United States Patent
Wolleb et al.

(10) Patent No.: US 11,279,709 B2
(45) Date of Patent: Mar. 22, 2022

(54) SPECIFICALLY SUBSTITUTED AZA-DIBENZOFURANS AND AZA-DIBENZOTHIOPHENES FOR ORGANIC ELECTRONIC DEVICES

(71) Applicant: IDEMITSU KOSAN CO., LTD., Chiyoda-ku (JP)

(72) Inventors: Annemarie Wolleb, Fehren (CH); Heinz Wolleb, Fehren (CH); Hideaki Nagashima, Ichihara (JP); Oliver Dosenbach, Bad Beilingen (DE); Takushi Shiomi, Chiba (JP)

(73) Assignee: IDEMITSU KOSAN CO., LTD., Chiyoda-ku (JP)

(*) Notice: Subject to any disclaimer, the term of this patent is extended or adjusted under 35 U.S.C. 154(b) by 339 days.

(21) Appl. No.: 16/329,443

(22) PCT Filed: Sep. 4, 2017

(86) PCT No.: PCT/JP2017/032595
§ 371 (c)(1),
(2) Date: Feb. 28, 2019

(87) PCT Pub. No.: WO2018/043761
PCT Pub. Date: Mar. 8, 2018

(65) Prior Publication Data
US 2019/0248804 A1  Aug. 15, 2019

(30) Foreign Application Priority Data
Sep. 5, 2016 (EP) .................................. 16187247

(51) Int. Cl.
*H01L 51/00* (2006.01)
*C07D 495/04* (2006.01)
(Continued)

(52) U.S. Cl.
CPC ....... *C07D 495/04* (2013.01); *C07D 491/048* (2013.01); *C09K 11/06* (2013.01);
(Continued)

(58) Field of Classification Search
None
See application file for complete search history.

(56) References Cited

U.S. PATENT DOCUMENTS 5,093,698 A * 3/1992 Egusa ................... H01L 51/506
257/40
8,415,031 B2   4/2013 Xia et al.
(Continued)

FOREIGN PATENT DOCUMENTS

EP    2 752 902 A1   7/2014
EP    3 162 806 A2   5/2017
(Continued)

OTHER PUBLICATIONS

International Search Report dated Nov. 21, 2017 in PCT/JP2017/032595 filed Sep. 4, 2017.

*Primary Examiner* — Robert S Loewe
(74) *Attorney, Agent, or Firm* — Oblon, McClelland, Maier & Neustadt, L.L.P.

(57) ABSTRACT

Specifically substituted aza-dibenzofurans and aza-dibenzothiophenes of formula (I) and their use in electronic devices, especially electroluminescent devices. When used as charge transport material, charge blocker material and/or host material in electroluminescent devices, the specifically substituted aza-dibenzofurans and aza-dibenzothiophenes may provide improved efficiency, stability, manufacturability, or spectral characteristics of electroluminescent devices and reduced driving voltage of electroluminescent devices. In formula (I) Y is S or O; one of $X^1$-$X^8$ is N; another $X^1$-$X^8$
(Continued)

is C-L(R$^9$)—[X$^9$X$^{10}$X$^{11}$]Ring; and the remaining X$^1$-X$^8$ are CR$^1$-CR$^8$ wherein R$^1$-R$^8$ are independently H, alkyl, alkenyl, aryl, etc.

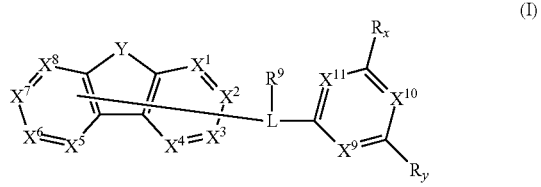

(I)

25 Claims, 1 Drawing Sheet

(51) Int. Cl.
C07D 491/048 (2006.01)
C09K 11/06 (2006.01)
H01L 51/50 (2006.01)

(52) U.S. Cl.
CPC ...... H01L 51/0054 (2013.01); H01L 51/0067 (2013.01); H01L 51/0071 (2013.01); H01L 51/0072 (2013.01); H01L 51/0073 (2013.01); H01L 51/5092 (2013.01); H01L 51/5096 (2013.01); C09K 2211/1007 (2013.01); C09K 2211/1011 (2013.01); C09K 2211/1033 (2013.01); C09K 2211/1037 (2013.01); C09K 2211/1051 (2013.01); C09K 2211/1059 (2013.01); C09K 2211/1092 (2013.01); H01L 51/0085 (2013.01); H01L 51/5016 (2013.01); H01L 51/5056 (2013.01); H01L 51/5072 (2013.01); H01L 51/5076 (2013.01)

(56) References Cited

U.S. PATENT DOCUMENTS

| | | | |
|---|---|---|---|
| 9,224,976 B2 * | 12/2015 | Sugisawa | H01L 51/5088 |
| 2007/0141387 A1 * | 6/2007 | Nakano | H01L 51/0072 |
| | | | 428/690 |
| 2013/0048964 A1 | 2/2013 | Takeda et al. | |
| 2013/0060037 A1 * | 3/2013 | Lin | H01L 27/32 |
| | | | 546/89 |
| 2014/0367667 A1 | 12/2014 | Iwakuma | |
| 2015/0207082 A1 | 7/2015 | Dyatkin et al. | |
| 2015/0349268 A1 | 12/2015 | Zeng et al. | |
| 2016/0028021 A1 * | 1/2016 | Zeng | C07D 251/24 |
| | | | 257/40 |
| 2016/0093808 A1 * | 3/2016 | Adamovich | H01L 51/001 |
| | | | 257/40 |
| 2016/0111654 A1 * | 4/2016 | Zoellner | H01L 51/0077 |
| | | | 257/40 |
| 2016/0233429 A1 * | 8/2016 | Xia | C09K 11/06 |
| 2016/0233436 A1 * | 8/2016 | Zeng | C09K 11/025 |
| 2017/0025618 A1 * | 1/2017 | Zheng | C09K 11/025 |
| 2017/0054087 A1 * | 2/2017 | Zeng | H05B 33/20 |
| 2017/0141325 A1 | 5/2017 | Lee et al. | |
| 2017/0253796 A1 | 9/2017 | Takeda et al. | |
| 2017/0362241 A1 * | 12/2017 | Nishimae | C09K 11/06 |
| 2018/0162843 A1 * | 6/2018 | Parham | C07D 405/14 |
| 2018/0208837 A1 * | 7/2018 | Ahn | H01L 51/0072 |
| 2019/0161497 A1 * | 5/2019 | Nishimae | H01L 51/5096 |

FOREIGN PATENT DOCUMENTS

| | | |
|---|---|---|
| JP | 5589251 B2 | 9/2014 |
| JP | 2015-126140 A | 7/2015 |
| KR | 10-2015-0122343 A | 11/2015 |
| WO | WO 2014/208755 A1 | 12/2014 |
| WO | WO 2015/072520 A1 | 5/2015 |
| WO | 2015/182872 A1 | 12/2015 |
| WO | WO 2015/199489 A2 | 12/2015 |
| WO | 2014/044722 A1 | 3/2017 |

* cited by examiner

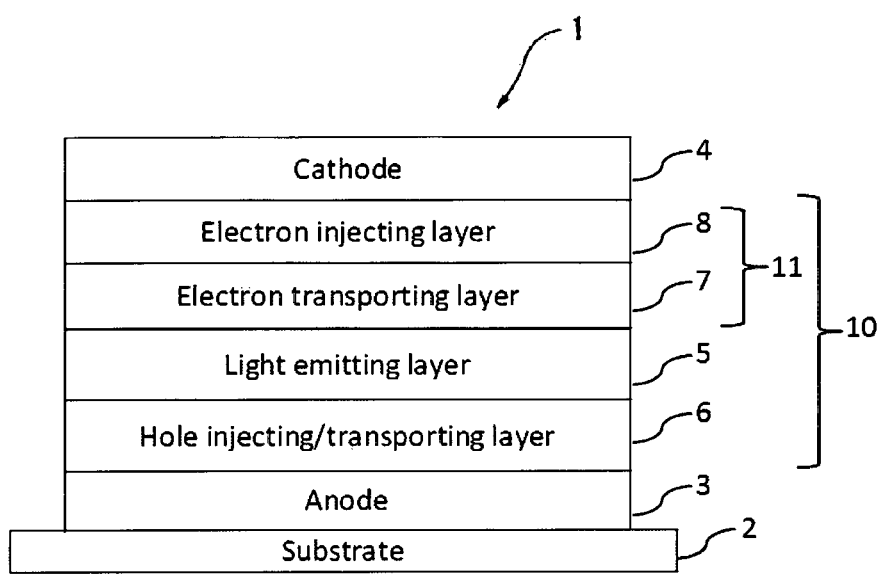

SPECIFICALLY SUBSTITUTED AZA-DIBENZOFURANS AND AZA-DIBENZOTHIOPHENES FOR ORGANIC ELECTRONIC DEVICES

The present invention relates to specifically substituted aza-dibenzofurans and aza-dibenzothiophenes and their use in electronic devices, especially electroluminescent devices. When used as charge transport material, charge blocker material and/or host material in electroluminescent devices, the specifically substituted aza-dibenzofurans and aza-dibenzothiophenes may provide improved efficiency, stability, manufacturability, or spectral characteristics of electroluminescent devices and reduced driving voltage of electroluminescent devices.

JP 2015126140 relates to an organic electroluminescent device comprising a triazine compound of the following formula (1) in an electron transport layer:

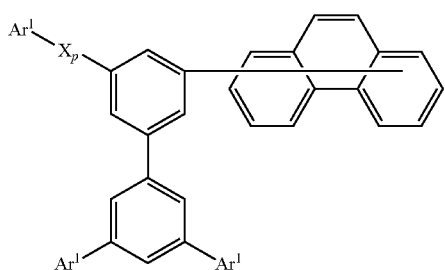
(1)

Compounds comprising an aza-dibenzofurane group or an aza-dibenzothiophene group are not disclosed in JP 2015126140.

WO 2014/208755 relates to a cyclic azine compound of formula (1) which is used for organic electroluminescent elements as electron transport material.

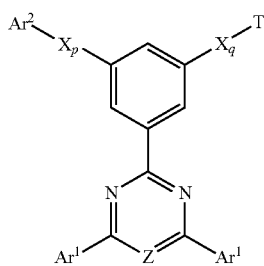
(1)

In WO 2014/208755 numerous specific compounds of formula (1) are mentioned. However, compounds comprising an aza-dibenzofurane group or an aza-dibenzothiophene group are not disclosed in WO 2014/208755.

WO 2014/044722 concerns aza-dibenzofurans of formula (I) for electronic applications

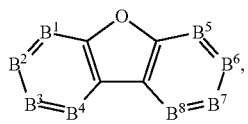
(I)

wherein at least one group $B^1$, $B^2$, $B^3$, $B^4$, $B^5$, $B^6$, $B^7$ or $B^8$ is N.

In WO 2014/044722 compounds like

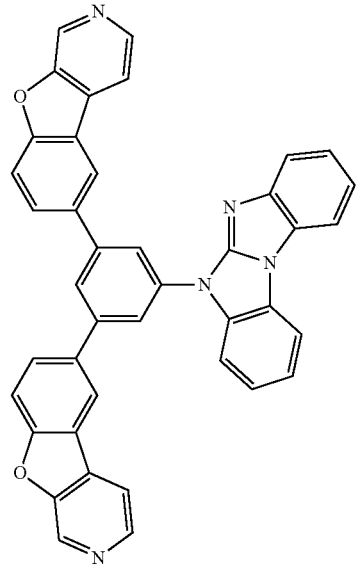
E-57 are disclosed. However, the compounds of formula (I) according to WO 2014/044722 do not comprise a triazine, pyrazine, pyrimidine or pyridazine group.

KR102015122343 discloses compounds of formula (1) for organic electronic elements

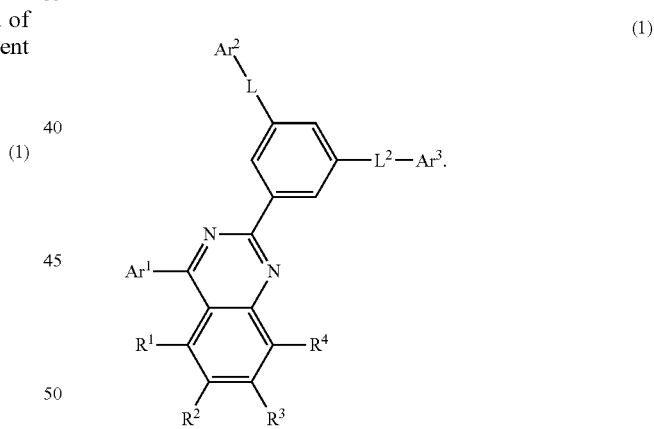
(1)

One mandatory group of the compounds of formula (1) is a fused group

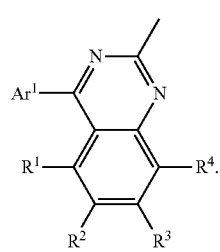

However, the compounds according to the present invention do not comprise a fused group

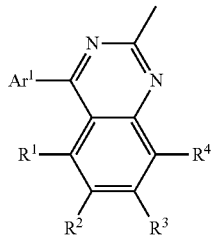

linked to a trivalent linking group.

WO 2015/182872 discloses compounds of the following formula as compounds for organic electronic devices.

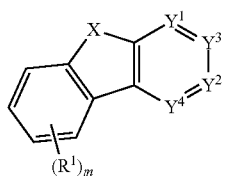

In WO 2015/182872 compounds like

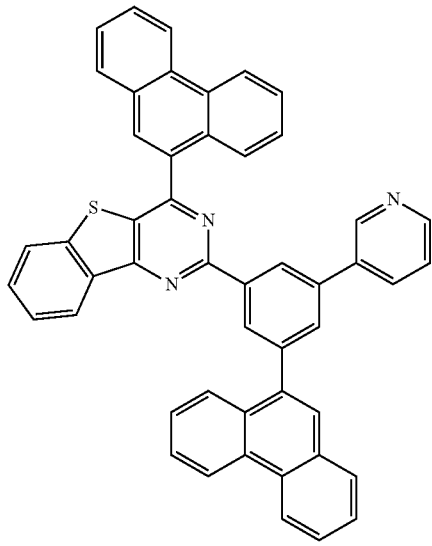

1-86 are disclosed. However, the compounds according to WO 2015/182872 do not comprise a triazine, pyrazine, pyrimidine or pyridazine group.

EP 2 752 902 discloses an aromatic heterocyclic derivative of formula (1), a material for an organic electroluminescent element and an organic electroluminescent element comprising the heterocyclic derivative

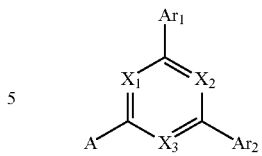

wherein A is a group of formula (2)

$$(HAr)_a\text{-}L_1\text{-} \tag{2},$$

and HAr is represented by formula (3)

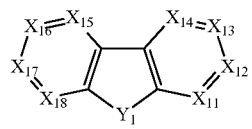

However, the compounds of the present application differ from the compounds disclosed in EP 2 752 902 in the residue attached to the trivalent linking group, which is a fused residue in the compounds according to the present invention.

WO 2015/072520 discloses a compound of formula (1), a material for an organic electroluminescence device, an organic electroluminescence device, and an electronic device comprising the compound of formula (1)

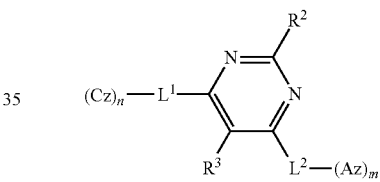

An example for a compound of formula (1) according to WO 2015/072520 is a compound of formula (13A)

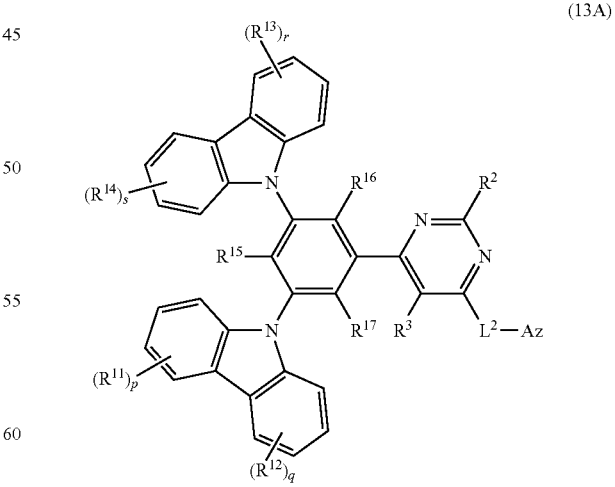

However, the compounds of the present application differ from the compounds disclosed in WO 2015/072520 in the presence of an aza-dibenzofurane group or an aza-dibenzothiophene group.

US2014/0367667 discloses a compound of formula (1) for use as material for an organic electroluminescence device and an organic electroluminescence device using the same

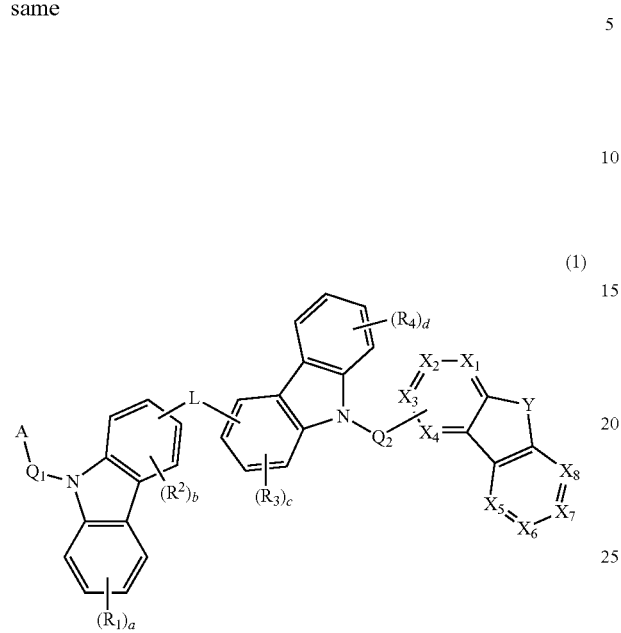

(1)

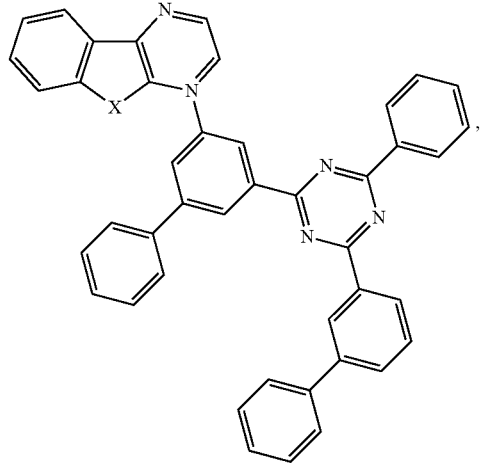

However, the compounds of the present application differ from the compounds disclosed in US2014/0367667 in the presence of a trivalent linking group directly attached to an aza-dibenzofurane group or an aza-dibenzothiophene group.

US2015/0207082 discloses compounds based on aza- and diazodibenzofurans and aza- and diaza dibenzothiophenes useful for electron transporting host material in green, red, yellow, and white phosphorescent emitting devices. The compounds are of formula (I): $G^1$-L-$G^2$, wherein $G^1$ is

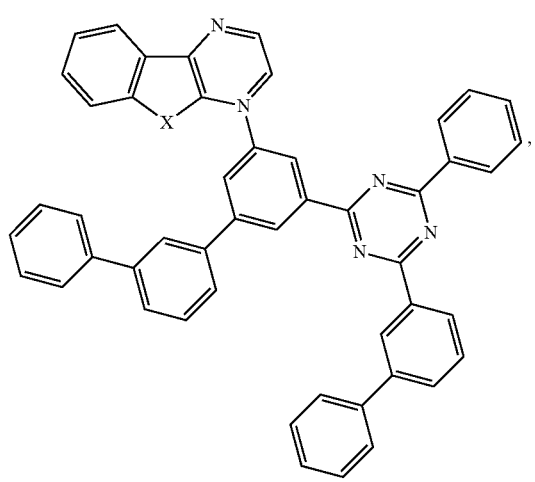

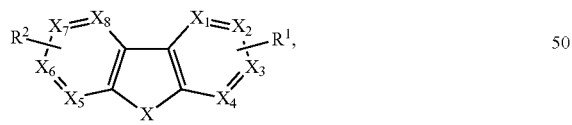

$G^2$ is a heteroaryl group having from 3 to 60 carbon atoms and from 1 to 6 heteroatoms, and L is a group consisting of a direct bond, benzene, biphenyl, terphenyl, naphthalene, triphenylene, dibenzofuran, dibenzothiophene, dibenzoselenophene, fluorine, pyridine, pyrimidine, pyridazine, pyrazine, quinolone, quinoxaline, naphtharidine, and combinations thereof; wherein L is optionally further unfused substituted with one or more groups selected from hydrogen, deuterium, alkyl, cycloalkyl, aralkyl, alkoxy, aryloxy, amino, silyl, aryl, heteroaryl, and combinations thereof. The following examples are shown in US2015/0207082

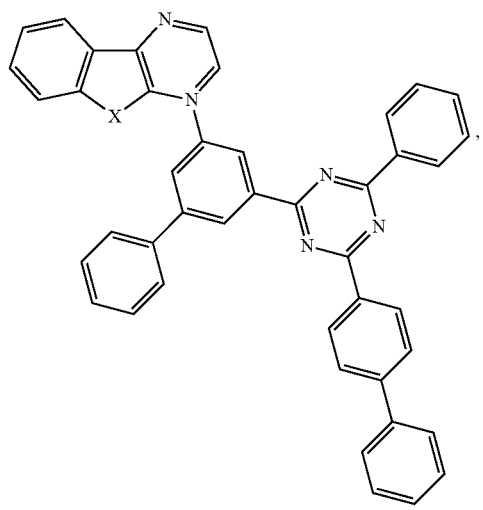

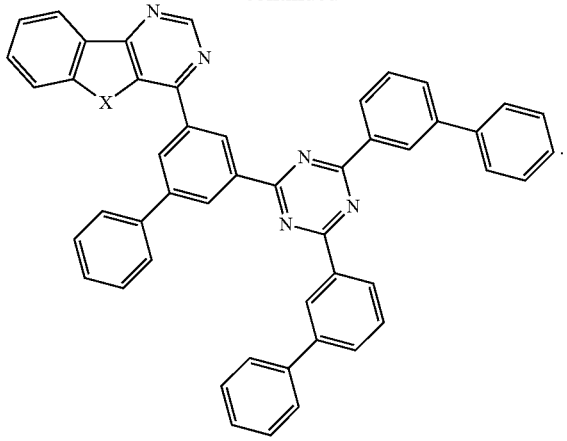

In most of the examples mentioned in US2015/0207082, L is a divalent linking group. The compounds of the present application differ from the compounds disclosed in US2015/0207082 in the residue attached to the trivalent linking group, which is a fused residue in the compounds according to the present invention.

US2015/0349268 discloses organic compounds containing triphenylene and triazine moieties. The compounds are expected to improve device performance when they are used in organic electroluminescent devices. The compounds are of formula (I):

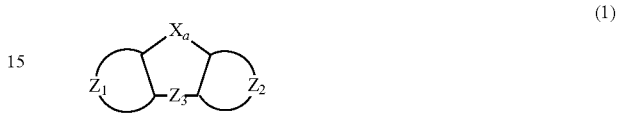

wherein
$G^1$ is triphenylene or aza-triphenylene;
$G^2$ and $G^3$ are each independently selected from the group consisting of benzene, biphenyl, terphenyl, dibenzofuran, dibenzothiophene, dibenzoselenophene, naphthalene, phenanthrene, benzofuran, benzothiophene, benzoselenophene, pyridine, pyrimidine, aza-dibenzothiophene, aza-dibenzofuran, aza-dibenzoselenophene, quinoline, isoquinoline, quinazoline, phenanthroline, and combinations thereof;
$L^1$, $L^2$ and $L^3$ are each independently selected from a group consisting of a direct bond, benzene, biphenyl, pyridine, pyramidine, phenylpyridine, and diphenylpyridine;
wherein $G^1$, $G^2$ and $G^3$, are each independently optionally further substituted with one or more substituents selected from the group consisting of deuterium, alkyl, alkoxyl, cycloalkyl, cycloalkoxyl, halogen, nitro, nitrile, silyl, benzene, biphenyl, terphenyl, naphthalene, phenanthrene, and combinations thereof;
$L^1$, $L^2$ and $L^3$ are each independently optionally further substituted with one or more substituents selected from the group consisting of deuterium, alkyl, alkoxyl, cycloalkyl, cycloalkoxyl, halogen, nitro, nitrile, silyl, benzene, biphenyl, terphenyl, naphthalene, phenanthrene, and combinations thereof; and
wherein at least one of $L^2$-$G^2$ and $L^3$-$G^3$ has more than six carbon atoms. However, the compounds of the present application differ from the compounds disclosed in US2015/0349268 in the presence of a trivalent linking group directly attached to an aza-dibenzofurane group or an aza-dibenzothiophene group and to a specific monocyclic heteroaryl group.

JP5589251 discloses a high emission luminance and long organic electroluminescence element material, an organic electroluminescent device, and a lighting device using the element, to provide a display device. The organic electroluminescent device material is characterized by a structure represented by the following general formula (1)


(1)

$X_a$ represents an oxygen atom, a sulfur atom, a selenium atom or a tellurium atom. $Z_1$, $Z_2$ each represents an aromatic hydrocarbon ring or an aromatic heterocyclic ring, either one is an aromatic heterocyclic ring. $Z_3$ represents a divalent linking group or merely a bond. However, the compounds of the present application differ from the compounds disclosed in JP5589251 in the presence of a trivalent linking group directly attached to an aza-dibenzofurane group or an aza-dibenzothiophene group.

U.S. Pat. No. 8,415,031 relates to compounds comprising an aza-dibenzo moiety having at least three benzene rings of the following formula: $Ar(L_i\text{-}D_i)_n$. Ar contains a condensed aromatic ring having at least three benzene rings and the condensed aromatic ring has a triplet energy lower than 440 nm. Ar is optionally further substituted. L is a single bond or a bivalent linking group. n is at least 1. i is an indexing variable that identifies n structures for $L_i$ and $D_i$ that may be the same or different for different values of i. Each $L_i$ is independently a single bond or a bivalent linking group. Each $D_i$ independently has the structure:

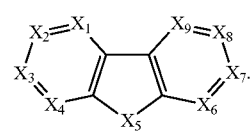

The compounds may be used in the electron transport layer of organic light emitting devices. U.S. Pat. No. 8,415,031 does not disclose compounds comprising a specifically substituted trivalent linking group.

Notwithstanding these developments, there remains a need for organic light emitting devices comprising new materials, especially host (=matrix) materials, charge transport materials, i.e. hole transport materials and electron transport materials, and/or charge/exciton blocker materials, i.e. electron/exciton blocker materials and hole/exciton blocker materials, to provide long lifetimes, improved efficiency, stability, manufacturability, driving voltage and/or spectral characteristics of electroluminescent devices.

Accordingly, it is an object of the present invention, with respect to the aforementioned related art, to provide further materials suitable for use in OLEDs and further applications in organic electronics. More particularly, it should be possible to provide charge transport materials, i.e. hole transport materials and electron transport materials, and/or charge/exciton blocker materials, i.e. electron/exciton blocker materials and hole/exciton blocker materials, and host (=matrix)

materials for use in OLEDs. The materials should be suitable especially for OLEDs which comprise at least one emitter, which is a phosphorescence emitter and/or a fluorescent emitter, for example at least one blue, green, red or yellow emitter, especially at least one blue emitter (e.g. fluorescent system), at least one green emitter or at least one red emitter.

Furthermore, the materials should be suitable for providing OLEDs which ensure good efficiencies, good operative lifetimes and a high stability to thermal stress, and a low use and operating voltage of the OLEDs.

Said object is solved by the compounds of formula (I)

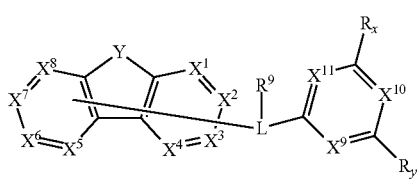

(I)

wherein
Y is S or O, preferably S;
$X^1$ is N or $CR^1$, preferably $CR^1$;
$X^2$ is N or $CR^2$, preferably $CR^2$;
$X^3$ is N or $CR^3$, preferably $CR^3$;
$X^4$ is N or $CR^4$, preferably N;
$X^5$ is N or $CR^5$, preferably $CR^6$;
$X^6$ is N or $CR^6$, preferably $CR^6$;
$X^7$ is N or $CR^7$, preferably $CR^7$;
$X^8$ is N or $CR^6$, preferably $CR^8$;
wherein one of $X^1$, $X^2$, $X^3$, $X^4$, $X^5$, $X^6$, $X^7$ and $X^8$ is N; and one of the remaining groups $X^1$, $X^2$, $X^3$, $X^4$, $X^5$, $X^6$, $X^7$ and $X^8$ is $CR^1$, $CR^2$, $CR^3$, $CR^4$, $CR^5$, $CR^6$, $CR^7$ or $CR^8$, wherein $R^1$, $R^2$, $R^3$, $R^4$, $R^5$, $R^6$, $R^7$ or $R^8$, preferably $R^1$, is

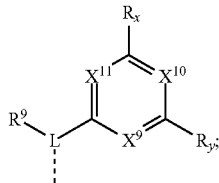

and the other of the remaining groups $X^1$, $X^2$, $X^3$, $X^4$, $X^5$, $X^6$, $X^7$ and $X^8$ are $CR^1$, $CR^2$, $CR^3$, $CR^4$, $CR^5$, $CR^6$, $CR^7$ or $CR^8$, wherein $R^1$, $R^2$, $R^3$, $R^4$, $R^5$, $R^6$, $R^7$ and $R^8$ are independently of each other H, CN, $NR^{65}R^{66}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group, which can optionally be substituted by G;
or adjacent groups $R^1$ and $R^2$, $R^2$ and $R^3$, $R^3$ and $R^4$, $R^5$ and $R^6$, $R^6$ and $R^7$, and/or $R^7$ and $R^8$ can optionally from together a ring, which can optionally be substituted by G; wherein— in the case that one of $X^1$ or $X^4$ is N—$R^2$ and $R^3$ do not form together a ring;
L is a trivalent $C_6$-$C_{24}$ arylene group or a trivalent $C_2$-$C_{24}$ heteroarylene group, preferably a trivalent $C_6$-$C_{14}$ arylene group or a trivalent $C_3$-$C_{13}$ heteroarylene group, more preferably a trivalent $C_6$ arylene group or a trivalent $C_3$-$C_5$ heteroarylene group;
$R^9$ is a fused $C_{10}$-$C_{24}$aryl group or a fused $C_{12}$-$C_{24}$ heteroaryl group, preferably, $R^9$ is selected from the group consisting of naphthyl, phenanthryl, anthryl, benzophenanthryl, benzanthryl, naphthacenyl, triphenylenyl, benzochrysenyl, fluorenyl, benzofluorenyl, dibenzofluorenyl, indenofluorenyl, benzindenofluorenyl, fluoranthenyl, benzofluoranthenyl, benzotriphenylenyl, quinolyl, isoquinolyl, quinazolinyl, quinoxalinyl, benzoquinolynyl, benzoisoquinolinyl, benzoquinazolinyl, benzoquinoxalinyl, naphthoquinolinyl, naphthoisoquinolinyl, naphthoquinazolinyl, naphthoquinoxalinyl, phenanthrolinyl, benzofuroquinolinyl, benzothienoquinolinyl, carbazolyl, benzocarbazolyl, dibenzocarbazolyl, indenocarbazolyl, benzofurocarbazolyl, benzothiocarbazolyl, indrocarbazolyl, benzimidazol[1,2-a]benzimadozolyl, dibenzofuranyl, dibenzothiophenyl, benzonaphthofuranyl, benzonaphthothiophenyl, benzophenanthrofuranyl, and benzophenanthrothiophenyl, wherein the groups mentioned above can optionally be substituted by G;
$X^9$, $X^{10}$ and $X^{11}$ are each independently N or $CR^{10}$, whereby at least two of $X^9$, $X^{10}$ and $X^{11}$ are N, preferably, $X^9$, $X^{10}$ and $X^{11}$ are N;
$R^{10}$ is H, $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G;
D is —CO—, —COO—, —S—, —SO—, —$SO_2$—, —O—, —$CR^{63}$=$CR^{64}$—, —$NR^{65}$—, —$POR^{72}$—, or —C≡C—, preferably —O—, —$NR^{65}$—;
E is —$OR^{69}$, —$SR^{69}$, —$NR^{65}R^{66}$, —$COR^{68}$, —$COOR^{67}$, —$CONR^{65}R^{66}$ or —CN, preferably —$NR^{65}R^{66}$, —CN,
G is E, or a $C_1$-$C_{24}$alkyl group, an unsubstituted $C_6$-$C_{24}$aryl group, a $C_6$-$C_{24}$aryl group, which is substituted by F, $C_1$-$C_{24}$alkyl, or $C_1$-$C_{24}$alkyl which is interrupted by O, an unsubstituted $C_2$-$C_{30}$heteroaryl group, or a $C_2$-$C_{30}$heteroaryl group, which is substituted by F, $C_1$-$C_{24}$alkyl, or $C_1$-$C_{24}$alkyl which is interrupted by O;
$R^{63}$ and $R^{64}$ are independently of each other unsubstituted $C_6$-$C_{18}$aryl; $C_6$-$C_{18}$aryl which is substituted by $C_1$-$C_{18}$alkyl or $C_1$-$C_{18}$alkoxy; $C_1$-$C_{18}$alkyl; or $C_1$-$C_{18}$alkyl which is interrupted by —O—;
$R^{65}$ and $R^{66}$ form together with the carbon atoms to which they are bonded a 5- or 6-membered ring, which can optionally be part of an anellated ring system, wherein the ring and/or anellated ring system can optionally be substituted by G;
$R^{67}$ is an unsubstituted $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; $R^{68}$ is H; an unsubstituted $C_6$-$C_{18}$aryl group; a $C_6$-$C_{18}$aryl group, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;
$R^{69}$ is an unsubstituted $C_6$-$C_{18}$aryl; a $C_6$-$C_{18}$aryl, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{71}$ is a $C_1$-$C_{18}$alkyl group, a $C_6$-$C_{18}$aryl group, or a $C_6$-$C_{18}$aryl group, which is substituted by $C_1$-$C_{18}$alkyl; and $R^{72}$ is a $C_1$-$C_{18}$alkyl group, an unsubstituted $C_6$-$C_{18}$aryl group, or a $C_6$-$C_{18}$aryl group, which is substituted by $C_1$-$C_{18}$alkyl;

$R^{73}$ and $R^{74}$ form together with the carbon atoms to which they are bonded a 5- or 6-membered ring, which can optionally be part of an anellated ring system, wherein the ring and/or anellated ring system can optionally be substituted by G;

$R_x$ and $R_y$ are independently of each other $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3$-$C_{18}$cycloalkyl group, which can optionally be substituted by G; a $C_6$-$C_{12}$aryl group, which can optionally be substituted by G, or a $C_2$-$C_{30}$heteroaryl group which can optionally be substituted by G;

wherein the dotted line is a bonding site.

BRIEF DESCRIPTION OF DRAWINGS

FIG. 1 shows a schematic configuration of one example of the organic EL device of the invention.

The specific substitution of the compounds of formula (I) gives rise to materials, especially host, charge transport or charge blocking materials, that are highly suitable in devices that emit blue, green or red light. Moreover, an improved electron injection, a balanced charge transport, i.e. hole transport or electron transport, and/or charge/exciton blocking, i.e. electron/exciton blocking or hole/exciton blocking, in devices is achieved resulting in low voltages, high external quantum efficiencies (EQE's) and/or long lifetimes.

The specifically substituted compounds of formula (I) according to the present invention are characterized by a lower LUMO level than the compounds disclosed in the related art. Further, the glass transition temperature (TG) of the specifically substituted compounds of the present invention is high and the morphology is improved, which results in a high stability of a device comprising said compounds. Further, the specifically substituted compounds of formula (I) show superior electron transport properties.

The compounds of the present invention may be used for electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and electroluminescent devices, such as, for example, organic light-emitting diodes (OLEDs).

Accordingly, a further subject of the present invention is directed to an electronic device, comprising a compound according to the present invention. The electronic device is preferably an electroluminescent device, such as an organic light-emitting diode (OLED).

The compounds of formula (I) can in principle be used in any layer of an EL device, but are preferably used as host, charge transport, i.e. hole transport or electron transport, and/or charge/exciton blocking, i.e. electron/exciton blocking or hole/exciton blocking, material. Particularly, the compounds of formula (I) are used as host material for green, red and blue light emitting phosphorescent or fluorescent emitters and/or as electron transport material, in combination with phosphorescent and/or fluorescent emitters.

Hence, a further subject of the present invention is directed to a charge transport, i.e. hole transport or electron transport, layer, preferably an electron transport layer, comprising a compound of formula (I) according to the present invention.

Hence, a further subject of the present invention is directed to a charge/exciton blocking, i.e. electron/exciton blocking or hole/exciton blocking, layer, preferably a hole/exciton blocking layer, comprising a compound of formula (I) according to the present invention.

A further subject of the present invention is directed to an emitting layer, comprising a compound of formula (I) according to the present invention. In said embodiment a compound of formula (I) is preferably used as host material or as co-host material together with one or more, preferably one, further host materials. More preferably, a combination of a compound of formula (I) and a co-host material together with a phosphorescent emitter is used.

A further subject of the present invention is directed to a hole/exciton blocking layer, comprising a compound of formula (I) according to the present invention.

A further subject of the present invention is directed to an electron/exciton blocking layer, comprising a compound of formula (I) according to the present invention.

The terms halogen, alkyl, alkoxy, cycloalkyl, aryl, aryloxy, aralkyl, heteroaryl, arylene, heteroarylene are known in the art and generally have the following meaning, if said groups are not further specified in specific embodiments mentioned below:

Halogen is fluorine, chlorine, bromine and iodine, preferably fluorine.

$C_1$-$C_{25}$alkyl, preferably $C_1$-$C_{24}$alkyl and more preferably $C_1$-$C_{18}$alkyl are typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

The alkyl groups mentioned above can optionally be substituted by E and/or interrupted by D. Preferably, the alkyl groups mentioned above are unsubstituted or can optionally be substituted by E.

$C_2$-$C_{25}$alkenyl, preferably $C_2$-$C_{24}$alkenyl and more preferably $C_2$-$C_{18}$alkenyl are typically linear or branched, where possible.

The alkenyl groups mentioned above can optionally be substituted by E and/or interrupted by D. Preferably, the alkenyl groups mentioned above are unsubstituted or can optionally be substituted by E.

$C_2$-$C_{25}$alkynyl, preferably $C_2$-$C_{24}$alkynyl and more preferably $C_2$-$C_{18}$alkynyl are typically linear or branched, where possible.

The alkynyl groups mentioned above can optionally be substituted by E and/or interrupted by D. Preferably, the alkynyl groups mentioned above are unsubstituted or can optionally be substituted by E.

$C_1$-$C_{25}$alkoxy groups and preferably $C_1$-$C_{51}$alkoxy groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

$C_3$-$C_{18}$cycloalkyl, preferably $C_5$-$C_{12}$cycloalkyl is for example cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl. The cycloalkyl groups may be unsubstituted or substituted by G.

$C_6$-$C_{60}$aryl, preferably $C_6$-$C_{30}$aryl, more preferably $C_6$-$C_{24}$aryl and most preferably $C_6$-$C_{18}$aryl, which is unsubstituted or optionally can be substituted by G, is most preferably phenyl, 4-methylphenyl, 4-methoxyphenyl, naphthyl, especially 1-naphthyl, or 2-naphthyl, biphenylyl, triphenylyl, fluoranthenyl, terphenylyl, pyrenyl, 2- or 9-fluorenyl, phenanthryl, or anthryl, which may be unsubstituted or substituted by G. Phenyl, 1-naphthyl and 2-naphthyl are examples of a $C_6$-$C_{10}$aryl group.

$C_6$-$C_{60}$heteroaryl, preferably $C_2$-$C_{30}$heteroaryl, more preferably $C_2$-$C_{13}$ heteroaryl represents a ring with five, six or seven ring atoms or a condensed ring system, wherein nitrogen, oxygen or sulfur are the possible heteroatoms, and is typically a heterocyclic group with five to 60 atoms, preferably with five to 30 atoms, more preferably with five to 13 atoms having at least six conjugated π-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, 4-imidazo[1,2-a]benzimidazoyl, 5-benzimidazo[1,2-a]benzimidazoyl, benzimidazolo[2,1-b][1,3]benzothiazolyl, carbazolyl, azatriphenylyl, azadibenzofuryl, azadibenzothiophenyl, azacarbazolyl, quinolonyl, isoquinolinyl, quinoxalinyl, quinazolinyl, phenanthrolinyl, phenanthridinyl, benzo[h]quinolonyl, benz[h]isoquinolinyl, benzo[f]isoquinolinyl, benzo[f]quinolinyl, benzo[h]quinazolinyl, benzo[f]quinazolinyl, dibenzo[f,h]quinolonyl, dibenzo[f,h]isoquinolonyl, dibenzo[f,h]quinoxalinyl, dibenzo[f,h]quinazolinyl or phenoxazinyl, which can be unsubstituted or substituted by G. Benzimidazo[1,2-a]benzimidazo-5-yl, benzimidazo[1,2-a]benzimidazo-2-yl, carbazolyl and dibenzofuranyl are examples of a $C_2$-$C_{14}$heteroaryl group.

A $C_2$-$C_{13}$heteroaryl group is for example, benzimidazo[1,2-a]benzimidazo-5-yl

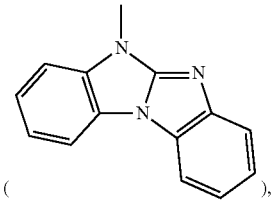 [SMILES: Cn1c2ccccc2n2c3ccccc3nc12]

( ), benzimidazo[1,2-a]benzimidazo-2-yl

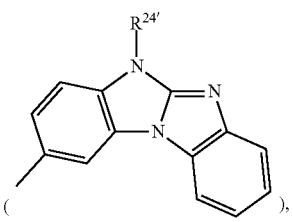

( ), benzimidazolo[2,1-b][1,3]benzothiazolyl, benzimidazolo[2,1-b][1,3]benzoxazole, carbazolyl, dibenzofuranyl, or dibenzotihophenyl, which can be unsubstituted or substituted by G, especially by $C_6$-$C_{10}$aryl, or $C_6$-$C_{10}$aryl, which is substituted by $C_1$-$C_4$alkyl; or $C_2$-$C_{13}$heteroaryl.

$C_1$-$C_{60}$heteroaryl, preferably $C_2$-$C_{30}$heteroaryl, more preferably $C_1$-$C_{24}$heteroaryl, most preferably $C_2$-$C_{13}$ heteroaryl means that the heteroaryl residue comprises at least one, preferably at least 2 carbon atoms and at most 60 carbon atoms in the base skeleton (without substituents). The further atoms in the heteroaryl base skeleton are heteroatoms (N, O and/or S).

$R^{24'}$ is in each case independently $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, phenanthronyl, triphenylenyl, fluoranthenyl or biphenylyl.

$C_1$-$C_{24}$heterocyclic group, preferably $C_1$-$C_{13}$heterocyclic group, more preferably $C_2$-$C_{13}$ heterocyclic group represents a ring with five, six or seven ring atoms or a condensed ring system, wherein nitrogen, oxygen or sulfur are the possible heteroatoms, and is typically a heterocyclic group with five to 24 atoms, preferably with five to 13 atoms. The heterocyclic group may be a $C_1$-$C_{24}$heteroaryl group as defined above or a $C_1$-$C_{24}$heterocycloalkyl group which may be unsubstituted or substituted by G. Typical $C_1$-$C_{24}$heterocycloalkyl groups are oxetan, tetrahydrofuran, tetrahydropyran, oxepane, dioxane, azetidine, pyrrolidine, piperidine, hexahydroazepine, hexahydrodiazepin, tetrahydrothiophene, thietan, tetrahydrothiopyran, thiepan, morpholine as well as bridged heterocycloalkyl systems such as oxabicyclo[4.4.0]decane and azabicyclo[2,2,1]undecane.

$C_6$-$C_{24}$arylene groups, preferably $C_6$-$C_{10}$arylene groups, which optionally can be substituted by G, preferably $C_6$-$C_{10}$arylene groups, which optionally can be substituted by G, are more preferably phenylene, 4-methylphenylene, 4-methoxyphenylene, naphthylene, especially 1-naphthylene, or 2-naphthylene, biphenylylene, triphenylylene, fluoranthenylene, terphenylylene, pyrenylene, 2- or 9-fluorenylene, phenanthrylene, or anthrylene, which may be unsubstituted or substituted by G. Preferred $C_6$-$C_{24}$arylene groups, preferably $C_6$-$C_{10}$arylene groups are 1,3-phenylene, 3,3'-biphenylylene, 3,3'-m-terphenylene, 2- or 9-fluorenylene, phenanthrylene, which may be unsubstituted or substituted by G.

$C_1$-$C_{30}$heteroarylene groups, preferably $C_2$-$C_{14}$heteroarylene groups, which are unsubstituted or optionally can be substituted by G, represent a ring with five to seven ring atoms or a condensed ring system, wherein nitrogen, oxygen or sulfur are the possible heteroatoms, and is typically a heterocyclic group with five to 30 atoms having at least six conjugated-electrons such as thienylene, benzothiophenylene, dibenzothiophenylene, thianthrenylene, furylene, furfurylene, 2H-pyranylene, benzofuranylene, isobenzofuranylene, dibenzofuranylene, phenoxythienylene, pyrrolylene, imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, chinolylene, isochinolylene, phthalazinylene, naphthyridinylene, chinoxalinylene, chinazolinylene, cinnolinylene, pteridinylene, carbolinylene, benzotriazolylene, benzoxazolylene, phenanthridinylene, acridinylene, pyrimidinylene, phenanthrolinylene, phenazinylene, isothiazolylene, phenothiazinylene, isoxazolylene, furazanylene, carbazolylene, benzimidazo[1,2-a]benzimidazo-2,5-ylene, or phenoxazinylene, which can be unsubstituted or substituted by G. Preferred $C_2$-$C_{30}$heteroarylen groups are pyridylene, triazinylene, pyrimidinylene, carbazolylene, dibenzofuranylene, azatriphenylylene, azadibenzofurylene, azadibenzothiophenylene, azacarbazolylene, quinolonylene, isoquinolinylene, quinoxalinylene, quinazolinylene, phenanthrolinylene, phenanthridinylene, benzo[h]quinolonylene, benz[h]isoquinolinylene, benzo[f]isoquinolinylene, benzo[f]quinolinylene, benzo[h]quinazolinylene, benzo[f]quinazolinylene, dibenzo[f,h]quinolonylene, dibenzo[f,h]isoquinolonylene, dibenzo[f,h]quinolonylene, dibenzo[f,h]quinazolinylene and benzimidazo[1,2-a]benzimidazo-2,5-ylene

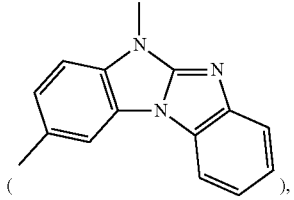 [SMILES: Cc1ccc2c(c1)n1c3ccccc3nc1n2C]

( ), which can be unsubstituted or substituted by G, preferably substituted by $C_6$-$C_{10}$aryl, $C_6$-$C_{10}$aryl which is substituted by $C_1$-$C_4$alkyl; or $C_2$-$C_{13}$heteroaryl.

If a substituent occurs more than one time in a group, it can be identical or different in each occurrence.

Halo-$C_1$-$C_8$alkyl is an alkyl group (as defined above) where at least one of the hydrogen atoms is replaced by a halogen atom. Examples are —$CF_3$, —$CF_2CF_3$, —$CF_2CF_2CF_3$, —$CF(CF_3)_2$, —$(CF_2)_3CF_3$, and —$C(CF_3)_3$.

The wording "substituted by G" means that one, or more, especially one, two or three substituents G might be present. Preferred substituents G are mentioned below.

The wording "substituted by E" means that one, or more, especially one, two or three substituents E might be present. Preferred substituents E are mentioned below.

As described above, the aforementioned alkyl groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl contains the unit D in the alkyl moiety. $C_1$-$C_{18}$alkyl substituted by one or more E and/or interrupted by one or more units D is, for example, $(CH_2CH_2O)_{1-9}$—$R_x$, where $R_x$ is H or $C_1$-$C_{10}$alkyl or $C_2$-$C_{10}$alkanoyl (e.g. CO—$CH(C_2H_5)C_4H_9$), $CH_2$—$CH(OR_y')$—$CH_2$—O—$R_y$, where $R_y$ is $C_1$-$C_{18}$alkyl, $C_5$-$C_{12}$cycloalkyl, phenyl, $C_7$-$C_{18}$phenylalkyl, and $R_y'$ embraces the same definitions as $R_y$ or is H.

An alkyl group substituted by E is, for example, an alkyl group where at least one of the hydrogen atoms is replaced by F. Examples are —$CF_3$, —$CF_2CF_3$, —$CF_2CF_2CF_3$, —$CF(CF_3)_2$, —$(CF_2)_3CF_3$, and —$C(CF_3)_3$.

D is —CO—, —COO—, —S—, —SO—, —$SO_2$—, —O—, —$NR^{65}$—, —$SiR^{70}R^{71}$—, —$POR^{72}$—, —$CR^{63}$=$CR^{64}$— or —C≡C—. Suitable residues $R^{63}$, $R^{64}$, $R^{65}$, $R^{70}R^{71}$ and $R^{72}$ are mentioned above. D is preferably —CO—, —COO—, —S—, —SO—, —$SO_2$—, —O—, —$NR^{65}$—, wherein $R^{65}$ is preferably $C_1$-$C_{18}$alkyl, such as methyl, ethyl, n-propyl, iso-propyl, n-butyl, isobutyl, or sec-butyl, or $C_6$-$C_{14}$aryl, such as phenyl, tolyl, naphthyl, triphenylyl or biphenylyl, or $C_2$-$C_{30}$heteroaryl, such as, for example, benzimidazo[1,2-a]benzimidazo-2-yl

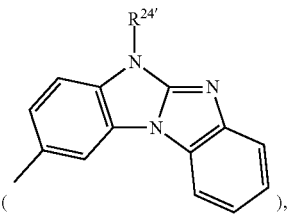

( ), carbazolyl, dibenzofuranyl, which can be unsubstituted or substituted especially by $C_6$-$C_{10}$aryl, or $C_6$-$C_{10}$aryl, which is substituted by $C_1$-$C_4$alkyl; or $C_2$-$C_{13}$heteroaryl.

E is —$OR^{69}$, —$SR^{69}$, —$NR^{65}R^{66}$, —$COR^{68}$, —$COOR^{67}$, —$CONR^{65}R^{66}$, —CN, —$SiR^{70}R^{71}R^{72}$, halogen or —$POR^{74}R^{75}$; preferably —$NR^{65}R^{66}$, —CN, —$SiR^{70}R^{71}R^{72}$ or —$POR^{74}R^{75}$; wherein $R^{65}$, $R^{66}$, $R^{67}$, $R^{68}$, $R^{69}$, $R^{70}$, $R^{71}$, $R^{72}$, $R^{73}$, $R^{74}$ and $R^{75}$ are preferably independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, triphenylyl or biphenylyl.

G is E, or a $C_1$-$C_{24}$alkyl group, a $C_6$-$C_{30}$aryl group, a $C_6$-$C_{30}$aryl group, which is substituted by F, $C_1$-$C_{24}$alkyl, or $C_1$-$C_{24}$alkyl which is interrupted by O; a $C_2$-$C_{60}$heteroaryl group, or a $C_2$-$C_{60}$heteroaryl group, which is substituted by F, $C_1$-$C_{18}$alkyl, or $C_1$-$C_{18}$alkyl which is interrupted by O. G is preferably —$OR^{69}$, —$SR^{69}$, —$NR^{65}R^{66}$; a $C_1$-$C_{18}$alkyl group, a $C_6$-$C_{18}$aryl group, a $C_6$-$C_{18}$aryl group, which is substituted by F, or $C_1$-$C_{18}$alkyl; a $C_2$-$C_{24}$heteroaryl group, or a $C_2$-$C_{24}$heteroaryl group, which is substituted by F, or $C_1$-$C_{18}$alkyl; wherein $R^{65}$, $R^{66}$ and $R^{69}$ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, or biphenylyl. More preferably, G is a $C_6$-$C_{18}$aryl group like phenyl, tolyl, triphenylyl or biphenylyl, phenanthryl, anthranyl or a $C_6$-$C_{24}$heteroaryl group like dibenzothiophenylyl, dibenzofuranyl, pyridyl, triazinyl, pyrimidinyl, azatriphenylyl, azadibenzofuryl, azadibenzothiophenyl, azacarbazolyl, quinolonyl, isoquinolinyl, quinoxalinyl, quinazolinyl, phenanthrolinyl, phenanthridinyl, benzo[h]quinolonyl, benz[h]isoquinolinyl, benzo[f]isoquinolinyl, benzo[f]quinolinyl, benzo[h]quinazolinyl, benzo[f]quinazolinyl, dibenzo[f,h]quinolonyl, dibenzo[f,h]isoquinolonyl, dibenzo[f,h]quinoxalinyl or dibenzo[f,h]quinazolinyl.

$X^1$, $X^2$, $X^3$, $X^4$, $X^5$, $X^6$, $X^7$ and $X^8$
$X^1$ is N or $CR^1$;
$X^2$ is N or $CR^2$;
$X^3$ is N or $CR^3$;
$X^4$ is N or $CR^4$;
$X^5$ is N or $CR^5$;
$X^6$ is N or $CR^6$;
$X^7$ is N or $CR^7$;
$X^8$ is N or $CR^8$;
wherein one of $X^1$, $X^2$, $X^3$, $X^4$, $X^5$, $X^6$, $X^7$ and $X^8$ is N; and one of the remaining groups $X^1$, $X^2$, $X^3$, $X^4$, $X^5$, $X^6$, $X^7$ and $X^8$ is $CR^1$, $CR^2$, $CR^3$, $CR^4$, $CR^5$, $CR^6$, $CR^7$ or $CR^8$, wherein $R^1$, $R^2$, $R^3$, $R^4$, $R^5$, $R^6$, $R^7$ or $R^8$ is

[structure]

and the other of the remaining groups $X^1$, $X^2$, $X^3$, $X^4$, $X^5$, $X^6$, $X^7$ and $X^8$ are $CR^1$, $CR^2$, $CR^3$, $CR^4$, $CR^5$, $CR^6$, $CR^7$ or $CR^8$, wherein $R^1$, $R^2$, $R^3$, $R^4$, $R^5$, $R^6$, $R^7$ and $R^8$ are independently of each other H, CN, $NR^{65}R^{66}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, $-OR^{69}$, $-SR^{69}$, $-COR^{68}$, $-COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group, which can optionally be substituted by G;
or adjacent groups $R^1$ and $R^2$, $R^2$ and $R^3$, $R^3$ and $R^4$, $R^5$ and $R^6$, $R^6$ and $R^7$, and/or $R^7$ and $R^8$ can optionally from together a ring, which can optionally be substituted by G; wherein—in the case that one of $X^1$ or $X^4$ is N—$R^2$ and $R^3$ do not form together a ring.

Preferred alkyl groups, alkenyl groups, alkynyl groups, cycloalkyl groups, aryl groups and heteroaryl groups as well as preferred groups E, D and G are mentioned above.

Further, suitable and preferred groups $R^{63}$ and $R^{64}$, $R^{65}$ and $R^{66}$, $R^{67}R^{68}$, $R^{69}$, $R^{71}$, $R^{72}$, $R^{73}$ and $R^{74}$ are mentioned above.

Preferably, $X^4$ or $X^1$ is N, more preferably $X^4$ is N, and one of the remaining groups $X^1$, $X^2$, $X^3$, $X^4$, $X^5$, $X^6$, $X^7$ and $X^8$ is $CR^1$, $CR^2$, $CR^3$, $CR^4$, $CR^5$, $CR^6$, $CR^7$ or $CR^8$, wherein $R^1$, $R^2$, $R^3$, $R^4$, $R^5$, $R^6$, $R^7$ or $R^8$ is

[structure]

and the other of the remaining groups $X_1$, $X_2$, $X_3$, $X_4$, $X^5$, $X^6$, $X^7$ and $X^8$ are $CR^1$, $CR^2$, $CR^3$, $CR^4$, $CR^5$, $CR^6$, $CR^7$ or $CR^8$, wherein $R^1$, $R^2$, $R^3$, $R^4$, $R^5$, $R^6$, $R^7$ and $R^8$ are independently of each other H, CN, $NR^{65}R^{66}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, $-OR^{69}$, $-SR^{69}$, $-COR^{68}$, $-COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group, which can optionally be substituted by G;
or adjacent groups $R^1$ and $R^2$, $R^5$ and $R^6$, $R^6$ and $R^7$, and/or $R^7$ and $R^8$ can optionally from together a ring, which can optionally be substituted by G.

Preferred compounds of the present invention are therefore compounds of formula (Ia)

(Ia)

[structure]

wherein the groups $R^1$, $R^2$, $R^3$, $R^5$, $R^6$, $R^7$, $R^8$, $R^9$, Y, L, $X^9$, $X^{10}$, $X^{11}$, $R_x$ and $R_y$ have the meanings mentioned above. Preferred meanings of the groups $R^1$, $R^2$, $R^3$, $R^5$, $R^6$, $R^7$, $R^8$, $R^9$, Y, L, $X^9$, $X^{10}$, $X^{11}$, $R_x$ and $R_y$ are mentioned below.

In a further preferred embodiment of the present invention,
$X^2$ is N or $CR^2$;
$X^3$ is N or $CR^3$;
$X^4$ is N or $CR^4$;
$X^5$ is N or $CR^5$;
$X^6$ is N or $CR^6$;
$X^7$ is N or $CR^7$;
$X^8$ is N or $CR^8$;
wherein $X^1$ is $CR^1$, wherein $R^1$ is

[structure]

one of the remaining groups $X^2$, $X^3$, $X^4$, $X^5$, $X^6$, $X^7$ and $X^8$ is N;
and the other of the remaining groups $X^2$, $X^3$, $X^4$, $X^5$, $X^6$, $X^7$ and $X^8$ are $CR^2$, $CR^3$, $CR^4$, $CR^5$, $CR^6$, $CR^7$ or $CR^8$, wherein $R^2$, $R^3$, $R^4$, $R^5$, $R^6$, $R^7$ and $R^8$ are independently of each other H, CN, $NR^{65}R^{66}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, $-OR^{69}$, $-SR^{69}$, $-COR^{68}$, $-COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group, which can optionally be substituted by G;
or adjacent groups $R^2$ and $R^3$, $R^3$ and $R^4$, $R^5$ and $R^6$, $R^6$ and $R^7$, and/or $R^7$ and $R^8$ can optionally from together a ring, which can optionally be substituted by G; wherein—in the case that $X^4$ is N—$R^2$ and $R^3$ do not form together a ring.

Most preferably, $X^4$ is N and $X^1$ is $CR^1$, wherein $R^1$ is

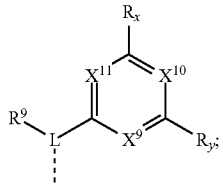

and the other of the remaining groups $X^2$, $X^3$, $X^5$, $X^6$, $X^7$ and $X^8$ are $CR^2$, $CR^3$, $CR^5$, $CR^6$, $CR^7$ or $CR^8$, wherein $R^2$, $R^3$, $R^5$, $R^6$, $R^7$ and $R^8$ are independently of each other H, CN, $NR^{65}R^{66}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group, which can optionally be substituted by G;

or adjacent groups $R^5$ and $R^6$, $R^6$ and $R^7$, and/or $R^7$ and $R^8$ can optionally from together a ring, which can optionally be substituted by G.

Most preferred compounds of the present invention are therefore compounds of formula (Iaa)

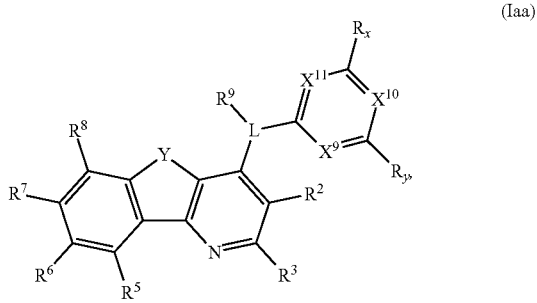

(Iaa)

wherein the groups $R^2$, $R^3$, $R^5$, $R^6$, $R^7$, $R^8$, $R^9$, Y, L, $X^9$, $X^{10}$, $X^{11}$, $R_x$ and $R_y$ have the meanings mentioned above. Preferred meanings of the groups $R^2$, $R^3$, $R^5$, $R^6$, $R^7$, $R^8$, $R^9$, Y, L, $X^9$, $X^{10}$, $X^{11}$, $R_x$ and $R_y$ are mentioned below.
$R^1$, $R^2$, $R^3$, $R^4$, $R^5$, $R^6$, $R^7$ and $R^8$ $R^1$, $R^2$, $R^3$, $R^4$, $R^5$, $R^6$, $R^7$ and $R^8$ are independently of each other H, CN, $NR^{65}R^{66}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group, which can optionally be substituted by G;

or adjacent groups $R^1$ and $R^2$, $R^2$ and $R^3$, $R^3$ and $R^4$, $R^5$ and $R^6$, $R^6$ and $R^7$, and/or $R^7$ and $R^8$ can optionally from together a ring, which can optionally be substituted by G; wherein—in the case that one of $X^1$ or $X^4$ is N—$R^2$ and $R^3$ do not form together a ring.

Preferred alkyl groups, alkenyl groups, alkynyl groups, cycloalkyl groups, aryl groups and heteroaryl groups as well as preferred groups E, D and G are mentioned above.

Further, suitable and preferred groups $R^{63}$ and $R^{64}$, $R^{65}$ and $R^{66}$, $R^{67}R^{68}$, $R^{69}$, $R^{71}$, $R^{72}$, $R^{73}$ and $R^{74}$ are mentioned above.

Preferred groups $R^1$, $R^2$, $R^3$, $R^4$, $R^5$, $R^6$, $R^7$ and $R^8$ are independently of each other H, CN, $NR^{65}R^{66}$, $C_1$-$C_{18}$alkyl, such as methyl, ethyl, n-propyl, iso-propyl, n-butyl, isobutyl, sec-butyl, hexyl, octyl, or 2-ethyl-hexyl, $C_6$-$C_{14}$aryl, such as phenyl, tolyl, naphthyl, triphenyl or biphenyl, or $C_2$-$C_{30}$heteroaryl such as pyridyl or phenylpyridyl.

More preferably, $R^1$, $R^2$, $R^3$, $R^4$, $R^5$, $R^6$, $R^7$ and $R^8$ are independently of each other H, CN, phenyl, naphthyl, triphenyl, biphenyl, pyridyl or phenylpyridyl.

Most preferably, $R^1$, $R^2$, $R^3$, $R^4$, $R^5$, $R^6$, $R^7$ and $R^8$ are H or phenyl.

Preferably, in the compounds of formula (I) according to the present invention, 0, one, two, three or four, preferably 0, one or two, more preferably 0 or one of the groups $R^1$, $R^2$, $R^3$, $R^4$, $R^5$, $R^6$, $R^7$ and $R^8$ are different from H and the other of $R^1$, $R^2$, $R^3$, $R^4$, $R^5$, $R^6$, $R^7$ and $R^8$ are H. Groups and preferred group $R^1$, $R^2$, $R^3$, $R^4$, $R^5$, $R^6$, $R^7$ and $R^8$ which are different from H are mentioned above. Most preferably, 0 or one groups $R^1$, $R^2$, $R^3$, $R^4$, $R^5$, $R^6$, $R^7$ and $R^8$ are different from H, i.e. all groups $R^1$, $R^2$, $R^3$, $R^4$, $R^5$, $R^6$, $R^7$ and $R^8$ are H or one of the groups $R^1$, $R^2$, $R^3$, $R^4$, $R^5$, $R^6$, $R^7$ and $R^8$ is different from H, preferably phenyl, and all other groups are H.

According to the present invention, adjacent groups $R^1$ and $R^2$, $R^2$ and $R^3$, $R^3$ and $R^4$, $R^5$ and $R^6$, $R^6$ and $R^7$, and/or $R^7$ and $R^8$ can optionally from together a ring, which can optionally be substituted by G; wherein—in the case that one of $X^1$ or $X^4$ is N—$R^2$ and $R^3$ do not form together a ring.

Preferably, adjacent groups $R^1$ and $R^2$, $R^2$ and $R^3$, $R^3$ and $R^4$, $R^5$ and $R^6$, $R^6$ and $R^7$, and/or $R^7$ and $R^8$ can optionally from together a 6 membered ring system, which can optionally be substituted by G; wherein—in the case that one of $X^1$ or $X^4$ is N—$R^2$ and $R^3$ do not form together a ring.

The six membered ring system is preferably a ring structure of the following formula:

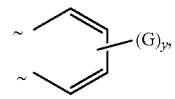

wherein G is defined above, and y is 0, 1, 2, 3 or 4, preferably 0, 1 or 2, more preferably 0 or 1, most preferably 0; and are bonding sites to the atoms to which the two adjacent groups of the groups $R^1$ to $R^8$ are bonded. Preferably, the two adjacent groups $R^1$ and $R^2$, $R^2$ and $R^3$, $R^3$ and $R^4$, $R^5$ and $R^6$, $R^6$ and $R^7$, and/or $R^7$ and $R^8$ may form together with the atoms to which they are bonded an aromatic 6 membered ring structure, which can optionally be substituted by G; wherein—in the case that one of $X^1$ or $X^4$ is N—$R^2$ and $R^3$ do not form together a ring.

Most preferably, adjacent groups $R^1$ and $R^2$, $R^2$ and $R^3$, $R^3$ and $R^4$, $R^5$ and $R^6$, $R^6$ and $R^7$, and/or $R^7$ and $R^8$ do not from together a ring, which can optionally be substituted by G.
$R^9$ $R^9$ is a fused $C_{10}$-$C_{24}$ aryl group or a fused $C_{12}$-$C_{24}$ heteroaryl group. Suitable and preferred aryl groups and heteroaryl groups are mentioned above.

Preferably, $R^9$ is selected from the group consisting of naphthyl, phenanthryl, anthryl, benzophenanthryl, benzanthryl, naphthacenyl, triphenylenyl, benzochrysenyl, fluorenyl, benzofluorenyl, dibenzofluorenyl, indenofluorenyl, benzindenofluorenyl, fluoranthenyl, benzofluoranthenyl, benzotriphenylenyl, quinolyl, isoquinolyl, quinazolinyl, quinoxalinyl, benzoquinolynyl, benzoisoquinolinyl, benzoquinazolinyl, benzoquinoxalinyl, naphthoquinolinyl, naphthoisoquinolinyl, naphthoquinazolinyl, naphthoquinoxalinyl, phenanthrolinyl, benzofuroquinolinyl, benzothienoquinolinyl, carbazolyl, benzocarbazolyl, dibenzocarbazolyl, indenocarbazolyl, benzofurocarbazolyl, benzothiocarbazolyl, indrocarbazolyl, benzimidazo[1,2-a]benzimadozolyl, dibenzofuranyl, dibenzothiophenyl, benzonaphthofuranyl, benzonaphthothiophenyl, benzophenanthrofuranyl, benzophenanthrothiophenyl, wherein the groups mentioned above can optionally be substituted by G.

More preferably, $R^9$ is selected from the group consisting of

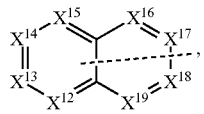  (1)

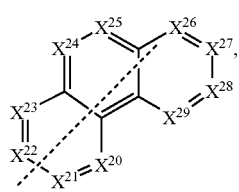  (2)

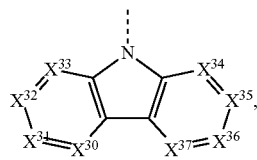  (3)

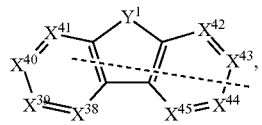  (4)

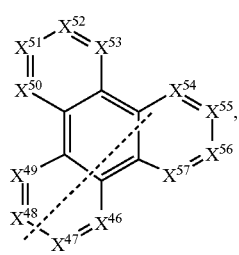  (5a)

-continued

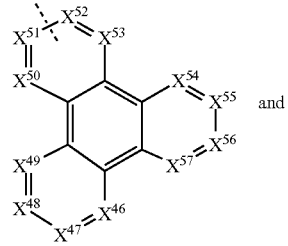  (5b)

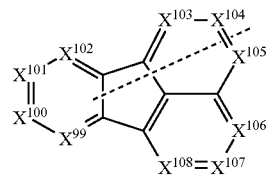  (9)

wherein $Y^1$ in formula (4) is $NR^{58}$, S, O or $CR^{59}R^{60}$, preferably S or O;

$X^{12}$ to $X^{57}$ are $CR^{12}$ to $CR^{57}$ or N and $X^{99}$ to $X^{108}$ are $CR^{99}$ to $CR^{108}$ or N, wherein 0, 1 or 2, preferably 0, of $X^{12}$ to $X^{19}$ in formula (1) are N, 0, 1 or 2, preferably 0, of $X^{20}$ to $X^{29}$ in formula (2) are N, 0, 1 or 2, preferably 0, of $X^{30}$ to $X^{37}$ in formula (3) are N, 0, 1 or 2, preferably 0, of $X^{38}$ to $X^{45}$ in formula (4) are N, 0, 1 or 2, preferably 0, of $X^{46}$ to $X^{57}$ in formula (5a) are N, 0, 1 or 2, preferably 0, of $X^{46}$ to $X^{57}$ in formula (5b) are N, and 0, 1 or 2, preferably 0, of $X^{99}$ to $X^{108}$ in formula (9) are N; whereby in formulae (1), (2), (3), (4), (5), (5b) and (9) two N atoms are not directly adjacent to each other;

$R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$ and $R^{47}$ and $R^{99}$, $R^{100}$, $R^{101}$, $R^{102}$, $R^{103}$, $R^{104}$, $R^{105}$, $R^{106}$, $R^{107}$ and $R^{108}$ are independently of each other H, $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G; preferably independently of each other H, $NR^{73}R^{74}$, a $C_1$-$C_{25}$alkyl group, which can optionally be substituted by E, and or interrupted by D, —$OR^{69}$, —$SR^{69}$, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G; or two adjacent groups of the groups $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$ and $R^{48}$ and $R^{99}$, $R^{100}$, $R^{101}$, $R^{102}$, $R^{103}$, $R^{104}$, $R^{105}$, $R^{106}$, $R^{107}$ and $R^{108}$ can optionally from together a ring, which can optionally be substituted by G; preferably H, a $C_1$-$C_{25}$alkyl group, which can optionally be substituted by E, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G; most preferably H;

$R^{58}$ is a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G; preferably a $C_1$-$C_{25}$alkyl group, which can optionally be substituted by E, $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G; more preferably a $C_6$-$C_{24}$aryl group, which can optionally be substituted by G, or a $C_2$-$C_{30}$heteroaryl group which can optionally be substituted by G; most preferably phenyl;

$R^{59}$ and $R^{60}$ are independently of each other H; an unsubstituted $C_6$-$C_{18}$aryl group; a $C_6$-$C_{18}$aryl group, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{67}$ is an unsubstituted $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—;

$R^{68}$ is H; an unsubstituted $C_6$-$C_{18}$aryl group; a $C_6$-$C_{18}$aryl group, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{69}$ is an unsubstituted $C_6$-$C_{18}$aryl; a $C_6$-$C_{18}$aryl, which is substituted by $C_1$-$C_{18}$alkyl or $C_1$-$C_{18}$ alkoxy; a $C_1$-$C_{16}$alkyl group; or a $C_1$-$C_1$alkyl group, which is interrupted by —O—;

$R^{71}$ is a $C_1$-$C_{18}$alkyl group, a $C_6$-$C_{18}$aryl group, or a $C_6$-$C_{18}$aryl group, which is substituted by $C_1$-$C_{18}$alkyl; and $R^{72}$ is a $C_1$-$C_{18}$alkyl group, an unsubstituted $C_6$-$C_{18}$aryl group, or a $C_6$-$C_{18}$aryl group, which is substituted by $C_1$-$C_{18}$alkyl;

$R^{73}$ and $R^{74}$ form together with the carbon atoms to which they are bonded a 5- or 6-membered ring, which can optionally be part of an anellated ring system, wherein the ring and/or annelated ring system can optionally be substituted by G;

wherein the dotted lines are bonding sites.

More preferably, $R^9$ is selected from the group consisting of

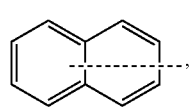

(1')

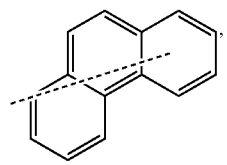

(2')

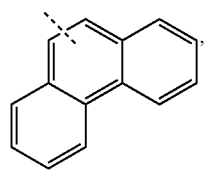

(2")

-continued

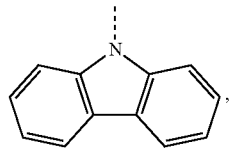

(3')

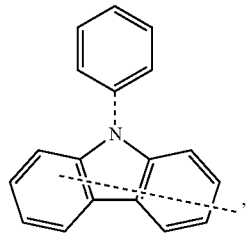

(4')

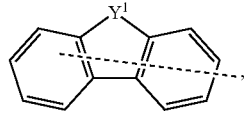

(4")

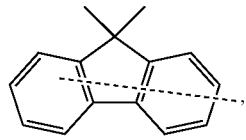

(4''')

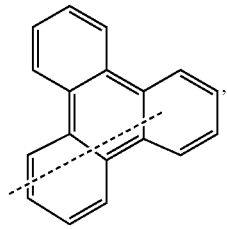

(5a')

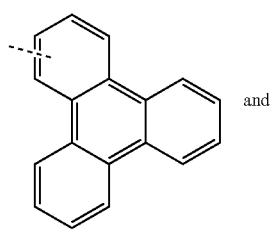

and (5b')

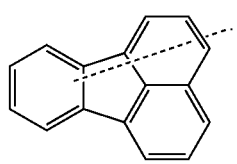

(9')

wherein $Y^1$ is O or S and the dotted lines are bonding sites.

Most preferably, $R^9$ is selected from the group consisting of formulas (1'), (2'), (2"), (4"), (5a'), (5b') and (9').

L

L is a trivalent $C_6$-$C_{24}$ arylene group or a trivalent $C_2$-$C_{24}$ heteroarylene group.

Preferably, L is selected from the group consisting of

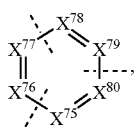
(6)

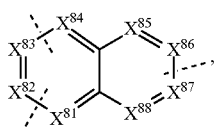
(7)

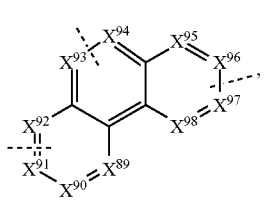
(8a)

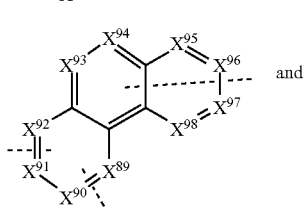
(8b)

and

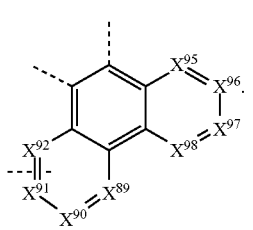
(8c)

wherein
$X^{75}$ to $X^{98}$ are $CR^{75}$ to $CR^{98}$ or N, wherein 0, 1, 2 or 3 of $X^{75}$ to $X^{80}$ in formula (6) are N, 0, 1 or 2, preferably 0, of $X^{81}$ to $X^{88}$ in formula (7) are N, 0, 1 or 2, preferably 0, of $X^{89}$ to $X^{98}$ in formula (8a) are N, 0, 1 or 2, preferably 0, of $X^{89}$ to $X^{98}$ in formula (8b) are N, 0, 1 or 2, preferably 0, of $X^{89}$ to $X^{98}$ in formula (8c) are N; whereby in formulae (6), (7), (8a), (8b) and (8c) two N atoms are not directly adjacent to each other;
$R^{75}$, $R^{76}$, $R^{77}$, $R^{78}$, $R^{79}$, $R^{80}$, $R^{81}$, $R^{82}$, $R^{83}$, $R^{84}$, $R^{85}$, $R^{86}$, $R^{87}$, $R^{88}$, $R^{89}$, $R^{90}$, $R^{91}$, $R^{92}$, $R^{93}$, $R^{94}$, $R^{95}$, $R^{96}$, $R^{97}$ and $R^{98}$ are independently of each other H, $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G; preferably independently of each other H, $NR^{73}R^{74}$, a $C_1$-$C_{25}$alkyl group, which can optionally be substituted by E, and or interrupted by D, —$OR^{69}$, —$SR^{69}$, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G; or two adjacent groups of the groups $R^{75}$, $R^{76}$, $R^{77}$, $R^{78}$, $R^{79}$, $R^{80}$, $R^{81}$, $R^{82}$, $R^{83}$, $R^{84}$, $R^{85}$, $R^{86}$, $R^{87}$, $R^{88}$, $R^{89}$, $R^{90}$, $R^{91}$, $R^{92}$, $R^{93}$, $R^{94}$, $R^{95}$, $R^{96}$, $R^{97}$ and $R^{98}$ can optionally from together a ring, which can optionally be substituted by G; preferably H, a $C_1$-$C_{25}$alkyl group, which can optionally be substituted by E, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G; most preferably H;
$R^{67}$ is an unsubstituted $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; $R^{68}$ is H; an unsubstituted $C_6$-$C_{18}$aryl group; a $C_6$-$C_{18}$aryl group, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;
$R^{69}$ is an unsubstituted $C_6$-$C_{18}$aryl; a $C_6$-$C_{18}$aryl, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;
$R^{71}$ is a $C_1$-$C_{18}$alkyl group, a $C_6$-$C_{18}$aryl group, or a $C_6$-$C_{18}$aryl group, which is substituted by $C_1$-$C_{18}$alkyl; and $R^{72}$ is a $C_1$-$C_{18}$alkyl group, an unsubstituted $C_6$-$C_{18}$aryl group, or a $C_6$-$C_{16}$aryl group, which is substituted by $C_1$-$C_{18}$alkyl;
$R^{73}$ and $R^{74}$ form together with the carbon atoms to which they are bonded a 5- or 6-membered ring, which can optionally be part of an anellated ring system, wherein the ring and/or annelated ring system can optionally be substituted by G;
wherein the dotted lines are bonding sites.

More preferably, L is selected from the group consisting of

(6′)

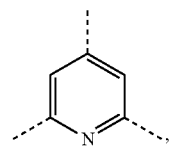
(6″)

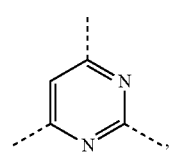
(6‴)

and
(6″″)

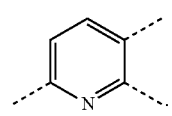
(6‴″)

Most preferably, L selected from the group consisting of

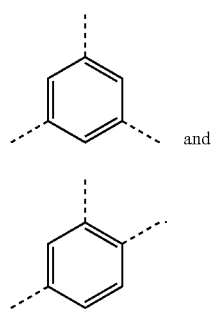

and

Y

Y is S or O, preferably S.

$X^9$, $X^{10}$ and $X^{11}$ $X^9$, $X^{10}$ and $X^{11}$ are each independently N or $CR^{10}$, whereby at least two of $X^9$, $X^{10}$ and $X^{11}$ are N, preferably, $X^9$, $X^{10}$ and $X^{11}$ are N;

$R^{10}$ is H, $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G;

preferably, $R^{10}$ is H, $NR^{73}R^{74}$, $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, triphenyl or biphenyl, or $C_2$-$C_{30}$heteroaryl such as pyridyl or phenylpyridyl.

more preferably, $R^{10}$ is H, phenyl, naphthyl, triphenyl, biphenyl, pyridyl or phenylpyridyl; most preferably, $R^{10}$ is H.

Preferred alkyl groups, alkenyl groups, alkynyl groups, cycloalkyl groups, aryl groups and heteroaryl groups as well as preferred groups E, D and G are mentioned above.

Further, suitable and preferred groups $R^{63}$ and $R^{64}$, $R^{65}$ and $R^{66}$, $R^{67}R^{68}$, $R^{69}$, $R^{71}$, $R^{72}$, $R^{73}$ and $R^{74}$ are mentioned above.

$R_x$ and $R_y$ $R_x$ and $R_y$ are independently of each other $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{12}$aryl group, which can optionally be substituted by G, or a $C_2$-$C_{30}$heteroaryl group which can optionally be substituted by G.

Preferred alkyl groups, alkenyl groups, alkynyl groups, cycloalkyl groups, aryl groups and heteroaryl groups as well as preferred groups E, D and G are mentioned above.

Further, suitable and preferred groups $R^{63}$ and $R^{64}$, $R^{65}$ and $R^{66}$, $R^{67}R^{68}$, $R^{69}$, $R^{71}$, $R^{72}$, $R^{73}$ and $R^{74}$ are mentioned above.

Preferred groups $R_x$ and $R_y$ are independently of each other $NR^{73}R^{74}$, $C_1$-$C_{18}$alkyl, such as methyl, ethyl, n-propyl, iso-propyl, n-butyl, isobutyl, sec-butyl, hexyl, octyl, or 2-ethyl-hexyl, $C_6$-$C_{14}$aryl, such as phenyl, tolyl, naphthyl, triphenyl, pyridylphenyl, or biphenyl, or $C_2$-$C_{30}$heteroaryl such as pyridyl or phenylpyridyl.

More preferably, $R_x$ and $R_y$ are independently of each other phenyl, naphthyl, triphenyl, biphenyl, pyridylphenyl, pyridyl or phenylpyridyl.

Most preferably, $R_x$ and $R_x$ are phenyl, pyridylphenyl, naphthyl or biphenyl.

The group

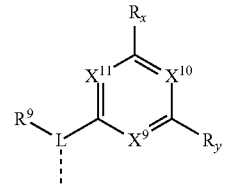

The definitions of suitable and preferred groups $R^9$, L, $X^9$, $X^{10}$, $X^{11}$, $R_x$ and R are mentioned above, Particularly preferred groups

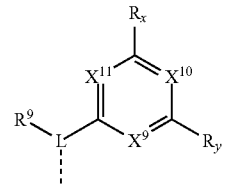

are selected from the group consisting of

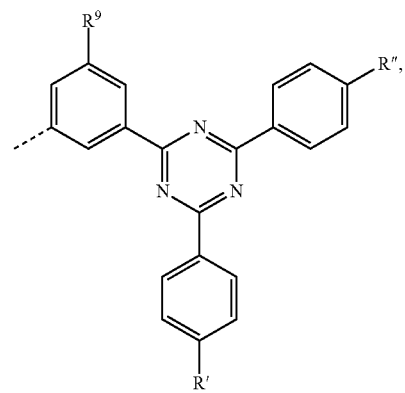

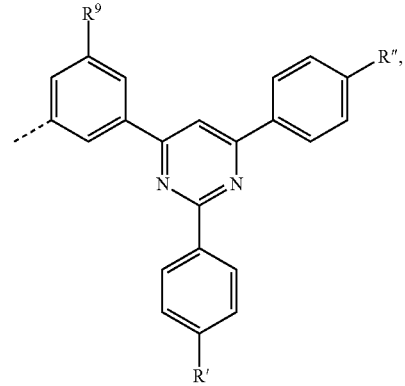

-continued
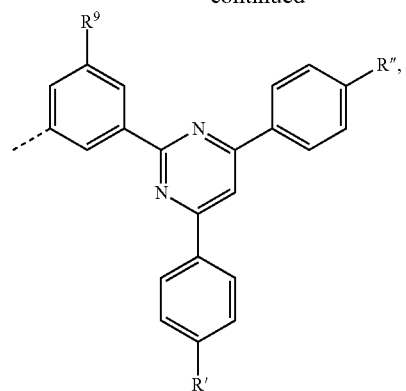
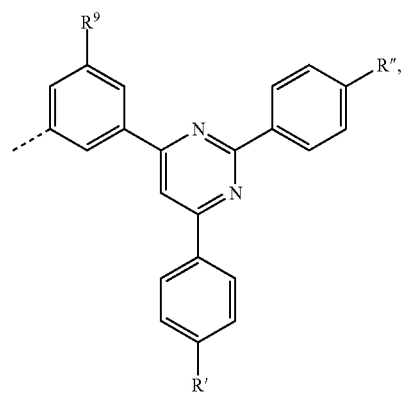
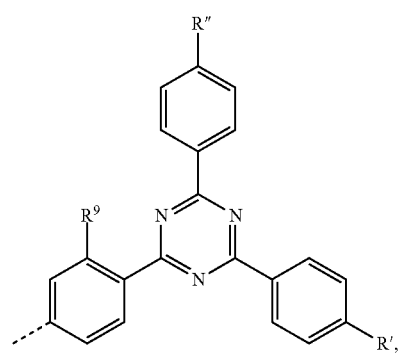
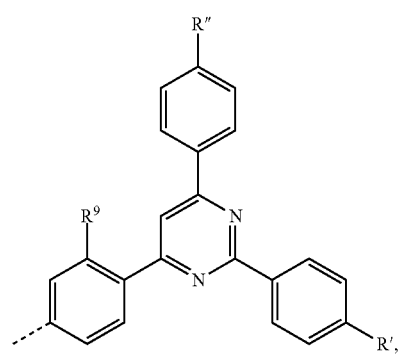
-continued
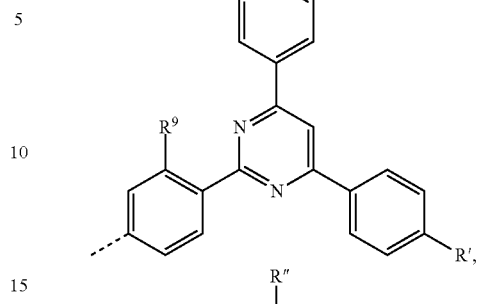
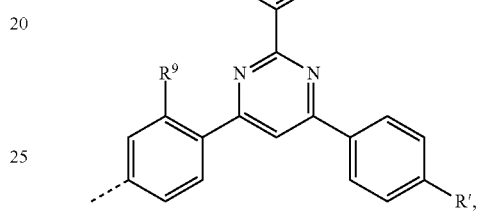
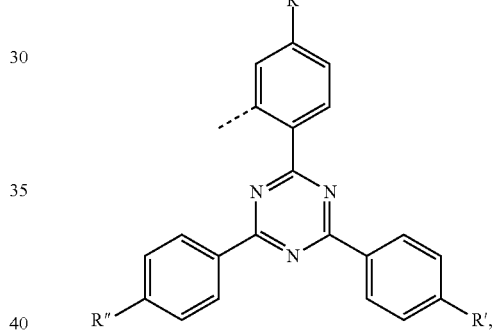

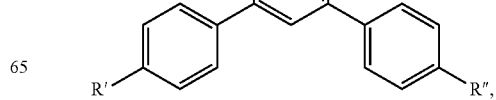

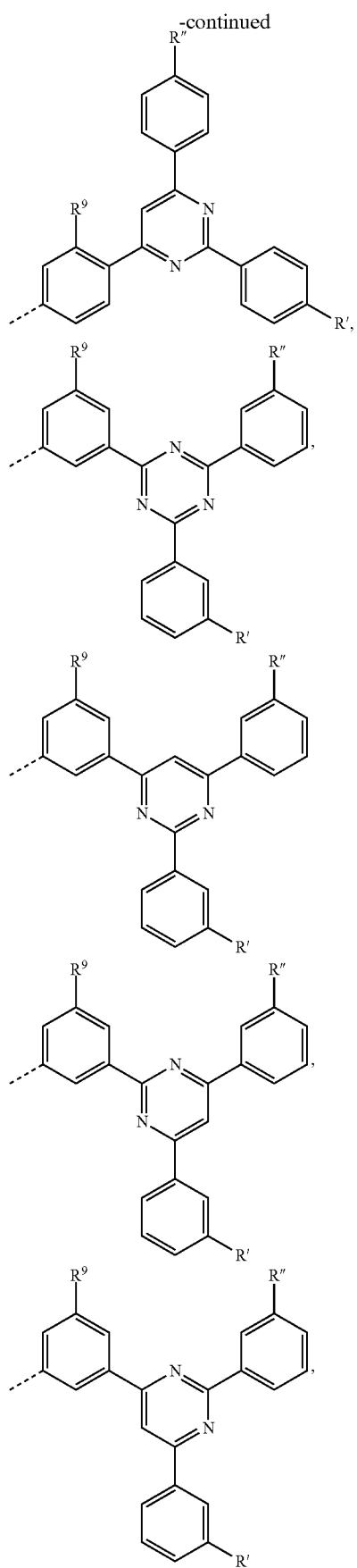
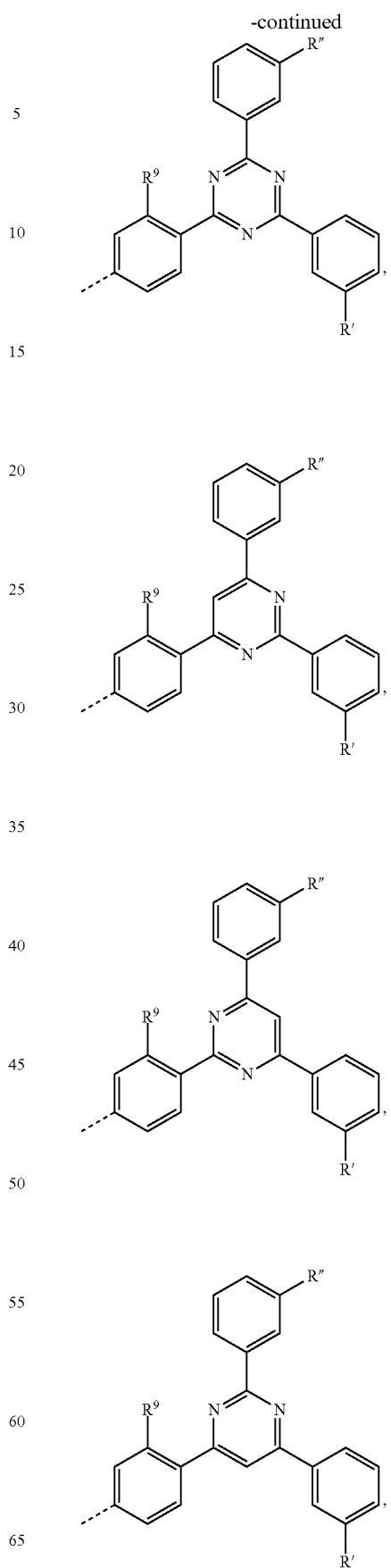

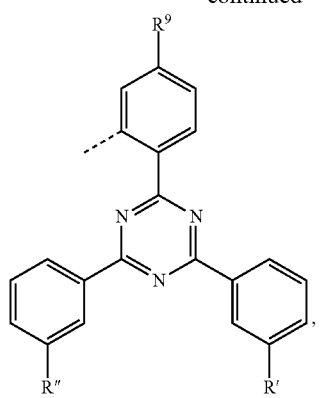
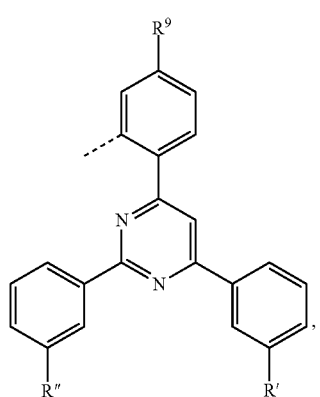
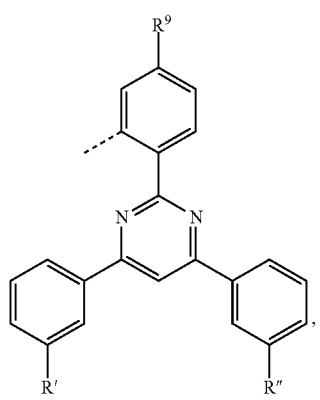
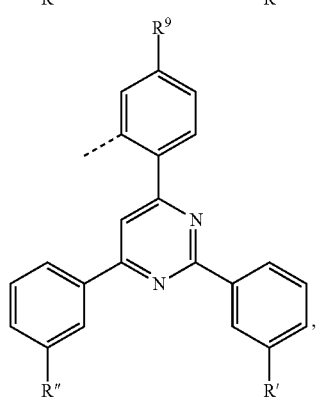
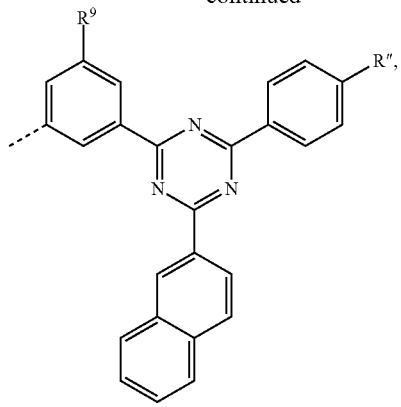
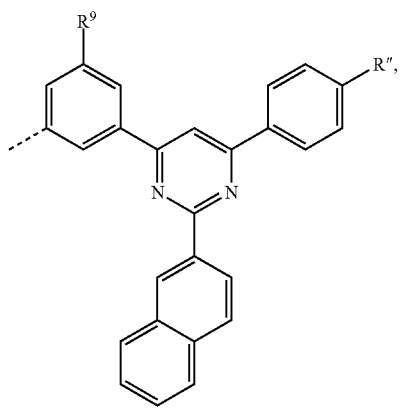
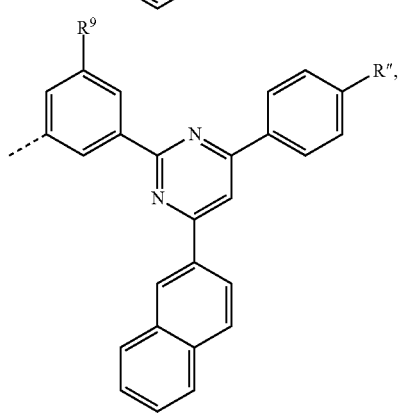

-continued

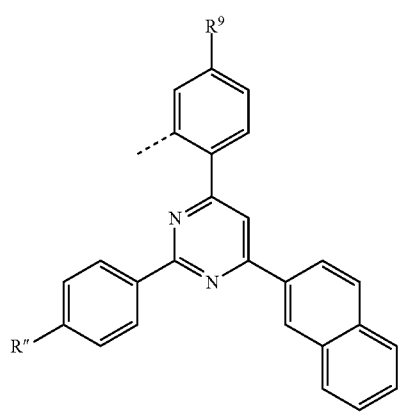
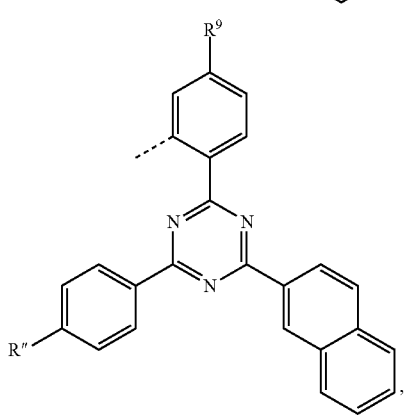
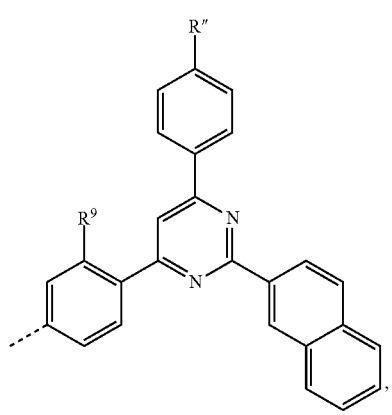
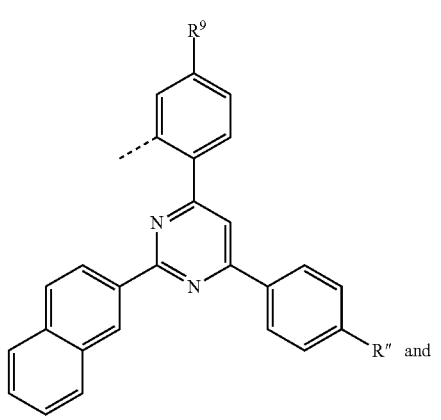
and
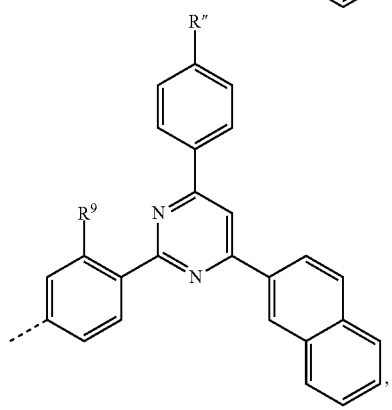
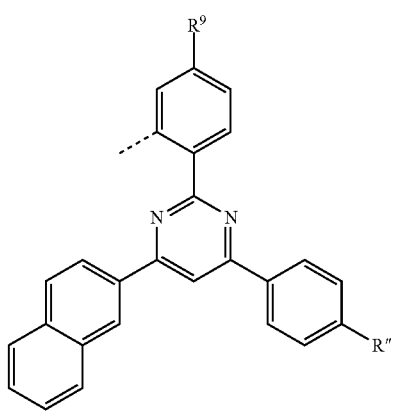

wherein
R⁹ is selected from the group consisting of (1')
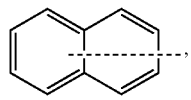

(2')
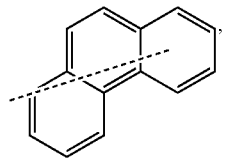

(2'')
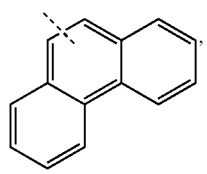

(3')
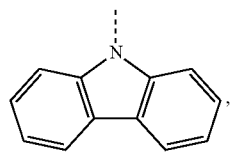

(4')
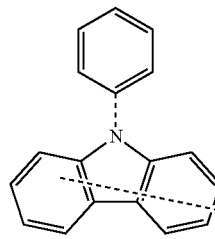

(4'')
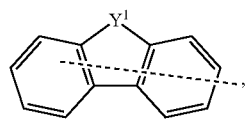

(4''')
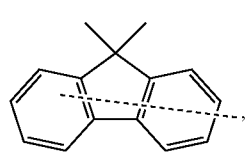

(5a')
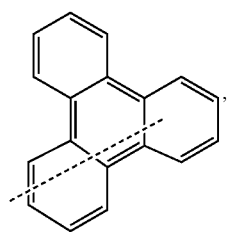

(5b')
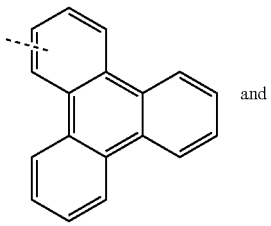

and (9')
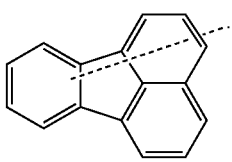

wherein $Y^1$ is O or S and the dotted lines are bonding sites;
R' and R" are each independently H, CN, phenyl or pyridyl; and the dotted lines are bonding sites.

Compounds of Formula (I)

Suitable and preferred compounds of formula (I) are mentioned above. More preferred compounds of formula (I) are compounds of formula (Ia) as mentioned above. Most preferred compounds of formula (I) are compounds of formula (Iaa) as mentioned above.

Particularly preferred compounds of formula (Iaa) are the following compounds:

(Iaaa)
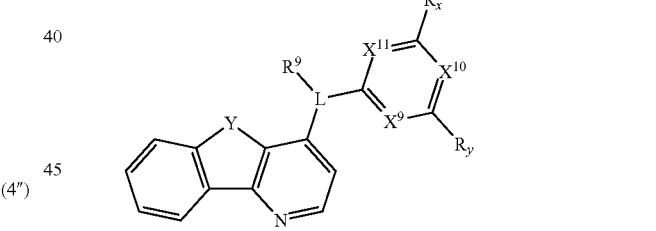

Wherein suitable and preferred groups Y, L, $R^9$, $X^0$, $X^{10}$, $X^{11}$, $R_x$ and $R_y$ as well as preferred groups

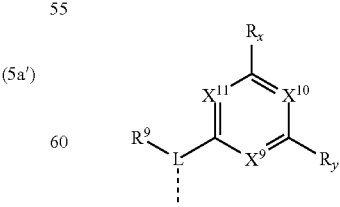

are mentioned above.

Examples for particularly preferred compounds of formula (Iaa) are the following compounds:

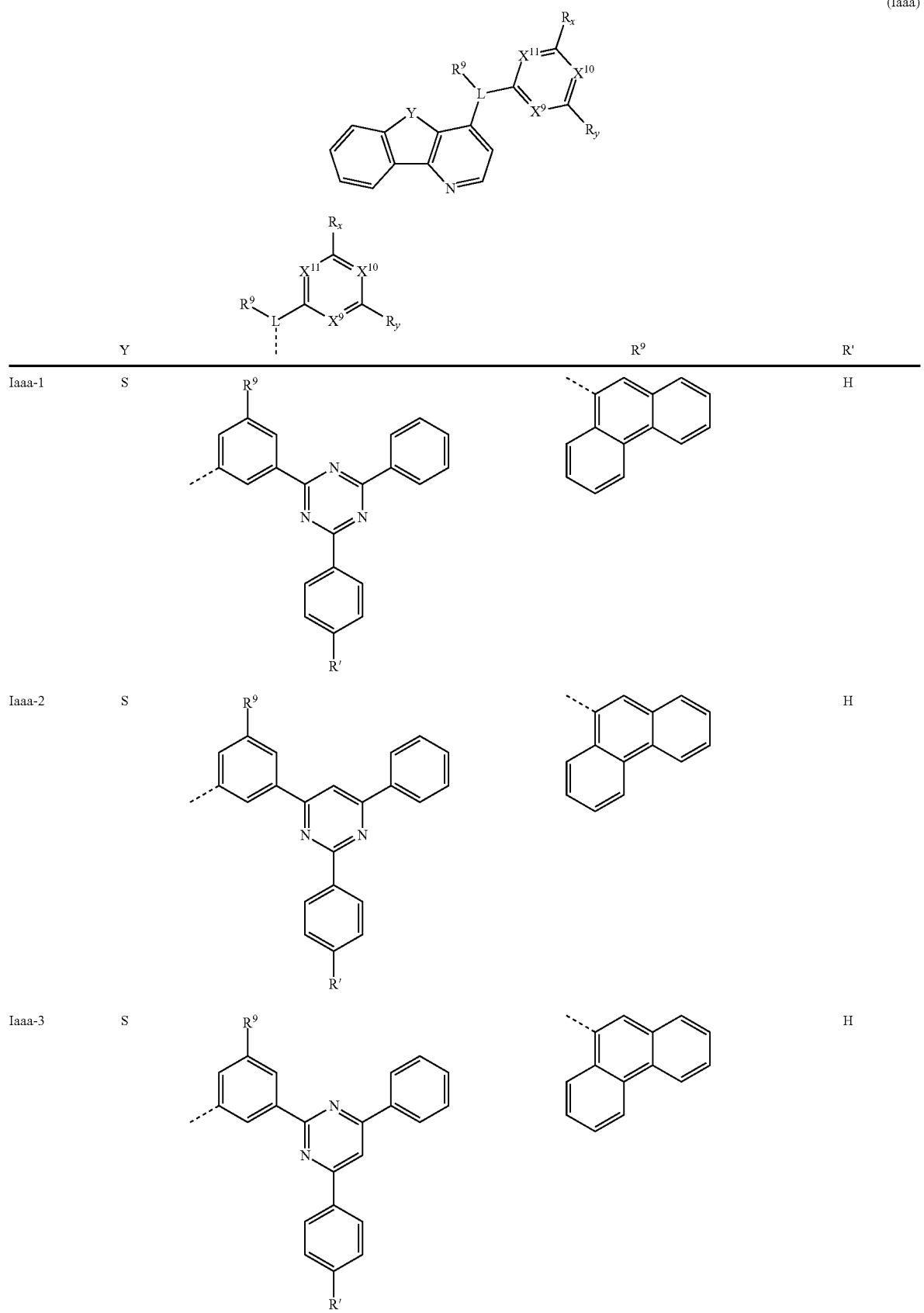

(Iaaa)
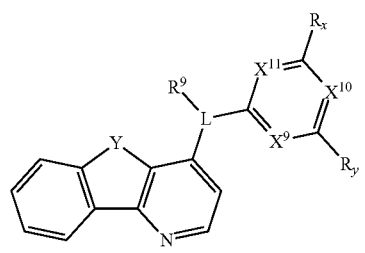
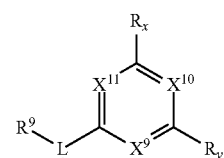
| | Y | | R⁹ | R' |
|---|---|---|---|---|
| Iaaa-4 | S | 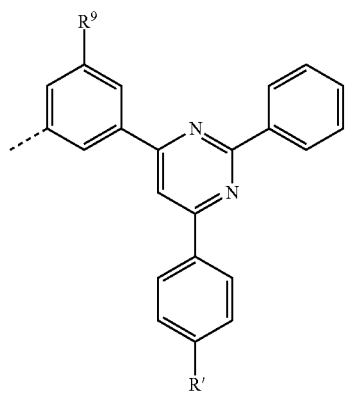 | 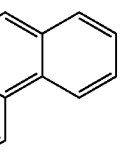 | H |
| Iaaa-5 | S | 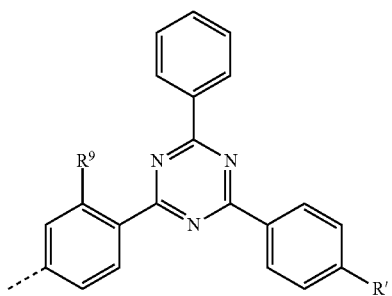 | 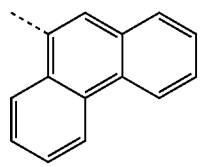 | H |
| Iaaa-6 | S | 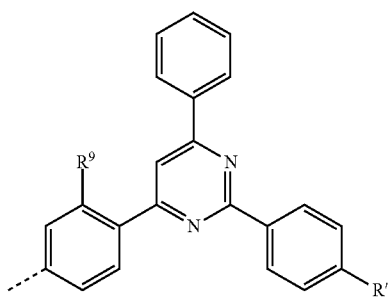 | 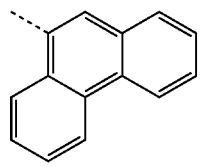 | H |

-continued
(Iaaa)
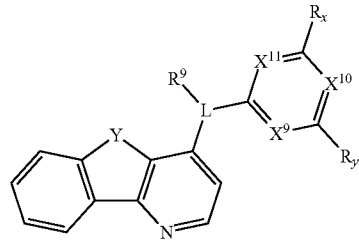
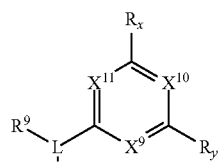
| | Y | R⁹ | R' |
|---|---|---|---|
| Iaaa-7 | S | 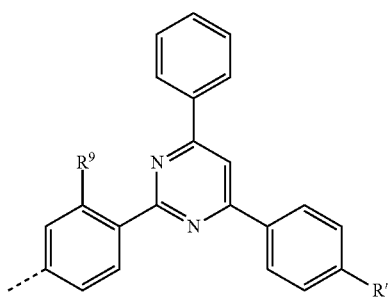 | 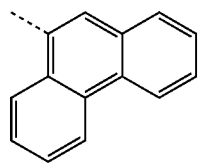 | H |
| Iaaa-8 | S | 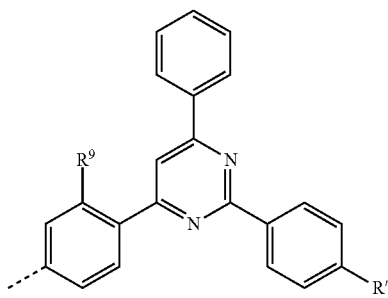 | 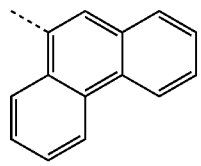 | H |
| Iaaa-9 | S | 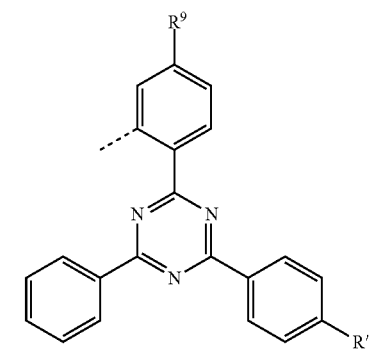 | 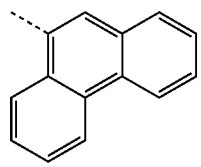 | H |

-continued
(Iaaa)
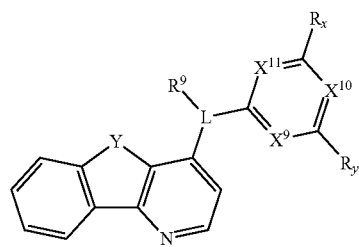
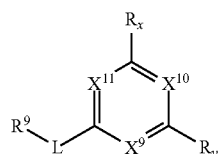
| | Y | | R⁹ | R' |
|---|---|---|---|---|
| Iaaa-10 | S | 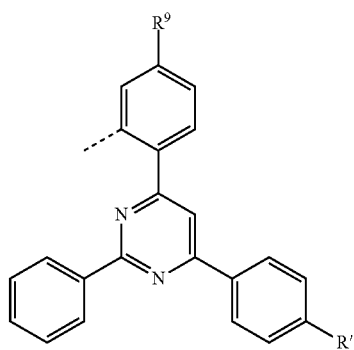 | 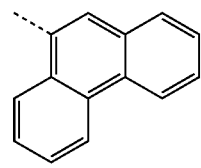 | H |
| Iaaa-11 | S | 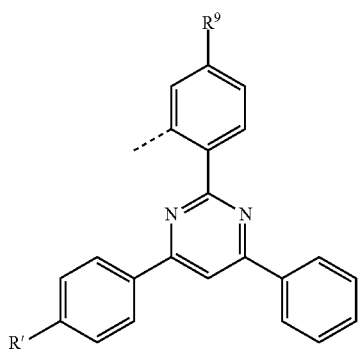 | 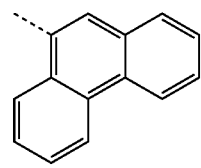 | H |
| Iaaa-12 | S | 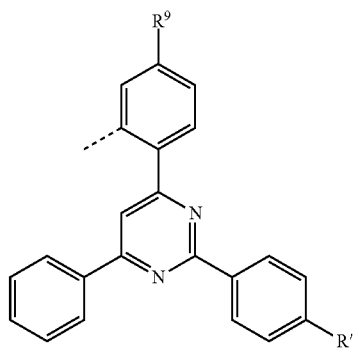 | 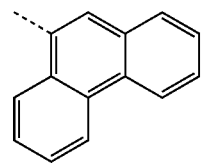 | H |

-continued
(Iaaa)
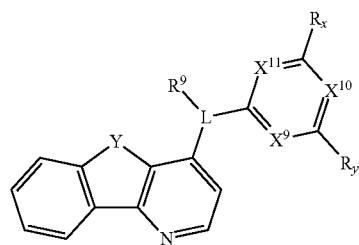
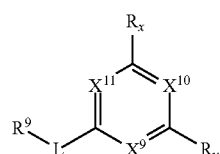
| | Y | | R⁹ | R' |
|---|---|---|---|---|
| Iaaa-13 | S | 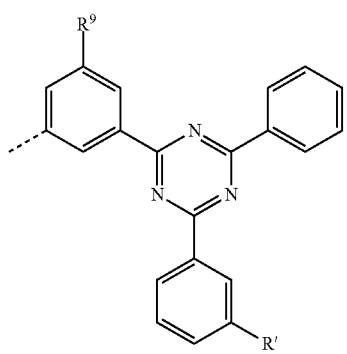 | 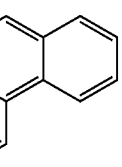 | H |
| Iaaa-14 | S | 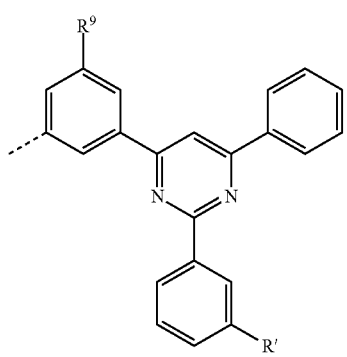 | 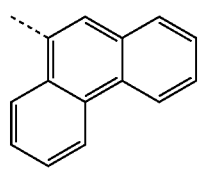 | H |
| Iaaa-15 | S | 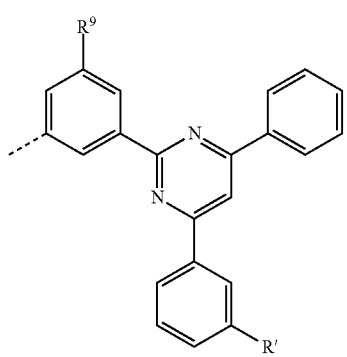 | 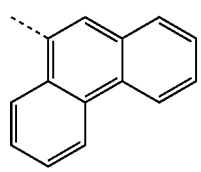 | H |

-continued
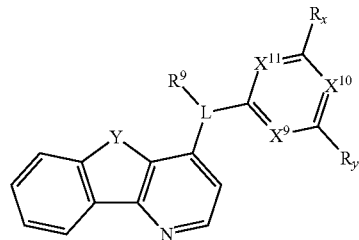
(Iaaa)
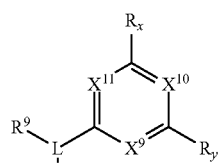
| | Y | R⁹ | R' |
|---|---|---|---|
| Iaaa-16 | S | 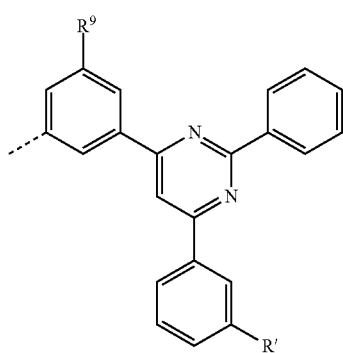 | 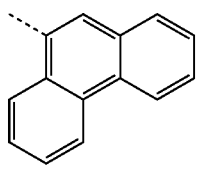 H |
| Iaaa-17 | S | 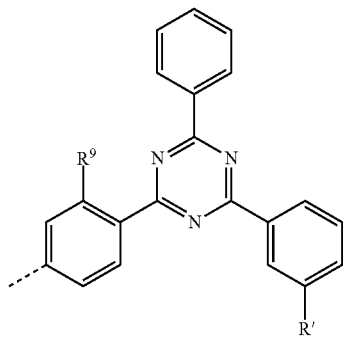 | 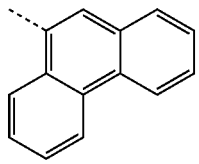 H |
| Iaaa-18 | S | 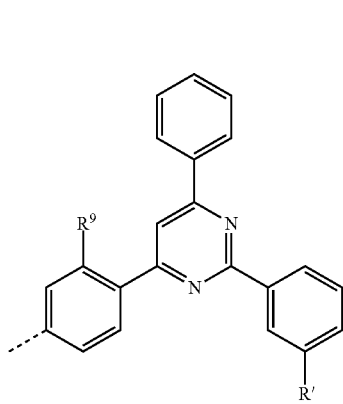 | 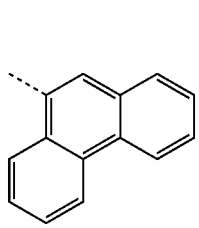 H |

-continued
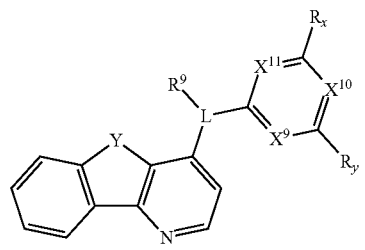
(Iaaa)
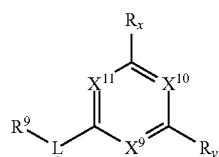
| | Y | R⁹ | R' |
|---|---|---|---|
| Iaaa-19 | S | 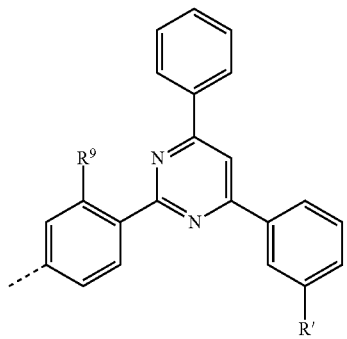 | 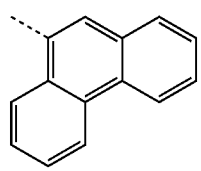 H |
| Iaaa-20 | S | 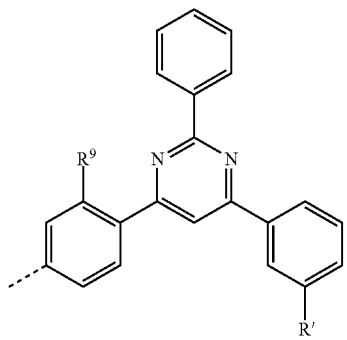 | 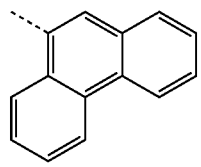 H |
| Iaaa-21 | S | 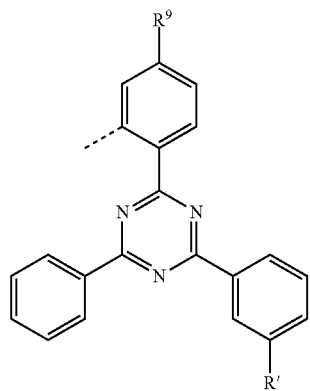 | 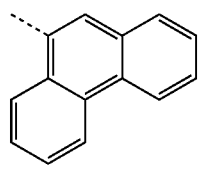 H |

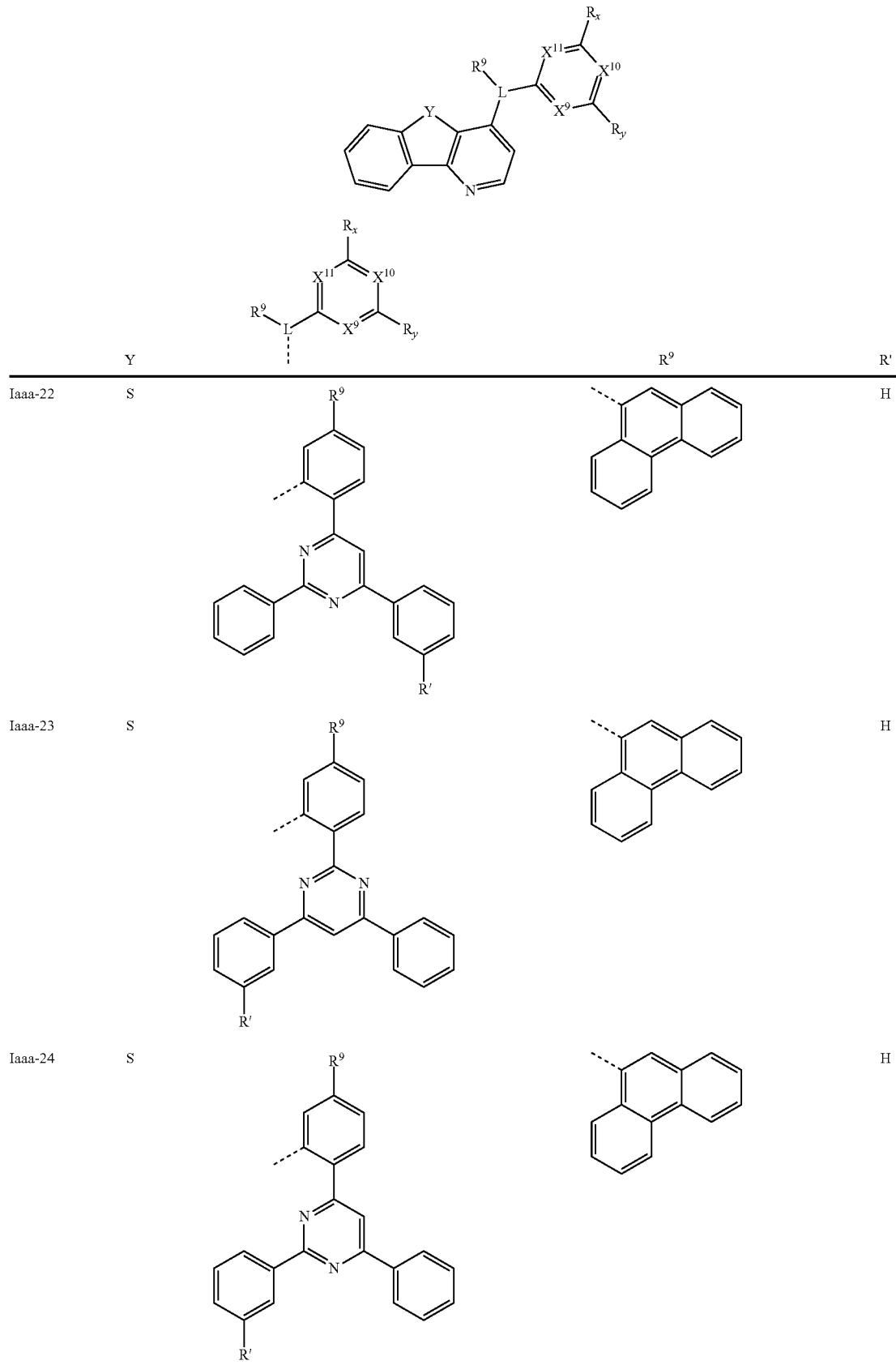

-continued
(Iaaa)
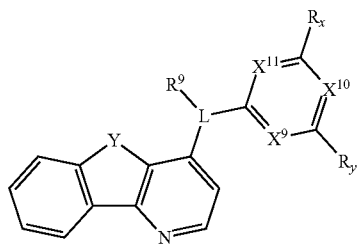
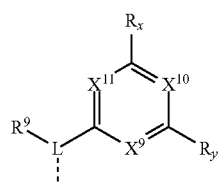
| | Y | R⁹ | R' |
|---|---|---|---|
| Iaaa-25 | S | 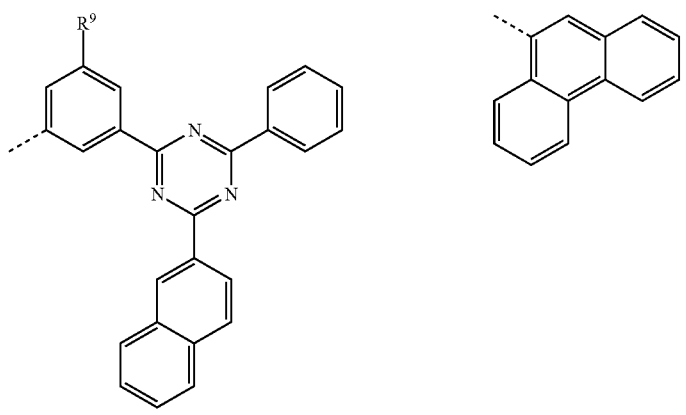 | — |
| Iaaa-26 | S | 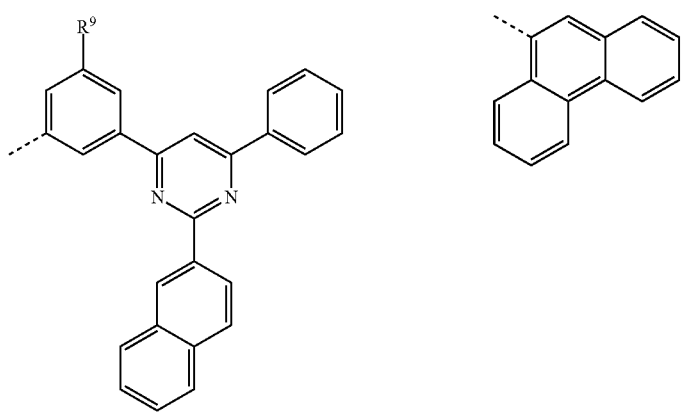 | — |

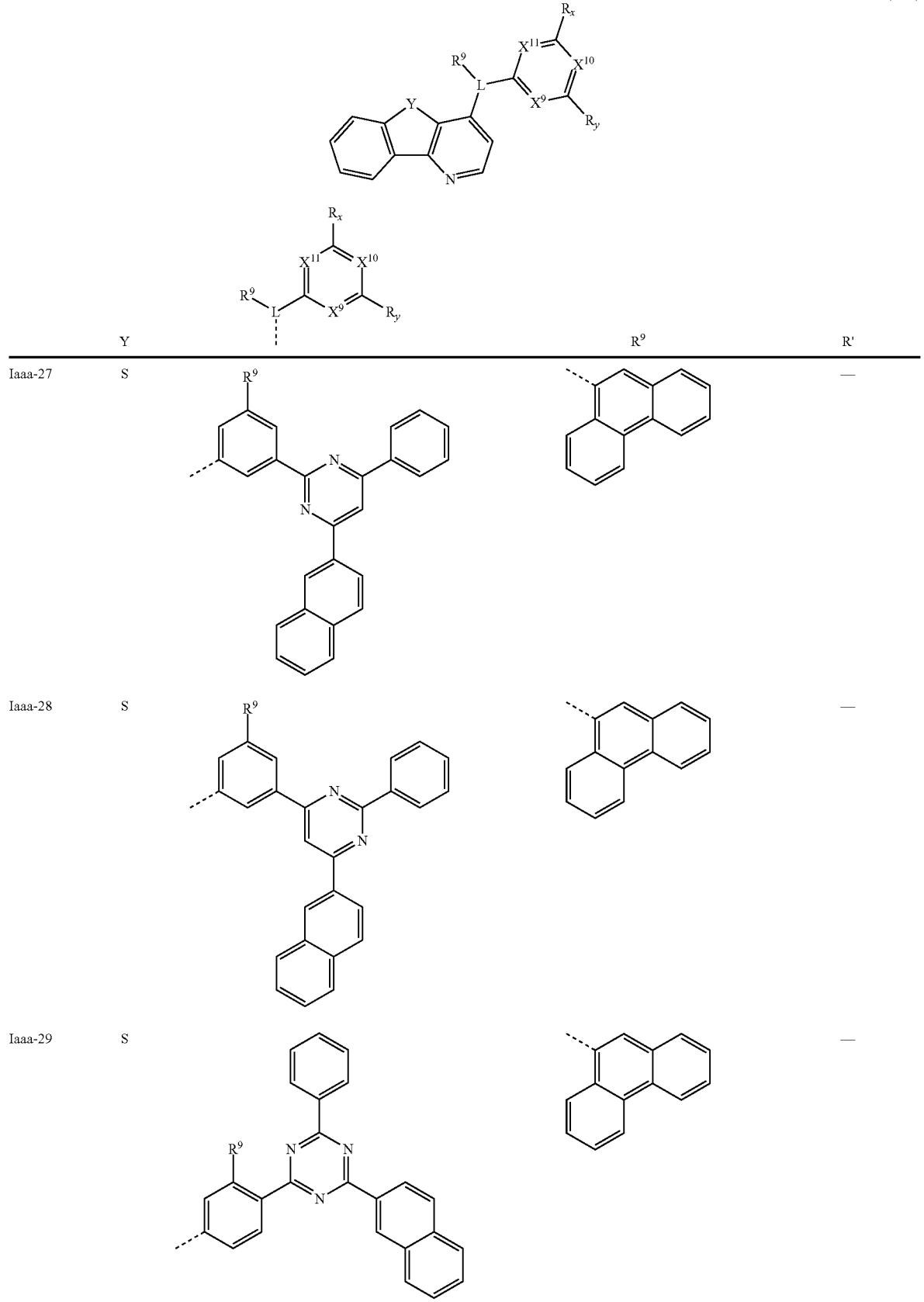

-continued
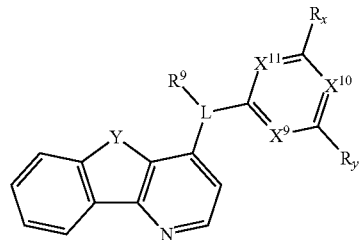
(Iaaa)
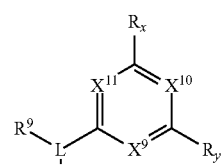
| | Y | | R⁹ | R' |
|---|---|---|---|---|
| Iaaa-30 | S | 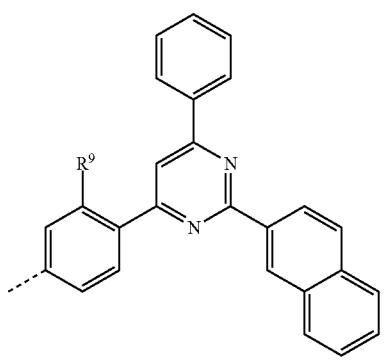 | 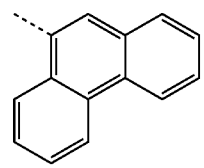 | — |
| Iaaa-31 | S | 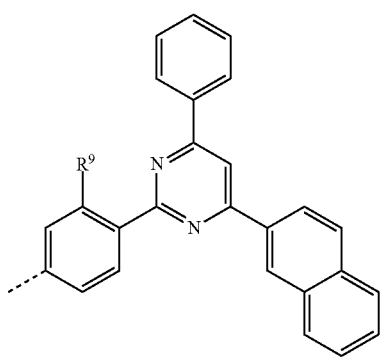 | 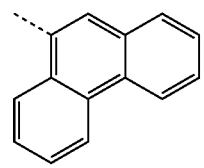 | — |
| Iaaa-32 | S | 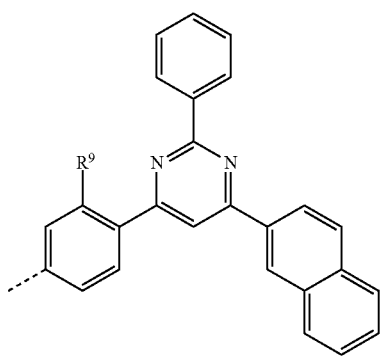 | 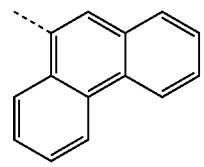 | — |

-continued
(Iaaa)
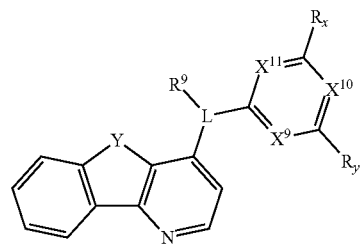
| | Y | 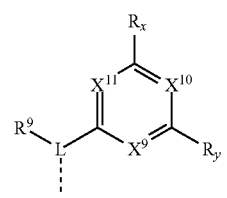 | R⁹ | R' |
|---|---|---|---|---|
| Iaaa-33 | S | |  | 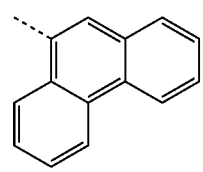 — |
| Iaaa-34 | S | |  | 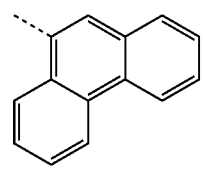 — |

-continued
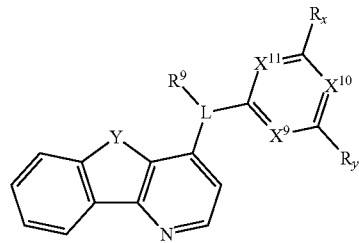
(Iaaa)
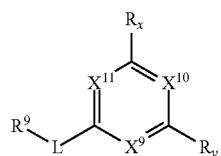
| | Y | R⁹ | R' |
|---|---|---|---|
| Iaaa-35 | S | 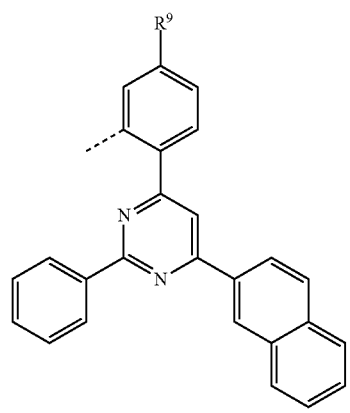 | 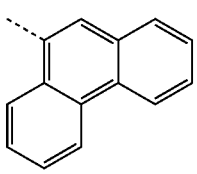 — |
| Iaaa-36 | S | 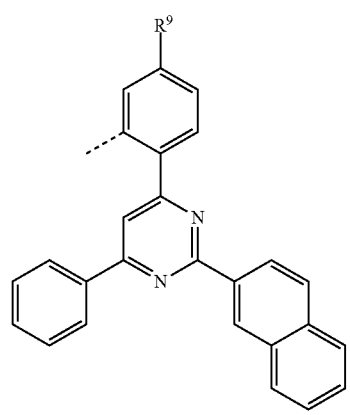 | 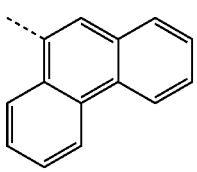 — |

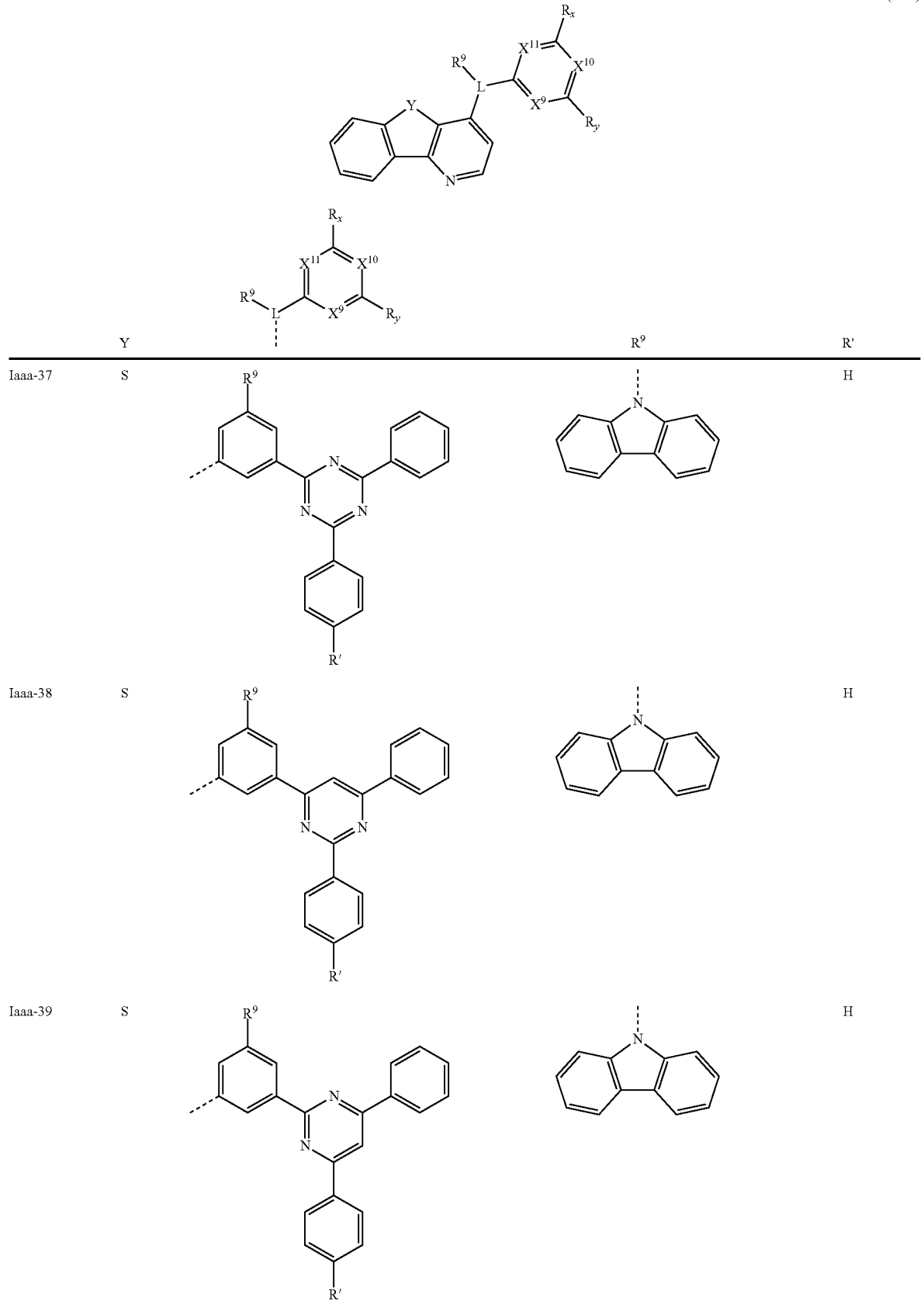

-continued
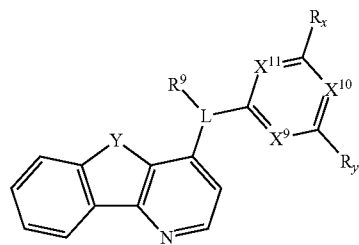
(Iaaa)
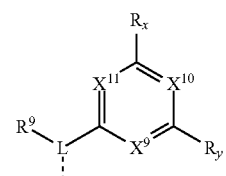
| | Y | | R⁹ | R' |
|---|---|---|---|---|
| Iaaa-40 | S | 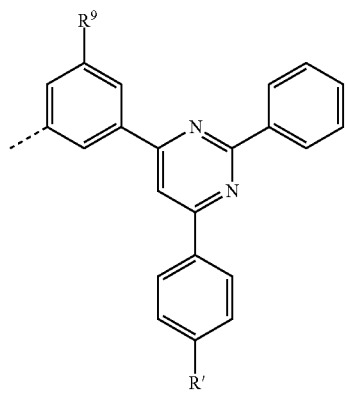 | 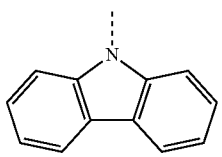 | H |
| Iaaa-41 | S | 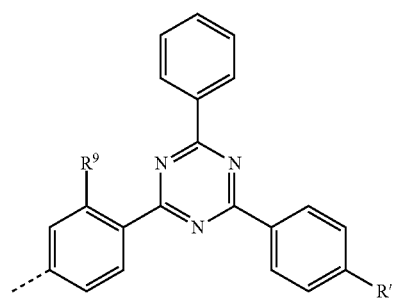 | 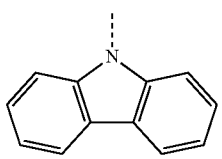 | H |
| Iaaa-42 | S | 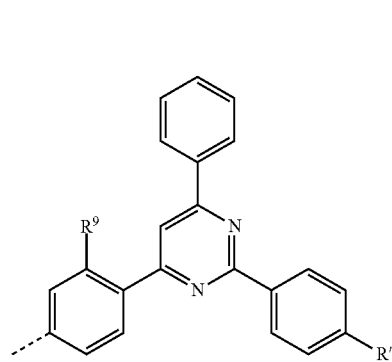 | 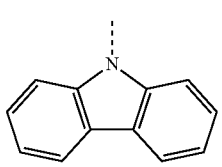 | H |

-continued
(Iaaa)
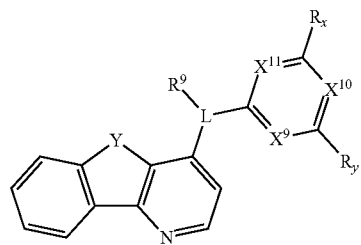
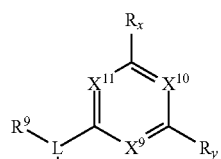
| | Y | R⁹ | R' |
|---|---|---|---|
| Iaaa-43 | S | 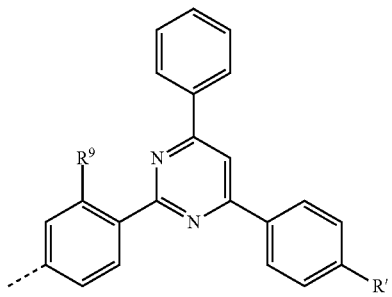 | 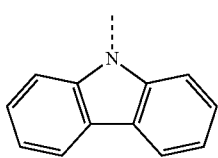 | H |
| Iaaa-44 | S | 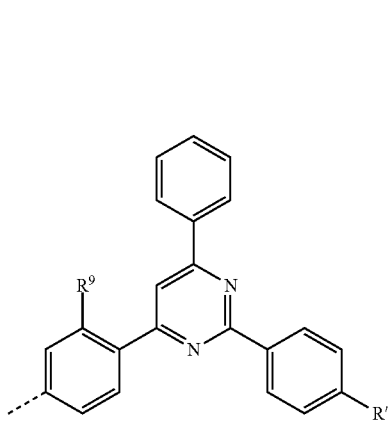 | 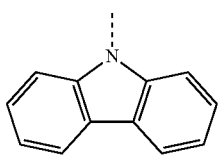 | H |
| Iaaa-45 | S | 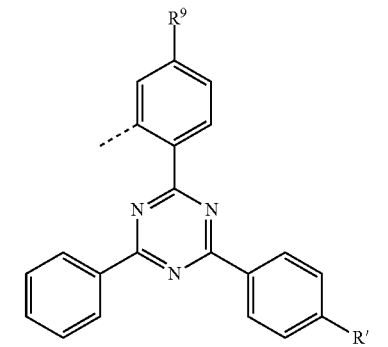 | 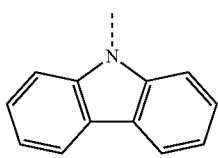 | H |

-continued
(Iaaa)
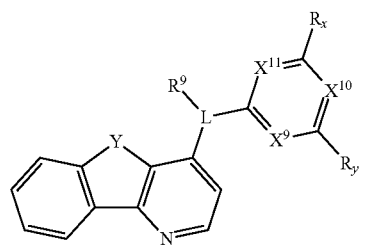
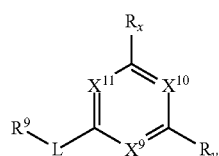
| | Y | | R⁹ | R' |
|---|---|---|---|---|
| Iaaa-46 | S | 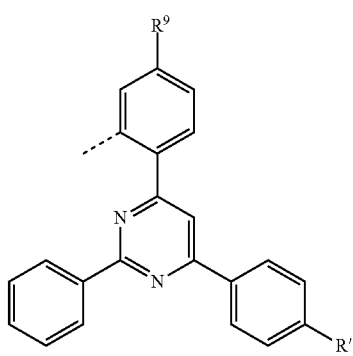 | 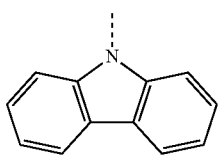 | H |
| Iaaa-47 | S | 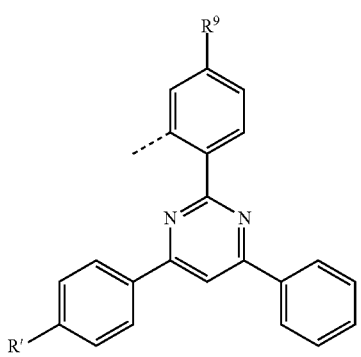 | 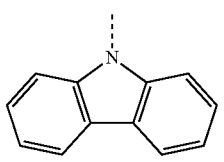 | H |
| Iaaa-48 | S | 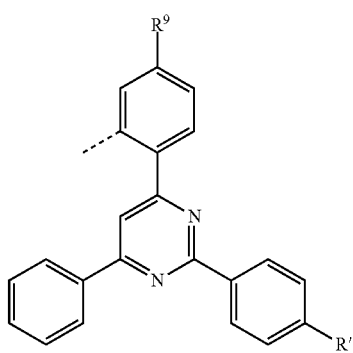 | 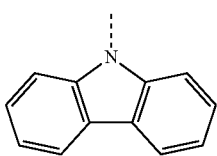 | H |

-continued
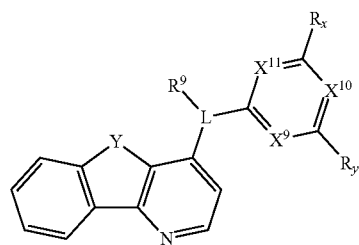
(Iaaa)
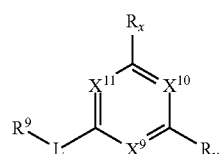
| | Y | | R⁹ | R' |
|---|---|---|---|---|
| Iaaa-49 | S | 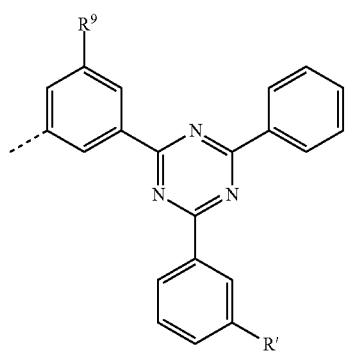 | 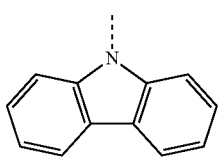 | H |
| Iaaa-50 | S | 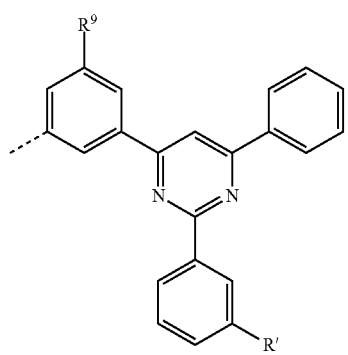 | 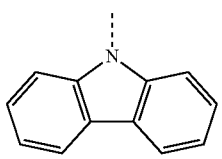 | H |
| Iaaa-51 | S | 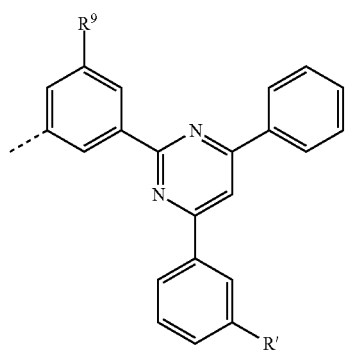 | 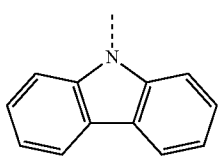 | H |

-continued
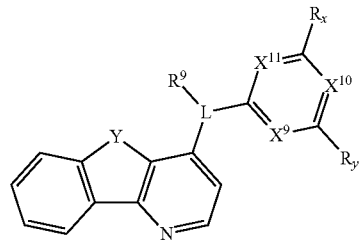
(Iaaa)
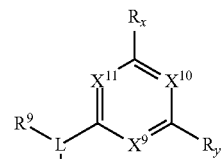
| | Y | | R⁹ | R' |
|---|---|---|---|---|
| Iaaa-52 | S | 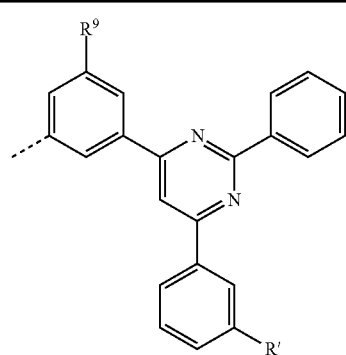 | 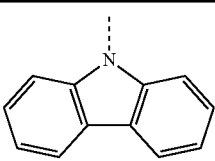 | H |
| Iaaa-53 | S | 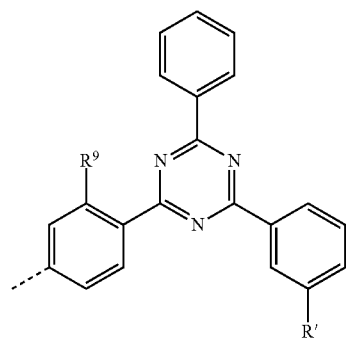 | 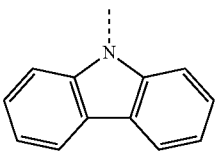 | H |
| Iaaa-54 | S | 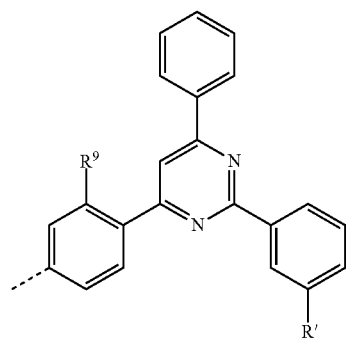 | 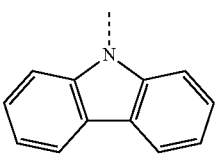 | H |

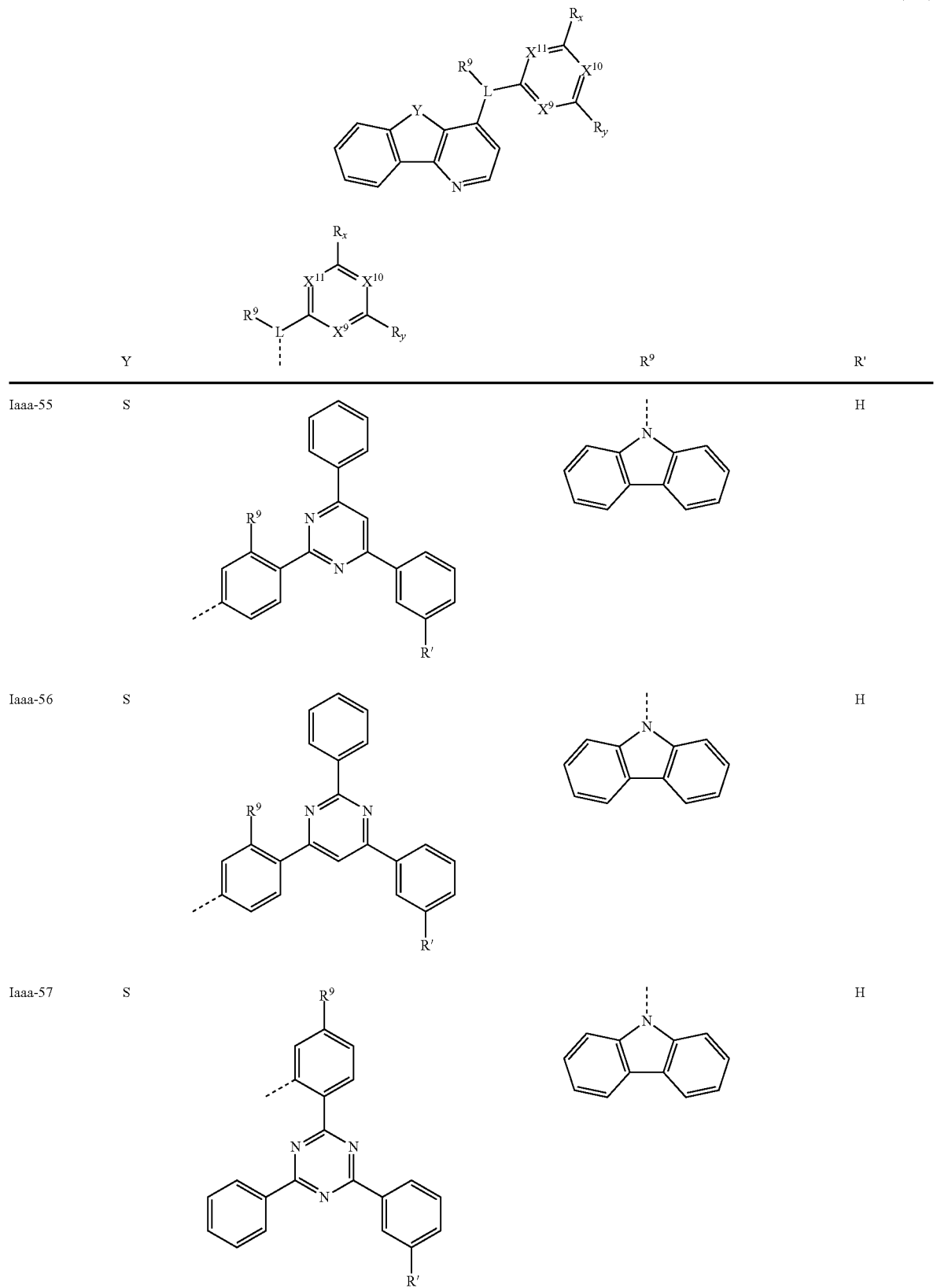

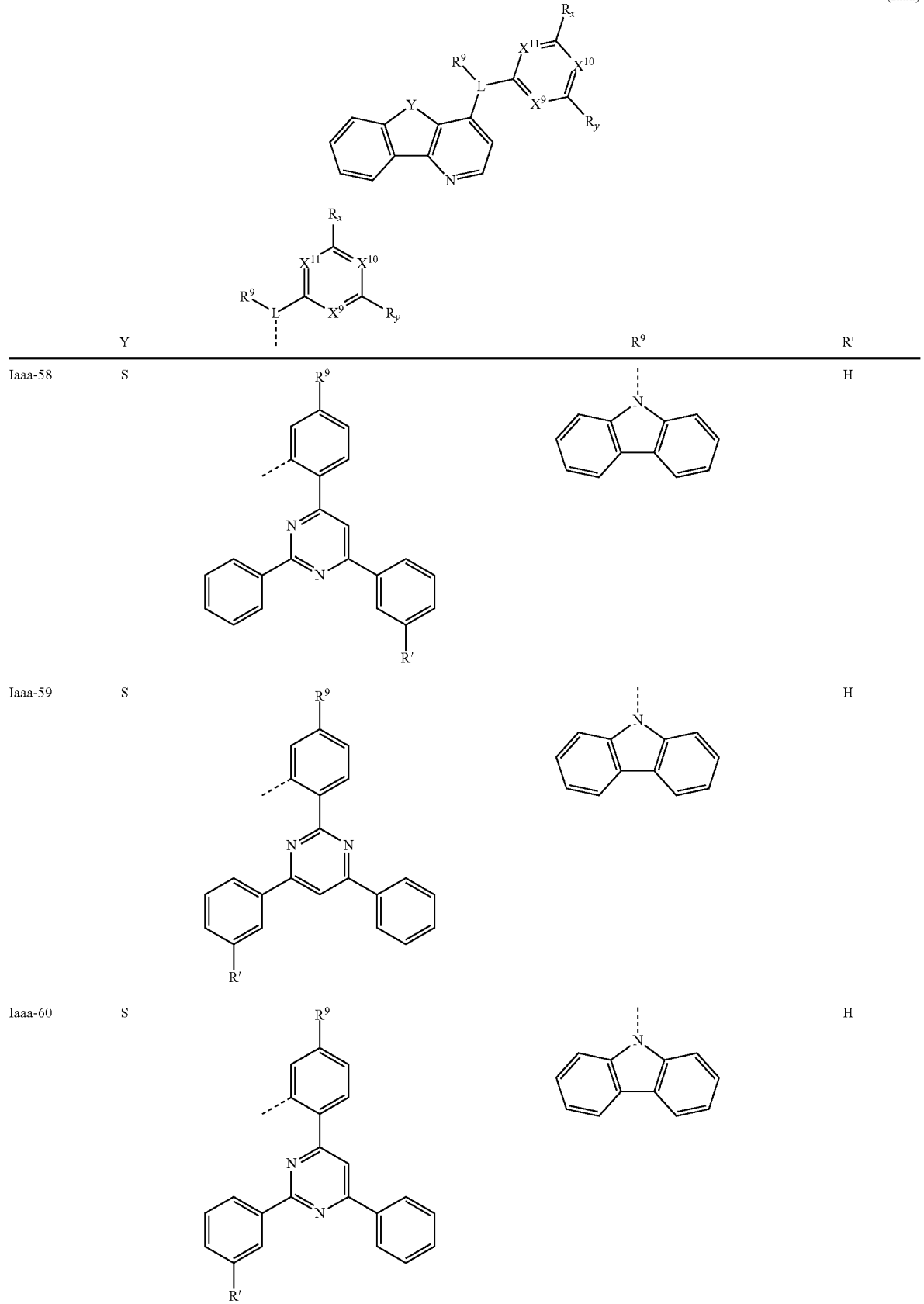

(Iaaa)
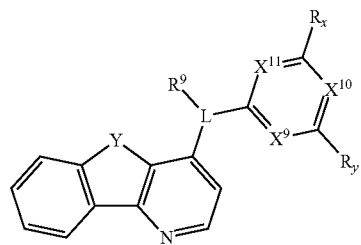
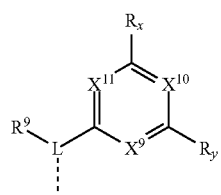
| | Y | | $R^9$ | R' |
|---|---|---|---|---|
| Iaaa-61 | S | 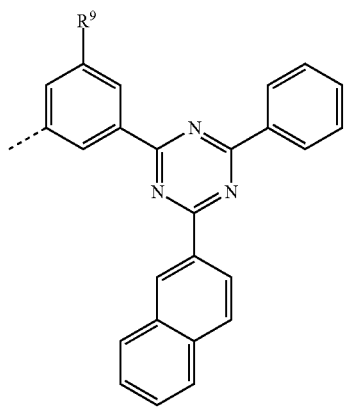 | 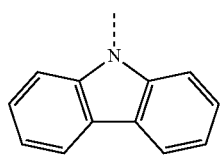 | H |
| Iaaa-62 | S | 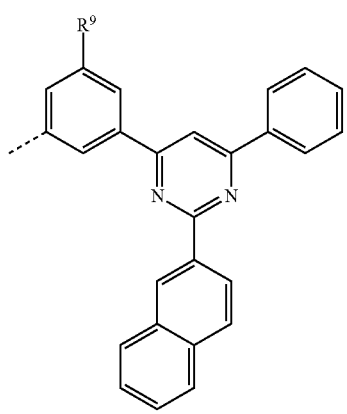 | 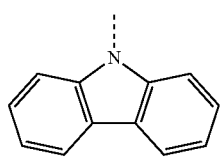 | — |

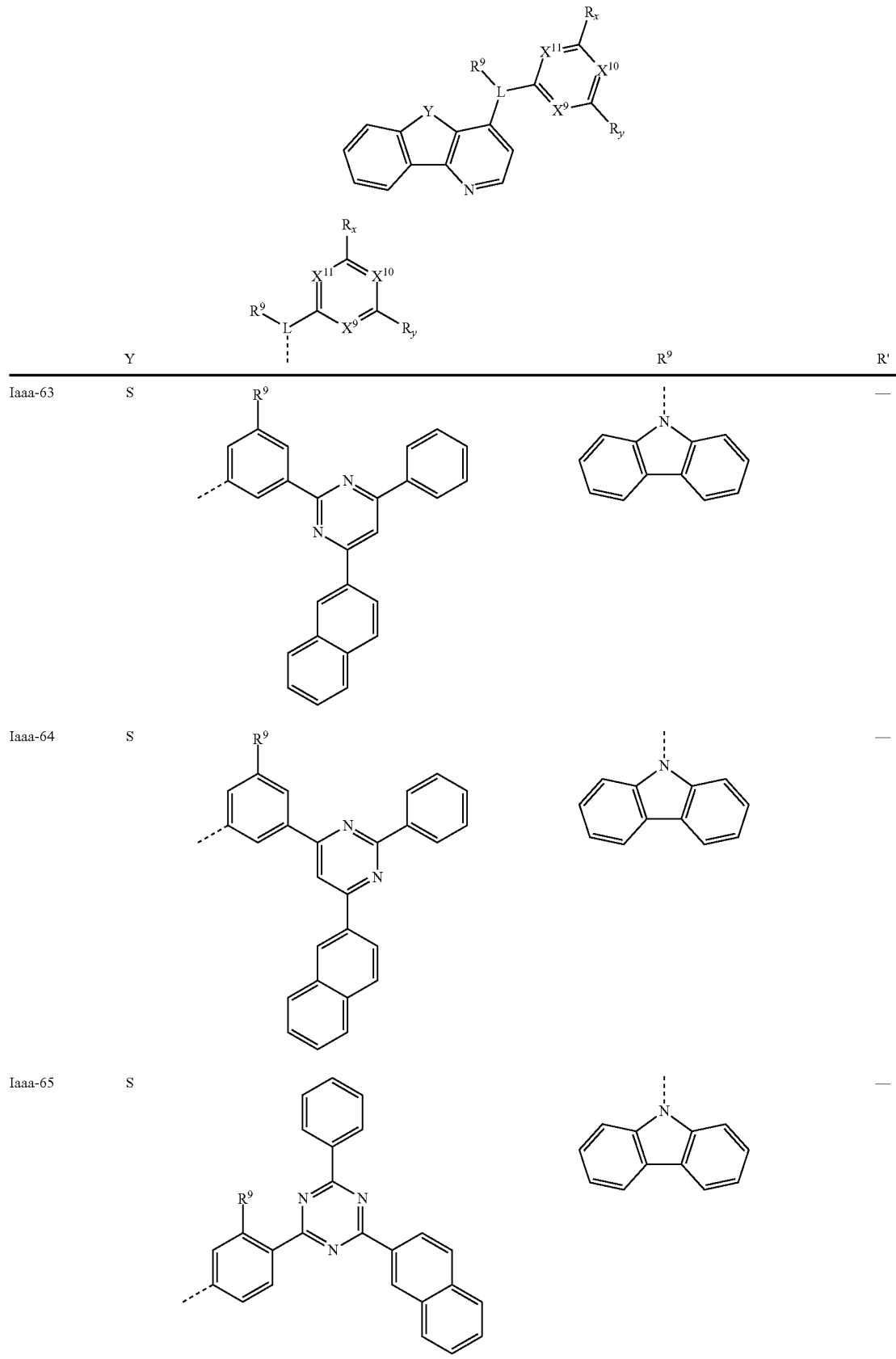

-continued
(Iaaa)
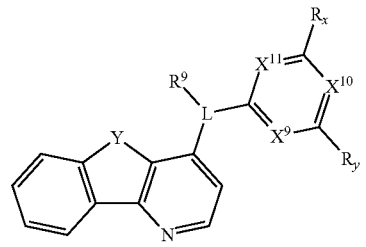
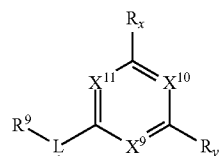
| | Y | | R⁹ | R' |
|---|---|---|---|---|
| Iaaa-66 | S | 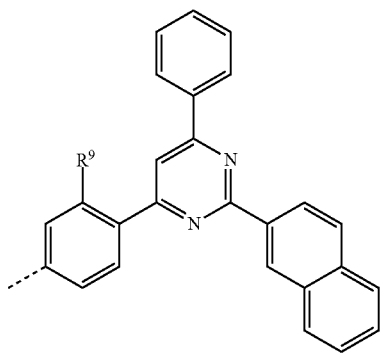 | 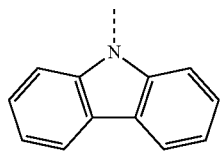 | — |
| Iaaa-67 | S | 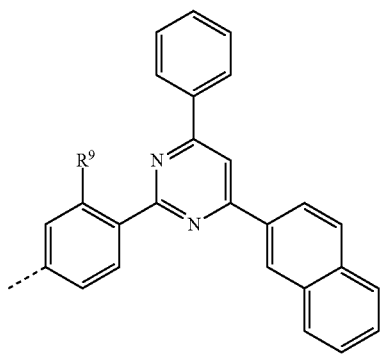 | 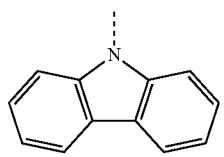 | — |
| Iaaa-68 | S | 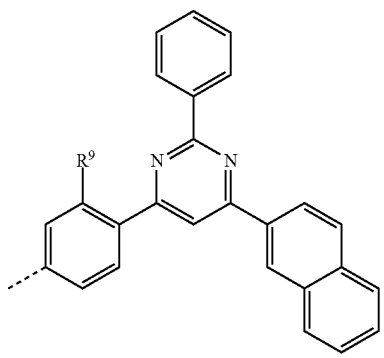 | 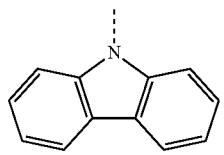 | — |

-continued
(Iaaa)
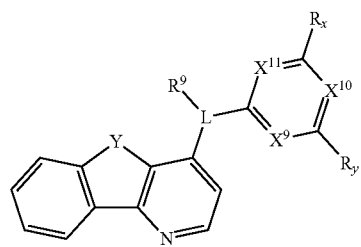
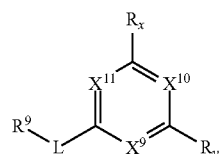
| | Y | | R⁹ | R' |
|---|---|---|---|---|
| Iaaa-69 | S | 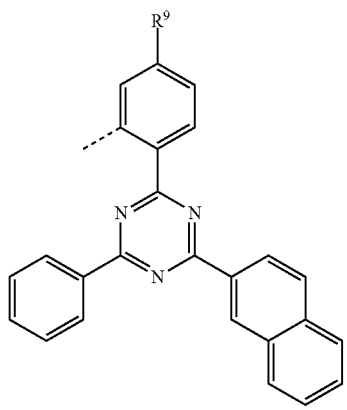 | 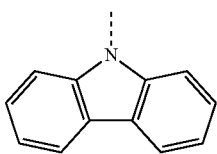 | — |
| Iaaa-70 | S | 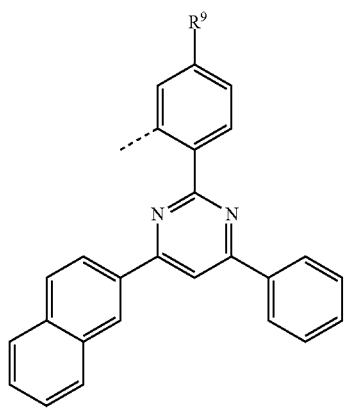 | 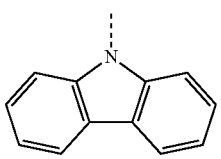 | — |

-continued
(Iaaa)
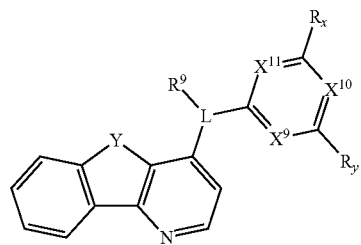
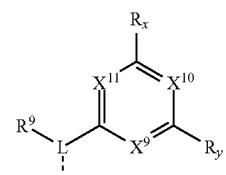
| | Y | R⁹ | R' |
|---|---|---|---|
| Iaaa-71 | S | 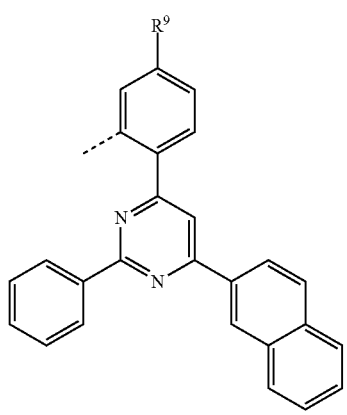 | 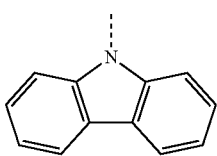 | — |
| Iaaa-72 | S | 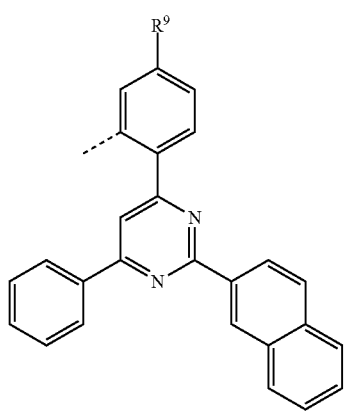 | 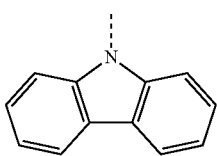 | — |

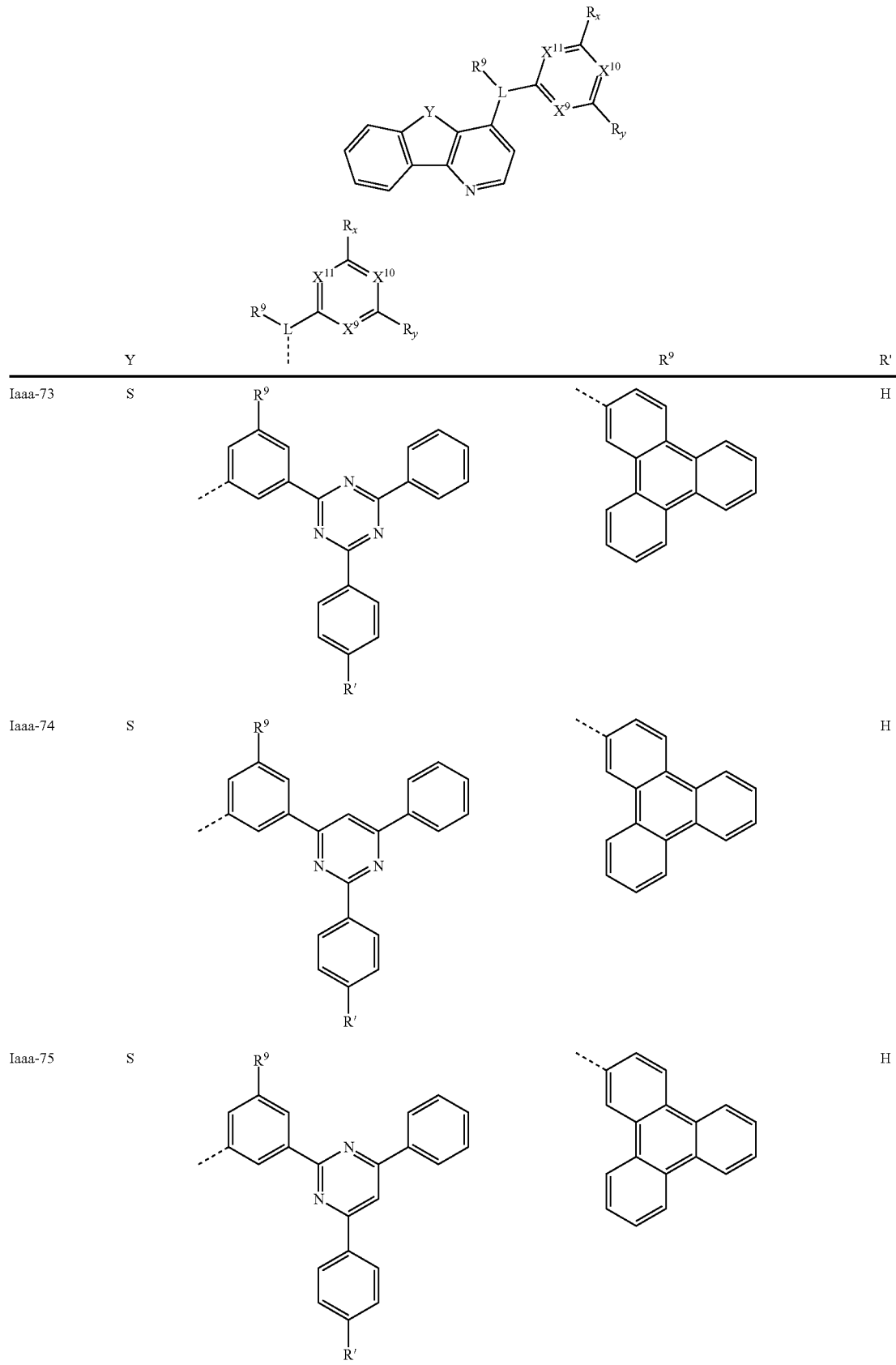

-continued
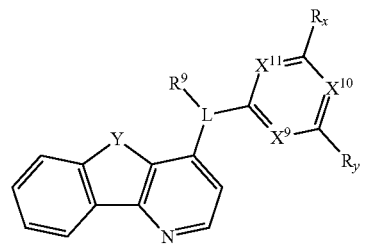
(Iaaa)
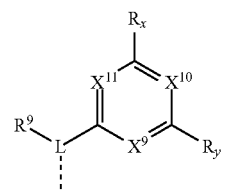
| | Y | | R⁹ | R' |
|---|---|---|---|---|
| Iaaa-76 | S | 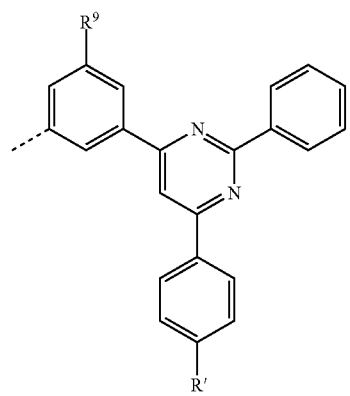 | 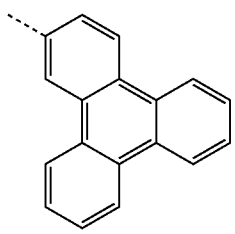 | H |
| Iaaa-77 | S | 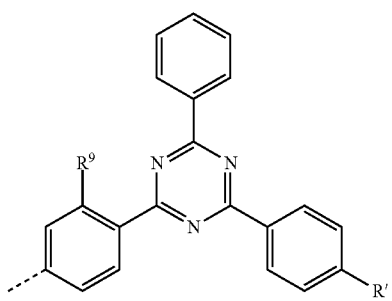 | 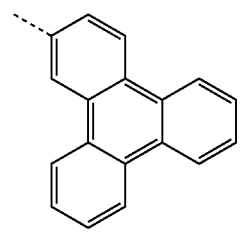 | H |
| Iaaa-78 | S | 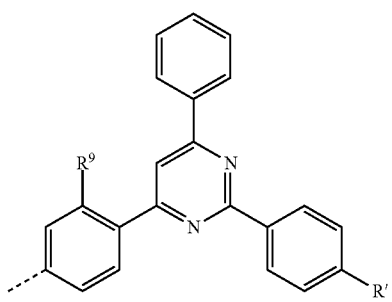 | 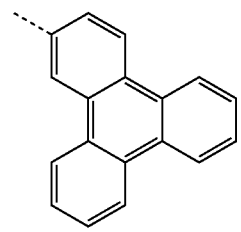 | H |

-continued
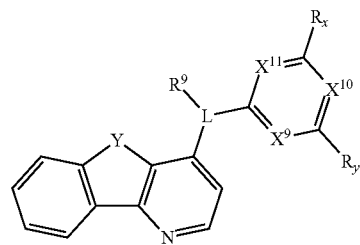
(Iaaa)
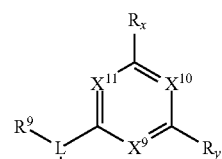
| | Y | | R⁹ | R' |
|---|---|---|---|---|
| Iaaa-79 | S | 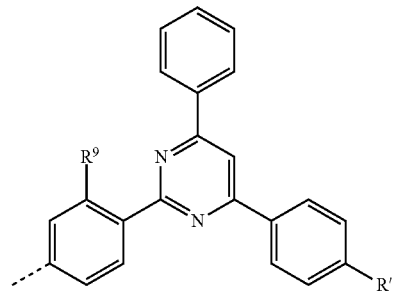 | 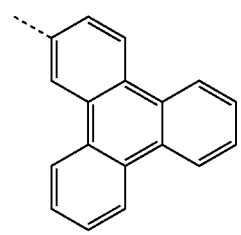 | H |
| Iaaa-80 | S | 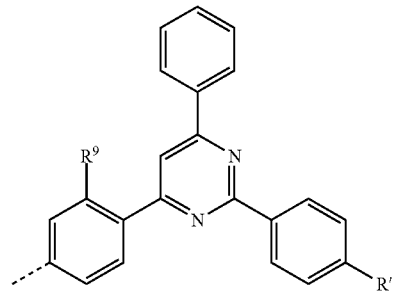 | 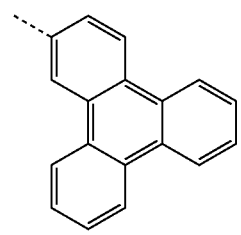 | H |
| Iaaa-81 | S | 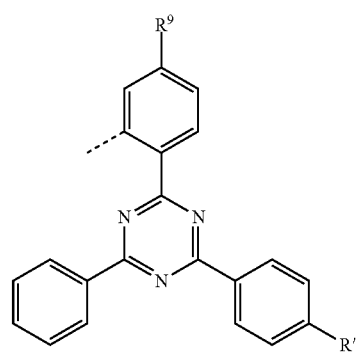 | 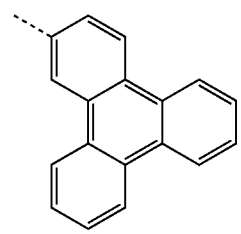 | H |

-continued
(Iaaa)
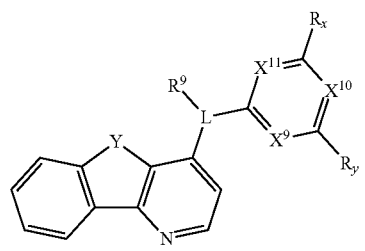
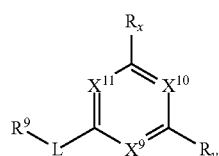
| | Y | | R⁹ | R' |
|---|---|---|---|---|
| Iaaa-82 | S | 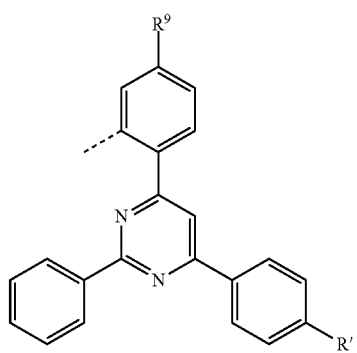 | 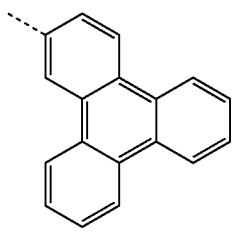 | H |
| Iaaa-83 | S | 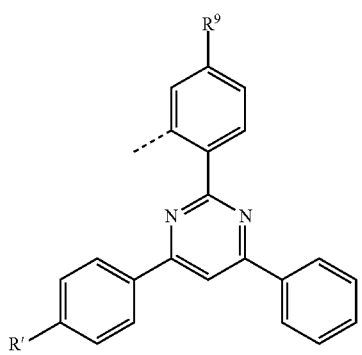 | 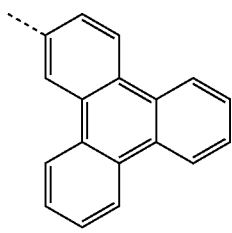 | H |
| Iaaa-84 | S | 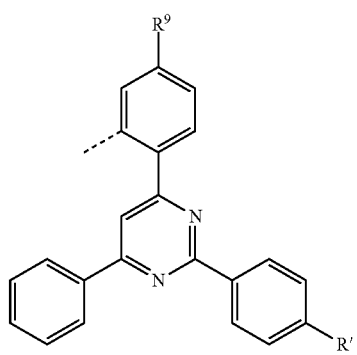 | 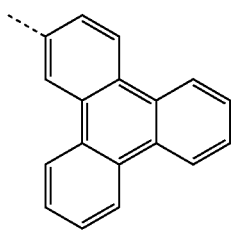 | H |

-continued
(Iaaa)
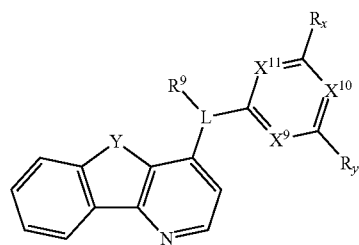
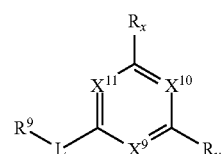
| | Y | R9 | R' |
|---|---|---|---|
| Iaaa-85 | S | 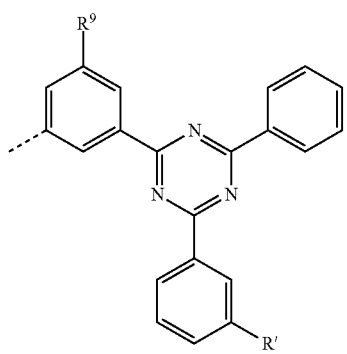 | 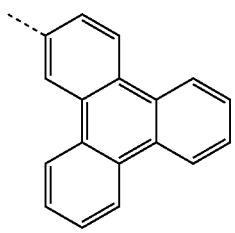 | H |
| Iaaa-86 | S | 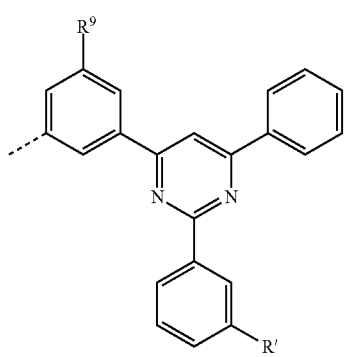 | 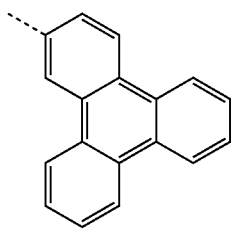 | H |
| Iaaa-87 | S | 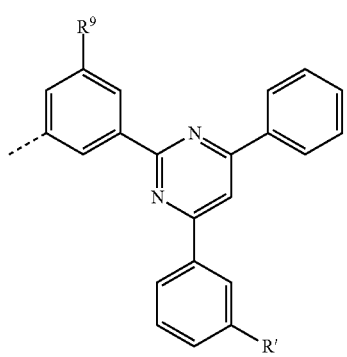 | 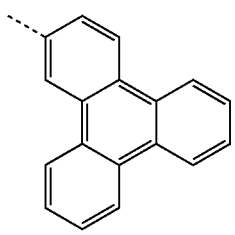 | H |

-continued
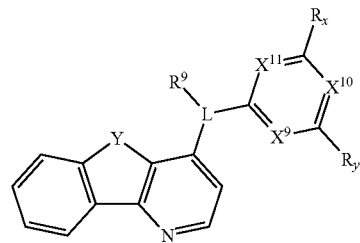
(Iaaa)
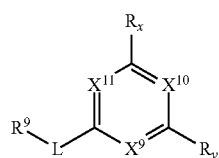
| | Y | R⁹ | R' |
|---|---|---|---|
| Iaaa-88 | S | 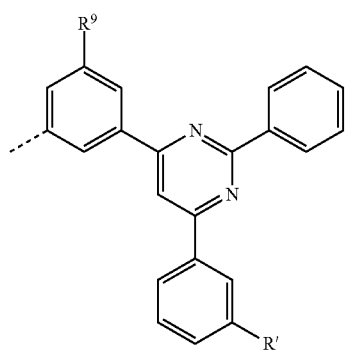 | 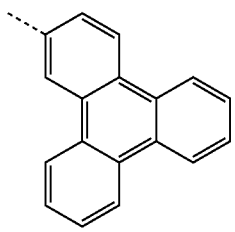 H |
| Iaaa-89 | S | 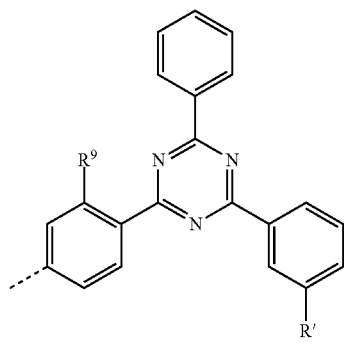 | 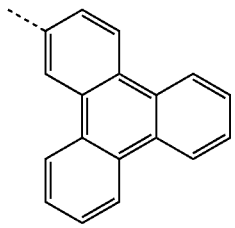 H |
| Iaaa-90 | S | 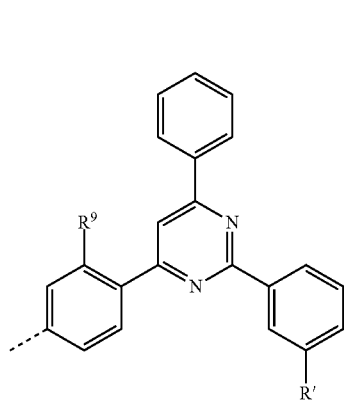 | 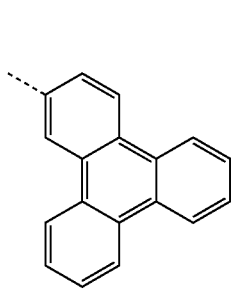 H |

-continued
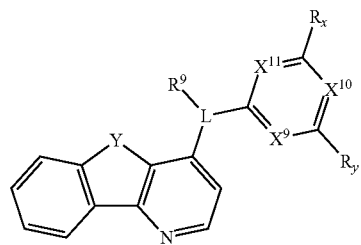
(Iaaa)
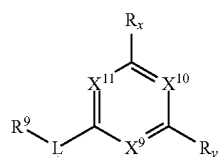
| | Y | | R⁹ | R' |
|---|---|---|---|---|
| Iaaa-91 | S | 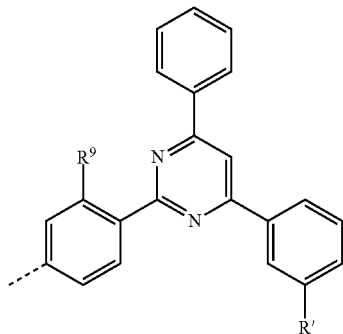 | 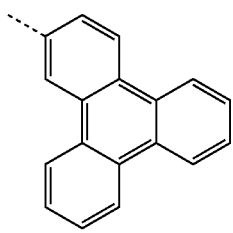 | H |
| Iaaa-92 | S | 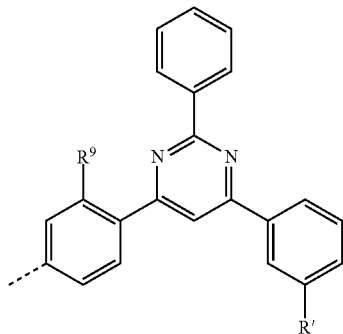 | 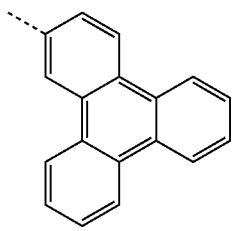 | H |
| Iaaa-93 | S | 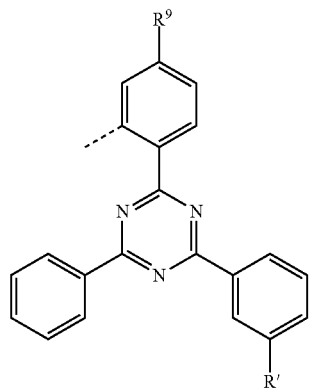 | 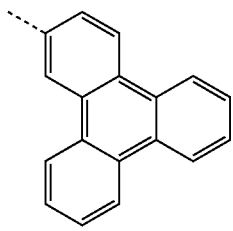 | H |

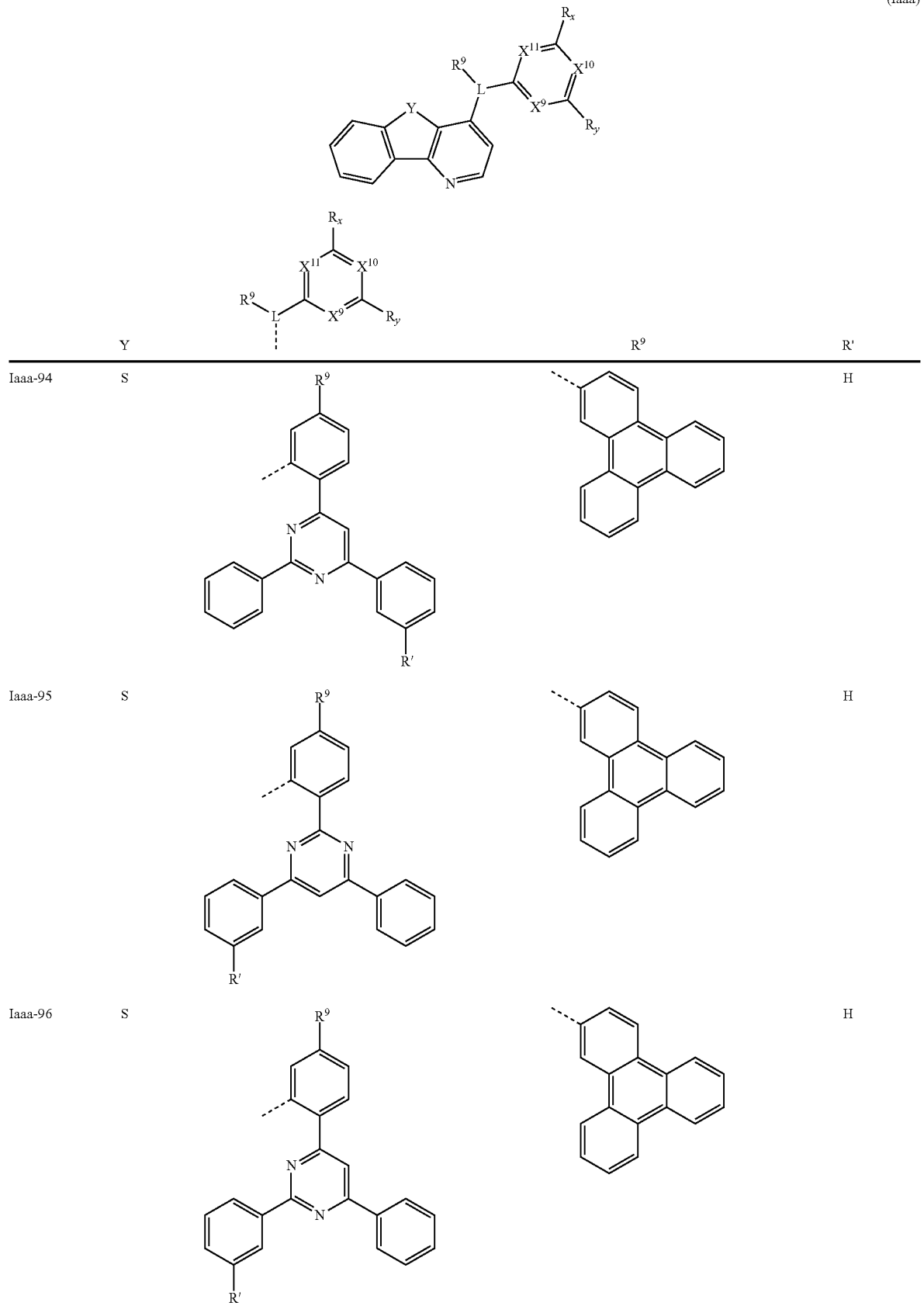

-continued
(Iaaa)
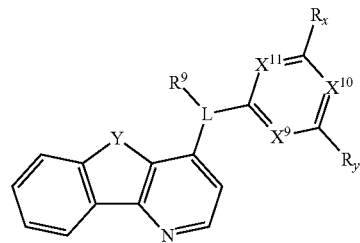
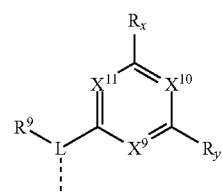
| | Y | R⁹ | R' |
|---|---|---|---|
| Iaaa-97 | S | 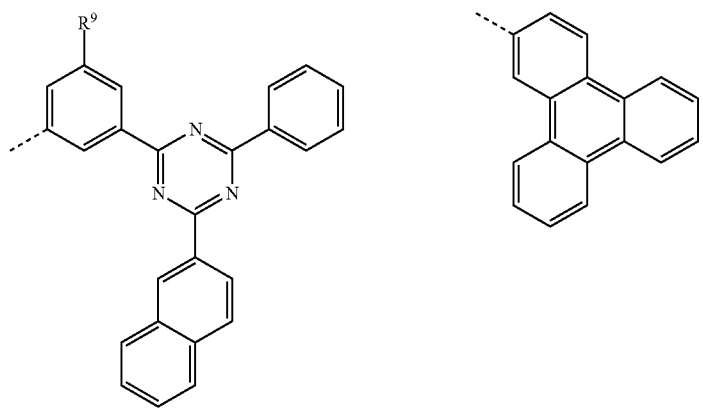 | — |
| Iaaa-98 | S | 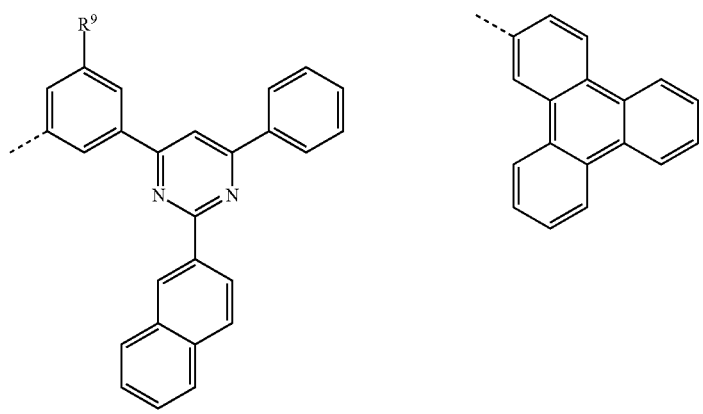 | — |

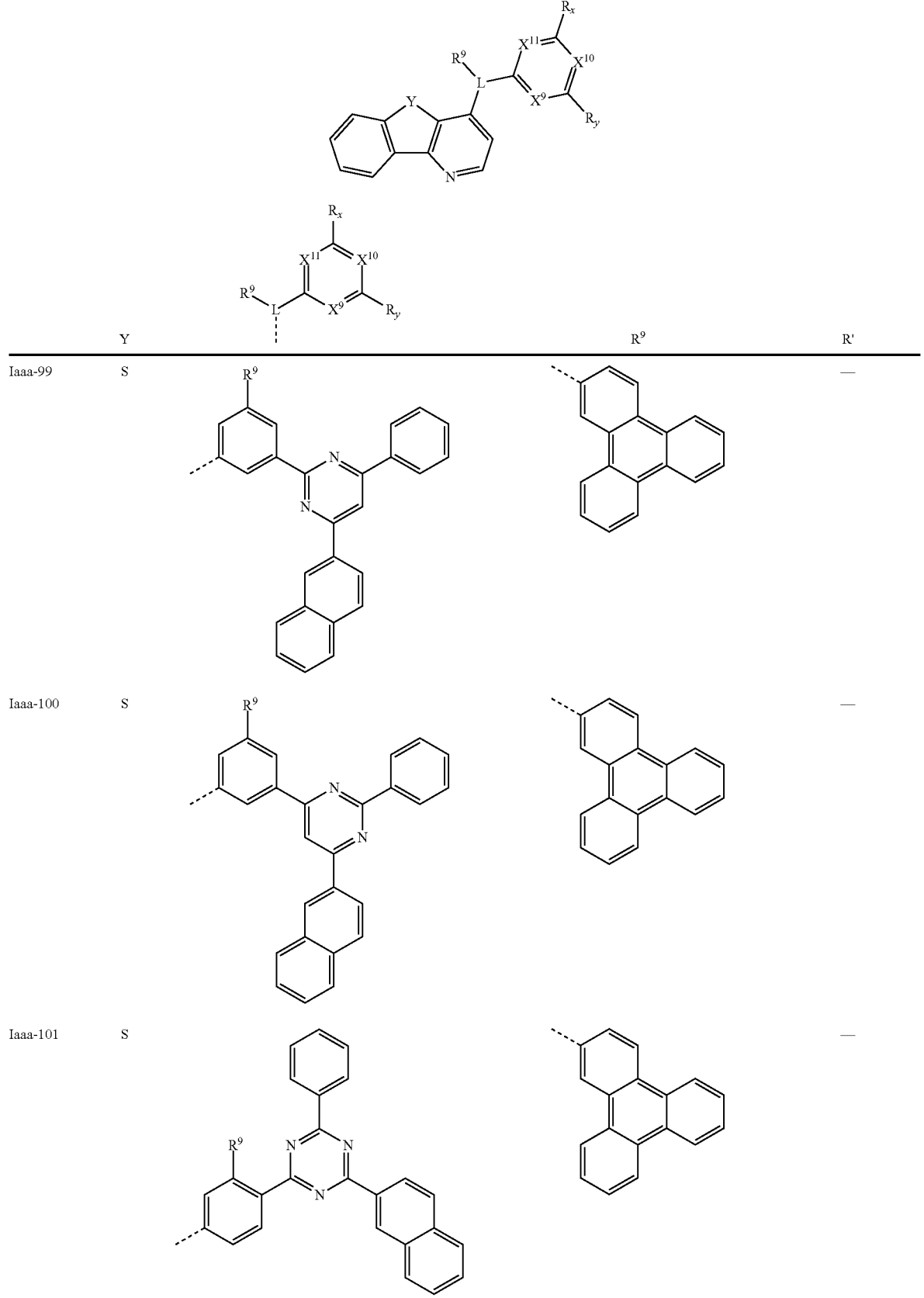

-continued
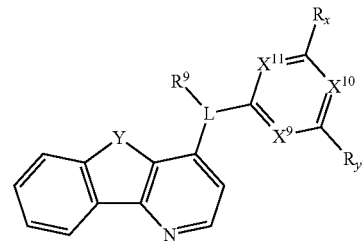
(Iaaa)
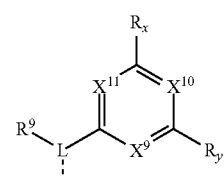
| | Y | R⁹ | R' |
|---|---|---|---|
| Iaaa-102 | S | 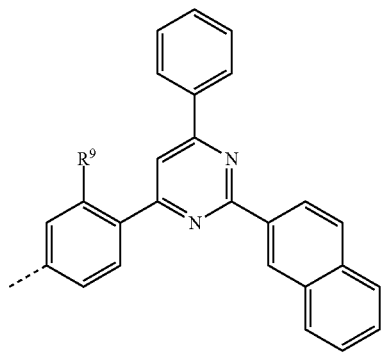 | 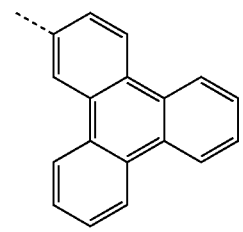 | — |
| Iaaa-103 | S | 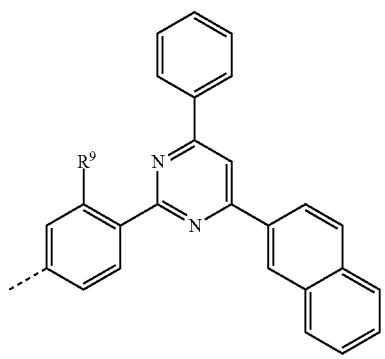 | 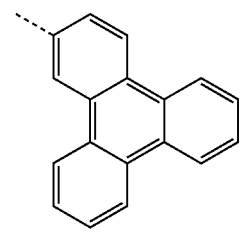 | — |
| Iaaa-104 | S | 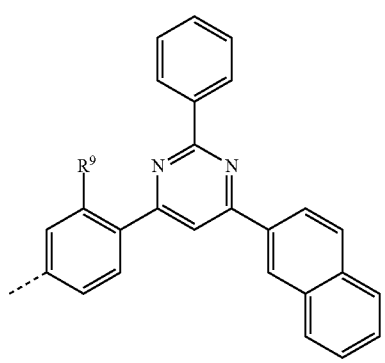 | 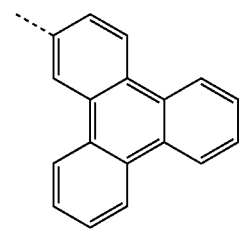 | — |

-continued
(Iaaa)
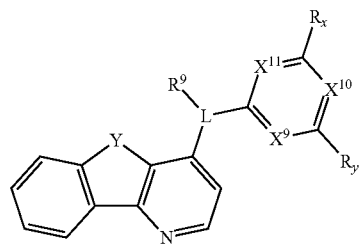
| | Y | 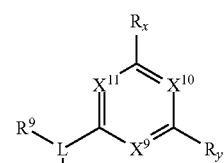 | R⁹ | R' |
|---|---|---|---|---|
| Iaaa-105 | S | 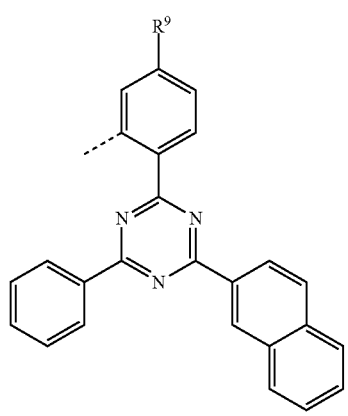 | 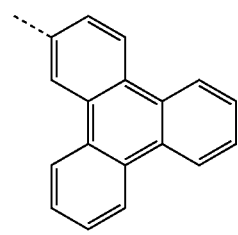 | — |
| Iaaa-106 | S | 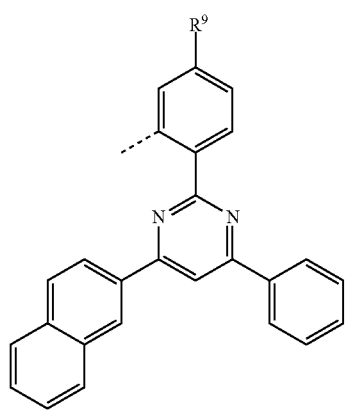 | 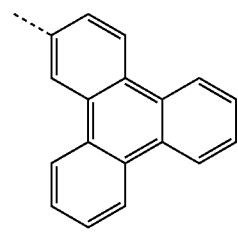 | — |

-continued
(Iaaa)
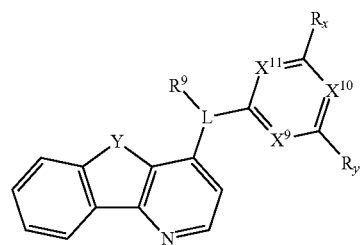
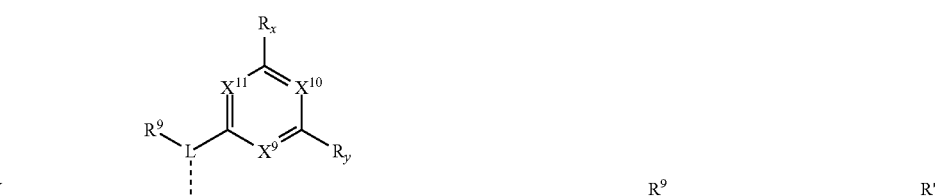
| | Y | R⁹ | R' |
|---|---|---|---|
| Iaaa-107 | S | 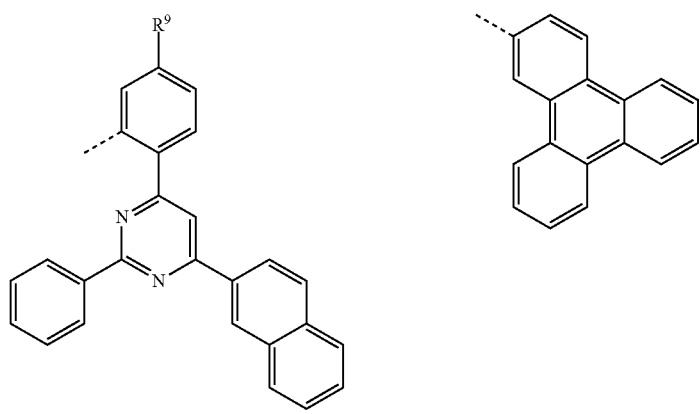 | — |
| Iaaa-108 | S | 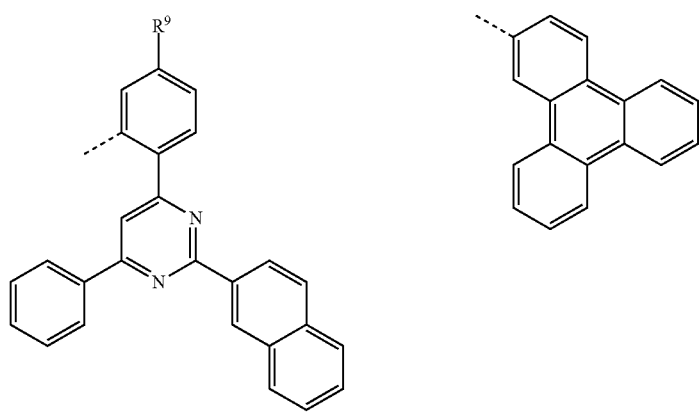 | — |

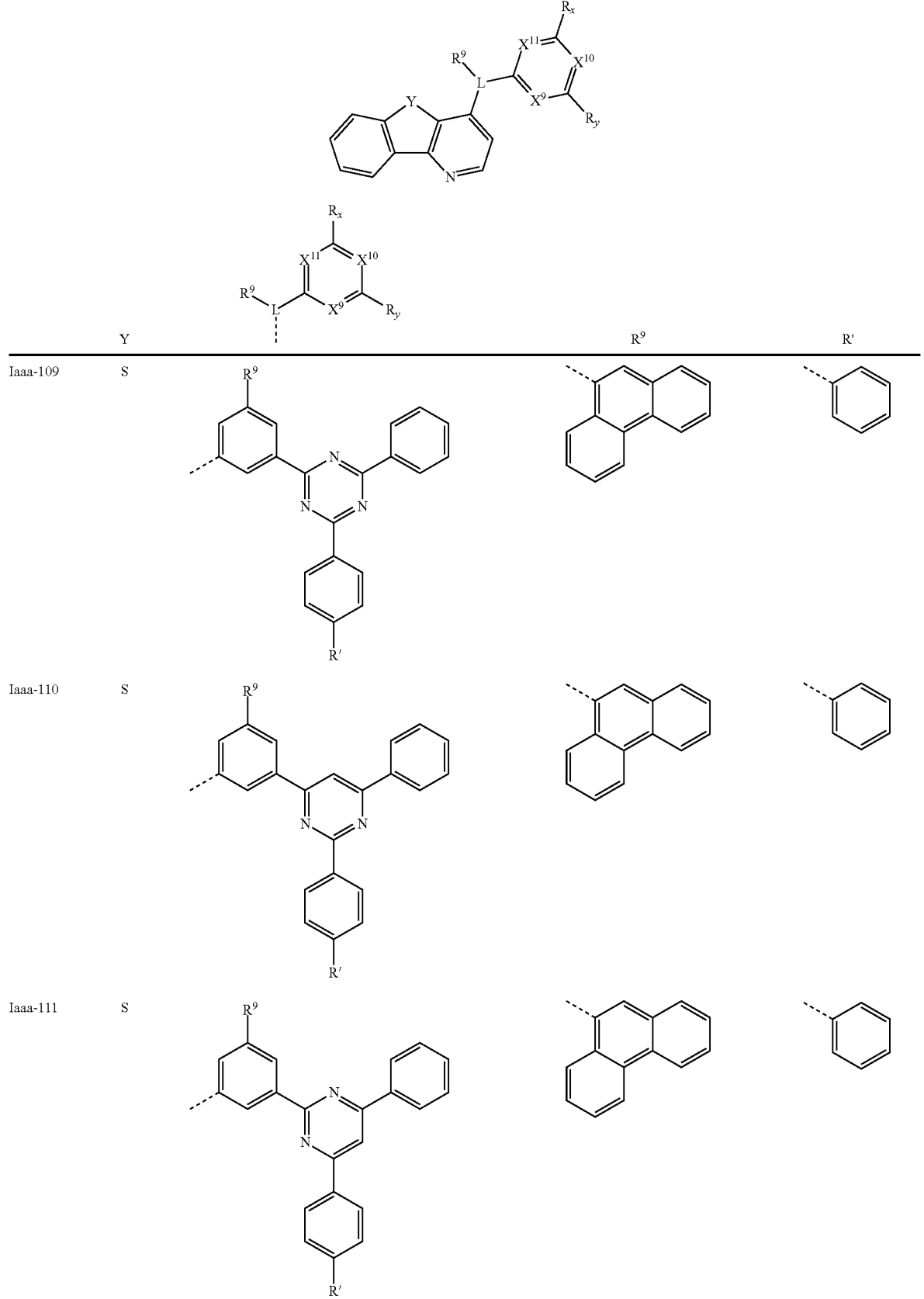

-continued
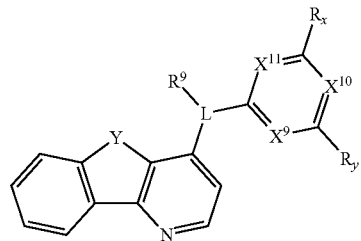
(Iaaa)
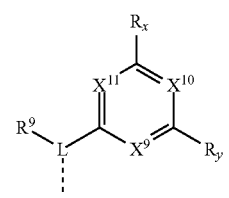
| | Y | | R⁹ | R' |
|---|---|---|---|---|
| Iaaa-112 | S | 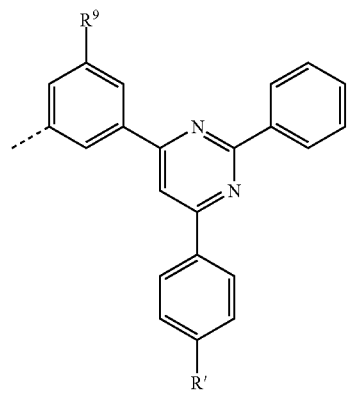 | 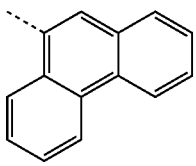 |  |
| Iaaa-113 | S | 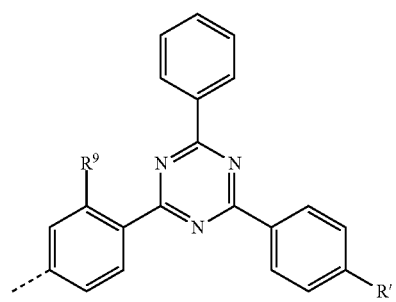 | 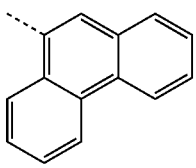 | 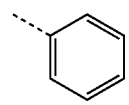 |
| Iaaa-114 | S | 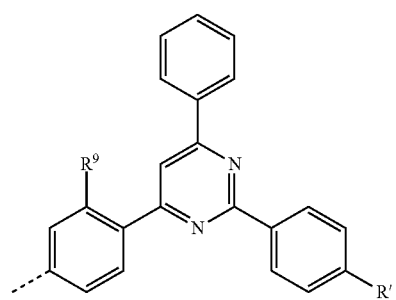 | 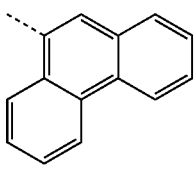 | 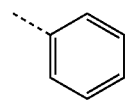 |

-continued
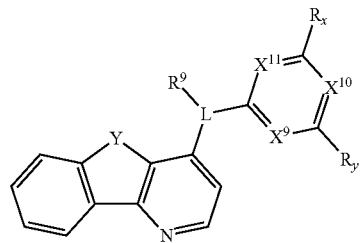
(Iaaa)
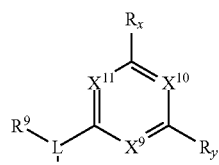
| | Y | | R⁹ | R' |
|---|---|---|---|---|
| Iaaa-115 | S |  |  | 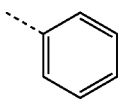 |
| Iaaa-116 | S | 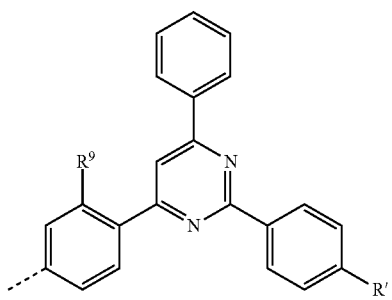 | 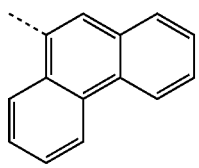 | 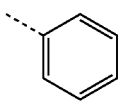 |
| Iaaa-117 | S | 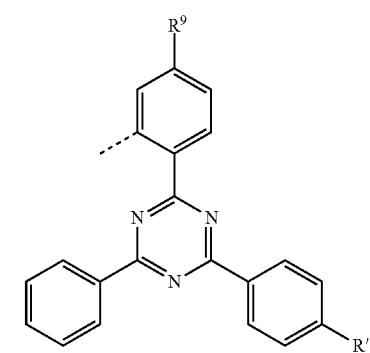 | 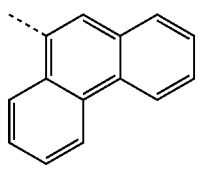 | 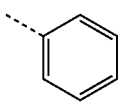 |

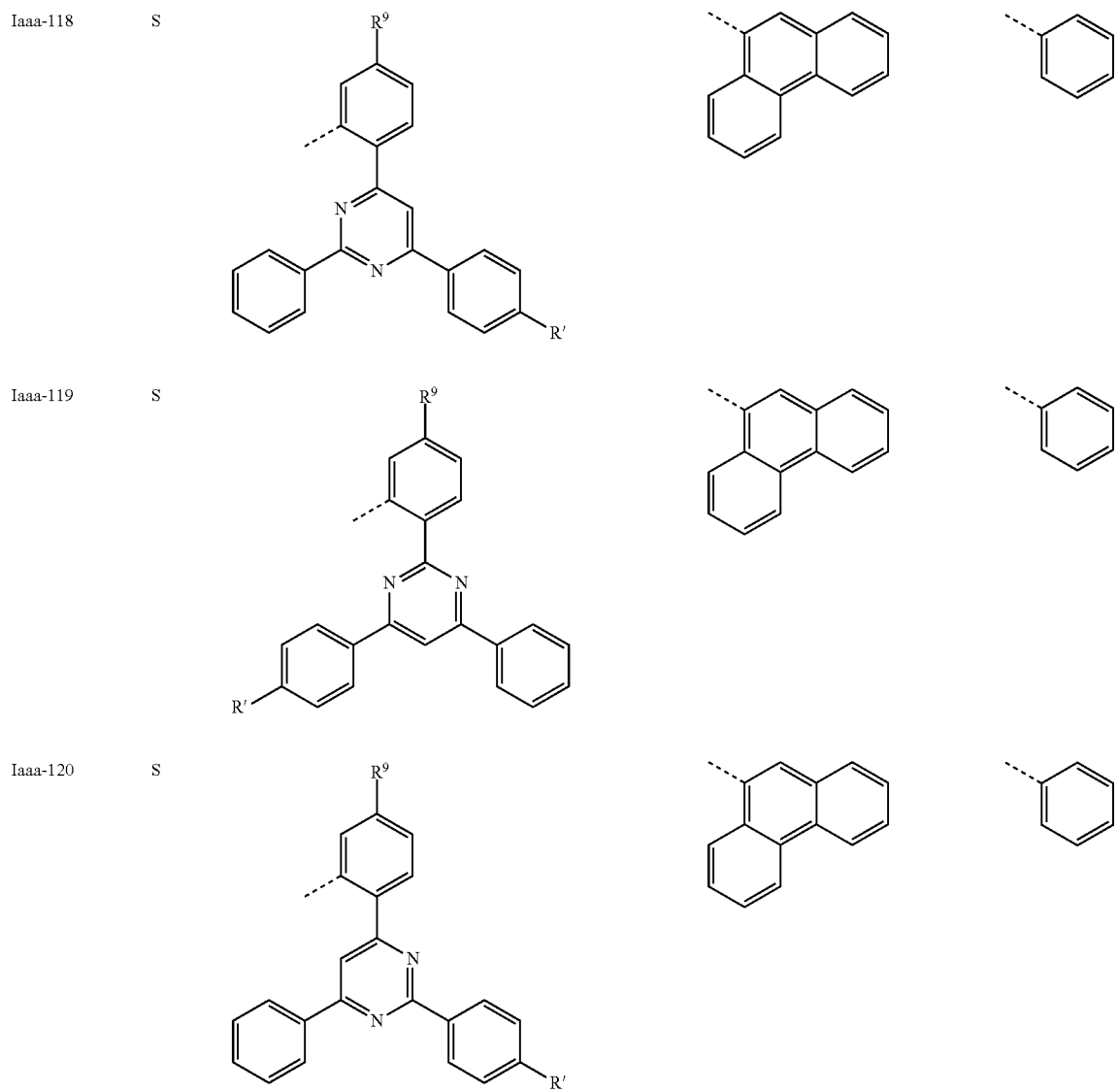

-continued
(Iaaa)
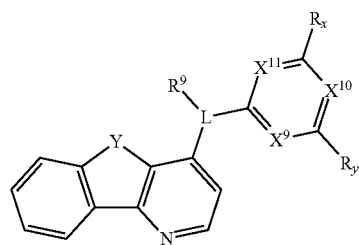
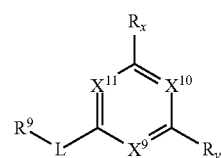
| | Y | | $R^9$ | R' |
|---|---|---|---|---|
| Iaaa-121 | S | 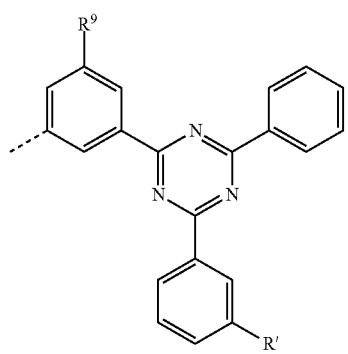 | 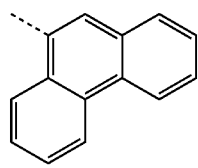 | 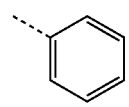 |
| Iaaa-122 | S | 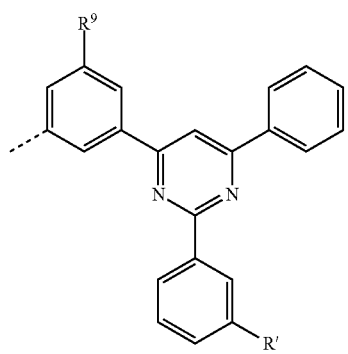 | 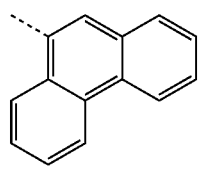 | 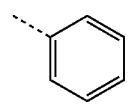 |
| Iaaa-123 | S | 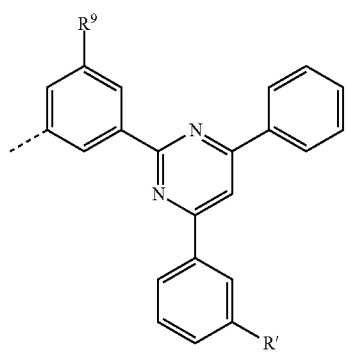 | 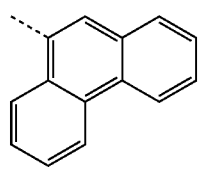 | 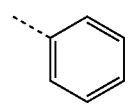 |

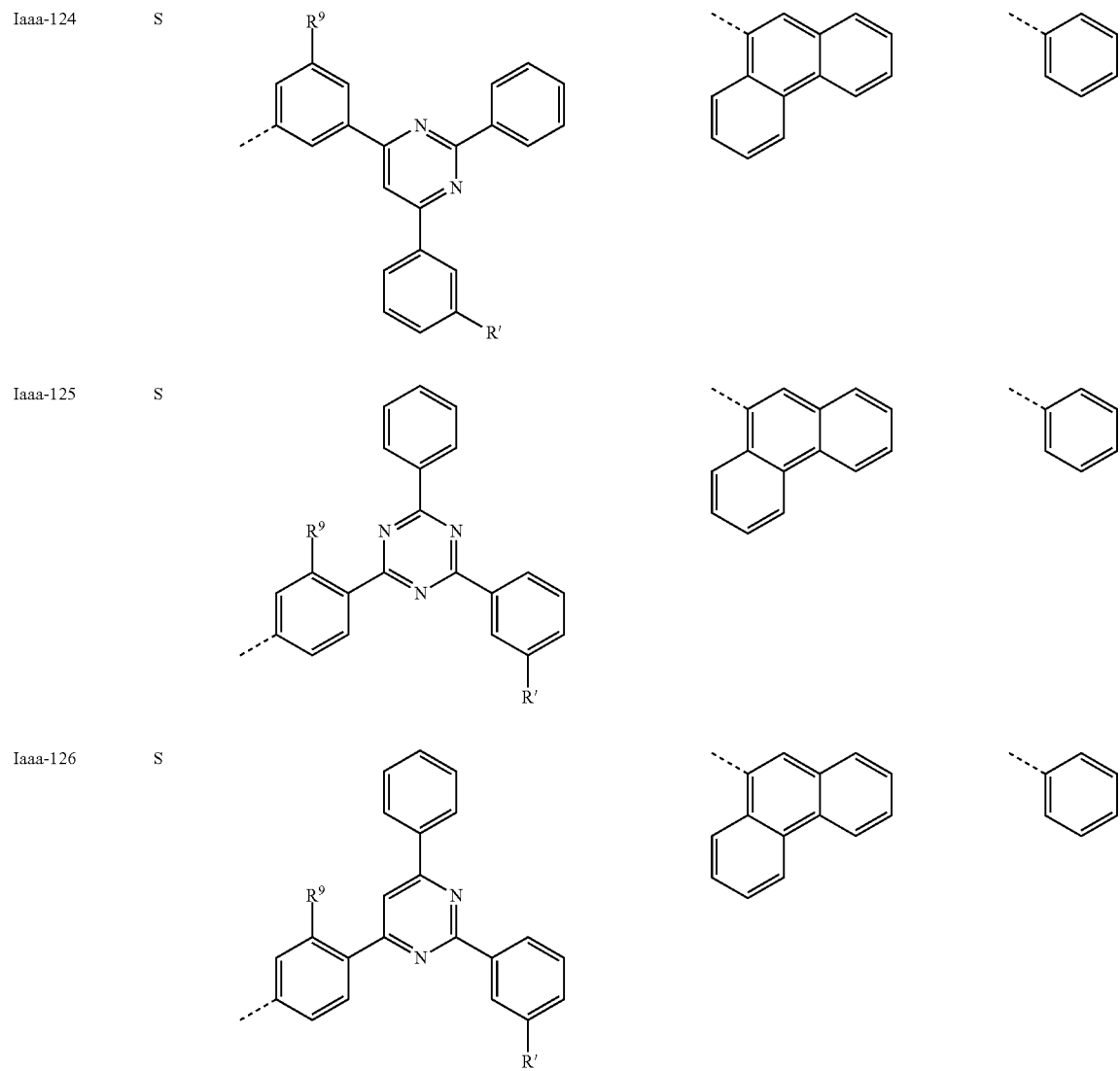

-continued
(Iaaa)
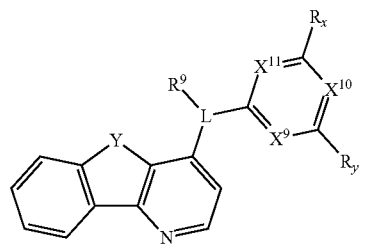
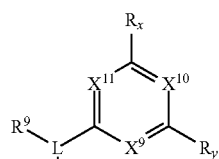
| | Y | | R⁹ | R' |
|---|---|---|---|---|
| Iaaa-127 | S | 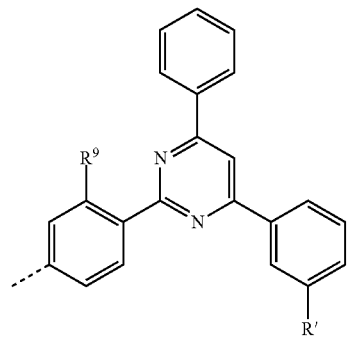 | 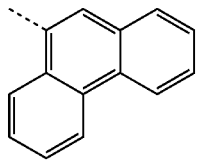 | 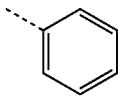 |
| Iaaa-128 | S | 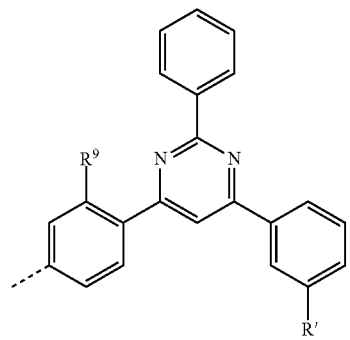 | 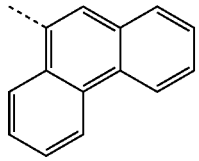 | 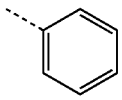 |
| Iaaa-129 | S | 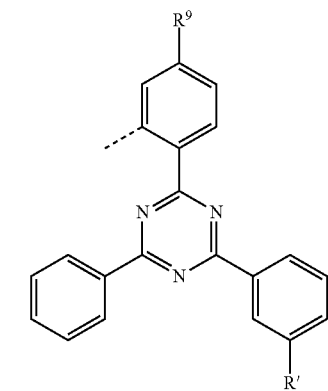 | 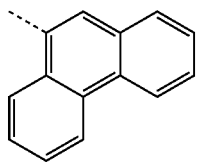 | 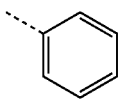 |

-continued
(Iaaa)
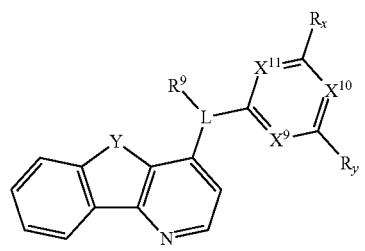
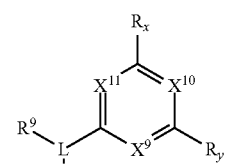
| | Y | | $R^9$ | R' |
|---|---|---|---|---|
| Iaaa-130 | S | 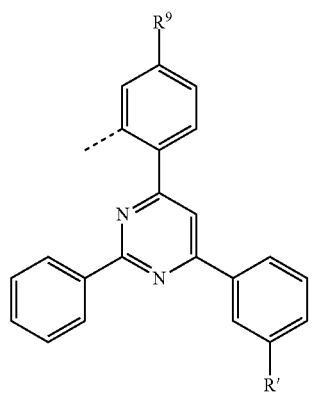 | 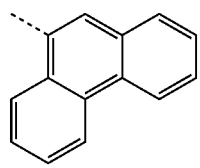 | 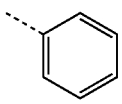 |
| Iaaa-131 | S | 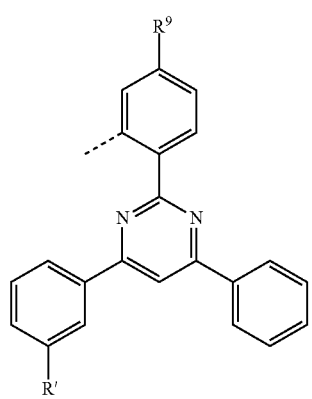 | 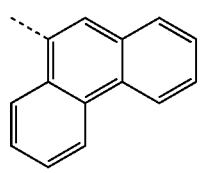 | 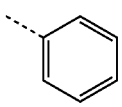 |

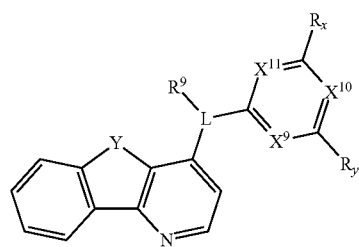
(Iaaa)
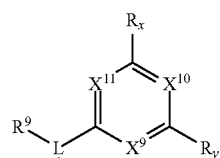
| | Y | | R⁹ | R' |
|---|---|---|---|---|
| Iaaa-132 | S | 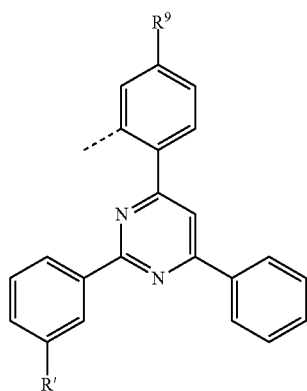 | 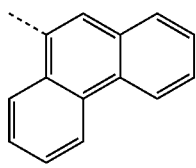 | 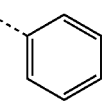 |
| Iaaa-133 | | | | |
| Iaaa-134 | | | | |
| Iaaa-135 | | | | |
| Iaaa-136 | S | 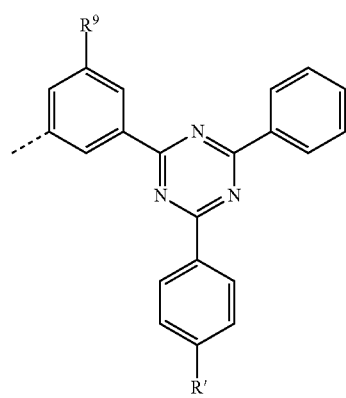 | 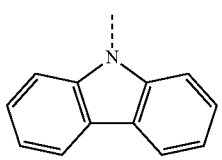 | 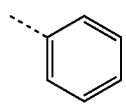 |

-continued
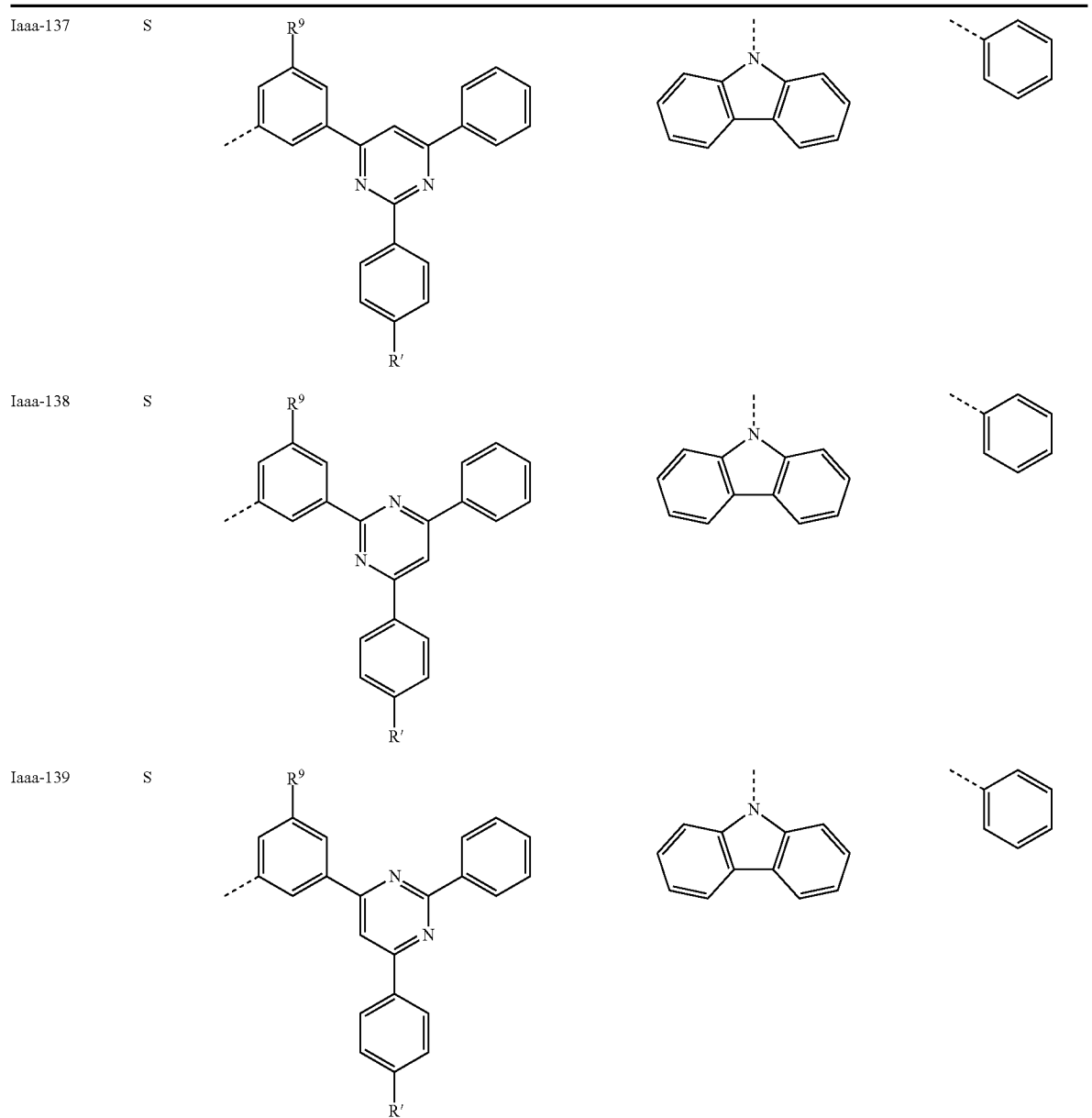

(Iaaa)
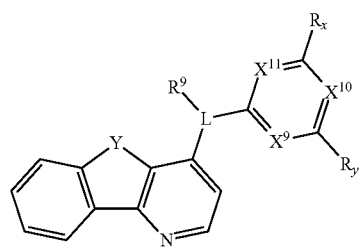
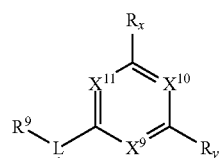
| | Y | | R⁹ | R' |
|---|---|---|---|---|
| Iaaa-140 | S | 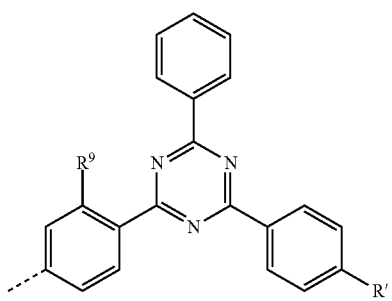 | 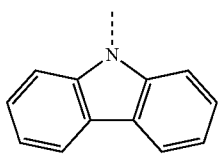 | 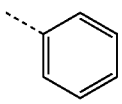 |
| Iaaa-141 | S | 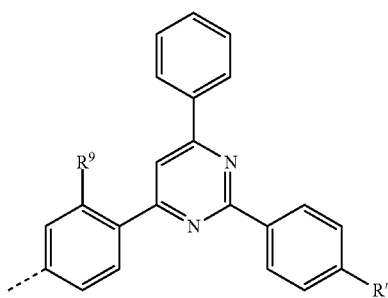 | 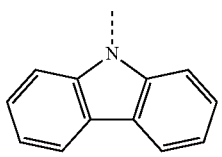 | 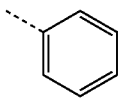 |
| Iaaa-142 | S | 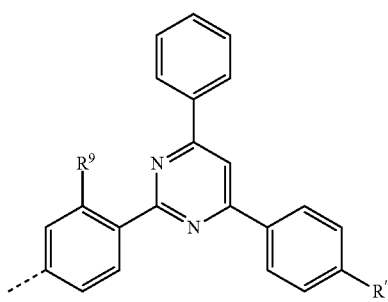 | 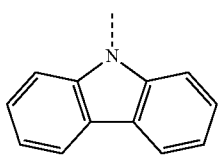 | 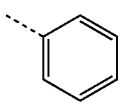 |

-continued
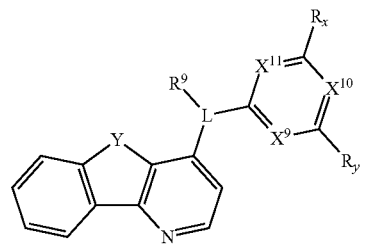
(Iaaa)
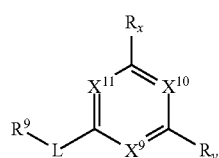
| | Y | | $R^9$ | R' |
|---|---|---|---|---|
| Iaaa-143 | S | 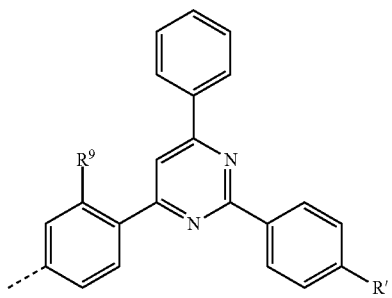 | 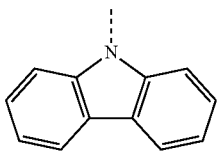 | 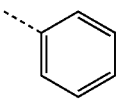 |
| Iaaa-144 | S | 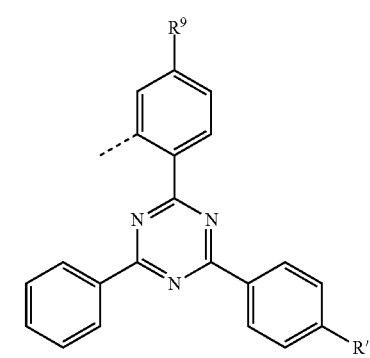 | 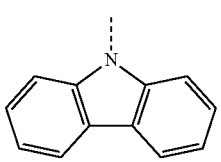 | 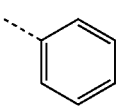 |
| Iaaa-145 | S | 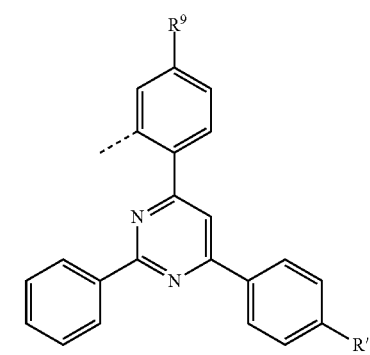 | 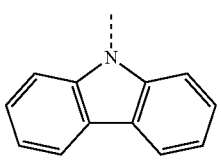 | 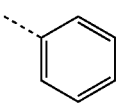 |

-continued
(Iaaa)
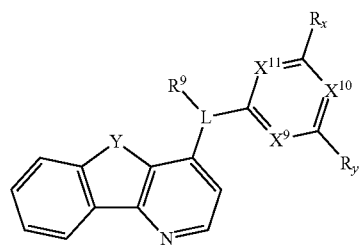
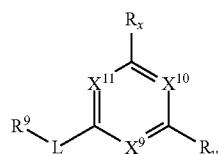
| | Y | | R⁹ | R' |
|---|---|---|---|---|
| Iaaa-146 | S | 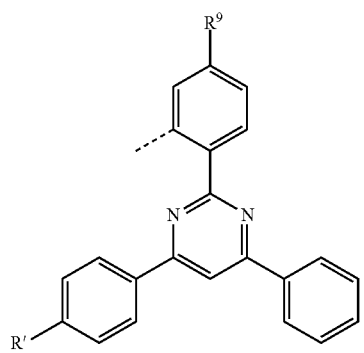 | 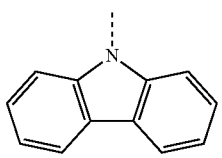 | 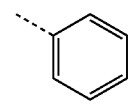 |
| Iaaa-147 | S | 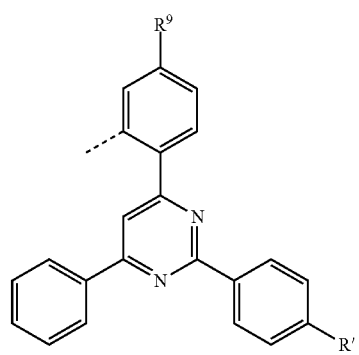 | 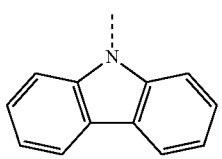 | 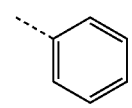 |
| Iaaa-148 | S | 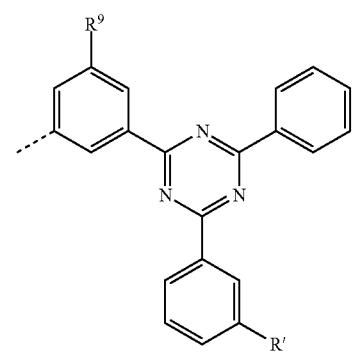 | 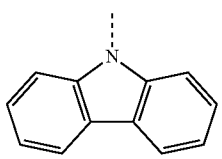 | 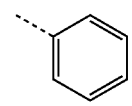 |

-continued
(Iaaa)
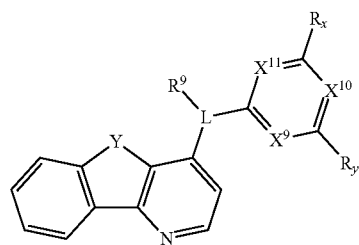
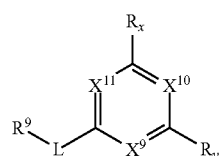
| | Y | R⁹ | R' |
|---|---|---|---|
| Iaaa-149 | S | 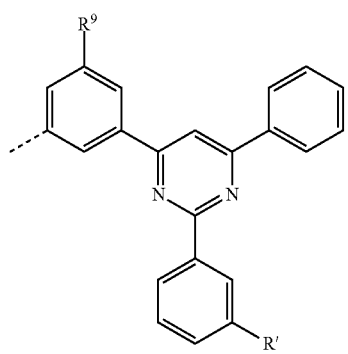 | 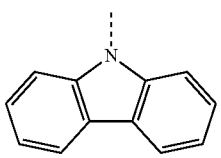 | 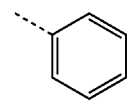 |
| Iaaa-150 | S | 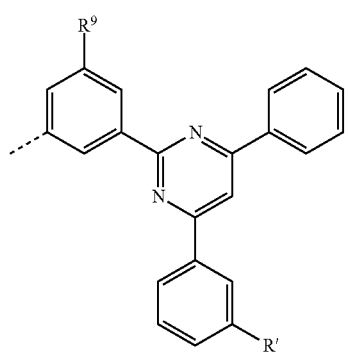 | 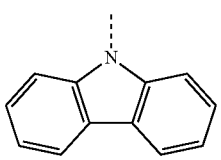 | 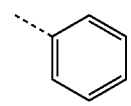 |
| Iaaa-151 | S | 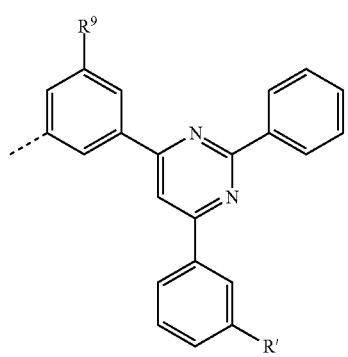 | 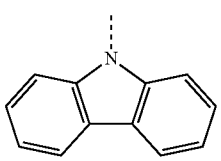 | 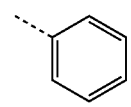 |

-continued
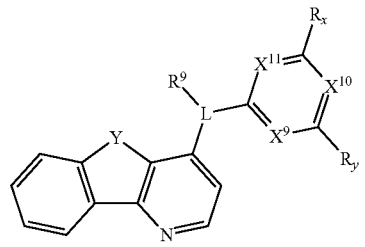
(Iaaa)
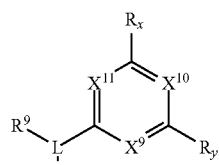
| | Y | | R⁹ | R' |
|---|---|---|---|---|
| Iaaa-152 | S | 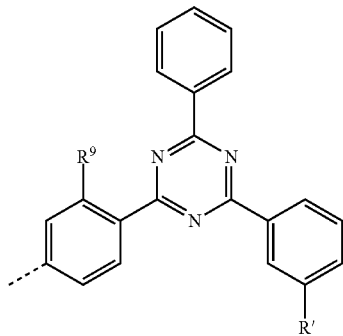 | 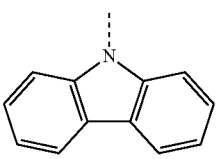 | 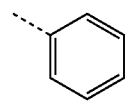 |
| Iaaa-153 | S | 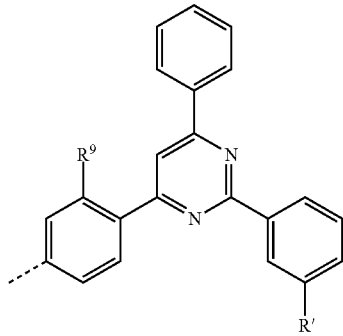 | 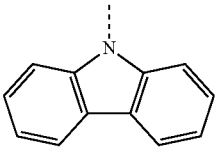 | 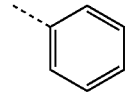 |
| Iaaa-154 | S | 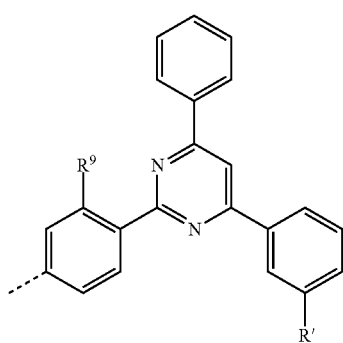 | 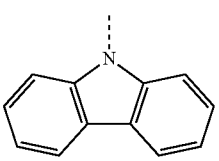 | 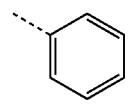 |

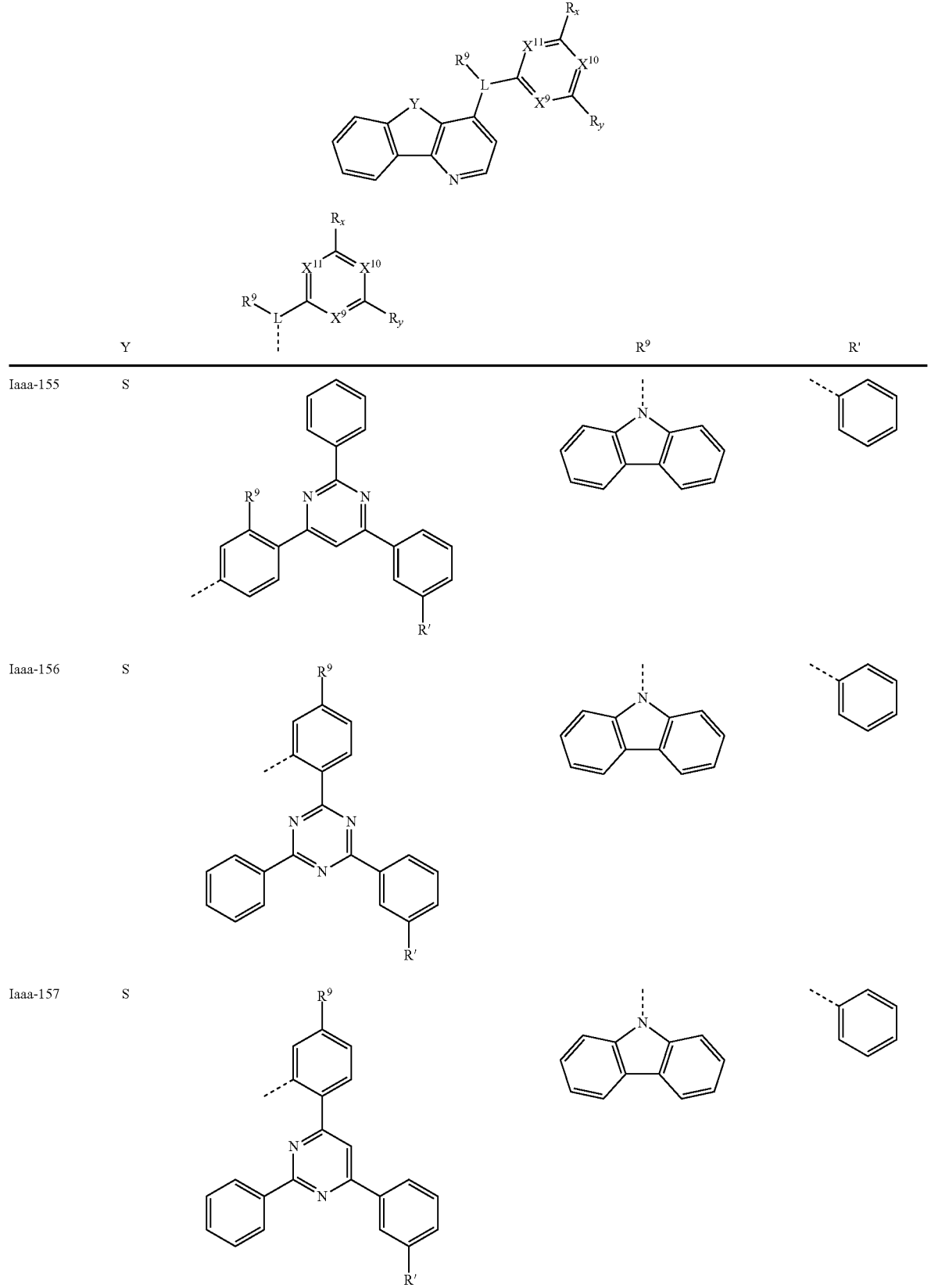

-continued
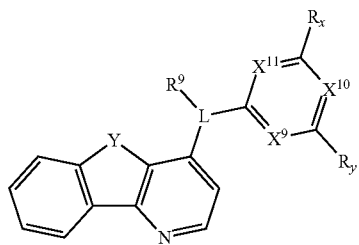
(Iaaa)
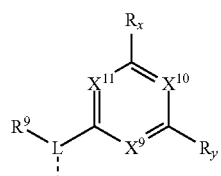
| | Y | R⁹ | R' |
|---|---|---|---|
| Iaaa-158 | S | 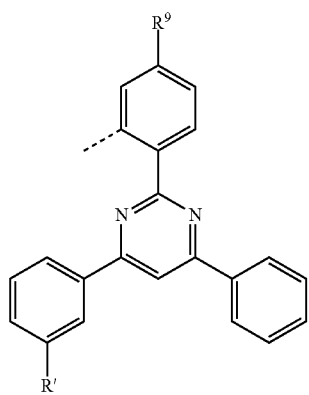 | 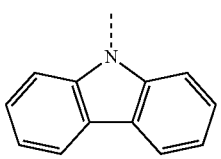 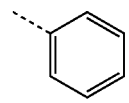 |
| Iaaa-159 | S | 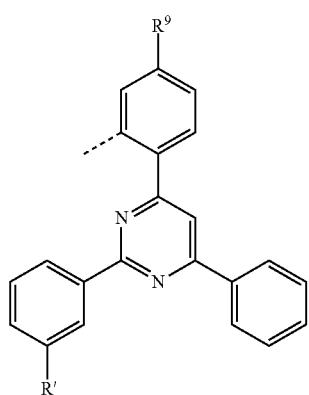 | 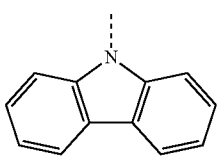 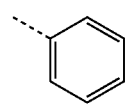 |

-continued
(Iaaa)
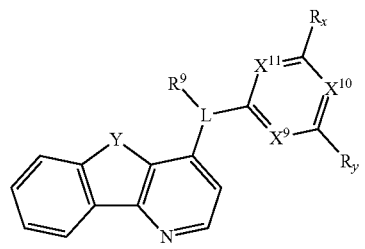
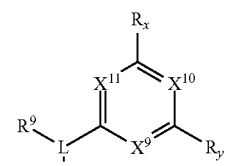
| | Y | | R⁹ | R' |
|---|---|---|---|---|
| Iaaa-160 | | | | |
| Iaaa-161 | | | | |
| Iaaa-162 | | | | |
| Iaaa-163 | S | 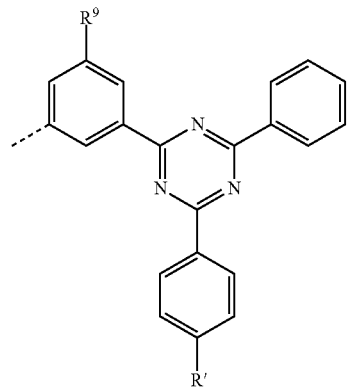 | 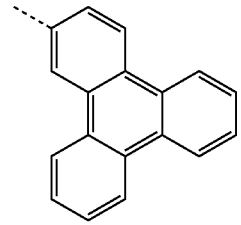 | 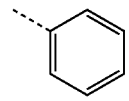 |
| Iaaa-164 | S | 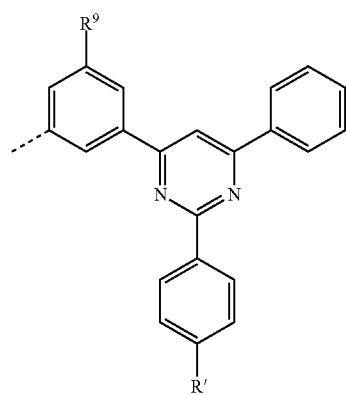 | 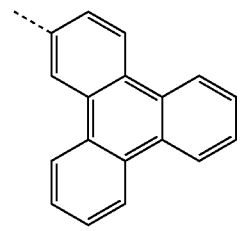 | 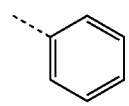 |

-continued
(Iaaa)
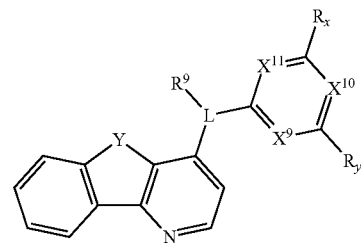
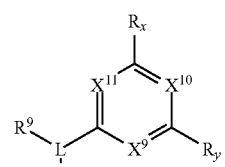
| | Y | | R⁹ | R' |
|---|---|---|---|---|
| Iaaa-165 | S | 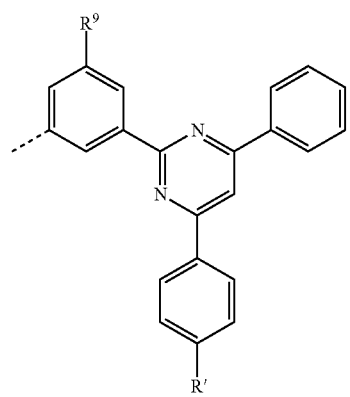 | 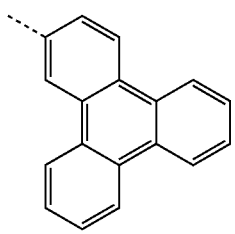 | 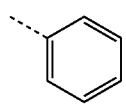 |
| Iaaa-166 | S | 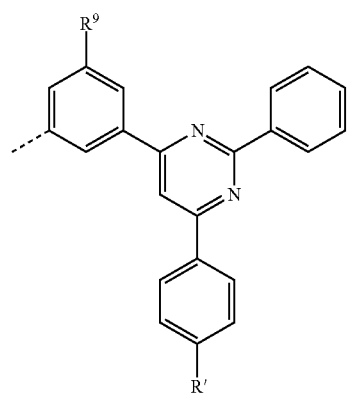 | 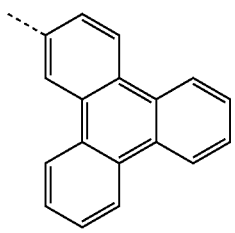 | 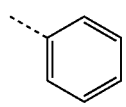 |
| Iaaa-167 | S | 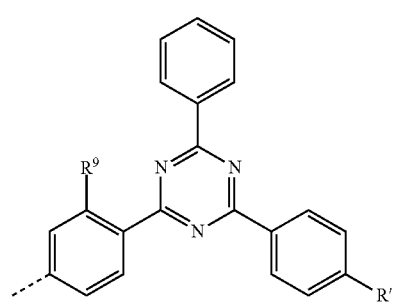 | 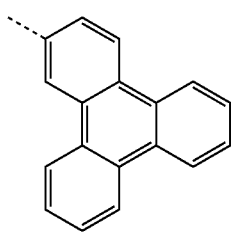 | 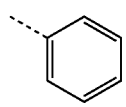 |

-continued
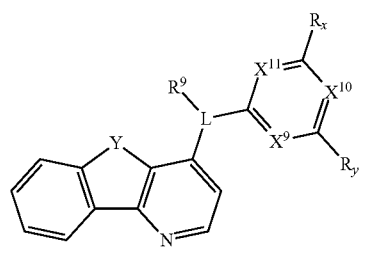
(Iaaa)
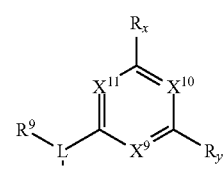
| | Y | | R⁹ | R' |
|---|---|---|---|---|
| Iaaa-168 | S | 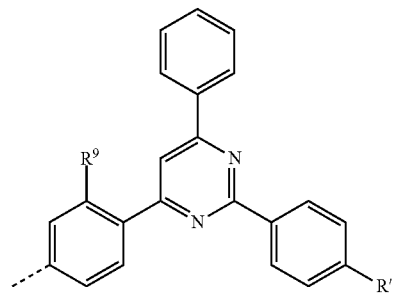 | 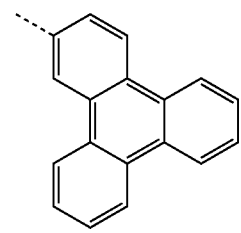 | 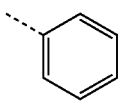 |
| Iaaa-169 | S | 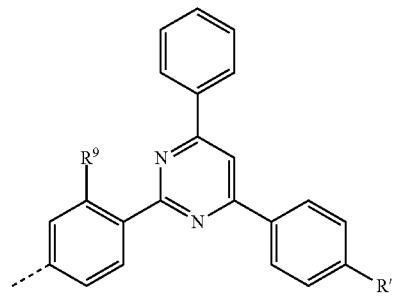 | 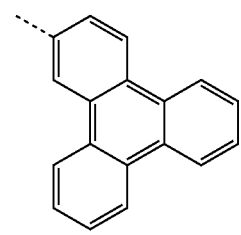 | 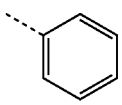 |
| Iaaa-170 | S | 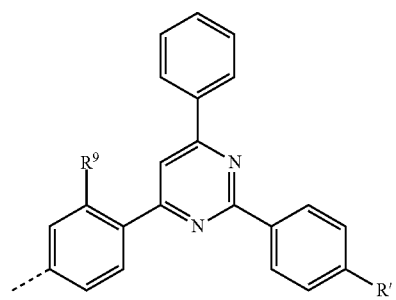 | 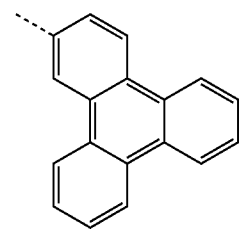 | 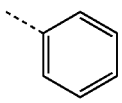 |

-continued
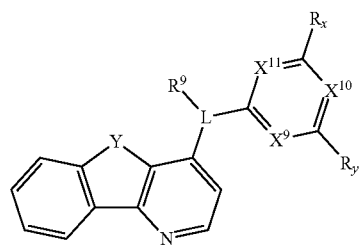
(Iaaa)
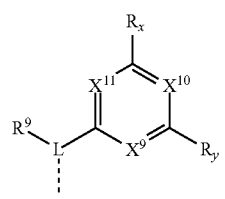
| | Y | | R⁹ | R' |
|---|---|---|---|---|
| Iaaa-171 | S | 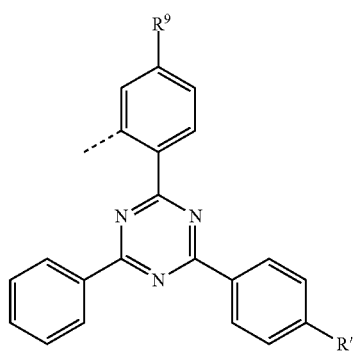 | 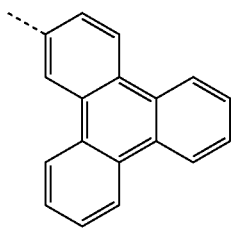 | 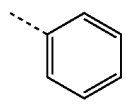 |
| Iaaa-172 | S | 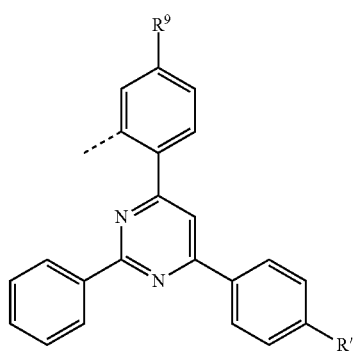 | 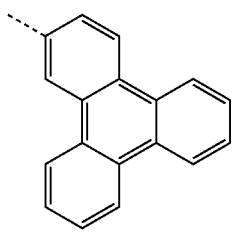 | 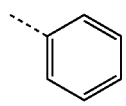 |
| Iaaa-173 | S | 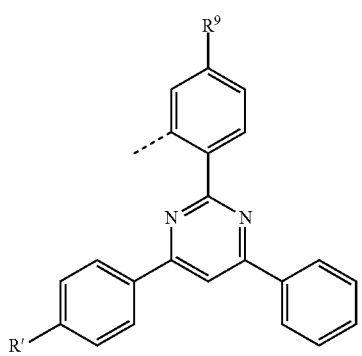 | 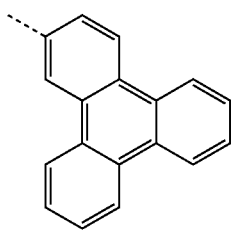 | 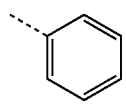 |

-continued
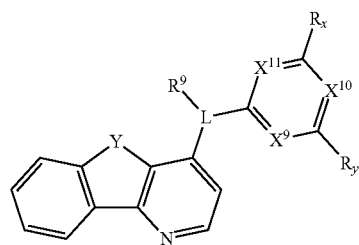
(Iaaa)
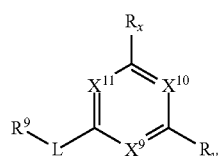
| | Y | | R⁹ | R' |
|---|---|---|---|---|
| Iaaa-174 | S | 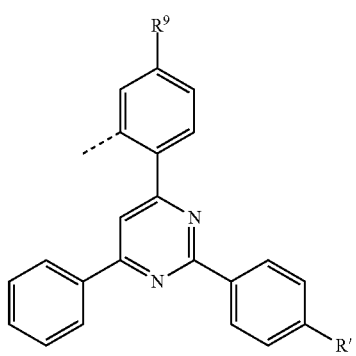 | 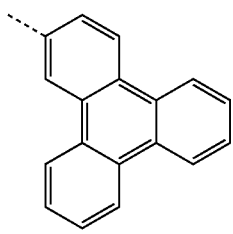 | 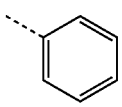 |
| Iaaa-175 | S | 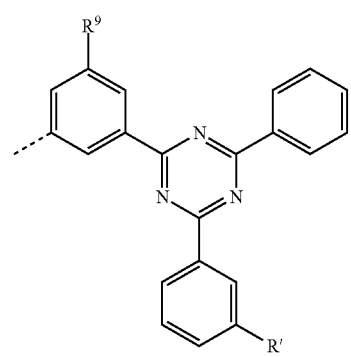 | 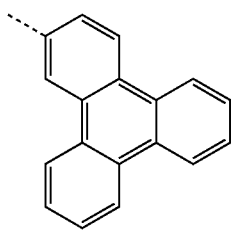 | 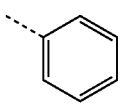 |
| Iaaa-176 | S | 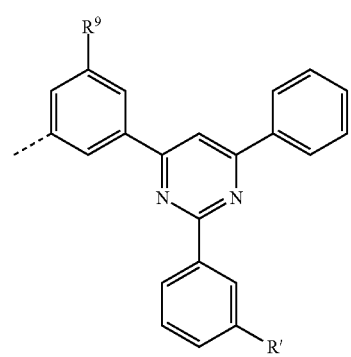 | 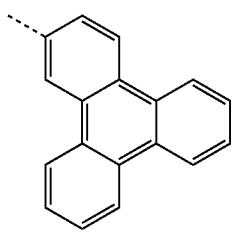 | 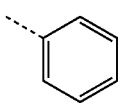 |

-continued
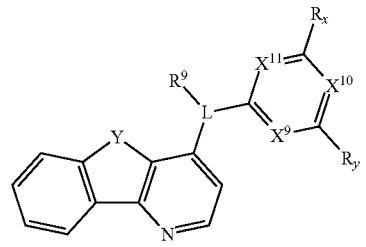
(Iaaa)
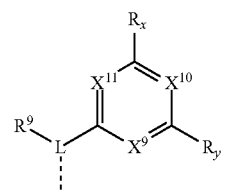
| | Y | | R⁹ | R' |
|---|---|---|---|---|
| Iaaa-177 | S | 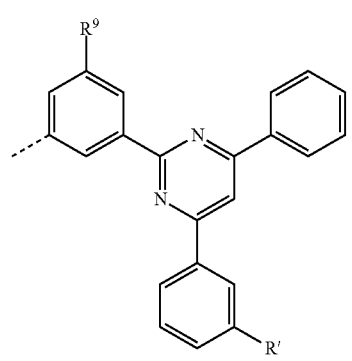 | 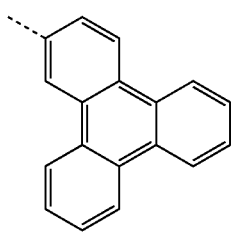 | 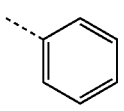 |
| Iaaa-178 | S | 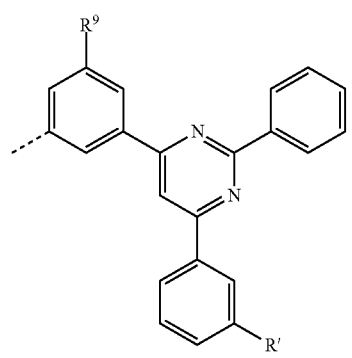 | 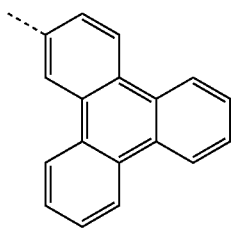 | 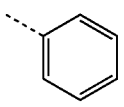 |
| Iaaa-179 | S | 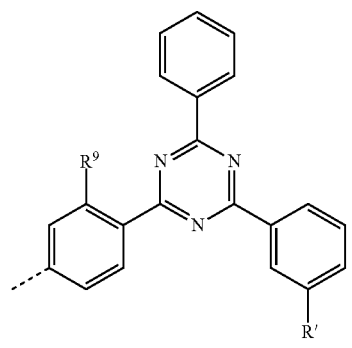 | 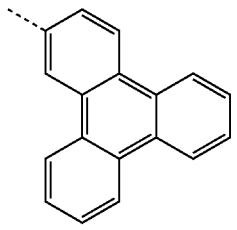 | 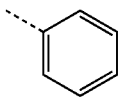 |

-continued
(Iaaa)
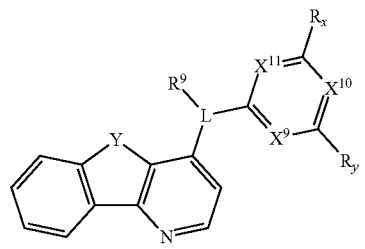
| | Y | | R⁹ | R' |
|---|---|---|---|---|
| Iaaa-180 | S | 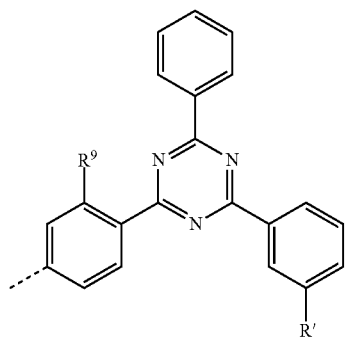 |  | 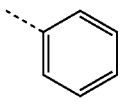 |
| Iaaa-181 | S | 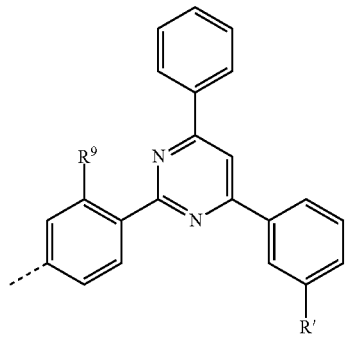 | 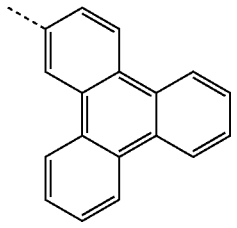 |  |
| Iaaa-182 | S | 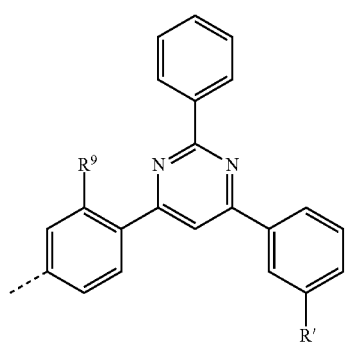 | 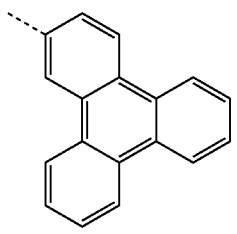 | 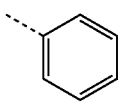 |

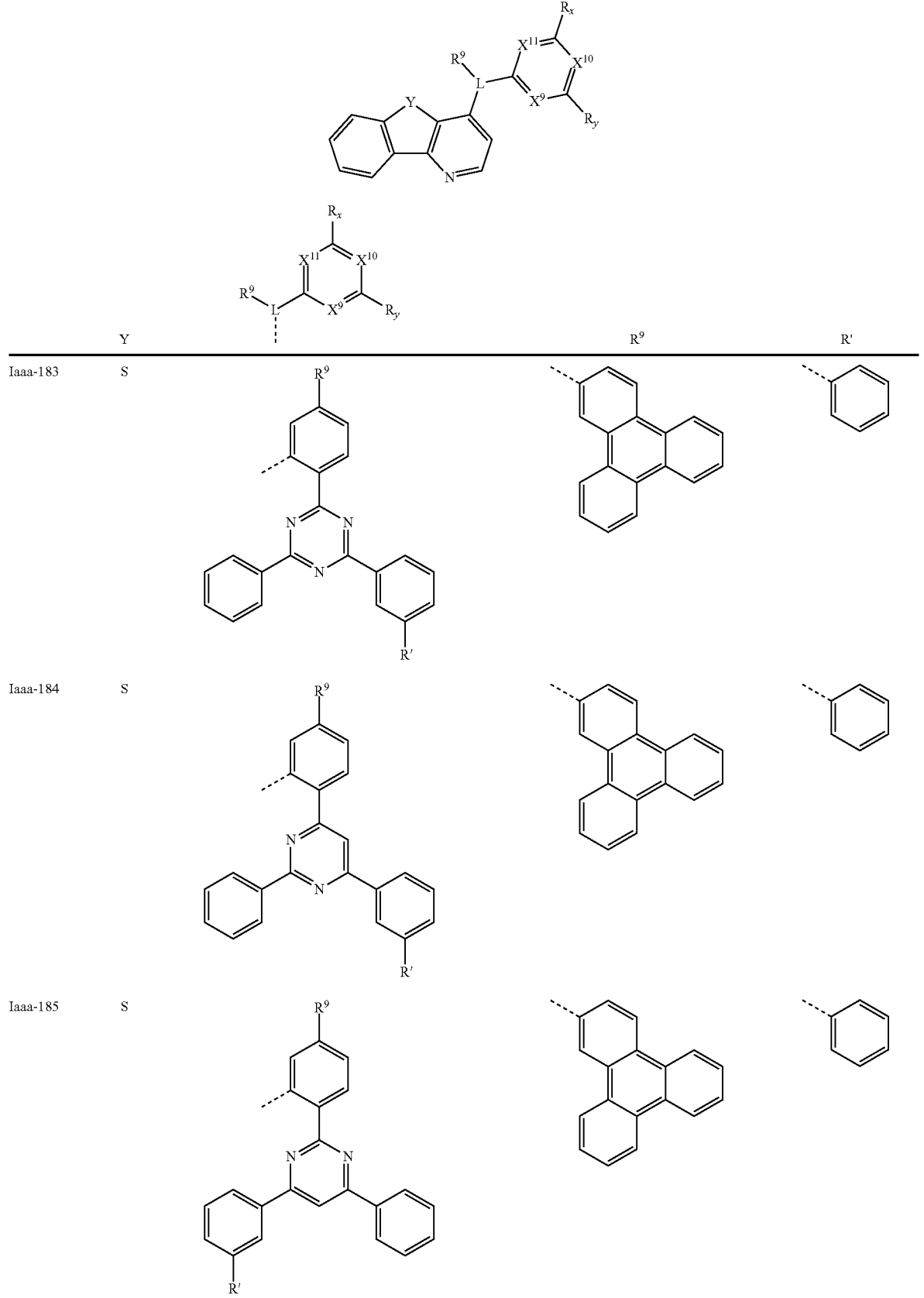

-continued
(Iaaa)
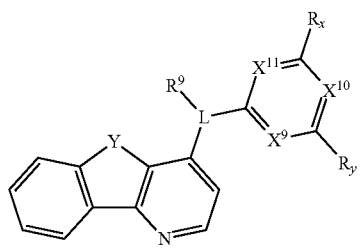
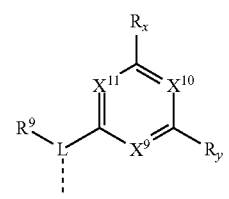
| | Y | R⁹ | R' |
|---|---|---|---|
| Iaaa-186 | S | 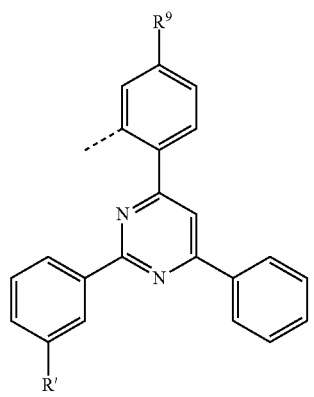 |  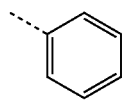 |
| Iaaa-187 | S |  |  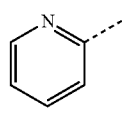 |

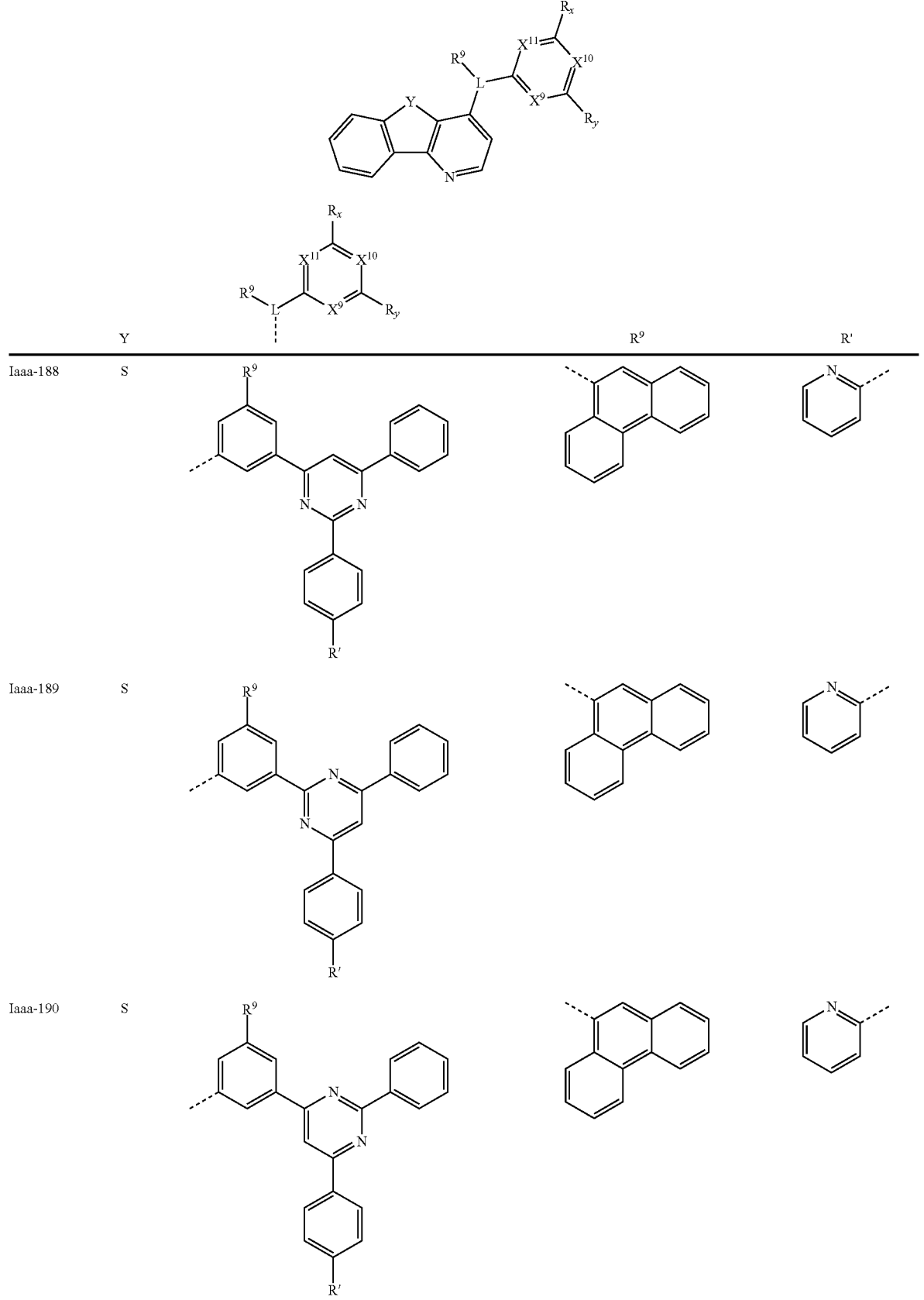

-continued
(Iaaa)
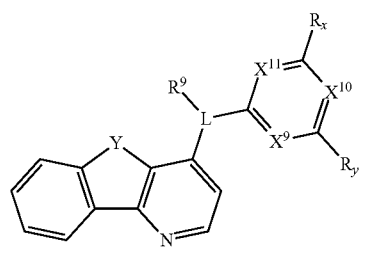
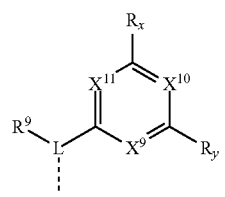
| | Y | R⁹ | R' |
|---|---|---|---|
| Iaaa-191 | S | 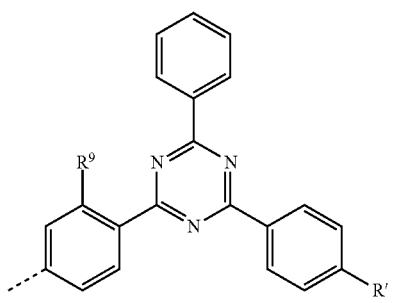 | 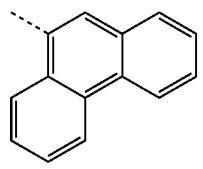 | 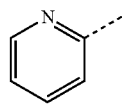 |
| Iaaa-192 | S | 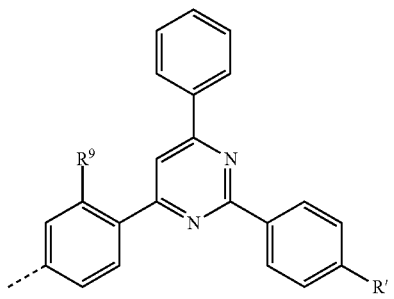 | 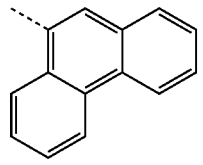 |  |
| Iaaa-193 | S | 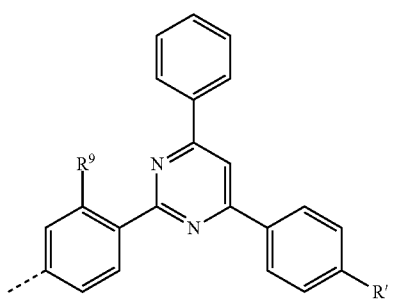 | 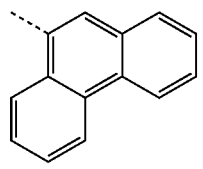 |  |

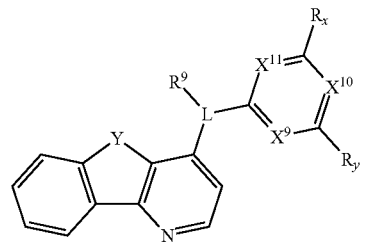
(Iaaa)
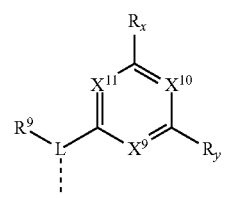
| | Y | | R⁹ | R' |
|---|---|---|---|---|
| Iaaa-194 | S | 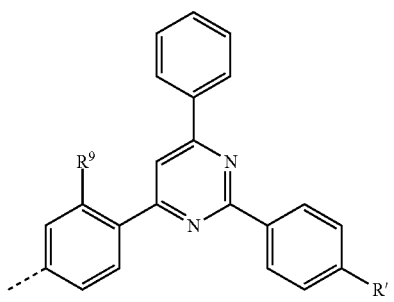 | 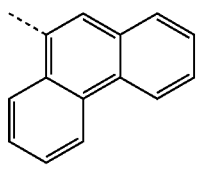 | 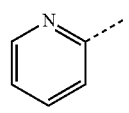 |
| Iaaa-195 | S | 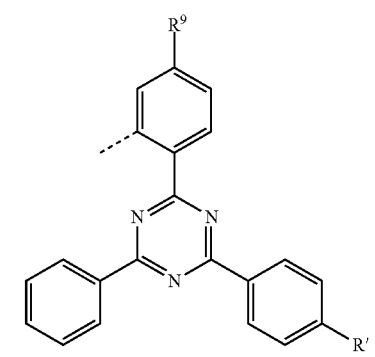 | 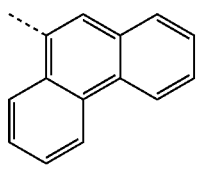 | 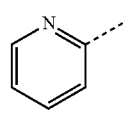 |
| Iaaa-196 | S | 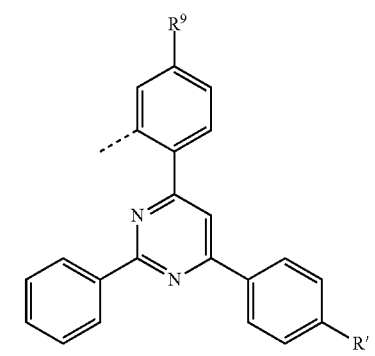 | 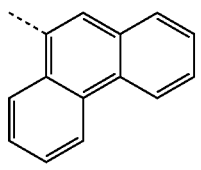 | 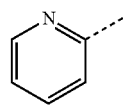 |

-continued
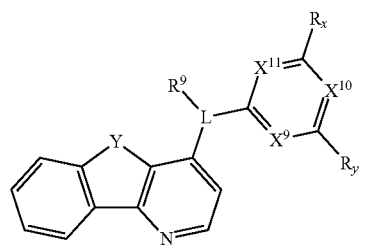
(Iaaa)
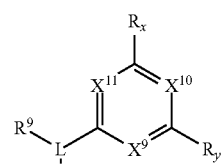
| | Y | | R⁹ | R' |
|---|---|---|---|---|
| Iaaa-197 | S | 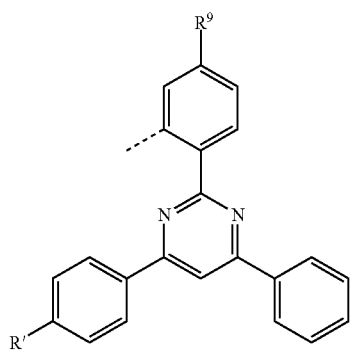 | 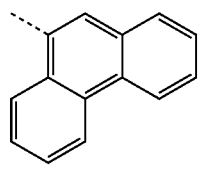 | 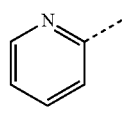 |
| Iaaa-198 | S | 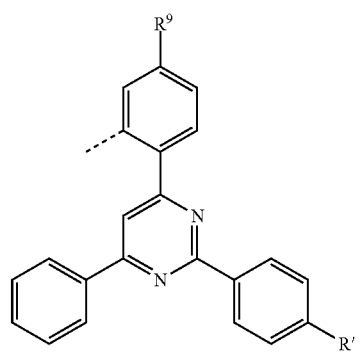 | 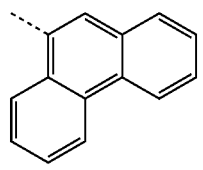 | 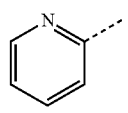 |
| Iaaa-199 | S | 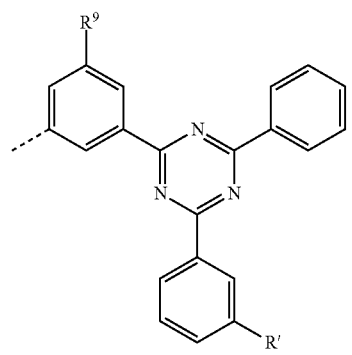 | 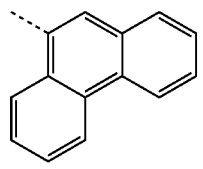 |  |

-continued
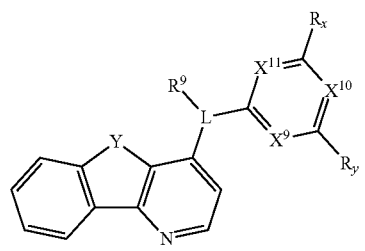
(Iaaa)

| | Y | | R⁹ | R' |
|---|---|---|---|---|
| Iaaa-200 | S | 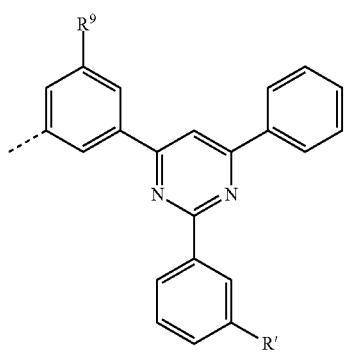 | 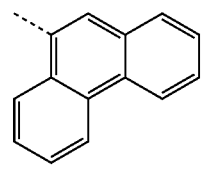 | 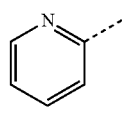 |
| Iaaa-201 | S | 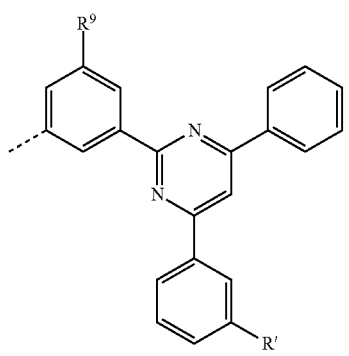 | 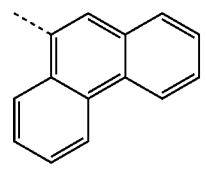 | 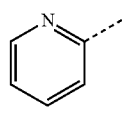 |
| Iaaa-202 | S | 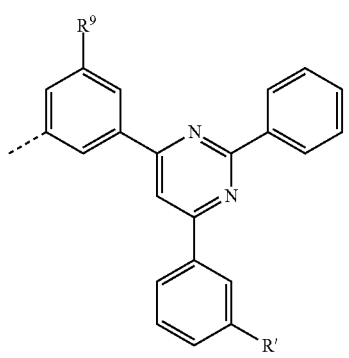 | 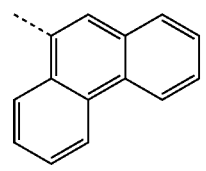 | 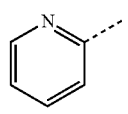 |

-continued
(Iaaa)
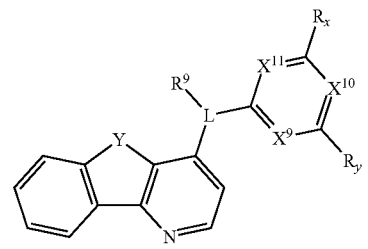
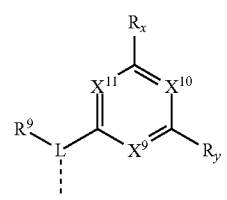
| | Y | | R⁹ | R' |
|---|---|---|---|---|
| Iaaa-203 | S | 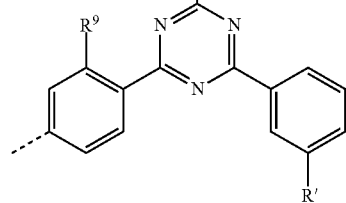 |  | 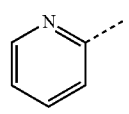 |
| Iaaa-204 | S | 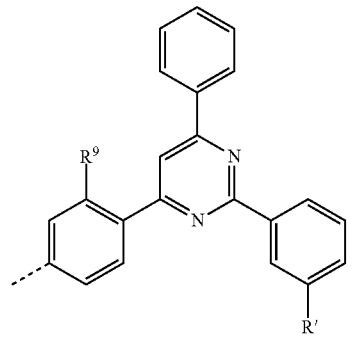 |  | 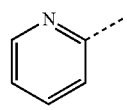 |
| Iaaa-205 | S | 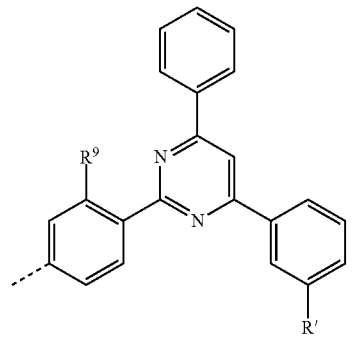 |  | 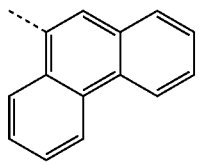 |

-continued
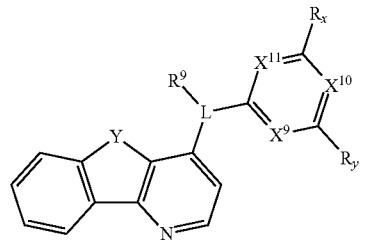
(Iaaa)
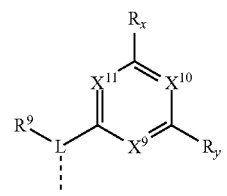
| | Y | | R⁹ | R' |
|---|---|---|---|---|
| Iaaa-206 | S |  | 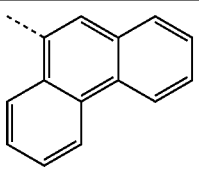 | 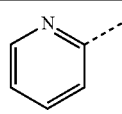 |
| Iaaa-207 | S |  | 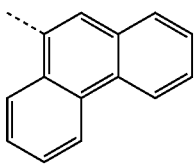 | 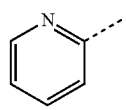 |
| Iaaa-208 | S | 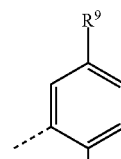 | 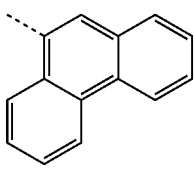 | 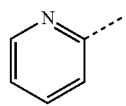 |

-continued
(Iaaa)
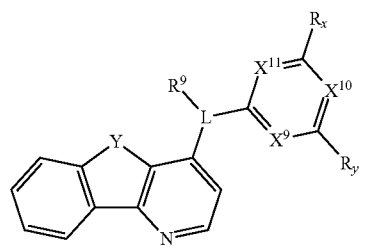
| | Y | | R⁹ | R' |
|---|---|---|---|---|
| Iaaa-209 | S | 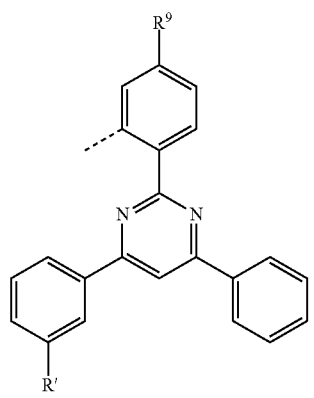 | 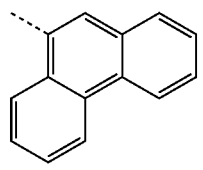 | 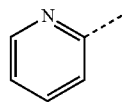 |
| Iaaa-210 | S | 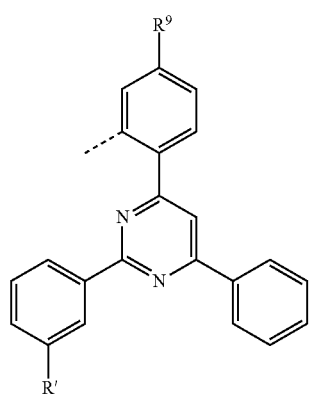 | 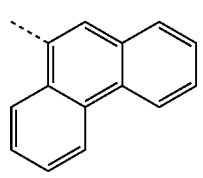 | 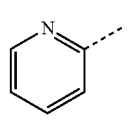 |

-continued

(Iaaa)
| | Y | | R⁹ | R' |
|---|---|---|---|---|
| Iaaa-211 | | | | |
| Iaaa-212 | | | | |
| Iaaa-213 | | | | |
| Iaaa-214 | S | 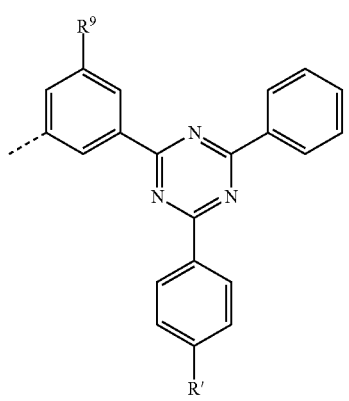 | 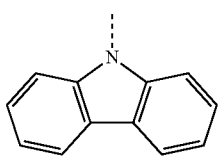 | 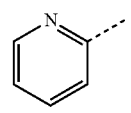 |
| Iaaa-215 | S | 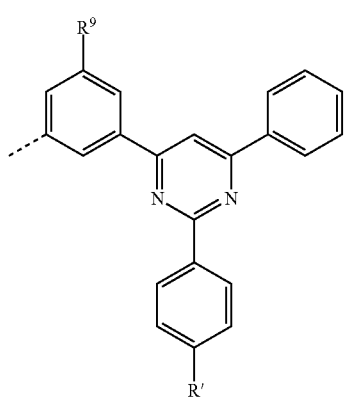 | 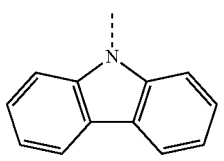 | 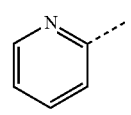 |

-continued
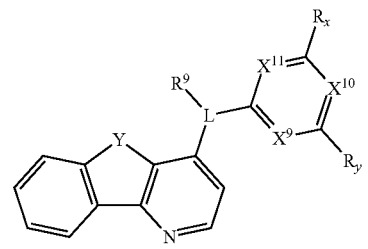
(Iaaa)
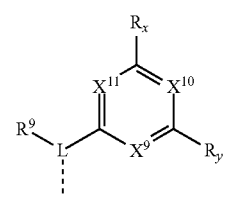
| | Y | | R⁹ | R' |
|---|---|---|---|---|
| Iaaa-216 | S | 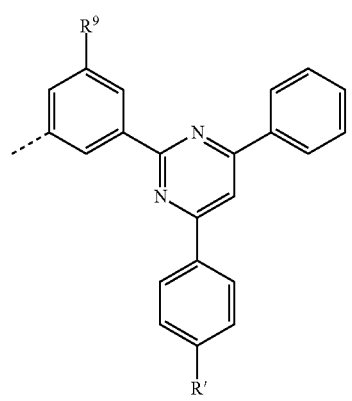 | 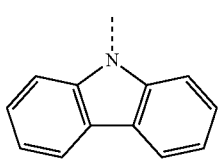 | 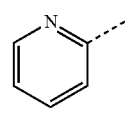 |
| Iaaa-217 | S | 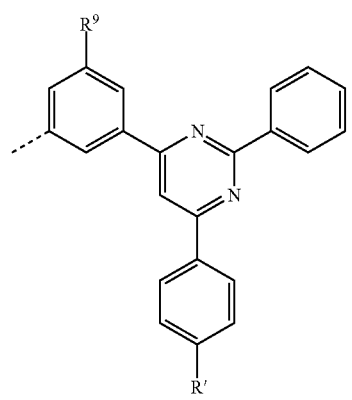 | 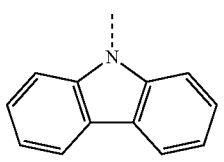 | 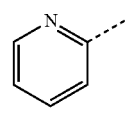 |
| Iaaa-218 | S | 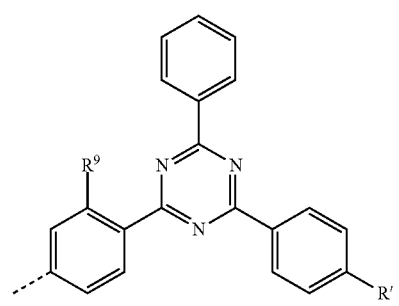 | 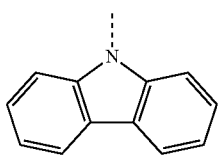 | 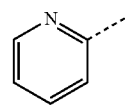 |

-continued
(Iaaa)
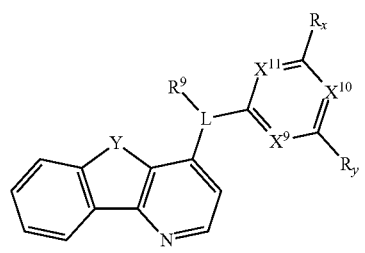
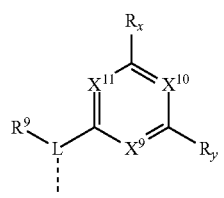
| | Y | R⁹ | R' |
|---|---|---|---|
| Iaaa-219 | S | 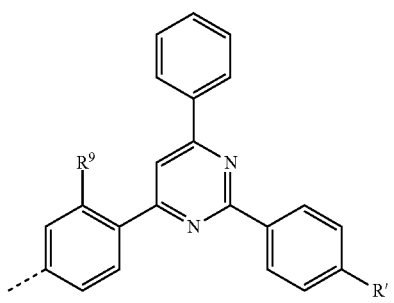 | 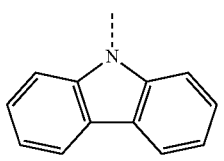 | 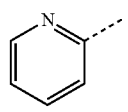 |
| Iaaa-220 | S | 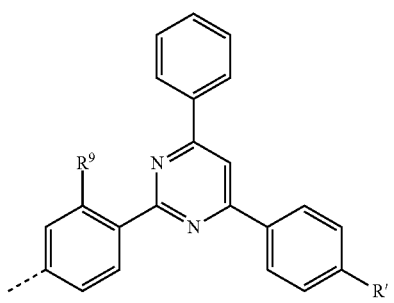 | 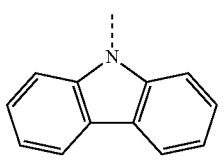 | 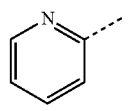 |
| Iaaa-221 | S | 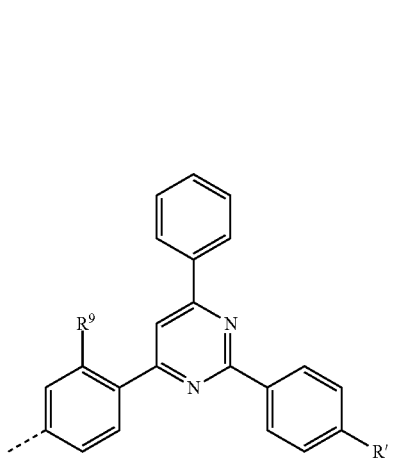 | 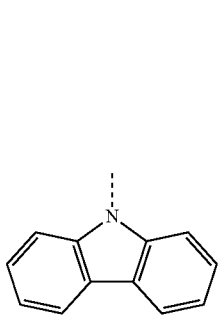 | 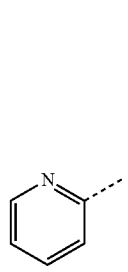 |

-continued
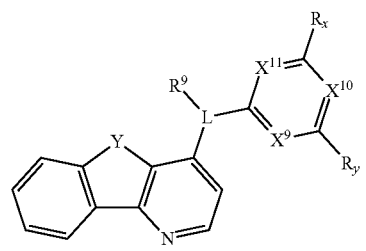
(Iaaa)
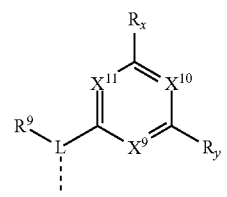
| | Y | | R⁹ | R' |
|---|---|---|---|---|
| Iaaa-222 | S | 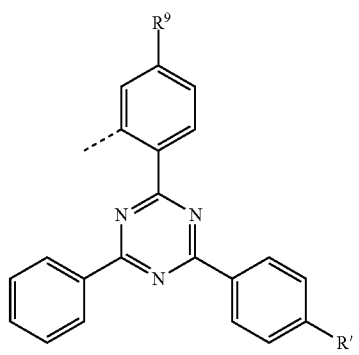 | 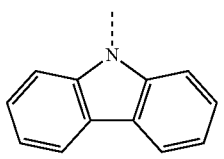 | 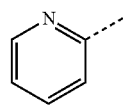 |
| Iaaa-223 | S | 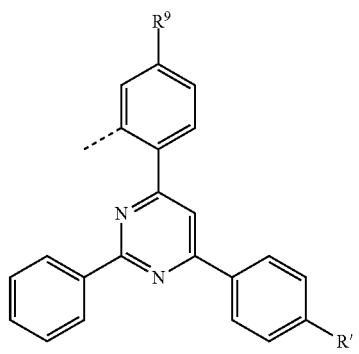 | 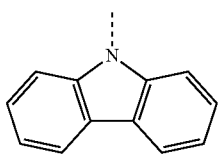 |  |
| Iaaa-224 | S | 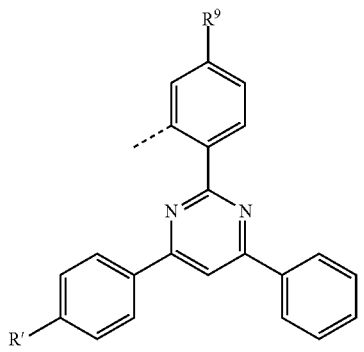 | 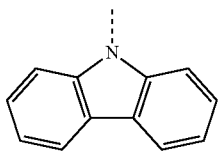 |  |

-continued
(Iaaa)
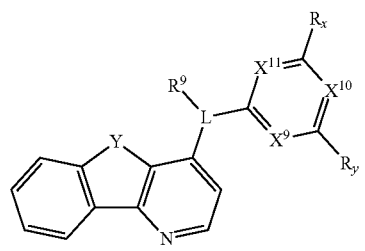
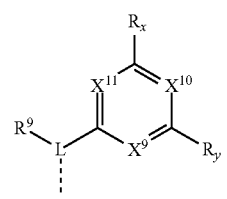
| | Y | | R⁹ | R' |
|---|---|---|---|---|
| Iaaa-225 | S | 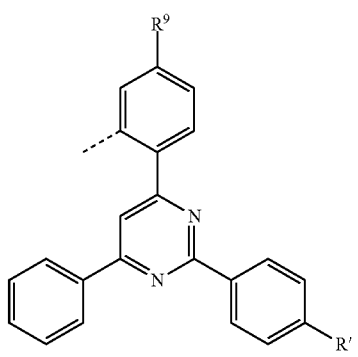 | 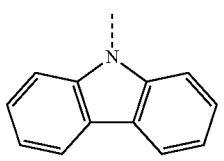 | 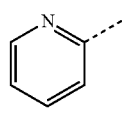 |
| Iaaa-226 | S | 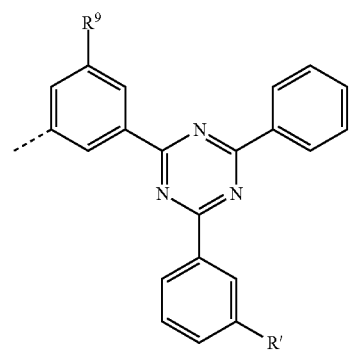 | 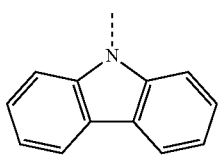 | 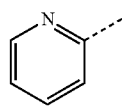 |
| Iaaa-227 | S | 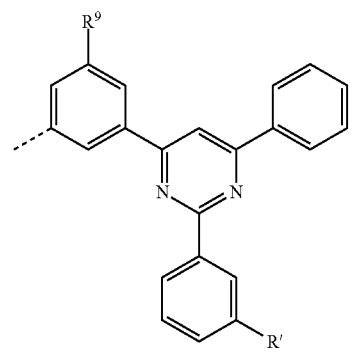 | 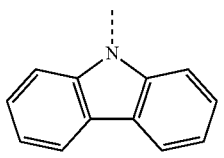 | 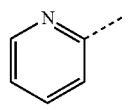 |

-continued
(Iaaa)
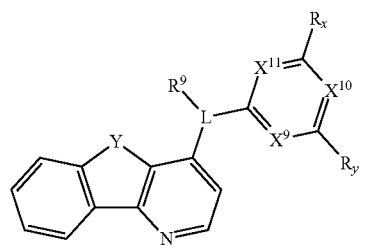
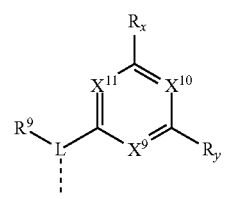
| | Y | | R⁹ | R' |
|---|---|---|---|---|
| Iaaa-228 | S | 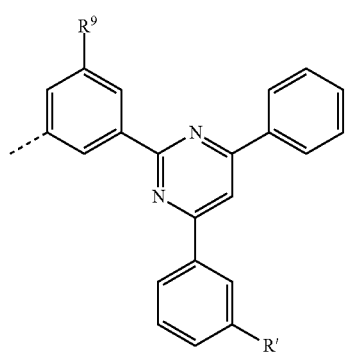 | 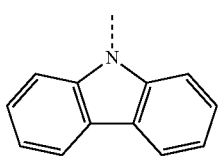 | 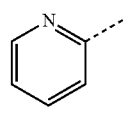 |
| Iaaa-229 | S | 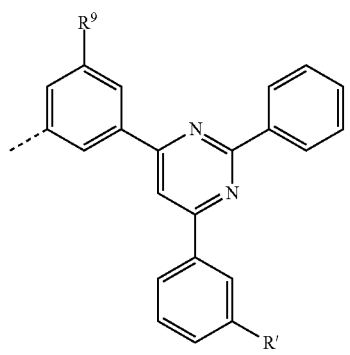 | 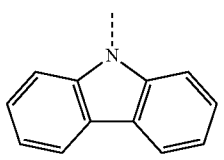 | 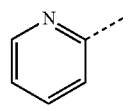 |
| Iaaa-230 | S | 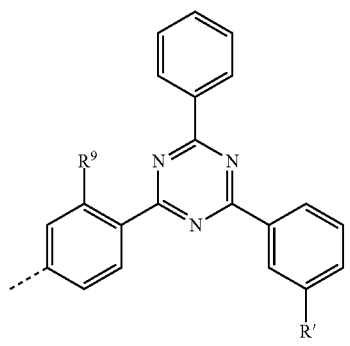 | 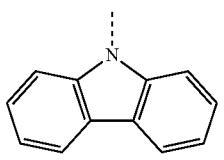 | 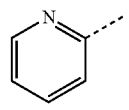 |

-continued
(Iaaa)
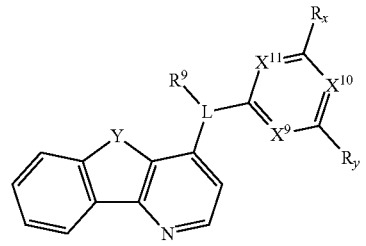
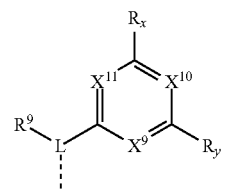
| | Y | | R⁹ | R' |
|---|---|---|---|---|
| Iaaa-231 | S | 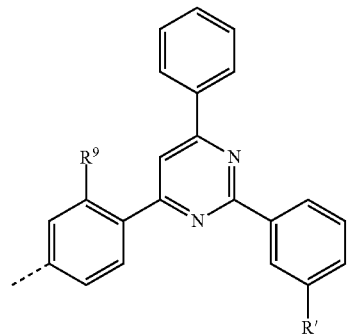 | 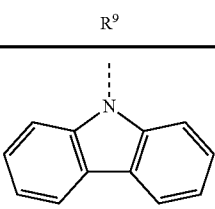 | 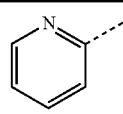 |
| Iaaa-232 | S | 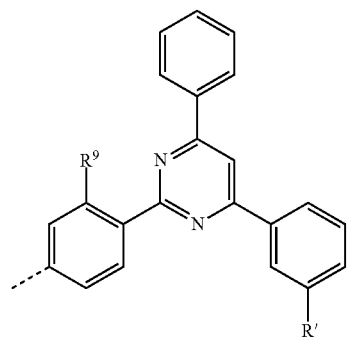 | 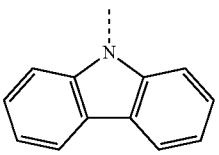 | 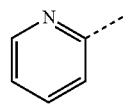 |
| Iaaa-233 | S | 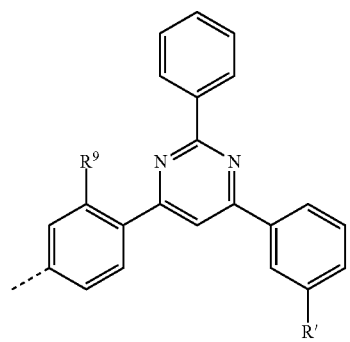 |  | 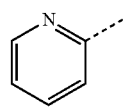 |

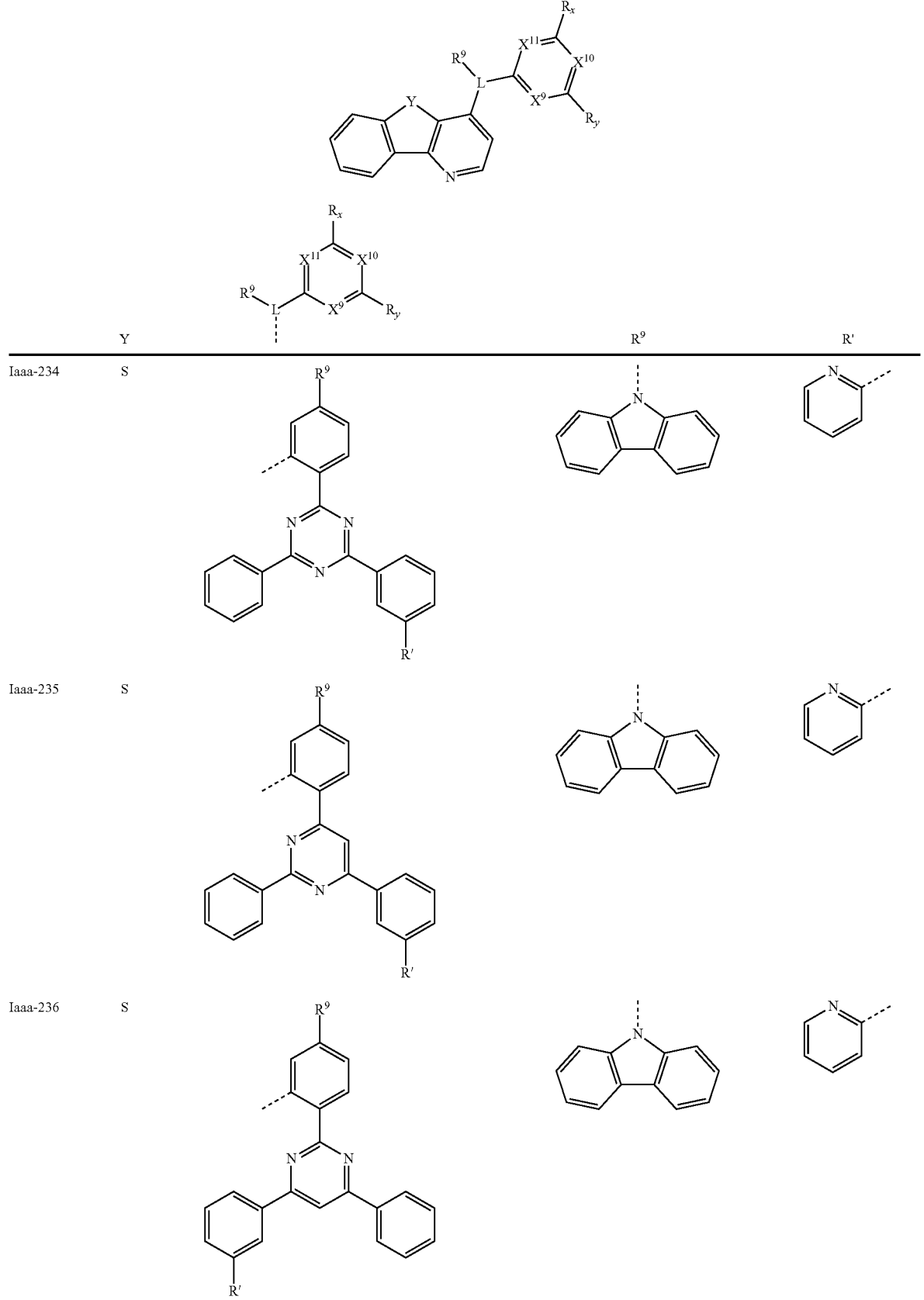

-continued
(Iaaa)
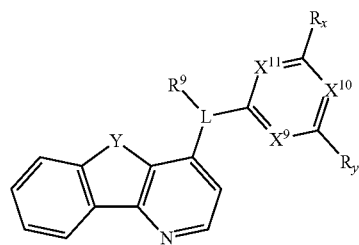
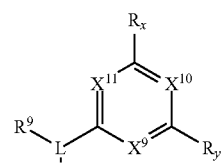
| | Y | | R⁹ | R' |
|---|---|---|---|---|
| Iaaa-237 | S | 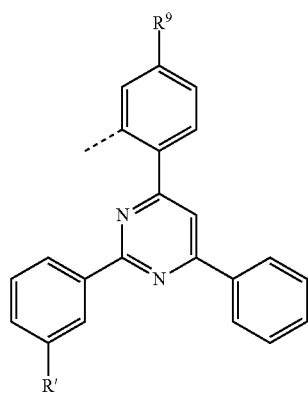 | 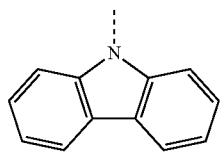 | 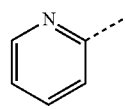 |
| Iaaa-238 | | | | |
| Iaaa-239 | | | | |
| Iaaa-240 | | | | |
| Iaaa-241 | S | 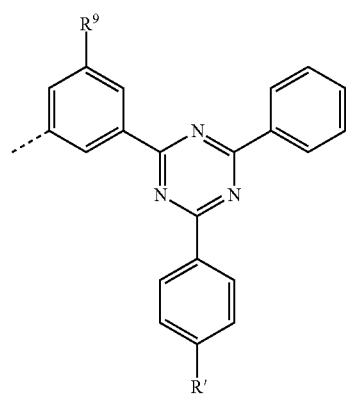 | 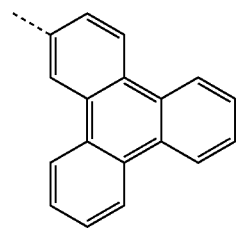 | 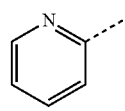 |

-continued
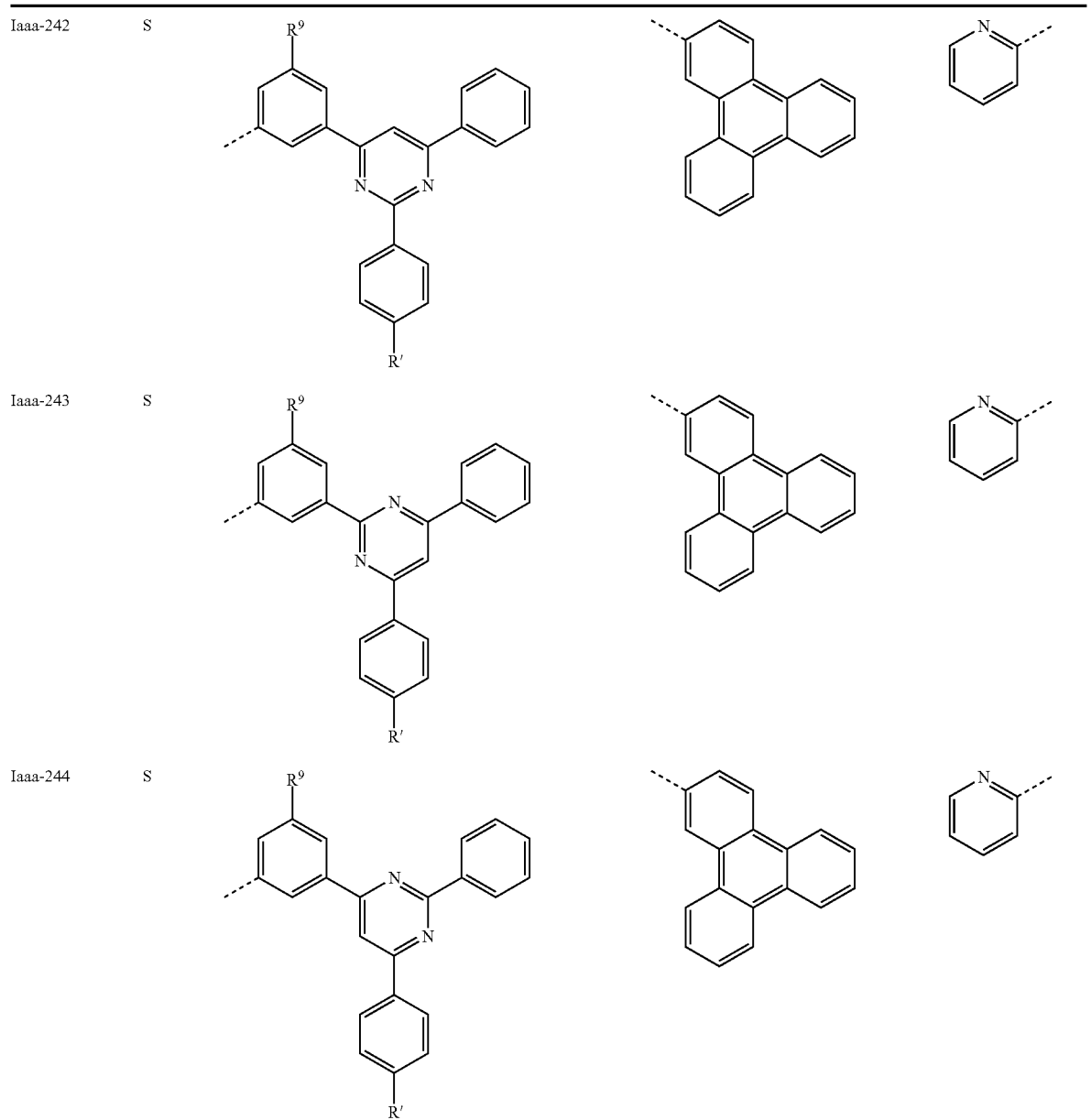

-continued
(Iaaa)
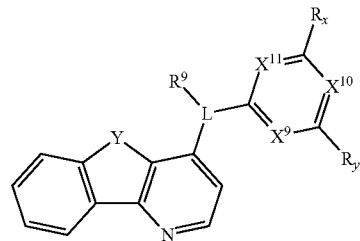
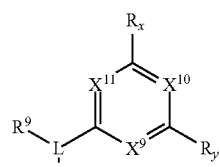
| | Y | | R⁹ | R' |
|---|---|---|---|---|
| Iaaa-245 | S | 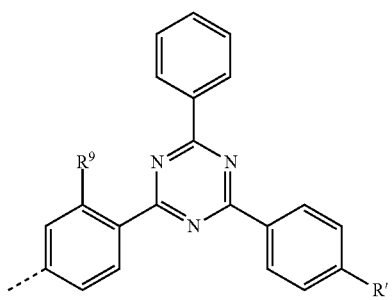 | 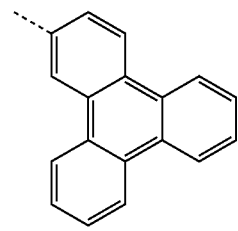 | 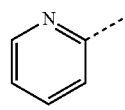 |
| Iaaa-246 | S | 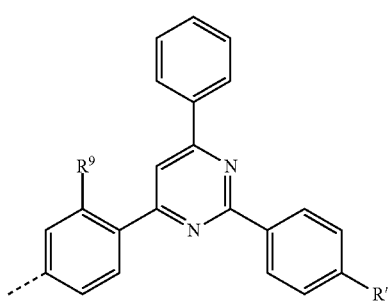 | 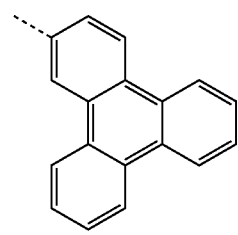 | 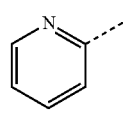 |
| Iaaa-247 | S | 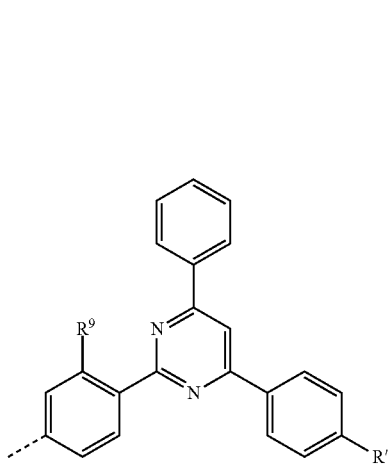 | 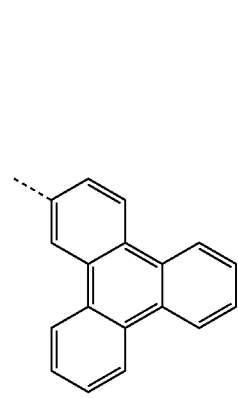 | 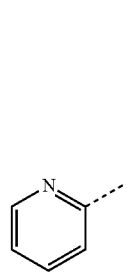 |

-continued
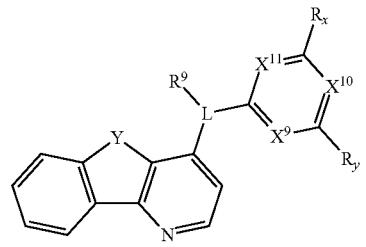
(Iaaa)
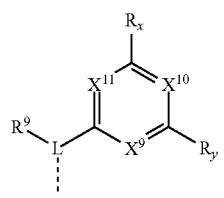
| | Y | | R⁹ | R' |
|---|---|---|---|---|
| Iaaa-248 | S | 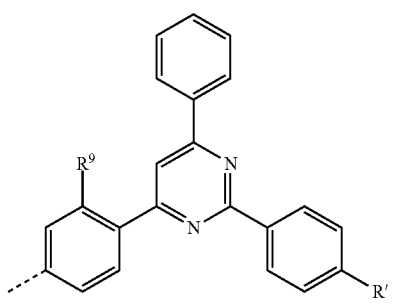 | 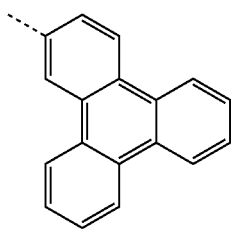 | 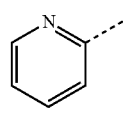 |
| Iaaa-249 | S | 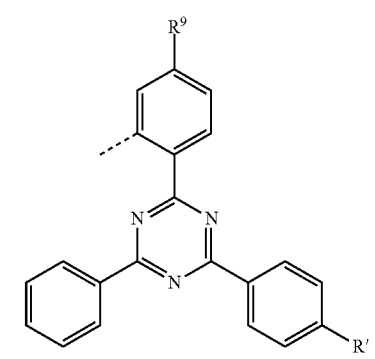 | 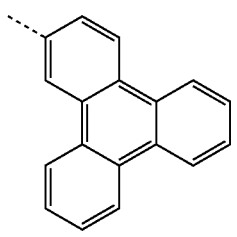 | 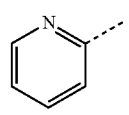 |
| Iaaa-250 | S |  |  |  |

-continued
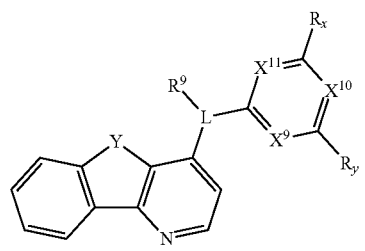
(Iaaa)
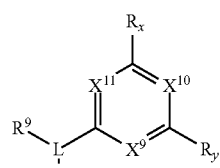
| | Y | | R⁹ | R' |
|---|---|---|---|---|
| Iaaa-251 | S | 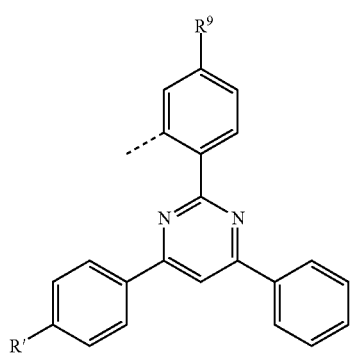 | 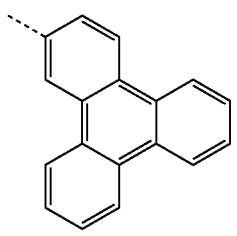 | 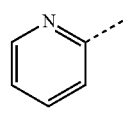 |
| Iaaa-252 | S | 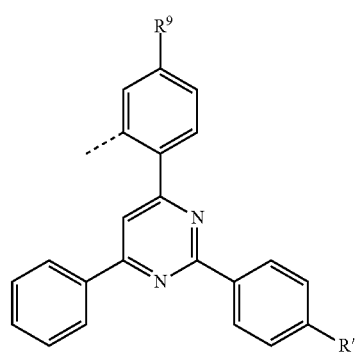 | 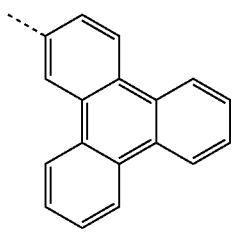 | 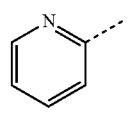 |
| Iaaa-253 | S | 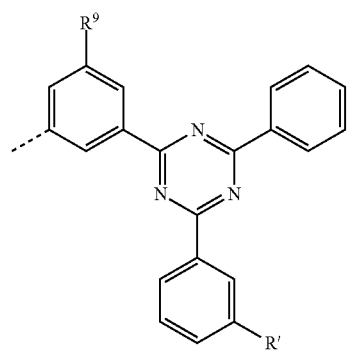 | 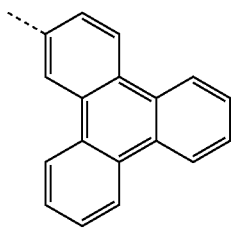 | 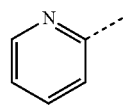 |

-continued
(Iaaa)
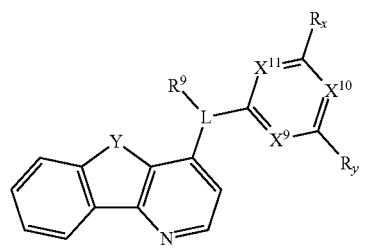
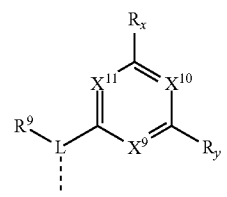
| | Y | | R⁹ | R' |
|---|---|---|---|---|
| Iaaa-254 | S | 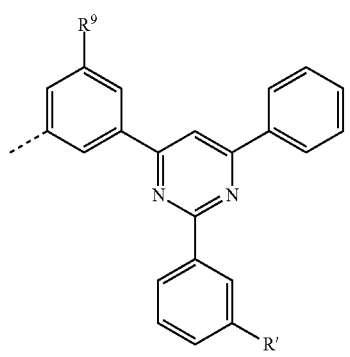 | 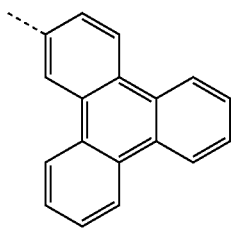 | 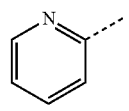 |
| Iaaa-255 | S | 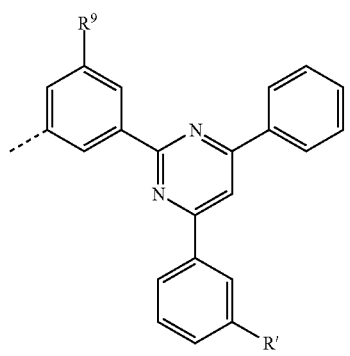 | 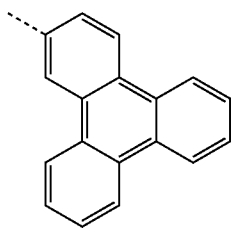 | 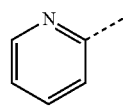 |
| Iaaa-256 | S | 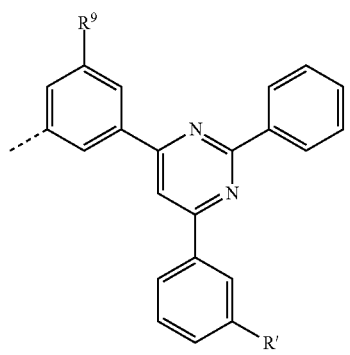 | 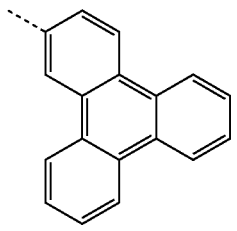 | 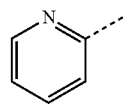 |

-continued
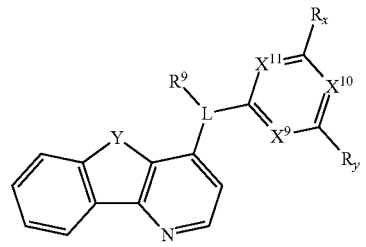
(Iaaa)
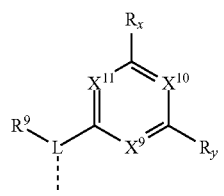
| | Y | | $R^9$ | $R'$ |
|---|---|---|---|---|
| Iaaa-257 | S | 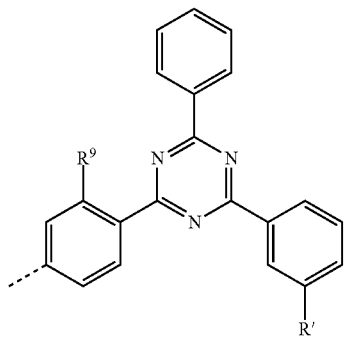 | 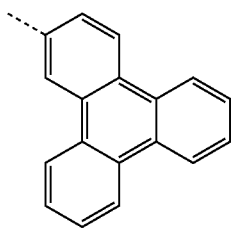 | 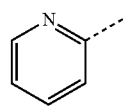 |
| Iaaa-258 | S | 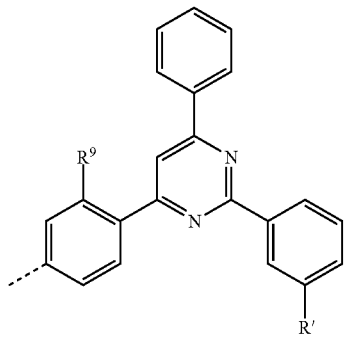 | 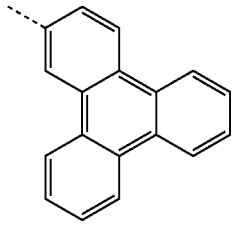 | 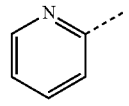 |
| Iaaa-259 | S | 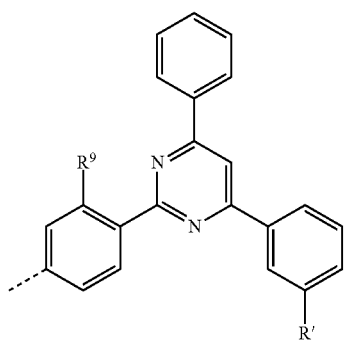 | 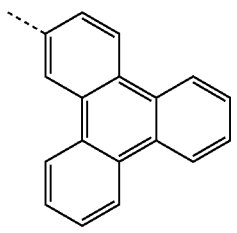 | 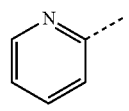 |

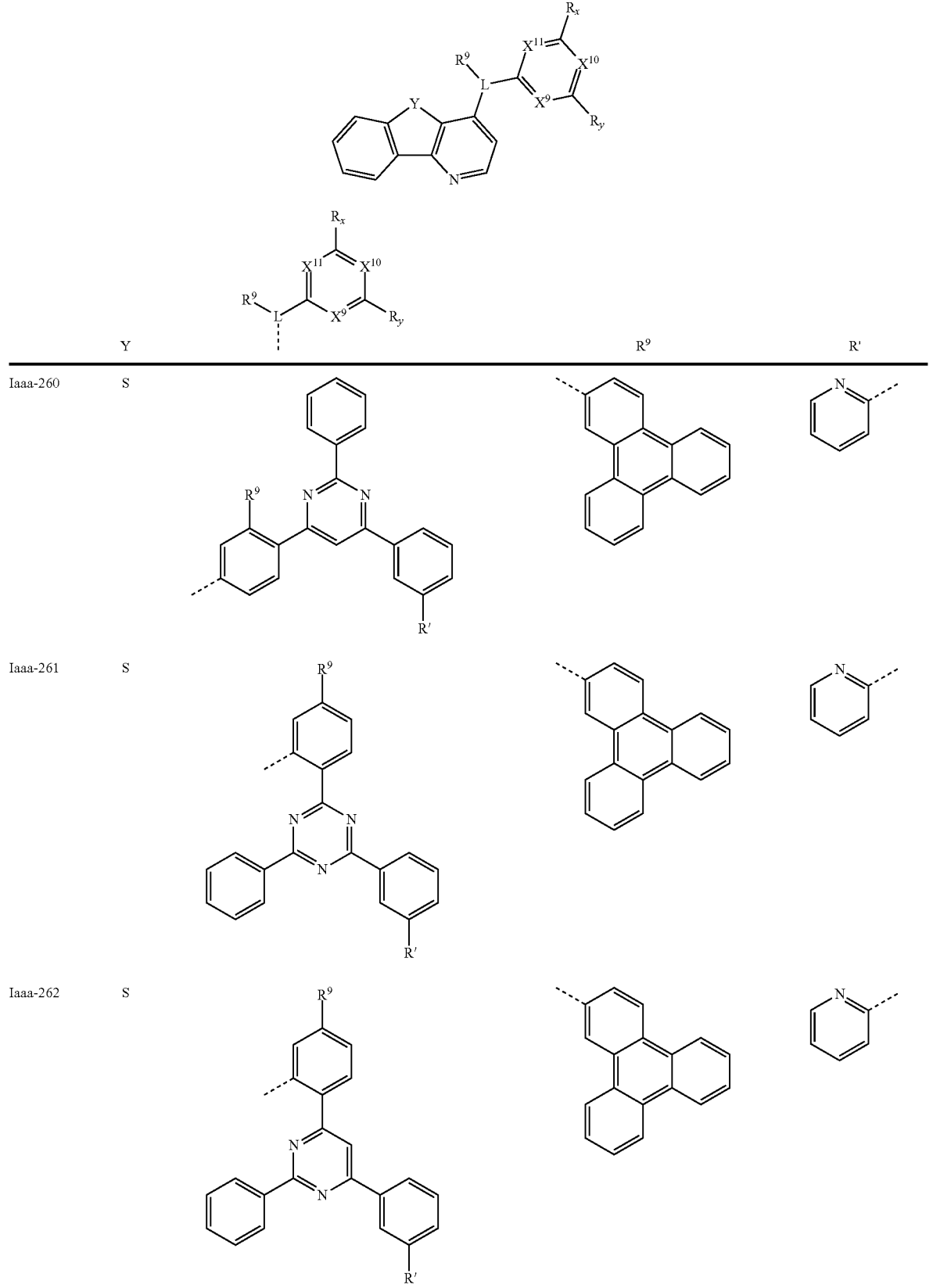

-continued
(Iaaa)
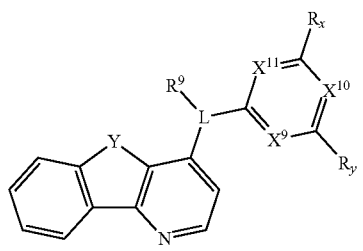
| | Y | | R⁹ | | R' |
|---|---|---|---|---|---|
| Iaaa-263 | S | 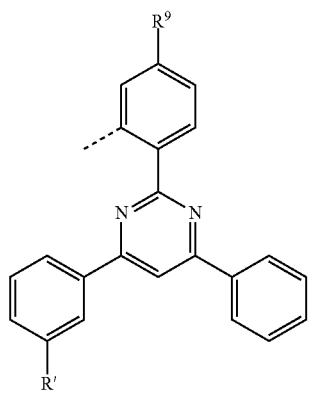 | 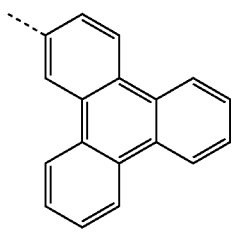 | | 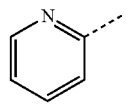 |
| Iaaa-264 | S | 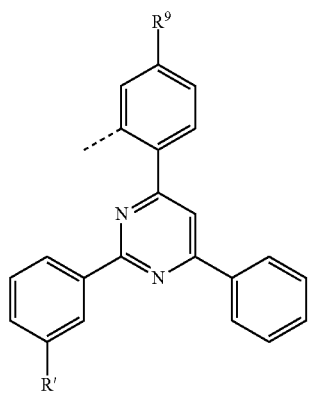 | 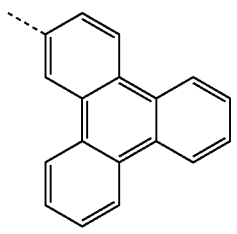 | | 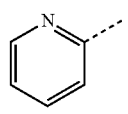 |

-continued
(Iaaa)
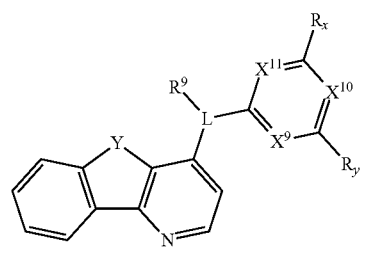
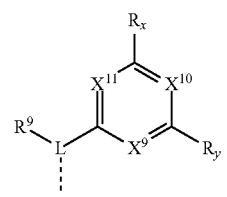
| | Y | R⁹ | R' |
|---|---|---|---|
| Iaaa-265 | | | |
| Iaaa-266 | | | |
| Iaaa-267 | | | |
| Iaaa-268 | S |  |  H |
| Iaaa-269 | S |  |  H |

-continued
(Iaaa)
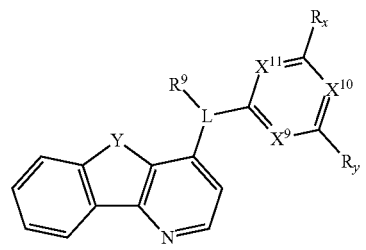
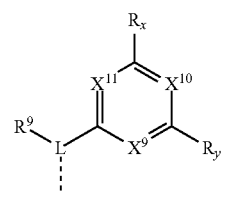
| | Y | | R⁹ | R' |
|---|---|---|---|---|
| Iaaa-270 | S | 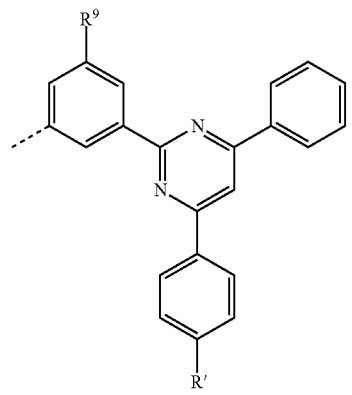 | 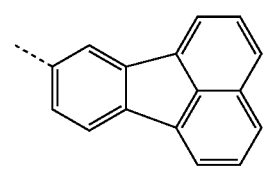 | H |
| Iaaa-271 | S | 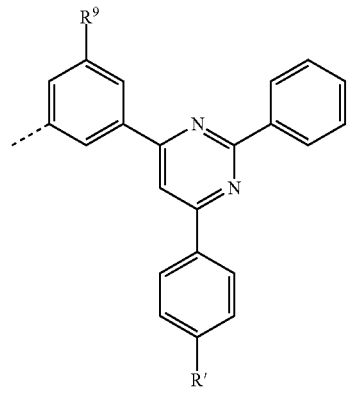 | 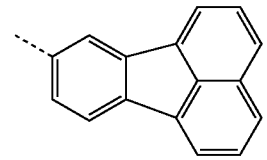 | H |
| Iaaa-272 | S | 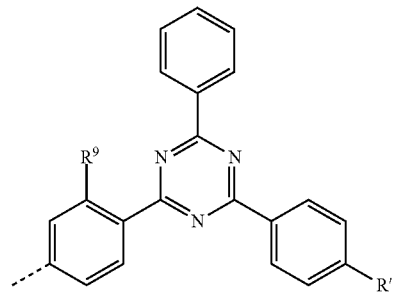 | 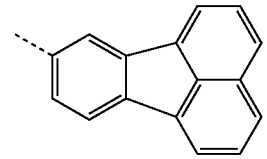 | H |

-continued
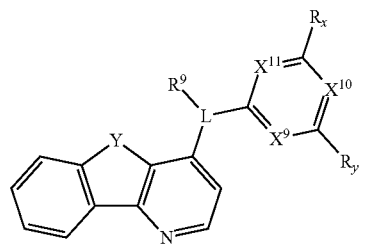
(Iaaa)
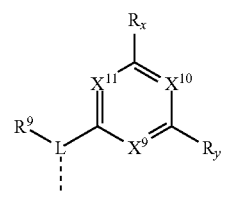
| | Y | | R⁹ | R' |
|---|---|---|---|---|
| Iaaa-273 | S | 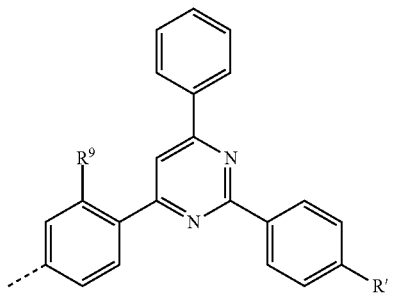 | 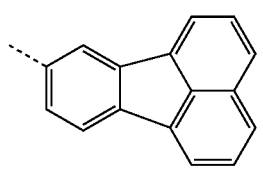 | H |
| Iaaa-274 | S | 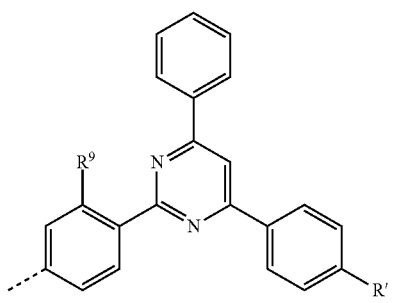 | 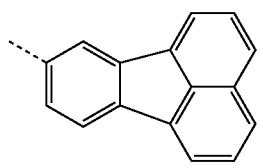 | H |
| Iaaa-275 | S | 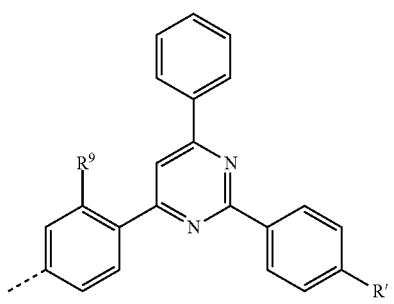 | 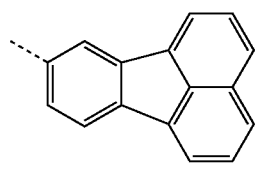 | H |

-continued
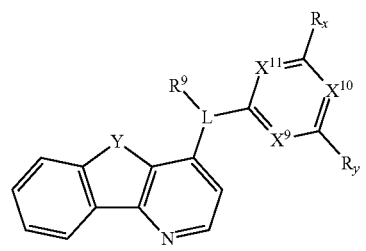
(Iaaa)
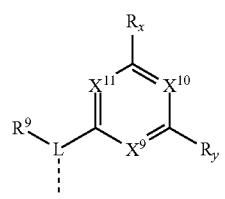
| | Y | | R⁹ | R' |
|---|---|---|---|---|
| Iaaa-276 | S | 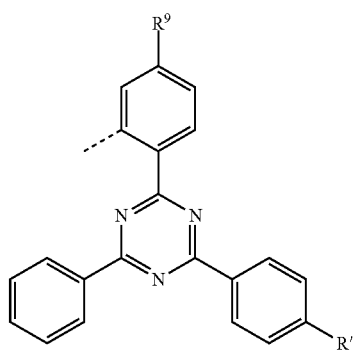 | 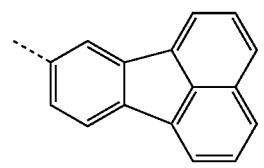 | H |
| Iaaa-277 | S | 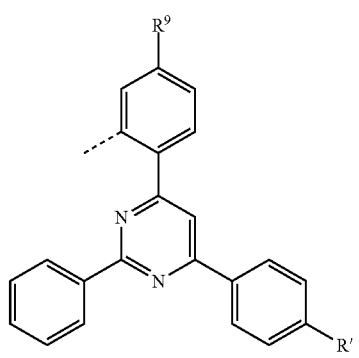 |  | H |
| Iaaa-278 | S | 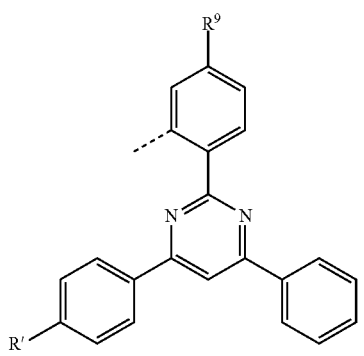 | 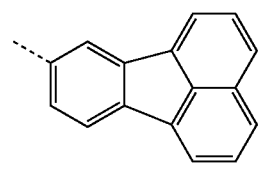 | H |

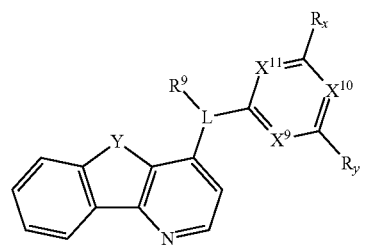
(Iaaa)
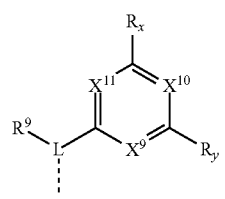
| | Y | R⁹ | | R' |
|---|---|---|---|---|
| Iaaa-279 | S | 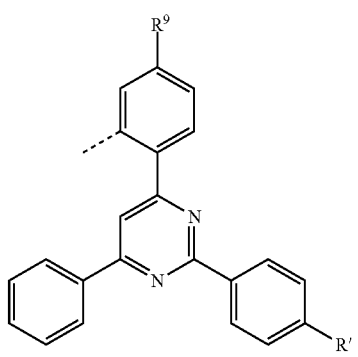 | 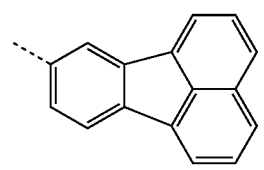 | H |
| Iaaa-280 | S | 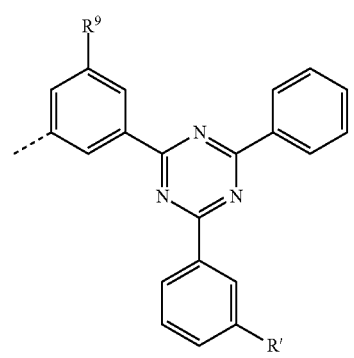 | 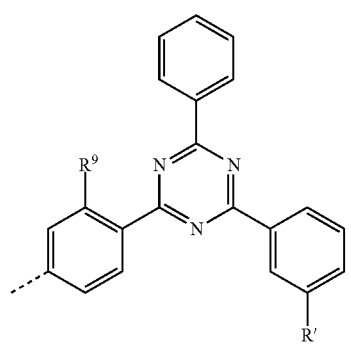 | H |
| Iaaa-281 | S | 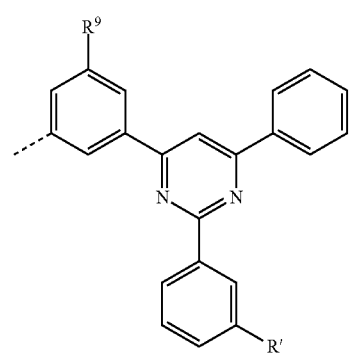 | 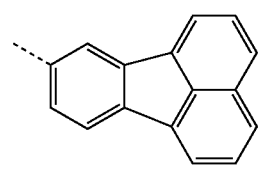 | H |

-continued
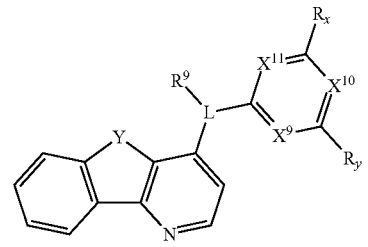
(Iaaa)
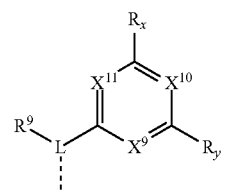
| | Y | | R⁹ | R' |
|---|---|---|---|---|
| Iaaa-282 | S | 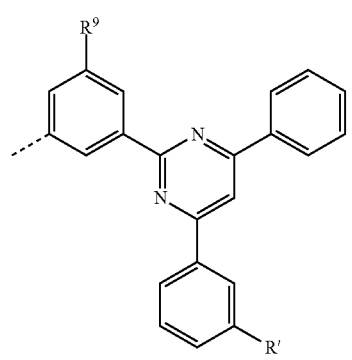 | | H |
| Iaaa-283 | S | 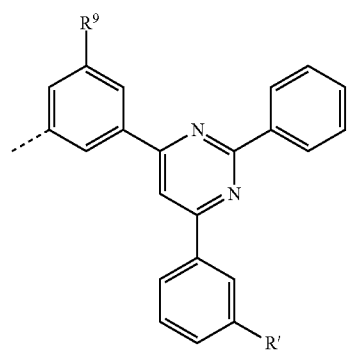 | | H |
| Iaaa-284 | S | 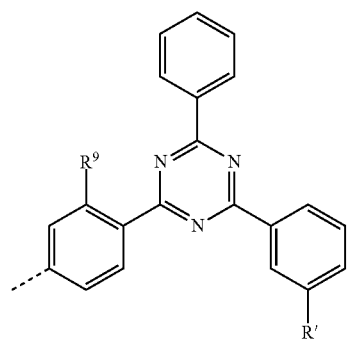 | | H |

-continued
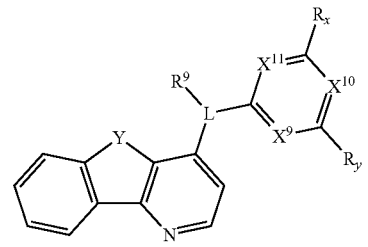
(Iaaa)
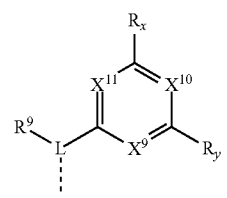
| | Y | | R⁹ | R' |
|---|---|---|---|---|
| Iaaa-285 | S | 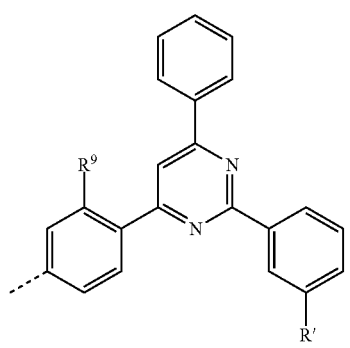 | 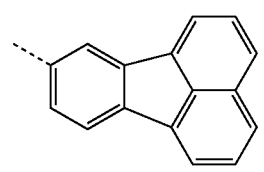 | H |
| Iaaa-286 | S | 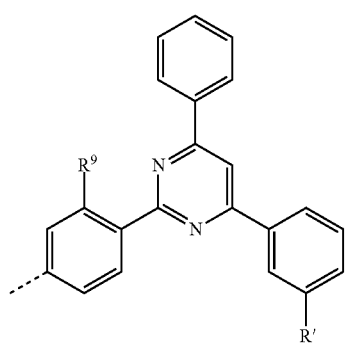 | 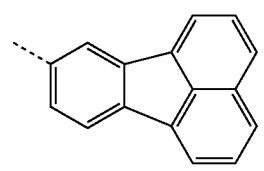 | H |
| Iaaa-287 | S | 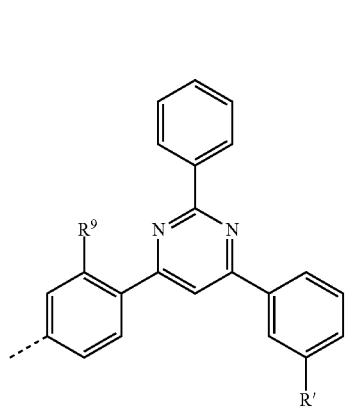 | 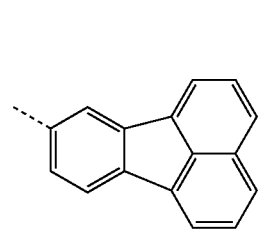 | H |

-continued
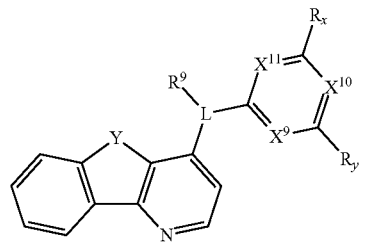
(Iaaa)
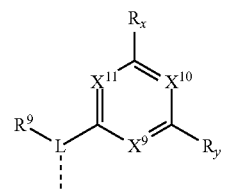
| | Y | R⁹ | R' |
|---|---|---|---|
| Iaaa-288 | S |  | 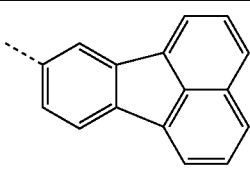 H |
| Iaaa-289 | S | 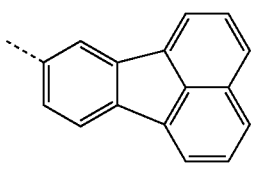 | 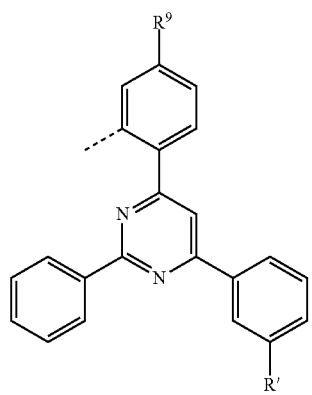 H |
| Iaaa-290 | S | 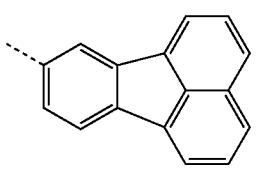 | 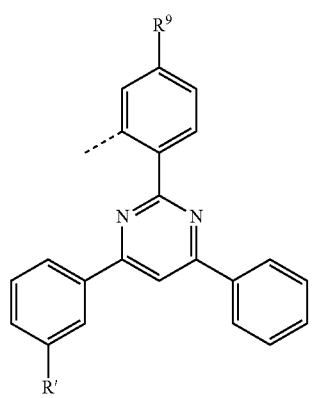 H |

-continued
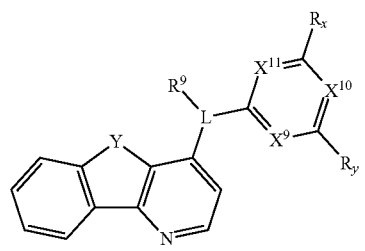
(Iaaa)
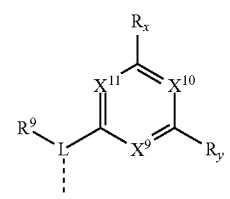
| | Y | R⁹ | | R' |
|---|---|---|---|---|
| Iaaa-291 | S | 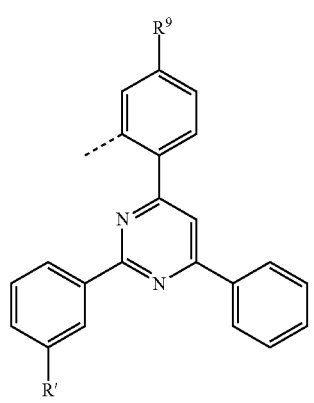 | 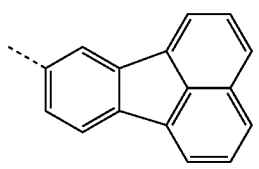 | H |
| Iaaa-292 | S | 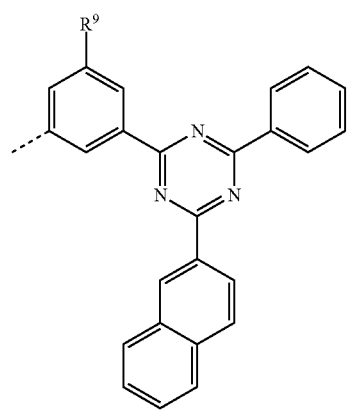 | | — |

-continued
(Iaaa)
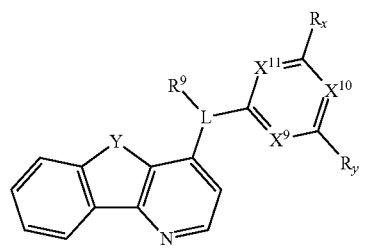
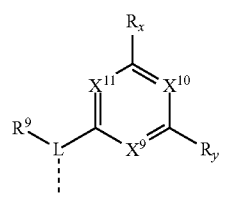
| | Y | | R⁹ | R' |
|---|---|---|---|---|
| Iaaa-293 | S | | 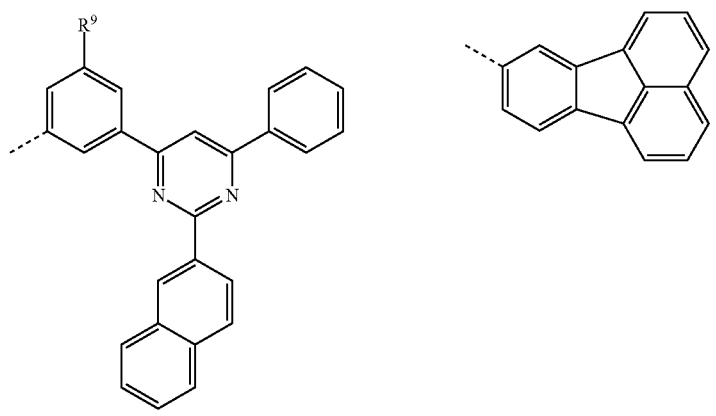 | — |
| Iaaa-294 | S | | 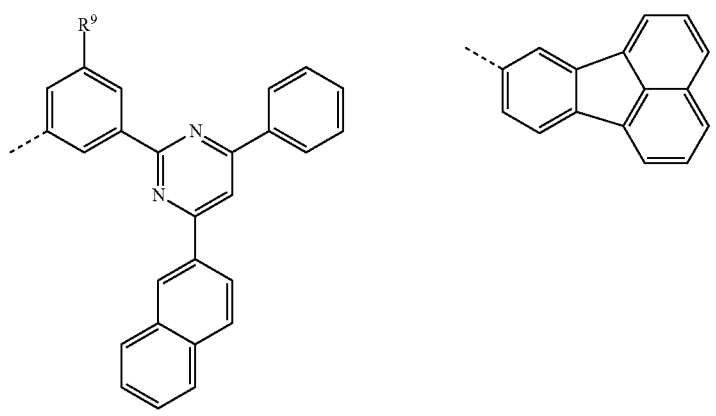 | — |

-continued
(Iaaa)
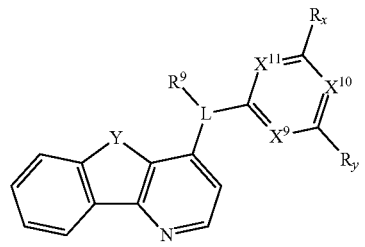
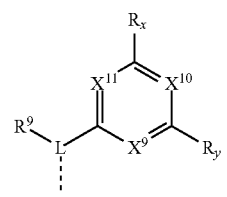
| | Y | R⁹ | | R' |
|---|---|---|---|---|
| Iaaa-295 | S | 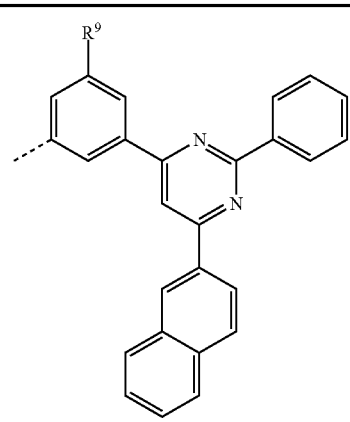 | 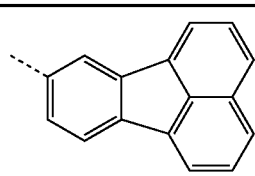 | — |
| Iaaa-296 | S | 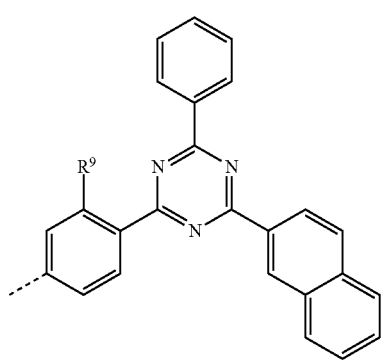 | 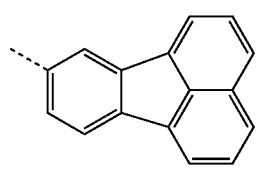 | — |
| Iaaa-297 | S | 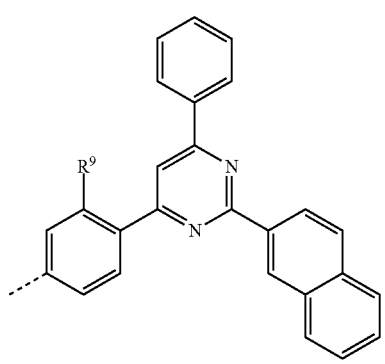 | 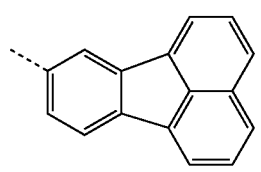 | — |

-continued
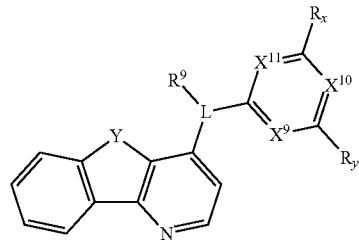
(Iaaa)
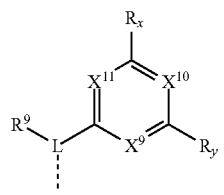
| | Y | | R⁹ | R' |
|---|---|---|---|---|
| Iaaa-298 | S | 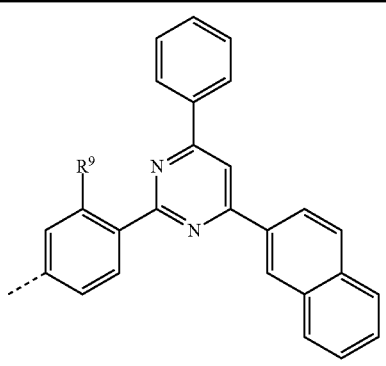 | 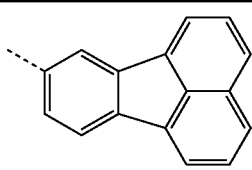 | — |
| Iaaa-299 | S | 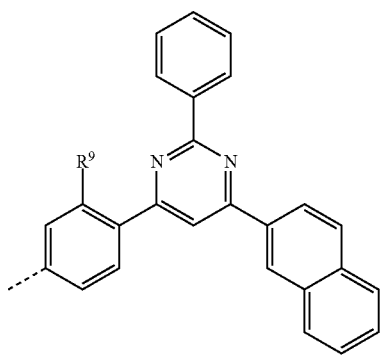 | 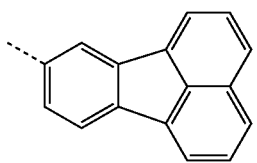 | — |
| Iaaa-300 | S | 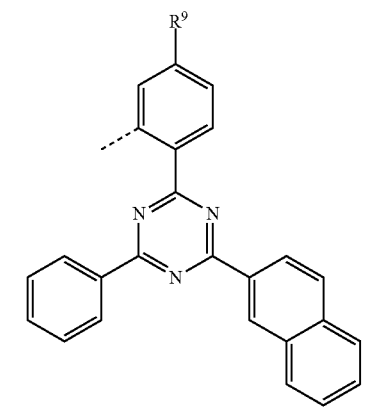 | 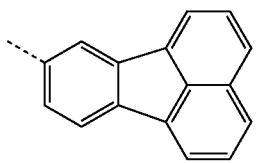 | — |

-continued
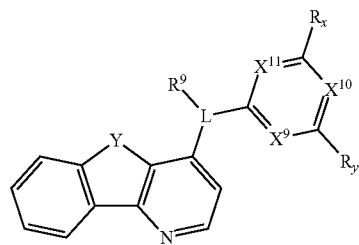
(Iaaa)
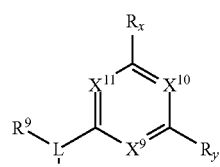
| | Y | R⁹ | R' |
|---|---|---|---|
| Iaaa-301 | S | 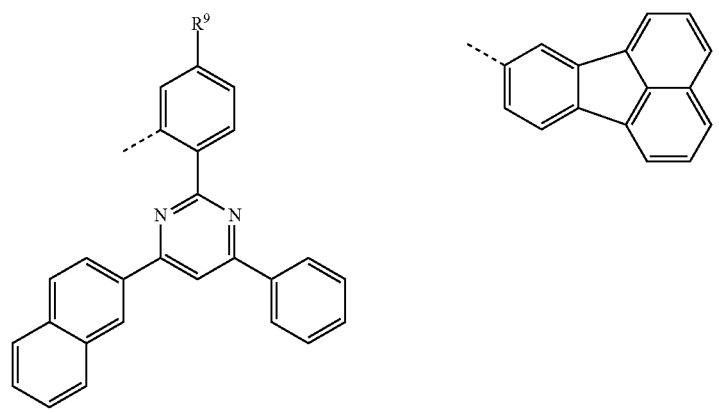 | — |
| Iaaa-302 | S | 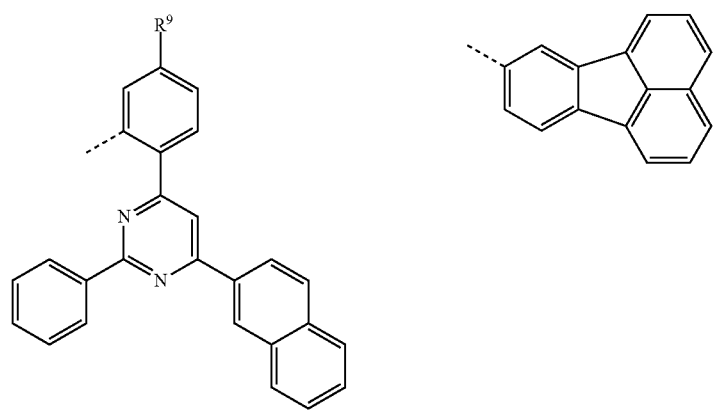 | — |

(Iaaa)
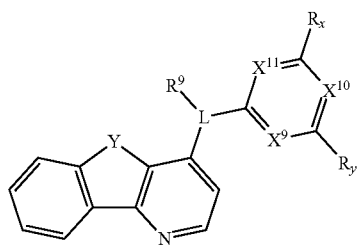
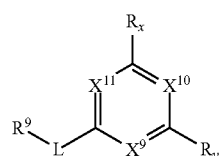
| | Y | R⁹ | R' |
|---|---|---|---|
| Iaaa-303 | S | 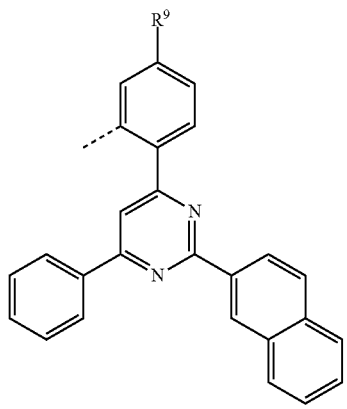 | 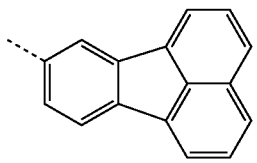 | — |
| Iaaa-304 | S | 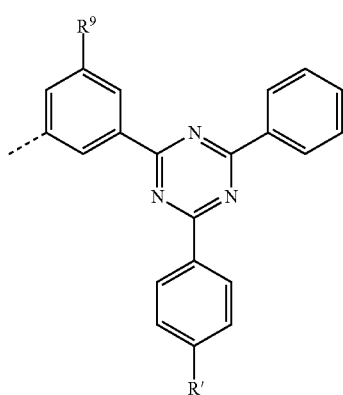 | 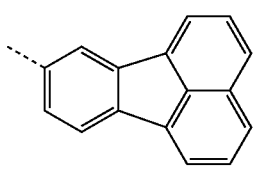 | 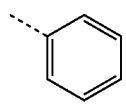 |

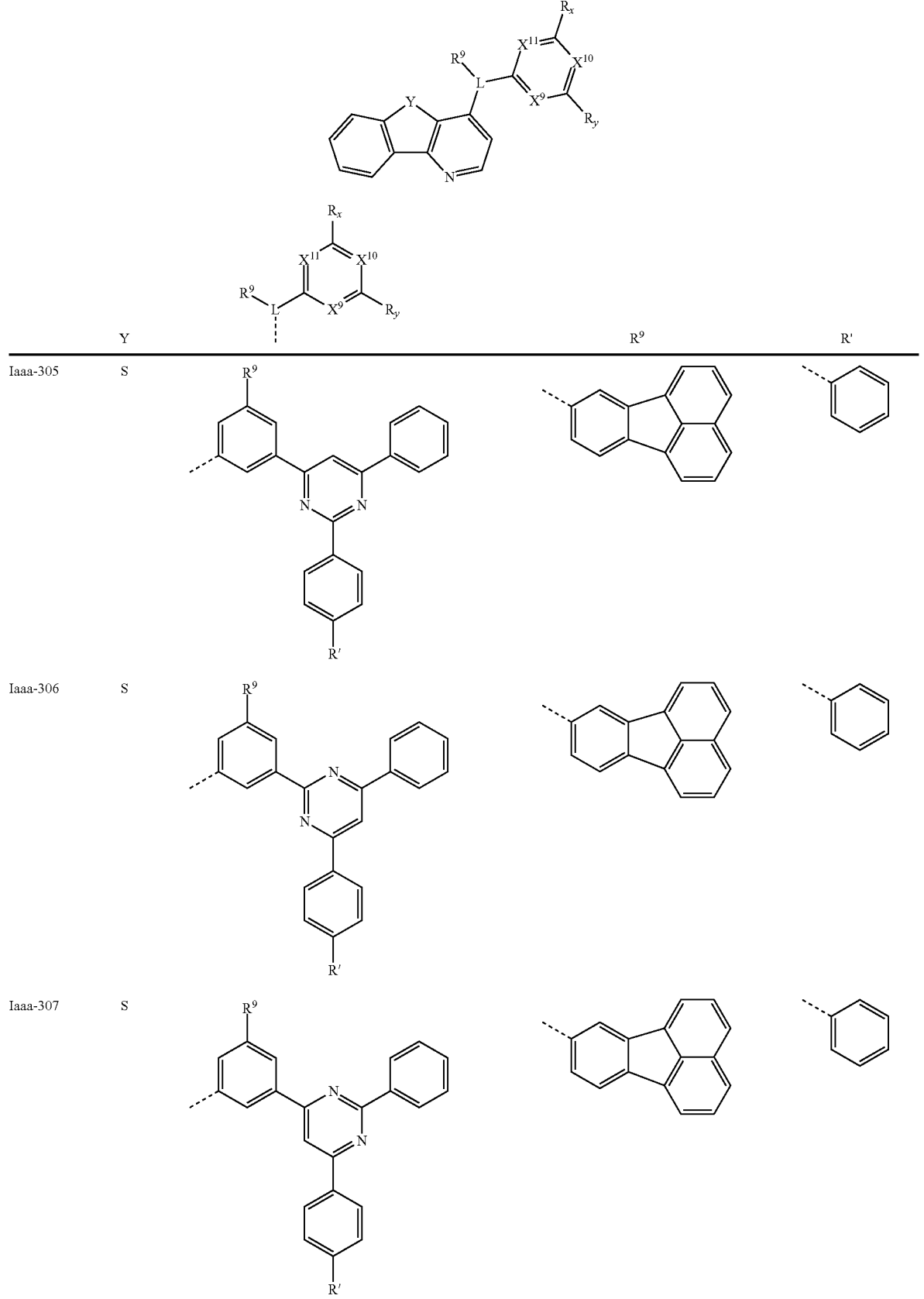

-continued
(Iaaa)
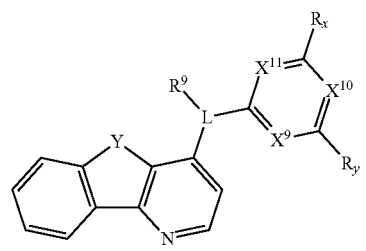
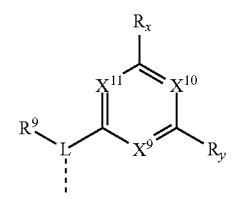
| Y | | R⁹ | R' |
|---|---|---|---|
| Iaaa-308 | S | 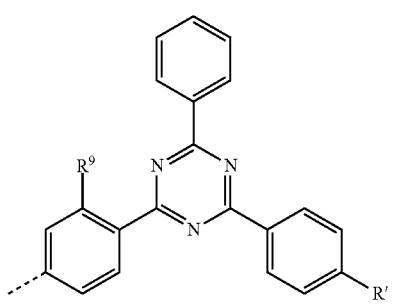 | 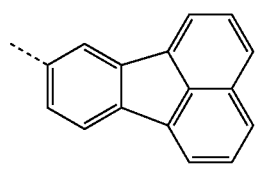 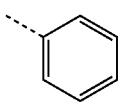 |
| Iaaa-309 | S | 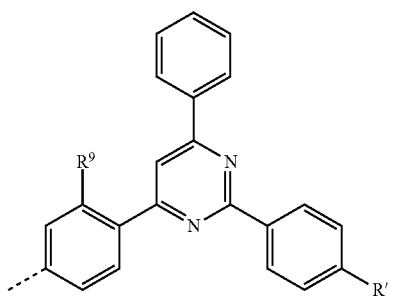 | 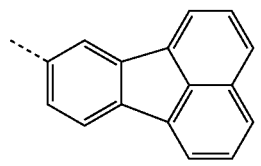 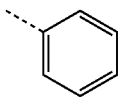 |
| Iaaa-310 | S | 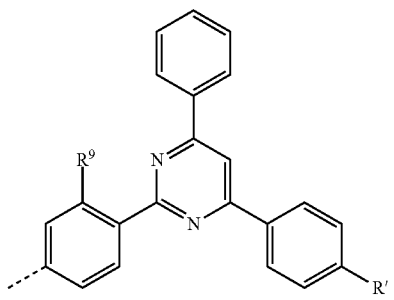 | 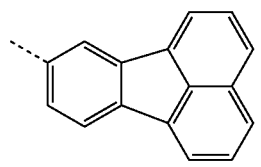 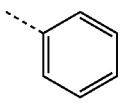 |

-continued
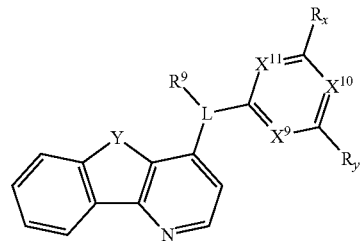
(Iaaa)
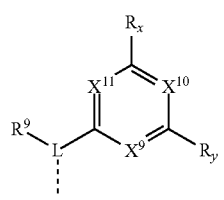
| | Y | | $R^9$ | R' |
|---|---|---|---|---|
| Iaaa-311 | S | 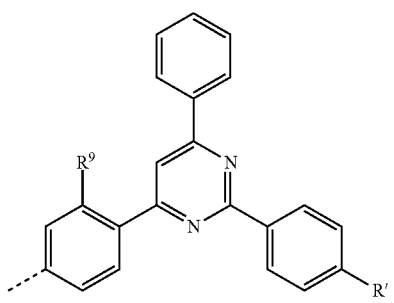 | 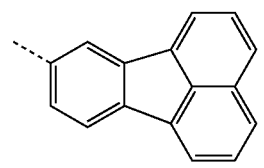 | 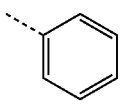 |
| Iaaa-312 | S | 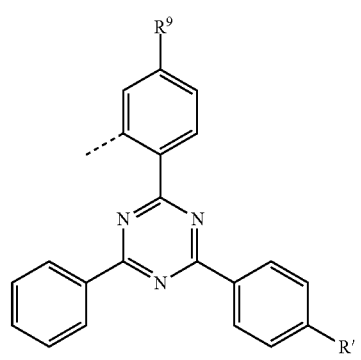 | 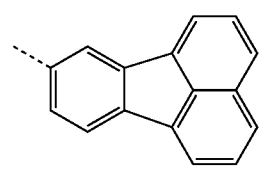 | 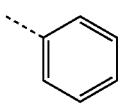 |
| Iaaa-313 | S | 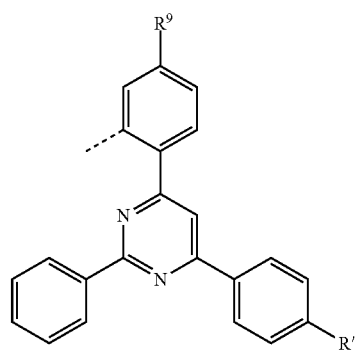 | 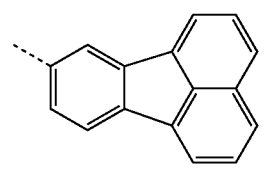 | 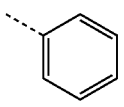 |

-continued
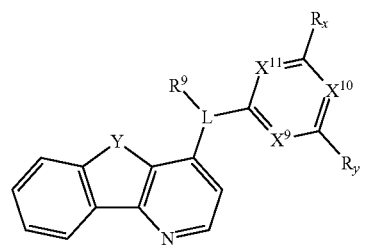
(Iaaa)
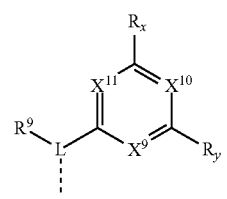
| | Y | R⁹ | R' |
|---|---|---|---|
| Iaaa-314 | S | 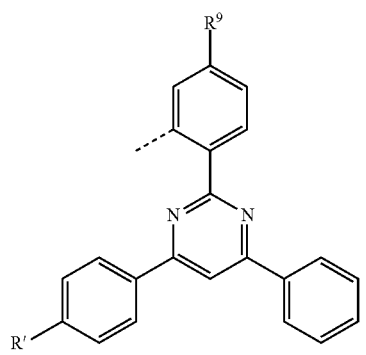 | 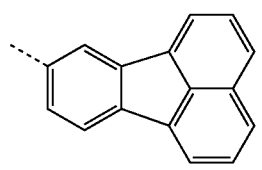 | 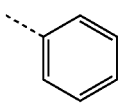 |
| Iaaa-315 | S | 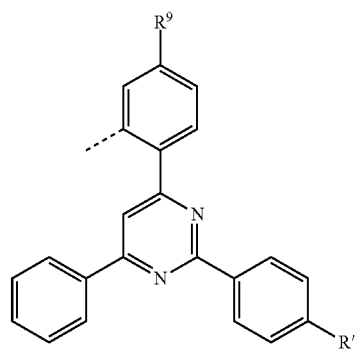 | 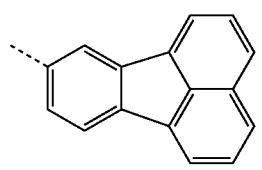 | 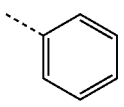 |
| Iaaa-316 | S | 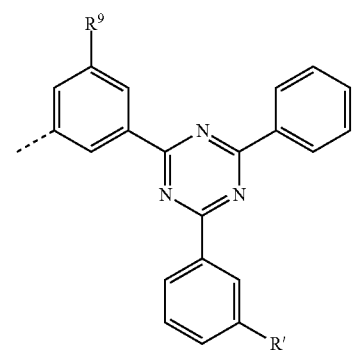 | 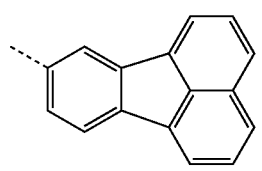 | 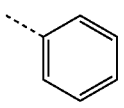 |

-continued
(Iaaa)
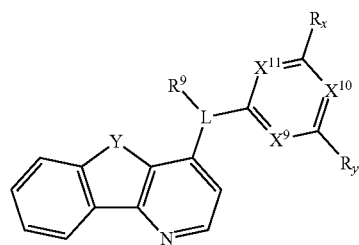
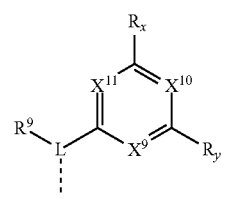
| | Y | | R⁹ | R' |
|---|---|---|---|---|
| Iaaa-317 | S | 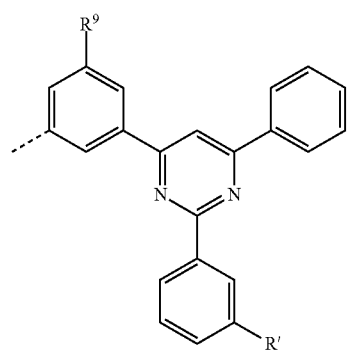 | 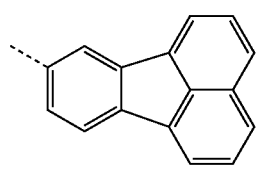 | 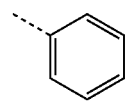 |
| Iaaa-318 | S | 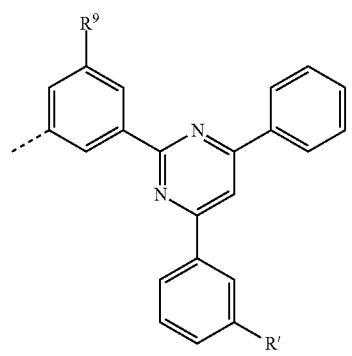 | 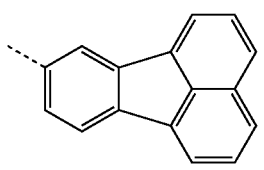 | 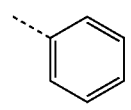 |
| Iaaa-319 | S | 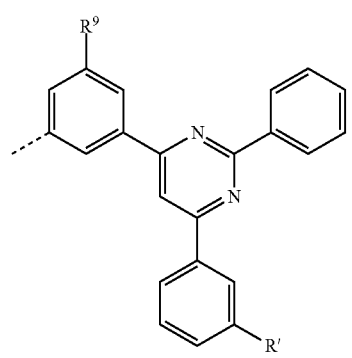 | 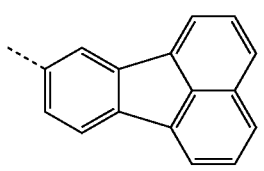 | 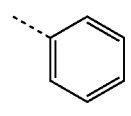 |

-continued
(Iaaa)
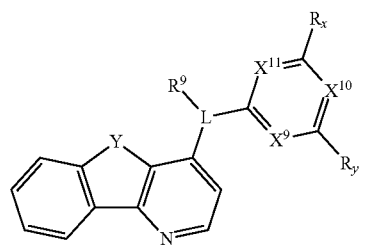
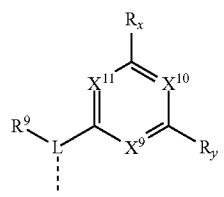
| | Y | | R⁹ | R' |
|---|---|---|---|---|
| Iaaa-320 | S | 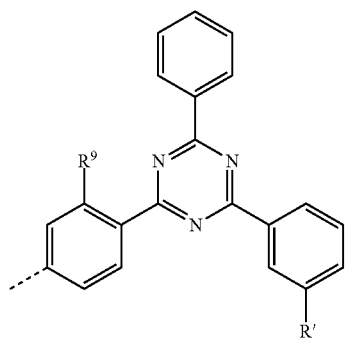 | 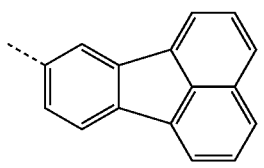 | 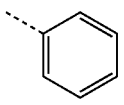 |
| Iaaa-321 | S | 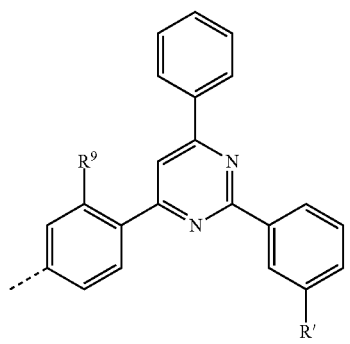 | 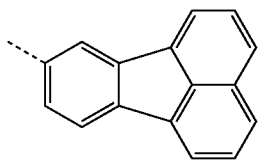 | 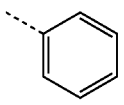 |
| Iaaa-322 | S | 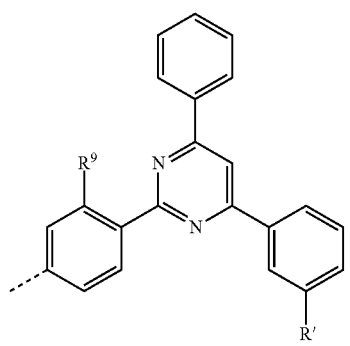 | 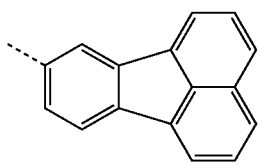 | 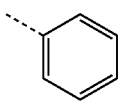 |

-continued
(Iaaa)
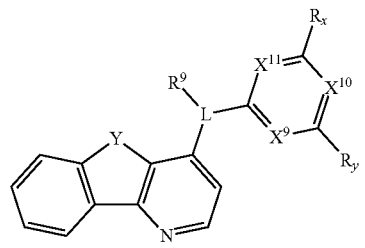
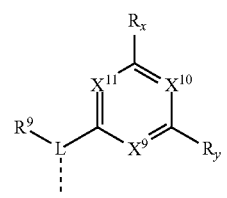
| | Y | | R⁹ | R' |
|---|---|---|---|---|
| Iaaa-323 | S | <br>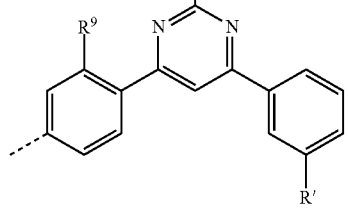 | 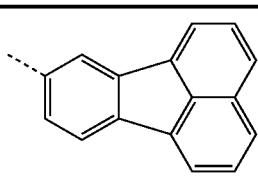 | 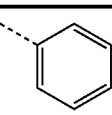 |
| Iaaa-324 | S | 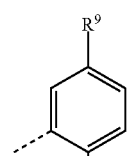 | 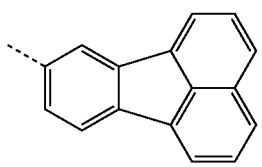 |  |
| Iaaa-325 | S | 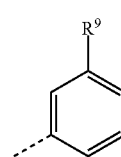 | 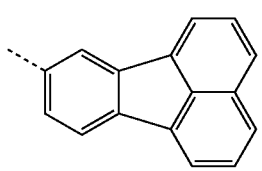 | |

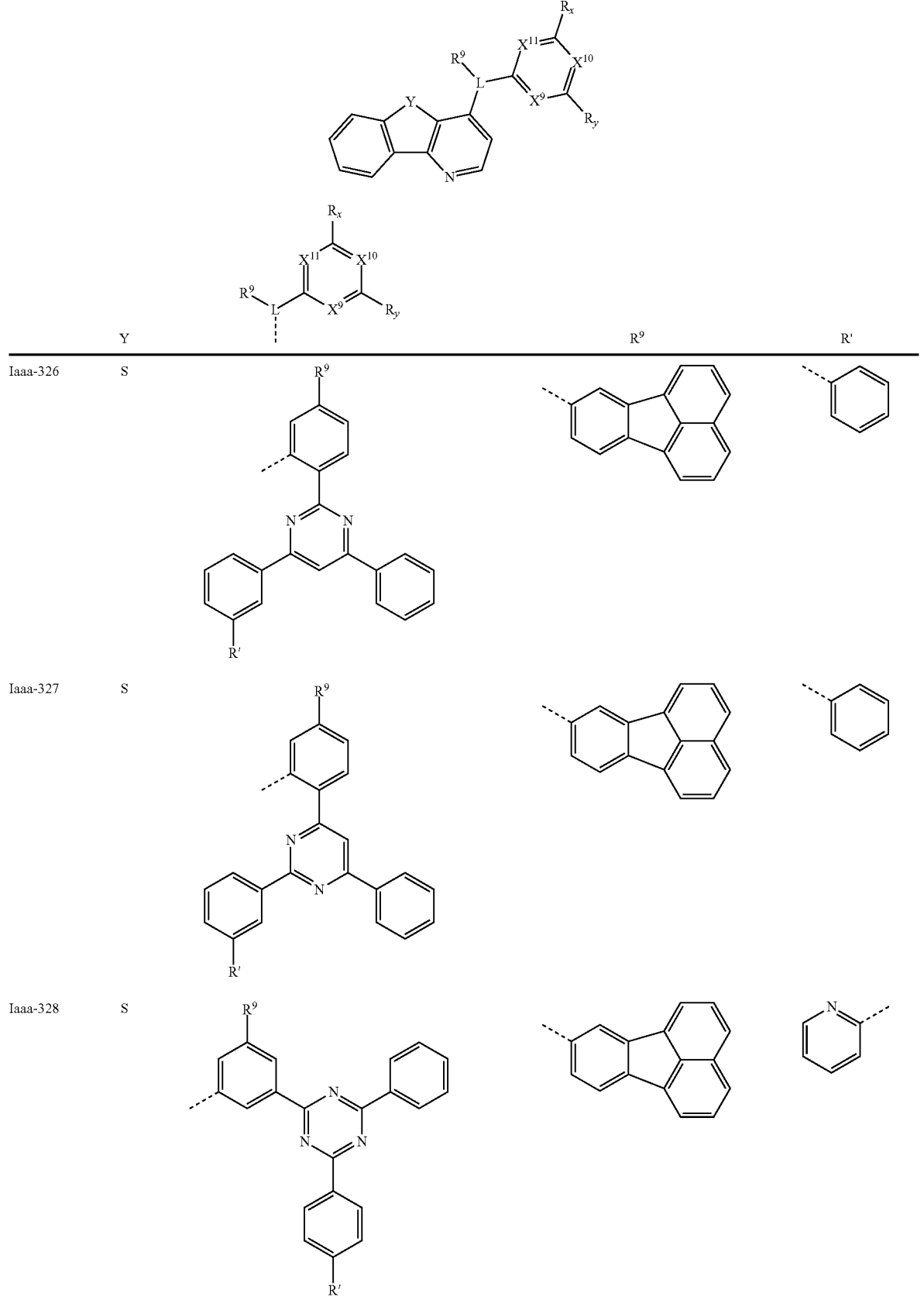

-continued
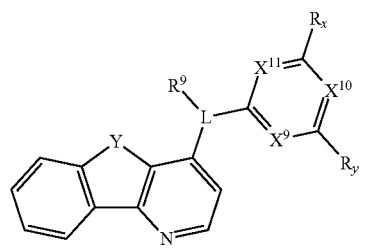
(Iaaa)
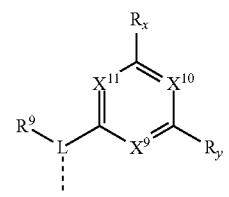
| | Y | | R⁹ | R' |
|---|---|---|---|---|
| Iaaa-329 | S | 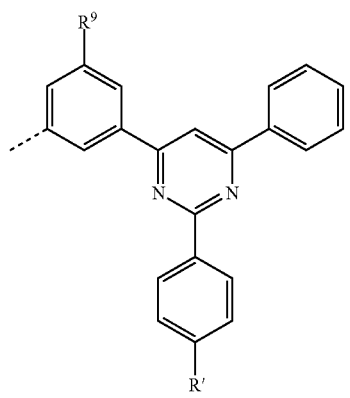 | 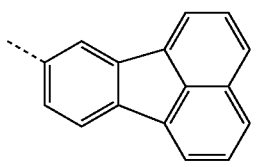 | 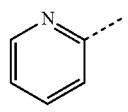 |
| Iaaa-330 | S | 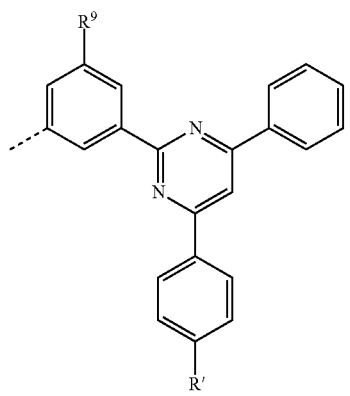 | 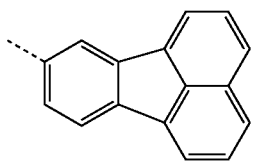 | 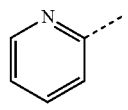 |

-continued
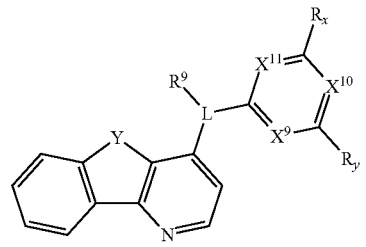
(Iaaa)
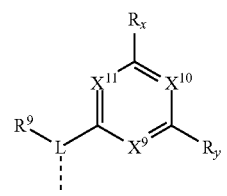
| | Y | | R⁹ | R' |
|---|---|---|---|---|
| Iaaa-331 | S | 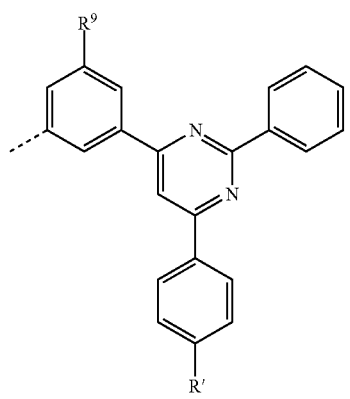 | 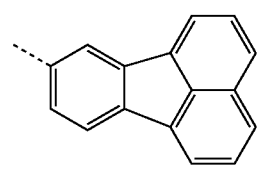 | 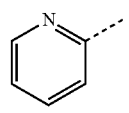 |
| Iaaa-332 | S | 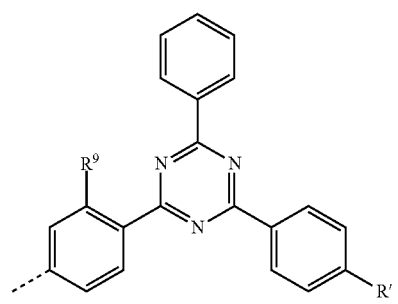 | 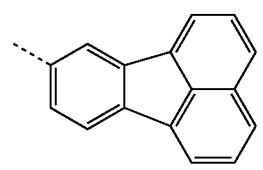 | 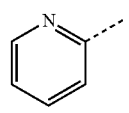 |
| Iaaa-333 | S | 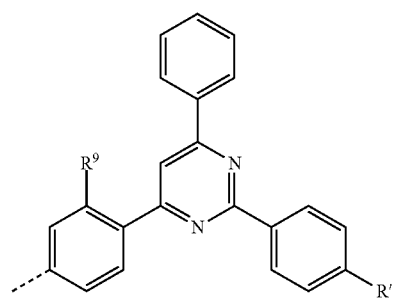 | 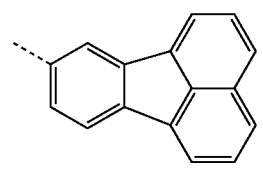 | 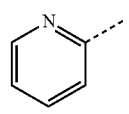 |

-continued
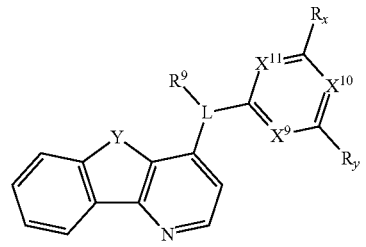
(Iaaa)
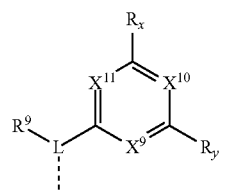
| | Y | R⁹ | R' |
|---|---|---|---|
| Iaaa-334 | S |  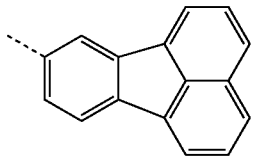 | 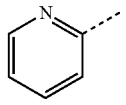 |
| Iaaa-335 | S |  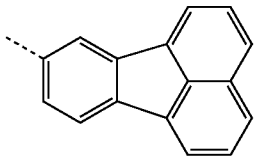 | 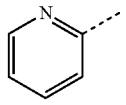 |
| Iaaa-336 | S | 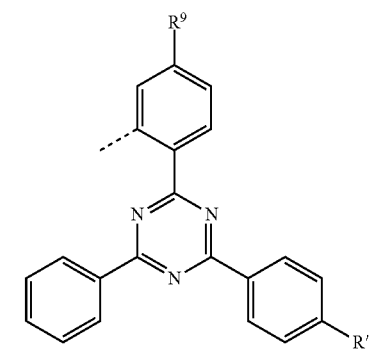 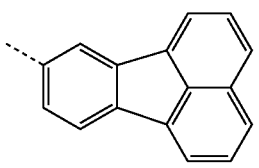 | 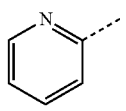 |

-continued
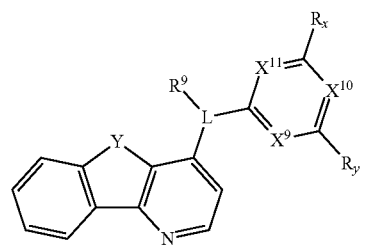
(Iaaa)
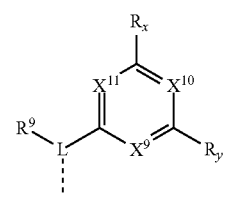
| | Y | | R⁹ | R' |
|---|---|---|---|---|
| Iaaa-337 | S | 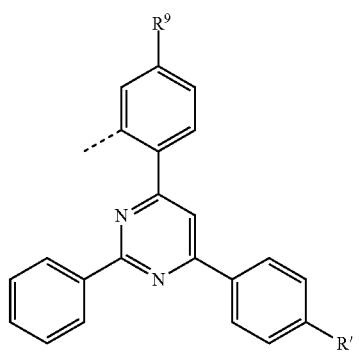 | 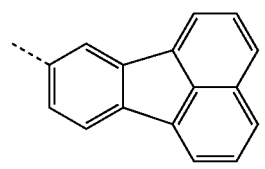 | 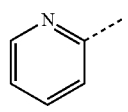 |
| Iaaa-338 | S | 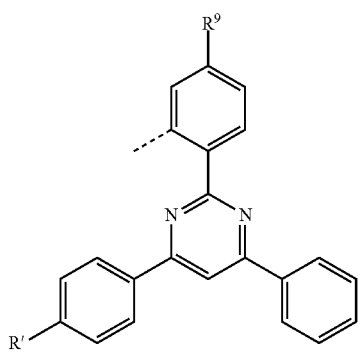 | 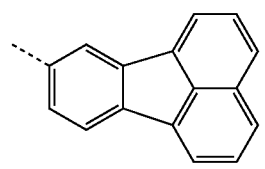 | 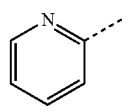 |
| Iaaa-339 | S | 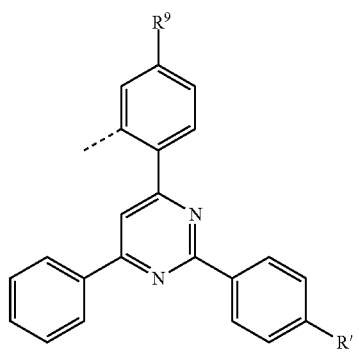 | 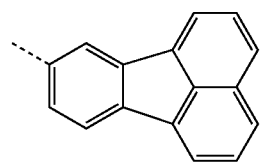 | 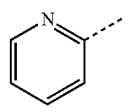 |

-continued
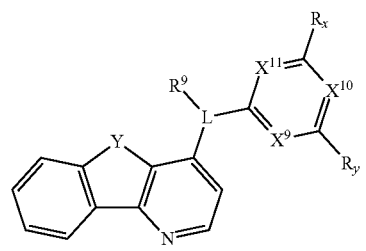
(Iaaa)
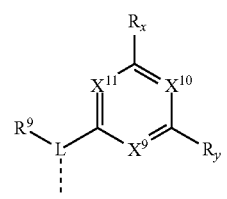
| | Y | | R⁹ | R' |
|---|---|---|---|---|
| Iaaa-340 | S | 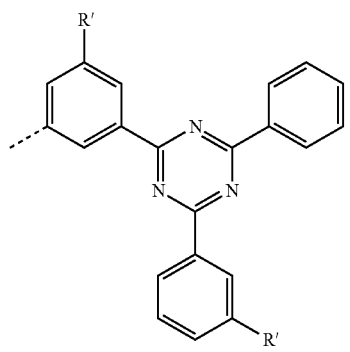 | 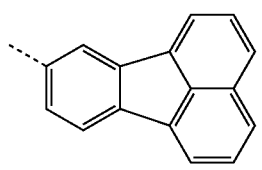 | 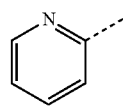 |
| Iaaa-341 | S | 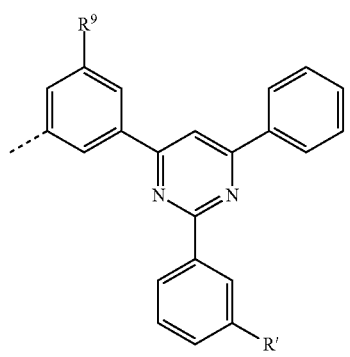 | 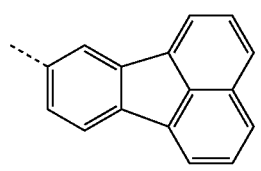 | 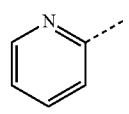 |
| Iaaa-342 | S | 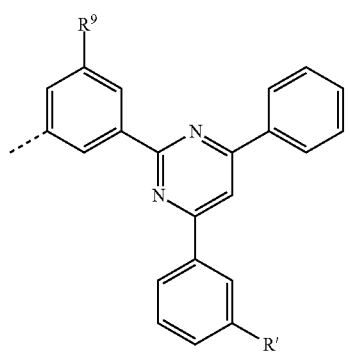 | 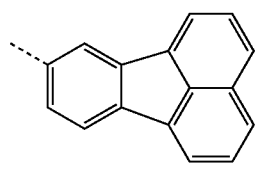 | 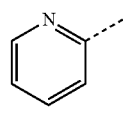 |

-continued
(Iaaa)
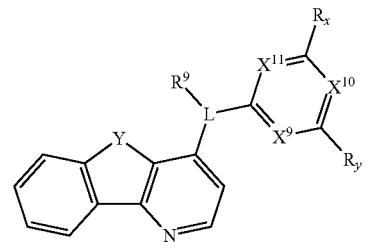
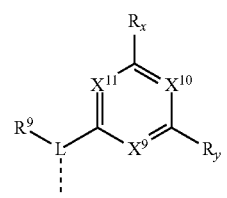
| | Y | | R⁹ | R' |
|---|---|---|---|---|
| Iaaa-343 | S | 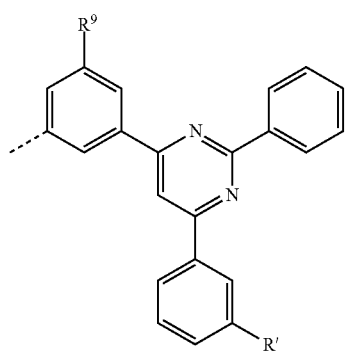 | 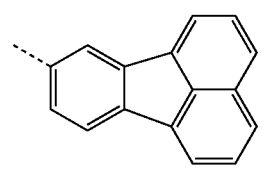 | 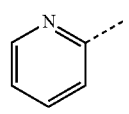 |
| Iaaa-344 | S | 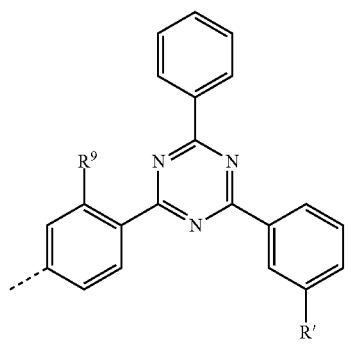 | 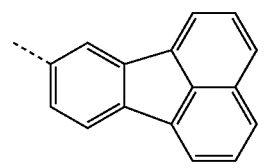 | 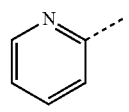 |
| Iaaa-345 | S | 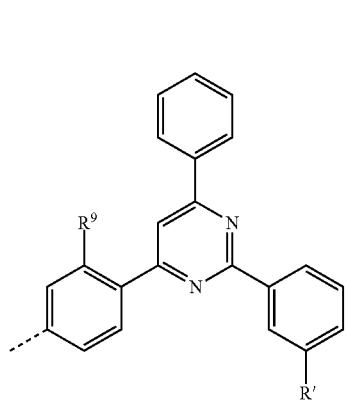 | 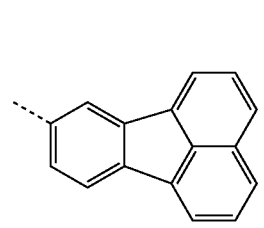 | 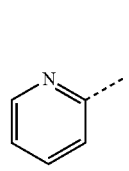 |

-continued
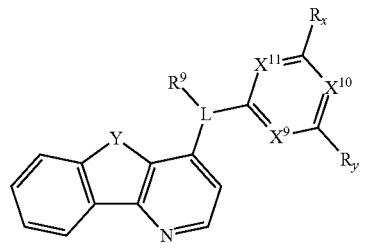
(Iaaa)
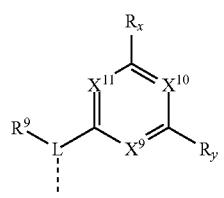
| | Y | | R⁹ | R' |
|---|---|---|---|---|
| Iaaa-346 | S | 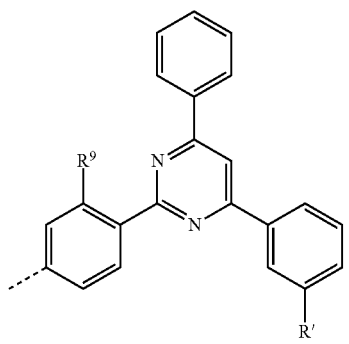 | 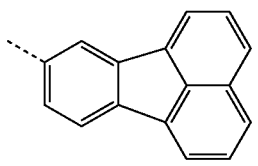 | 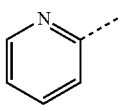 |
| Iaaa-347 | S | 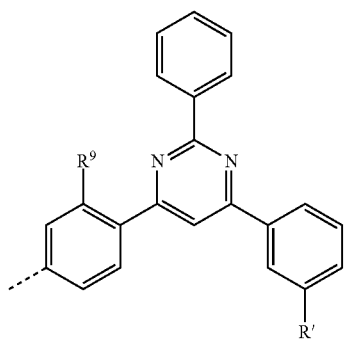 | 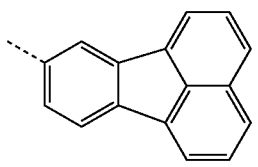 | 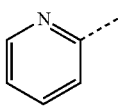 |
| Iaaa-348 | S | 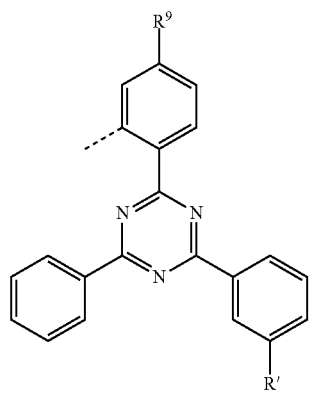 | 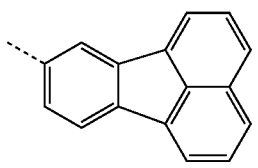 | 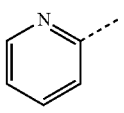 |

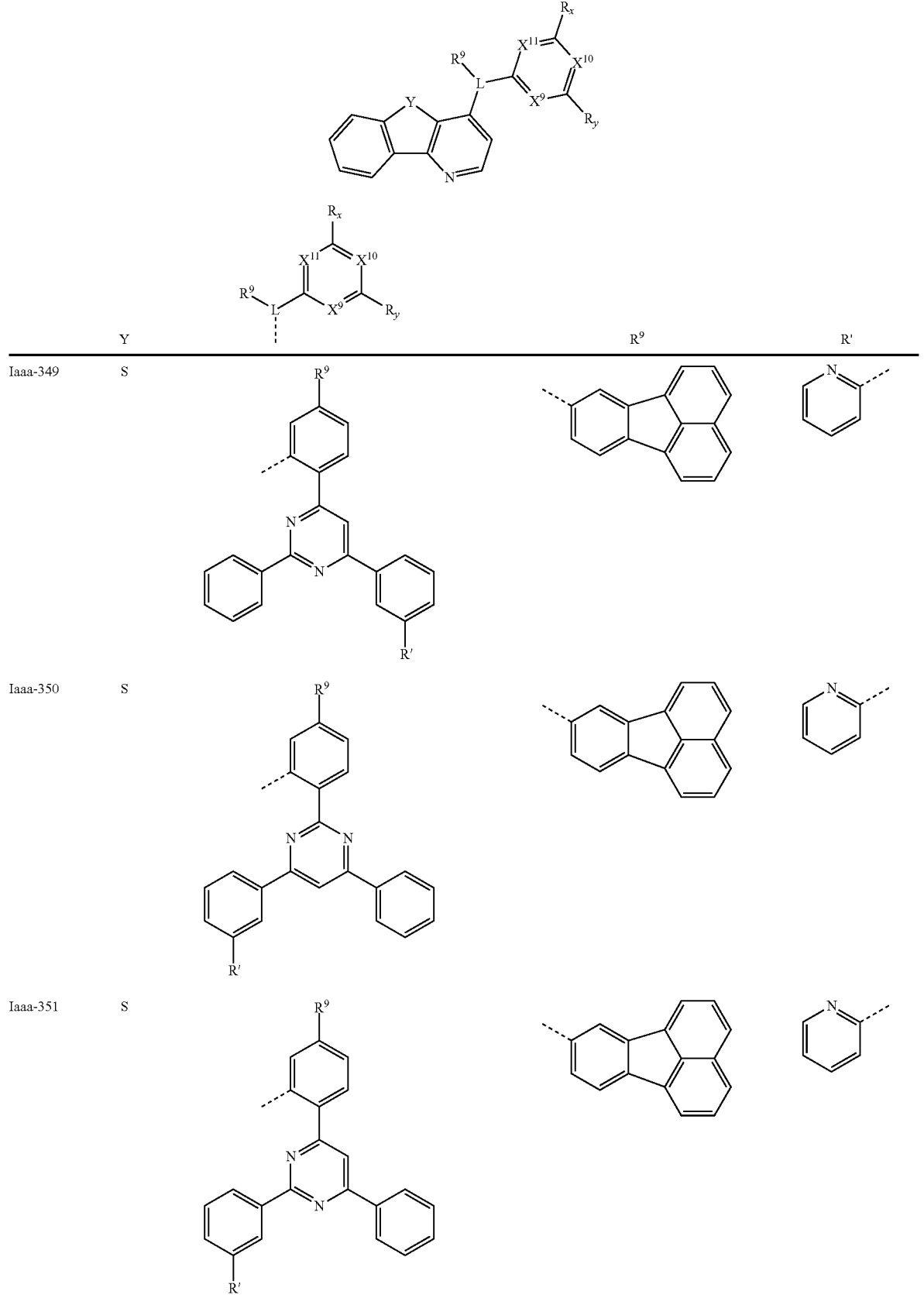

-continued
(Iaaa)
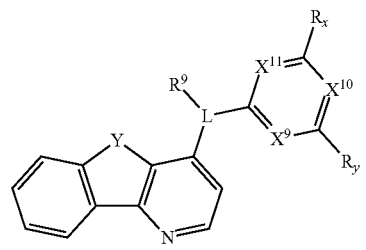
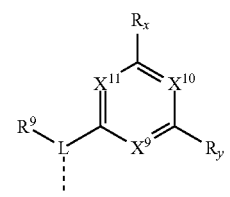
| | Y | R⁹ | | R' |
|---|---|---|---|---|
| Iaaa-352 | S | 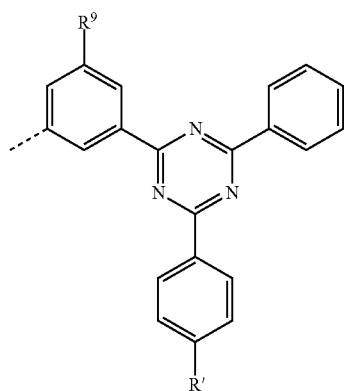 | 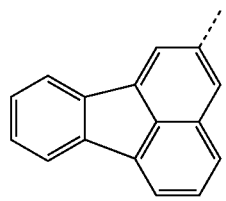 | H |
| Iaaa-353 | S | 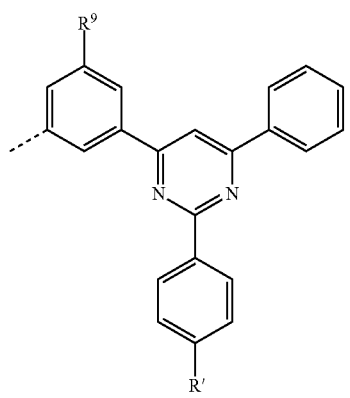 | 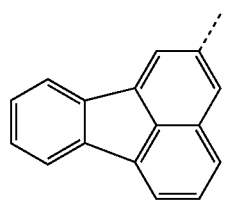 | H |

-continued
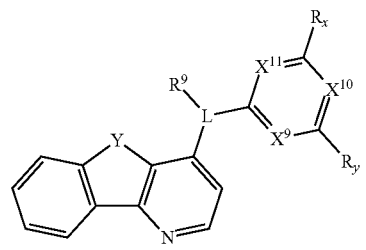
(Iaaa)

| | Y | | R⁹ | | R' |
|---|---|---|---|---|---|
| Iaaa-354 | S | 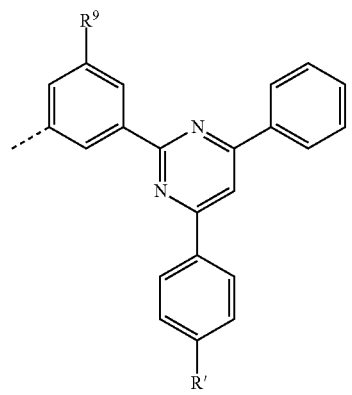 | | 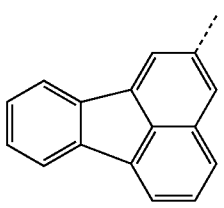 | H |
| Iaaa-355 | S | 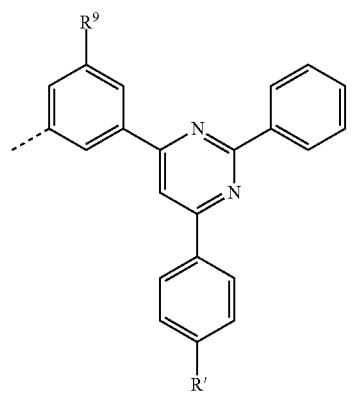 | | 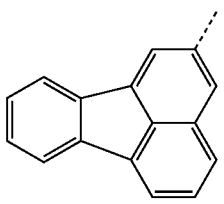 | H |
| Iaaa-356 | S | 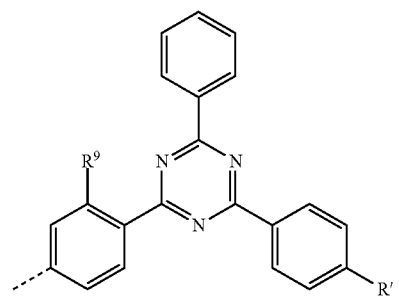 | | 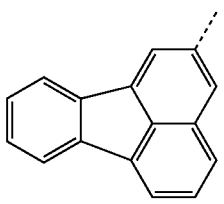 | H |

-continued
(Iaaa)
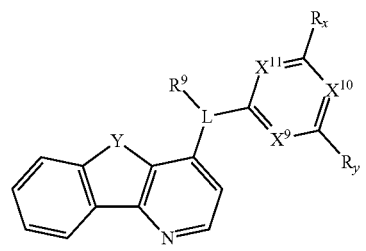

| | Y | | R⁹ | R' |
|---|---|---|---|---|
| Iaaa-357 | S | 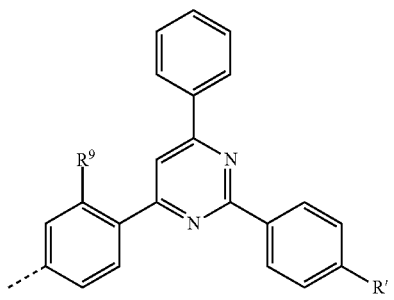 | 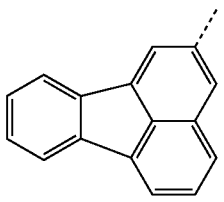 | H |
| Iaaa-358 | S | 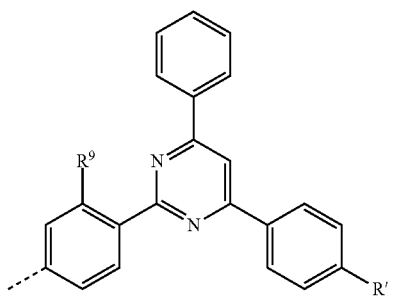 | 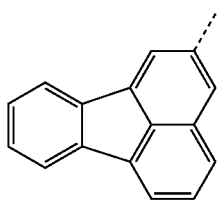 | H |
| Iaaa-359 | S | 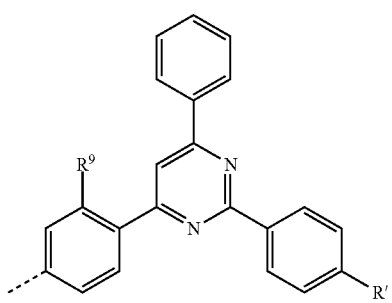 | 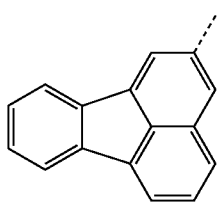 | H |

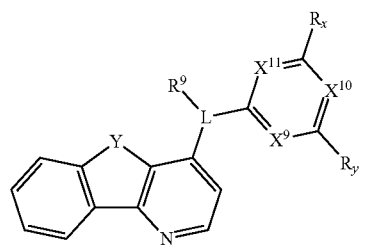
(Iaaa)
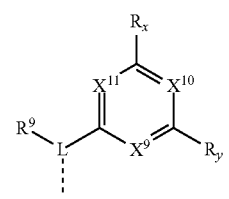
| | Y | R⁹ | R' |
|---|---|---|---|
| Iaaa-360 | S | 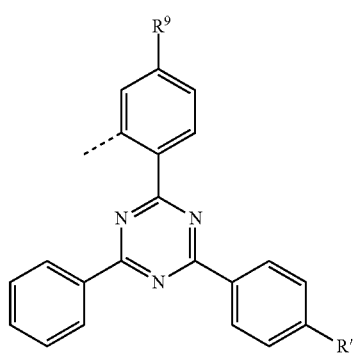 | 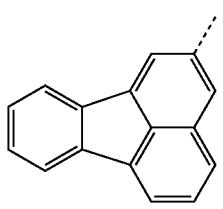 H |
| Iaaa-361 | S | 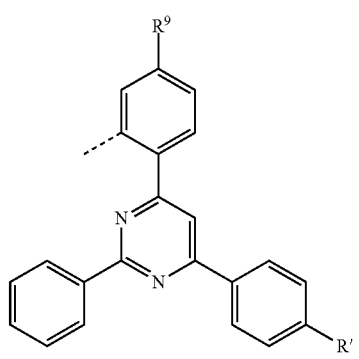 | 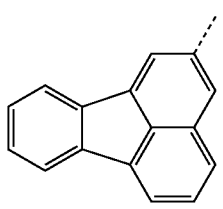 H |
| Iaaa-362 | S | 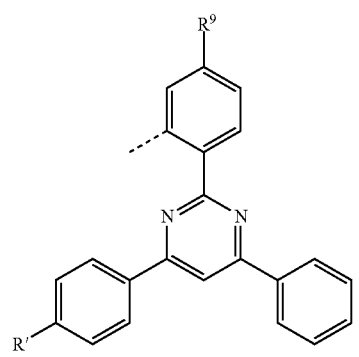 | 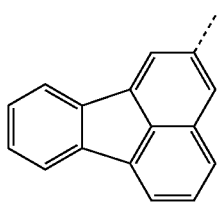 H |

-continued
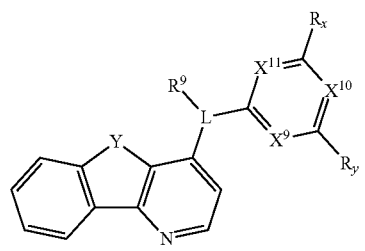
(Iaaa)
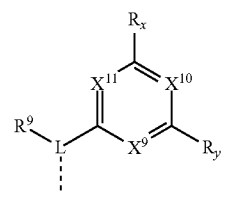
| | Y | R⁹ | R' |
|---|---|---|---|
| Iaaa-363 | S | 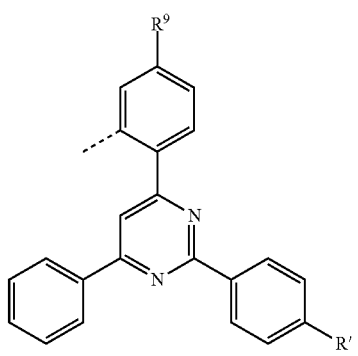 | 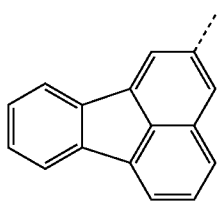 H |
| Iaaa-364 | S | 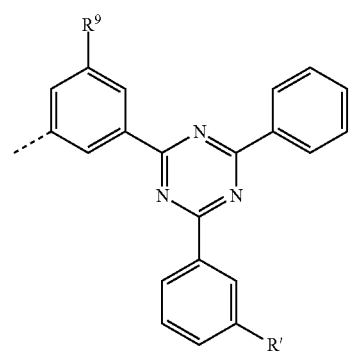 | 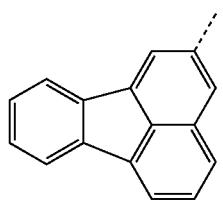 H |
| Iaaa-365 | S | 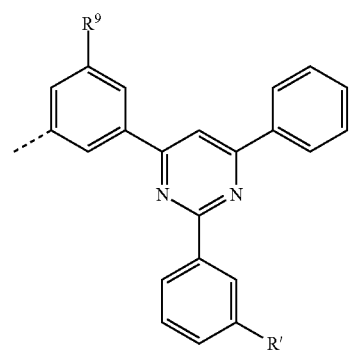 | 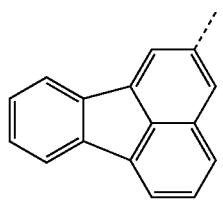 H |

-continued
(Iaaa)
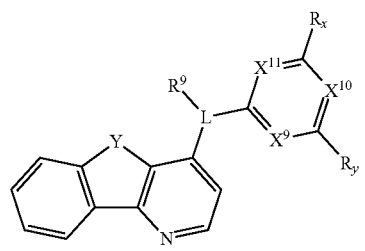
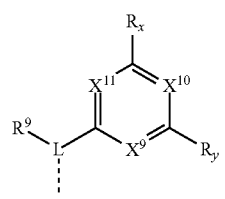
| | Y | R⁹ | R' |
|---|---|---|---|
| Iaaa-366 | S | 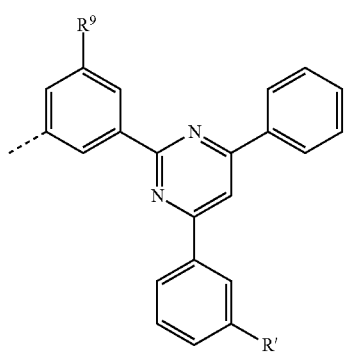 | 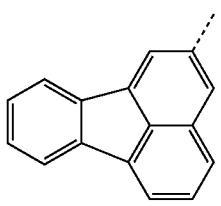 H |
| Iaaa-367 | S | 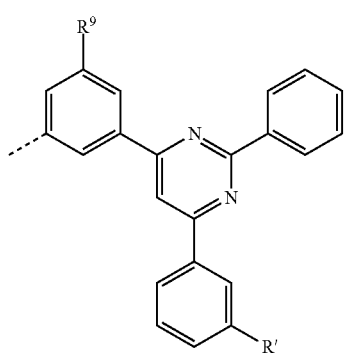 | 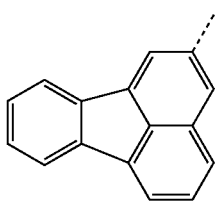 H |
| Iaaa-368 | S | 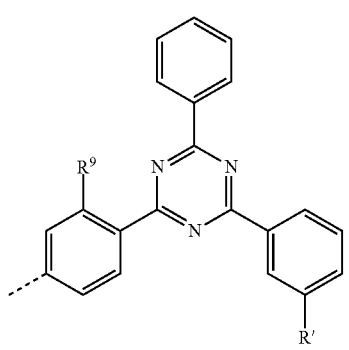 | 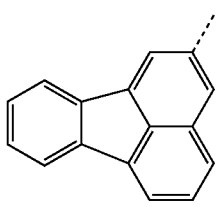 H |

-continued
(Iaaa)
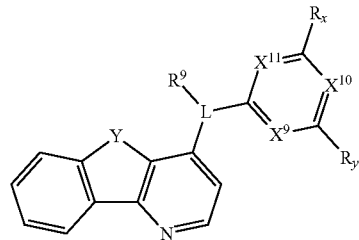
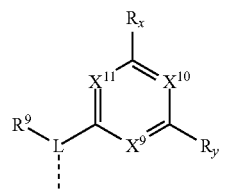
| | Y | | R⁹ | R' |
|---|---|---|---|---|
| Iaaa-369 | S | 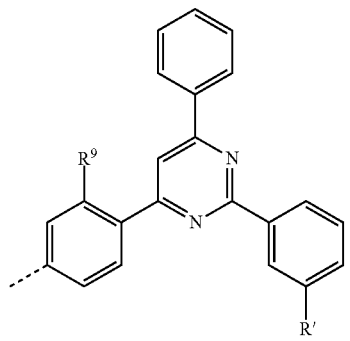 | 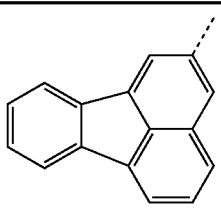 | H |
| Iaaa-370 | S | 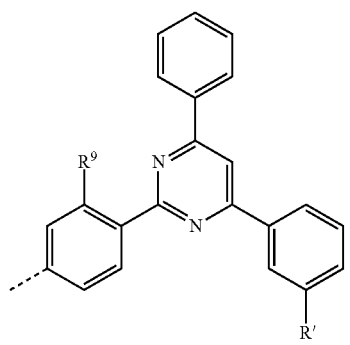 | 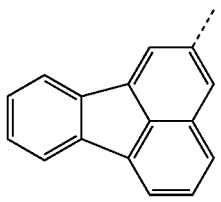 | H |
| Iaaa-371 | S | 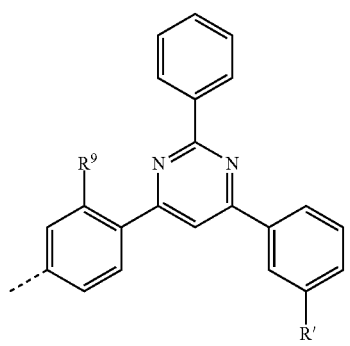 |  | H |

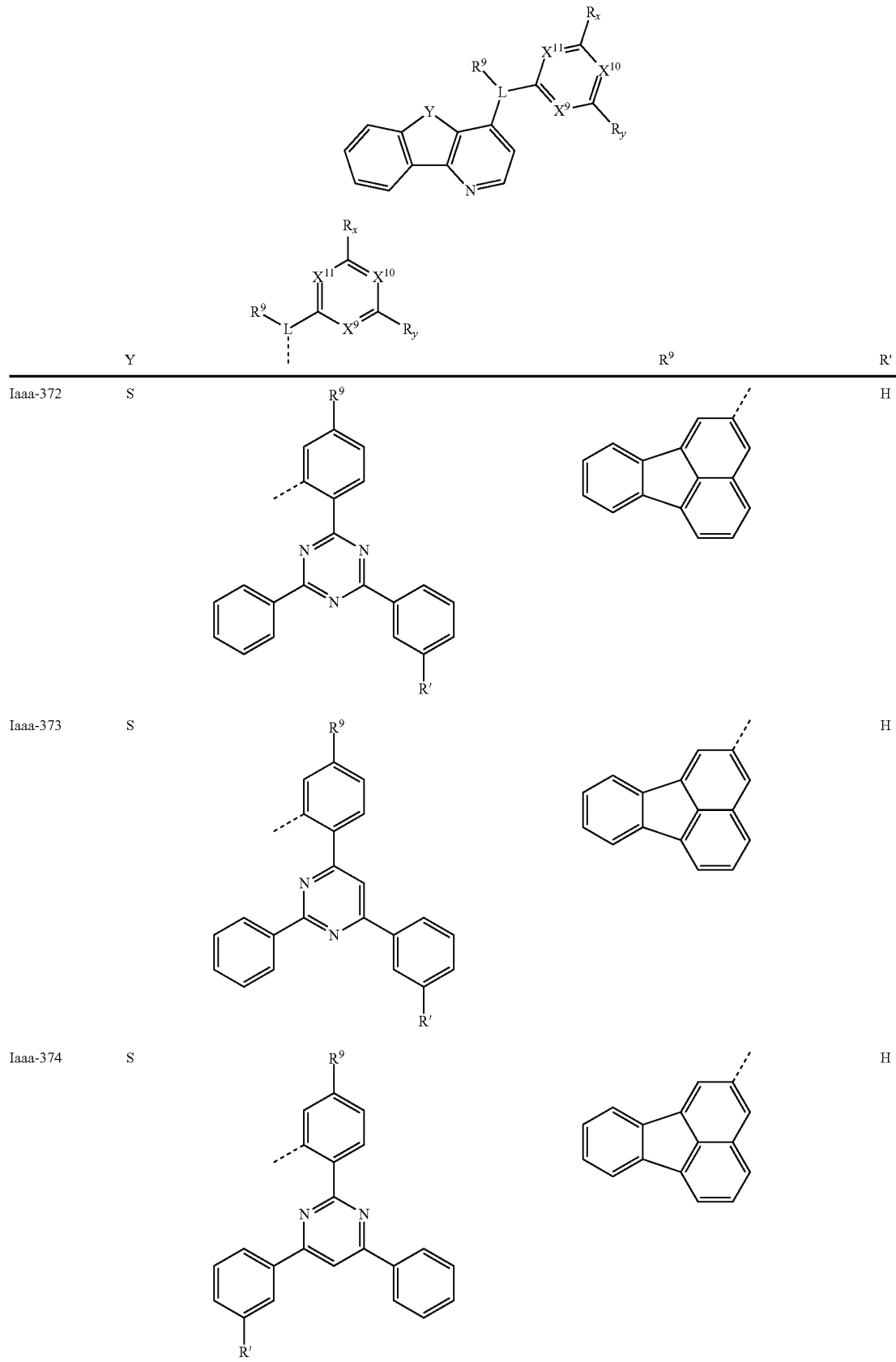

-continued
(Iaaa)
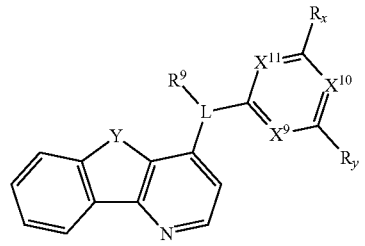
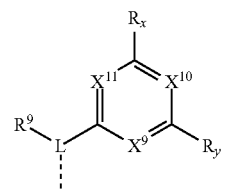
| | Y | R⁹ | R' |
|---|---|---|---|
| Iaaa-375 | S | 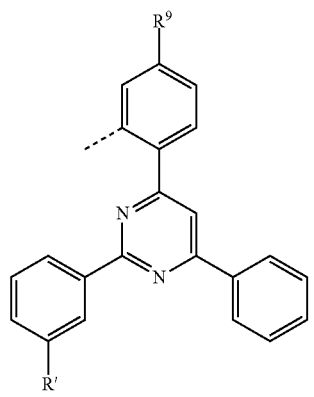 | 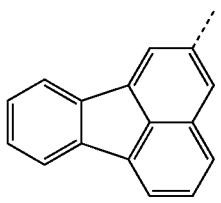 H |
| Iaaa-376 | S | 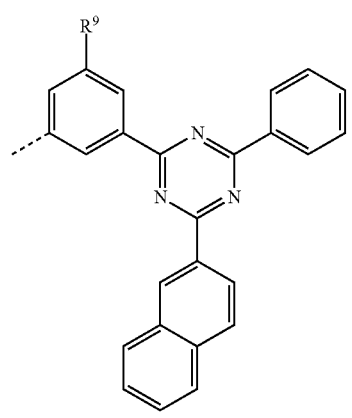 | 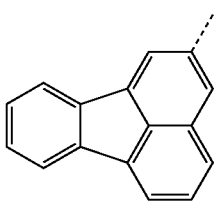 — |

-continued
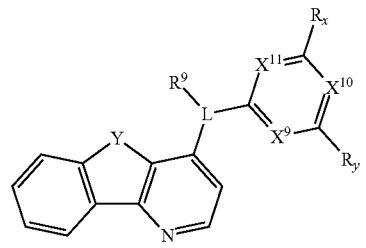
(Iaaa)

| | Y | R⁹ | R' |
|---|---|---|---|
| Iaaa-377 | S | 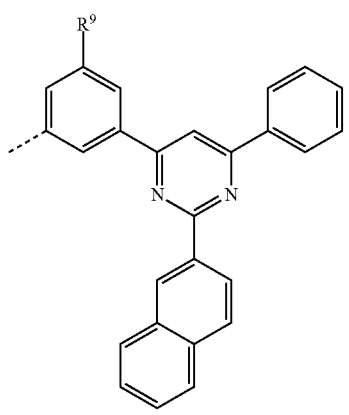 | 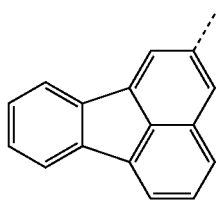 | — |
| Iaaa-378 | S | 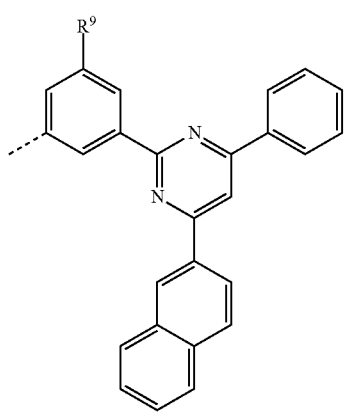 | 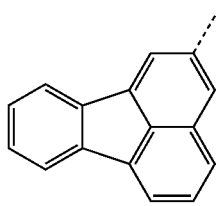 | — |

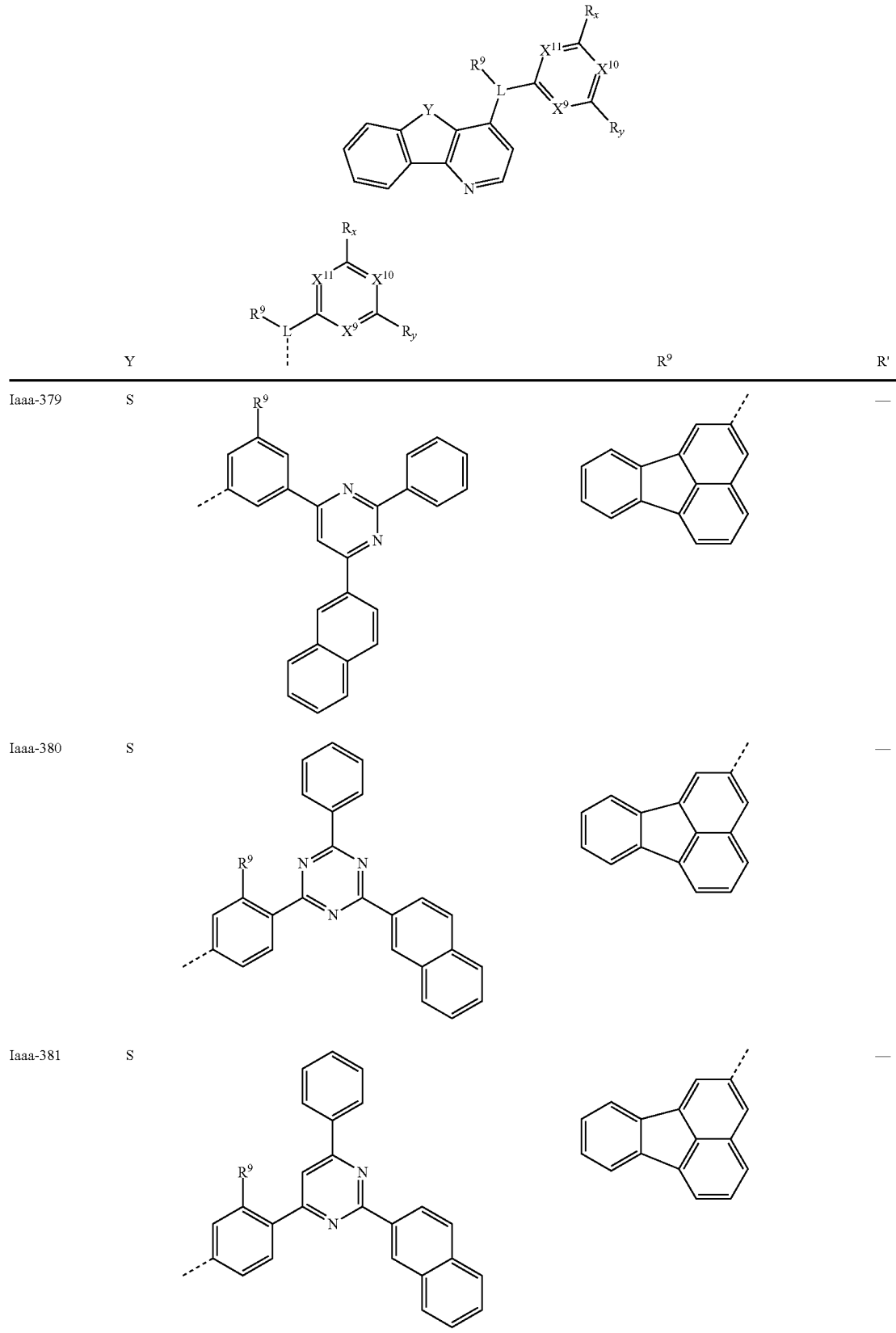

-continued
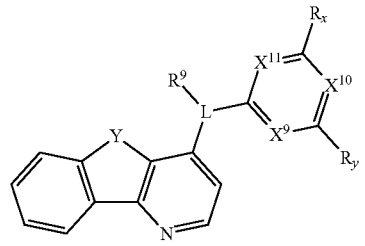
(Iaaa)
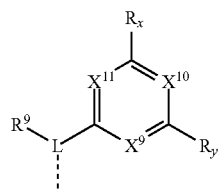
| | Y | R⁹ | R' |
|---|---|---|---|
| Iaaa-382 | S | 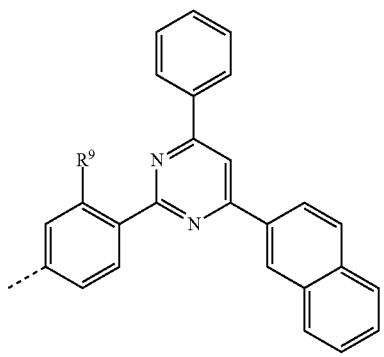 | 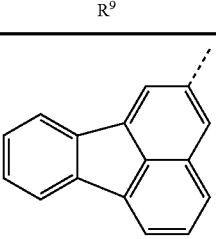 | — |
| Iaaa-383 | S | 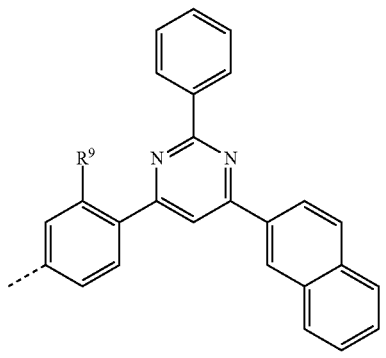 | 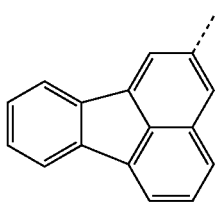 | — |
| Iaaa-384 | S | 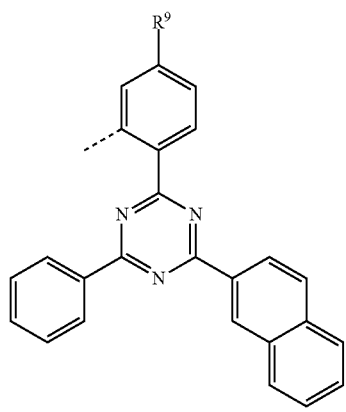 | 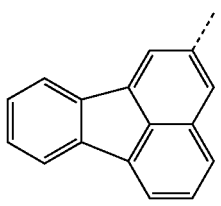 | — |

-continued
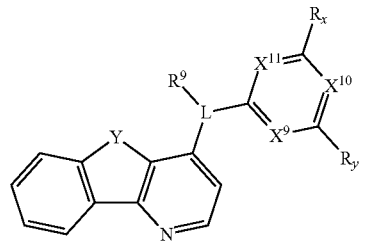
(Iaaa)
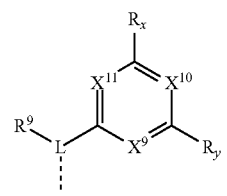
| | Y | R⁹ | R' |
|---|---|---|---|
| Iaaa-385 | S | 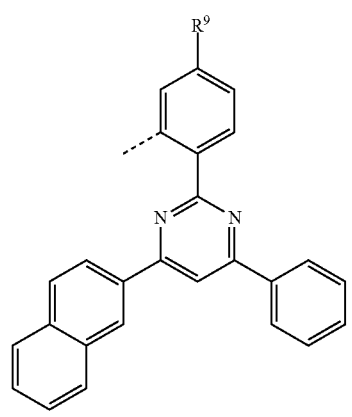 |  | — |
| Iaaa-386 | S | 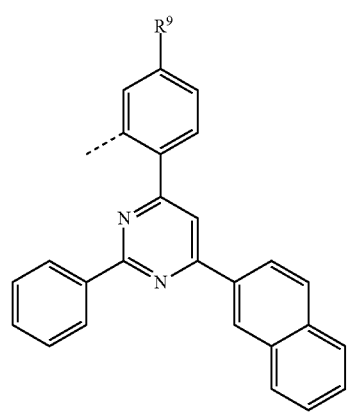 | 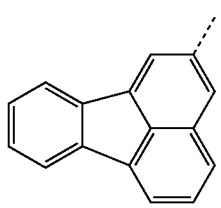 | — |

-continued
(Iaaa)
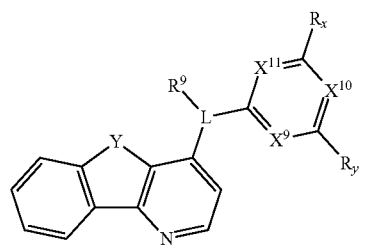
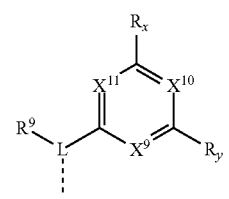
| | Y | | R⁹ | R' |
|---|---|---|---|---|
| Iaaa-387 | S | 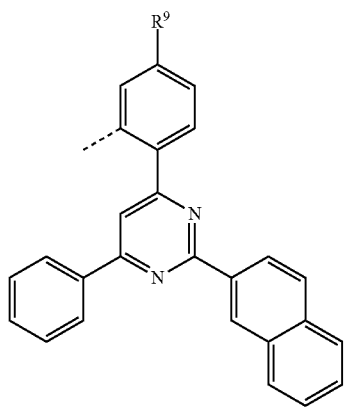 | 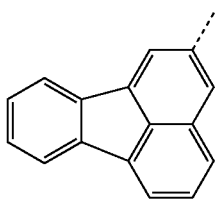 | — |
| Iaaa-388 | S | 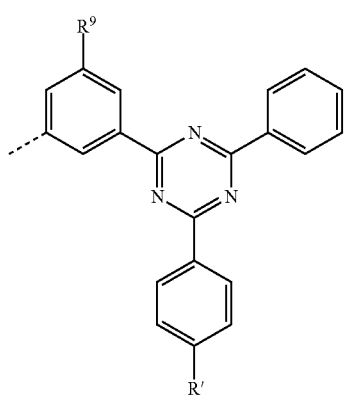 | 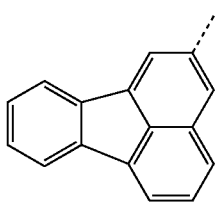 | 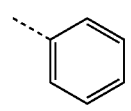 |

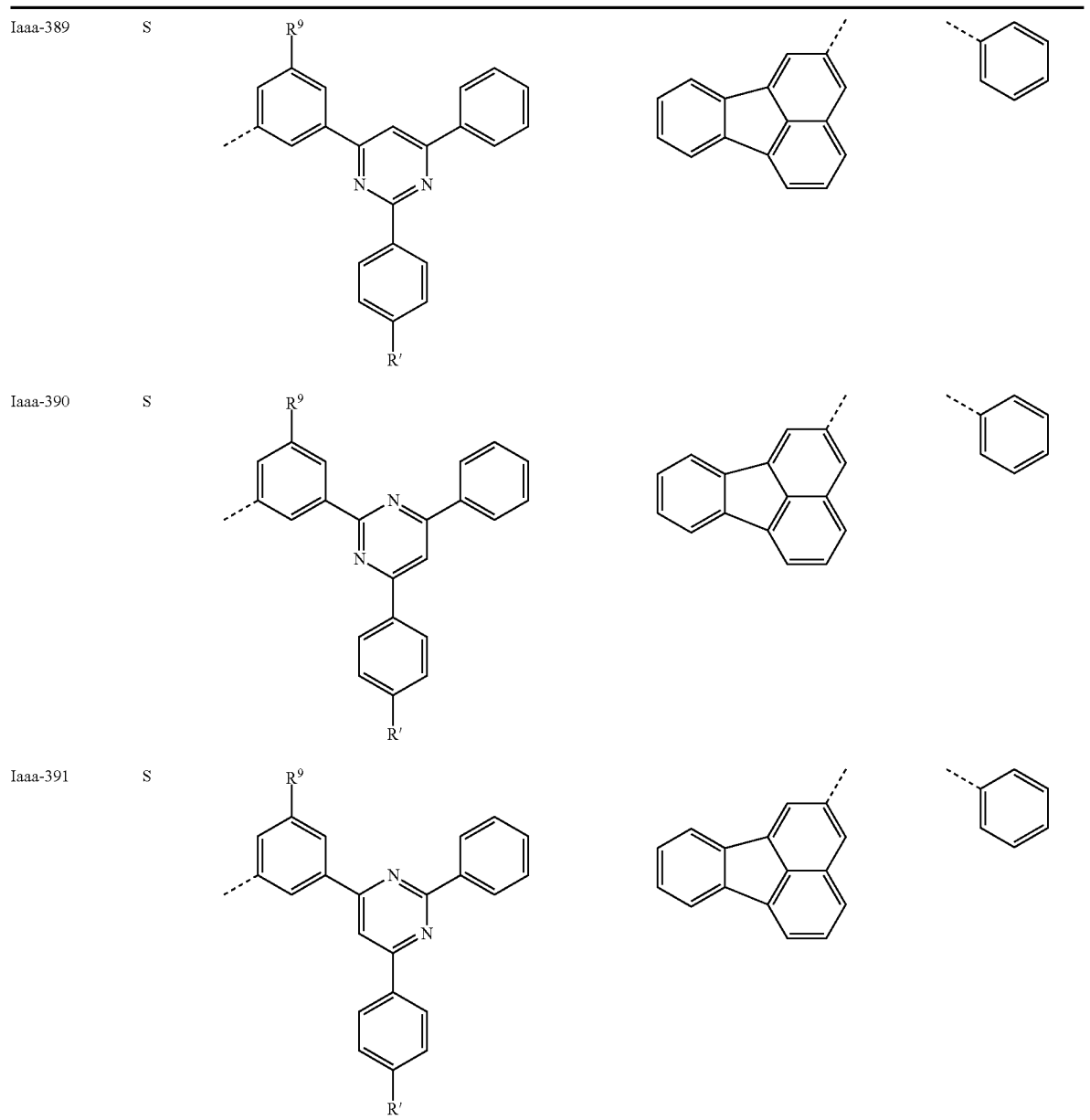

-continued
(Iaaa)
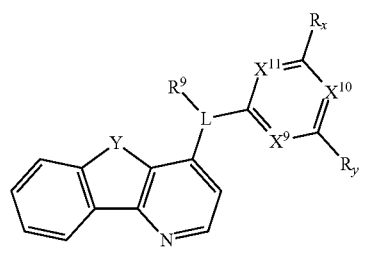
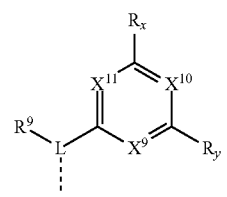
| | Y | R⁹ | R' |
|---|---|---|---|
| Iaaa-392 | S | 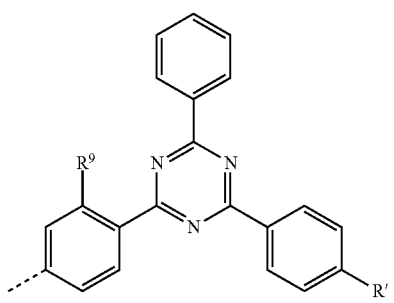 | 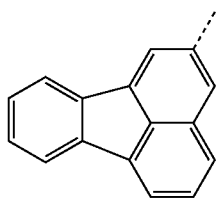 | 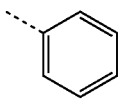 |
| Iaaa-393 | S | 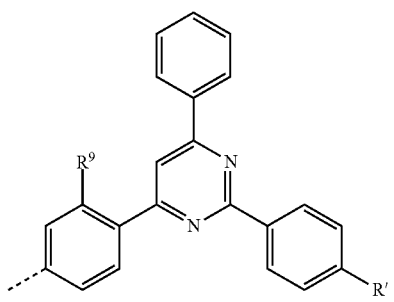 | 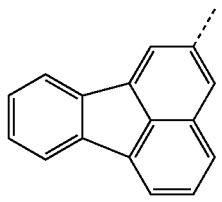 | 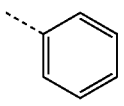 |
| Iaaa-394 | S | 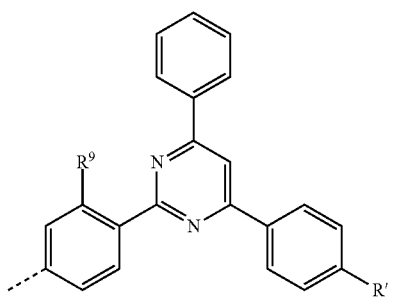 | 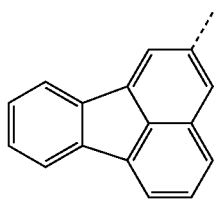 | 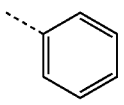 |

-continued
(Iaaa)
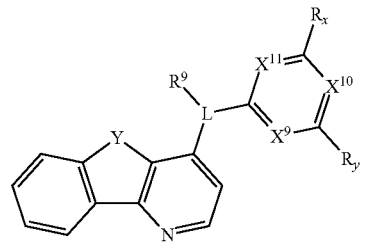
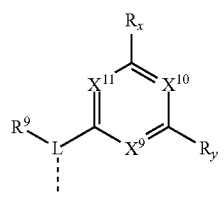
| | Y | | R⁹ | R' |
|---|---|---|---|---|
| Iaaa-395 | S | 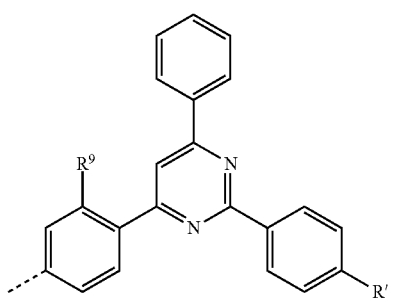 | 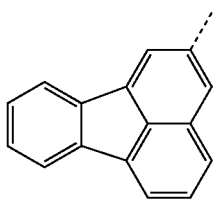 | 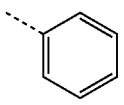 |
| Iaaa-396 | S | 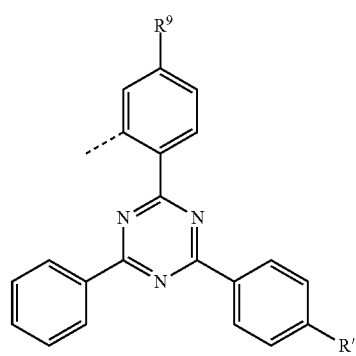 | 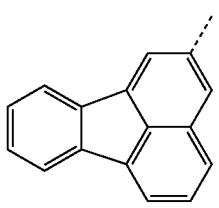 | 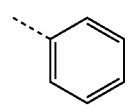 |
| Iaaa-397 | S | 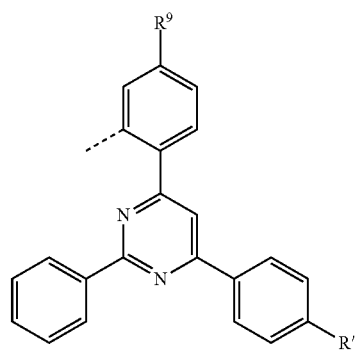 | 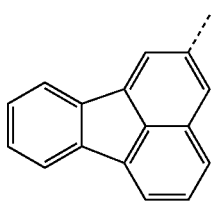 | 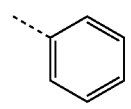 |

-continued
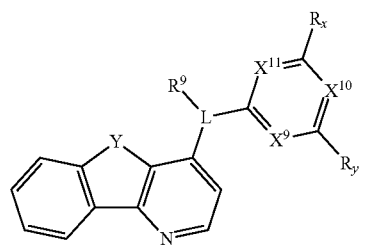
(Iaaa)
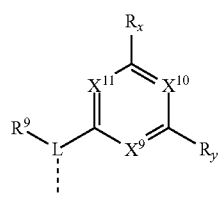
| | Y | R⁹ | R' |
|---|---|---|---|
| Iaaa-398 | S | 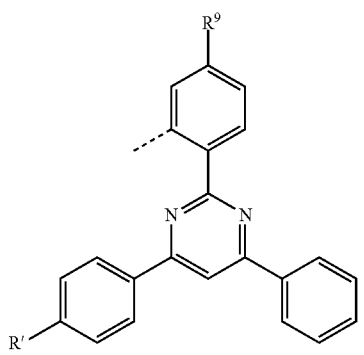 | 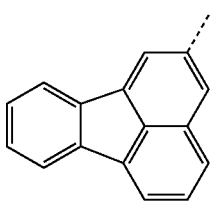 | 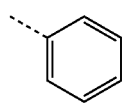 |
| Iaaa-399 | S | 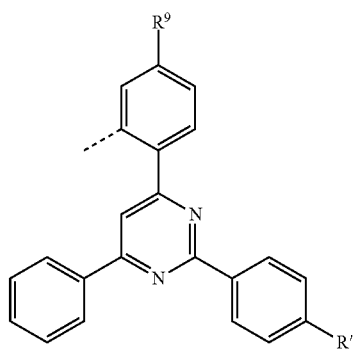 |  | 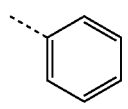 |
| Iaaa-400 | S | 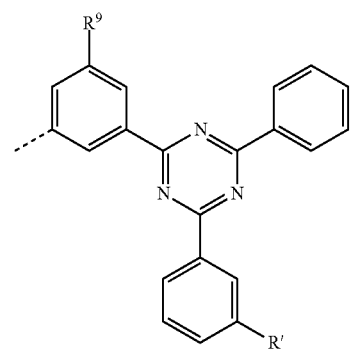 | 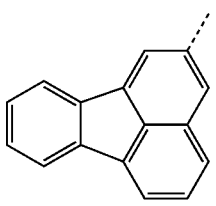 | 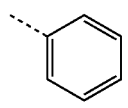 |

-continued
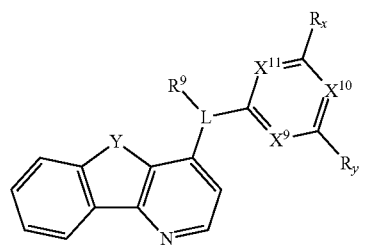
(Iaaa)
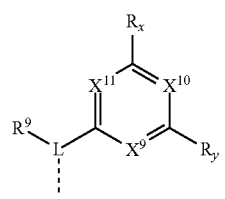
| | Y | R⁹ | R' |
|---|---|---|---|
| Iaaa-401 | S | 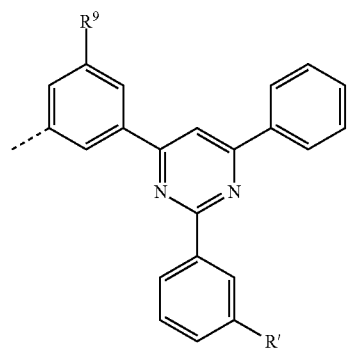 | 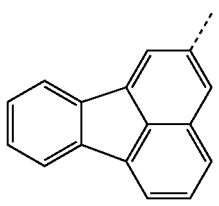 | 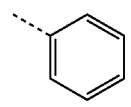 |
| Iaaa-402 | S | 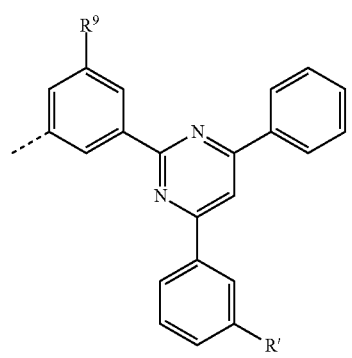 |  | 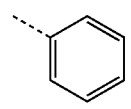 |
| Iaaa-403 | S | 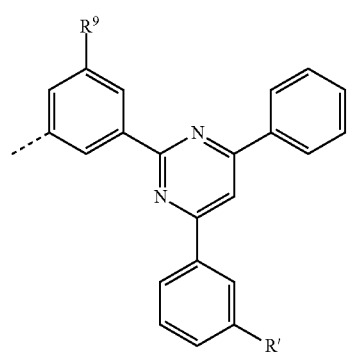 | 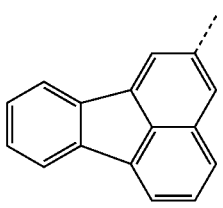 | 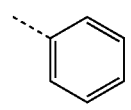 |

-continued
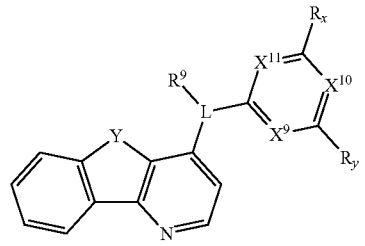
(Iaaa)
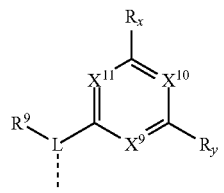
| | Y | | R⁹ | R' |
|---|---|---|---|---|
| Iaaa-404 | S | 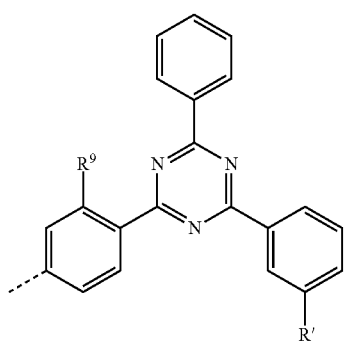 |  |  |
| Iaaa-405 | S | 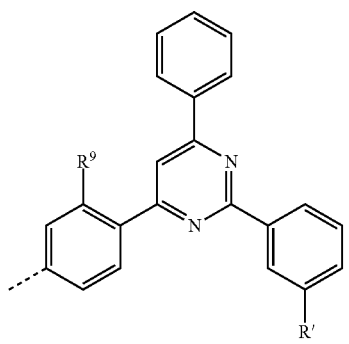 | 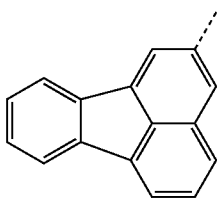 | 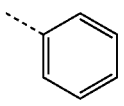 |
| Iaaa-406 | S | 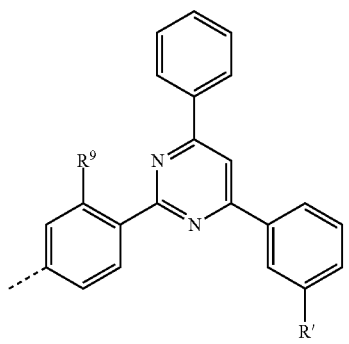 |  | 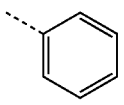 |

-continued
(Iaaa)
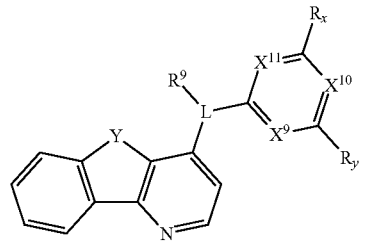
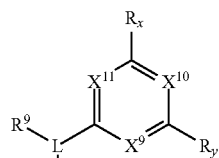
| | Y | | R⁹ | R' |
|---|---|---|---|---|
| Iaaa-407 | S | 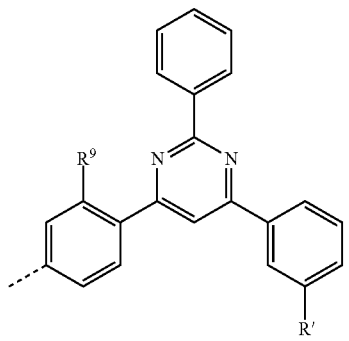 | 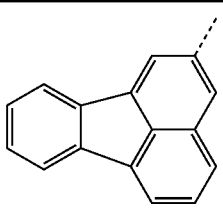 |  |
| Iaaa-408 | S | 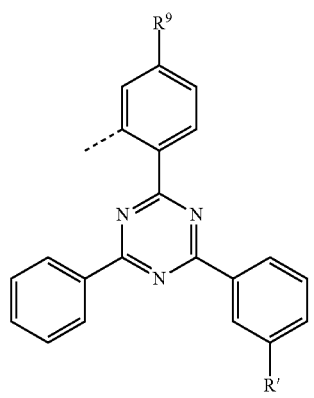 | 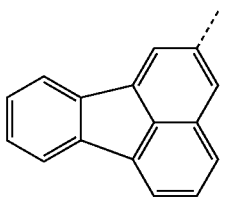 | 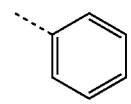 |
| Iaaa-409 | S | 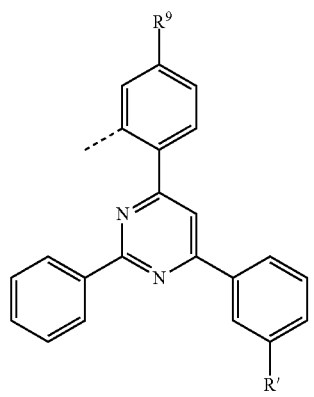 | 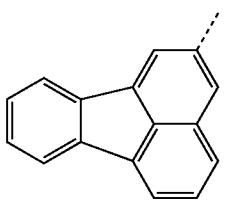 | 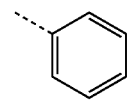 |

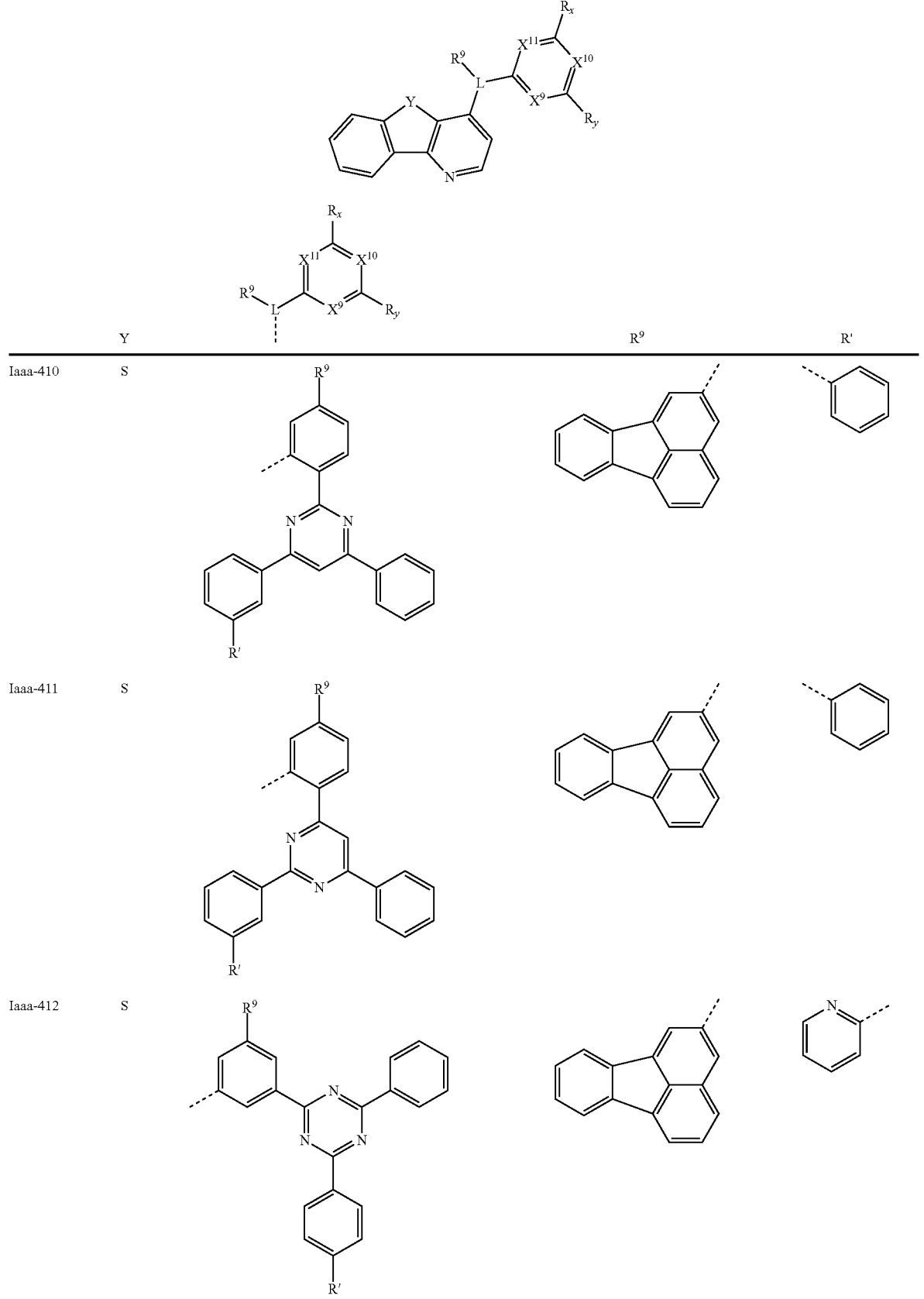

-continued
(Iaaa)
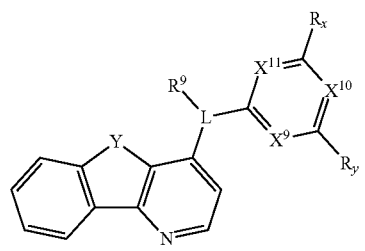
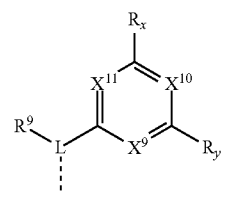
| | Y | | R⁹ | R' |
|---|---|---|---|---|
| Iaaa-413 | S | 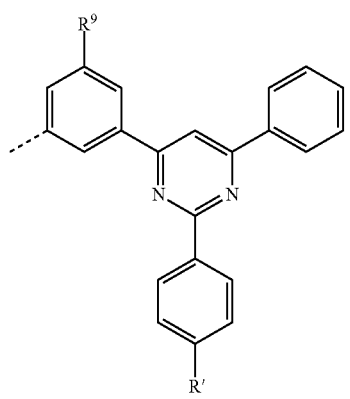 | 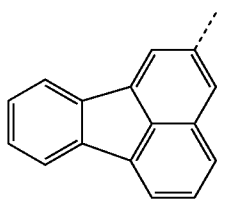 | 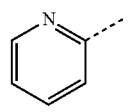 |
| Iaaa-414 | S | 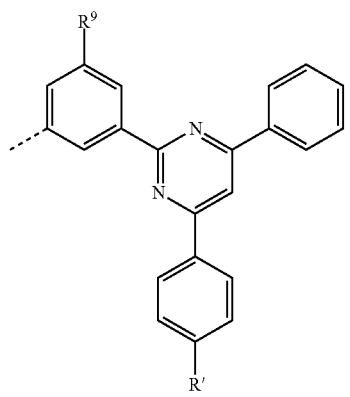 | 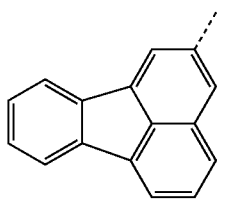 | 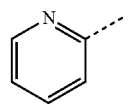 |

-continued
(Iaaa)
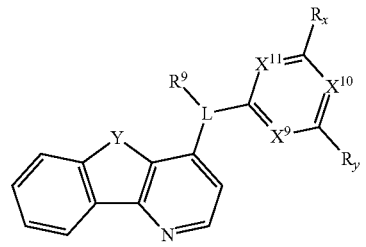
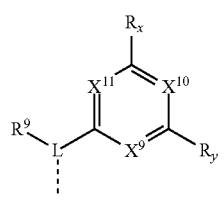
| | Y | R⁹ | R' |
|---|---|---|---|
| Iaaa-415 | S | 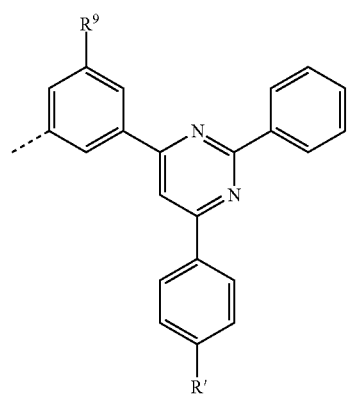 | 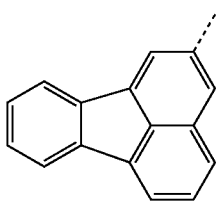 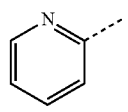 |
| Iaaa-416 | S | 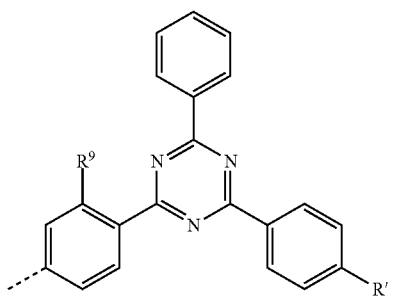 |  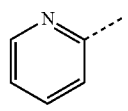 |
| Iaaa-417 | S | 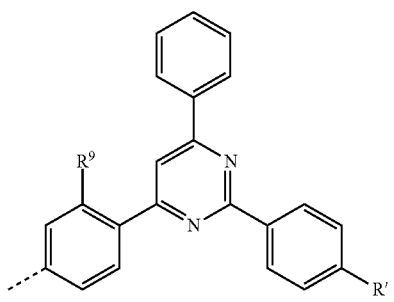 | 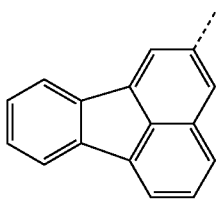 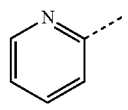 |

-continued
(Iaaa)
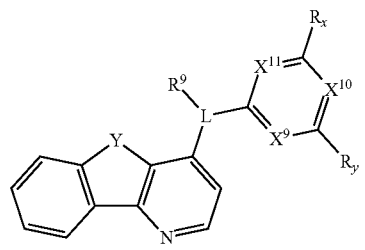
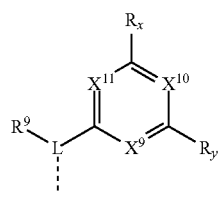
| | Y | R⁹ | R' |
|---|---|---|---|
| Iaaa-418 | S | 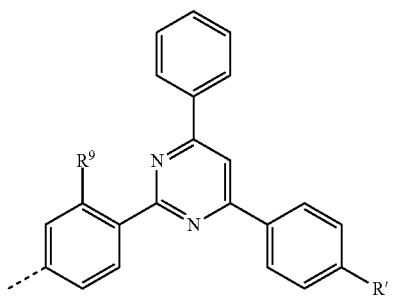 | 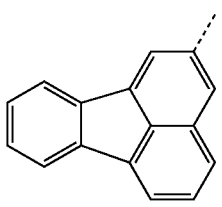 | 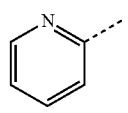 |
| Iaaa-419 | S |  |  | 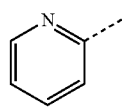 |
| Iaaa-420 | S | 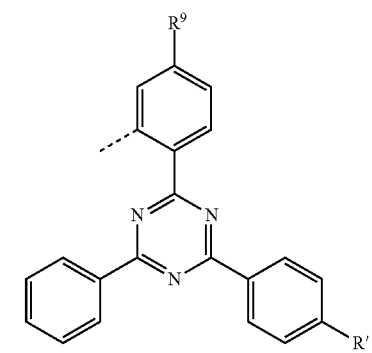 | 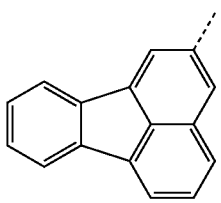 | 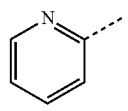 |

-continued
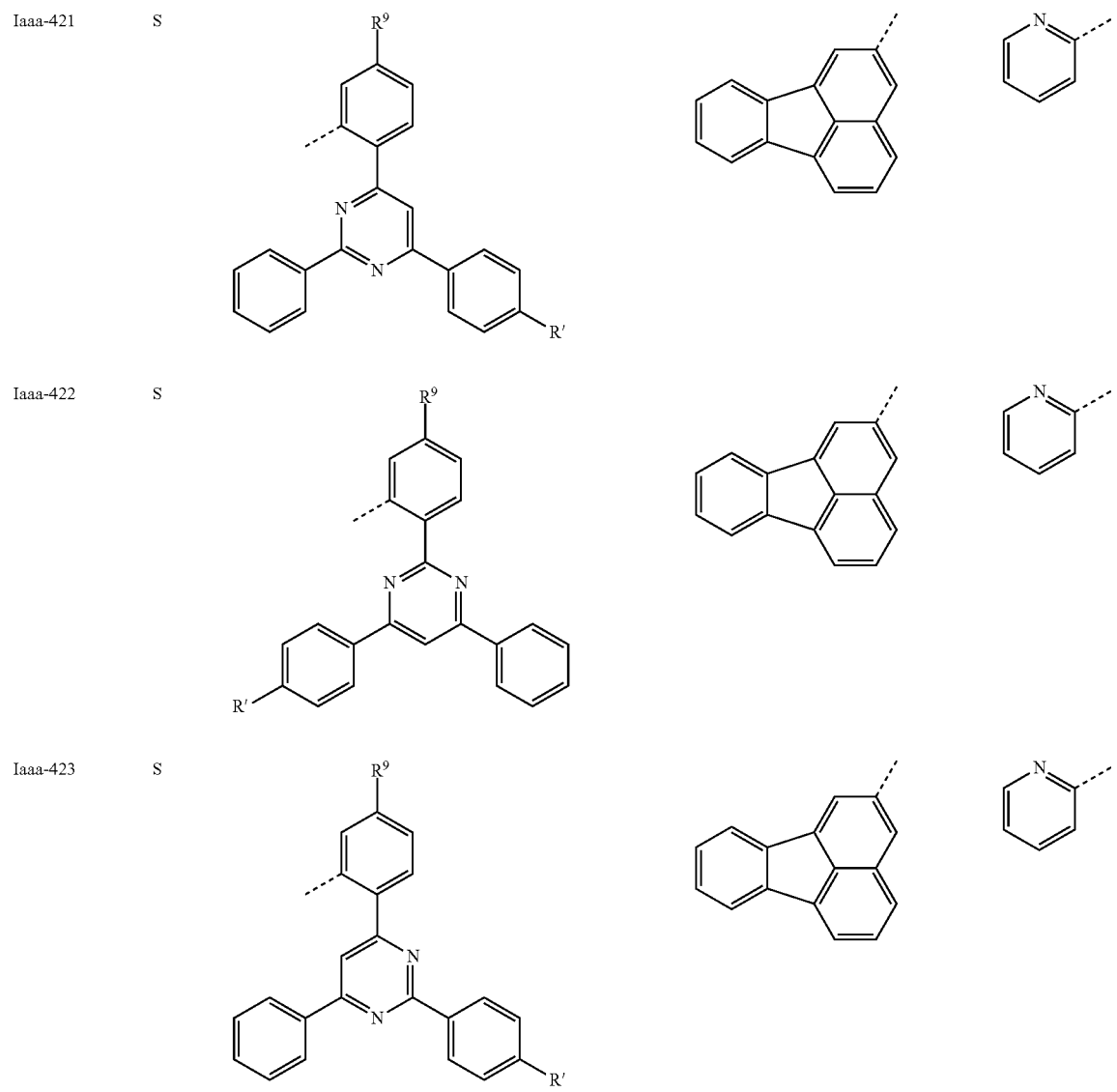

-continued
(Iaaa)
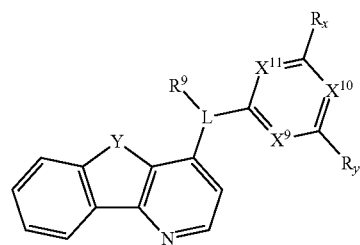
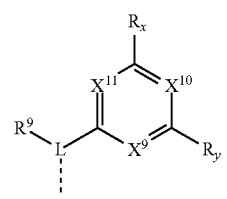
| | Y | | R⁹ | R' |
|---|---|---|---|---|
| Iaaa-424 | S | 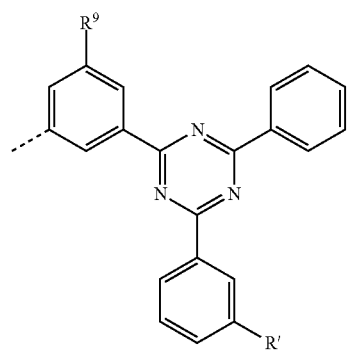 | 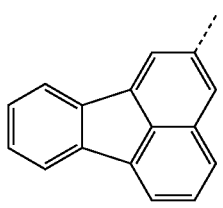 | 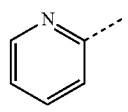 |
| Iaaa-425 | S | 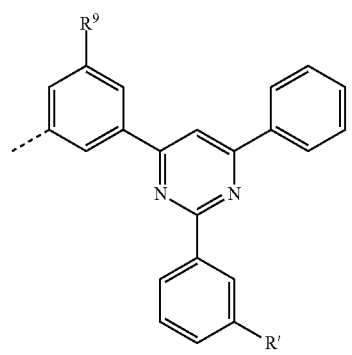 | 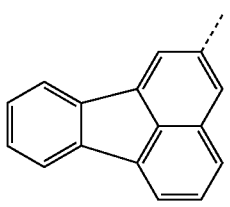 | 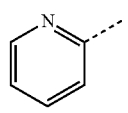 |
| Iaaa-426 | S | 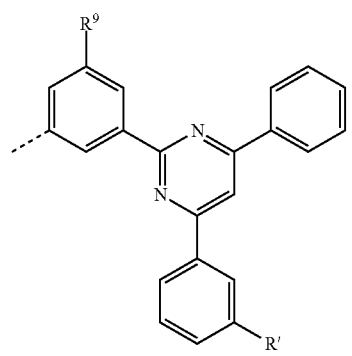 | 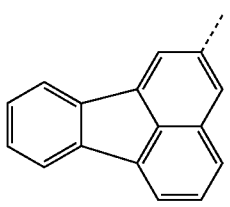 | 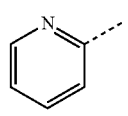 |

-continued
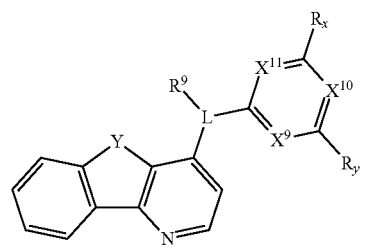
(Iaaa)
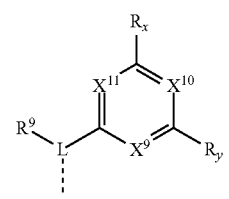
| | Y | R⁹ | R' |
|---|---|---|---|
| Iaaa-427 | S | 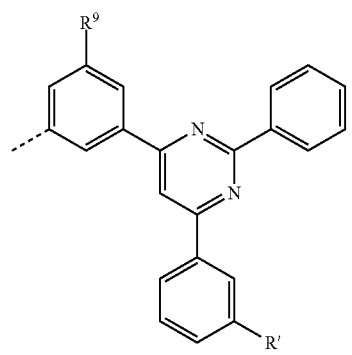 | 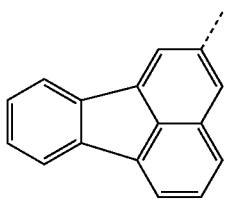 | 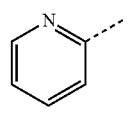 |
| Iaaa-428 | S | 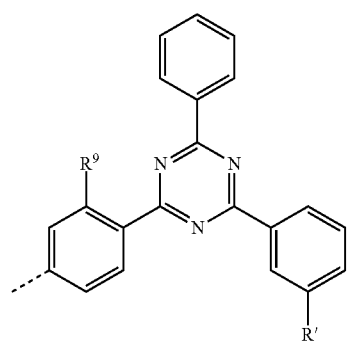 |  | 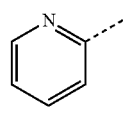 |
| Iaaa-429 | S | 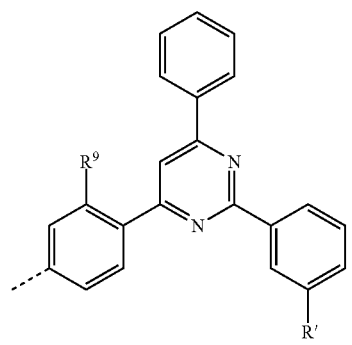 | 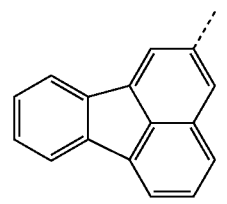 | 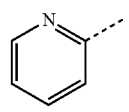 |

-continued
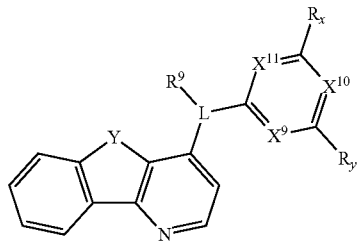
(Iaaa)
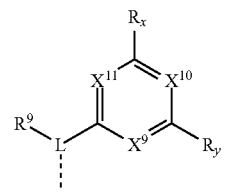
| | Y | | R⁹ | R' |
|---|---|---|---|---|
| Iaaa-430 | S | 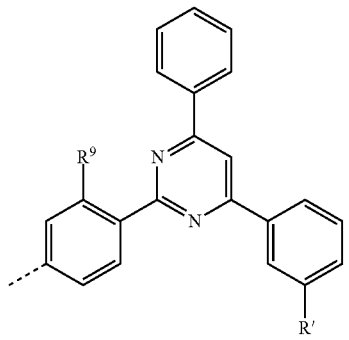 |  |  |
| Iaaa-431 | S | 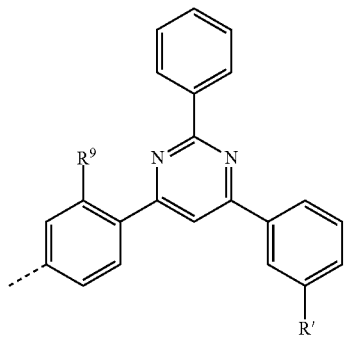 | 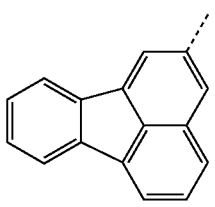 | 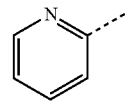 |
| Iaaa-432 | S | 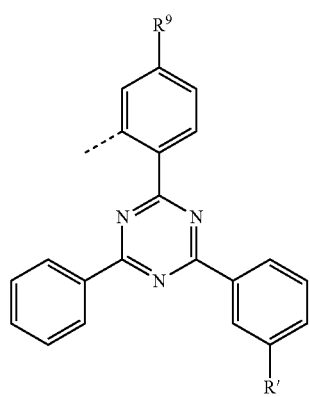 | 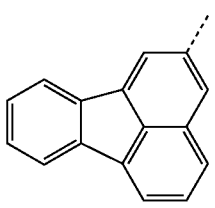 | 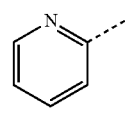 |

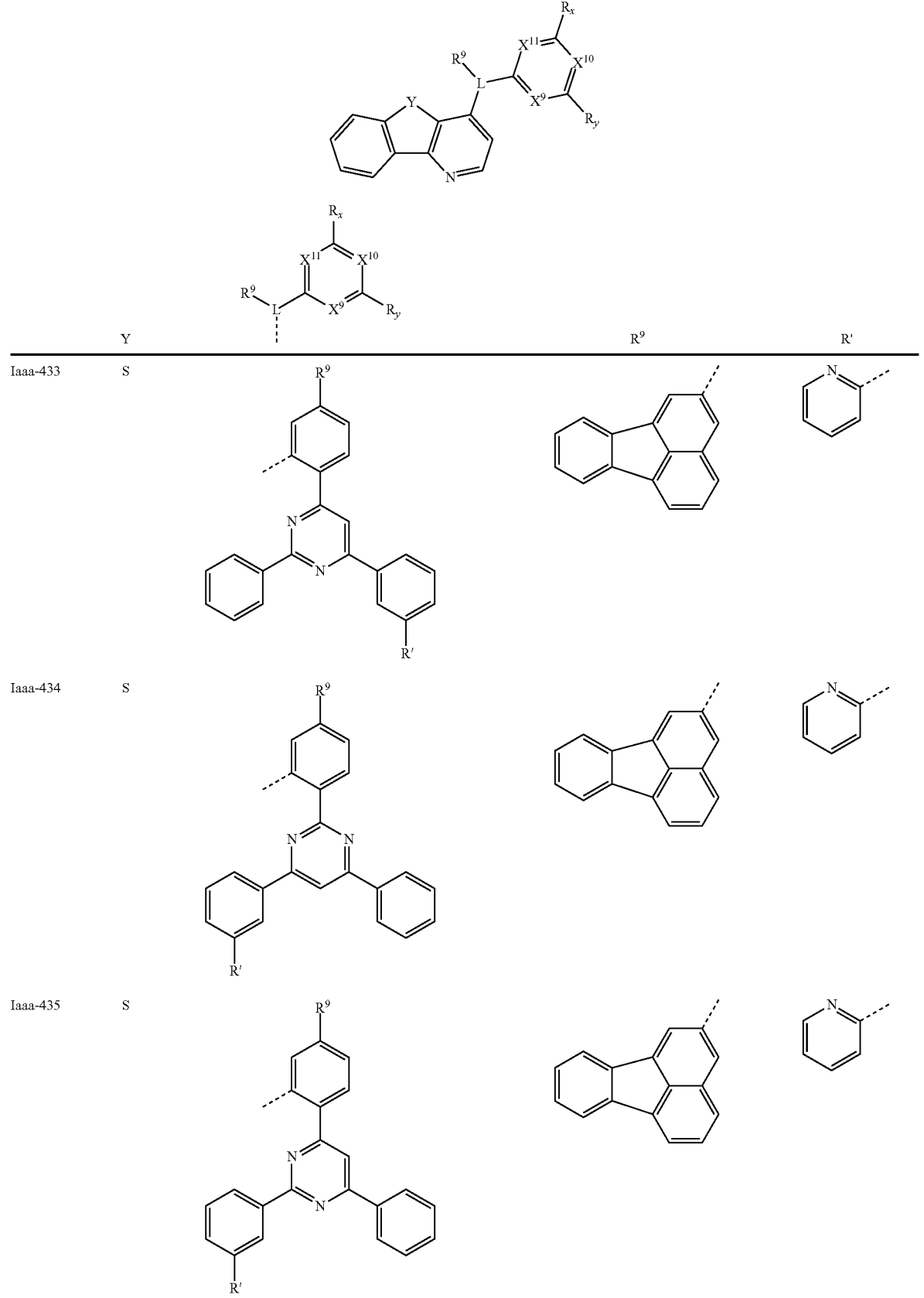

-continued
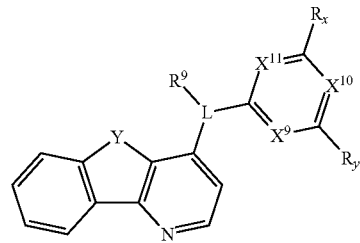
(Iaaa)

| | Y | | R⁹ | R' |
|---|---|---|---|---|
| Iaaa-436 | S | 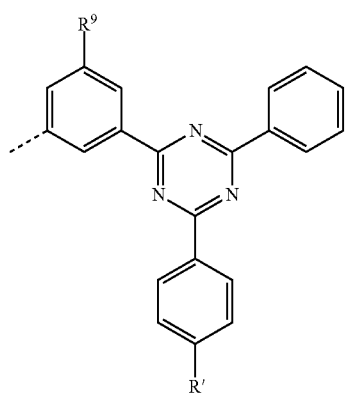 | 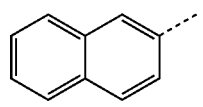 | H |
| Iaaa-437 | S | 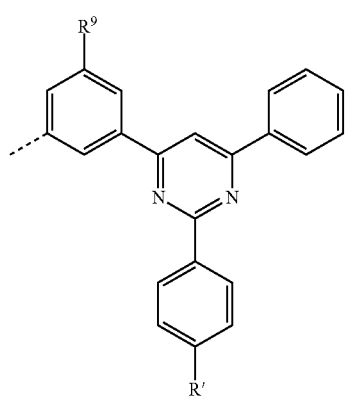 | 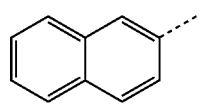 | H |

-continued
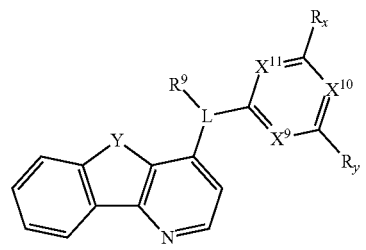
(Iaaa)
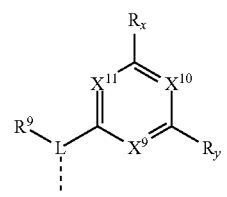
| | Y | | R⁹ | R' |
|---|---|---|---|---|
| Iaaa-438 | S | 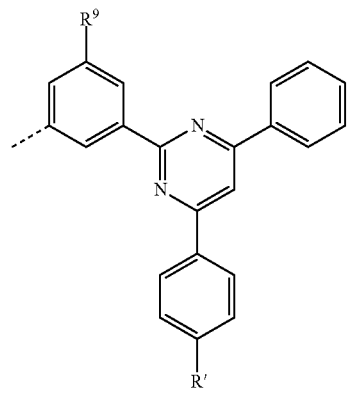 | 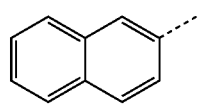 | H |
| Iaaa-439 | S | 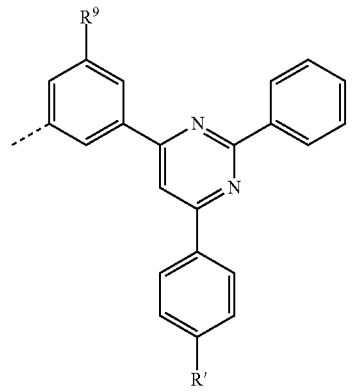 | 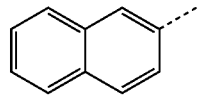 | H |
| Iaaa-440 | S | 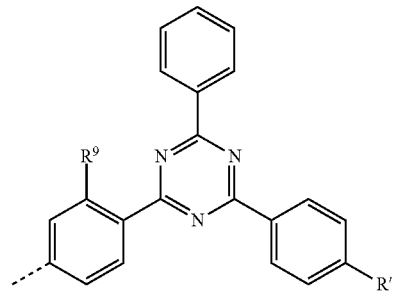 | 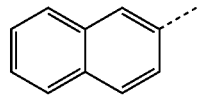 | H |

(Iaaa)
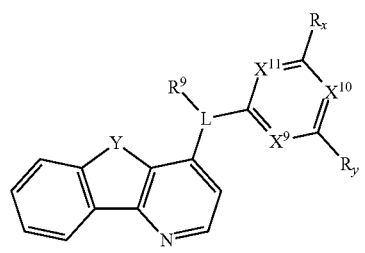
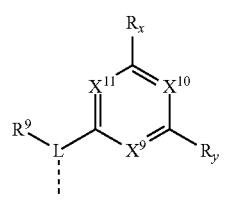
| | Y | R⁹ | R' |
|---|---|---|---|
| Iaaa-441 | S | 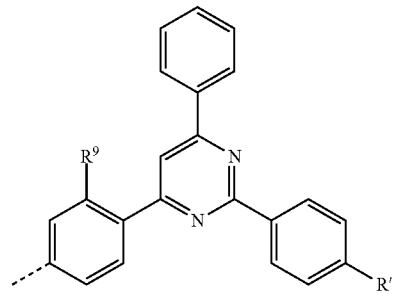  |  H |
| Iaaa-442 | S | 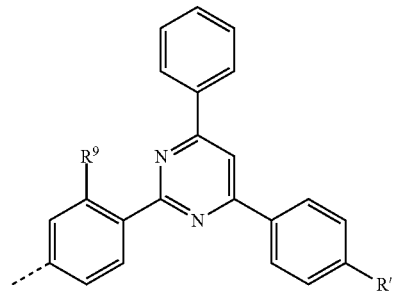  |  H |
| Iaaa-443 | S | 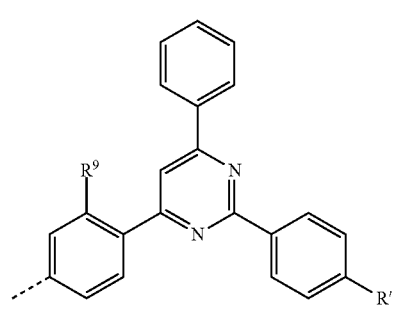 |  H |

(Iaaa)
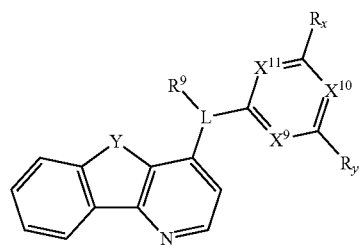
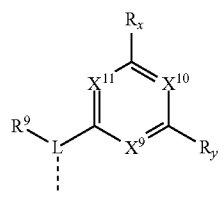
| | Y | R⁹ | R' |
|---|---|---|---|
| Iaaa-444 | S | 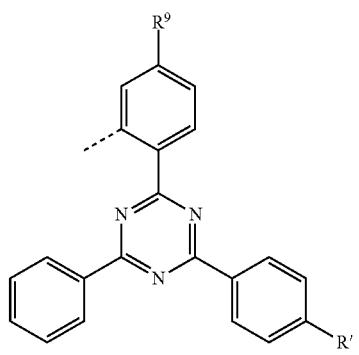 |  | H |
| Iaaa-445 | S | 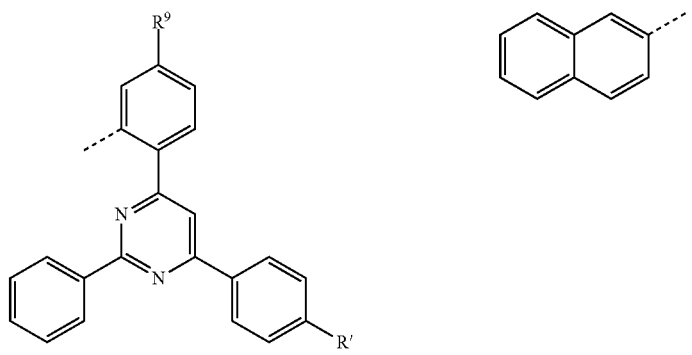 |  | H |
| Iaaa-446 | S | 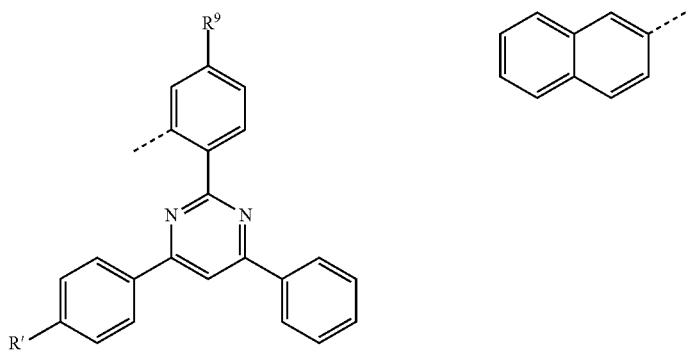 |  | H |

-continued
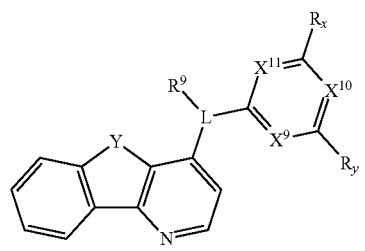
(Iaaa)
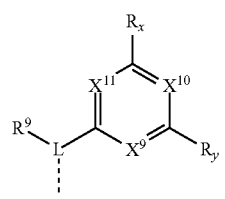
| | Y | R⁹ | R' |
|---|---|---|---|
| Iaaa-447 | S | 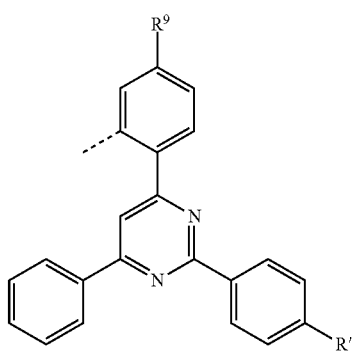 | 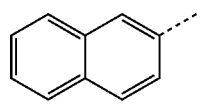 H |
| Iaaa-448 | S | 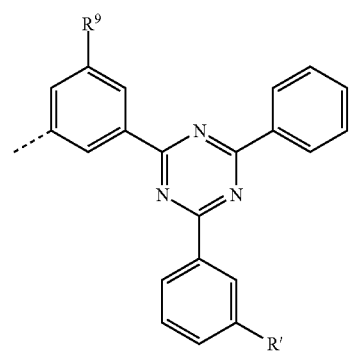 |  H |
| Iaaa-449 | S | 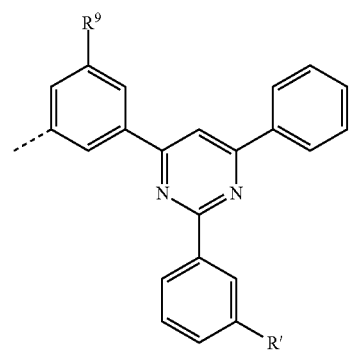 | 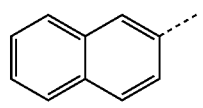 H |

(Iaaa)
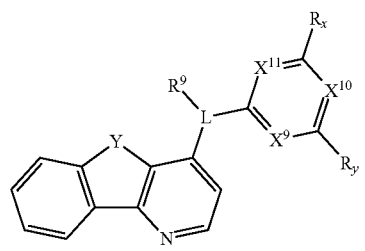
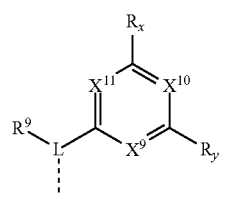
| | Y | | R⁹ | R' |
|---|---|---|---|---|
| Iaaa-450 | S | 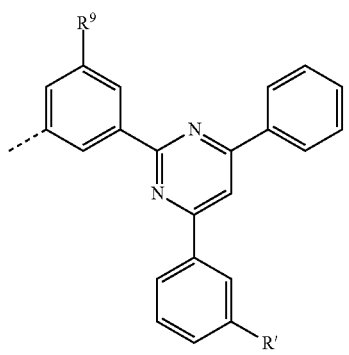 | 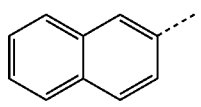 | H |
| Iaaa-451 | S | 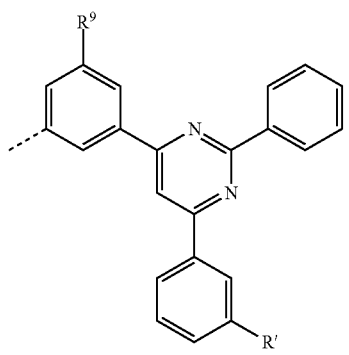 | 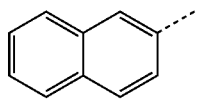 | H |
| Iaaa-452 | S | 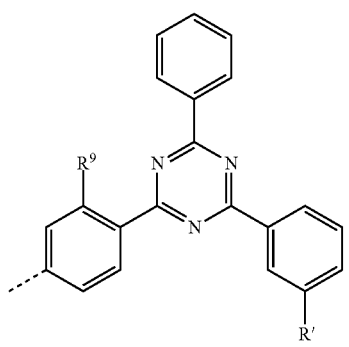 | 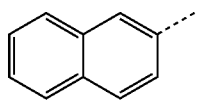 | H |

-continued
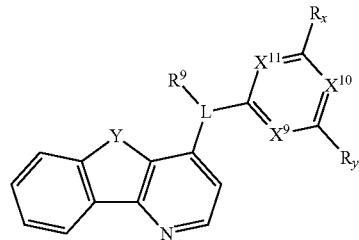
(Iaaa)
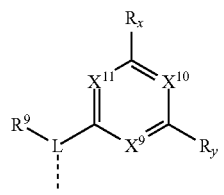
| | Y | R⁹ | R' |
|---|---|---|---|
| Iaaa-453 | S |  | 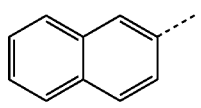 | H |
| Iaaa-454 | S |  | 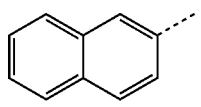 | H |
| Iaaa-455 | S | 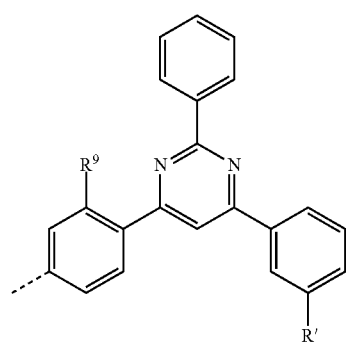 | 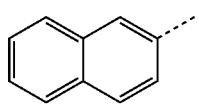 | H |

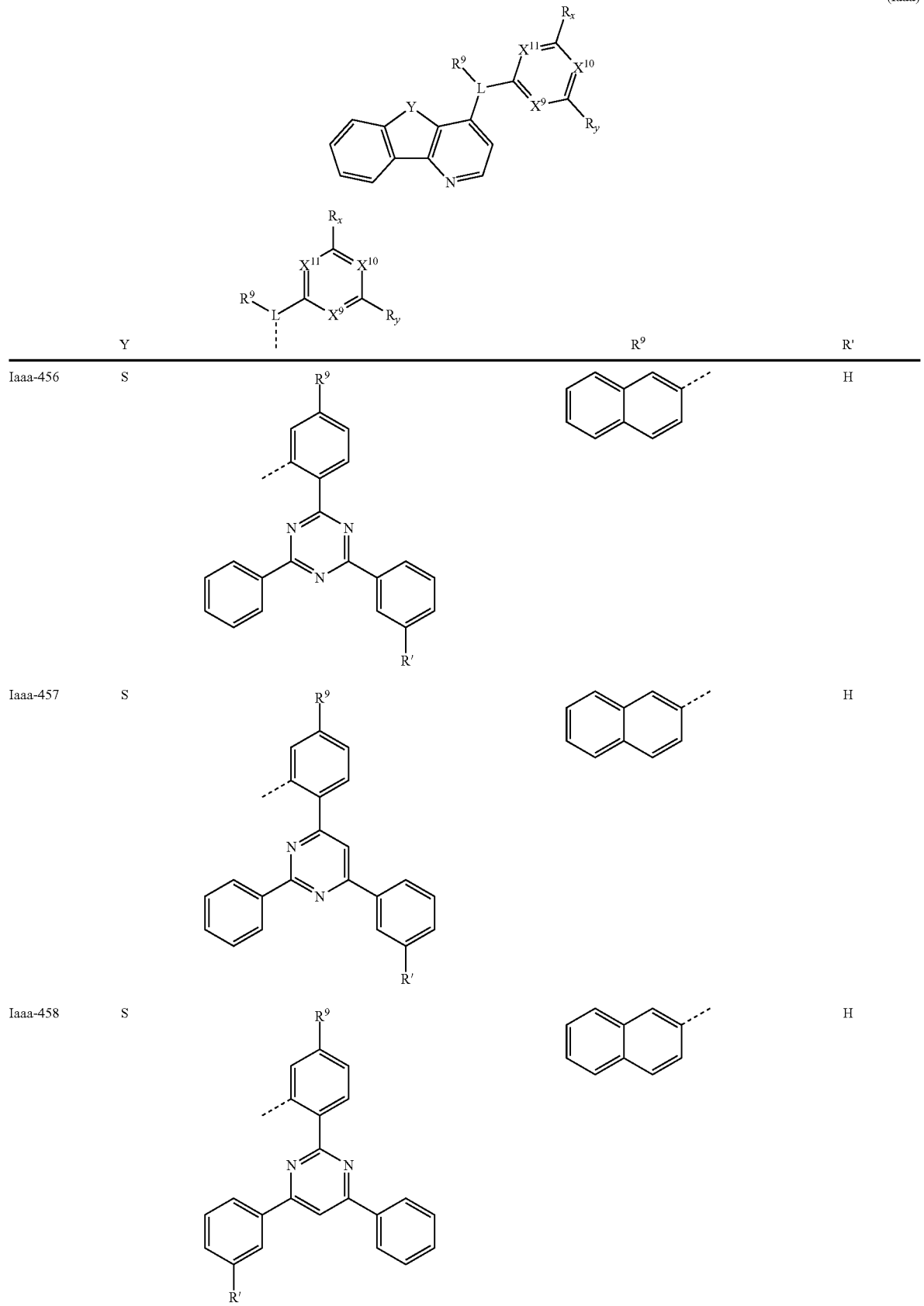

-continued
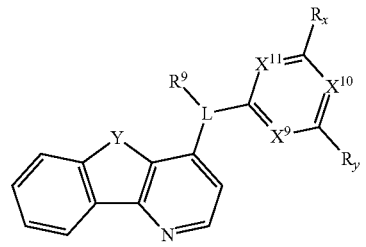
(Iaaa)
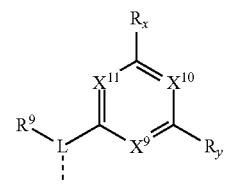
| | Y | | $R^9$ | R' |
|---|---|---|---|---|
| Iaaa-459 | S | 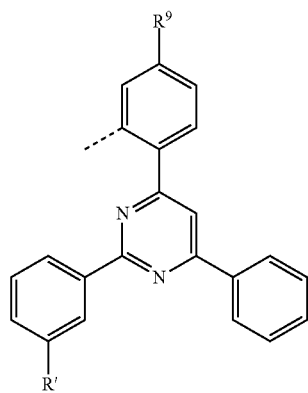 | 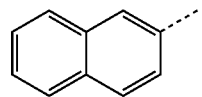 | — |
| Iaaa-460 | S | 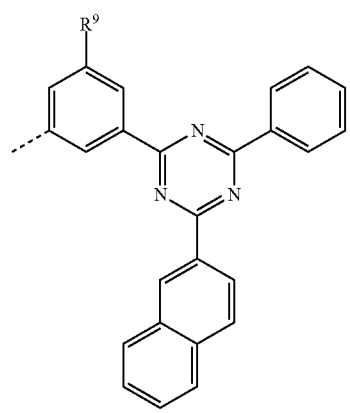 | 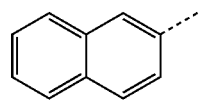 | — |

-continued
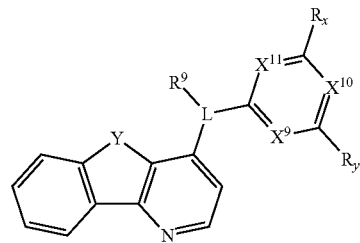
(Iaaa)
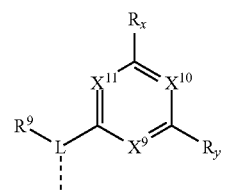
| | Y | | R⁹ | R' |
|---|---|---|---|---|
| Iaaa-461 | S | 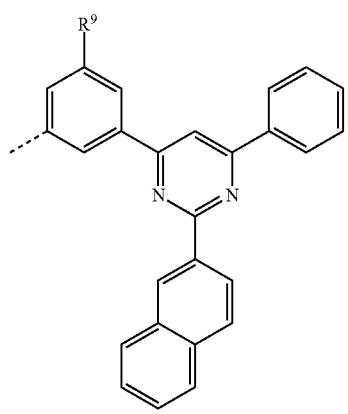 | 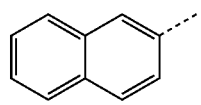 | — |
| Iaaa-462 | S | 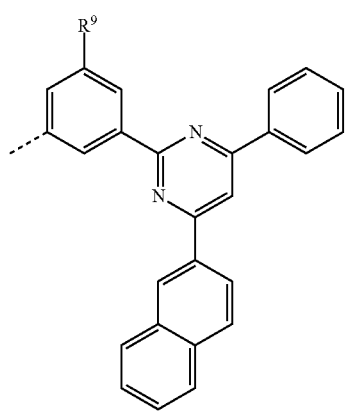 | 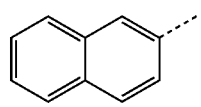 | — |

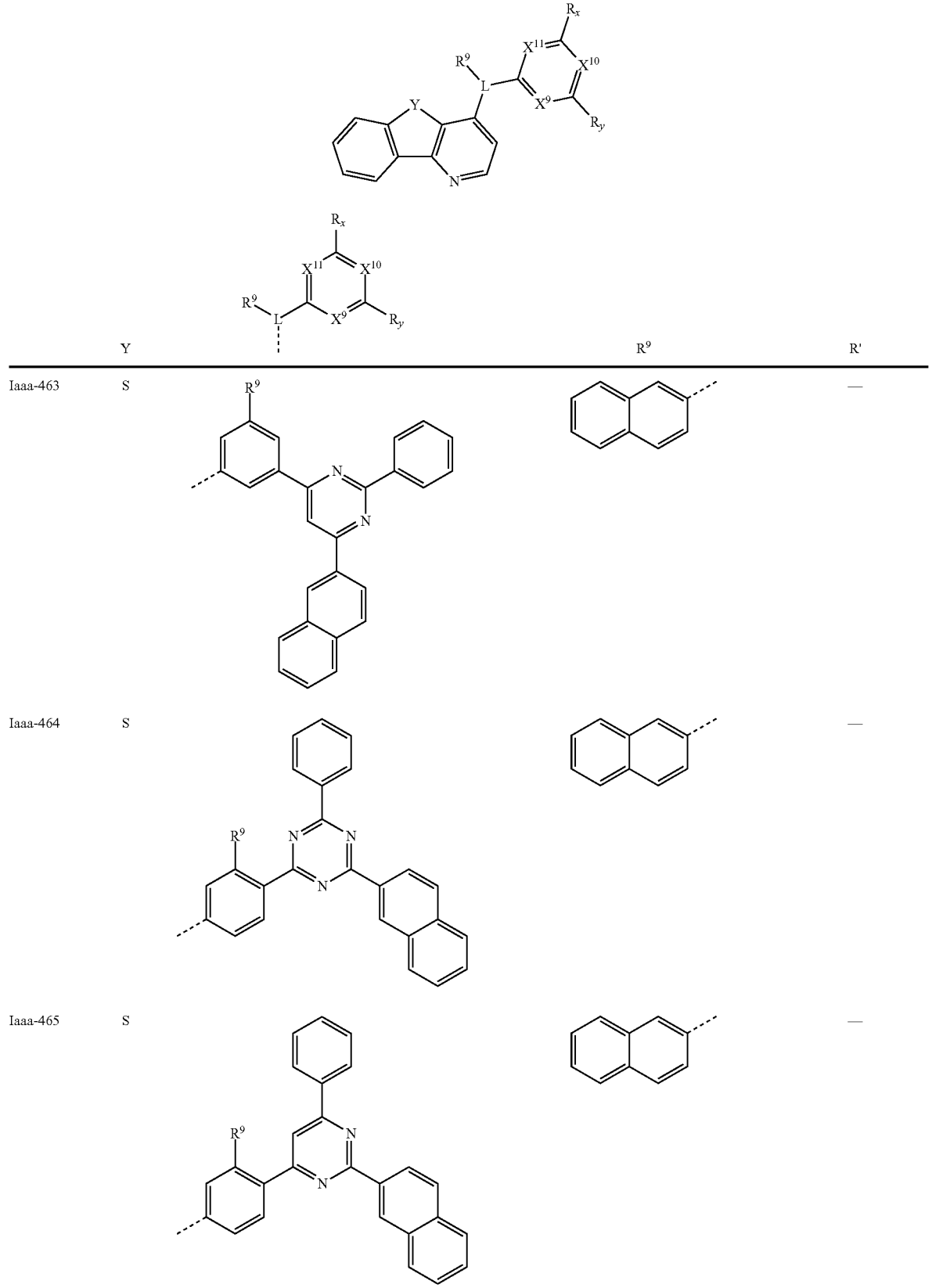

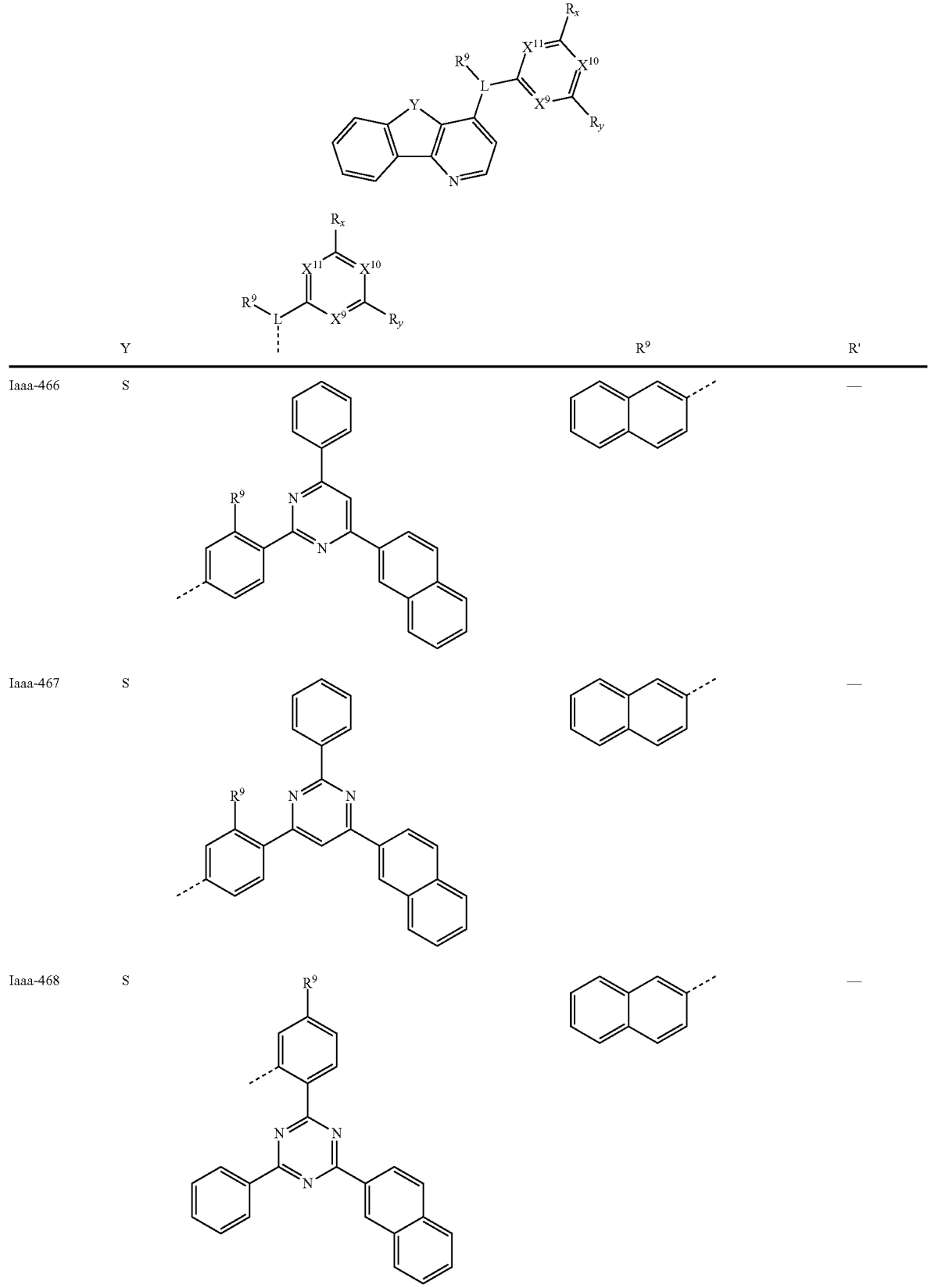

-continued
(Iaaa)
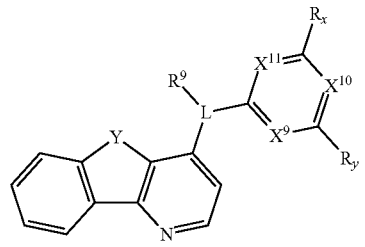
| | Y | R⁹ | R' |
|---|---|---|---|
| Iaaa-469 | S | 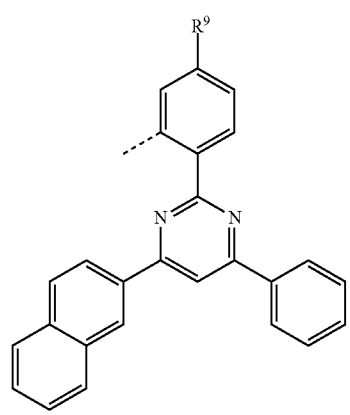 |  — |
| Iaaa-470 | S | 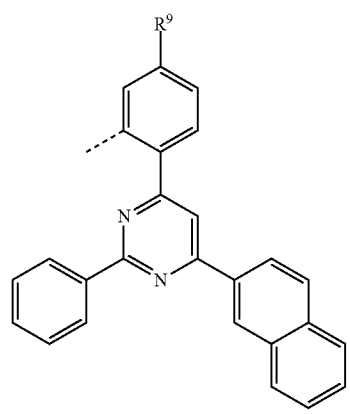 | 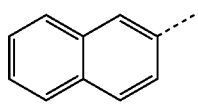 — |

-continued
(Iaaa)
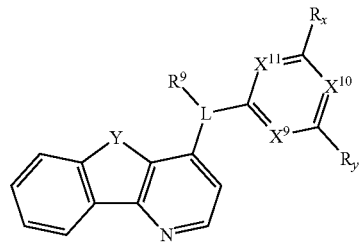
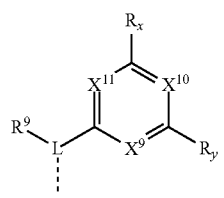
| | Y | | R⁹ | R' |
|---|---|---|---|---|
| Iaaa-471 | S | 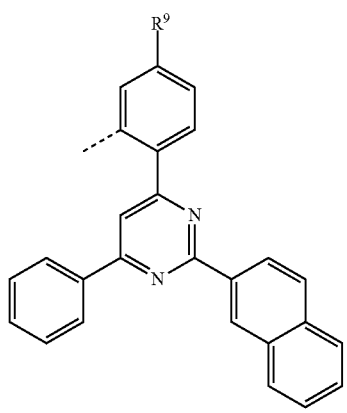 | 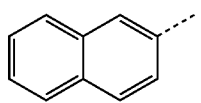 | — |
| Iaaa-472 | S | 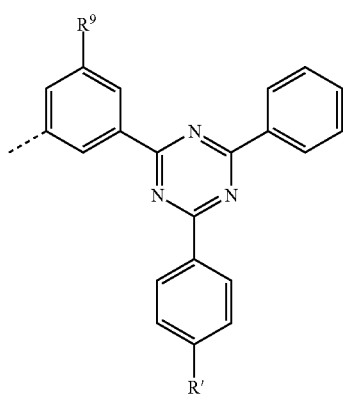 | 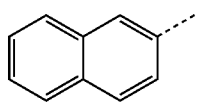 | 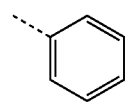 |

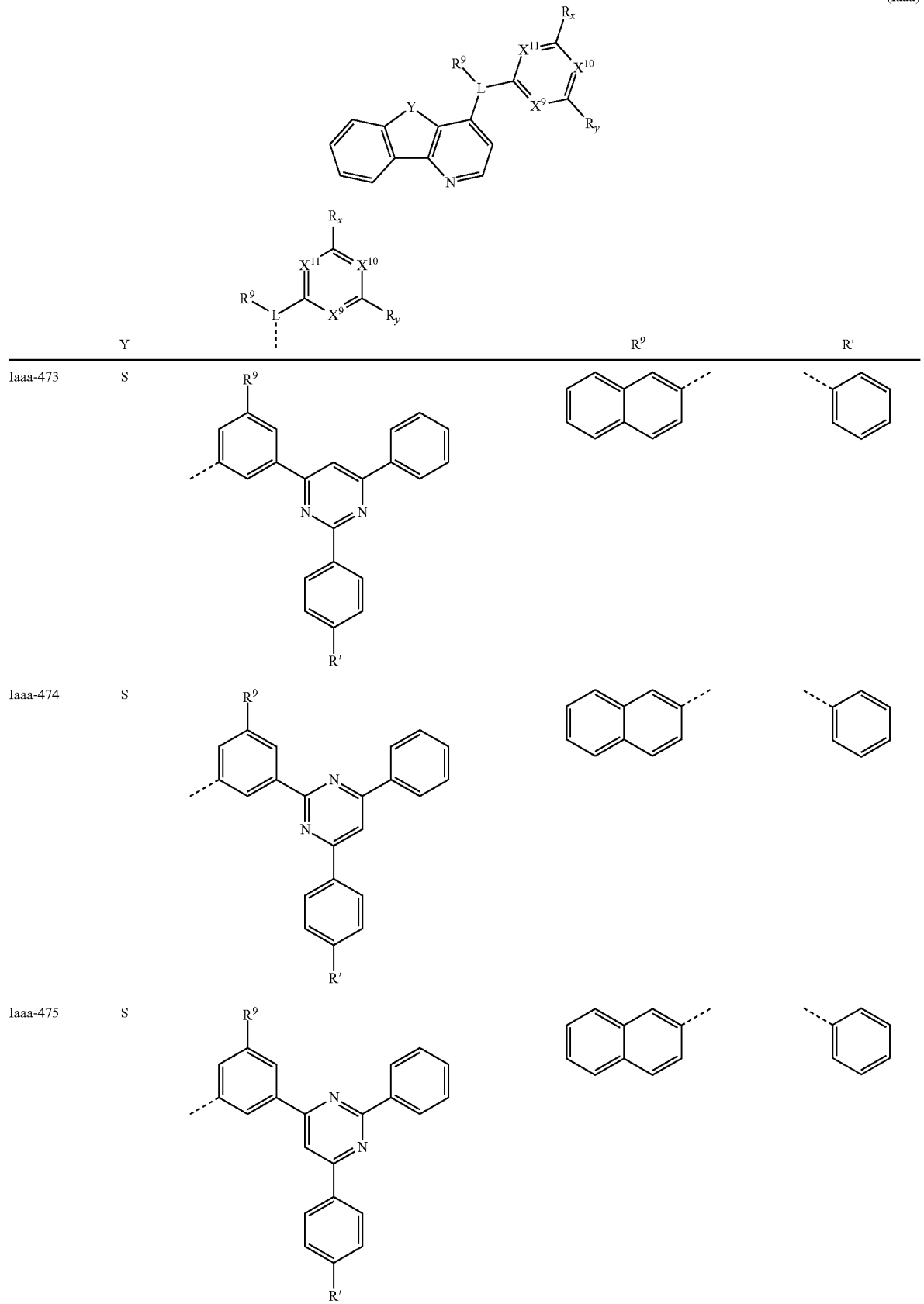

-continued
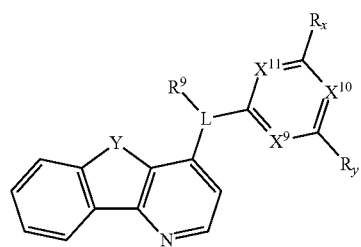
(Iaaa)
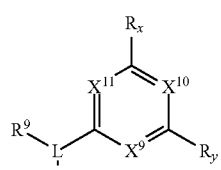
| | Y | R⁹ | R' |
|---|---|---|---|
| Iaaa-476 | S | 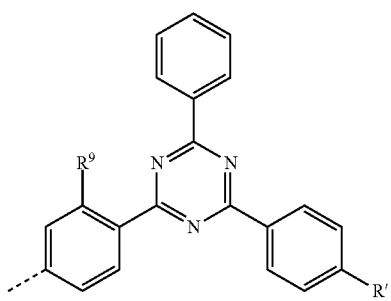 | 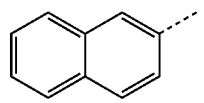 | 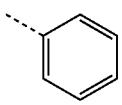 |
| Iaaa-477 | S | 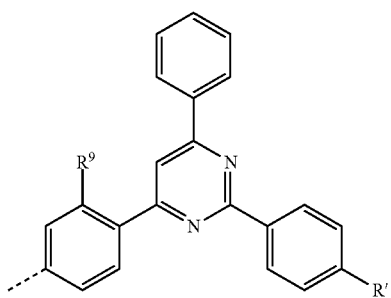 | 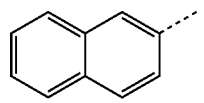 | 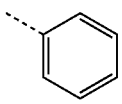 |
| Iaaa-478 | S | 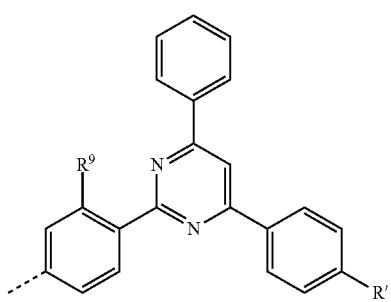 | 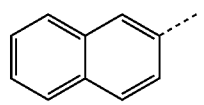 |  |

-continued
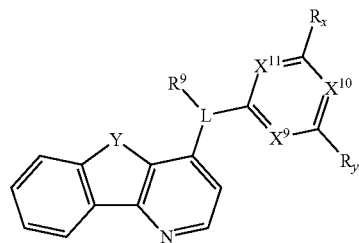
(Iaaa)
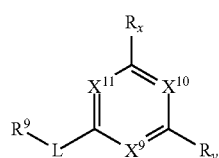
| | Y | | R⁹ | R' |
|---|---|---|---|---|
| Iaaa-479 | S | 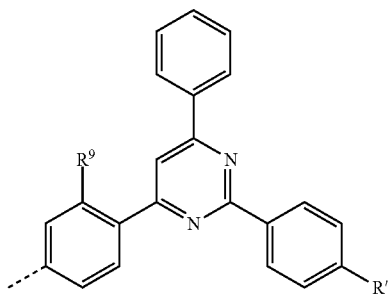 | 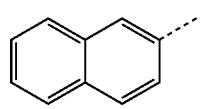 | 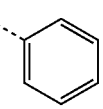 |
| Iaaa-480 | S | 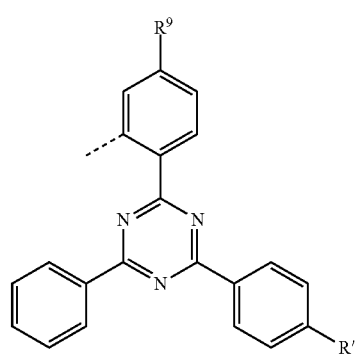 | 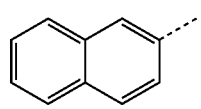 |  |
| Iaaa-481 | S | 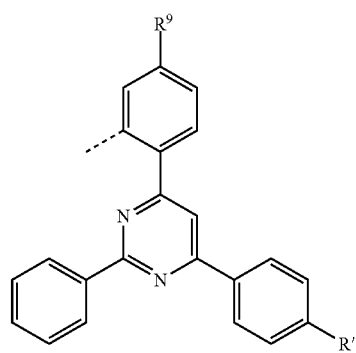 | 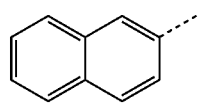 |  |

-continued
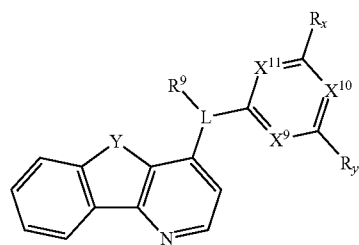
(Iaaa)
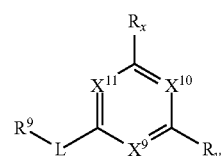
| | Y | | R⁹ | R' |
|---|---|---|---|---|
| Iaaa-482 | S | 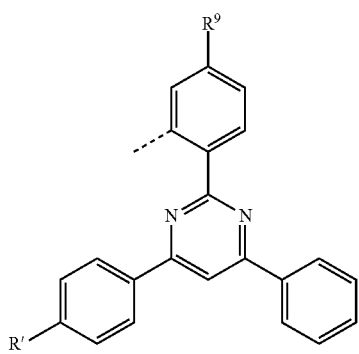 | 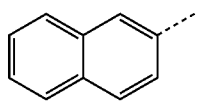 | 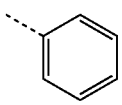 |
| Iaaa-483 | S | 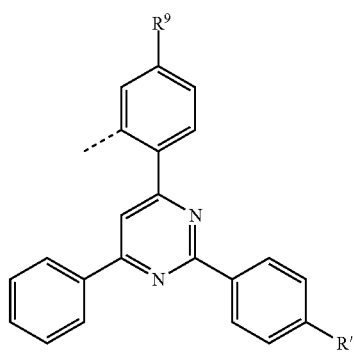 | 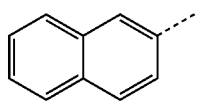 | 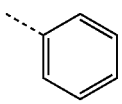 |
| Iaaa-484 | S | 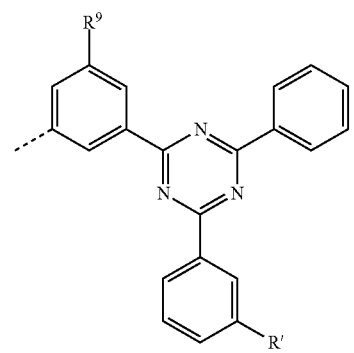 | 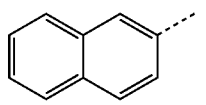 | 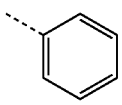 |

-continued
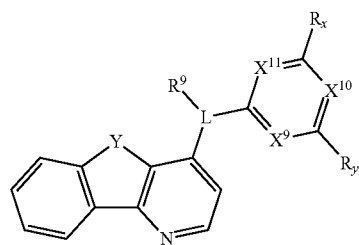
(Iaaa)
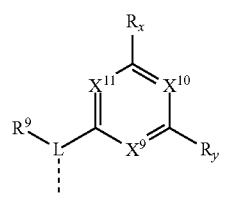
| | Y | R⁹ | R' |
|---|---|---|---|
| Iaaa-485 | S | 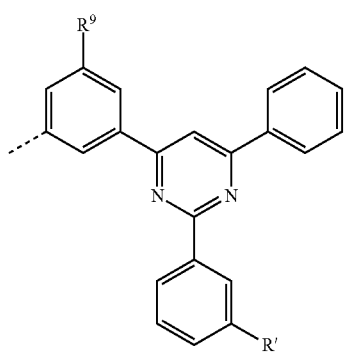 | 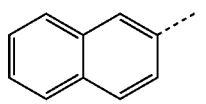 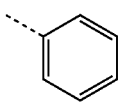 |
| Iaaa-486 | S | 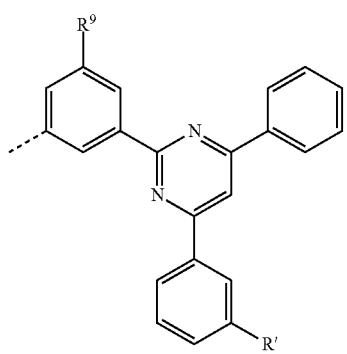 | 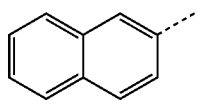 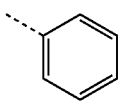 |
| Iaaa-487 | S | 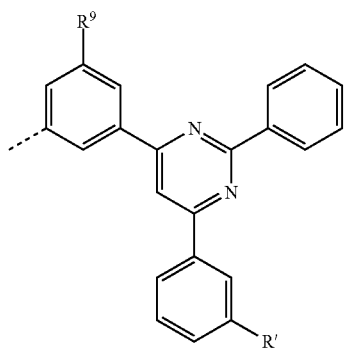 | 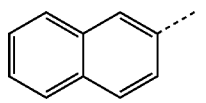  |

-continued
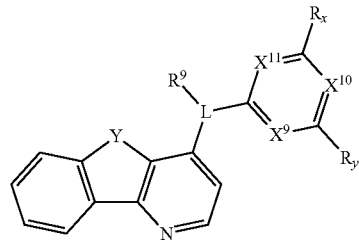
(Iaaa)
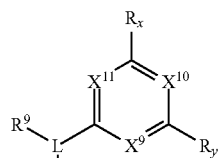
| | Y | | R⁹ | R' |
|---|---|---|---|---|
| Iaaa-488 | S | 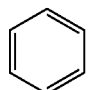 | 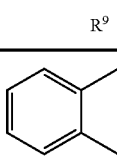 | 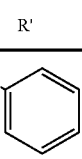 |
| Iaaa-489 | S | 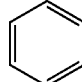 | 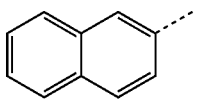 | 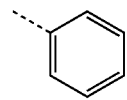 |
| Iaaa-490 | S | 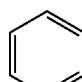 | 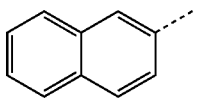 | 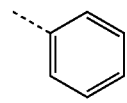 |
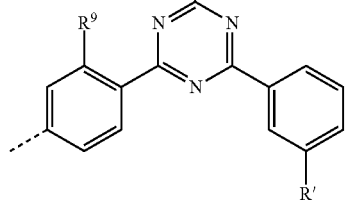
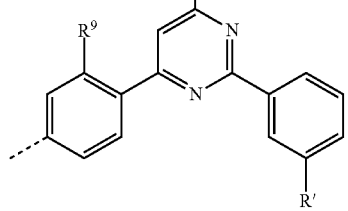
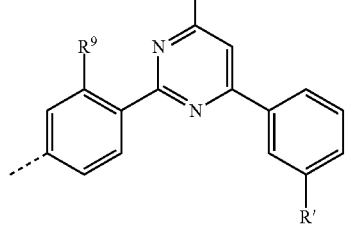

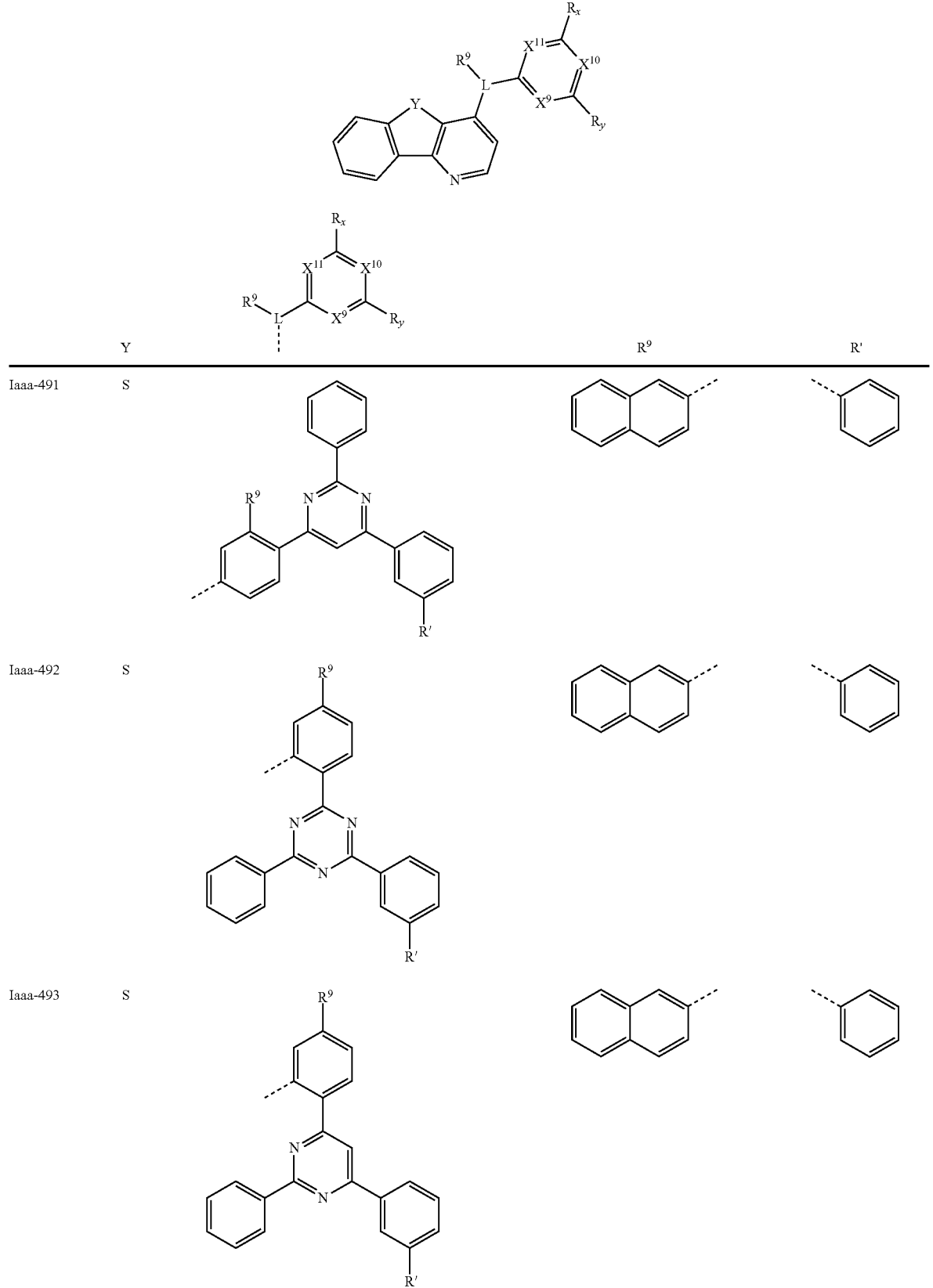

-continued
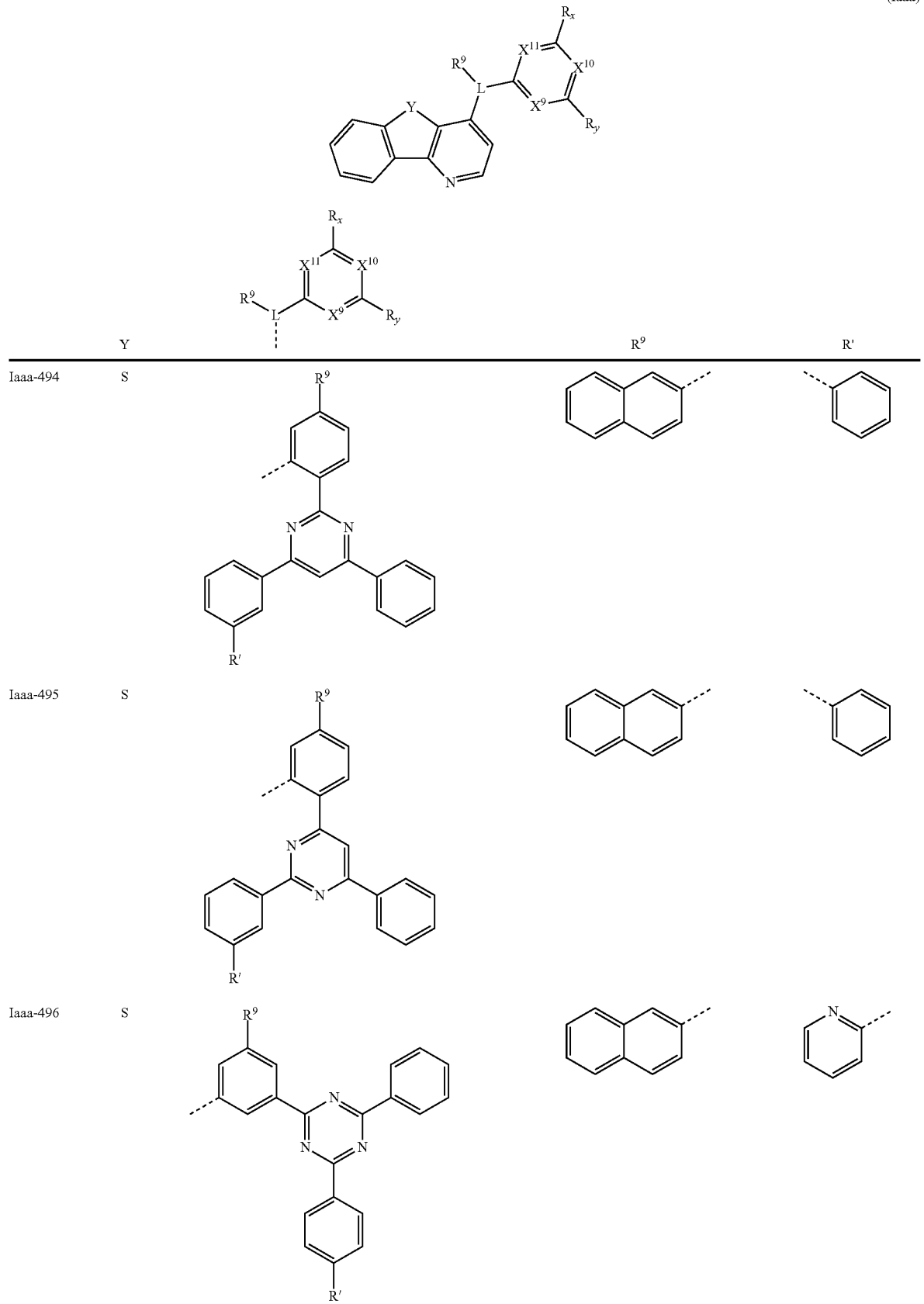

-continued
(Iaaa)
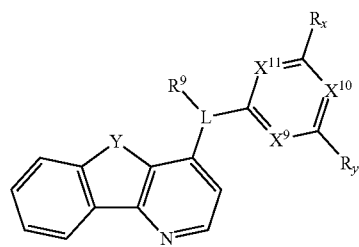
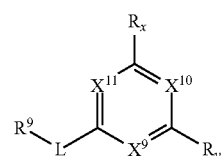
| | Y | | R⁹ | R' |
|---|---|---|---|---|
| Iaaa-497 | S | 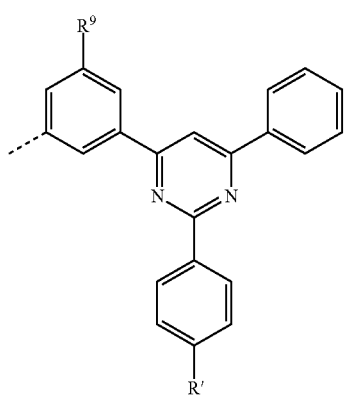 | 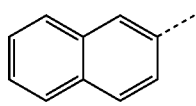 | 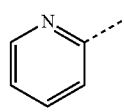 |
| Iaaa-498 | S | 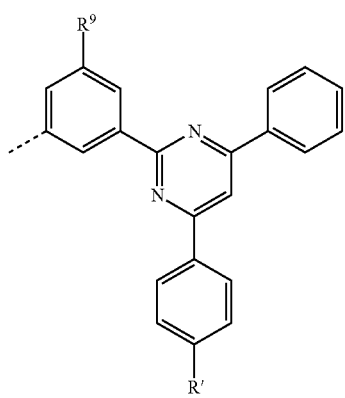 | 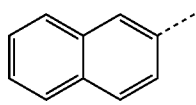 | 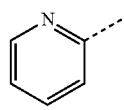 |

-continued
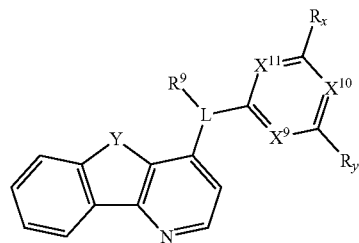
(Iaaa)
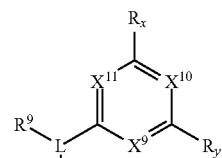
| | Y | R⁹ | R' |
|---|---|---|---|
| Iaaa-499 | S | 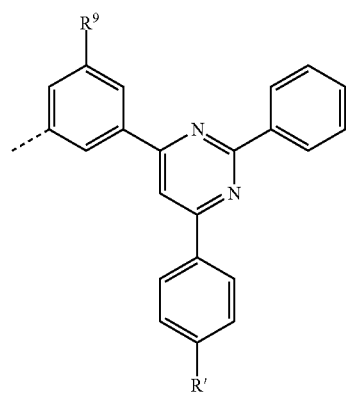 | 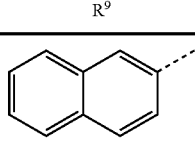 | 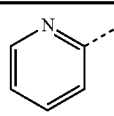 |
| Iaaa-500 | S | 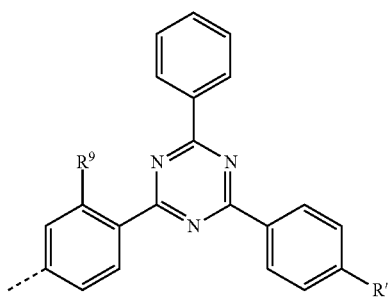 | 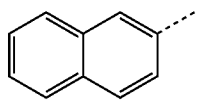 | 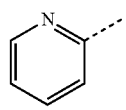 |
| Iaaa-501 | S | 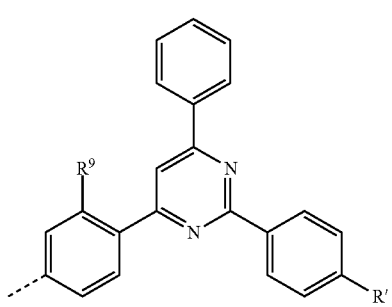 | 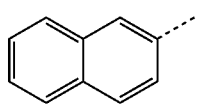 | 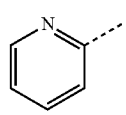 |

-continued
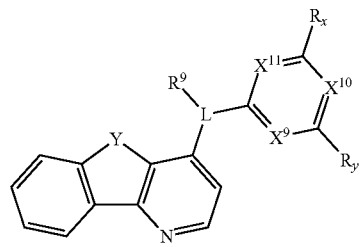
(Iaaa)
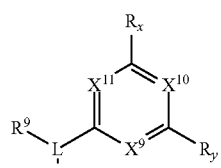
| | Y | R⁹ | R' |
|---|---|---|---|
| Iaaa-502 | S | 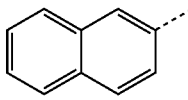 | 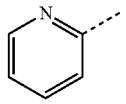 |
| |  | | |
| Iaaa-503 | S | 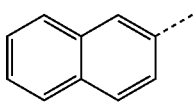 | 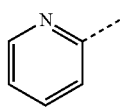 |
| | 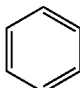 | | |
| Iaaa-504 | S | 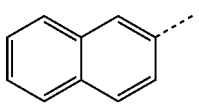 | 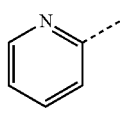 |
| | 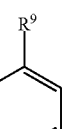 | | |

-continued
(Iaaa)
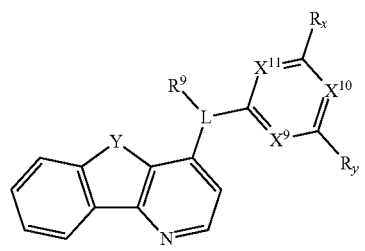
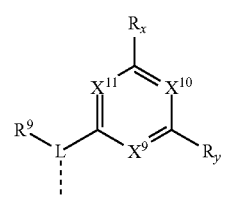
| | Y | | $R^9$ | $R'$ |
|---|---|---|---|---|
| Iaaa-505 | S | 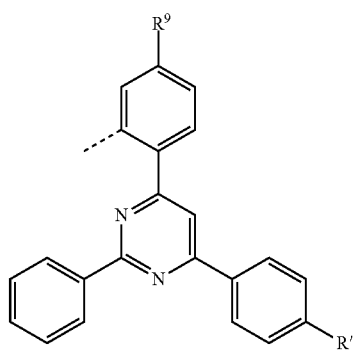 | 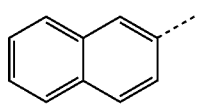 | 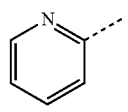 |
| Iaaa-506 | S | 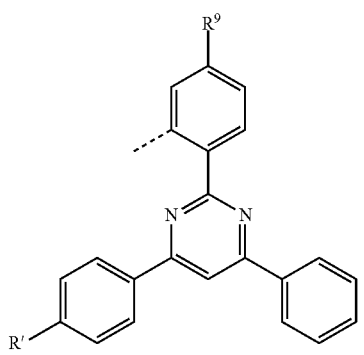 | 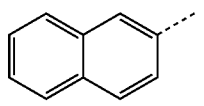 | 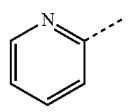 |
| Iaaa-507 | S | 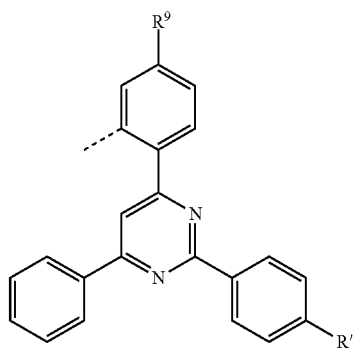 | 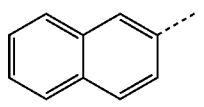 | 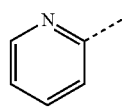 |

-continued
(Iaaa)
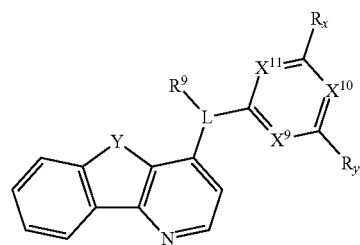
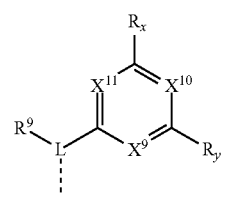
| | Y | R⁹ | R' |
|---|---|---|---|
| Iaaa-508 | S | 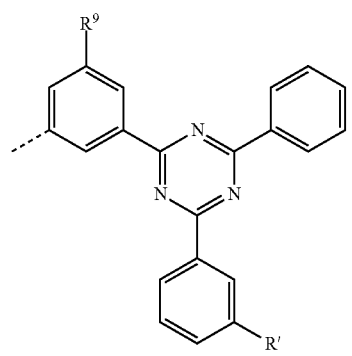 | 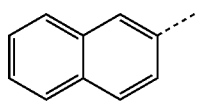 | 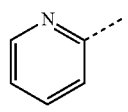 |
| Iaaa-509 | S | 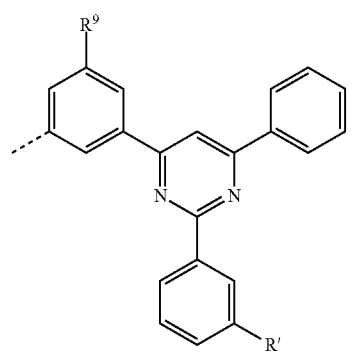 | 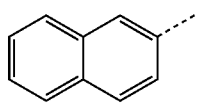 |  |
| Iaaa-510 | S | 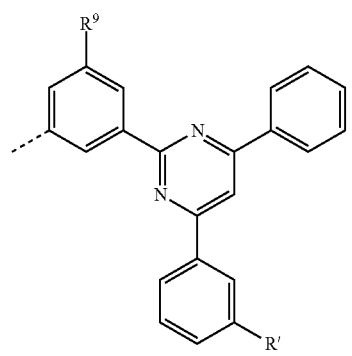 | 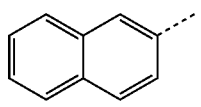 |  |

-continued
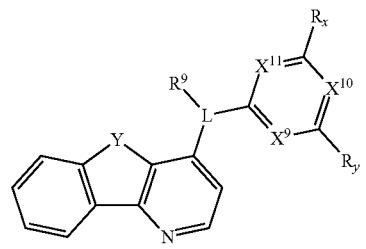
(Iaaa)
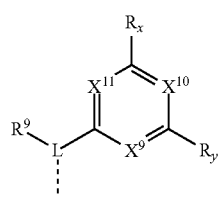
| | Y | | R⁹ | R' |
|---|---|---|---|---|
| Iaaa-511 | S | 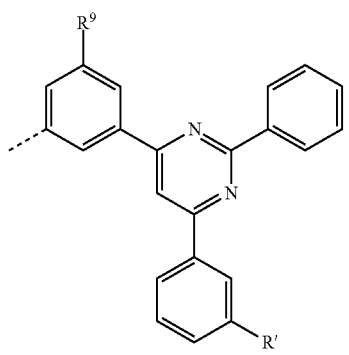 | 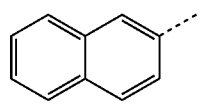 | 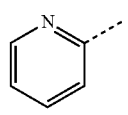 |
| Iaaa-512 | S | 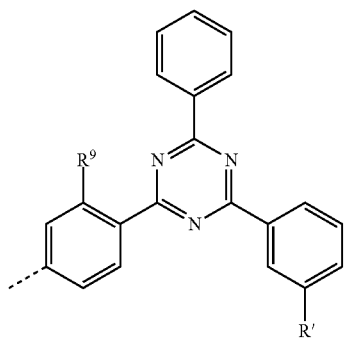 | 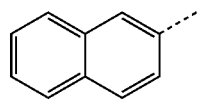 | 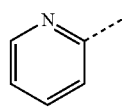 |
| Iaaa-513 | S | 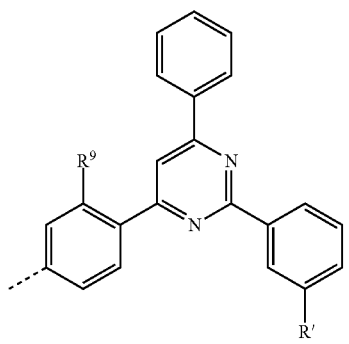 | 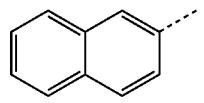 | 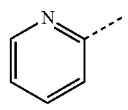 |

-continued
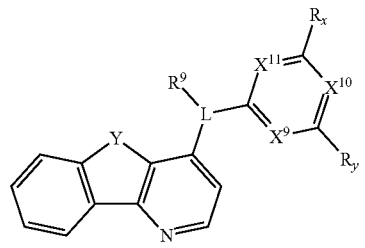
(Iaaa)
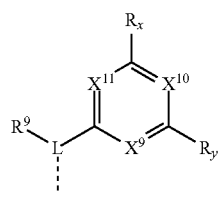
| | Y | | R⁹ | R' |
|---|---|---|---|---|
| Iaaa-514 | S |  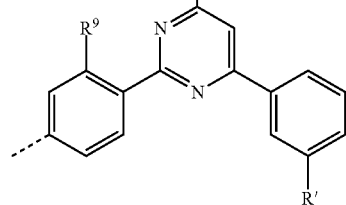 | 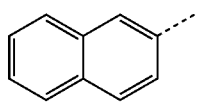 | 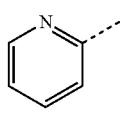 |
| Iaaa-515 | S |  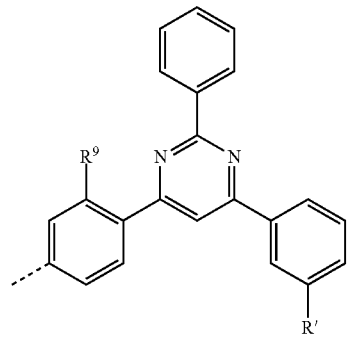 | 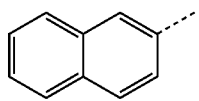 | 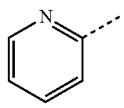 |
| Iaaa-516 | S |  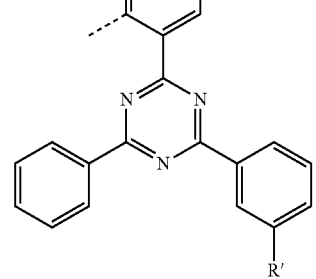 | 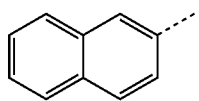 | 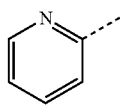 |

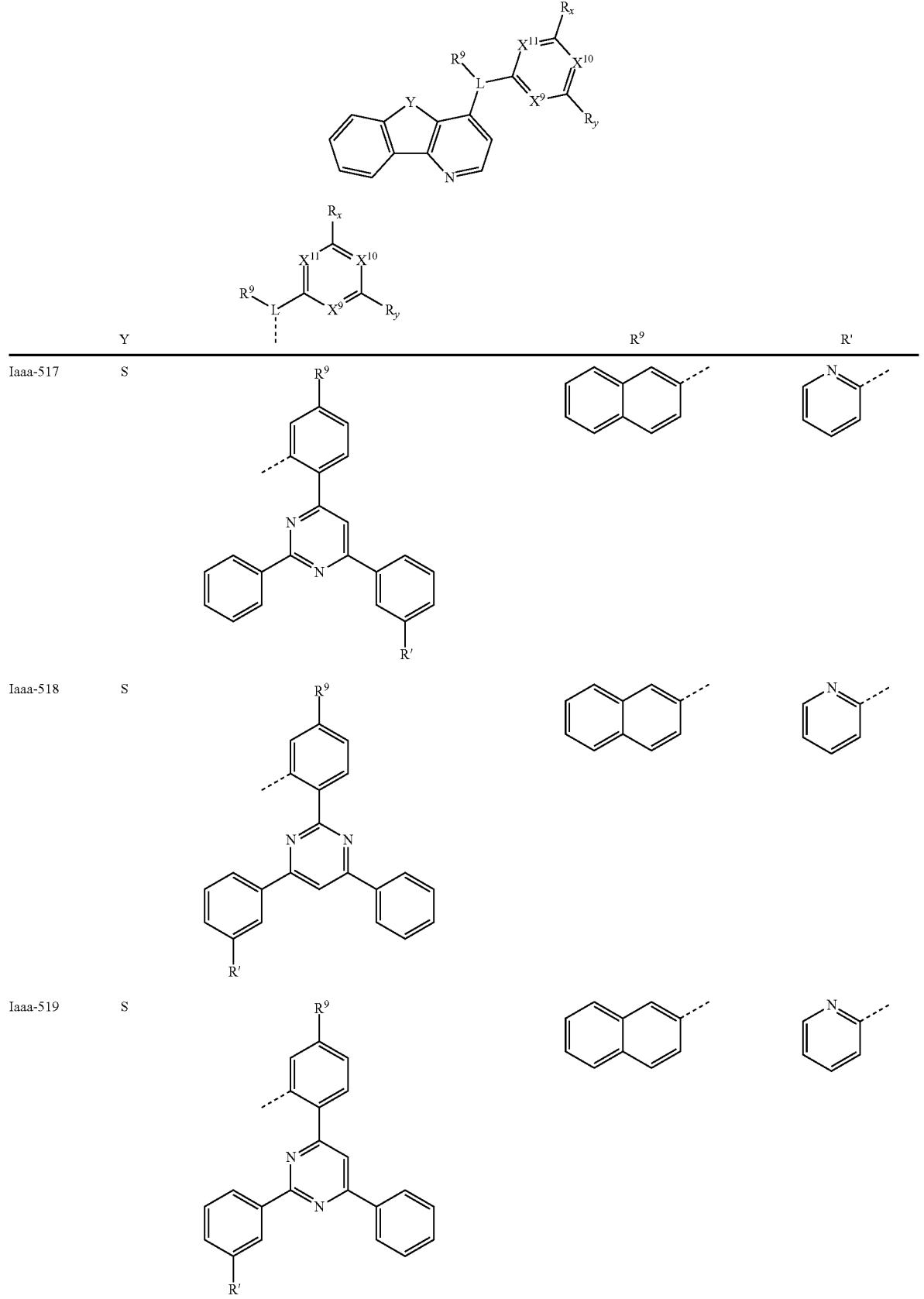

-continued
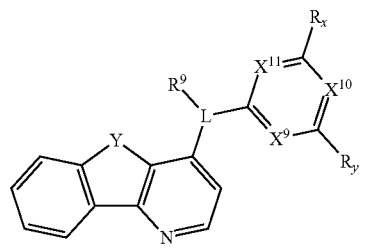
(Iaaa)

| | Y | | R⁹ | R' |
|---|---|---|---|---|
| Iaaa-520 | S | 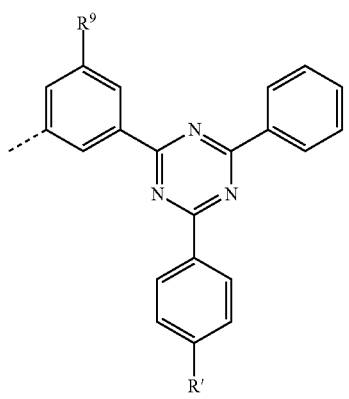 | 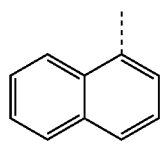 | H |
| Iaaa-521 | S | 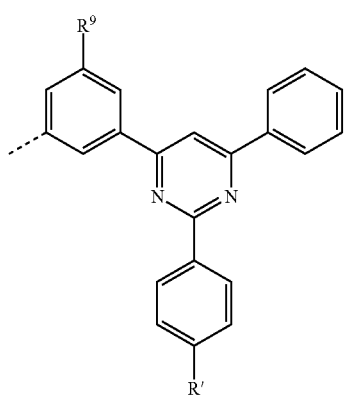 |  | H |

-continued
(Iaaa)
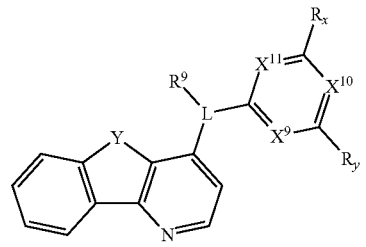
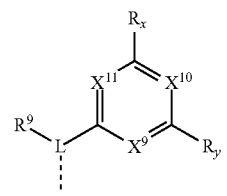
| | Y | | R⁹ | R' |
|---|---|---|---|---|
| Iaaa-522 | S | 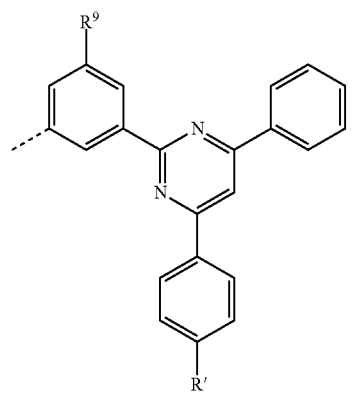 | 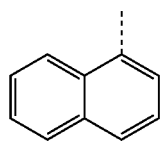 | H |
| Iaaa-523 | S | 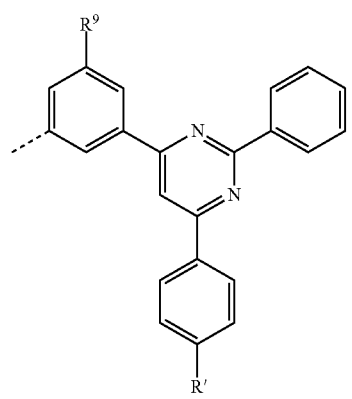 | 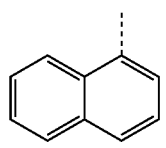 | H |
| Iaaa-524 | S | 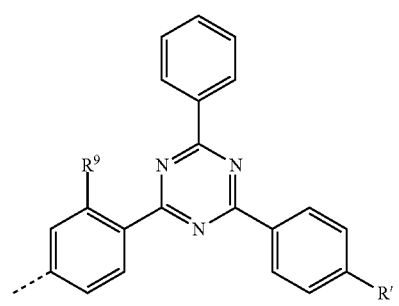 | 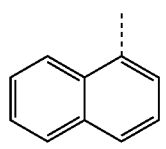 | H |

-continued
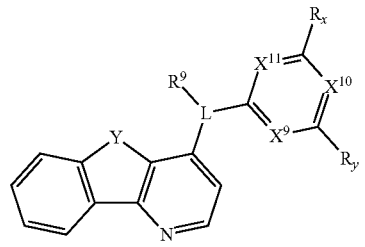
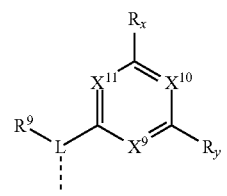
| | Y | R⁹ | R' |
|---|---|---|---|
| Iaaa-525 | S | 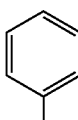 | H |
| Iaaa-526 | S |  | H |
| Iaaa-527 | S | 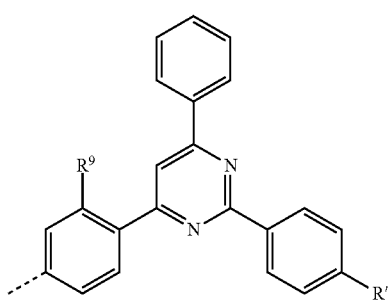 | 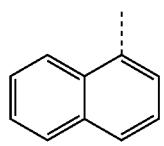 | H |

-continued
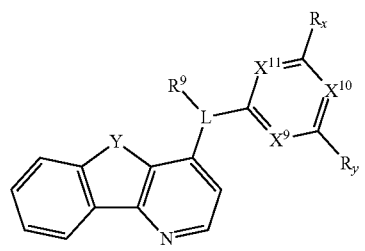
(Iaaa)

| | Y | | R⁹ | R' |
|---|---|---|---|---|
| Iaaa-528 | S | 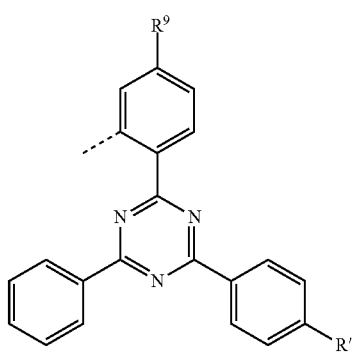 | 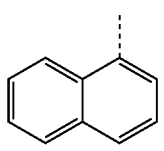 | H |
| Iaaa-529 | S | 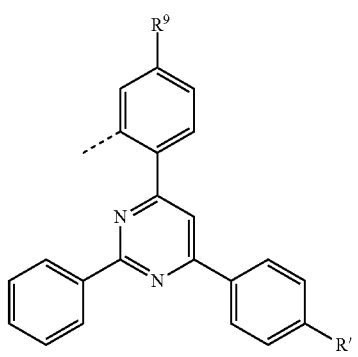 | 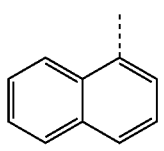 | H |
| Iaaa-530 | S | 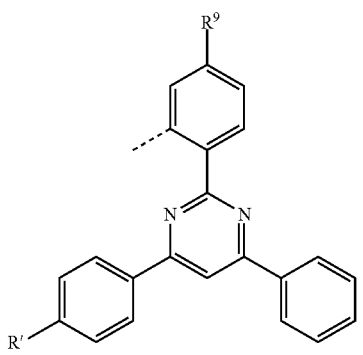 | 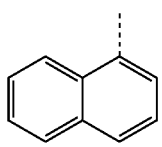 | H |

-continued
(Iaaa)
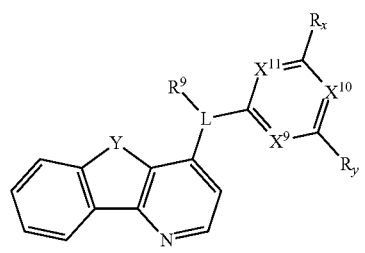
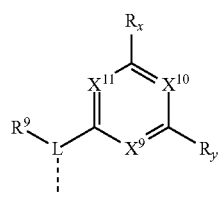
| | Y | | R⁹ | R' |
|---|---|---|---|---|
| Iaaa-531 | S | 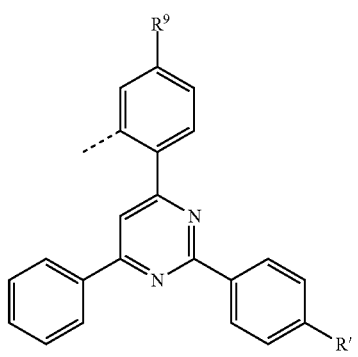 | 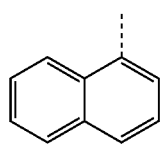 | H |
| Iaaa-532 | S | 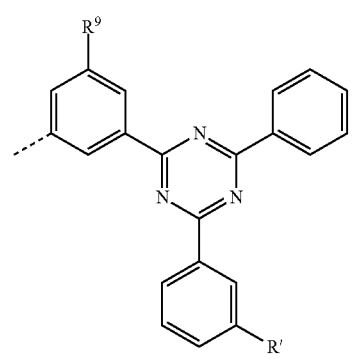 | 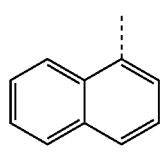 | H |
| Iaaa-533 | S |  |  | H |

-continued
(Iaaa)
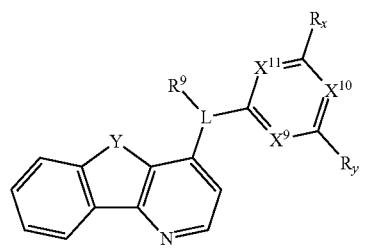
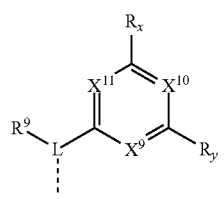
| | Y | R⁹ | | R' |
|---|---|---|---|---|
| Iaaa-534 | S | 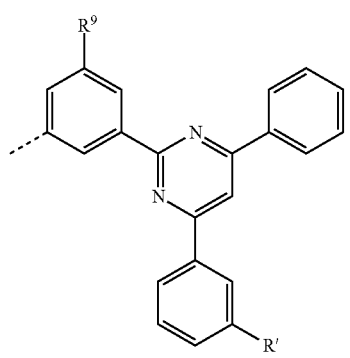 | | H |
| Iaaa-535 | S | 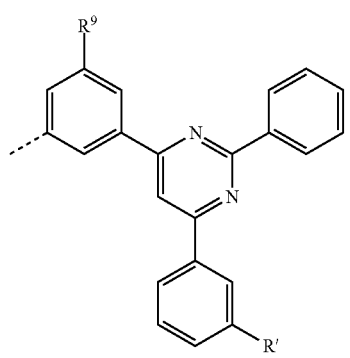 | | H |
| Iaaa-536 | S | 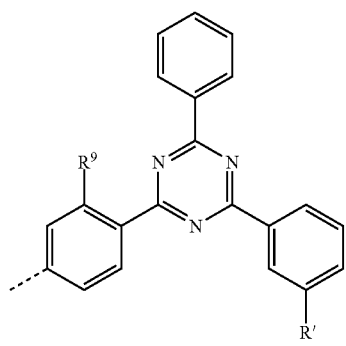 | | H |

-continued
(Iaaa)
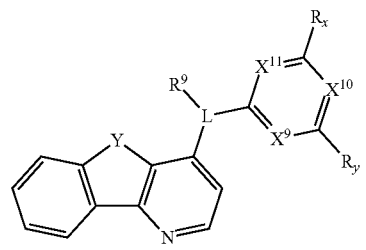
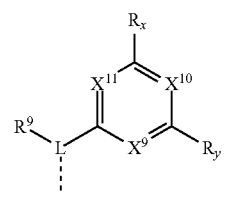
| | Y | | R⁹ | R' |
|---|---|---|---|---|
| Iaaa-537 | S | 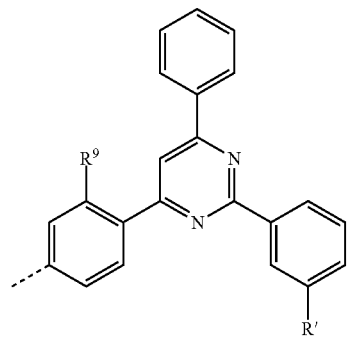 | 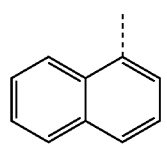 | H |
| Iaaa-538 | S | 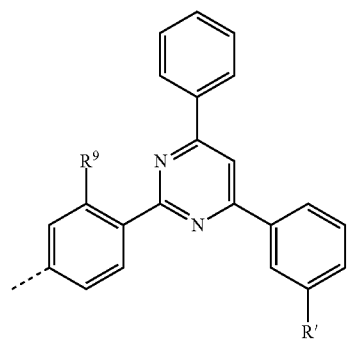 | 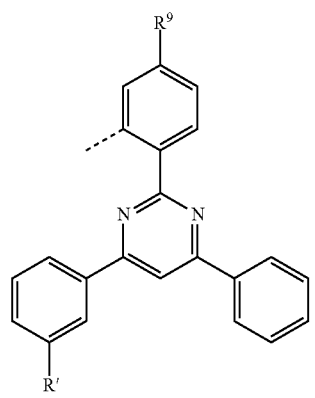 | H |
| Iaaa-539 | S | 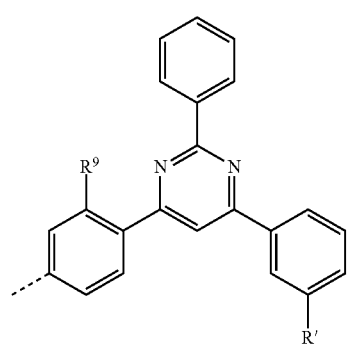 | 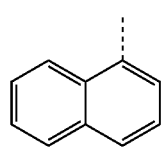 | H |

-continued
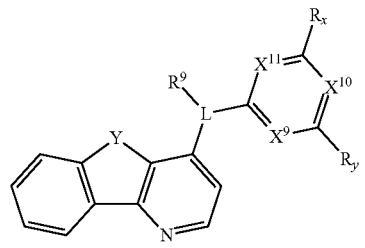
(Iaaa)
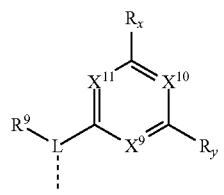
| | Y | | R⁹ | R' |
|---|---|---|---|---|
| Iaaa-540 | S | 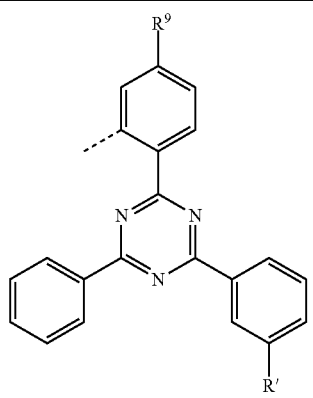 | 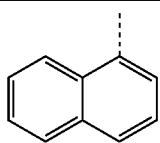 | H |
| Iaaa-541 | S | 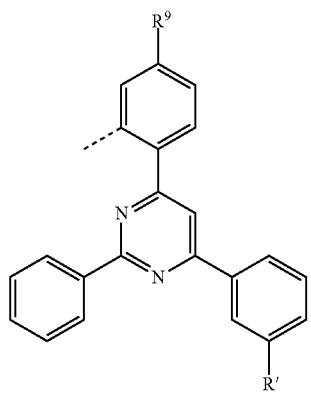 | 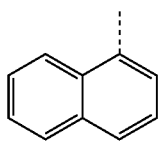 | H |
| Iaaa-542 | S | 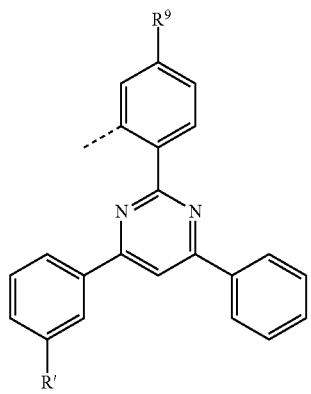 | 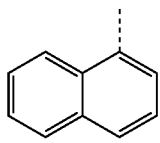 | H |

-continued
(Iaaa)
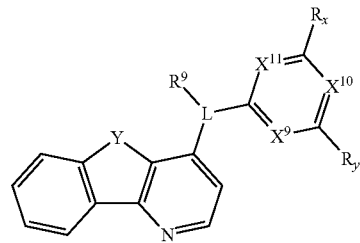
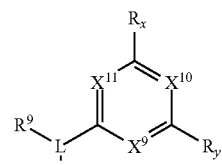
| | Y | | R⁹ | R' |
|---|---|---|---|---|
| Iaaa-543 | S | 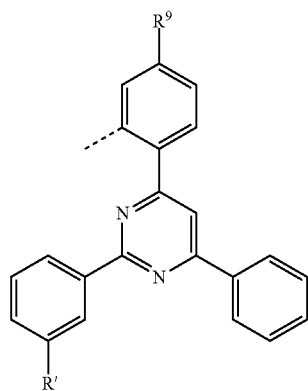 | 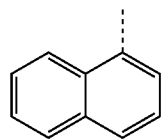 | H |
| Iaaa-544 | S | 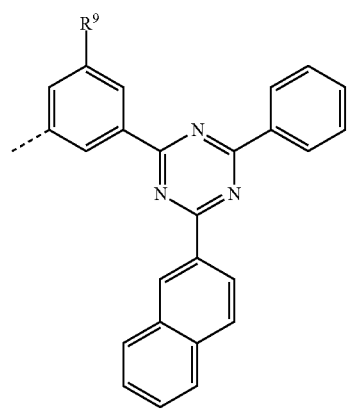 | 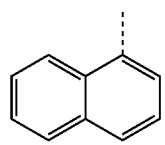 | — |

-continued
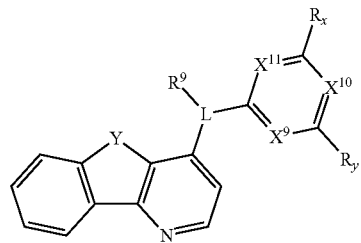
(Iaaa)
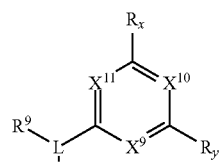
| | Y | R⁹ | R' |
|---|---|---|---|
| Iaaa-545 | S | 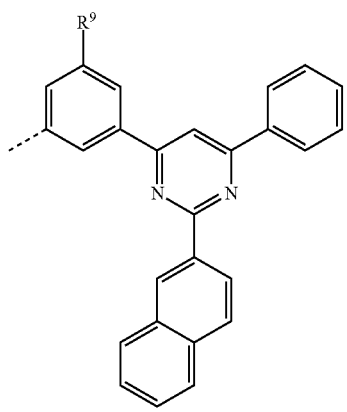 | 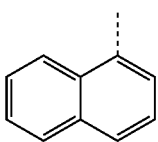 | — |
| Iaaa-546 | S | 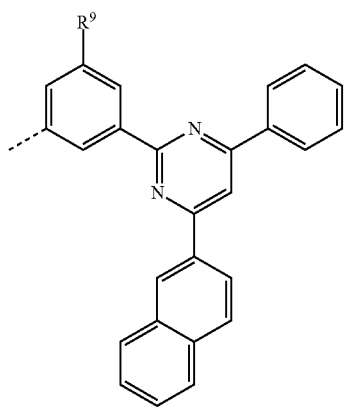 | 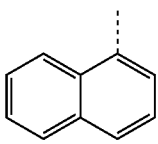 | — |

-continued
(Iaaa)
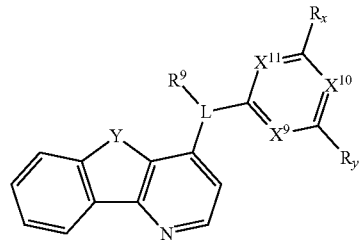
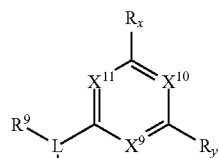
| | Y | R⁹ | | R' |
|---|---|---|---|---|
| Iaaa-547 | S | 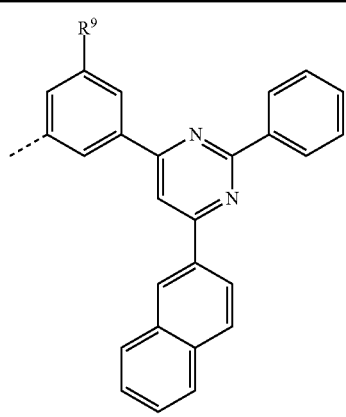 | 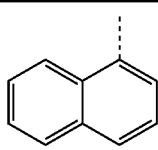 | — |
| Iaaa-548 | S | 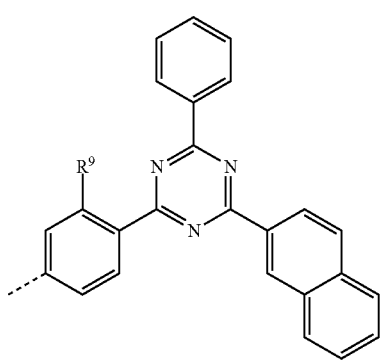 | 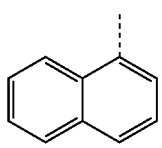 | — |
| Iaaa-549 | S | 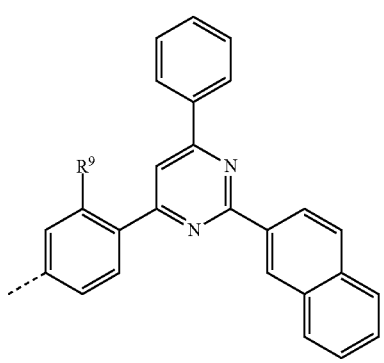 | 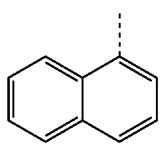 | — |

-continued
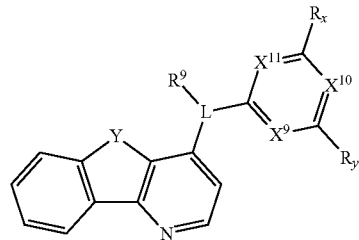
(Iaaa)
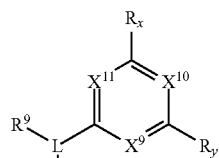
| | Y | | R⁹ | R' |
|---|---|---|---|---|
| Iaaa-550 | S | 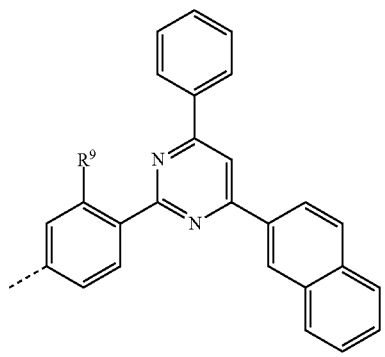 | 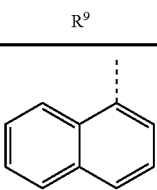 | — |
| Iaaa-551 | S | 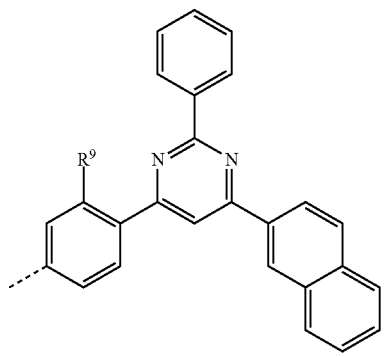 | 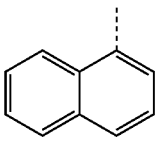 | — |
| Iaaa-552 | S | 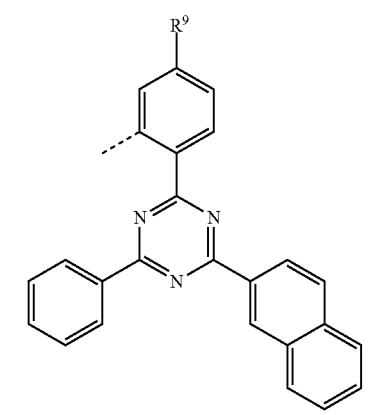 | 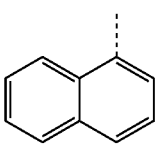 | — |

-continued
(Iaaa)
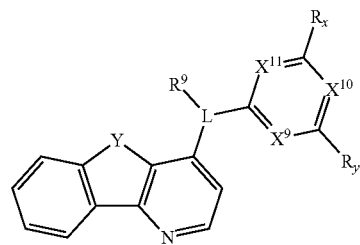
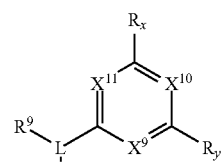
| | Y | | R⁹ | R' |
|---|---|---|---|---|
| Iaaa-553 | S | 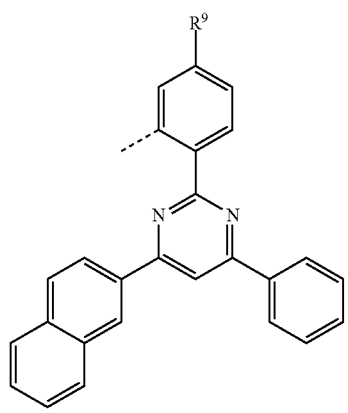 | 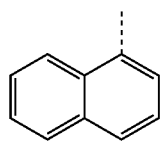 | — |
| Iaaa-554 | S | 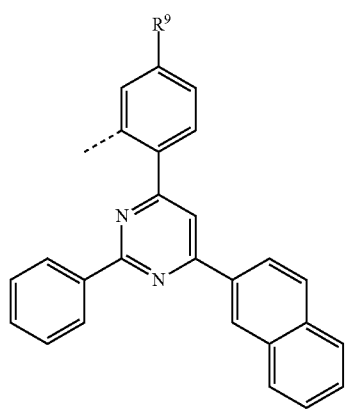 | 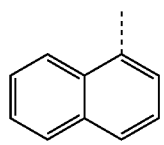 | — |

-continued
(Iaaa)
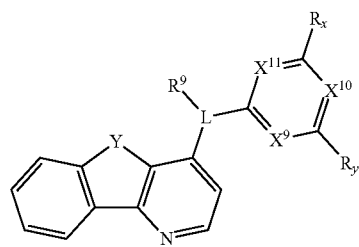
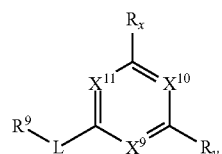
| | Y | | R⁹ | R' |
|---|---|---|---|---|
| Iaaa-555 | S | 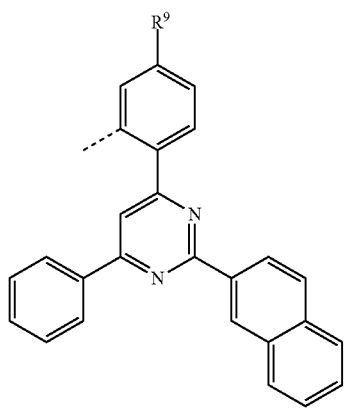 | 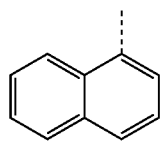 | — |
| Iaaa-556 | S | 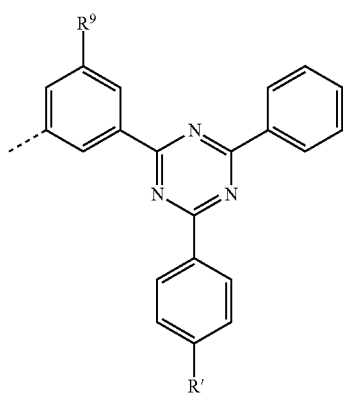 | 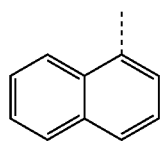 |  |

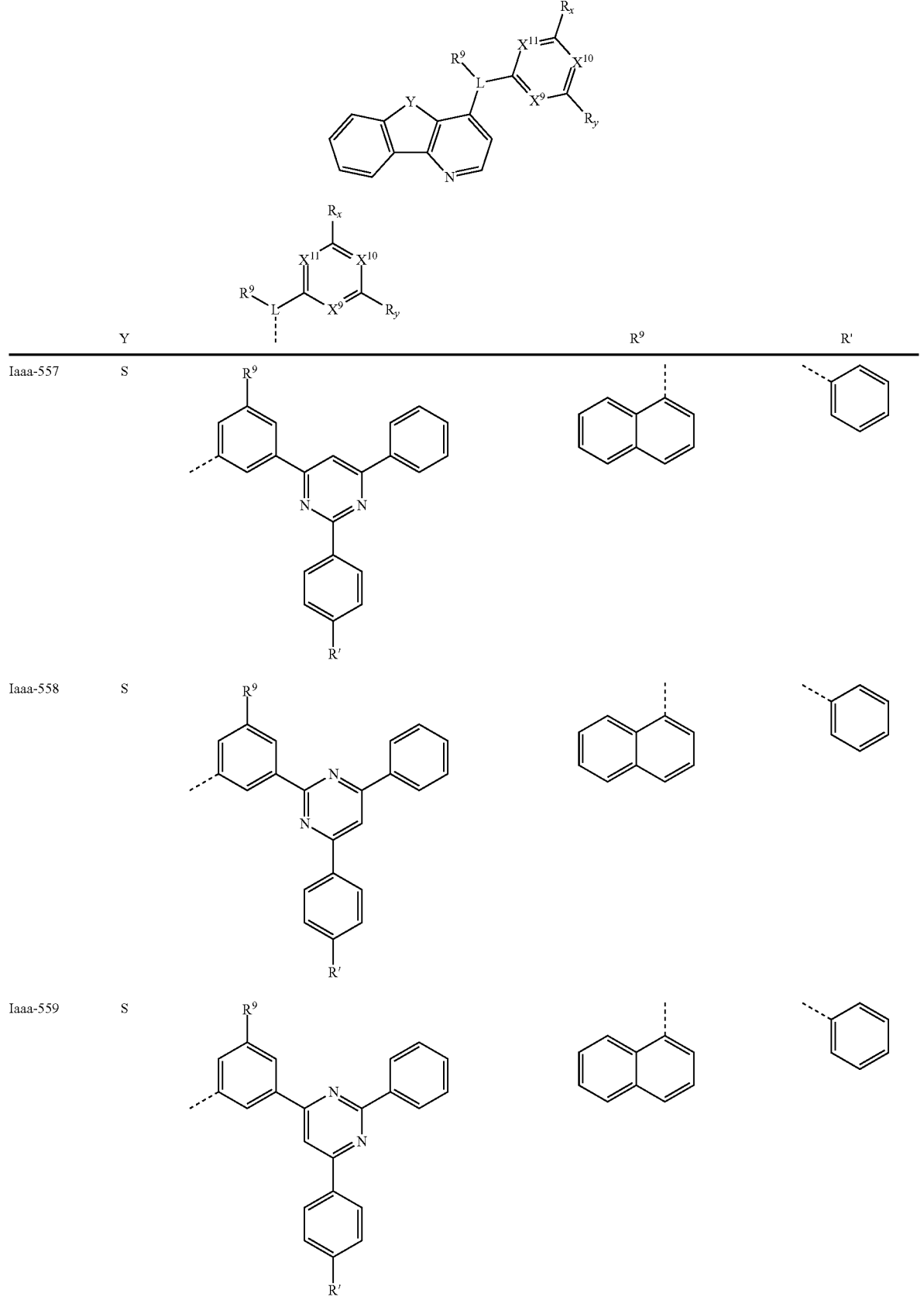

-continued
(Iaaa)
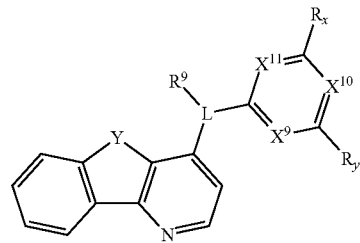
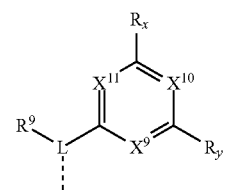
| | Y | | R⁹ | R' |
|---|---|---|---|---|
| Iaaa-560 | S | 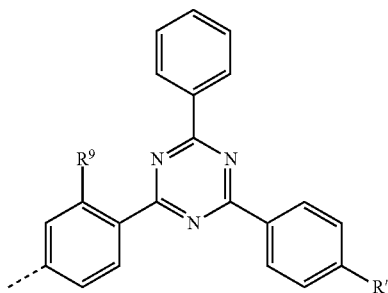 | 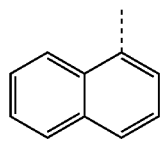 | 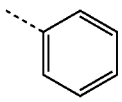 |
| Iaaa-561 | S | 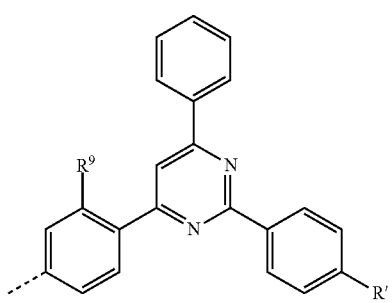 | 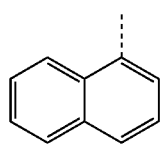 | 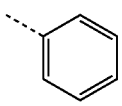 |
| Iaaa-562 | S | 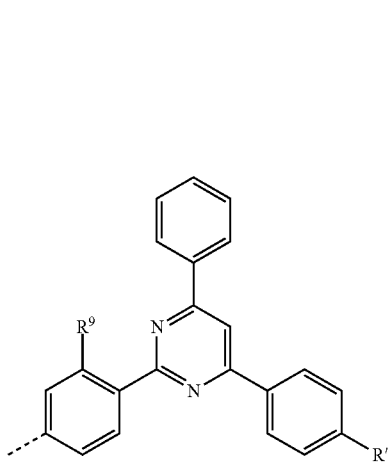 | 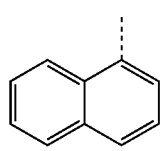 | 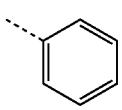 |

-continued
(Iaaa)
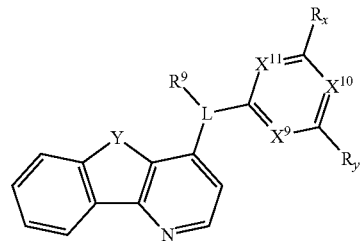
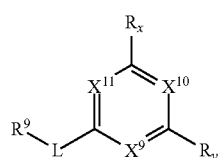
| | Y | | R⁹ | R' |
|---|---|---|---|---|
| Iaaa-563 | S | 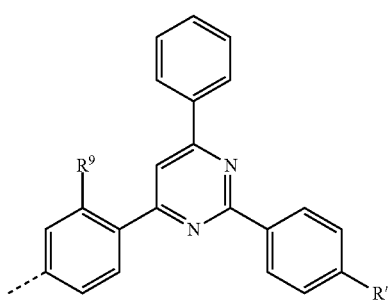 | 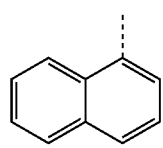 | 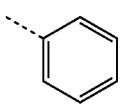 |
| Iaaa-564 | S | 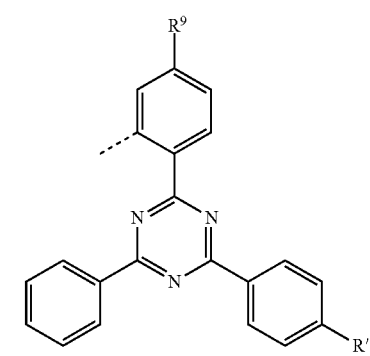 | 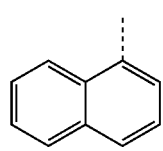 | 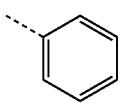 |
| Iaaa-565 | S | 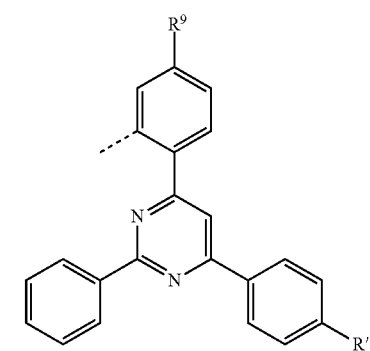 | 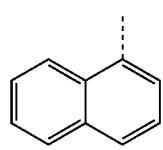 | 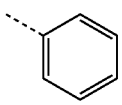 |

-continued
(Iaaa)
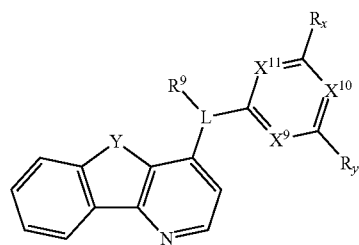
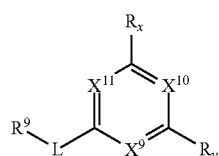
| | Y | R⁹ | R' |
|---|---|---|---|
| Iaaa-566 | S | 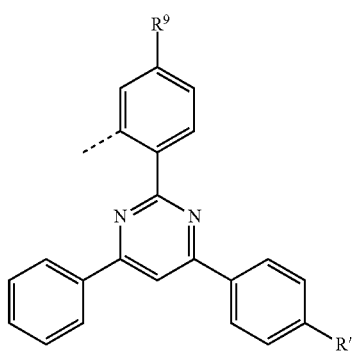 | 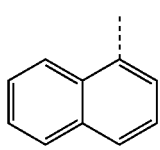 | 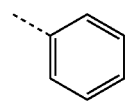 |
| Iaaa-567 | S | 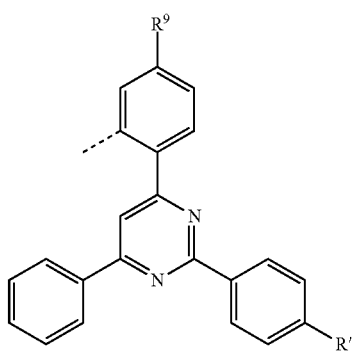 | 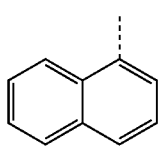 | 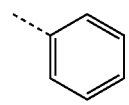 |
| Iaaa-568 | S | 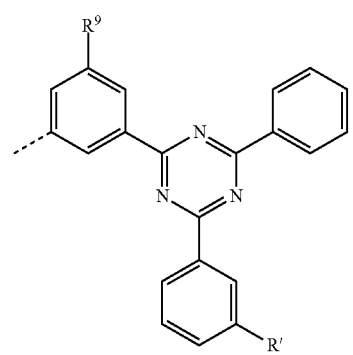 | 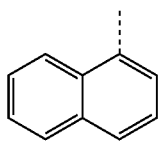 | 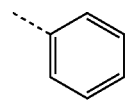 |

-continued
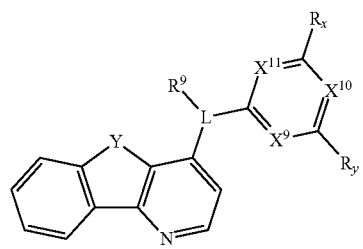
(Iaaa)
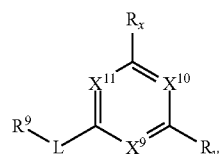
| | Y | R⁹ | R' |
|---|---|---|---|
| Iaaa-569 | S | 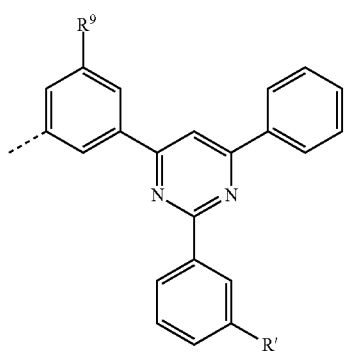 | 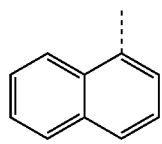 | 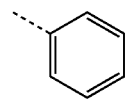 |
| Iaaa-570 | S | 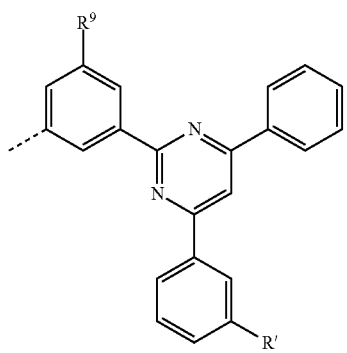 | 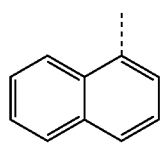 | 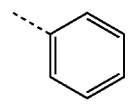 |
| Iaaa-571 | S | 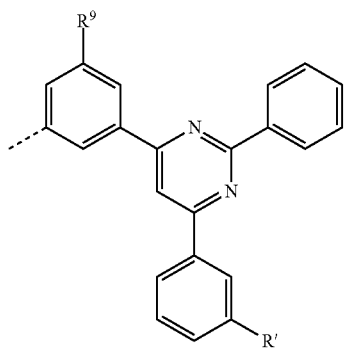 | 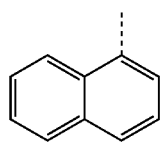 | 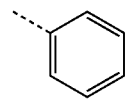 |

-continued
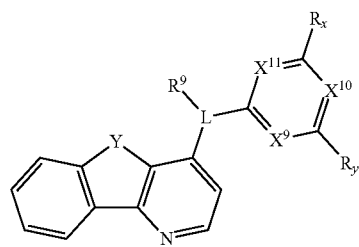
(Iaaa)
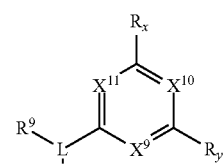
| | Y | R⁹ | R' |
|---|---|---|---|
| Iaaa-572 | S | 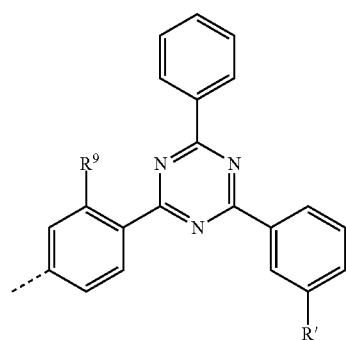 | 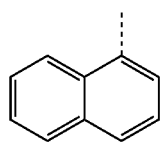 | 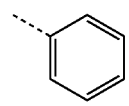 |
| Iaaa-573 | S | 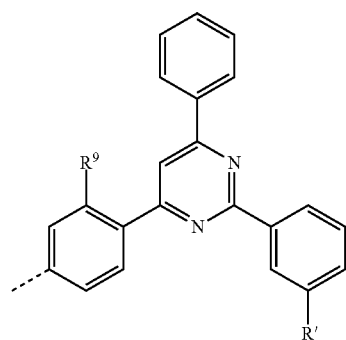 | 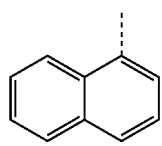 | 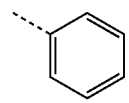 |
| Iaaa-574 | S | 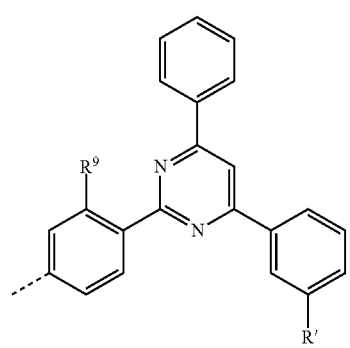 | 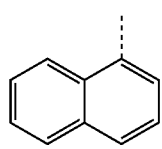 | 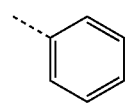 |

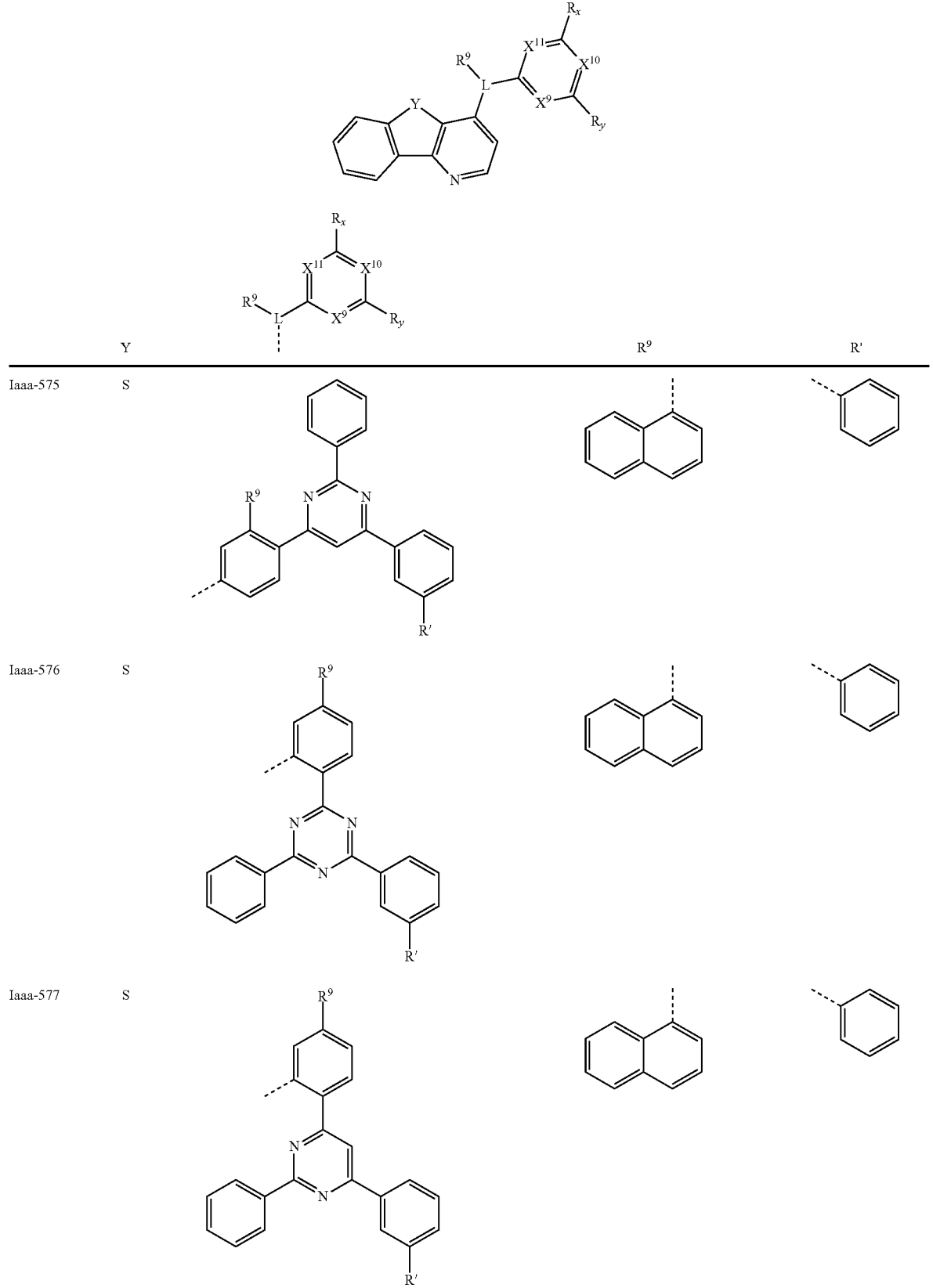

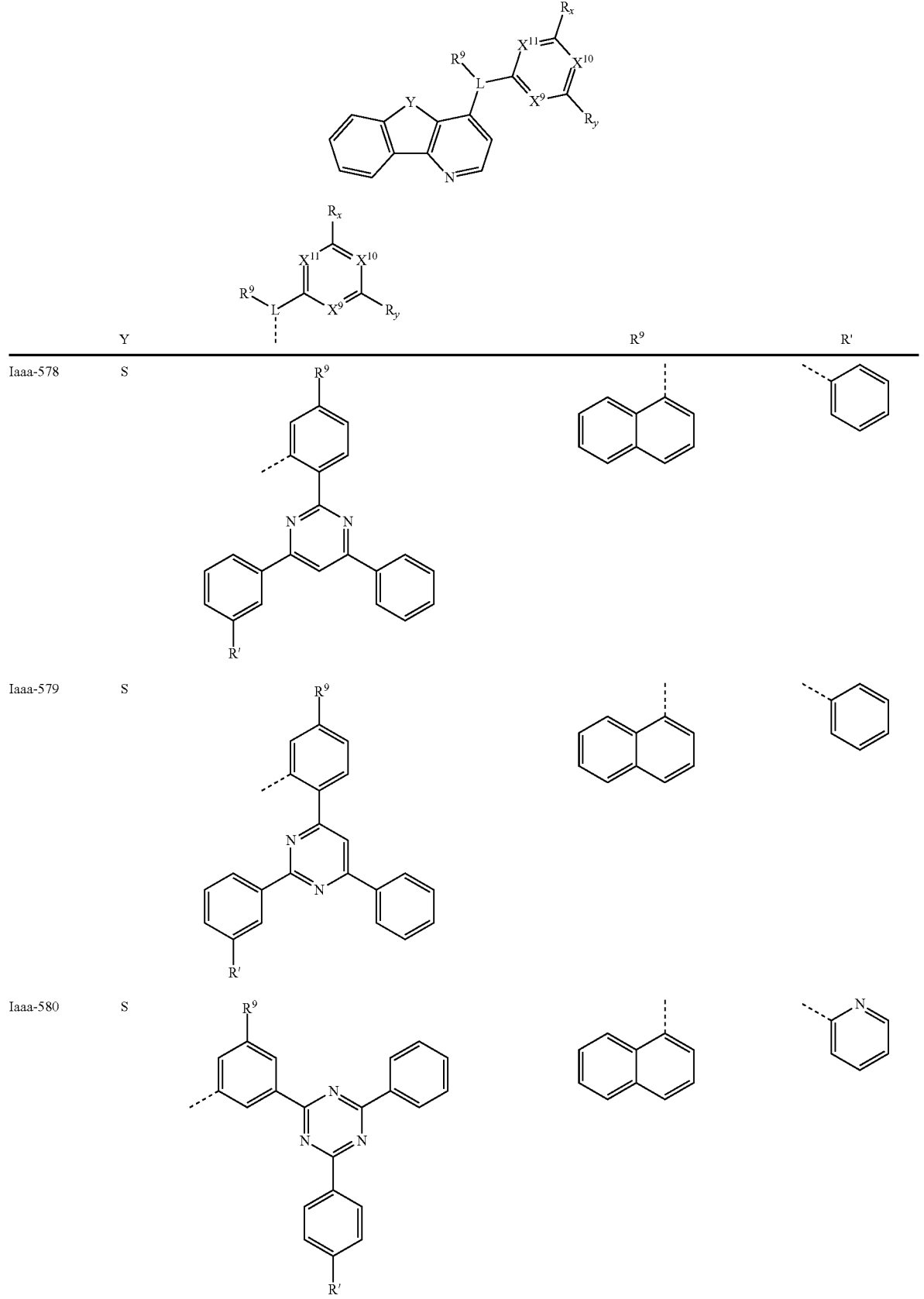

(Iaaa)
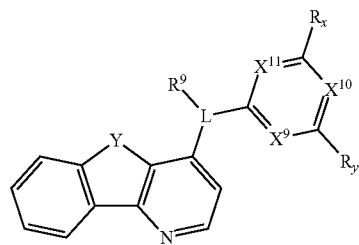
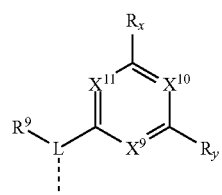
| | Y | | R⁹ | R' |
|---|---|---|---|---|
| Iaaa-581 | S | 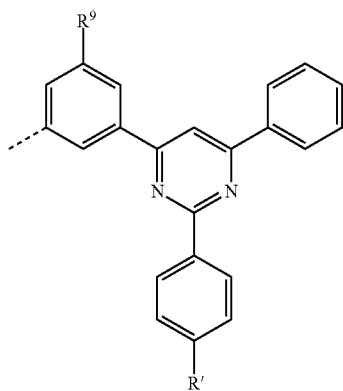 | 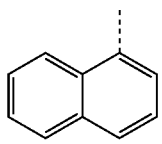 | 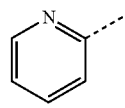 |
| Iaaa-582 | S | 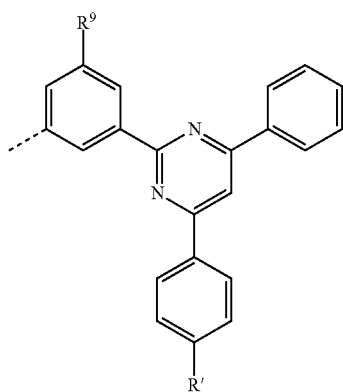 | 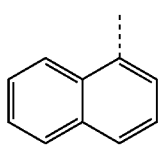 | 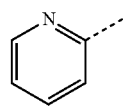 |

-continued
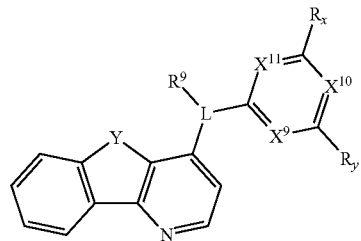
(Iaaa)
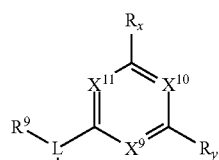
| | Y | R⁹ | R' |
|---|---|---|---|
| Iaaa-583 | S | 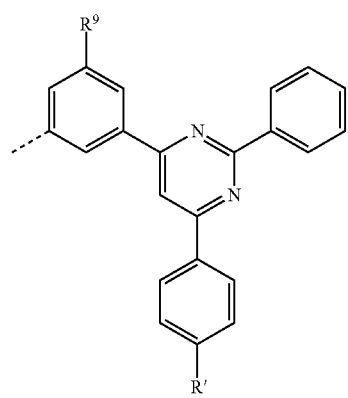 | 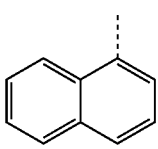 | 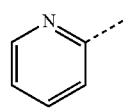 |
| Iaaa-584 | S | 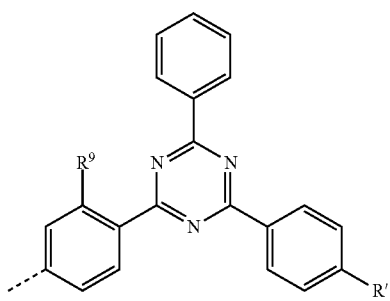 | 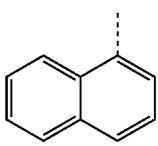 | 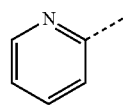 |
| Iaaa-585 | S | 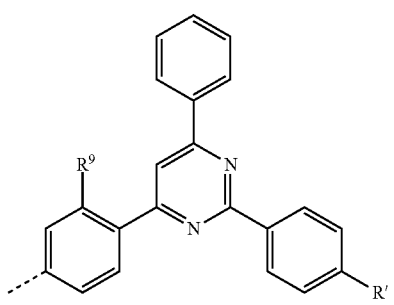 | 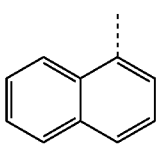 | 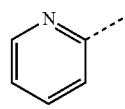 |

-continued
(Iaaa)
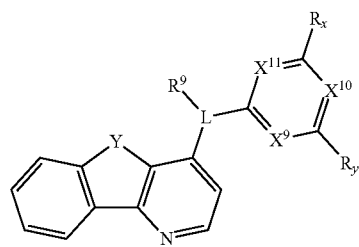
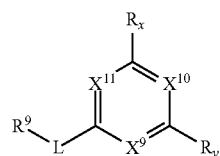
| | Y | | R⁹ | R' |
|---|---|---|---|---|
| Iaaa-586 | S | 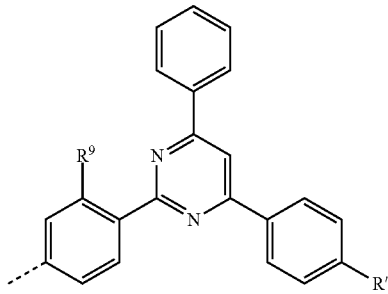 | 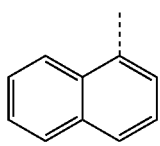 | 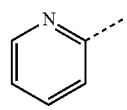 |
| Iaaa-587 | S | 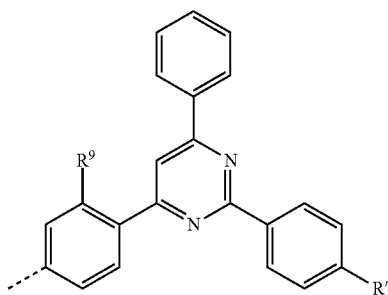 | 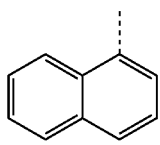 | 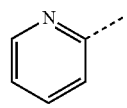 |
| Iaaa-588 | S | 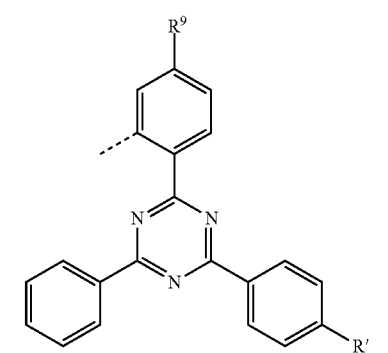 | 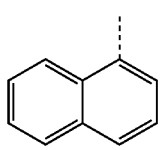 | 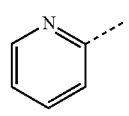 |

-continued
(Iaaa)
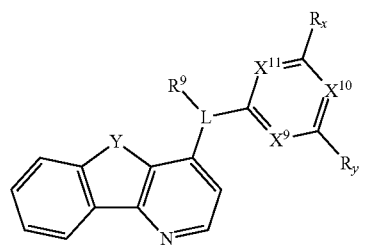
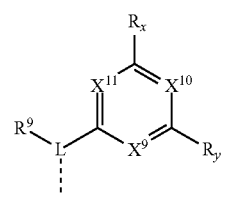
| | Y | | R⁹ | R' |
|---|---|---|---|---|
| Iaaa-589 | S | (phenyl-pyrimidine with phenyl and R' substituents, R⁹) | naphthyl | pyridin-2-yl |
| Iaaa-590 | S | (phenyl-pyrimidine with R' and phenyl substituents, R⁹) | naphthyl | pyridin-2-yl |
| Iaaa-591 | S | (phenyl-pyrimidine with phenyl and R' substituents, R⁹) | naphthyl | pyridin-2-yl |

-continued
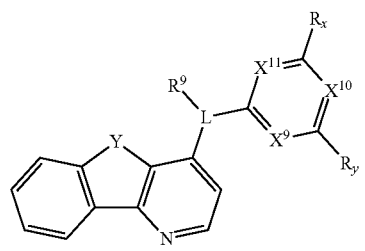
(Iaaa)
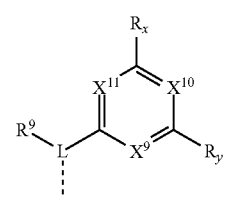
| | Y | | R⁹ | R' |
|---|---|---|---|---|
| Iaaa-592 | S | 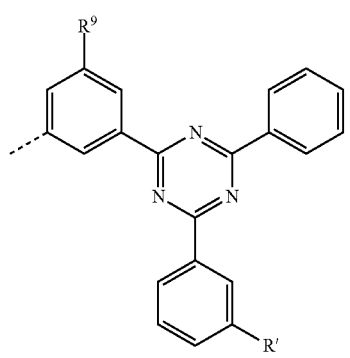 | 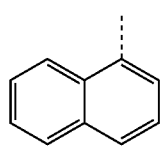 | 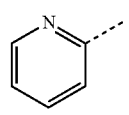 |
| Iaaa-593 | S | 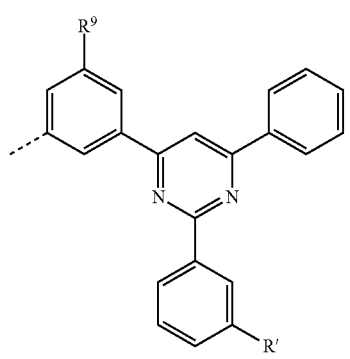 | 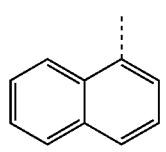 | 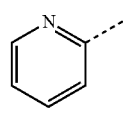 |
| Iaaa-594 | S | 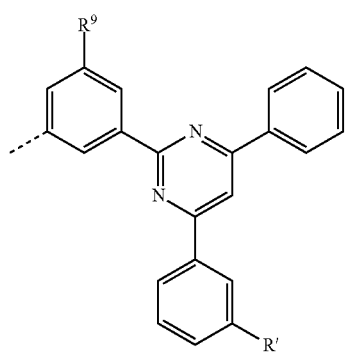 | 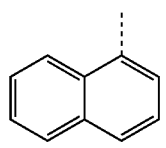 | 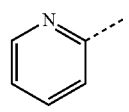 |

-continued
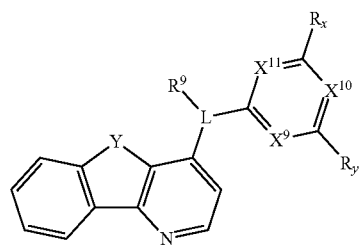
(Iaaa)
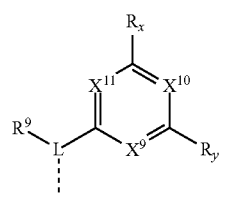
| | Y | R9 | | R' |
|---|---|---|---|---|
| Iaaa-595 | S | 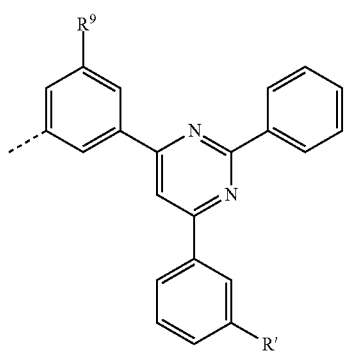 | 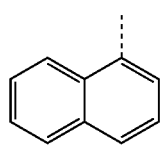 | 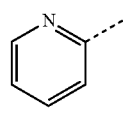 |
| Iaaa-596 | S | 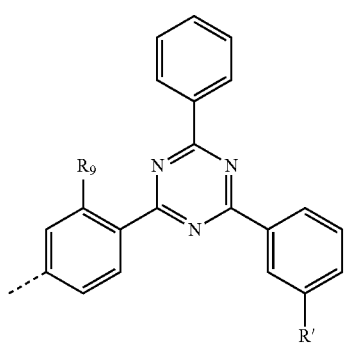 | 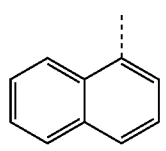 | 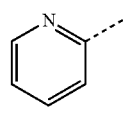 |
| Iaaa-597 | S | 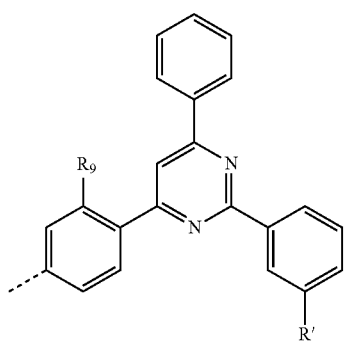 | 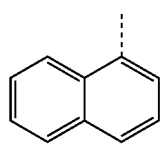 | 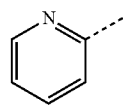 |

-continued
(Iaaa)
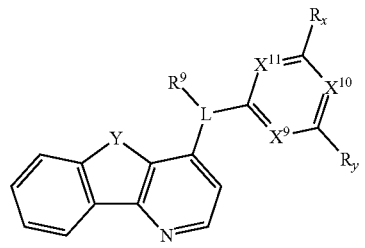
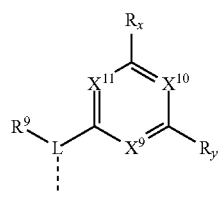
| | Y | | R⁹ | R' |
|---|---|---|---|---|
| Iaaa-598 | S | 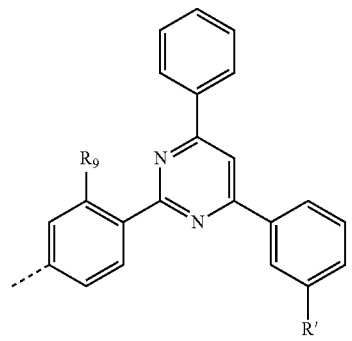 | 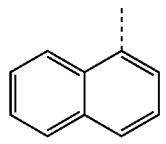 | 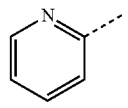 |
| Iaaa-599 | S | 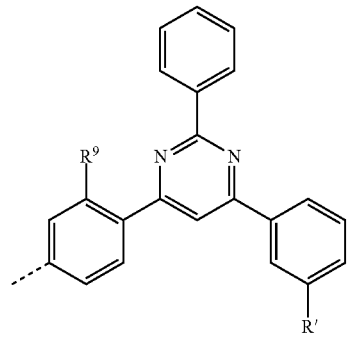 | 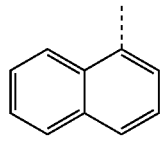 | 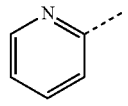 |
| Iaaa-600 | S | 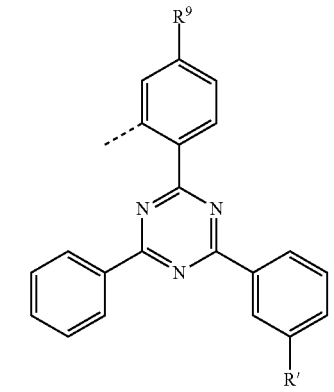 | 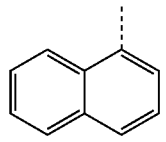 | 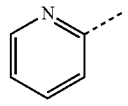 |

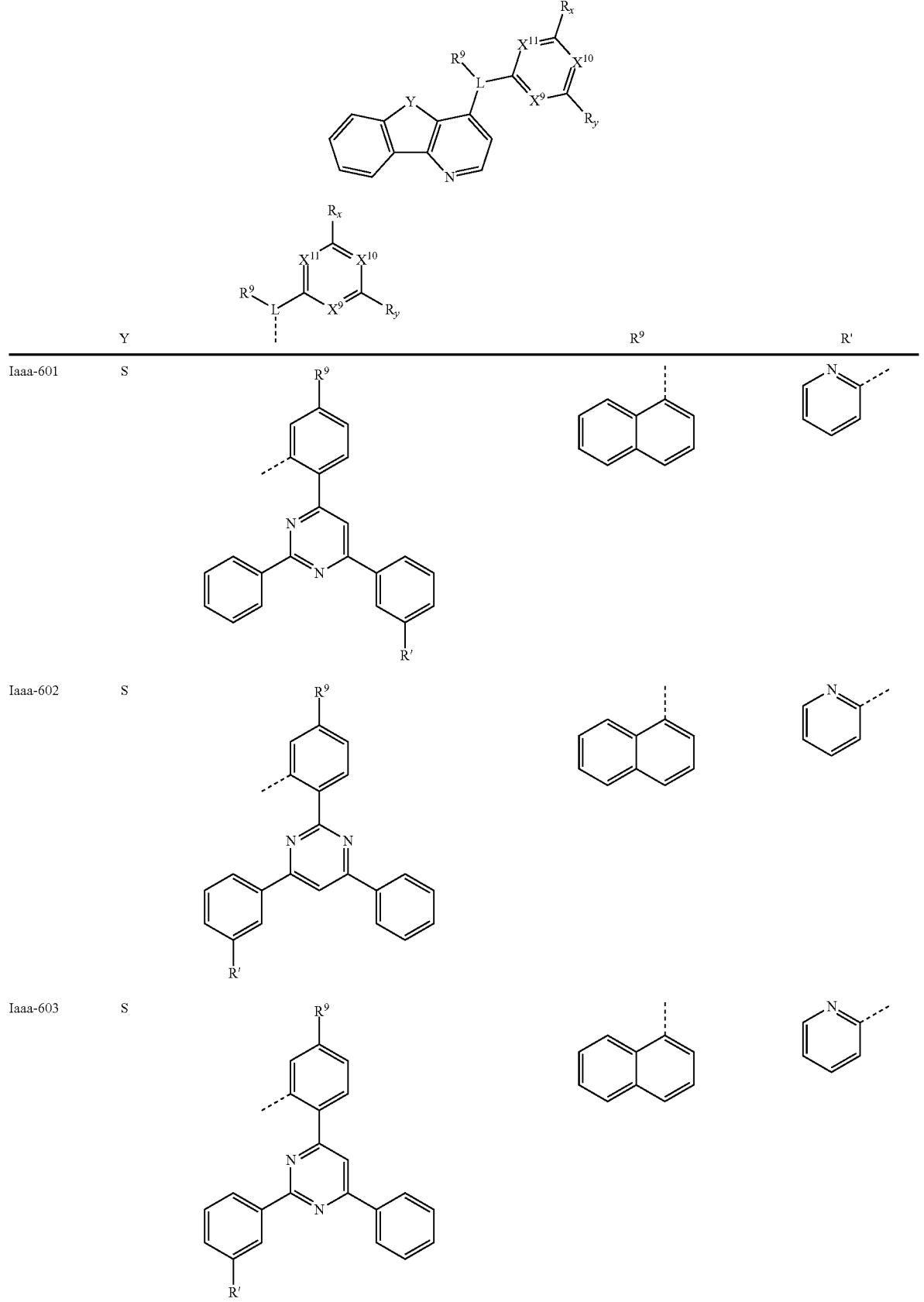

-continued
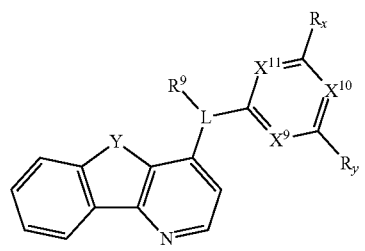
(Iaaa)
| | Y | 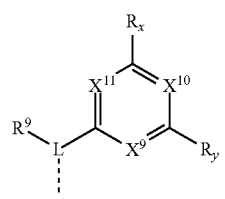 | R⁹ | R' |
|---|---|---|---|---|
| Iaaa-604 | O | 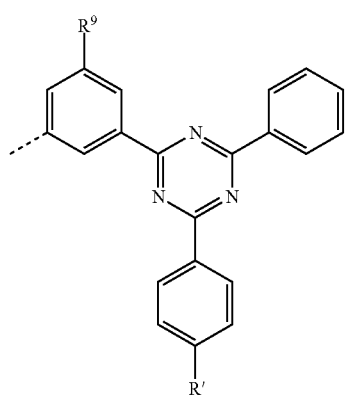 | 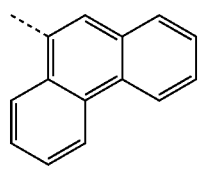 | H |
| Iaaa-605 | O | | | H |

-continued
(Iaaa)
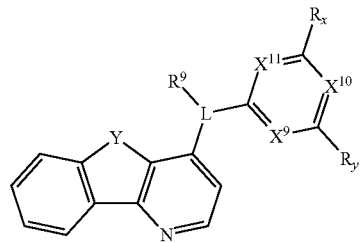
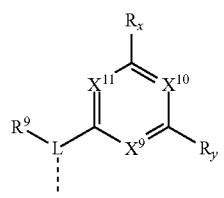
| | Y | | R⁹ | R' |
|---|---|---|---|---|
| Iaaa-606 | O | 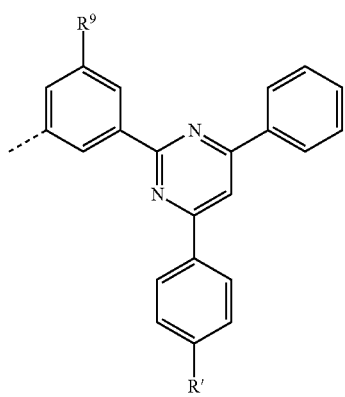 | 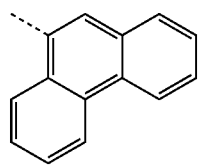 | H |
| Iaaa-607 | O | 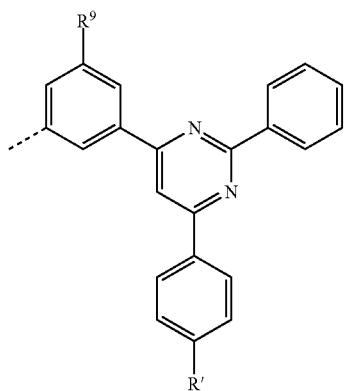 | 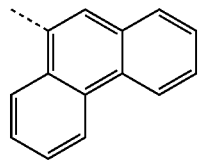 | H |
| Iaaa-608 | O | 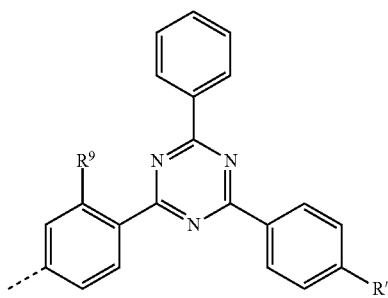 | 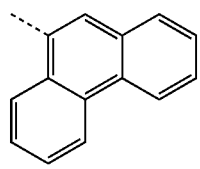 | H |

-continued
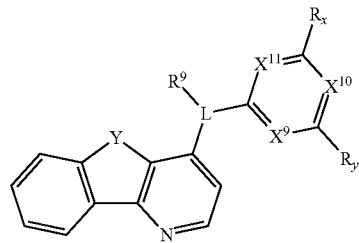
(Iaaa)
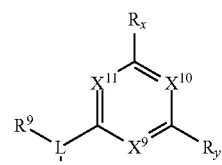
| | Y | | R⁹ | R' |
|---|---|---|---|---|
| Iaaa-609 | O | 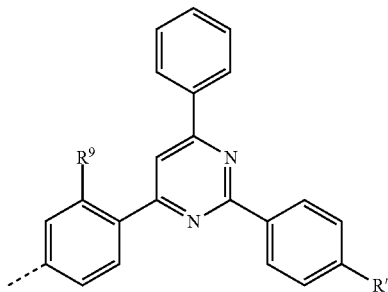 | 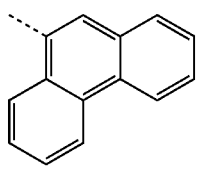 | H |
| Iaaa-610 | O | 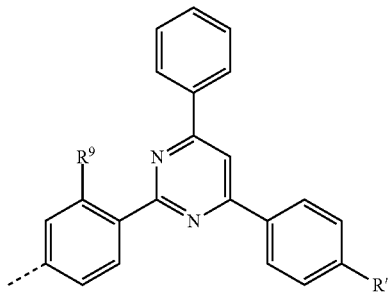 | 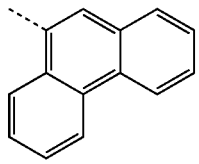 | H |
| Iaaa-611 | O | 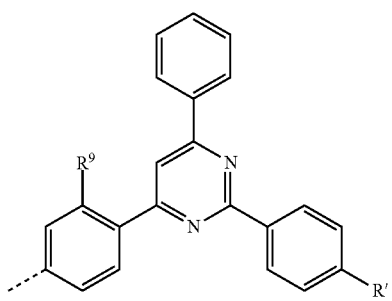 | 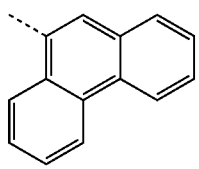 | H |

-continued
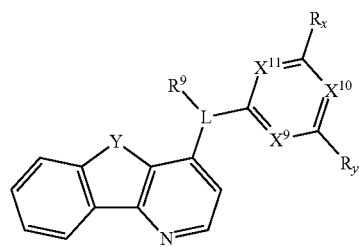
(Iaaa)
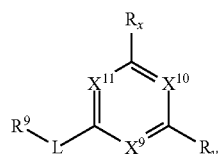
| | Y | | R⁹ | R' |
|---|---|---|---|---|
| Iaaa-612 | O | 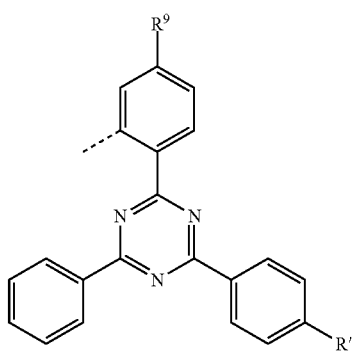 | 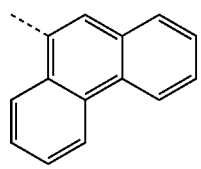 | H |
| Iaaa-613 | O | 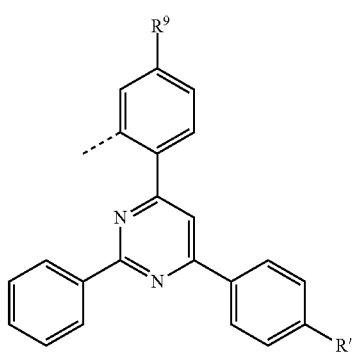 | 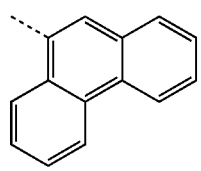 | H |
| Iaaa-614 | O | 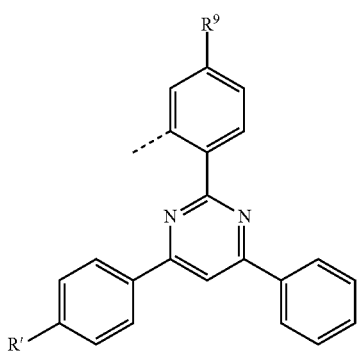 | 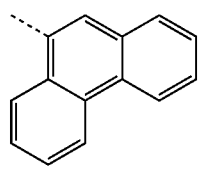 | H |

-continued
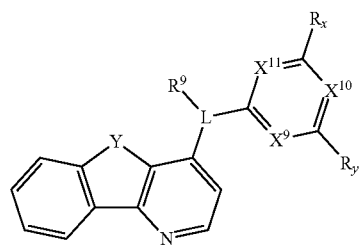
(Iaaa)
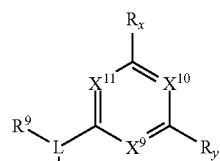
| | Y | | R⁹ | R' |
|---|---|---|---|---|
| Iaaa-615 | O | 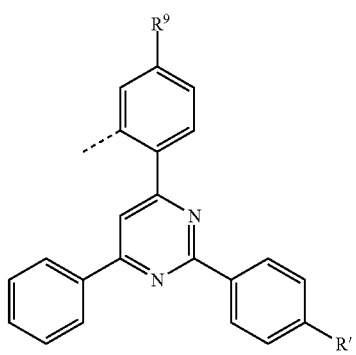 | 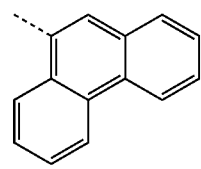 | H |
| Iaaa-616 | O | 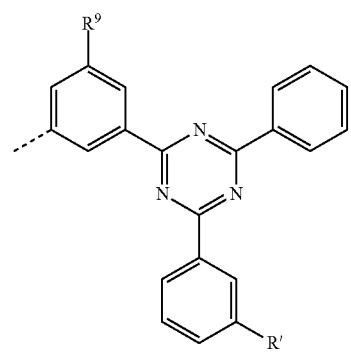 | 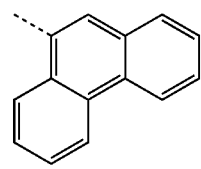 | H |
| Iaaa-617 | O | 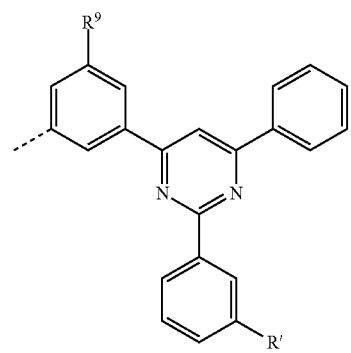 | 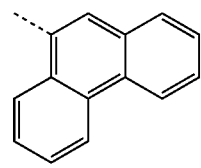 | H |

-continued
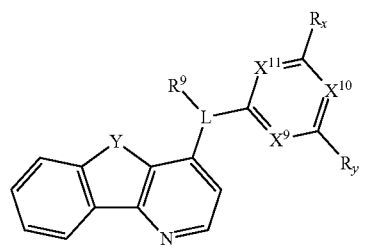
(Iaaa)
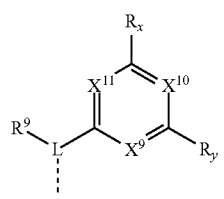
| | Y | | R⁹ | R' |
|---|---|---|---|---|
| Iaaa-618 | O | 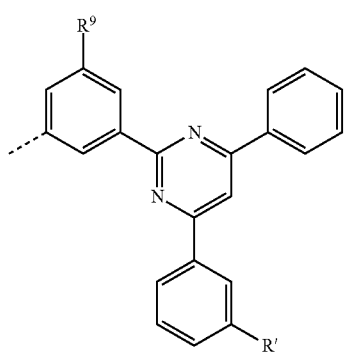 | 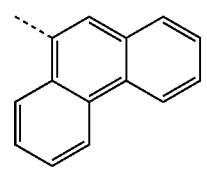 | H |
| Iaaa-619 | O | 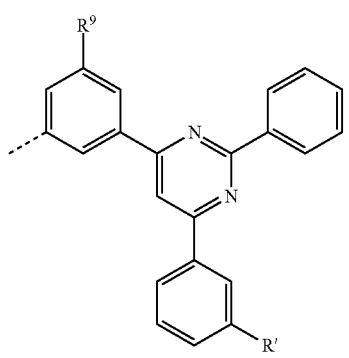 | 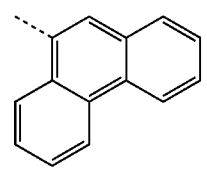 | H |
| Iaaa-620 | O | 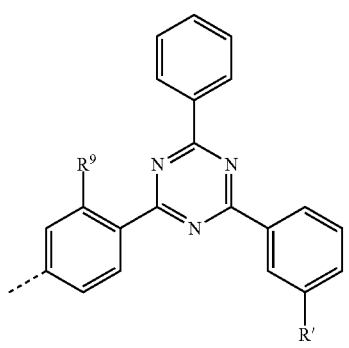 | 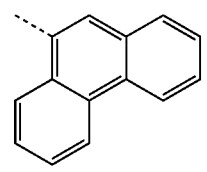 | H |

-continued
(Iaaa)
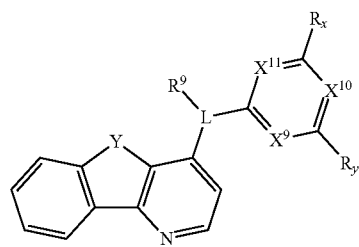
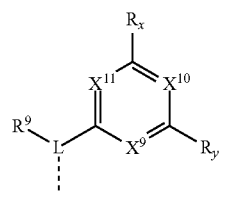
| | Y | | R⁹ | R' |
|---|---|---|---|---|
| Iaaa-621 | O | 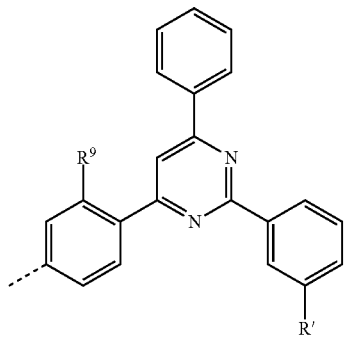 | 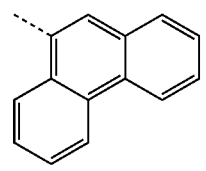 | H |
| Iaaa-622 | O | 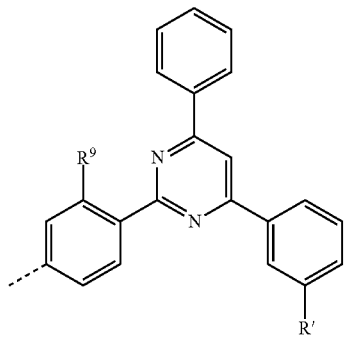 | 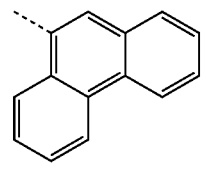 | H |
| Iaaa-623 | O | 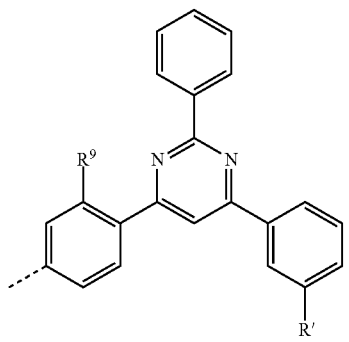 | 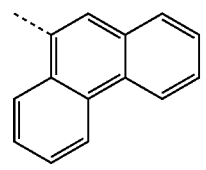 | H |

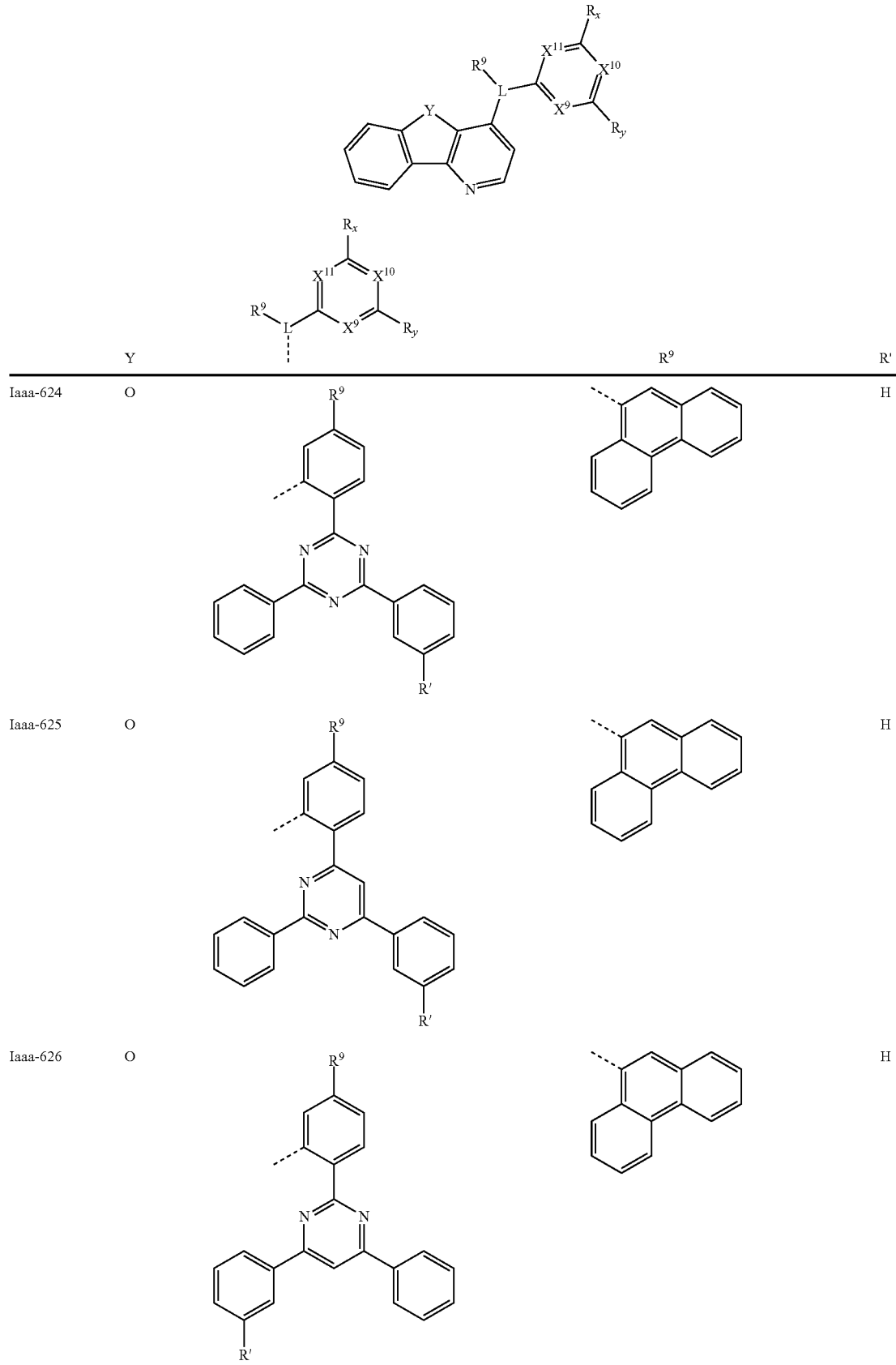

-continued
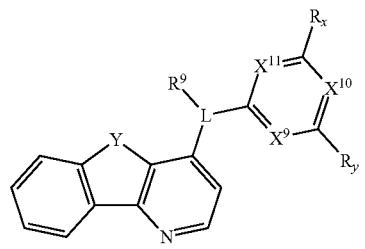
(Iaaa)
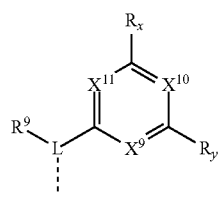
| | Y | | $R^9$ | R' |
|---|---|---|---|---|
| Iaaa-627 | O | 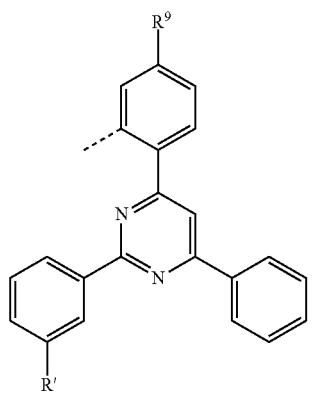 | 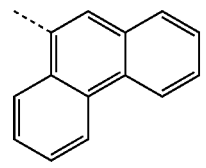 | H |
| Iaaa-628 | O | 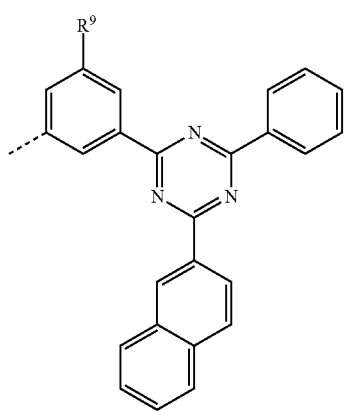 | 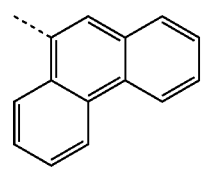 | — |

-continued
(Iaaa)
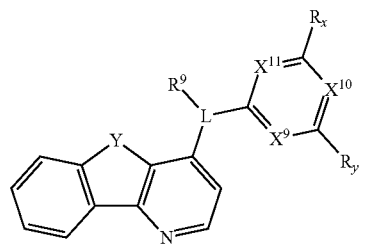
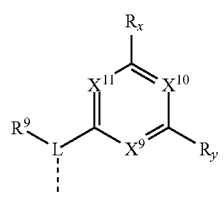
| | Y | | R⁹ | R' |
|---|---|---|---|---|
| Iaaa-629 | O | 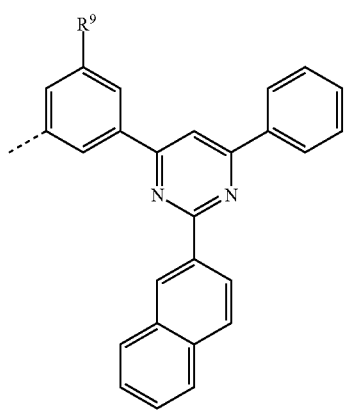 | 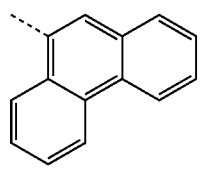 | — |
| Iaaa-630 | O | 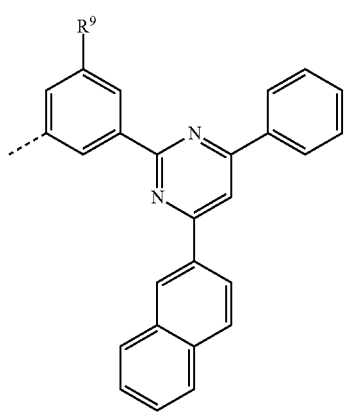 | 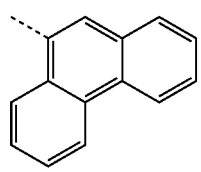 | — |

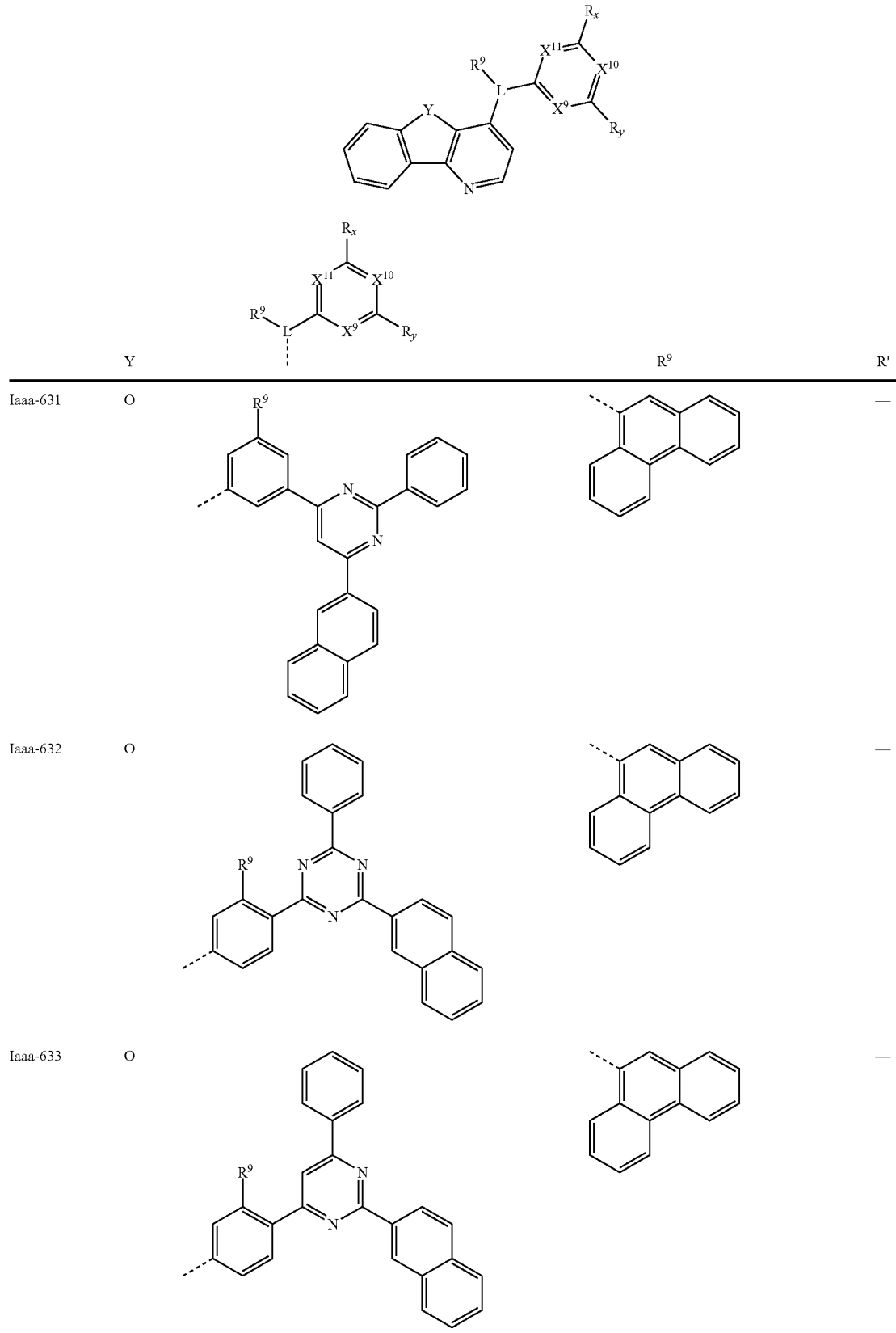

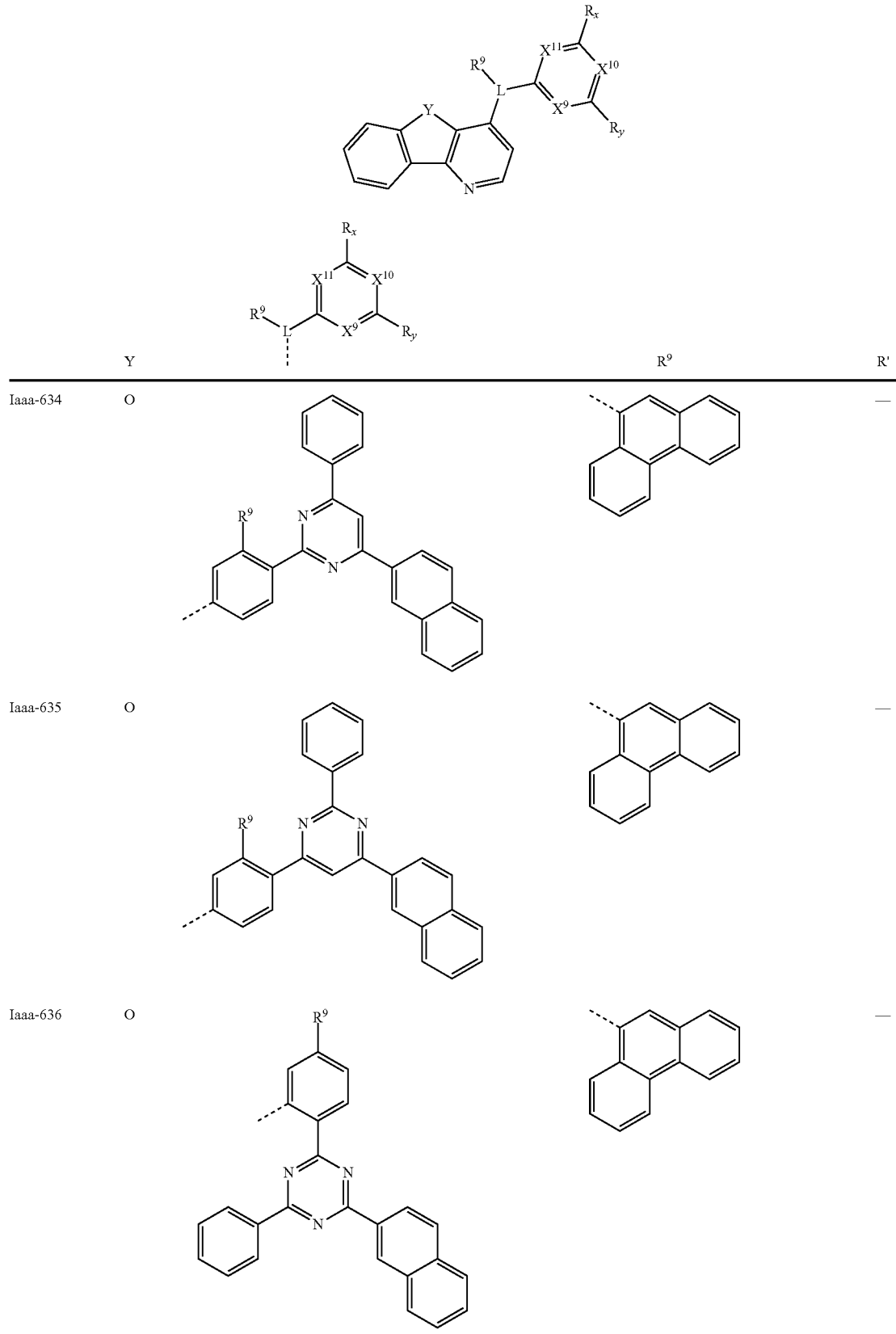

-continued
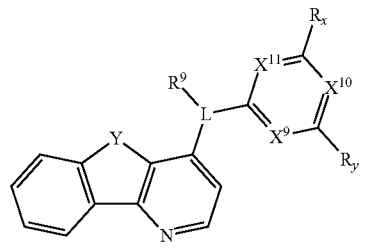
(Iaaa)
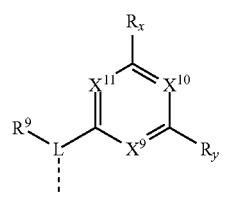
| | Y | R⁹ | R' |
|---|---|---|---|
| Iaaa-637 | O |  |  — |
| Iaaa-638 | O | 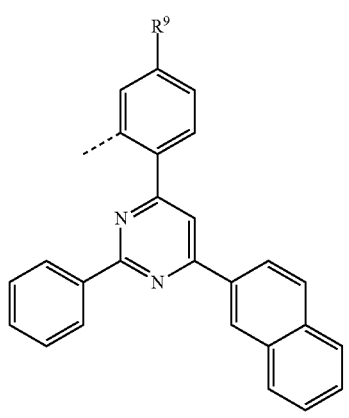 | 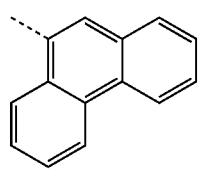 — |

-continued
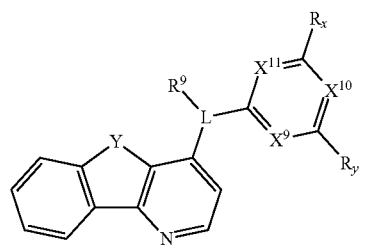
(Iaaa)

| | Y |  | R⁹ | R' |
|---|---|---|---|---|
| Iaaa-639 | O | 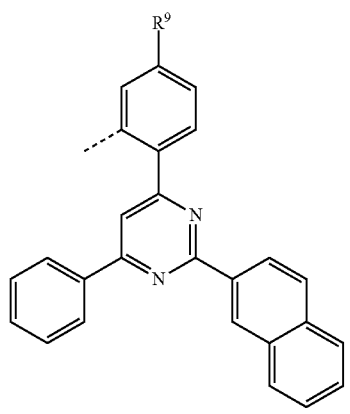 | 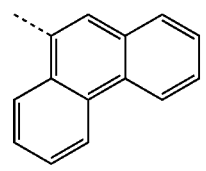 | — |
| Iaaa-640 | O | 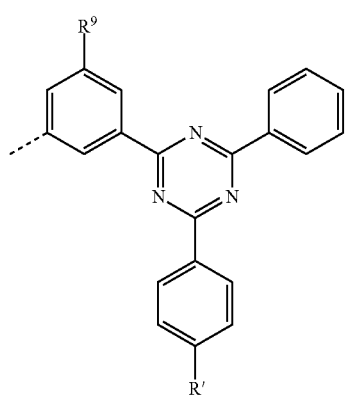 | 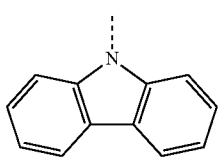 | H |

-continued
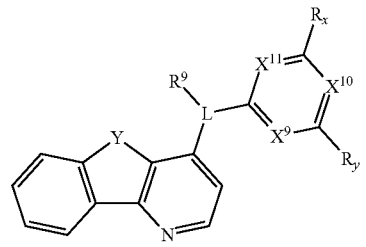
(Iaaa)
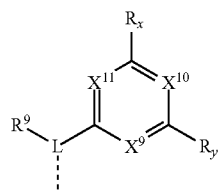
| | Y | R⁹ | | R' |
|---|---|---|---|---|
| Iaaa-641 | O | 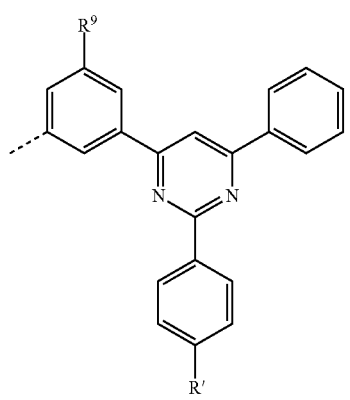 | | H |
| Iaaa-642 | O | 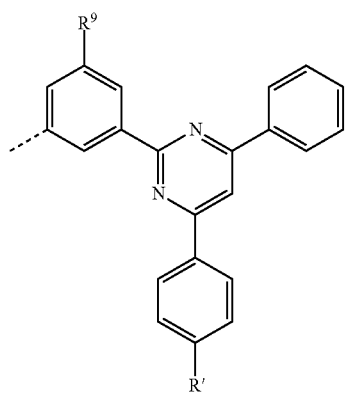 | | H |
| Iaaa-643 | O | 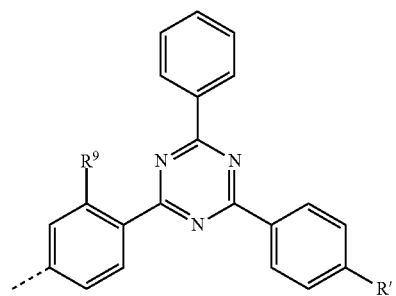 | 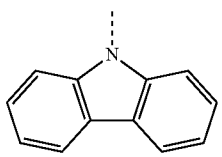 | H |

-continued
(Iaaa)
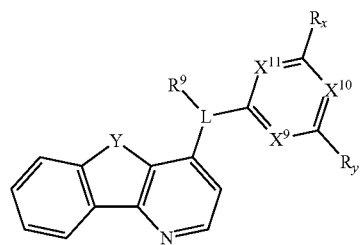
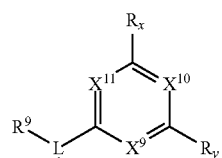
| | Y | | R⁹ | R' |
|---|---|---|---|---|
| Iaaa-644 | O | 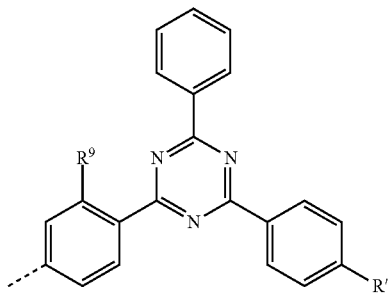 | 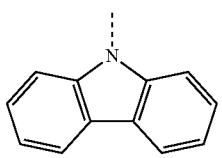 | H |
| Iaaa-645 | O | 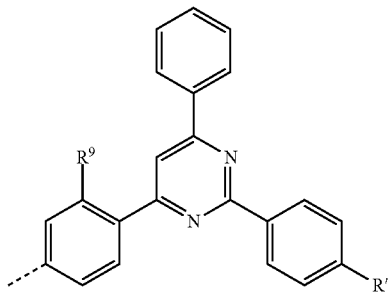 | 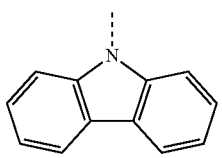 | H |
| Iaaa-646 | O | 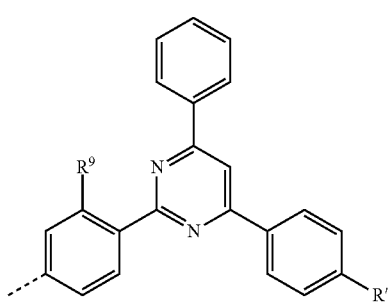 | 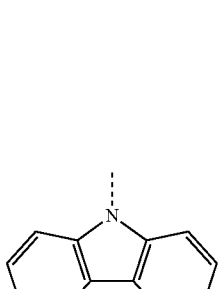 | H |

(Iaaa)
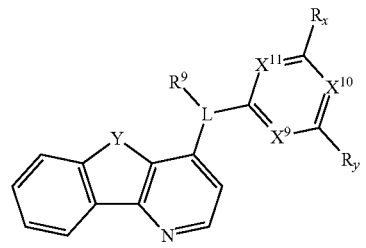
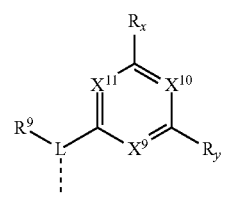
| | Y | | R⁹ | R' |
|---|---|---|---|---|
| Iaaa-647 | O | 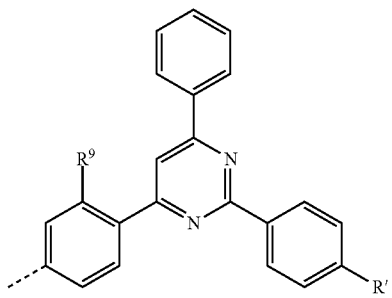 | 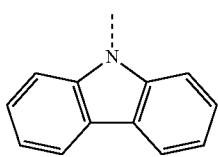 | H |
| Iaaa-648 | O | 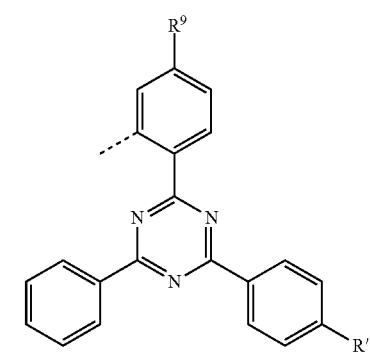 | 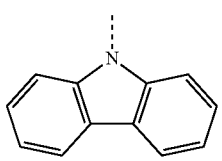 | H |
| Iaaa-649 | O | 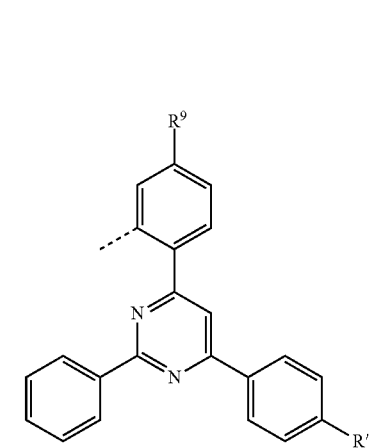 | 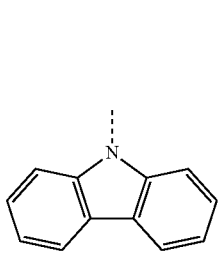 | H |

-continued
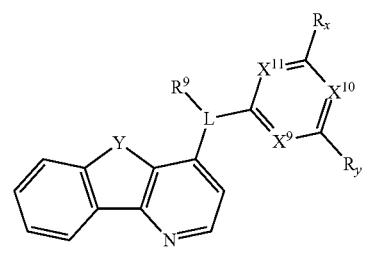
(Iaaa)
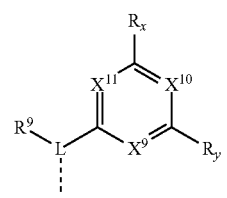
| | Y | | R⁹ | R' |
|---|---|---|---|---|
| Iaaa-650 | O | 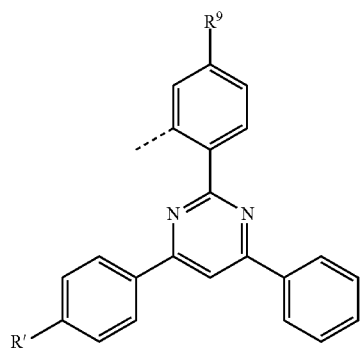 | 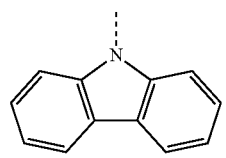 | H |
| Iaaa-651 | O | 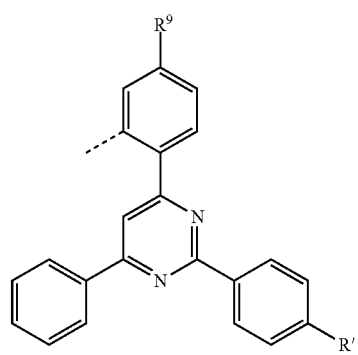 | 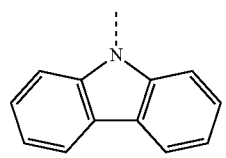 | H |
| Iaaa-652 | O | 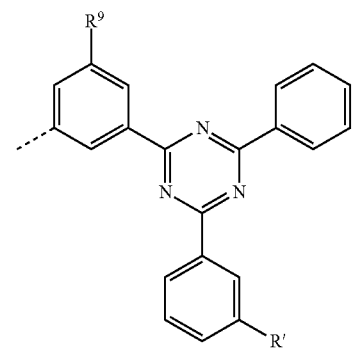 | 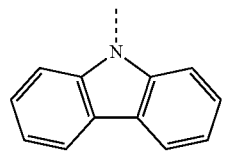 | H |

-continued
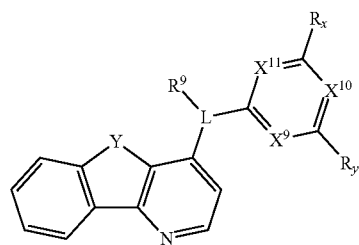
(Iaaa)
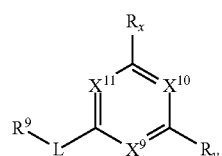
| | Y | | R⁹ | R' |
|---|---|---|---|---|
| Iaaa-653 | O | 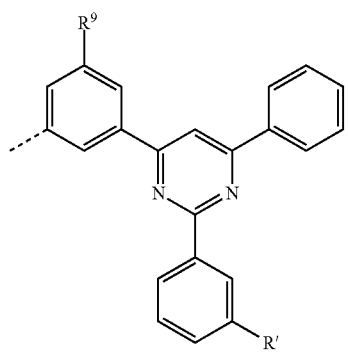 | 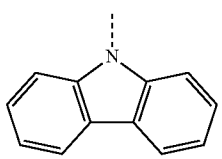 | H |
| Iaaa-654 | O | 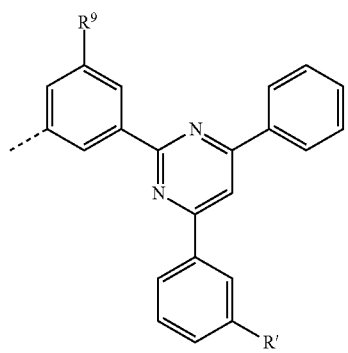 | 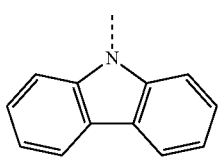 | H |
| Iaaa-655 | O | 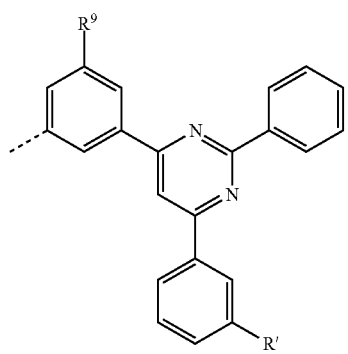 | 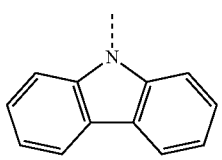 | H |

-continued
(Iaaa)
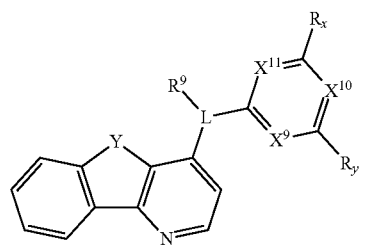
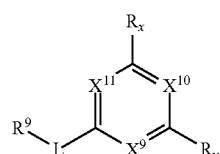
| | Y | | R⁹ | R' |
|---|---|---|---|---|
| Iaaa-656 | O | 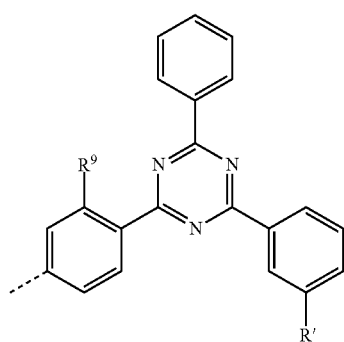 | 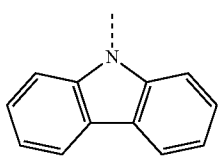 | H |
| Iaaa-657 | O | 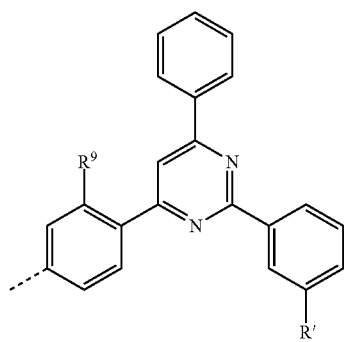 | 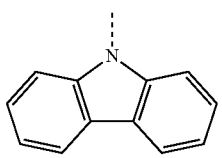 | H |
| Iaaa-658 | O | 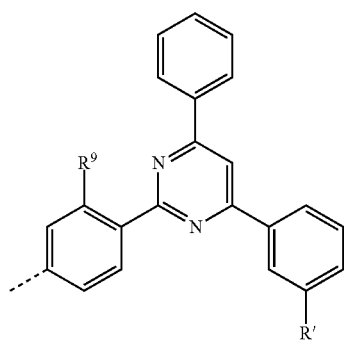 | 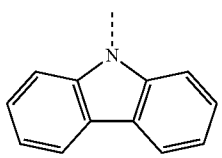 | H |

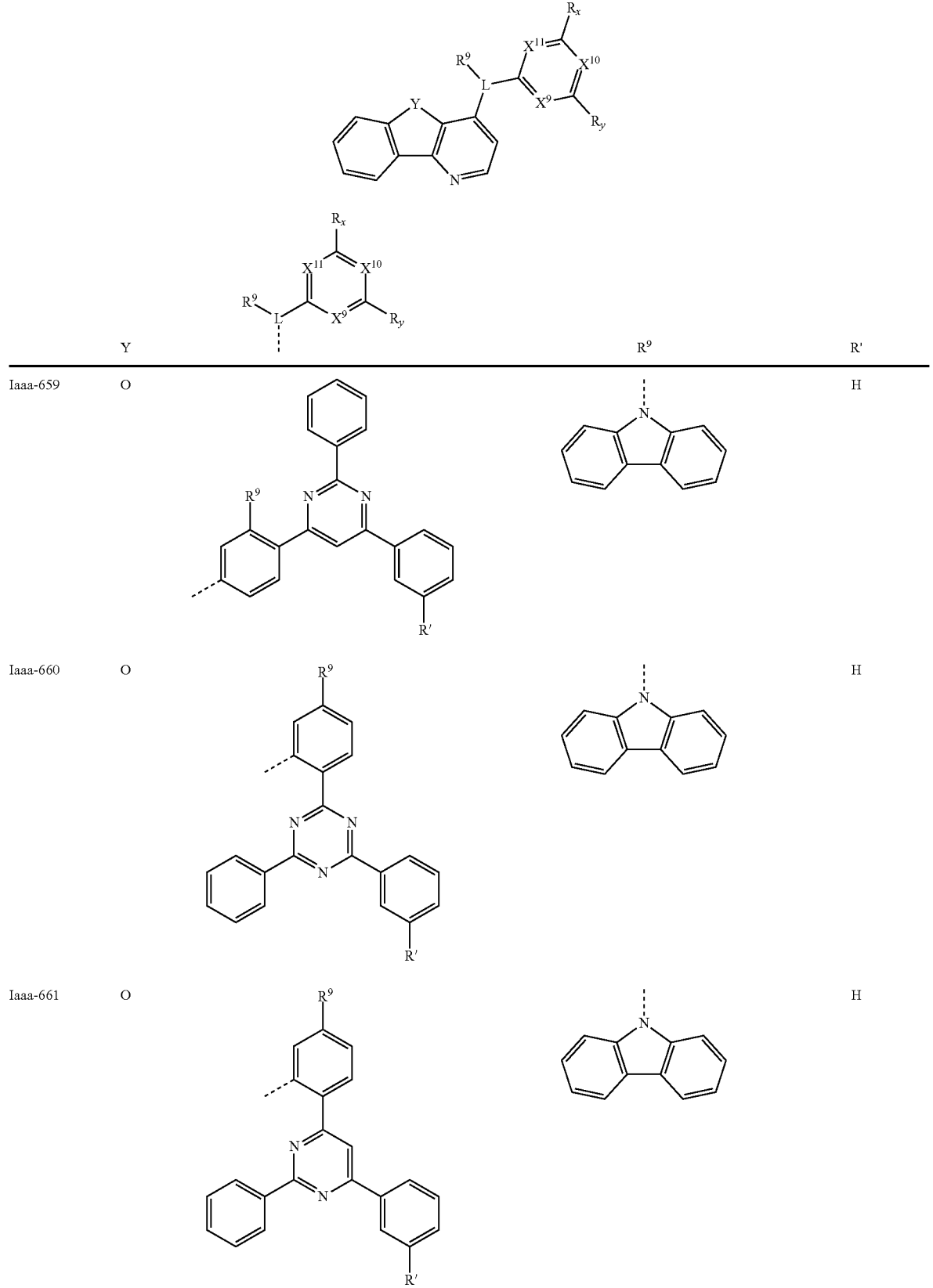

-continued
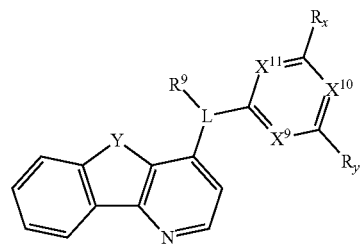
(Iaaa)
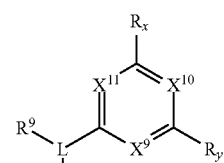
| | Y | | R⁹ | R' |
|---|---|---|---|---|
| Iaaa-662 | O | 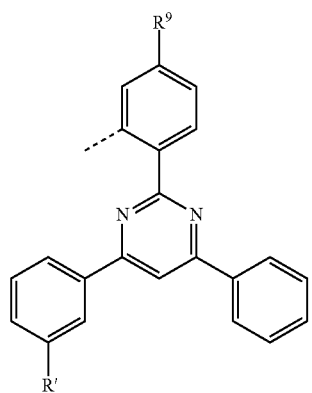 | 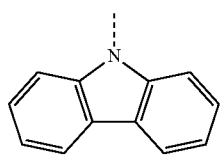 | H |
| Iaaa-663 | O | 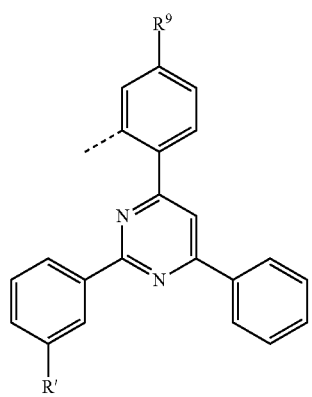 | 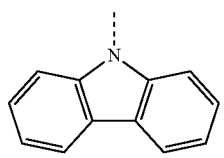 | H |

-continued
(Iaaa)
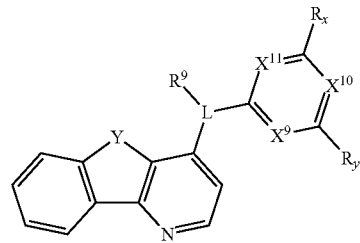
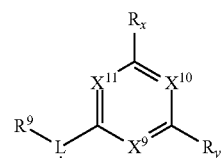
| | Y | R⁹ | R' |
|---|---|---|---|
| Iaaa-664 | O | 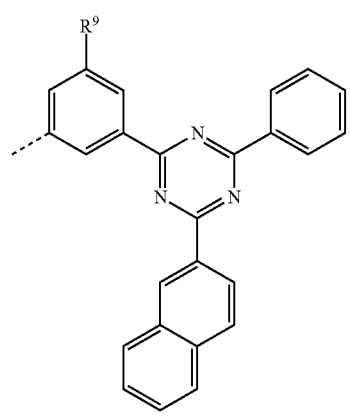 | 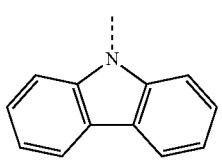 | — |
| Iaaa-665 | O | 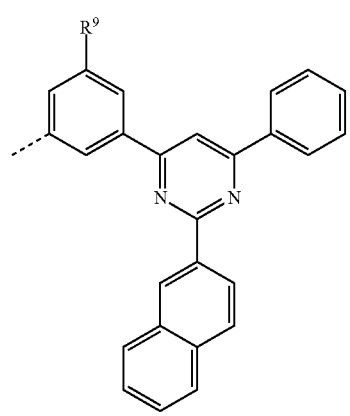 | 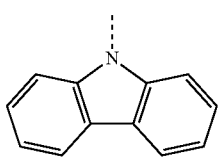 | — |

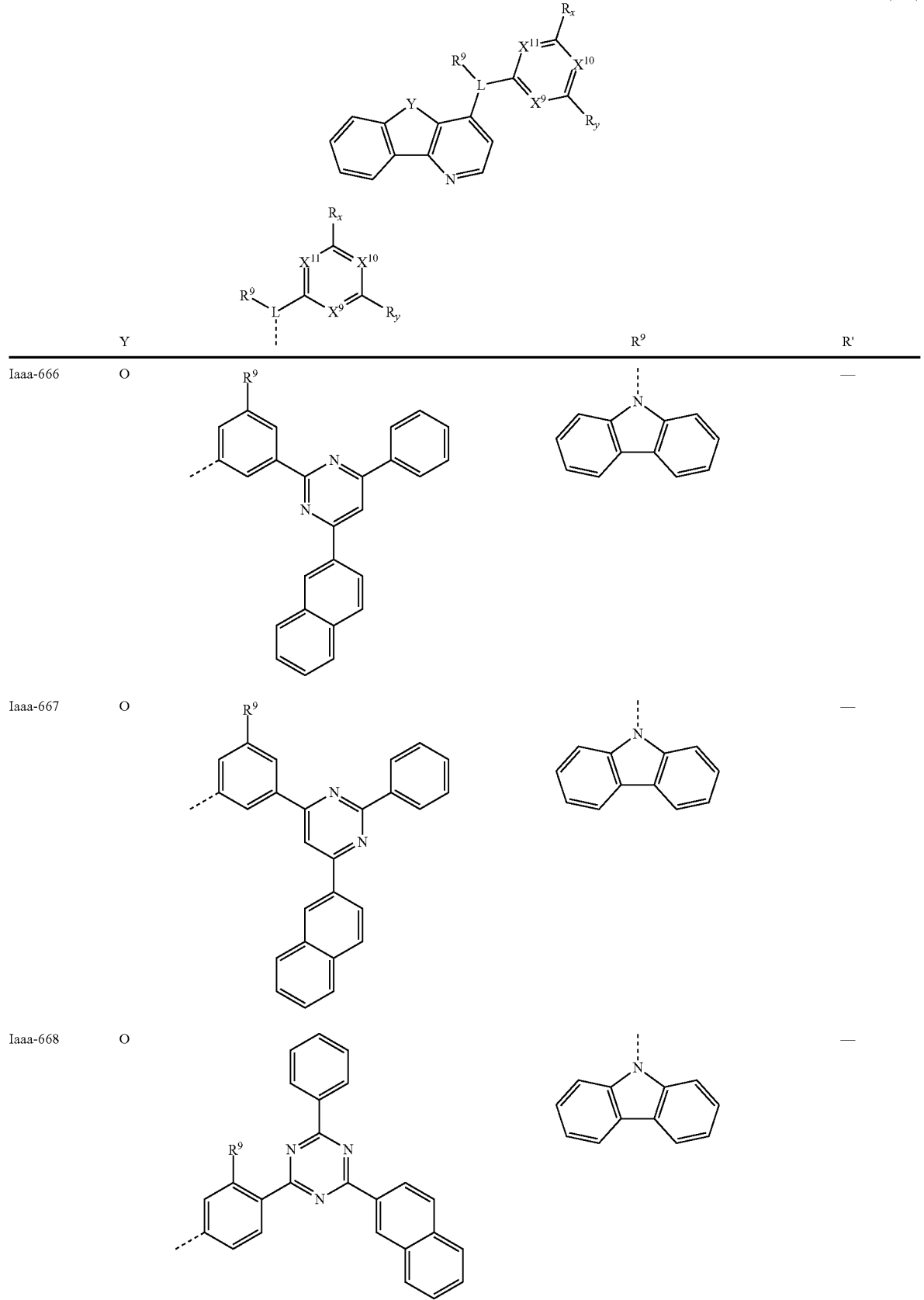

-continued
(Iaaa)
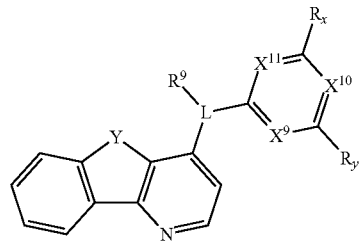
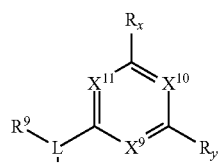
| Y | | R⁹ | R' |
|---|---|---|---|
| Iaaa-669 | O | 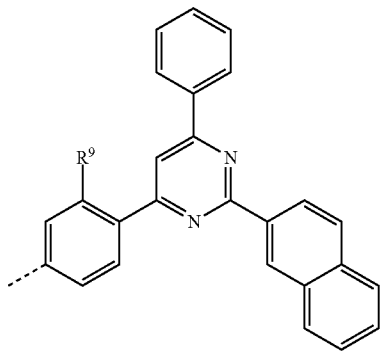 | 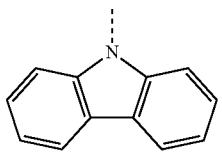 | — |
| Iaaa-670 | O | 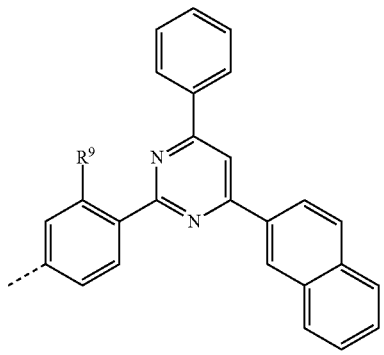 | 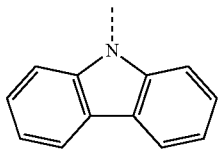 | — |
| Iaaa-671 | O | 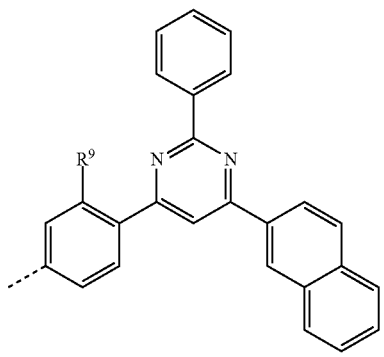 | 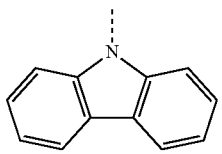 | — |

-continued
(Iaaa)
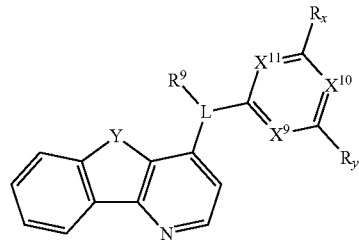
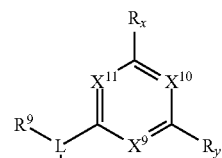
| | Y | R⁹ | | R' |
|---|---|---|---|---|
| Iaaa-672 | O | 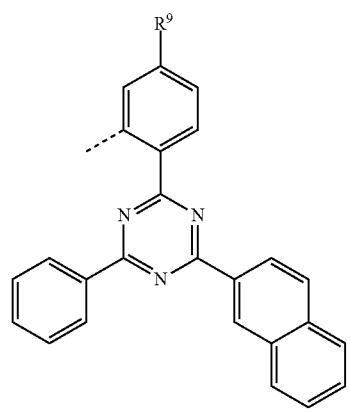 | 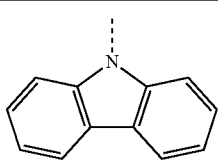 | — |
| Iaaa-673 | O | 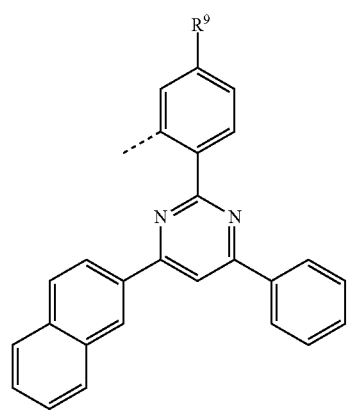 | 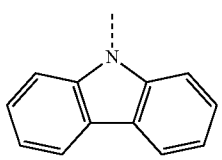 | — |

-continued
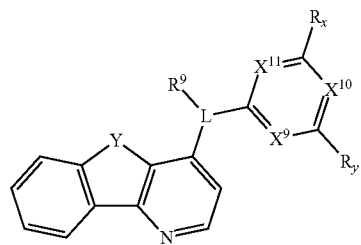
(Iaaa)
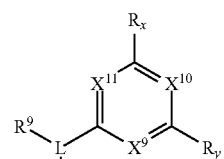
| | Y | R⁹ | R' |
|---|---|---|---|
| Iaaa-674 | O | 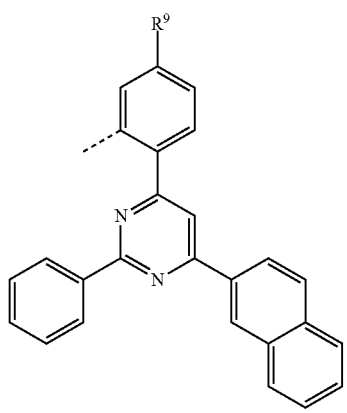 | 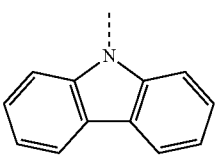 — |
| Iaaa-675 | O | 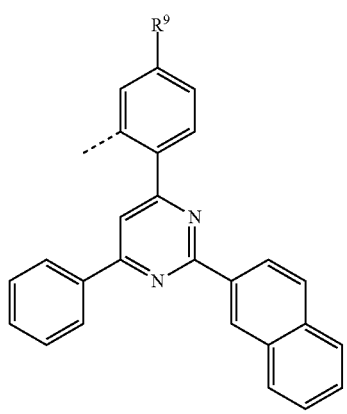 | 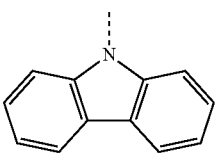 — |

-continued
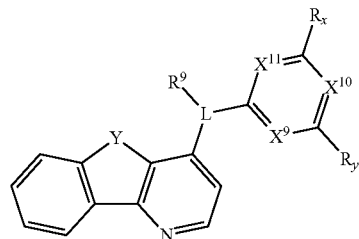
(Iaaa)
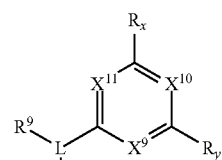
| | Y | | R⁹ | R' |
|---|---|---|---|---|
| Iaaa-676 | O | 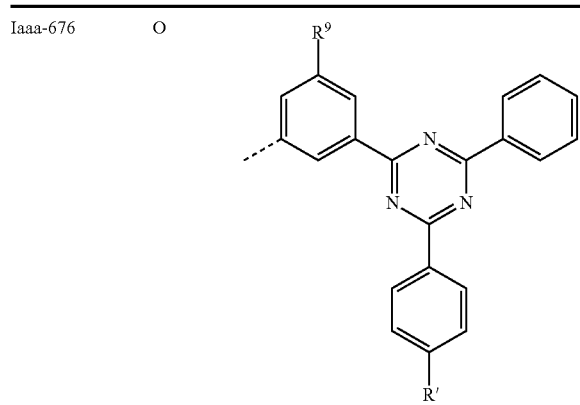 | 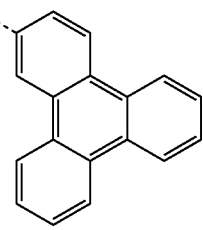 | H |
| Iaaa-677 | O | 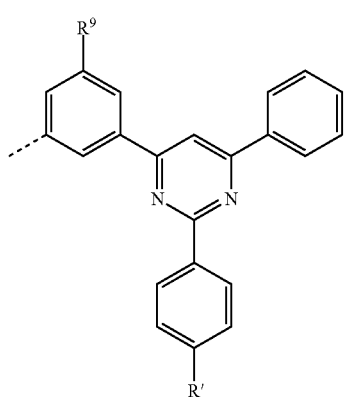 | 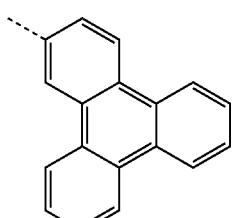 | H |
| Iaaa-678 | O | 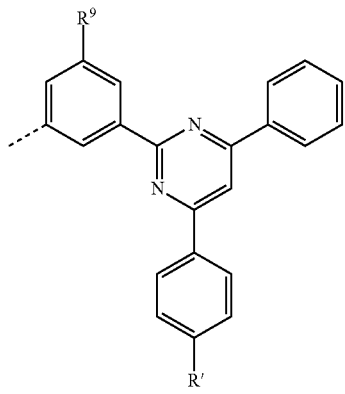 | 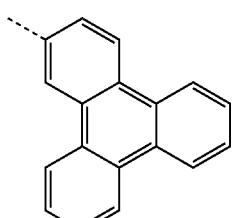 | H |

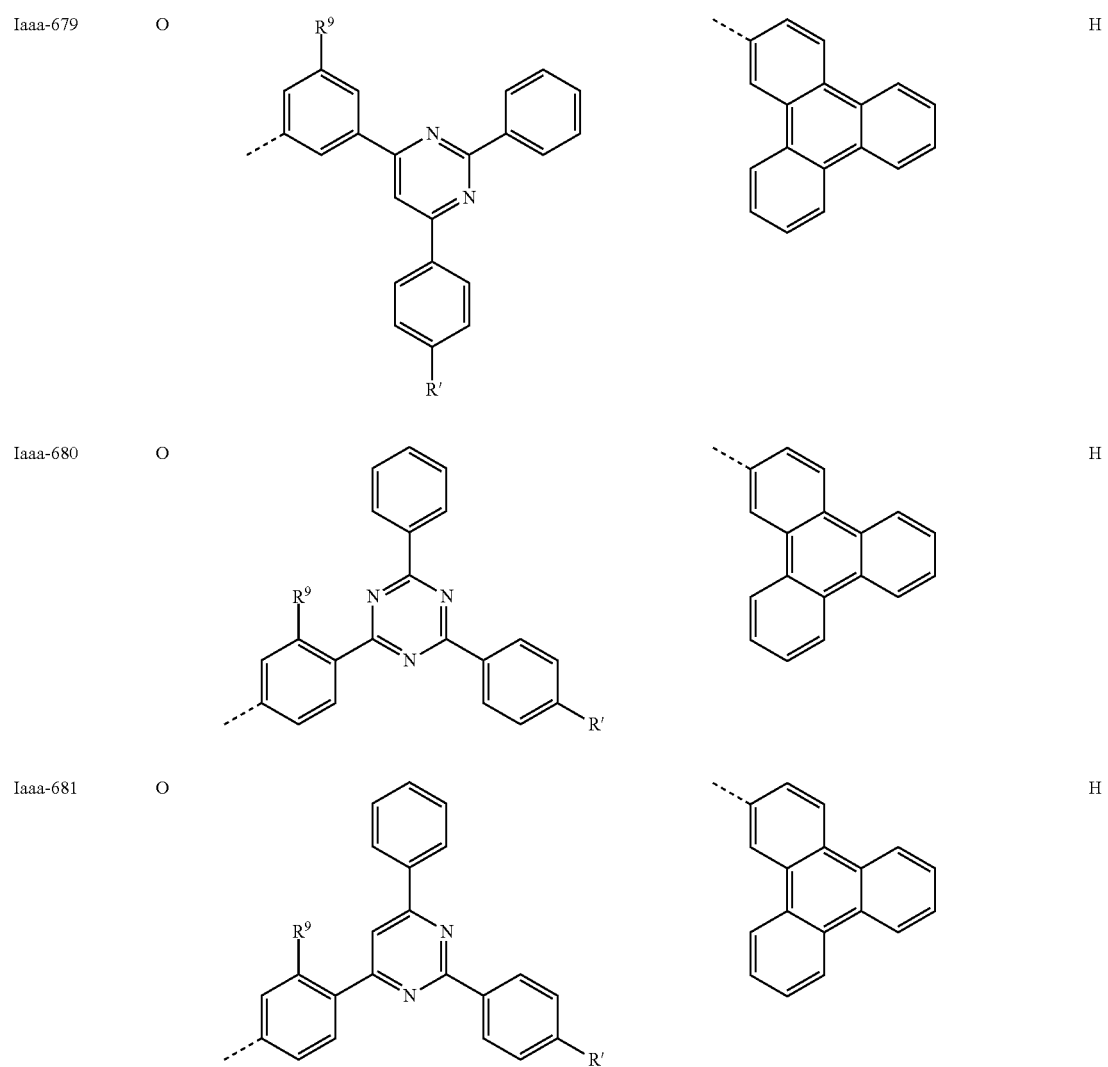

-continued
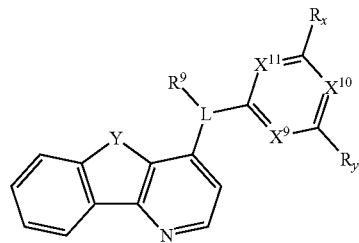
(Iaaa)
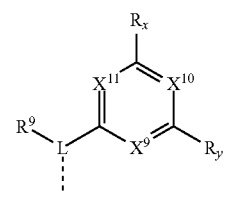
| | Y | | R⁹ | R' |
|---|---|---|---|---|
| Iaaa-682 | O | 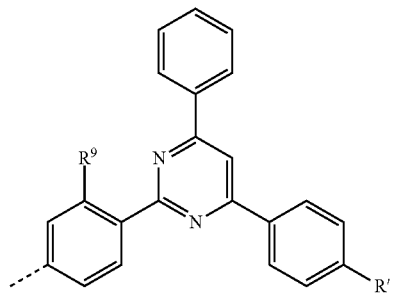 | 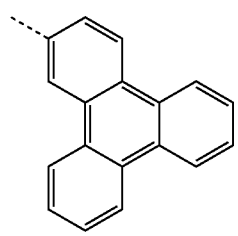 | H |
| Iaaa-683 | O | 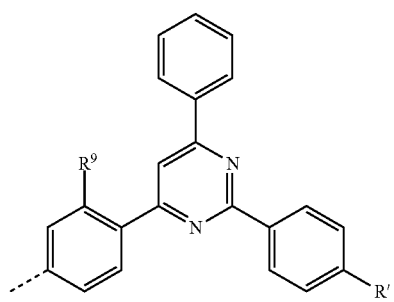 | 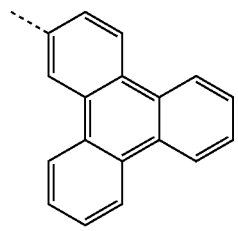 | H |
| Iaaa-684 | O | 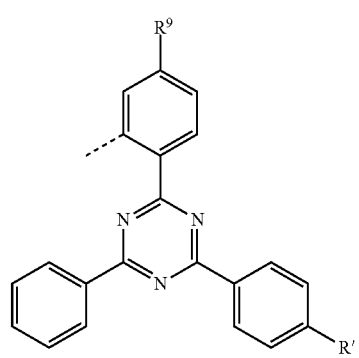 | 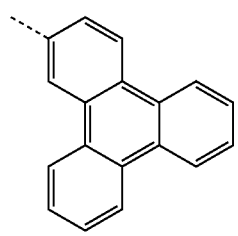 | H |

-continued
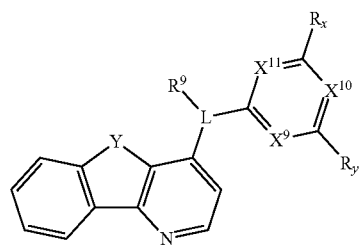
(Iaaa)
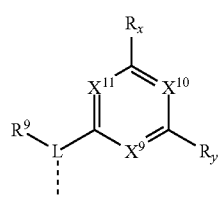
| | Y | | R⁹ | R' |
|---|---|---|---|---|
| Iaaa-685 | O | 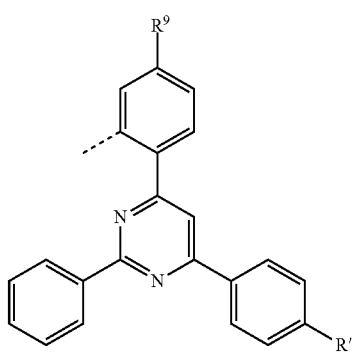 | 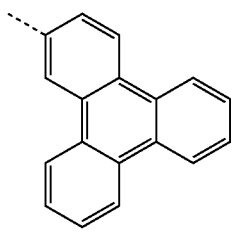 | H |
| Iaaa-686 | O | 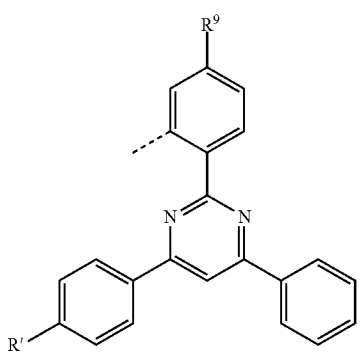 | 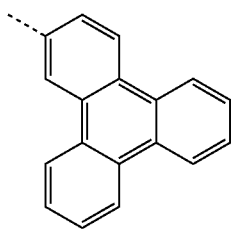 | H |
| Iaaa-687 | O | 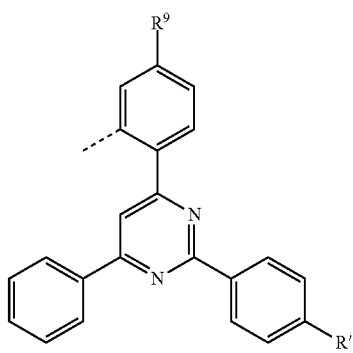 | 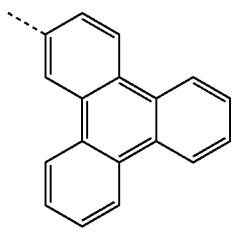 | H |

-continued
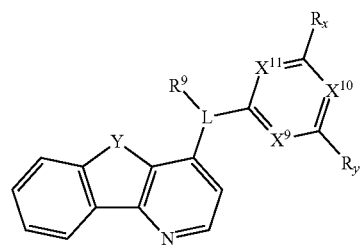
(Iaaa)
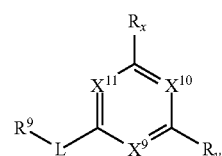
| | Y | | R⁹ | R' |
|---|---|---|---|---|
| Iaaa-688 | O |  | 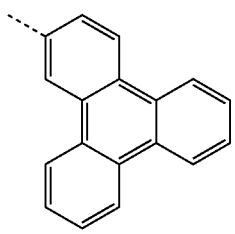 | H |
| Iaaa-689 | O | 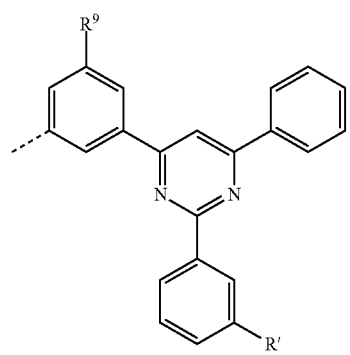 | 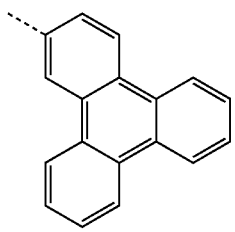 | H |
| Iaaa-690 | O | 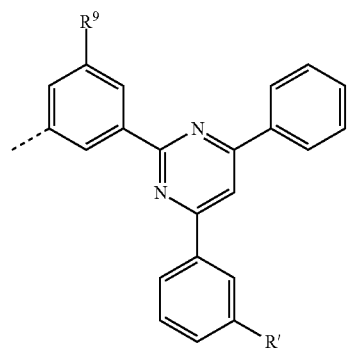 | 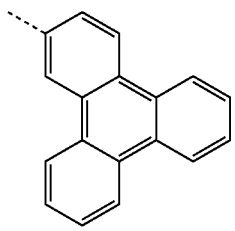 | H |

-continued
(Iaaa)
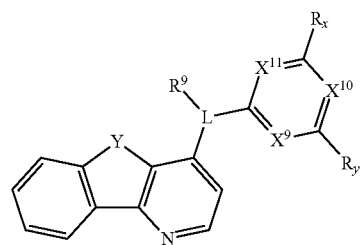
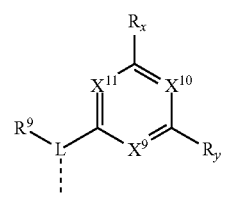
| | Y | R⁹ | | R' |
|---|---|---|---|---|
| Iaaa-691 | O | 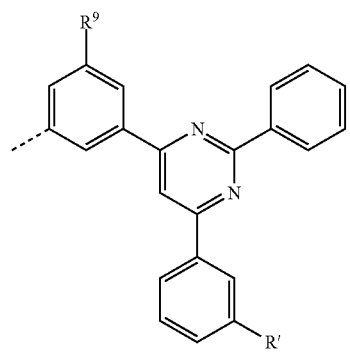 | | H |
| Iaaa-692 | O | 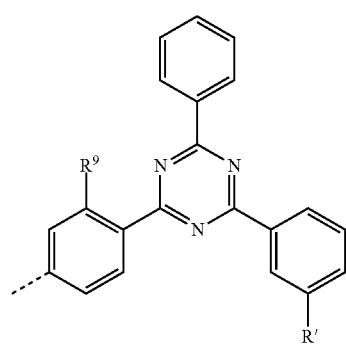 | | H |
| Iaaa-693 | O | 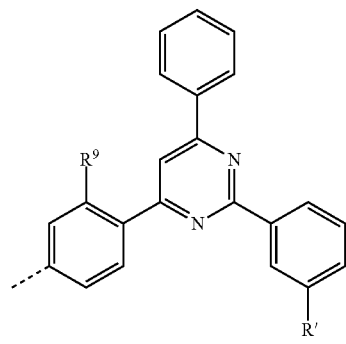 | | H |

-continued
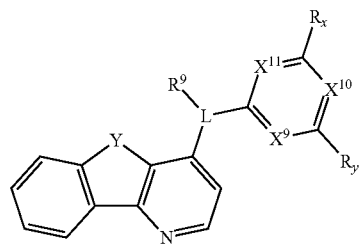
(Iaaa)
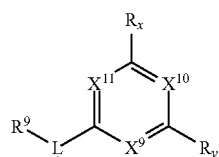
| | Y | | R⁹ | R' |
|---|---|---|---|---|
| Iaaa-694 | O | 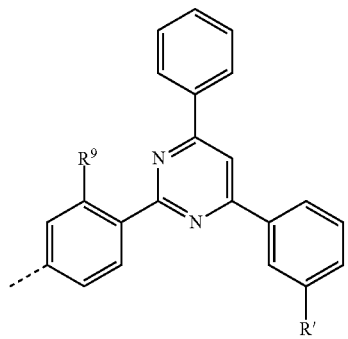 | 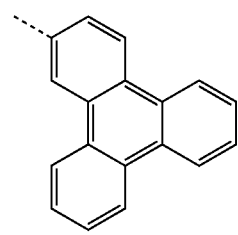 | H |
| Iaaa-695 | O | 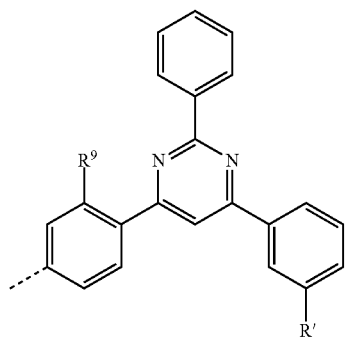 | 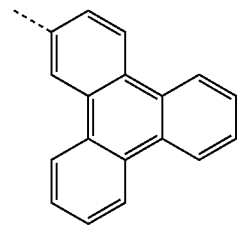 | H |
| Iaaa-696 | O | 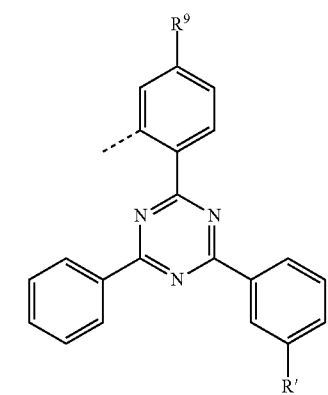 | 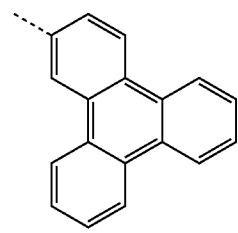 | H |

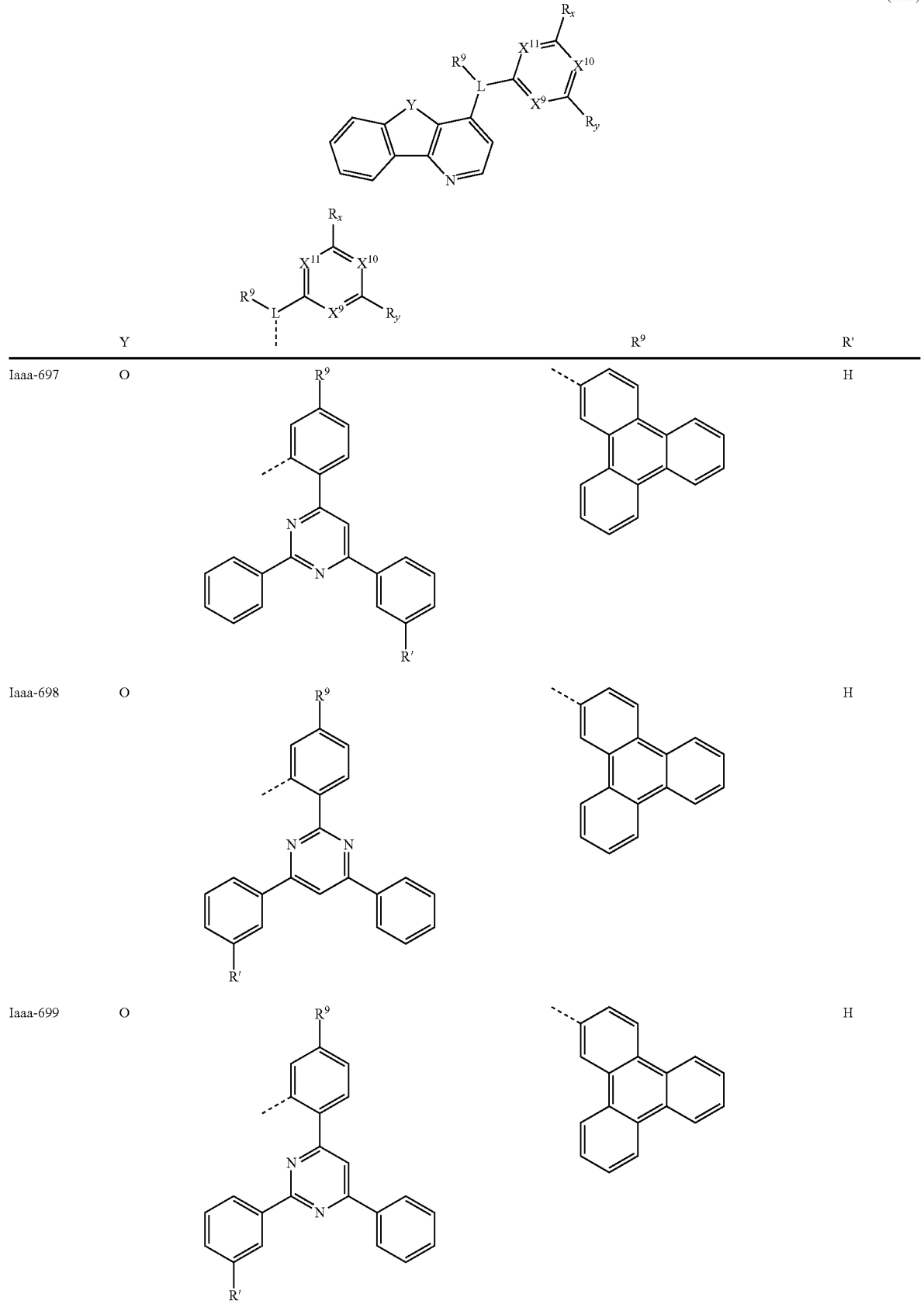

-continued
(Iaaa)
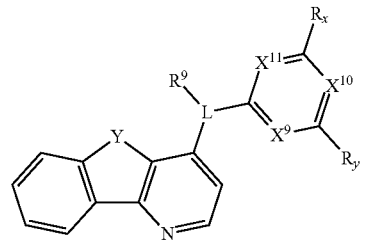
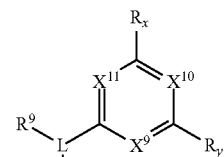
| | Y | | R⁹ | R' |
|---|---|---|---|---|
| Iaaa-700 | O | 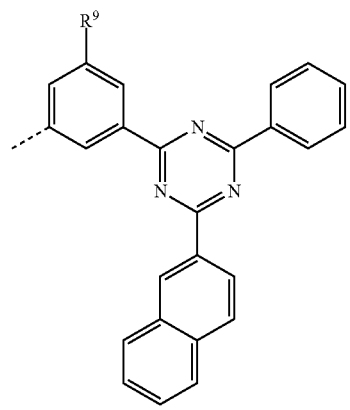 | 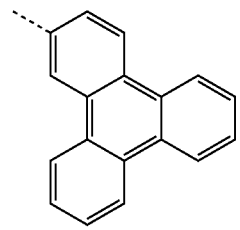 | — |
| Iaaa-701 | O | 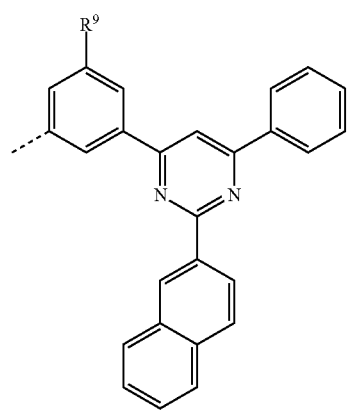 | 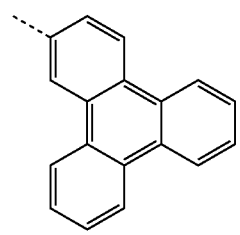 | — |

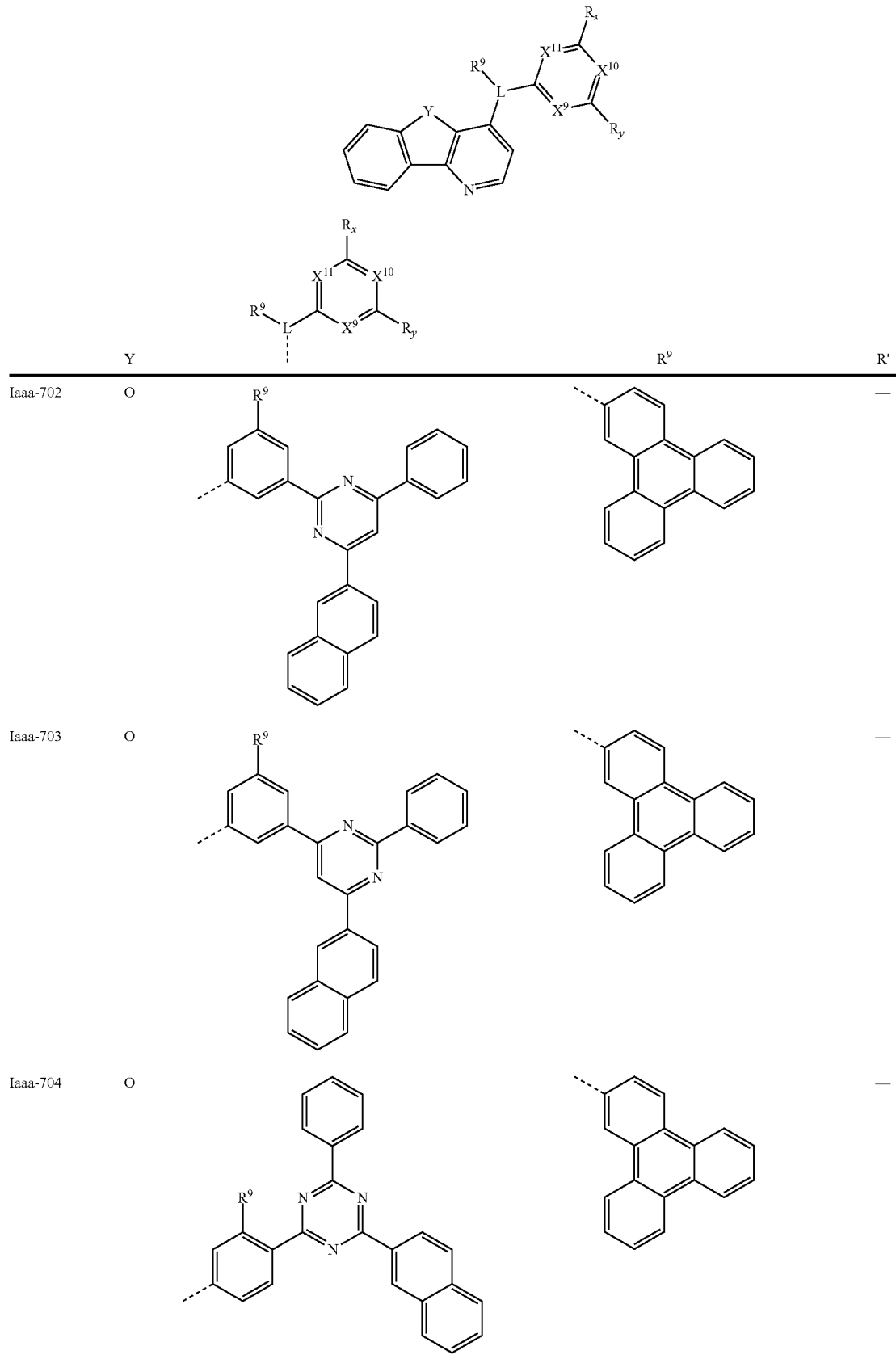

-continued
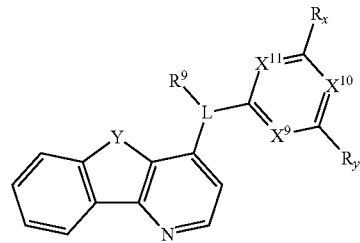
(Iaaa)
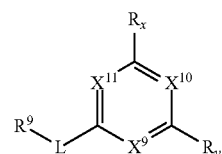
| | Y | R⁹ | R' |
|---|---|---|---|
| Iaaa-705 | O | 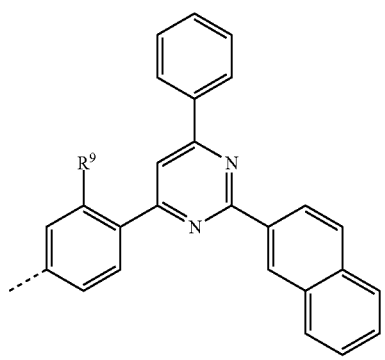 | 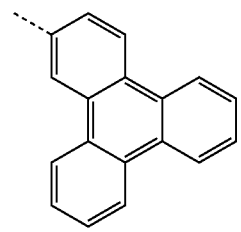 | — |
| Iaaa-706 | O | 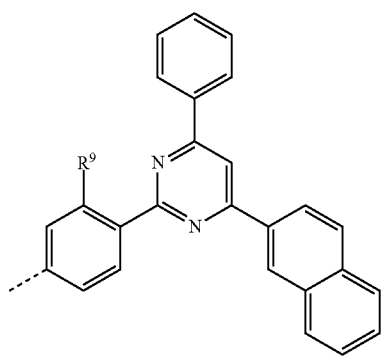 |  | — |
| Iaaa-707 | O | 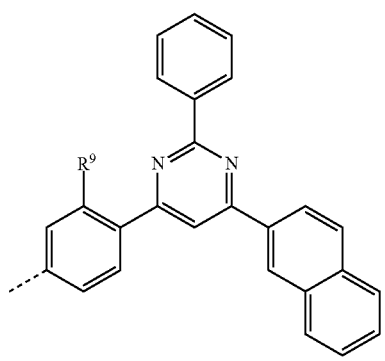 | 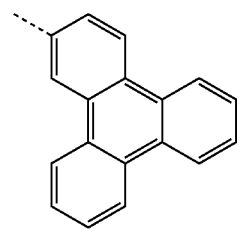 | — |

-continued
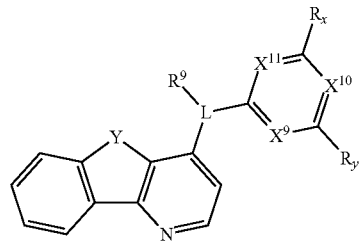
(Iaaa)
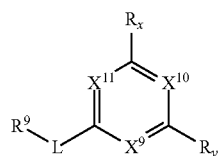
| | Y | | R⁹ | R' |
|---|---|---|---|---|
| Iaaa-708 | O | 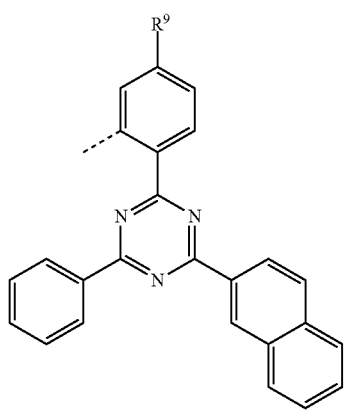 | 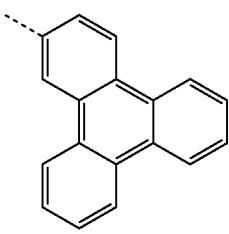 | — |
| Iaaa-709 | O | 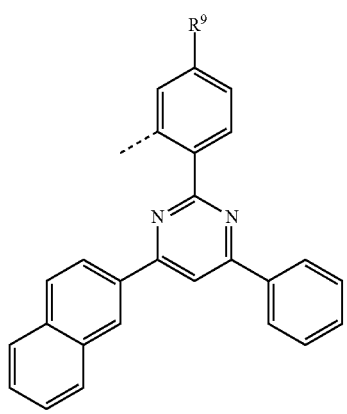 | 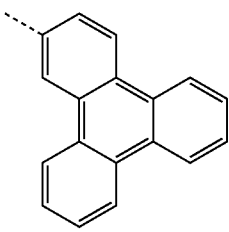 | — |

-continued
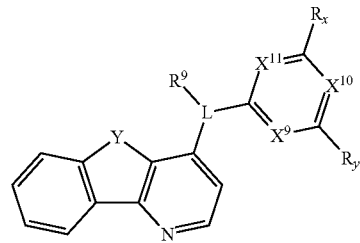
(Iaaa)
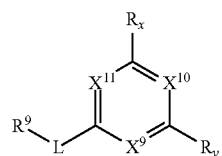
| | Y | R⁹ | R' |
|---|---|---|---|
| Iaaa-710 | O | 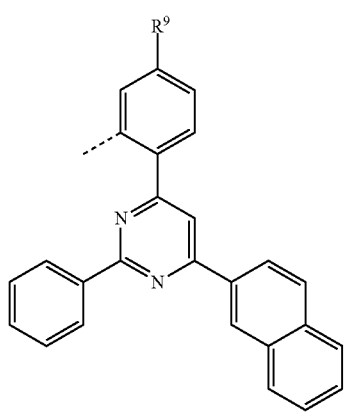 | 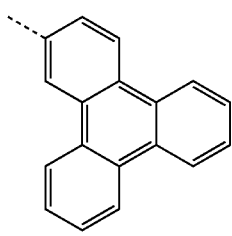 |
| Iaaa-711 | O | 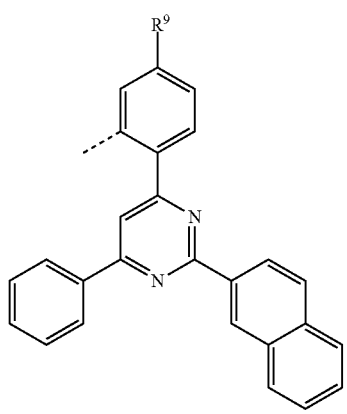 | 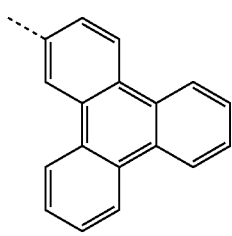 |

-continued
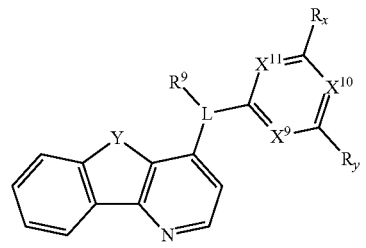
(Iaaa)
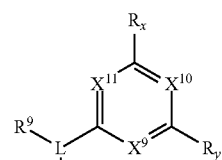
| | Y | | R⁹ | R' |
|---|---|---|---|---|
| Iaaa-712 | O | 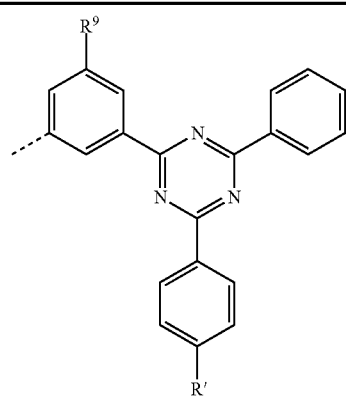 | 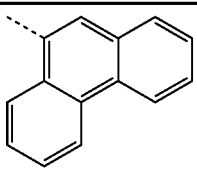 |  |
| Iaaa-713 | O | 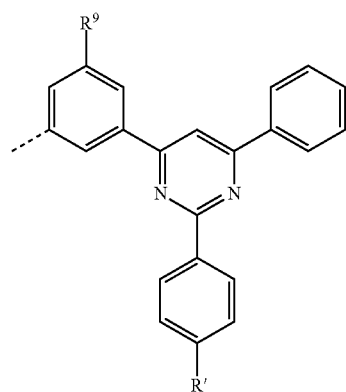 | | |
| Iaaa-714 | O | 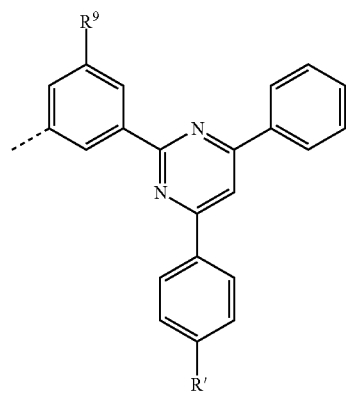 | |  |

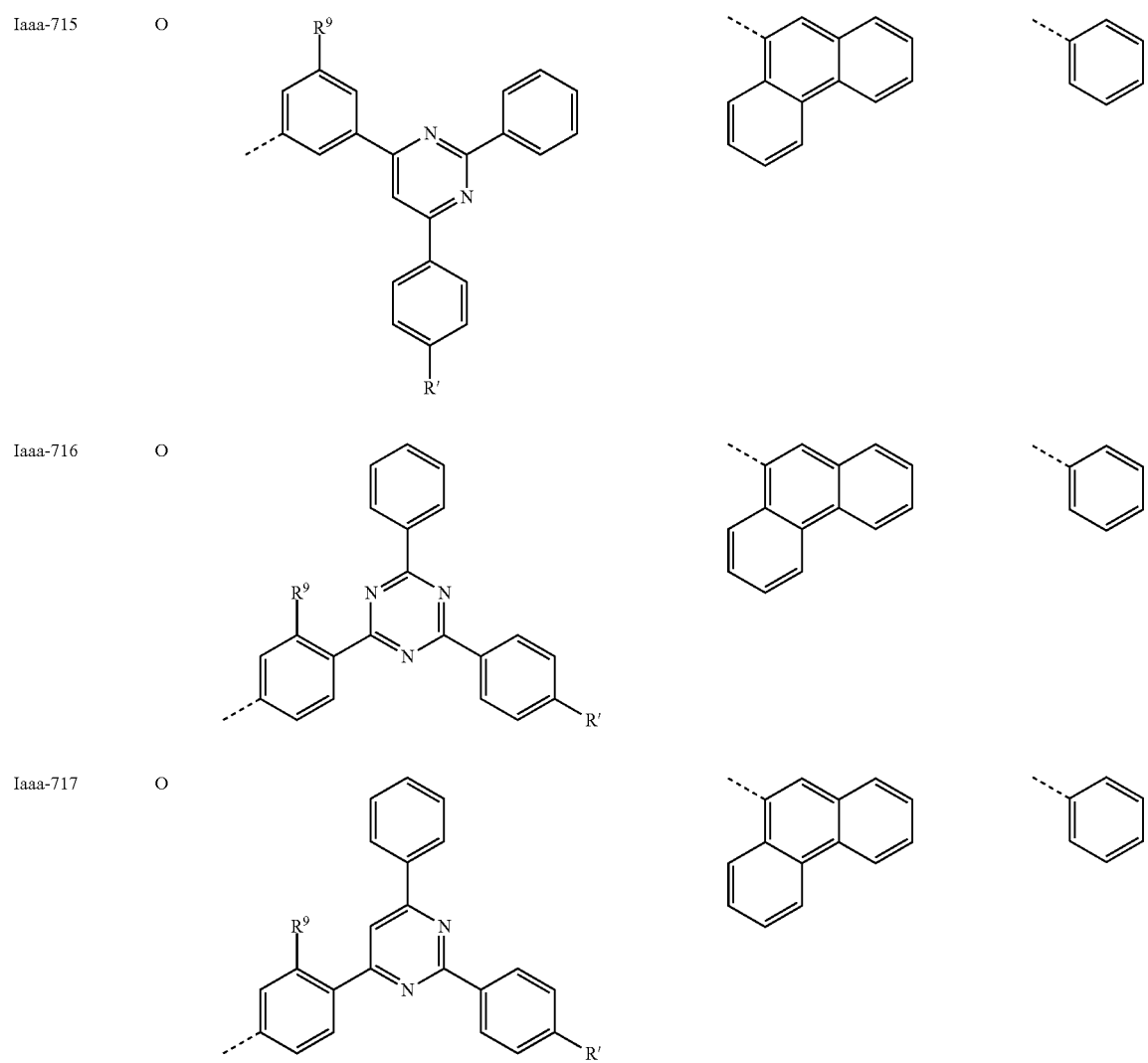

-continued
(Iaaa)
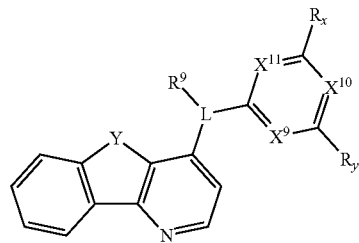
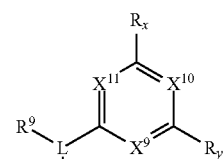
| | Y | | R⁹ | R' |
|---|---|---|---|---|
| Iaaa-718 | O | 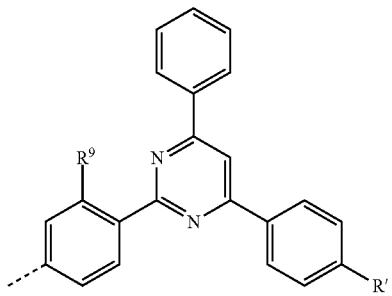 | 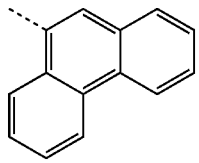 | 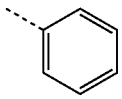 |
| Iaaa-719 | O | 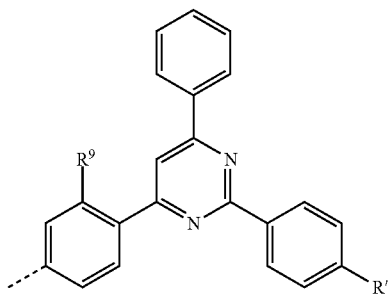 | 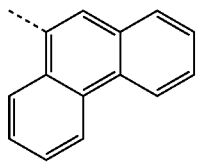 | 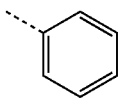 |
| Iaaa-720 | O | 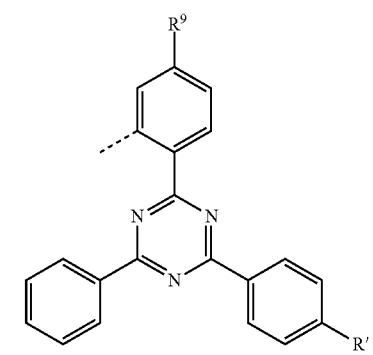 | 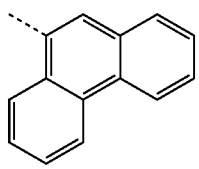 | 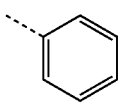 |

-continued
(Iaaa)
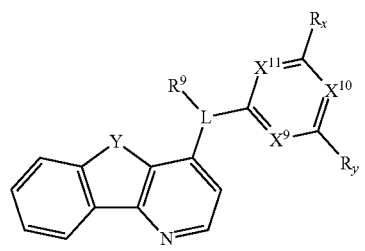
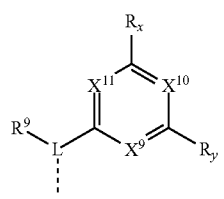
| | Y | | R⁹ | R' |
|---|---|---|---|---|
| Iaaa-721 | O | 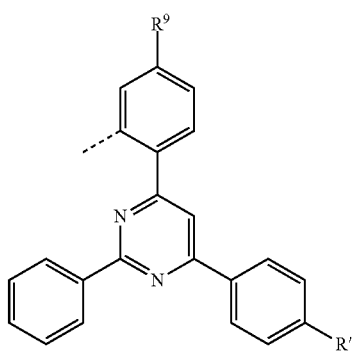 | 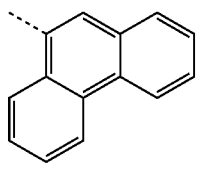 | 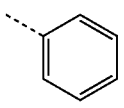 |
| Iaaa-722 | O | 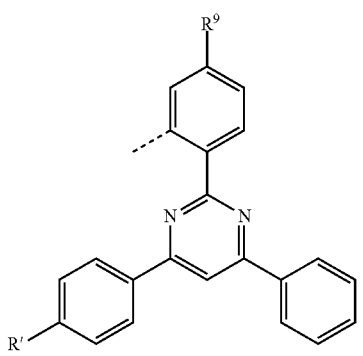 | 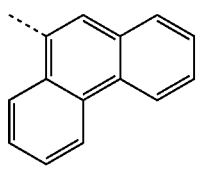 | 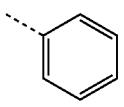 |
| Iaaa-723 | O | 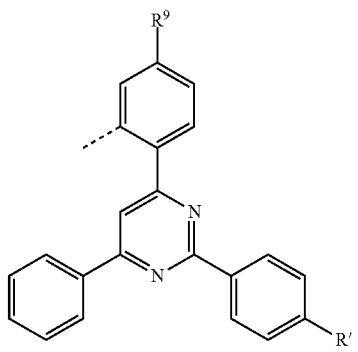 | 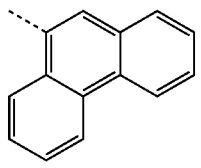 | 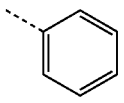 |

-continued
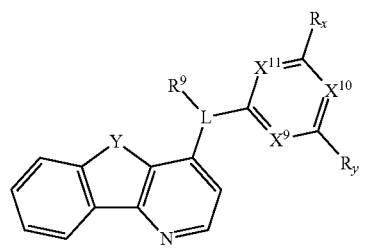
(Iaaa)
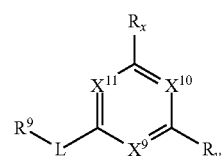
| | Y | | R⁹ | R' |
|---|---|---|---|---|
| Iaaa-724 | O | 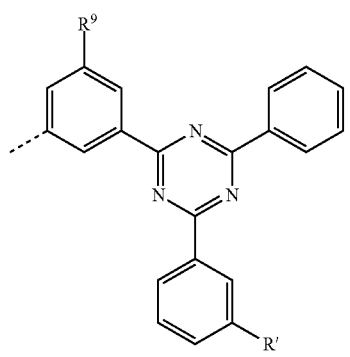 | 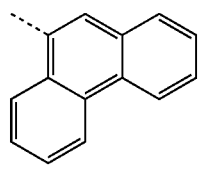 | 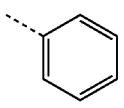 |
| Iaaa-725 | O | 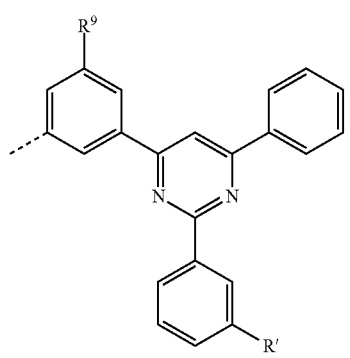 | 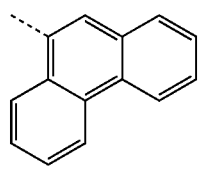 | 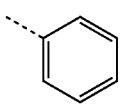 |
| Iaaa-726 | O | 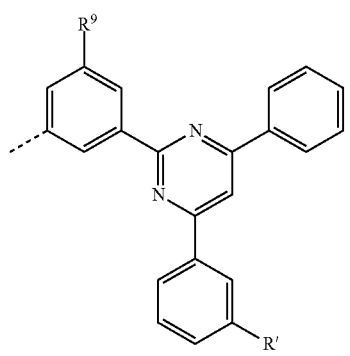 | 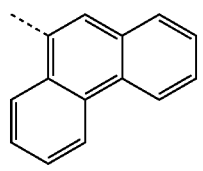 | 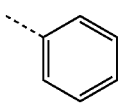 |

-continued
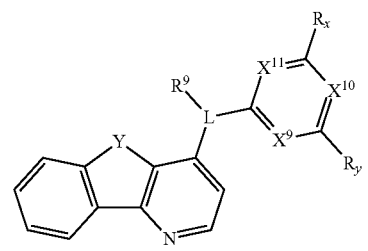
(Iaaa)
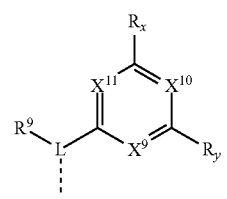
| | Y | | $R^9$ | R' |
|---|---|---|---|---|
| Iaaa-727 | O | 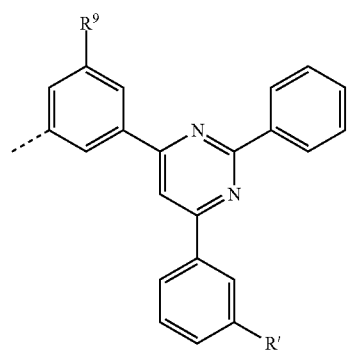 | 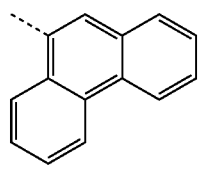 | 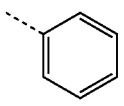 |
| Iaaa-728 | O | 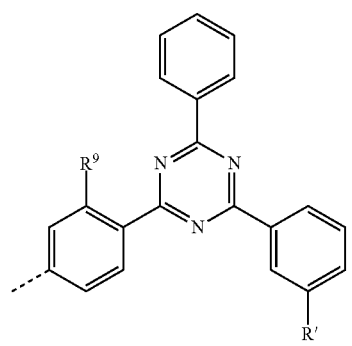 | 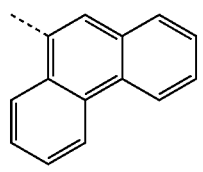 | 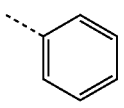 |
| Iaaa-729 | O | 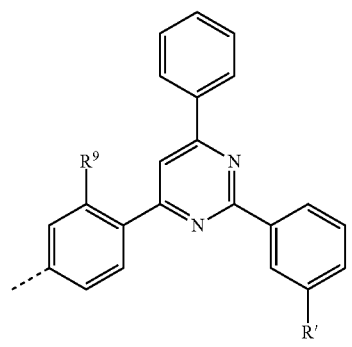 | 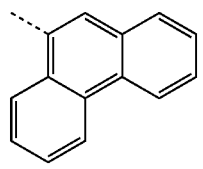 | 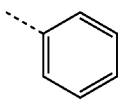 |

-continued
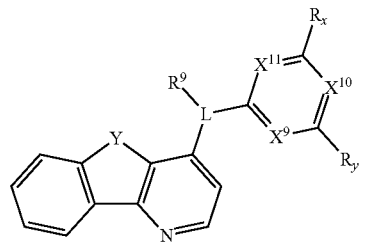
(Iaaa)
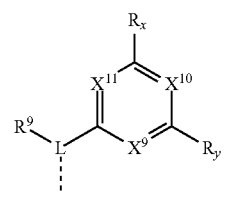
| | Y | | R⁹ | R' |
|---|---|---|---|---|
| Iaaa-730 | O | 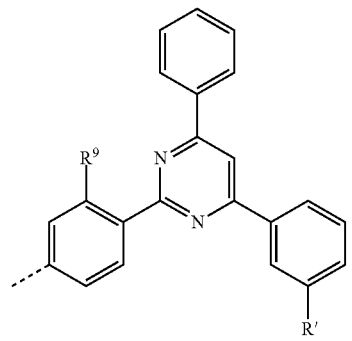 | 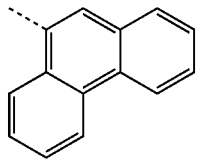 | 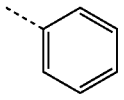 |
| Iaaa-731 | O | 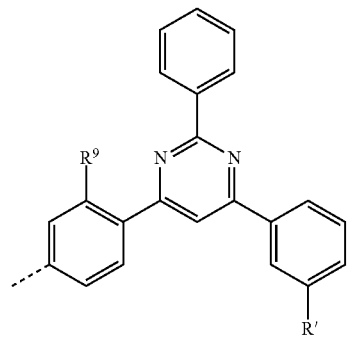 | 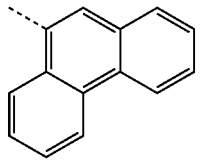 | 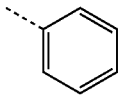 |
| Iaaa-732 | O | 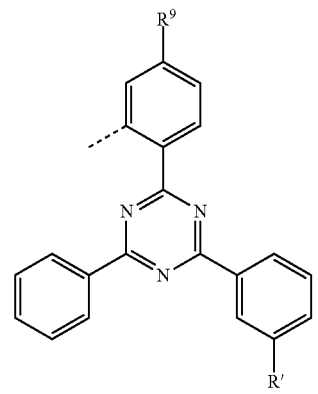 | 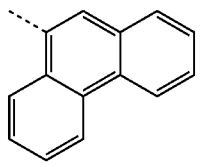 | 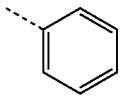 |

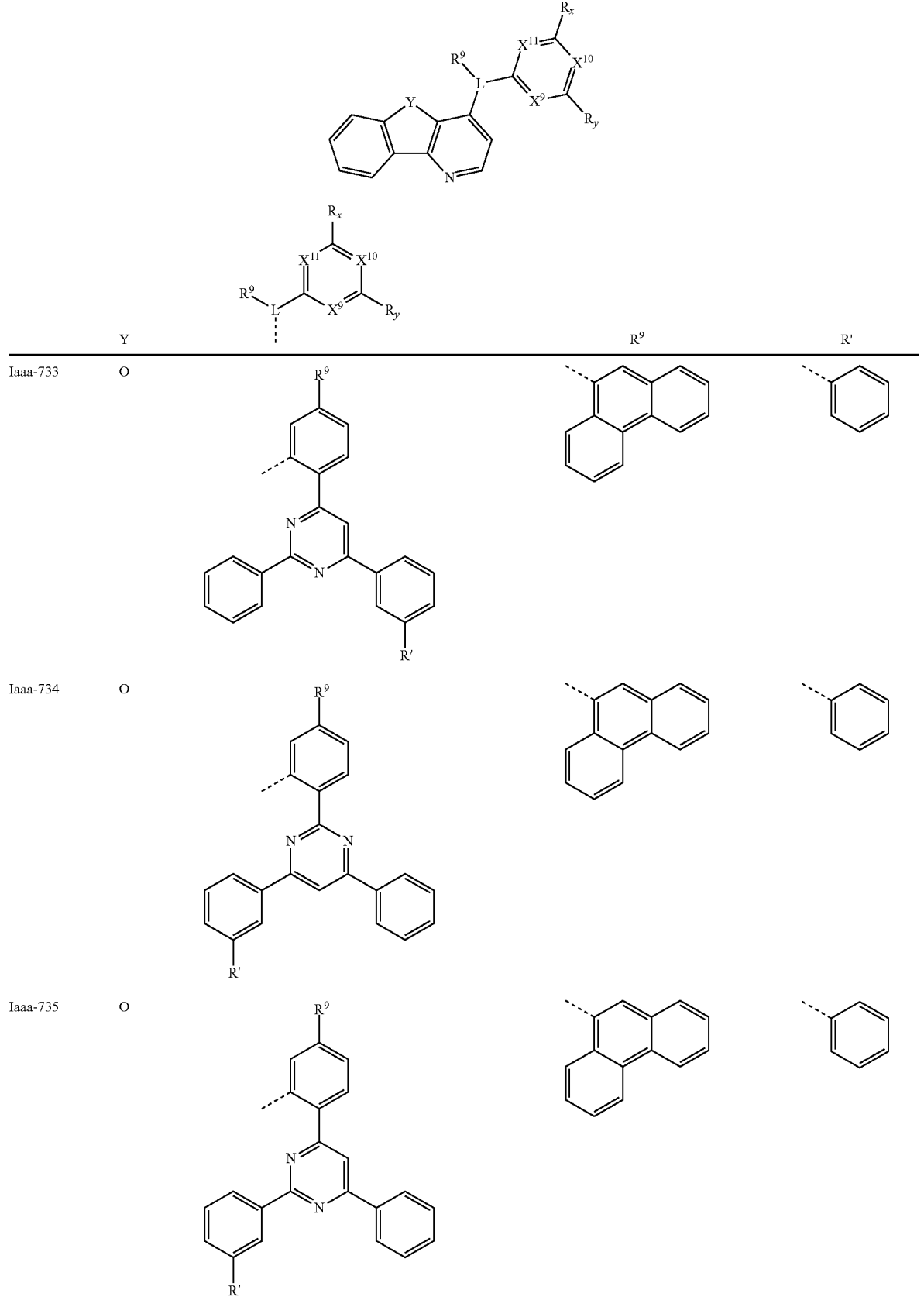

-continued
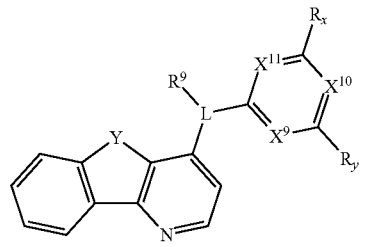
(Iaaa)
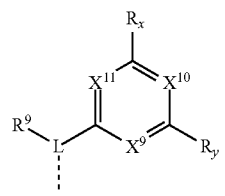
| | Y | R⁹ | R' |
|---|---|---|---|
| Iaaa-736 | | | |
| Iaaa-737 | | | |
| Iaaa-738 | | | |
| Iaaa-739 | O | 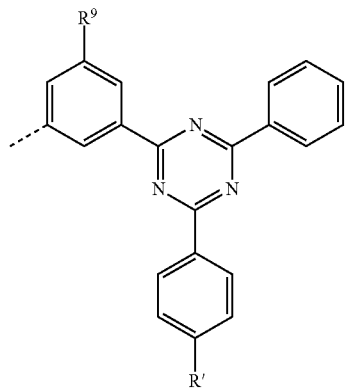 | 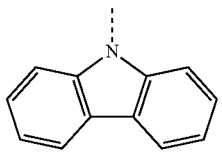 | 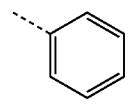 |
| Iaaa-740 | O | 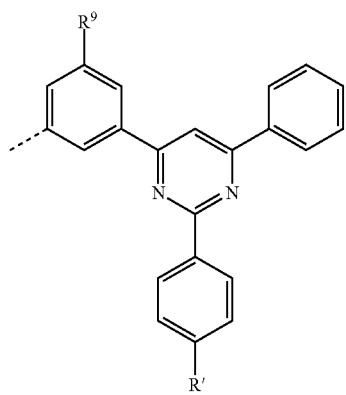 | 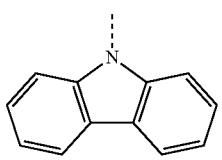 | 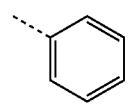 |

-continued
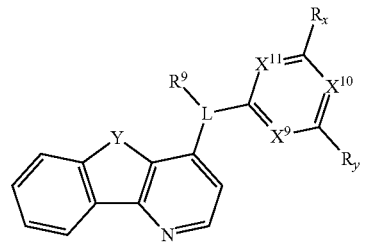
(Iaaa)
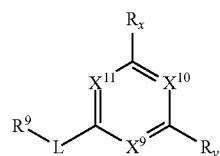
| | Y | | R⁹ | R' |
|---|---|---|---|---|
| Iaaa-741 | O | 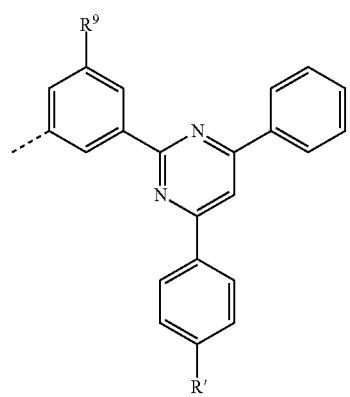 | 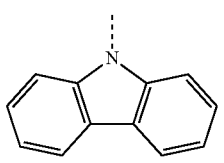 | 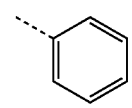 |
| Iaaa-742 | O | 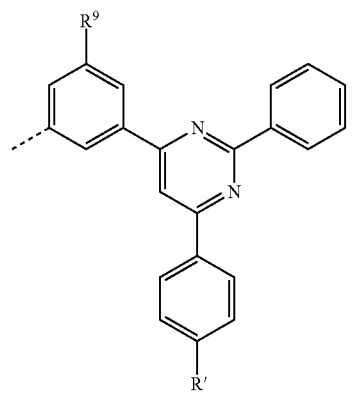 | 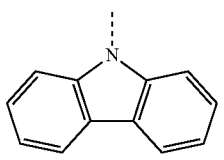 | 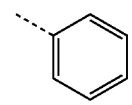 |
| Iaaa-743 | O | 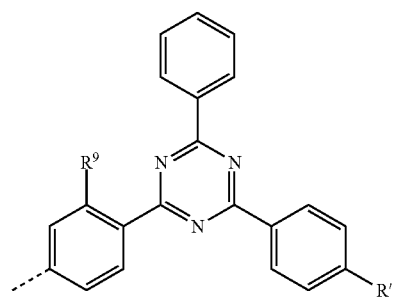 | 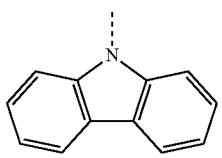 | 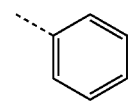 |

-continued
(Iaaa)
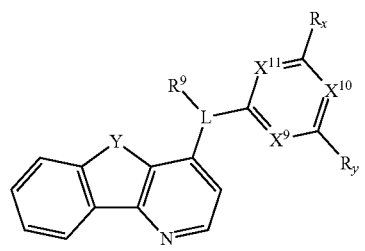
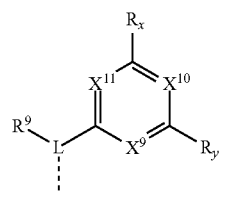
| | Y | R⁹ | R' |
|---|---|---|---|
| Iaaa-744 | O | 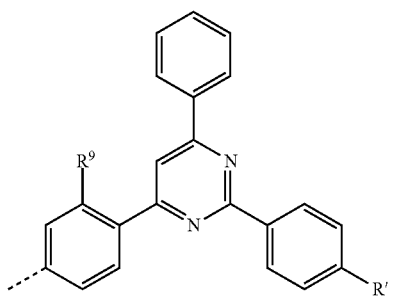 | 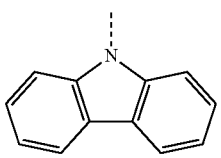 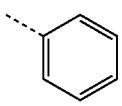 |
| Iaaa-745 | O | 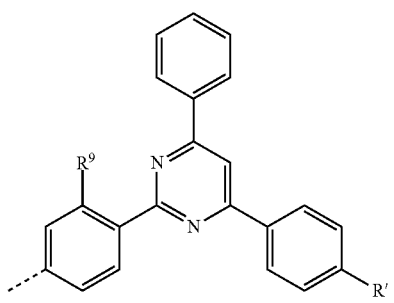 |  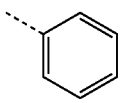 |
| Iaaa-746 | O | 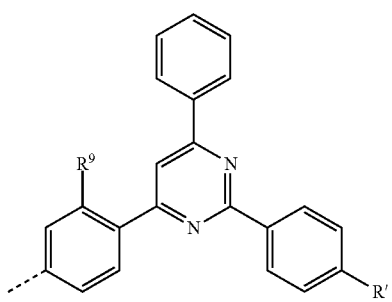 | 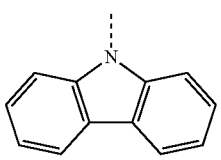 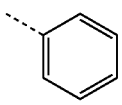 |

(Iaaa)
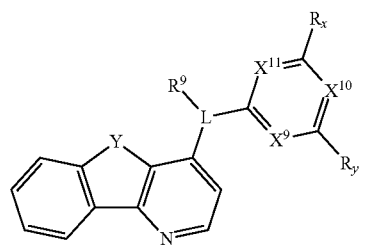
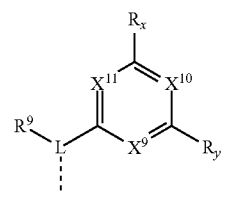
| | Y | | R⁹ | R' |
|---|---|---|---|---|
| Iaaa-747 | O | 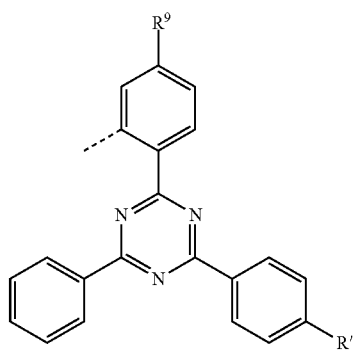 | 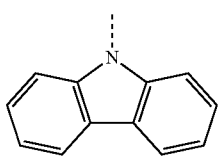 | 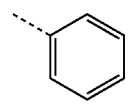 |
| Iaaa-748 | O | 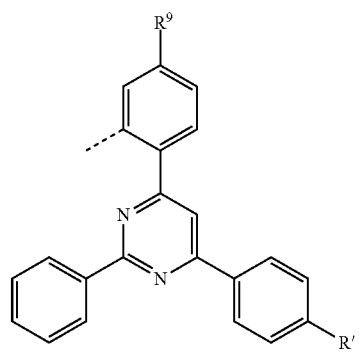 | 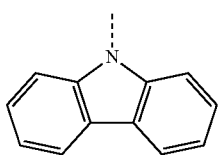 | 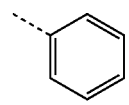 |
| Iaaa-749 | O | 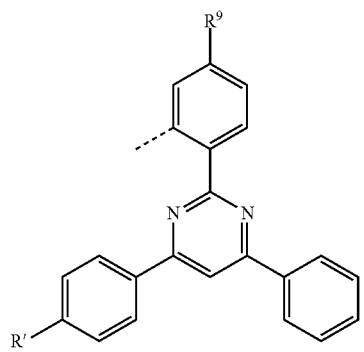 | 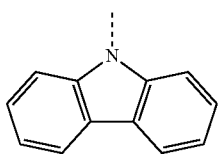 | 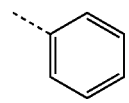 |

-continued
(Iaaa)
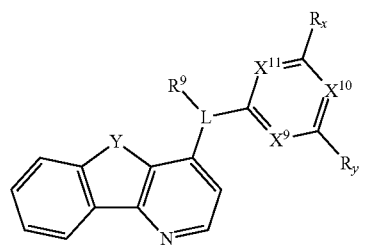
| | Y | | R⁹ | R' |
|---|---|---|---|---|
| Iaaa-750 | O | 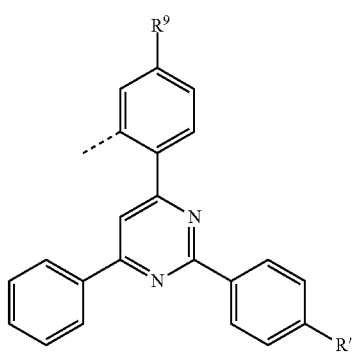 |  | 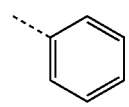 |
| Iaaa-751 | O | 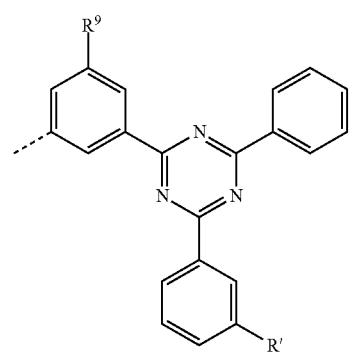 | 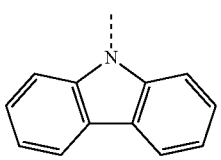 |  |
| Iaaa-752 | O | 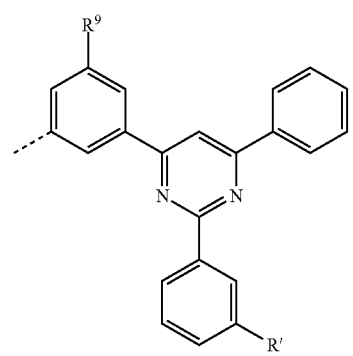 | 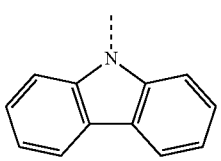 | 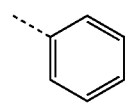 |

-continued
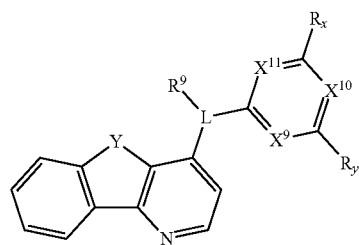
(Iaaa)
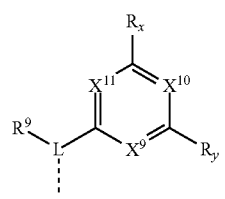
| | Y | | R⁹ | R' |
|---|---|---|---|---|
| Iaaa-753 | O | 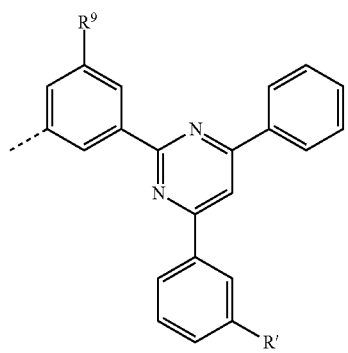 | 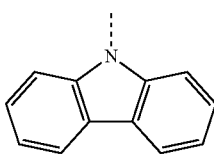 | 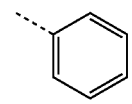 |
| Iaaa-754 | O | 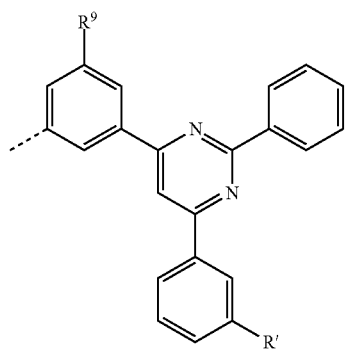 | 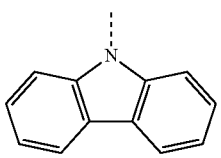 | 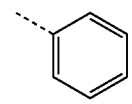 |
| Iaaa-755 | O | 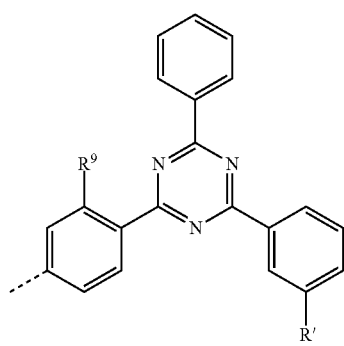 | 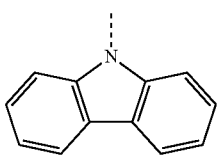 | 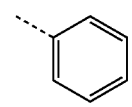 |

-continued
(Iaaa)
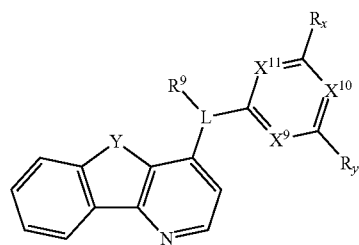
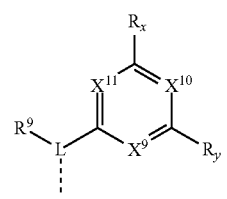
| | Y | R⁹ | R' |
|---|---|---|---|
| Iaaa-756 | O | 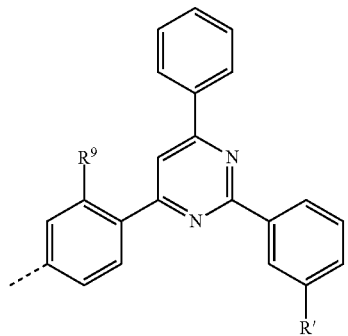 | 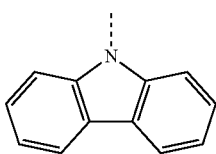 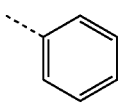 |
| Iaaa-757 | O | 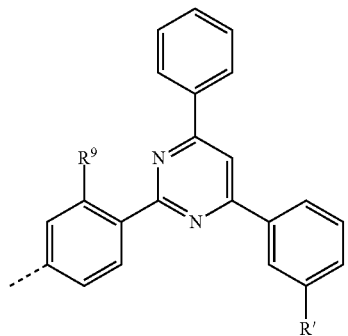 | 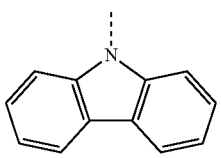 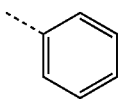 |
| Iaaa-758 | O | 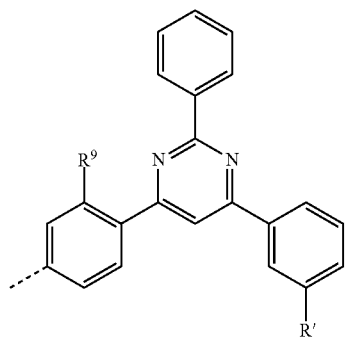 | 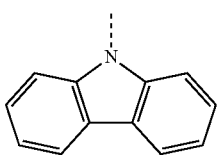 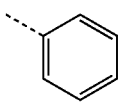 |

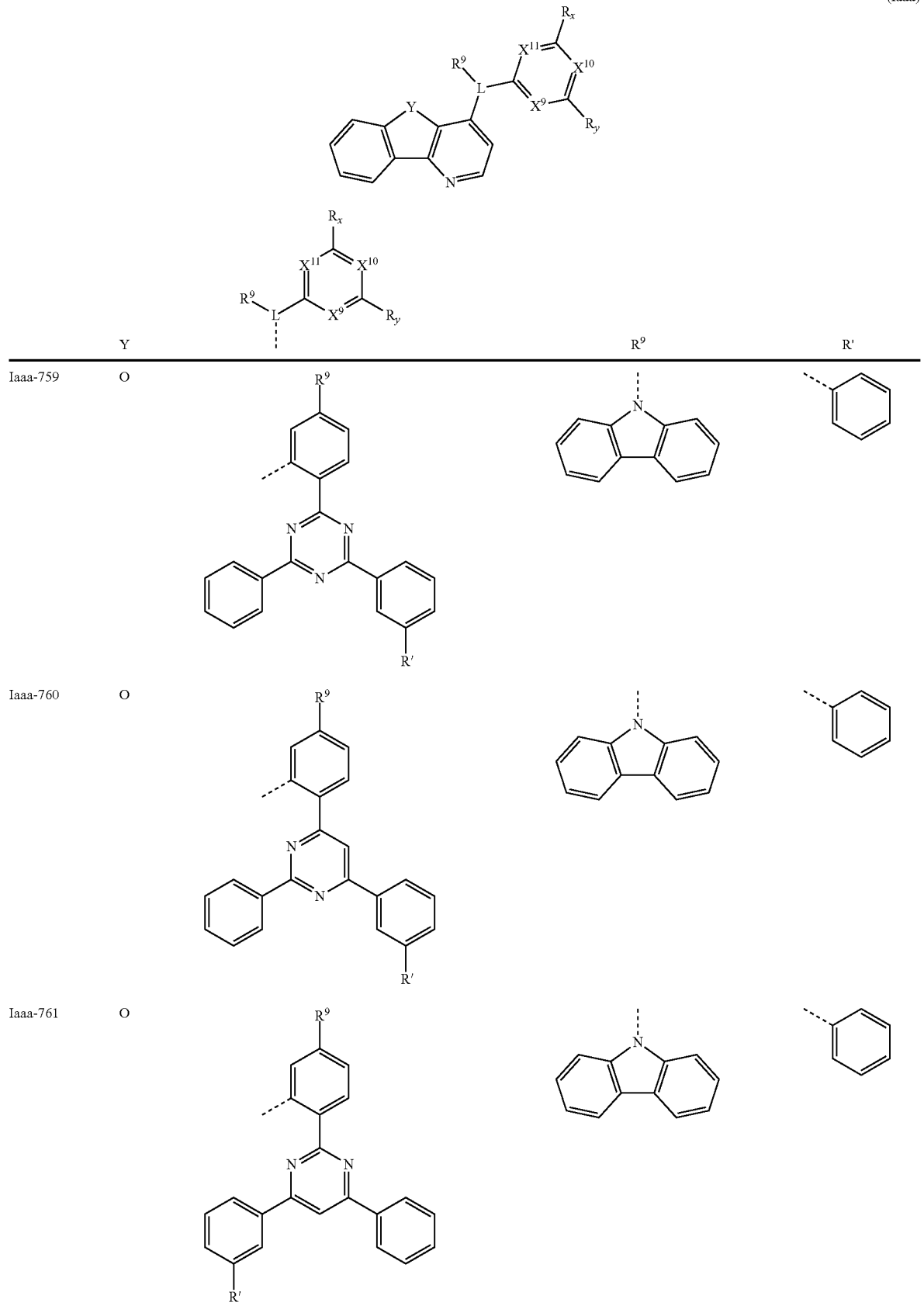

(Iaaa)
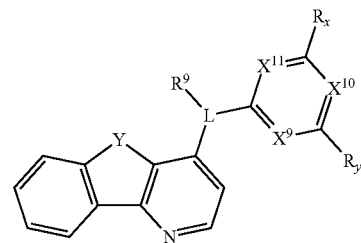
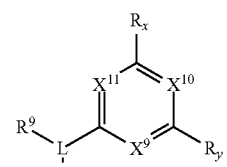
| | Y | | R⁹ | R' |
|---|---|---|---|---|
| Iaaa-762 | O | 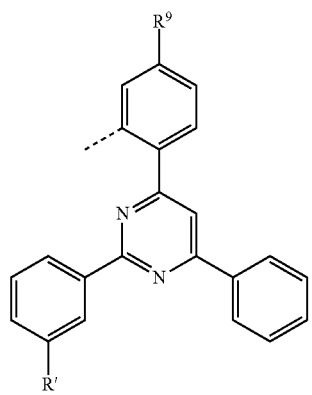 | 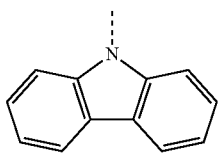 | 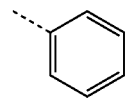 |
| Iaaa-763 | | | | |
| Iaaa-764 | | | | |
| Iaaa-765 | | | | |
| Iaaa-766 | O | 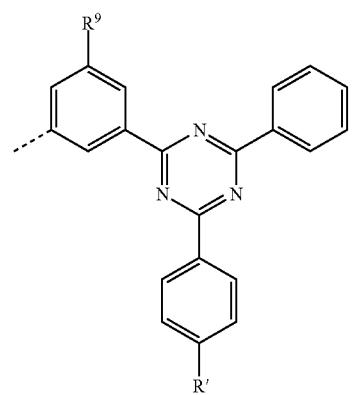 | 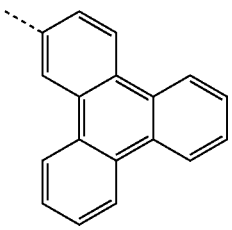 | 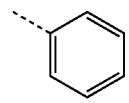 |

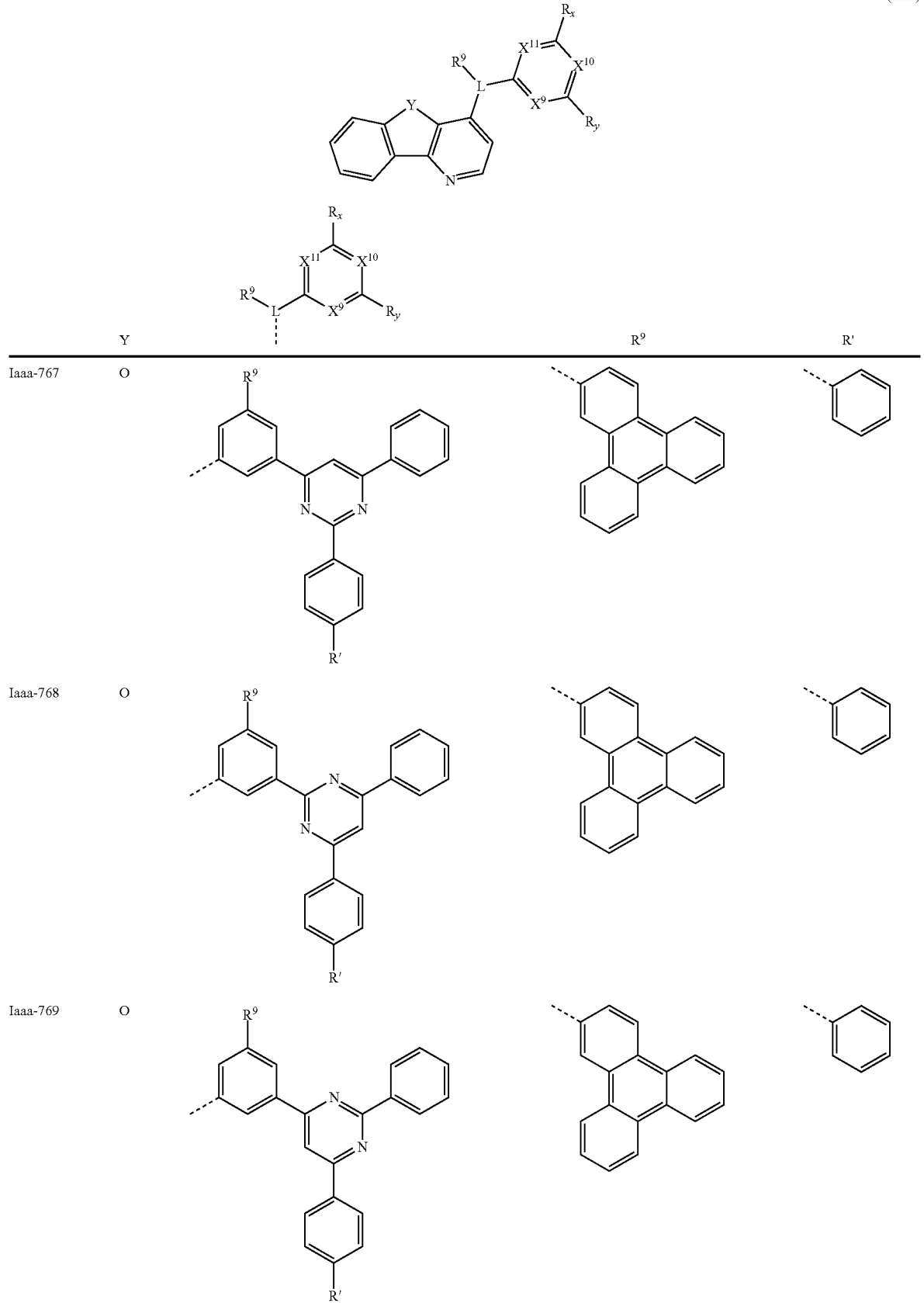

-continued
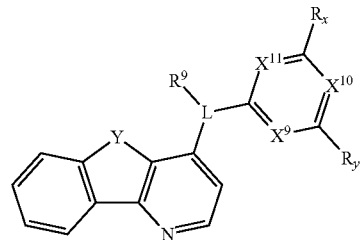
(Iaaa)
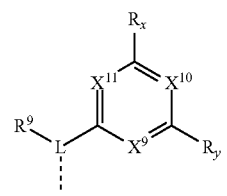
| | Y | R⁹ | R' |
|---|---|---|---|
| Iaaa-770 | O | 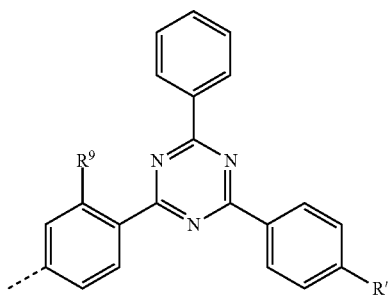 | 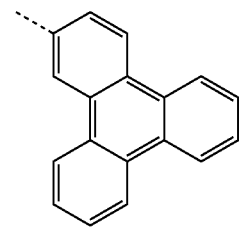 | 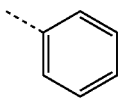 |
| Iaaa-771 | O | 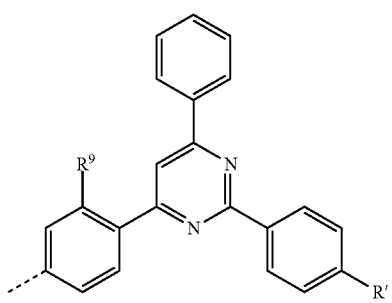 | 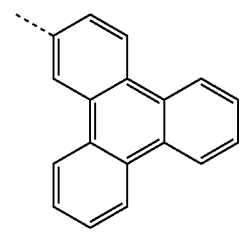 | 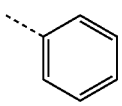 |
| Iaaa-772 | O | 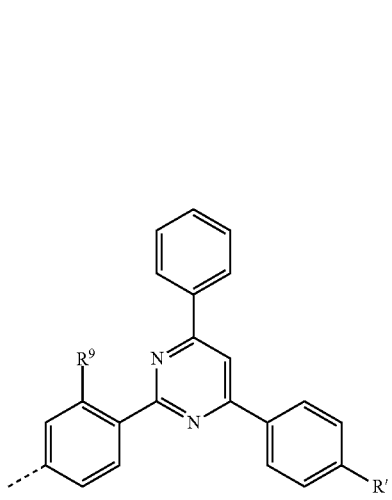 | 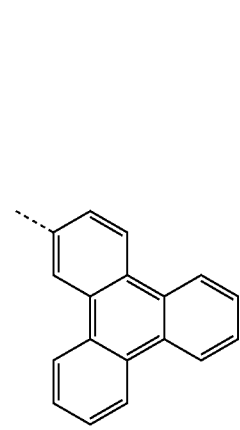 |  |

-continued
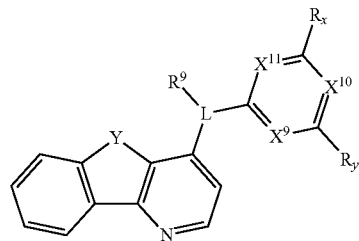
(Iaaa)
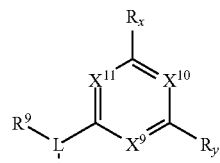
| | Y | | R⁹ | R' |
|---|---|---|---|---|
| Iaaa-773 | O | 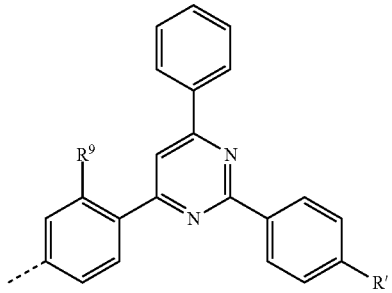 | 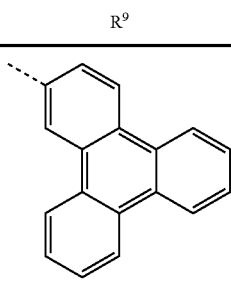 | 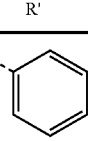 |
| Iaaa-774 | O | 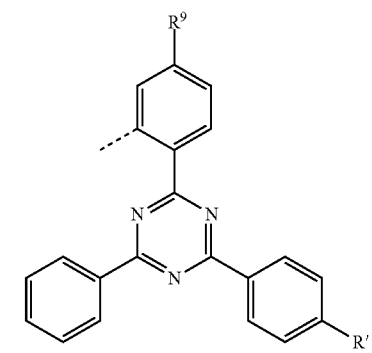 | 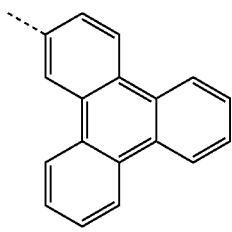 | 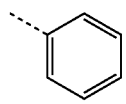 |
| Iaaa-775 | O | 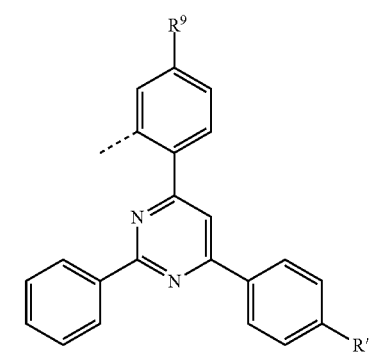 | 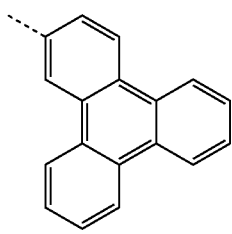 | 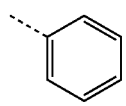 |

-continued
(Iaaa)
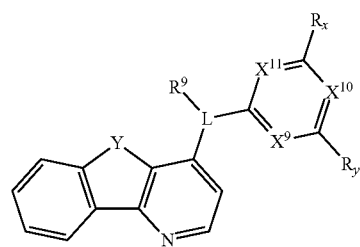
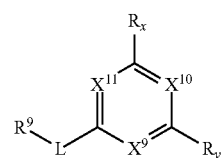
| | Y | R⁹ | R' |
|---|---|---|---|
| Iaaa-776 | O | 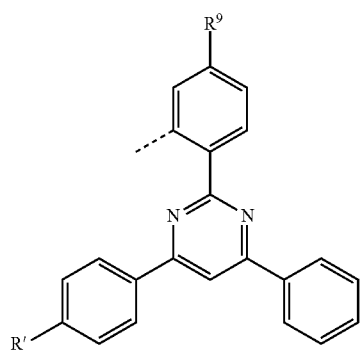 | 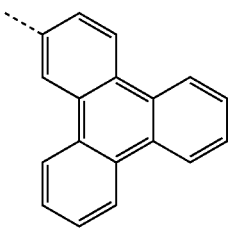 | 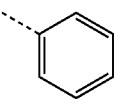 |
| Iaaa-777 | O | 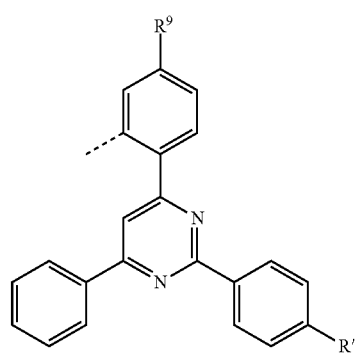 | 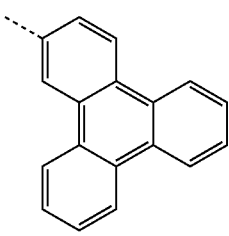 | 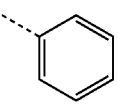 |
| Iaaa-778 | O | 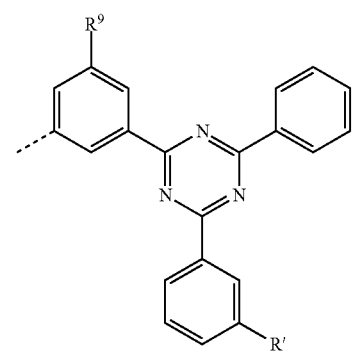 | 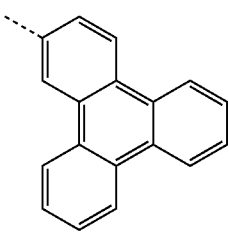 | 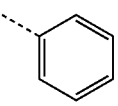 |

-continued
(Iaaa)
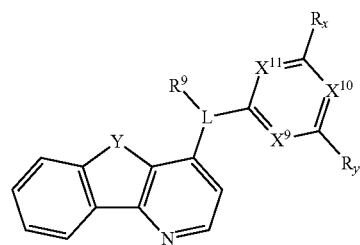
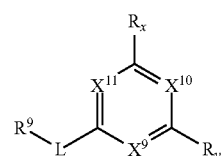
| | Y | | $R^9$ | R' |
|---|---|---|---|---|
| Iaaa-779 | O | 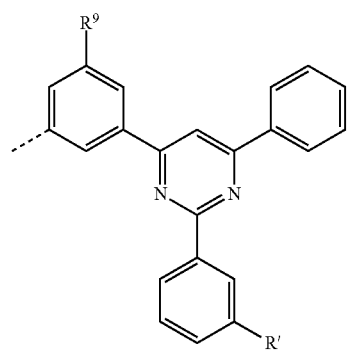 | 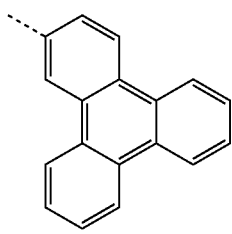 | 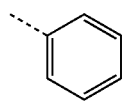 |
| Iaaa-780 | O | 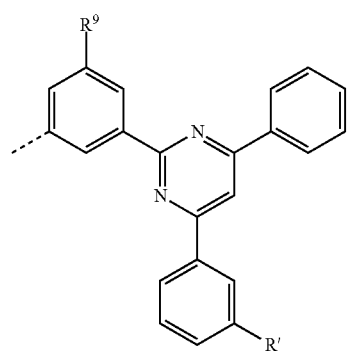 | 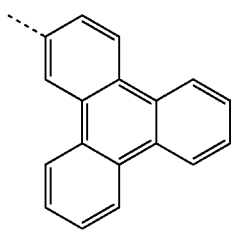 | 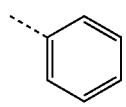 |
| Iaaa-781 | O | 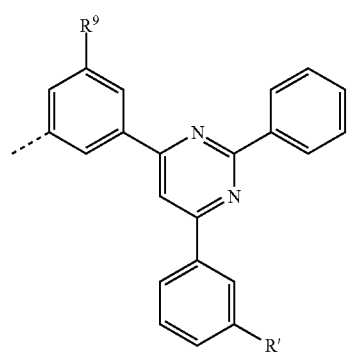 | 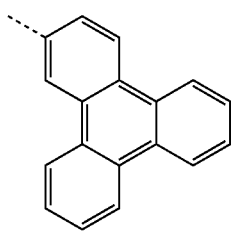 | 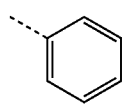 |

(Iaaa)
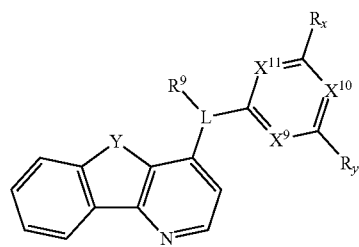
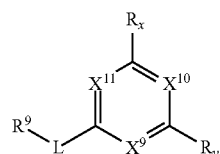
| | Y | | R⁹ | R' |
|---|---|---|---|---|
| Iaaa-782 | O | 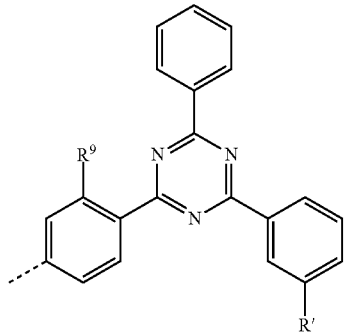 | 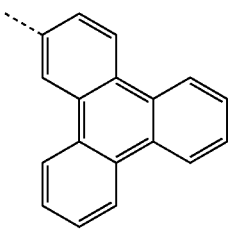 | 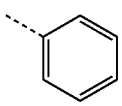 |
| Iaaa-783 | O | 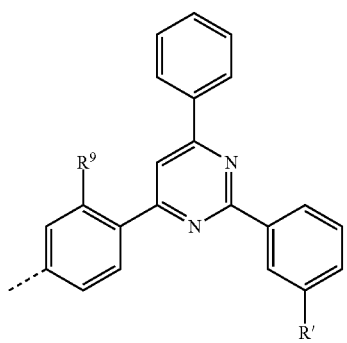 | 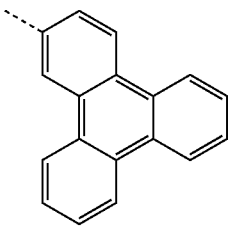 | 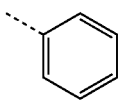 |
| Iaaa-784 | O | 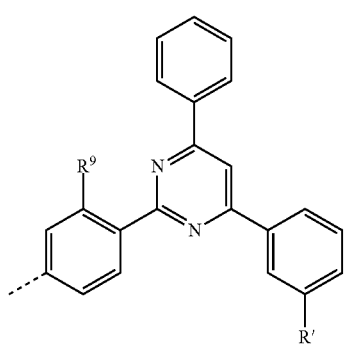 | 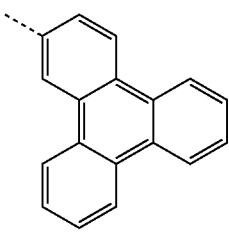 | 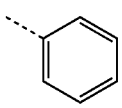 |

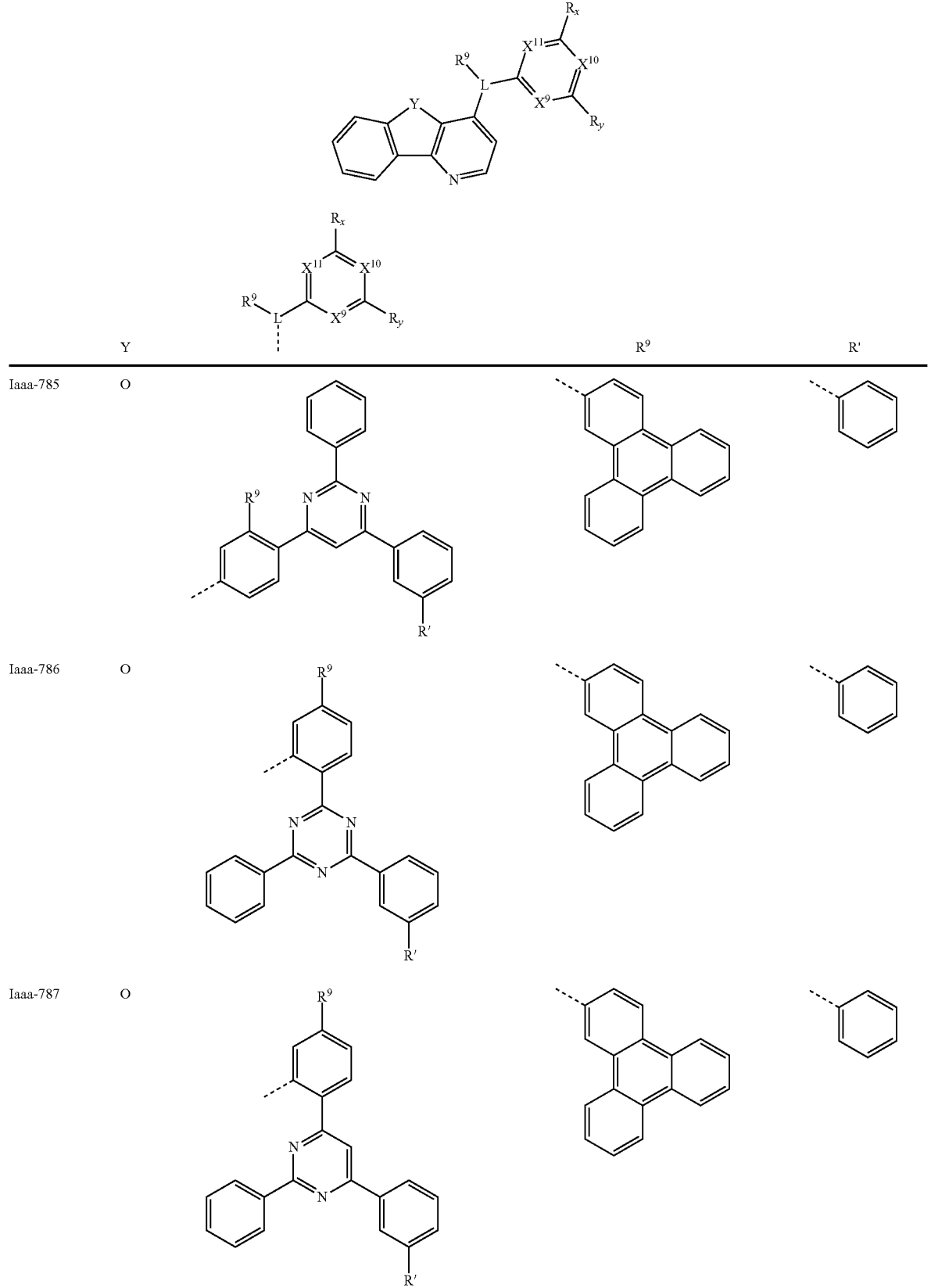

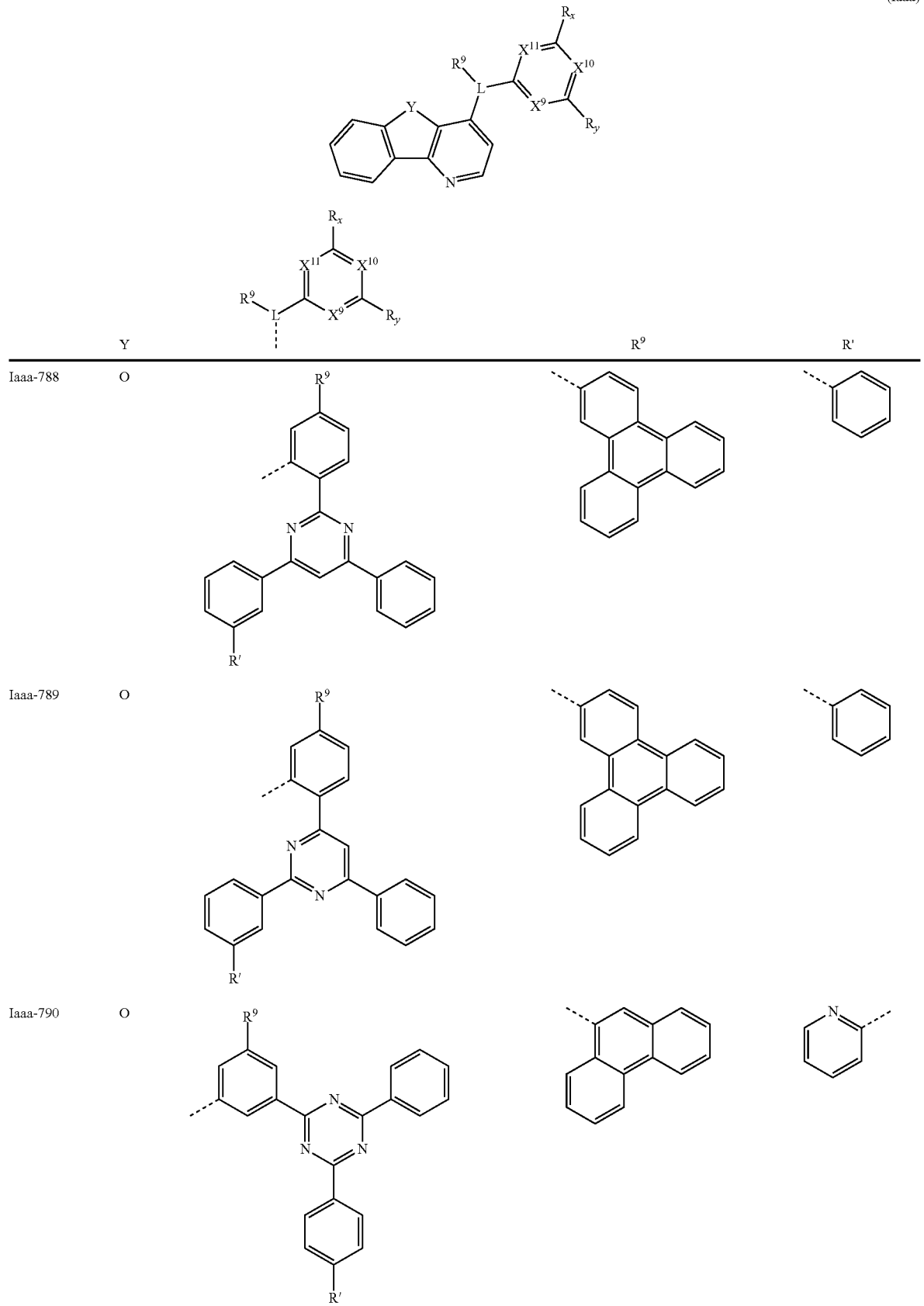

-continued
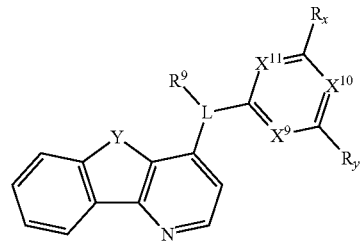
(Iaaa)
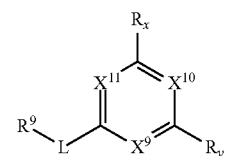
| | Y | | R⁹ | R' |
|---|---|---|---|---|
| Iaaa-791 | O | 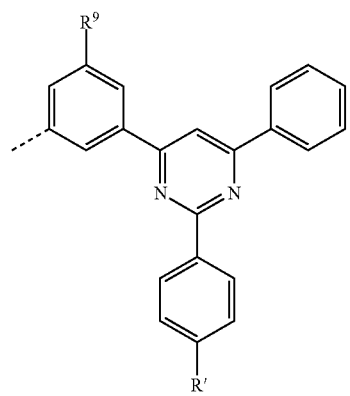 | 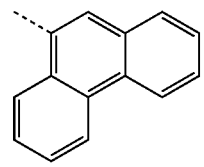 | 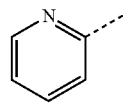 |
| Iaaa-792 | O | 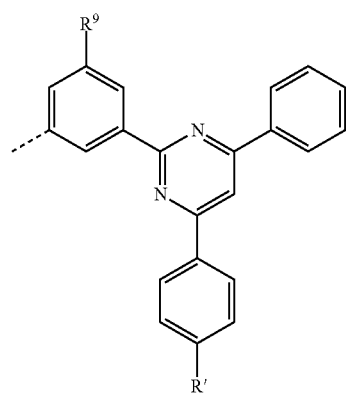 | 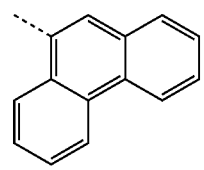 | 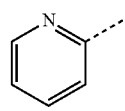 |

-continued
(Iaaa)
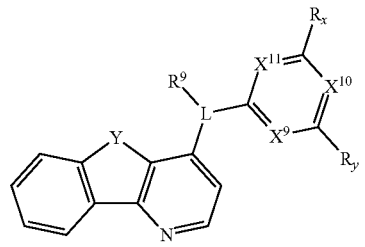
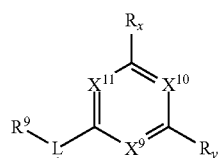
| | Y | | R⁹ | R' |
|---|---|---|---|---|
| Iaaa-793 | O | 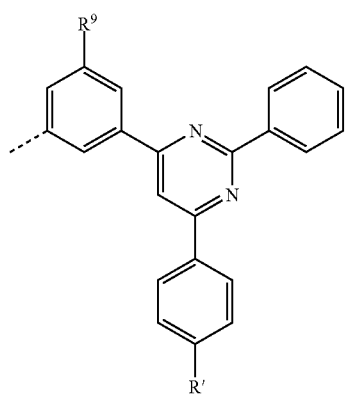 | 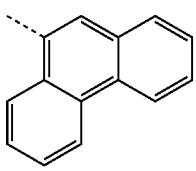 | 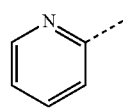 |
| Iaaa-794 | O | 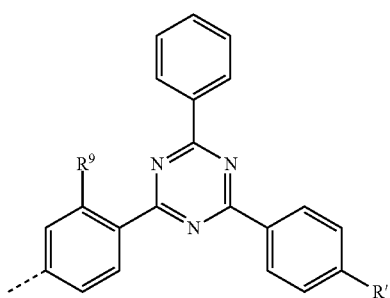 | 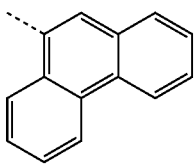 |  |
| Iaaa-795 | O | 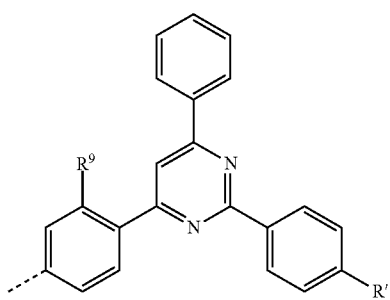 | 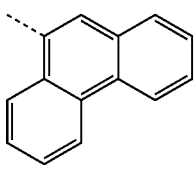 |  |

-continued
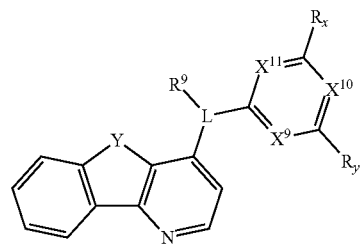
(Iaaa)
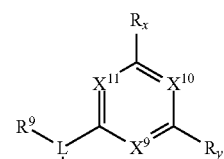
| | Y | | $R^9$ | R' |
|---|---|---|---|---|
| Iaaa-796 | O | 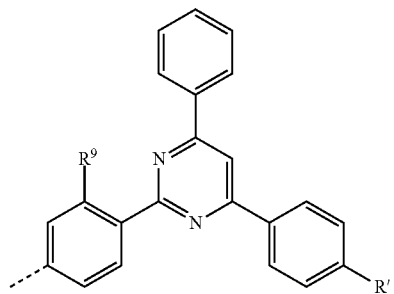 | 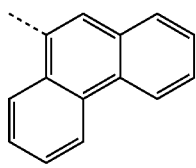 | 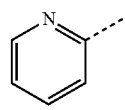 |
| Iaaa-797 | O | 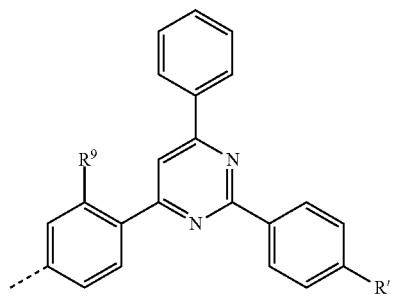 | 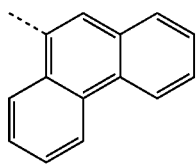 | 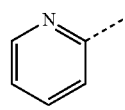 |
| Iaaa-798 | O | 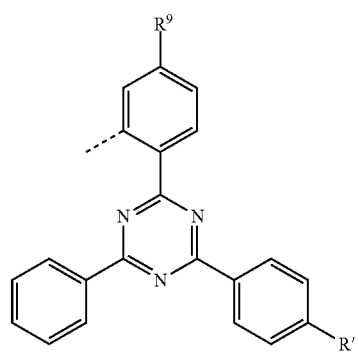 | 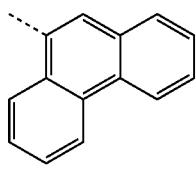 | 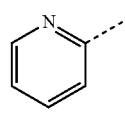 |

-continued
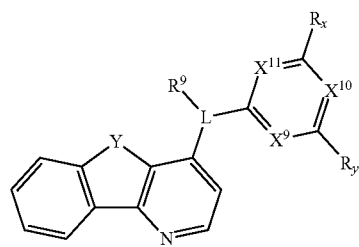
(Iaaa)
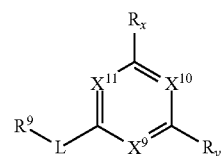
| | Y | | R⁹ | R' |
|---|---|---|---|---|
| Iaaa-799 | O | 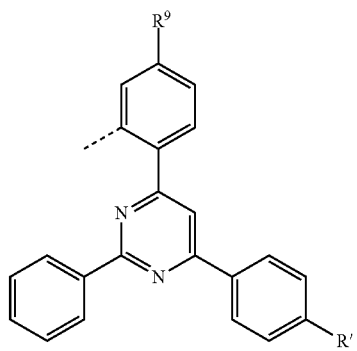 | 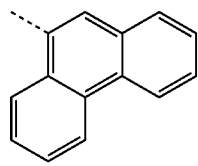 | 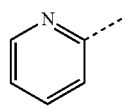 |
| Iaaa-800 | O | 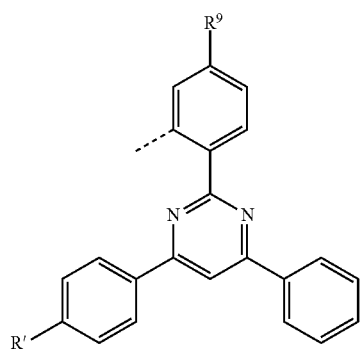 | 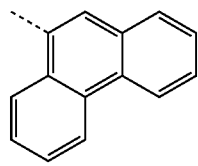 | 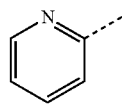 |
| Iaaa-801 | O | 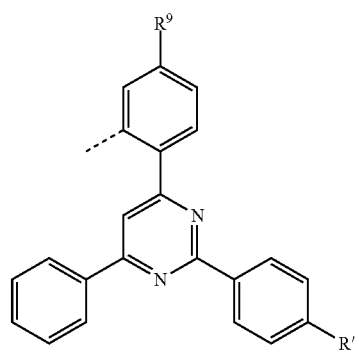 | 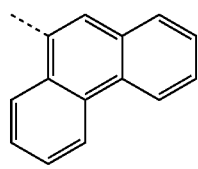 | 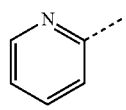 |

-continued
(Iaaa)
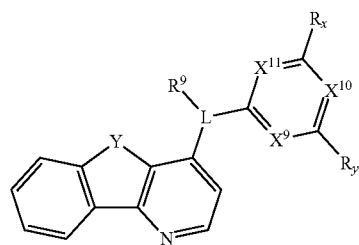
| | Y | | $R^9$ | R' |
|---|---|---|---|---|
| | | 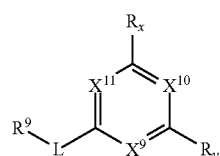 | | |
| Iaaa-802 | O | 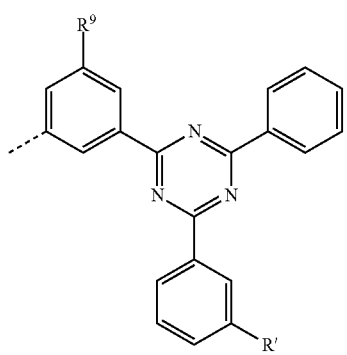 | 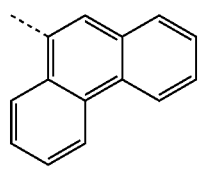 | 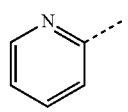 |
| Iaaa-803 | O | 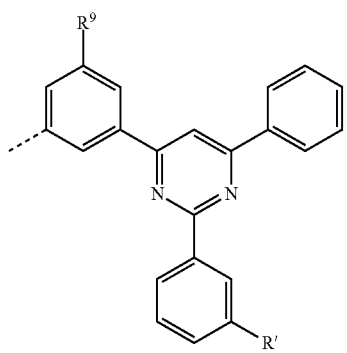 | 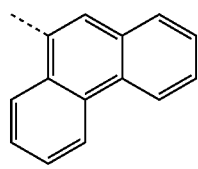 | 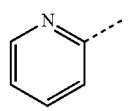 |
| Iaaa-804 | O | 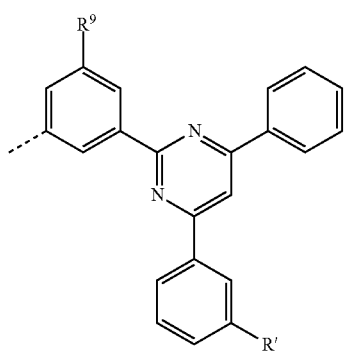 | 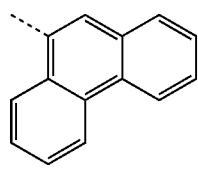 | 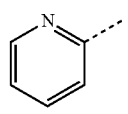 |

-continued
(Iaaa)
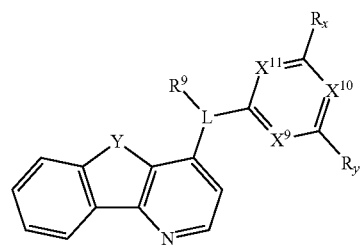
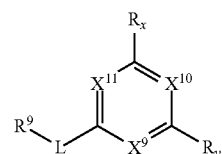
| | Y | | R⁹ | R' |
|---|---|---|---|---|
| Iaaa-805 | O | 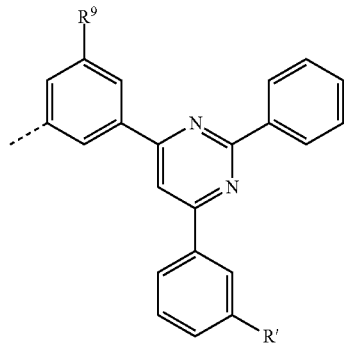 | 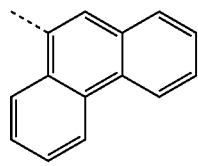 | 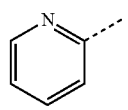 |
| Iaaa-806 | O | 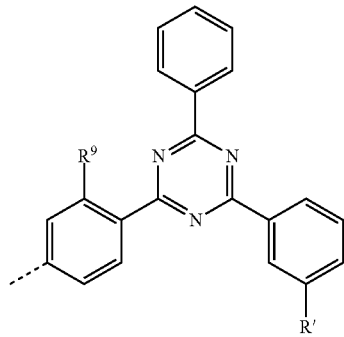 | 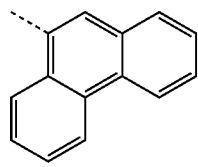 | 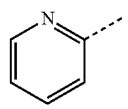 |
| Iaaa-807 | O | 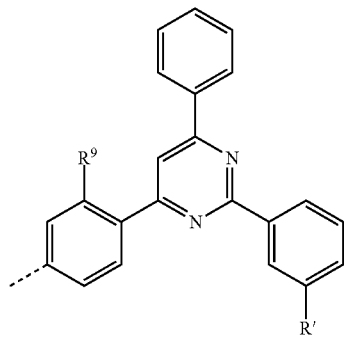 | 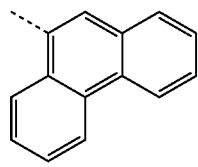 | 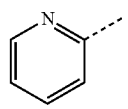 |

-continued
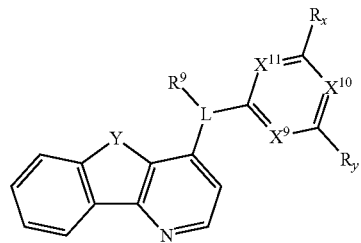
(Iaaa)
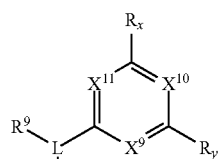
| | Y | R⁹ | R' |
|---|---|---|---|
| Iaaa-808 | O | 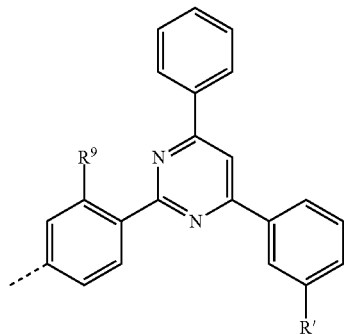 | 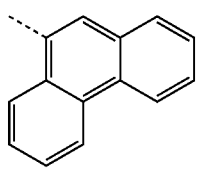 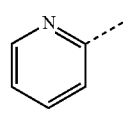 |
| Iaaa-809 | O | 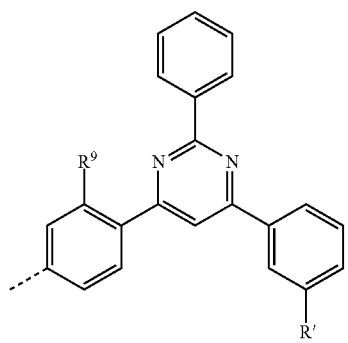 | 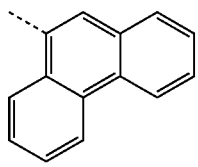 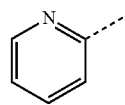 |
| Iaaa-810 | O | 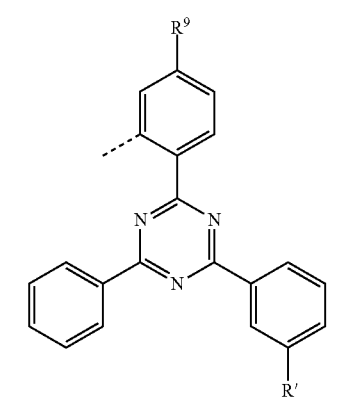 | 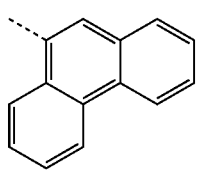 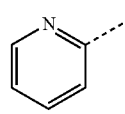 |

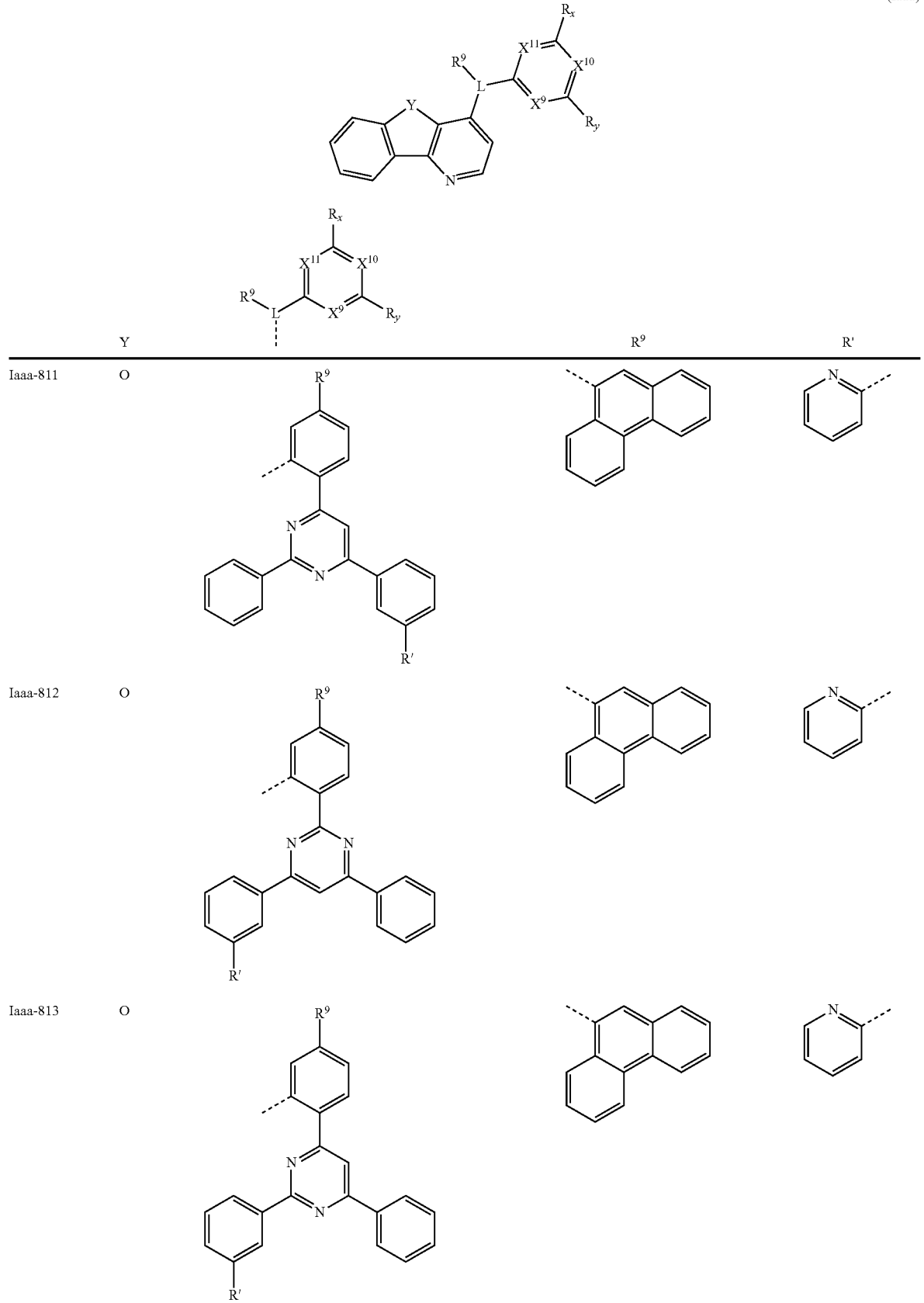

-continued
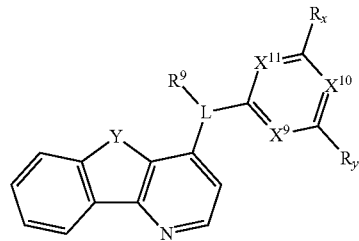
(Iaaa)
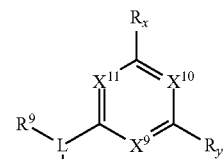
| | Y | R⁹ | R' |
|---|---|---|---|
| Iaaa-814 | | | |
| Iaaa-815 | | | |
| Iaaa-816 | | | |
| Iaaa-817 | O | 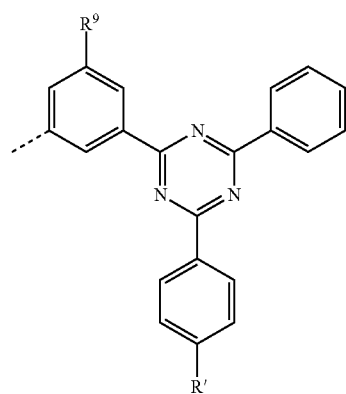 | 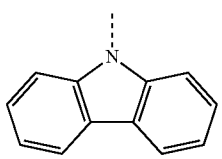 | 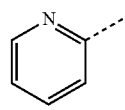 |
| Iaaa-818 | O | 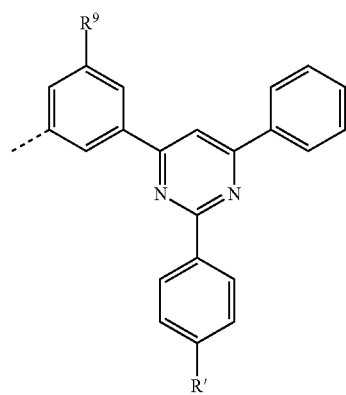 | 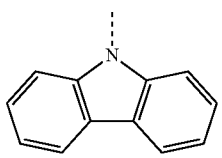 | 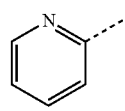 |

-continued
(Iaaa)
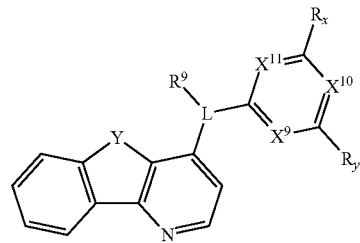
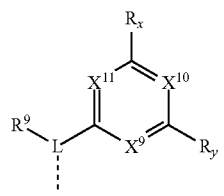
| | Y | | R⁹ | R' |
|---|---|---|---|---|
| Iaaa-819 | O | 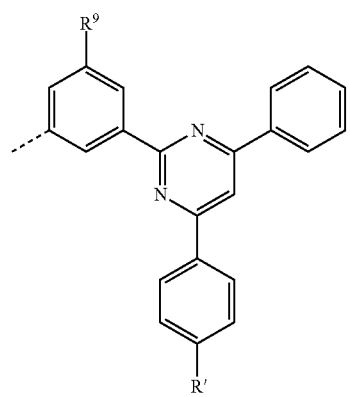 | 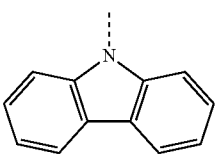 | 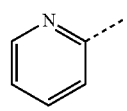 |
| Iaaa-820 | O | 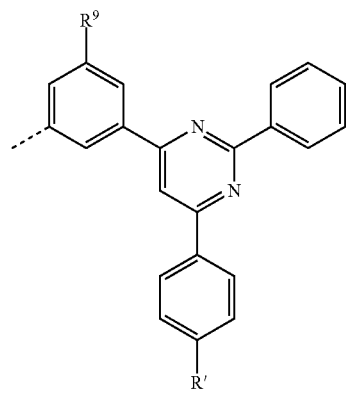 | 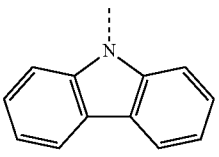 | 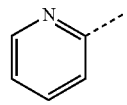 |
| Iaaa-821 | O |  |  |  |

-continued
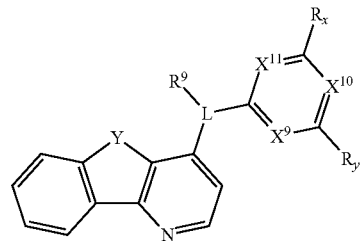
(Iaaa)
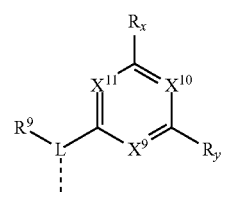
| | Y | | R⁹ | R' |
|---|---|---|---|---|
| Iaaa-822 | O | 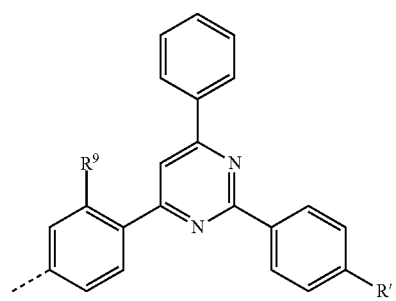 | 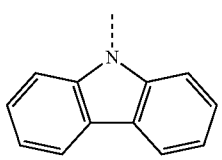 | 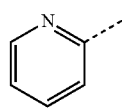 |
| Iaaa-823 | O | 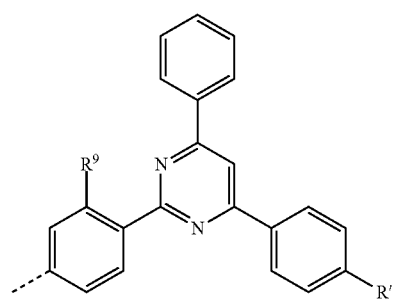 | 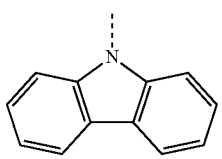 | 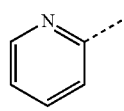 |
| Iaaa-824 | O | 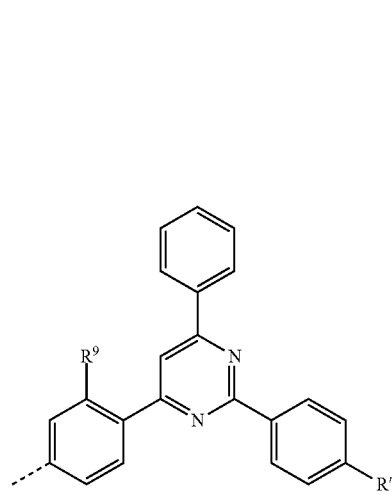 | 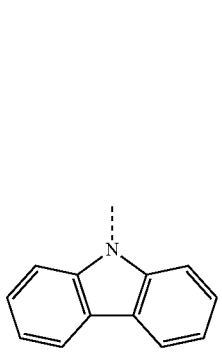 | 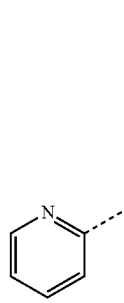 |

-continued
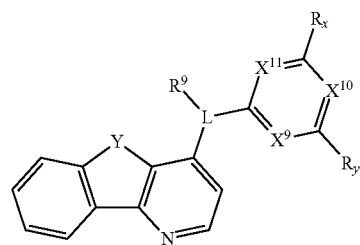
(Iaaa)
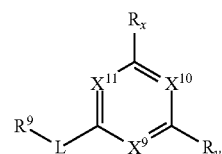
| | Y | | R⁹ | R' |
|---|---|---|---|---|
| Iaaa-825 | O | 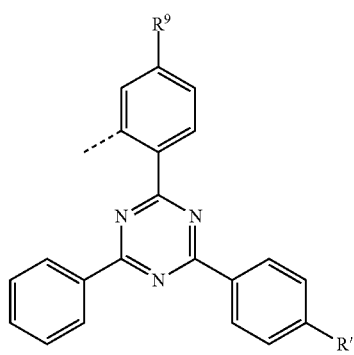 | 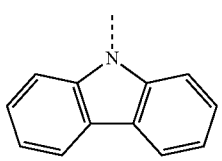 | 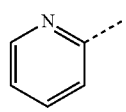 |
| Iaaa-826 | O | 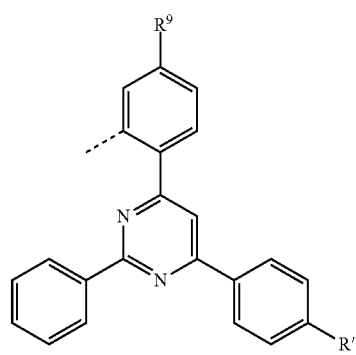 | 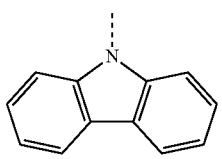 | 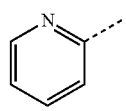 |
| Iaaa-827 | O | 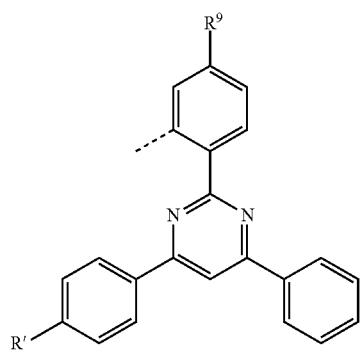 | 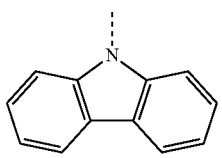 | 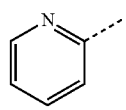 |

-continued
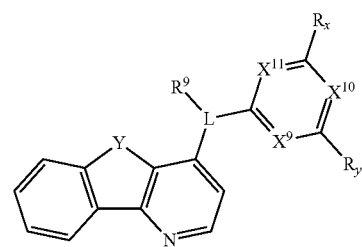
(Iaaa)
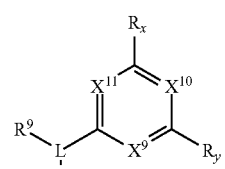
| | Y | | R⁹ | R' |
|---|---|---|---|---|
| Iaaa-828 | O | 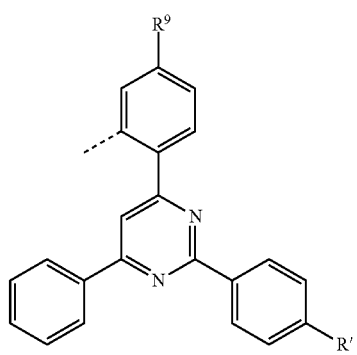 | 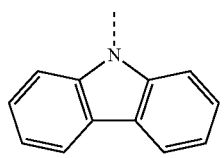 | 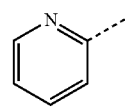 |
| Iaaa-829 | O | 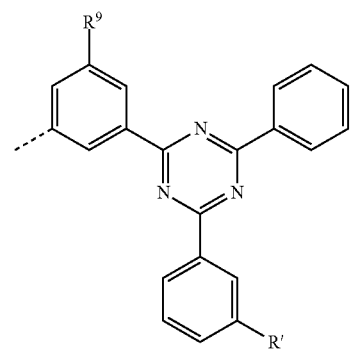 | 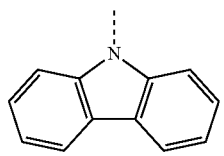 | 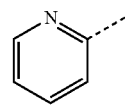 |
| Iaaa-830 | O | 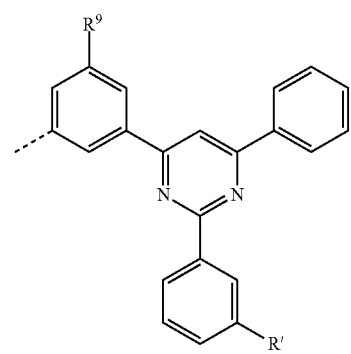 | 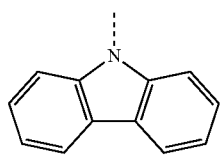 | 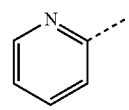 |

-continued
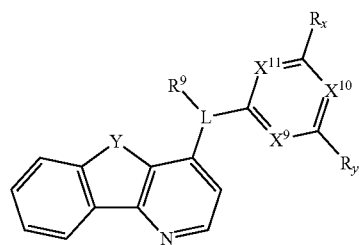
(Iaaa)
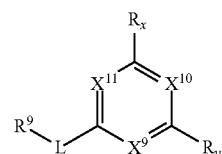
| | Y | | R⁹ | R' |
|---|---|---|---|---|
| Iaaa-831 | O |  | 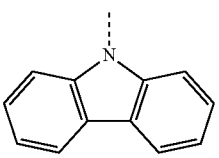 | 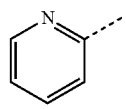 |
| Iaaa-832 | O | 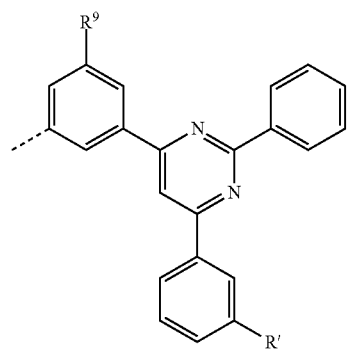 |  | 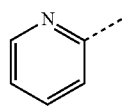 |
| Iaaa-833 | O | 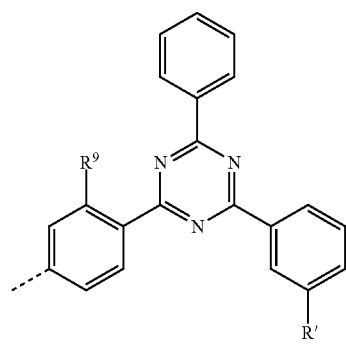 | 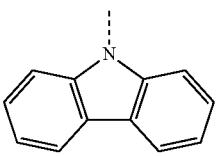 |  |

-continued
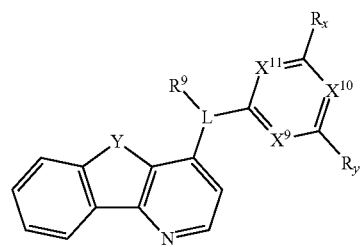
(Iaaa)
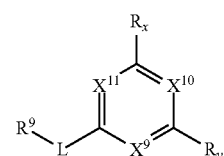
| | Y | | R⁹ | R' |
|---|---|---|---|---|
| Iaaa-834 | O | 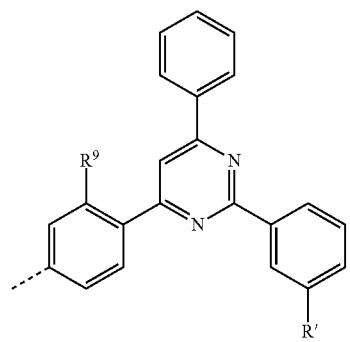 | 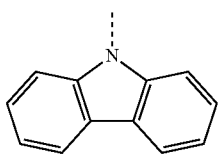 | 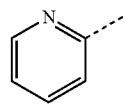 |
| Iaaa-835 | O | 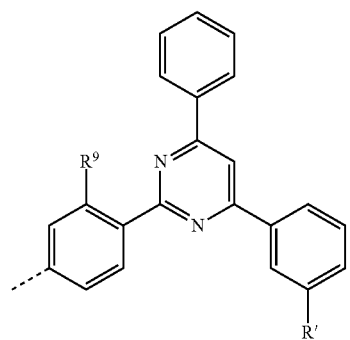 | 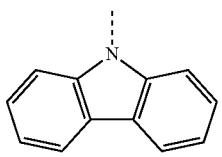 | 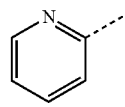 |
| Iaaa-836 | O |  | 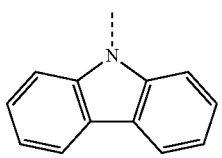 |  |

-continued
(Iaaa)
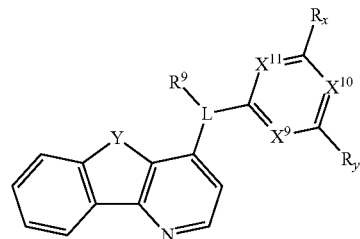
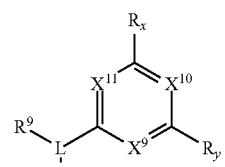
| | Y | | R⁹ | R' |
|---|---|---|---|---|
| Iaaa-837 | O | 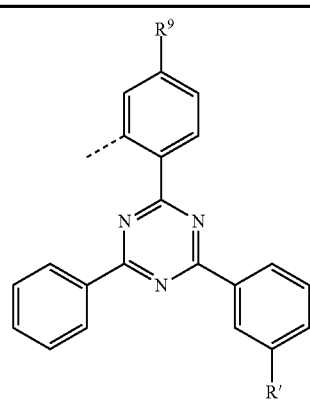 | 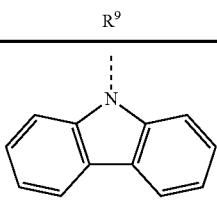 | 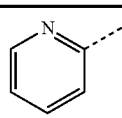 |
| Iaaa-838 | O | 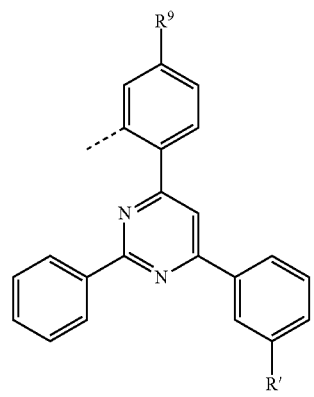 | 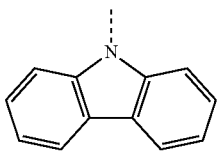 | 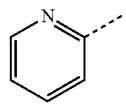 |
| Iaaa-839 | O | 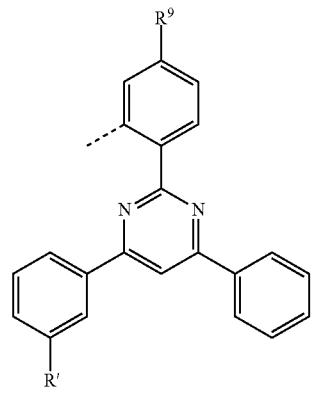 | 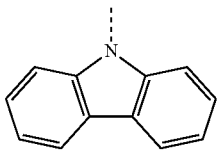 | 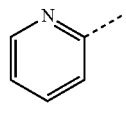 |

(Iaaa)
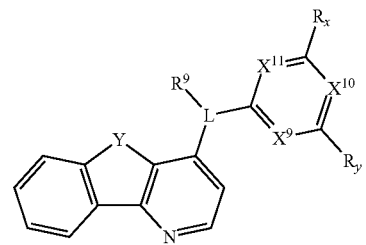
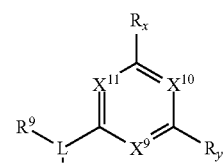
| | Y | | R⁹ | R' |
|---|---|---|---|---|
| Iaaa-840 | O | 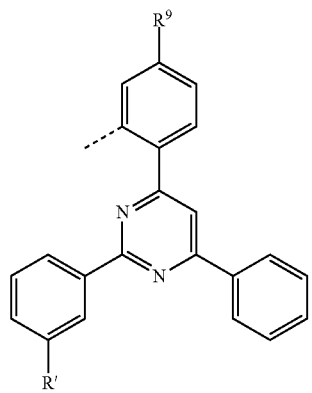 | 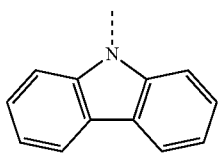 | 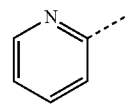 |
| Iaaa-841 | | | | |
| Iaaa-842 | | | | |
| Iaaa-843 | | | | |
| Iaaa-844 | O | 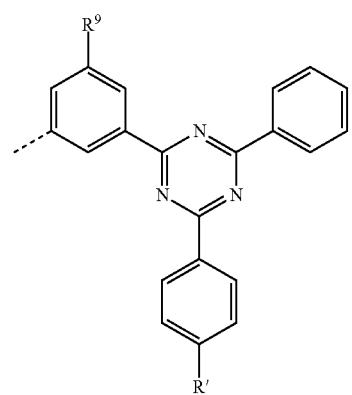 |  | 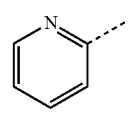 |

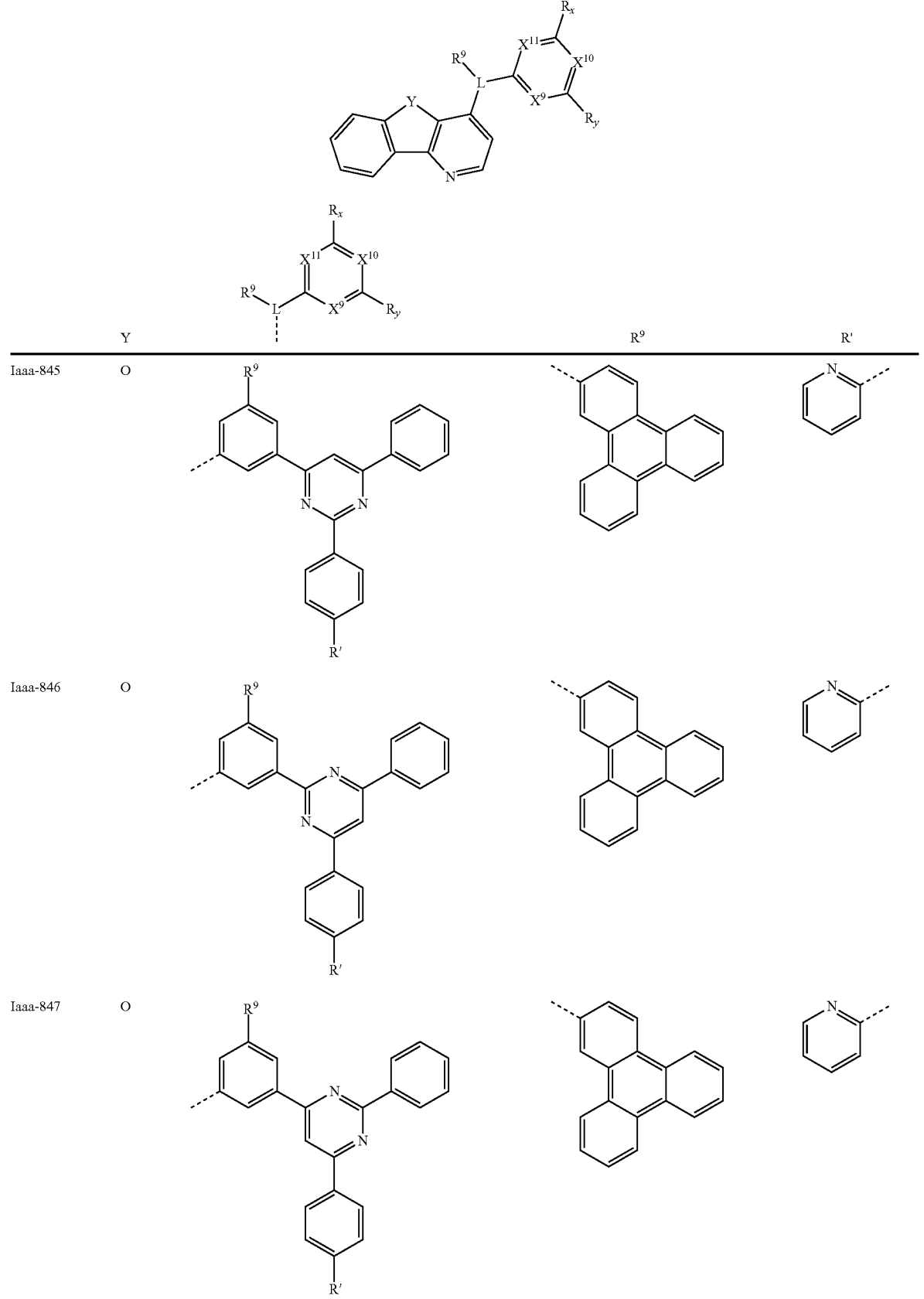

-continued
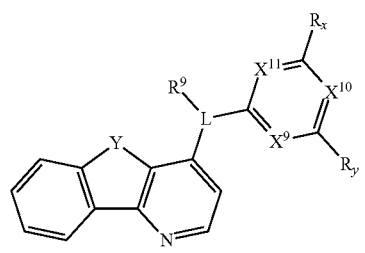
(Iaaa)
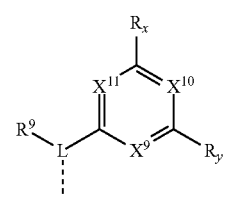
| | Y | | $R^9$ | R' |
|---|---|---|---|---|
| Iaaa-848 | O | 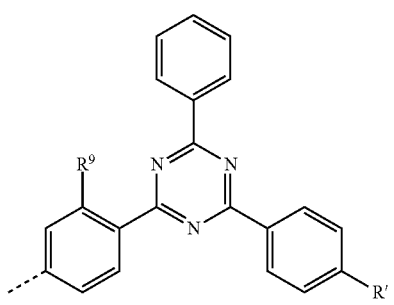 | 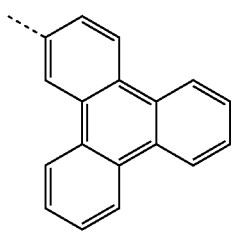 | 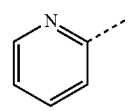 |
| Iaaa-849 | O | 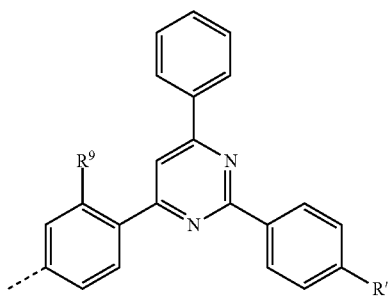 | 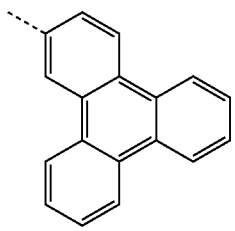 | 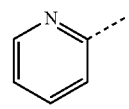 |
| Iaaa-850 | O | 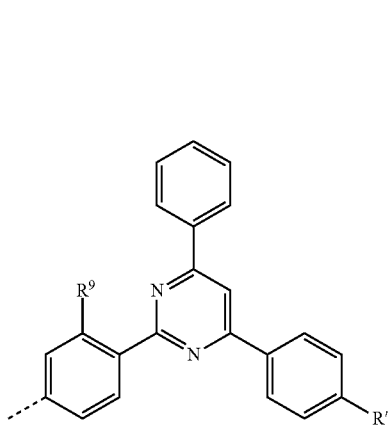 | 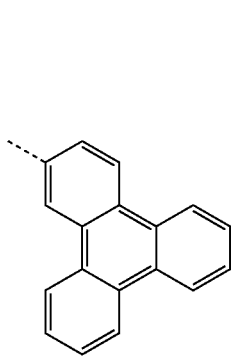 | 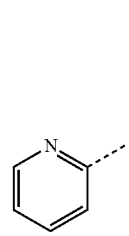 |

-continued
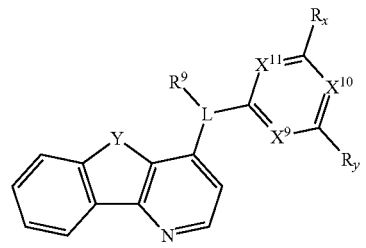
(Iaaa)
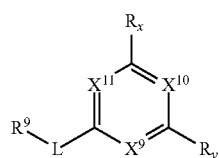
| | Y | R⁹ | R' |
|---|---|---|---|
| Iaaa-851 | O | 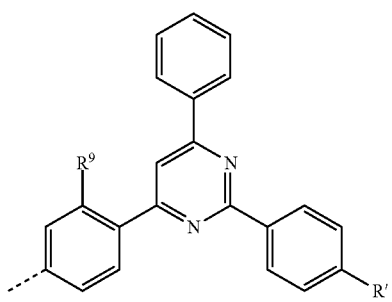 | 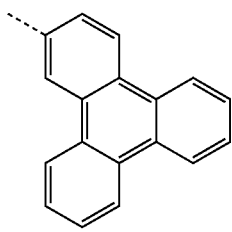 | 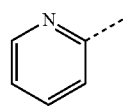 |
| Iaaa-852 | O | 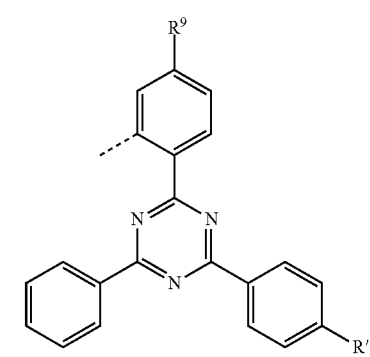 | 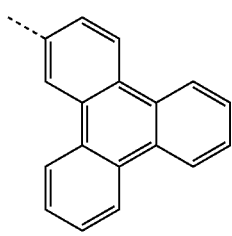 | 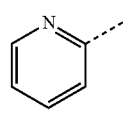 |
| Iaaa-853 | O | 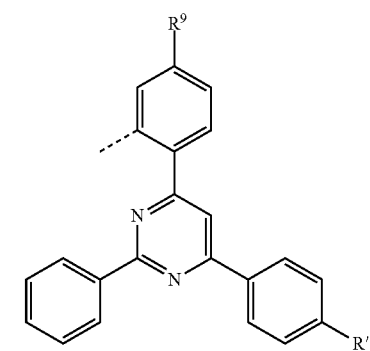 | 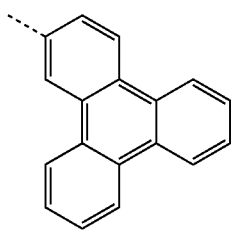 | 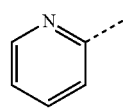 |

-continued
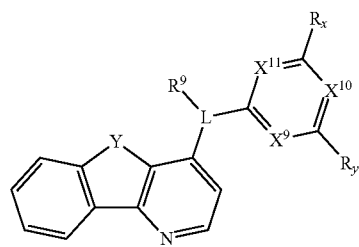
(Iaaa)
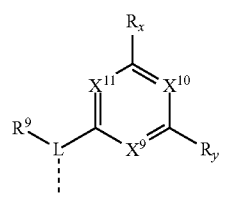
| | Y | R⁹ | R' |
|---|---|---|---|
| Iaaa-854 | O | 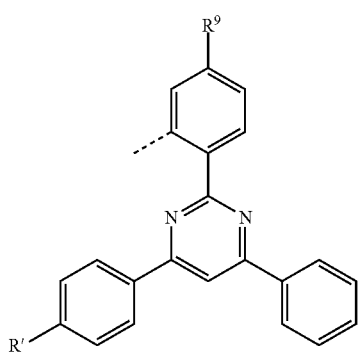 | 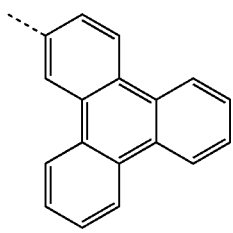 | 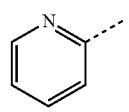 |
| Iaaa-855 | O | 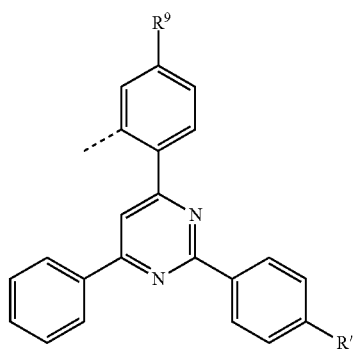 | 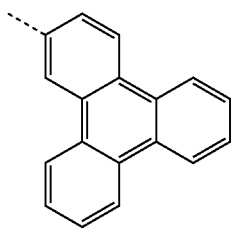 | 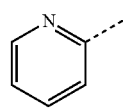 |
| Iaaa-856 | O | 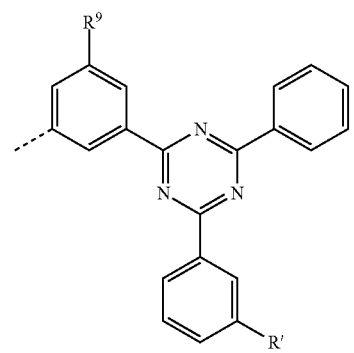 | 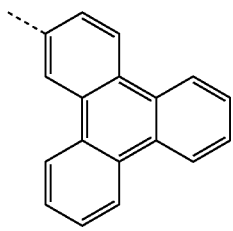 | 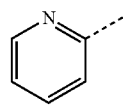 |

-continued
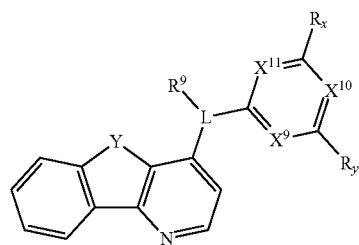
(Iaaa)
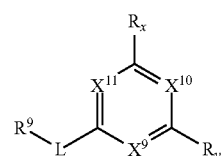
| | Y | | R⁹ | R' |
|---|---|---|---|---|
| Iaaa-857 | O | 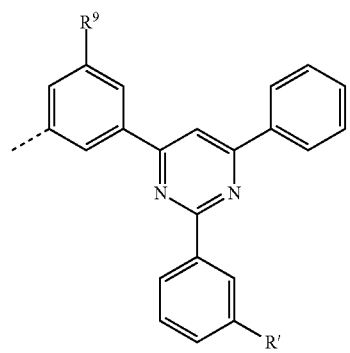 | 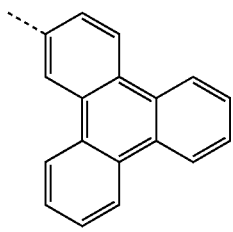 | 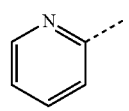 |
| Iaaa-858 | O | 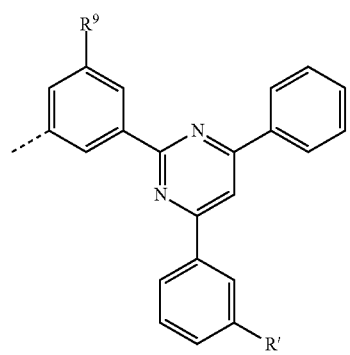 | 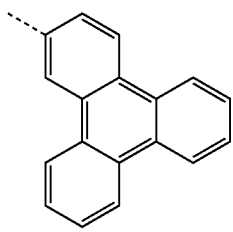 | 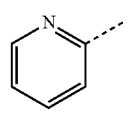 |
| Iaaa-859 | O | 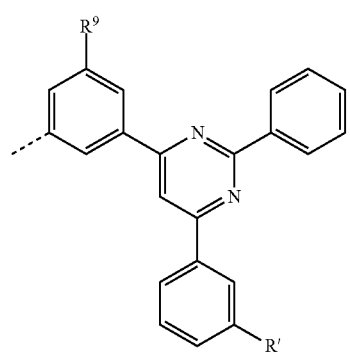 | 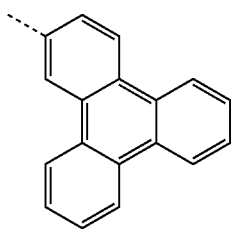 | 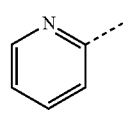 |

-continued
(Iaaa)
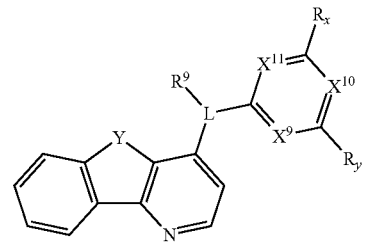
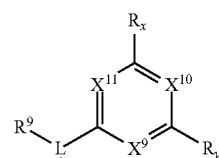
| | Y | | R⁹ | R' |
|---|---|---|---|---|
| Iaaa-860 | O | 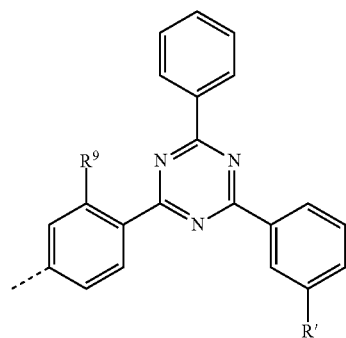 | 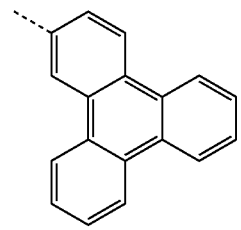 | 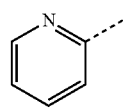 |
| Iaaa-861 | O | 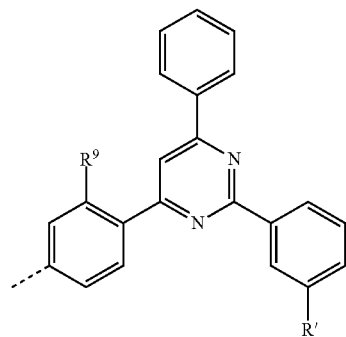 | 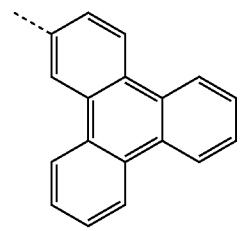 | 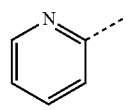 |
| Iaaa-862 | O | 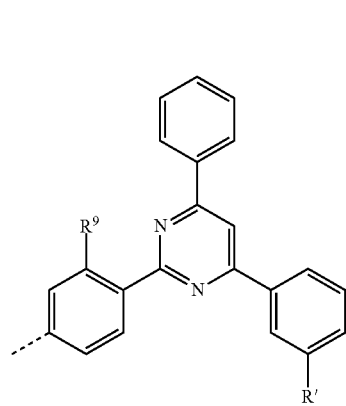 | 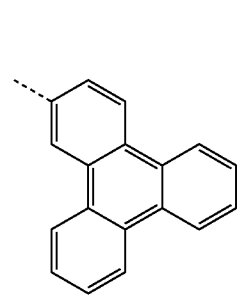 | 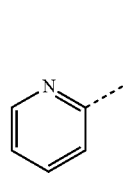 |

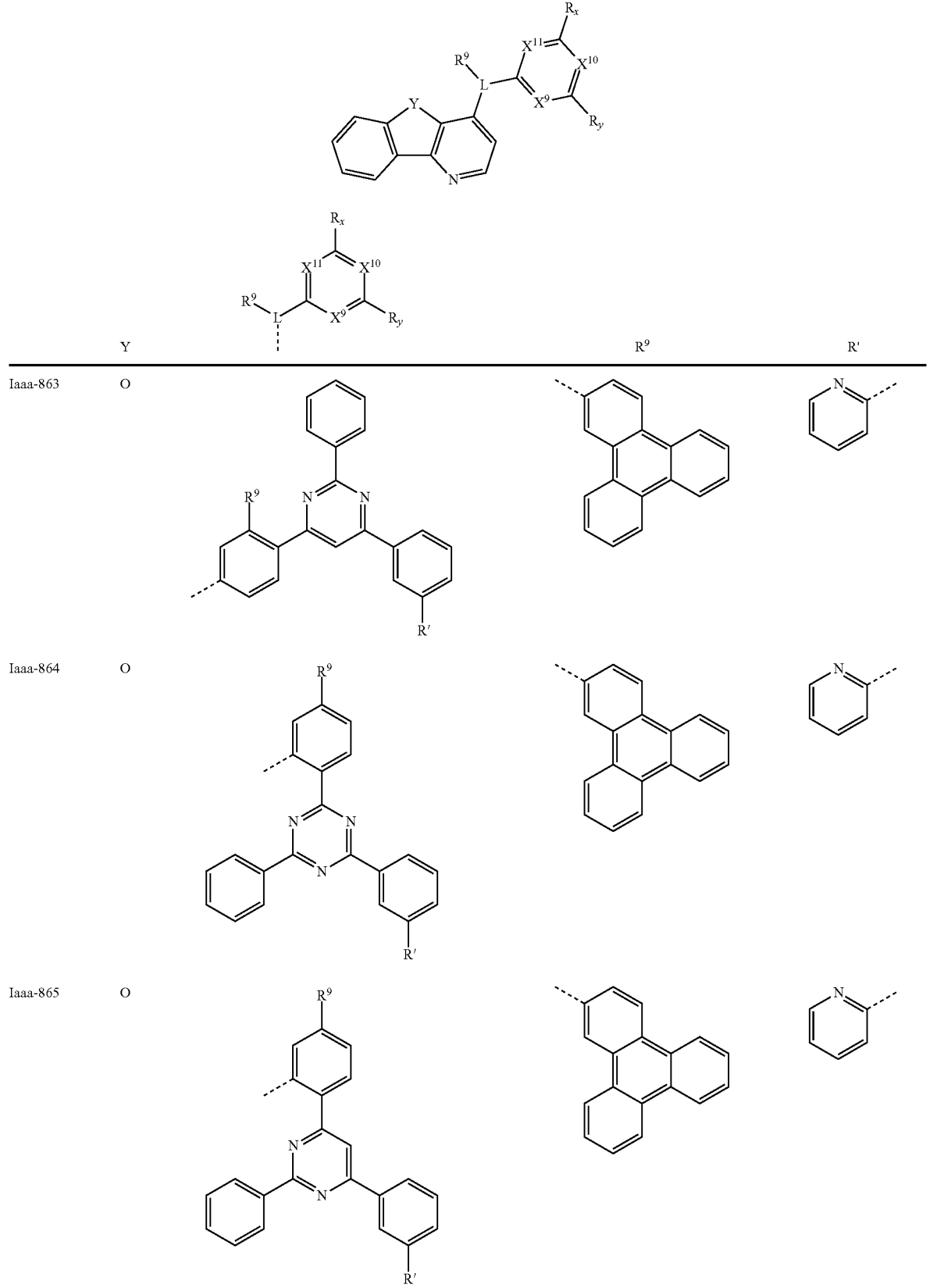

-continued
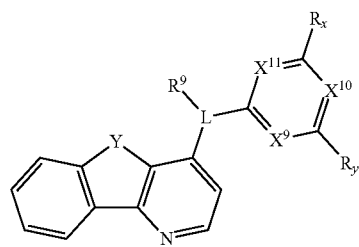
(Iaaa)
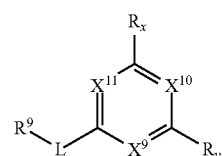
| | Y | | R⁹ | R' |
|---|---|---|---|---|
| Iaaa-866 | O | 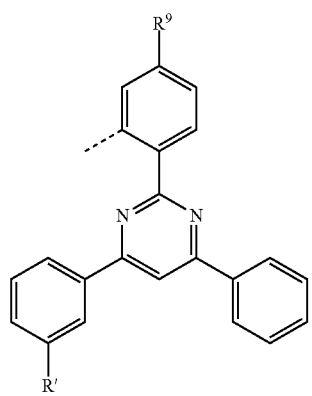 | 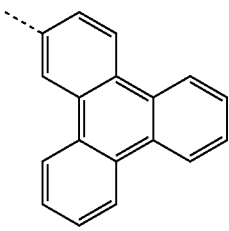 | 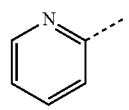 |
| Iaaa-867 | O | 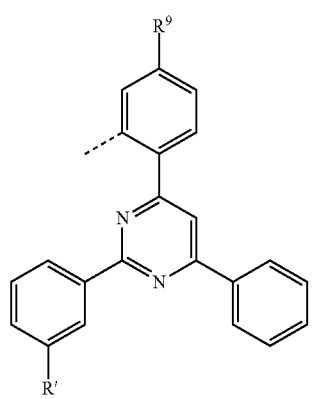 | 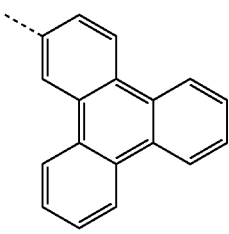 | 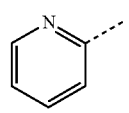 |

-continued
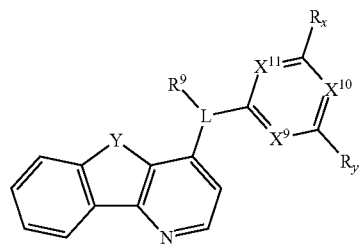
(Iaaa)
| | Y | 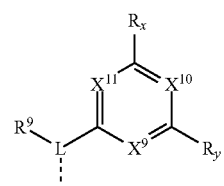 | R⁹ | R' |
|---|---|---|---|---|
| Iaaa-868 | | | | |
| Iaaa-869 | | | | |
| Iaaa-870 | | | | |
| Iaaa-871 | O | 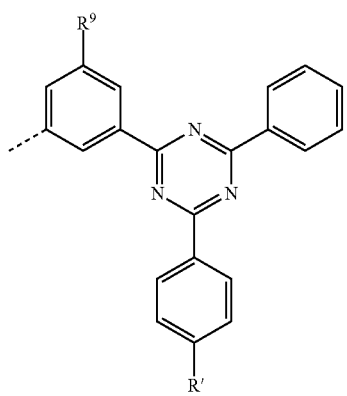 | 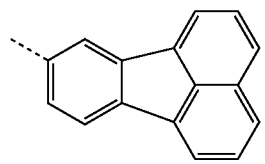 | H |
| Iaaa-872 | O | 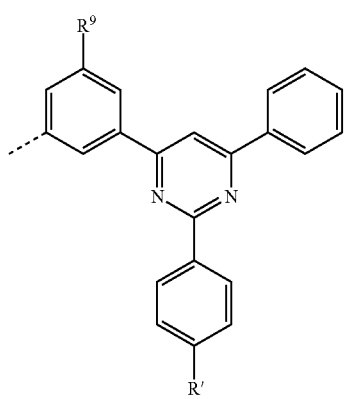 | 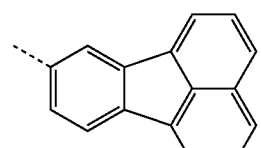 | H |

-continued
(Iaaa)
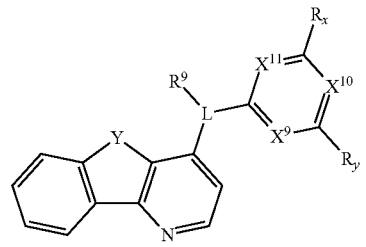
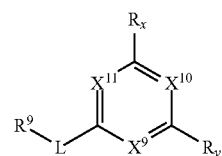
| | Y | | R⁹ | R' |
|---|---|---|---|---|
| Iaaa-873 | O | 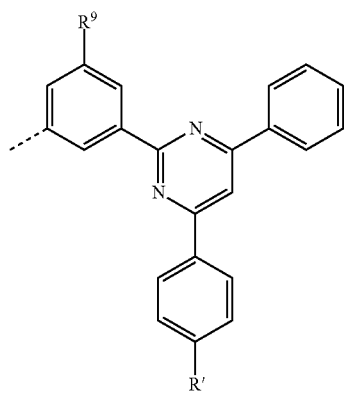 | 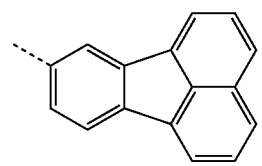 | H |
| Iaaa-874 | O | 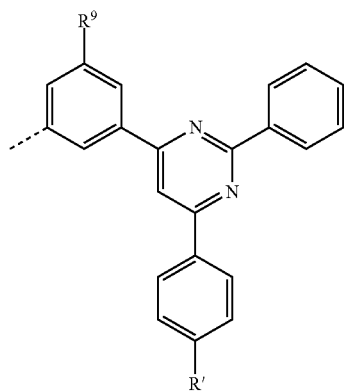 | 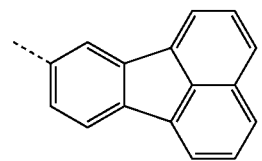 | H |
| Iaaa-875 | O | 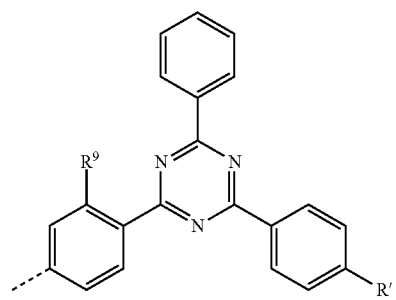 | 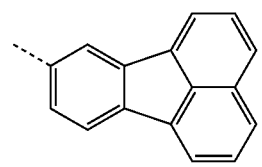 | H |

-continued
(Iaaa)
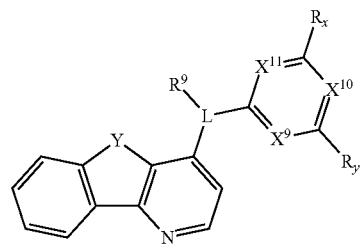
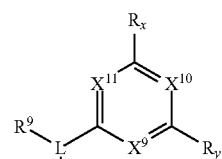
| | Y | | R⁹ | R' |
|---|---|---|---|---|
| Iaaa-876 | O | 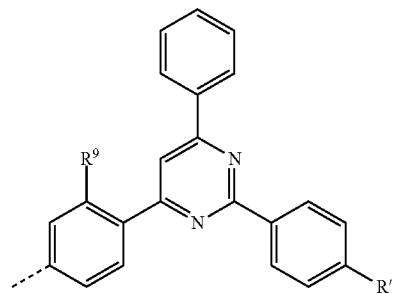 | 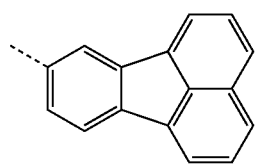 | H |
| Iaaa-877 | O | 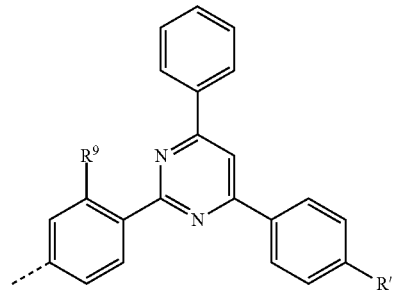 | 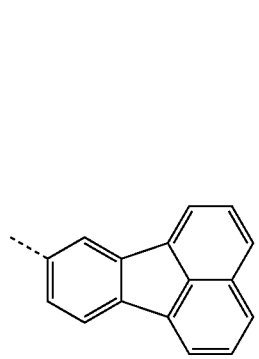 | H |
| Iaaa-878 | O | 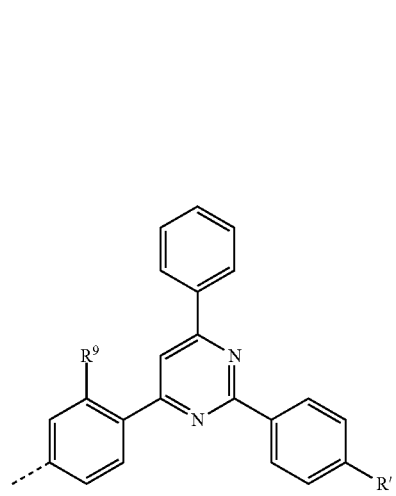 | | H |

-continued
(Iaaa)
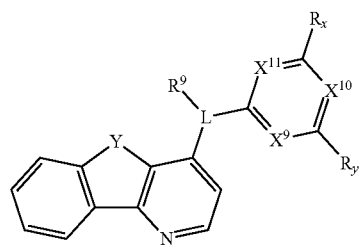
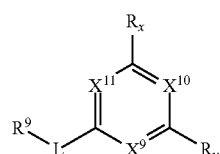
| | Y | | R⁹ | R' |
|---|---|---|---|---|
| Iaaa-879 | O | 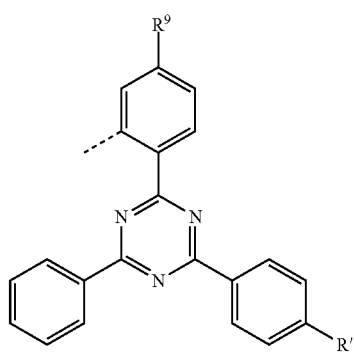 | 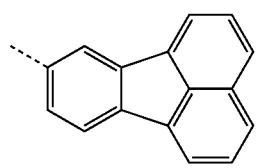 | H |
| Iaaa-880 | O | 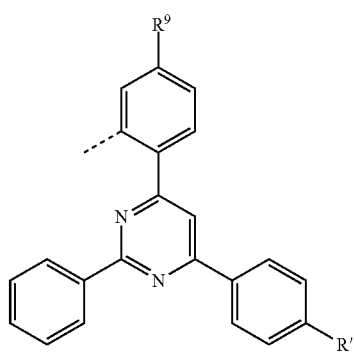 | 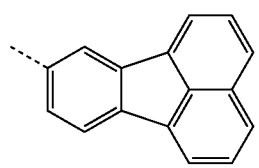 | H |
| Iaaa-881 | O | 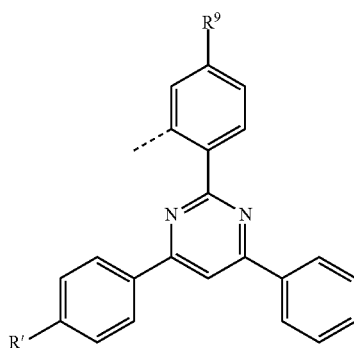 | 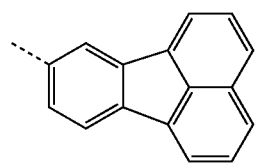 | H |

-continued
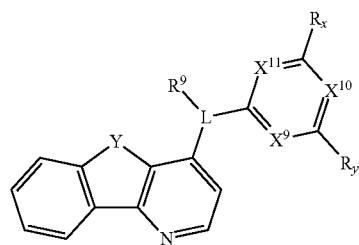
(Iaaa)
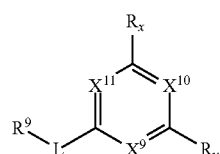
| | Y | | R⁹ | R' |
|---|---|---|---|---|
| Iaaa-882 | O | 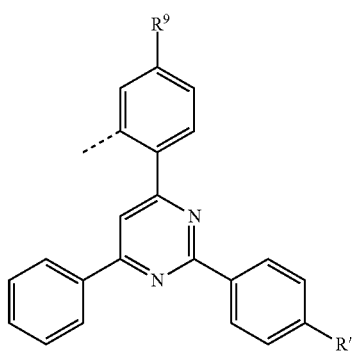 | 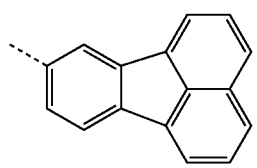 | H |
| Iaaa-883 | O | 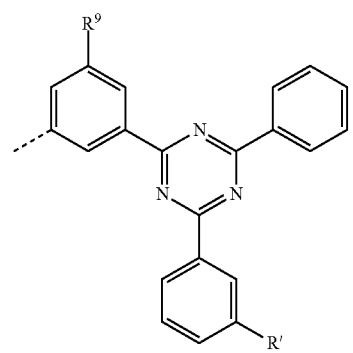 | 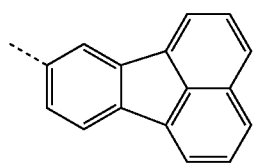 | H |
| Iaaa-884 | O | 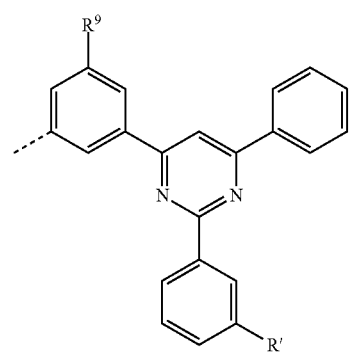 | 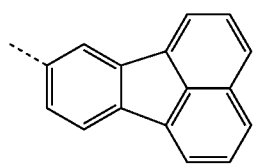 | H |

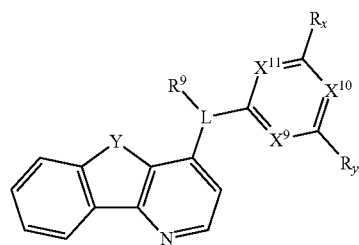
(Iaaa)
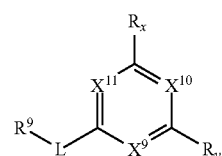
| | Y | | R⁹ | R' |
|---|---|---|---|---|
| Iaaa-885 | O | 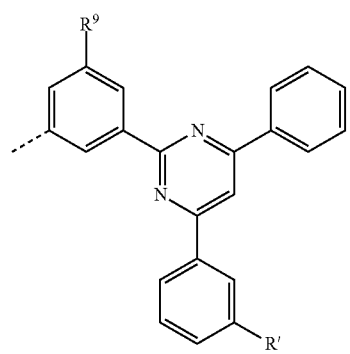 | 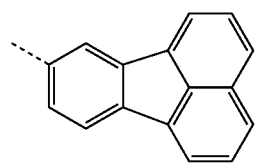 | H |
| Iaaa-886 | O | 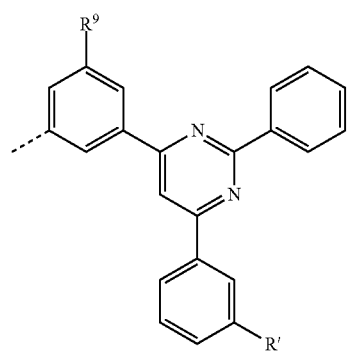 | 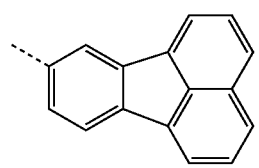 | H |
| Iaaa-887 | O | 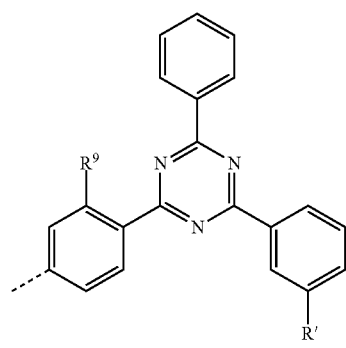 | 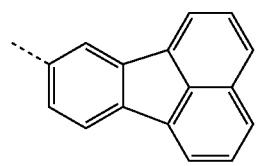 | H |

-continued
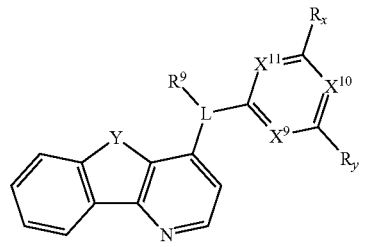
(Iaaa)
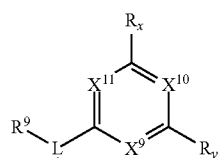
| | Y | | $R^9$ | R' |
|---|---|---|---|---|
| Iaaa-888 | O | 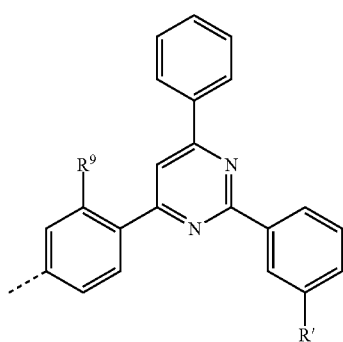 | 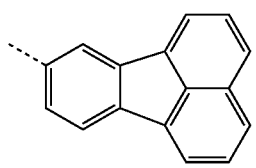 | H |
| Iaaa-889 | O | 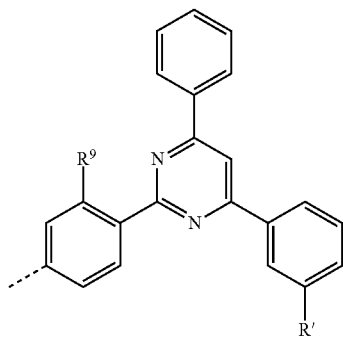 | 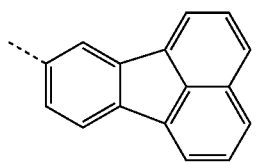 | H |
| Iaaa-890 | O | 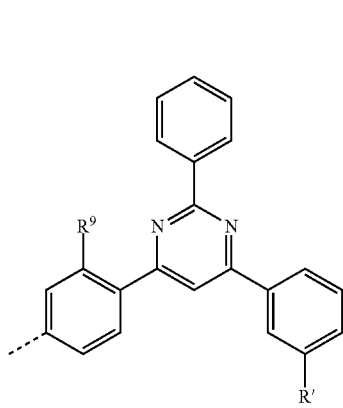 | 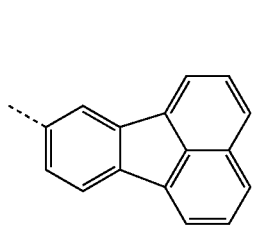 | H |

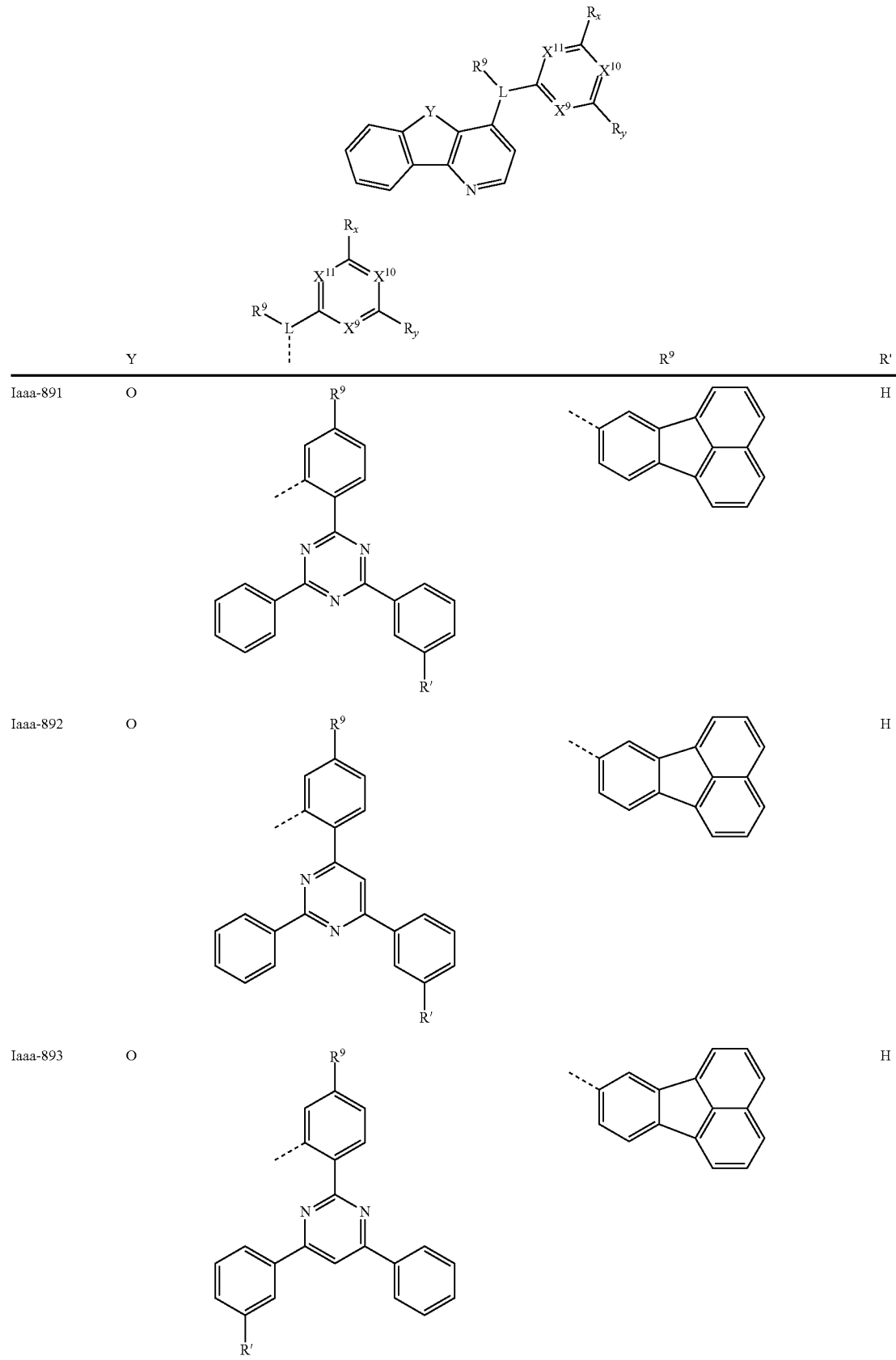

-continued
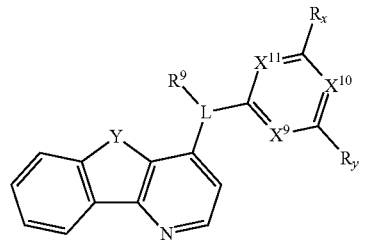
(Iaaa)
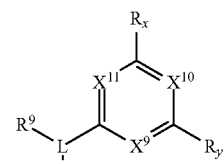
| | Y | R⁹ | R' |
|---|---|---|---|
| Iaaa-894 | O | 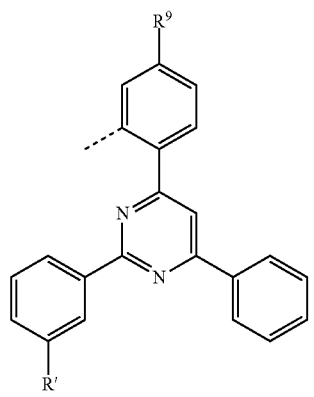 | 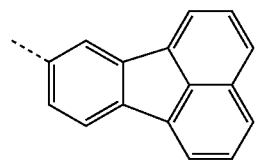 | H |
| Iaaa-895 | O | 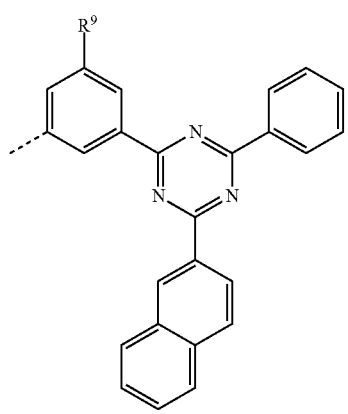 | 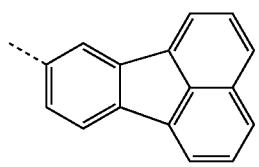 | — |

-continued
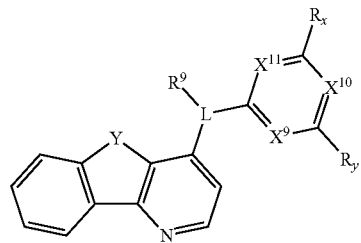
(Iaaa)
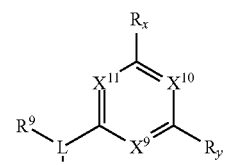
| | Y | R⁹ | R' |
|---|---|---|---|
| Iaaa-896 | O | 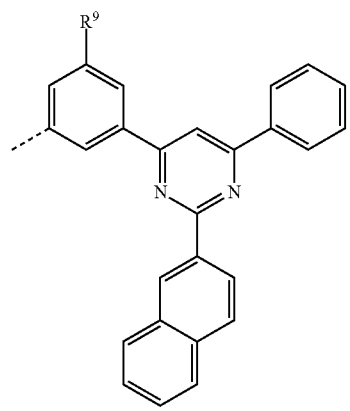 | 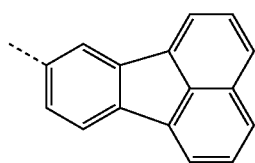 | — |
| Iaaa-897 | O | 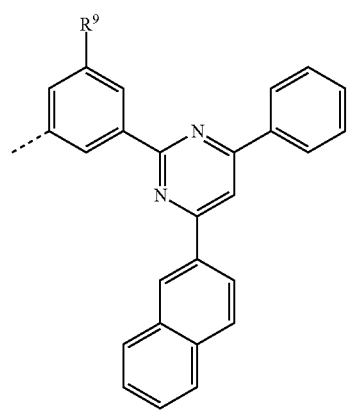 | 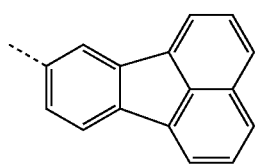 | — |

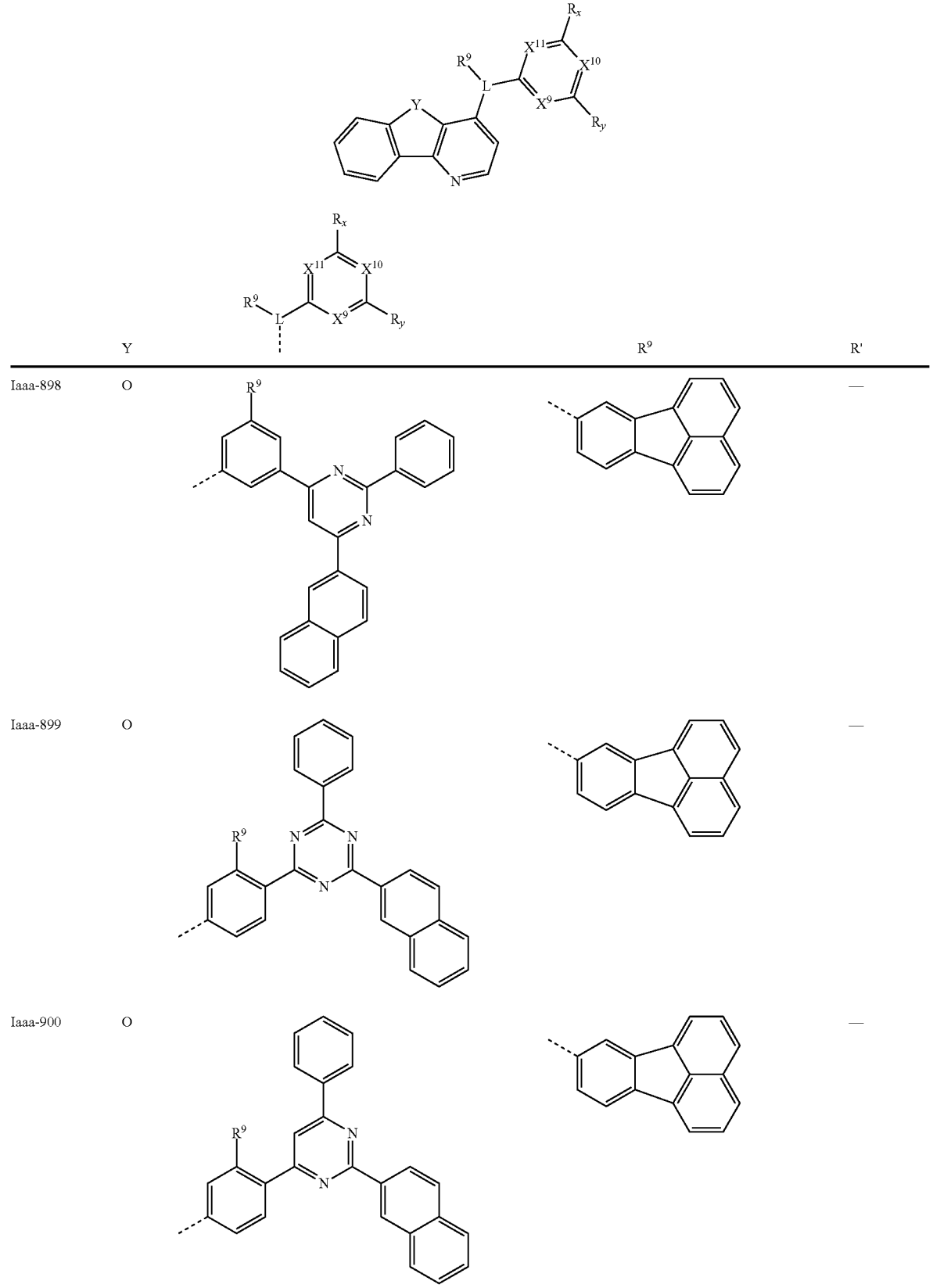

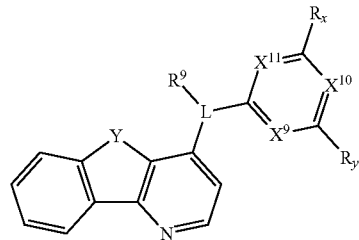
(Iaaa)
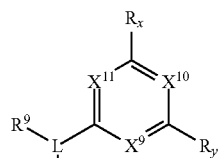
| | Y | R⁹ | | R' |
|---|---|---|---|---|
| Iaaa-901 | O | 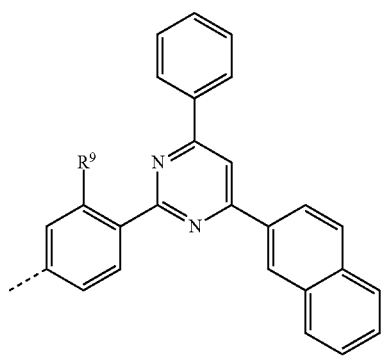 | 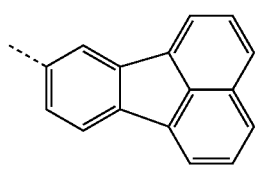 | — |
| Iaaa-902 | O | 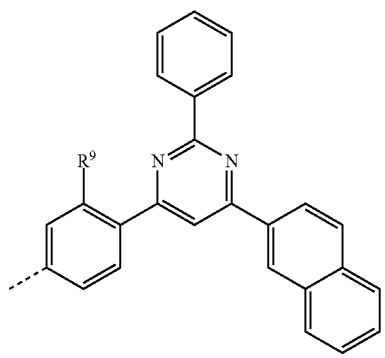 | 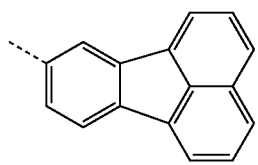 | — |
| Iaaa-903 | O | 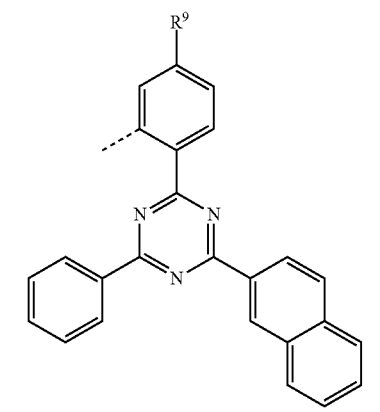 | 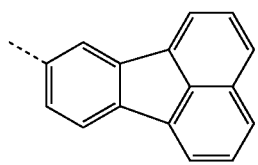 | — |

-continued
(Iaaa)
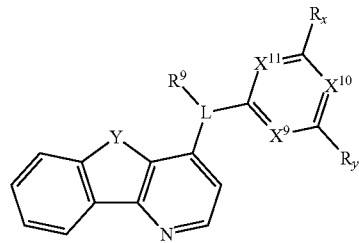
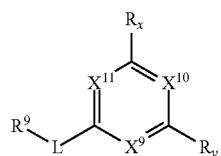
| | Y | R⁹ | R' |
|---|---|---|---|
| Iaaa-904 | O | 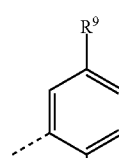 | 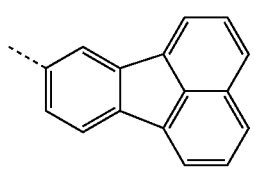 — |
| Iaaa-905 | O | 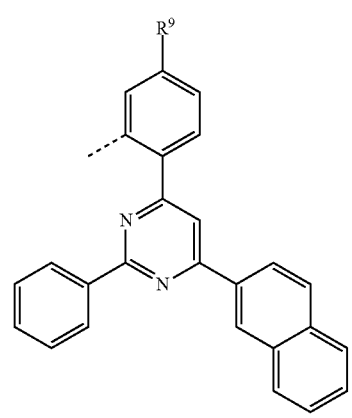 | 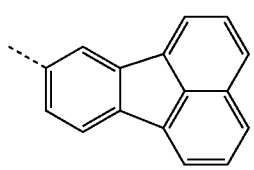 — |

-continued
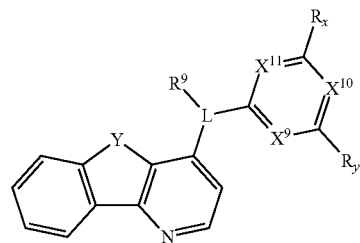
(Iaaa)
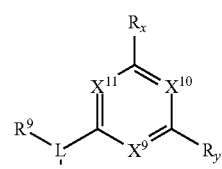
| | Y | R⁹ | R' |
|---|---|---|---|
| Iaaa-906 | O | 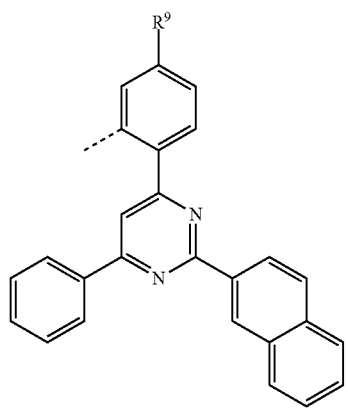 | 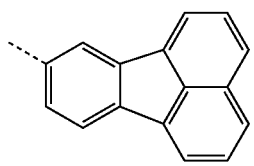 | — |
| Iaaa-907 | O | 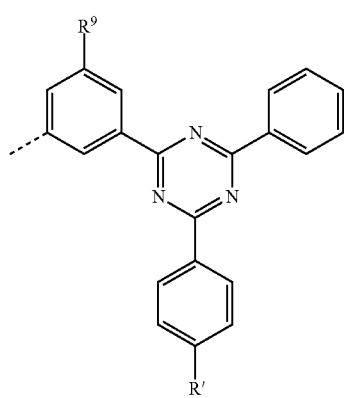 | 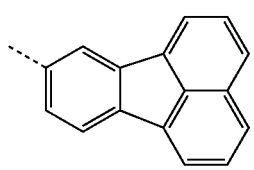 | 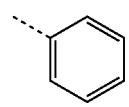 |

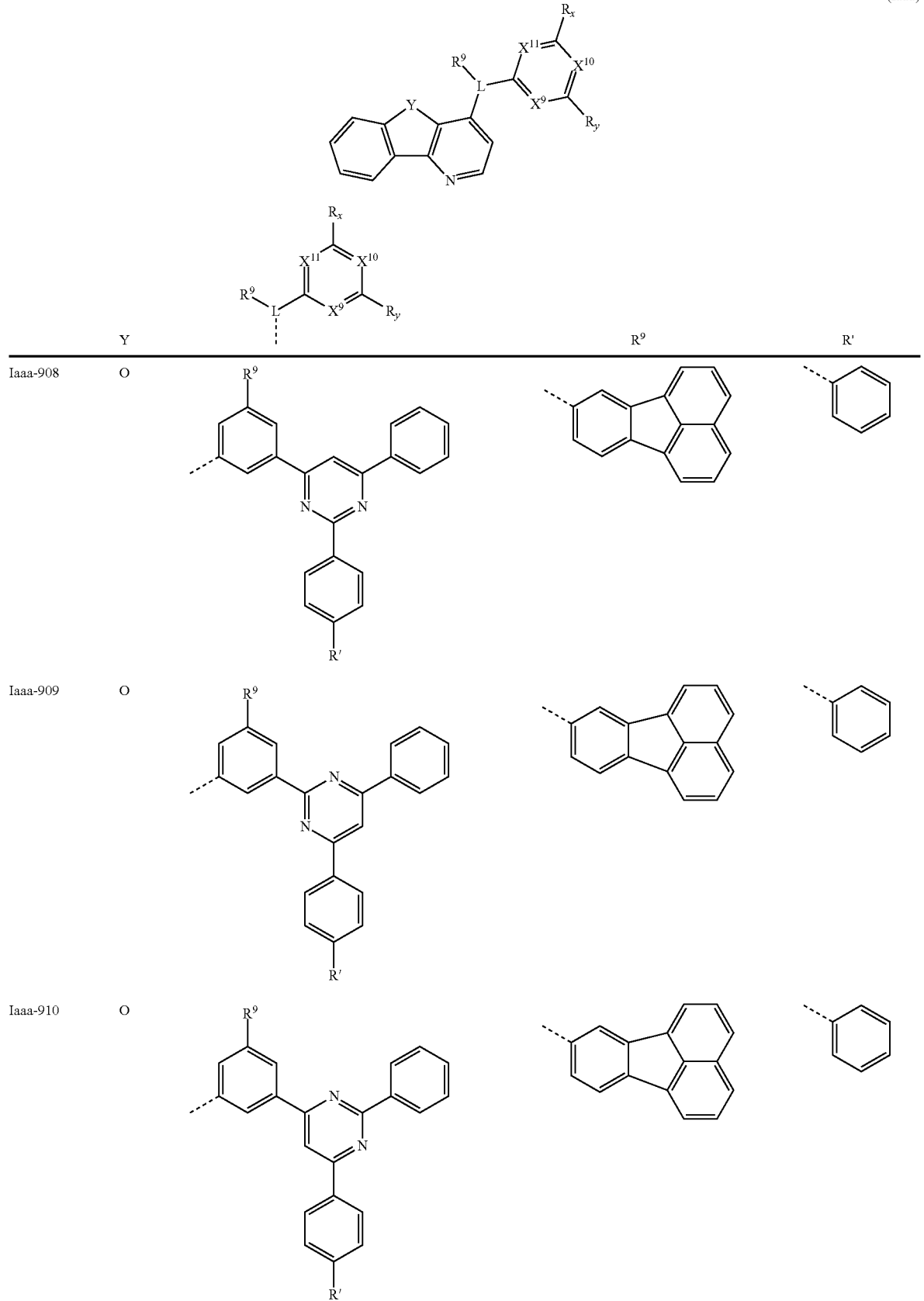

-continued
(Iaaa)
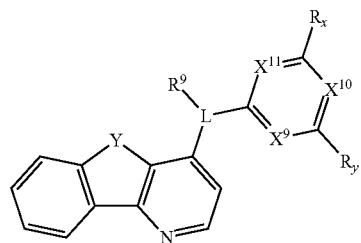
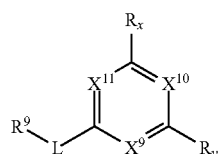
| Y | | R⁹ | R' |
|---|---|---|---|
| Iaaa-911 | O | 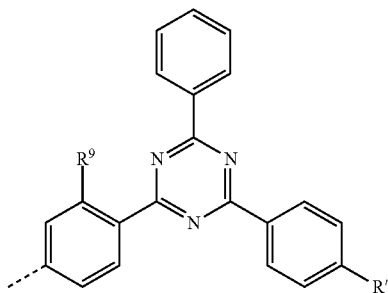 | 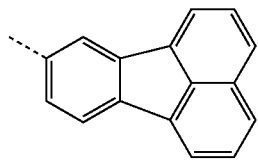 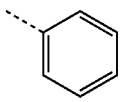 |
| Iaaa-912 | O | 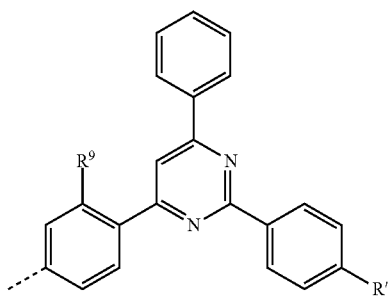 | 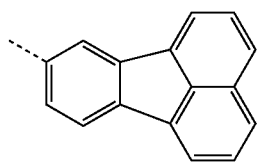 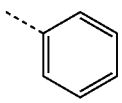 |
| Iaaa-913 | O | 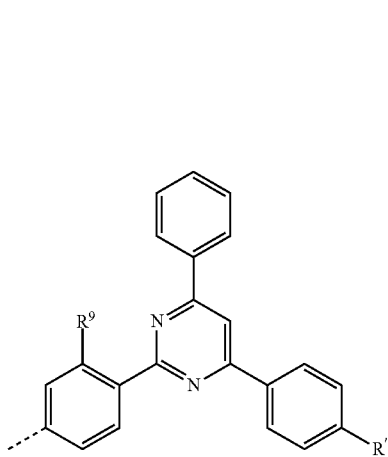 | 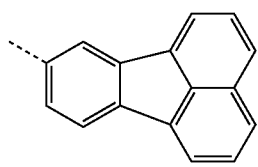 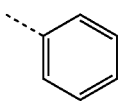 |

-continued
(Iaaa)
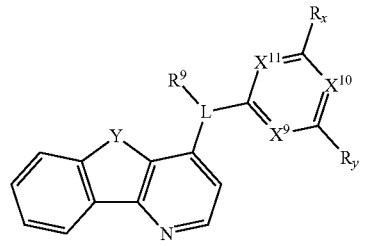
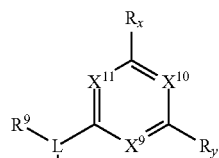
| | Y | | R⁹ | R' |
|---|---|---|---|---|
| Iaaa-914 | O | 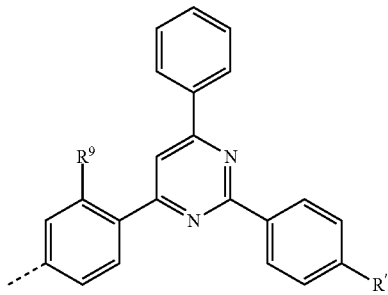 | 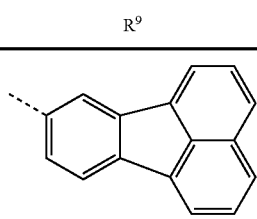 | 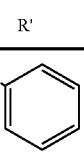 |
| Iaaa-915 | O | 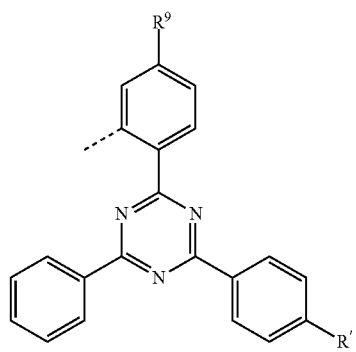 | 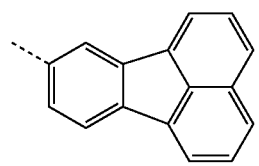 | 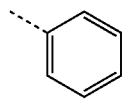 |
| Iaaa-916 | O | 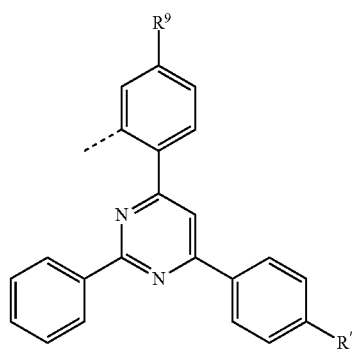 | 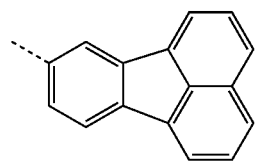 | 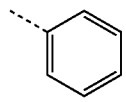 |

-continued
(Iaaa)
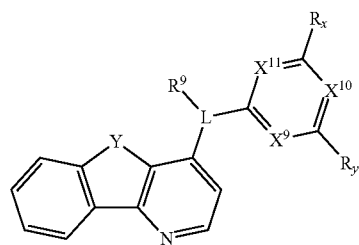
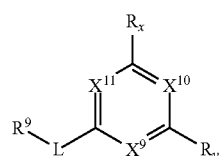
| | Y | | R⁹ | R' |
|---|---|---|---|---|
| Iaaa-917 | O | 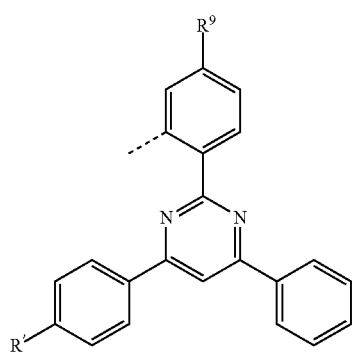 | 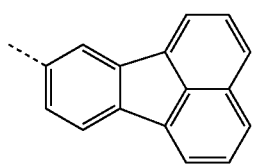 | 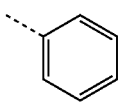 |
| Iaaa-918 | O | 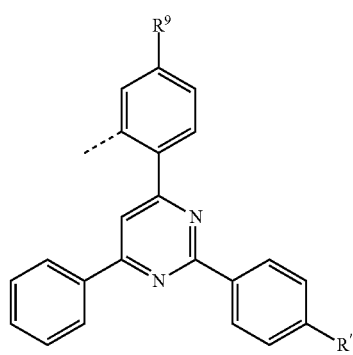 | 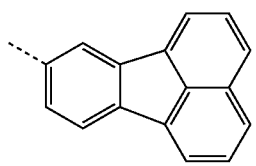 | 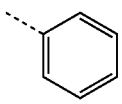 |
| Iaaa-919 | O | 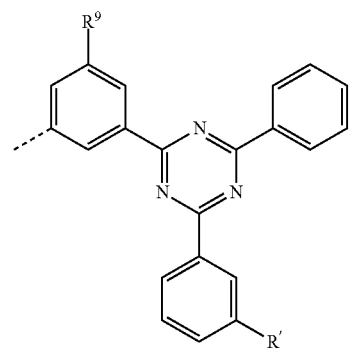 | 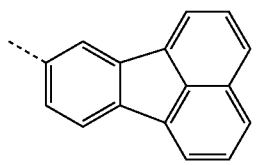 | 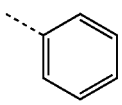 |

-continued
(Iaaa)
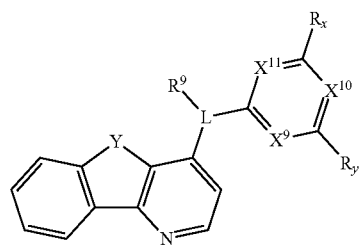
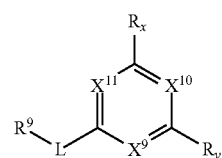
| | Y | | R⁹ | R' |
|---|---|---|---|---|
| Iaaa-920 | O | 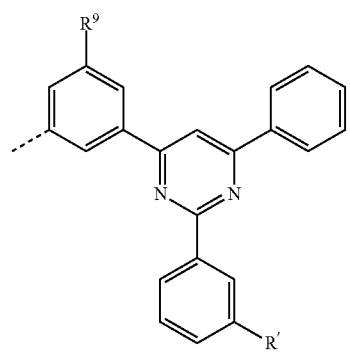 | 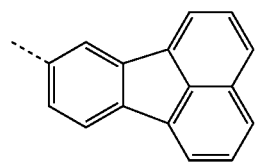 | 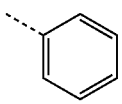 |
| Iaaa-921 | O | 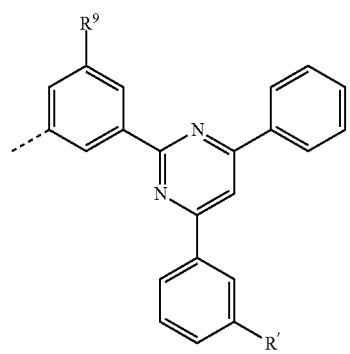 | 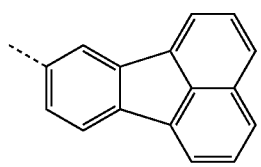 | 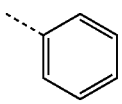 |
| Iaaa-922 | O | 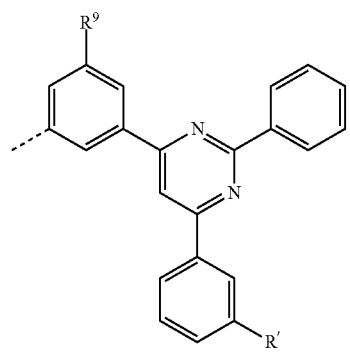 | 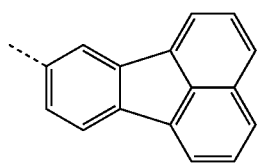 | 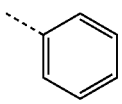 |

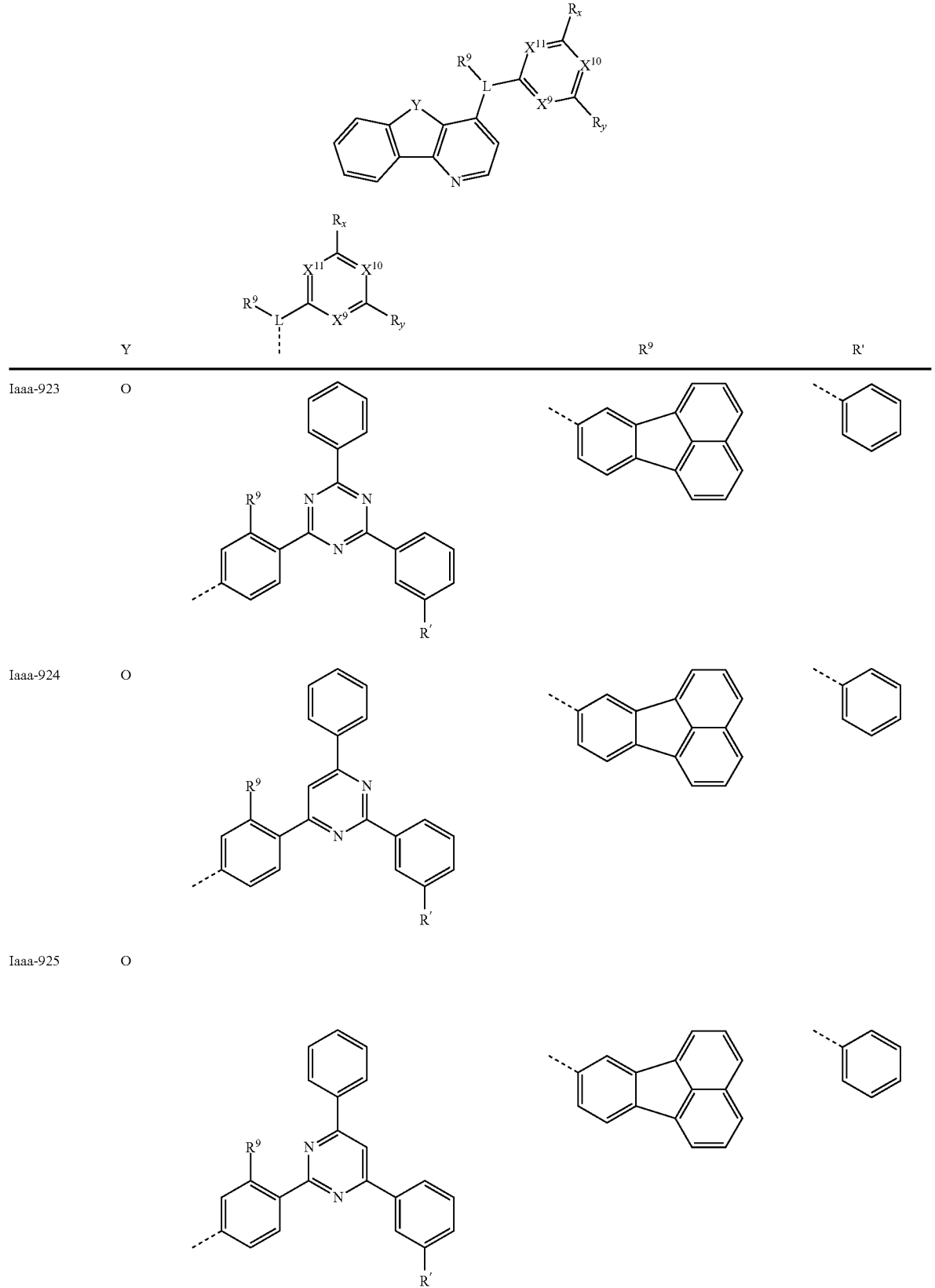

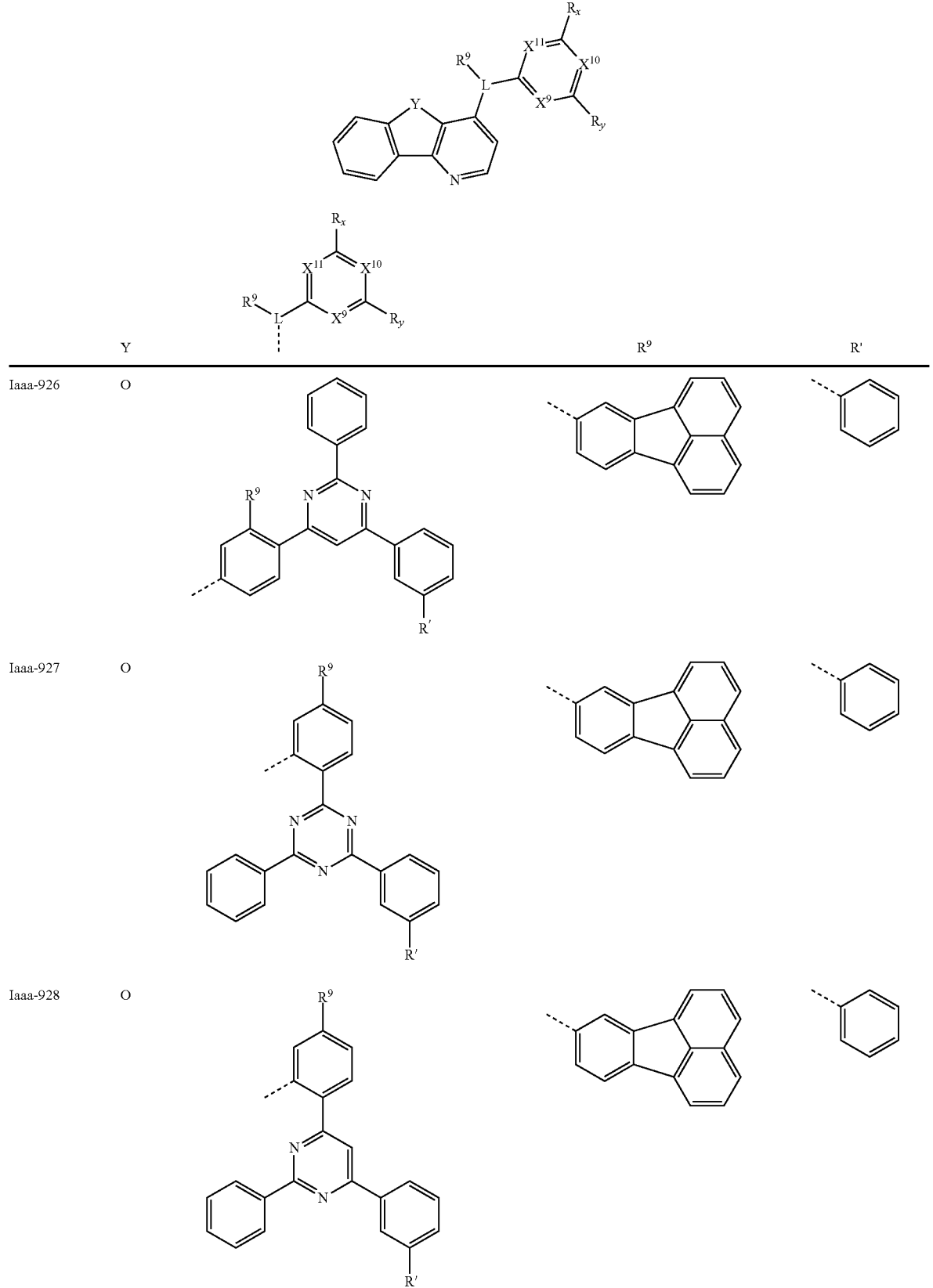

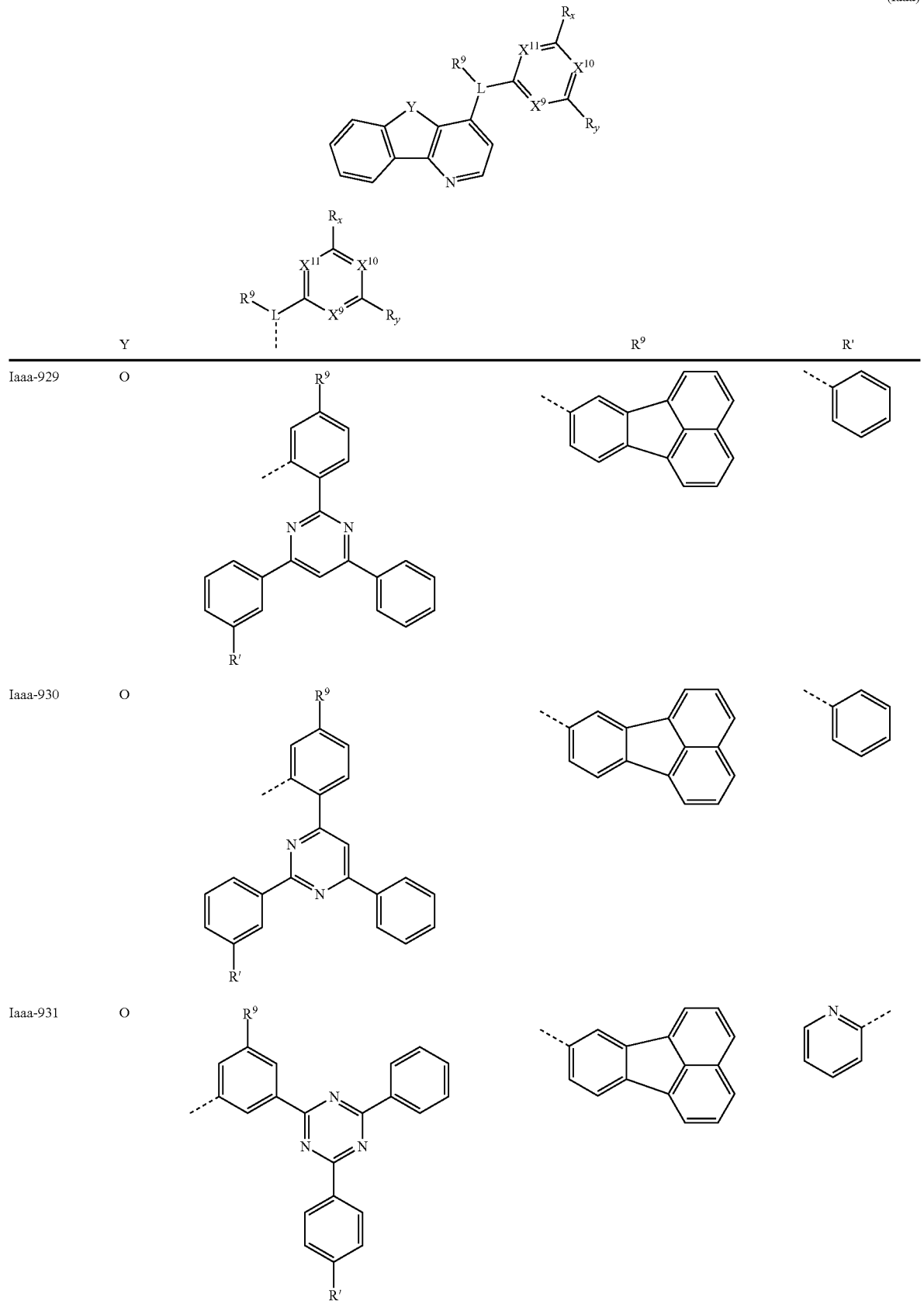

-continued
(Iaaa)
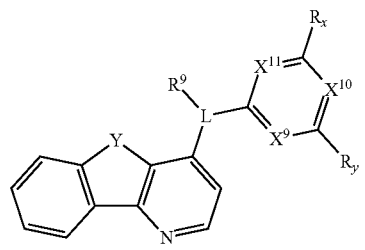
| | Y | 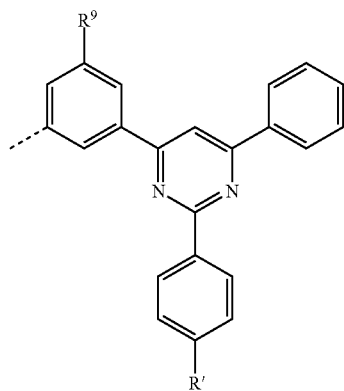 | $R^9$ | $R'$ |
|---|---|---|---|---|
| Iaaa-932 | O | 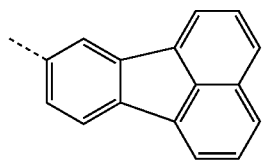 | 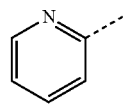 | |
| Iaaa-933 | O | 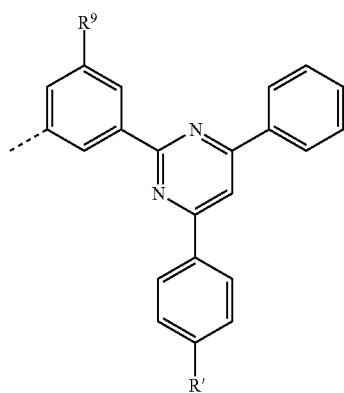 | 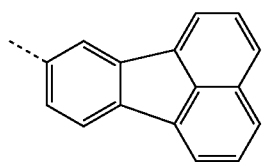 | 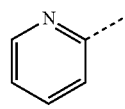 |

-continued
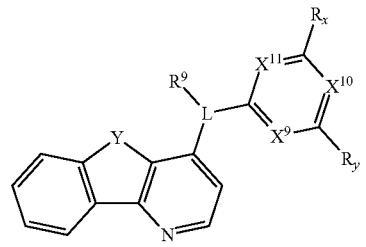
(Iaaa)
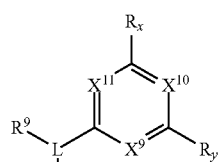
| | Y | | $R^9$ | R' |
|---|---|---|---|---|
| Iaaa-934 | O | 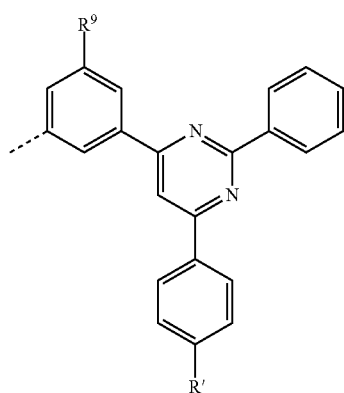 | 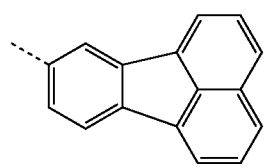 | 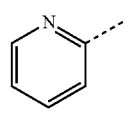 |
| Iaaa-935 | O | 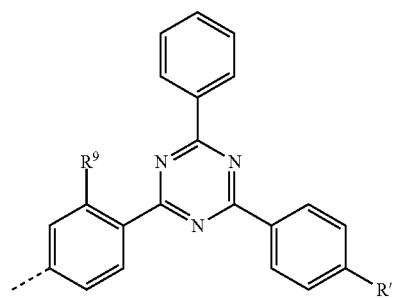 | 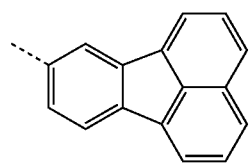 | 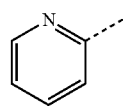 |
| Iaaa-936 | O | 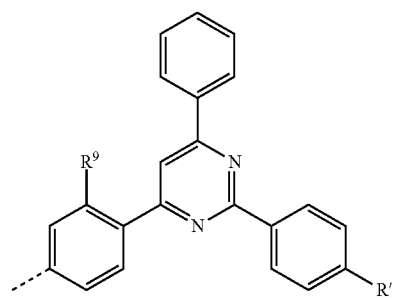 | 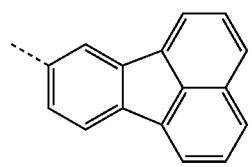 | 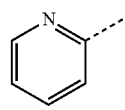 |

-continued
(Iaaa)
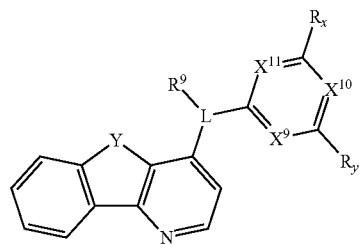
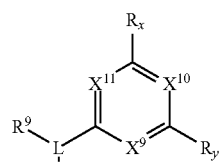
| | Y | | R⁹ | R' |
|---|---|---|---|---|
| Iaaa-937 | O | 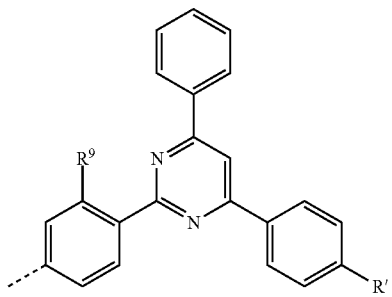 | 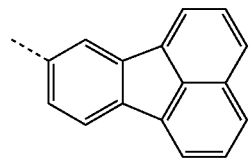 | 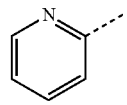 |
| Iaaa-938 | O | 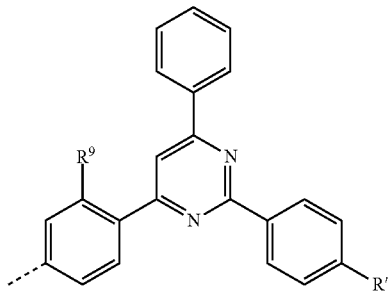 | 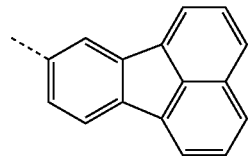 | 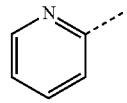 |
| Iaaa-939 | O | 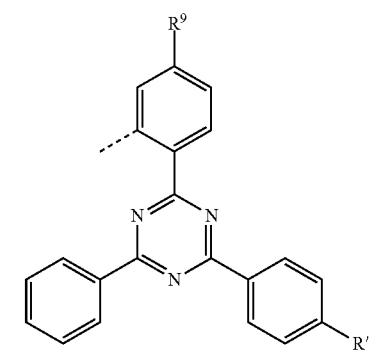 | 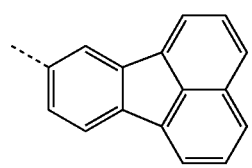 | 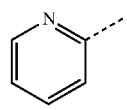 |

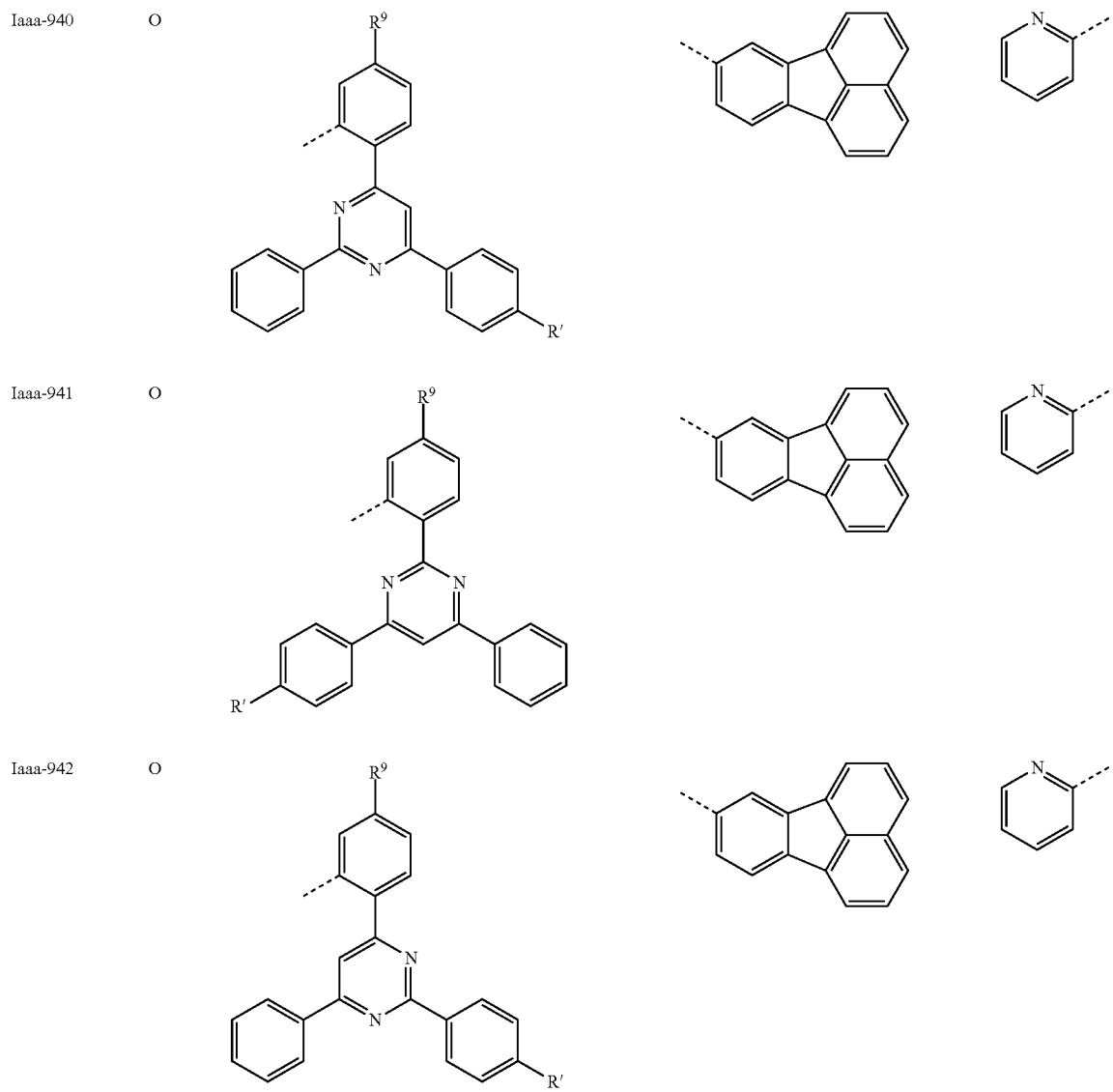

-continued
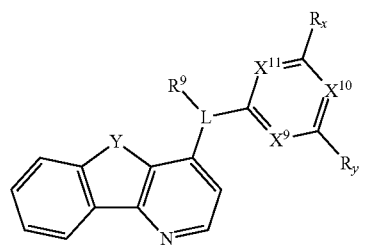
(Iaaa)
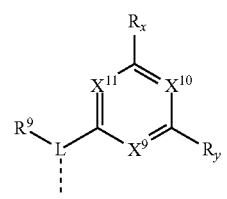
| | Y | R⁹ | | R' |
|---|---|---|---|---|
| Iaaa-943 | O | 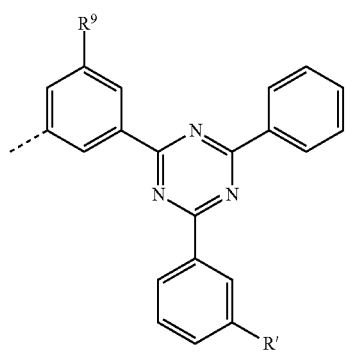 | 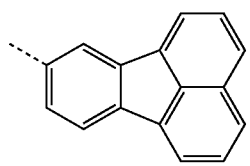 | 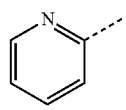 |
| Iaaa-944 | O | 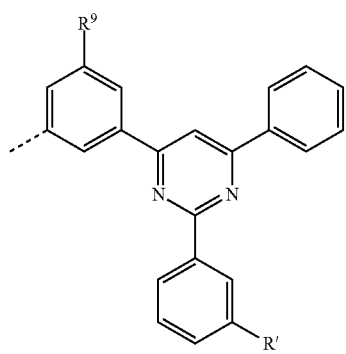 | 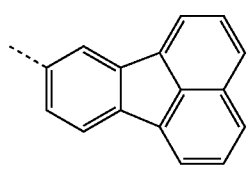 | 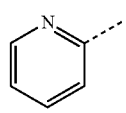 |
| Iaaa-945 | O | 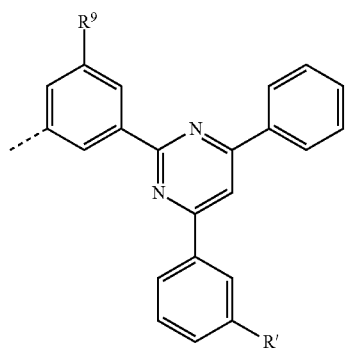 | 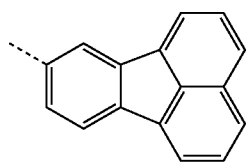 | 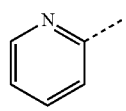 |

-continued
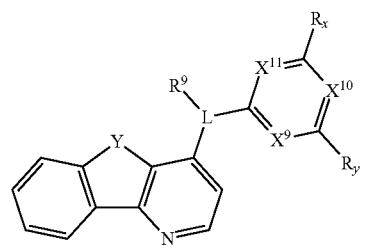
(Iaaa)
| | Y | | R⁹ | R' |
|---|---|---|---|---|
| Iaaa-946 | O | 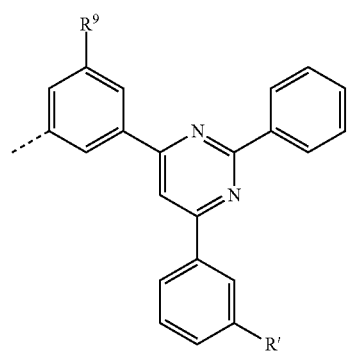 | 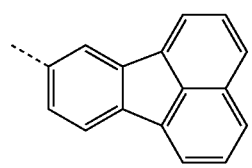 | 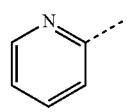 |
| Iaaa-947 | O | 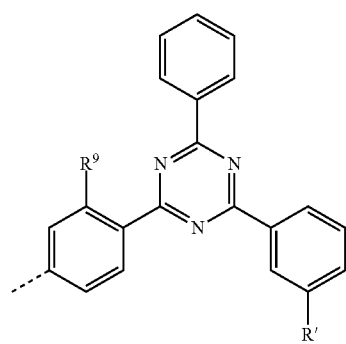 | 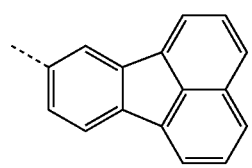 | 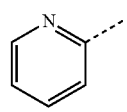 |
| Iaaa-948 | O | 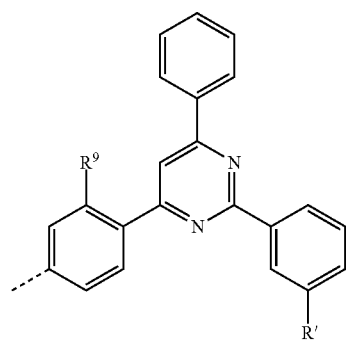 | 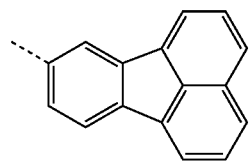 | 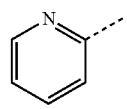 |

-continued
(Iaaa)
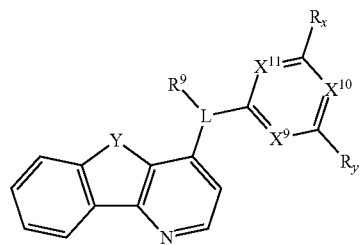
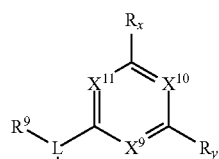
| | Y | | R⁹ | R' |
|---|---|---|---|---|
| Iaaa-949 | O | 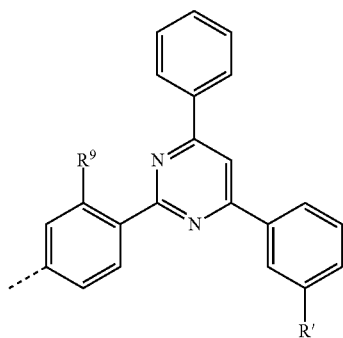 | 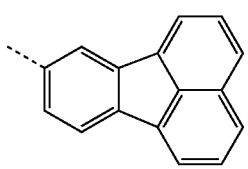 | 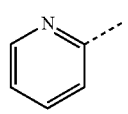 |
| Iaaa-950 | O | 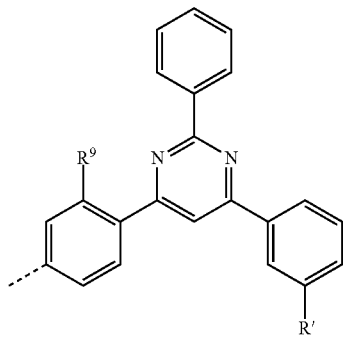 | 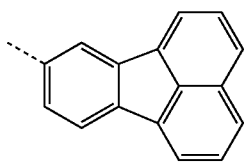 | 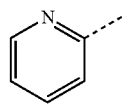 |
| Iaaa-951 | O | 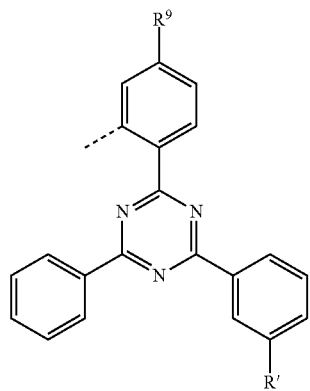 | 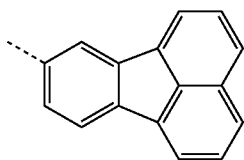 | 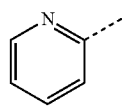 |

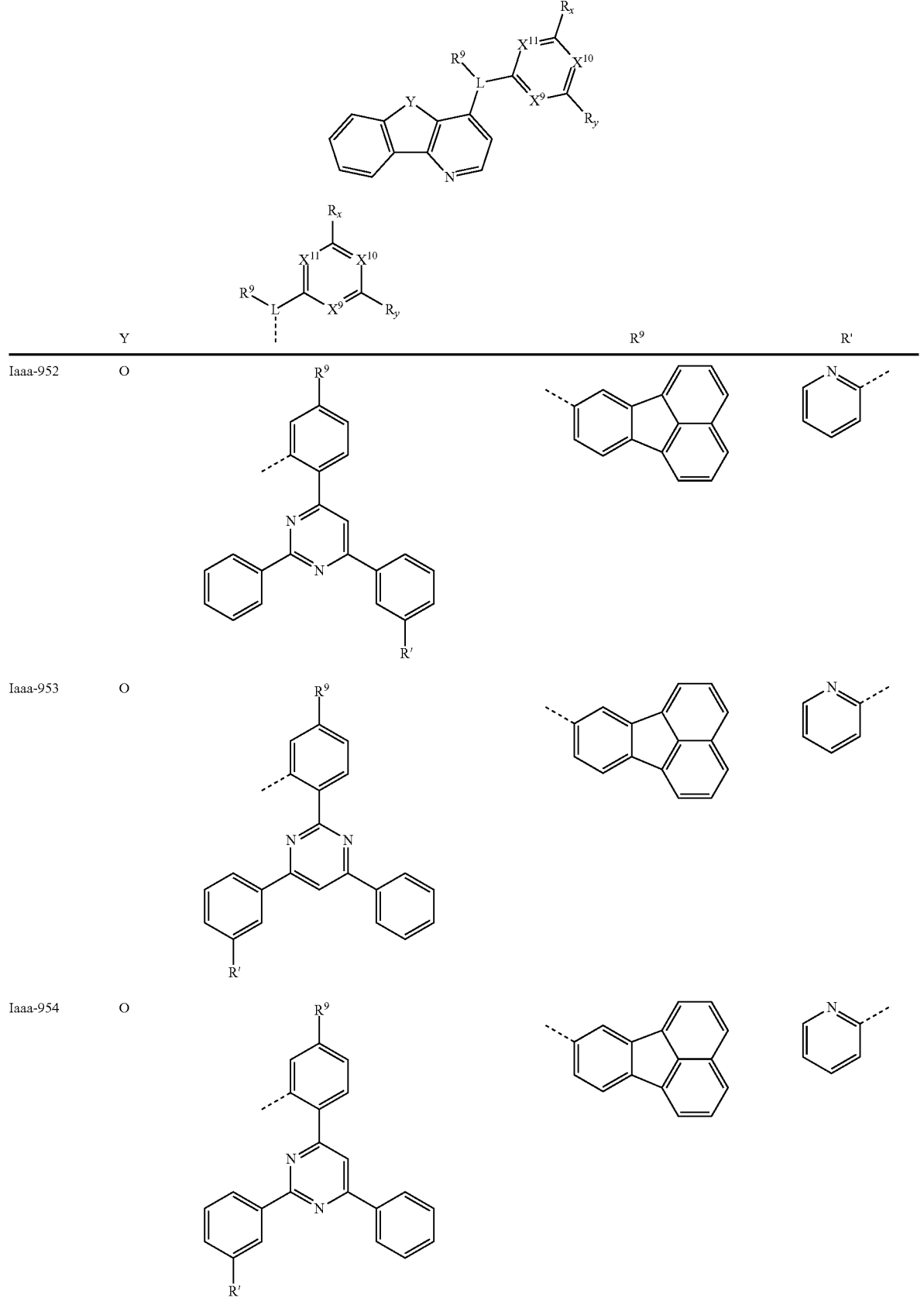

-continued
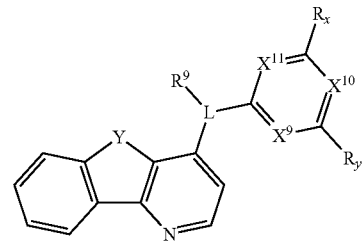
(Iaaa)
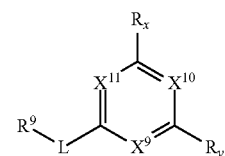
| | Y | R⁹ | | R' |
|---|---|---|---|---|
| Iaaa-955 | O | 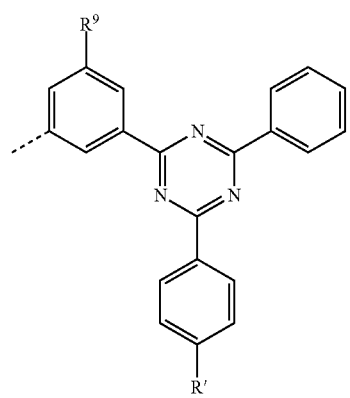 | 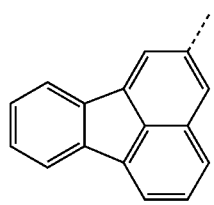 | H |
| Iaaa-956 | O | 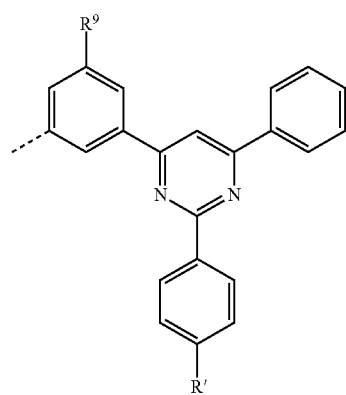 | 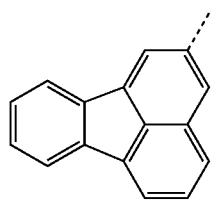 | H |

-continued
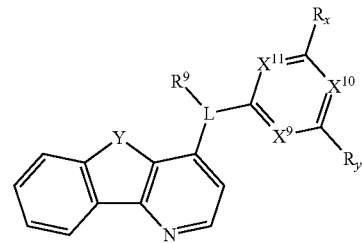
(Iaaa)
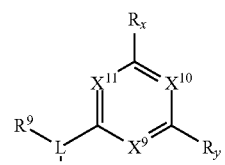
| | Y | | $R^9$ | R' |
|---|---|---|---|---|
| Iaaa-957 | O | 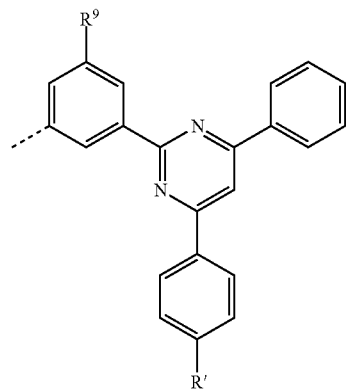 | 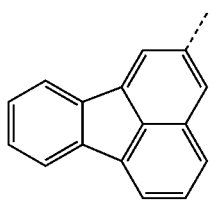 | H |
| Iaaa-958 | O | 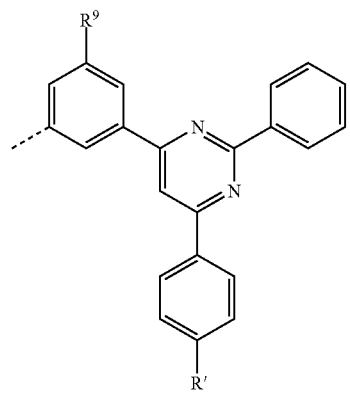 | 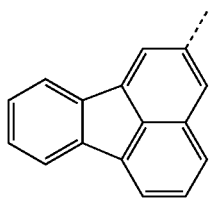 | H |
| Iaaa-959 | O | 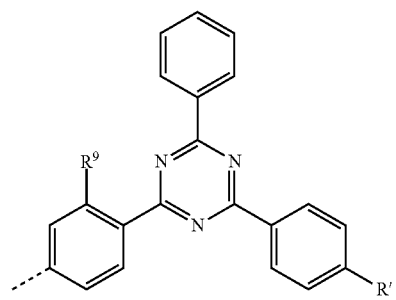 | 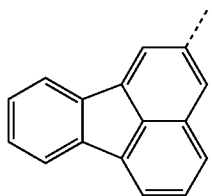 | H |

-continued
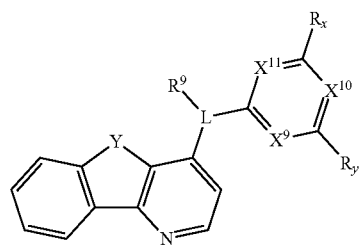
(Iaaa)
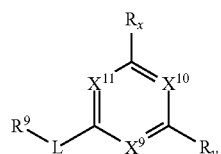
| | Y | R⁹ | R' |
|---|---|---|---|
| Iaaa-960 | O | 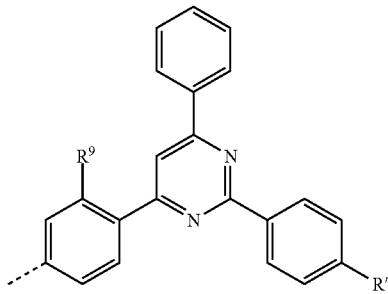 | 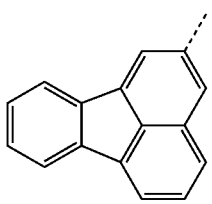 H |
| Iaaa-961 | O | 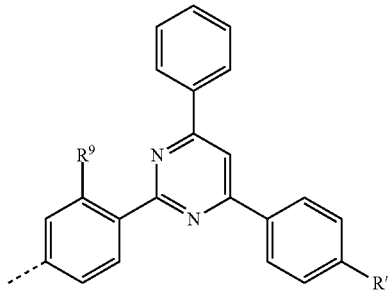 | 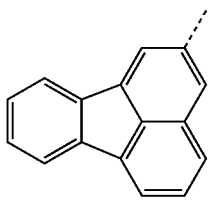 H |
| Iaaa-962 | O | 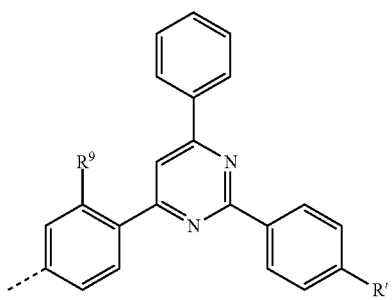 | 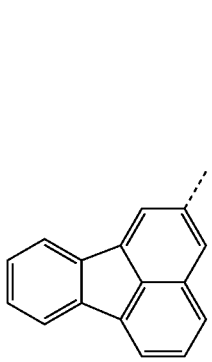 H |

-continued
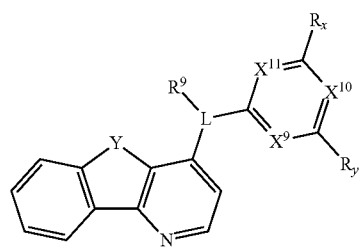
(Iaaa)
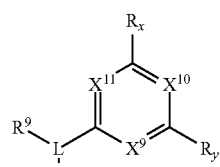
| | Y | | R⁹ | R' |
|---|---|---|---|---|
| Iaaa-963 | O | 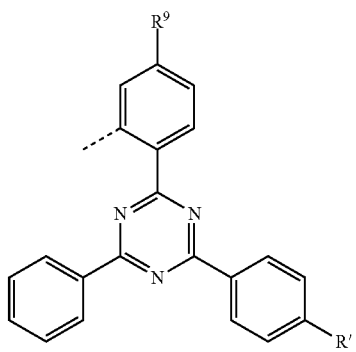 | 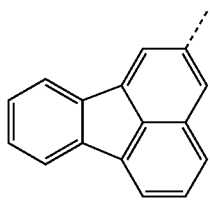 | H |
| Iaaa-964 | O | 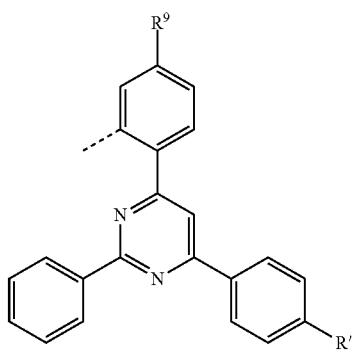 | 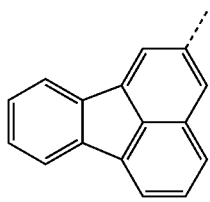 | H |
| Iaaa-965 | O | 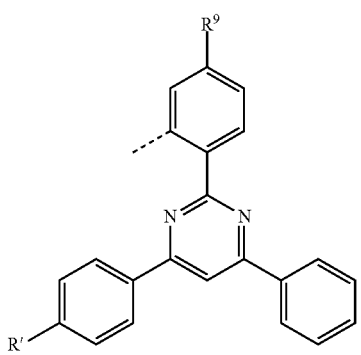 | 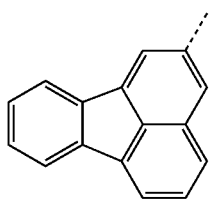 | H |

-continued
(Iaaa)
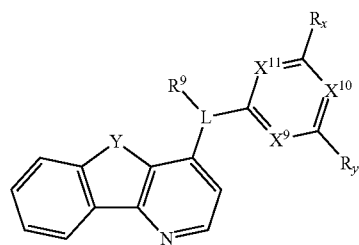
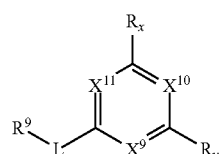
| | Y | | R⁹ | R' |
|---|---|---|---|---|
| Iaaa-966 | O | 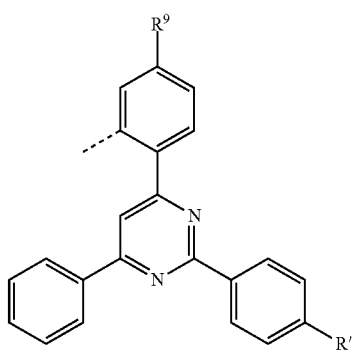 | 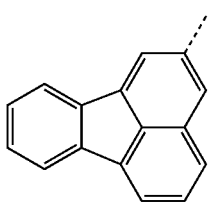 | H |
| Iaaa-967 | O | 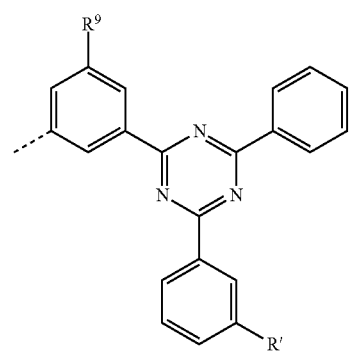 | 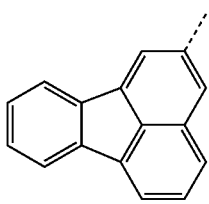 | H |
| Iaaa-968 | O | 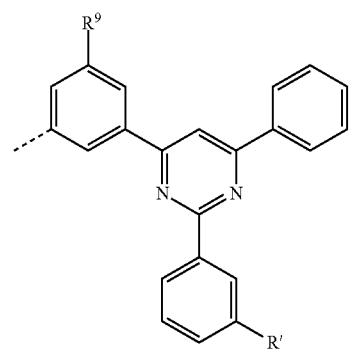 | 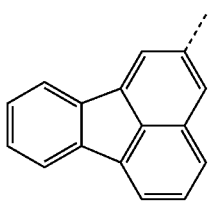 | H |

-continued
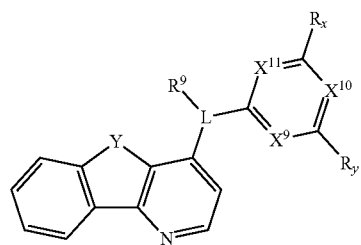
(Iaaa)
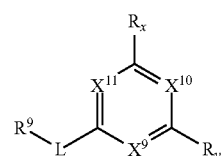
| | Y | R⁹ | | R' |
|---|---|---|---|---|
| Iaaa-969 | O | 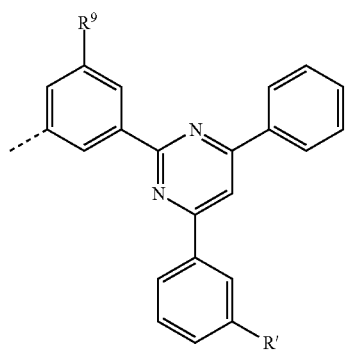 | 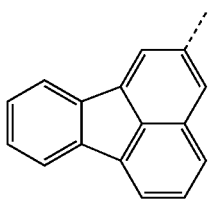 | H |
| Iaaa-970 | O | 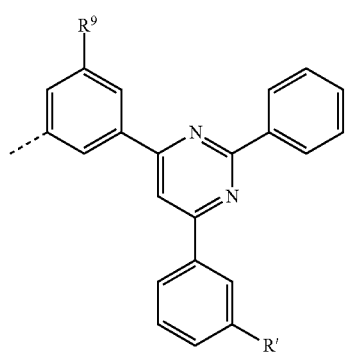 | 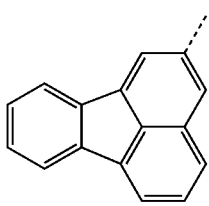 | H |
| Iaaa-971 | O | 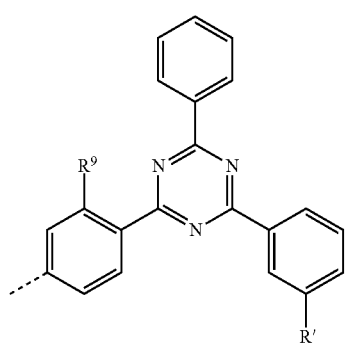 |  | H |

-continued
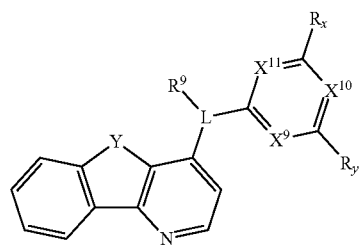
(Iaaa)
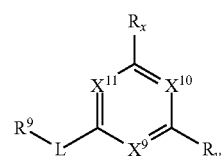
| | Y | R⁹ | R' |
|---|---|---|---|
| Iaaa-972 | O | 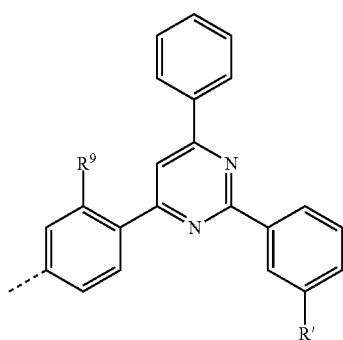 | 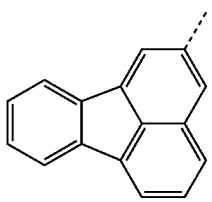 H |
| Iaaa-973 | O | 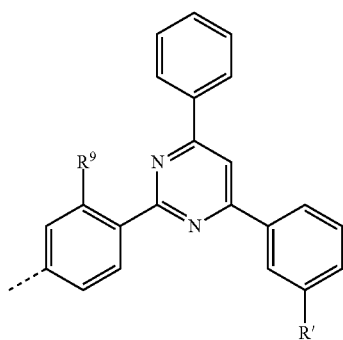 | 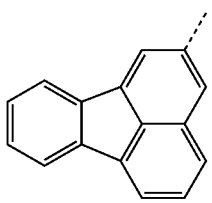 H |
| Iaaa-974 | O | 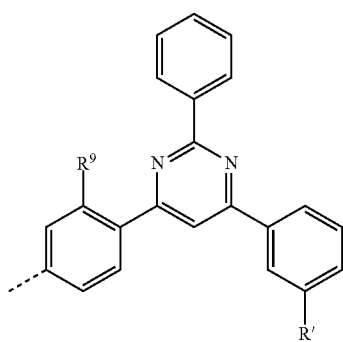 | 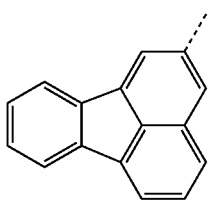 H |

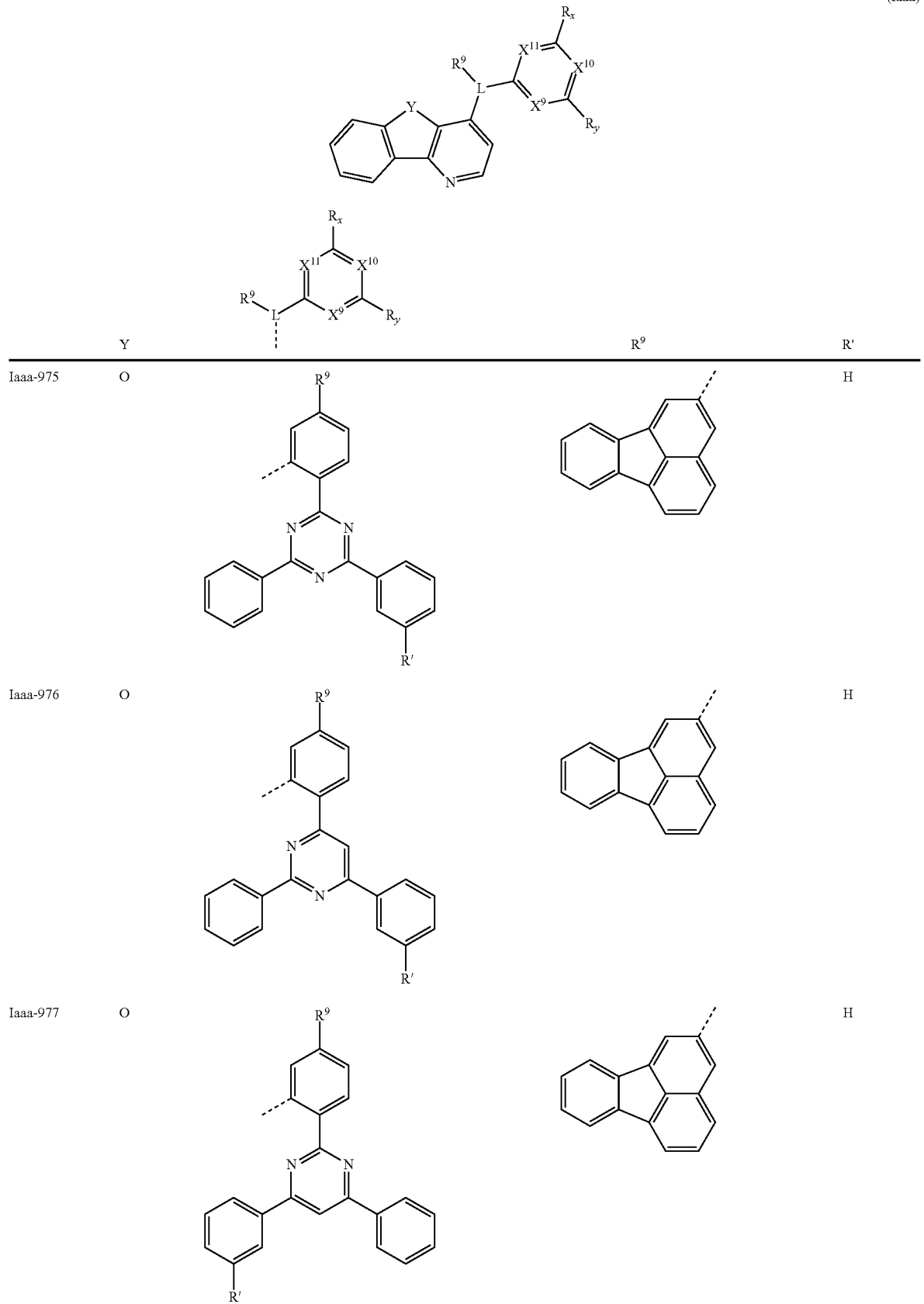

-continued
(Iaaa)
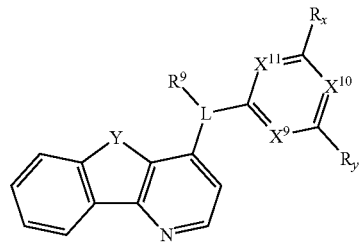
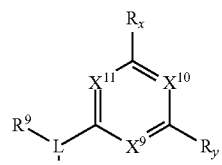
| | Y | R⁹ | R' |
|---|---|---|---|
| Iaaa-978 | O | 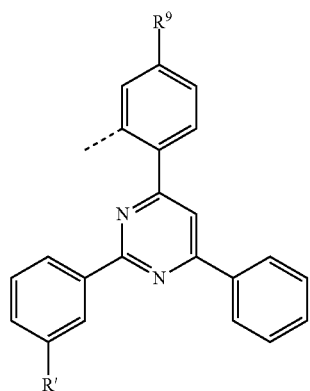 | 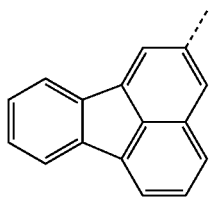 H |
| Iaaa-979 | O | 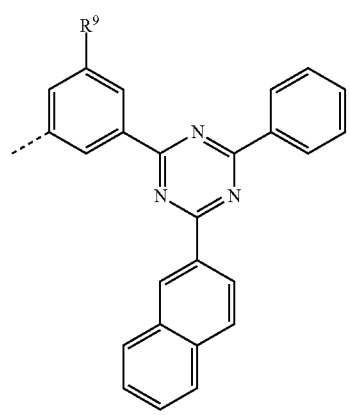 | 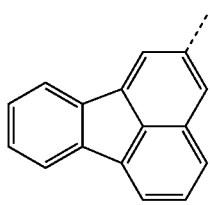 — |

-continued
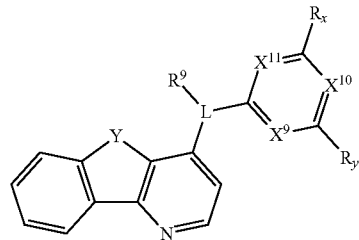
(Iaaa)
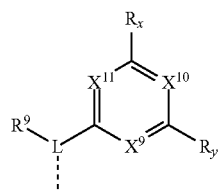
| | Y | R⁹ | R' |
|---|---|---|---|
| Iaaa-980 | O | 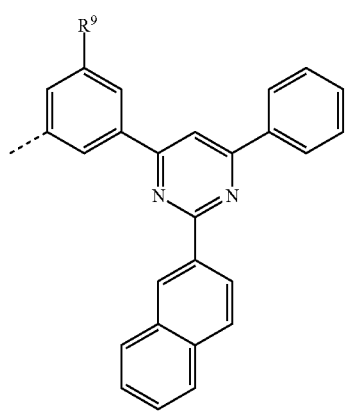 | 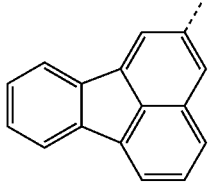 | — |
| Iaaa-981 | O | 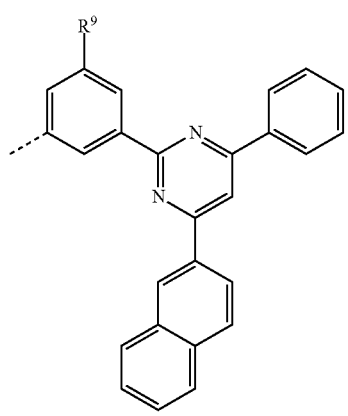 | 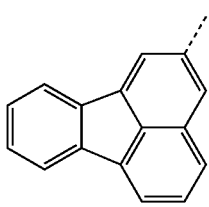 | — |

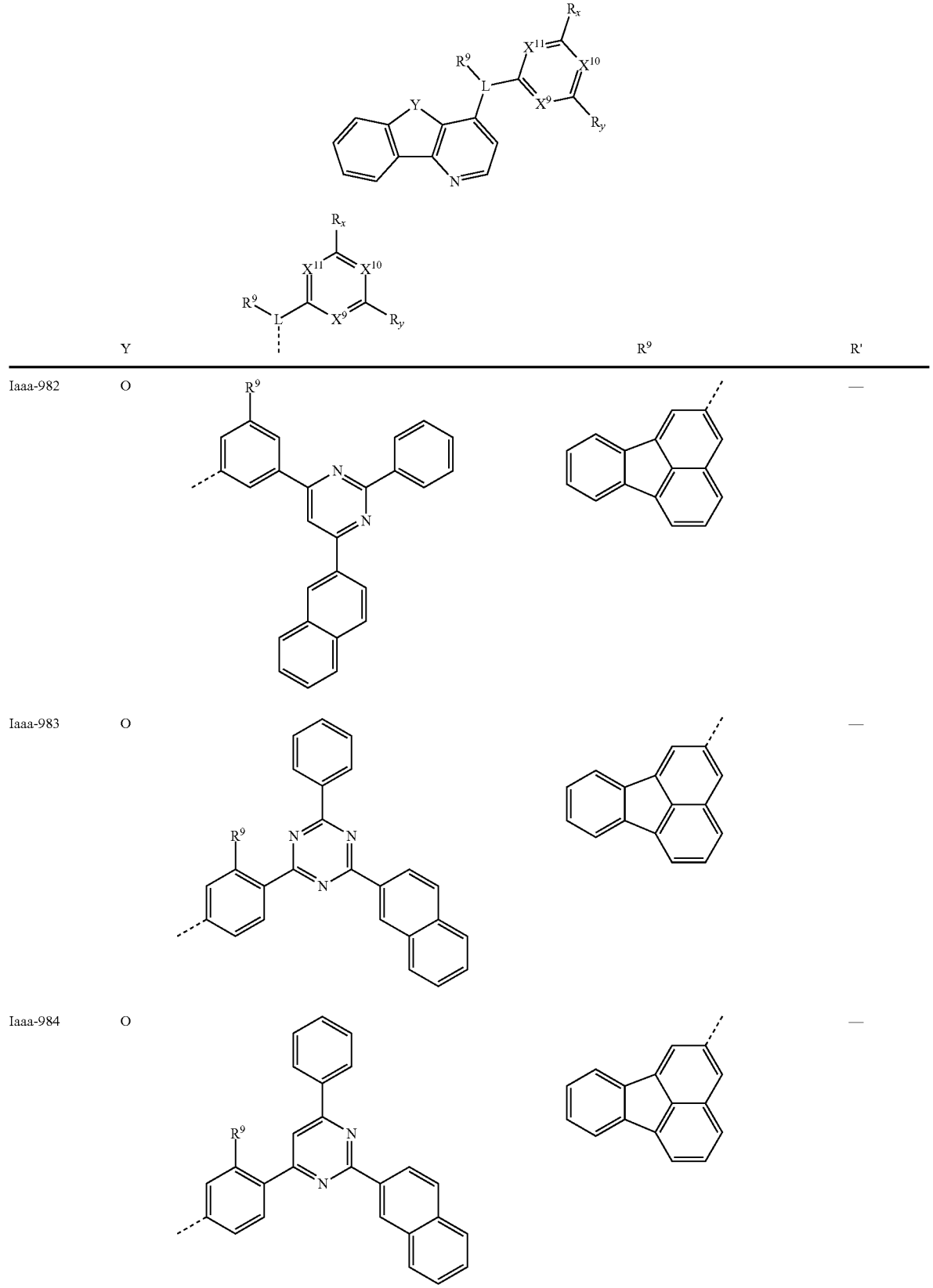

-continued
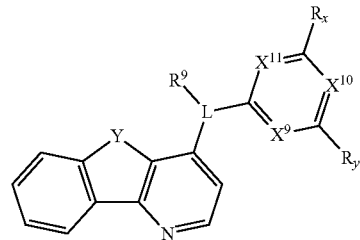
(Iaaa)
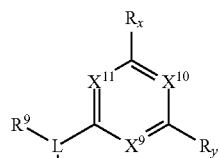
| | Y | R⁹ | R' |
|---|---|---|---|
| Iaaa-985 | O | 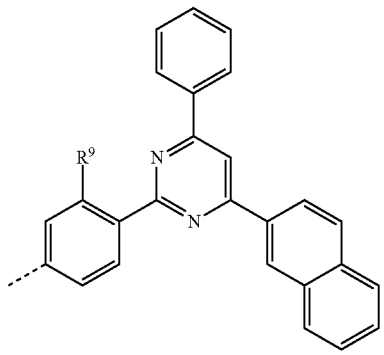 | 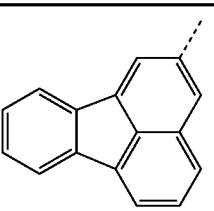 | — |
| Iaaa-986 | O | 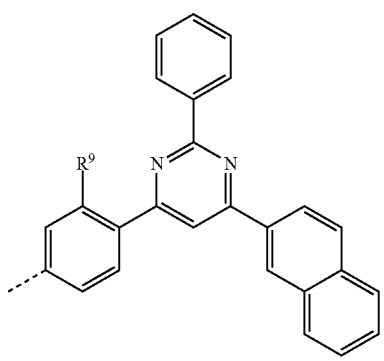 | 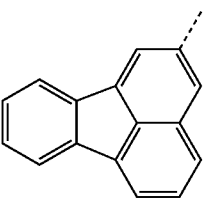 | — |
| Iaaa-987 | O | 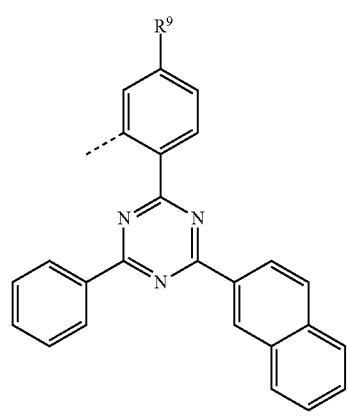 | 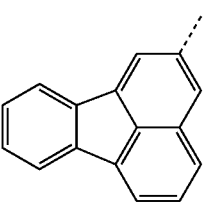 | — |

-continued
(Iaaa)
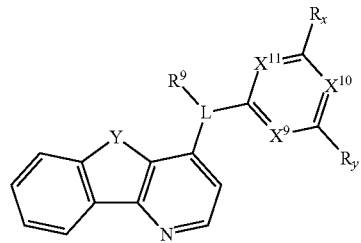
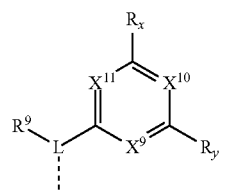
| | Y | | R⁹ | R' |
|---|---|---|---|---|
| Iaaa-988 | O | 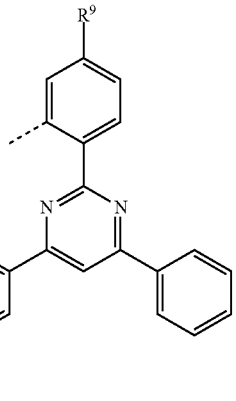 | 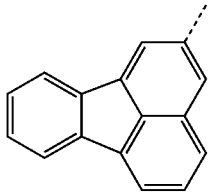 | — |
| Iaaa-989 | O | 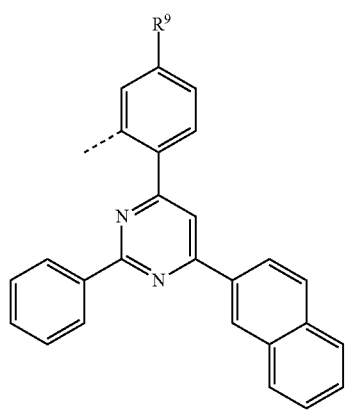 | 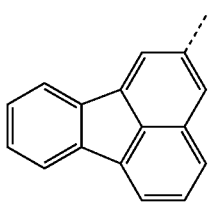 | — |

-continued
(Iaaa)
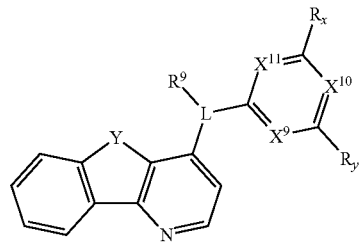
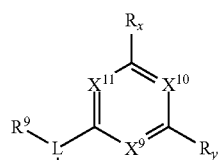
| | Y | | R⁹ | R' |
|---|---|---|---|---|
| Iaaa-990 | O | 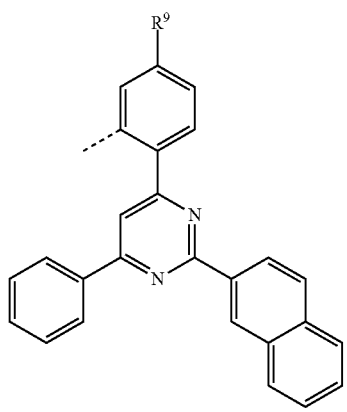 | 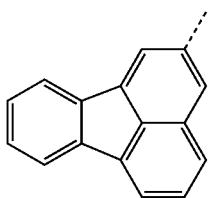 | — |
| Iaaa-991 | O | 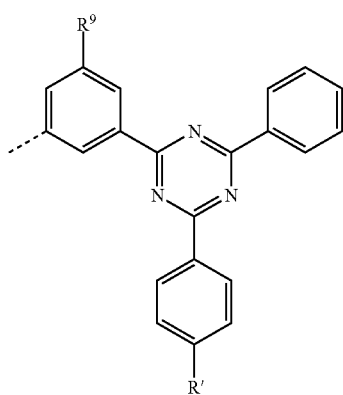 | 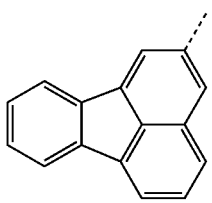 | 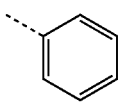 |

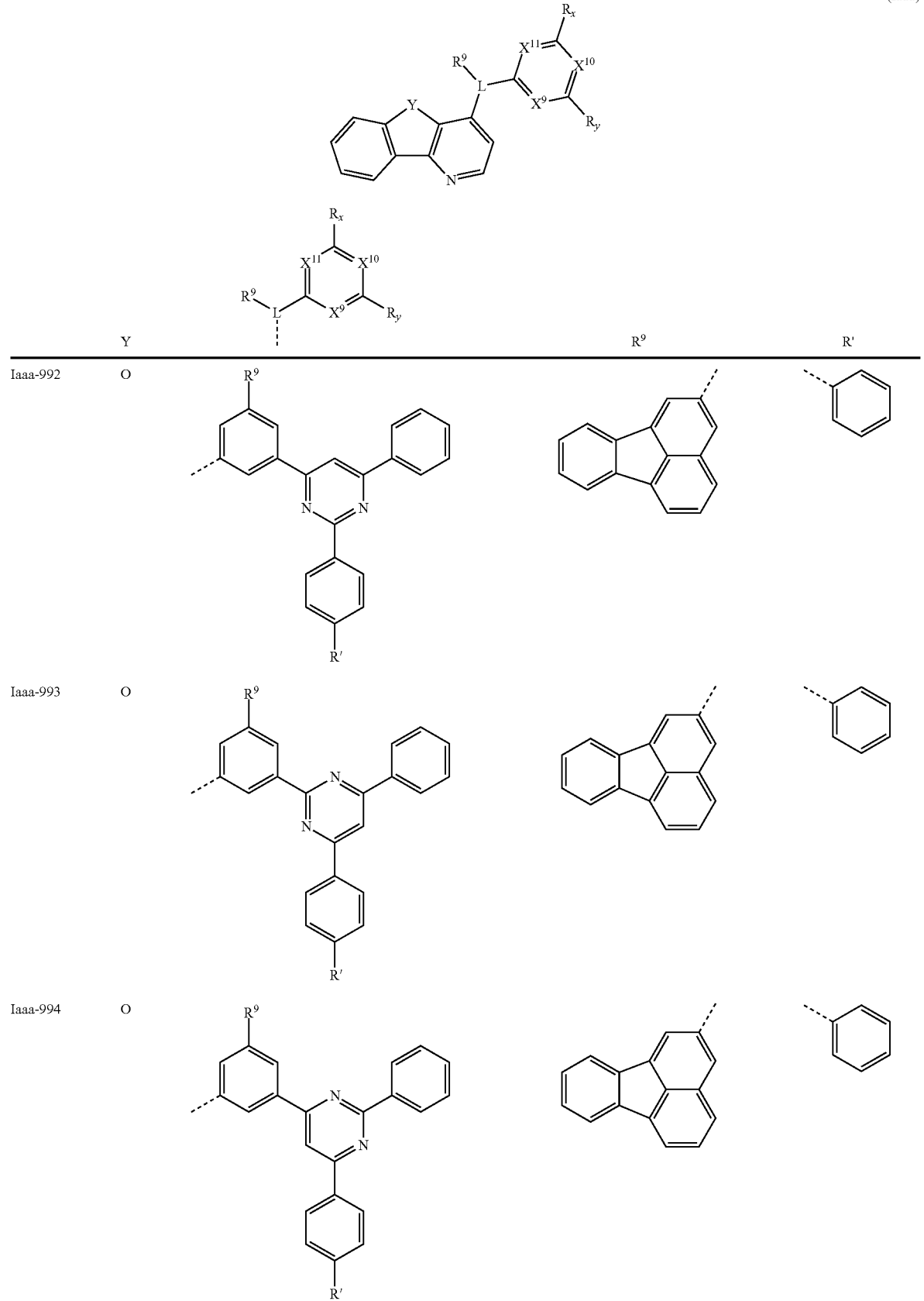

-continued
(Iaaa)
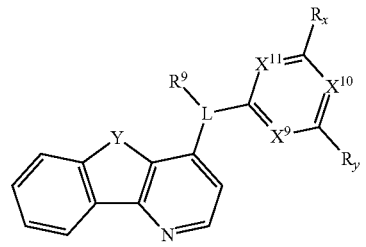
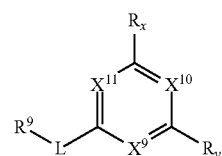
| | Y | | R⁹ | R' |
|---|---|---|---|---|
| Iaaa-995 | O | 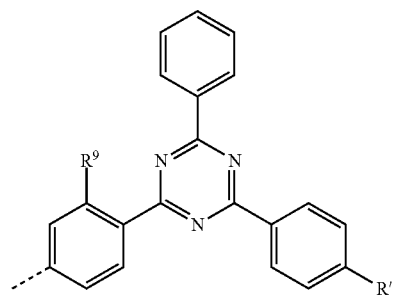 | 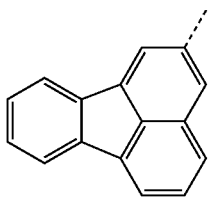 | 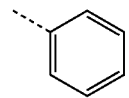 |
| Iaaa-996 | O | 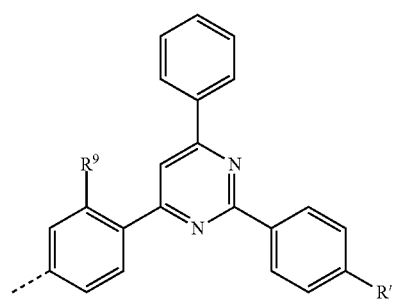 | 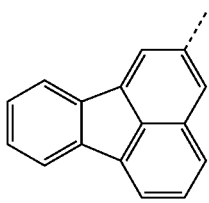 | 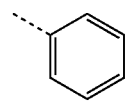 |
| Iaaa-997 | O | 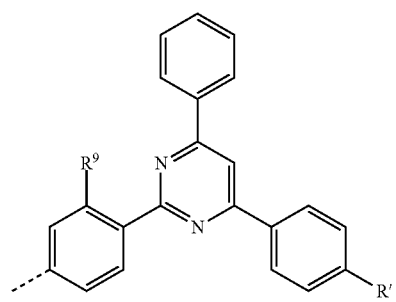 | 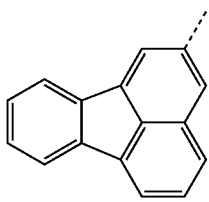 | 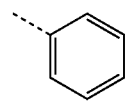 |

-continued
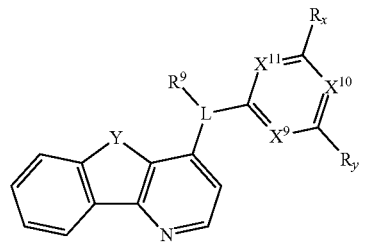
(Iaaa)
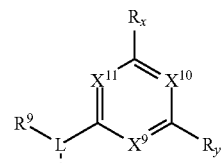
| | Y | R⁹ | R' |
|---|---|---|---|
| Iaaa-998 | O | 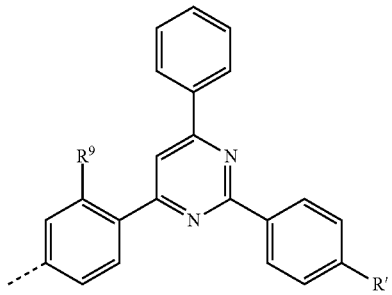 | 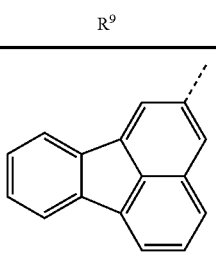 |  |
| Iaaa-999 | O | 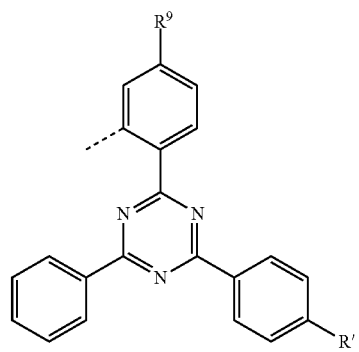 | 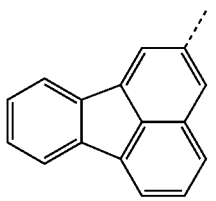 | 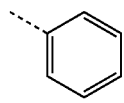 |
| Iaaa-1000 | O | 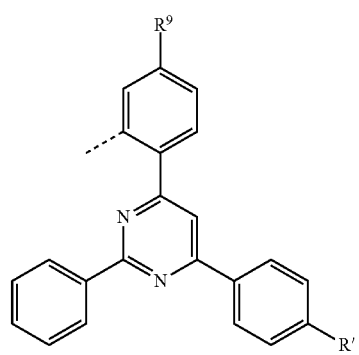 | 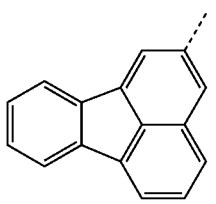 | 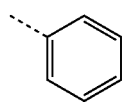 |

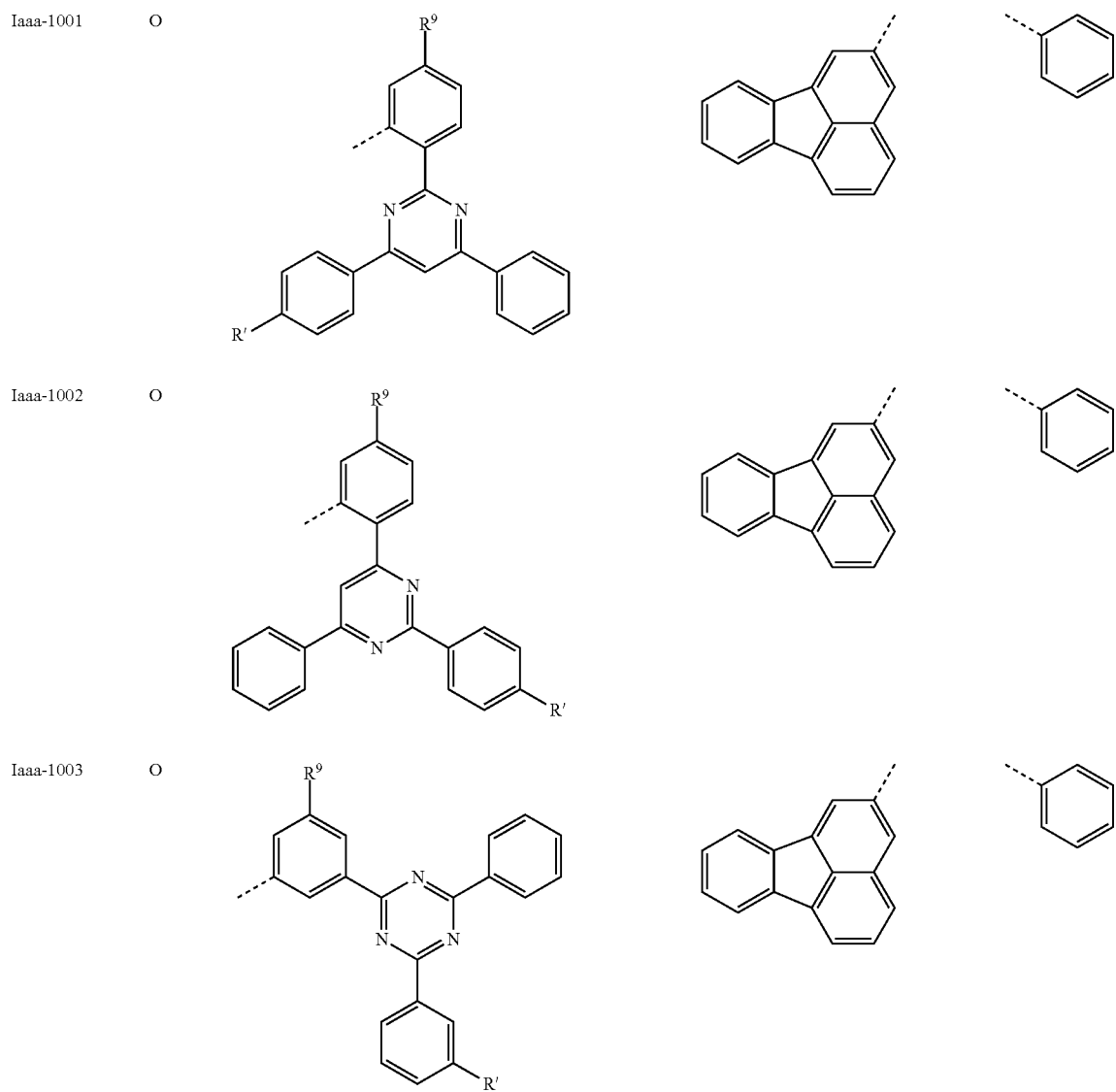

-continued
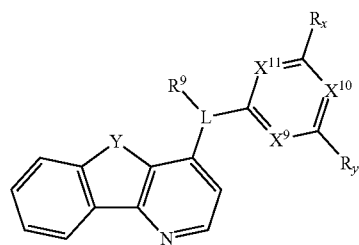
(Iaaa)
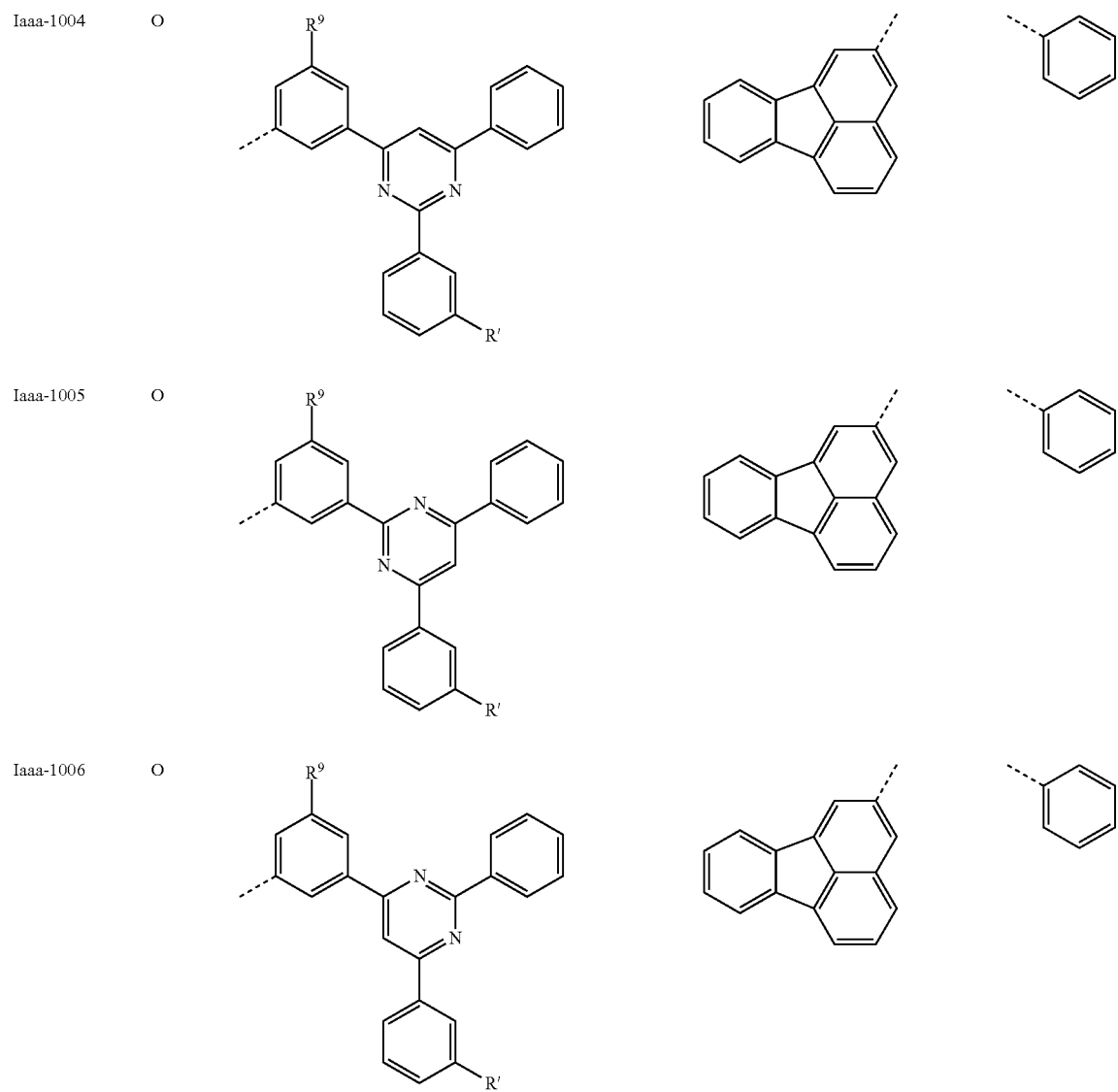

-continued
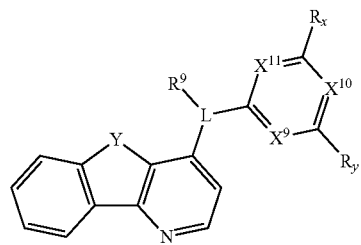
(Iaaa)
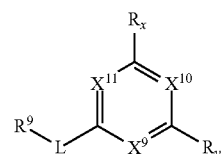
| | Y | R⁹ | R' |
|---|---|---|---|
| Iaaa-1007 | O | 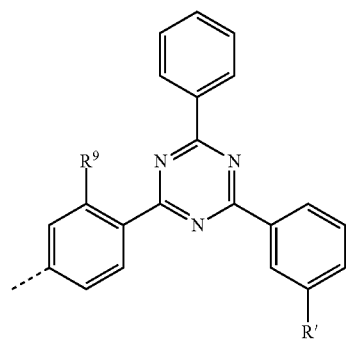 | 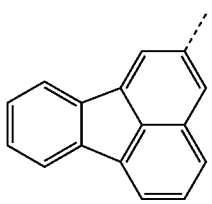 | 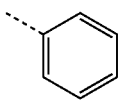 |
| Iaaa-1008 | O | 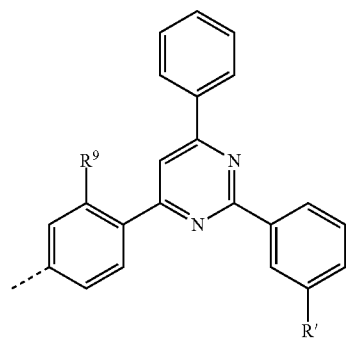 | 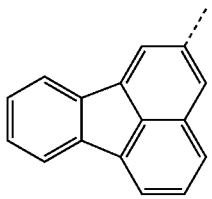 | 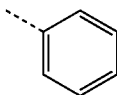 |
| Iaaa-1009 | O | 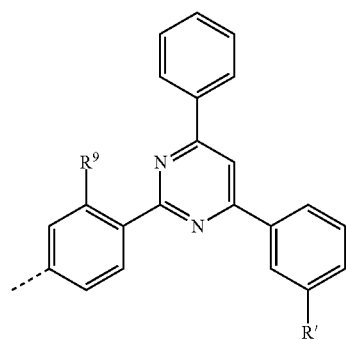 | 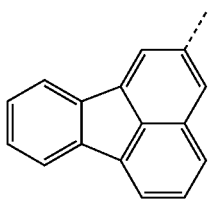 | 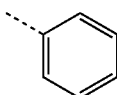 |

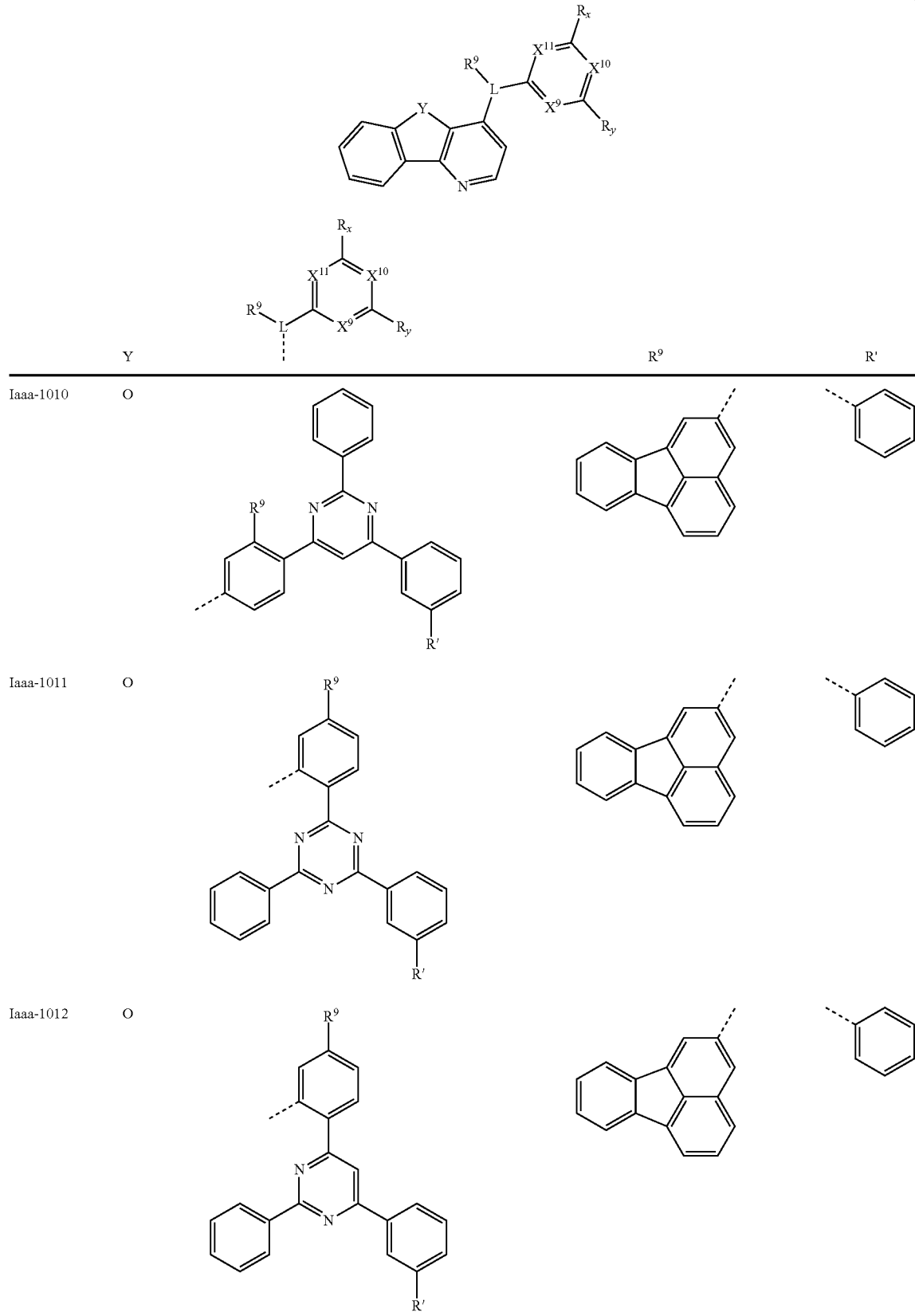

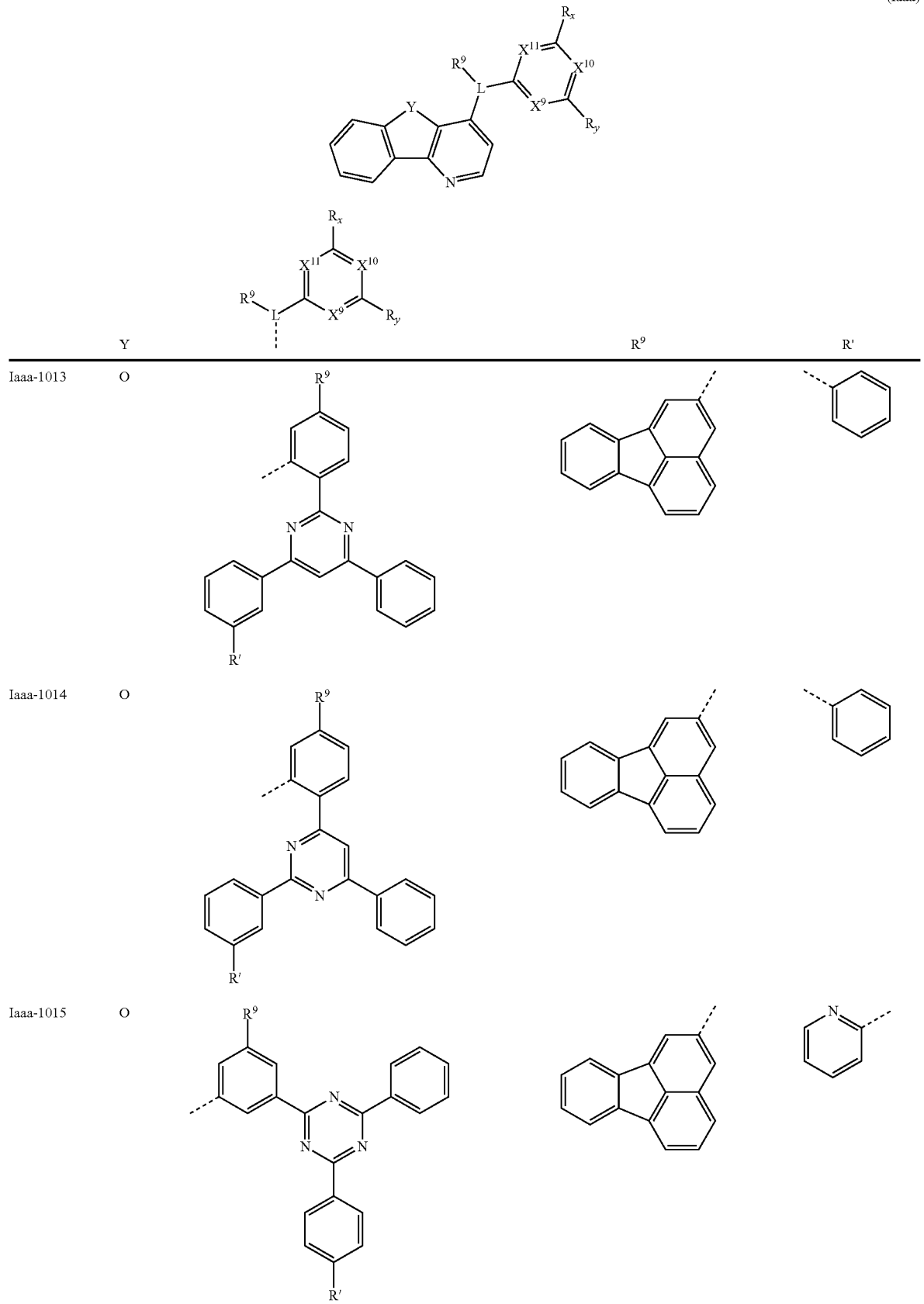

-continued
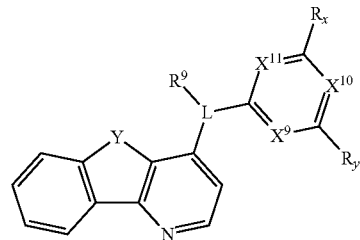
(Iaaa)
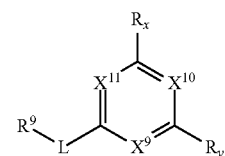
| | Y | | R⁹ | R' |
|---|---|---|---|---|
| Iaaa-1016 | O | 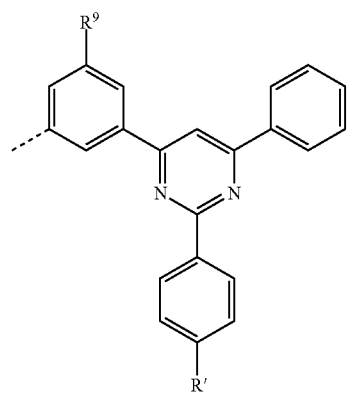 | 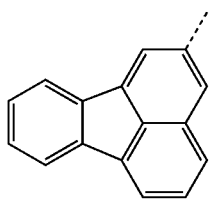 | 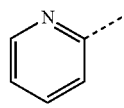 |
| Iaaa-1017 | O | 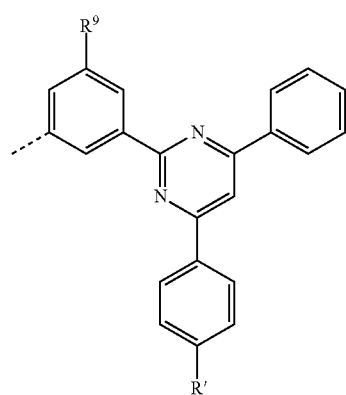 | 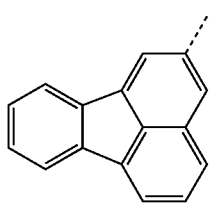 | 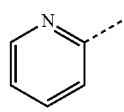 |

-continued
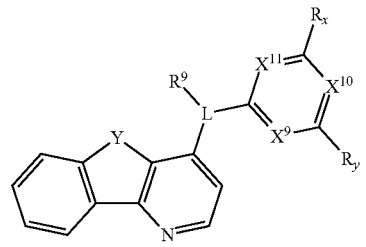
(Iaaa)
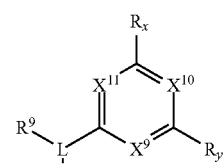
| | Y | | $R^9$ | $R'$ |
|---|---|---|---|---|
| Iaaa-1018 | O | 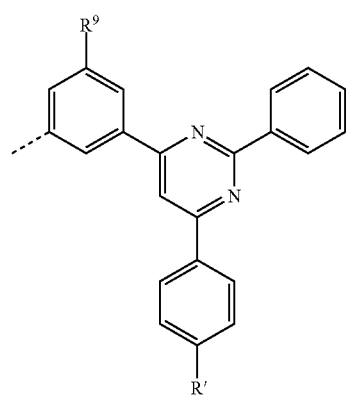 | 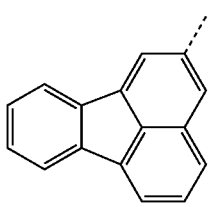 | 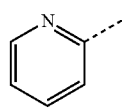 |
| Iaaa-1019 | O | 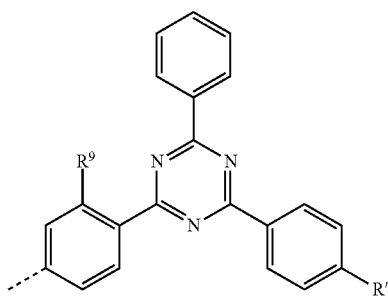 | 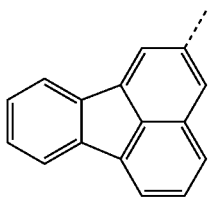 | 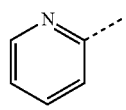 |
| Iaaa-1020 | O | 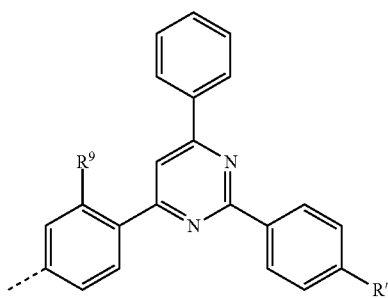 | 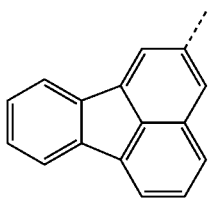 | 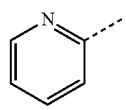 |

-continued
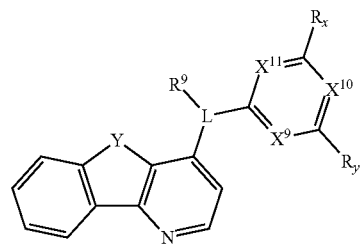
(Iaaa)
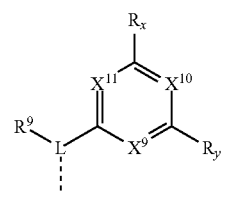
| | Y | R⁹ | R' |
|---|---|---|---|
| Iaaa-1021 | O | 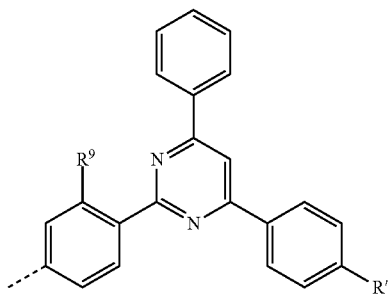 | 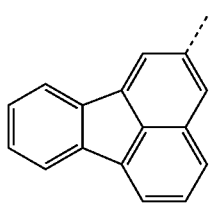 | 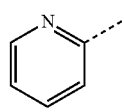 |
| Iaaa-1022 | O | 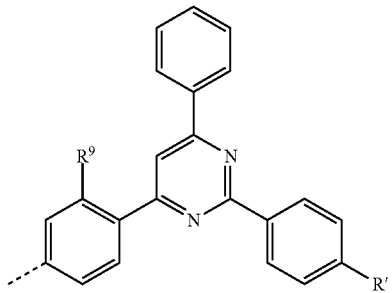 | 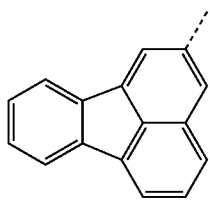 | 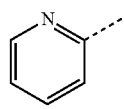 |
| Iaaa-1023 | O | 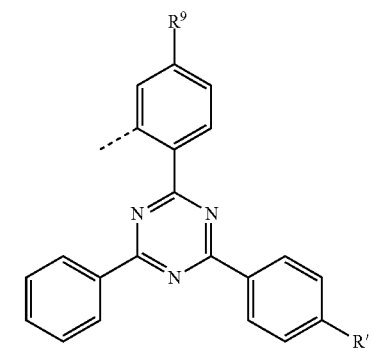 | 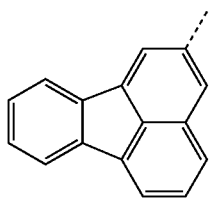 | 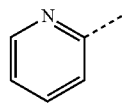 |

-continued
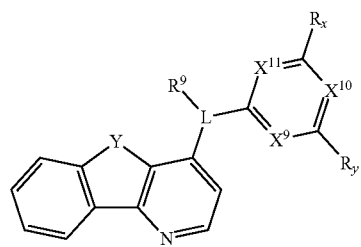
(Iaaa)
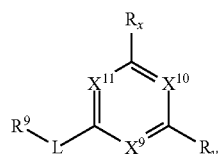
| | Y | R⁹ | R' |
|---|---|---|---|
| Iaaa-1024 | O | 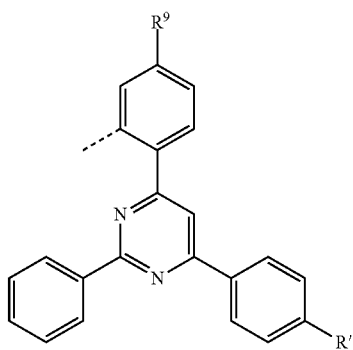 | 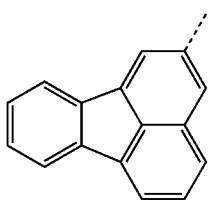 | 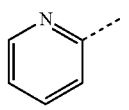 |
| Iaaa-1025 | O | 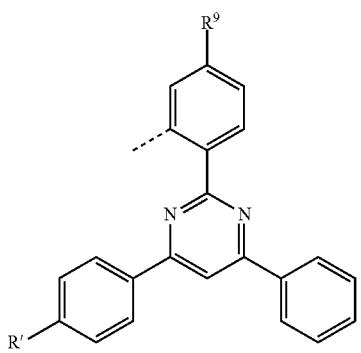 | 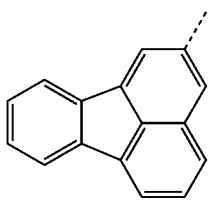 | 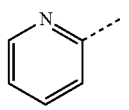 |
| Iaaa-1026 | O | 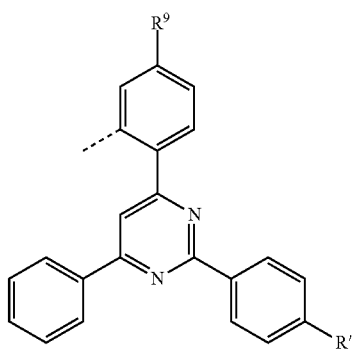 | 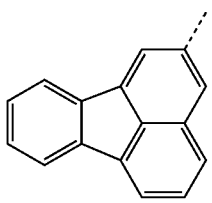 | 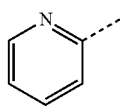 |

-continued
(Iaaa)
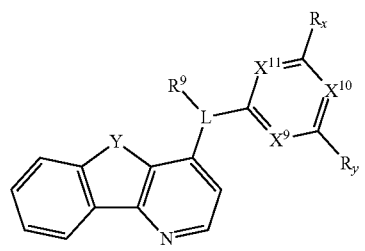
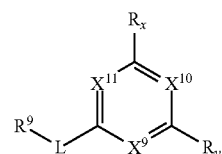
| | Y | R9 | R' |
|---|---|---|---|
| Iaaa-1027 | O | 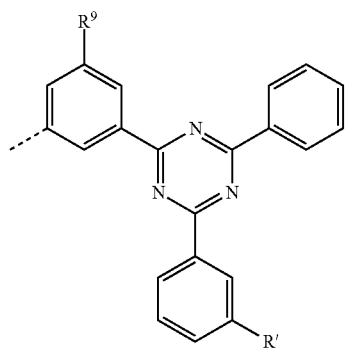 | 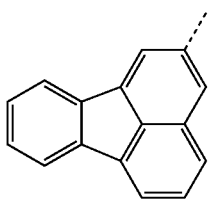 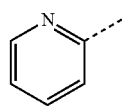 |
| Iaaa-1028 | O | 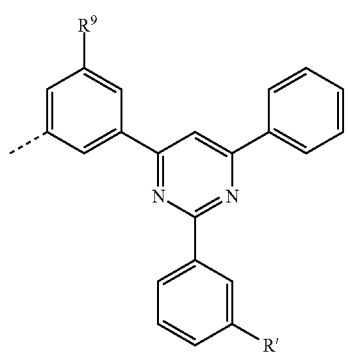 | 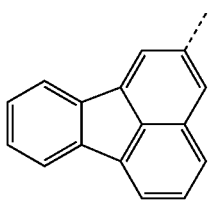 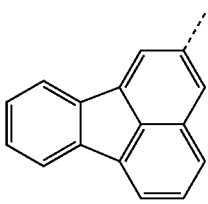 |
| Iaaa-1029 | O | 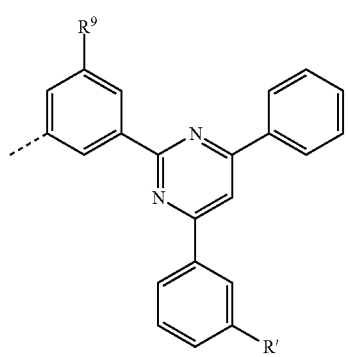 | 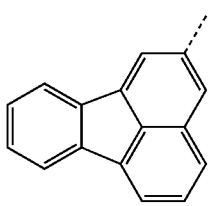 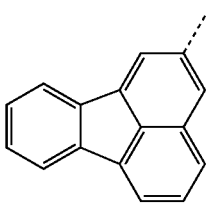 |

-continued
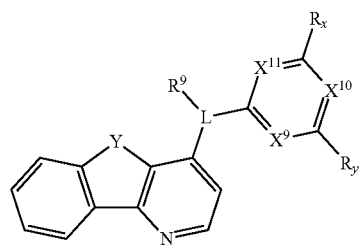
(Iaaa)
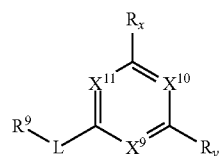
| | Y | R⁹ | | R' |
|---|---|---|---|---|
| Iaaa-1030 | O | 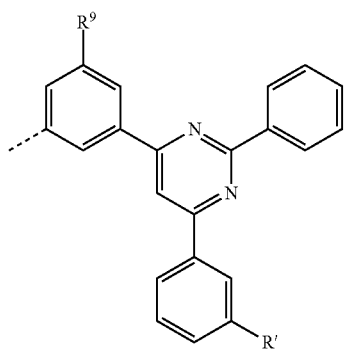 | 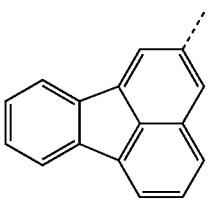 | 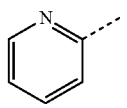 |
| Iaaa-1031 | O | 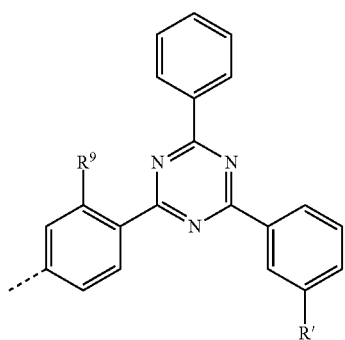 | 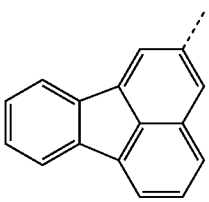 | 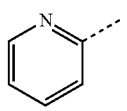 |
| Iaaa-1032 | O | 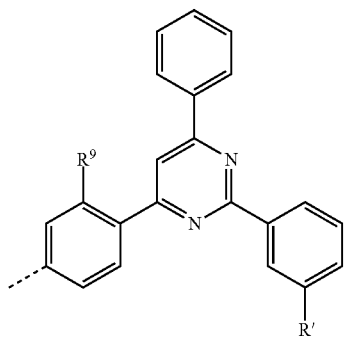 | 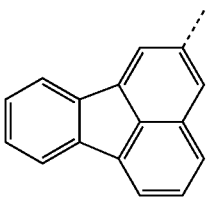 | 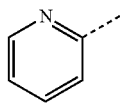 |

-continued
(Iaaa)
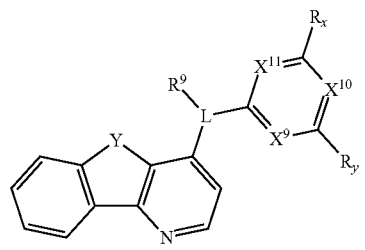
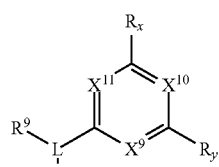
| | Y | | R⁹ | R' |
|---|---|---|---|---|
| Iaaa-1033 | O | 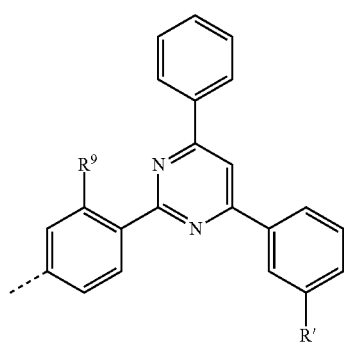 | 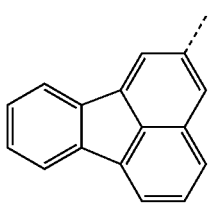 | 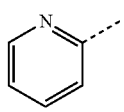 |
| Iaaa-1034 | O | 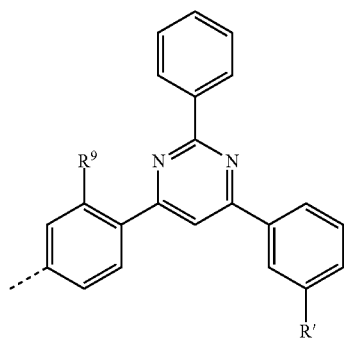 | 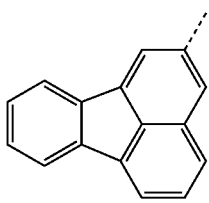 | 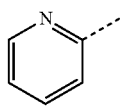 |
| Iaaa-1035 | O | 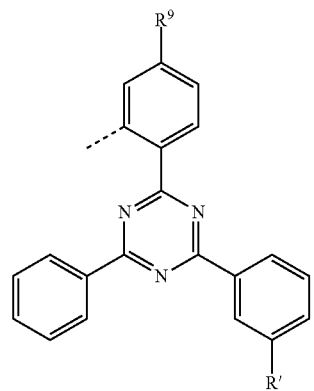 | 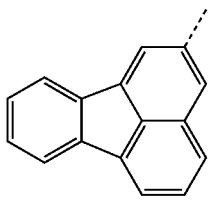 | 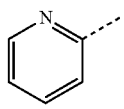 |

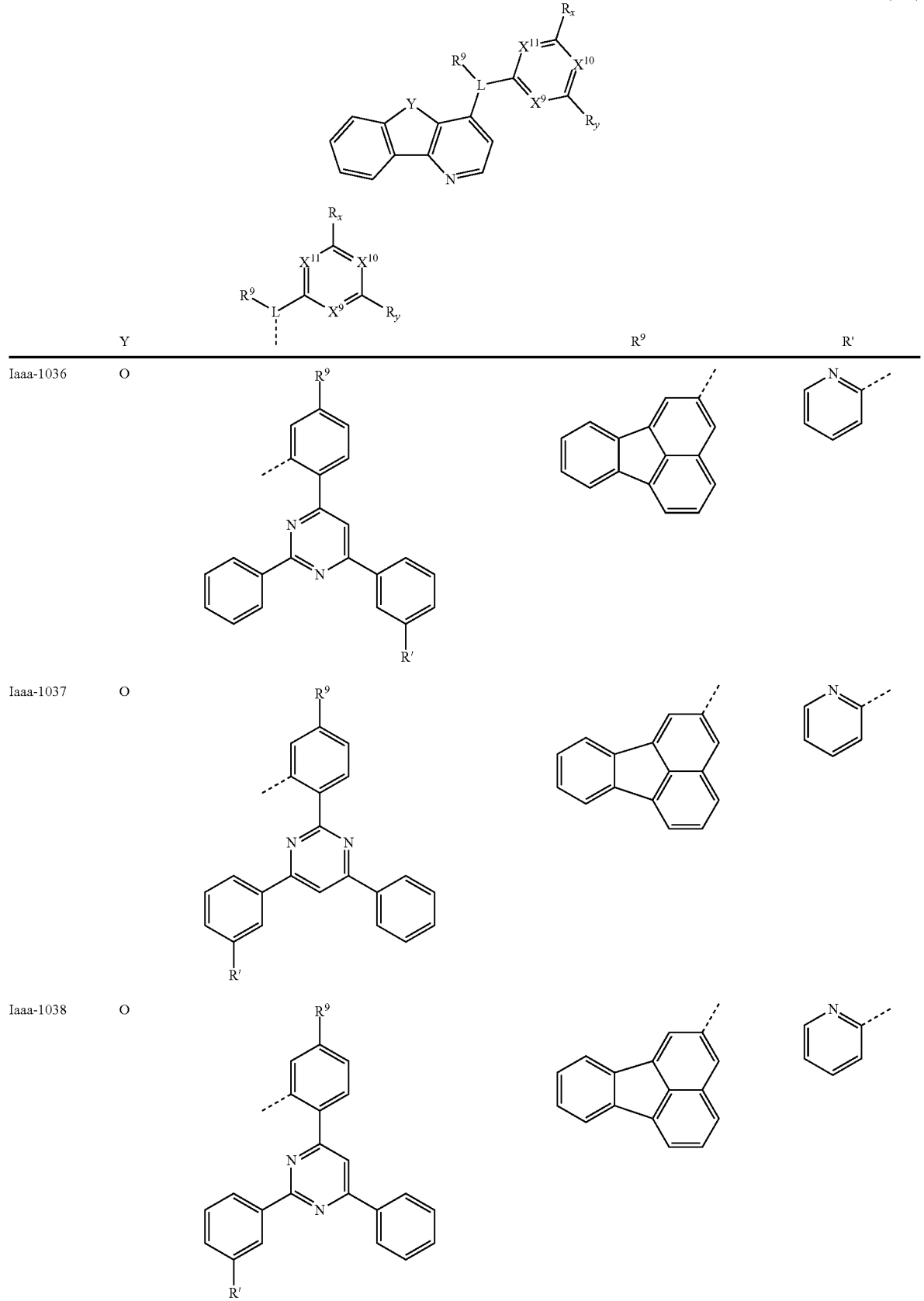

-continued
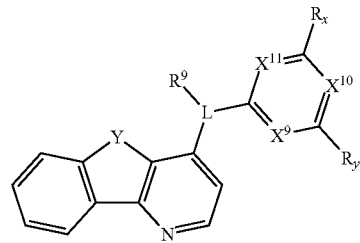
(Iaaa)
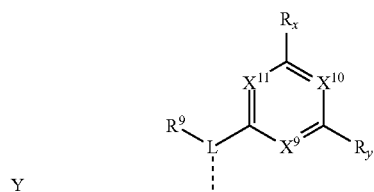
| | Y | R⁹ | R' |
|---|---|---|---|
| Iaaa-1039 | O | 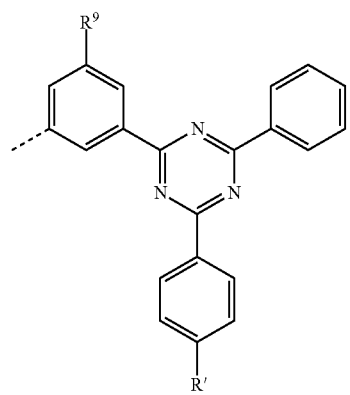 | 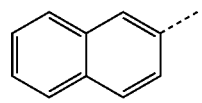 | H |
| Iaaa-1040 | O | 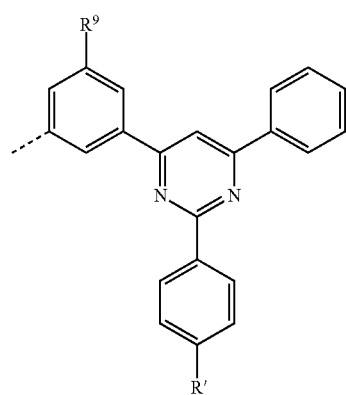 | 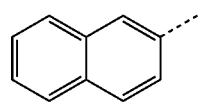 | H |

-continued
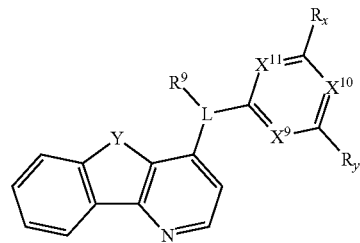
(Iaaa)
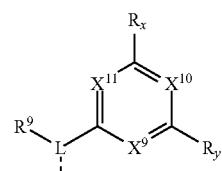
| | Y | | R⁹ | R' |
|---|---|---|---|---|
| Iaaa-1041 | O | 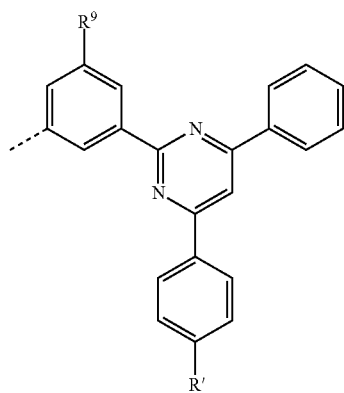 | 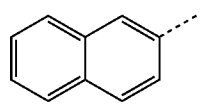 | H |
| Iaaa-1042 | O | 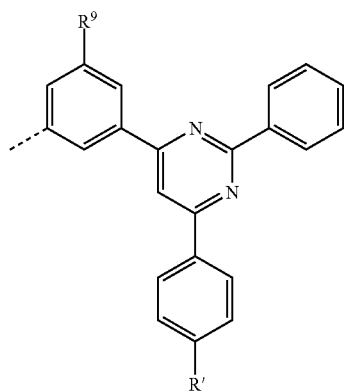 | 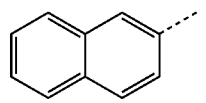 | H |
| Iaaa-1043 | O | 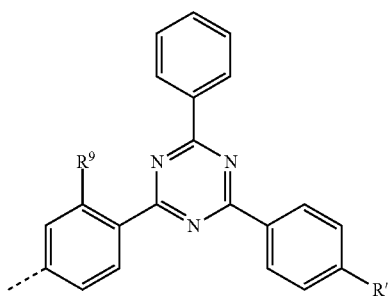 | 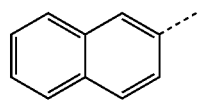 | H |

-continued
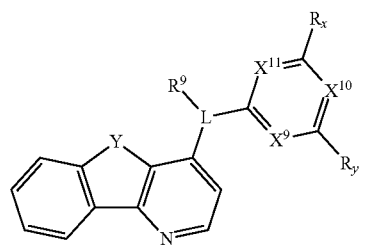
(Iaaa)
| | Y | R⁹ | R' |
|---|---|---|---|
| Iaaa-1044 | O |  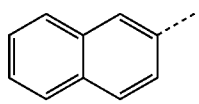 | H |
| Iaaa-1045 | O | 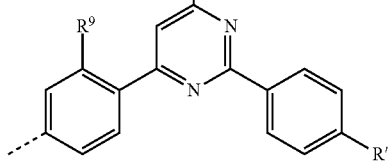  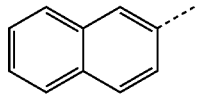 | H |
| Iaaa-1046 | O | 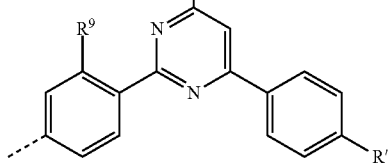 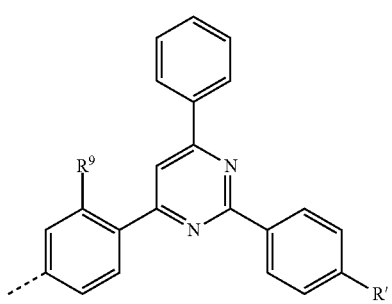 | H |

-continued
(Iaaa)
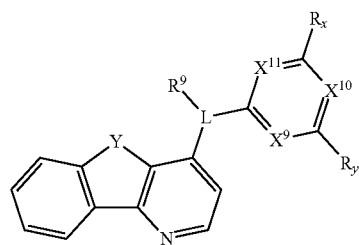
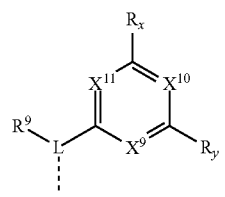
| | Y | | R⁹ | R' |
|---|---|---|---|---|
| Iaaa-1047 | O | 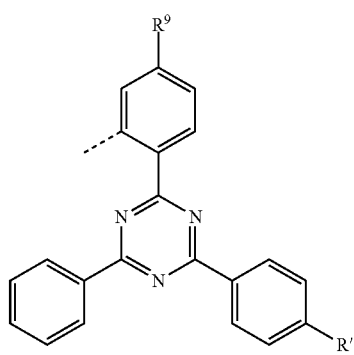 | 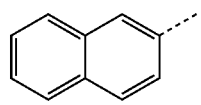 | H |
| Iaaa-1048 | O | 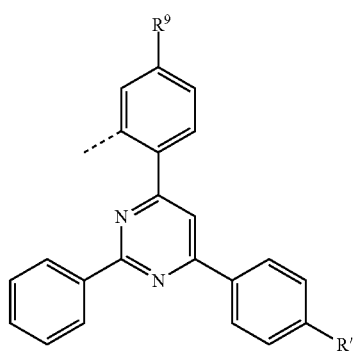 | 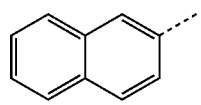 | H |
| Iaaa-1049 | O | 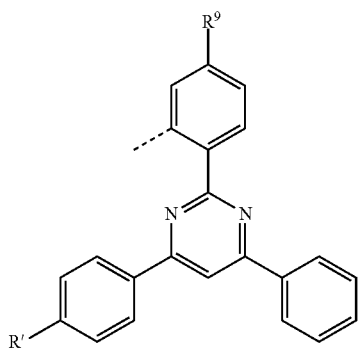 | 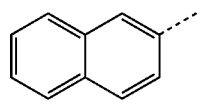 | H |

-continued
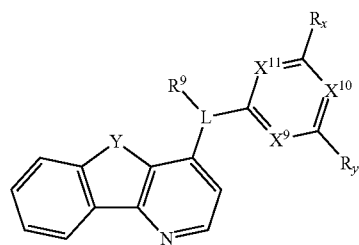
(Iaaa)
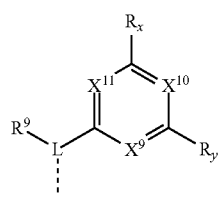
| | Y | | R⁹ | R' |
|---|---|---|---|---|
| Iaaa-1050 | O | 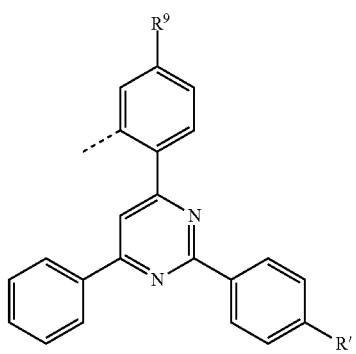 | 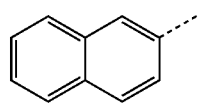 | H |
| Iaaa-1051 | O | 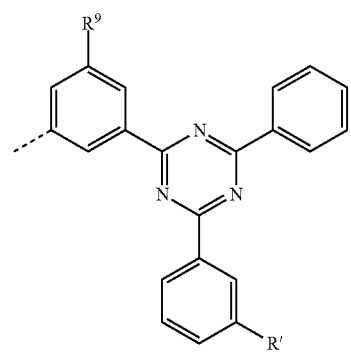 | 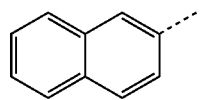 | H |
| Iaaa-1052 | O | 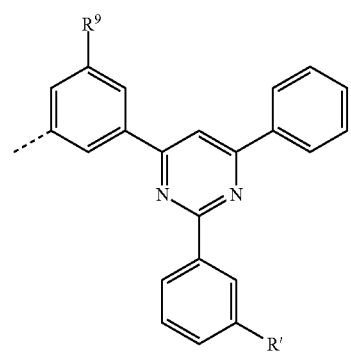 | 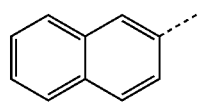 | H |

(Iaaa)
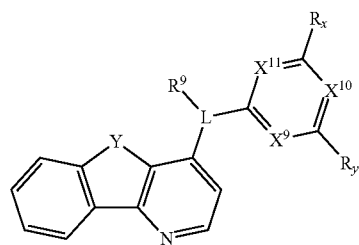
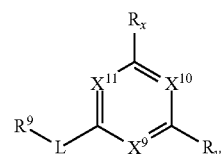
| | Y | | R⁹ | R' |
|---|---|---|---|---|
| Iaaa-1053 | O | 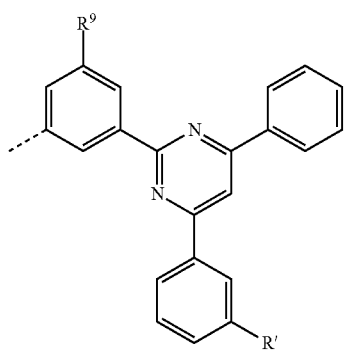 | 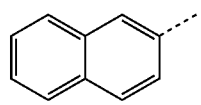 | H |
| Iaaa-1054 | O | 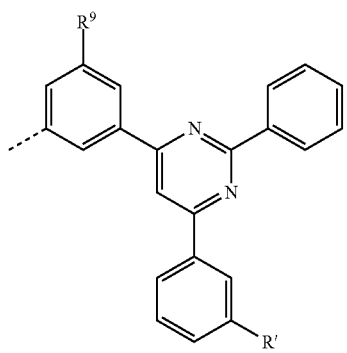 | 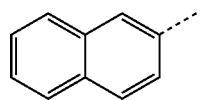 | H |
| Iaaa-1055 | O | 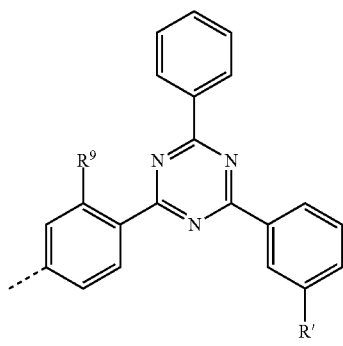 | 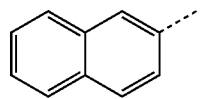 | H |

-continued
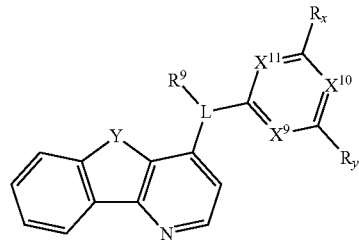
(Iaaa)
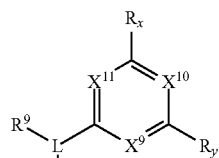
| | Y | | R⁹ | R' |
|---|---|---|---|---|
| Iaaa-1056 | O | 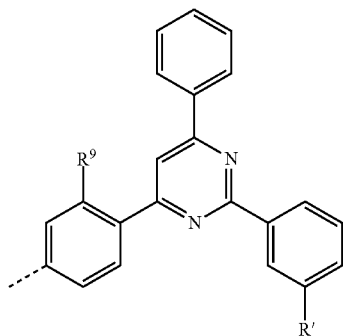 | 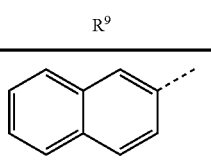 | H |
| Iaaa-1057 | O | 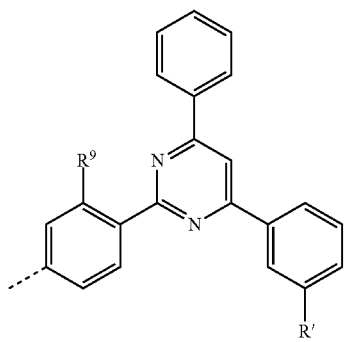 | 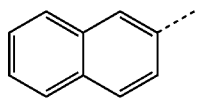 | H |
| Iaaa-1058 | O | 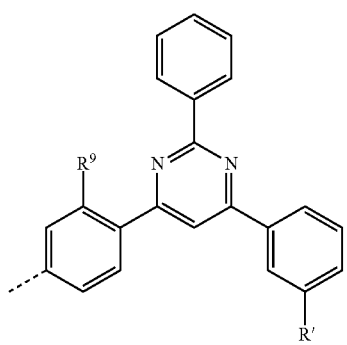 | 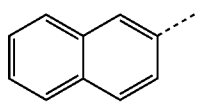 | H |

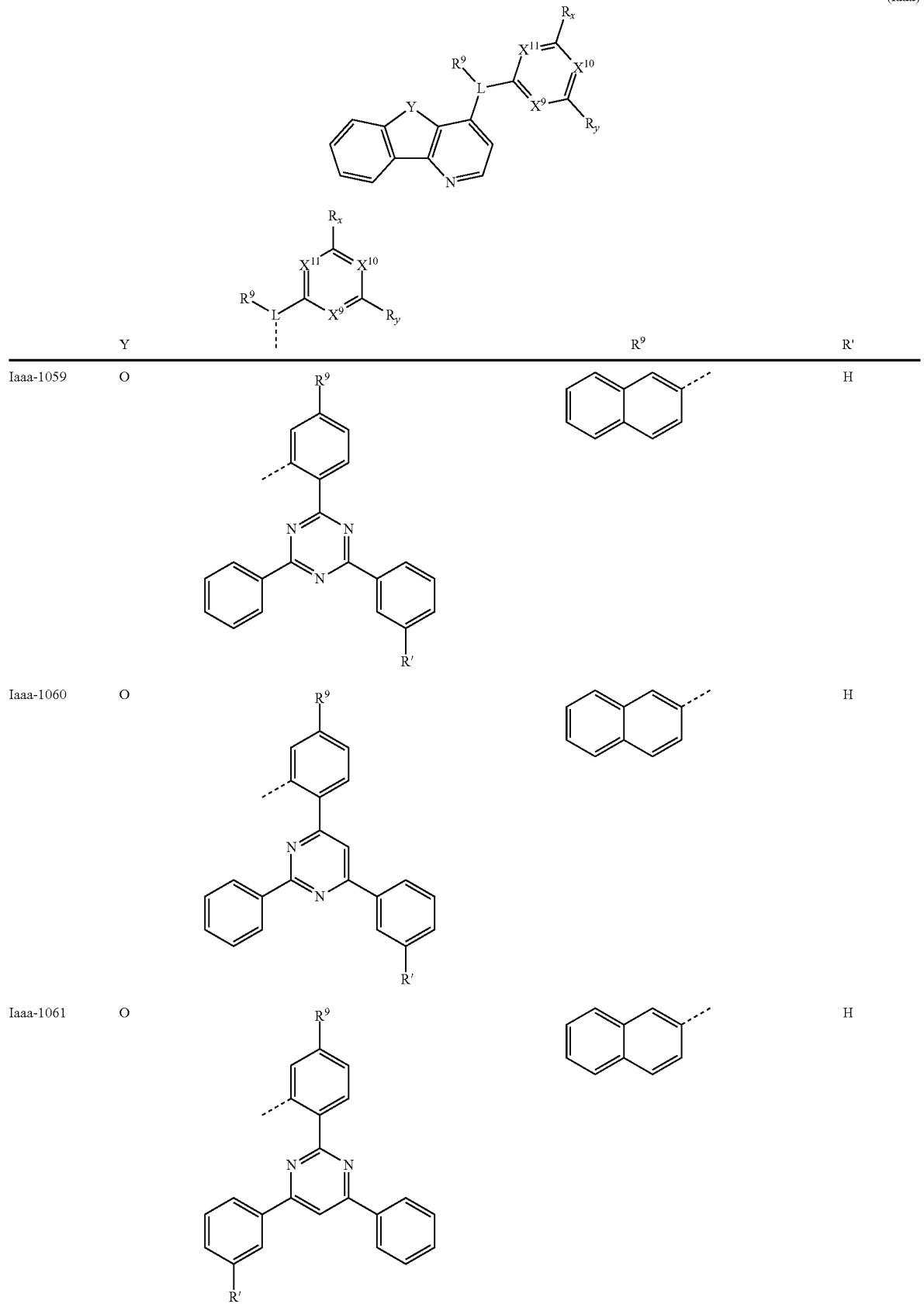

-continued
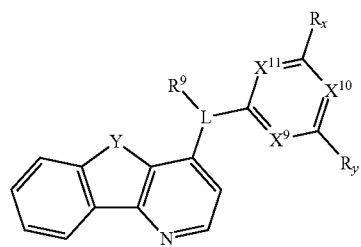
(Iaaa)
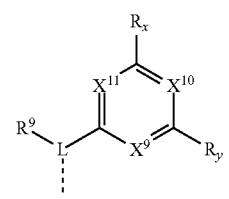
| | Y | | R⁹ | R' |
|---|---|---|---|---|
| Iaaa-1062 | O | 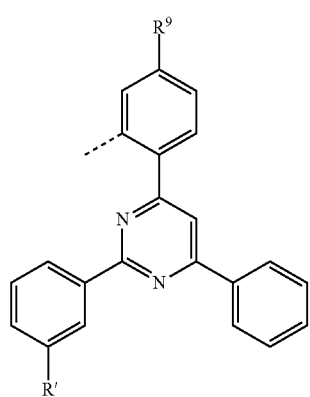 | 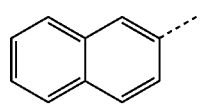 | H |
| Iaaa-1063 | O | 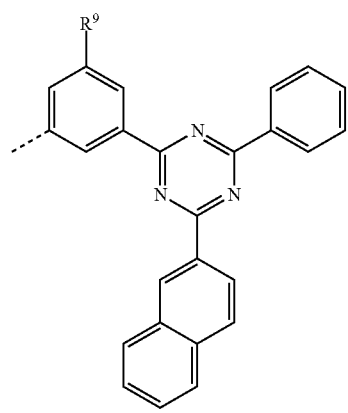 | 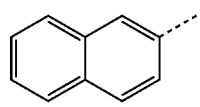 | — |

-continued
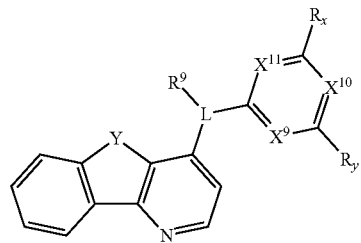
(Iaaa)
| | Y | 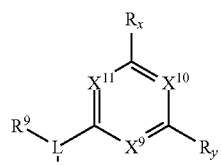 | R⁹ | R' |
|---|---|---|---|---|
| Iaaa-1064 | O | 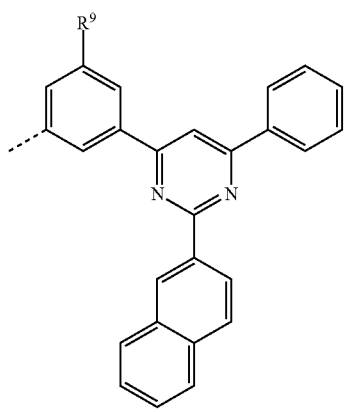 | 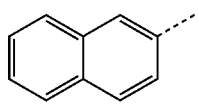 | — |
| Iaaa-1065 | O | 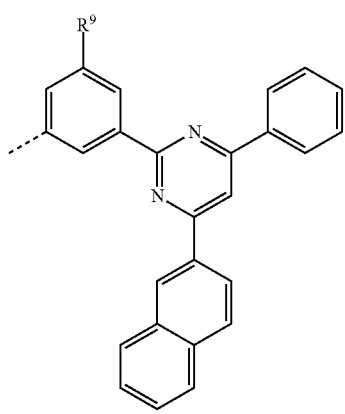 | 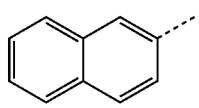 | — |

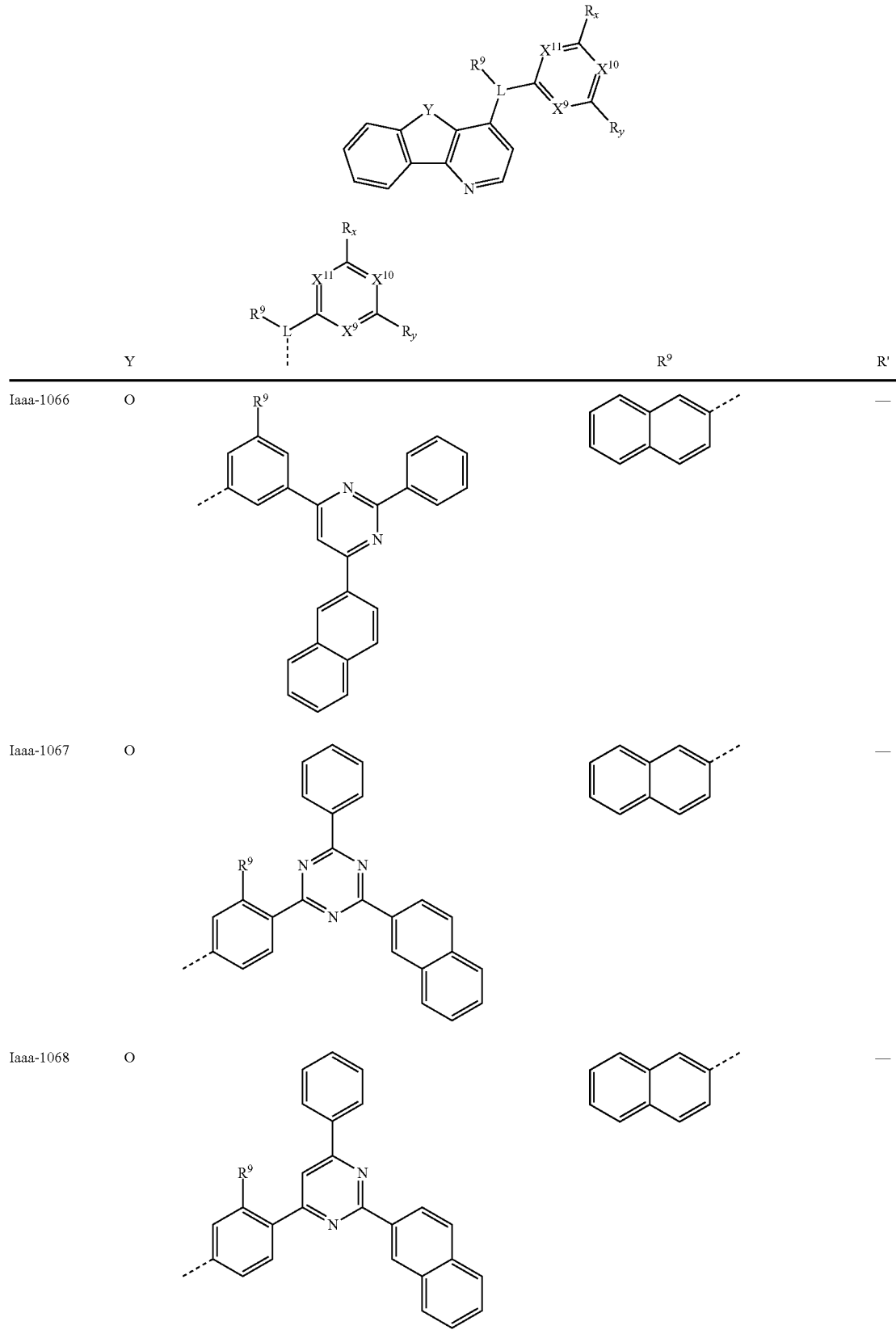

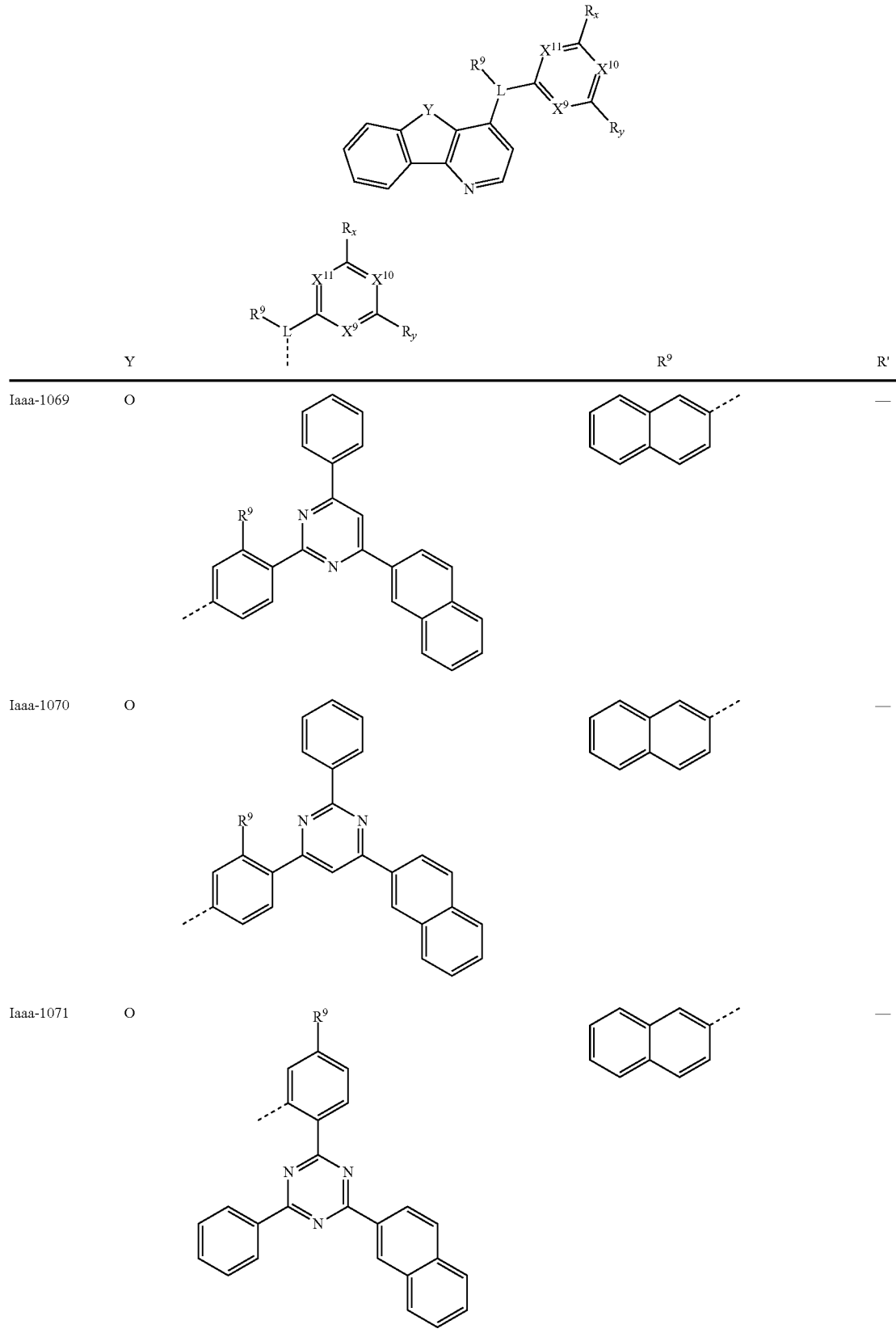

-continued
(Iaaa)
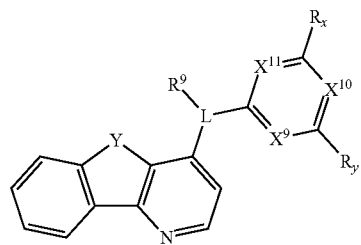
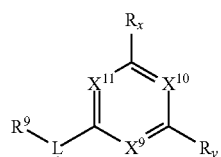
| | Y | | $R^9$ | R' |
|---|---|---|---|---|
| Iaaa-1072 | O | 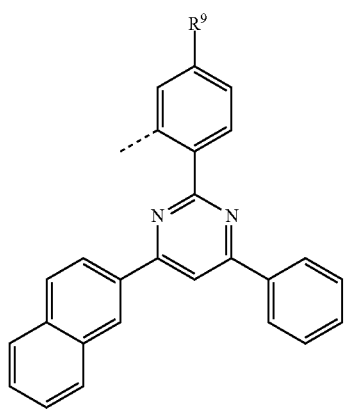 | 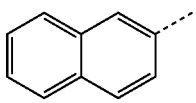 | — |
| Iaaa-1073 | O | 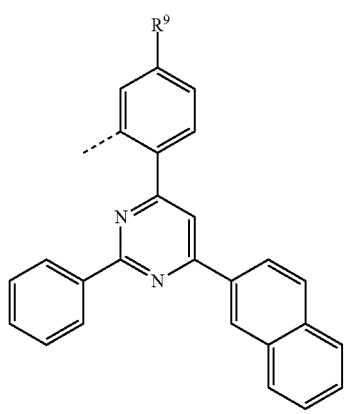 | 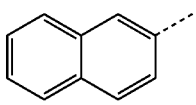 | — |

-continued
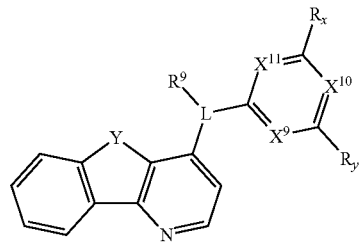
(Iaaa)
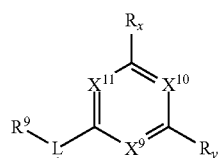
| | Y | R⁹ | R' |
|---|---|---|---|
| Iaaa-1074 | O | 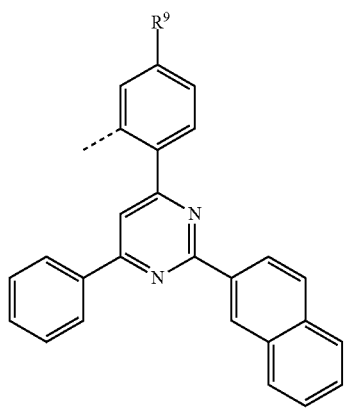 | 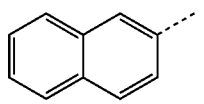 | — |
| Iaaa-1075 | O | 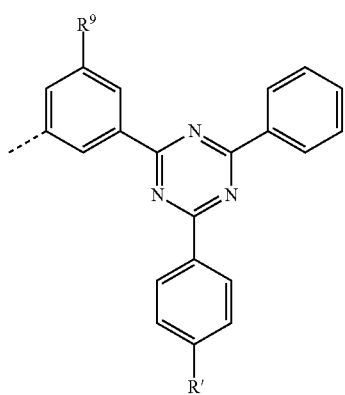 | 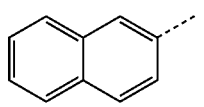 | 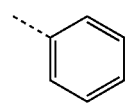 |

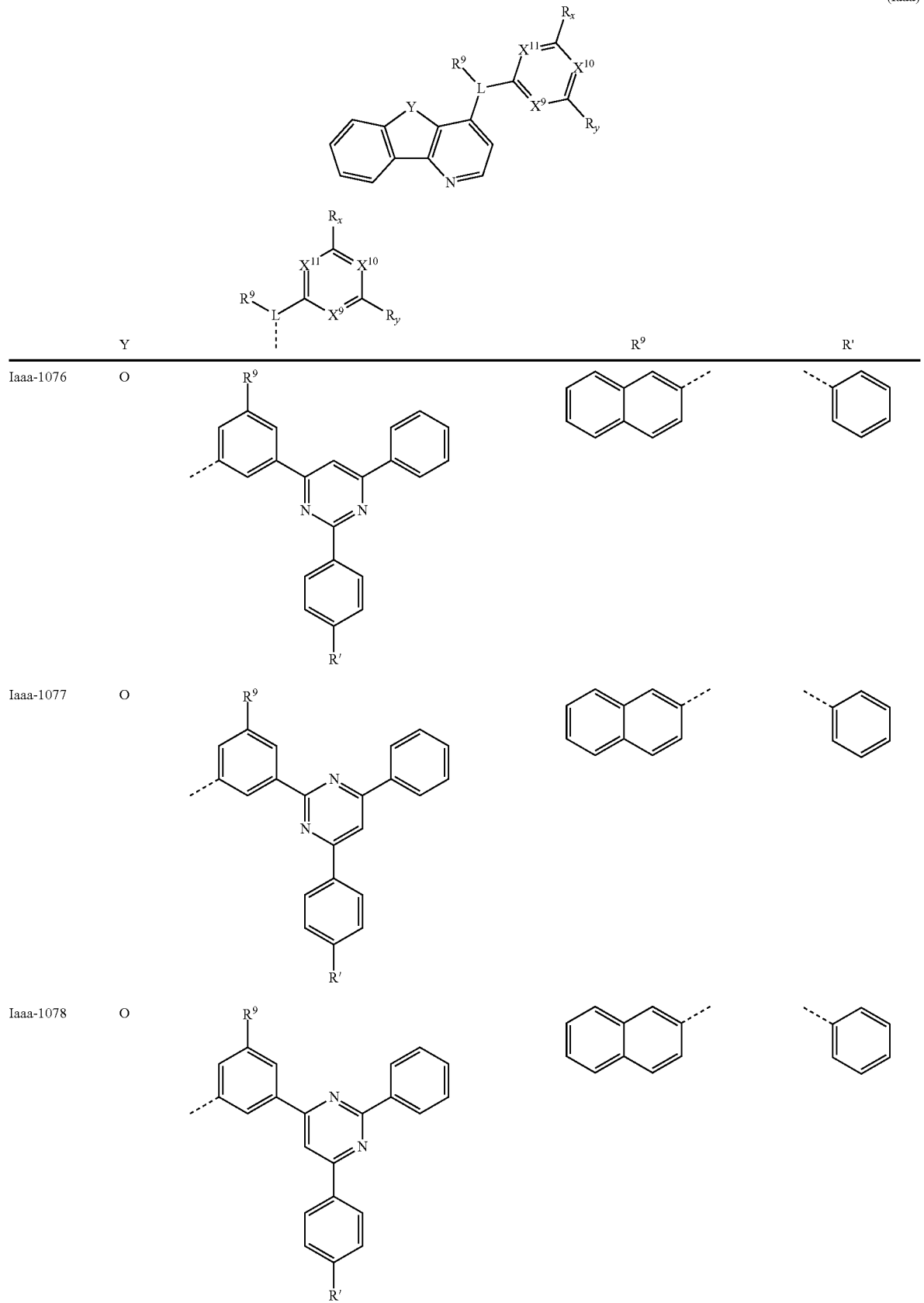

-continued
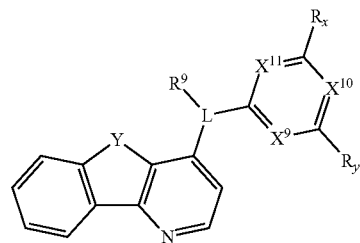
(Iaaa)
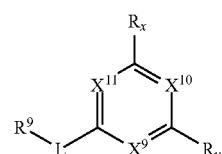
| | Y | | R⁹ | R' |
|---|---|---|---|---|
| Iaaa-1079 | O | 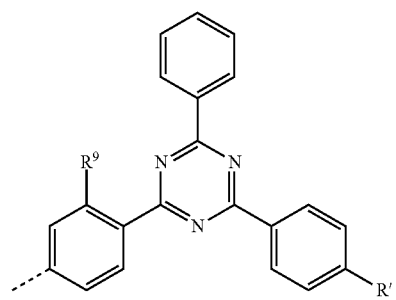 | 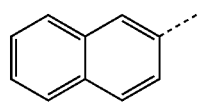 | 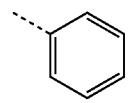 |
| Iaaa-1080 | O | 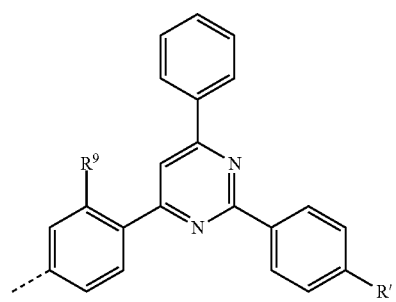 | 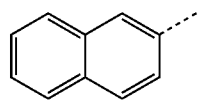 | 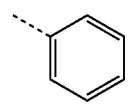 |
| Iaaa-1081 | O | 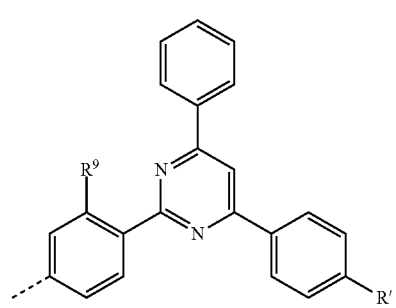 | 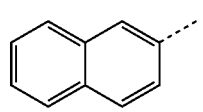 | 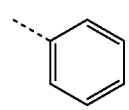 |

-continued
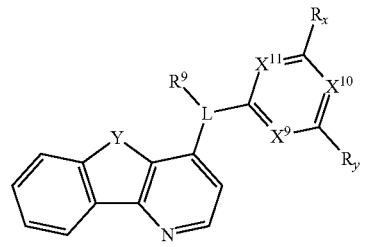
(Iaaa)
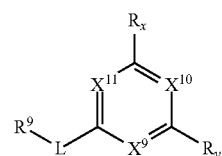
| | Y | R⁹ | R' |
|---|---|---|---|
| Iaaa-1082 | O | 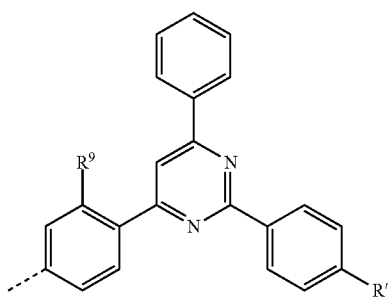 | 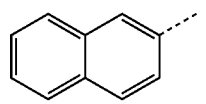 | 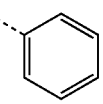 |
| Iaaa-1083 | O | 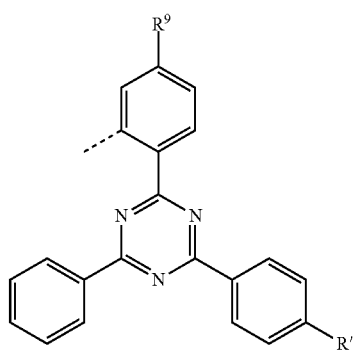 | 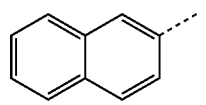 |  |
| Iaaa-1084 | O | 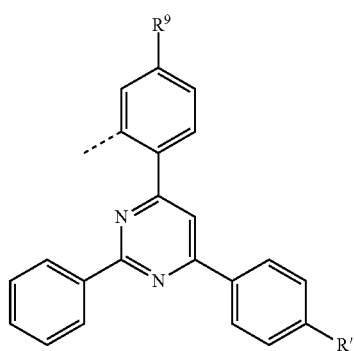 | 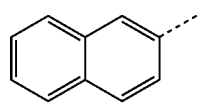 |  |

-continued
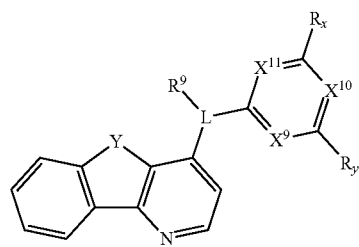
(Iaaa)
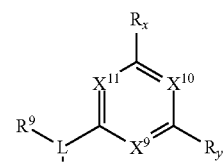
| | Y | | R⁹ | R' |
|---|---|---|---|---|
| Iaaa-1085 | O | 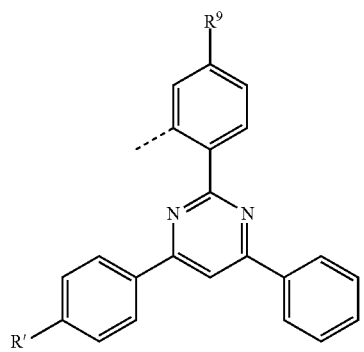 | 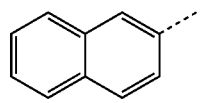 | 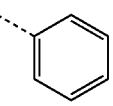 |
| Iaaa-1086 | O | 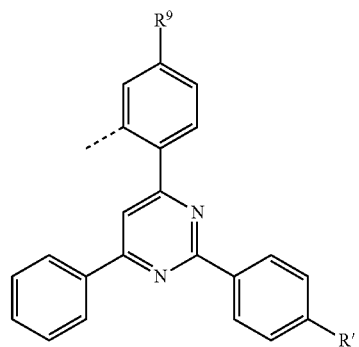 | 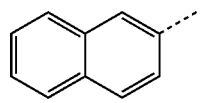 | 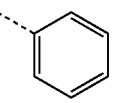 |
| Iaaa-1087 | O | 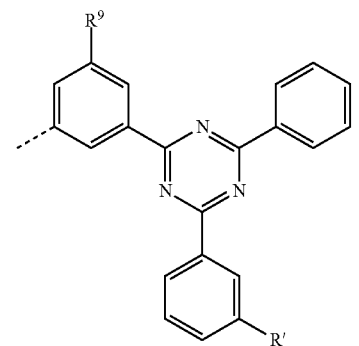 | 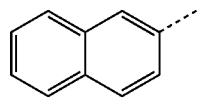 | 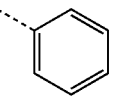 |

-continued
(Iaaa)
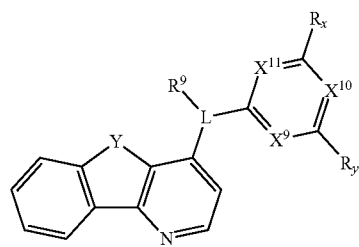
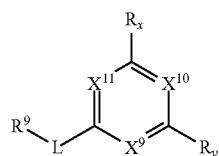
| | Y | R⁹ | R' |
|---|---|---|---|
| Iaaa-1088 | O | 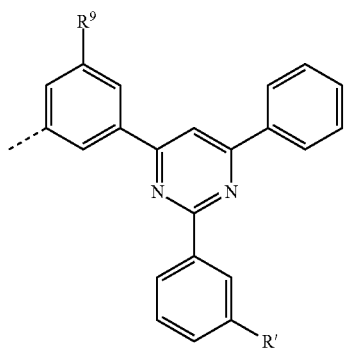 | 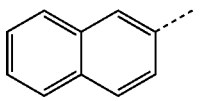 | 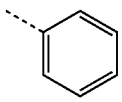 |
| Iaaa-1089 | O | 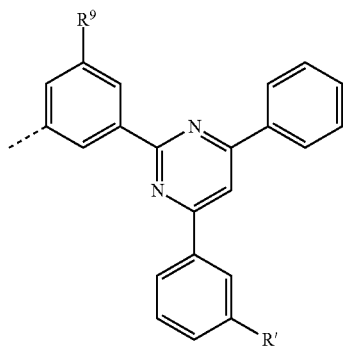 | 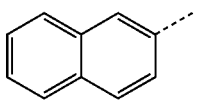 | 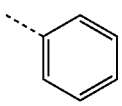 |
| Iaaa-1090 | O | 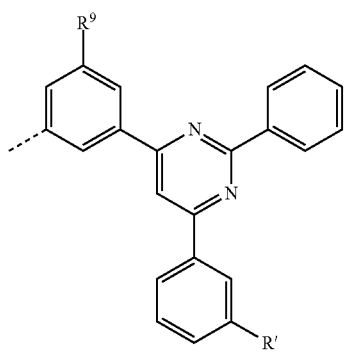 | 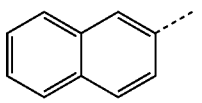 | 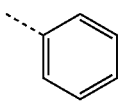 |

-continued
(Iaaa)
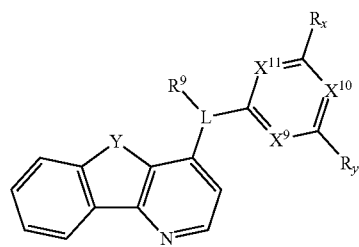
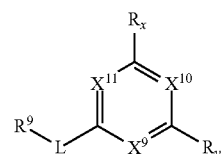
| | Y | | R⁹ | R' |
|---|---|---|---|---|
| Iaaa-1091 | O | 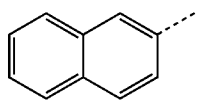 | 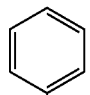 | 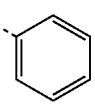 |
| Iaaa-1092 | O | 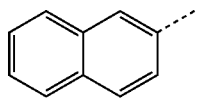 | 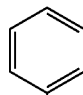 |  |
| Iaaa-1093 | O | 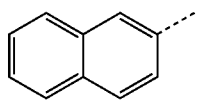 |  |  |

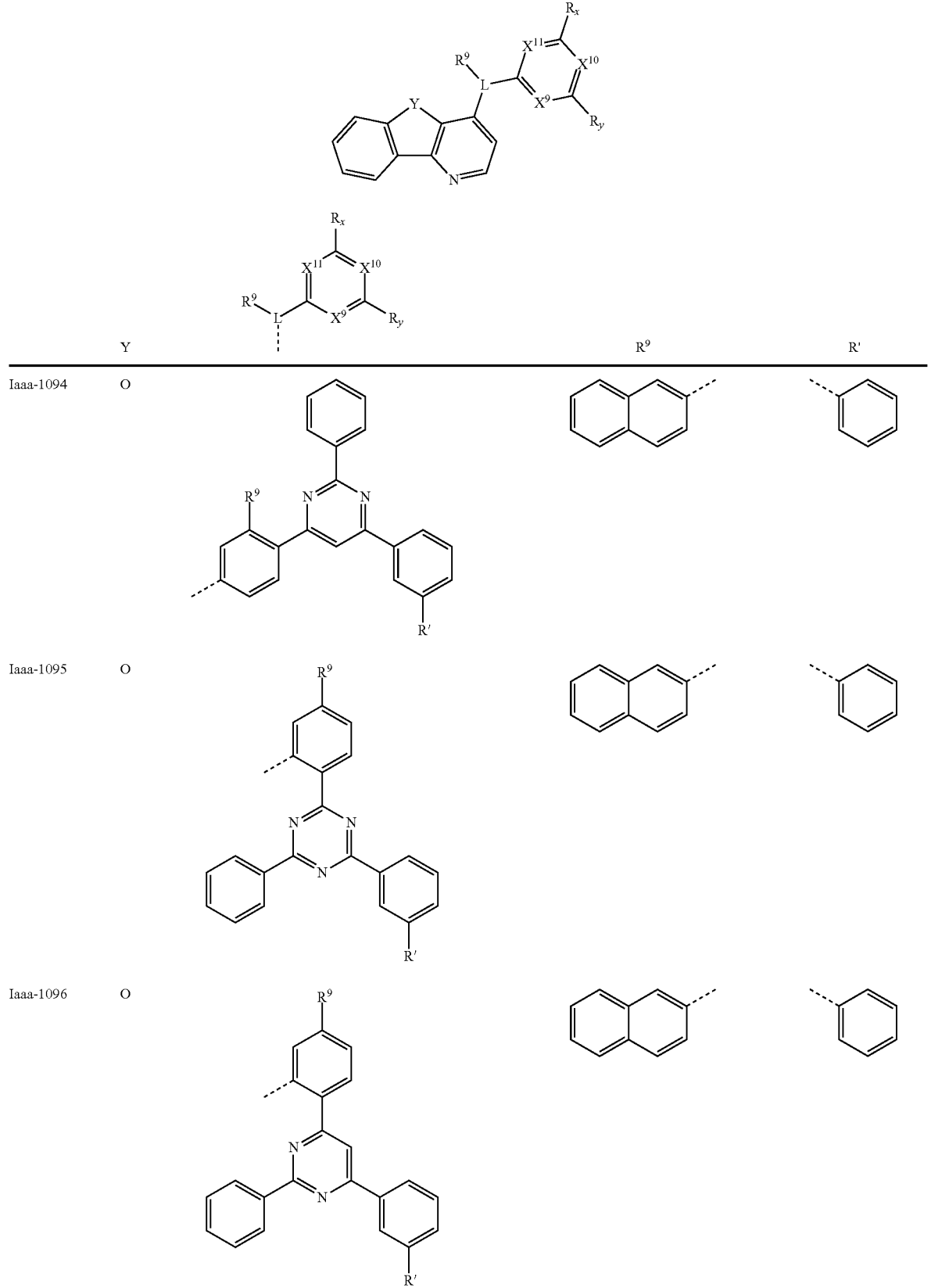

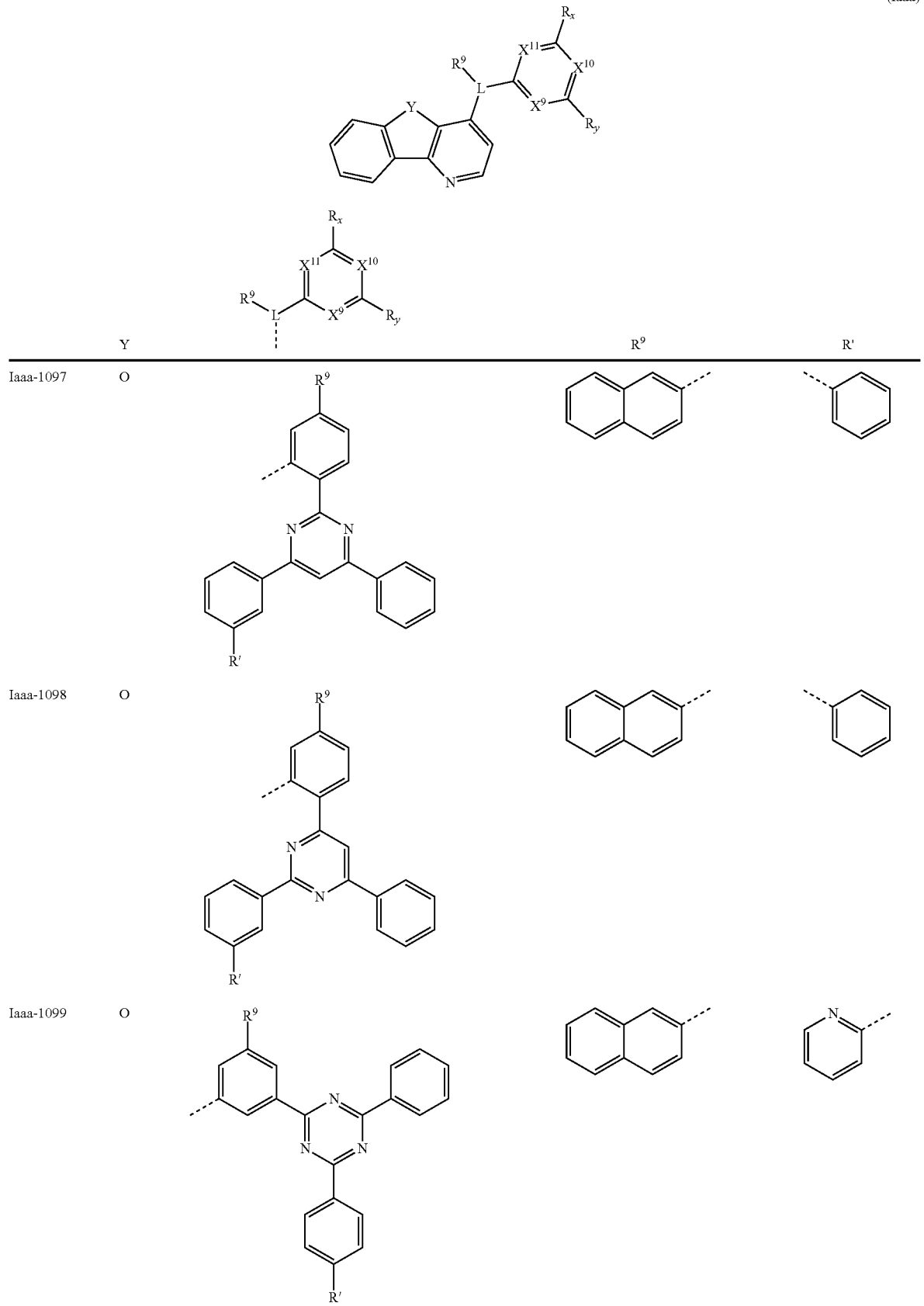

-continued
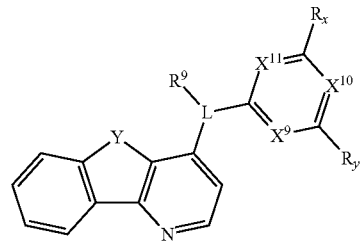
(Iaaa)
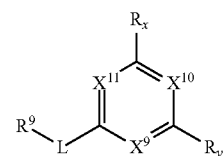
| | Y | R⁹ | R' |
|---|---|---|---|
| Iaaa-1100 | O | 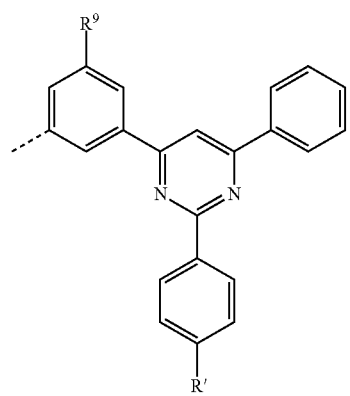 | 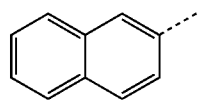 | 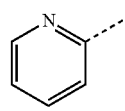 |
| Iaaa-1101 | O | 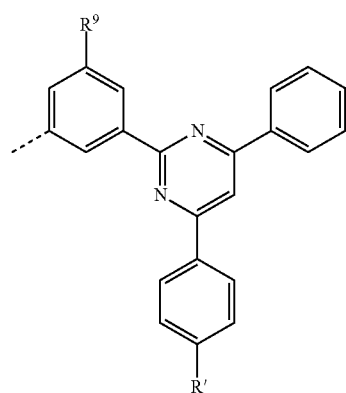 | 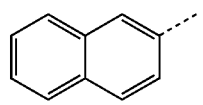 | 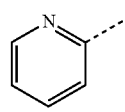 |

-continued
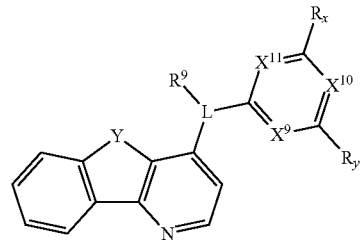
(Iaaa)
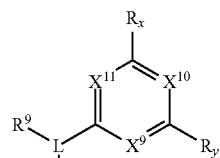
| | Y | | R⁹ | R' |
|---|---|---|---|---|
| Iaaa-1102 | O | 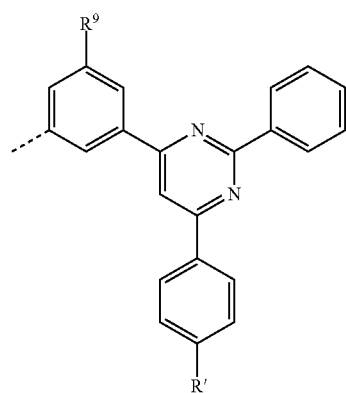 | 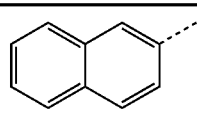 | 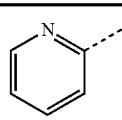 |
| Iaaa-1103 | O | 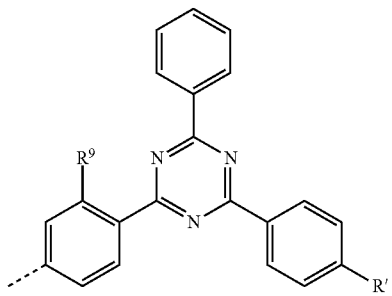 | 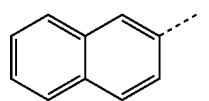 | 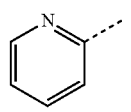 |
| Iaaa-1104 | O | 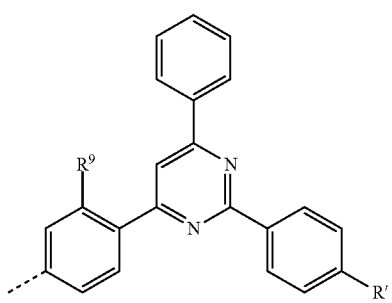 | | |

-continued
(Iaaa)
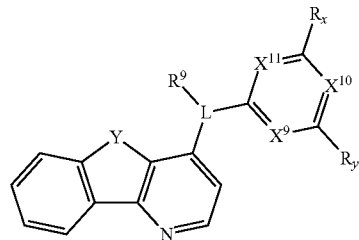
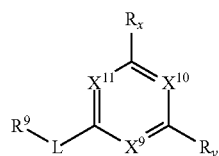
| | Y | | R⁹ | R' |
|---|---|---|---|---|
| Iaaa-1105 | O |  | 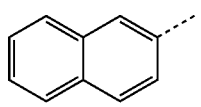 | 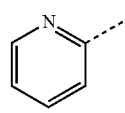 |
| Iaaa-1106 | O | 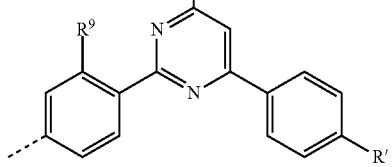 | 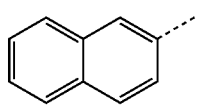 | 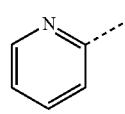 |
| Iaaa-1107 | O | 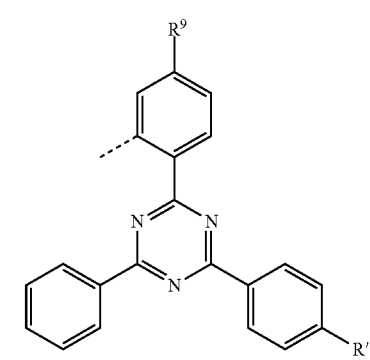 |  |  |

-continued
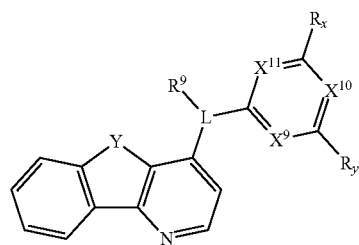
(Iaaa)
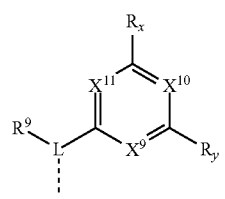
| | Y | | R⁹ | R' |
|---|---|---|---|---|
| Iaaa-1108 | O | [structure: phenyl-pyrimidine with phenyl and p-R' phenyl substituents, R⁹ on attached phenyl] | [naphthyl] | [2-pyridyl] |
| Iaaa-1109 | O | [structure: phenyl-pyrimidine at 2-position with 4,6-diphenyl, R' on one phenyl, R⁹ on attached phenyl] | [naphthyl] | [2-pyridyl] |
| Iaaa-1110 | O | [structure: phenyl-pyrimidine with phenyl and p-R' phenyl substituents] | [naphthyl] | [2-pyridyl] |

-continued
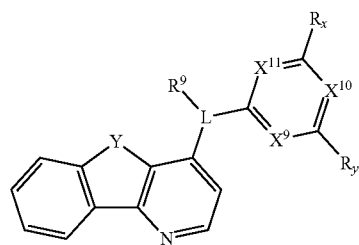
(Iaaa)
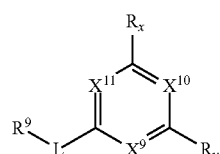
| | Y | | $R^9$ | $R'$ |
|---|---|---|---|---|
| Iaaa-1111 | O | 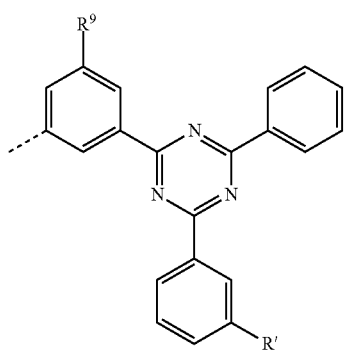 | 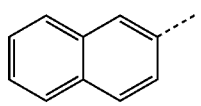 | 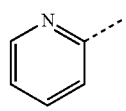 |
| Iaaa-1112 | O | 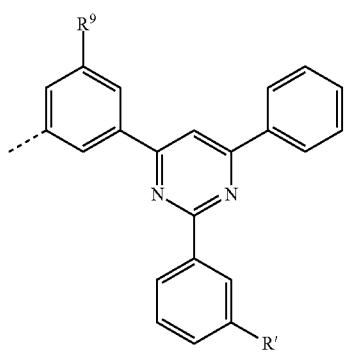 | 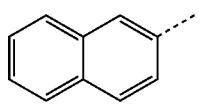 | 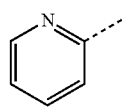 |
| Iaaa-1113 | O | 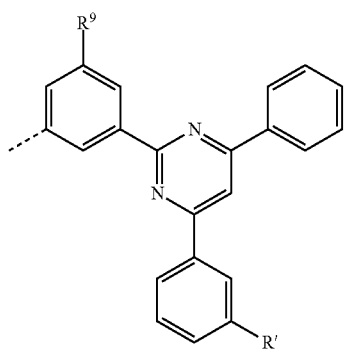 | 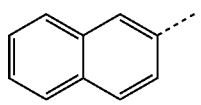 | 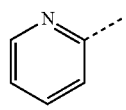 |

-continued
(Iaaa)
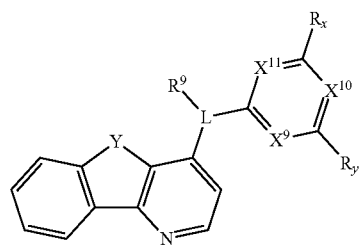
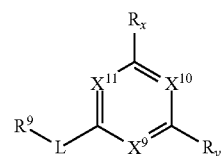
| | Y | | R⁹ | R' |
|---|---|---|---|---|
| Iaaa-1114 | O | 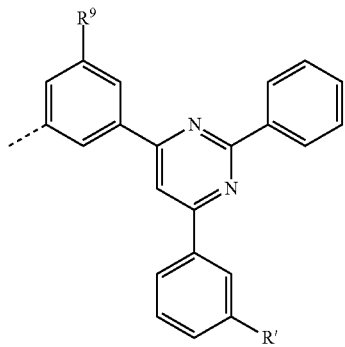 | 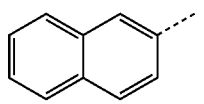 | 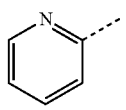 |
| Iaaa-1115 | O | 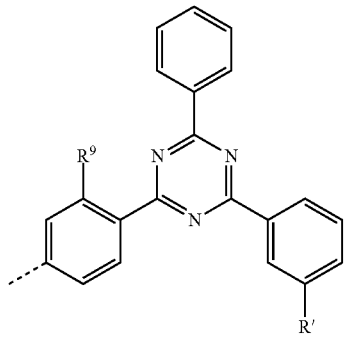 | 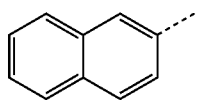 | 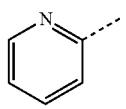 |
| Iaaa-1116 | O | 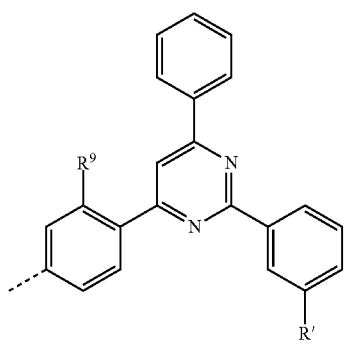 | 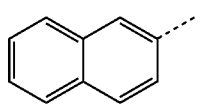 | 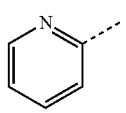 |

(Iaaa)
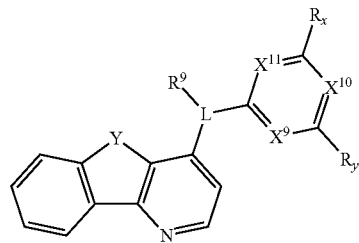
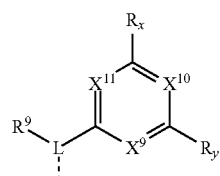
| | Y | | R⁹ | R' |
|---|---|---|---|---|
| Iaaa-1117 | O |  | 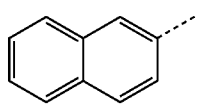 | 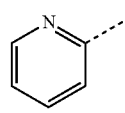 |
| Iaaa-1118 | O | 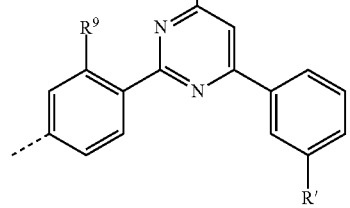 | 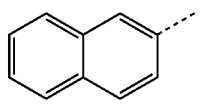 | 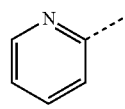 |
| Iaaa-1119 | O | 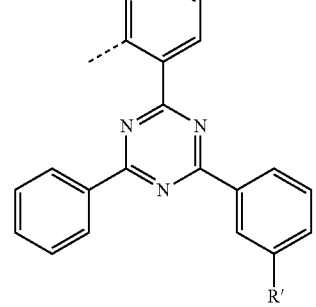 | 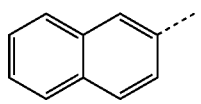 | 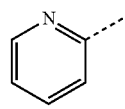 |

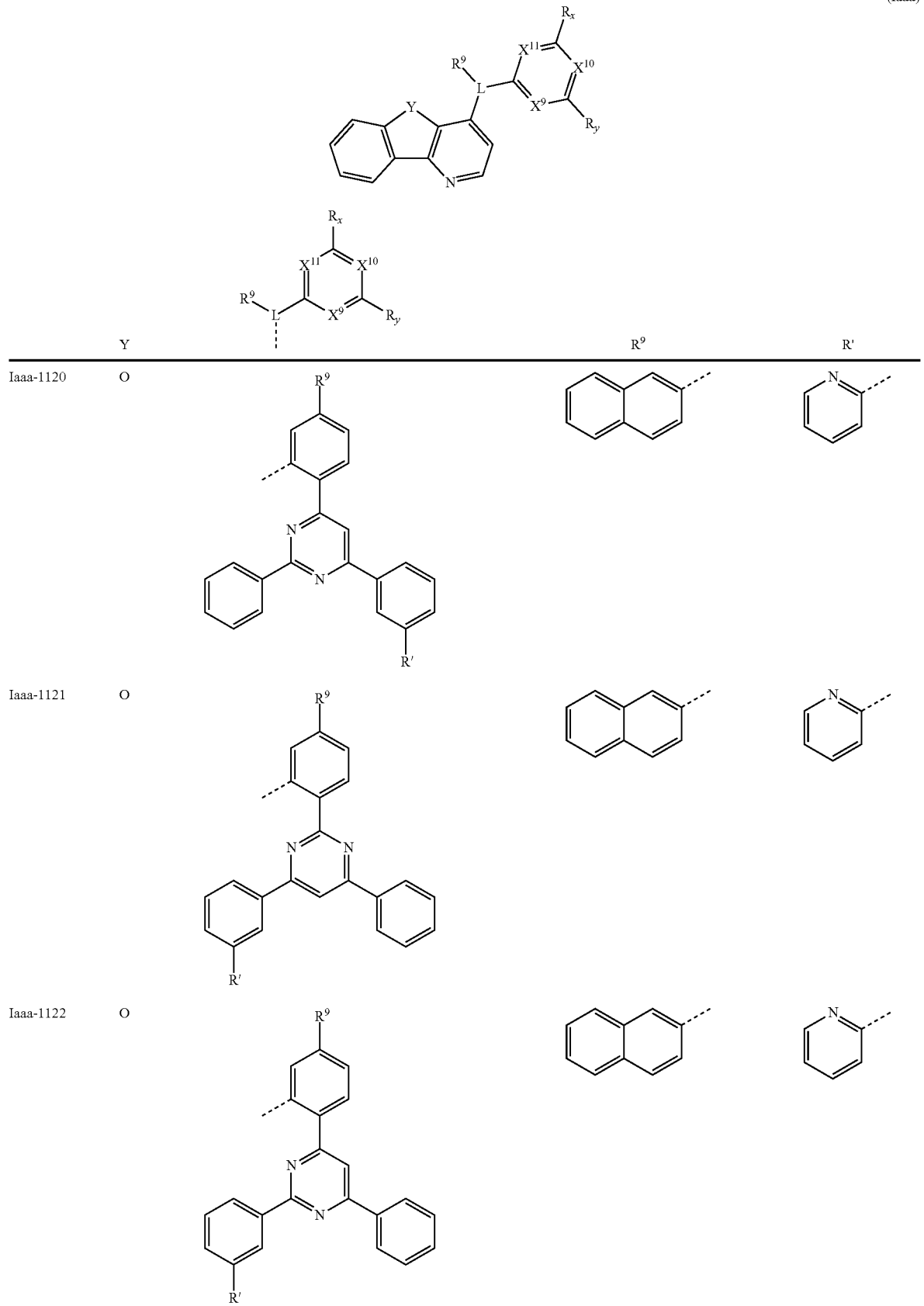

-continued
(Iaaa)
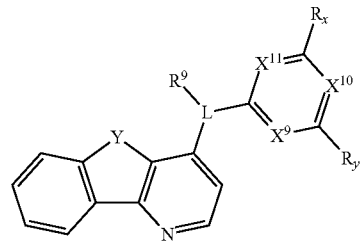
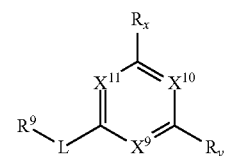
| | Y | R⁹ | R' |
|---|---|---|---|
| Iaaa-1123 | O | 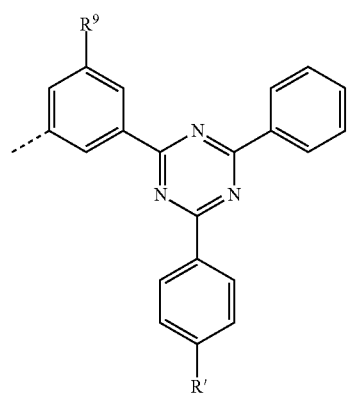 | 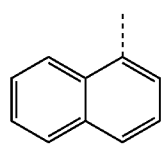 H |
| Iaaa-1124 | O | 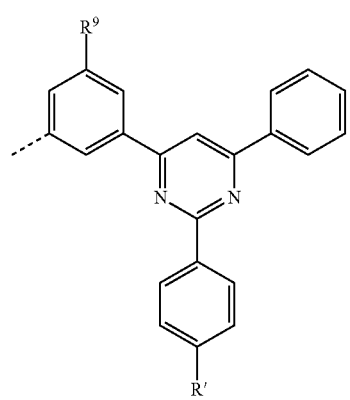 | 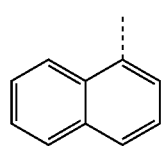 H |

-continued
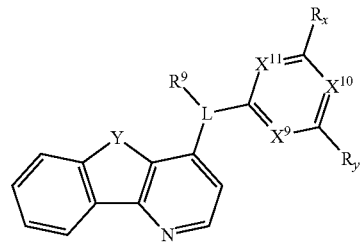
(Iaaa)
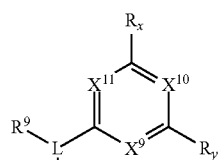
| | Y | R⁹ | R' |
|---|---|---|---|
| Iaaa-1125 | O | 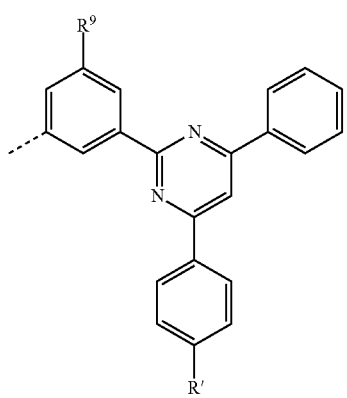 | 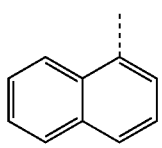 | H |
| Iaaa-1126 | O | 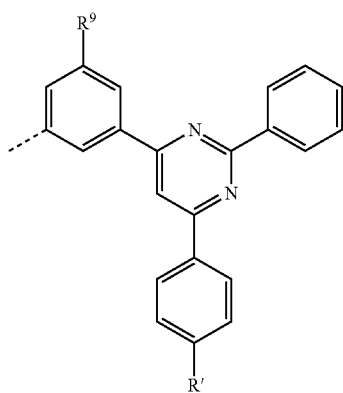 | 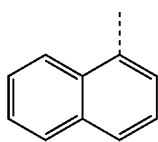 | H |
| Iaaa-1127 | O | 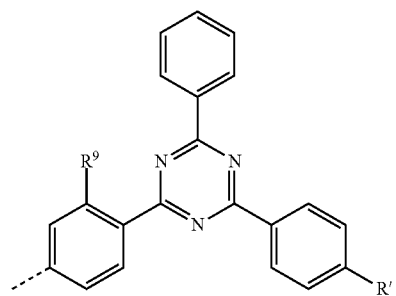 | 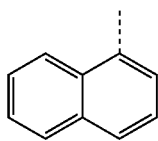 | H |

-continued
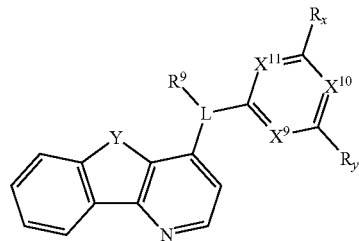
(Iaaa)
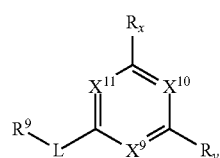
| | Y | | R⁹ | R' |
|---|---|---|---|---|
| Iaaa-1128 | O | 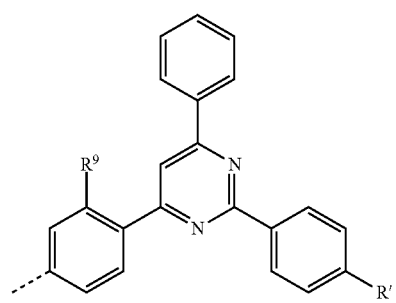 | 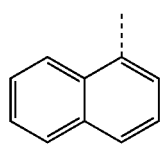 | H |
| Iaaa-1129 | O | 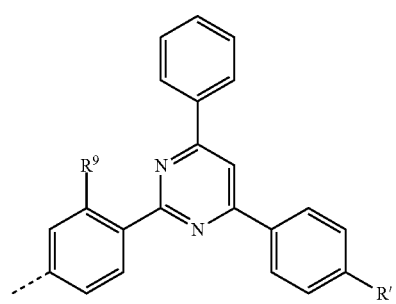 | 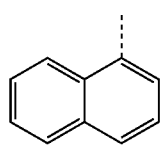 | H |
| Iaaa-1130 | O | 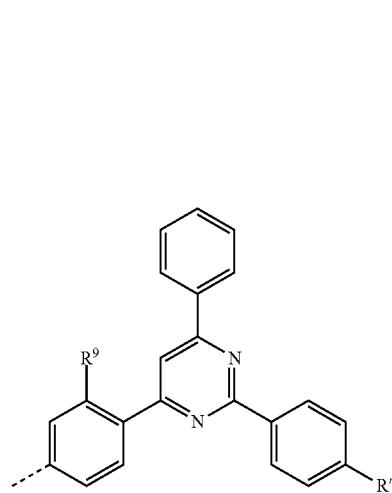 | 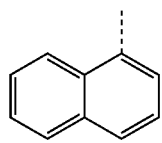 | H |

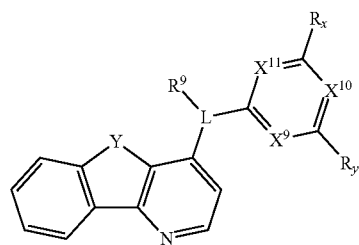
(Iaaa)
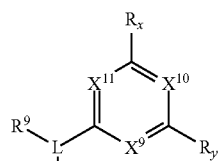
| | Y | R⁹ | R' |
|---|---|---|---|
| Iaaa-1131 | O | 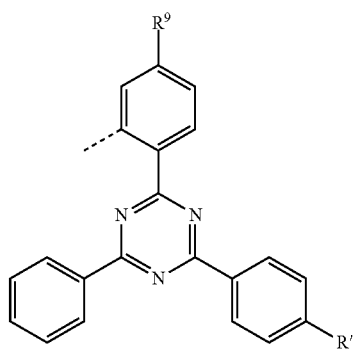 | 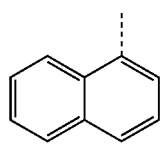 H |
| Iaaa-1132 | O | 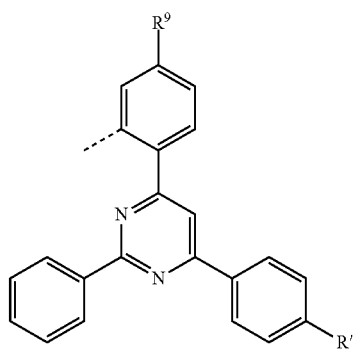 | 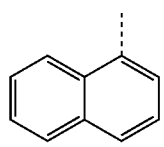 H |
| Iaaa-1133 | O | 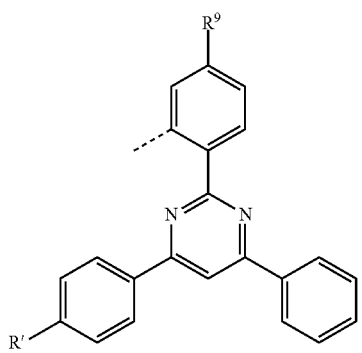 | 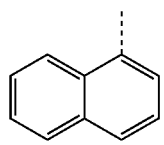 H |

-continued
(Iaaa)
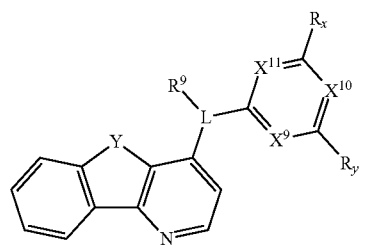
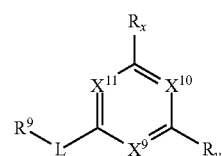
| | Y | R⁹ | | R' |
|---|---|---|---|---|
| Iaaa-1134 | O | 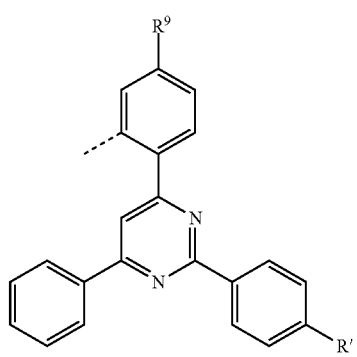 | 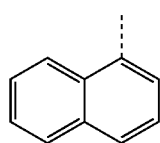 | H |
| Iaaa-1135 | O | 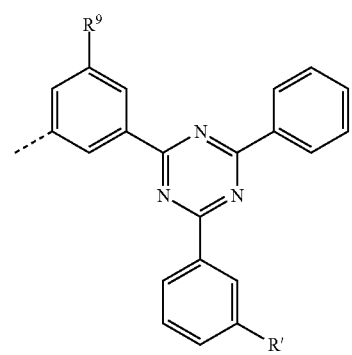 | 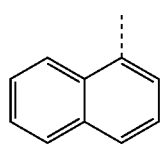 | H |
| Iaaa-1136 | O | 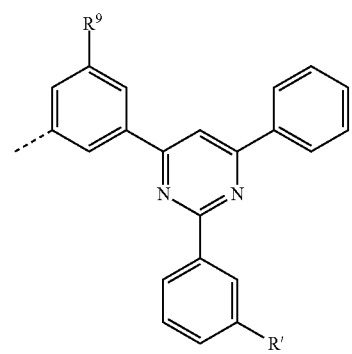 | 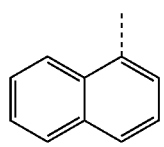 | H |

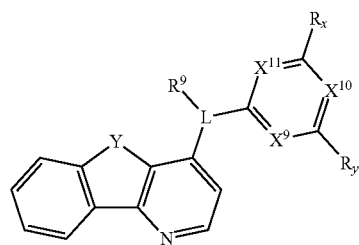
(Iaaa)
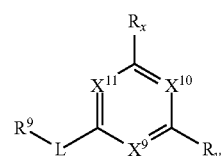
| | Y | R⁹ | | R' |
|---|---|---|---|---|
| Iaaa-1137 | O | 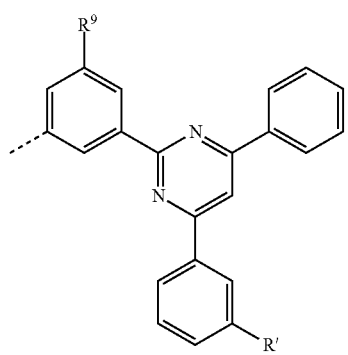 | 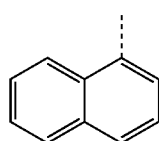 | H |
| Iaaa-1138 | O | 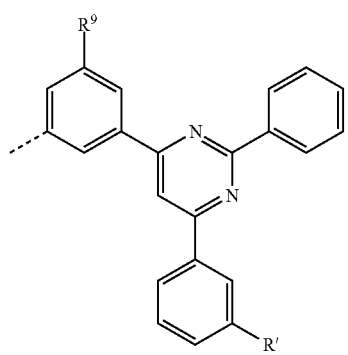 | 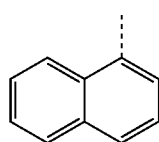 | H |
| Iaaa-1139 | O | 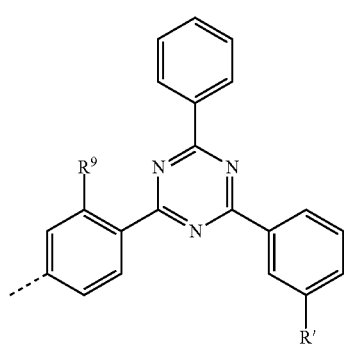 | 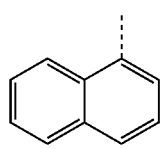 | H |

-continued
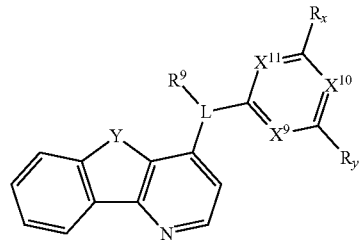
(Iaaa)
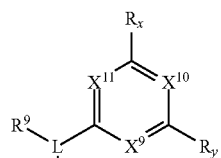
| | Y | R⁹ | | R' |
|---|---|---|---|---|
| Iaaa-1140 | O | 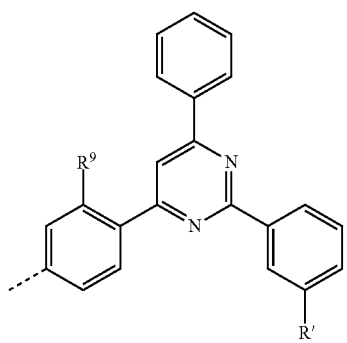 | 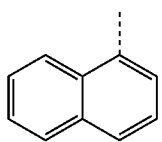 | H |
| Iaaa-1141 | O | 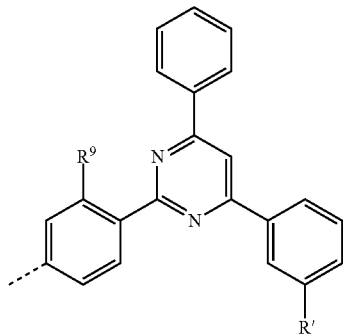 | 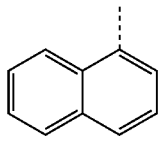 | H |
| Iaaa-1142 | O | 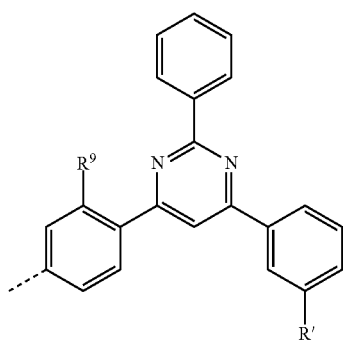 | 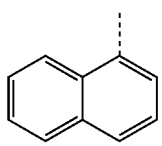 | H |

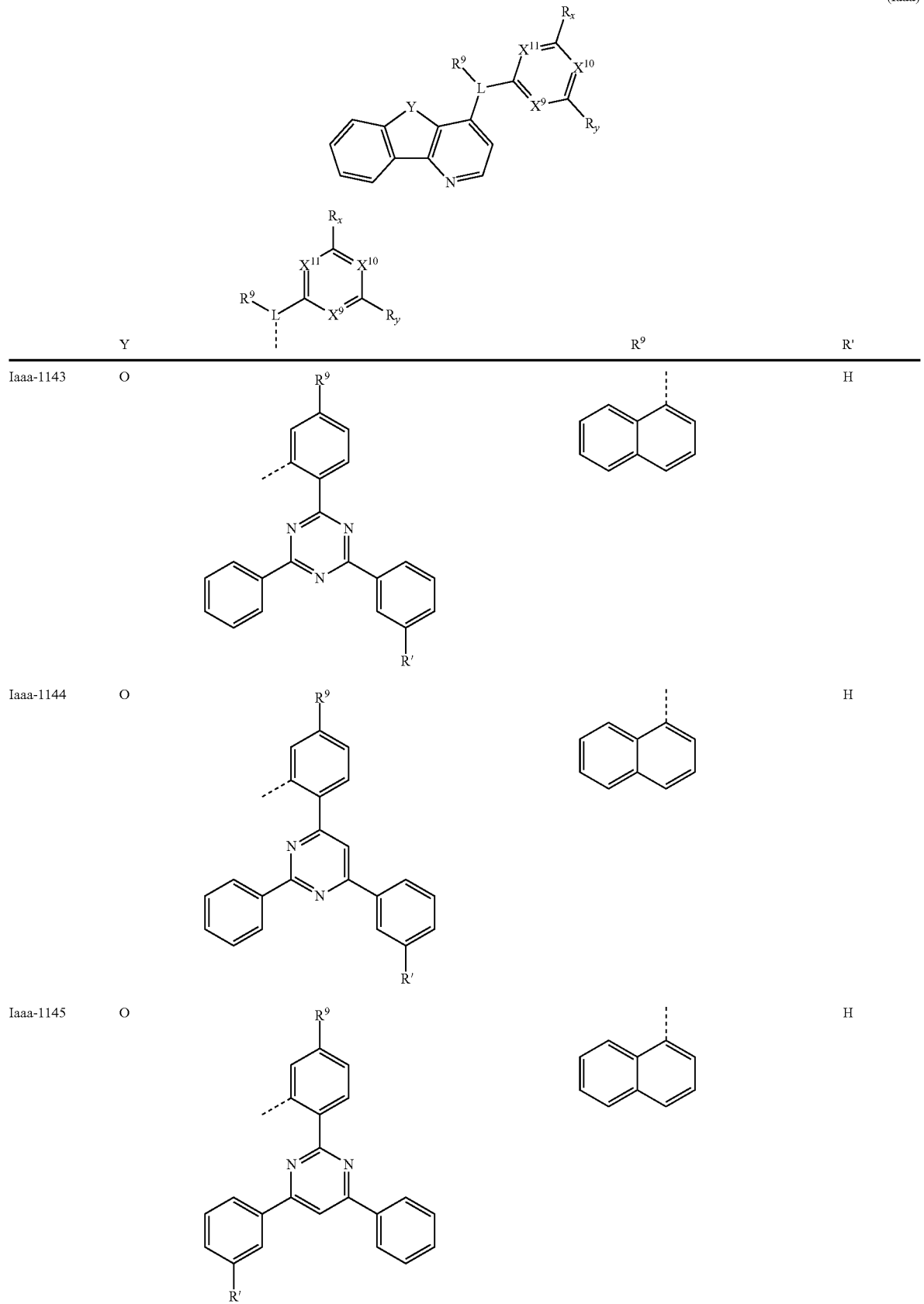

-continued
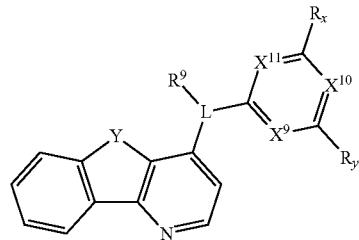
(Iaaa)
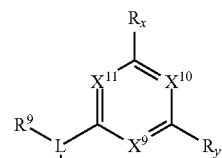
| | Y | R⁹ | R' |
|---|---|---|---|
| Iaaa-1146 | O | 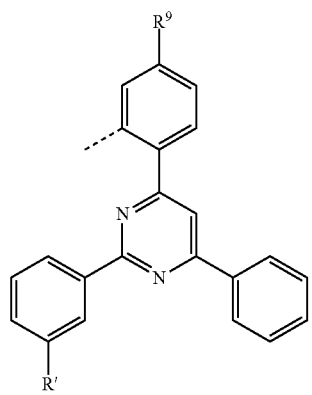 | 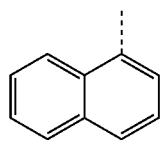 | H |
| Iaaa-1147 | O | 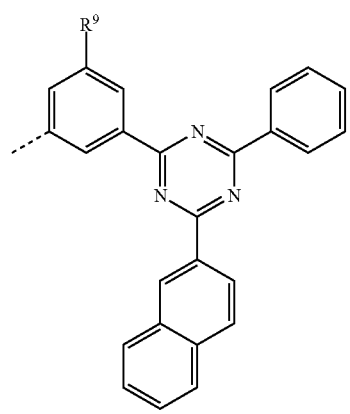 | 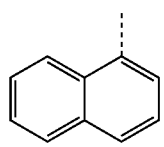 | — |

-continued
(Iaaa)
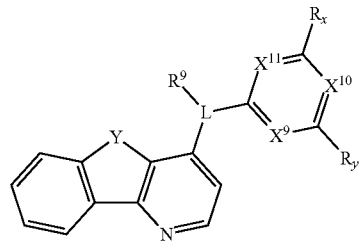
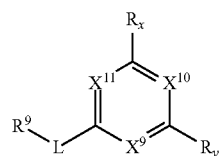
| | Y | R⁹ | R' |
|---|---|---|---|
| Iaaa-1148 | O | 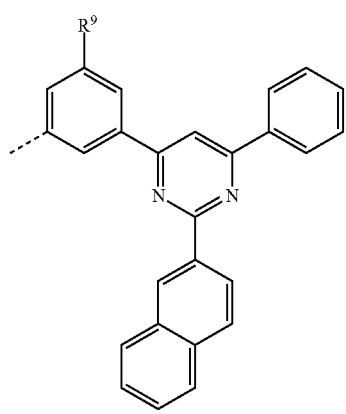 | 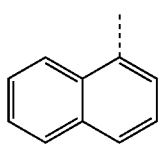 | — |
| Iaaa-1149 | O | 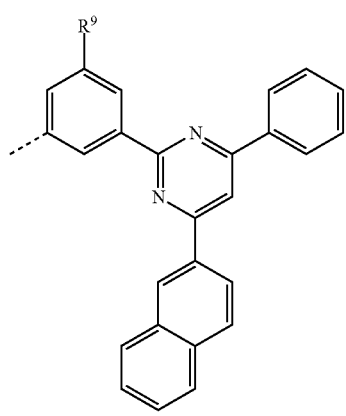 | 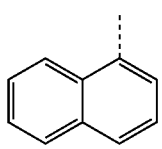 | — |

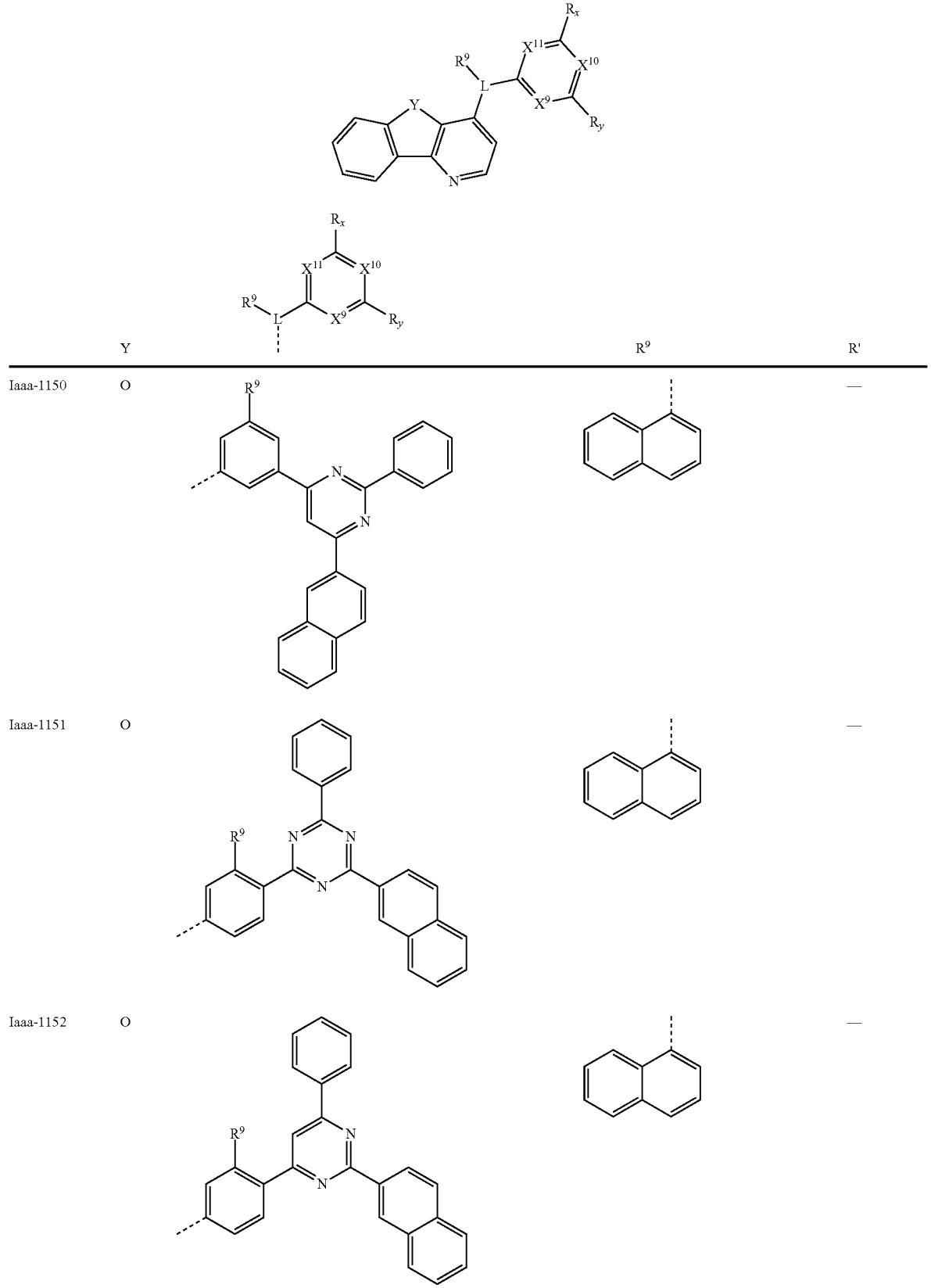

-continued
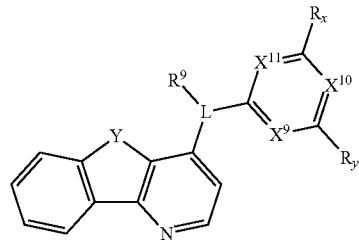
(Iaaa)
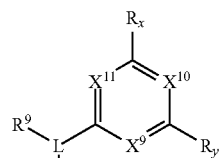
| | Y | R⁹ | R' |
|---|---|---|---|
| Iaaa-1153 | O | 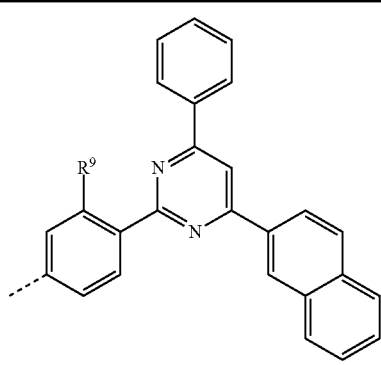 | 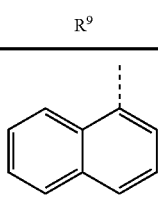 | — |
| Iaaa-1154 | O | 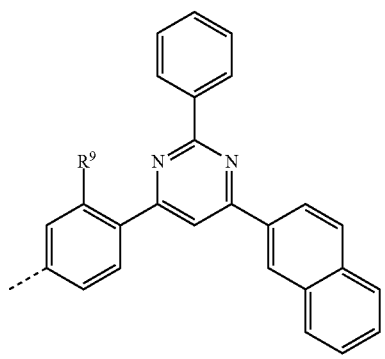 | 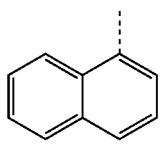 | — |
| Iaaa-1155 | O | 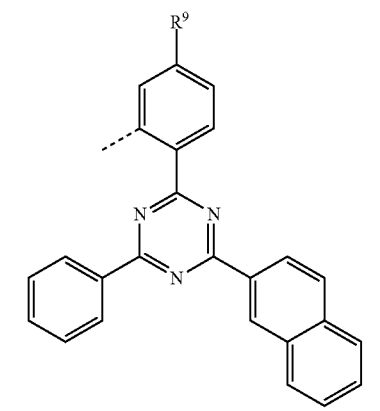 | 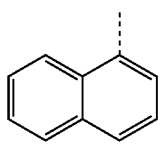 | — |

-continued
(Iaaa)
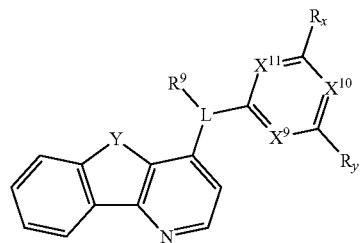
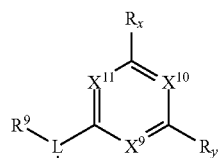
| | Y | R⁹ | R' |
|---|---|---|---|
| Iaaa-1156 | O | 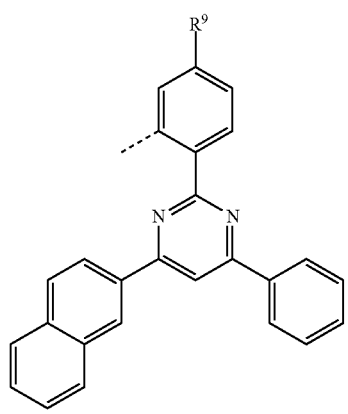 | 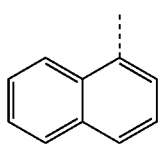 | — |
| Iaaa-1157 | O | 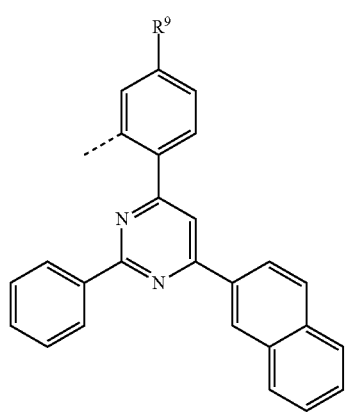 | 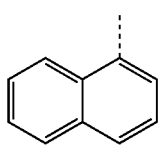 | — |

-continued
(Iaaa)
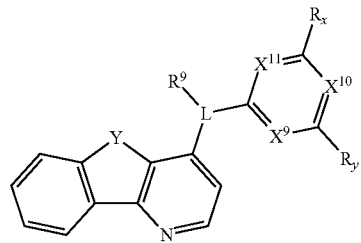
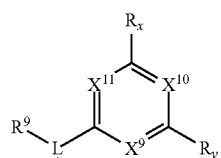
| | Y | | R⁹ | R' |
|---|---|---|---|---|
| Iaaa-1158 | O | 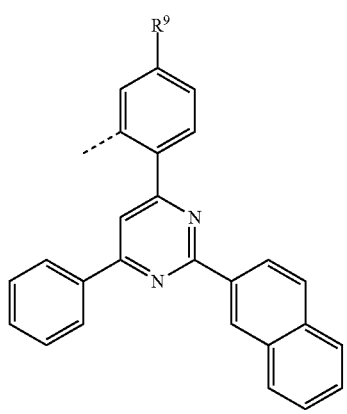 | 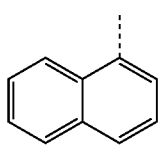 | — |
| Iaaa-1159 | O | 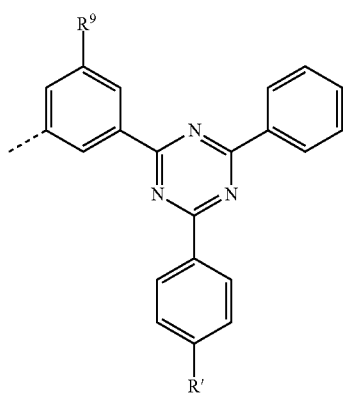 | 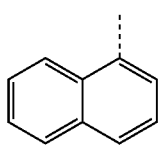 | 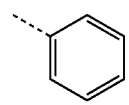 |

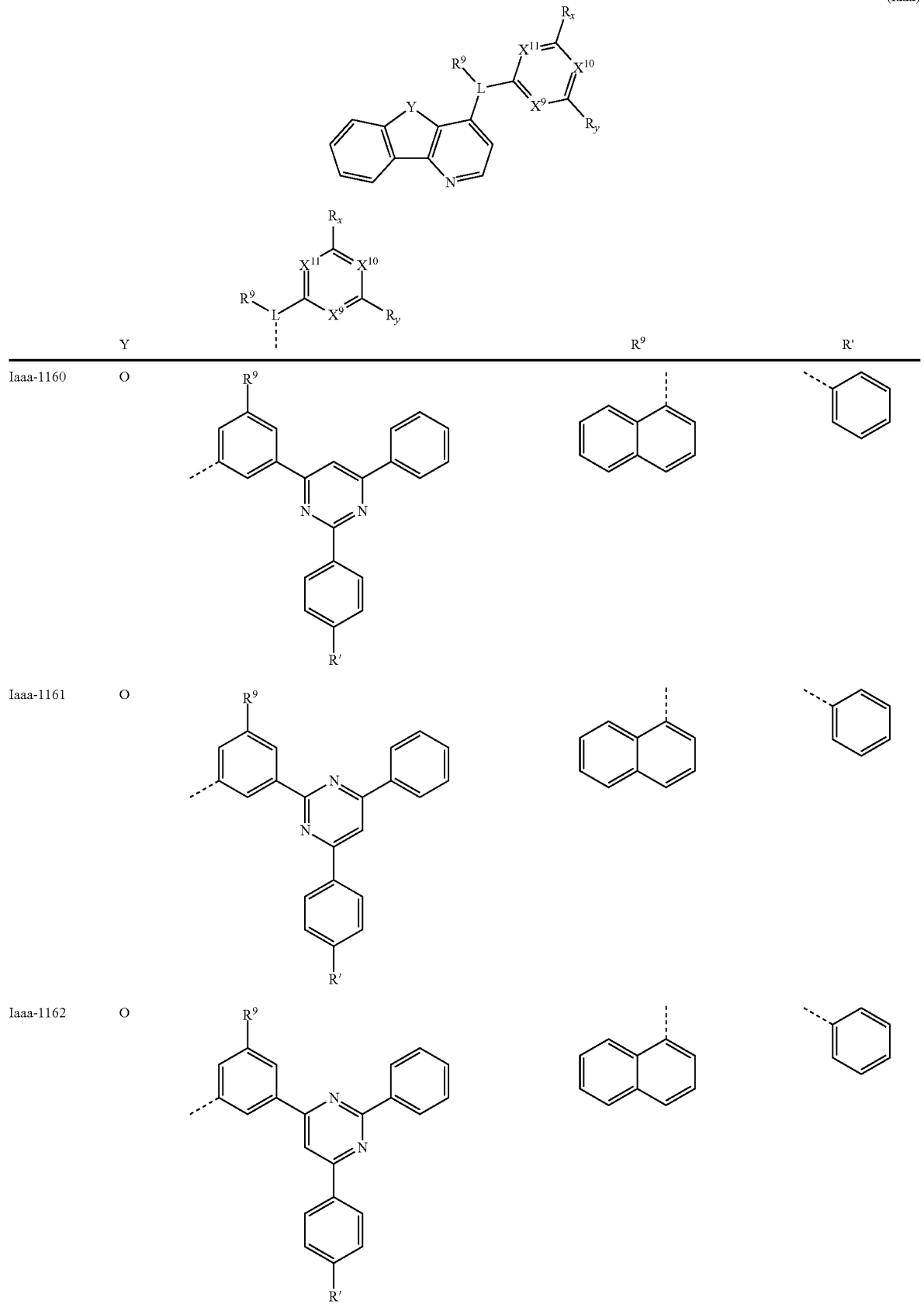

-continued
(Iaaa)
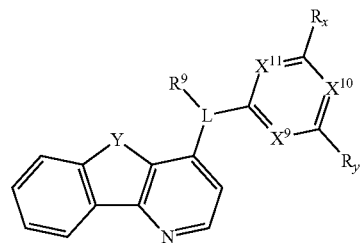
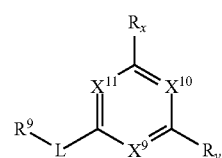
| | Y | | R⁹ | R' |
|---|---|---|---|---|
| Iaaa-1163 | O | 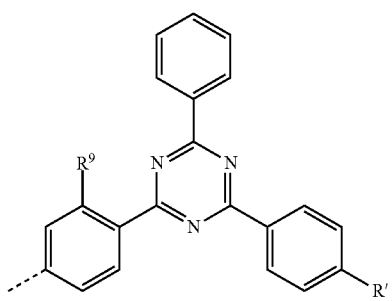 | 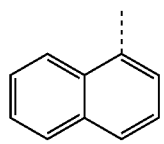 | 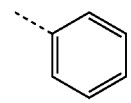 |
| Iaaa-1164 | O | 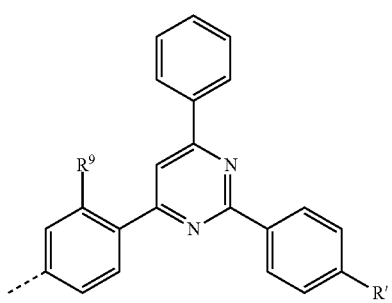 | 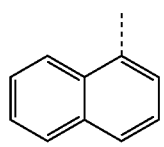 | 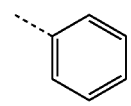 |
| Iaaa-1165 | O | 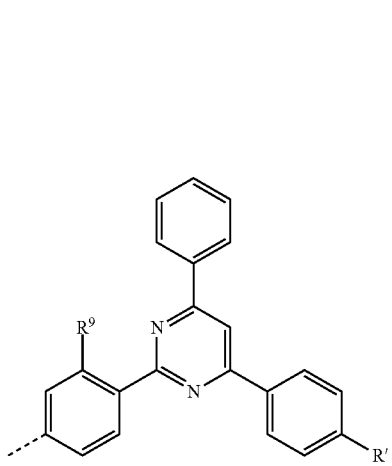 | 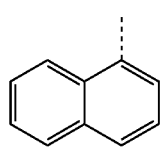 | 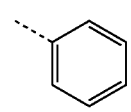 |

-continued
(Iaaa)
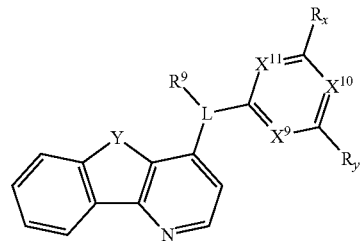
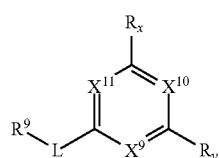
| | Y | | R⁹ | R' |
|---|---|---|---|---|
| Iaaa-1166 | O | 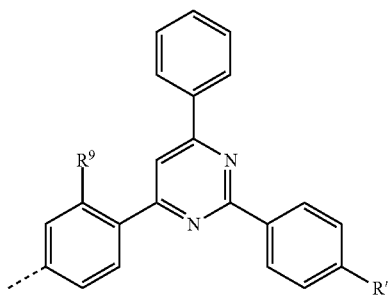 | 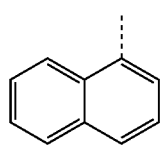 | 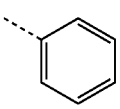 |
| Iaaa-1167 | O | 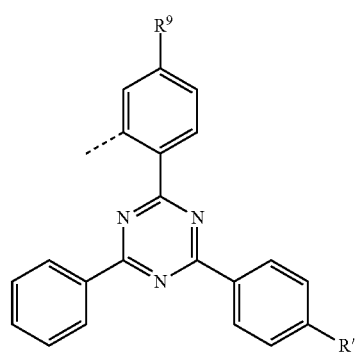 | 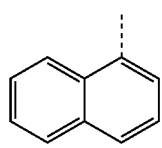 | 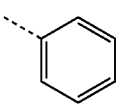 |
| Iaaa-1168 | O | 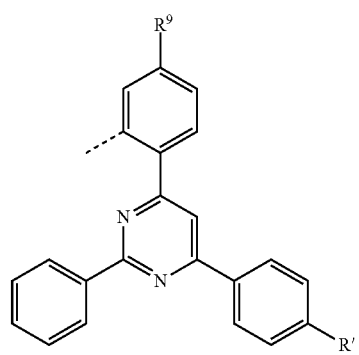 | 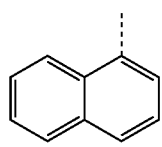 | 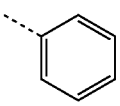 |

-continued
(Iaaa)
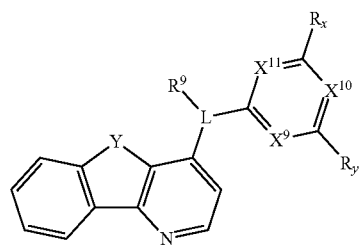
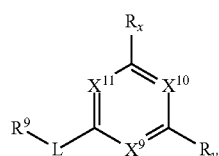
| | Y | | R⁹ | R' |
|---|---|---|---|---|
| Iaaa-1169 | O | 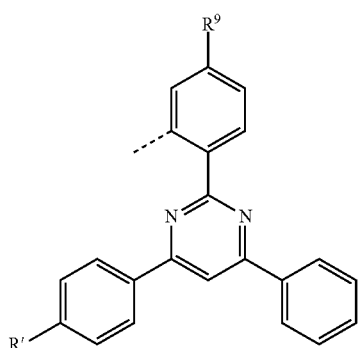 | 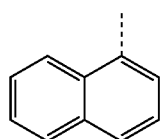 | 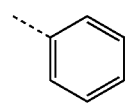 |
| Iaaa-1170 | O | 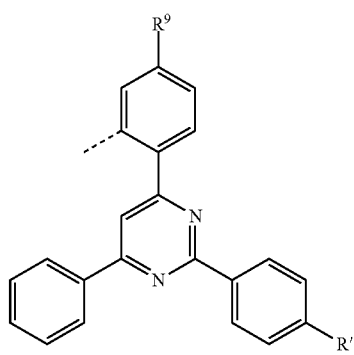 | 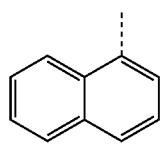 | 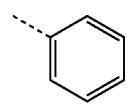 |
| Iaaa-1171 | O | 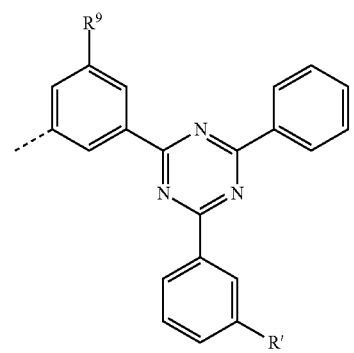 | 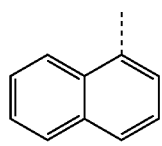 | 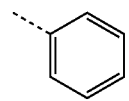 |

-continued
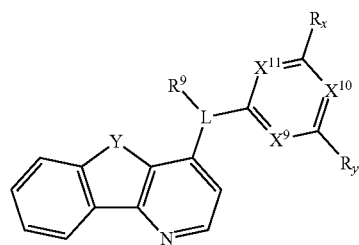
(Iaaa)
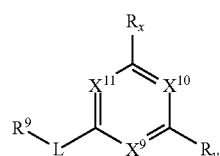
| | Y | R⁹ | R' |
|---|---|---|---|
| Iaaa-1172 | O | 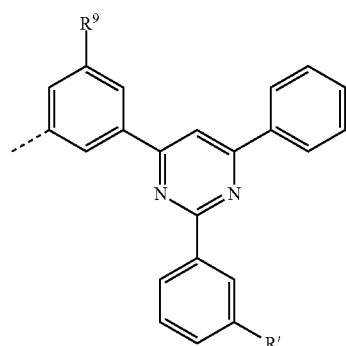 | 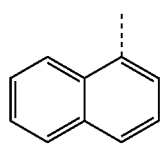 | 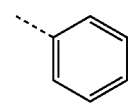 |
| Iaaa-1173 | O | 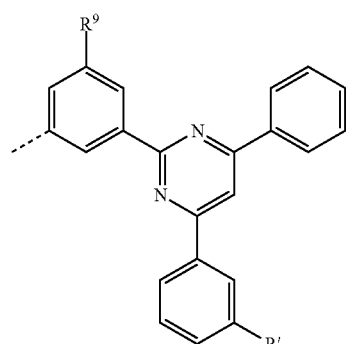 | 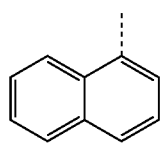 | 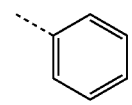 |
| Iaaa-1174 | O | 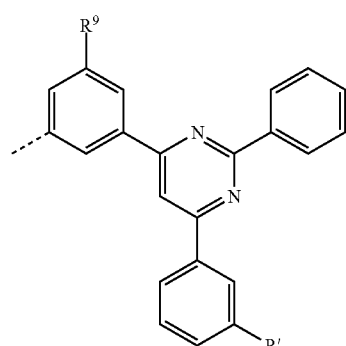 | 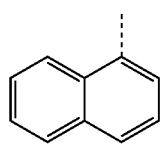 | 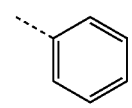 |

-continued
(Iaaa)
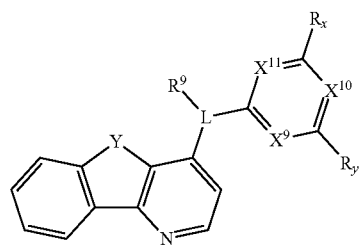
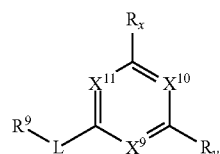
| | Y | R⁹ | R' |
|---|---|---|---|
| Iaaa-1175 | O | 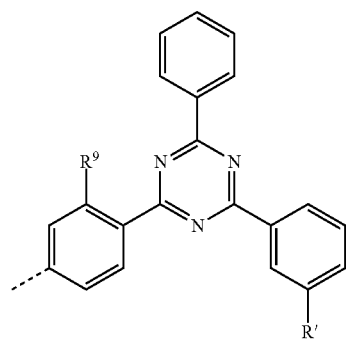 | 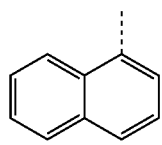 | 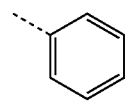 |
| Iaaa-1176 | O | 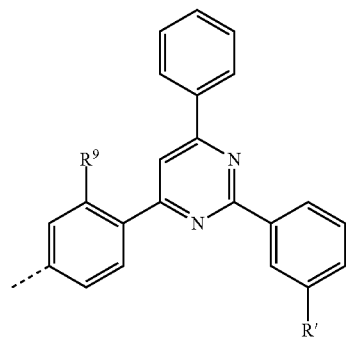 | 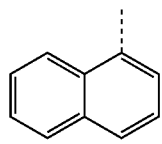 | 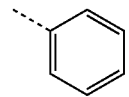 |
| Iaaa-1177 | O | 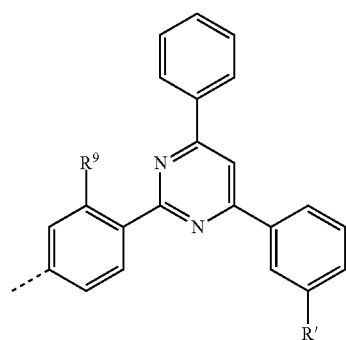 | 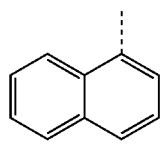 | 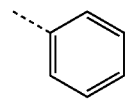 |

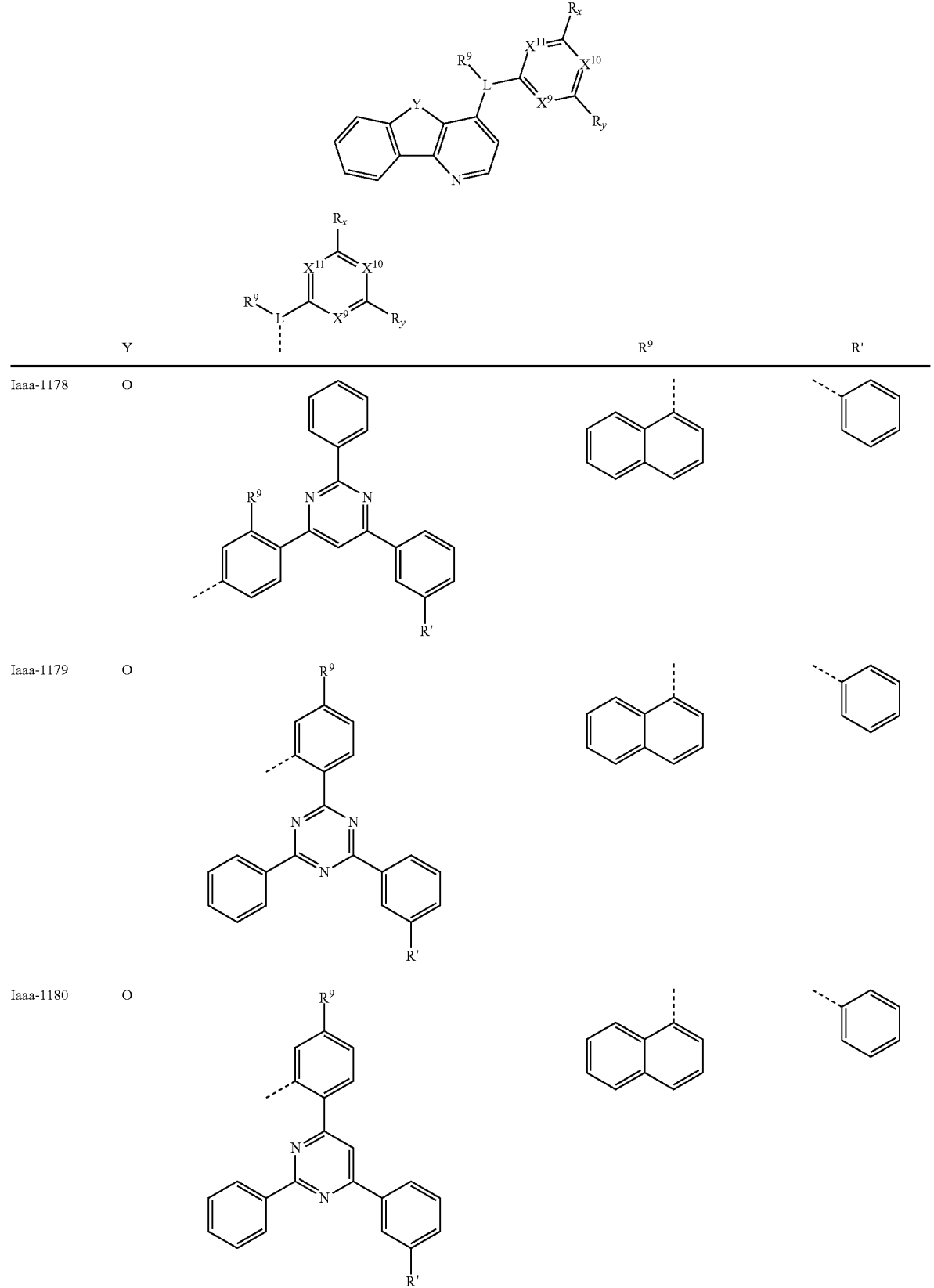

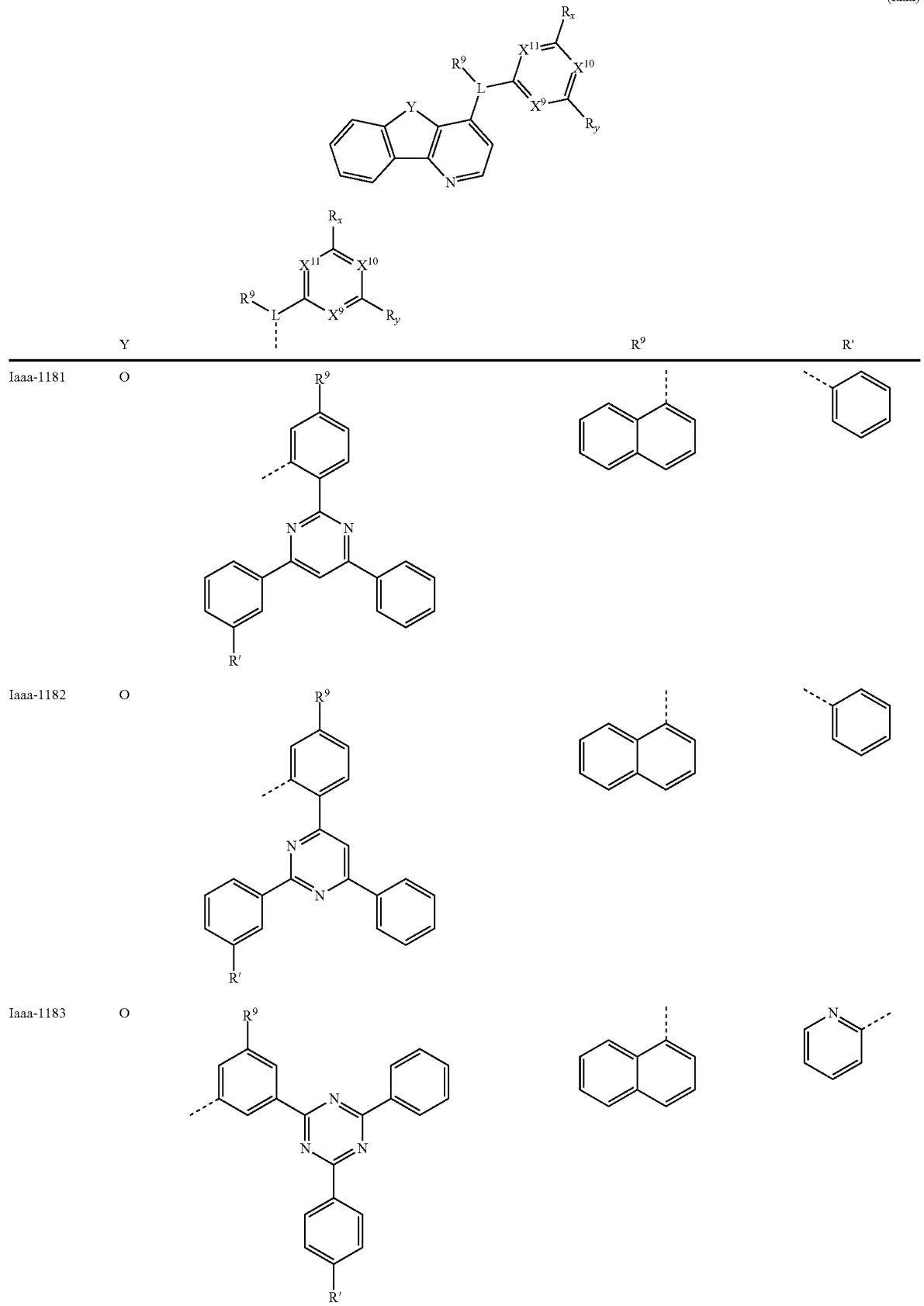

-continued
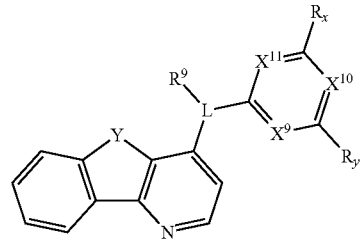
(Iaaa)
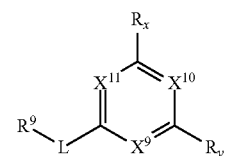
| | Y | R⁹ | | R' |
|---|---|---|---|---|
| Iaaa-1184 | O | 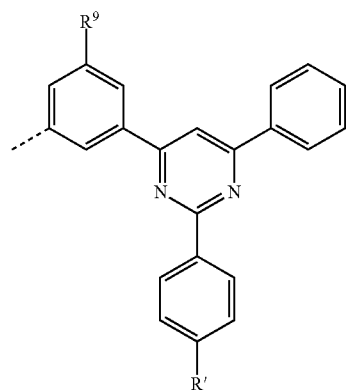 | 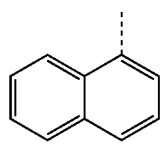 | 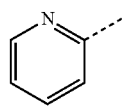 |
| Iaaa-1185 | O | 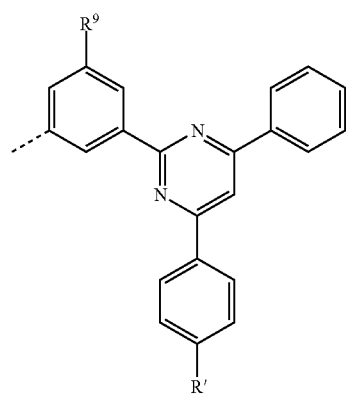 | 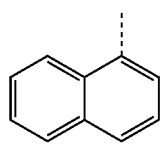 | 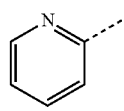 |

-continued
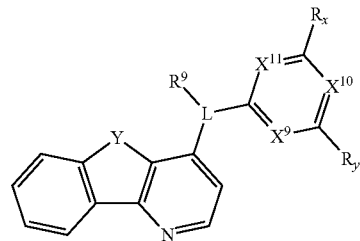
(Iaaa)
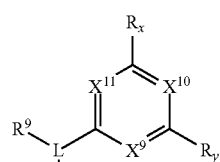
| | Y | R⁹ | R' |
|---|---|---|---|
| Iaaa-1186 | O | 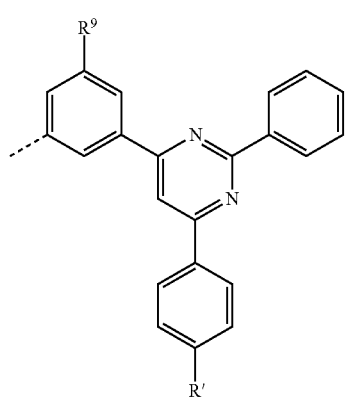 | 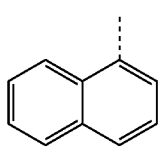 | 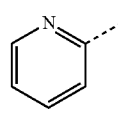 |
| Iaaa-1187 | O | 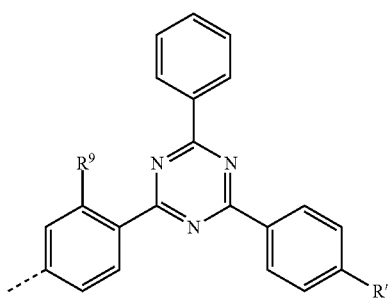 | 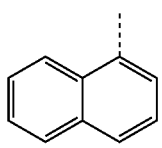 | 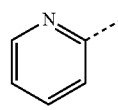 |
| Iaaa-1188 | O | 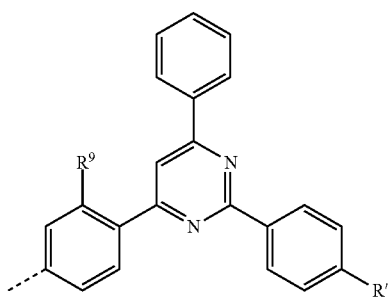 | 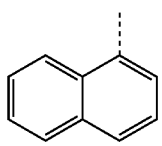 | 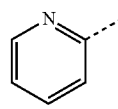 |

-continued
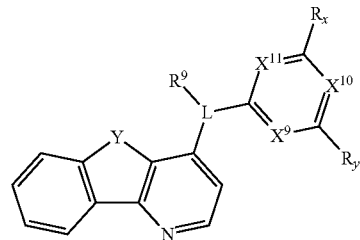
(Iaaa)
| | Y | | R⁹ | R' |
|---|---|---|---|---|
| Iaaa-1189 | O | 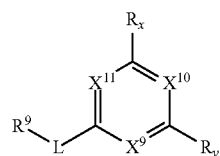 | 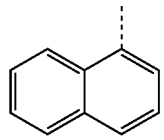 | 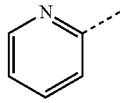 |
| Iaaa-1190 | O | 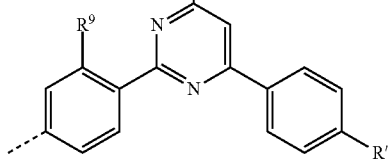 | 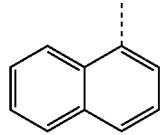 | 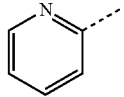 |
| Iaaa-1191 | O | 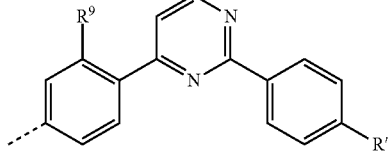 | 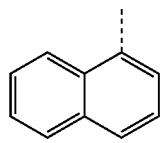 | 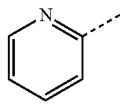 |

-continued
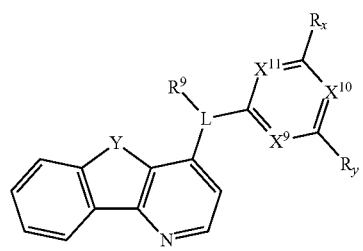
(Iaaa)
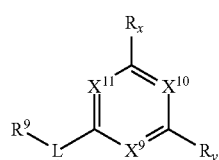
| | Y | R⁹ | R' |
|---|---|---|---|
| Iaaa-1192 | O | 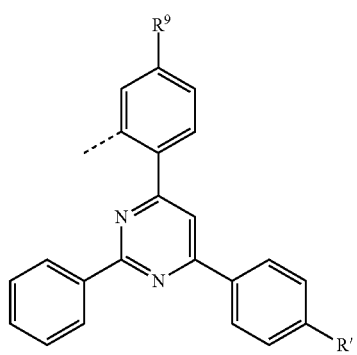 | 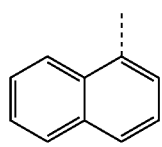 | 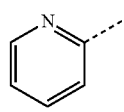 |
| Iaaa-1193 | O | 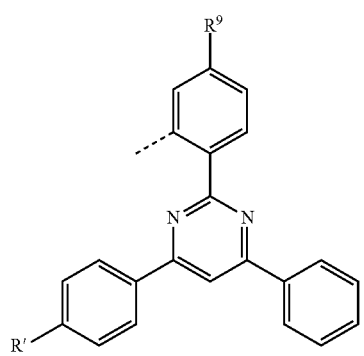 | 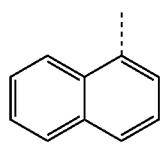 | 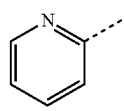 |
| Iaaa-1194 | O | 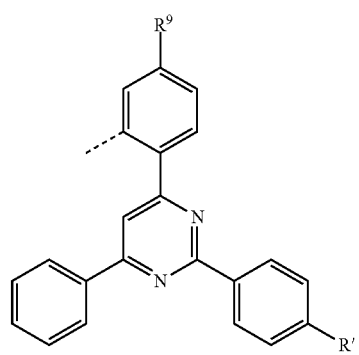 | 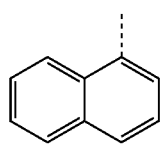 | 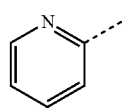 |

-continued
(Iaaa)
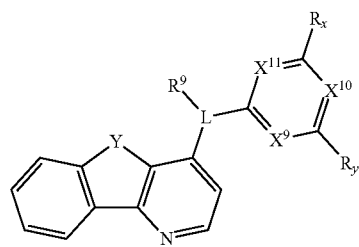
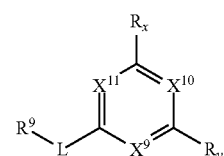
| | Y | | R⁹ | R' |
|---|---|---|---|---|
| Iaaa-1195 | O | 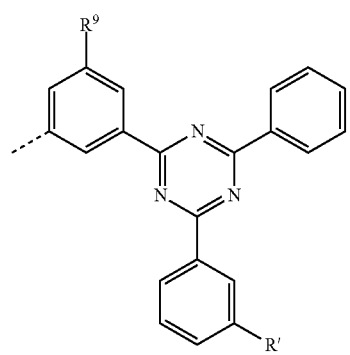 | 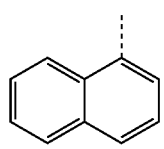 | 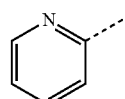 |
| Iaaa-1196 | O | 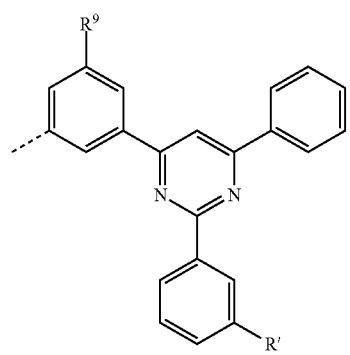 | 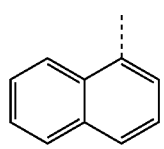 | 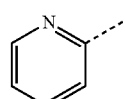 |
| Iaaa-1197 | O | 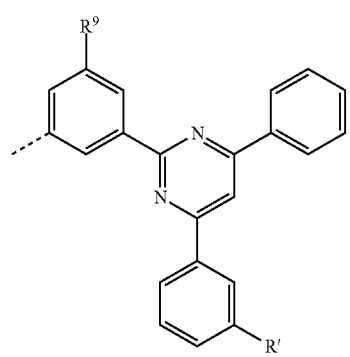 | 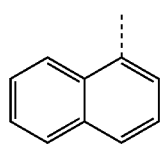 | 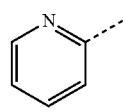 |

-continued
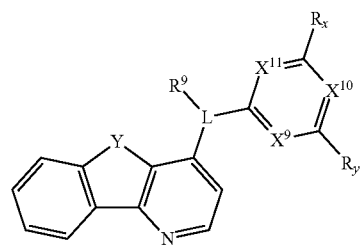
(Iaaa)
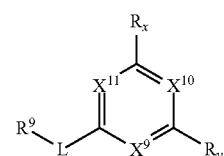
| | Y | R⁹ | R' |
|---|---|---|---|
| Iaaa-1198 | O | 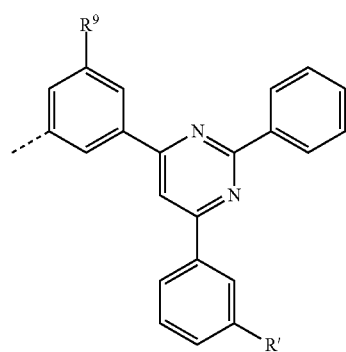 | 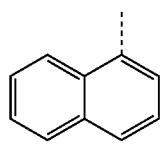 | 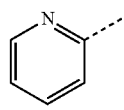 |
| Iaaa-1199 | O | 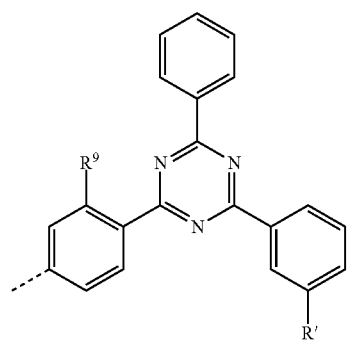 | 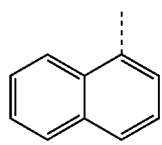 | 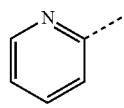 |
| Iaaa-1200 | O | 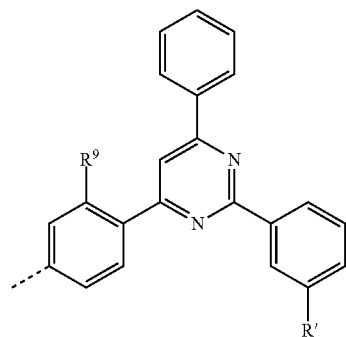 | 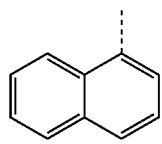 | 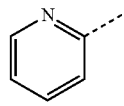 |

-continued
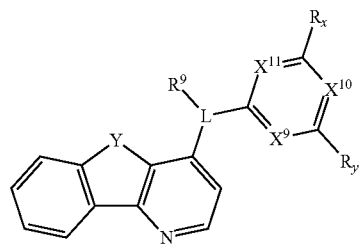
(Iaaa)
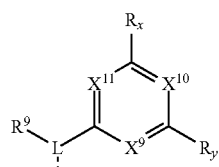
| | Y | R⁹ | R' |
|---|---|---|---|
| Iaaa-1201 | O | 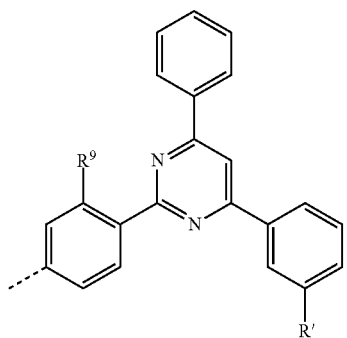 | 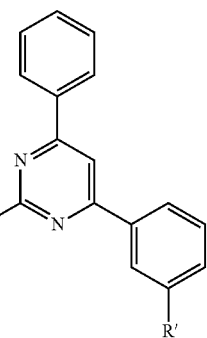 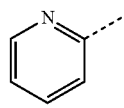 |
| Iaaa-1202 | O | 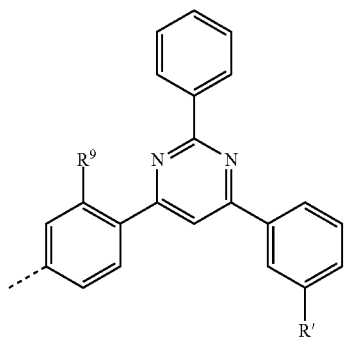 | 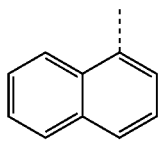 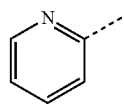 |
| Iaaa-1203 | O | 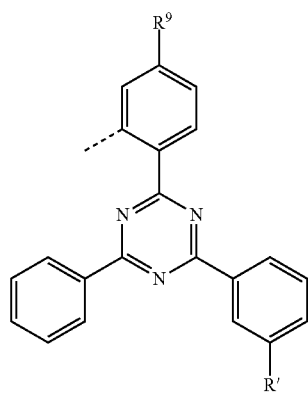 | 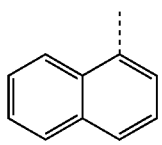 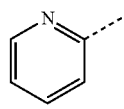 |

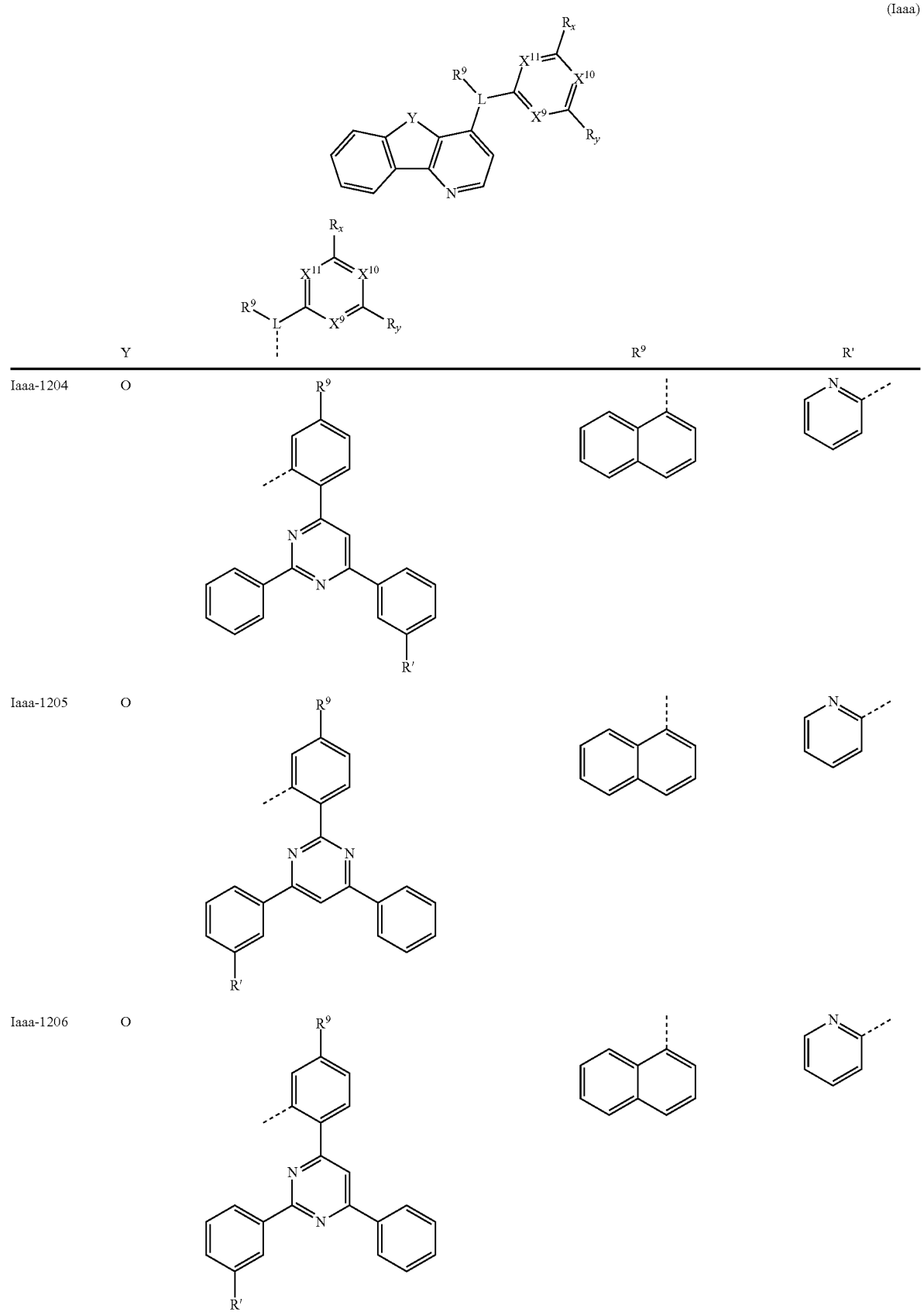

-continued
(Iaaa)
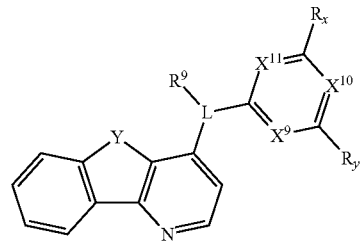
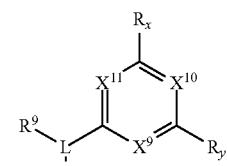
| | Y | R⁹ | | R' |
|---|---|---|---|---|
| Iaaa-1207 | O | 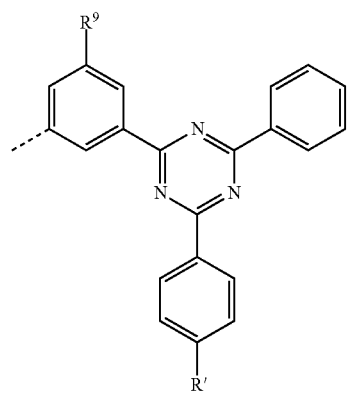 | 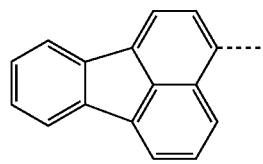 | H |
| Iaaa-1208 | O | 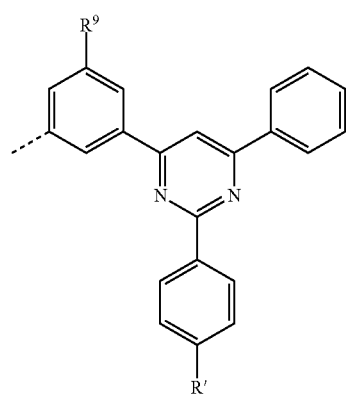 | 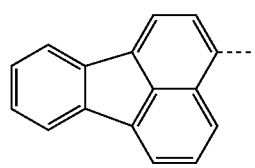 | H |

-continued
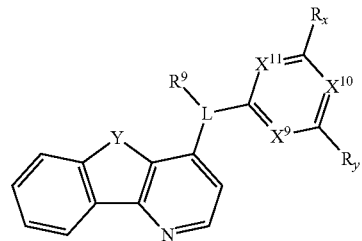
(Iaaa)
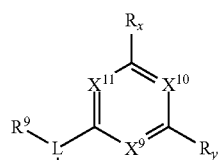
| | Y | R⁹ | R' |
|---|---|---|---|
| Iaaa-1209 | O | 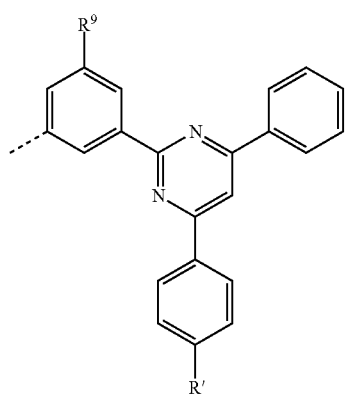 | 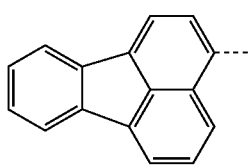 H |
| Iaaa-1210 | O | 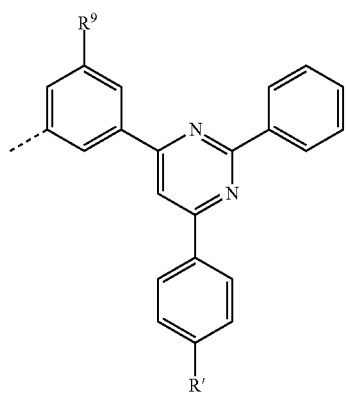 | 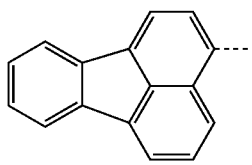 H |
| Iaaa-1211 | O | 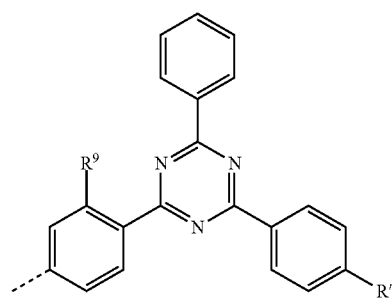 | 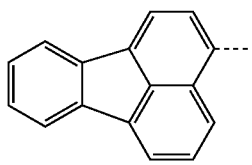 H |

-continued
(Iaaa)
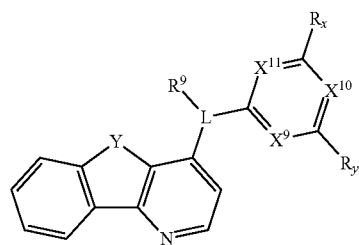
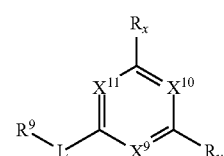
| | Y | | $R^9$ | R' |
|---|---|---|---|---|
| Iaaa-1212 | O | 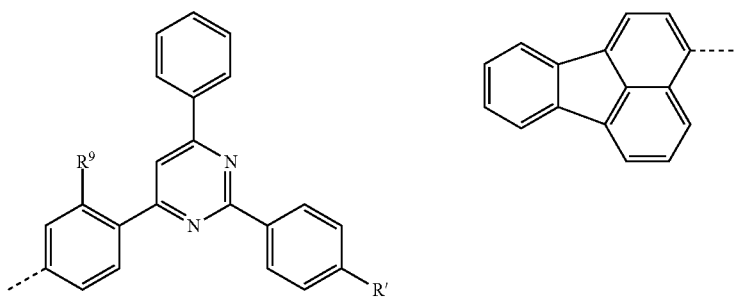 | | H |
| Iaaa-1213 | O | 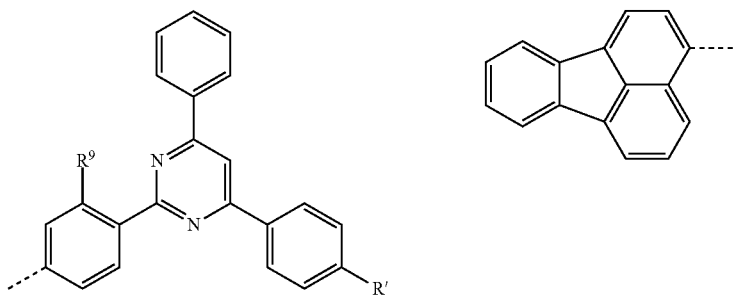 | | H |
| Iaaa-1214 | O | 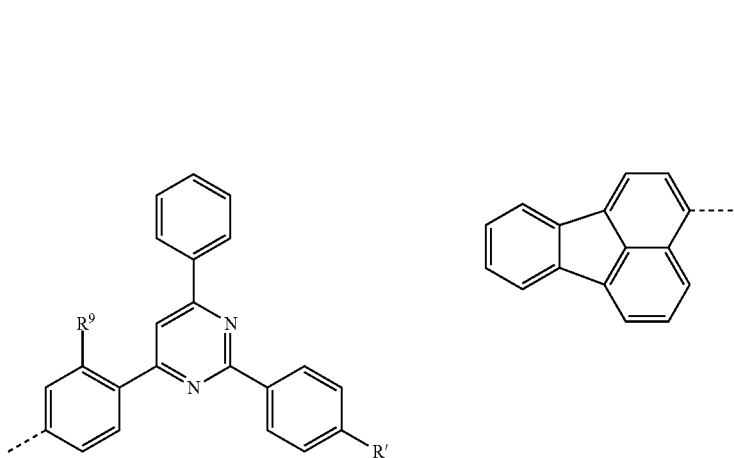 | | H |

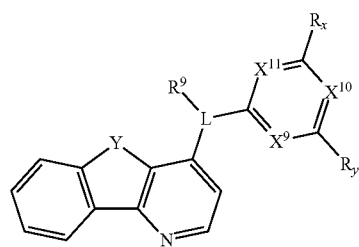
(Iaaa)
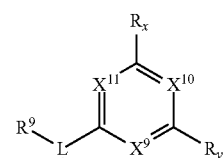
| | Y | R⁹ | R' |
|---|---|---|---|
| Iaaa-1215 | O | 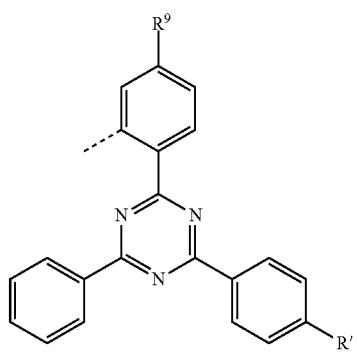 | 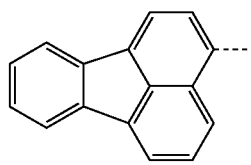 H |
| Iaaa-1216 | O | 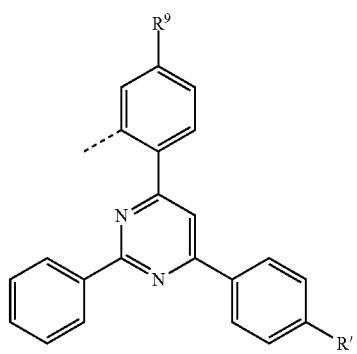 | 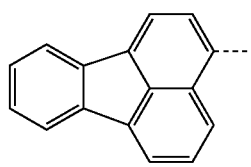 H |
| Iaaa-1217 | O | 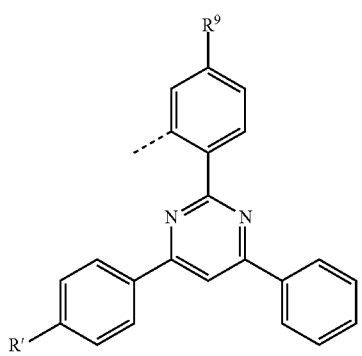 | 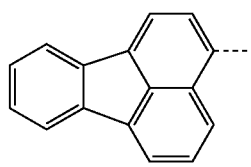 H |

-continued
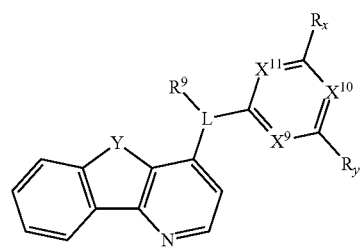
(Iaaa)
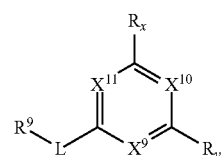
| | Y | R⁹ | | R' |
|---|---|---|---|---|
| Iaaa-1218 | O | 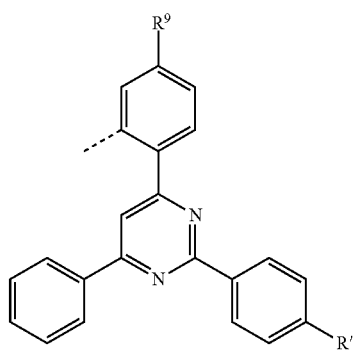 | 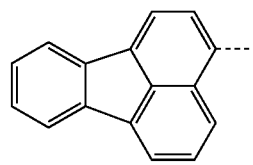 | H |
| Iaaa-1219 | O | 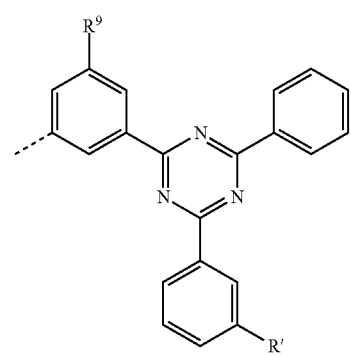 | 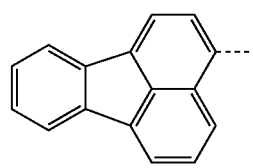 | H |
| Iaaa-1220 | O | 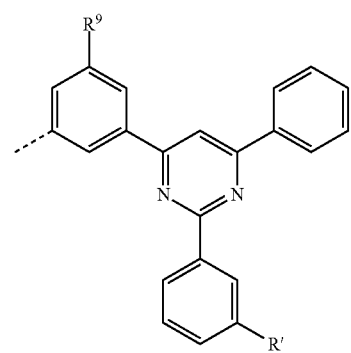 | 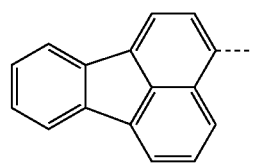 | H |

(Iaaa)
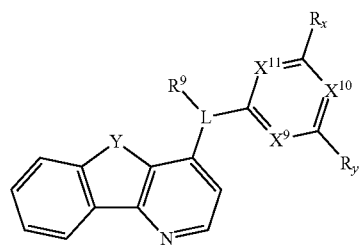
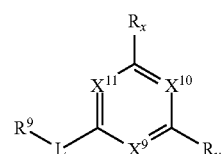
| | Y | R⁹ | R' |
|---|---|---|---|
| Iaaa-1221 | O | 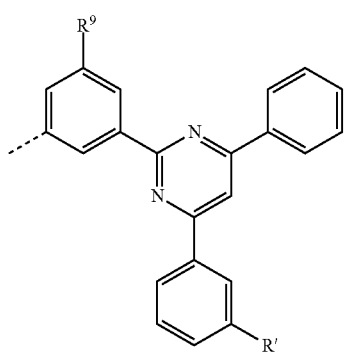 | 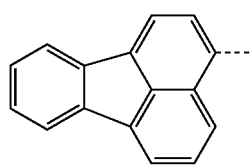 H |
| Iaaa-1222 | O | 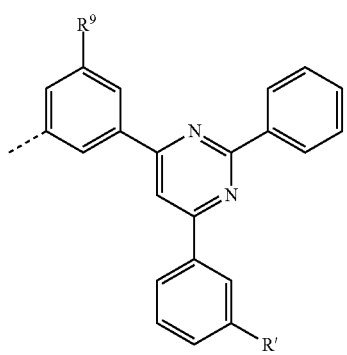 | 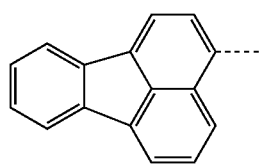 H |
| Iaaa-1223 | O | 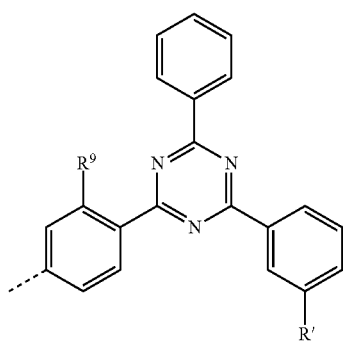 | 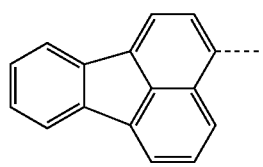 H |

(Iaaa)
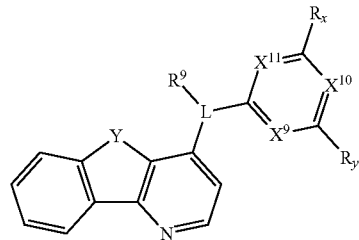
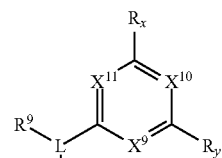
| | Y | | R⁹ | R' |
|---|---|---|---|---|
| Iaaa-1224 | O | 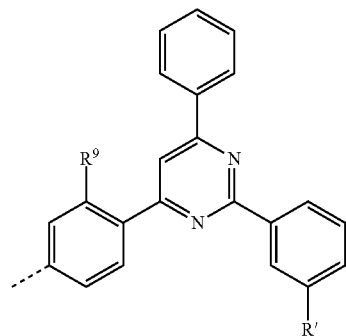 | 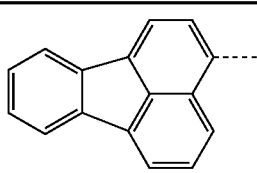 | H |
| Iaaa-1225 | O | 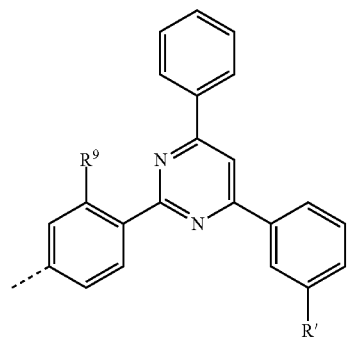 | 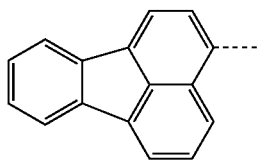 | H |
| Iaaa-1226 | O | 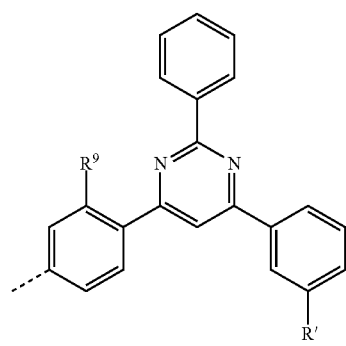 | 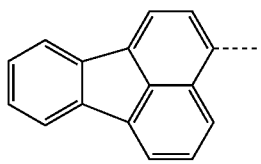 | H |

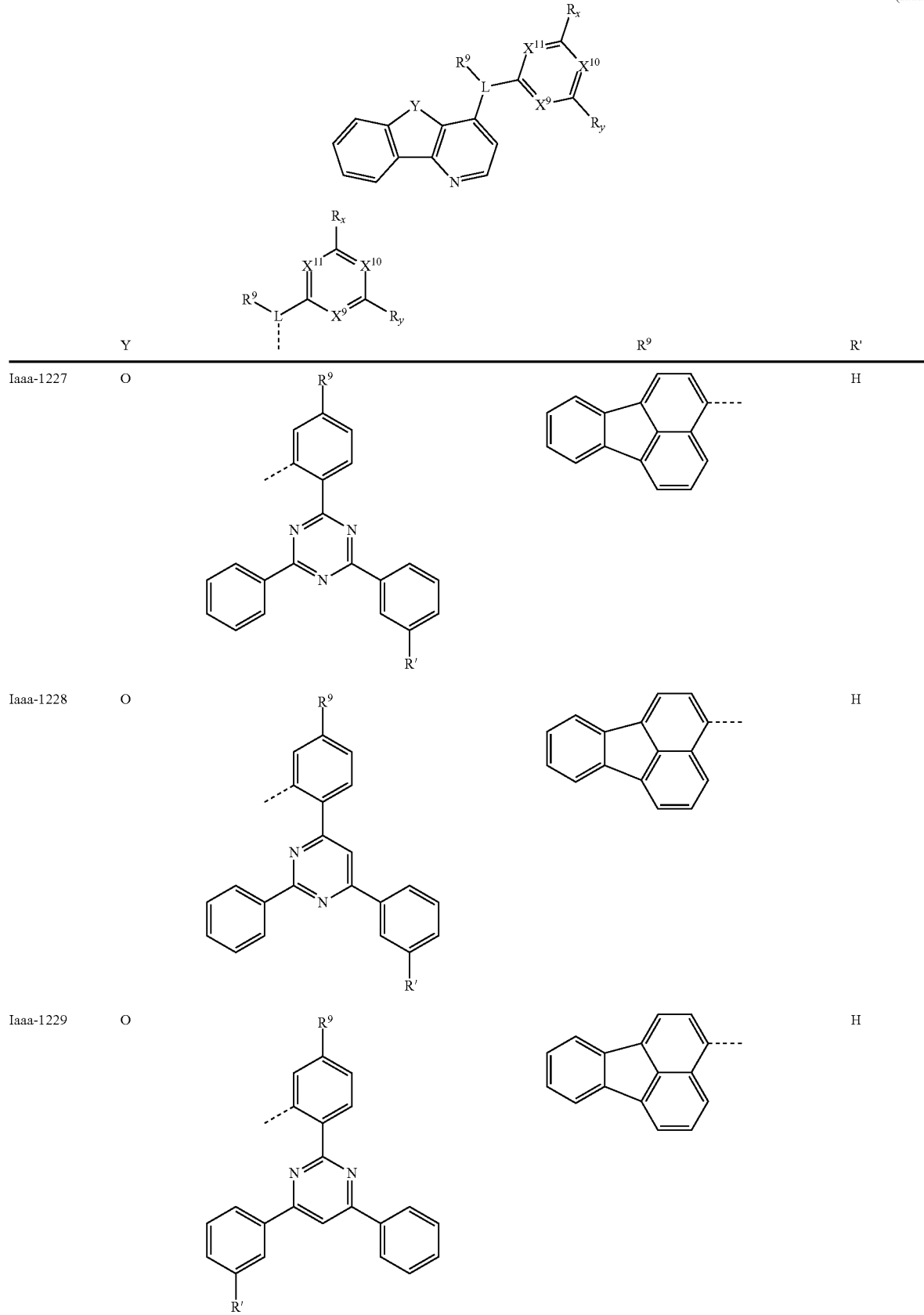

-continued
(Iaaa)
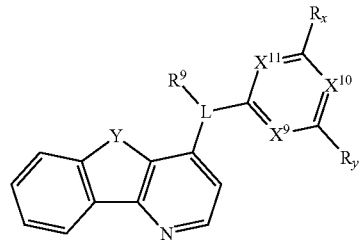
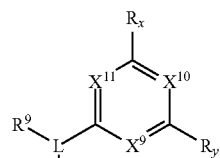
| | Y | | R⁹ | R' |
|---|---|---|---|---|
| Iaaa-1230 | O | 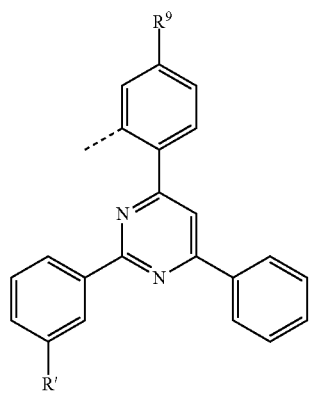 | 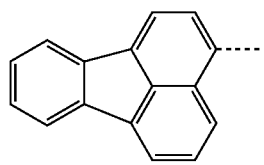 | H |
| Iaaa-1231 | O | 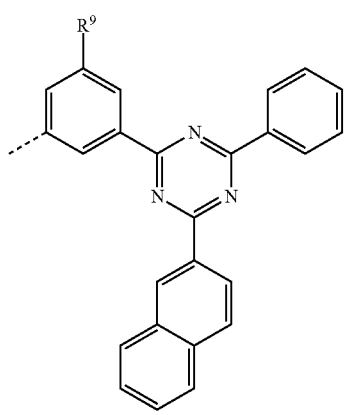 | 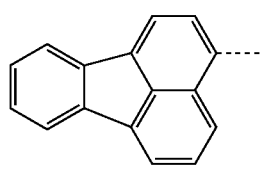 | — |

-continued
(Iaaa)
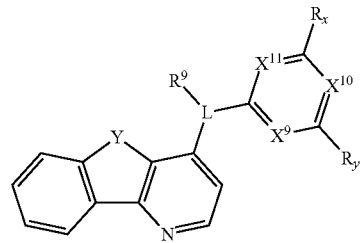
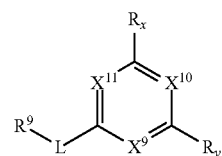
| | Y | R⁹ | | R' |
|---|---|---|---|---|
| Iaaa-1232 | O | 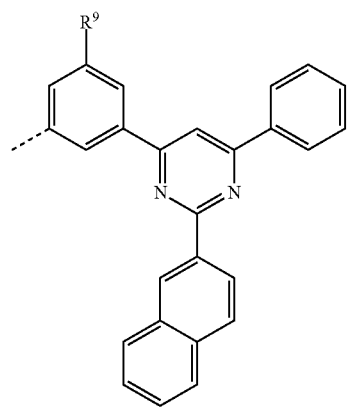 | 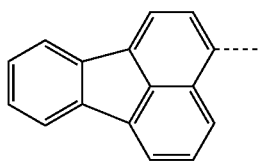 | — |
| Iaaa-1233 | O | 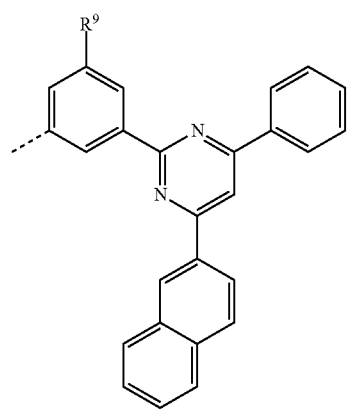 | 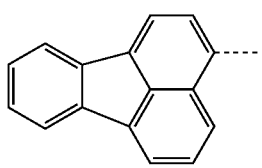 | — |

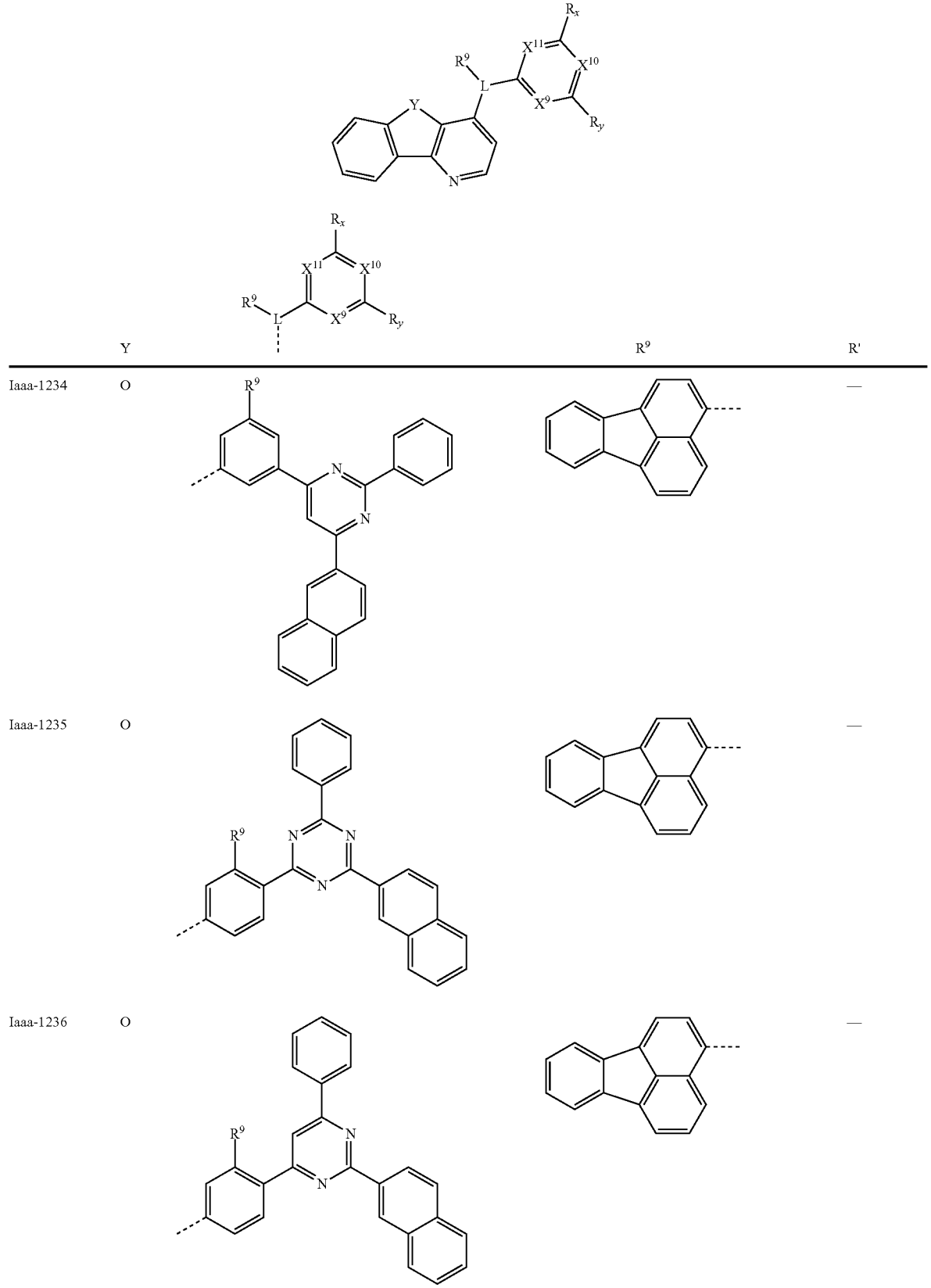

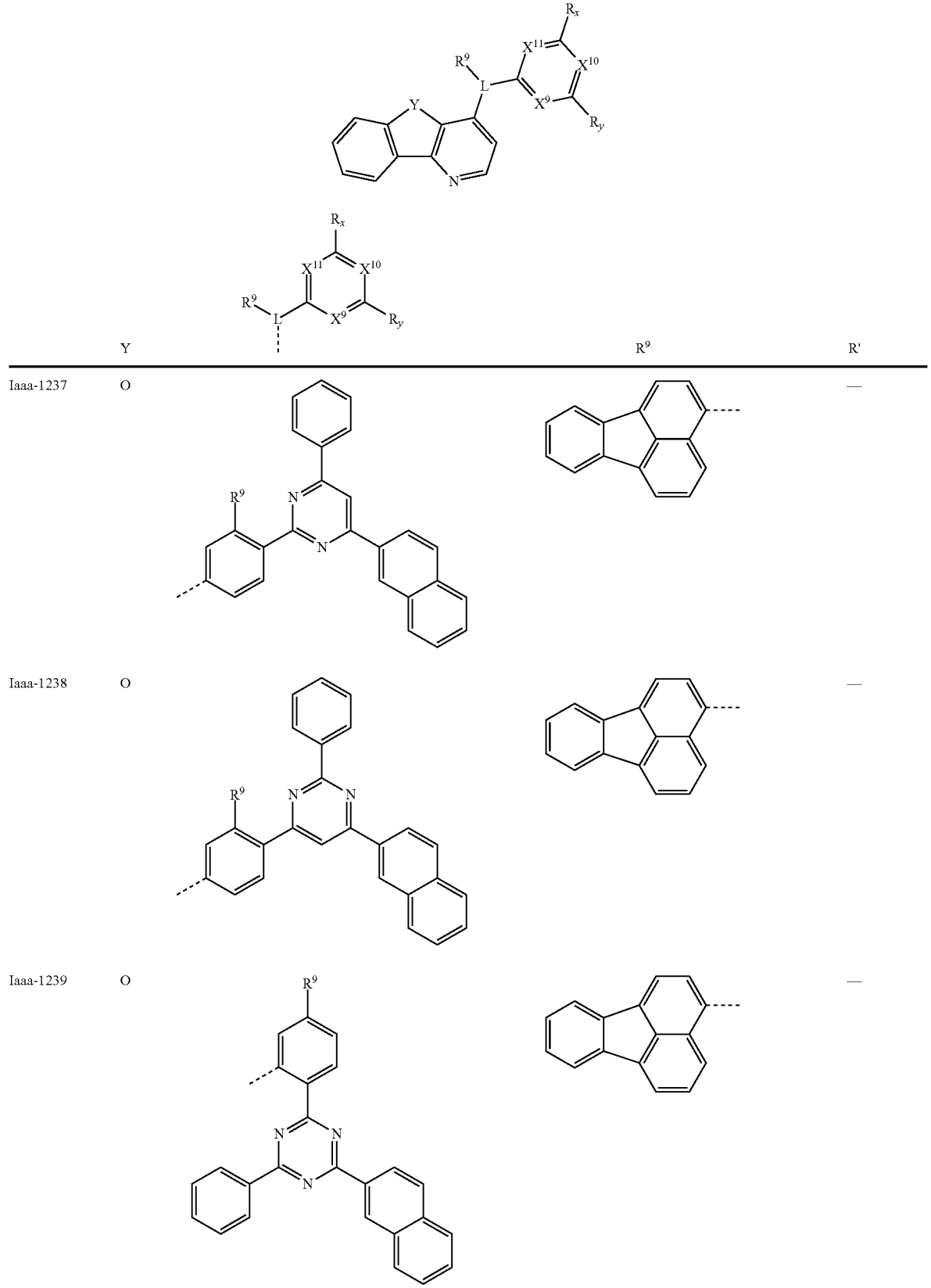

-continued
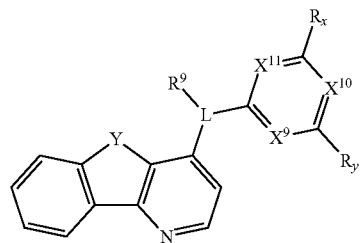
(Iaaa)
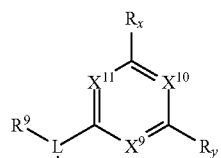
| | Y | R⁹ | R' |
|---|---|---|---|
| Iaaa-1240 | O | 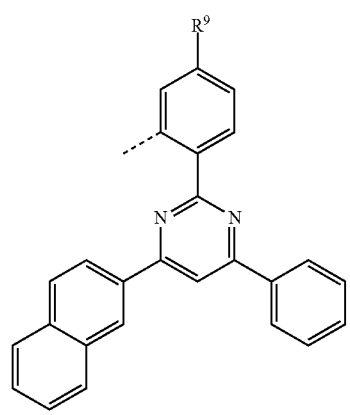 | 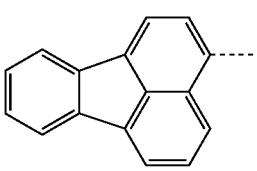 | — |
| Iaaa-1241 | O | | | — |
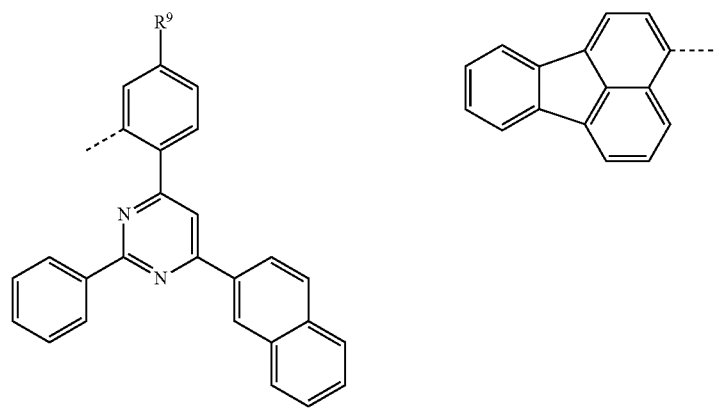

-continued
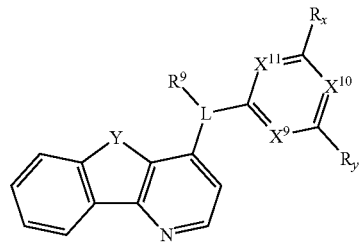
(Iaaa)
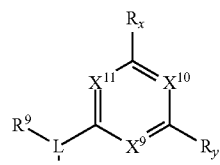
| | Y | R⁹ | | R' |
|---|---|---|---|---|
| Iaaa-1242 | O | 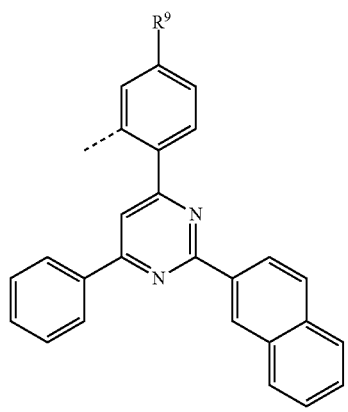 | 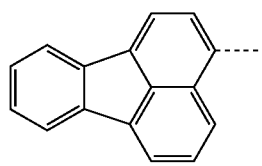 | — |
| Iaaa-1243 | O | 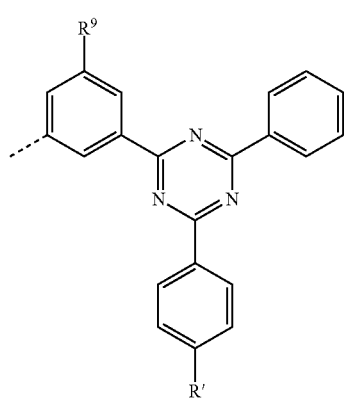 | 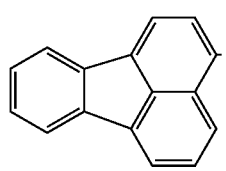 | 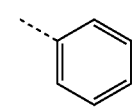 |

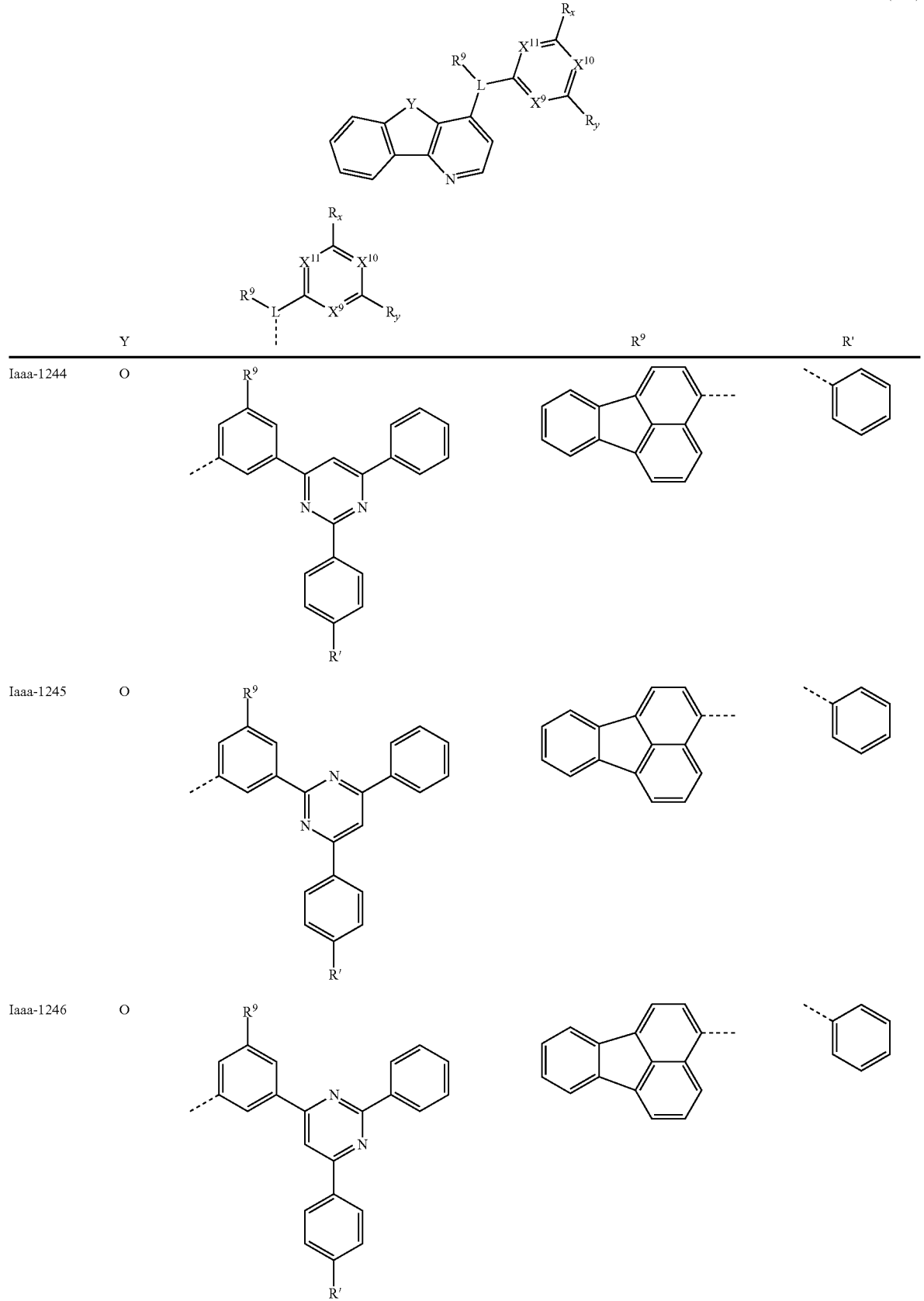

-continued
(Iaaa)
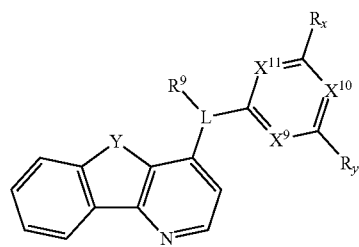
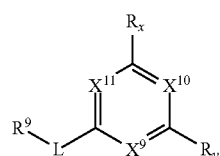
| | Y | | R⁹ | R' |
|---|---|---|---|---|
| Iaaa-1247 | O | 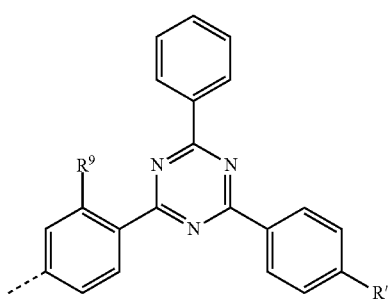 | 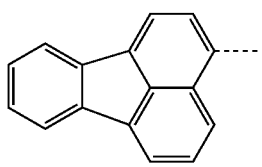 | 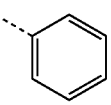 |
| Iaaa-1248 | O | 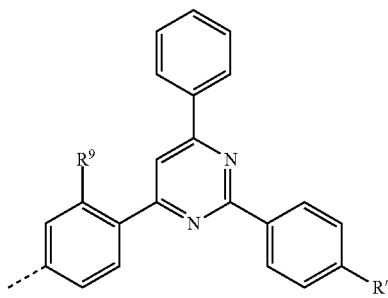 | 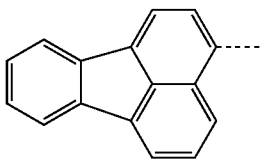 | 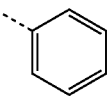 |
| Iaaa-1249 | O | 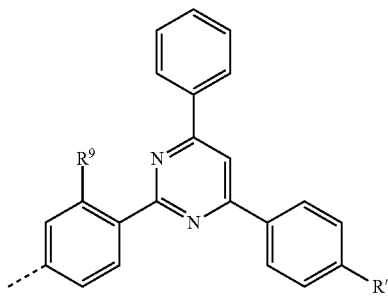 | 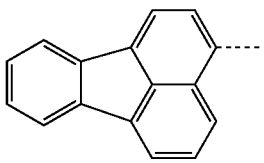 | 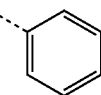 |

-continued
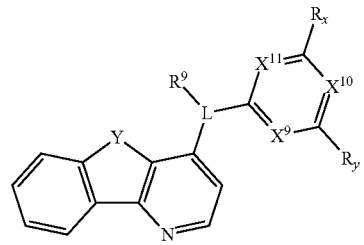
(Iaaa)
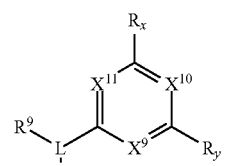
| | Y | R⁹ | R' |
|---|---|---|---|
| Iaaa-1250 | O | 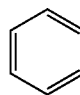 |  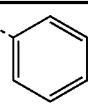 |
| Iaaa-1251 | O | 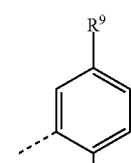 | 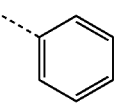 |
| Iaaa-1252 | O | 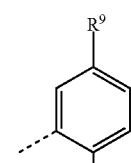 | 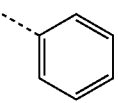 |

-continued
(Iaaa)
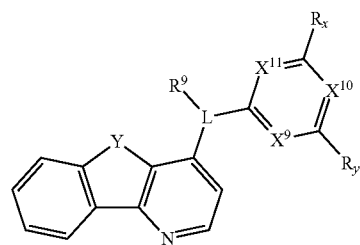
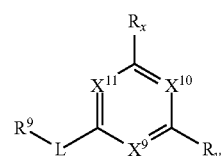
| | Y | | R⁹ | R' |
|---|---|---|---|---|
| Iaaa-1253 | O | 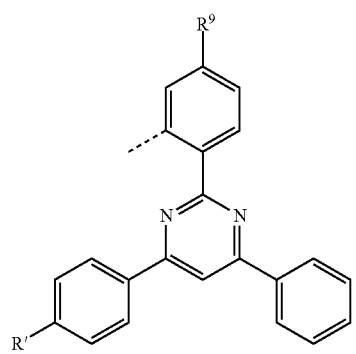 | 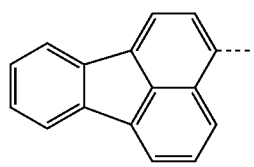 | 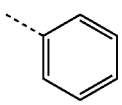 |
| Iaaa-1254 | O | 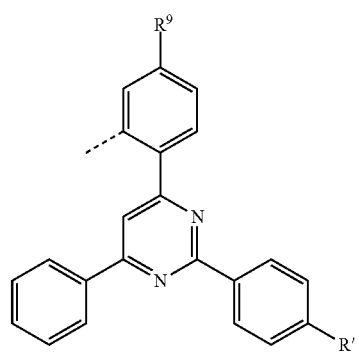 | 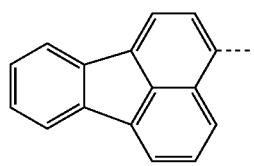 | 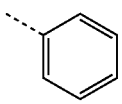 |
| Iaaa-1255 | O | 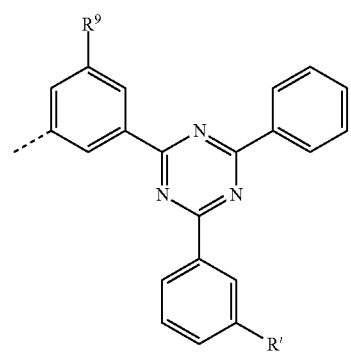 | 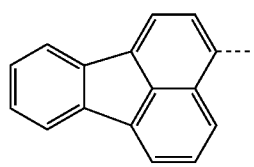 | 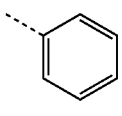 |

-continued
(Iaaa)
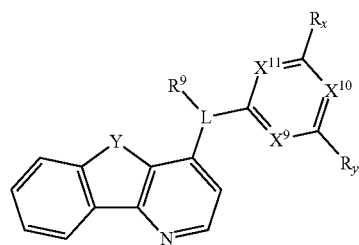
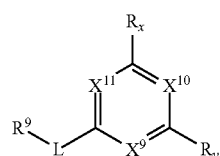
| | Y | | R⁹ | R' |
|---|---|---|---|---|
| Iaaa-1256 | O | 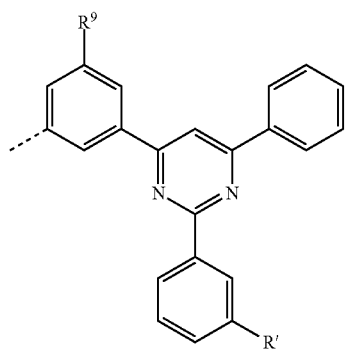 | 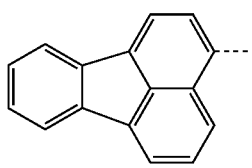 | 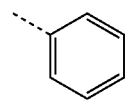 |
| Iaaa-1257 | O | 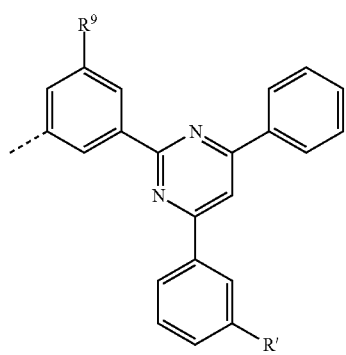 | 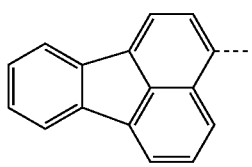 | 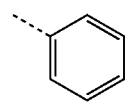 |
| Iaaa-1258 | O | 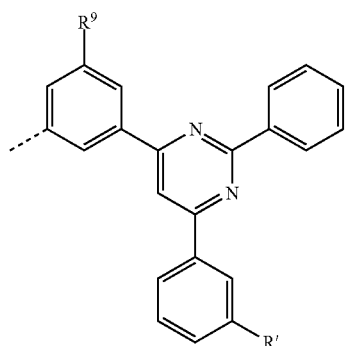 | 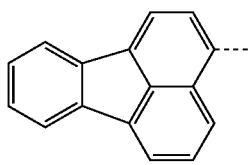 | 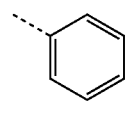 |

-continued
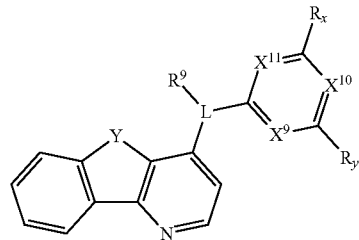
(Iaaa)
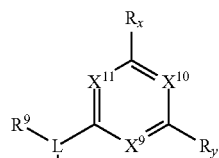
| | Y | | R⁹ | R' |
|---|---|---|---|---|
| Iaaa-1259 | O | 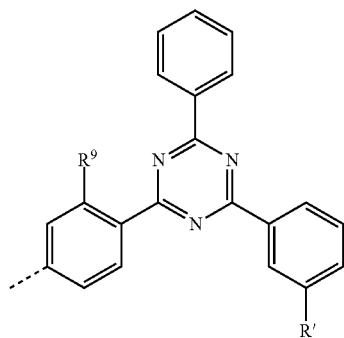 | 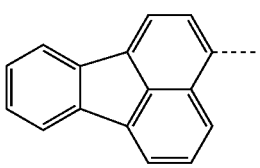 |  |
| Iaaa-1260 | O | 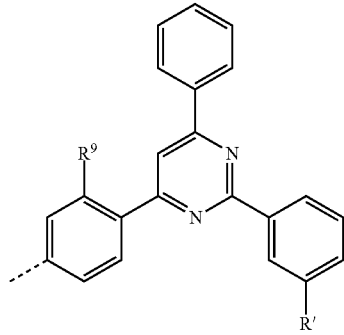 | 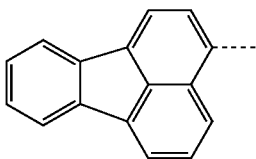 | 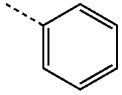 |
| Iaaa-1261 | O | 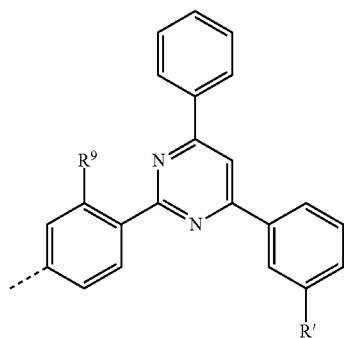 | 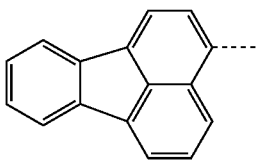 | 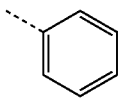 |

-continued
(Iaaa)
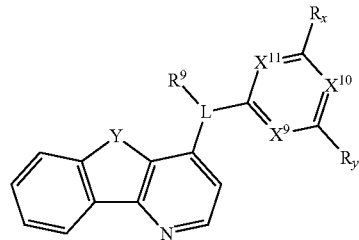
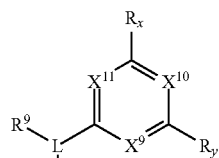
| | Y | | R⁹ | R' |
|---|---|---|---|---|
| Iaaa-1262 | O | 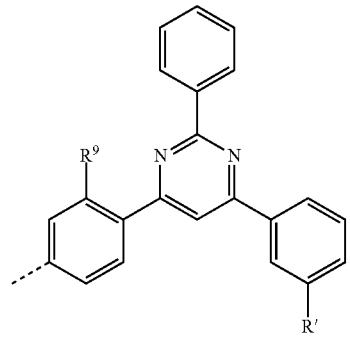 | 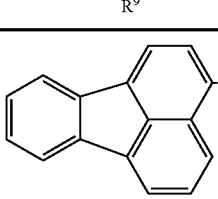 | 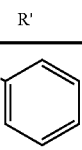 |
| Iaaa-1263 | O | 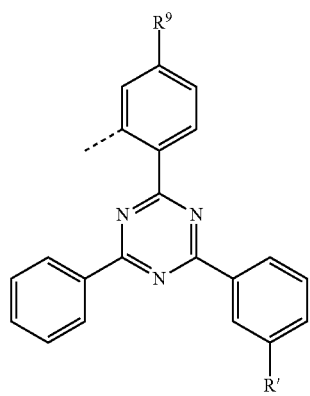 | 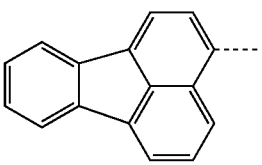 | 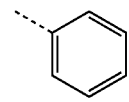 |
| Iaaa-1264 | O | 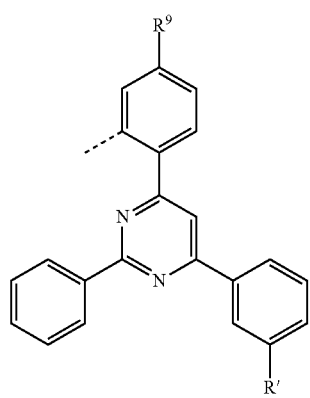 | 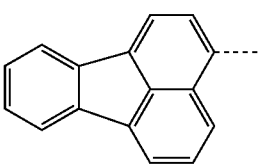 | 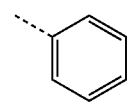 |

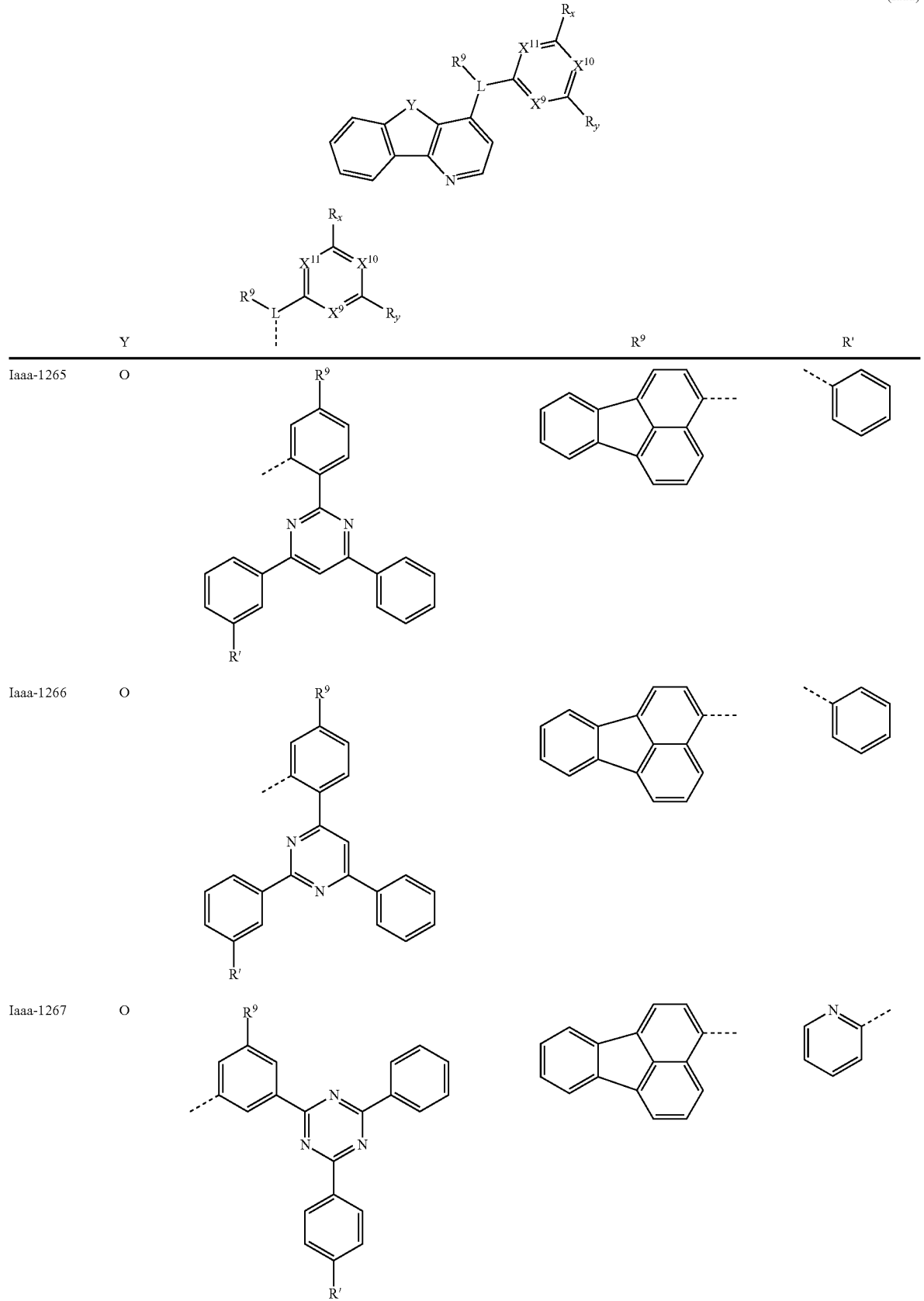

(Iaaa)
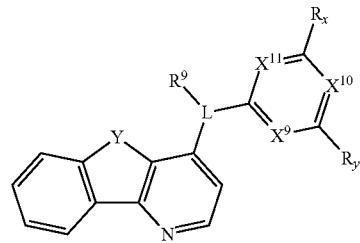
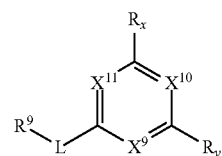
| | Y | R⁹ | | R' |
|---|---|---|---|---|
| Iaaa-1268 | O | 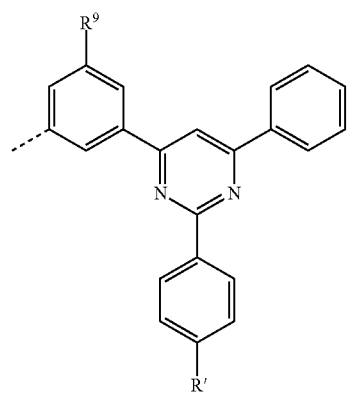 | 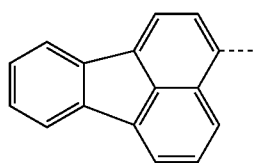 | 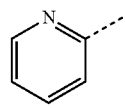 |
| Iaaa-1269 | O | 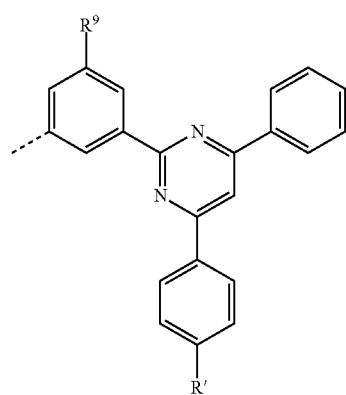 | 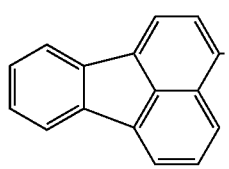 | 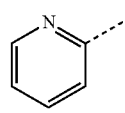 |

-continued
(Iaaa)
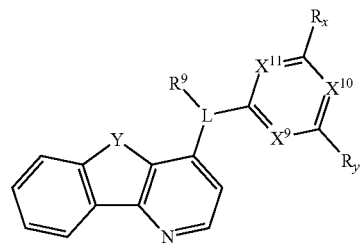
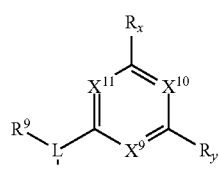
| | Y | R9 | | R' |
|---|---|---|---|---|
| Iaaa-1270 | O | 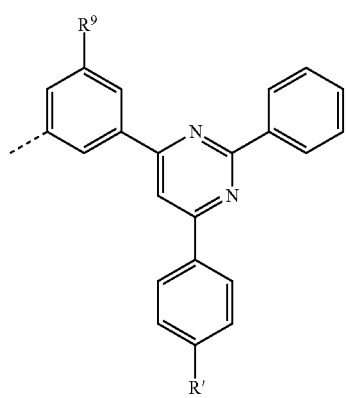 | 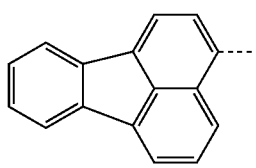 | 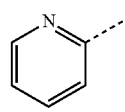 |
| Iaaa-1271 | O | 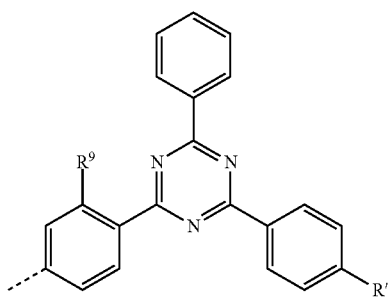 | 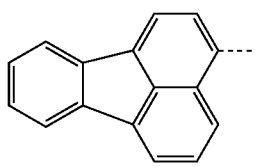 | 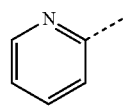 |
| Iaaa-1272 | O | 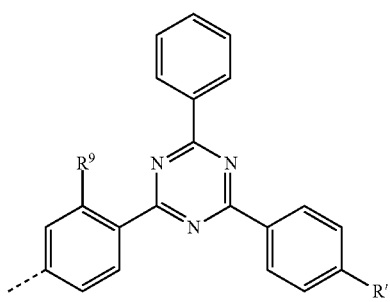 | 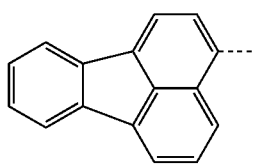 | 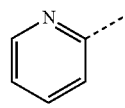 |

(Iaaa)
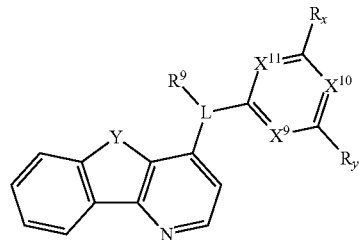
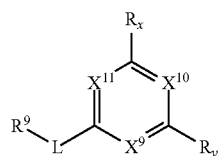
| | Y | R⁹ | R' |
|---|---|---|---|
| Iaaa-1273 | O | 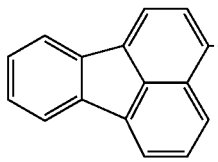 | 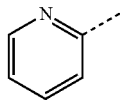 |
| | | 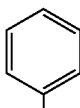 | |
| | | 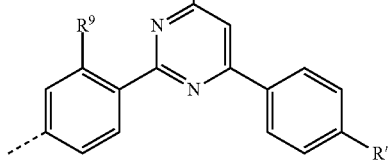 | |
| Iaaa-1274 | O | 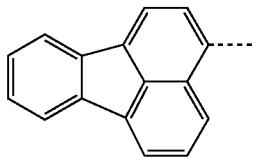 | 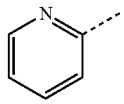 |
| | | 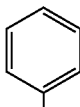 | |
| | | 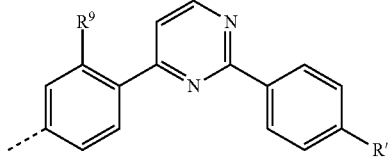 | |
| Iaaa-1275 | O | 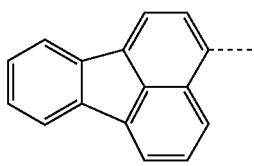 | 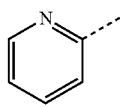 |
| | | 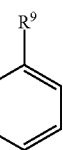 | |
| | | 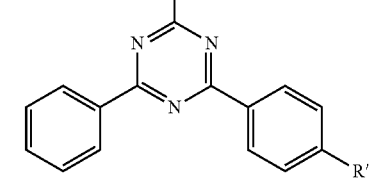 | |

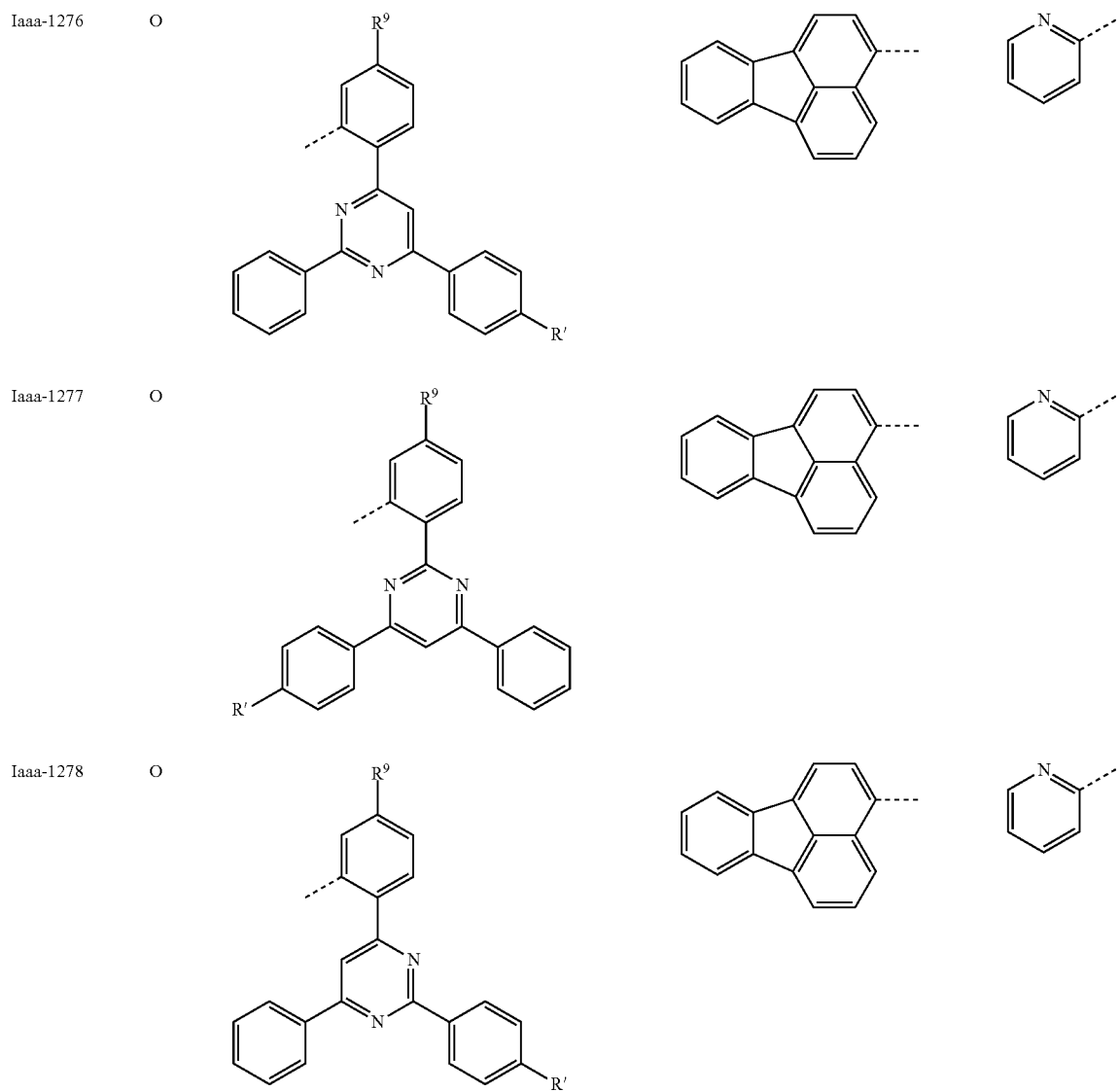

-continued
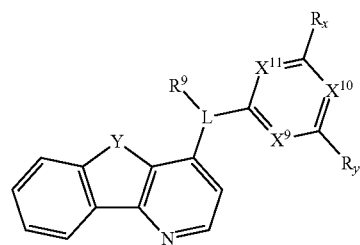
(Iaaa)
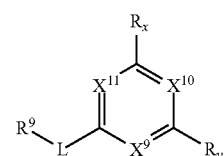
| | Y | R⁹ | | R' |
|---|---|---|---|---|
| Iaaa-1279 | O | 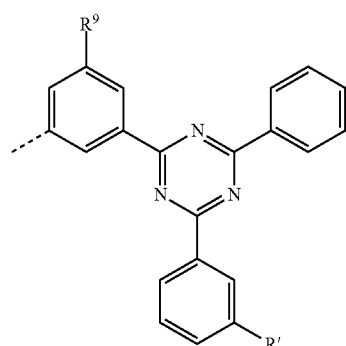 | 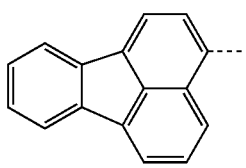 | 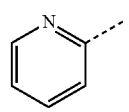 |
| Iaaa-1280 | O | 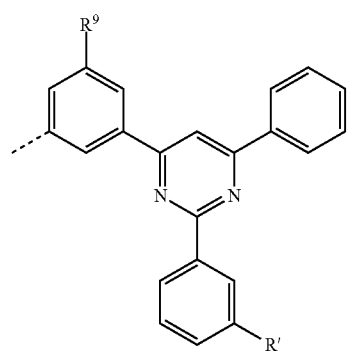 | 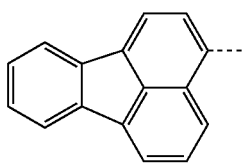 | 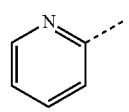 |
| Iaaa-1281 | O | 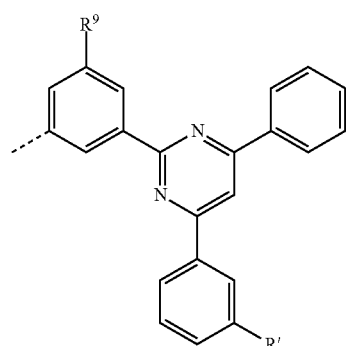 | 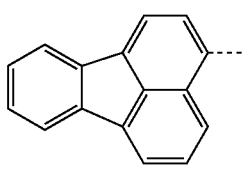 | 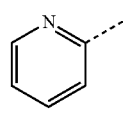 |

-continued
(Iaaa)
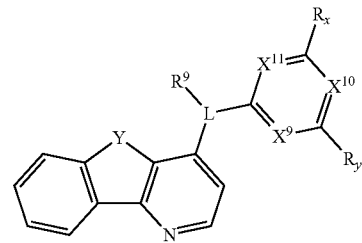
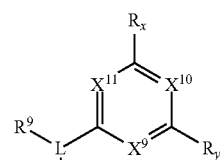
| | Y | | R⁹ | R' |
|---|---|---|---|---|
| Iaaa-1282 | O | 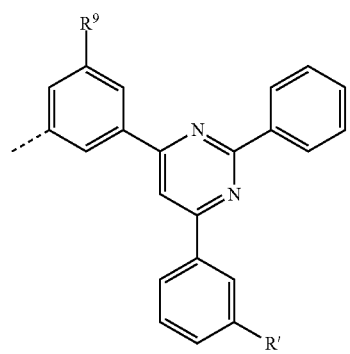 | 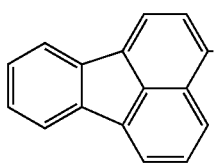 | 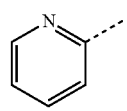 |
| Iaaa-1283 | O | 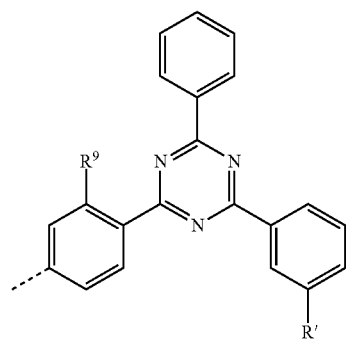 |  | 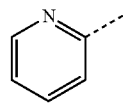 |
| Iaaa-1284 | O | 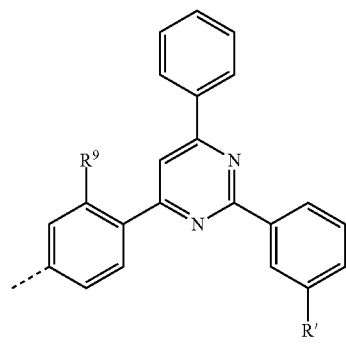 | 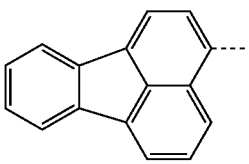 | 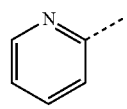 |

-continued
(Iaaa)
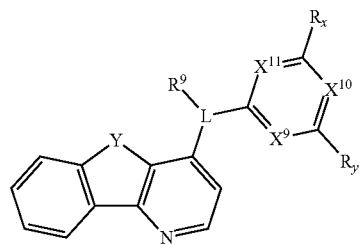
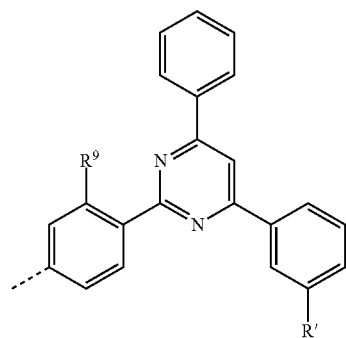
| | Y | | R⁹ | R' |
|---|---|---|---|---|
| Iaaa-1285 | O | 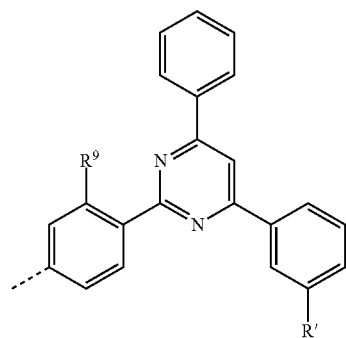 | 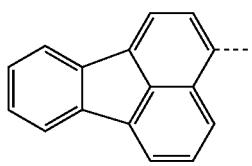 | 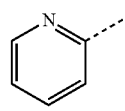 |
| Iaaa-1286 | O | 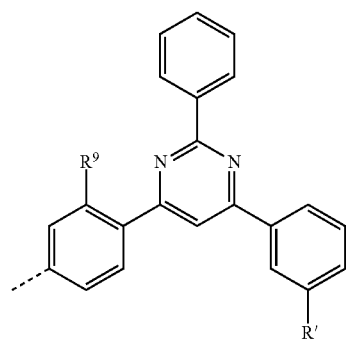 | 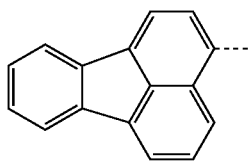 | 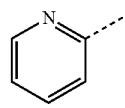 |
| Iaaa-1287 | O | 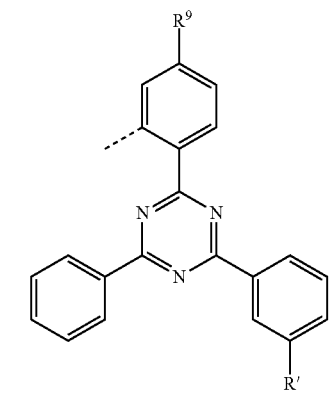 | 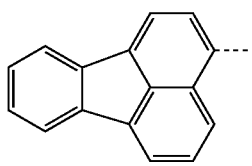 | 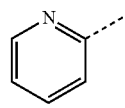 |

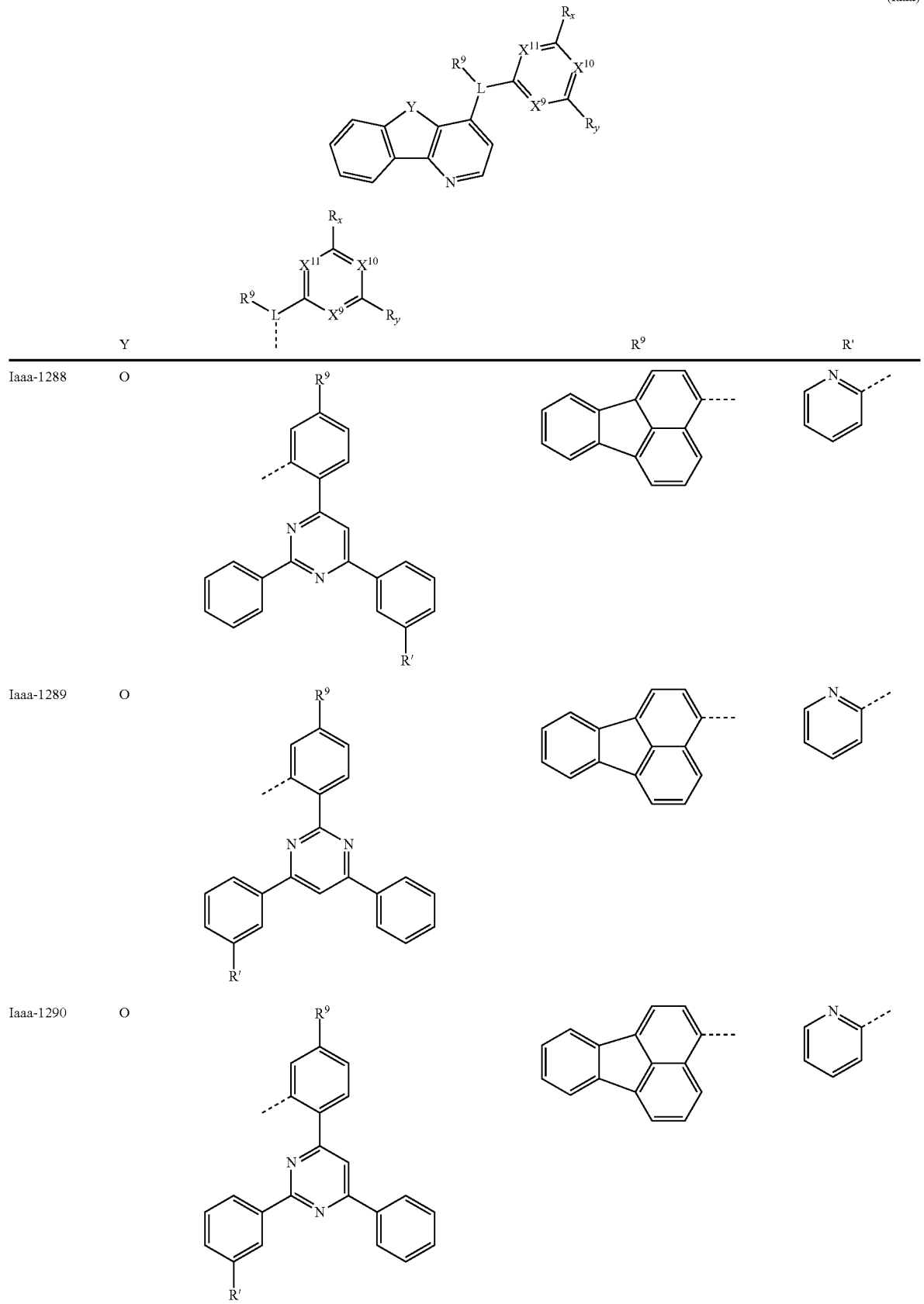

(Iaaa)
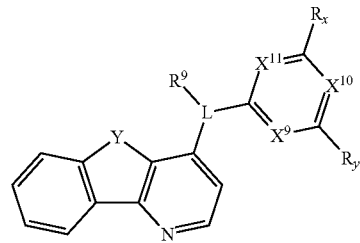
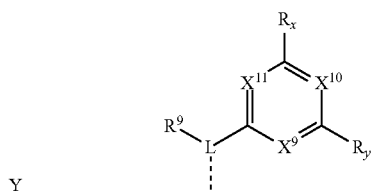
| | Y | R⁹ | R' |
|---|---|---|---|
| Iaaa-1291 | S | 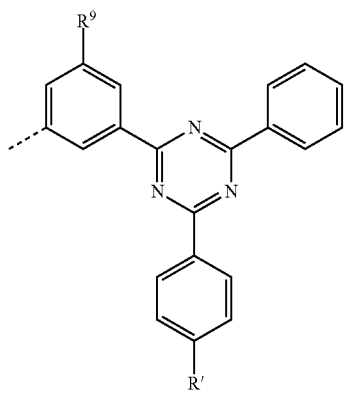 | 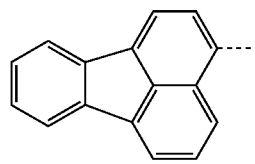 H |
| Iaaa-1292 | S | 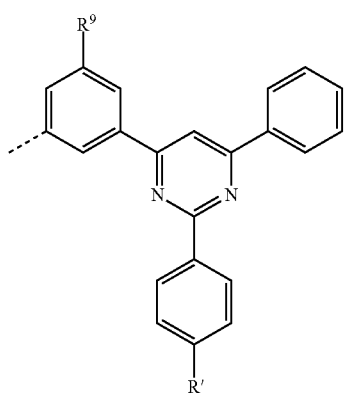 | 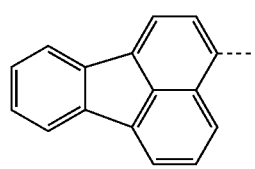 H |

-continued
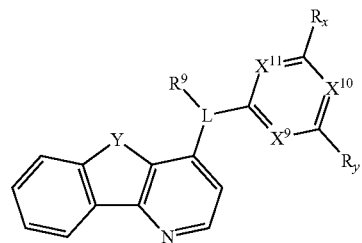
(Iaaa)
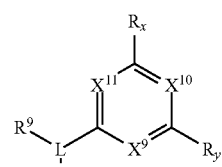
| | Y | | R⁹ | R' |
|---|---|---|---|---|
| Iaaa-1293 | S | 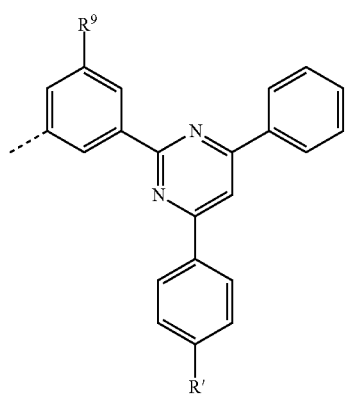 | 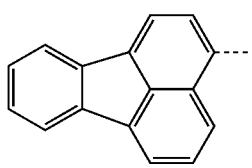 | H |
| Iaaa-1294 | S | 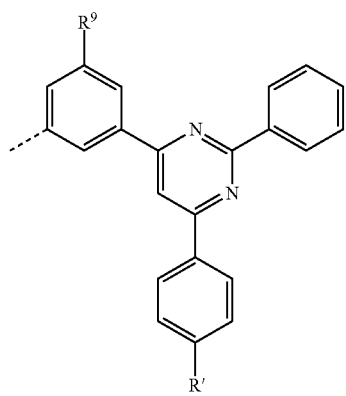 | 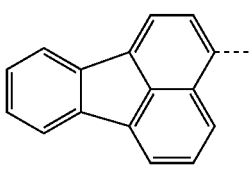 | H |
| Iaaa-1295 | S | 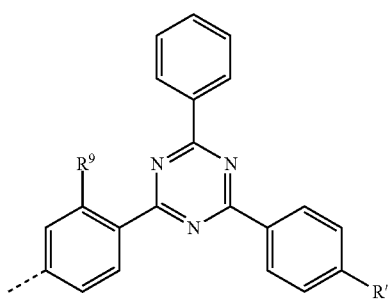 | 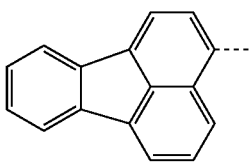 | H |

-continued
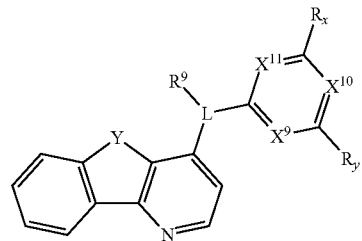
(Iaaa)
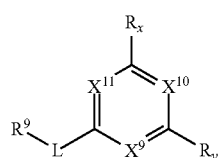
| | Y | | R⁹ | R' |
|---|---|---|---|---|
| Iaaa-1296 | S | 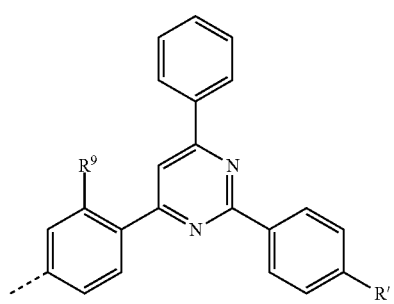 | 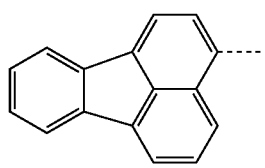 | H |
| Iaaa-1297 | S | 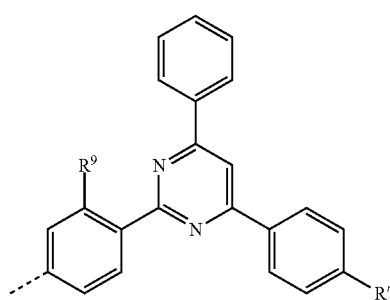 | 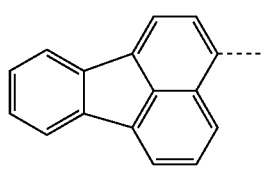 | H |
| Iaaa-1298 | S | 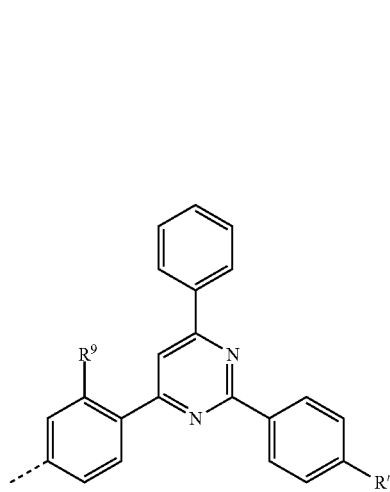 | 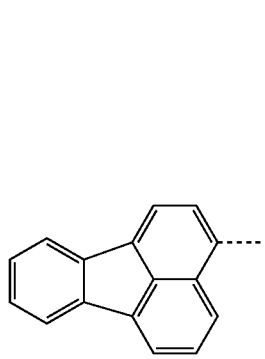 | H |

-continued
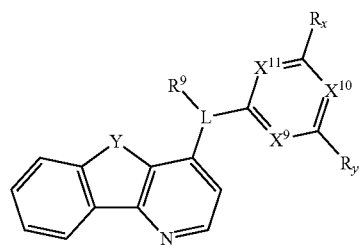
(Iaaa)
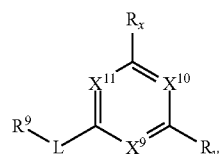
| | Y | R⁹ | | R' |
|---|---|---|---|---|
| Iaaa-1299 | S | 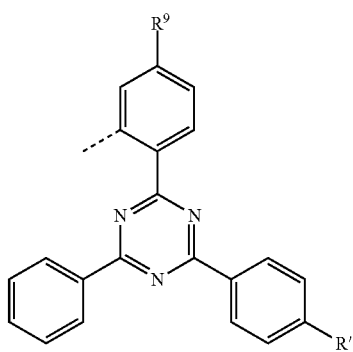 | 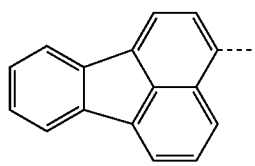 | H |
| Iaaa-1300 | S | 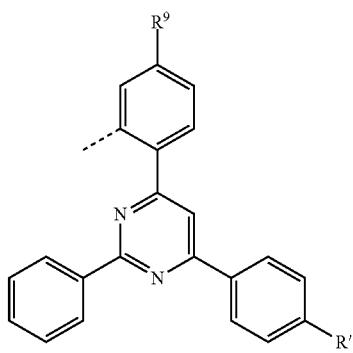 | 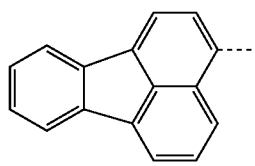 | H |
| Iaaa-1301 | S | 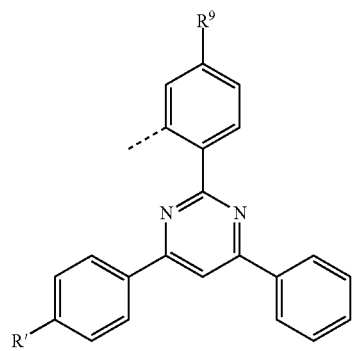 | 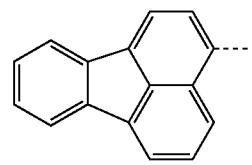 | H |

-continued
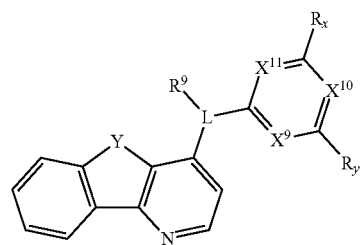
(Iaaa)
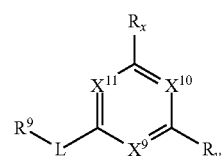
| | Y | | R⁹ | R' |
|---|---|---|---|---|
| Iaaa-1302 | S | 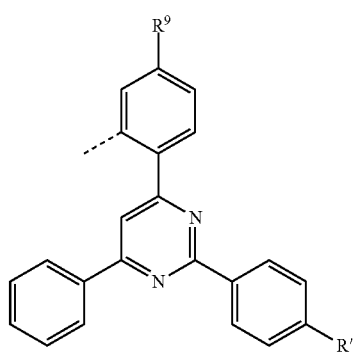 | 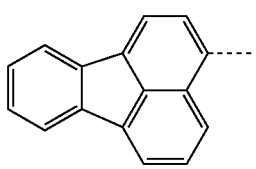 | H |
| Iaaa-1303 | S | 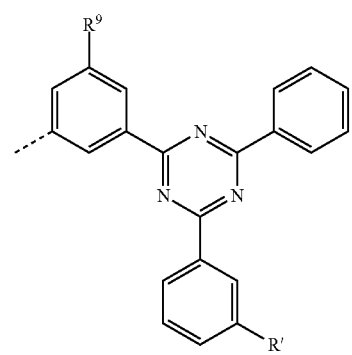 | 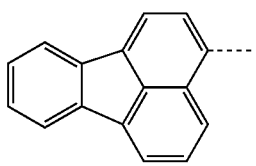 | H |
| Iaaa-1304 | S | 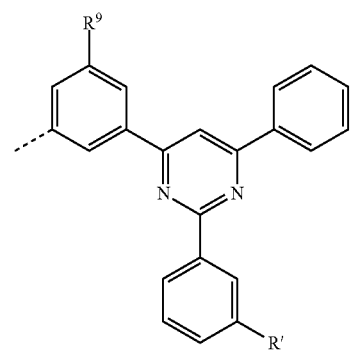 | 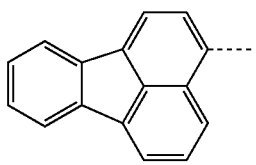 | H |

-continued
(Iaaa)
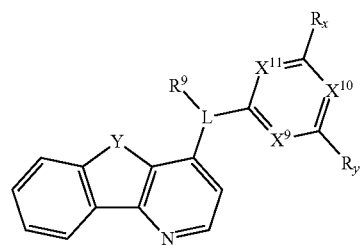
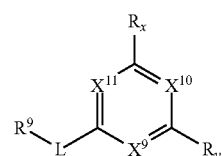
| | Y | R⁹ | | R' |
|---|---|---|---|---|
| Iaaa-1305 | S | 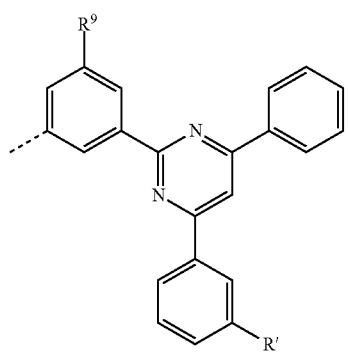 | 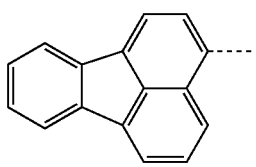 | H |
| Iaaa-1306 | S | 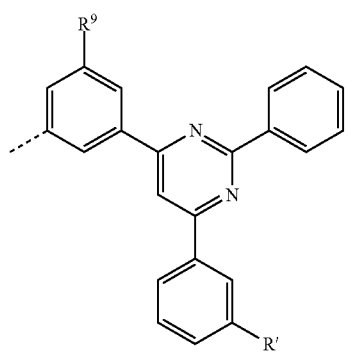 | 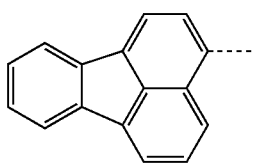 | H |
| Iaaa-1307 | S | 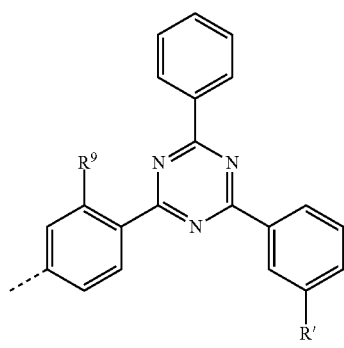 | 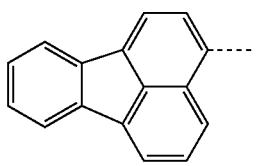 | H |

-continued
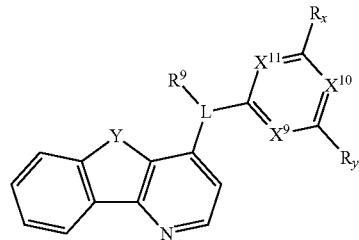
(Iaaa)
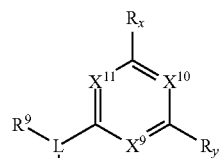
| | Y | R⁹ | R' |
|---|---|---|---|
| Iaaa-1308 | S | 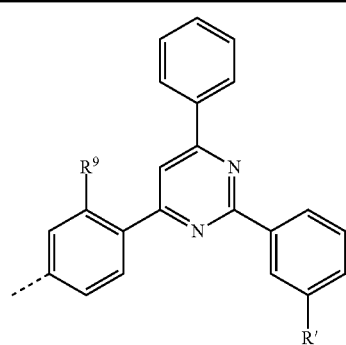 | 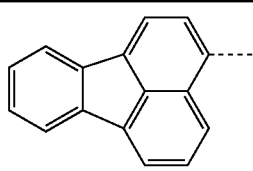 H |
| Iaaa-1309 | S | 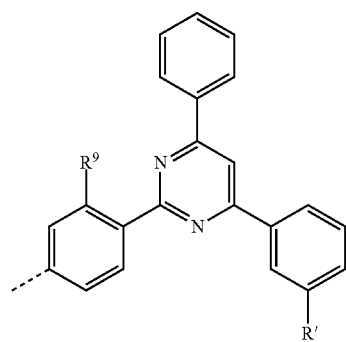 | 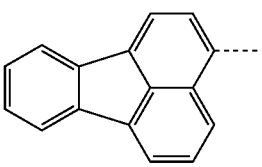 H |
| Iaaa-1310 | S | 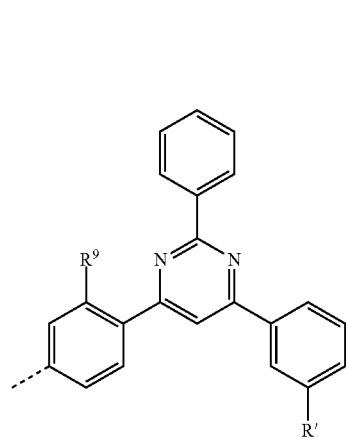 | 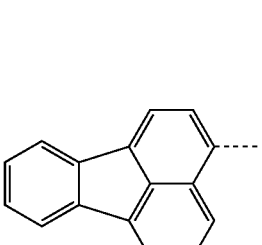 H |

-continued
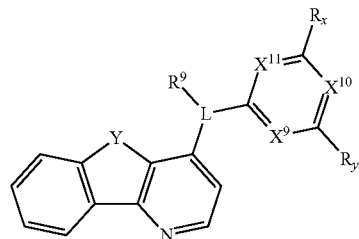
(Iaaa)
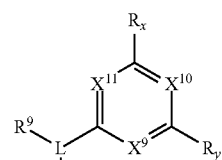
| | Y | | R⁹ | R' |
|---|---|---|---|---|
| Iaaa-1311 | S | 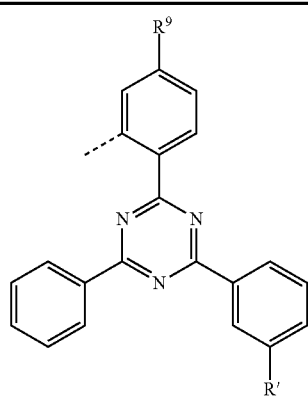 | 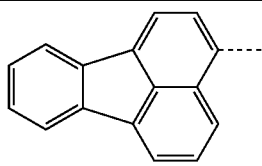 | H |
| Iaaa-1312 | S | 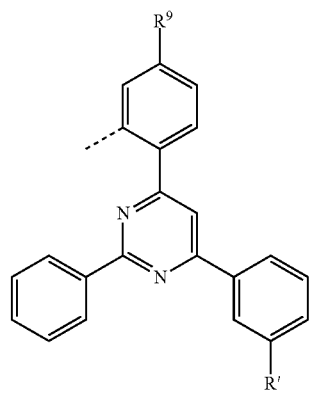 | 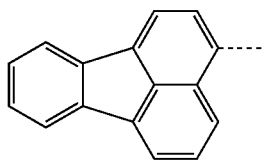 | H |
| Iaaa-1313 | S | 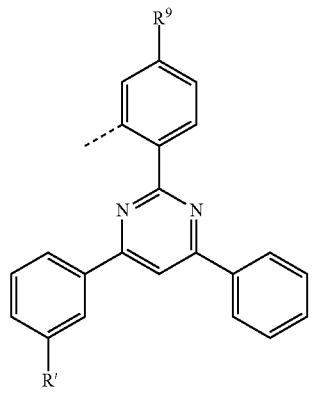 | 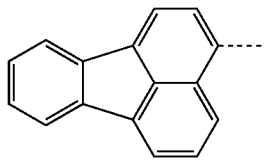 | H |

-continued
(Iaaa)
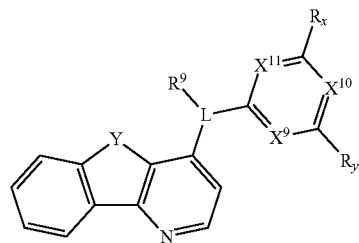
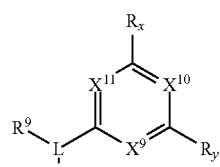
| | Y | R[9] | R' |
|---|---|---|---|
| Iaaa-1314 | S | 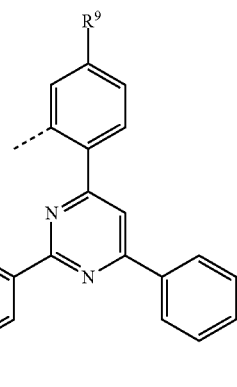 | 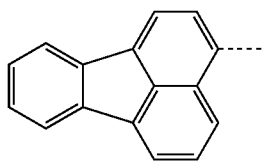 H |
| Iaaa-1315 | S | 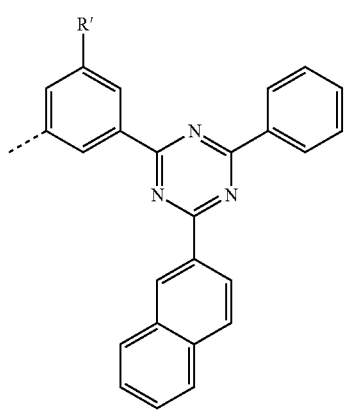 | 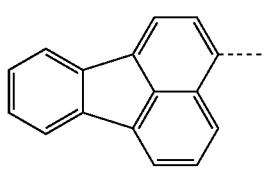 — |

-continued
(Iaaa)
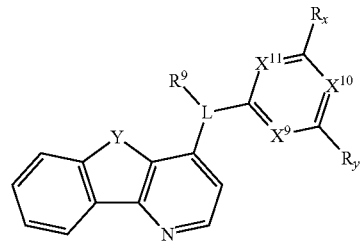
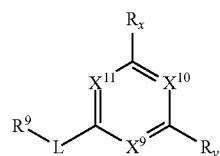
| | Y | R⁹ | R' |
|---|---|---|---|
| Iaaa-1316 | S | 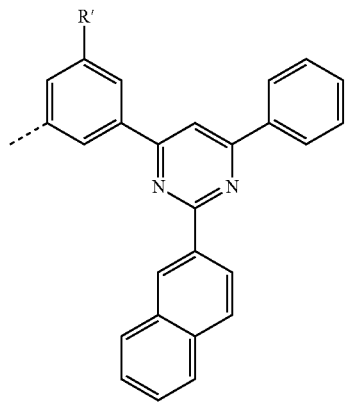 | 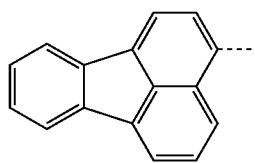 | — |
| Iaaa-1317 | S | 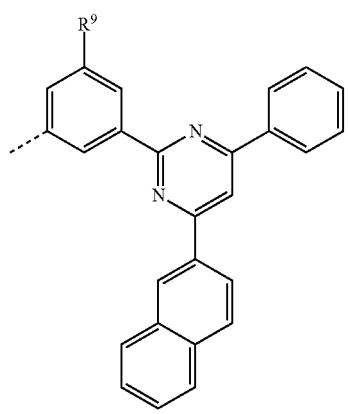 | 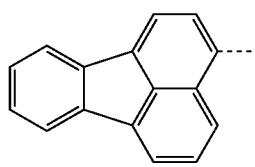 | — |

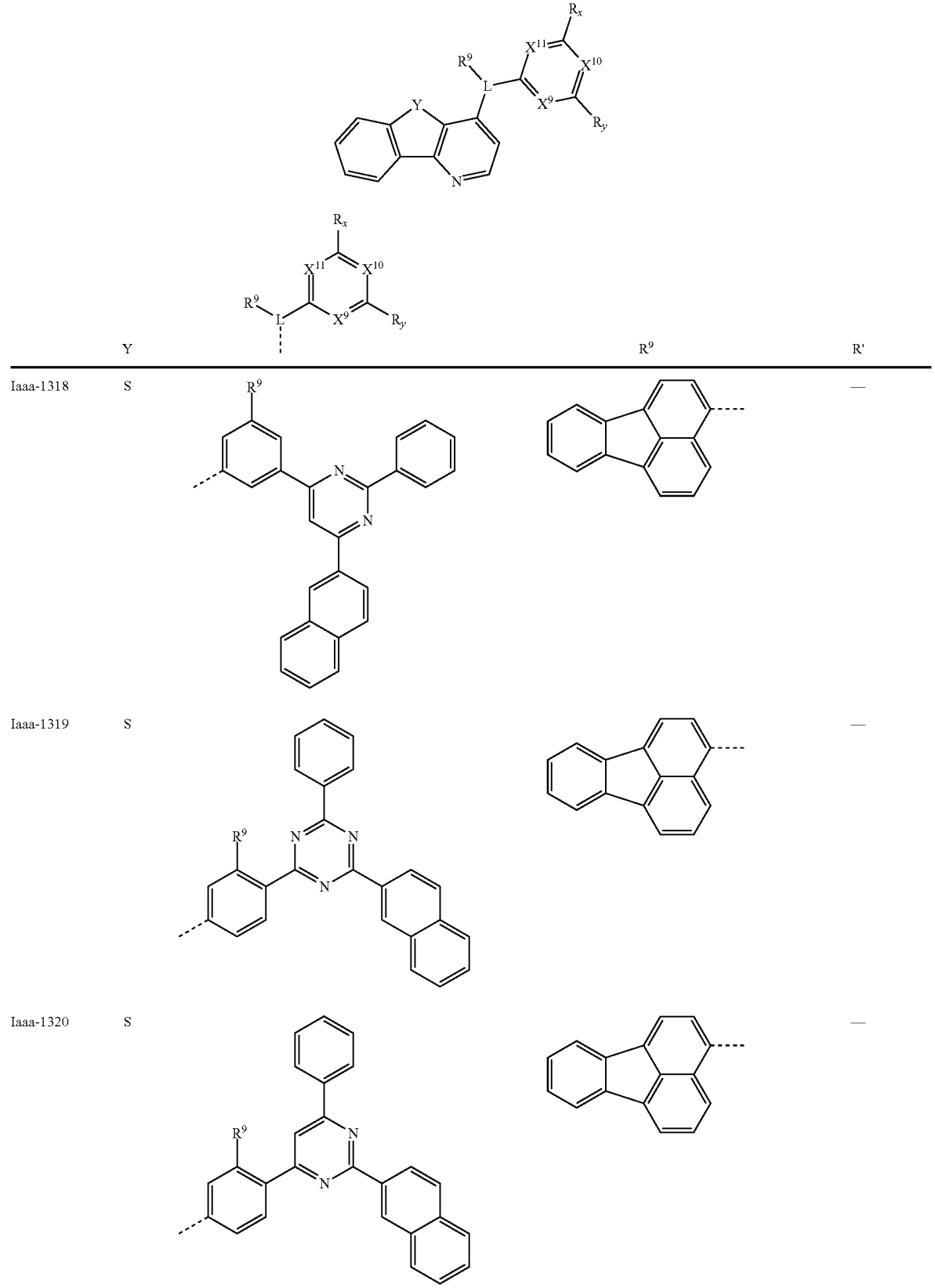

-continued
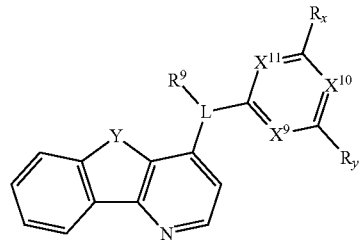
(Iaaa)
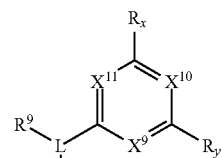
| | Y | R⁹ | R' |
|---|---|---|---|
| Iaaa-1321 | S | 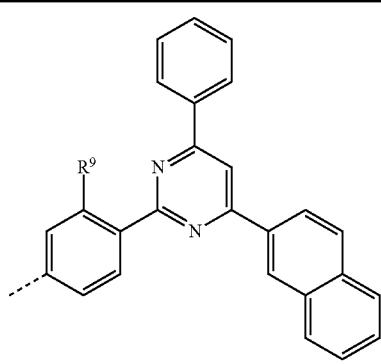 | 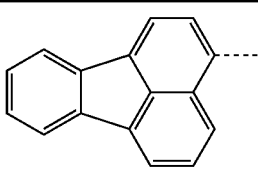 | — |
| Iaaa-1322 | S | 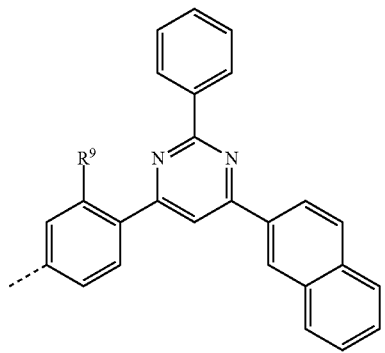 | 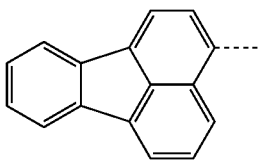 | — |
| Iaaa-1323 | S | 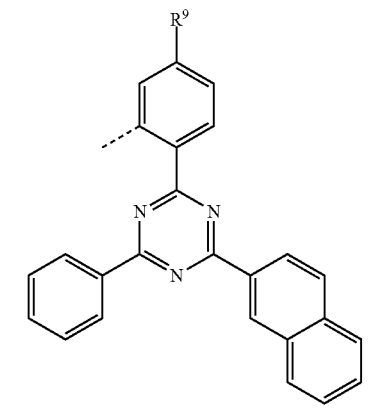 | 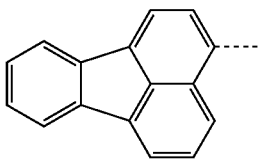 | — |

-continued
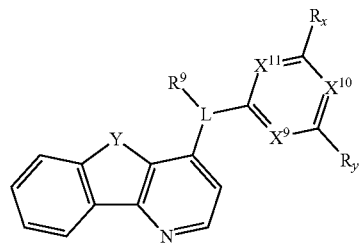
(Iaaa)
| | Y | R⁹ | R' |
|---|---|---|---|
| Iaaa-1324 | S | 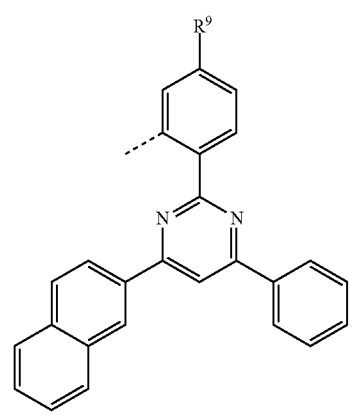 | 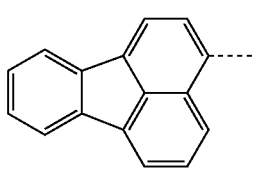 | — |
| Iaaa-1325 | S | 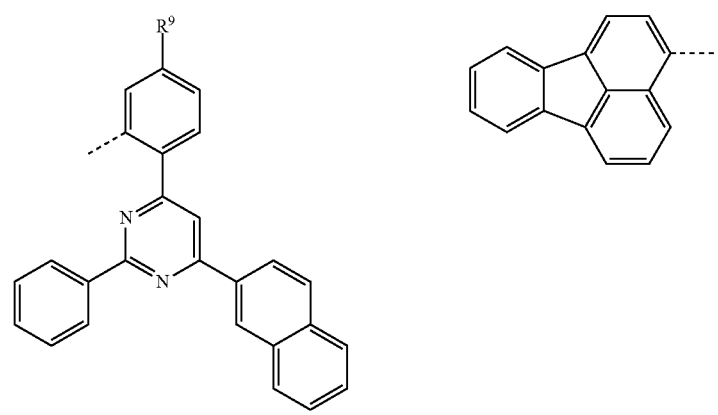 | | — |

-continued
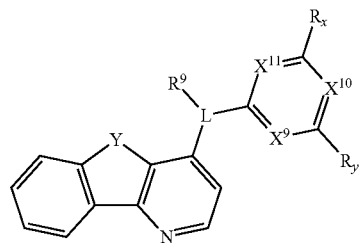
(Iaaa)
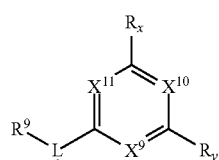
| | Y | | R⁹ | R' |
|---|---|---|---|---|
| Iaaa-1326 | S | 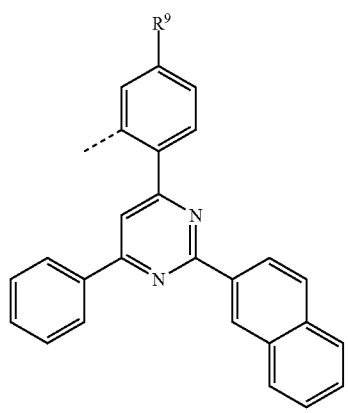 | 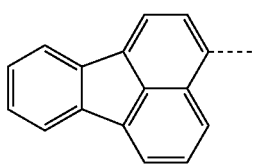 | — |
| Iaaa-1327 | S | 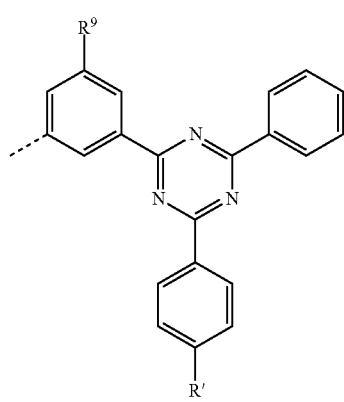 | 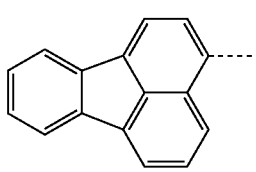 | 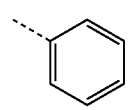 |

-continued
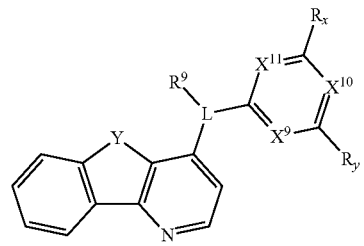
(Iaaa)
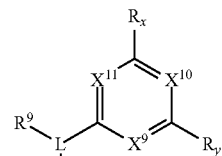
| | Y | R⁹ | | R' |
|---|---|---|---|---|
| Iaaa-1328 | S | 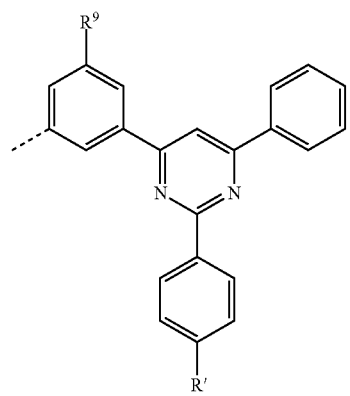 | 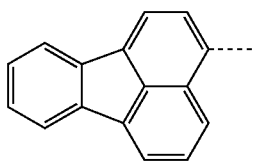 |  |
| Iaaa-1329 | S | 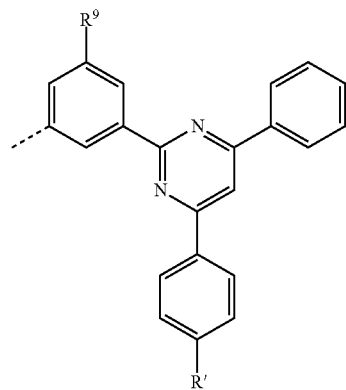 | 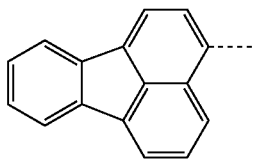 |  |
| Iaaa-1330 | S | 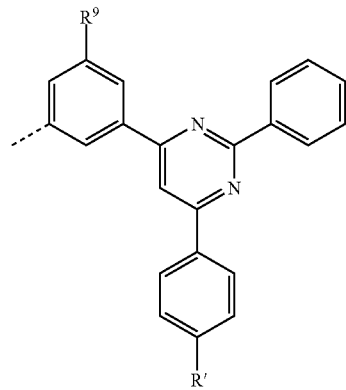 | 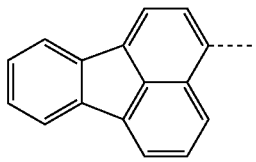 |  |

-continued
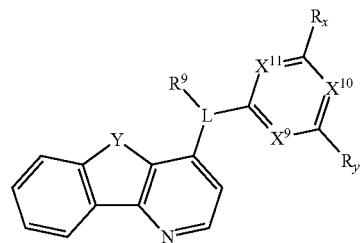
(Iaaa)
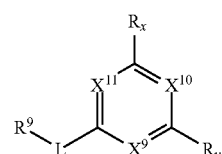
| | Y | | R9 | R' |
|---|---|---|---|---|
| Iaaa-1331 | S | 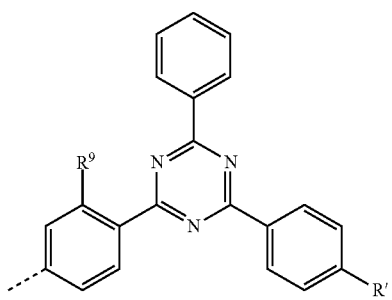 | 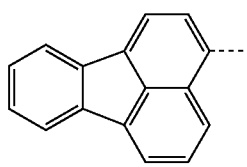 | 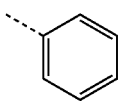 |
| Iaaa-1332 | S | 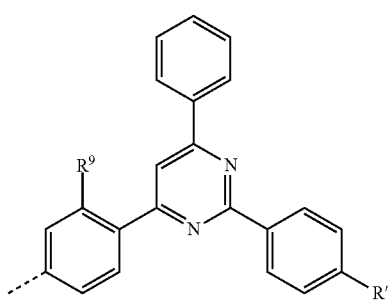 | 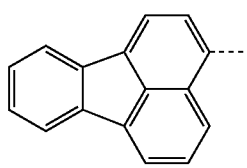 | 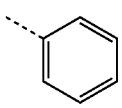 |
| Iaaa-1333 | S | 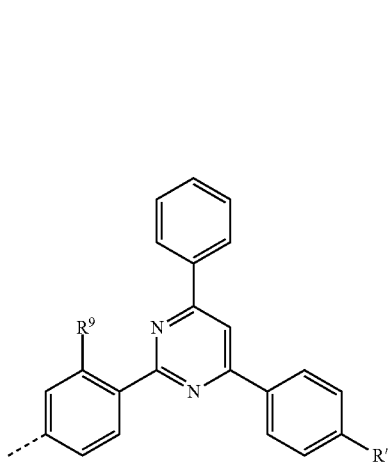 | 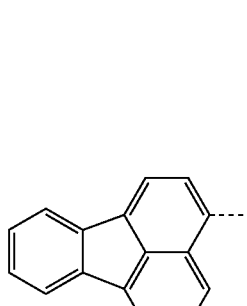 |  |

-continued
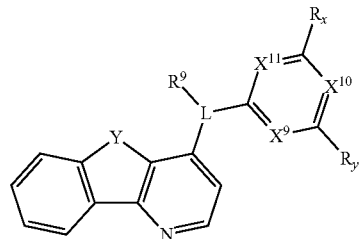
(Iaaa)
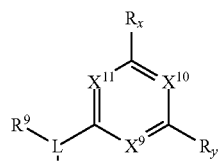
| | Y | R⁹ | R' |
|---|---|---|---|
| Iaaa-1334 | S | 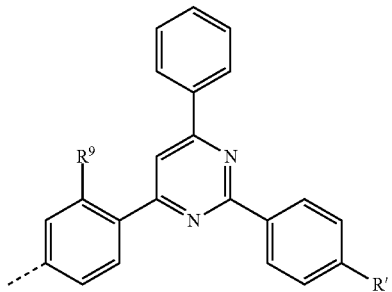 | 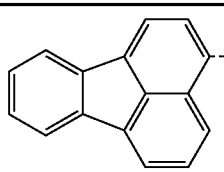 | 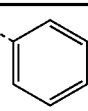 |
| Iaaa-1335 | S | 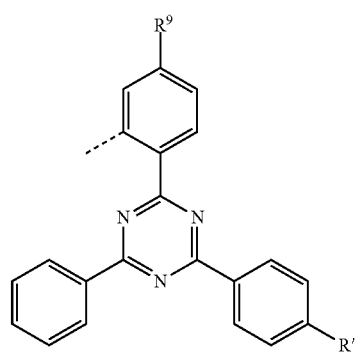 | 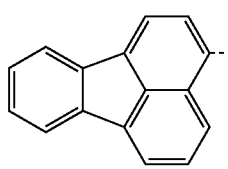 | 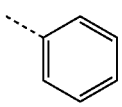 |
| Iaaa-1336 | S | 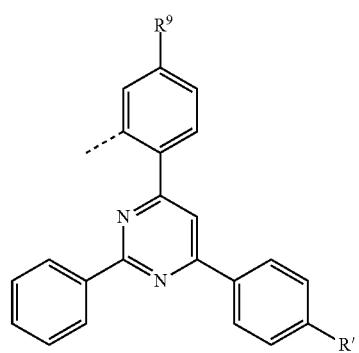 | 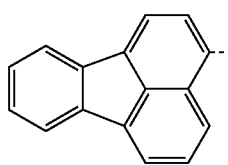 | 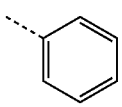 |

-continued
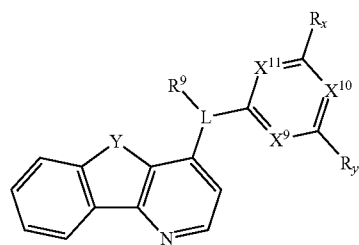
(Iaaa)
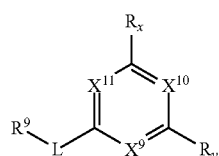
| | Y | R⁹ | R' |
|---|---|---|---|
| Iaaa-1337 | S | 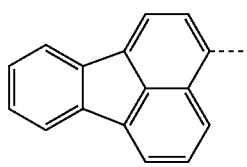 | 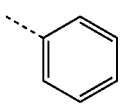 |
| | | 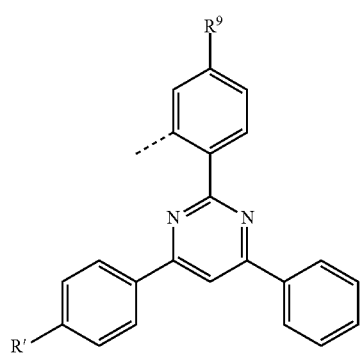 | |
| Iaaa-1338 | S | 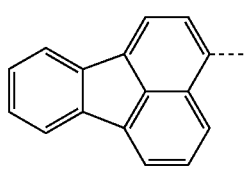 | 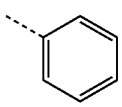 |
| | | 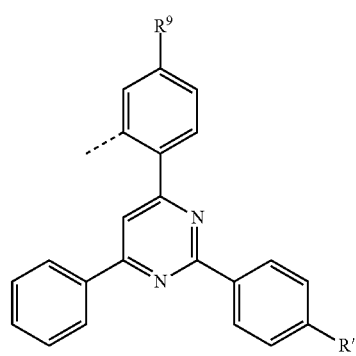 | |
| Iaaa-1339 | S | 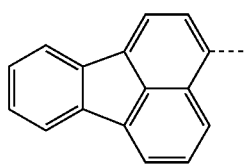 | 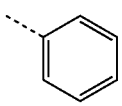 |
| | | 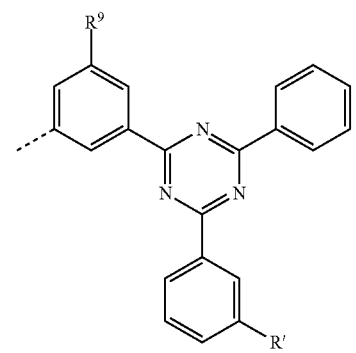 | |

-continued
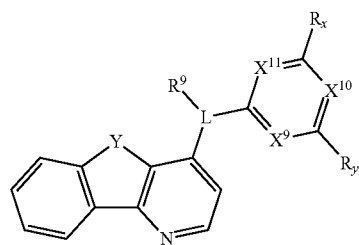
(Iaaa)
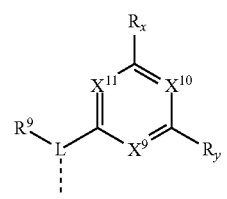
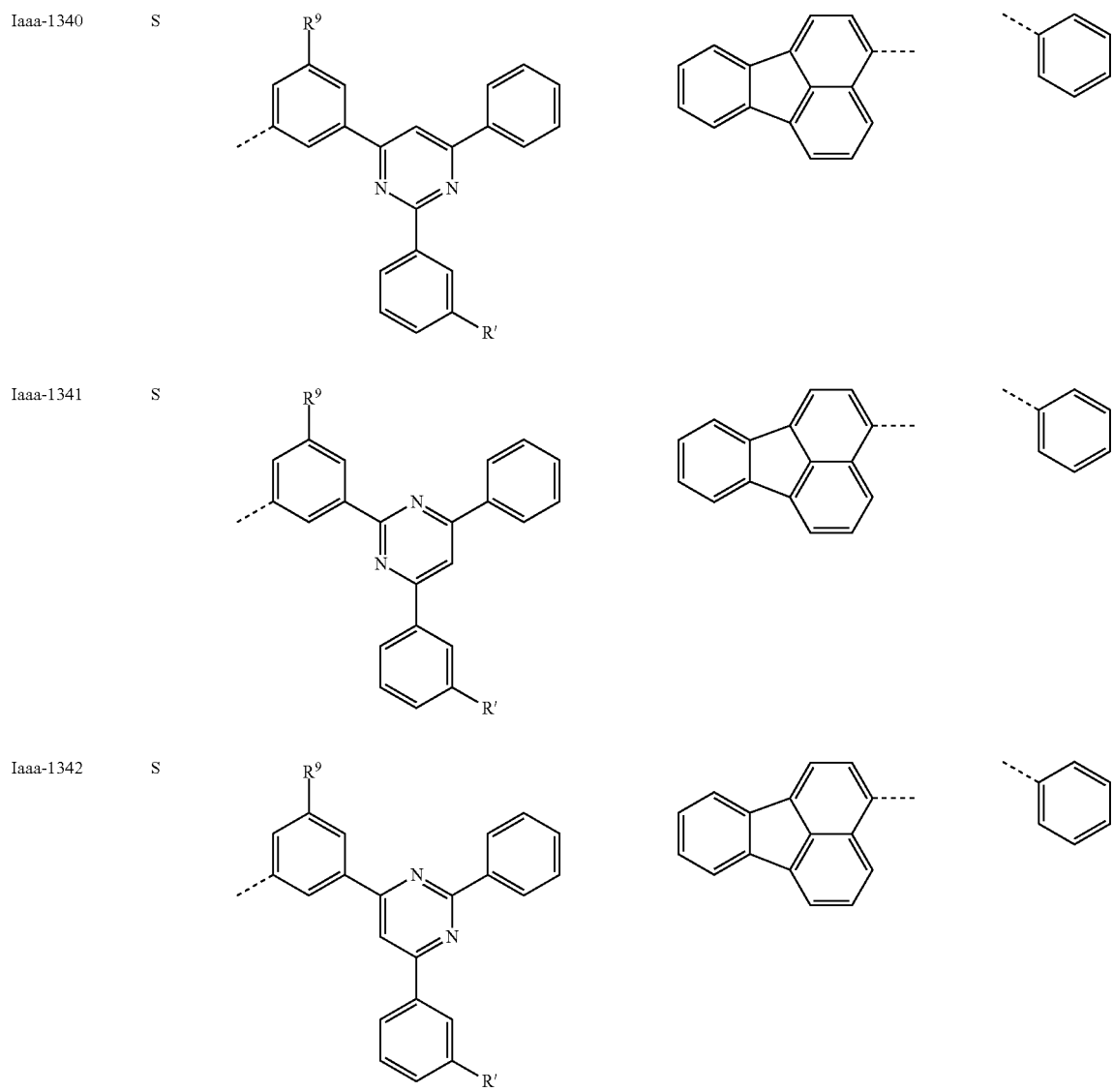

-continued
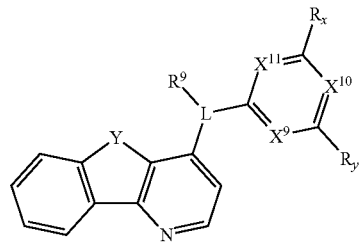
(Iaaa)
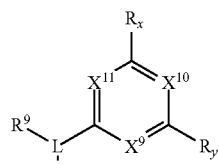
| | Y | | $R^9$ | $R'$ |
|---|---|---|---|---|
| Iaaa-1343 | S | 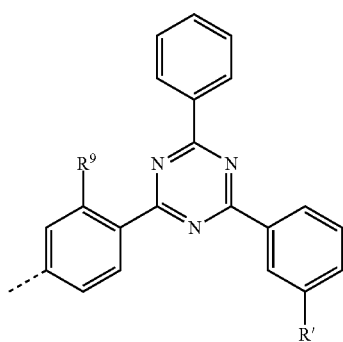 | 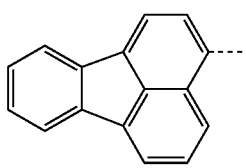 | 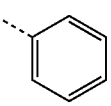 |
| Iaaa-1344 | S | 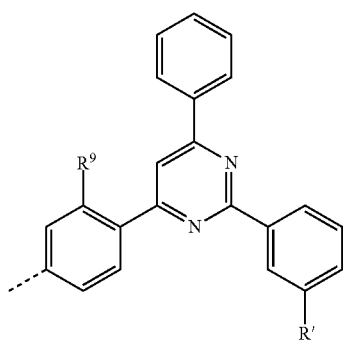 | 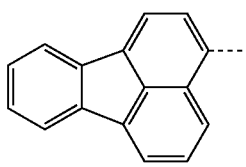 | 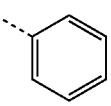 |
| Iaaa-1345 | S | 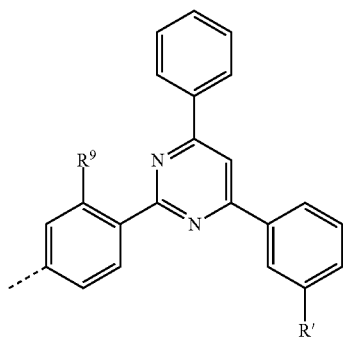 | 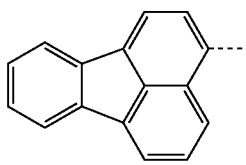 | 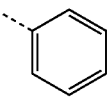 |

-continued
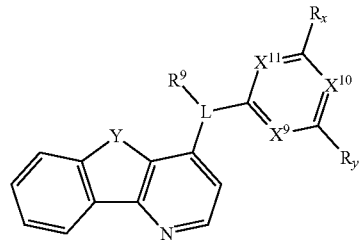
(Iaaa)
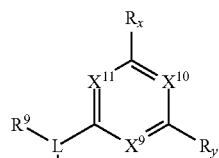
| | Y | R⁹ | | R' |
|---|---|---|---|---|
| Iaaa-1346 | S | 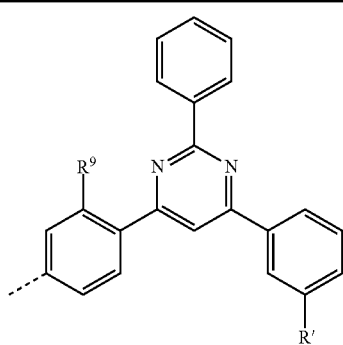 | 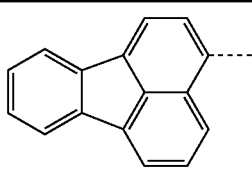 | 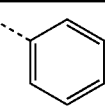 |
| Iaaa-1347 | S | 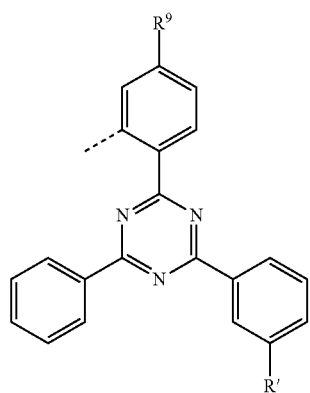 | 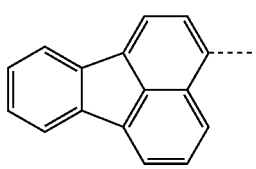 | 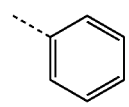 |
| Iaaa-1348 | S | 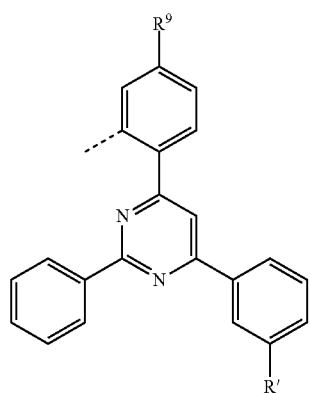 | 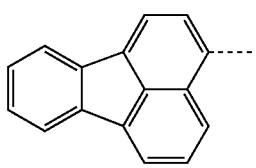 | 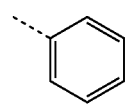 |

-continued
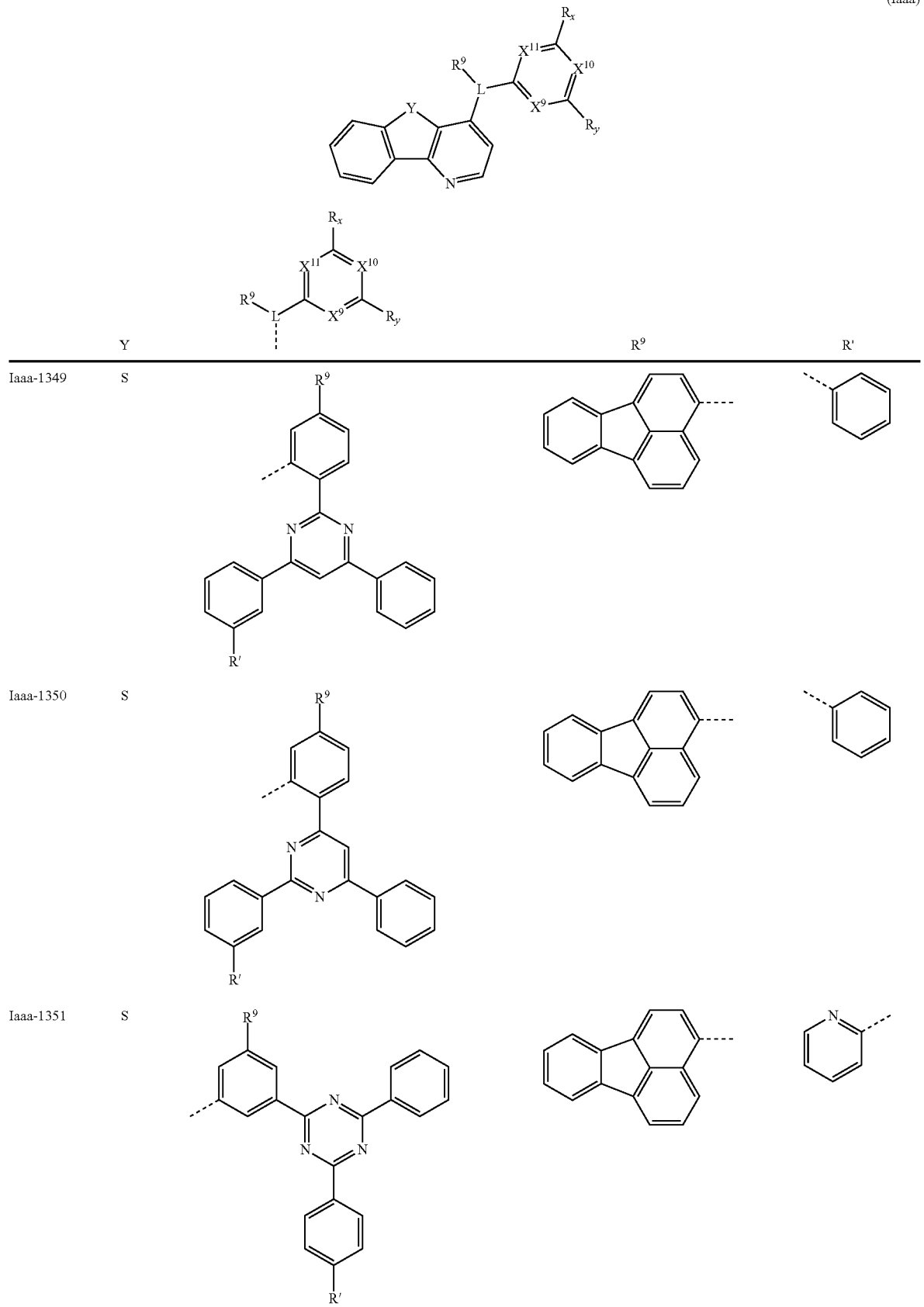

-continued
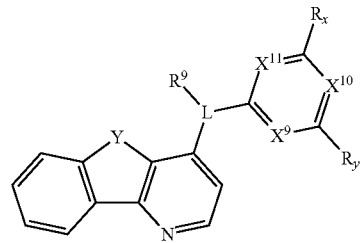
(Iaaa)
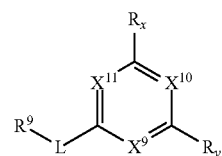
| | Y | R⁹ | | R' |
|---|---|---|---|---|
| Iaaa-1352 | S | 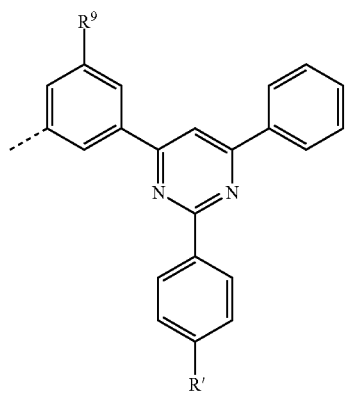 | 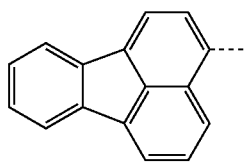 | 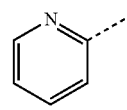 |
| Iaaa-1353 | S | 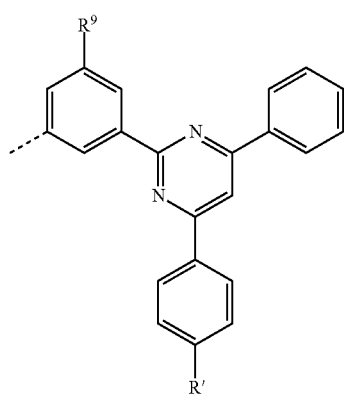 | 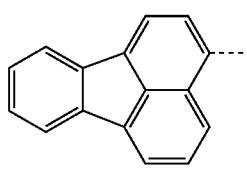 | 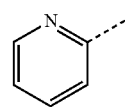 |

(Iaaa)
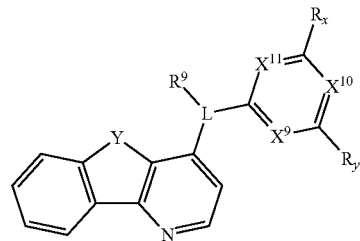
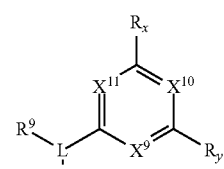
| | Y | | $R^9$ | R' |
|---|---|---|---|---|
| Iaaa-1354 | S | 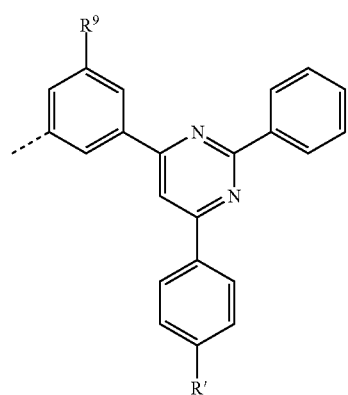 | 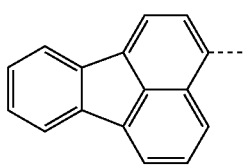 | 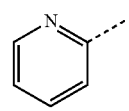 |
| Iaaa-1355 | S | 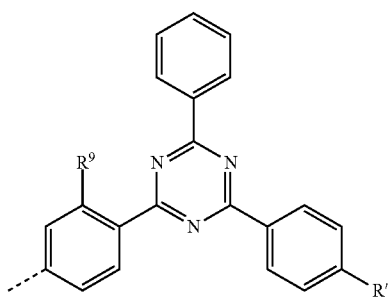 | 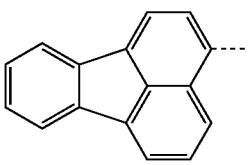 | 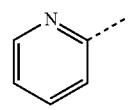 |
| Iaaa-1356 | S | 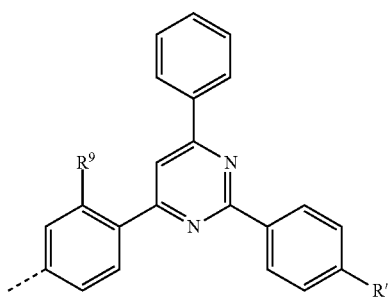 | 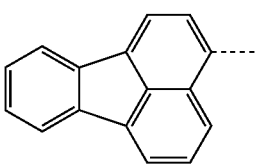 | 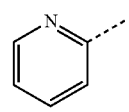 |

-continued
(Iaaa)
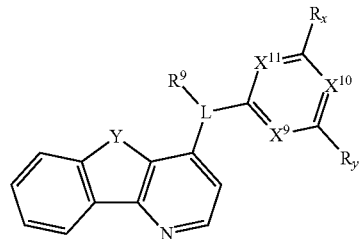
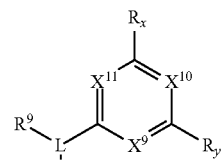
| | Y | | R⁹ | R' |
|---|---|---|---|---|
| Iaaa-1357 | S | 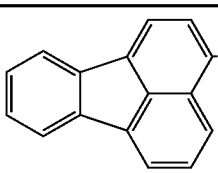 | 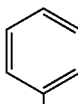 | 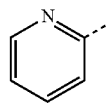 |
| Iaaa-1358 | S | 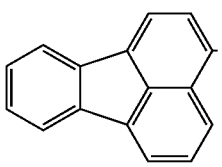 | 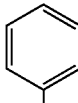 | 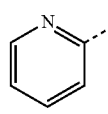 |
| Iaaa-1359 | S | 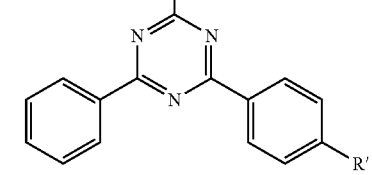 | 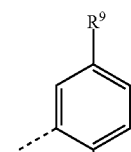 | 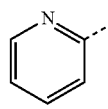 |
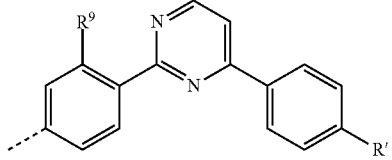
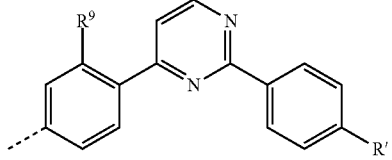
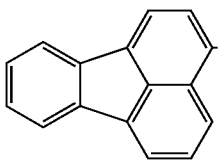

-continued
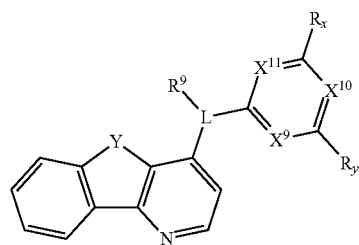
(Iaaa)
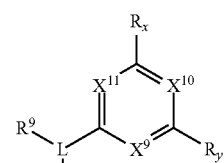
| | Y | | R⁹ | R' |
|---|---|---|---|---|
| Iaaa-1360 | S | (4-R⁹-phenyl at 4-position of 2-phenylpyrimidine-6-(4-R'-phenyl)) | fluoranthene | 2-pyridyl |
| Iaaa-1361 | S | (4-R⁹-phenyl at 2-position of 4,6-diphenylpyrimidine with R' on one phenyl) | fluoranthene | 2-pyridyl |
| Iaaa-1362 | S | (4-R⁹-phenyl at 4-position of 2-(4-R'-phenyl)-6-phenylpyrimidine) | fluoranthene | 2-pyridyl |

-continued
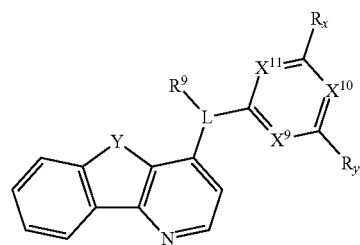
(Iaaa)
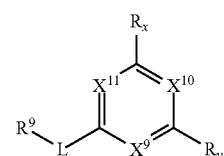
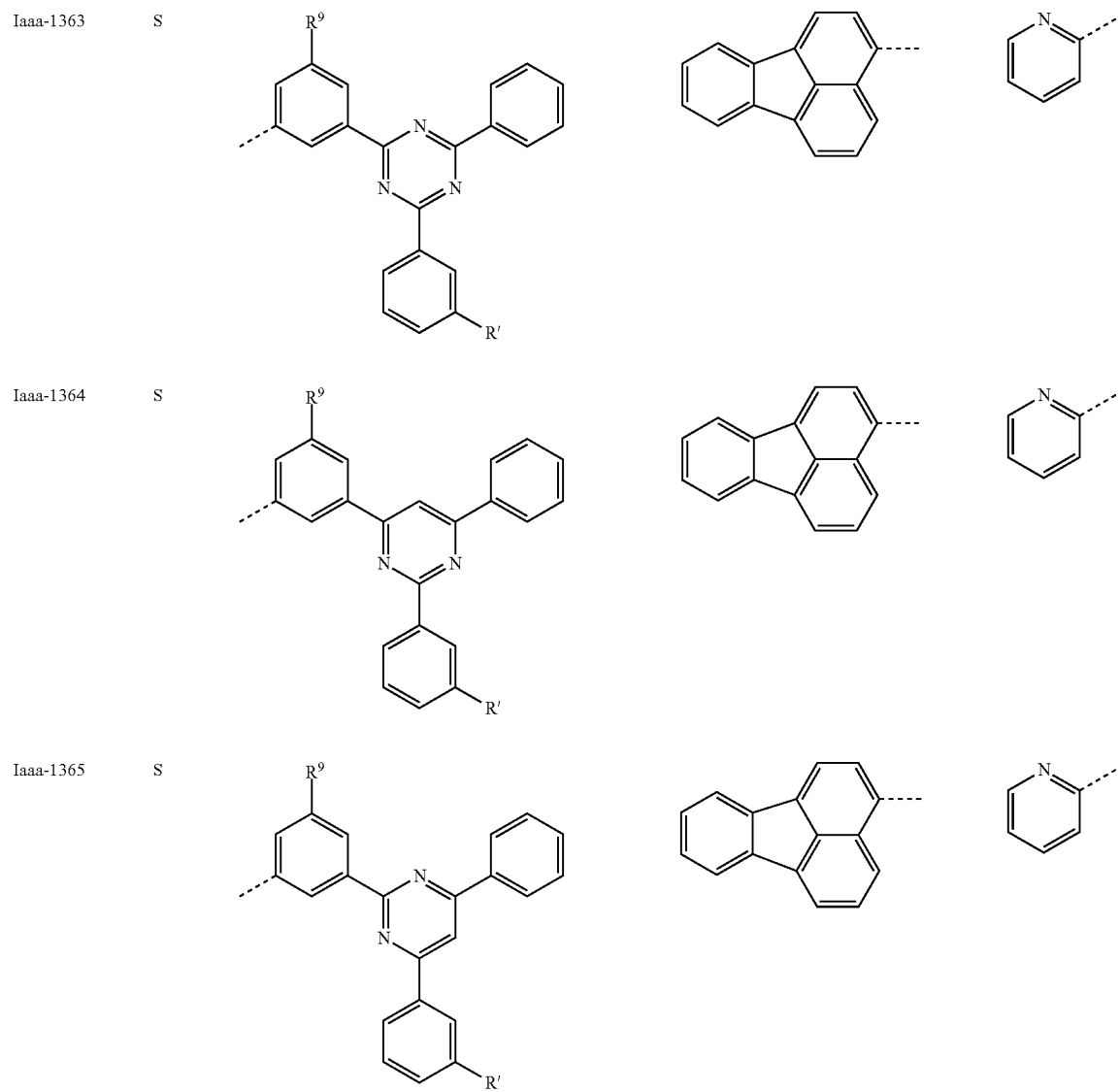

-continued
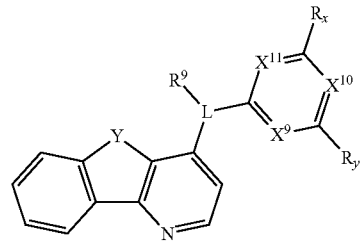
(Iaaa)
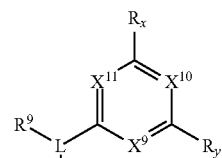
| | Y | R⁹ | R' |
|---|---|---|---|
| Iaaa-1366 | S | 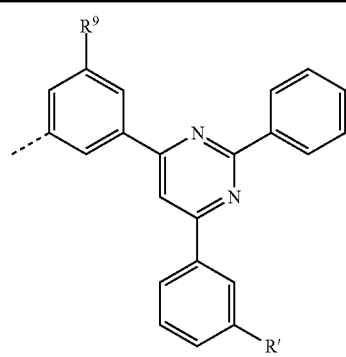 | 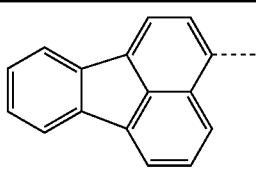 | 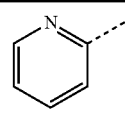 |
| Iaaa-1367 | S | 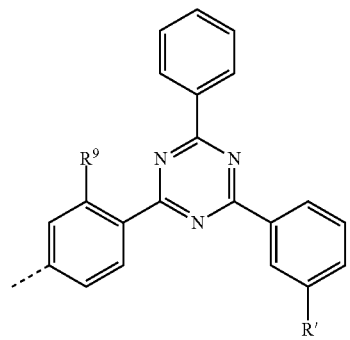 | 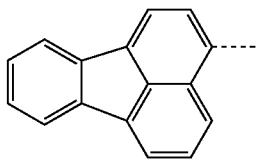 | 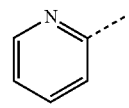 |
| Iaaa-1368 | S | 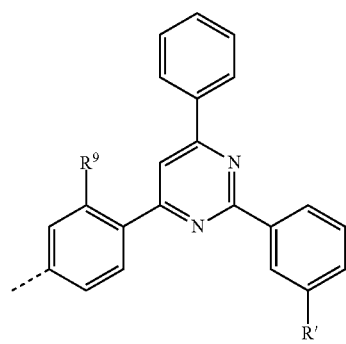 | 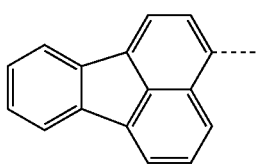 | 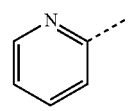 |

-continued
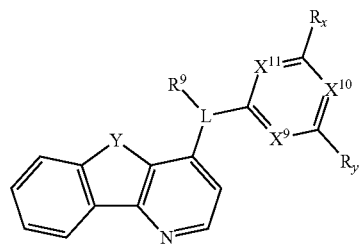
(Iaaa)
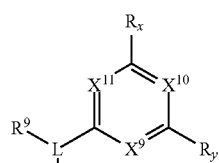
| | Y | | R⁹ | R' |
|---|---|---|---|---|
| Iaaa-1369 | S | 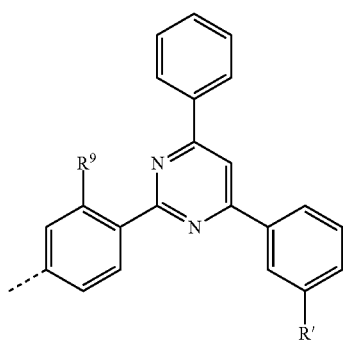 | 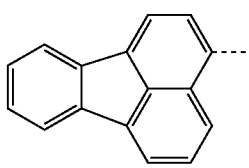 | 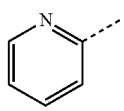 |
| Iaaa-1370 | S | 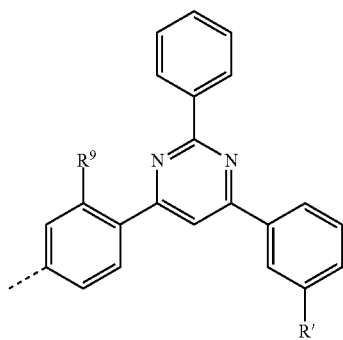 | 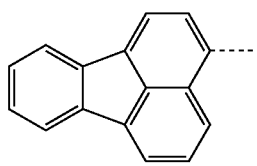 | 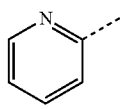 |
| Iaaa-1371 | S | 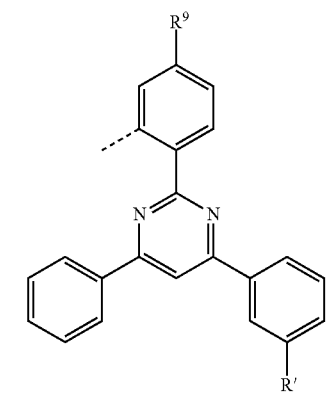 | 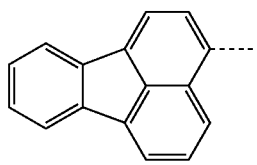 | 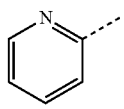 |

-continued
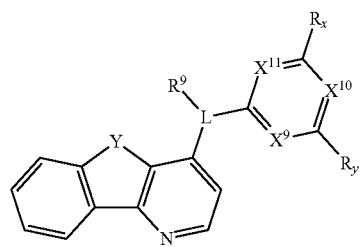
(Iaaa)
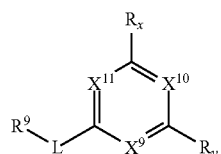
| | Y | | R⁹ | R' |
|---|---|---|---|---|
| Iaaa-1372 | S | 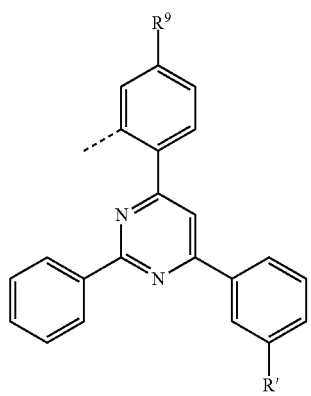 | 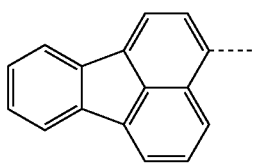 | 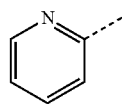 |
| Iaaa-1373 | S | 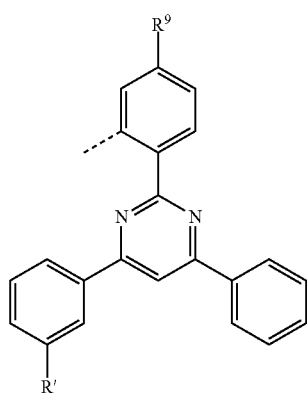 | 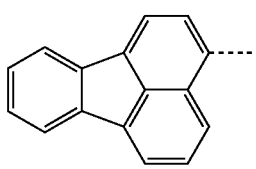 | 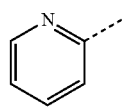 |

-continued
(Iaaa)
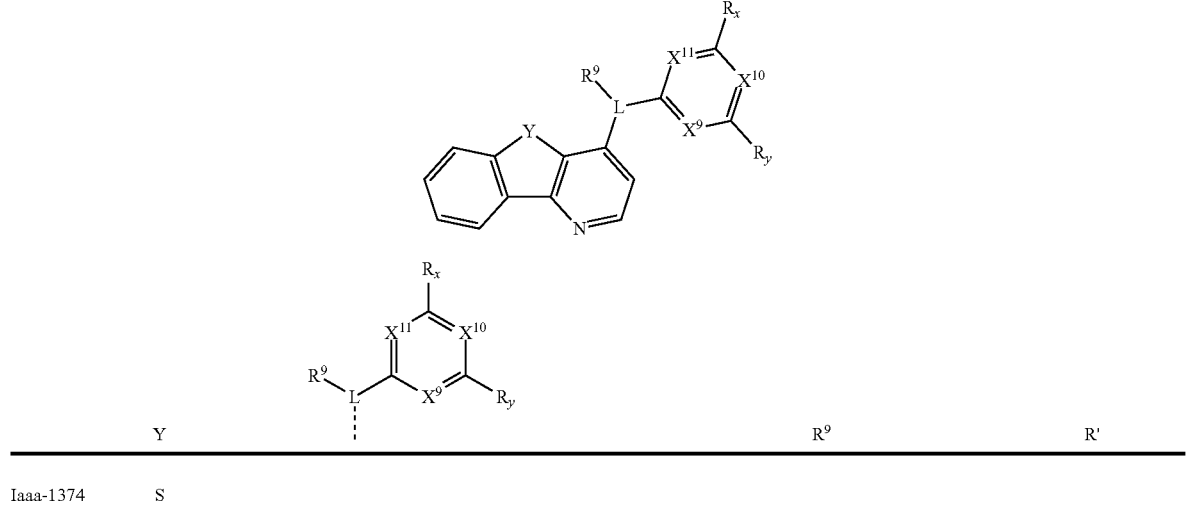
| Y | R⁹ | R' |
|---|----|----|
| Iaaa-1374 | S | |
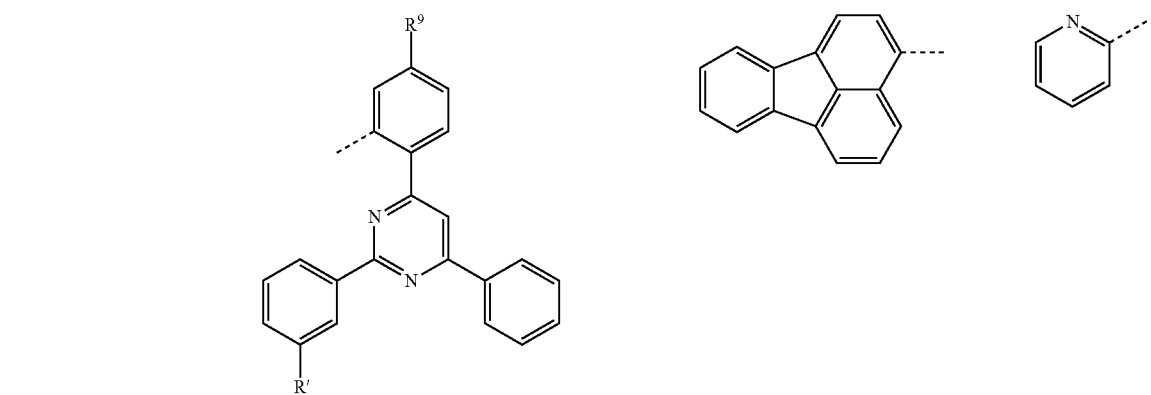
wherein the dotted lines are bonding sites.
Most preferred compounds of formula (I) are the following compounds:
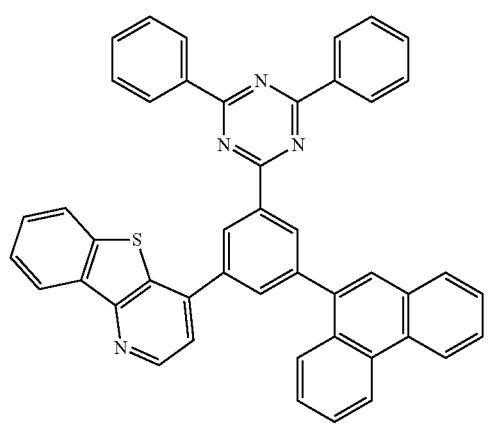
-continued
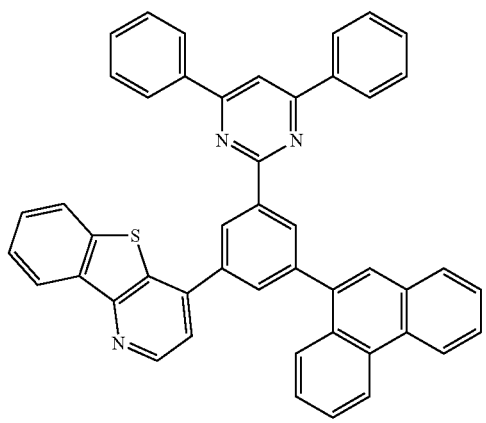

1001
-continued
1002
-continued
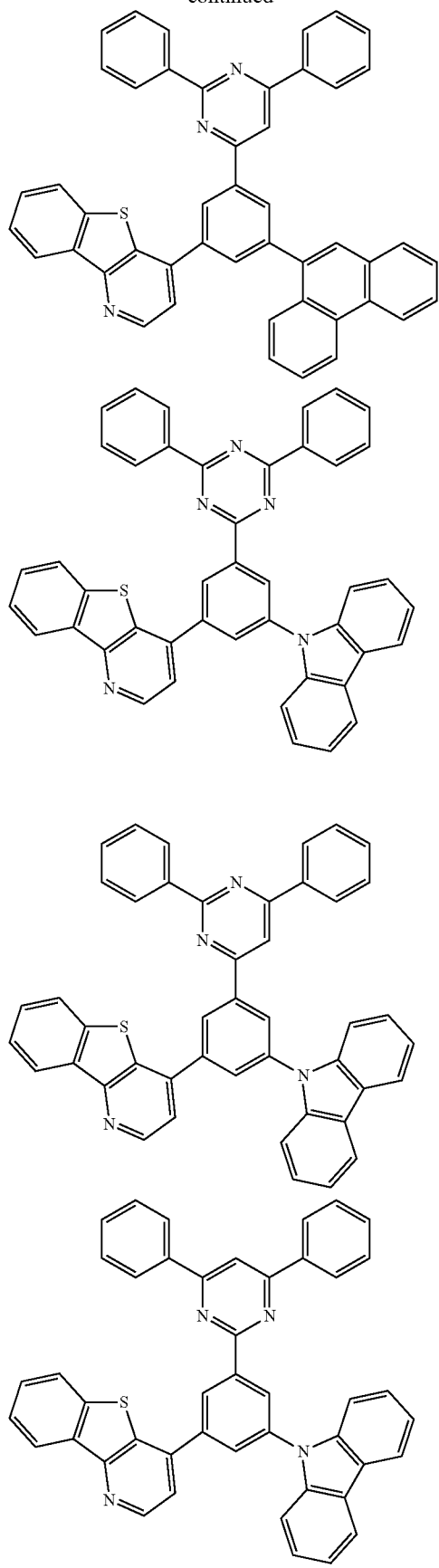
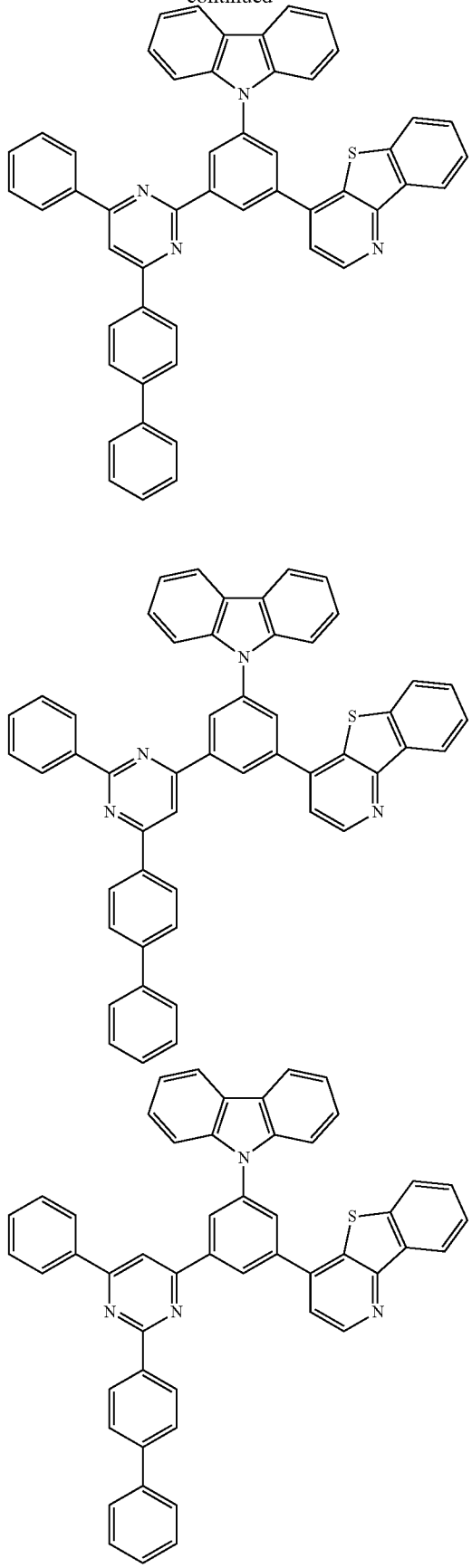

1003
-continued
1004
-continued
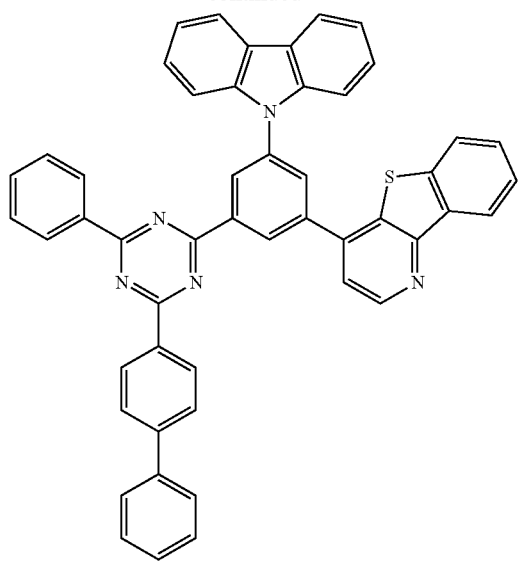
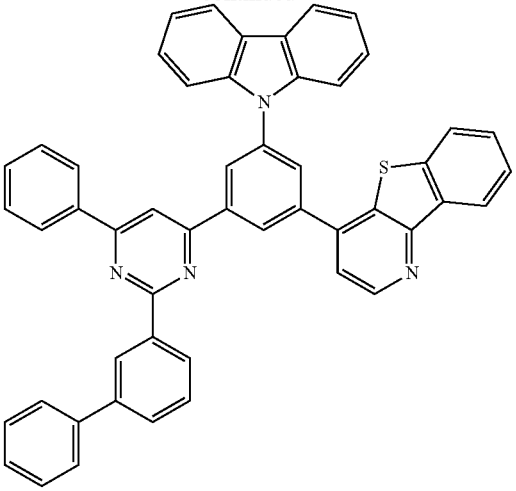
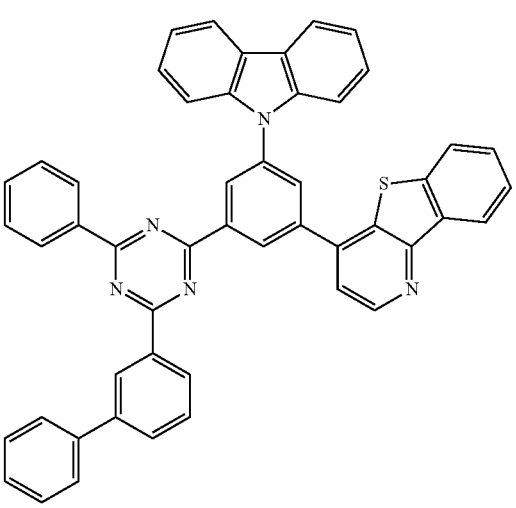
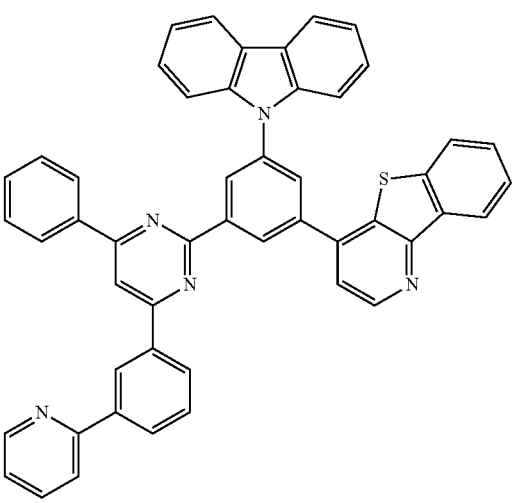

1005
-continued
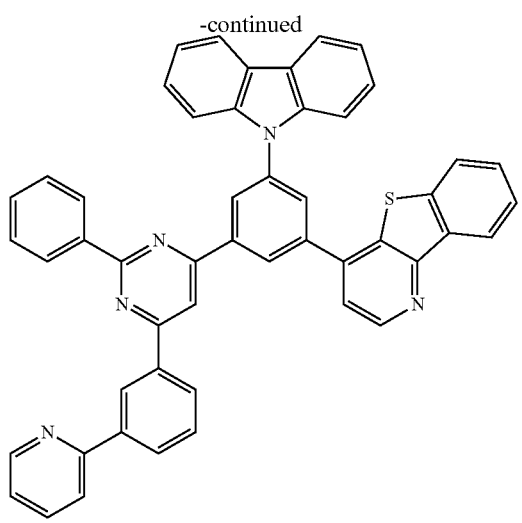
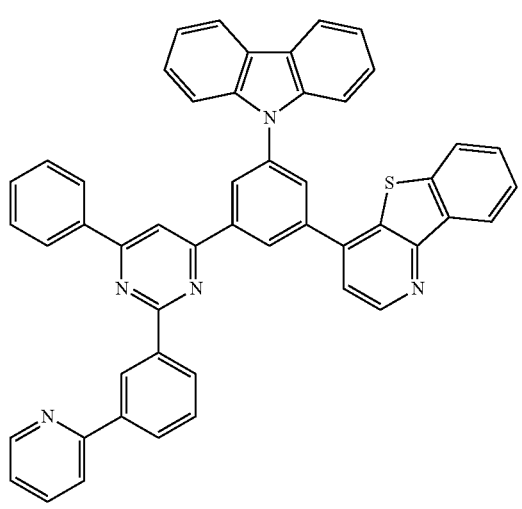
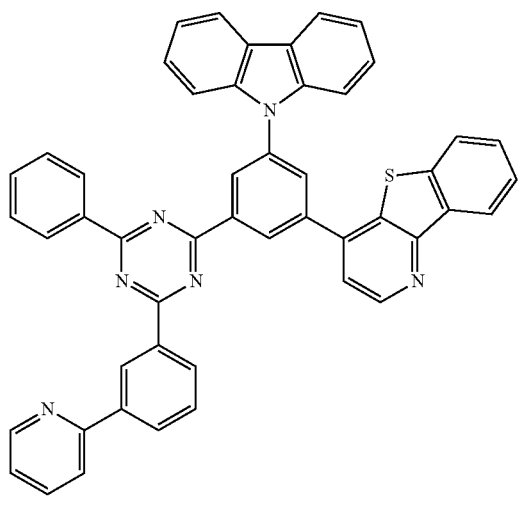
1006
-continued
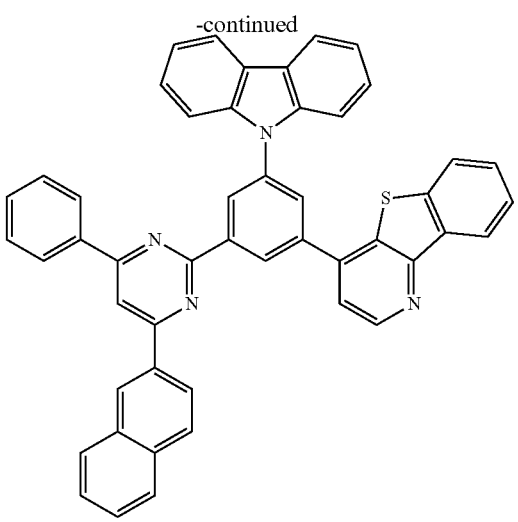
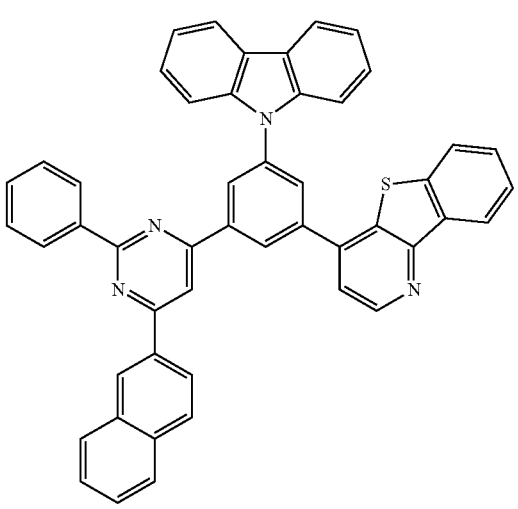
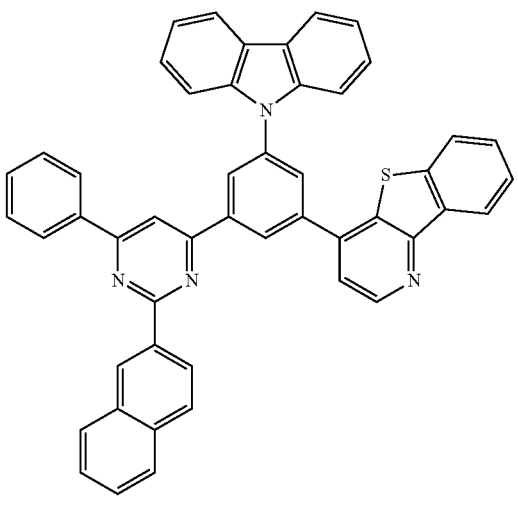

1007
-continued
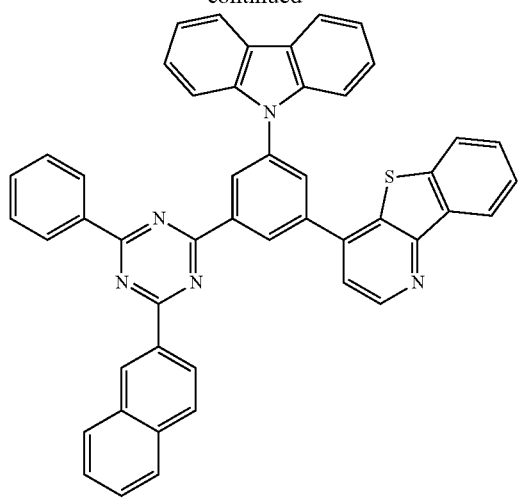
1008
-continued
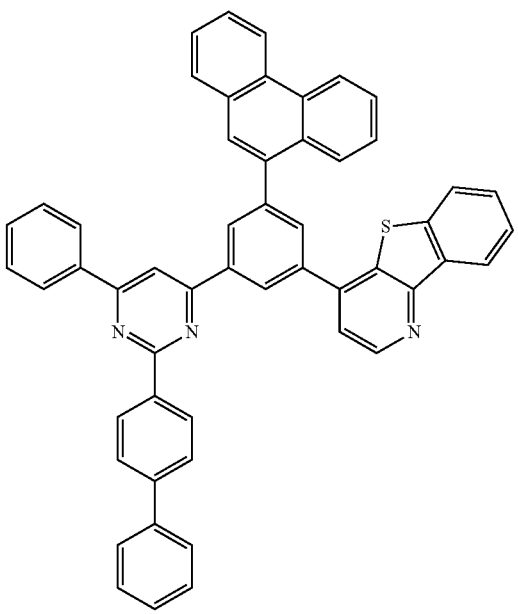
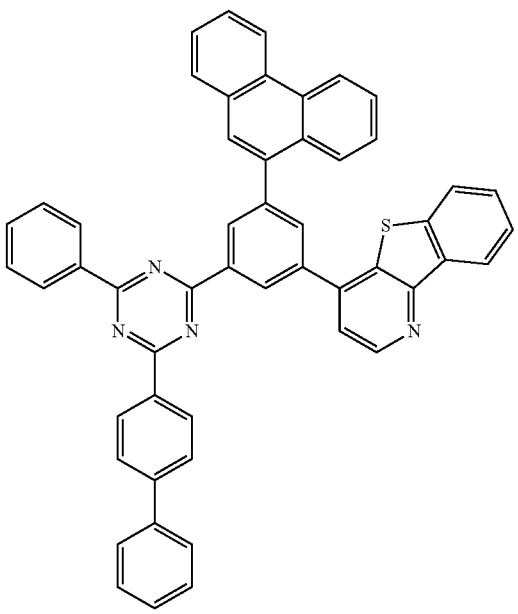

1009
-continued
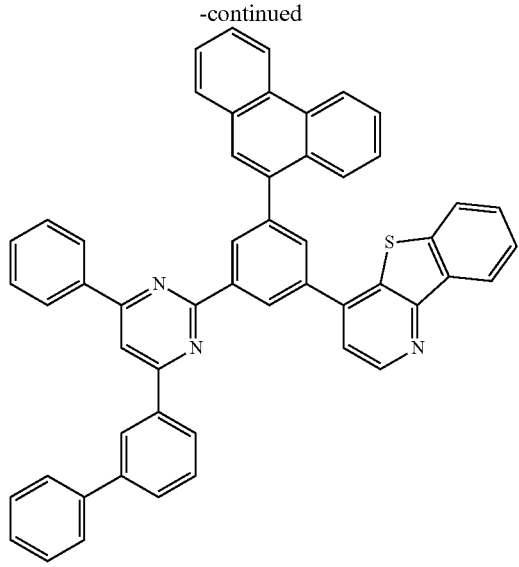
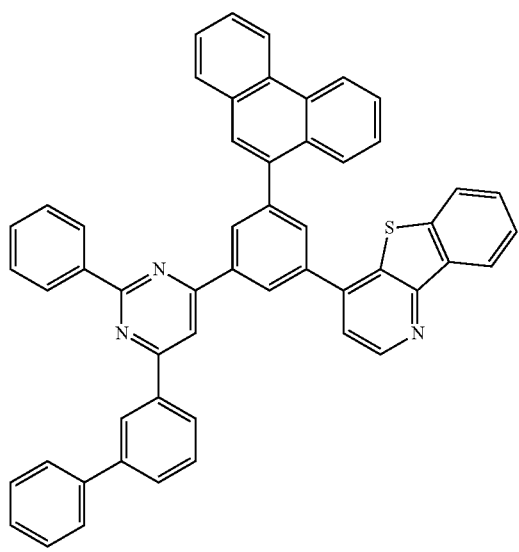
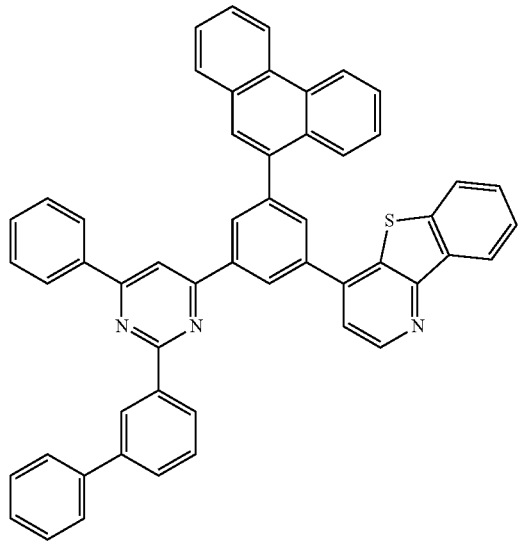
1010
-continued
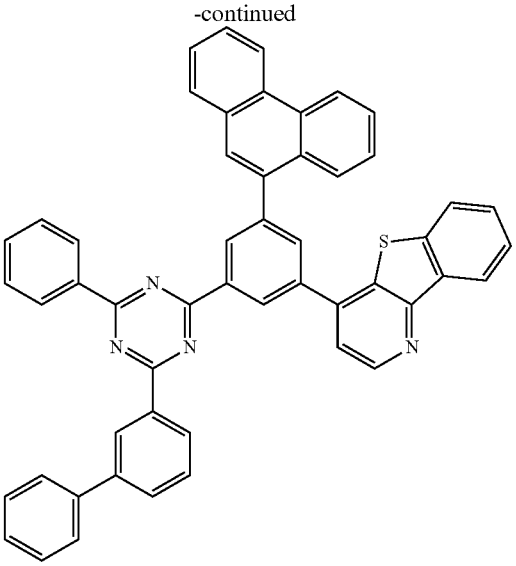
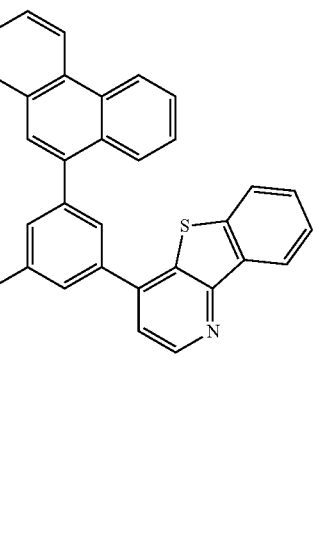
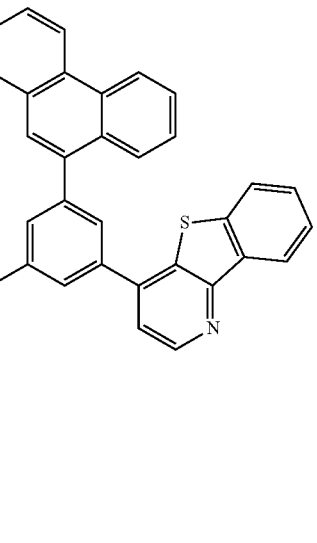

1011
-continued
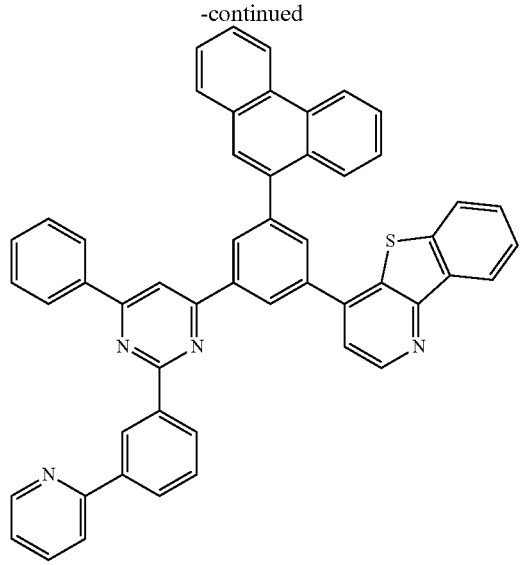
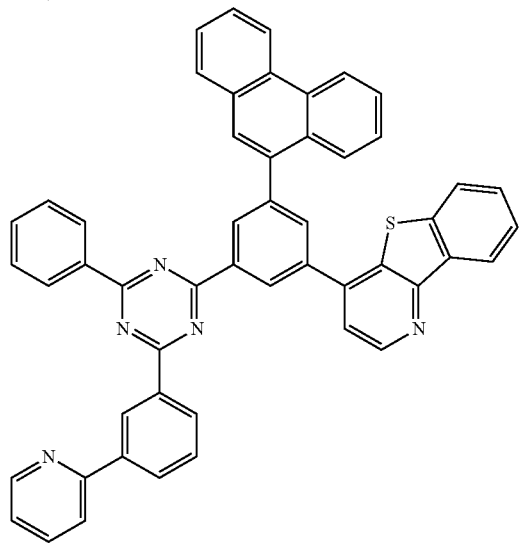
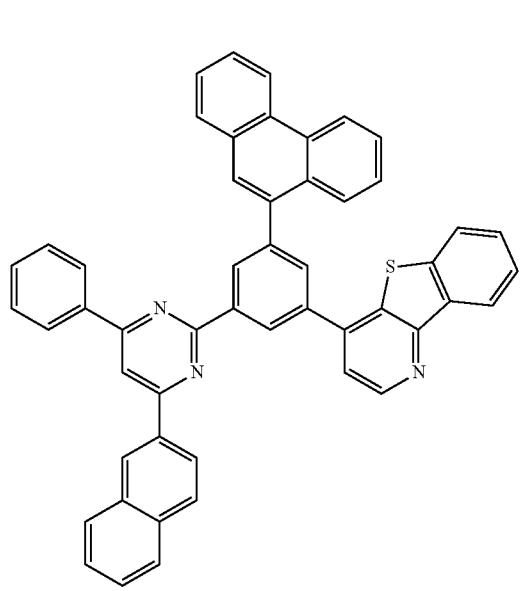
1012
-continued
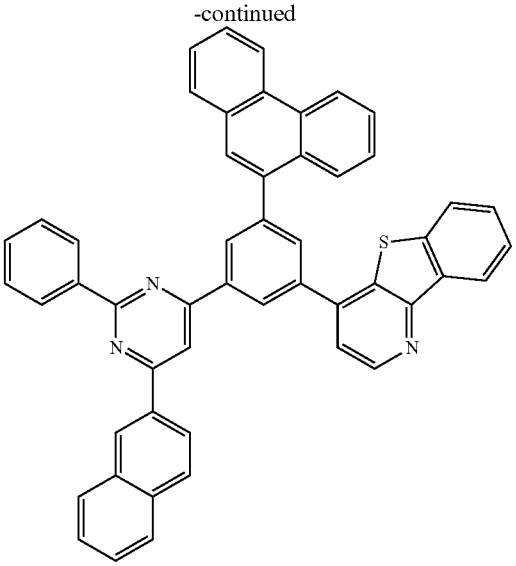
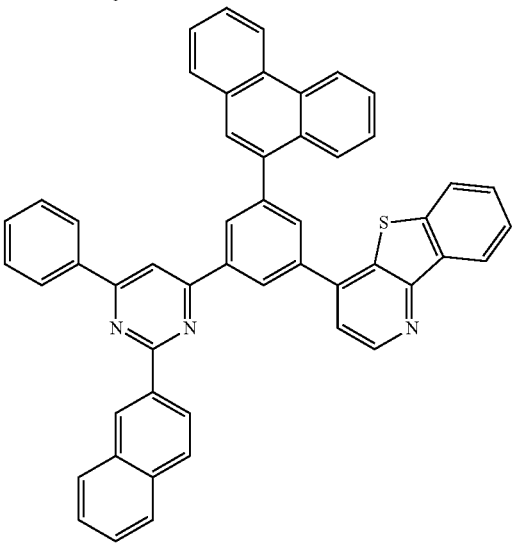
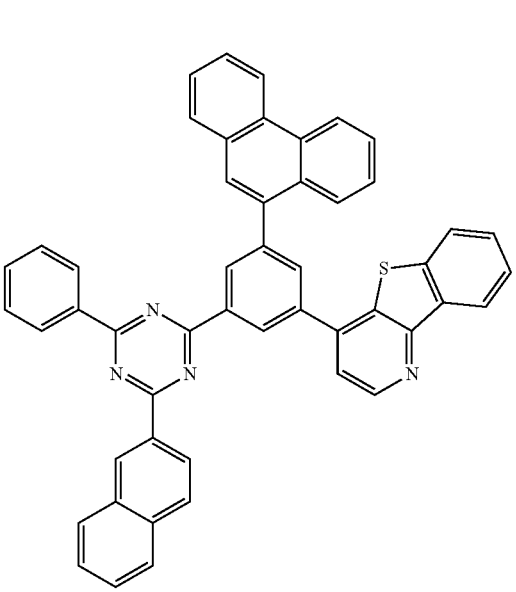

1013
-continued
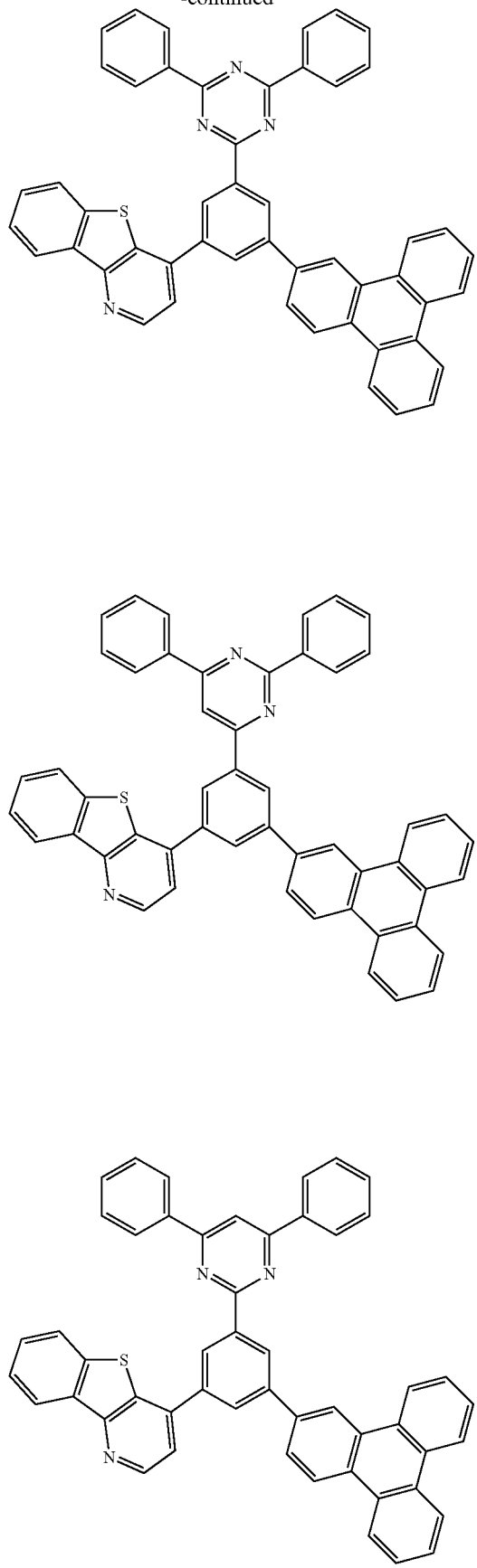
1014
-continued
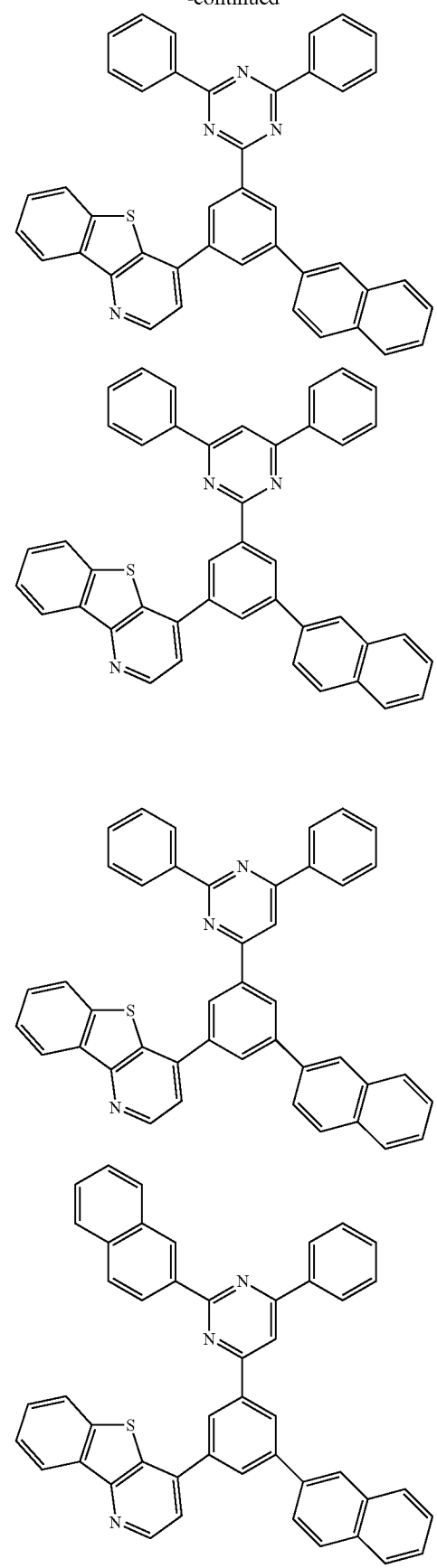

| 1015 -continued | 1016 -continued |
|---|---|
| 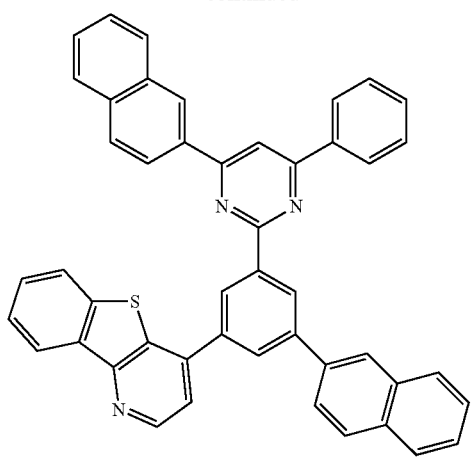 | 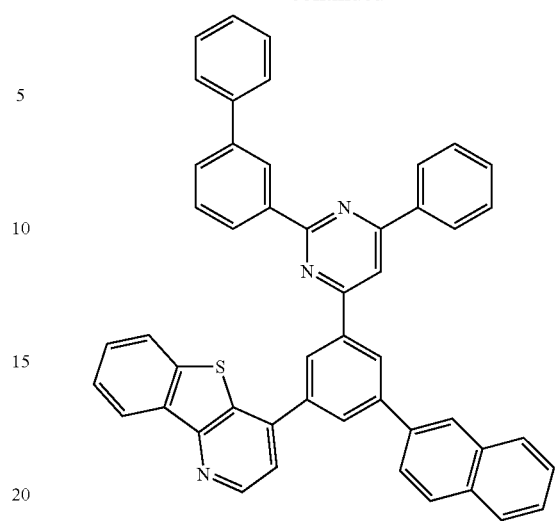 |
| 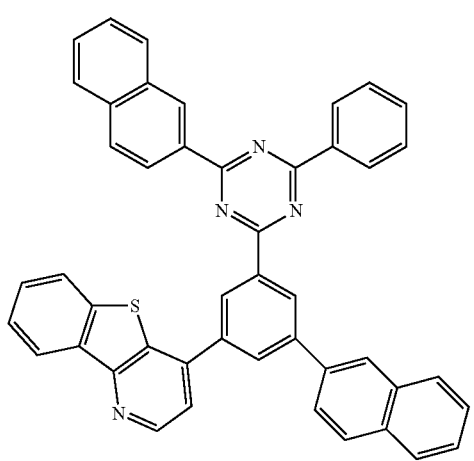 | 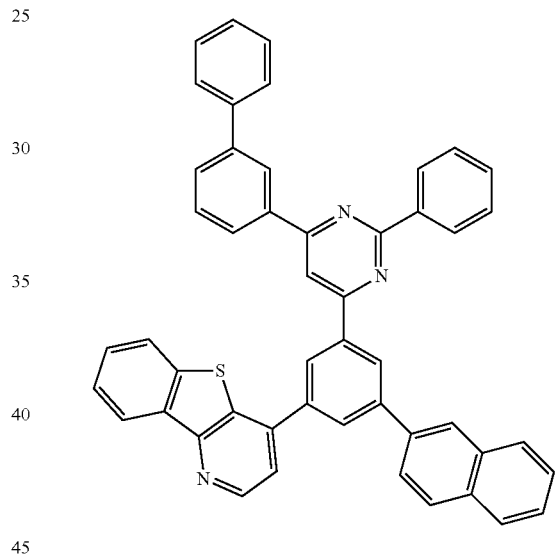 |
| 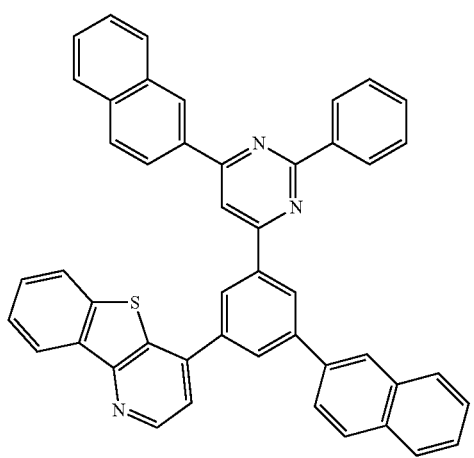 | 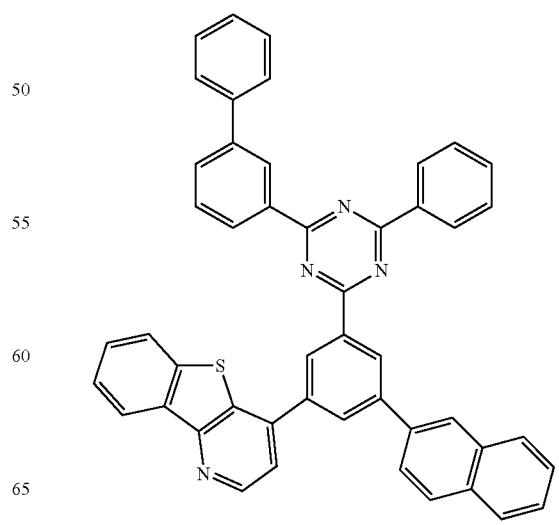 |

1017
-continued
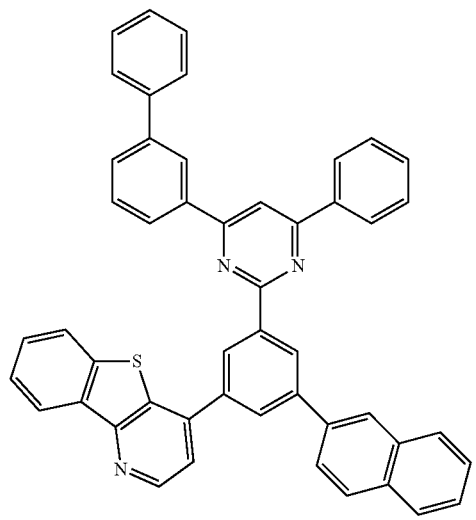
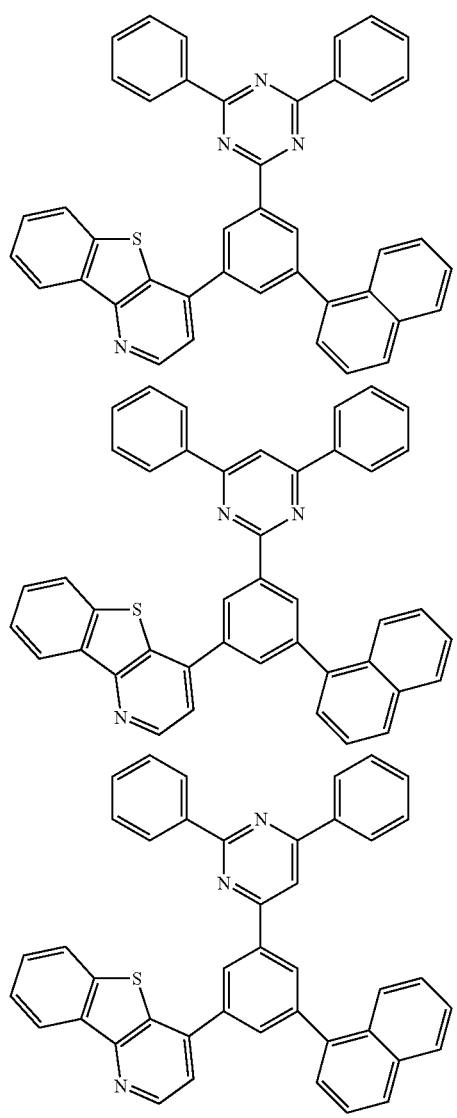
1018
-continued
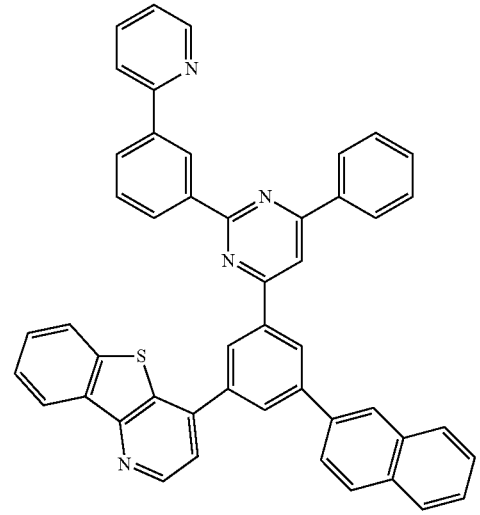
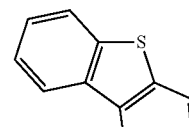
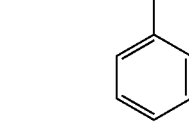
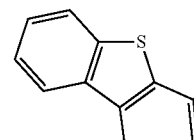
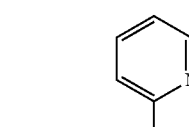
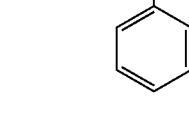
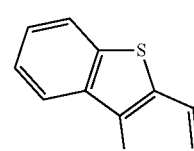

1019
-continued
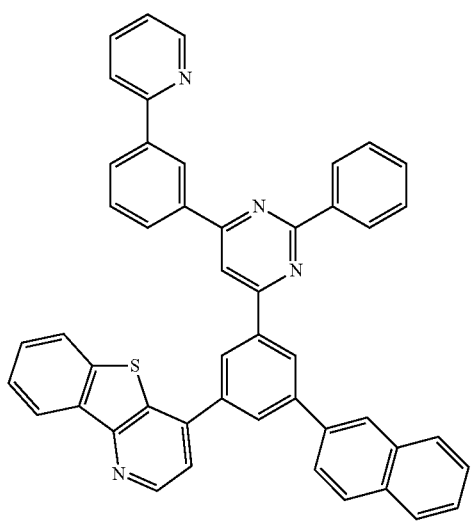
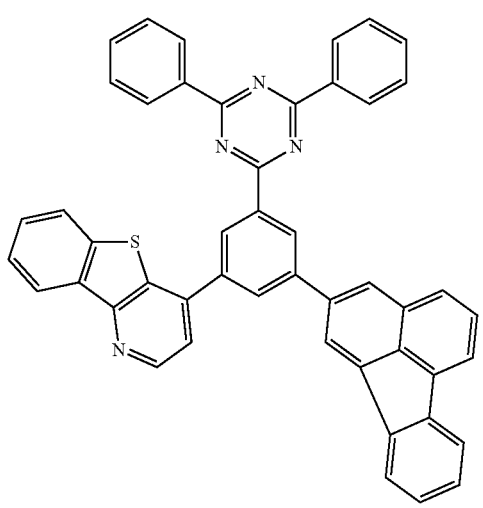
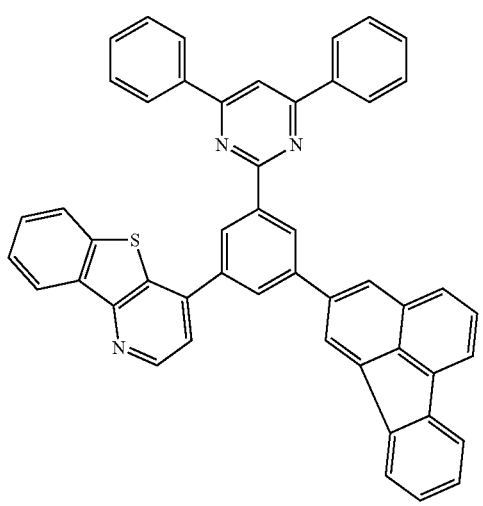
1020
-continued
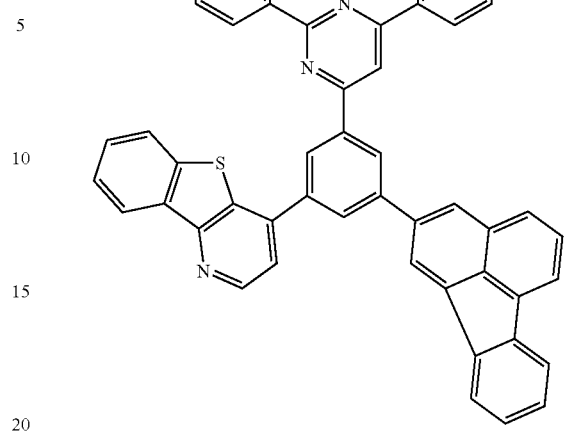

1021
-continued
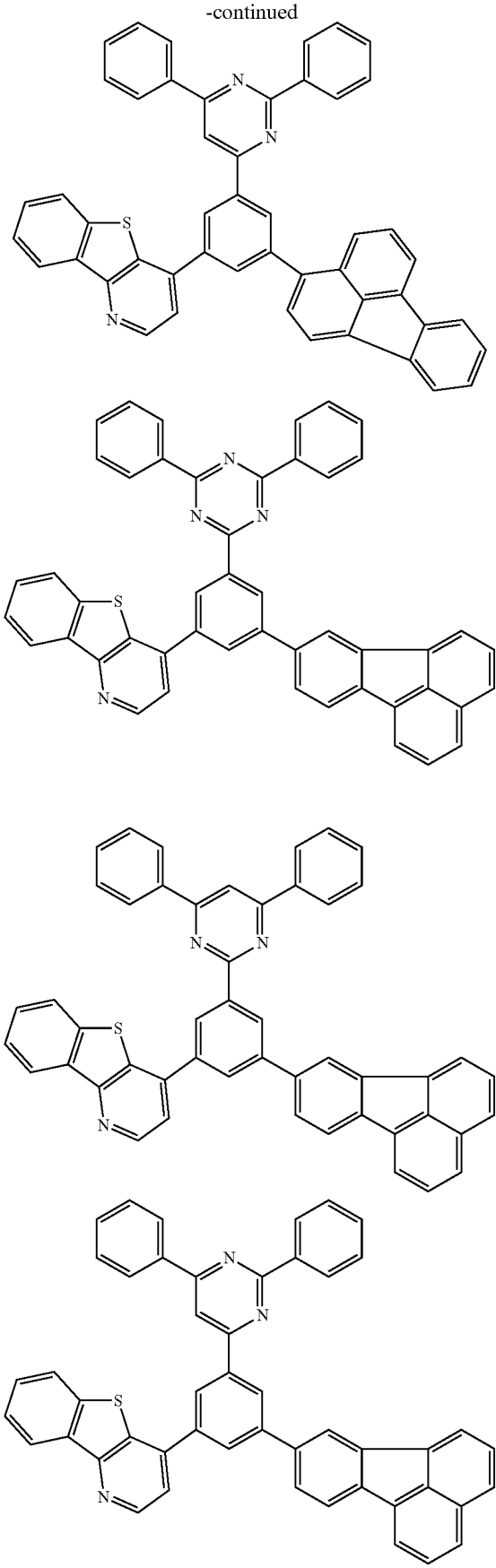
1022
-continued
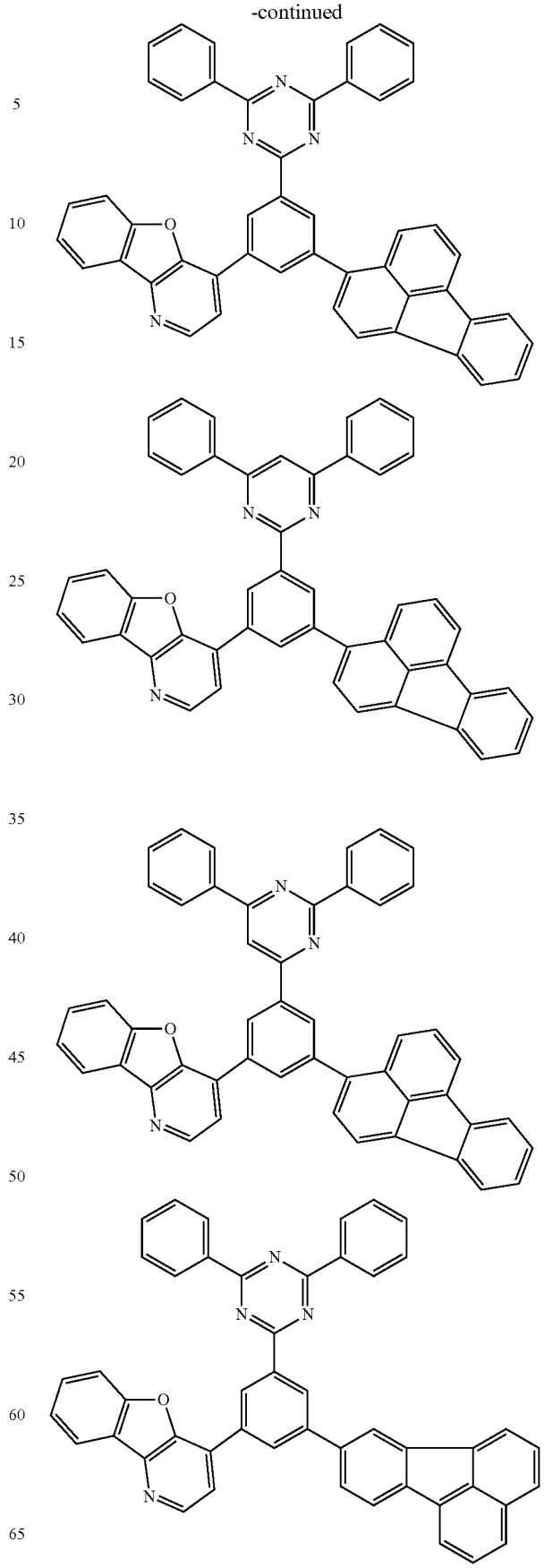

1023
-continued
1024
-continued
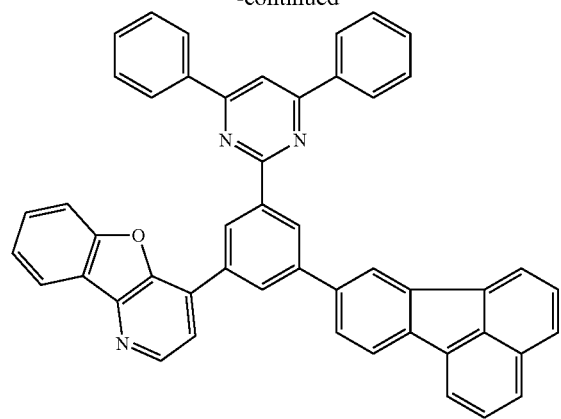
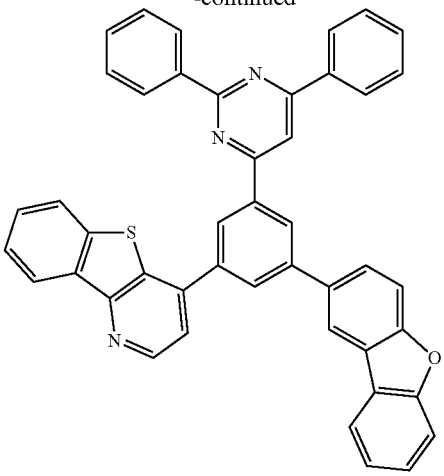
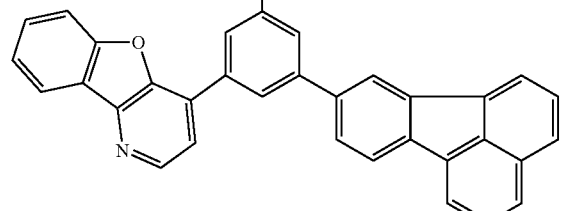
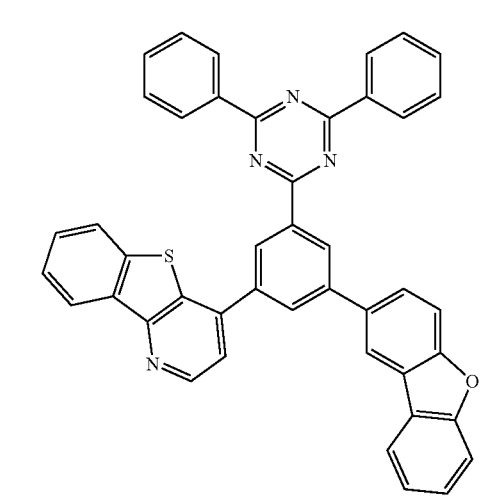
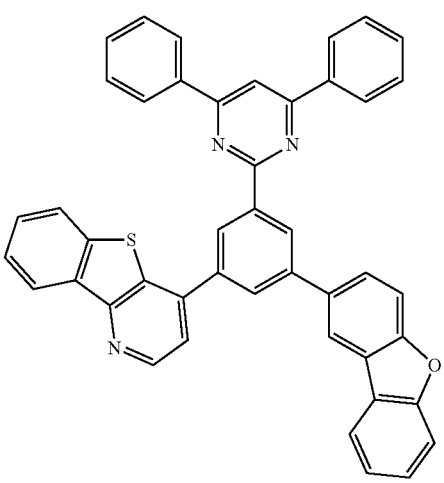
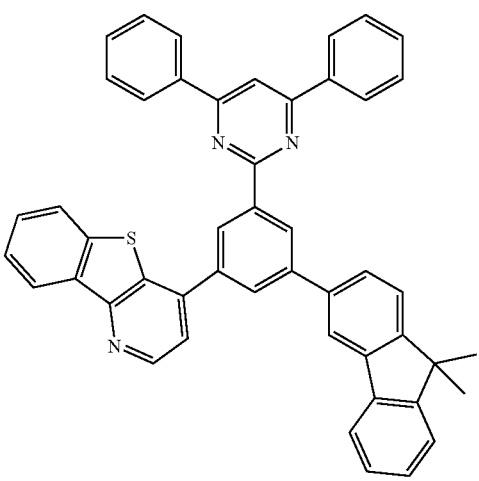

1025
-continued
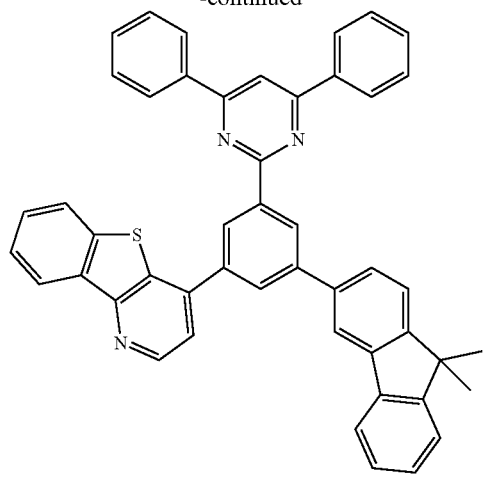
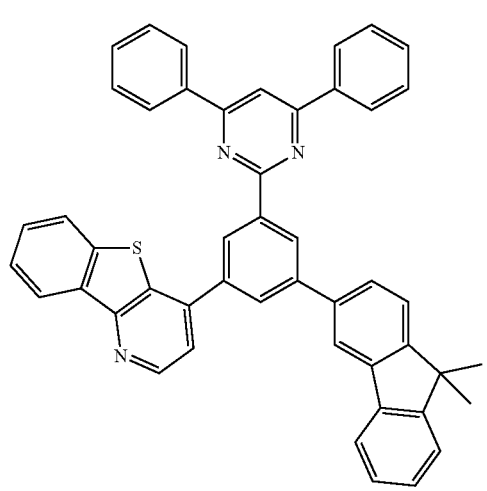
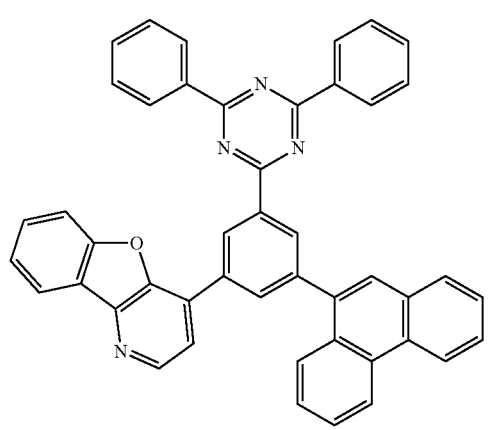
1026
-continued
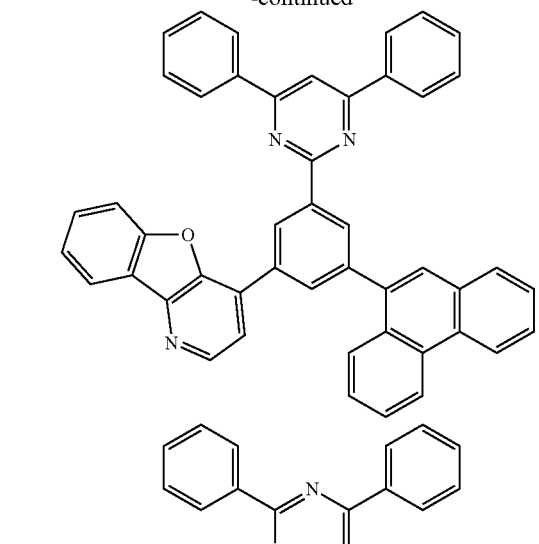
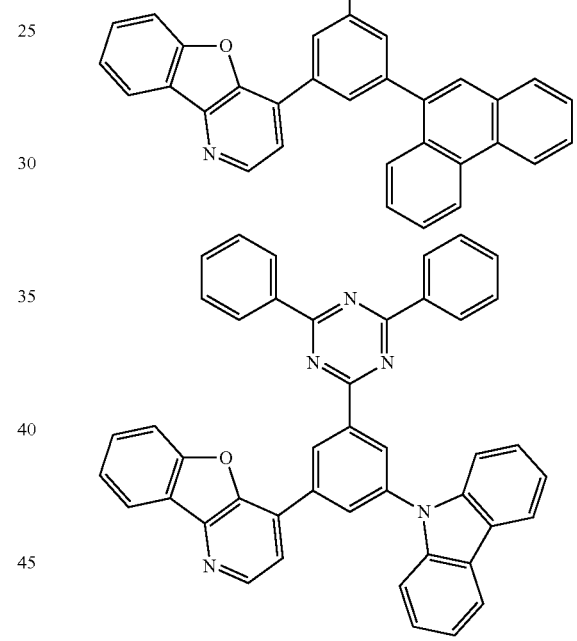
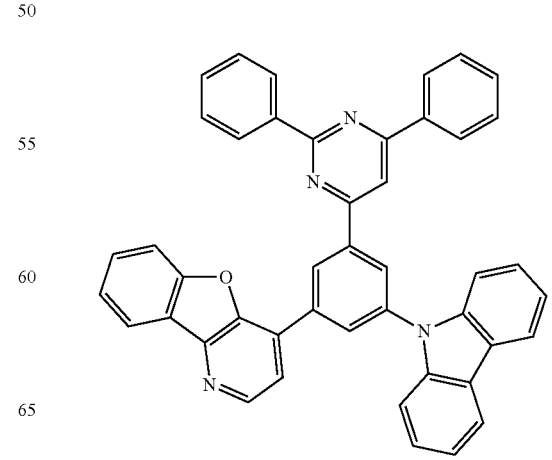

1027
-continued
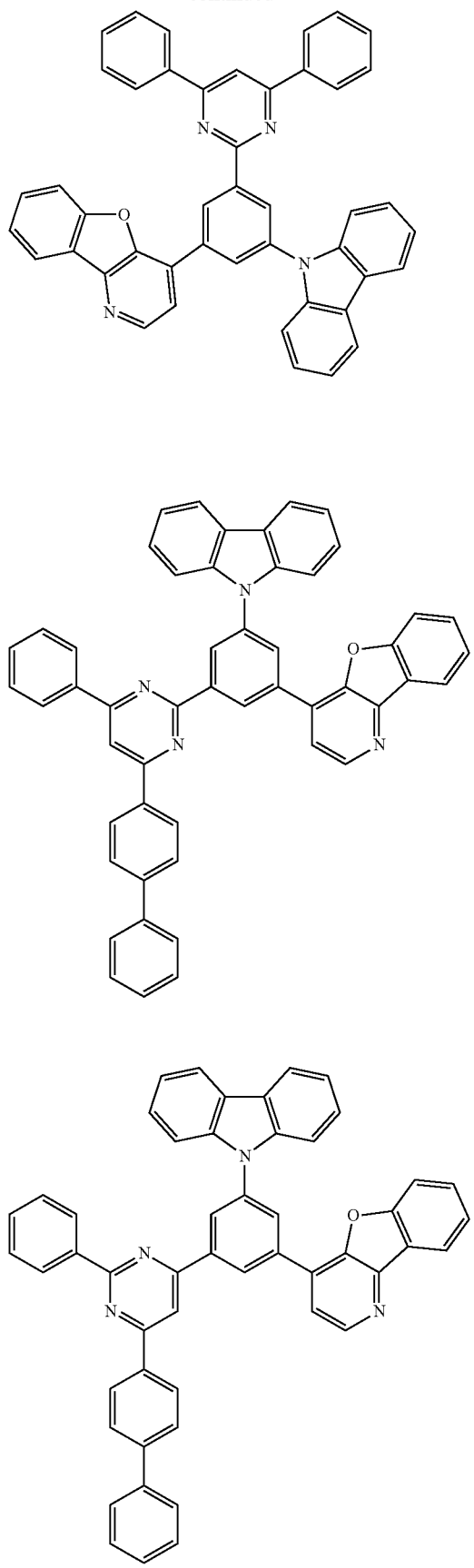
1028
-continued
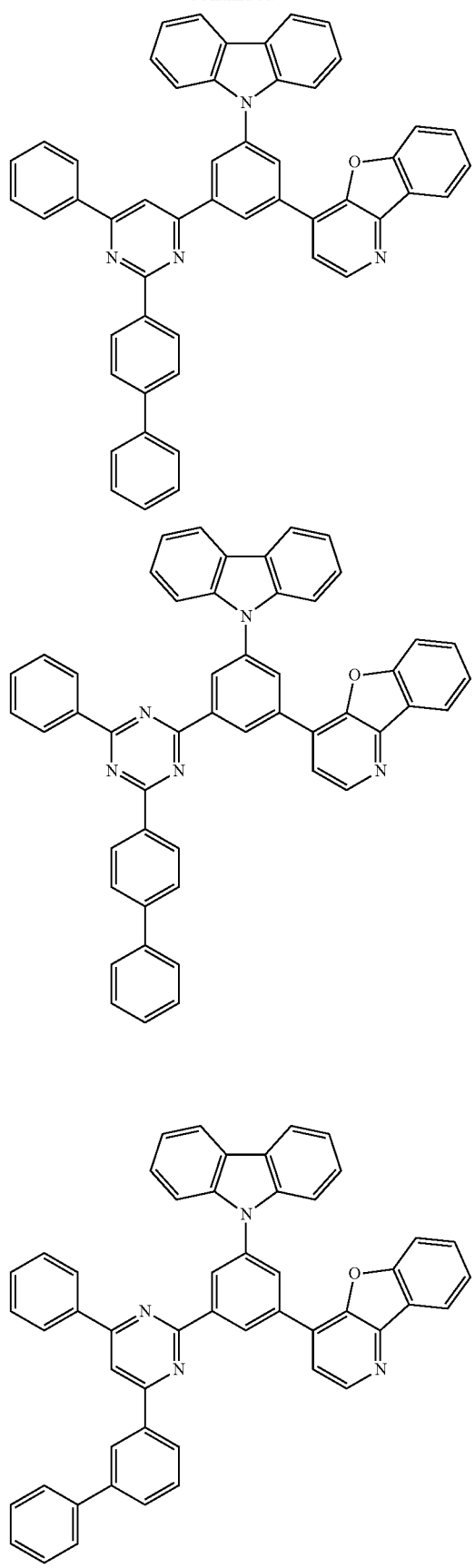

1029
-continued
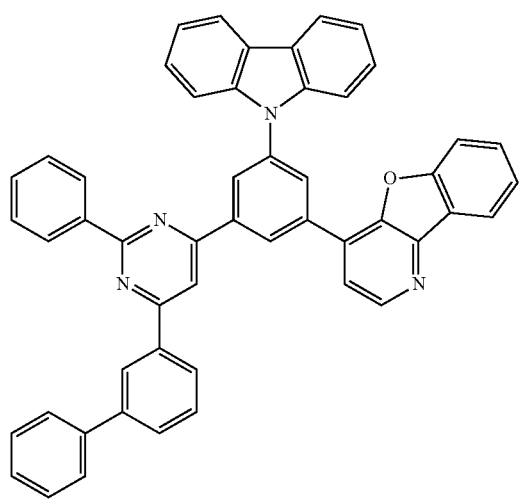
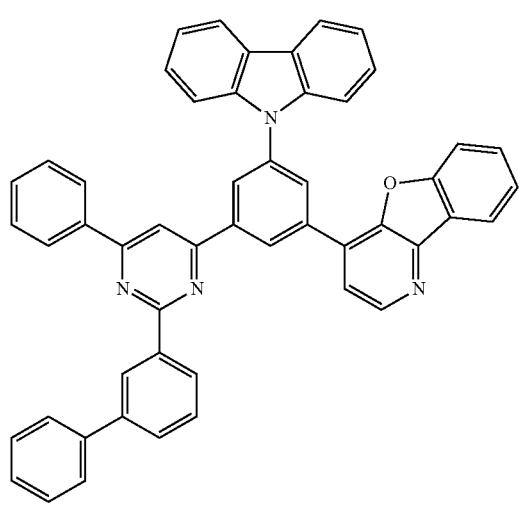
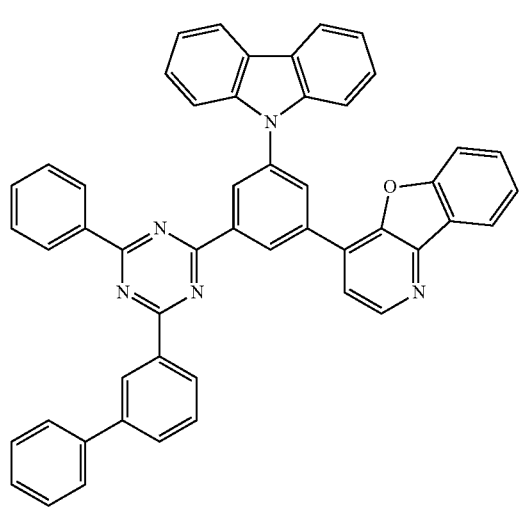
1030
-continued
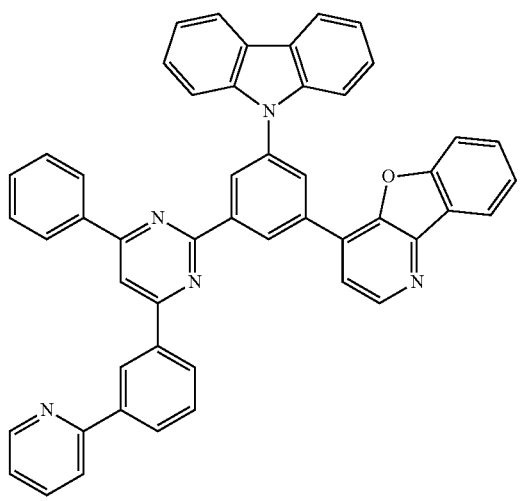
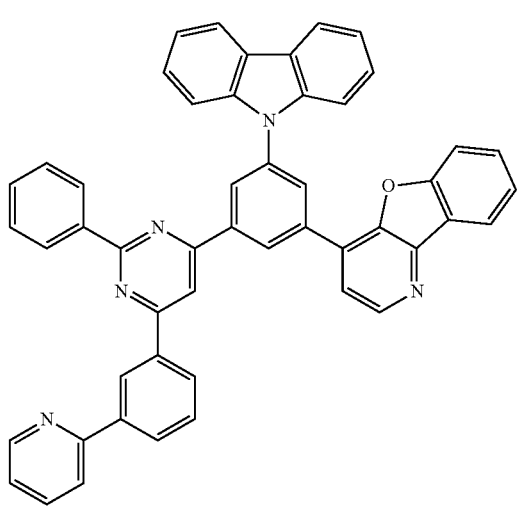
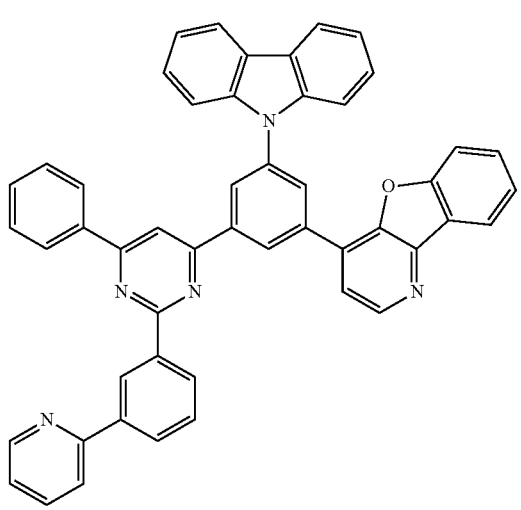

1031
-continued
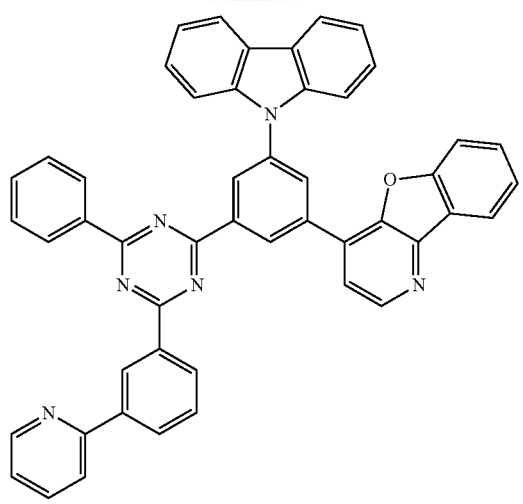
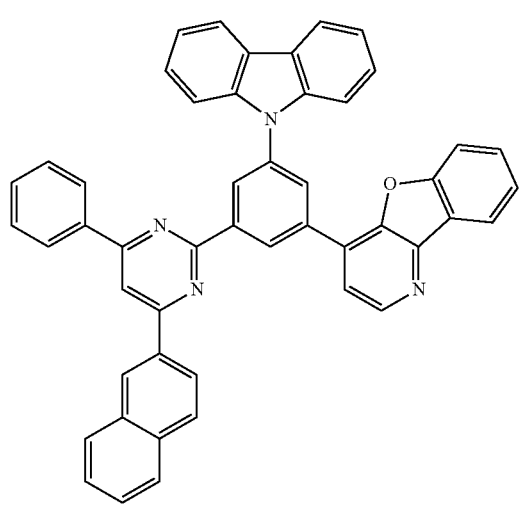
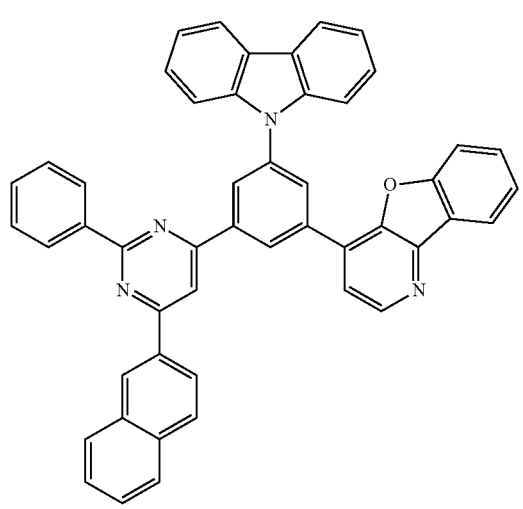
1032
-continued
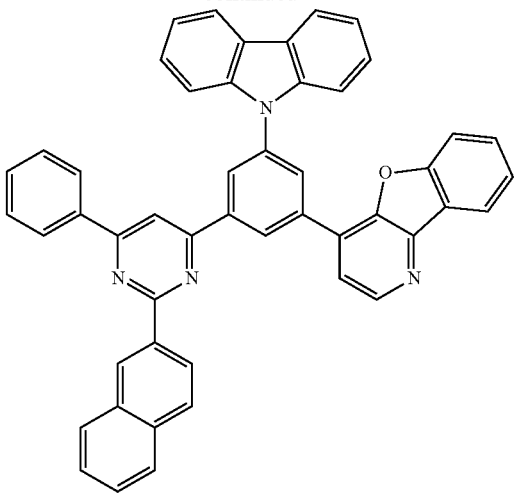
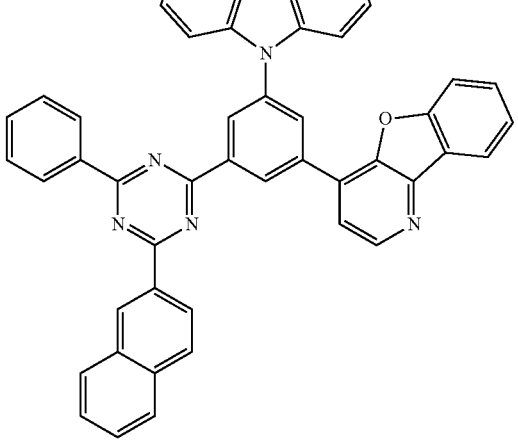
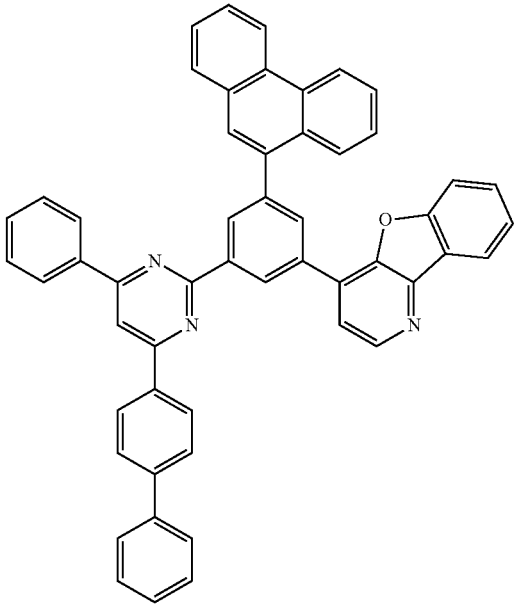

1033
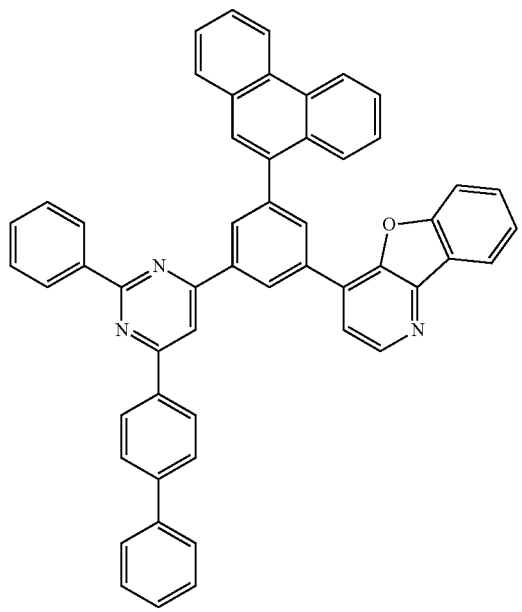
1034
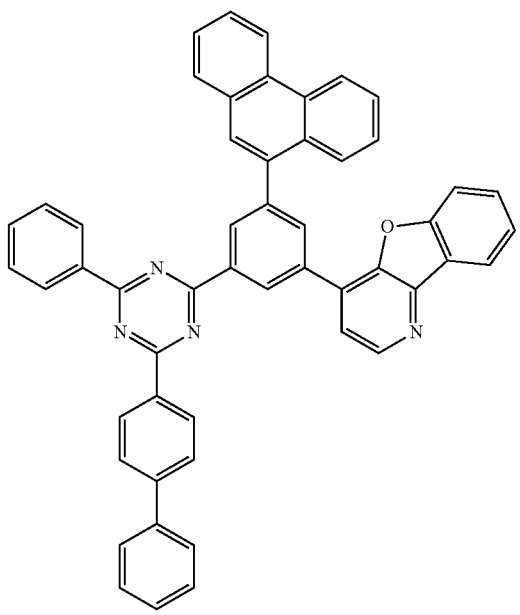
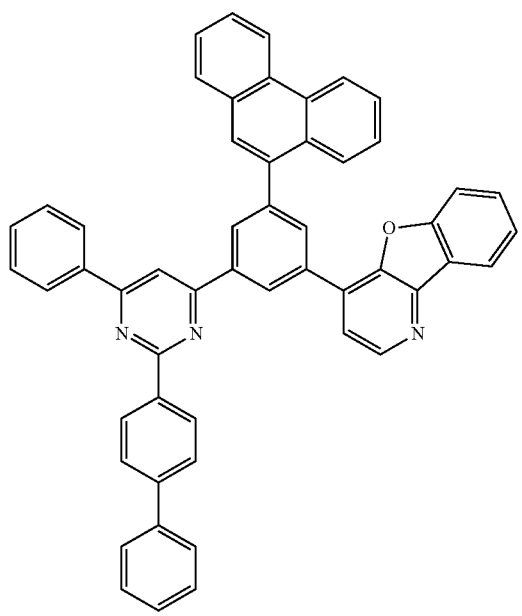
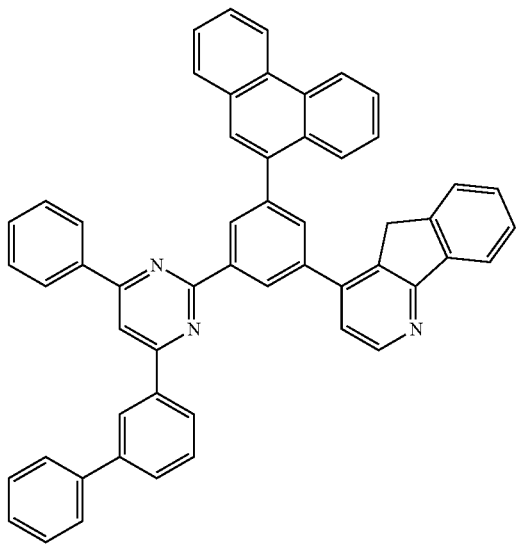

1035
-continued
1036
-continued
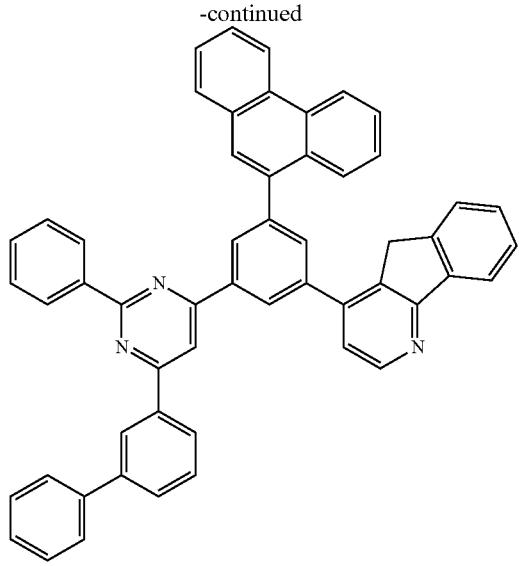
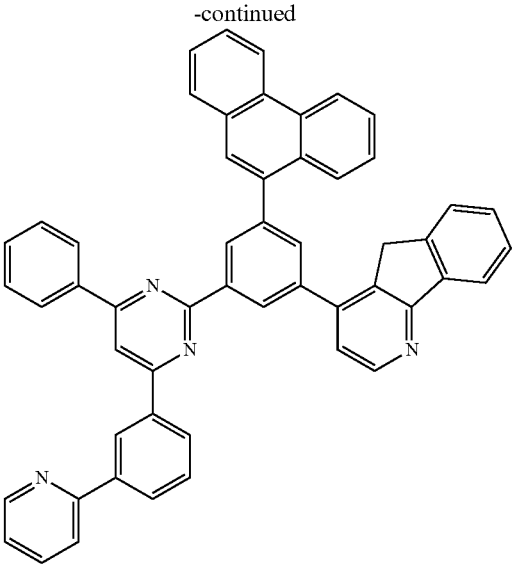

1037
-continued
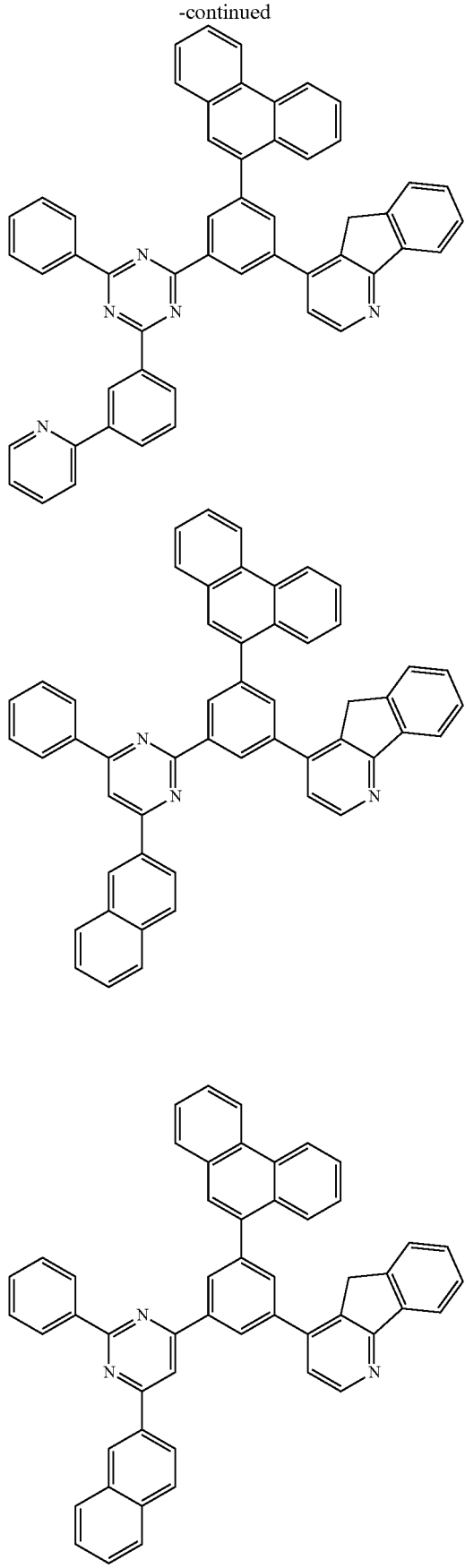
1038
-continued
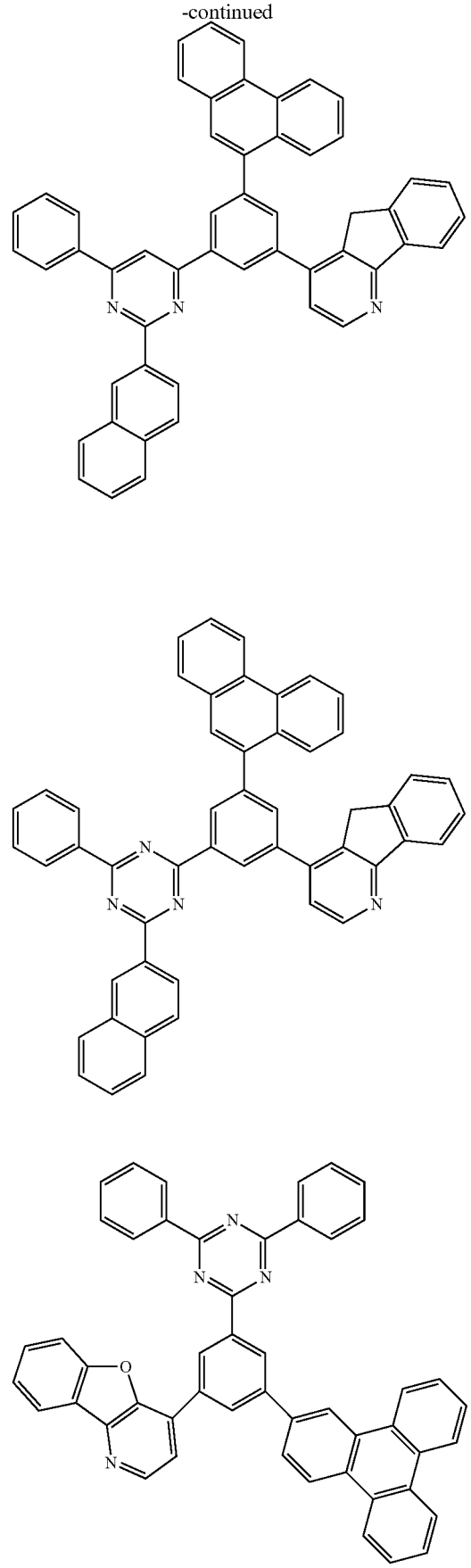

1039
-continued
1040
-continued
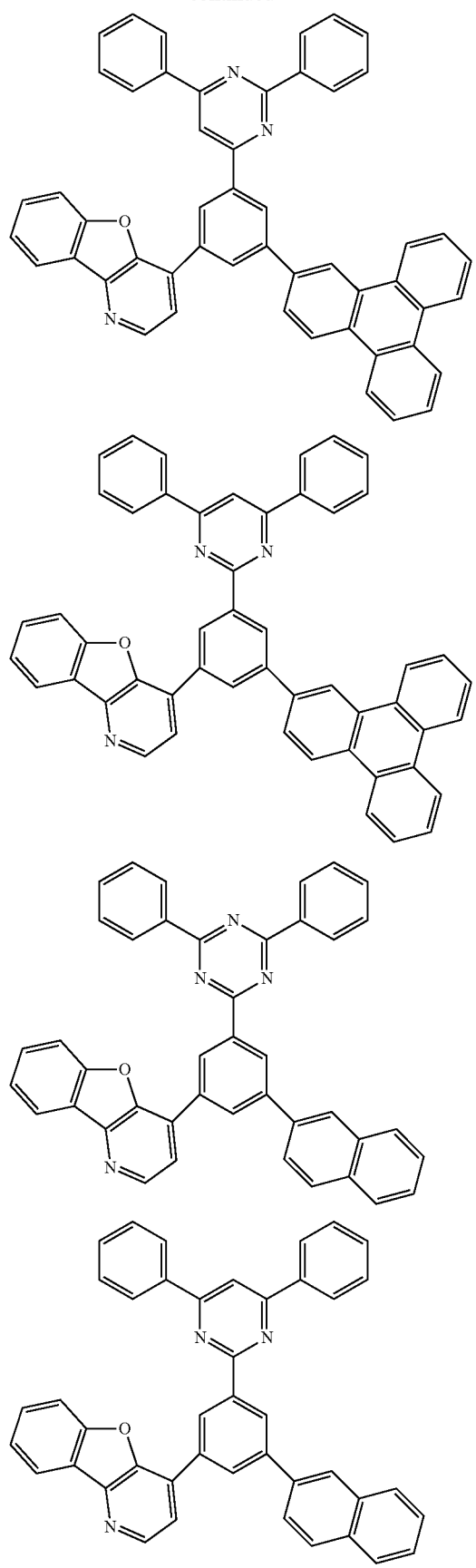

1041
-continued
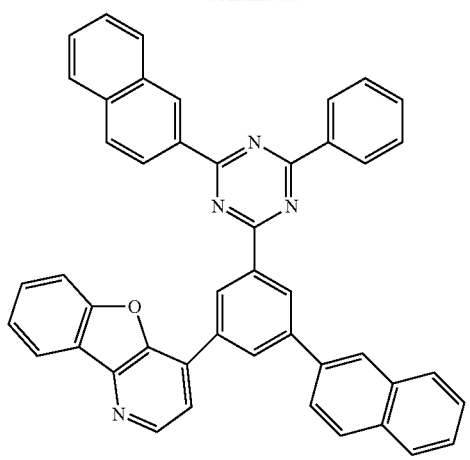
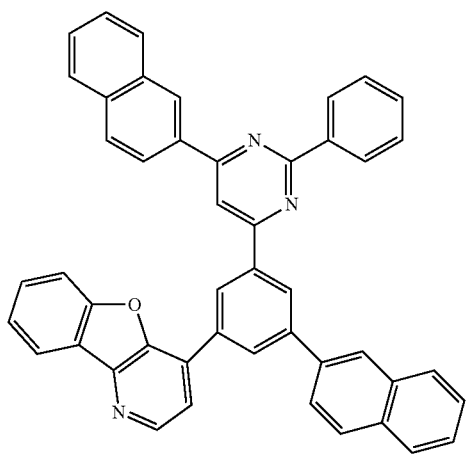
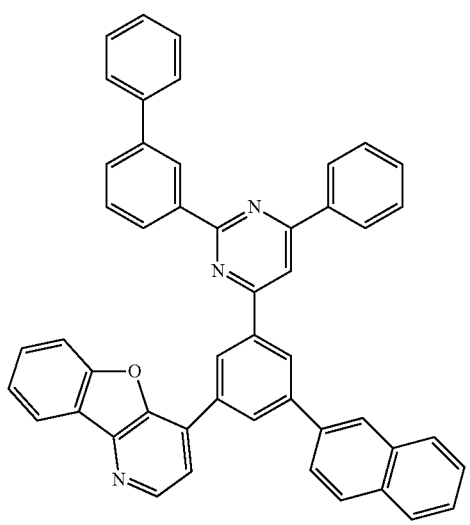
1042
-continued
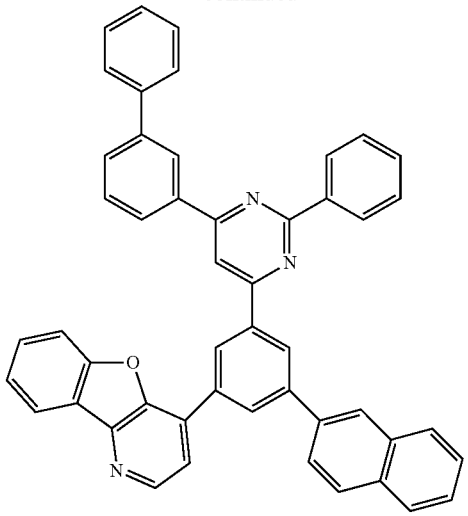
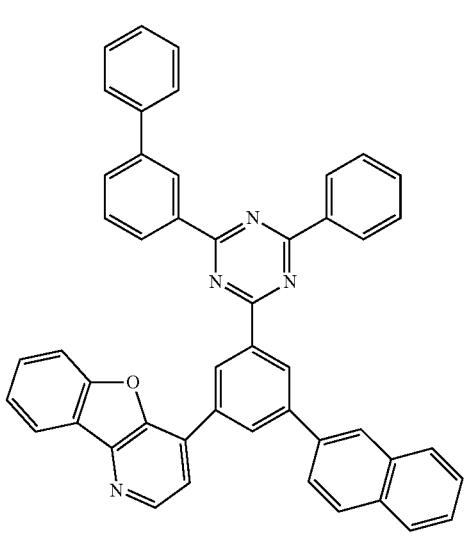
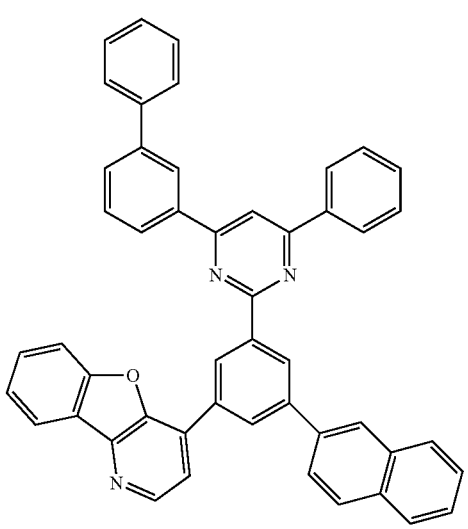

1043
-continued
1044
-continued
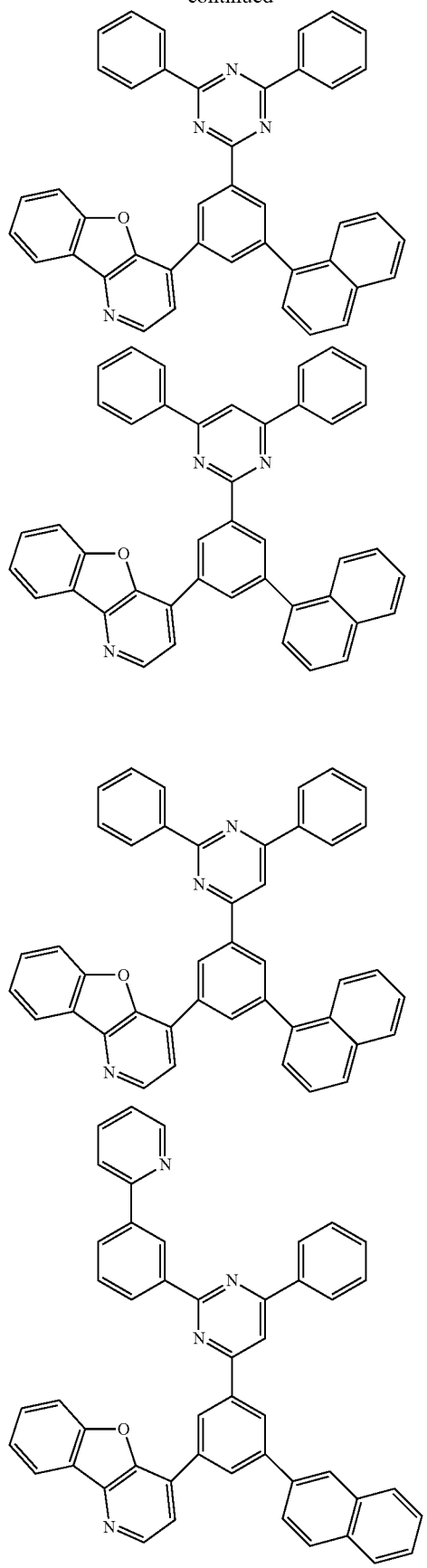
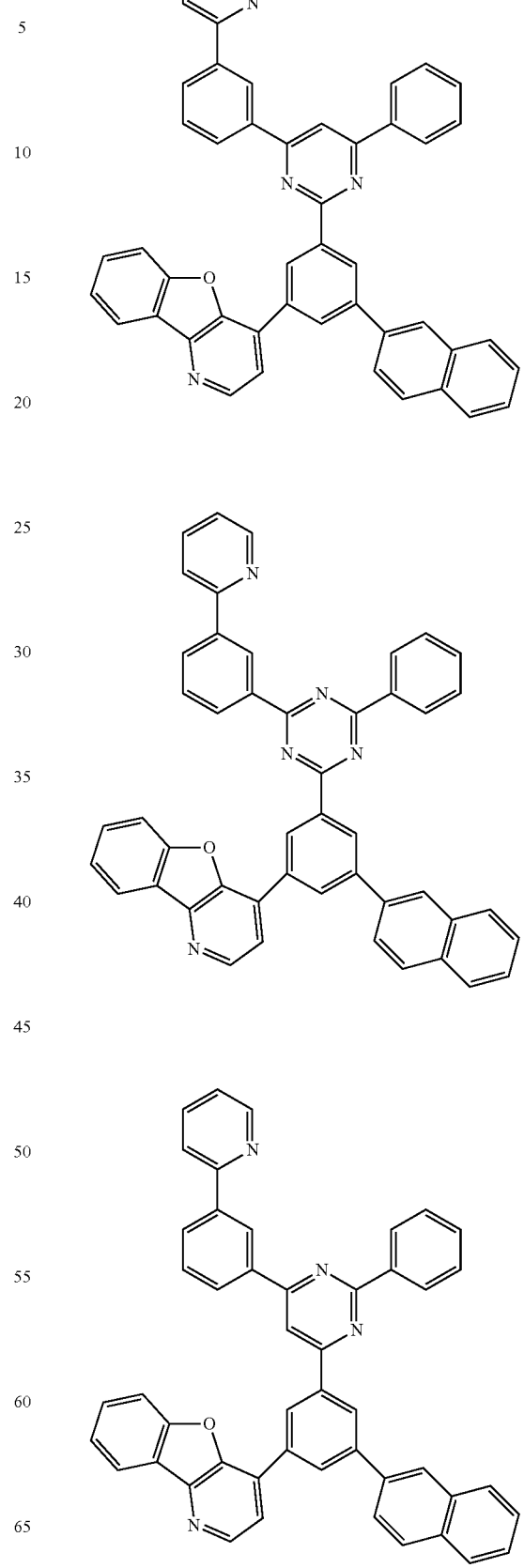

1045
-continued
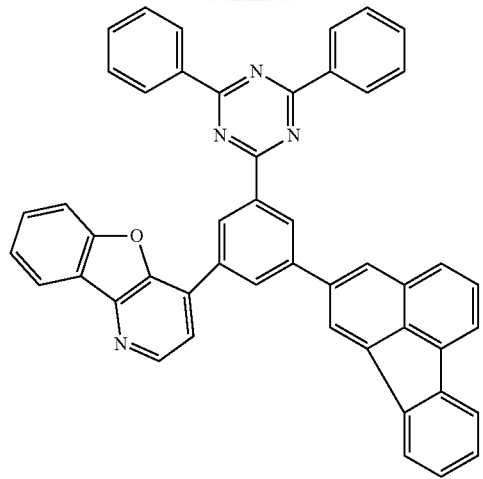
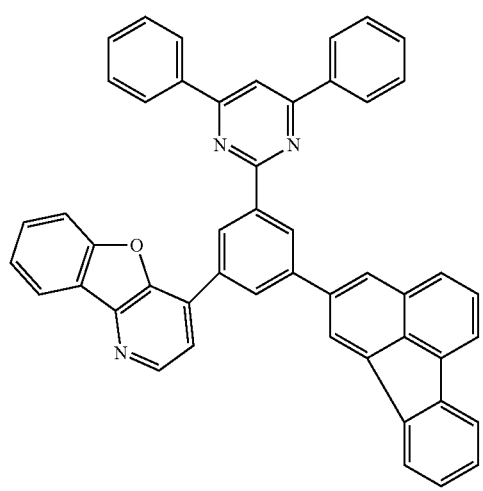
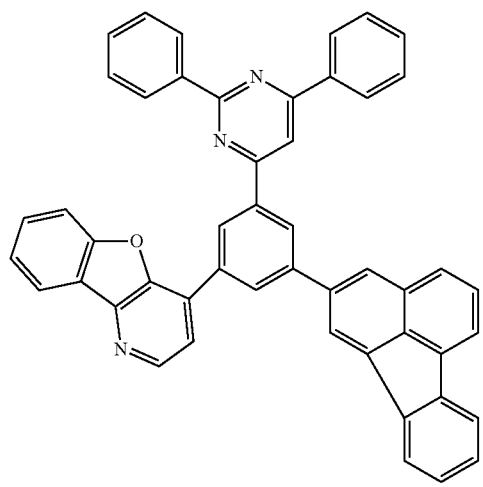
1046
-continued
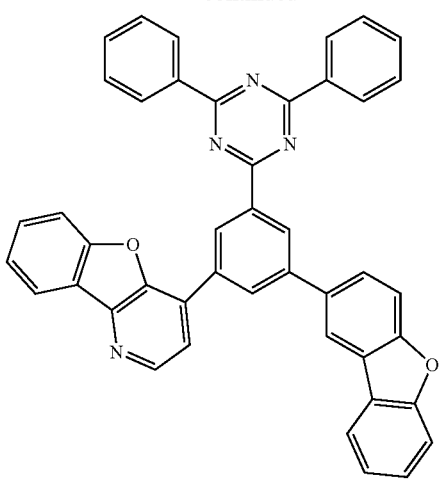
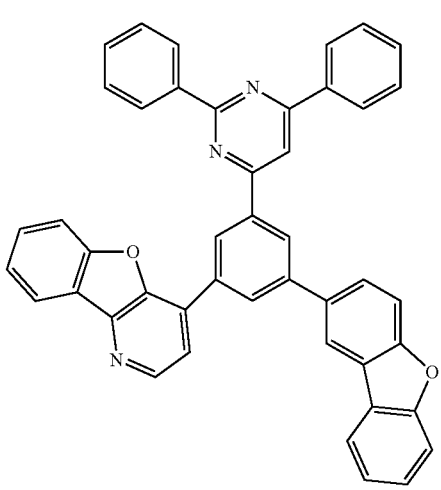
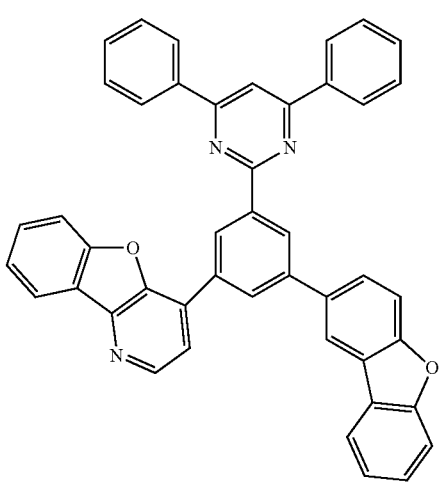

1047
-continued
1048
-continued
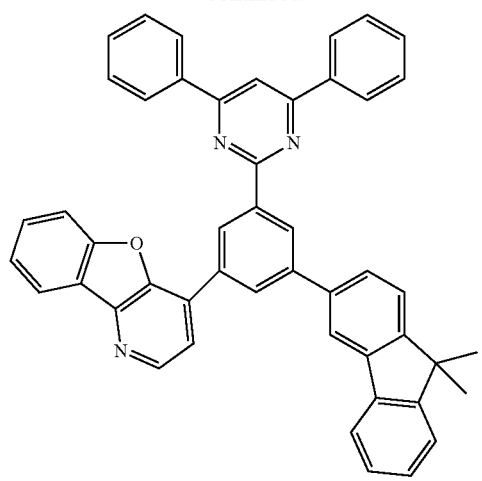
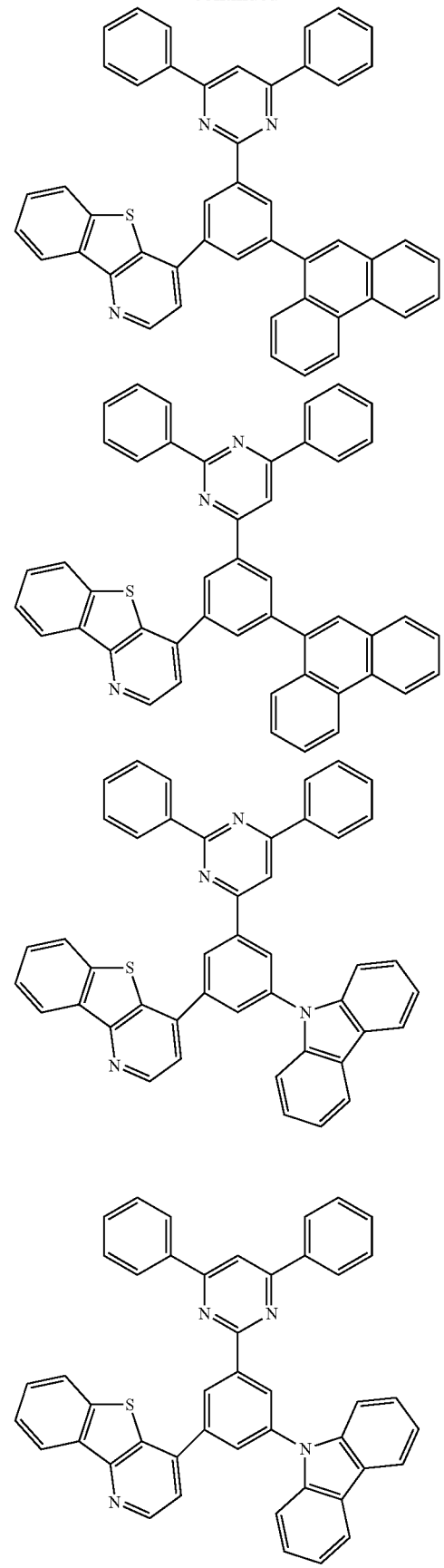

1049
-continued
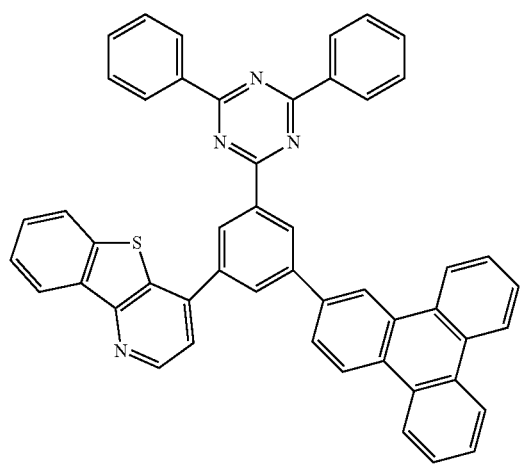
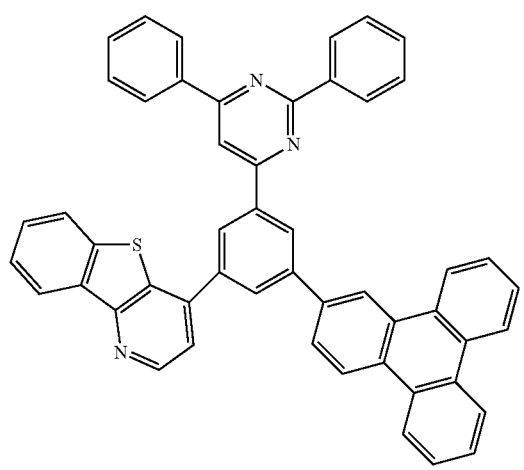
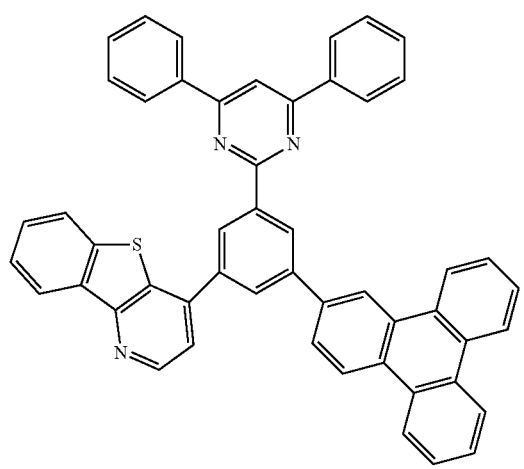
1050
-continued
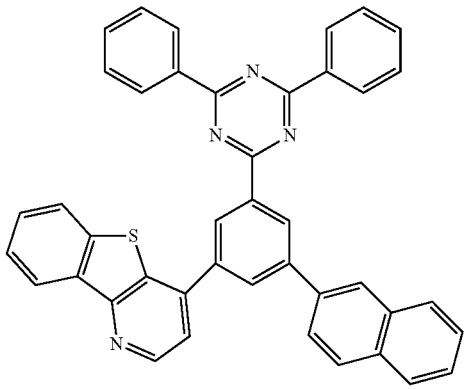
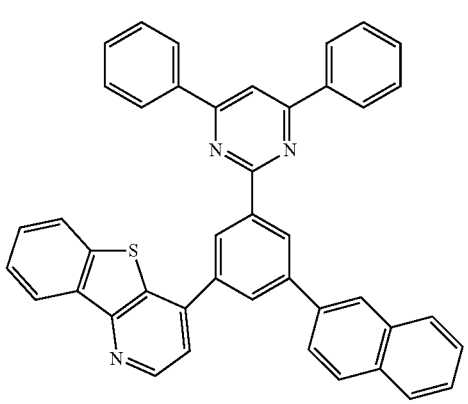
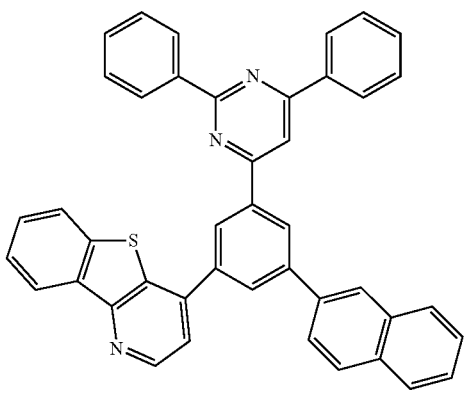
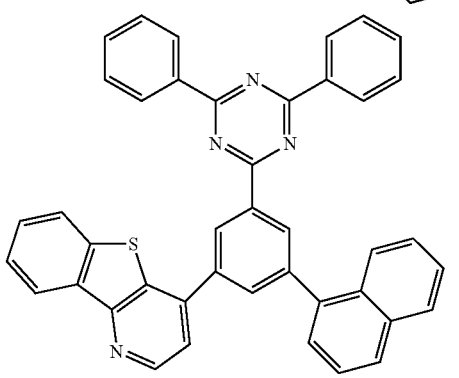

1051
-continued
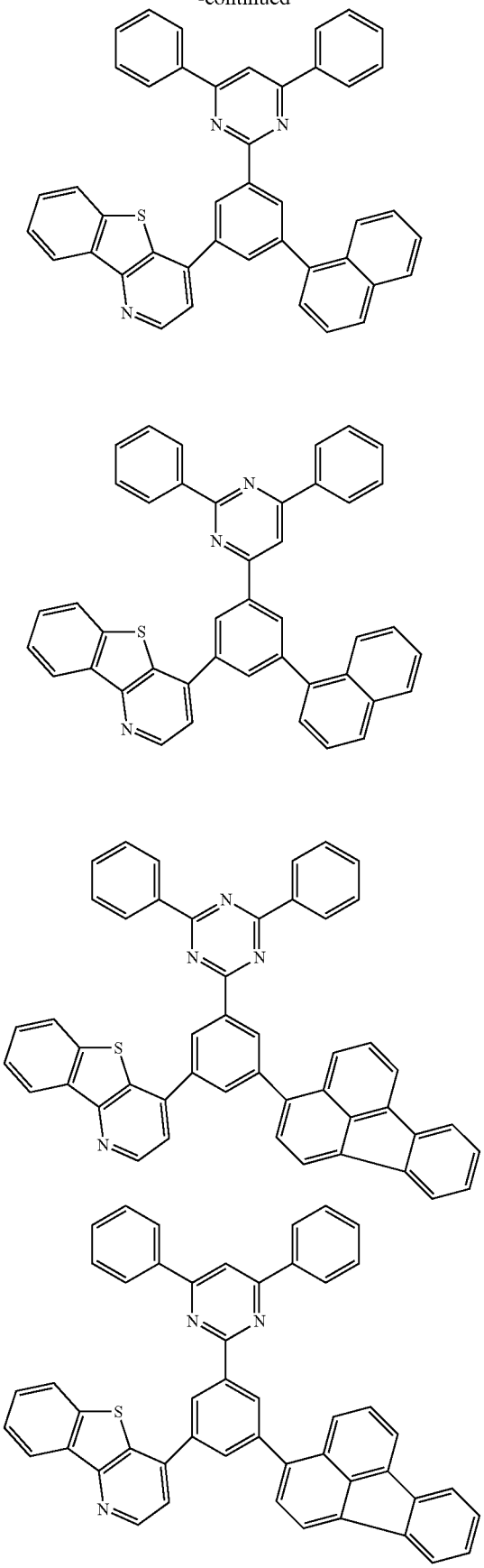
1052
-continued
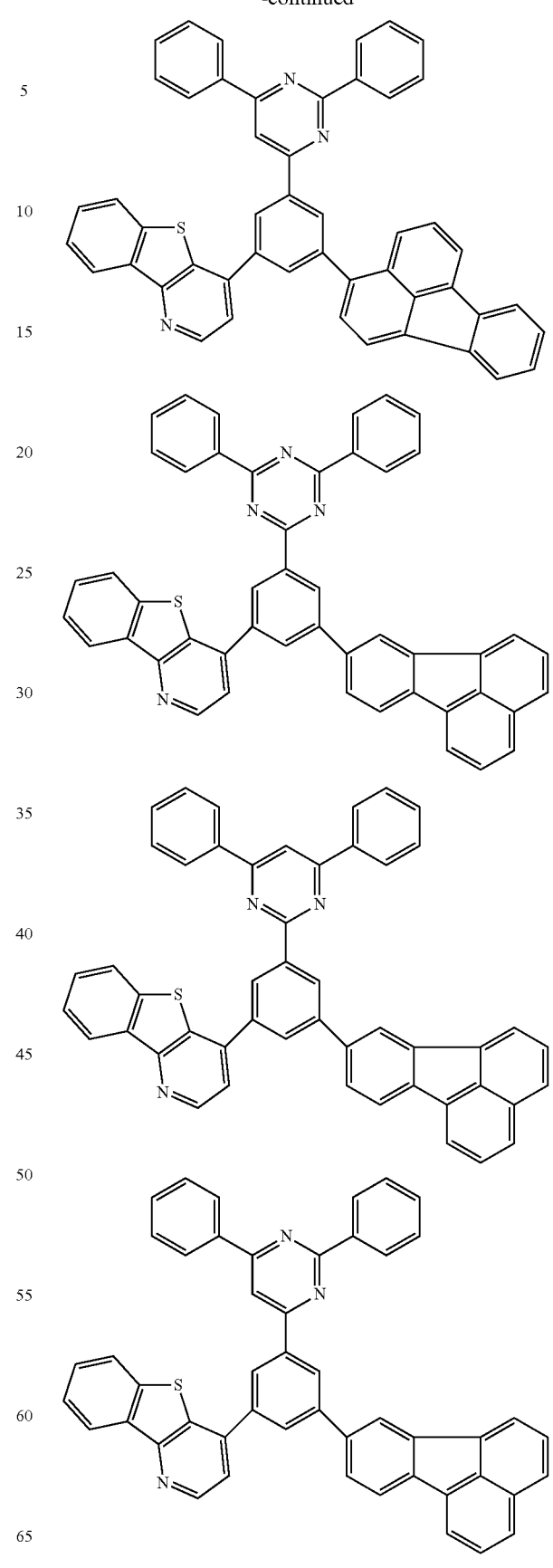

1053
-continued
1054
-continued
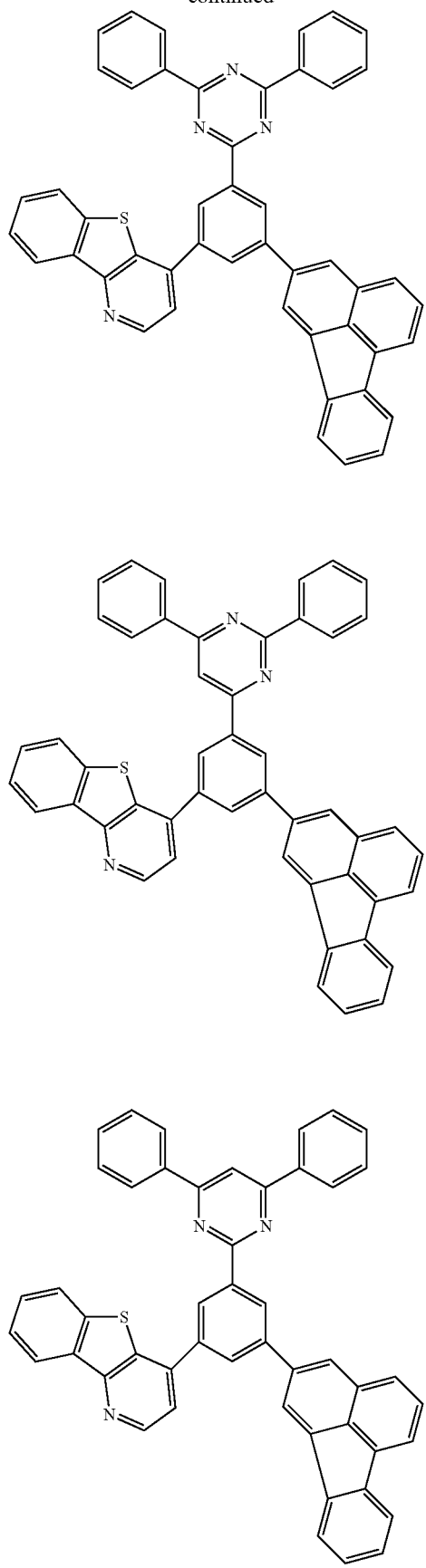
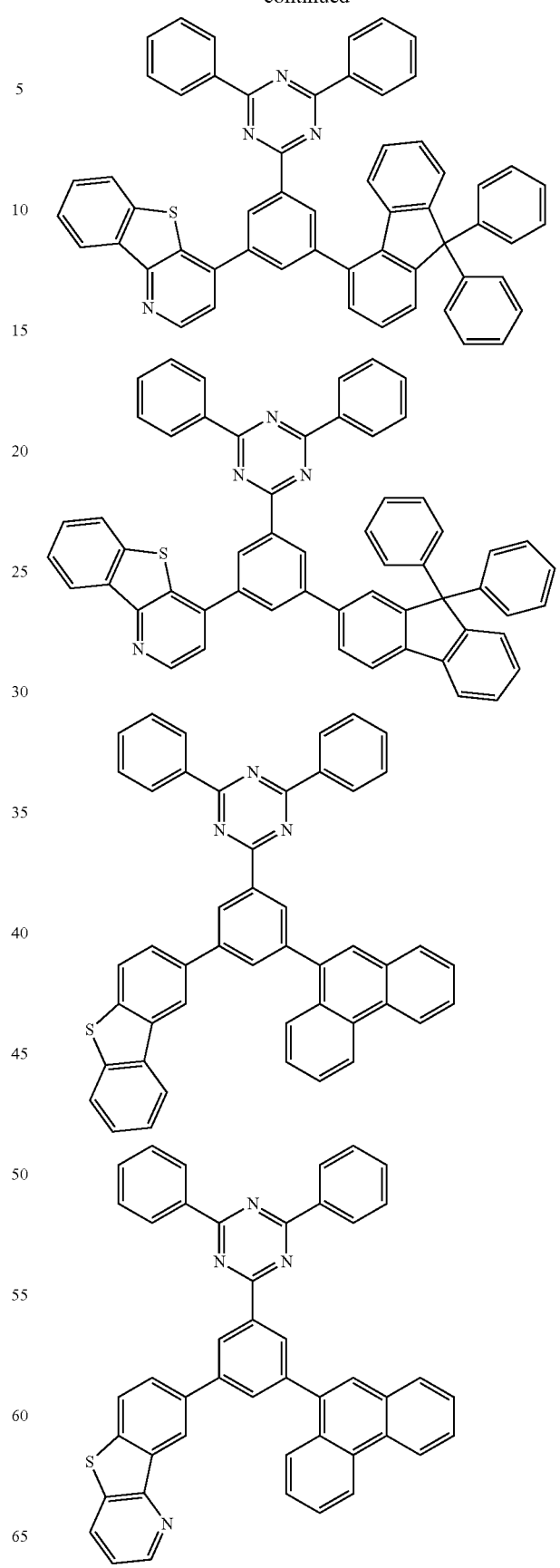

1055
-continued
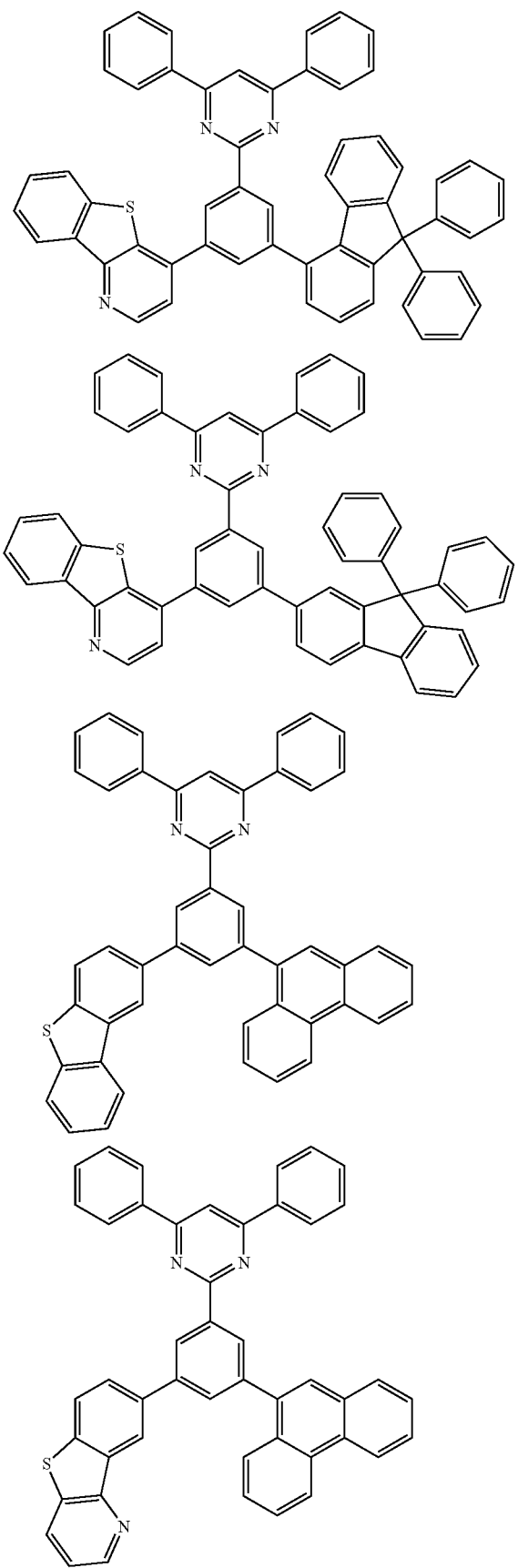
1056
-continued
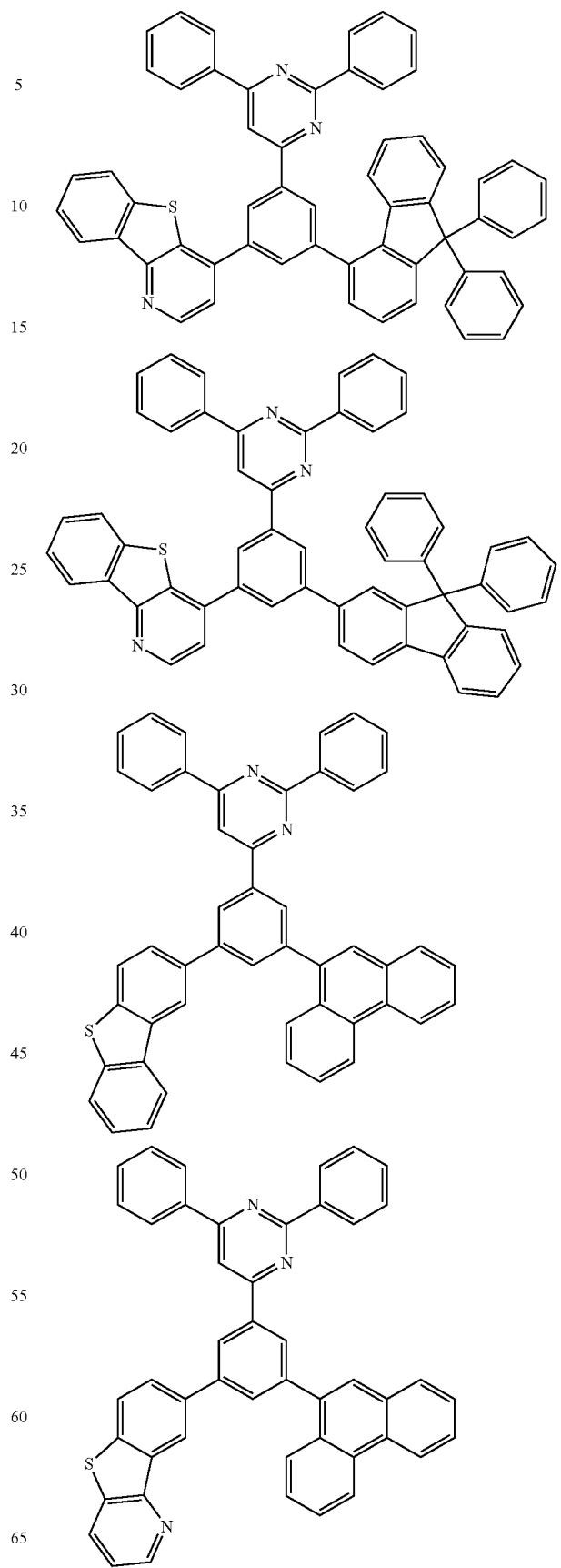

1057
-continued
1058
-continued
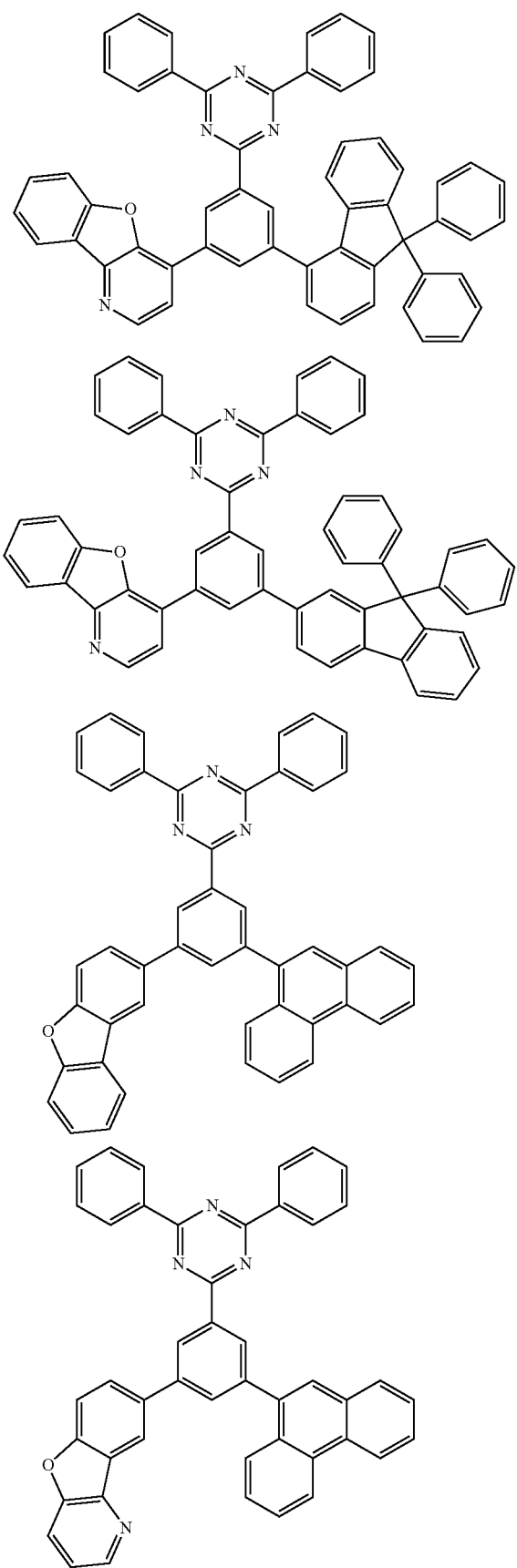
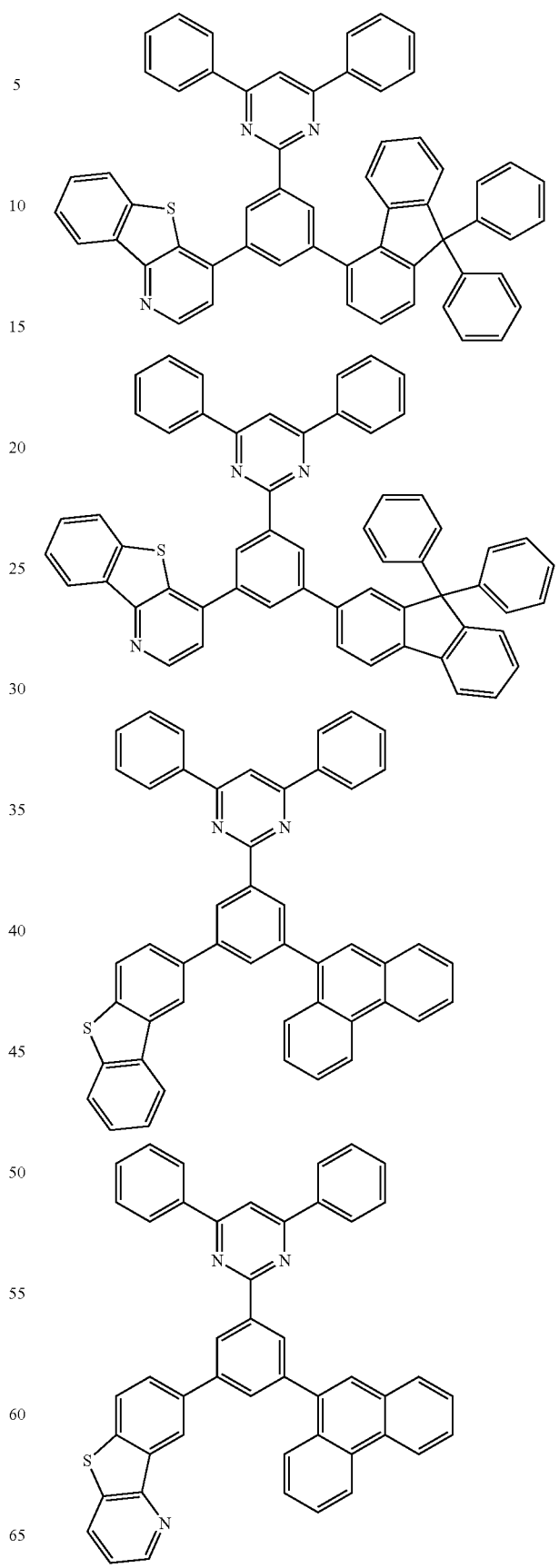

| 1059 -continued | 1060 -continued |
|---|---|
| 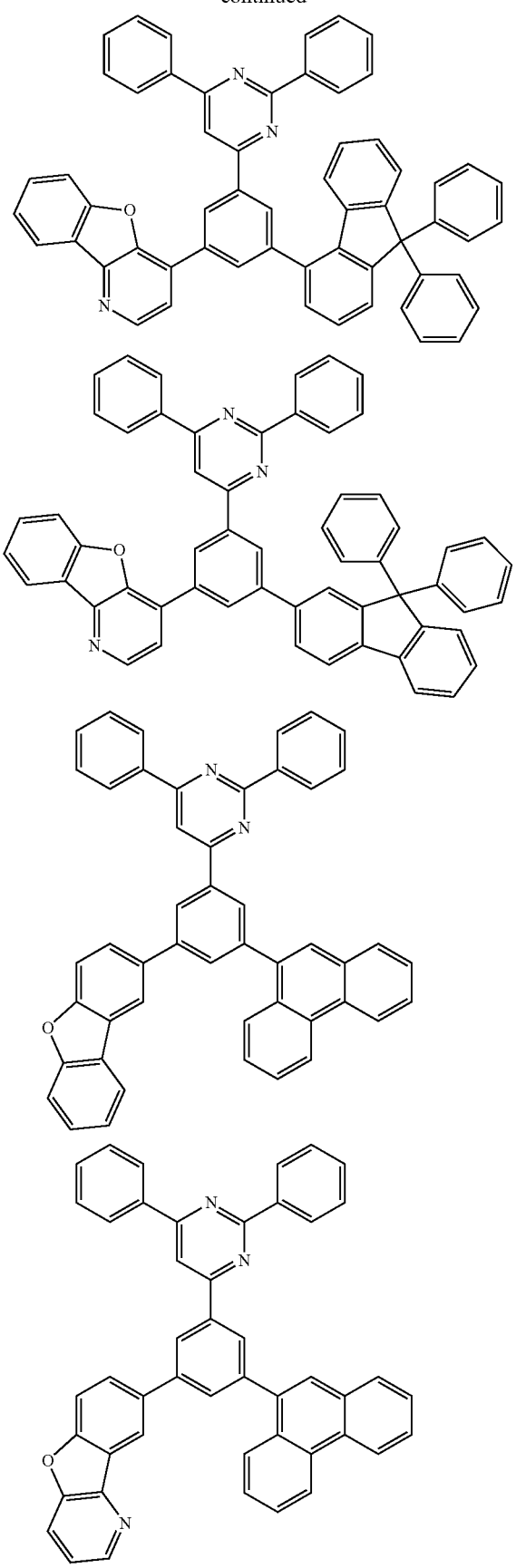 | 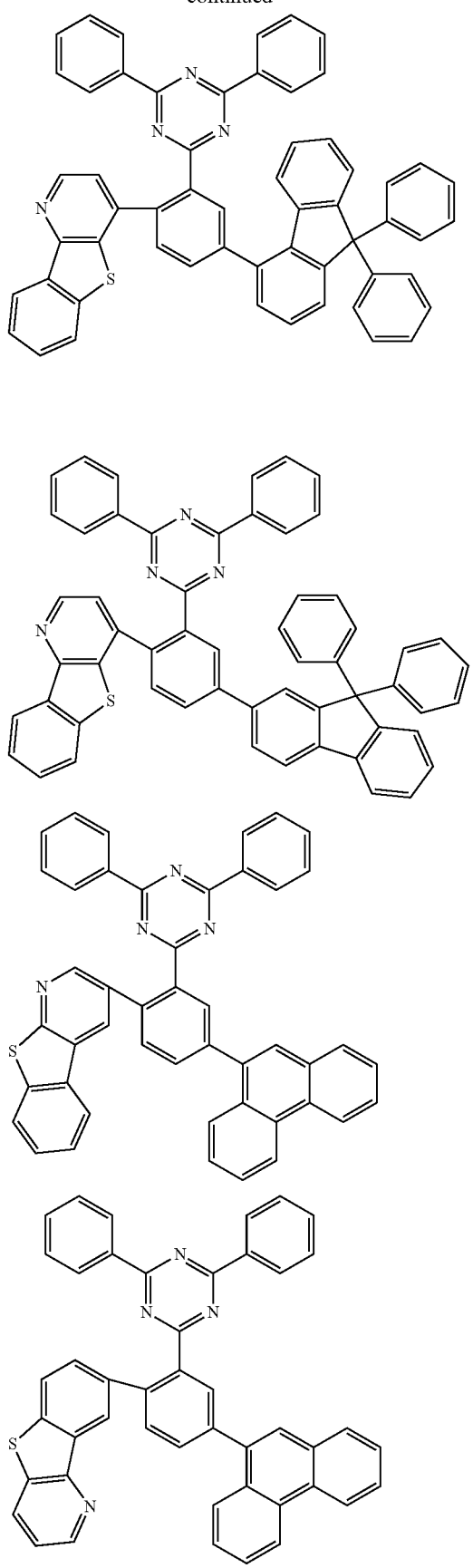 |

1061
-continued
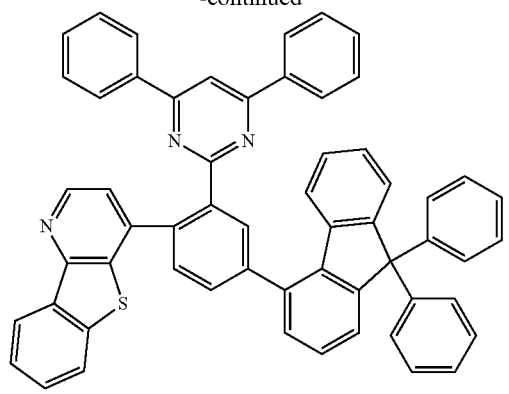
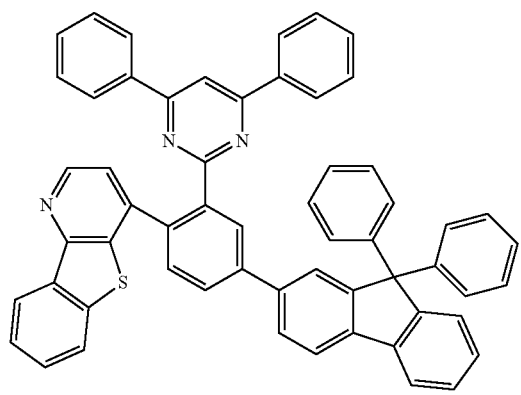
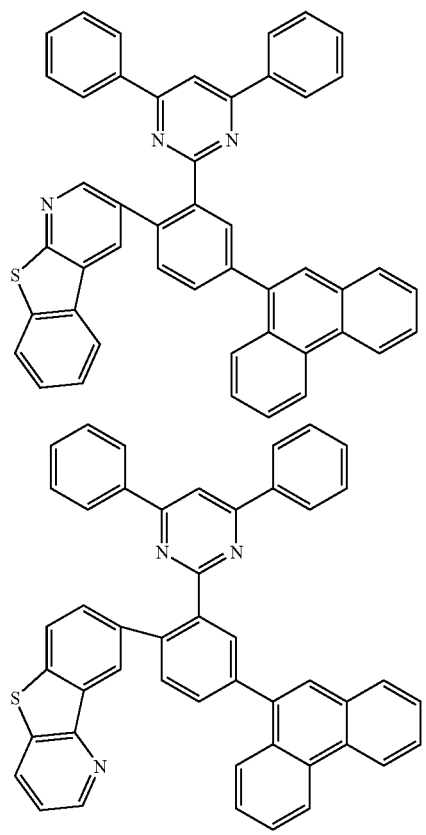
1062
-continued
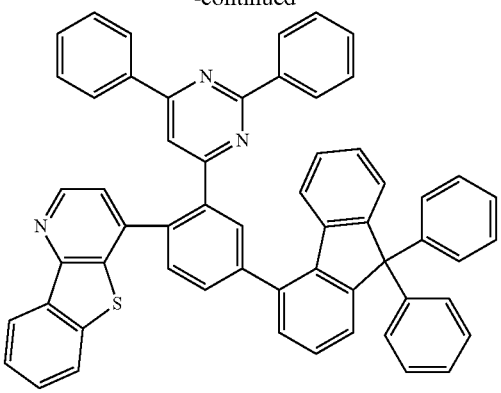
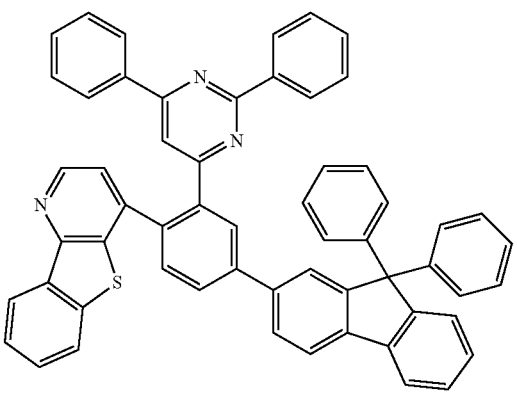
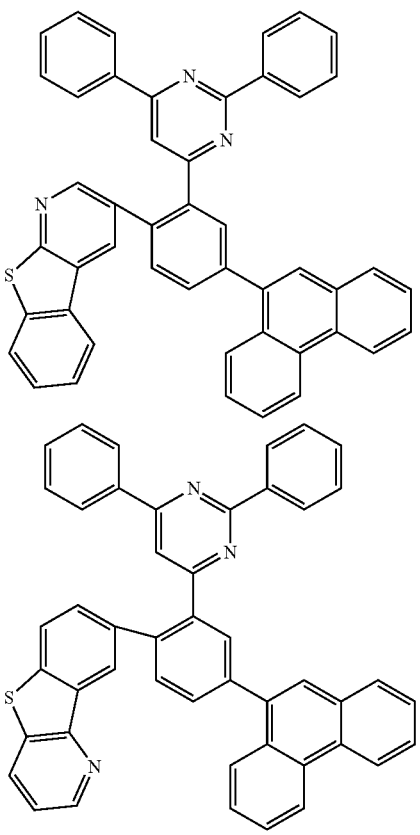

1063
-continued
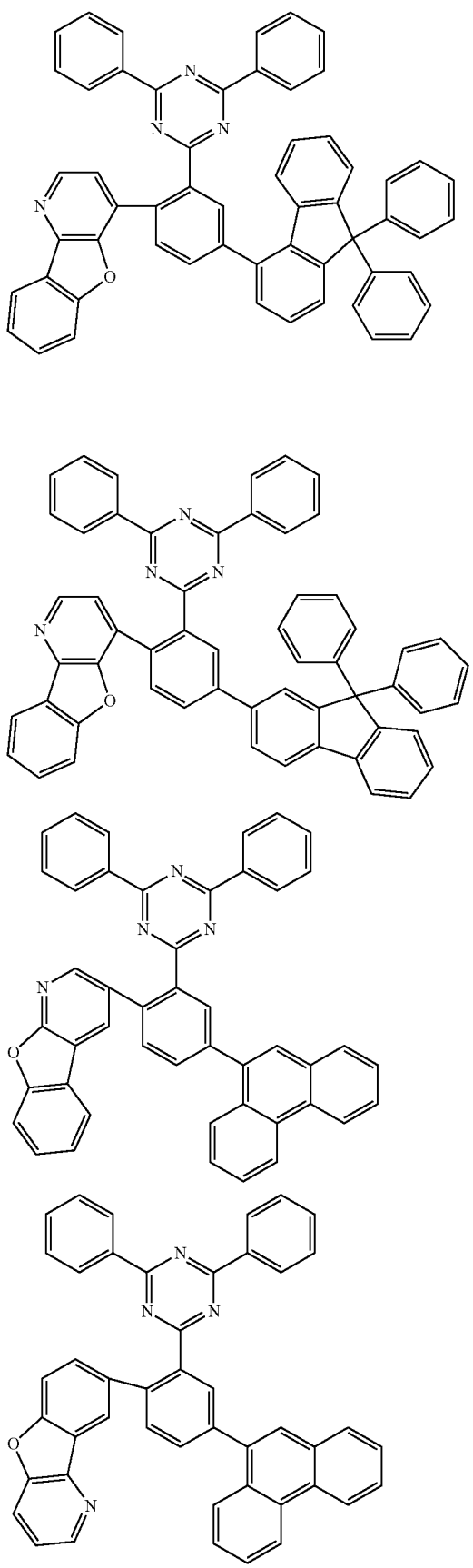
1064
-continued
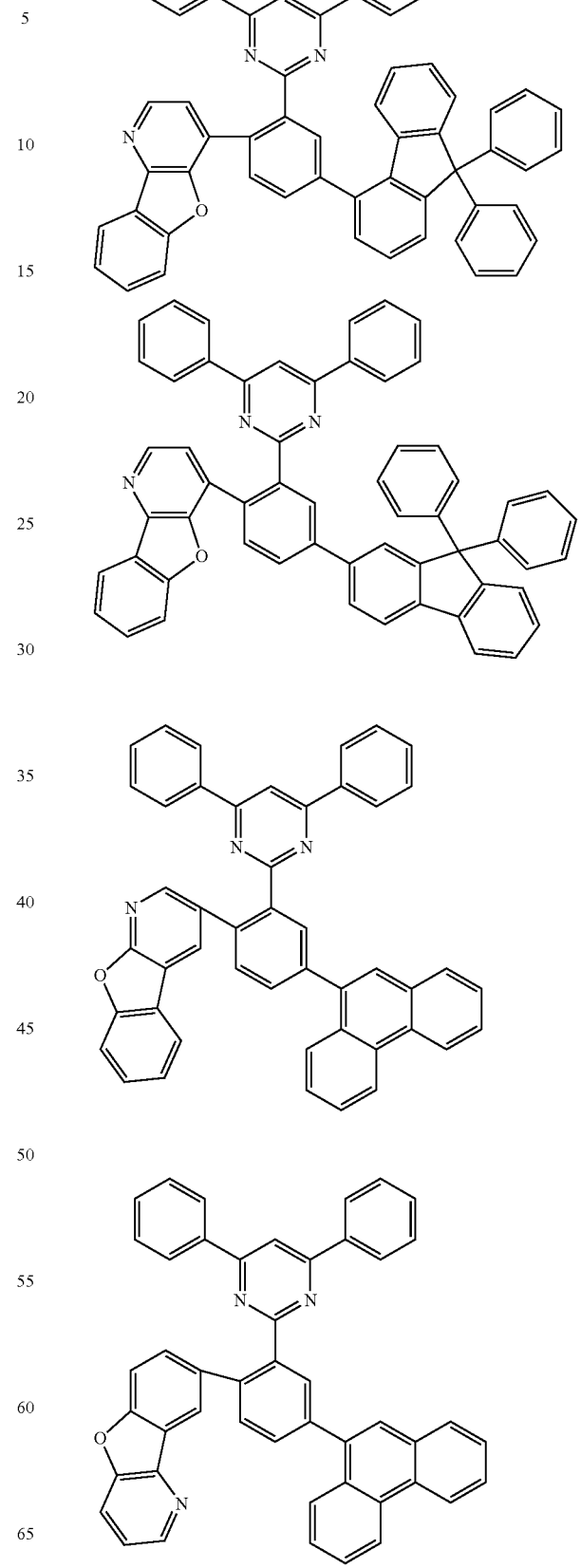

1065
-continued
1066
-continued
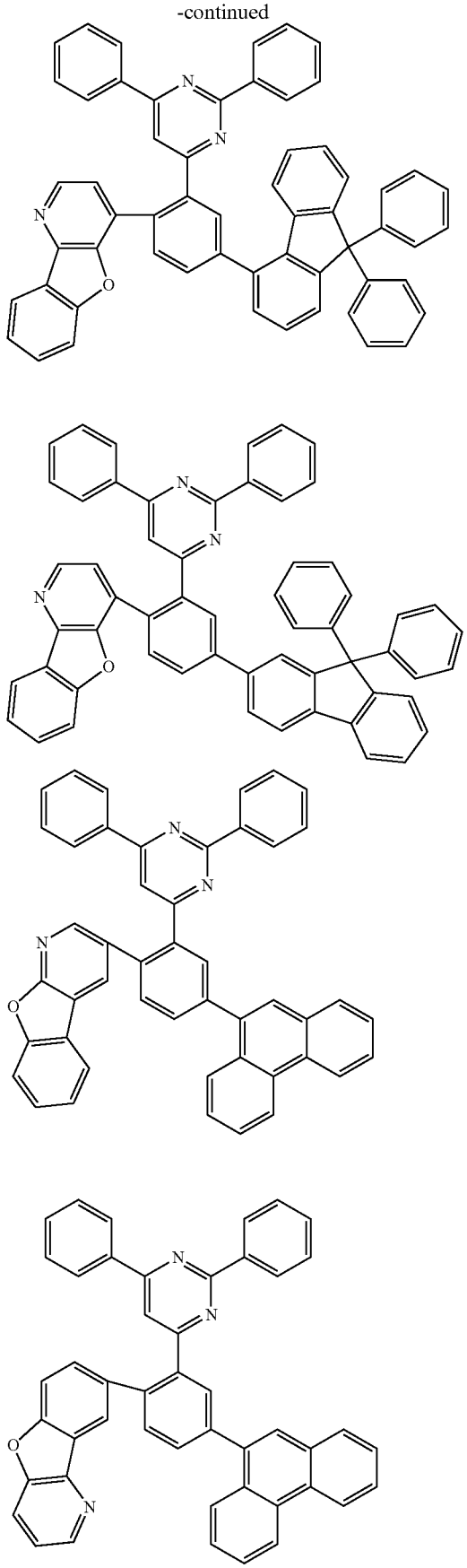
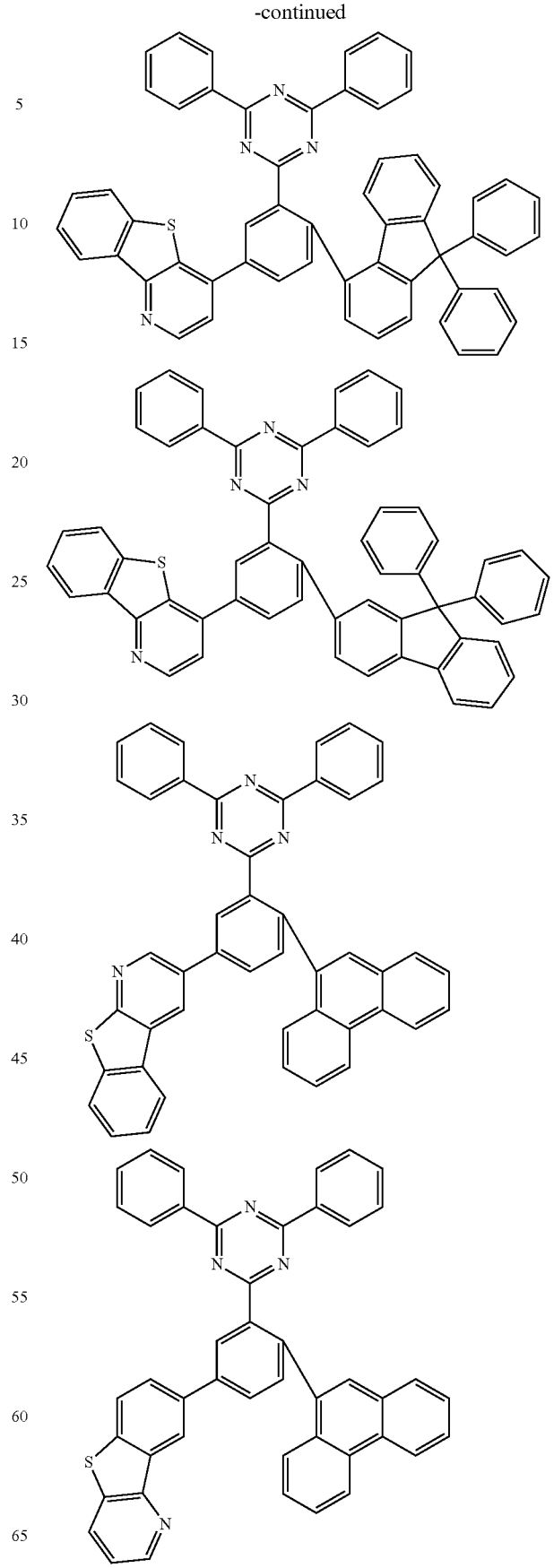

1067
-continued
1068
-continued
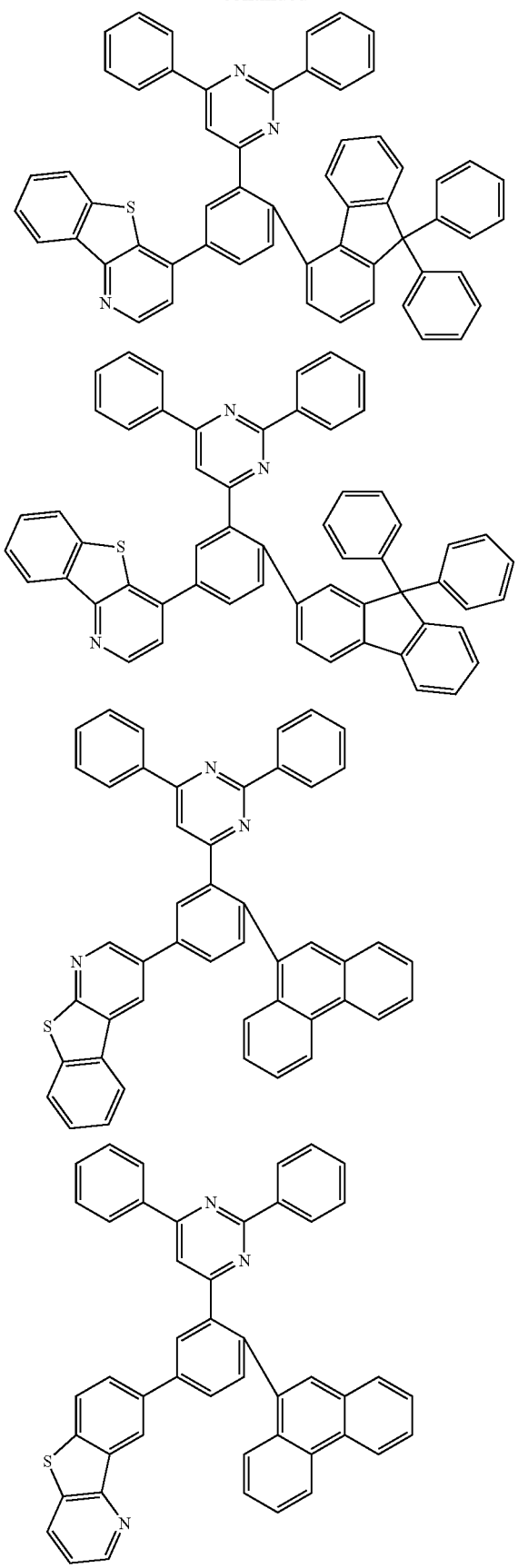
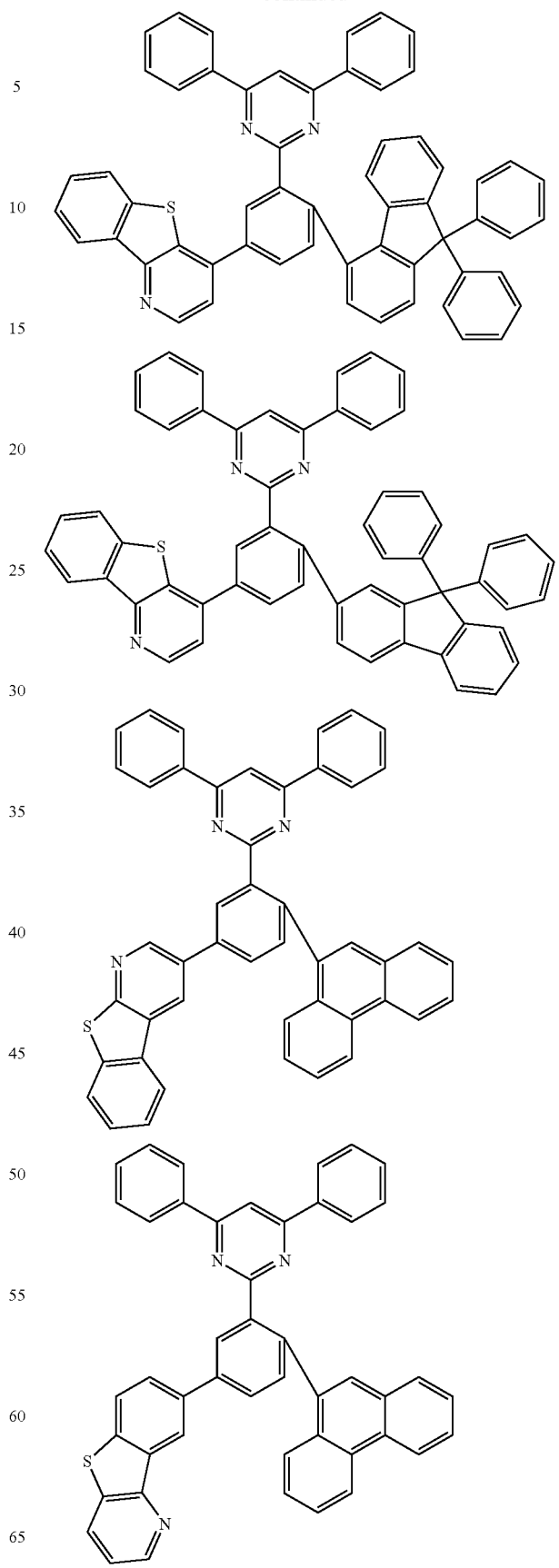

1069
-continued
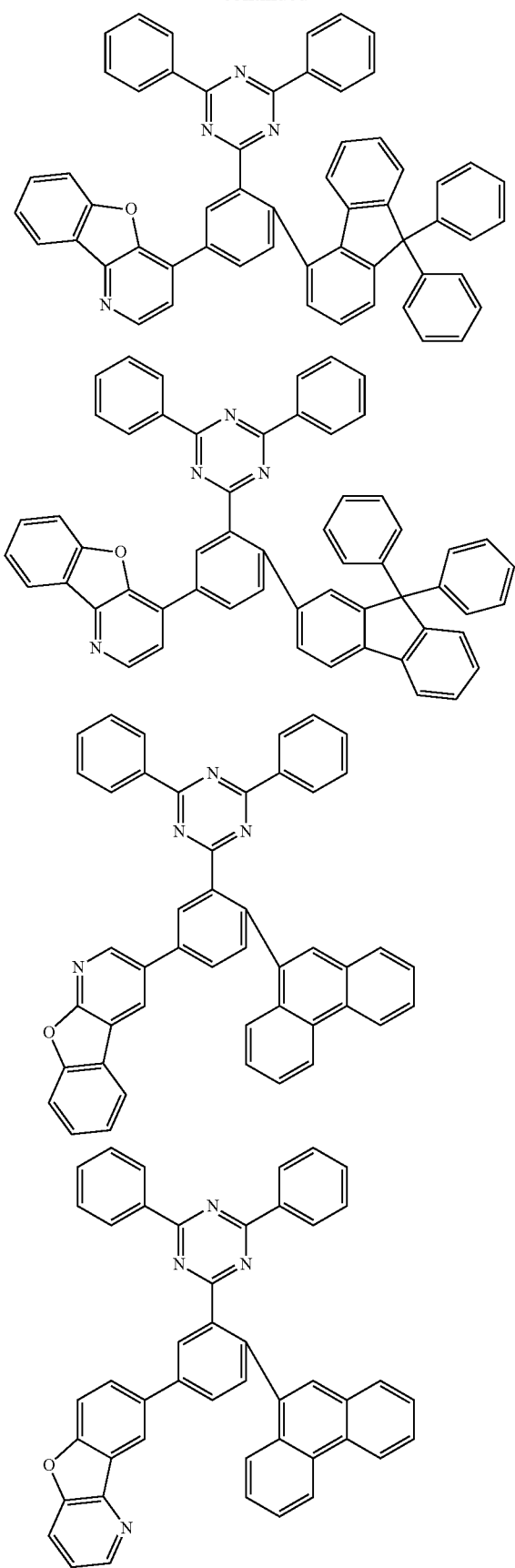
1070
-continued
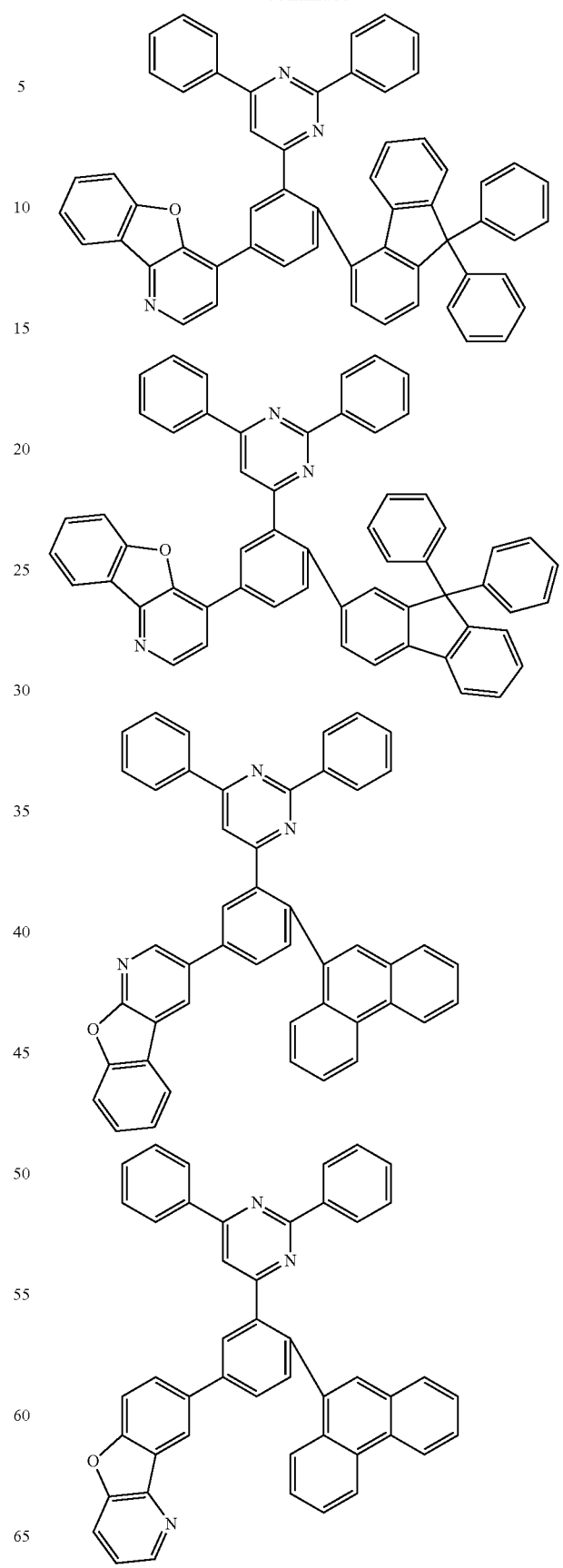

1071
-continued
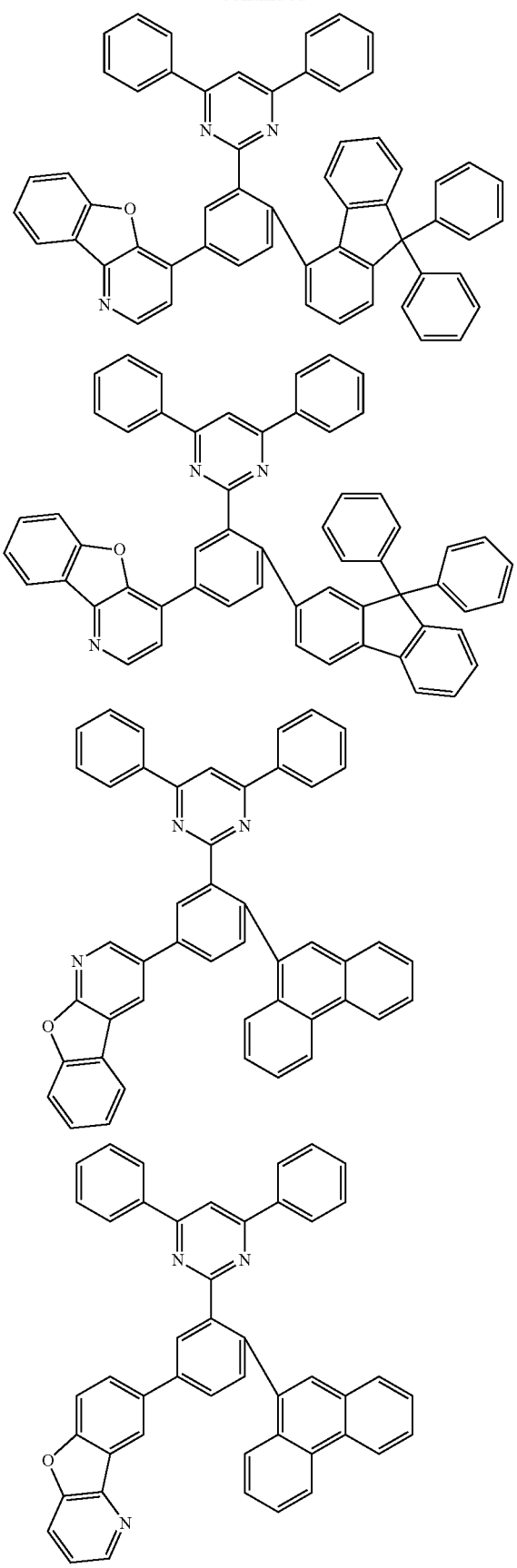
1072
-continued
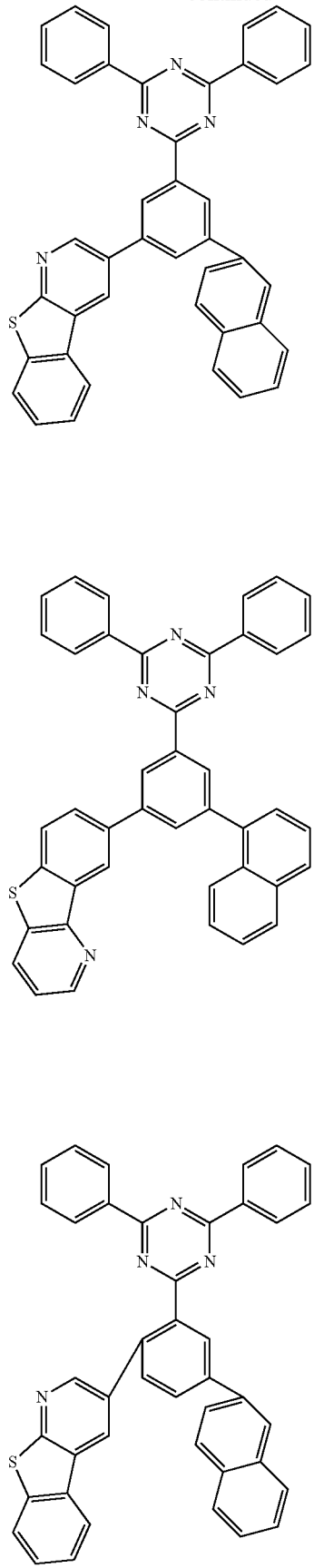

1073
-continued
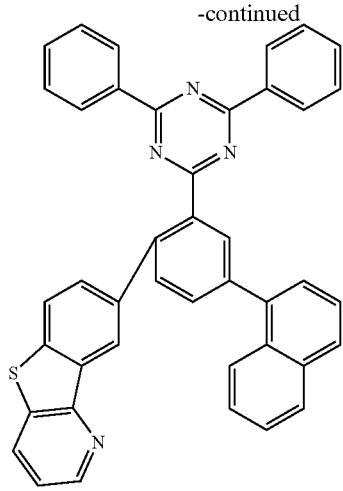
1074
-continued
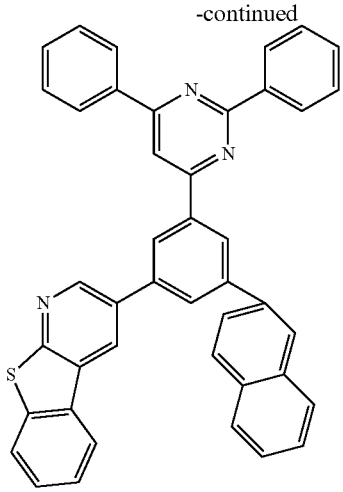
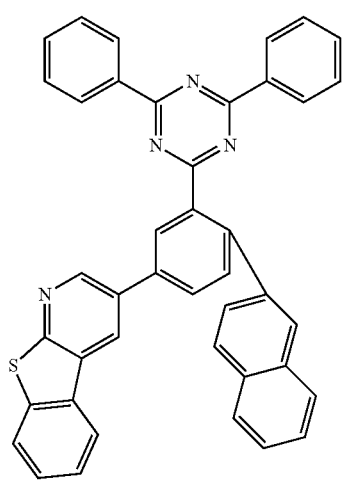
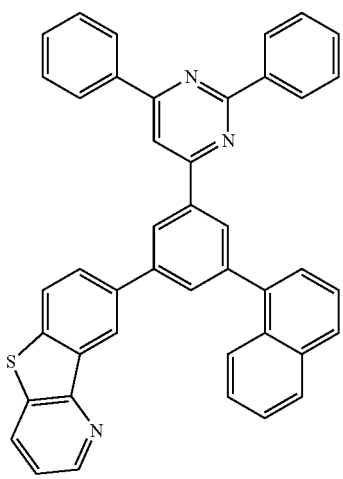
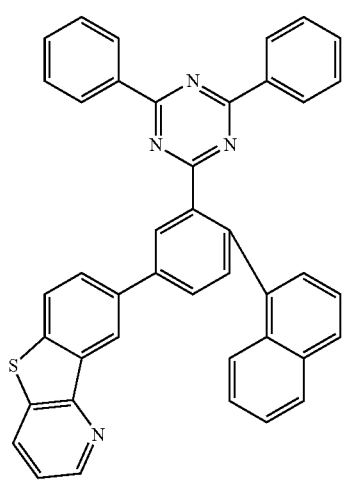
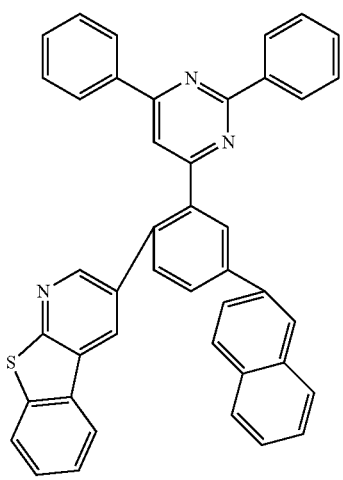

1075
-continued
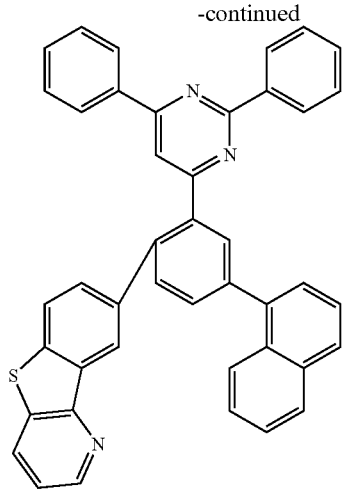
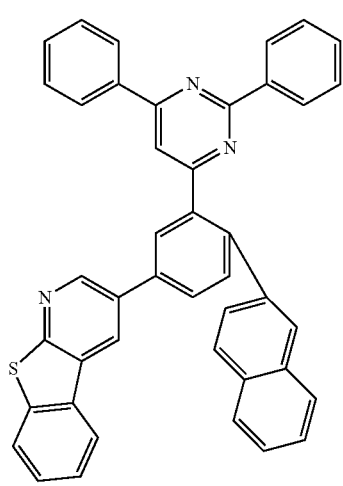
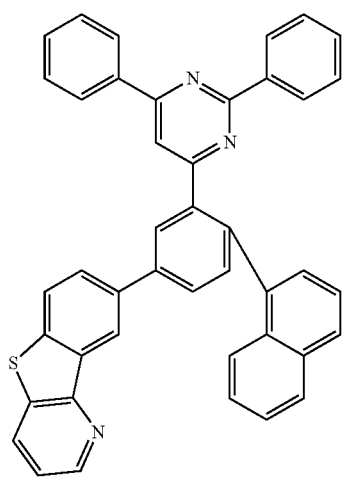
1076
-continued
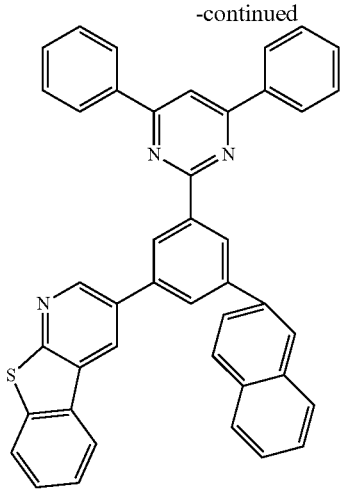
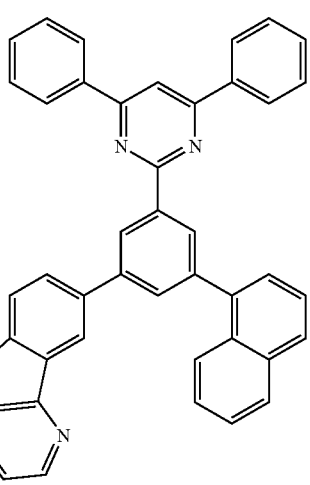
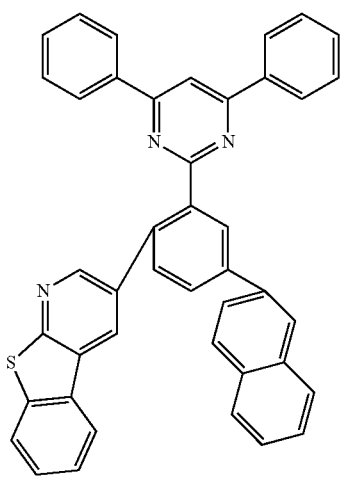

1077
-continued
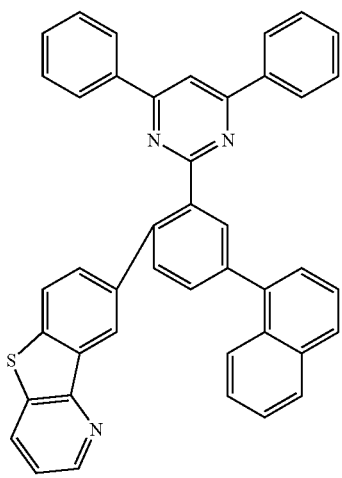
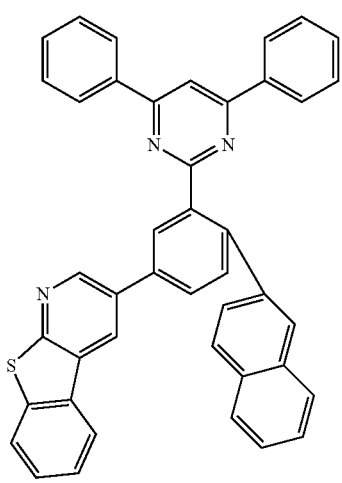
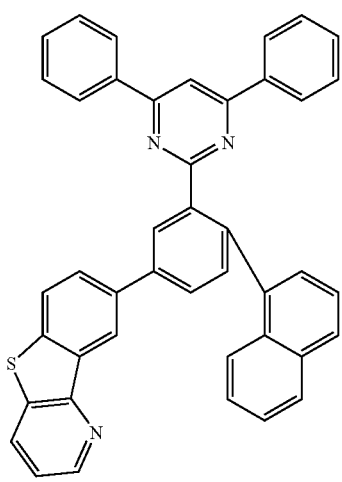
1078
-continued
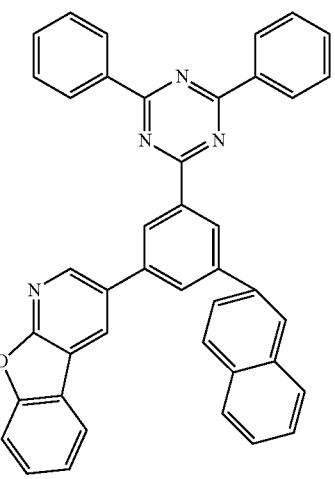
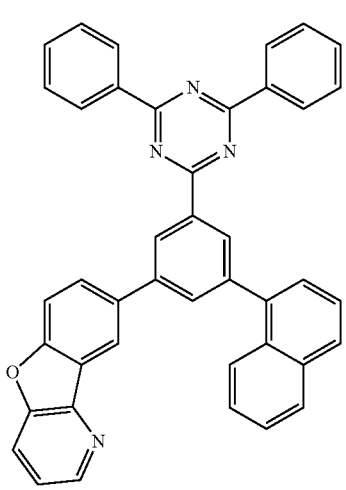
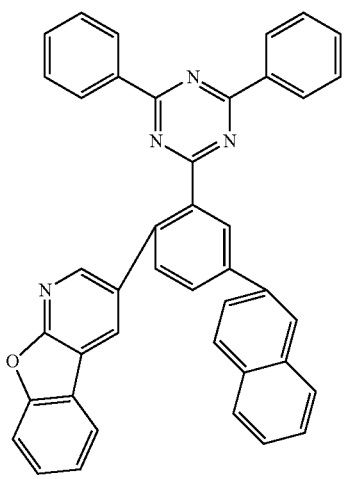

1079
-continued
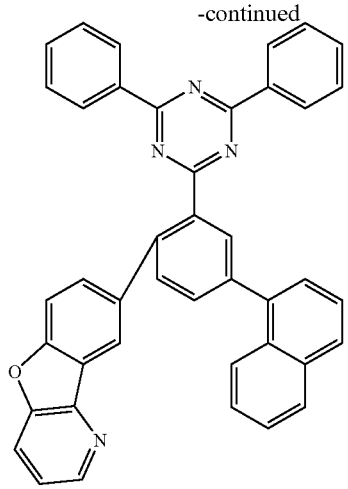
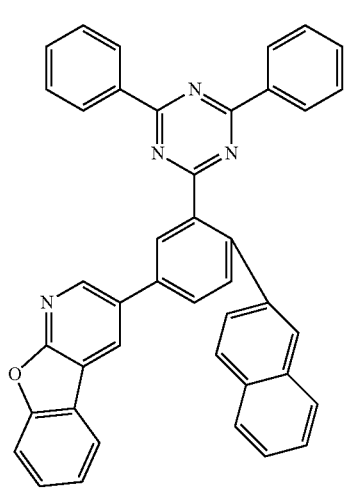
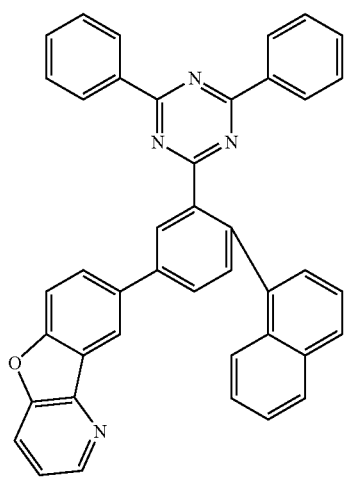
1080
-continued
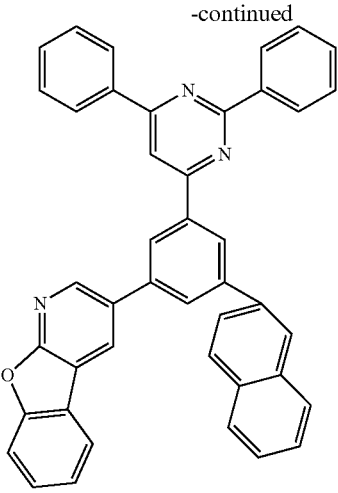
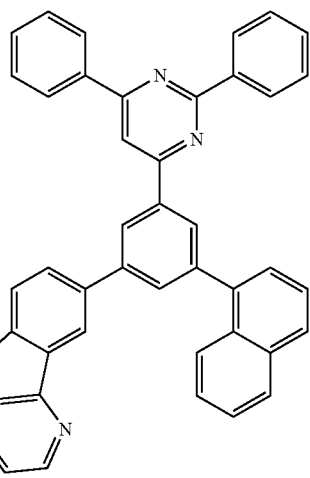
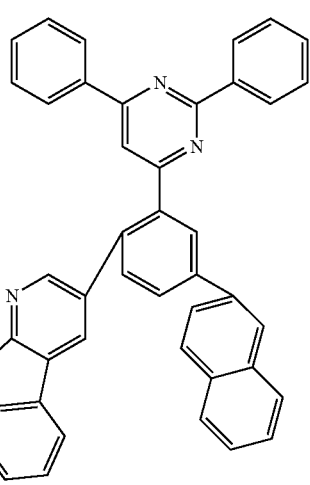

1081
-continued
1082
-continued
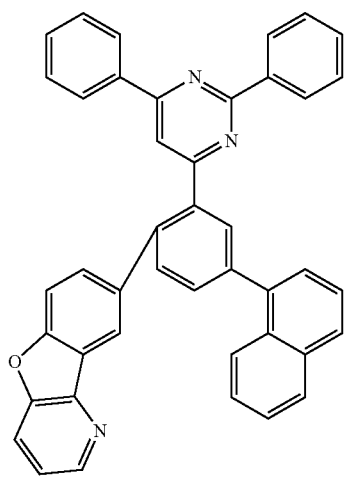
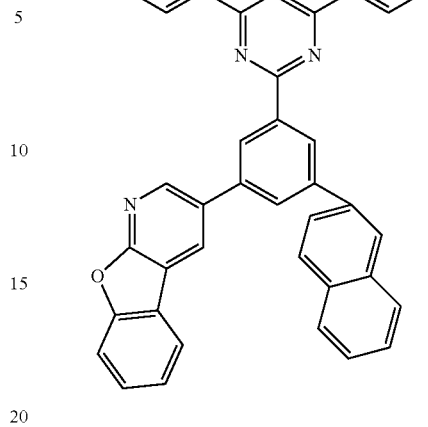
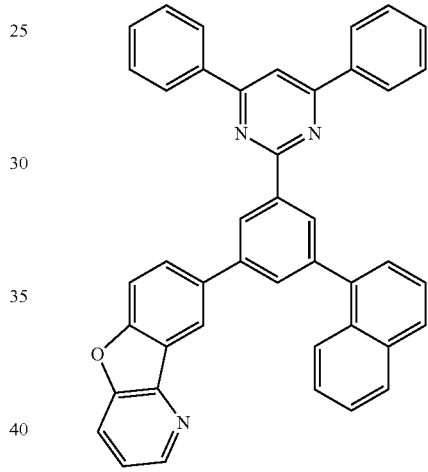
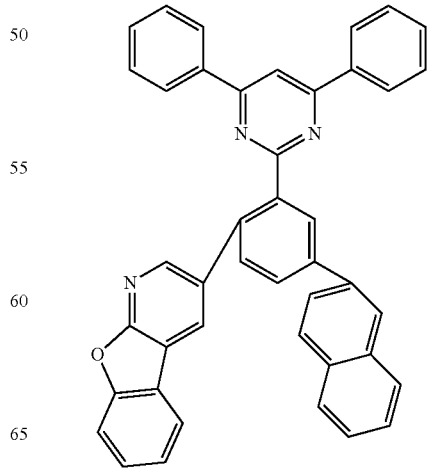

-continued
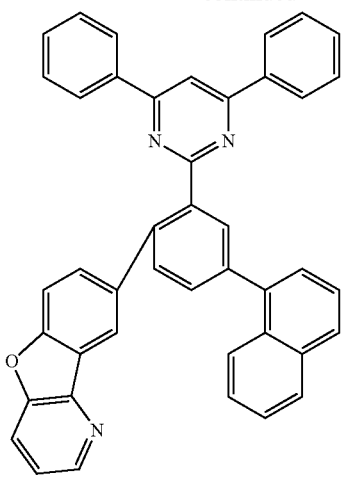
Most preferred are the following compounds:
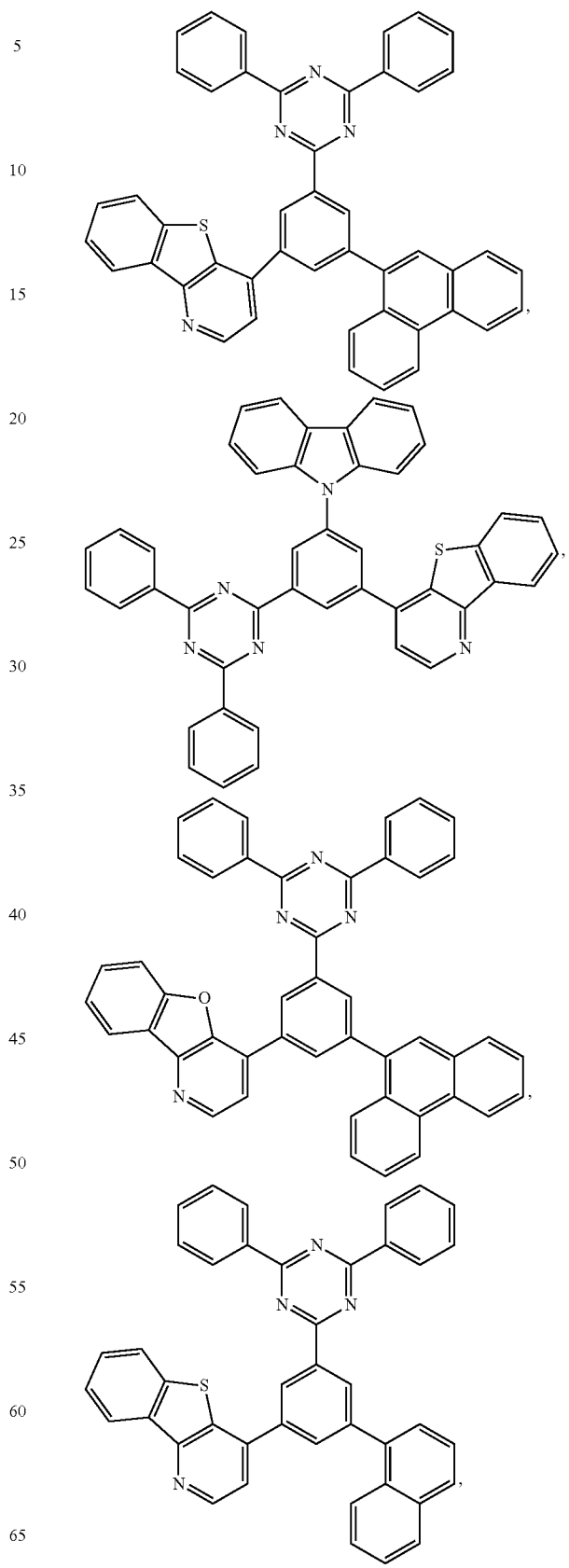

1085
-continued

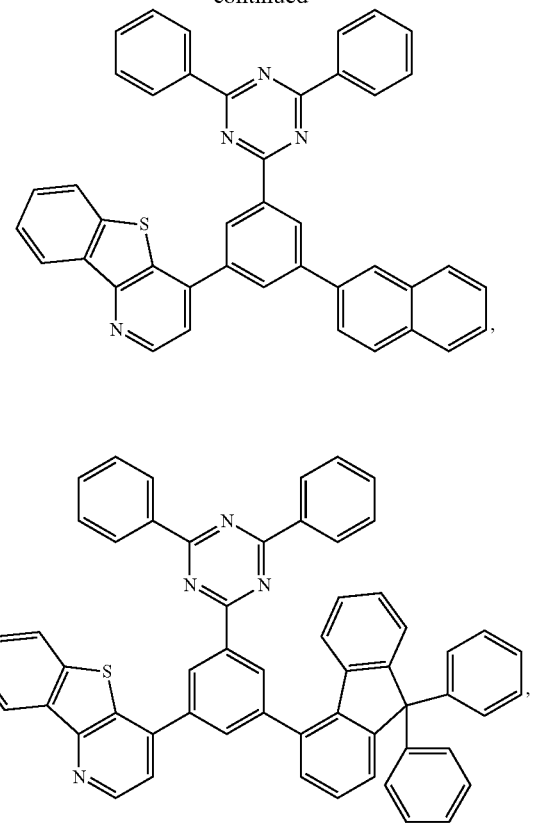

1086
-continued

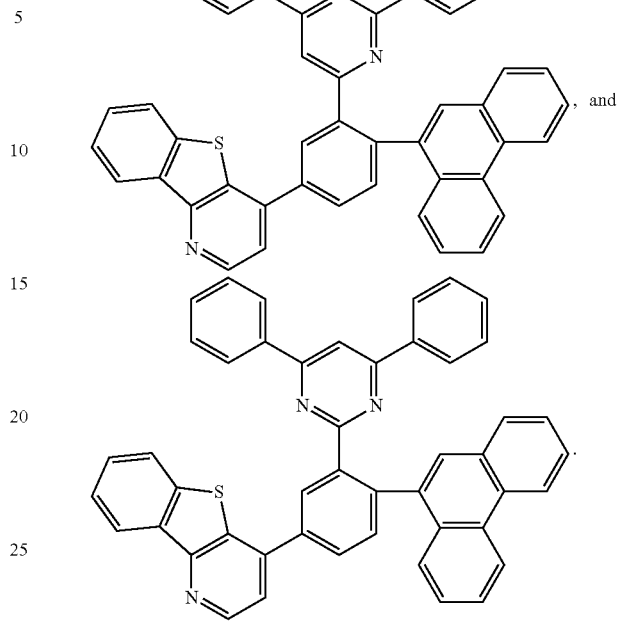

Synthesis of the Compounds of Formula (I)

Generally, the compounds of formula (I') mentioned below are prepared in analogy to the preparation processes described in the related art, e.g. WO2015063046, WO2014044722 and WO2015114102.

Structure (I):

A general process for the preparation of the basic structure (I')

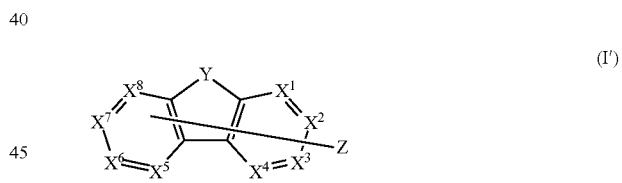

wherein

Z is Hal or —B(OR")$_2$ wherein R" is H or a $C_1$-$C_3$ alkyl group or a phenyl group, provided that two R" may be same or different, and the two R"s may form a ring together with the two oxygen atoms and the boron atom;

wherein one of $X^1$, $X^2$, $X^3$, $X^4$, $X^5$, $X^6$, $X^7$ and $X^8$ is N; and one of the remaining groups $X^1$, $X^2$, $X^3$, $X^4$, $X^5$, $X^6$, $X^7$ and $X^8$ is $CR^1$, $CR^2$, $CR^3$, —$CR^4$, $CR^5$, $CR^6$, $CR^7$ or $CR^8$, wherein $R^1$, $R^2$, $R^3$, $R^4$, $R^5$, $R^6$, $R^7$ or $R^8$ is Z;

and all other groups are defined above and below;

is based for example on the disclosure in WO2009086028 (compound 50), J. of the Kenya Chem. Soc., 1(1) (1999) 5-9, WO2015063046, JP2011084531, US2010/0187984, WO2014044722, US20090134784, and J. Liu, J. Org. Chem. 73, 2951 (2008):

Benzothiopheno[3,2-b]pyridine is for example synthesized according to WO2009086028 (compound 50), then iodinated via lithiation in ortho position:

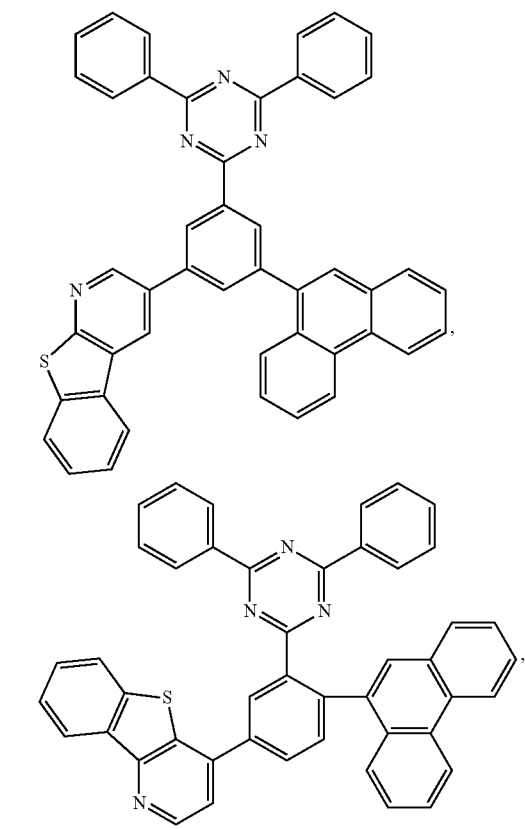

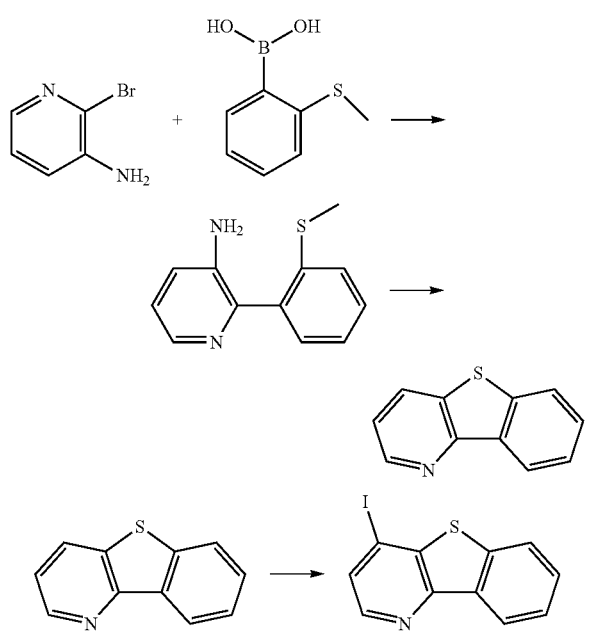

Iodination of benzothiopheno[3,2-b]pyridine with iodine via lithiation is for example described in WO2009/086028:

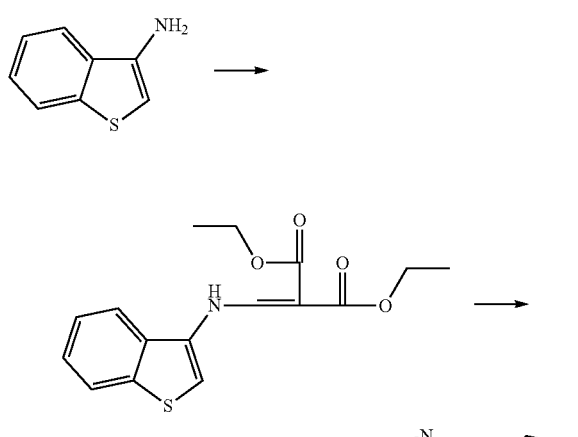

In J. of the Kenya Chem. Soc., 1(1) (1999) 5-9, the synthesis of 4-chlorobenzothiopheno[3,2-b]pyridine is described.

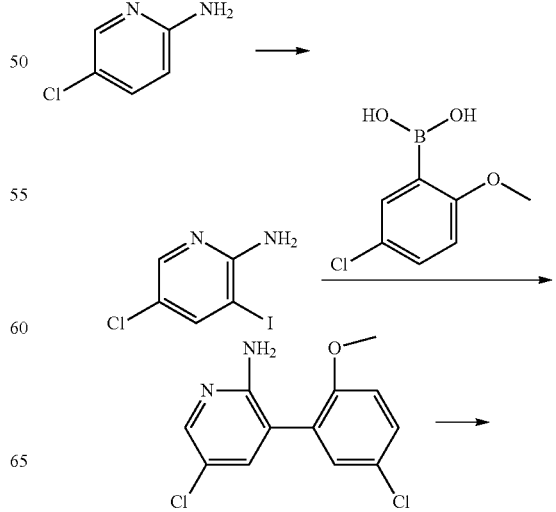

3-Bromobenzothiopheno[2,3-b,]pyridine is for example synthesized according to WO2015063046:

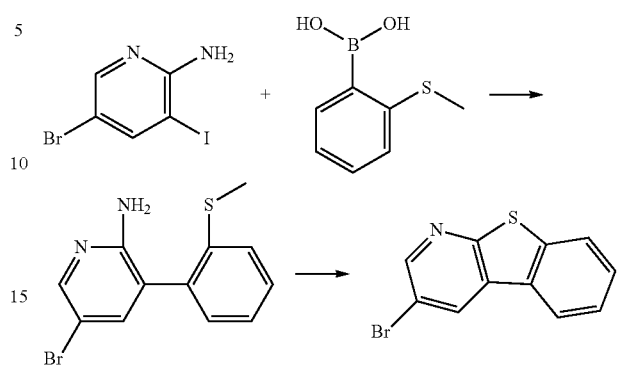

JP2011084531 describes the synthesis of benzofuro[3,2-b]pyridine in two steps starting from 2-bromopyridin-3-ol using a base catalyzed cyclisation. The brominated compound is received by bromination with bromine in the presence of silver sulfate:

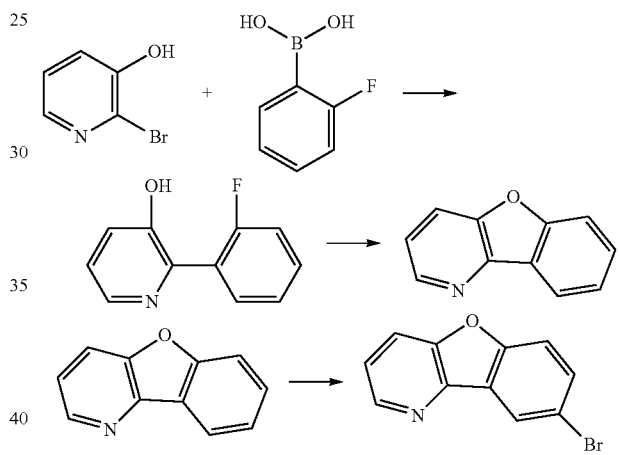

US2010/0187984 describes the synthesis of 3,6-dichloro-benzofuro[2,3-b]pyridine in three steps starting from 2-amino-5-chloropyridine:

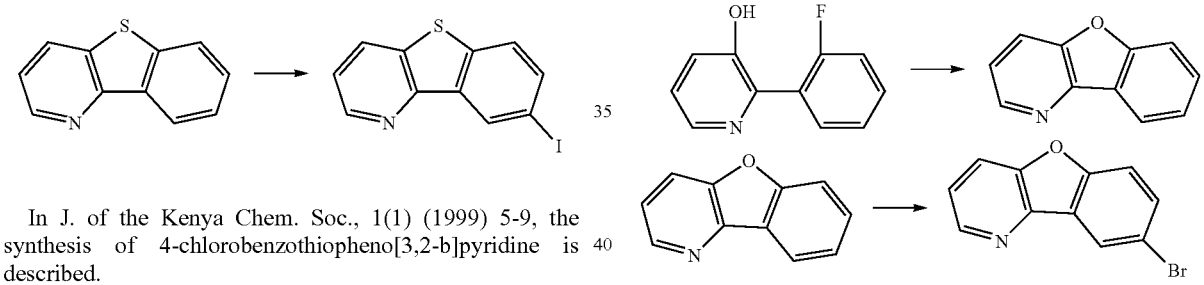

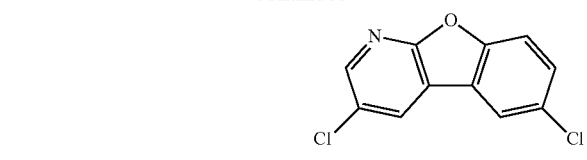

Accordingly 3,6-dibromo-benzofuro[2,3-b]pyridine is for example synthesized as described in WO2014044722:

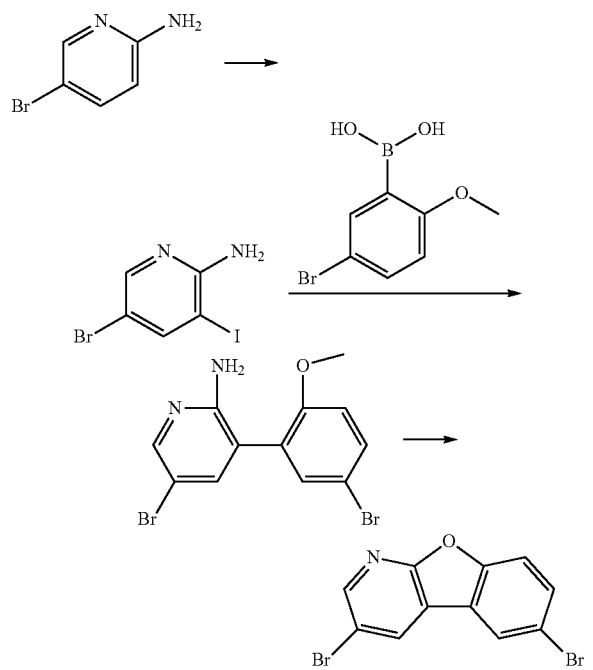

6-Chlorobenzofuro[2,3-b]pyridine is for example synthesized according to US20090134784:

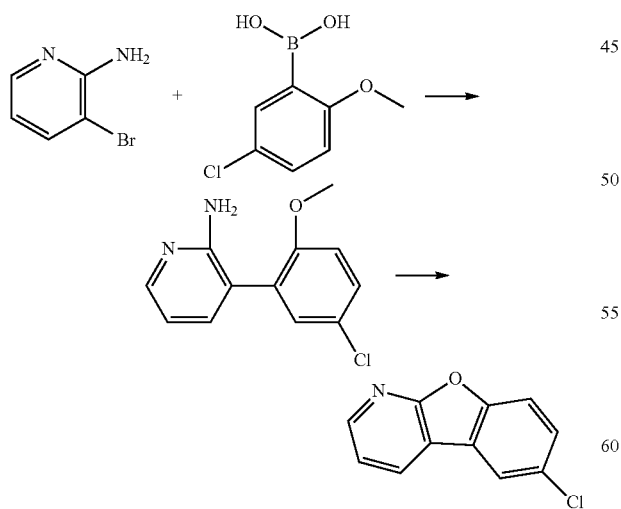

J. Liu, J. Org. Chem. 73, 2951 (2008) describes the synthesis of benzofuro[2,3-c]pyridine using a copper catalyzed cyclisation step:

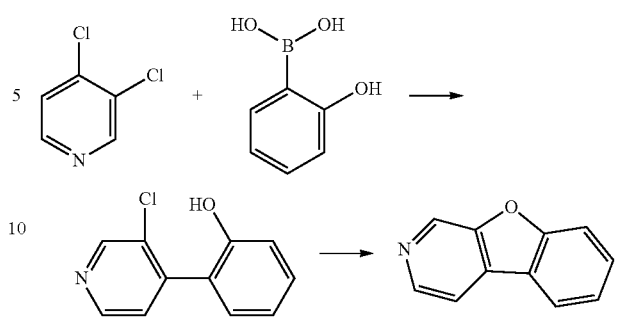

WO2014044722 describes the synthesis of 6-bromobenzofuro[2,3-c]pyridine.

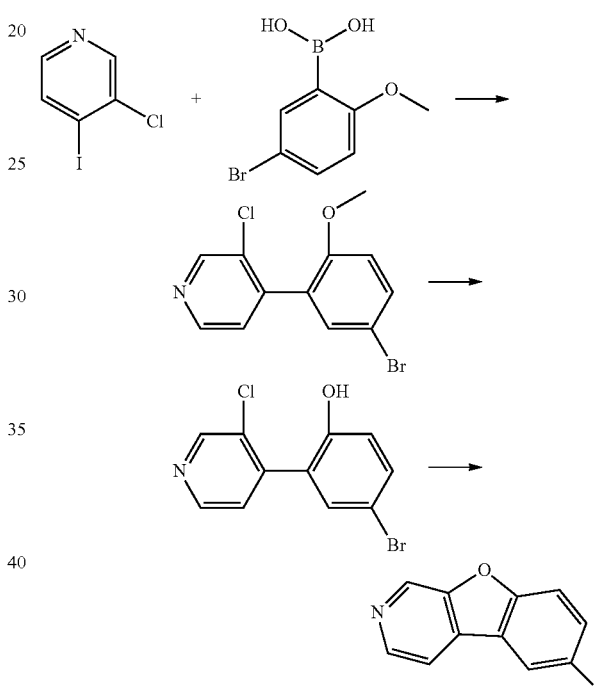

Compounds of formula (I'), wherein Z is —B(OR")$_2$ are prepared analogously to the reactions mentioned above, wherein Z is Hal.

A functionalization of the basic structure (I') mentioned above with a group of formula

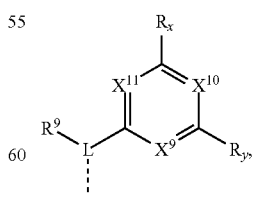

wherein the groups $R^9$, $X^9$, $X^{10}$, $X^{11}$, L, $R_x$ and $R_y$, are described above and below, is preferably carried out by coupling the basic structure (I') at the halogenated or boron-treated position with a compound of formula

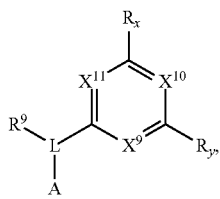

wherein A is —B(OR")$_2$ wherein R" is H or a C$_1$-C$_3$alkyl group or a phenyl group, provided that two R" may be same or different, and the two R"s may form a ring together with the two oxygen atoms and the boron atom, or Hal;
in the presence of a catalyst and in the presence of a base;
wherein
Hal is halogen, preferably Cl, Br or I.

The coupling is preferably a Suzuki-Miyaura reaction (coupling). The general conditions for the Suzuki-Miyaura reaction are for example disclosed in US2014/0330013. Especially in paragraphs [136]-[137].
Concerning —B(OR")$_2$ Preferably, R" is H, CH$_3$, CH(CH$_3$)$_2$, CH$_2$CH$_2$CH$_3$, and phenyl, when two R"s from a ring together with the boron atom bonded to the two R's via the two oxygen atoms, B(OR")$_2$ preferably includes the following groups

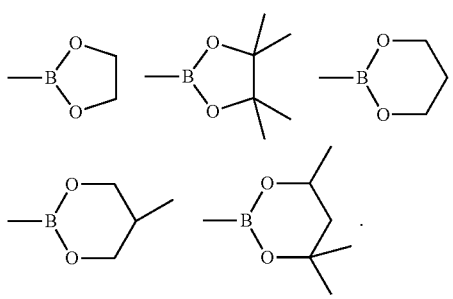

Coupling

Preferably, the base is K$_3$PO$_4$, Na$_2$CO$_3$, K$_2$CO$_3$, Cs$_2$CO$_3$ or KOAc The reaction is preferably carried out in the presence of a catalyst. Suitable catalysts are for example tetrakis(triphenylphospin)-palladium(0), [1,1'-bis(diphenylphosphino)ferrocene]-dichloropalladium(II) complex with dichloromethane, combination of tri-t-butyl-phosphoniumtetrafluoroborat with tris(dibenzylideneacetone)dipalladium(0) or palladium(II) acetate and combination of dicyclohexyl-[2-(2,6-dimethoxyphenyl)phenyl]phosphane with tris(dibenzylideneacetone)dipalladium(0) or palladium(II) acetate.

In the following, an example is shown, wherein R$^3$ in formula (I') is Z and R$^6$ is as defined above, but not H:

8-chlorobenzofuro[3,2-b]pyridine, synthesized according to US20090134784, is coupled with substituent, then converted to the N-oxid and brominated:

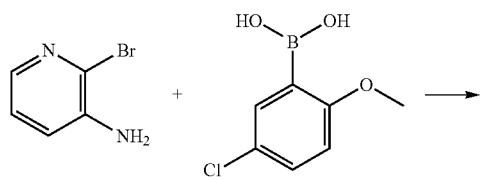

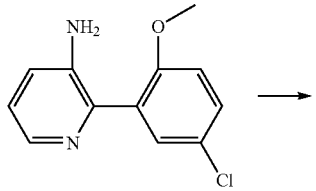

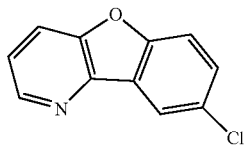

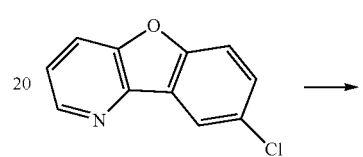

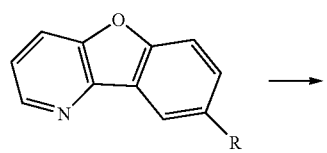

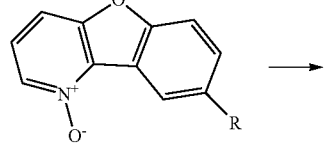

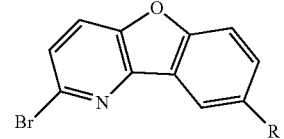

Details of the reaction step and process conditions are mentioned above and in the examples of the present application.

The present invention therefore further relates to a process for the preparation of a compound of formula (I) according to the present application comprising the step:

Coupling a Compound of Formula (I')

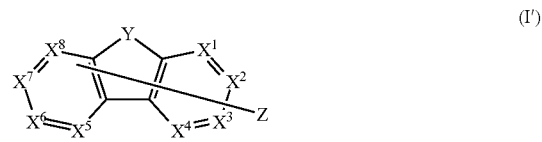

wherein
Z is Hal or —B(OR")$_2$ wherein R" is H or a C$_1$-C$_3$ alkyl group or a phenyl group, provided that two R" may be same or different, and the two R"s may form a ring together with the two oxygen atoms and the boron atom;

with a compound of formula A

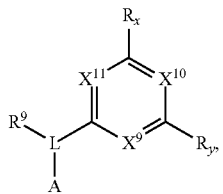

wherein A is —B(OR")$_2$ wherein R" is H or a C$_1$-C$_3$-alkyl group or a phenyl group, provided that two R" may be same or different, and the two R"s may form a ring together with the two oxygen atoms and the boron atom, or Hal;
in the presence of a catalyst and in the presence of a base;
wherein
Hal is halogen, preferably Cl, Br or I,
Y is S or O;
X$^1$ is N or CR$^1$;
X$^2$ is N or CR$^2$;
X$^3$ is N or CR$^3$;
X$^4$ is N or CR$^4$;
X$^5$ is N or CR$^5$;
X$^6$ is N or CR$^6$;
X$^7$ is N or CR$^7$;
X$^8$ is N or CR$^8$;
wherein one of X$^1$, X$^2$, X$^3$, X$^4$, X$^5$, X$^6$, X$^7$ and X$^8$ is N; and one of the remaining groups X$^1$, X$^2$, X$^3$, X$^4$, X$^5$, X$^6$, X$^7$ and X$^8$ is CR$^1$, CR$^2$, CR$^3$, CR$^4$, CR$^5$, CR$^6$, CR$^7$ or CR$^8$, wherein R$^1$, R$^2$, R$^3$, R$^4$, R$^5$, R$^6$, R$^7$ or R$^8$ is Z;
the other of R$^1$, R$^2$, R$^3$, R$^4$, R$^5$, R$^6$, R$^7$ and R$^8$ which are not Z are independently of each other H, CN, NR$^{65}$R$^{66}$, a C$_1$-C$_{25}$alkyl group, which can optionally be substituted by E and or interrupted by D, a C$_2$-C$_{25}$alkenyl group, which can optionally be substituted by E, and or interrupted by D, a C$_2$-C$_{25}$alkynyl group, which can optionally be substituted by E, and or interrupted by D, —OR$^{69}$, —SR$^{69}$, —COR$^{68}$, —COOR$^{67}$, a C$_3$C$_{18}$cycloalkyl group, which can optionally be substituted by G; a C$_6$-C$_{24}$aryl group, which can optionally be substituted by G, or a C$_2$-C$_{30}$heteroaryl group; which can optionally be substituted by G;
or adjacent groups R$^1$ and R$^2$, R$^2$ and R$^3$, R$^3$ and R$^4$, R$^5$ and R$^6$, R$^6$ and R$^7$, land/or R$^7$ and R$^8$ can optionally from together a ring, which can optionally be substituted by G; wherein—in the case that one of X$^1$ or X$^4$ is N—R$^2$ and R$^3$ do not form together a ring;
L is a trivalent C$_6$-C$_{24}$ arylene group or a trivalent C$_2$-C$_{24}$ heteroarylene group;
R$^9$ is a fused C$_{10}$-C$_{24}$ aryl group or a fused C$_{12}$-C$_{24}$ heteroaryl group;
X$^9$, X$^{10}$ and X$^{11}$ are each independently N or CR$^{10}$, whereby at least two of X$^9$, X$^{10}$ and X$^{11}$ are N, preferably, X$^9$, X$^{10}$ and X$^{11}$ are N;
R$^{10}$ is H, NR$^{73}$R$^{74}$, a C$_1$-C$_{25}$alkyl group, which can optionally be substituted by E, and or interrupted by D, a C$_2$-C$_{25}$alkenyl group, which can optionally be substituted by E, and or interrupted by D, a C$_2$-C$_{25}$alkynyl group, which can optionally be substituted by E, and or interrupted by D, —OR$^{69}$, —SR$^{69}$, —COR$^{68}$, —COOR$^{67}$, a C$_3$C$_{18}$cycloalkyl group, which can optionally be substituted by G; a C$_6$-C$_{24}$aryl group, which can optionally be substituted by G, or a C$_2$-C$_{30}$heteroaryl group which can optionally be substituted by G;

D is —CO—, —COO—, —S—, —SO—, —SO$_2$—, —O—, —CR$^{63}$=CR$^{64}$—, —NR$^{65}$—, —POR$^{72}$—, or —C=C—, preferably —O—, —NR$^{65}$—;
E is —OR$^{69}$, —SR$^{69}$, —NR$^{65}$R$^{66}$, —COR$^{68}$, —COOR$^{67}$, —CONR$^{65}$R$^{66}$ or —CN, preferably —NR$^{65}$R$^{66}$, —CN, G is E, or a C$_1$-C$_{24}$alkyl group, an unsubstituted C$_6$-C$_{24}$aryl group, a C$_6$-C$_{24}$aryl group, which is substituted by F, C$_1$-C$_{24}$alkyl, or C$_1$-C$_{24}$alkyl which is interrupted by O, an unsubstituted C$_2$-C$_{30}$heteroaryl group, or a C$_2$-C$_{30}$heteroaryl group, which is substituted by F, C$_1$-C$_{24}$alkyl, or C$_1$-C$_{24}$alkyl which is interrupted by O;
R$^{63}$ and R$^{64}$ are independently of each other unsubstituted C$_6$-C$_{18}$aryl; C$_6$-C$_{18}$aryl which is substituted by C$_1$-C$_{18}$alkyl or C$_1$-C$_{18}$alkoxy; C$_1$-C$_{18}$alkyl; or C$_1$-C$_8$alkyl which is interrupted by —O—;
R$^{65}$ and R$^{66}$ form together with the carbon atoms to which they are bonded a 5- or 6-membered ring, which can optionally be part of an anellated ring system, wherein the ring and/or annelated ring system can optionally be substituted by G;
R$^{67}$ is an unsubstituted C$_6$-C$_{18}$aryl group; a C$_6$-C$_{16}$aryl group, which is substituted by C$_1$-C$_{18}$alkyl, or C$_1$-C$_{18}$alkoxy; a C$_1$-C$_{18}$alkyl group; or a C$_1$-C$_{18}$alkyl group, which is interrupted by —O—;
R$^{68}$ is H; an unsubstituted C$_6$-C$_{18}$aryl group; a C$_6$-C$_{18}$aryl group, which is substituted by C$_1$-C$_{18}$alkyl or C$_1$-C$_{18}$alkoxy; a C$_1$-C$_{18}$alkyl group; or a C$_1$-C$_{18}$alkyl group, which is interrupted by —O—;
R$^{69}$ is an unsubstituted C$_6$-C$_{18}$aryl; a C$_6$-C$_{18}$aryl, which is substituted by C$_1$-C$_{18}$alkyl or C$_1$-C$_{18}$alkoxy; a C$_1$-C$_{18}$alkyl group; or a C$_1$-C$_{18}$alkyl group, which is interrupted by —O—;
R$^{71}$ is a C$_1$-C$_{18}$alkyl group, a C$_6$-C$_{18}$aryl group, or a C$_6$-C$_{18}$aryl group, which is substituted by C$_1$-C$_{18}$alkyl; and R$^{72}$ is a C$_1$-C$_{18}$alkyl group, an unsubstituted C$_6$-C$_{18}$aryl group, or a C$_6$-C$_8$aryl group, which is substituted by C$_1$-C$_{18}$alkyl;
R$^{73}$ and R$^{74}$ form together with the carbon atoms to which they are bonded a 5- or 6-membered ring, which can optionally be part of an anellated ring system, wherein the ring and/or annelated ring system can optionally be substituted by G;
R$_x$ and R$_y$ are independently of each other NR$^{73}$R$^{74}$, a C$_1$-C$_{25}$alkyl group, which can optionally be substituted by E, and or interrupted by D, a C$_2$-C$_{25}$alkenyl group, which can optionally be substituted by E, and or interrupted by D, a C$_2$-C$_{25}$alkynyl group, which can optionally be substituted by E, and or interrupted by D, —OR$^{69}$, —SR$^{69}$, —COR$^{68}$, —COOR$^{67}$, a C$_3$C$_{18}$cycloalkyl group, which can optionally be substituted by G; a C$_6$-C$_{12}$aryl group, which can optionally be substituted by G, or a C$_2$-C$_{30}$heteroaryl group which can optionally be substituted by G.

Preferred compounds of formula (I) and the corresponding groups are mentioned above.

Compounds of Formula (I) in Organic Electronics Applications

It has been found that the compounds of the formula (I) are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs).

The term organic EL device is used interchangeable with the term organic light-emitting diode (OLED) in the following; i.e. both terms have the same meaning, in the sense of the present application.

The organic transistor generally includes a semiconductor layer formed from an organic layer with charge transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor. The layers with charge transport capacity may comprise the compounds of formula (I).

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e, a layer with p-type semiconductor properties or hole transport capacity, and a layer formed with n-type semiconductor properties or charge transport capacity. In addition, it is possible for further layers known to those skilled in the art to be present in the organic solar cell. The layers with charge transport capacity may comprise the compounds of formula (I).

The compounds of formula (I) being particularly suitable in OLEDs for use as matrix material in a light-emitting layer and/or as charge and/or exciton blocker material i.e as electron/exciton blocker material or as hole/exciton blocker material, and/or charge transport material, i.e. hole transport material or electron transport material, especially in combination with a phosphorescence emitter and/or fluorescence emitter.

In the case of use of the inventive compounds of formula (I) in OLEDs, OLEDs which have good efficiencies and a long lifetime and which can be operated especially at a low use and operating voltage are obtained. The inventive compounds of formula (I) are suitable especially for use as matrix and/or charge transport, i.e. hole or electron transport, and/or charge blocker material, i.e. hole or electron blocker material, for blue, green and red. The blue emitters employed are usually fluorescent emitters. The other emitters employed are usually fluorescent or phosphorescent emitters, preferably phosphorescent emitters. Furthermore, the compounds of the formula (I) can be used as conductor/complementary materials in organic electronics applications selected from switching elements and organic solar cells. (In the sense of the present application, the terms matrix and host are used interchangeable).

Compounds of the Formula (I) as Matrix Material in an Emission Layer

Most preferably, the compounds of the formula (I) are used as matrix materials (host materials), preferably in an emission layer of an OLED, more preferably in an emission layer of an OLED comprising at least one compound of the formula (I) and at least one emitter material, wherein the emitter material is preferably a fluorescent or phosphorescent emitter material.

The present invention therefore relates to an emission layer (light-emitting layer) comprising at least one compound of the formula (I) and at least one emitter material. Suitable emitter materials are mentioned above and below. Suitable structures of the emission layer are mentioned below.

The present invention further relates to an OLED comprising an emission layer (light-emitting layer) comprising at least one compound of the formula (I) and at least one emitter material.

In the emission layer or one of the emission layers of an OLED, it is also possible to combine an emitter material with at least one matrix material of the compound of the formula (I) and one or more, preferably one, further matrix materials (co-host). This may achieve a high quantum efficiency, low driving voltage and/or long lifetime of this devices.

It is likewise possible that the compounds of the formula (I) are present in two or three of the following layers: in the light-emitting layer (preferably as matrix material), in the blocking layer (as charge blocker material) and/or in the charge transport layer (as charge transport material).

When a compound of the formula (I) is used as matrix (host) material in an emission layer and additionally as charge blocking material and/or as charge transport material, owing to the chemical identity or similarity of the materials, an improved interface between the emission layer and the adjacent material, which can lead to a decrease in the voltage with equal luminance and to an extension of the lifetime of the OLED. Moreover, the use of the same material as charge transport material and/or as charge blocker material and as matrix of an emission layer allows the production process of an OLED to be simplified, since the same source can be used for the vapor deposition process of the material of one of the compounds of the formula the compound of the formula (I)

Suitable structures of organic electronic devices, especially organic light-emitting-diodes (OLED), are known to those skilled in the art and are specified below.

Compounds of the Formula (I) as Electron Transporting Material

In a further most preferred embodiment, the compounds of the formula (I) are used as electron transporting materials, preferably in an OLED, more preferably in an OLED comprising at least one fluorescent or phosphorescent emitter material.

The present invention therefore relates to an electron-transporting layer comprising at, least one compound of the formula (I).

The present invention further relates to an OLED comprising an electron transporting layer comprising at least one compound of the formula (I) and an emission layer comprising at least one emitter material. Suitable emitter materials are mentioned above and below. Suitable structures of the electron transporting layer are mentioned below.

In a preferred embodiment, the electron-transporting layer comprising at least one compound of the formula (I) of the invention further comprises a reducing dopant.

Examples of the reducing dopant include a donating metal, a donating metal compound, and a donating metal complex. The reducing dopant may be used, alone or in combination of two or more.

The reducing dopant referred to herein is an electron-donating material. The electron-donating material is a material which generates radical anions by the interaction with a coexisting organic material in the electron transporting layer or an organic material in a layer adjacent to the electron transporting layer, or a material having an electron-donating radical.

The donating metal is a metal having a work function of 3.8 eV or less, preferably an alkali metal, an alkaline earth metal, or a rare earth metal and more preferably Cs, Li, Na, Sr, K, Mg, Ca, Ba, Yb, Eu, or Ce.

The donating metal compound is a compound comprising the above donating metal, preferably a compound comprising an alkali metal, an alkaline earth metal, or a rare earth metal, and more preferably a halide, an oxide, a carbonate, or a borate of these metals for example, a compound represented by MOx (M: donating metal, x: 0.5 to 1.5) MFx (x: 1 to 3), or M(CO$_3$)x (x: 0.5 to 1.5).

The donating metal complex is a complex comprising the above donating metal, preferably an organic metal complex of an alkali metal, an alkaline earth metal or a rare earth metal, and more preferably an organic metal complex represented by formula (I): M-(Q)$_n$, wherein M is a donating metal, Q is a ligand, preferably a carboxylic acid derivative, a diketone derivative, or a quinoline derivative, and n is an integer of 1 to 4.

Examples of the donating metal complex include water-mill-shaped tungsten compounds described in JP 2005-72012A and phthalocyanine compounds having an alkali metal or an alkaline earth metal as the central metal, which are described in JP 11-345687A.

The reducing dopant is preferably at least one selected from the group consisting of an alkali metal, an alkaline earth metal, a rare earth metal, an alkali metal oxide, an alkali metal halide, an alkaline earth metal oxide, an alkaline earth metal halide, a rare earth metal oxide, a rare earth metal halide, an organic complex having an alkali metal, an organic complex having an alkaline earth metal, and an organic complex having a rare earth metal, and more preferably a 8-quinolinol complex of an alkali metal.

Examples of the Alkali Metal Include:

Li (lithium, work function: 2.93 eV), Na (sodium, work function: 2.36 eV), K (potassium, work function: 2.3 eV), Rb (rubidium, work function: 2.16 eV), and Cs (cesium, work function: 1.95 eV).

The values of work functions are based on Handbook of Chemistry (Pure Chemistry II, 1984, p. 493, edited by The Chemical Society of Japan). The same applies hereafter.

Preferred examples of the alkaline earth metals are: Ca (calcium, work function: 2.9 eV), Mg (magnesium, work function: 3.66 eV), Ba (barium, work function: 2.52 eV), and Sr (strontium, work function: 2.0 to 2.5 eV).

The work function of strontium is based of Physics of Semiconductor Device (N.Y., Wiley, 1969, p. 366).

Preferred examples of the rare earth metal are: Yb (ytterbium, work function: 2.6 eV), Eu (europium, work function: 2.5 eV), Gd (gadolinium, work function: 3.1 eV), and Er (erbium, work function: 2.5 eV).

Examples of the alkali metal oxide include Li$_2$O, LiO, and NaO. The alkaline earth metal oxide is preferably CaO, BaO, SrO, BeO, or MgO.

Examples of the alkali metal halide include a fluoride, for example, LiF, NaF, CsF, and KF and a chloride, for example, LiCl, KCl, and NaCl.

The alkaline earth metal halide is preferably a fluoride, such as CaF$_2$, BaF$_2$, SrF$_2$, MgF$_2$, and BeF$_2$ and a halide other than fluoride.

The content of the compound of the formula (I) in the electron transporting layer is preferably 50% by mass or more, i.e. 50 to 100% by weight and more preferably 60% by mass or more, i.e. 60 to 100% by weight, based on the weight of the electron transporting layer.

The present invention further provides an organic light-emitting diode (OLED) comprising an anode and a cathode and a light-emitting layer arranged between the anode and the cathode, and if appropriate at least one further layer selected from the group consisting of at least one blocking layer for holes/excitons, at least one blocking layer for electrons/excitons, at least one hole injection layer, at least one hole transport layer, at least one electron injection layer and at least one electron transport layer, wherein the at least one compound of the formula (I) is present in the light-emitting layer and/or in at least one of the further layers. The at least one compound of the formula (I) is preferably present in the light-emitting layer and/or the charge blocking layer and/or the charge transport layer.

In a preferred embodiment of the present invention at least one compound of the formula (I) is used as charge transport, i.e. electron transport or hole transport material, especially as electron transport material. Examples of preferred compounds, of the formula (I) are shown above.

In a further preferred embodiment of the present invention, at least one compound of the formula (I) is used as charge/exciton blocker, i.e. electron/exciton blocker or hole/exciton blocker material, especially as hole/exciton blocker material. Examples of preferred compounds of the formula (I) are shown above.

The present application further relates to a light-emitting layer comprising at least one compound of the formula (I), preferably as host material or co-host material. Examples of preferred compounds of the formula (I) are shown above.

The material for an organic EL device (OLED) of the invention comprises the compound represented by the above formula (I). The content of the above-mentioned compound in the material for an organic EL device is not particularly restricted. For example, it may be 1 mass % or more, preferably 10 mass % or more, more preferably 50 mass % or more, further preferably 80 mass % or more, and particularly preferably 90 mass % or more. The content may be 100 mass %. As other materials than those represented by the formula (I), materials used in the emitting layer, the electron-transporting layer, the hole-transporting layer or the like (mentioned later) can be given.

The material for an organic EL device of the invention is effective as the material for an organic EL device, and can be used as a host material in the emitting layer of a fluorescent emitting unit or as a host material in the emitting layer of a phosphorescent emitting unit. In any of a fluorescent emitting unit and a phosphorescent emitting unit, the material is effective as a material for an anode-side organic thin film layer provided between an anode and an emitting layer of an organic EL device or as a material for a cathode-side organic thin film layer provided between a cathode and an emitting layer of an organic EL device. That is, it is effective as a material for a hole-transporting layer, a hole-injecting layer, an electron-transporting layer, an electron-injecting layer, a hole-blocking layer, an electron-blocking layer, or the like.

Meanwhile, the "emitting unit" means the minimum unit that comprises one or more organic layers, one of which being an emitting layer, and can emit light by recombination of holes and electrons injected.

Organic EL Device (OLED)

The organic EL device as one embodiment of the invention comprises one or more organic thin film layers including an emitting layer between a cathode and an anode, and at least one layer of the organic thin film layers comprises the above-mentioned material for an organic EL device.

As examples of the organic thin film layers that comprise the above-mentioned material for an organic EL device, an anode-side organic thin film layer (hole transporting layer, hole-injecting layer, or the like), an emitting layer, a cathode-side organic thin film layer (electron-transporting layer, electron-injecting layer, or the like) provided between a cathode and an emitting layer, a spacing layer, a barrier layer or the like can be given. The examples are not limited thereto. The above-mentioned material for an organic EL device may be contained in any of the above-mentioned layers, and can be used as a host material or a dopant material in the emitting layer of a fluorescent emitting unit, a host material in the emitting layer of a phosphorescent emitting unit, a hole-transporting layer, an electron-transporting layer or the like of an emitting unit.

The organic EL device of the invention may be a fluorescent or phosphorescent monochromatic emitting device or may be a fluorescent/phosphorescent hybrid white emitting device. It may be a simple emitting device having a single emitting unit or a tandem emitting device having plural emitting units. Among them, the organic EL device may preferably be a phosphorescent or fluorescent emitting device.

As the representative device structure of a simple-type organic EL device, the following device configuration can be given.
(1) Anode/Emitting Unit/Cathode The emitting unit mentioned above may be a stacked type emitting unit comprising plural phosphorescent emitting layers or plural fluorescent emitting layers. In this case, in order to prevent diffusion of excitons generated in the phosphorescent emitting layer to the fluorescent emitting layer, a spacing layer may be provided between the emitting layers. The representative layer configuration of the emitting unit is given below.
(a) Hole-transporting layer/Emitting layer (/Electron-transporting layer)
(b) Hole-transporting layer/First phosphorescent emitting layer/Second phosphorescent emitting layer (/Electron-transporting layer)
(c) Hole-transporting layer/Phosphorescent emitting layer/Spacing layer/Fluorescent emitting layer (/Electron-transporting layer)
(d) Hole-transporting layer/First phosphorescent emitting layer/Second phosphorescent emitting layer/Spacing layer/Fluorescent emitting layer (/Electron-transporting layer)
(e) Hole-transporting layer/First phosphorescent emitting layer/Spacing layer/Second phosphorescent emitting layer/Spacing layer/Fluorescent emitting layer (/Electron-transporting layer)
(f) Hole-transporting layer/Phosphorescent emitting layer/Spacing layer/First fluorescent emitting layer/Second fluorescent emitting layer (/Electron-transporting layer)
(g) Hole-transporting layer/Electron barrier layer/Emitting layer (/Electron-transporting layer)
(h) Hole-transporting layer/Emitting layer/Hole barrier layer (/Electron-transporting layer)
(i) Hole-transporting layer/Fluorescent emitting layer/Triplet barrier layer (/Electron-transporting layer)

The phosphorescent or fluorescent emitting layer as mentioned above can emit different colors of light. Specifically, in the stacked emitting layer (d), a layer configuration of the hole-transporting layer/first phosphorescent emitting layer (red emission)/second phosphorescent emitting layer (green emission)/spacing layer/fluorescent emitting layer (blue emission)/electron-transporting layer or the like can be given.

Between each emitting layer and the hole-transporting layer or the spacing layer, an electron-barrier layer may be provided appropriately. Between each emitting layer and the electron-transporting layer, a hole-barrier layer may be provided appropriately. Due to provision of an electron-barrier layer or a hole-barrier layer, electrons or holes can be confined within the emitting layer, whereby possibility of recombination of carriers in the emitting layer can be increased, and the life can be improved.

As the represented device configuration of a tandem organic EL device, the following device configuration can be given.
(2) Anode/First Emitting Unit/Intermediate Layer/Second Emitting Unit/Cathode Here, as the first emitting unit and the second emitting unit, the same emitting units as those mentioned above can independently be given, for example.

In general, the intermediate layer is called an intermediate electrode, an intermediate conductive layer, a carrier-generating layer, an electron-withdrawing layer, and a known material configuration that supplies electrons to the first emitting unit and supplies holes to the second emitting unit can be used.

FIG. 1 shows a schematic configuration of one example of the organic EL device of the invention. The organic EL device 1 comprises a substrate 2, an anode 3, a cathode 4 and an emitting unit 10 provided between the anode 3 and the cathode 4. The emitting unit 10 comprises an emitting layer 5 preferably comprising a host material and a dopant. A hole-injecting and transporting layer 6 or the like may be provided between the emitting layer 5 and the anode 3 and an electron-injecting layer 8 and an electron transporting layer 7 or the like (electron injecting and transporting unit 11) may be provided between the emitting layer 5 and the cathode 4. An electron-barrier layer may be provided on the anode 3 side of the emitting layer 5 and a hole-barrier layer may be provided on the cathode 4 side of the emitting layer 5. Due to such configuration, electrons or holes can be confined in the emitting layer 5, whereby possibility of generation of excitons in the emitting layer 5 can be improved.

Herein, a host that is combined with a fluorescent dopant is referred to as a fluorescent host and a host that is combined with a phosphorescent dopant is referred to as a phosphorescent host. The fluorescent host and the phosphorescent host are, not distinguished only by the molecular structure thereof. That is, the phosphorescent host means a material constituting a phosphorescent emitting layer that contains a phosphorescent dopant and does not mean a material that cannot be used as a material constituting a fluorescent dopant. The same can be applied to a fluorescent host.
Substrate The organic EL device is usually formed on a transparent substrate. The transparent substrate is a substrate for supporting the organic EL device, and is preferably a flat and smooth substrate having a 400-to-700-nm-visible-light transmittance of 50% or more. Specific examples thereof include glass plates and polymer plates. Examples of the glass plate include those obtained by using as raw materials soda-lime glass, barium/strontium-containing, glass, lead glass, aluminosilicate glass, borosilicate glass, barium borosilicate glass, quartz, or the like. Examples of the polymer plate include those obtained by using as raw materials polycarbonate, acrylic polymer, polyethylene terephthalate, polyethersulfide, polysulfone, or the like.
Anode The anode of the organic EL device plays a role for injecting holes into its hole-transporting layer or emitting layer. It is effective to use one having a work function of 4.5 eV or more. As specific examples of the anode material, indium tin oxide alloy (ITO), tin oxide (NESA), indium zinc oxide, gold, silver, platinum, copper, and the like can be given. The anode can be formed by forming these electrode materials into a thin film by vapor deposition sputtering or the like. In the case where emission from the emitting layer is taken out through the anode the transmittance of the anode to the emission is preferably more than 10%. The sheet resistance of the anode is preferably several hundred Ω/□ or less. The film thickness of the anode, which varies depending upon the material thereof, is usually from 10 nm to 1 μm, preferably from 10 to 200 nm.

Cathode

The cathode plays a role for injecting electrons into its electron-injecting layer, electron-transporting layer or emitting layer. The cathode is preferably formed of a material having a small work function. The cathode material is not particularly restricted. As specific examples of the cathode material, indium, aluminum, magnesium, a magnesium-indium alloy, a magnesium-aluminum alloy, an aluminum-lithium alloy, an aluminum-scandium-lithium alloy a magnesium-silver alloy or the like can be given. As in the case of the anode, the cathode can be formed by forming the materials into a thin film by a deposition method, a sputtering method, or the like. If necessary, emission can be outcoupled from the cathode side.

Emitting Layer

The emitting layer is an organic layer having an emitting function, and where a doping system is used, it comprises a host material and a dopant material. The host material has a function of accelerating recombination of electrons and holes and confining excitons within the emitting layer. The dopant material has a function of emitting efficiently excitons obtained by recombination.

In the case of a phosphorescent device, the host material has a function of confining excitons mainly generated by a dopant within the emitting layer.

Here, in the emitting layer, a double host (also referred to as a host/cohost) that adjusts the carrier balance in the emitting layer may be used by combining an electron-transporting host and a hole-transporting host or by other methods. It is preferred that the emitting layer comprise a first host material and a second host material and that the first host material be the material for the organic EL device according to the invention.

Double dopant may be used in which two or more types of dopant materials having a high quantum yield are incorporated, and each dopant emits light. Specifically, by allowing a host, a red dopant and a green dopant to be co-deposited, yellow emission from the common emitting layer, whereby yellow emission is realized.

As for the emitting layer, by allowing plural emitting layers to be a stacked body, electrons and holes are accumulated in the interface of the emitting layers, whereby the recombination region is concentrated in the interface of the emitting layers. As a result, the quantum efficiency is improved.

Easiness in injection of holes to the emitting layer and easiness in injection of electrons to the emitting layer may differ. Further, the hole-transporting performance and the electron-transporting performance indicated by the mobility of holes and electrons in the emitting layer may differ from each other.

The emitting layer can be formed by a known method such as a deposition method, a spin coating method, a LB method (Langmuir Blodgett method) or the like, for example. The emitting layer can also be formed by forming a solution obtained by dissolving a binder such as a resin and material compounds in a solvent into a thin film by a spin coating method and the like.

The emitting layer is preferably a molecular deposited film. The "molecular deposited film" means a thin film formed by deposition of a raw material compound in a vapor phase or a film formed by solidification of a raw material compound in a solution state or a liquid phase state. Normally, this molecular deposited film differs from a thin film (molecular accumulated film) formed by a LB method in aggregation structure or high-order structure, or differ in function derived from such difference in structure.

Emitter (Dopant Material)

The dopant material is usually selected from a known fluorescent dopant showing fluorescent emission or a known phosphorescent dopant showing phosphorescent emission.

A phosphorescent dopant (phosphorescent emitting material) that forms the emitting layer is a compound that can emit light from triplet excited state. The phosphorescent dopant is hot limited as long as it can emit from triplet excited state. The phosphorescent dopant is preferably an organic metal complex containing at least one metal selected from Ir, Pt, Os, Au, Cu, Re and Ru and a ligand. It is preferred that the ligand have an ortho-metalated bond. In respect of a high phosphorescent quantum yield and capability of improving external quantum yield of an emitting device, the phosphorescent dopant is preferably a compound having a metal atom selected from Ir, Os and Pt. Further preferable are a metal complex such as an iridium complex, an osmium complex and a platinum complex, with an ortho-metalated complex being more preferable. Among them, an iridium complex and a platinum complex are more preferable, and an ortho-metalated iridium complex is particularly preferable.

The content of the emitter materials (dopants), preferably the phosphorescent emitter materials, in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided. The further component in the emitting layer is usually one or more host material, which is preferably present in an amount of 30 to 99.9% by mass, more preferably 70 to 99% by mass, wherein the sum of the emitter material(s) and the host material(s) is 100% by mass.

Suitable metal complexes (dopants, especially phosphorescent dopants) for use in the inventive OLEDs, preferably as emitter material, are described; for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2; WO02006/115301 A1, WO 2006/067074 A1, WO 2006/056418, WO 20061214811 A1, WO2007095118 A2, WO 2007/115970, WO 2007/115981, WO 2008/000727, WO2010129323, WO2010056669, WO10086089, US2011/0057559, WO2011/106344, US2011/0233528; WO2012/048266 and WO2012/172482.

Further suitable metal complexes are the commercially available metal complexes tris(2-phenylpyridine)iridium (III), iridium(III) tris(2-(4-tolyl)pyridinato-N,$C^{2'}$), bis(2-phenylpyridine)(acetylacetonato)iridium(III), iridium(III) tris(1-phenylisoquinoline), iridium(III) bis(2,2'-benzothienyl)pyridinato-N,$C^{3'}$)(acetylacetonate), tris(2-phenylquinoline)iridium(III), iridium(III) bis(2-(4,6-difluorophenyl)pyridinato-N,$C^{2}$)picolinate, iridium(III) bis(1-phenylisoquinoline)(acetylacetonate), bis(2-phenylquinoline)(acetylacetonato)iridium(III), iridium(III) bis(di-benzo[f,h]quinoxaline)(acetylacetonate), iridium(III)

bis(2-methyldibenzo[f,h]quinoxaline)(acetylacetonate) and tris(3-methyl-1-phenyl-4-trimethylacetyl-5-pyrazolino)terbium(III), bis[1-(9,9-dimethyl-9H-fluoren-2-yl)isoquinoline](acetylacetonato)iridium(I II), bis(2-phenylbenzothiazolato)(acetylacetonato)iridium(11*l*), bis(2-(9,9-dihexylfluorenyl)-1-pyridine)(acetylacetonato)iridium(III), bis(2-benzo[b]thiophen-2-ylpyridine)(acetylacetonato)iridium(III).

In addition, the following commercially available materials are suitable: tris(dibenzoylacetonato)mono(phenanthroline)europium(III), tris(dibenzoylmethane)mono(phenanthroline)europium(III), tris(dibenzoylmethane)mono(5-aminophenanthroline)europium(I II), tris(di-2-naphthoylmethane)mono(phenanthroline)europium(II), tris(4-bromobenzoylmethane)mono(phenanthroline)europium(III), tris(di(biphenyl)methane)mono(phenanthroline)europium(III), tris(dibenzoylmethane)mono(4,7-diphenylphenanthroline)europium(III), tris(dibenzoylmethane)mono(4,7-di-methylphenanthroline)europium(III), tris(dibenzoylmethane)mono(4,7-dimethylphenanthrolinedisulfonic acid)europium(III) disodium salt, tris[di(4-(2-(2-ethoxyethoxy)ethoxy)benzoylmethane)]mono(phenanthroline)europium(III) and tris[di[4-(2-(2-ethoxyethoxy)ethoxy)benzoylmethane)]mono(5-aminophenanthroline)europium(III), osmium(III) bis(3-(trifluoromethyl)-5-(4-tert-butylpyridyl)-1,2,4-triazolato) diphenylmethylphosphine, osmium(III) bis(3-(trifluoromethyl)-5-(2-pyridyl)-1,2,4-triazole) dimethylphenylphosphine, osmium(III) bis(3-(trifluoromethyl)-5-(4-tert-butylpyridyl)-1,2,4-triazolato) dimethylphenylphosphine, osmium(III) bis(3-(trifluoromethyl)-5-(2-pyridyl)pyrazolato) dimethylphenylphosphine, tris[4,4'-di-tert-butyl(2,2')-bipyridine]ruthenium(III), osmium(III) bis(2-(9,9-dibutylfluorenyl)-1-isoquinoline(acetylacetonate).

Particularly suitable metal complexes are described in US2014048784, US2012223295, US2014367667, US2013234119, US2014001446, US2014231794, US2014008633, WO2012108388 and WO02012108389. The emitters mentioned in US2013234119, paragraph [0222], are exemplified. Selected emitters, especially red emitters, of said emitters mentioned in US2013234119, paragraph [0222], are:

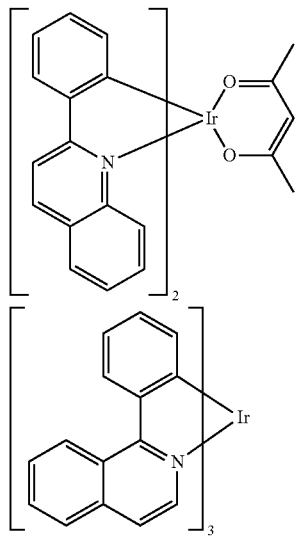

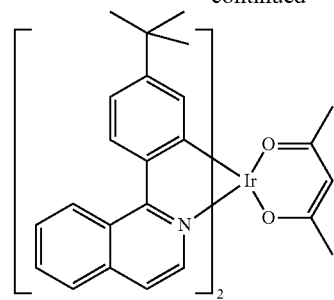

-continued

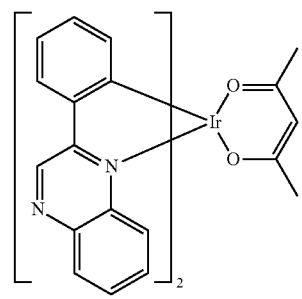

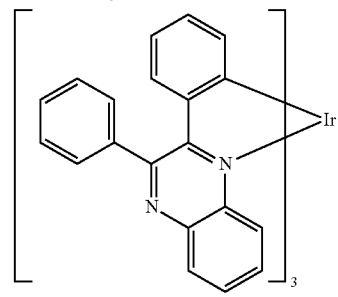

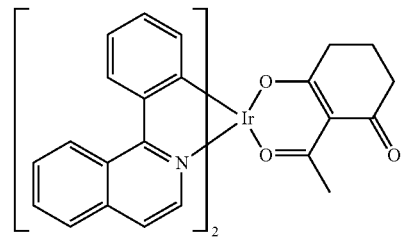

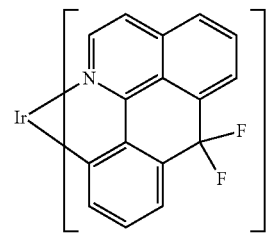

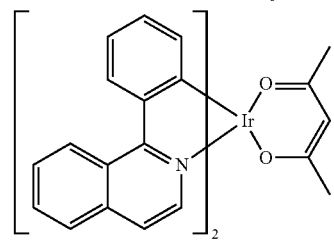

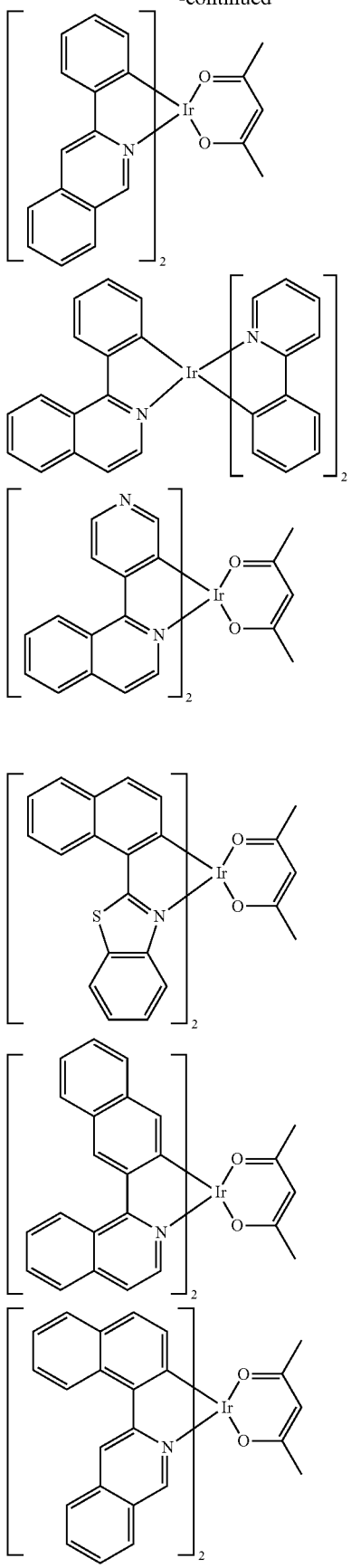
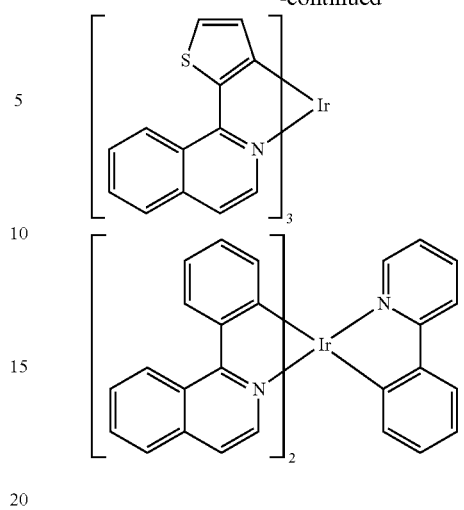
Further suitable Emitters are mentioned in: Mrs Bulletin, 2007, 32, 694:
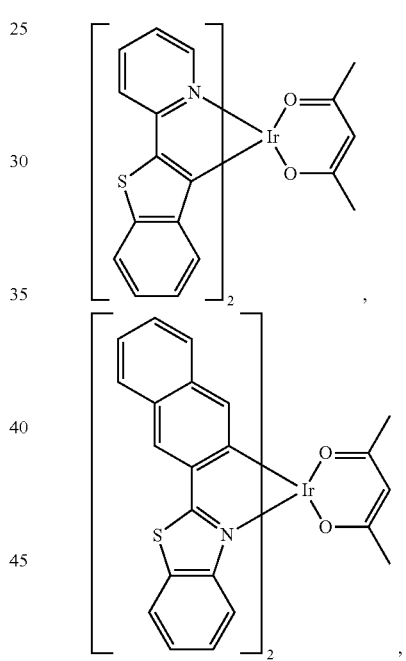
Further suitable Emitters are mentioned in: WO2009100991:
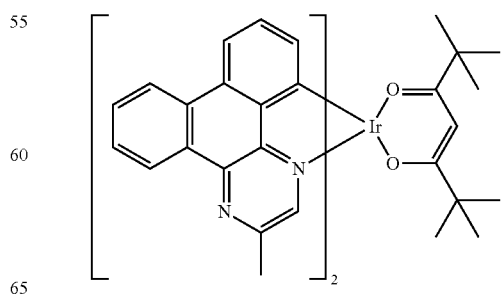

Further suitable Emitters are mentioned in: WO02008101842:
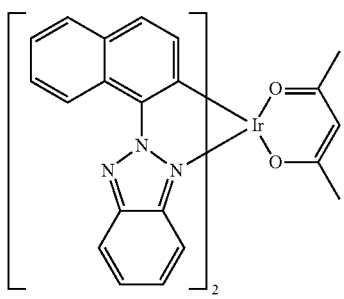
Further suitable Emitters are mentioned in: US 20140048784, especially in paragraph [0159]:
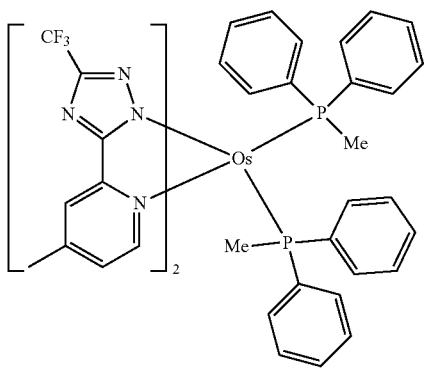
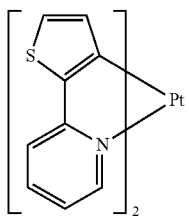
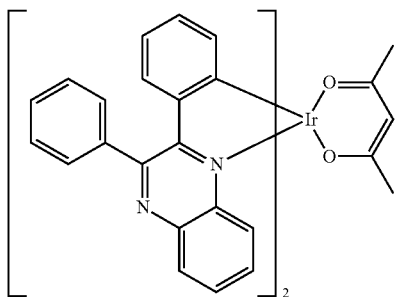
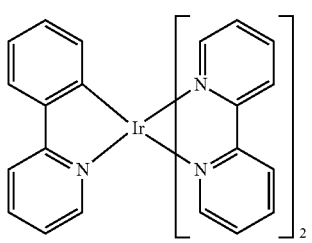
-continued
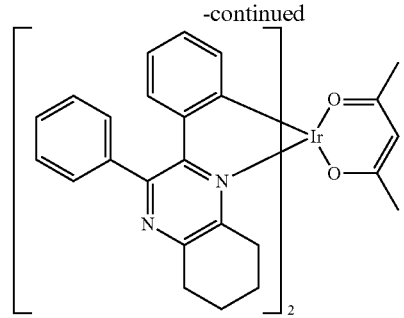
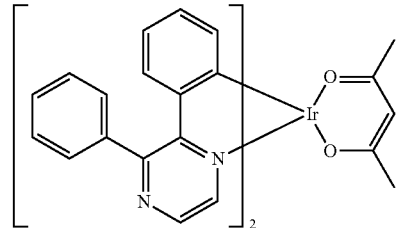
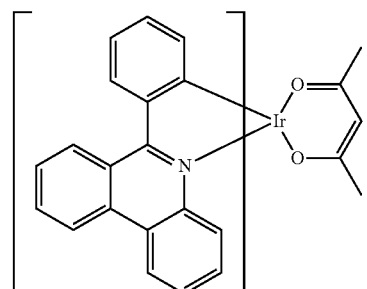
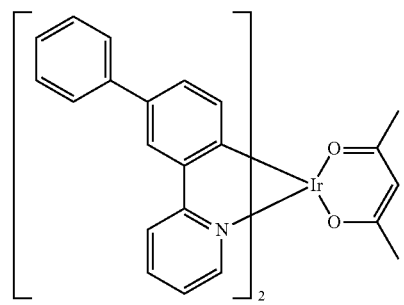
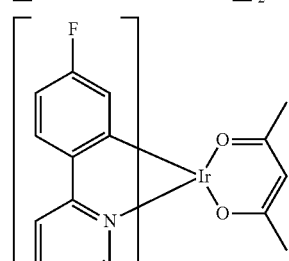
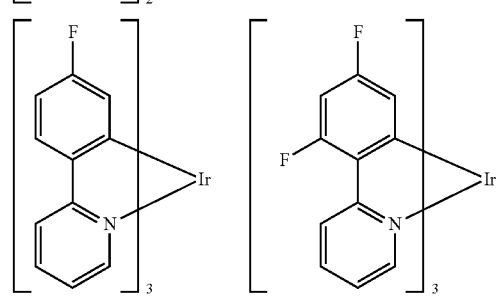

1109
-continued
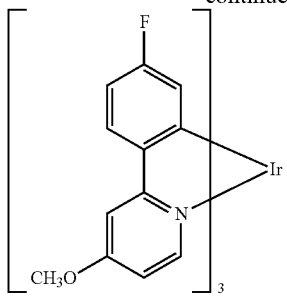
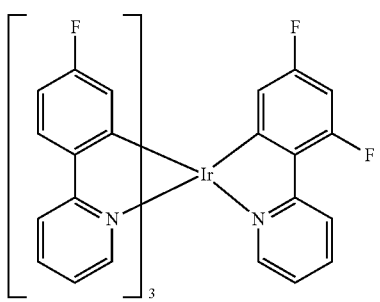
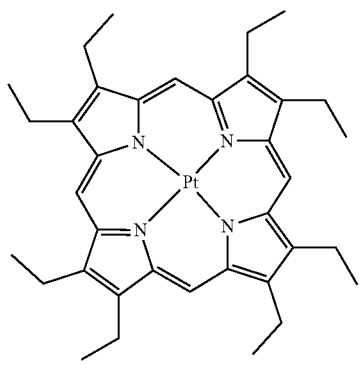
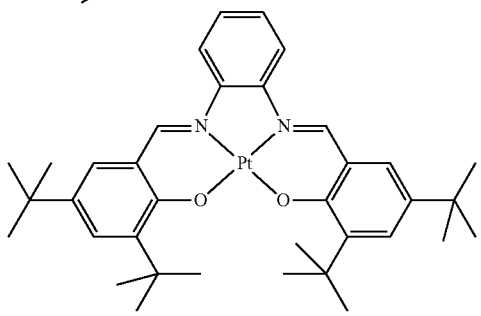
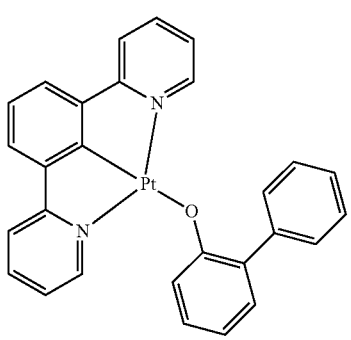
1110
-continued
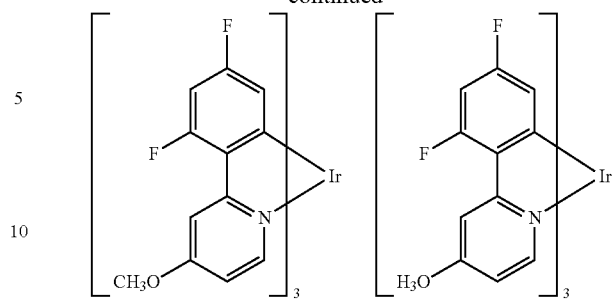
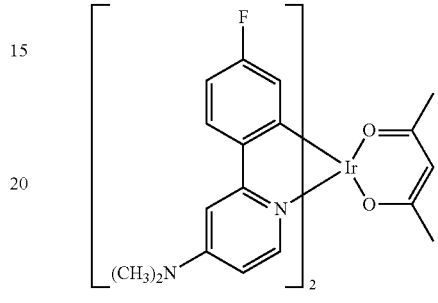
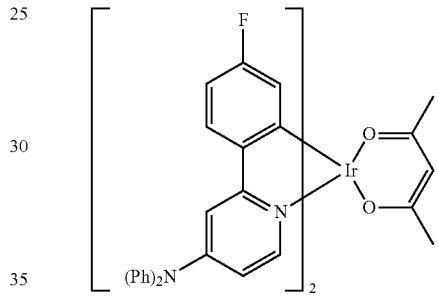
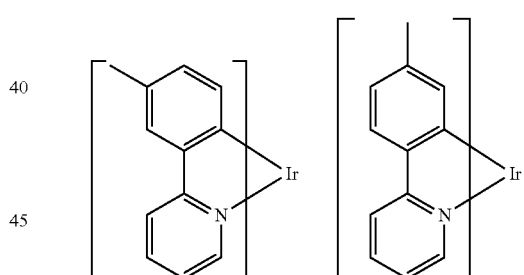
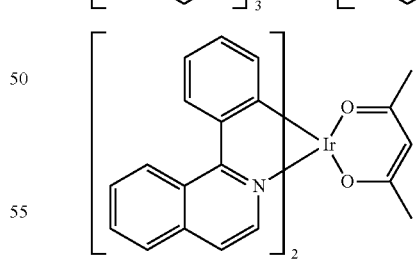
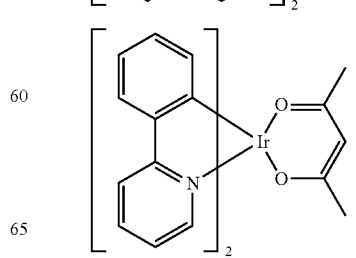

1111
-continued
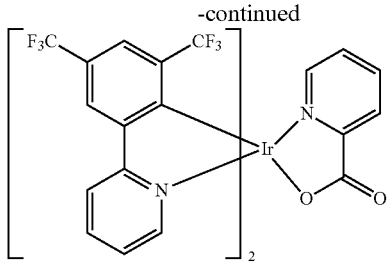
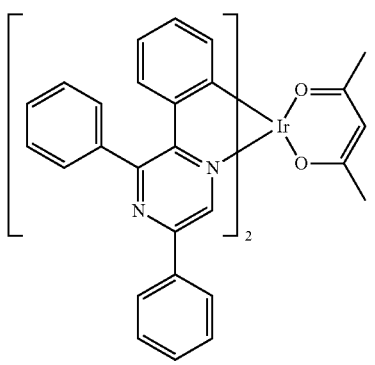
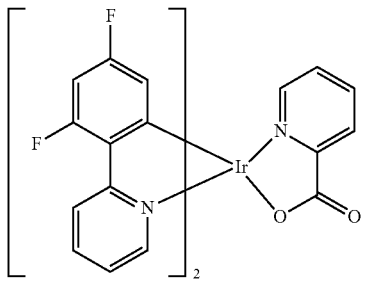
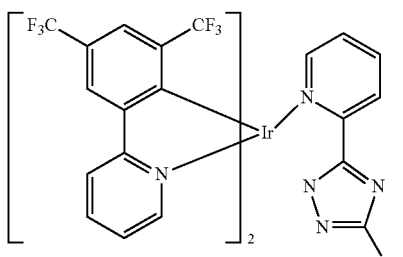
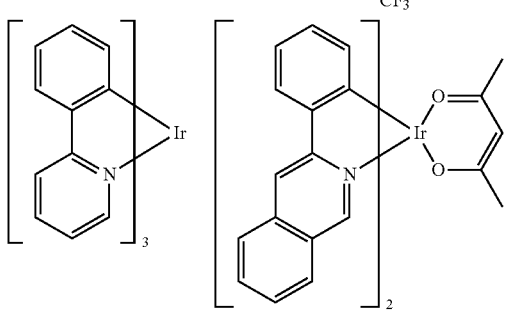
1112
-continued
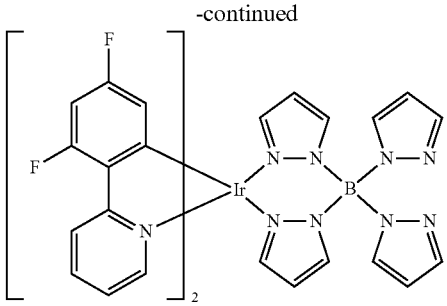
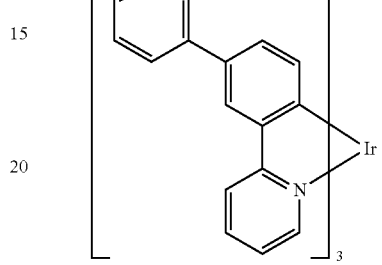
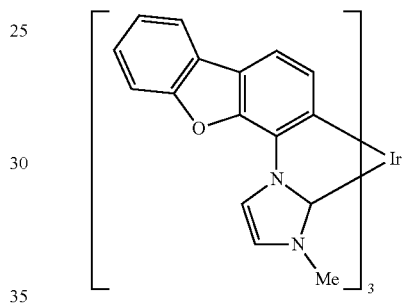
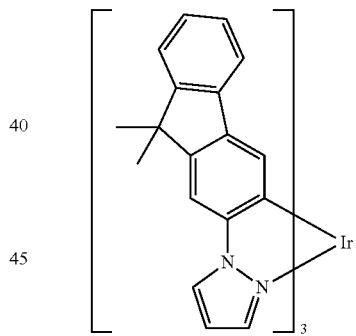
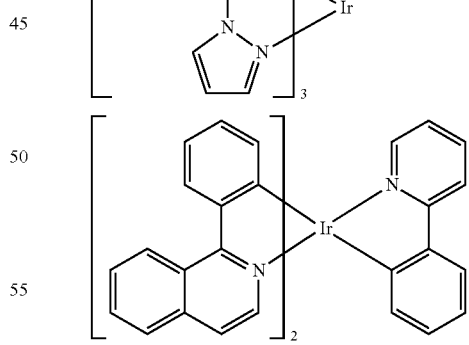
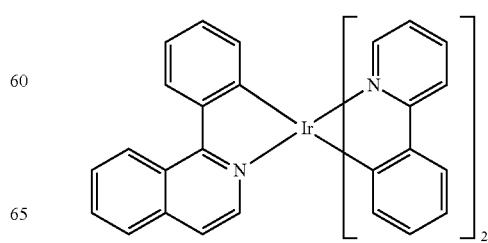

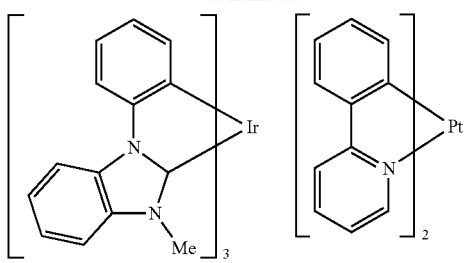
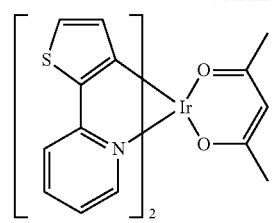
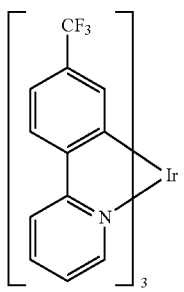
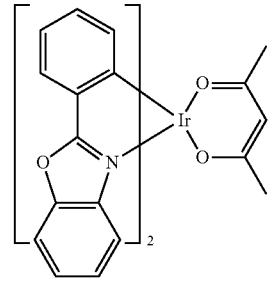
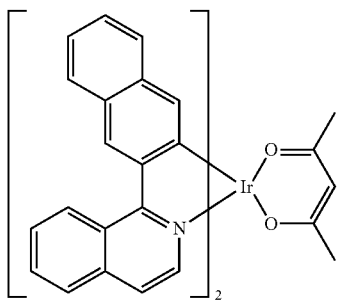
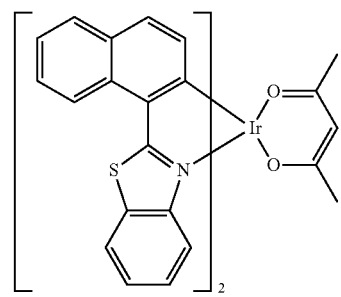
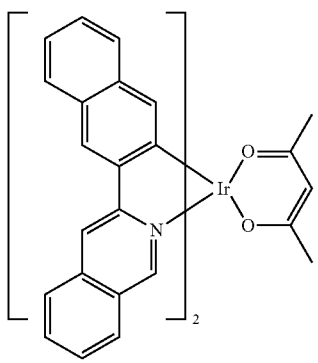
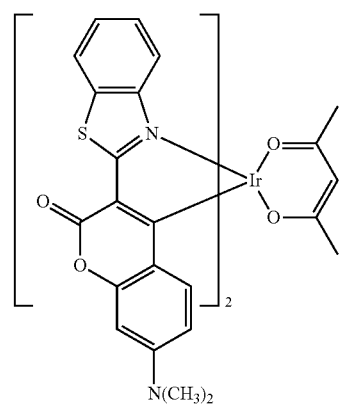
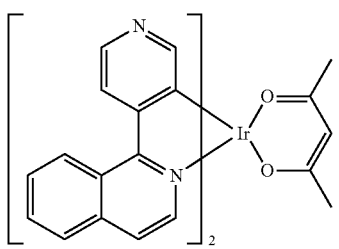
Further suitable red emitters are shown in WO 2008/109824. Preferred red emitters according to this document are the following compounds:
Compound 1
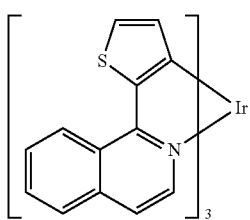
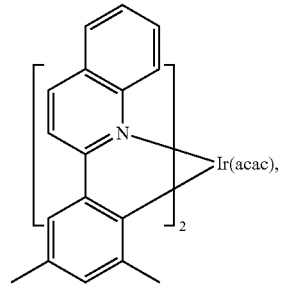

Compound 2
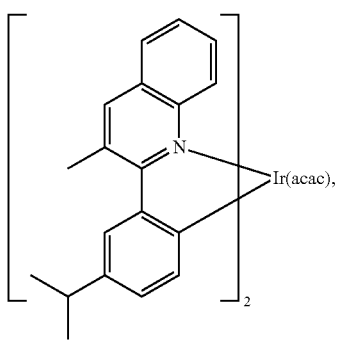
Compound 3
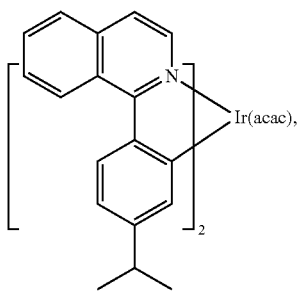
Compound 4
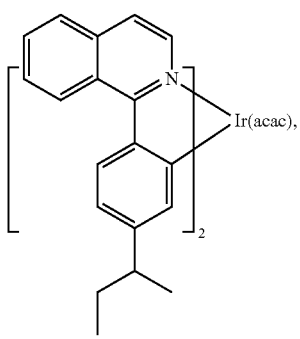
Compound 5
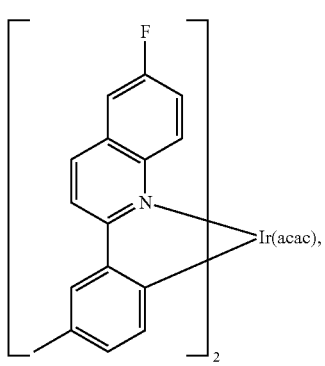
Compound 6
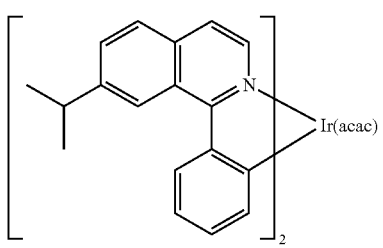
Compound 7
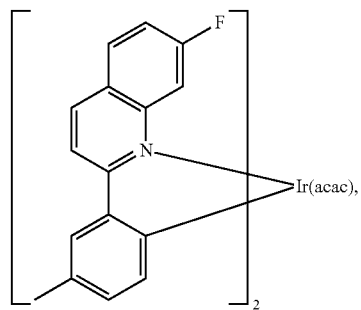
Compound 8
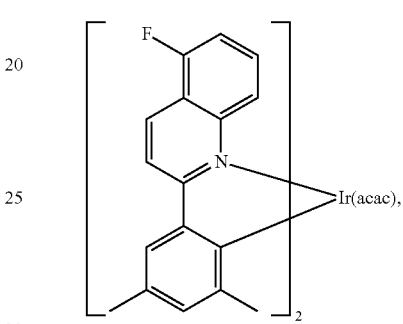
Compound 9
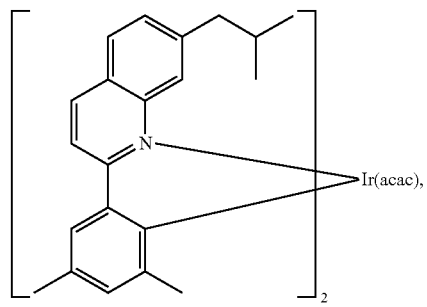
Compound 10
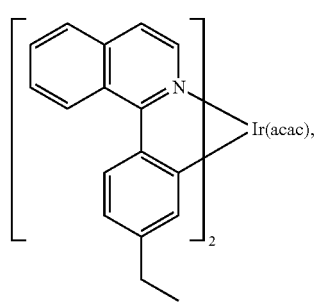
Compound 11
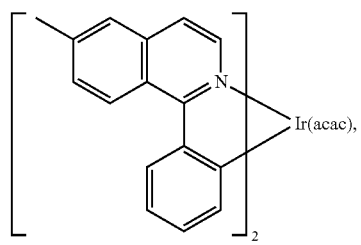

Compound 12
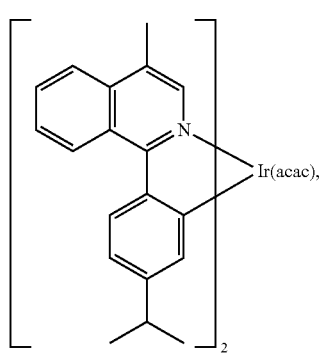
Compound 13
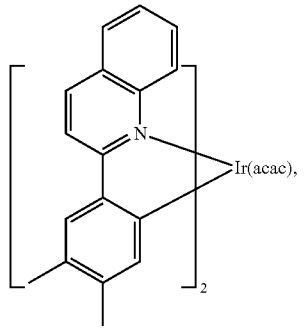
Compound 14
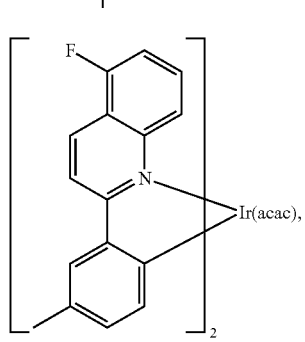
Compound 15
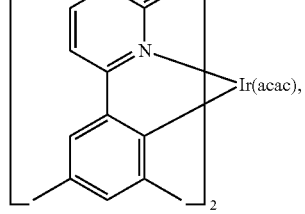
Compound 16
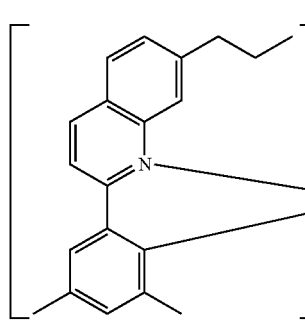
Compound 17
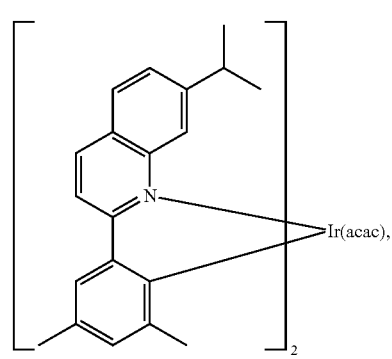
Compound 18
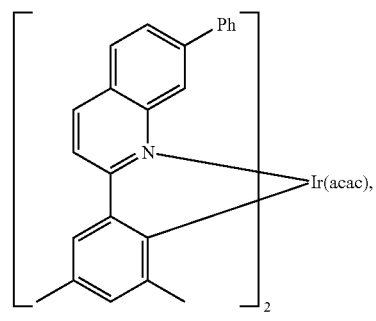
Compound 19
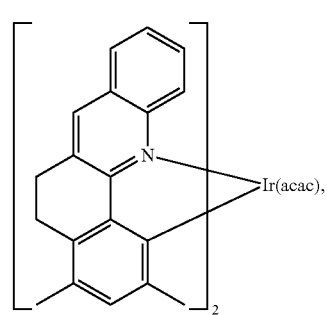
Compound 20
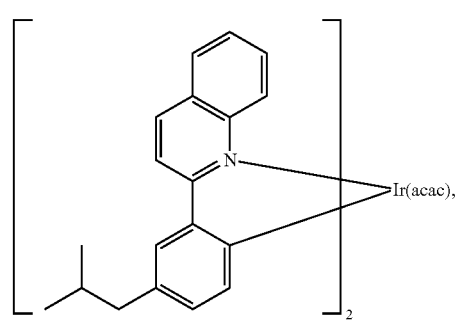
Compound 21
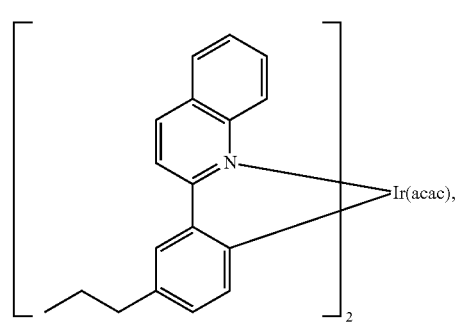

-continued

Compound 22

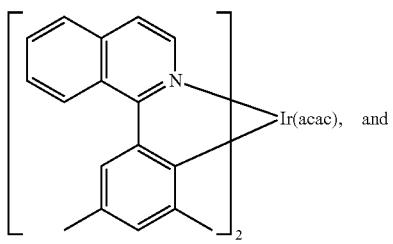

Compound 23

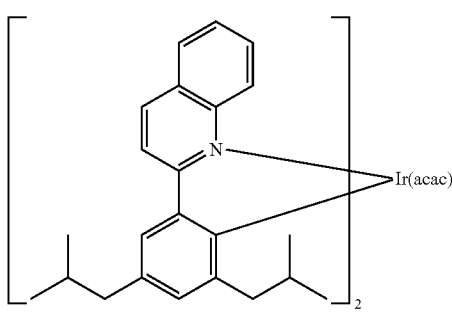

Compound 24

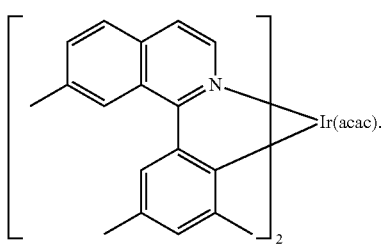

The emitter materials (dopants), preferably the phosphorescent emitter materials, may be used alone or in combination of two or more.

The compounds of formula (I) are also useful in combination with fluorescent dopants, especially as electron transport material, preferably in combination with a blue fluorescent dopant. Preferred blue fluorescent dopants that may be present in the light emitting layer of the OLED according to the present invention are for example polycyclic amine derivatives as mentioned in EP 2924029. Particularly preferred aromatic amine derivatives are selected from compounds according to the following formula (20A):

(20A)

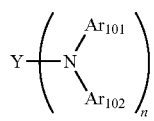

In the formula (20A), Y is a substituted or unsubstituted fused aromatic hydrocarbon group including 10 to 50 ring carbon atoms.

$Ar_{101}$, and $Ar_{102}$ are independently a substituted or unsubstituted aryl group including 6 to 50 ring carbon atoms or a substituted or unsubstituted heterocyclic ring group including 5 to 50 ring atoms.

Specific examples of Y include the above-mentioned fused aryl group. Y is preferably a substituted or unsubstituted anthryl group, a substituted or unsubstituted pyrenyl group or a substituted or unsubstituted chrysenyl group.

n is an integer of 1 to 4. It is preferred that n be an integer of 1 to 2.

The above-mentioned formula (20A) is preferably one represented by the following formulas (21A) to (24A).

(21A)

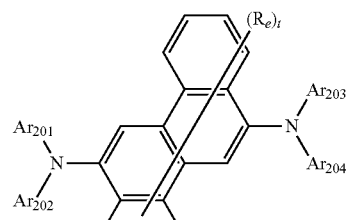

(22A)

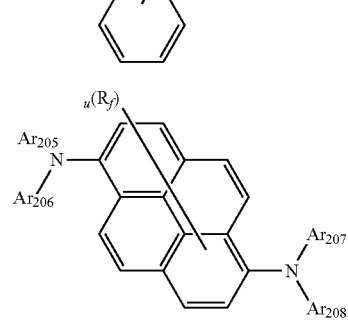

(23A)

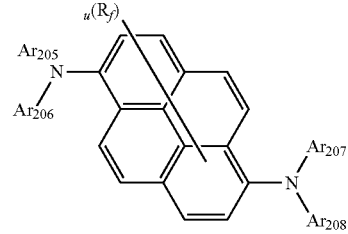

(24A)

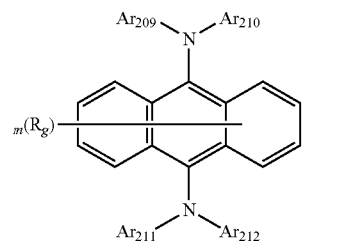

In the formulas (21A) to (24A), Re, $R_f$ and $R_g$ are independently a substituted or unsubstituted alkyl group including 1 to 20 carbon atoms, a substituted or unsubstituted alkenyl group including 2 to 50 carbon atoms, a substituted or unsubstituted alkynyl group including 2 to 5.0 carbon atoms, a substituted or unsubstituted aralykyl group including 1 to 20 carbon atoms, a substituted or unsubstituted cycloalkyl group including 3 to 20 ring carbon atoms, a, substituted or unsubstituted alkoxy group including 1 to 20 carbon atoms, a substituted, or unsubstituted aryloxy group including 6 to 20 ring carbon atoms, a substituted or unsubstituted aryl group including 6 to 50 ring carbon atoms, a substituted or unsubstituted silyl group, a substituted or unsubstituted alkyl germanium group including 1 to 50 carbon atoms or a substituted or unsubstituted aryl germanium group including 6 to 50 ring carbon atoms. $R_e$, $R_f$ and $R_g$ may independently be bonded to any of the bonding positions of the benzene rings that constitutes the fused polycyclic skeleton.

As preferable examples of $R_e$, $R_f$ and $R_g$, a substituted or unsubstituted aryl group including 6 to 50 ring carbon atoms can be given. More preferably, $R_e$, $R_f$ and $R_g$ are a substituted or unsubstituted phenyl group, a substituted or unsubstituted naphthyl group, or the like.

t is an integer of 0 to 10. u is an integer of 0 to 18 m is an integer of 0 to 10. $Ar_{201}$ to $Ar_{218}$ are independently an aryl group including 6 to 50 ring carbon atoms or a substituted or unsubstituted heterocyclic group including 5 to 50 ring atoms.

Preferred examples of $Ar_{201}$ to $Ar_{218}$ include a substituted or unsubstituted phenyl group, a substituted or unsubstituted dibenzofuranyl group or the like. As preferable examples of the substituent of $Ar_{201}$ to $Ar_{218}$, an alkyl group, a cyano group and, a substituted or unsubstituted silyl group can be given.

In the formulas (21A) to (24A), as examples of the alkyl group, the alkoxy group, the aryl group, the aryloxy group and the heterocyclic group, those exemplified above can be given.

As the alkenyl group including 2 to 50, preferably 2 to 30 more preferably 2 to 20, and particularly preferably 2 to 10, carbon atoms, a vinyl group; an allyl group, a 1-butenyl group, a 2-butenyl group, a 3-butenyl group, a 1,3-butanedienyl group, a 1-methylvinyl group, a styryl group, a 2,2-diphenylvinyl group, a 1,2-diphenylvinyl group, a 1-methylallyl group, a 1,1-dimethylallyl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, a 3-phenyl-1-butenyl group or the like can be given. Preferred are a styryl group, a 2,2-diphenylvinyl group, a 1,2-diphenylvinyl group or the like.

As the alkynyl group including 2 to 50 (preferably 2 to 30, more preferably 2 to 20, particularly preferably 2 to 10) carbon atoms, a propargyl group, a 3-pentynyl group or the like can be given.

As the alkyl germanium group, a methylhydrogermyl group, a trimethylgermyl group, a triethylgermyl group, a tripropylgermyl group, a dimethyl-t-butylgermyl group or the like can be given.

As the aryl germanium group, a phenyldihydrogermyl group, a diphenylhydrogermy group, a triphenylgermyl group, a tritolylgermyl group, a trinaphthylgermyl group or the like can be given.

As the styrylamine compound and the styryldiamine compound, those represented by the following formulas (17A) and (18A) are preferable.

(17A)

(18A)

In the formula (17A), $Ar_{301}$ is a k-valent group; a k-valent group corresponding to a phenyl group, a naphthyl group, a biphenyl group, a terphenyl group, a stilbene group, a styrylaryl group and a distyrylaryl group. $Ar_{302}$ and $Ar_{303}$ are independently an aryl group including 6 to 20 ring carbon atoms, and $Ar_{301}$, $Ar_{302}$ and $Ar_{303}$ may be substituted.

k is an integer of 1 to 4, with an integer of 1 and 2 being preferable. Any one of $Ar_{301}$ to $Ar_{303}$ is a group including a styryl group. It is further preferred that at least one of $Ar_{302}$ and $Ar_{303}$ be substituted by a styryl group.

As for the aryl group including 6 to 20 ring carbon atoms, the above-mentioned aryl group can be specifically given. Preferable examples include a phenyl group, a naphthyl group, an anthranyl group, a phenanthryl group, a terphenyl group or the like.

In the formula (18A), $Ar_{304}$ to $Ar_{306}$ are a v-valent substituted or unsubstituted aryl group including 6 to 40 ring carbon atoms. v is an integer of 1 to 4, with an integer of 1 and 2 being preferable.

Here, as the aryl group including 6 to 40 ring carbon atoms in the formula (18A), the above-mentioned aryl group can be specifically given. A naphthyl group; an anthranyl group, a chrysenyl group, a pyrenyl group or an aryl group represented by the formula (20A) is preferable.

As preferable substituents that substitute on the aryl group, an alkyl group, including 1 to 6 carbon atoms, an alkoxy group including 1 to 6 carbon atoms, an aryl group including 6 to 40 ring carbon atoms, an amino group substituted by an aryl group including 6 to 40 ring carbon atoms, an ester group including an aryl group that includes 5 to 40 ring carbon atoms, an ester group including an alkyl group that includes 1 to 6 carbon atoms, a cyano group, a nitro group, a halogen atom or the like can be given.

Host (Matrix) Materials

The light-emitting layer may comprise further components in addition to the emitter material. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, be a small molecule, for example 4,4'-N,N'-dicarbazolebiphenyl (CDP=CBP) or tertiary aromatic amines, for example Tris(4-carbazoyl-9-ylphenyl) amine (TCTA).

In the case that one or more phosphorescent emitter materials are used in the light emitting layer, one or more phosphorescent hosts are employed as host material. The phosphorescent host is a compound which confines the triplet energy of the phosphorescent dopant efficiently in the light emitting layer to cause the phosphorescent dopant to emit light efficiently.

In a preferred embodiment, the light-emitting layer is formed of at least one emitter material and of at least one of the matrix materials mentioned in this application. According to a preferred embodiment, the electronic device according to the present invention, preferably the OLED according to the present invention, comprises at least one compound of the formula (I) as matrix (host) material.

According to one embodiment, the light-emitting layer comprises at least one emitter material and at least two matrix materials, wherein one of the matrix materials is a compound, of the formula (I) and the other matrix material(s) is/are used as co-host(s). Suitable other host materials than the compounds of formula (I) (co-hosts) are mentioned below According to another embodiment, the light-emitting layer comprises at least one emitter material and a compound of the formula (I) as a single matrix (host) material. Examples of preferred compounds of formula (I) useful as single host material are shown above.

The compounds of the formula (I) are suitable as single host material as well as host material, together with one or more further host materials (co-host). Suitable further host materials are mentioned below. "Further host materials" means in the sense of the present application, host materials different from the compounds of formula (I). However, it is also possible to use two or more different compounds of formula (I) as host material in the light-emitting layer in an OLED of the present application.

In a more preferred embodiment, the light-emitting layer is formed from 0.1 to 70% by weight, preferably 1 to 30% by weight, of at least one of the aforementioned emitter materials and 30 to 99:9% by weight, preferably 70 to 99% by weight, of at least one of the matrix materials mentioned in the specification—in one embodiment at least one compound of the formula (I)—where the sum total of the emitter material and of the matrix material adds up to 100% by weight.

In a further more preferred embodiment, the light-emitting layer comprises a compound of formula (I) as matrix material, at least one further matrix material (co-host) and at least one emitter material. In said embodiment, the light-emitting layer is formed from 0.1 to 70% by weight, preferably 1 to 30% by weight, of the at least one emitter material and 30 to 99.9% by weight, preferably 70 to 99% by weight, of a compound of the formula (I) and the further matrix material, where the sum total of the at least one emitter material, the further matrix material and of the compound of formula (I) adds up to 100% by weight.

The content ratio of the compound of the formula (I) as first host material and the second matrix material as co-host in the light emitting layer is not particularly limited and may be selected accordingly, and the ratio of first host material: second host material is preferably 1:99 to 99:1, more preferably 10:90 to 90:10, each based on mass.

The phosphorescent host is a compound having a function of allowing a phosphorescent dopant to emit light efficiently by efficiently confining the triplet energy of the phosphorescent dopant in the emitting layer. The material for an organic EL device according to the invention is preferable as the phosphorescent host. The emitting layer may comprise one kind of the material for an organic EL device according to the invention or may comprise two or more kinds of the material for an organic EL device according to the invention.

When the material for an organic EL device according to the invention is used as a host material of the emitting layer, the emission wavelength of the phosphorescent dopant contained in the emitting layer is not particularly restricted. It is preferred that at least one kind of the phosphorescent dopant materials contained in the emitting layer have a peak of an emission wavelength of 490 nm or more and 700 nm or less, more preferably 490 nm or more and 650 nm or less. As for the emission color of the emitting layer, red, yellow and green are preferable, for example. By using the compound according to the invention as the host material and by forming an emitting layer by doping the phosphorescent dopant having such an emission wavelength, it is possible to obtain a long-lived organic EL device.

In the organic EL device according to the invention, other compounds than the material for an organic EL device according to the invention can appropriately be selected as the phosphorescent host according to the above-mentioned purpose.

The material for an organic EL device according to the invention and other compounds may be used in combination as the phosphorescent host material in the same emitting layer. When plural emitting layers are present, as the phosphorescent host material for one of these emitting layers, the material for an organic EL device according to the invention is used, and as the phosphorescent host material for one of other emitting layers other compounds than the material for an organic EL device according to the invention may be used. The material for an organic EL device according to the invention can be used in an organic layer other than the emitting layer. In that case, as the phosphorescent host of the emitting layer, other compounds than the material for an organic EL device according to the invention may be used.

As for the compound other than the material for an organic EL device according to the invention, as specific examples of the compound that is preferable as the phosphorescent host, carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethane derivatives, anthrone derivatives, diphenylquinone derivatives, thiopyrandioxide derivatives, carbodiimide derivatives, fluorenylidene methane derivatives, distyrylpyrazine derivatives and heterocyclic tetracarboxylic anhydrides of naphthaleneperylene or the like, metal complexes of phthalocyanine derivatives and 8-quinolinol derivatives, various metal complex polysilane compounds represented by metal complexes having metal phthalocyanine benzoxazole or benzothiazole as a ligand, poly(N-vinylcarbazole) derivatives aniline-based copolymers, conductive polymer oligomers such as thiophene oligomers and polythiophene, and polymer compounds such as polythiophene derivatives, polyphenylene derivatives, polyphenylene vinylene derivatives and polyfluorene derivatives can be given. The phosphorescent host may be used alone or in combination of two or more. As specific examples, the following compounds can be given.

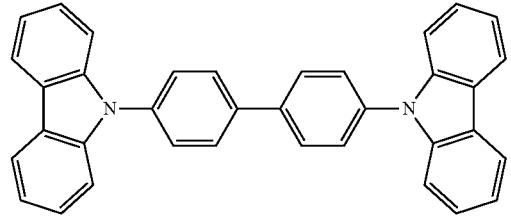

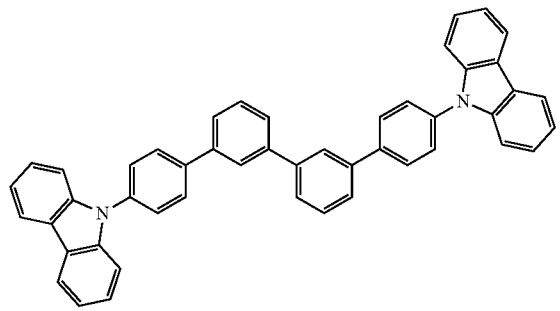

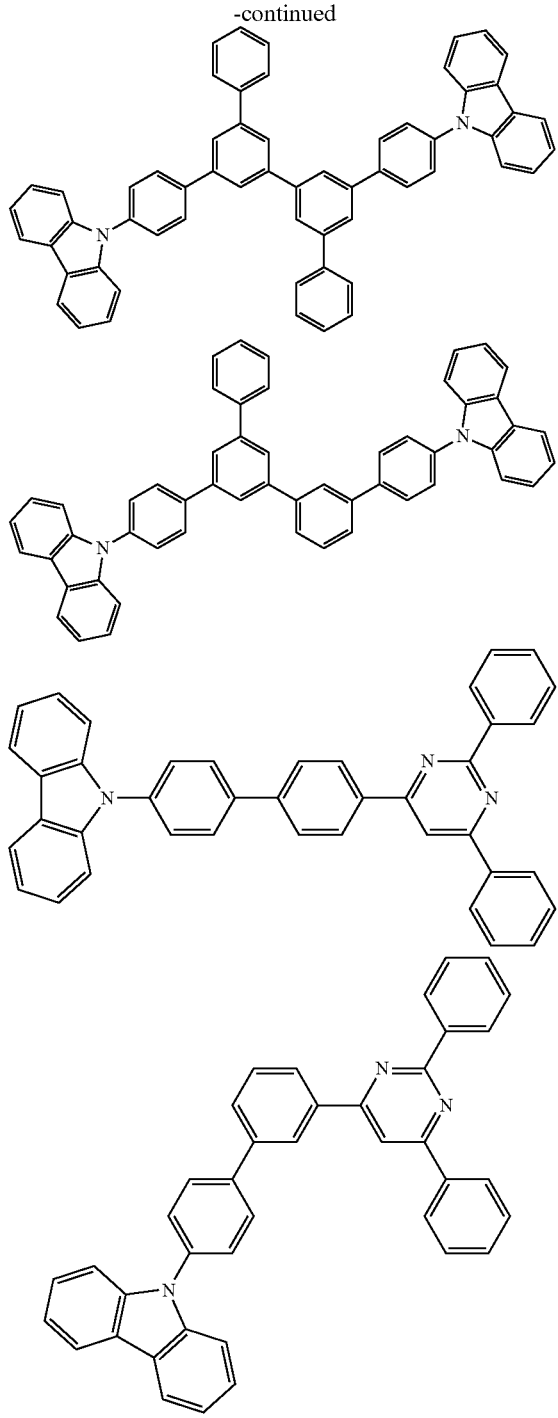

If the emitting layer comprises the first host material and the second host, material, the material for an organic EL device according to the invention may be used as the first host material and other compounds than the material for an organic EL device according to the invention may be used as the second host material. The "first host material" and the "second host material" as referred to herein mean that the plural host materials contained in the emitting layer differ from each other in structure, and are not determined by the content of each host material in the emitting layer.

The second host material is not particularly restricted, and compounds other than the material for an organic EL device according to the invention and the same compound mentioned above as being preferable as the phosphorescent host can be given. As the second host, a carbazole derivative, an arylamine derivative, a fluorenone derivative and an aromatic tertiary amine compound are preferable.

The organic EL device of the invention may have an emitting layer that contains a fluorescent emitting material (i.e. fluorescent emitting layer). As the fluorescent emitting layer, a known fluorescent emitting material can be used. As the fluorescent emitting material, at least one selected from an anthracene derivative, a fluororanthene derivative, a styrylamine derivative and an arylamine derivative is preferable. An anthracene derivative and an arylamine derivative are more preferable. In particular, an anthracene derivative is preferable as a host material, and an arylamine derivative is preferable as a dopant. Specifically, preferable materials disclosed in WO2010/134350 or WO2010/134352 can be selected. The material for an organic EL device of the invention may be used as a fluorescent emitting material for the fluorescent emitting layer, or may be used as a host material for the fluorescent emitting layer.

The ring carbon atoms of the anthracene derivative as a fluorescent emitting layer is preferably 26 to 100, more preferably 26 to 80, and further preferably 26 to 60. As the anthracene derivative, more specifically, an anthracene derivative represented by the following formula (10A) is preferable.

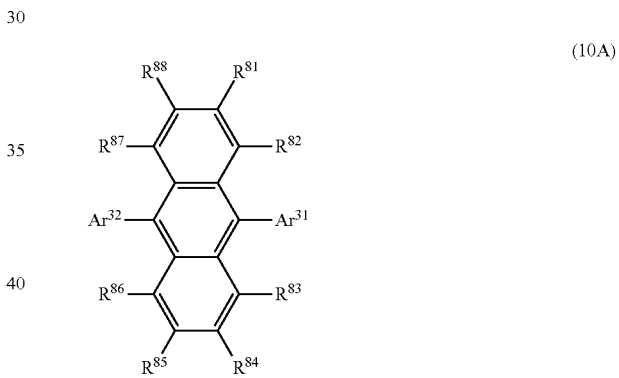

(10A)

In the formula (10A), $Ar^{31}$ and $Ar^{32}$ are independently a substituted or unsubstituted aryl group including 6 to 50 ring carbon atoms or a heterocyclic group including 5 to 50 ring atoms.

$R^{81}$ to $R^{88}$ are independently a hydrogen atom, a substituted or unsubstituted aryl group including 6 to 50 ring carbon atoms, a substituted or unsubstituted heterocyclic group including 5 to 50 ring atoms, an alkyl group including 1 to 50 carbon atoms, a substituted or unsubstituted alkoxy group including 1 to 50 carbon atoms, a substituted or unsubstituted aralkyl group including 7 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, a substituted or unsubstituted silyl group, a carboxy group, a halogen atom, a cyano group, a nitro group or a hydroxyl group.

As the above-mentioned any aryl group including 6 to 50 ring carbon atoms, an aryl group including 6 to 40 ring carbon atoms is preferable, with an aryl group including 6 to 30 ring carbon atoms being more preferable.

As the above-mentioned any heterocyclic group including 5 to 50 ring atoms, a heterocyclic group including 5 to 40 ring atoms is preferable, with a heterocyclic group including 5 to 30 ring atoms being more preferable.

As the above-mentioned alkyl group including 1 to 50 carbon atoms, an alkyl group including 1 to 30 carbon atoms is preferable, an alkyl group including 1 to 10 carbon atoms are more preferable, with an alkyl group including 1 to 5 carbon atoms being further preferable.

As the above-mentioned alkoxy group including 1 to 50 carbon atoms, an alkoxy group including 1 to 30 carbon atoms is preferable, an alkoxy group including 1 to 10 carbon atoms is more preferable, with an alkoxy group including 1 to 5 carbon atoms being further preferable.

As the above-mentioned aralkyl group including 7 to 50 carbon atoms, an aralkyl group including 7 to 30 carbon atoms is preferable, with an aralkyl group including 7 to 20 carbon atoms being more preferable.

As the above-mentioned aryloxy group including 6 to 50 ring carbon atoms, an aryloxy group including 6 to 40 ring carbon atoms is preferable, with an aryloxy group including 6 to 30 ring carbon atoms being more preferable.

As the above-mentioned arylthio group including 6 to 50 ring carbon atoms, an arylthio group including 6 to 40 ring carbon atoms is preferable, with an arylthio group including 6 to 30 ring carbon atoms being more preferable.

As the above-mentioned alkoxycarbonyl group including 2 to 50 carbon atoms, an alkoxycarbonyl group including 2 to 30 carbon atoms is preferable, an alkoxycarbonyl group including 2 to 10 carbon atoms is more preferable, with an alkoxycarbonyl group including 2 to 5 carbon atoms being further preferable.

As the above-mentioned halogen atom, a fluorine atoms, a chlorine atom, a bromine atom or the like may be given.

In particular, $Ar^{31}$ and $Ar^{32}$ are preferably a substituted or unsubstituted aryl group including 6 to 50 ring carbon atoms.

In the formula (10A-1), $Ar^{33}$ is a substituted or unsubstituted aryl group including 6 to 50 ring carbon atoms or a heterocyclic group including 5 to 50 ring atoms. $R^{81}$ to $R^{88}$ are as defined above. $R^{89}$ is the same as defined for $R^{81}$ to $R^{88}$. a is an integer of 1 to 7.

Preferable examples of $R^{81}$ to $R^{88}$ are the same as defined above. Preferable examples of $R^{89}$ are the same as those for $R^{81}$ to $R^{88}$. a is preferably an integer of 1 to 3, with 1 or 2 being more preferable.

As the aryl group including 6 to 50 ring carbon atoms represented by $Ar^{33}$, an aryl group including 6 to 40 ring carbon atoms is preferable, an aryl group including 16 to 30 ring carbon atoms is more preferable, an aryl group including 6 to 20 ring carbon atoms is further preferable, with an aryl group including 6 to 12 ring carbon atoms being particularly preferable.

As the arylamine derivative as the fluorescent emitting material, an aryldiamine derivative is preferable, an aryldiamine derivative having a pyrene skeleton is more preferable, and an aryldiamine derivative having a pyrene skeleton and a dibenzofurane skeleton is further preferable.

As the aryldiamine derivative, more specifically, the arylamine derivative represented by the following formula (11A) is preferable.

(11A)

In the formula (11A), $Ar^{34}$ to $Ar^{37}$ are independently a substituted or unsubstituted aryl group including 6 to 50 ring carbon atoms or a substituted or unsubstituted heteroaryl group including 5 to 50 ring atoms.

$L^{21}$ is a substituted or unsubstituted arylene group including 6 to 50 ring carbon atoms or a substituted or unsubstituted heteroarylene group including 5 to 50 ring atoms.

As the aryl group including 6 to 50 ring carbon atoms, an aryl group including 6 to 30 ring carbon atoms is preferable, an aryl group including 6 to 20 ring carbon atoms is more preferable, an aryl group including 6 to 12 ring carbon atoms is further preferable, with a phenyl group and a naphthyl group being particularly preferable.

As the heteroaryl group including 5 to 50 ring atoms, a heteroaryl group including 5 to 40 ring atoms is preferable, a heteroaryl group including 5 to 30 ring atoms is more preferable and a heteroaryl group including 5 to 20 ring atoms is further preferable. As the heteroaryl group; a carbazolyl group, a dibenzofuranyl group, a dibenzofuranyl group or the like can be given, and a dibenzofuranyl group is preferable. As the preferable substituent of the heteroaryl group, an aryl group including 6 to 30 (preferably 6 to 20, more preferably 6 to 12)-ring carbon atoms can be given, with a phenyl group and a naphthyl group being more preferable.

As the arylene group including 6 to 50 ring carbon atoms, an arylene group-including 6 to 40 ring carbon atoms is preferable, an arylene group including 6 to 30 ring carbon atoms is more preferable, an arylene group including 6 to 20 ring carbon atoms is further, preferable, with a pyrenyl group being particularly preferable.

The thickness of the emitting layer is preferably 5 to 50 nm, more preferably −7 to 50 nm, and further preferably 10 to 50 nm. If the thickness is 5 nm or more, the formation of the emitting layer is facilitated. If the thickness is 50 nm or less, an increase in driving voltage can be avoided.

Electron-Donating Dopant

In the organic EL device according to the invention, it is preferred that an electron-donating dopant be contained in the interfacial region between the cathode and the emitting unit. Due to such a configuration, the organic EL device can have an increased luminance or a long life. Here, the electron-donating dopant means one having a metal with a work function of 3.8 eV or less. As specific examples thereof, at least one selected from an alkali metal, an alkali metal complex, an alkali metal compound, an alkaline earth metal an alkaline earth metal complex, an alkaline earth metal compound, a rare earth-metal, a rare earth metal complex and a rare earth metal compound or the like can be mentioned.

As the alkali metal, Na (work function: 2.36 eV), K (work function: 2.28 eV), Rb (work function: 2.16 eV), Cs (work function: 1.95 eV) and the like can be given. One having a work function of 2.9 eV or less is particularly preferable. Among them K, Rb and Cs are preferable. Rb or Cs is further preferable. Cs is most preferable. As the alkaline earth metal, Ca (work function: 2.9 eV), Sr (work function: 2.0 eV to 2.5 eV), Ba (work-function: 22.52 eV) and the like can be given. One having a work function of 2.9 eV or less is particularly preferable. As the rare-earth metal, Sc, Y, Ce, Tb, Yb and the like can be given. One having a work function of 2.9 eV or less is particularly preferable.

Examples of the alkali metal compound include an alkali oxide such as $Li_2O$, $Cs_2O$ or $K_2O$, and an alkali halide such as LiF, NaF, CsF and KF. Among them, LiF, $Li_2O$ and NaF are preferable. Examples of the alkaline earth metal compound include BaO, SrO, CaO, and mixtures thereof such as $Ba_xSr_{1-x}O$ (0<x<1) and $Ba_xCa_{1-x}O$ (0<x<1). Among them, BaO, SrO and CaO are preferable. Examples of the rare earth metal compound include $YbF_3$, $ScF_3$, $ScO_3$, $Y_2O_3$, $Ce_2O_3$, $GdF_3$ and $TbF_3$. Among these, $YbF_3$, $ScF_3$ and $TbF_3$ are preferable.

The alkali metal complexes, the alkaline earth metal complexes and the rare earth metal complexes are not particularly limited as long as they contain, as a metal ion, at least one of alkali metal ions, alkaline earth metal ions, and rare earth metal ions. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, and derivatives thereof.

Regarding the addition form of the electron-donating dopant, it is preferred that the electron-donating dopant be formed in a shape of a layer or an island in the interfacial region. A preferred method for the formation is a method in which an organic compound (a light emitting material or an electron-injecting material) for forming the interfacial region is deposited simultaneously with deposition of the electron-donating dopant by a resistant heating deposition method, thereby dispersing the electron-donating dopant in the organic compound. The dispersion concentration of the organic compound: the electron-donating dopant (molar ratio) is 100:1 to 1:100, preferably 5:1 to 1:5.

In a case where the electron-donating dopant is formed into the shape of a layer, the light-emitting material or electron-injecting material which serves as an organic layer in the interface is formed into the shape of a layer. After that, a reductive dopant is solely deposited by the resistant heating deposition method to form a layer preferably having a thickness of from 0.1 nm to 15 nm. In a case where the electron-donating dopant is formed into the shape of an island, the emitting material or the electron-injecting material which serves as an organic layer in the interface is formed into the shape of an island. After that, the electron-donating dopant is solely deposited by the resistant heating deposition method to form an island preferably having a thickness of from 0.05 nm to 1 nm.

The ratio of the main component and the electron-donating dopant in the organic EL device according to the invention is main component:electron-donating dopant=5:1 to 1:5 in terms of molar ratio, more preferably 2:1 to 1:2.

Electron-Transporting Layer

The electron-transporting layer is an organic layer that is-formed between the emitting layer and the cathode and has a function of transporting electrons from the cathode to the emitting, layer. When the electron-transporting layer is formed of plural layers, an organic layer that is nearer to the cathode is often defined as the electron-injecting layer. The electron-injecting layer has a function of injecting electrons from the cathode efficiently to the organic layer unit. The material for an organic EL device of the invention is also preferable as an electron-transporting layer material that constitutes an electron-transporting layer.

As the electron-transporting material used in the electron-transporting layer other than the material for an organic EL device of the invention, an aromatic heterocyclic compound having one or more hetero atoms in the molecule may preferably be used. In particular, a nitrogen-containing ring derivative is preferable. As the nitrogen-containing ring derivative, an aromatic ring having a nitrogen-containing six-membered or five-membered ring skeleton or a fused aromatic ring compound having a nitrogen-containing six-membered or five-membered ring skeleton is preferable.

As the nitrogen-containing ring derivative, a nitrogen-containing ring metal chelate complex represented by the following formula (A) is preferable, for example.

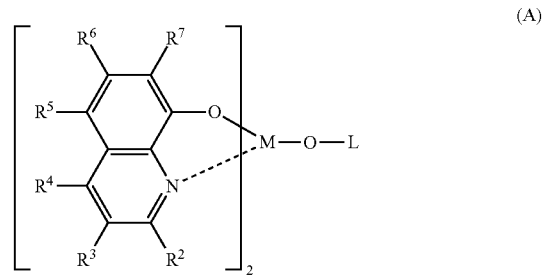

(A)

$R^2$ to $R^7$ in the formula (A), that is a nitrogen-containing ring metal chelate complex, are independently a hydrogen atom, a heavy hydrogen atom, a hydrogen atom, a hydroxy group, an amino group, a hydrocarbon group including 1 to 40 carbon atoms, an alkoxy group including 1 to 40 carbon atoms, an aryloxy group including 6 to 50 carbon atoms, an alkoxycarbonyl group or an aromatic heterocyclic group including 5 to 50 ring carbon atoms. They may be substituted.

As the halogen atom, fluorine, chlorine, bromine, iodine or the like can be given, for example.

As examples of the amino group that may be substituted, an alkylamino group, an arylamino group and an aralkylamino group can be given.

The alkylamino group and the aralkylamino group are represented by $-NQ^1Q^2$. $Q^1$ and $Q^2$ are independently an alkyl group including 1 to 20 carbon atoms or an aralkyl group including 1 to 20 carbon atoms. One of $Q^1$ and $Q^2$ may be a hydrogen atom or a heavy hydrogen atom.

The arylamino group is represented by $-NAr^1Ar^2$, and $Ar^1$ and $Ar^2$ are independently a non-fused aromatic hydrocarbon group or fused aromatic hydrocarbon group, including 6 to 50 carbon atoms. One of $Ar^1$ and $Ar^2$ may be either a hydrogen atom or a heavy hydrogen atom.

The hydrocarbon group including 1 to 40 carbon atoms includes an alkyl group, an alkenyl group, a cycloalkyl group, an aryl group and an aralkyl group.

The alkoxycarbonyl group is represented by $-COOY'$ and Y' is an alkyl group including 1 to 20 carbon atoms.

M is aluminum (Al), gallium (Ga) or indium (In), and M is preferably In.

L is a group represented by the following formula (A') or (A").

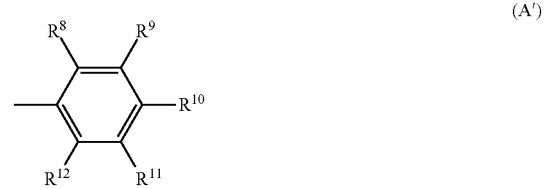

(A')

-continued

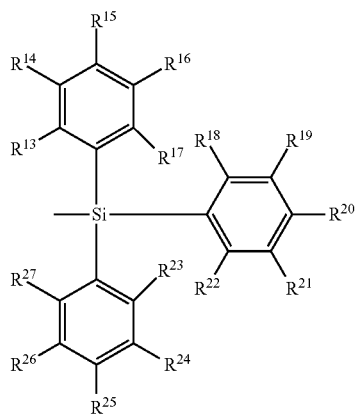

(A")

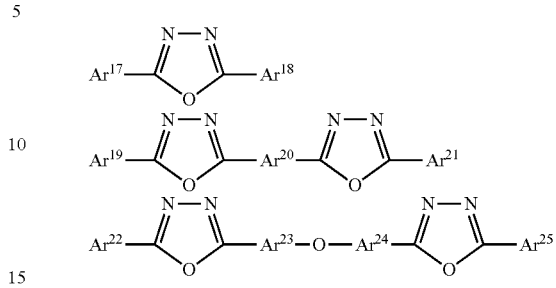

In the formula (A'), $R^8$ to $R^{12}$ are independently a hydrogen atom, a heavy hydrogen atom or a substituted or unsubstituted hydrocarbon group including 1 to 40 carbon atoms, and adjacent groups may form a ring structure. In the formula (A"), $R^{13}$ to $R^{27}$ are independently a hydrogen atom, a heavy hydrogen atom or a substituted or unsubstituted hydrocarbon group including 1 to 40 carbon atoms, and adjacent groups may form a ring structure.

The hydrocarbon group including 1 to 40 carbon atoms represented by $R^8$ to $R^{12}$ and $R^{13}$ to $R^{27}$ in the formulas (A') and (A") is the same as the hydrocarbon group represented by $R^2$ to $R^7$ in the formula (A) that is a nitrogen-containing ring metal chelate complex. As the divalent group formed when the adjacent groups of $R^8$ to $R^{12}$ and $R^{13}$ to $R^{27}$ form a ring structure, a tetramethylene group, a pentamethylene group, a hexamethylene group, a diphenylmethane-2,2'-diyl group, a diphenylethane-3,3'-diyl group, a diphenylpropane-4,4'-diyl group or the like can be mentioned.

As the electron-transmitting material used in the electron-transmitting layer, a metal complex of 8-hydroxyquinoline or a derivative thereof, an oxadiazole derivative and a nitrogen-containing heterocyclic derivative are preferable. Specific examples of the metal complex of the 8-hydroxyquinoline or the derivative thereof include metal chelate oxynoid compounds containing a chelate of oxine (generally, 8-quinolinol or 8-hydroxyquinoline). For example, tris(8-quinolinol)aluminum can be used. As the oxadiazole derivative, the following can be given, for example.

In the formula, $Ar^{17}$, $Ar^{18}$, $Ar^{19}$, $Ar^{21}$, $Ar^{22}$ and $Ar^{25}$ are independently a substituted or unsubstituted aromatic hydrocarbon group or fused aromatic hydrocarbon group including 6 to 50 carbon atoms. $Ar^{17}$ and $Ar^{18}$, $Ar^{19}$ and $Ar^{21}$ and $Ar^{22}$ and $Ar^{25}$ may be the same as or different from each other. As the aromatic hydrocarbon group or the fused aromatic hydrocarbon, group, a phenyl group, a naphthyl group, a biphenyl group, an anthranyl group, a perylenyl group, a pyrenyl group or the like can be mentioned. As the substituent of these groups, an alkyl group including 1 to 10 carbon atoms, an alkoxy group including 1 to 10 carbon atoms, a cyano group or the like can be given.

$Ar^{20}$, $Ar^{23}$ and $Ar^{24}$ are independently a substituted or unsubstituted divalent aromatic hydrocarbon group or fused aromatic hydrocarbon group including 6 to 50 carbon atoms, and $Ar^{23}$ and $Ar^{24}$ may be the same as or different from each other. As the divalent aromatic hydrocarbon group or the fused aromatic hydrocarbon group, a phenylene group, a naphthylene group, a biphenylene group, an anthranylene group, a perylenylene group; a pyrenylene group or the like can be given. As the substituent of these, an alkyl group including 1 to 10 carbon atoms, an alkoxy group including 1 to 10 carbon atoms, a cyano group or the like can be given.

As these electron-transmitting compounds, those having excellent thin film-forming capability can be preferably used. As specific examples of these electron-transmitting compounds, the following can be given.

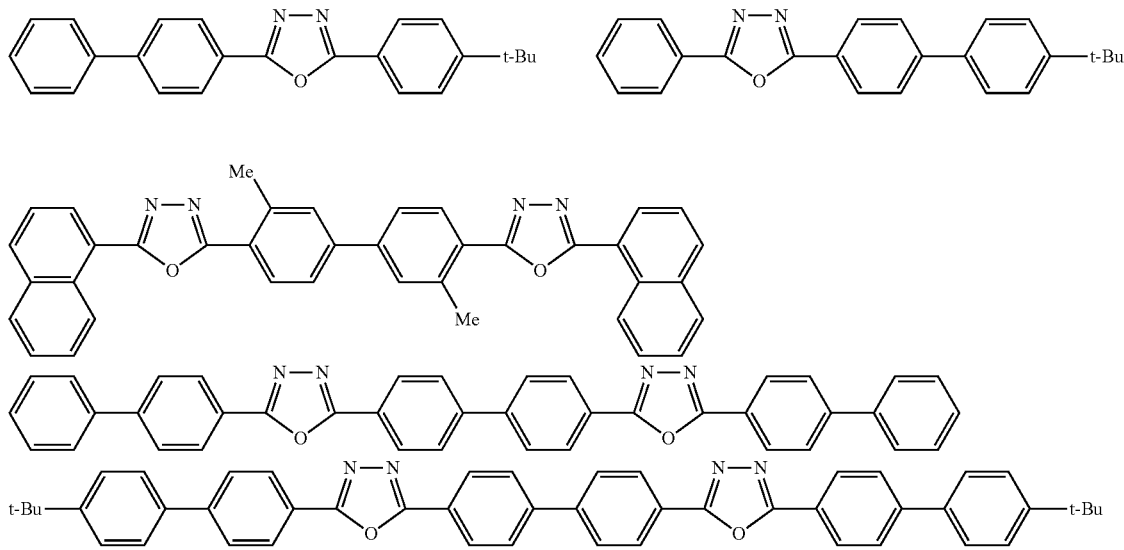

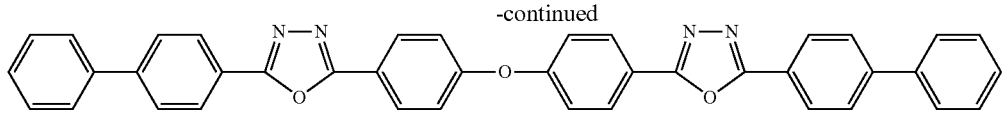

The nitrogen-containing heterocyclic derivative as the electron-transmitting compound is a nitrogen-containing heterocyclic derivative that comprises an organic compound represented by the following formula and is not a metal complex can be given. For example, a five-membered ring or a six-membered ring having a skeleton represented by the following formula (B) or one having a structure represented by the following formula (C) can be mentioned.

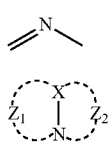

(B)

(C)

In the formula (C), X is a carbon atom or a nitrogen atom. $Z_1$ and $Z_2$ are independently a group of atoms capable of forming a nitrogen-containing heterocyclic ring.

The nitrogen-containing heterocyclic ring derivative is further preferably an organic compound having a nitrogen-containing aromatic polycyclic ring group composed of a five-membered ring or a six-membered ring. Further, in the case of the nitrogen-containing aromatic polycyclic ring group, a nitrogen-containing aromatic polycyclic organic compound having a skeleton obtained by combining the above formulas (B) and (C) or the above formula (B) and the following formula (D) is preferable.

(D)

The nitrogen-containing group in the nitrogen-containing aromatic polycyclic organic compound can be selected from the nitrogen-containing heterocyclic groups represented by the following formulas, for example.

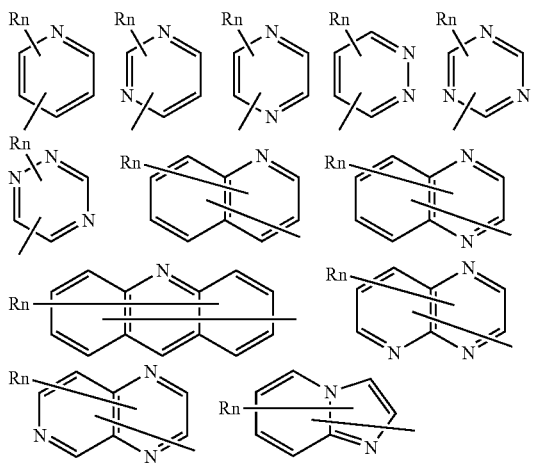

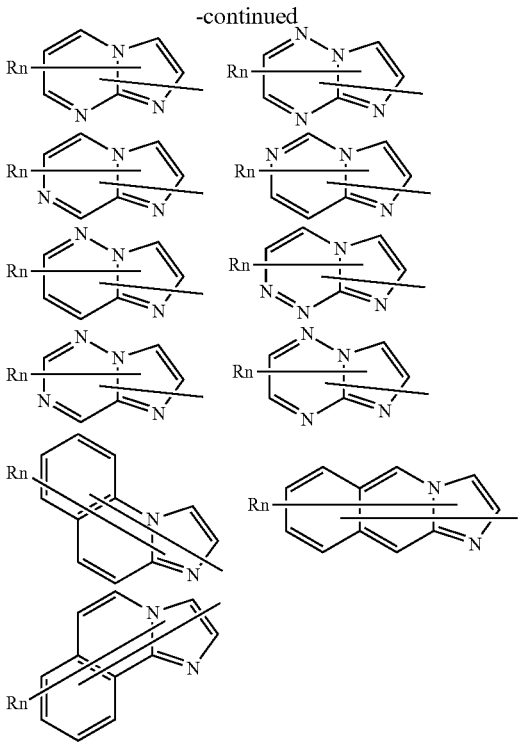

In each of the above formulas, R is an aromatic hydrocarbon group or fused aromatic hydrocarbon group including 6 to 40 carbon atoms, an aromatic heterocyclic group or fused aromatic heterocyclic group including 3 to 40 carbon atoms, an alkyl group including 1 to 20 carbon atoms or an alkoxy group including 1 to 20 carbon atoms. n is an integer of 0 to 5, and when n is an integer of 2 or more, plural Rs may be the same as or different from each other.

As further preferable specific compounds, a nitrogen-containing heterocyclic derivative represented by the following formula (D1) can be mentioned.

$$HAr\text{-}L^1\text{-}Ar^1\text{-}Ar^2 \tag{D1}$$

In the formula (D1), HAr is a substituted or unsubstituted nitrogen-containing heterocyclic ring group including 3 to 40 carbon atoms, $L^1$ is a single bond, a substituted or unsubstituted aromatic hydrocarbon group or fused aromatic hydrocarbon group including 6 to 40 carbon atoms or a substituted or unsubstituted aromatic heterocyclic group or fused aromatic heterocyclic group including 3 to 40 carbon atoms, $Ar^1$ is a substituted or unsubstituted divalent aromatic hydrocarbon group including 6 to 40 carbon atoms, and $Ar^2$ is a substituted or unsubstituted aromatic hydrocarbon group or fused aromatic hydrocarbon group including 6 to 40 carbon atoms or a substituted or unsubstituted aromatic heterocyclic group or fused-aromatic heterocyclic group including 3 to 40 carbon atoms.

HAr is selected from the following group, for example.

1135
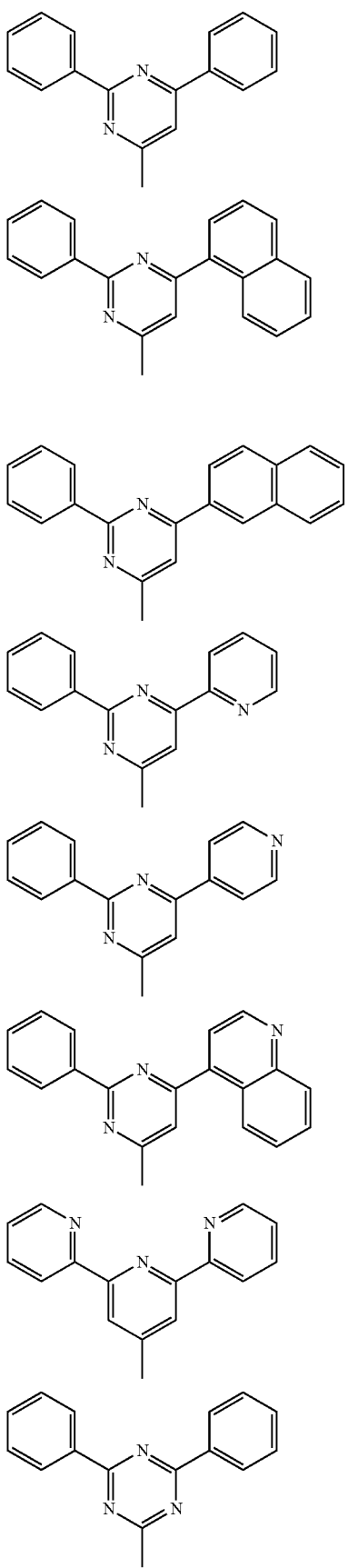
1136
-continued
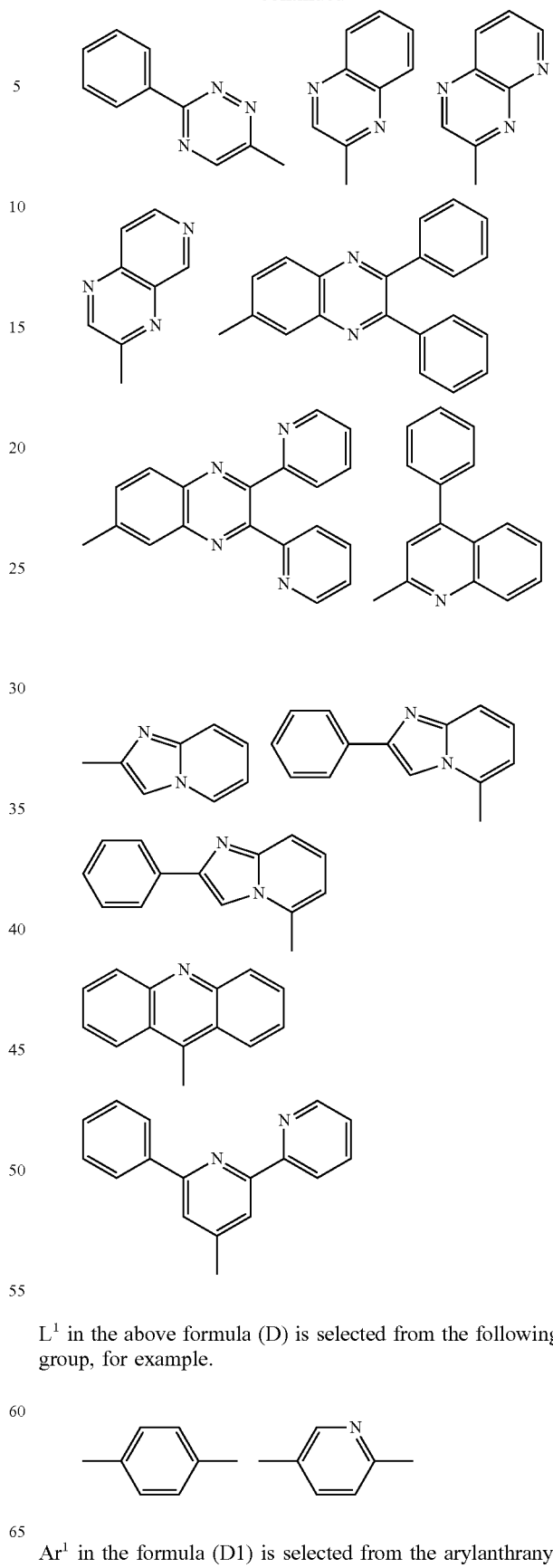
L¹ in the above formula (D) is selected from the following group, for example.
Ar¹ in the formula (D1) is selected from the arylanthranyl group in the following formulas (D2) and (D3).

(D2)
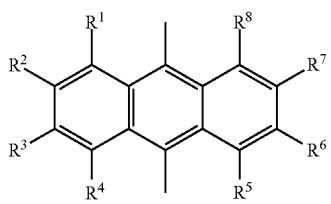

(D3)
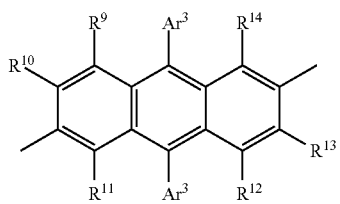

In the formulas (D2) and (D3), $R^1$ to $R^{14}$ are independently a hydrogen atom, a heavy hydrogen atom, a halogen atom, an alkyl group including 1 to 20 carbon atoms, an alkoxy group including 1 to 20 carbon atoms, an aryloxy group including 6 to 40 carbon atoms, a substituted or unsubstituted aromatic hydrocarbon group or fused aromatic hydrocarbon group including 6 to 40 carbon atoms or a substituted or unsubstituted aromatic heterocyclic group or fused aromatic heterocyclic group including 3 to 40 carbon atoms, $Ar^3$ is a substituted or unsubstituted aromatic hydrocarbon group or fused aromatic hydrocarbon group including 6 to 40 carbon atoms or a substituted or unsubstituted aromatic heterocyclic group or fused aromatic heterocyclic group including 3 to 40 carbon atoms. The nitrogen-containing heterocyclic derivative may be one in which all of $R^1$ to $R^8$ are a hydrogen atom or a heavy hydrogen atom.

$Ar^2$ in the formula (D1) is selected from the following group, for example.

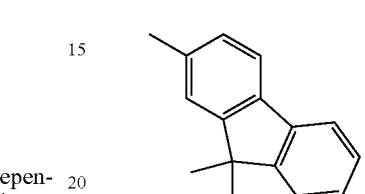

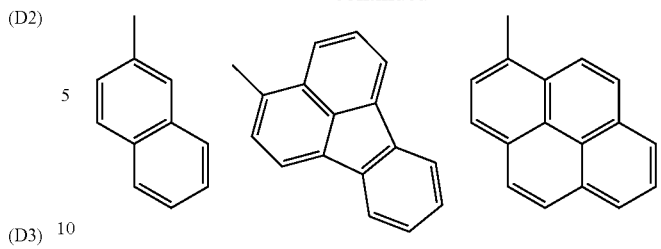

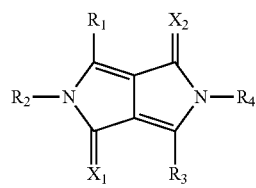

As the nitrogen-containing aromatic polycyclic organic compound as the electron-transmitting compound, in addition to those mentioned above, the following compounds can preferably be used.

(D4)

$$R_2-N\underset{X_1}{\overset{R_1\quad X_2}{\diagup\!\!\!\diagdown}}N-R_4$$
$$\quad\quad\quad R_3$$

In the formula (D4), $R_1$ to $R_4$ are independently a hydrogen atom, a heavy hydrogen atom, a substituted or unsubstituted aliphatic group including 1 to 20 carbon atoms, a substituted or unsubstituted alicyclic group including 3 to 20 carbon atoms, a substituted or unsubstituted aromatic ring group including 6 to 50 carbon atoms or a substituted or unsubstituted heterocyclic group including 3 to 50 carbon atoms; and $X_1$ and $X_2$ are independently an oxygen atom, a sulfur atom or a dicyanomethylene group.

As the electron-transmitting compound, the following compound is preferably used.

(D5)
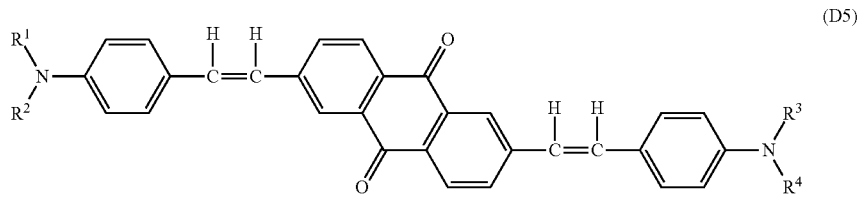

In the formula (D5), $R^1$, $R^2$, $R^3$ and $R^4$ are groups that are the same as or different from each other, and are an aromatic hydrocarbon group or a fused-aromatic hydrocarbon group represented by the following formula (D6).

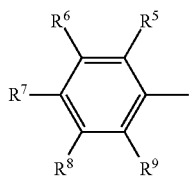
(D6)

In the formula (D6), $R^5$, $R^6$, $R^7$, $R^8$ and $R^9$ are groups that are the same as or different from each other, and are a hydrogen atom, a heavy hydrogen atom, a saturated or unsaturated alkoxy group including 1 to 20 carbon atoms, a saturated or unsaturated alkyl group including 1 to 20 carbon atoms, an amino group or an alkylamino group including 1 to 20 carbon atoms. At least one of $R^5$, $R^6$, $R^7$, $R^8$ and $R^9$ is a group other than a hydrogen atom or a heavy hydrogen atom.

Further, the electron-transmitting compound may be a high molecular compound that comprises the nitrogen-containing heterocyclic group or the nitrogen-containing heterocyclic derivative.

It is particularly preferred that the electron-transporting layer of the organic EL device according to the invention contains at least one of the nitrogen-containing heterocyclic derivatives represented by the following formulas (E) to (G):

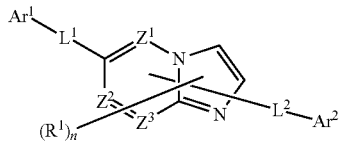
(E)

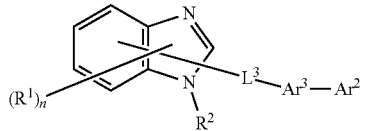
(F)

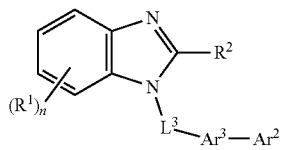
(G)

In the formulas (E) to (G), $Z^1$, $Z^2$ and $Z^3$ are independently a nitrogen atom or a carbon atom.

$R^1$ and $R^2$ are independently a substituted or unsubstituted aryl group including 6 to 50 ring carbon atoms, a substituted or unsubstituted heteroaryl group including 5 to 50 ring atoms, a substituted or unsubstituted alkyl group including 1 to 20 carbon atoms, a substituted or unsubstituted haloalkyl group including 1 to 20 carbon atoms or a substituted or unsubstituted alkoxy group including 1 to 20 carbon-atoms. n is an integer of 0 to 5. When n is an integer of 2 or more, plural $R^1$s may be the same or different. The two adjacent $R^1$s may be bonded to each other to form a substituted or unsubstituted hydrocarbon ring.

$Ar^1$ is a substituted or unsubstituted aryl group including 6 to 50 ring carbon atoms or a substituted or unsubstituted heteroaryl group including 5 to 50 ring atoms.

$Ar^2$ is a hydrogen atom, a substituted or unsubstituted alkyl group including 1 to 20 carbon atoms, a substituted or unsubstituted haloalkyl group including 1 to 20 carbon atoms, a substituted or unsubstituted alkoxy group including 1 to 20 carbon atoms, a substituted or unsubstituted aryl group including 6 to 50 ring carbon atoms or a substituted or unsubstituted heteroaryl group including 5 to 50 ring atoms.

Any one of $Ar^1$ and $Ar^2$ is a substituted or unsubstituted fused aromatic hydrocarbon ring group including 10 to 50 ring carbon atoms or a substituted or unsubstituted fused aromatic heterocyclic group including 9 to 50 ring atoms.

$Ar^3$ is a substituted or unsubstituted arylene group including 6 to 50 ring carbon atoms or a substituted or unsubstituted heteroarylene group including 5 to 50 ring atoms.

$L^1$, $L^2$ and $L^3$ are independently a single bond, a substituted or unsubstituted arylene-group including 6 to 50 ring carbon atoms or a substituted or unsubstituted divalent fused aromatic heterocyclic group including 9 to 50 ring atoms.

As the aryl group including 6 to 50 ring carbon atoms, a phenyl group, a naphthyl group, an anthryl group, a phenanthryl group, a naphthacenyl group, a chrysenyl group, a pyrenyl group, a biphenyl group, a terphenyl group, a tolyl group, a fluoranthenyl group and a fluorenyl group can be mentioned.

As the heteroaryl group including 5 to 50 ring atoms, a pyrrolyl group, a furyl group, a thienyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, a triazolyl group, a pyrazinyl group, a pyridazinyl group, a triazinyl group, a, quinoxalinyl group, an acridinyl group, an imidazo[1,2-a]pyridinyl group, an imidazo[1,2-a]pyrimidinyl group or the like can be given.

As the alkyl group including 1 to 20 carbon atoms, a methyl group, an ethyl group, a propyl group, a butyl group, a pentyl group, a hexyl group or the like can be given.

As the haloalkyl group including 1 to 20 carbon atoms, a group obtained by substituting one or two or more hydrogen atoms in the alkyl group with at least one halogen atom selected from fluorine, chlorine, iodine and bromine can be given.

As the alkoxy group including 1 to 20 carbon atoms, a group having the alkyl group as an alkyl moiety can be given.

As the arylene group including 6 to 50 ring carbon atoms, a group obtained by removing one hydrogen atom from the aryl group can be given.

As the divalent fused aromatic heterocyclic group including 9 to 50 ring atoms, a group obtained by removing one hydrogen atom from the fused aromatic heterocyclic group mentioned above as the heteroaryl group can be given.

The film thickness of the electron-transporting layer is not particularly restricted, but is preferably 1 nm to 100 nm.

As the constituting elements of the electron-injecting layer that can be provided in adjacent to the electron-transporting layer, in addition to the nitrogen-containing ring derivative, as an inorganic compound, it is preferable to use an insulator or a semiconductor. If the electron-injecting layer is formed of an insulator or a semiconductor, current leakage can be effectively prevented, whereby electron-injecting properties can be improved.

As such an insulator, it is preferable to use at least one metal compound selected from the group consisting of an alkali metal chalcogenide, an alkaline earth metal chalcogenide, a halide of an alkali metal and a halide of an alkaline earth metal. It is preferred that the electron-injecting layer be formed of these alkali metal chalcogenides or the like, since the electron-injecting property can be further improved. Specifically, as preferable alkali metal chalcogenides, $Li_2O$, $K_2O$, $Na_2S$, $Na_2Se$ and $Na_2O$ can be given. As preferable alkaline earth metal chalcogenides, CaO, BaO, SrO, BeO, BaS and CaSe can be given, for example. As preferable halides of an alkali metal, LiF, NaF, KF, LiCl, KCl, NaCl and the like can be given; for example. As preferable halides of an alkaline earth metal, a fluoride such as $CaF_2$, $BaF_2$, $SrF_2$, $MgF_2$ and $BeF_2$ and a halide other than a fluoride can be given, for example.

As the semiconductor, an oxide, a nitride or a nitric oxide containing at least one element selected from Ba, Ca, Sr, Yb, Al, Ga, In, Li, Na, Cd, Mg, Si, Ta, Sb and Zn or the like can be given, for example. They can be used singly or in combination of two or more. Further, it is preferred that an inorganic compound constituting the electron-injecting layer be a finely-crystallized or amorphous insulating thin film. If the electron-injecting layer is formed of these insulting thin films, more homogenous thin film is formed, and hence, pixel defects such as dark spots can be decreased. As such an inorganic compound, alkali metal chalcogenide, alkaline earth metal chalcogenide, a halide of an alkali metal and a halide of an alkaline earth metal or the like can be given, for example.

If such an insulator or a semiconductor is used, the preferable thickness of the layer is about 0.1 nm to 15 nm. The electron-injecting layer in the invention may preferably comprise the above-mentioned electron-donating dopant.

Hole-Transporting Layer

The hole-transporting layer is an organic layer that is formed between the emitting layer and the anode, and has a function of transporting holes from the anode to the emitting layer. If the hole-transporting layer is composed of plural layers, an organic layer that is nearer to the anode may often be defined as the hole-injecting layer. The hole-injecting layer has a function of injecting holes efficiently to the organic layer unit from the anode.

As other materials that form the hole-transporting layer, an aromatic amine compound, for example, an aromatic amine derivative represented by the following formula (H) can preferably be used.

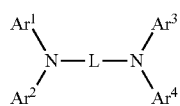
(H)

In the formula (H), $Ar^1$ to $Ar^4$ are a substituted or unsubstituted aromatic hydrocarbon group or fused aromatic hydrocarbon group including 6 to 50 ring carbon atoms, a substituted or unsubstituted aromatic heterocyclic group or fused aromatic heterocyclic group including 5 to 50 ring atoms, or a group formed by bonding of these aromatic hydrocarbon group or the fused aromatic hydrocarbon group with an aromatic heterocyclic group or a fused aromatic heterocyclic group.

In the formula (H), L is a substituted or unsubstituted aromatic hydrocarbon group or fused aromatic hydrocarbon group including 6 to 50 ring carbon atoms or a substituted or unsubstituted aromatic heterocyclic group or fused aromatic heterocyclic group including 5 to 50 ring atoms.

Specific examples of the compound represented by the formula (H) are shown below.

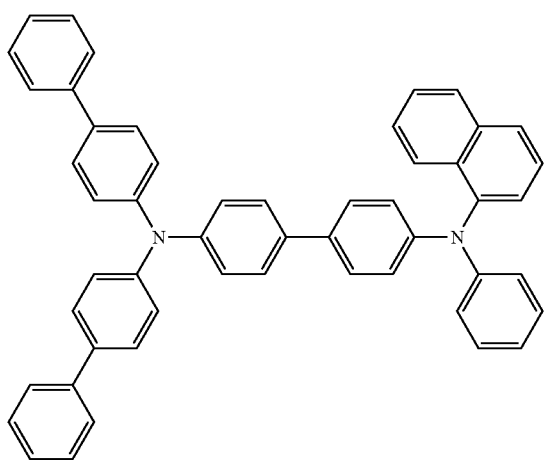

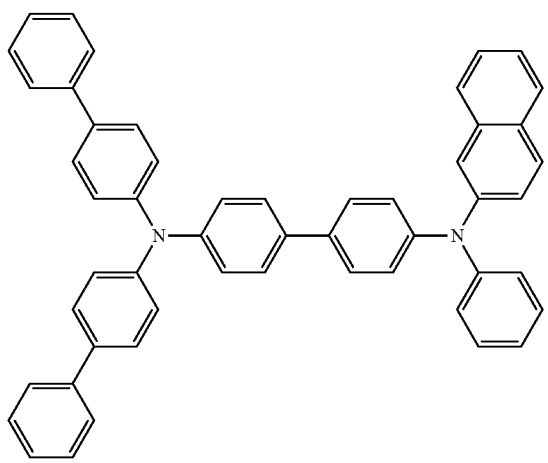

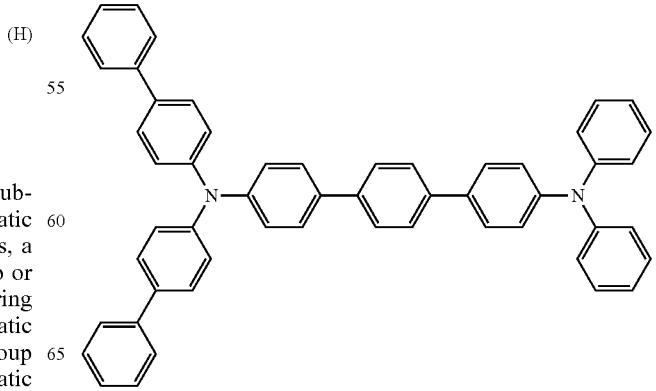

1143
-continued
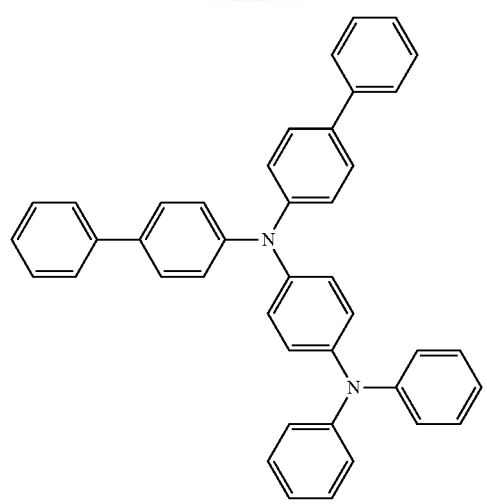
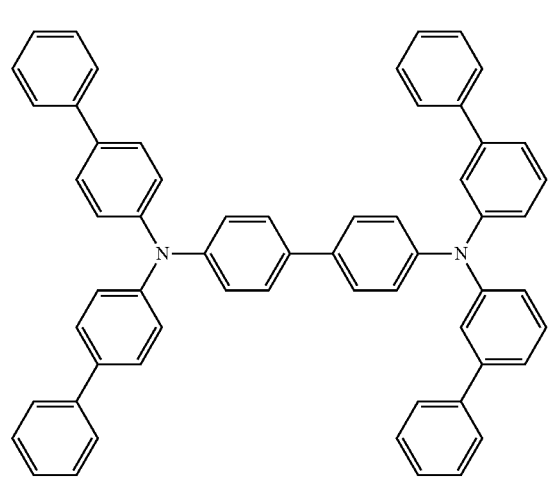
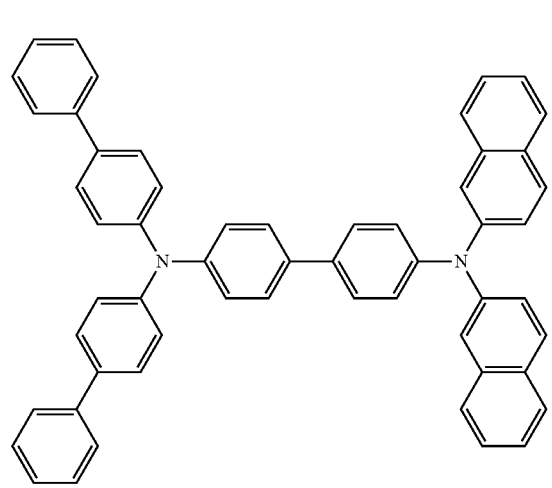
1144
-continued
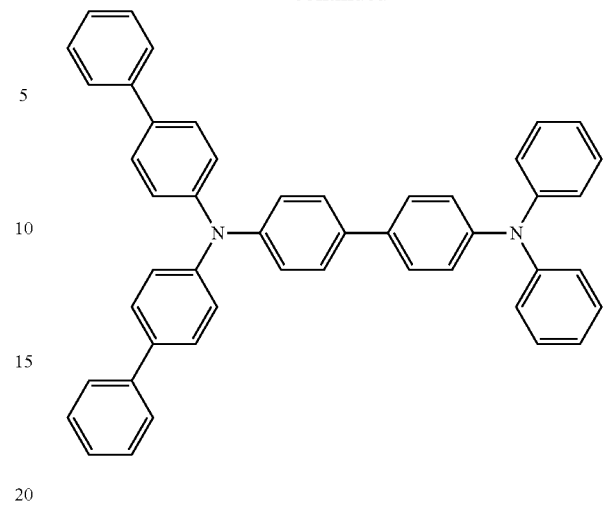
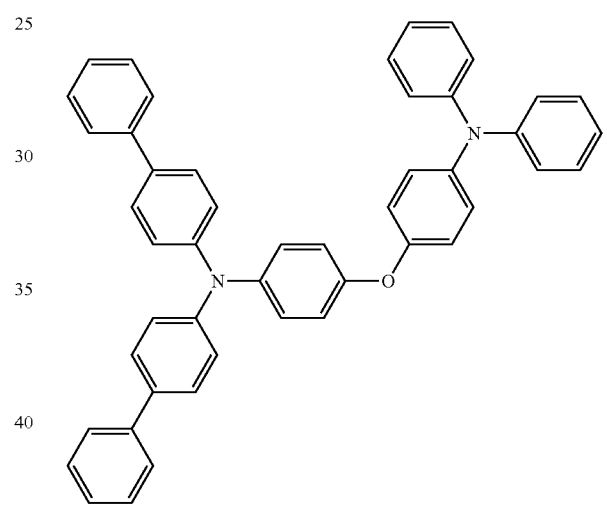
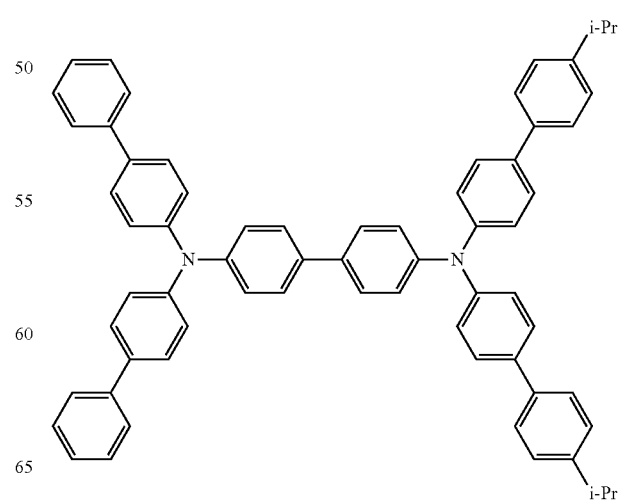

1145
-continued
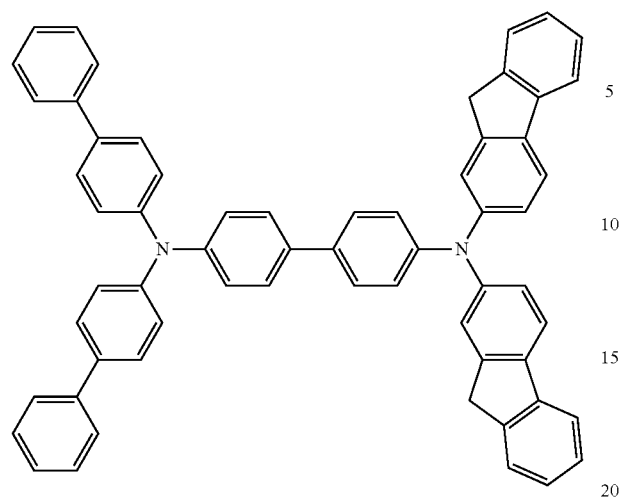
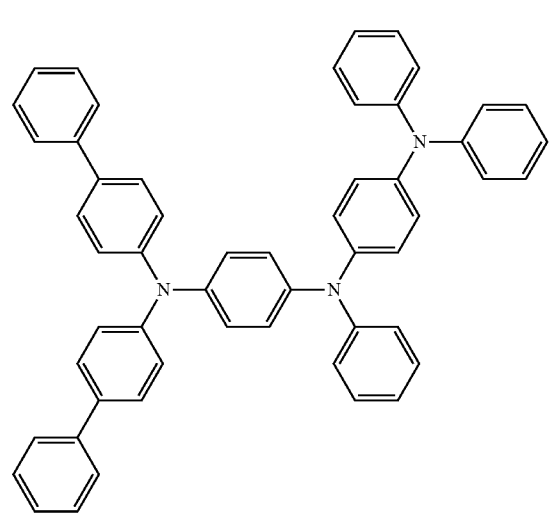
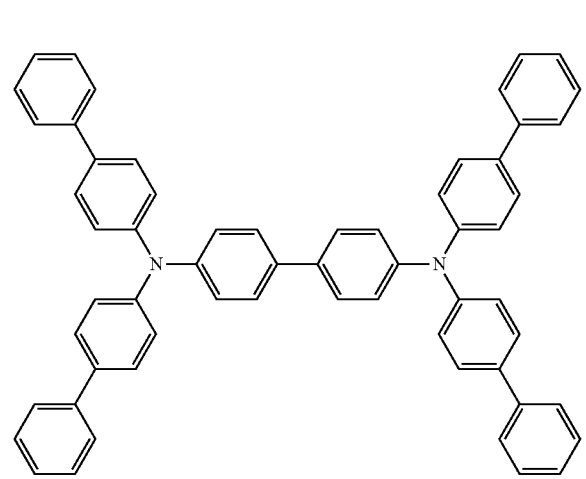
1146
-continued
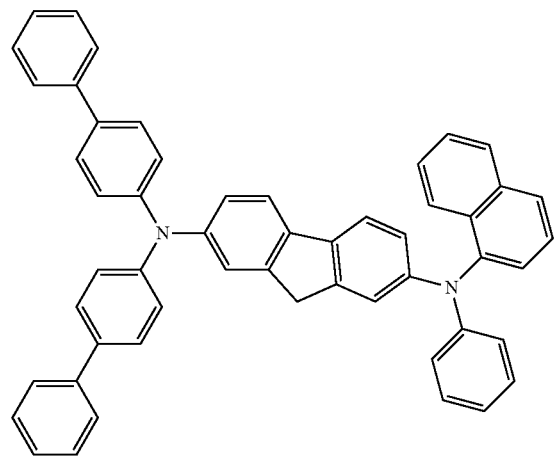
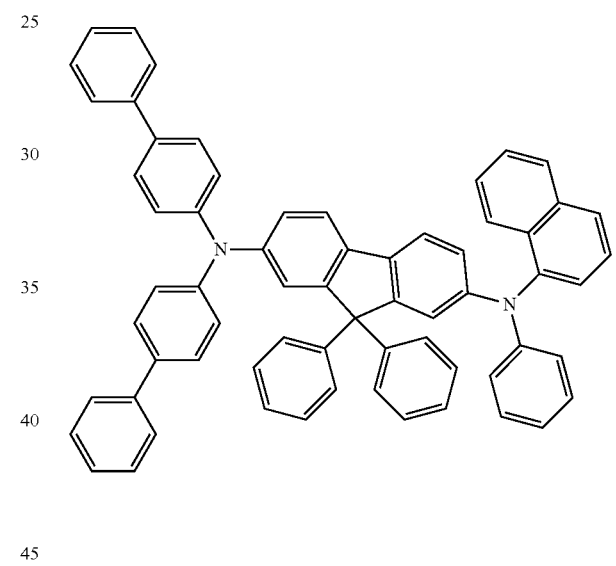
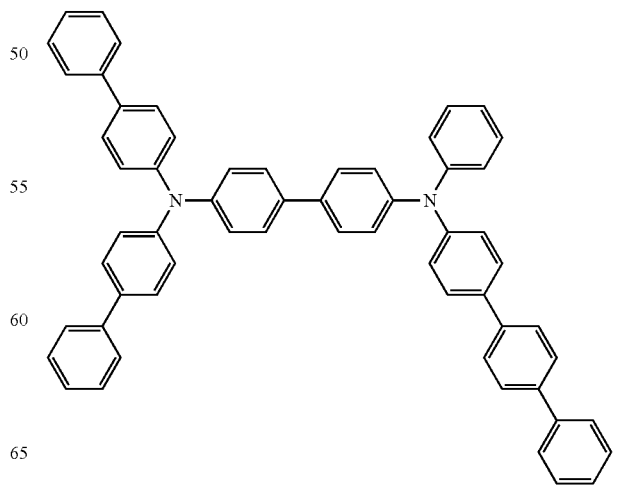

1147
-continued
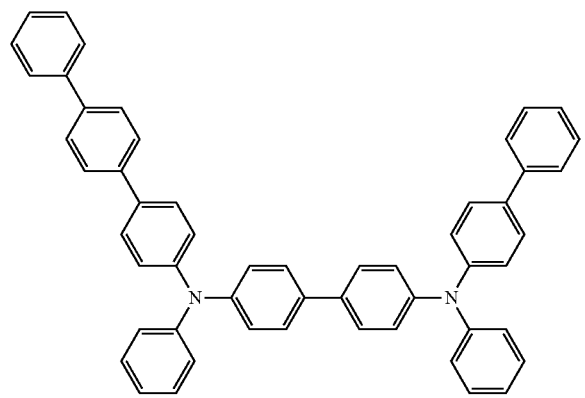
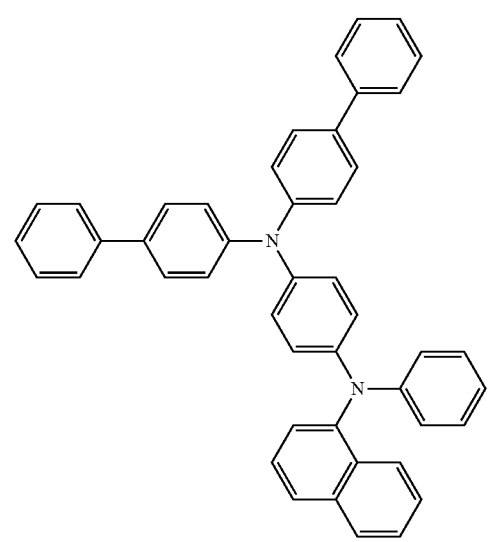
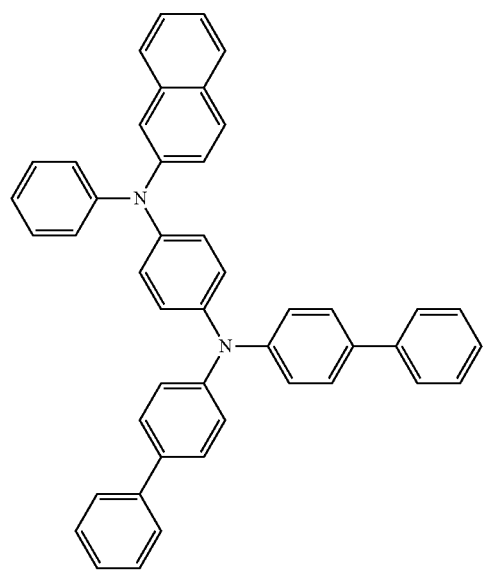
1148
-continued
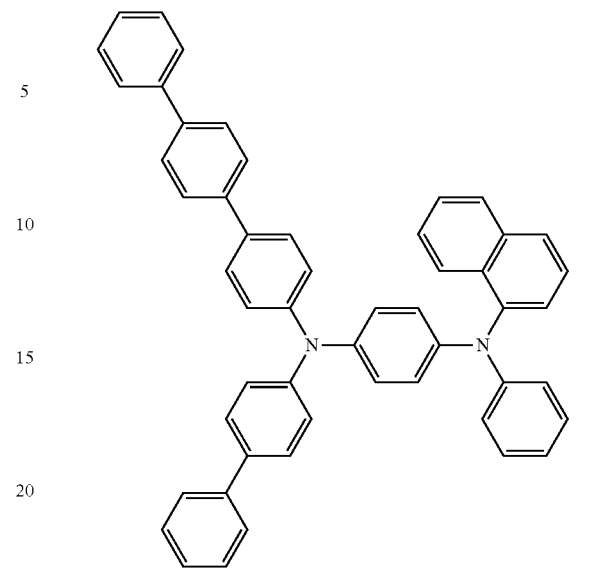
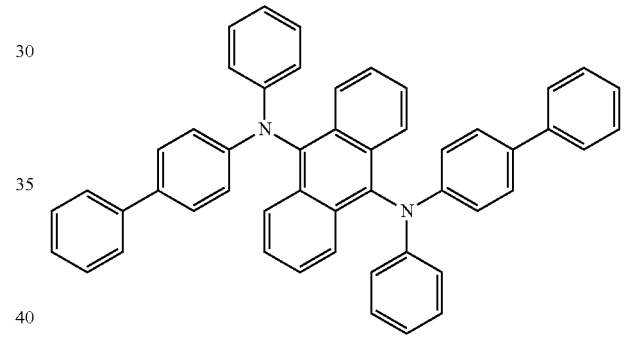
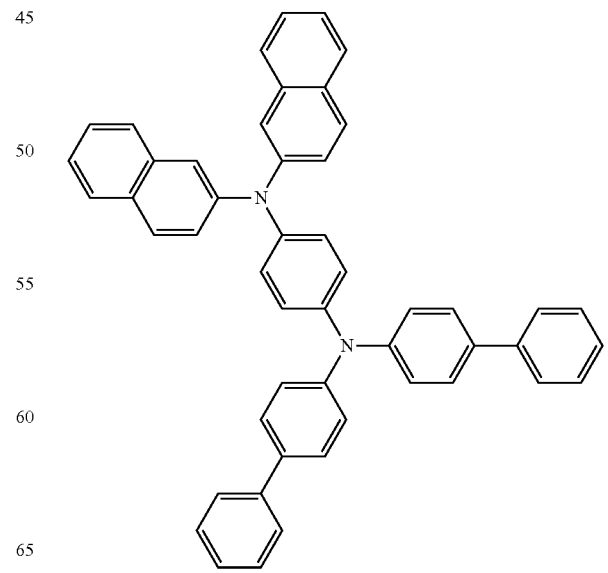

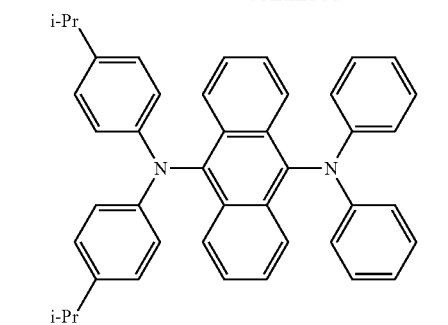
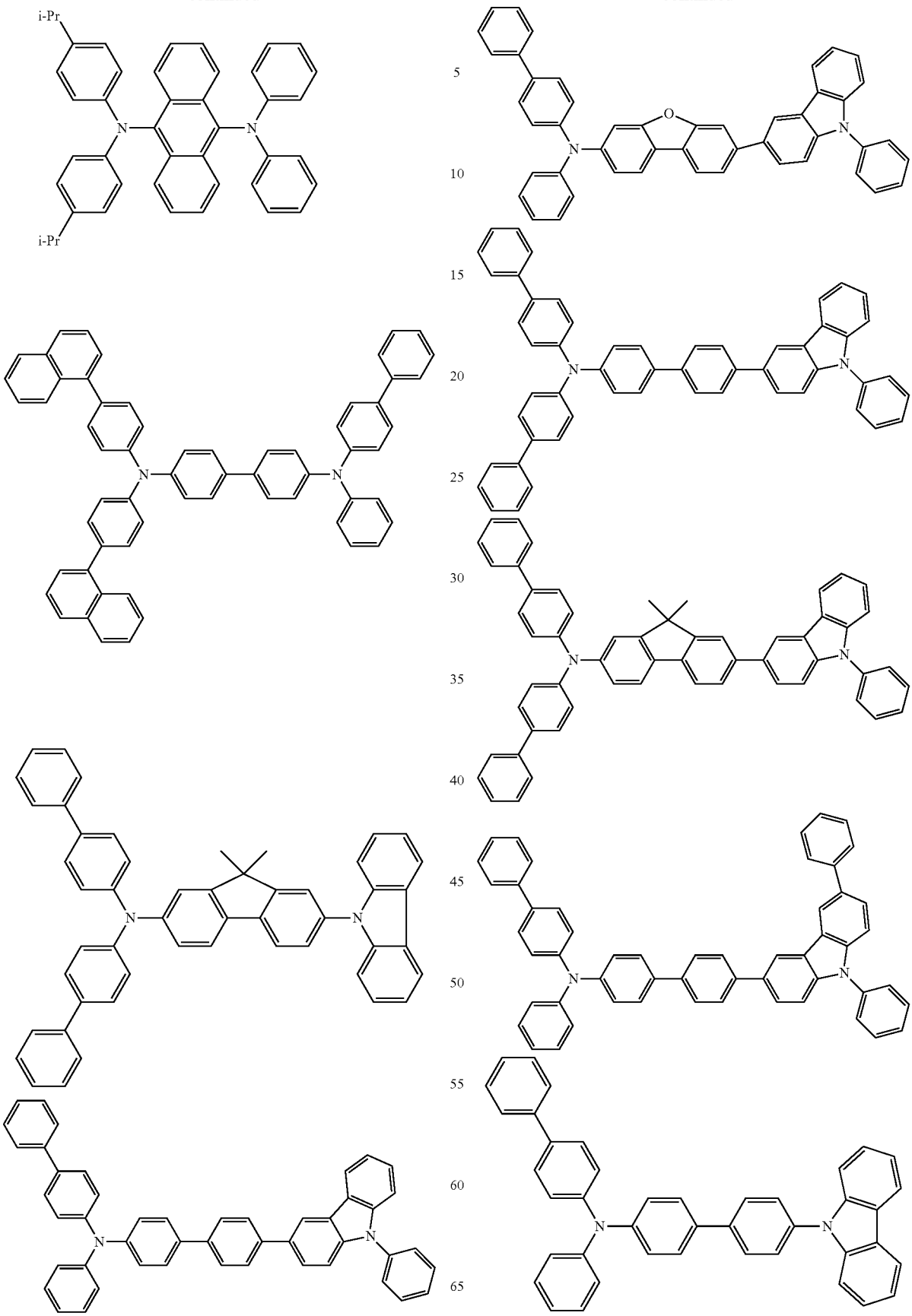

-continued
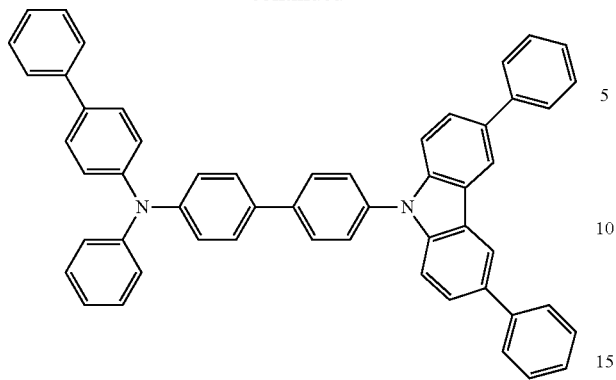
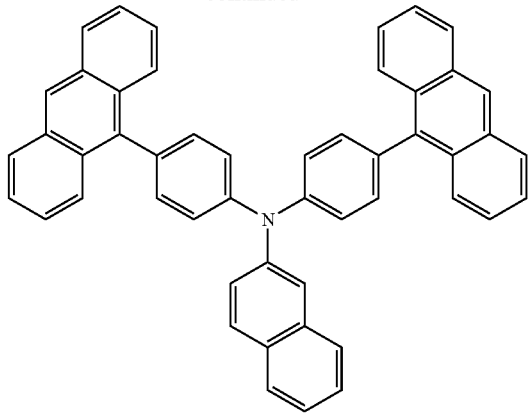
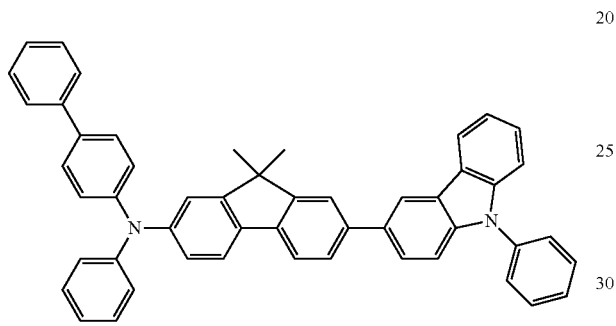
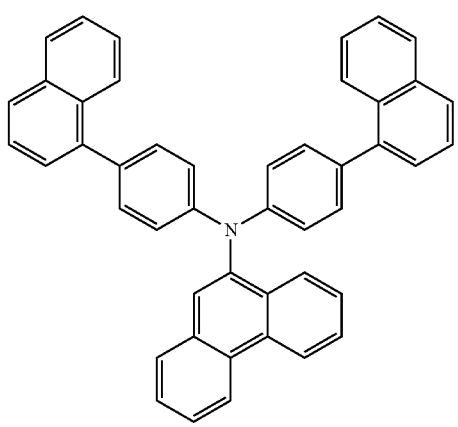
An aromatic amine represented by the following formula (J) is preferably used for forming the hole-transporting layer.
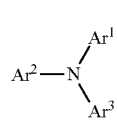
(J)
In the formula (J), Ar$^1$ to Ar$^3$ are as defined for Ar$^1$ to Ar$^4$ in the formula (H). Specific examples of the compound represented by the formula (J) will be shown below. The compound represented by the formula (J) is not limited to these.
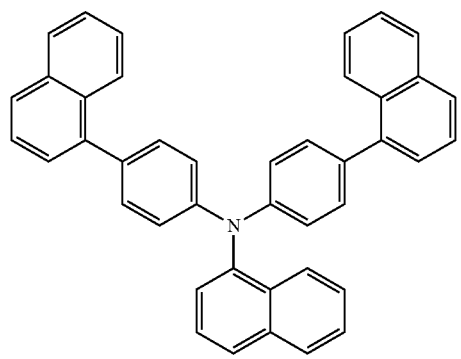
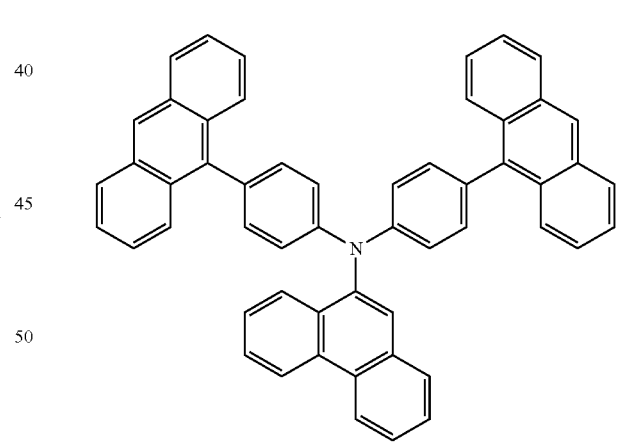

1153
-continued
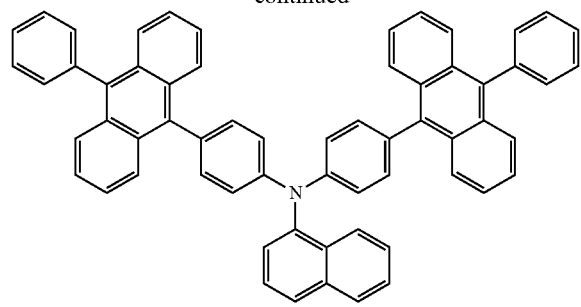
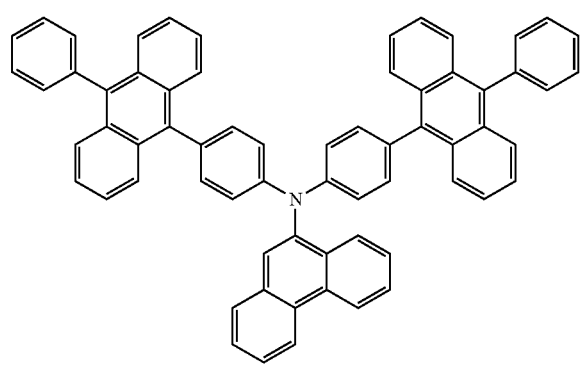
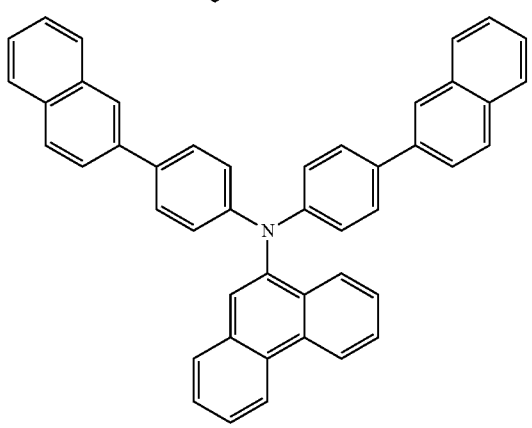
1154
-continued
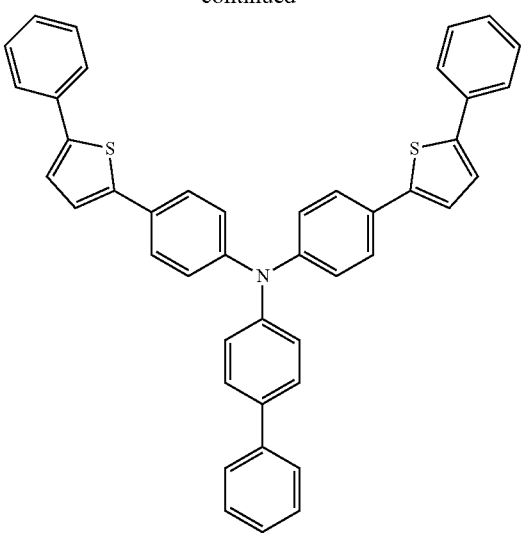
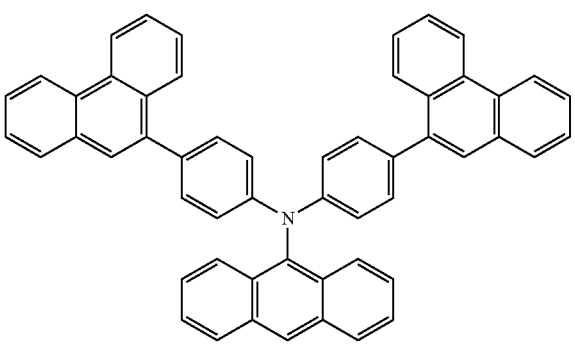
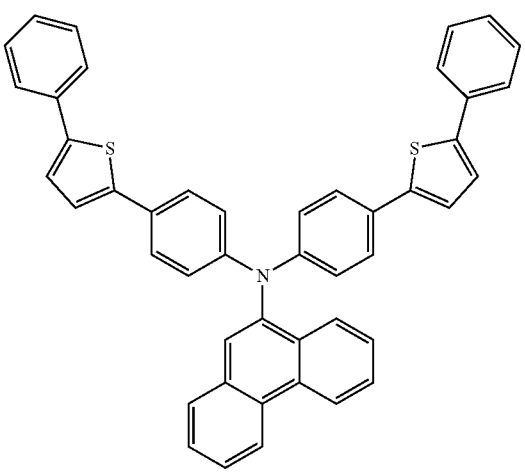

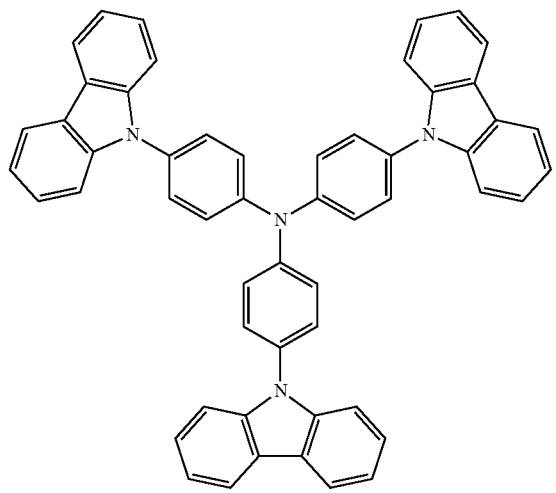
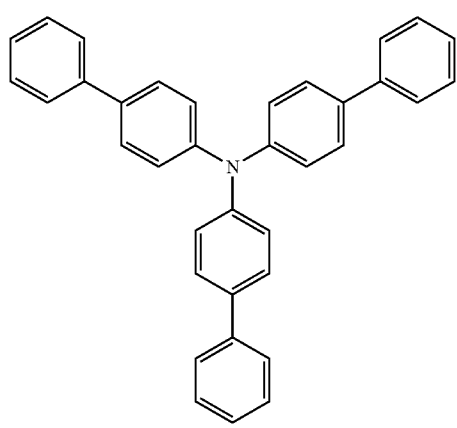
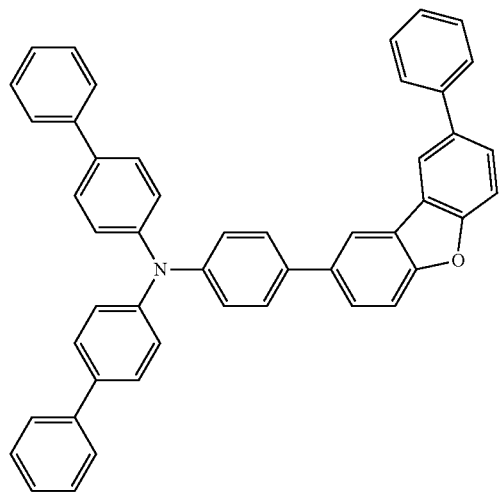
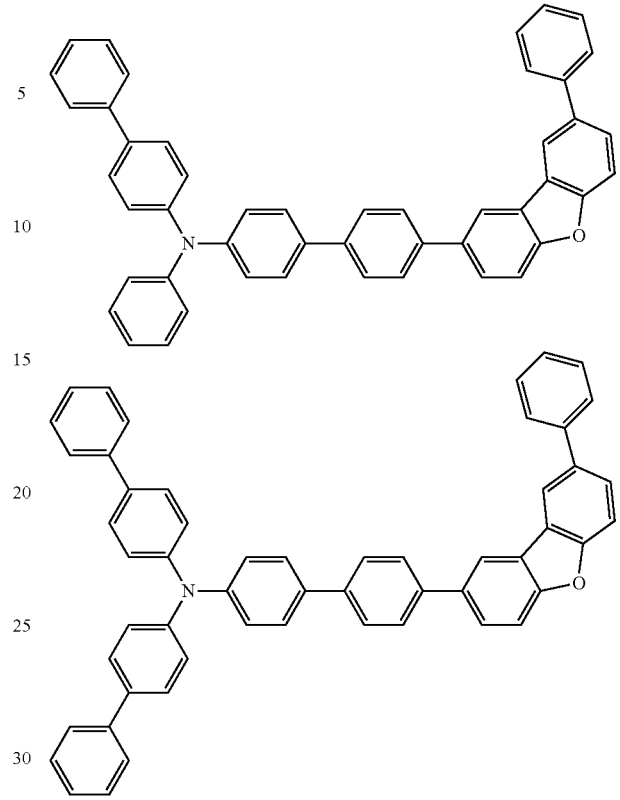

The hole-transporting layer of the organic EL device according to the invention may have a two-layer structure of a first hole-transporting layer (anode side) and a second hole-transporting layer (cathode side).

The thickness of the hole-transporting layer is not particularly restricted, but preferably 10 to 200 nm.

In the organic EL device according to the invention, a layer comprising an acceptor material may be stacked to the anode side of the hole-transporting layer or the first hole-transporting layer. As a result, a lowering in driving voltage or a decrease in production cost can be expected.

As the acceptor material, a compound represented by the following formula (K) is preferable.

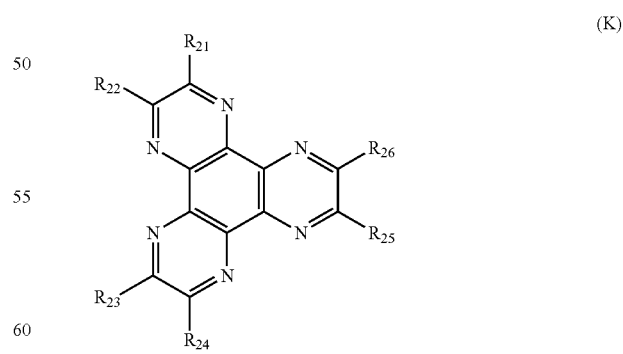

In the formula (K), $R_{21}$ to $R_{26}$, which may be the same as or different from, each other are independently a cyano group, —$CONH_2$, a carboxyl group or —$COOR_{27}$ ($R_{27}$ is an alkyl group including 1 to 20 carbon atoms or a cycloalkyl group including 3 to 20 carbon atoms); provided that, one or two or more pairs of $R_{21}$ and $R_{22}$; $R_{23}$ and $R_{24}$; and $R_{25}$ and $R_{26}$ may be bonded together to form a group represented by —CO—O—CO—.

As $R_{27}$, a methyl group, an ethyl group, an n-propyl group, an isopropyl group, an n-butyl group, an isobutyl group, a t-butyl group, a cyclopentyl group, a cyclohexyl group or the like can be given.

An example for an acceptor material K is

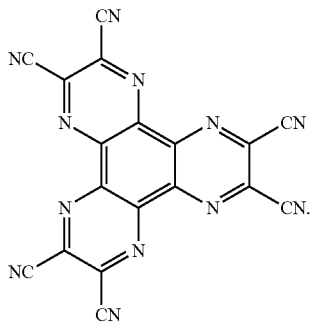 [SMILES: N#Cc1nc2c3nc(C#N)c(C#N)nc3c3nc(C#N)c(C#N)nc3c2nc1C#N]

The thickness of the layer that comprises an acceptor material is not particularly limited, but preferably 5 to 20 nm.

n/p Doping

In the hole-transporting layer or the electron-transporting layer mentioned above, as described in the Japanese Patent No. 3695714, the carrier injecting performance can be adjusted by doping (n) of a donor material or doping (p) of an acceptor material.

As representative examples of the n-doping, a method in which an electron-transporting material is doped with a metal such as Li and Cs can be mentioned. As the represented example of the p-doping, a method in which a hole-transporting material is doped with an acceptor material such as $F_4TCNQ$ (2,3,5,6-tetrafluoro-7,7,8,8-tetracyanoquinodimethane) can be given.

Spacing Layer

The spacing layer is a layer provided between the fluorescent emitting layer and the phosphorescent emitting layer when the fluorescent emitting layer and the phosphorescent emitting layer are stacked in order to prevent diffusion of excitons generated in the phosphorescent emitting layer to the fluorescent emitting layer or in order to adjust the carrier balance. Further, the spacing layer can be provided between the plural phosphorescent emitting layers.

Since the spacing layer is provided between the emitting layers, the material for the spacing layer is preferably a material having both electron-transporting properties and hole-transporting properties. In order to prevent diffusion of the triplet energy in adjacent phosphorescent emitting layers, it is preferred that the spacing layer have a triplet energy of 2.6 eV or more. As the material used for the spacing layer, the same material as those used in the above-mentioned hole-transporting layer can be given.

Barrier Layer

It is preferred that the organic EL device according to the invention have a barrier layer such as an electron-barrier layer, a hole-barrier layer and a triplet barrier layer in a part that is adjacent to the emitting layer. Here, the electron-barrier layer is a layer that serves to prevent leakage of electrons from the emitting layer to the hole-transporting layer, and the hole-barrier layer is a layer that serves to prevent leakage of holes from the emitting layer to the electron-transporting layer.

The triplet barrier layer prevents diffusion of triplet excitons generated in the emitting layer to the surrounding layers, and has a function of preventing energy deactivation of triplet excitons on molecules in the electron-transporting layer other than the emitting dopant by confining the triplet excitons within the emitting layer.

When the triplet barrier layer is provided, in the phosphorescent emitting device, the following is considered. The triplet energy of the phosphorescent emitting dopant is taken as $E^T_d$ and the triplet energy of the compound used as the triplet barrier layer is taken, as $E^T_{TB}$. If the energy relationship $E^T_d < E^T_{TB}$ is satisfied, in respect of energy, the triple excitons of the phosphorescent emitting dopant is confined (i.e. the triplet excitons cannot be moved to other molecules), whereby the energy deactivation route other than emission on the dopant is, cut off, leading to efficient emission. However, even when the relationship $E^T_d < E^T_{TB}$ is established, if the energy difference $\Delta E^T = E^T_{TB} - E^T_d$ is small, it is thought that, in an environment at around room temperature where the device is actually driven, due to thermal energy of the surrounding area, the triplet excitons can move to other molecules by endothermically overcoming this energy difference $\Delta E^T$. In particular, in the case of phosphorescent emission that has a longer exciton life as compared with fluorescent emission, effects of the endothermic move of excitons relatively tend to appear. Relative to the thermal energy at room temperature a larger energy difference $\Delta E^T$ is preferable. The energy difference $\Delta E^T$ is further preferably 0.1 eV or more, and particularly preferably 0.2 eV or more. On the other hand, in a fluorescent device, as the triplet barrier layer of the TTF device configuration disclosed in WO2010/134350A1, the material for an organic EL device according to the invention can be used.

The electron mobility of the material constituting the triplet barrier layer is desirably $10^{-6}$ cm$^2$/Vs or more in a field intensity range of 0.04 to 0.5 MV/cm. As the method for measuring the electron mobility of an organic material, several methods that include the Time of Flight method are known. Here, the electron mobility means an electron mobility that is determined by the impedance spectroscopy.

The electron mobility of the electron-injecting layer is desirably $10^{-6}$ cm$^2$/Vs or more in a field intensity range of 0.04 to 0.5 MV/cm. The reason is that, by this electron mobility, injection of electrons from the cathode to the electron-transporting layer is promoted, and as a result injection of electrons to adjacent barrier layer, and emitting layer is promoted, enabling the device to be driven at a lower voltage.

The organic EL device of the invention can be used as an emitting device in a panel module used in various displays.

The organic EL device according to the invention can be used as a display element of a TV, a mobile phone and a PC; or an electronic apparatus such as lightings or the like.

The OLEDs (organic EL devices) can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper. In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays % on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES

I Preparation Examples

Example 1: Compound (1)

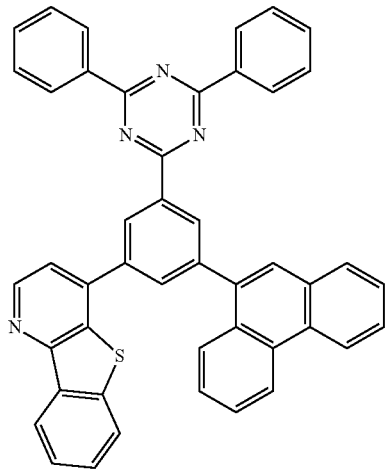

(1)

a)

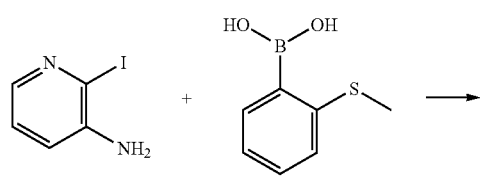

Benzothiopheno[3,2-b]pyridine is synthesized according to WO2009086028 (compound 50).

The structure was confirmed by $^1$H-NMR.

b)

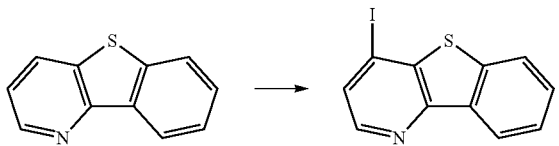 [SMILES: c1ccc2c(c1)sc1cccnc12 ; Ic1ccnc2c1sc1ccccc12]

2.914 g (28.8 mmol) of diisopropylamine are dissolved in 25 ml of THF under nitrogen at room temperature and cooled to −78° C. 10.8 ml (27 mmol) of n=butyllithium (2.5 M) are added drop by drop within 10 minutes at −78° C. The reaction mixture is warmed to room temperature within 20 minutes. 3.33 g (18 mmol) of benzothiopheno[3,2-b]pyridine are dissolved in 325 ml of THF under nitrogen at room temperature and heated in a water bath to get the starting material into solution. The clear solution is cooled to −78° C. The LDA solution prepared as described above is now added drop by drop within 15 minutes and the reaction mixture is stirred at −78° C. for 20 minutes. 9.132 g (32.4 mmol) of diiodoethan are added, the reaction mixture is stirred for 5 minutes at −78° C. and then warmed to room-temperature. After stirring 90 minutes at room temperature, the solution is poured on 200 ml of a 5% solution of Na$_2$SO$_4$, the phases are separated and the water phase is extracted with 200 ml of ethyl acetate. The organic phases are washed twice with 200 ml of brine each, dried over Na$_2$SO$_4$, filtered and the solvent is evaporated to get 5.75 g of brown crystals as crude product. The crude product is purified by flash chromatography using toluene as eluent yielding 2.99 g (53%) of 4-iodobenzothiopheno[3,2-b]pyridine.

$^1$H NMR (400 MHz, CDCl$_3$): δ 8.49 (d, J=7.2 Hz, 1H), 8.37 (d, J=4.8 Hz, 1H), 7.88 (d, J=7.2 Hz, 1H), 7.77 (d, J=4.8 Hz, 1H), 7.62-7.55 (m, 2H)

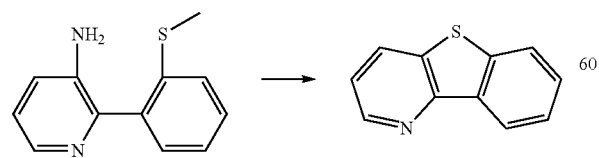

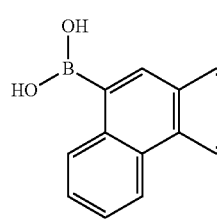

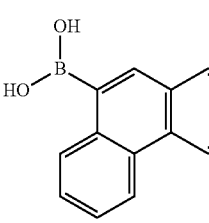

1161

-continued

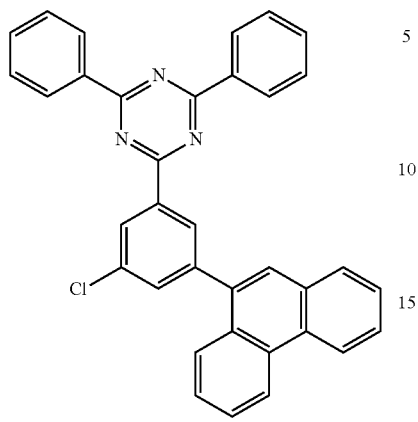

24.40 g (57.6 mmol) of 2-(3-bromo-5-chloro-phenyl)-4,6-diphenyl-1,3,5-triazine, (synthesized according to known procedures), 12.80 g (57.6 mmol) of 9-phenanthrylboronic acid and 86 ml (173 mmol) of a 2M sodium carbonate solution are suspended in 450 ml of DME and evacuated and purged with argon 4 times. Then argon is bubbled through for 30 minutes. 1.33 g (1.15 mmol) of tetrakis(triphenylphospin)-palladium(0) are added under argon and argon is bubbled through for another 5 minutes. Then the reaction mixture is heated to 85° C. After stirring under argon for 14 hours at this temperature, the reaction mixture is cooled to room temperature and filtered. The residue is washed with hot toluene to give 25.7 g (85%) of 2-[3-chloro-5-(9-phenanthryl)phenyl]-4,6-diphenyl-1,3,5-triazine.

$^1$H NMR (400 MHz, Chloroform-d) δ 8.89-8.71 (m, 8H), 7.96 (dd, J=7.8, 1.5 Hz, 1H), 7.91 (dd, J=8.3, 1.3 Hz, 1H), 7.83-7.63 (m, 5H), 7.64-7.52 (m, 7H).

d)

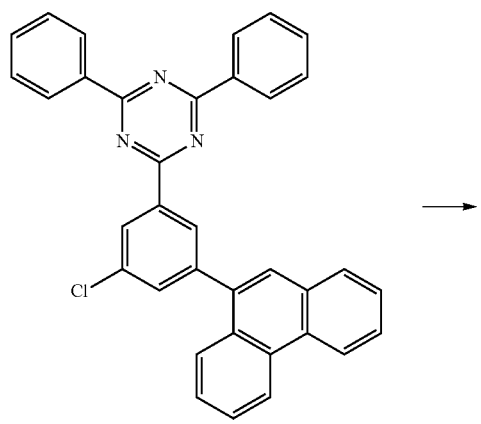

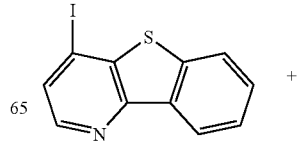

1162

-continued

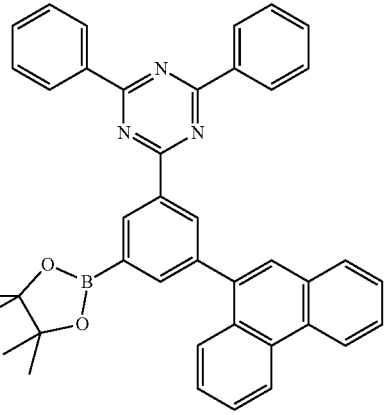

8.58 g (16.50 mmol) of 2-[3-chloro-5-(9-phenanthryl)phenyl]-4,6-diphenyl-1,3,5-triazine, 4.61 g (18.15 mmol) of 4,4,5,5-tetramethyl-2-(4,4,5,5-tetramethyl-1,3,2-dioxaborolan-2-yl)-1,3,2-dioxaborolane and 4.05 g (41.25 mmol) of potassium acetate are mixed and evacuated and purged with argon 3 times. Then 85 ml of dioxane are added and the white suspension is again evacuated and purged with argon 4 times. Then argon is bubbled through for 15 minutes. 0.203 g (0.495 mmol) of dicyclohexyl-[2-(2,6-dimethoxyphenyl)phenyl]phosphane and 0.227 g (0.248 mmol) of Pd$_2$(dba)$_3$ are added under argon and the suspension is heated to 115° C. After stirring at this temperature for 4 hours, the reaction mixture is cooled to room temperature. 250 ml of water and 150 ml of chloroform are added to the orange suspension, which is stirred and filtered through hyflo into the separation funnel, while washing with 200 ml of chloroform. The phases are separated, the water phase is extracted with 100 ml of chloroform, the combined organic phases are washed with 200 ml of water, dried over Na$_2$SO$_4$, filtered and the solvent is removed in vacuum.

The crude product is recrystallized from 60 ml of toluene and dried at high vacuum to give 9.39 g (93%) of 2-[3-(9-phenanthryl)-5-(4,4,5,5-tetramethyl-1,3,2-dioxaborolan-2-yl)phenyl]-4,6-diphenyl-1,3,5-triazine.

δ$^1$H NMR (400 MHz, Chloroform-d) δ 9.25 (t, J=1.5 Hz, 1H), 9.03 (t, J=1.8 Hz, 1H), 8.92-8.60 (m, 6H), 8.24 (t, J=1.5 Hz, 1H), 8.06-7.86 (m, 2H), 7.83 (s, 1H), 7.75-7.48 (m, 10H), 1.43 (s, 12H).

e)

1163
-continued

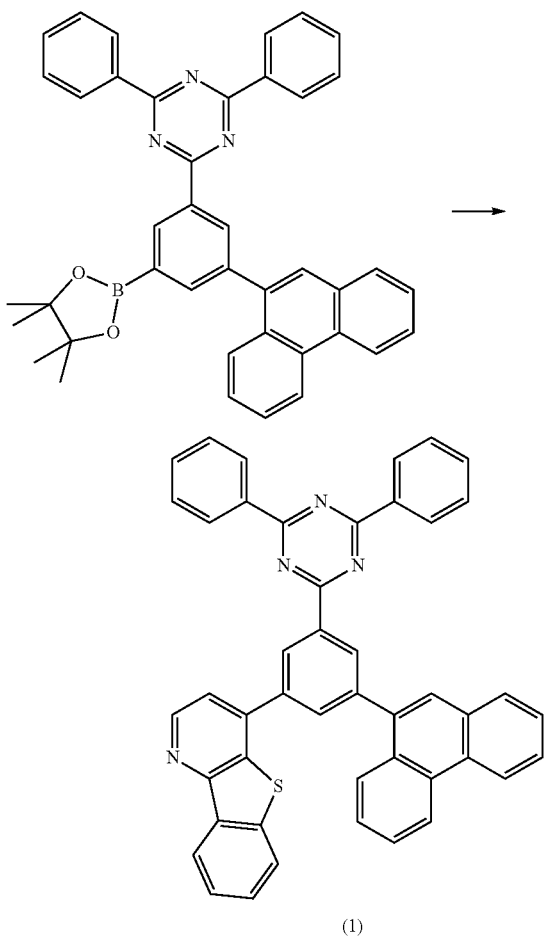

(1)

0.996 g (3.20 mmol) of 4-iodobenzothiopheno[3,2-b]pyridine, 2.06 g (3.36 mmol) of 2-[3-(9-phenanthryl)-5-(4,4,5,5-tetramethyl-1,3,2-dioxaborolan-2-yl)phenyl]-4,6-diphenyl-1,3,5-triazine and 1.33 g (9.60 mmol) of potassium carbonate are suspended in 30 ml of toluene, 8 ml of ethanol and 4 ml of water, then the mixture is evacuated and purged with argon 4 times. Argon is bubbled through the suspension for 15 minutes. 0.185 g (0.16 mmol) of tetrakis(triphenylphospin)-palladium(0) are added under argon and the reaction mixture is heated to reflux. After stirring under argon for 14 hours, the reaction mixture is cooled to room temperature. 100 ml of chloroform and 100 ml of a sodium cyanide solution (5%) are added and the reaction mixture is stirred and heated to reflux for 2 hours. The two-phase suspension is cooled to room temperature and then centrifuged for 10 minutes. The precipitate is filtered, washed twice with 20 ml of water and 20 ml of chloroform each and dried at high vacuum to give 1:364 g of white crystals. The crude product is recrystallized from 25 ml of chlorobenzene, filtered and dried at high vacuum to give 1.17 g (55%) of 4-[3-(4,6-diphenyl-1,3,5-triazin-2-yl)-5-(9-phenanthryl)phenyl]benzothiopheno[3,2-b]pyridine.

$^1$H NMR (400 MHz, Chloroform-d) δ 9.36 (t, J=1.7 Hz, 1H), 9.09 (t, J=1.5 Hz, 1H), 8.93 (d, J=4.9 Hz, 1H), 8.86 (dd, J=8.5, 1.2 Hz, 1H), 8.83-8.75 (m, 5H), 8.23 (t, J=1.7 Hz, 1H), 8.07 (dd, J=8.3, 1.3 Hz, 1H), 8.00 (dd, J=7.8, 1.4 Hz, 1H), 7.95-7.86 (m, 2H), 7.79-7.50 (m, 14H).

1164

Example 2: Compound (2)

a)

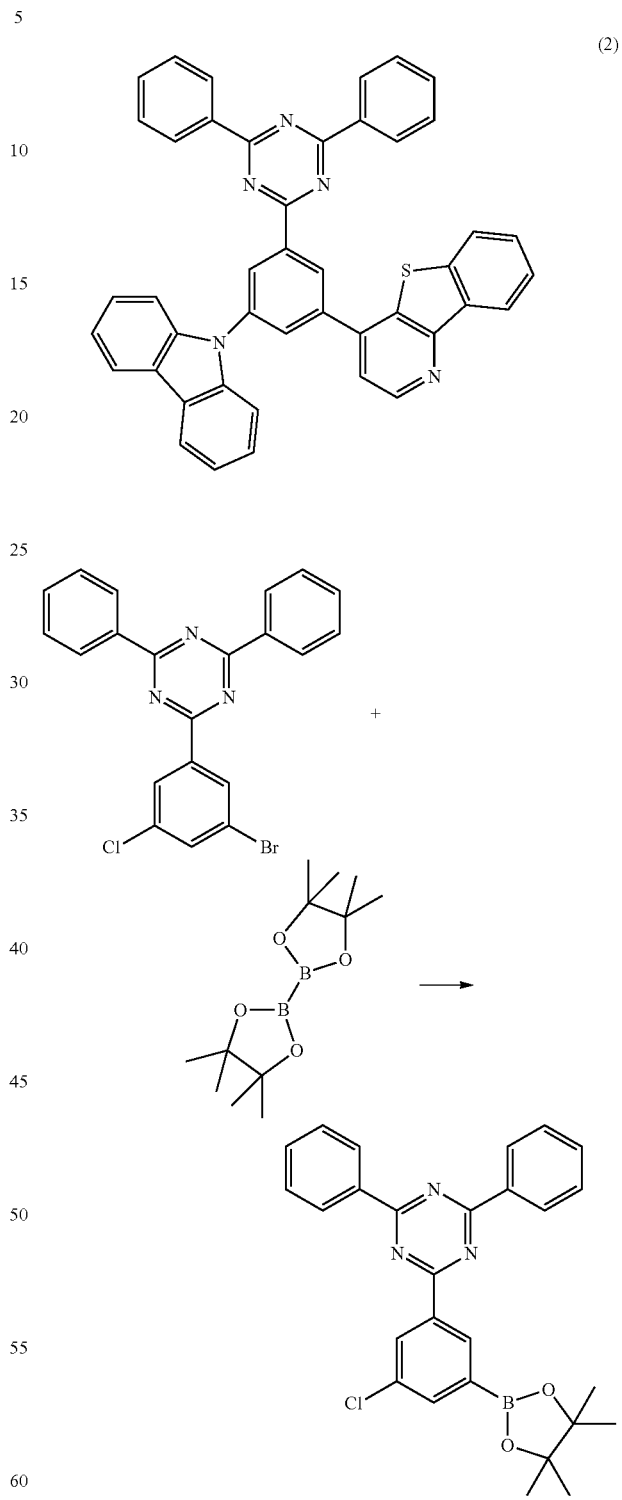

6.34 g (15.00 mmol) of 2-(3-bromo-5-chloro-phenyl)-4,6-diphenyl-1,3,5-triazine (synthesized according to known procedures), 4.0 g (15.75 mmol) of 4,4,5,5-tetrameramethyl-2-(4,4,5,5-tetramethyl-1,3,2-dioxaborolan-2-yl)-1,3,2-dioxaborolane and 3.68 g (37.5 mmol) of potassium acetate are charged in a round bottomed flask and evacuated and purged with argon 3 times. Then 70 ml of DMF are added and the white suspension is again evacuated and purged with argon 4 times. Then argon is bubbled through for 15 minutes. 0.245 g (030 mmol) of [1,1-Bis'(diphenylphosphino)ferrocene]-dichloropalladium(II)-dichlormethankomplex are added under argon and the suspension is heated to 85° C. After stirring at this temperature under argon for 6 hours, the reaction mixture is cooled to room temperature. The dark brown suspension is poured on 400 ml of water, stirred, filtered and washed with water and methanol. The residue is dissolved in warm toluene, then filtered through silicagel and washed with toluene. The solvent of the filtrate is removed under reduced pressure to give 6.69 g (94%) of light brown crystals of 2-[3-chloro-5-(4,4,5,5-tetramethyl-1,3,2-dioxaborolan-2-yl)phenyl]-4,6-diphenyl-1,3,5-triazine.

$^1$H NMR (400 MHz, Chloroform-d) δ 9.00 (t, J=1.3 Hz, 1H), 8.90-8:67 (m, 5H), 8.03 (d, J=2.8 Hz, 1H), 7.75-7.46 (m, 6H), 1.43 (s, 12H).

b)

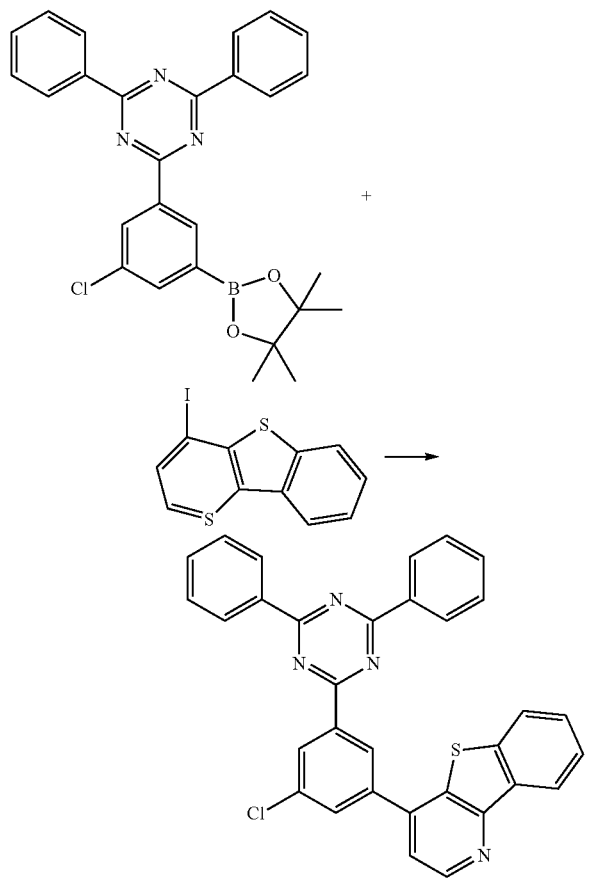

1.87 g (6.0 mmol) of 4-iodobenzothiopheno[3,2-b]pyridine, 3.10 g (6.60 mmol) of 2-[3-chloro-5-(4,4,5,5-tetramethyl-1,3,2-dioxaborolan-2-yl)phenyl]-4,6-diphenyl-1,3,5-triazine and 2.49 g (18.0 mmol) of potassium carbonate are suspended in 55 ml of toluene, 17 ml of ethanol and 9 ml of water, then the mixture is evacuated and purged with argon 4 times. Then argon is bubbled through for 30 minutes. 0.555 g (0.480 mmol) of tetrakis(triphenylphospin)-palladium(0) are added under argon and argon is bubbled through for another 5 minutes. Then the reaction mixture is heated to 85° C. After stirring under argon for 7 hours at this temperature, the reaction mixture is cooled to room temperature. 30 ml of water and 40 ml of toluene are added and after stirring the brown suspension is filtered, washed with water and toluene and dried at high vacuum. 1.79 g (56%) of 4-[3-chloro-5-(4,6-diphenyl-1,3,5-triazin-2-yl)phenyl]benzothiophen[3,2-b]pyridine are obtained.

$^1$H NMR (400 MHz, Chloroform-d) δ 9.12 (s, 1H), 8.90 (d, J=4.8 Hz, 1H), 8.86 (t, J=1.8 Hz, 1H), 8.82-8.75 (m, 4H), 8.62-8.55 (m, 1H), 7.99 (t, J=1.9 Hz, 1H), 7.93-7.86 (m, 1H), 7.65-7.53 (m, 9H).

c)

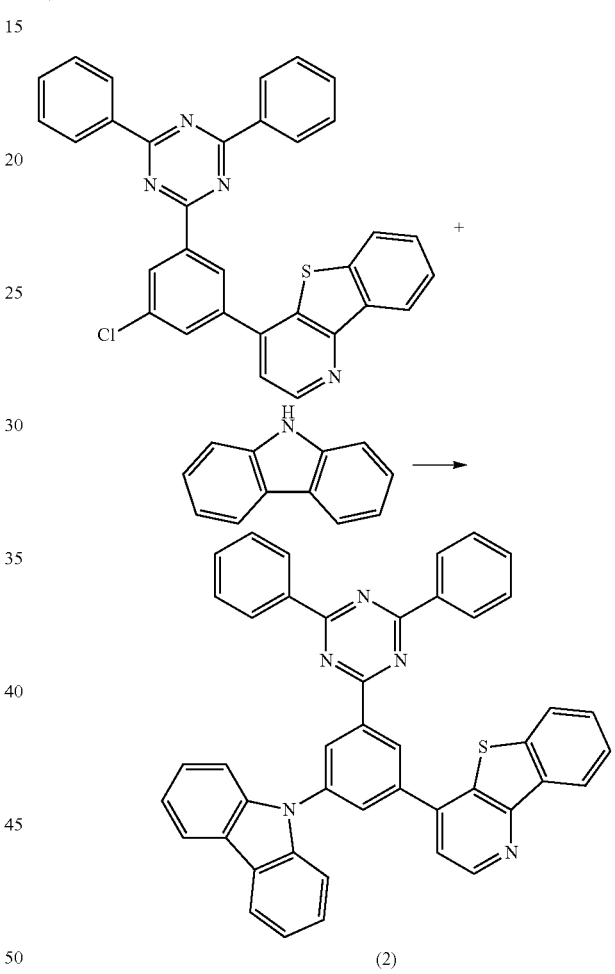

(2)

1.53 g (2.90 mmol) of 4-[3-chloro-5-(4,6-diphenyl-1,3,5-triazin-2-yl)phenyl]benzothiopheno[3,2-b]pyridine, 2.43 g (14.50 mmol) of 9-H-carbazole and 1.30 g (11.6 mmol) of potassium; 2-methylpropan-2-olate are suspended in 50 ml of o-xylene. The mixture is evacuated and purged with argon 4 times, then argon is bubbled through for 10 minutes. 0.119 g (0:290 mmol) of dicyclohexyl-[2-(2,6-dimethoxyphenyl)phenyl]phosphane and 0.133 g (0.145 mmol) of Pd(dba)$_3$ are added under argon and argon is bubbled through for another 5 minutes. Then the reaction mixture is heated to reflux. After stirring under argon for 3 hours the reaction mixture is cooled to room temperature. 7 ml of water and 80 ml of ethanol are added, the mixture is heated to reflux, filtered and the residue is washed with ethanol and dried at high vacuum. The product is purified by combiflash chromatography using toluene/ethyl acetate as eluent. The product is further purified by recrystallization from 1,2-dichlorobenzene; the residue is washed with toluene and heptane and dried at high vacuum. 1.520 g (79%) of 4-[3-carbazol-9-yl-5-(4,6-diphenyl-1,3,5-triazin-2-yl)phenyl]benzothiopheno[3,2-b]pyridine are obtained.

$^1$H NMR (400 MHz, DMSO-d) δ 9.32 (t, J=1.6 Hz, 1H), 9.05 (t, J=1.8 Hz, 1H), 8.96 (d, J=4.9 Hz, 1H), 8.78-8.70 (m, 4H), 8.53 (dd, J=7.5, 1.7 Hz, 1H), 8.38 (t, J=2.0 Hz, 1H), 8.31 (d, J=7.7 Hz, 2H), 8.16-8.11 (m, 1H), 7.94 (d, J=4.8 Hz, 1H), 7.75-7.59 (m, 10H), 7.53 (ddd, J=8.2, 7.0, 1.2 Hz, 2H), 7.37 (t, J=7.4 Hz, 2H).

Example 3: Compound (3)

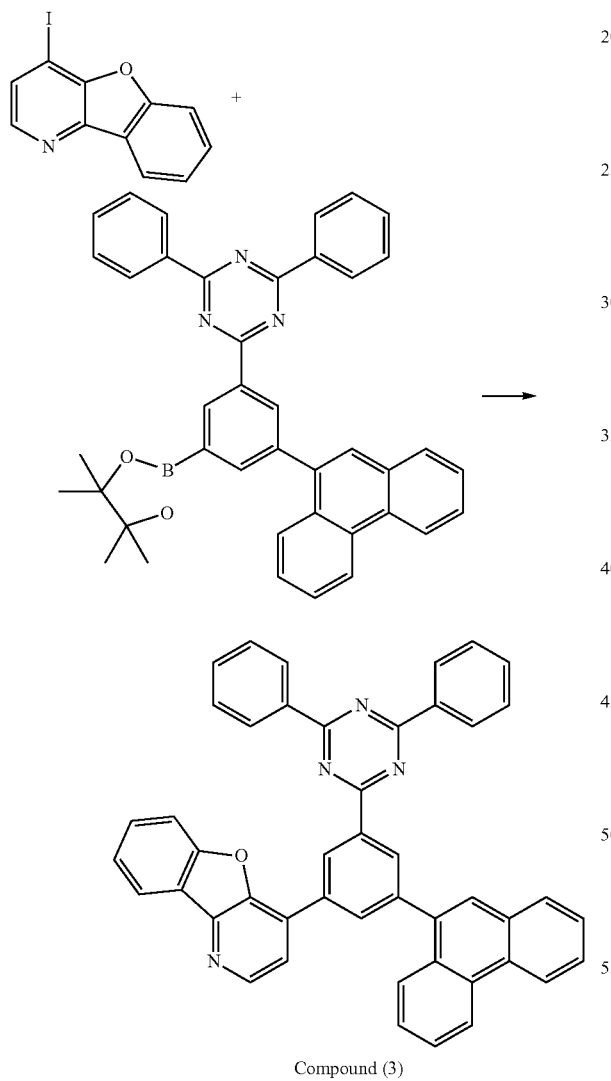

Compound (3)

Compound (3) is obtained by the same synthesis as in the synthesis of the compound (1) except that 4-iodobenzofuro[3,2-b]pyridine is used instead of 4-iodobenzothiopheno[3,2-b]pyridine. The yield is 65%. The result of mass analysis is m/e=652, and the aforementioned compound (3) (exact mass: 652.22) is identified.

Example 4: Compound (4)

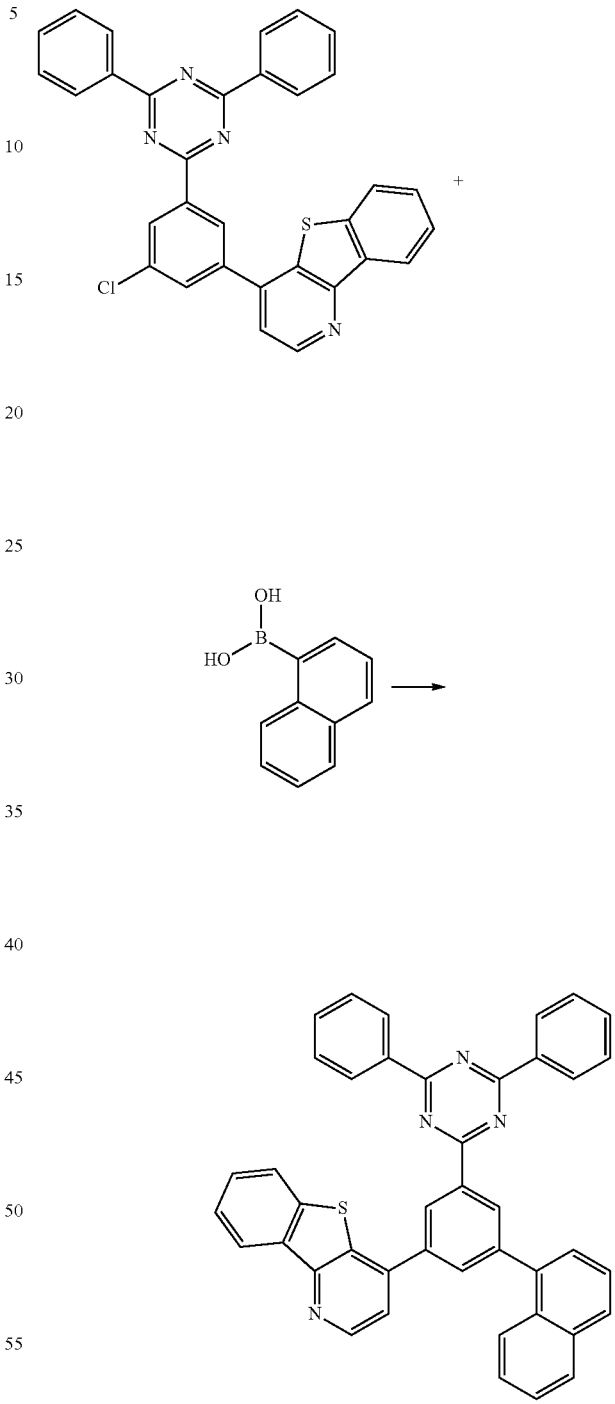

Compound (4)

Compound (4) is obtained by the same synthesis as in the synthesis of the compound (2) except that in 1-naphthylboronic acid is used instead of 9-H-carbazole. The yield is 30%. The result of mass analysis is m/e=618, and the aforementioned compound (4) (exact mass: 618.19) is identified.

Example 5: Compound (5)

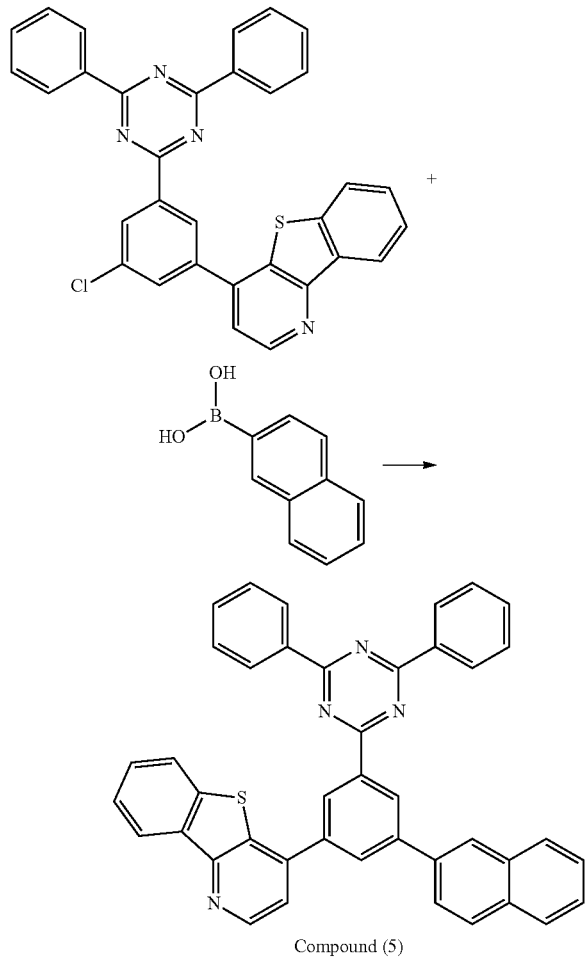

Compound (5)

Compound (5) is obtained by the same synthesis as in the synthesis of the compound (2) except that 2-naphthylboronic acid is used instead of 9-H-carbazole. The yield is 40%. The result of mass analysis is m/e=618, and the aforementioned compound (5) (exact mass: 61:8.19) is identified.

Example 6: Compound (6)

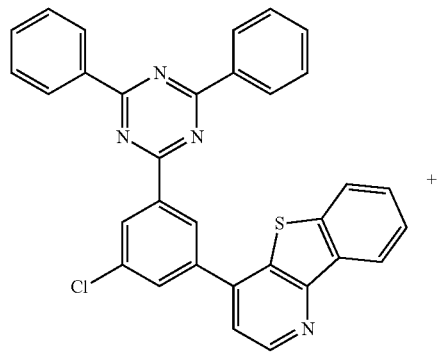

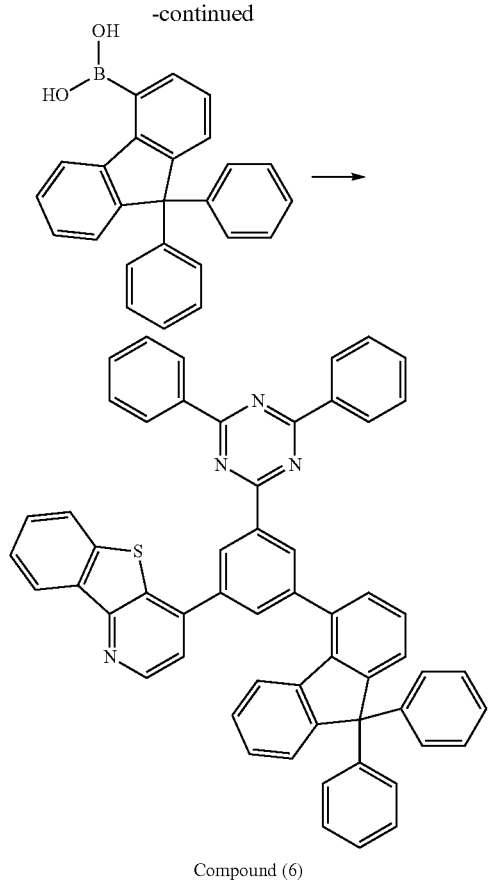

Compound (6)

Compound (6) is obtained by the same synthesis as in the synthesis of the compound (2) except that (9,9-diphenylfluoren-4-yl)boronic acid is used instead of 9-H-carbazole. The yield is 40%. The result of mass analysis is m/e=808, and the aforementioned compound (6) (exact mass: 808.27) is identified.

Example 7: Compound (7)

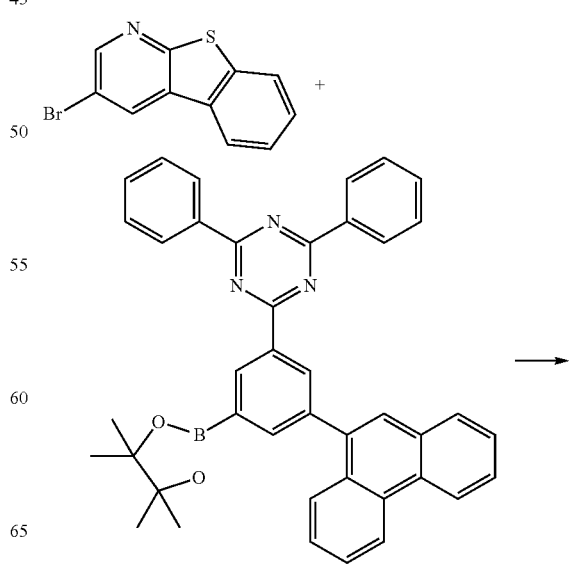

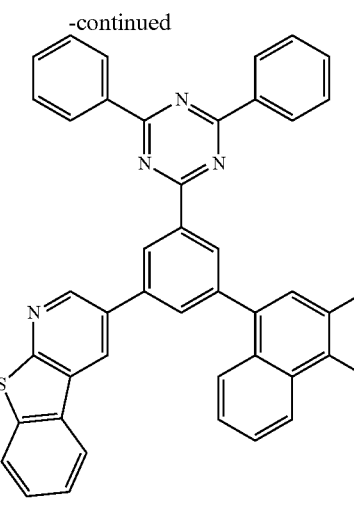

Compound (7)

Compound (7) is obtained by the same synthesis as in the synthesis of the compound (1) except that 3-bromobenzothiopheno[2,3-b]pyridine is used instead of 4-iodobenzothiopheno[3,2-b]pyridine. The yield is 70%. The result of mass analysis is m/e=1668, and the aforementioned compound (7) (exact mass: 668.20) is identified.

Example 8: Compound (8)

Intermediate 1

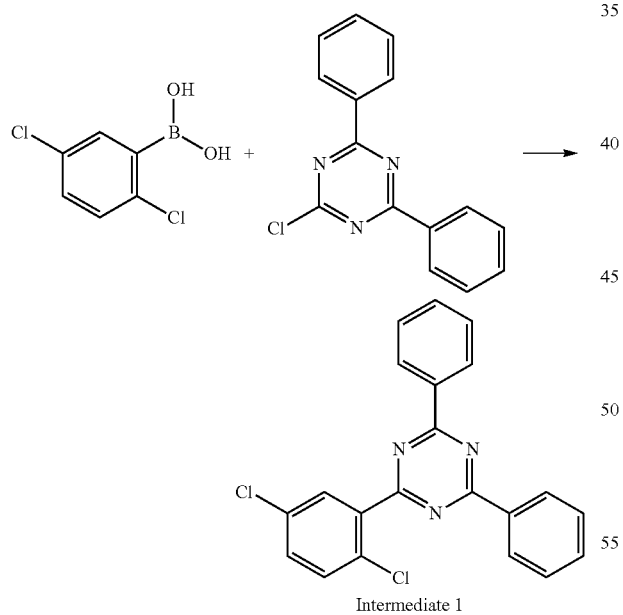

Intermediate 1

Under an argon atmosphere, to a mixture of 2,5-dichlorophenylboronic acid (11.4 g, 60:0 mmol), 2-chloro-4,6-diphenyl-1,3,5-triazine (16.1 g, 60.0 mmol), tetrakis(triphenylphosphine) palladium(0) (0.693 g, 0.600 mmol), and sodium carbonate (12.7 g, 120 mmol), 1,2-dimethoxyethane (300 mL) and water (150 mL) are added, and the mixture is stirred under heating and refluxing for 8 hours. After completing the reaction, the mixture is cooled to room temperature, the phases are separated, and then organic phase is concentrated under reduced pressure. The mixture is dissolved in dichloromethane and passed through silica gel column chromatography. The resulting solution is concentrated under reduced pressure to provide intermediate 1 (18.2 g, 48.0 mmol). The yield of the intermediate 1 is 80%.

Intermediate 2

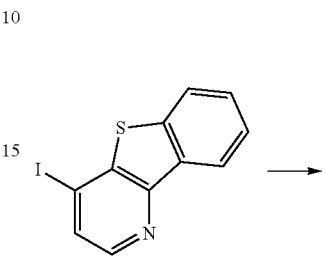

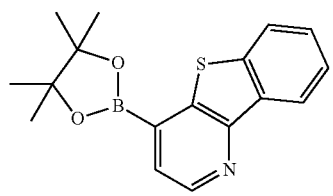

Intermediate 2

Under an argon atmosphere, to a mixture of 4-iodobenzothiopheno[3,2-b]pyridine (18.6 g, 59.9 mmol), bis(pinacolato)diboron (18.3 g, 71.9 mmol), tris(dibenzylideneacetone) dipalladium(0) (1.10 g, 2.20 mmol), X-phos (2-dicyclohexylphosphino-2',4',6'-triisopropylbiphenyl) (2.29 g, 4.79 mmol), and potassium acetate (16.6 g, 120.0 mmol), 1,4-dioxane (600 mL) is added, and the mixture is stirred under heating and refluxing for 8 hours. After completing the reaction, the mixture is cooled to room temperature, toluene (300 mL) and water (300 mL) are added, the phases are separated, and then organic phase is concentrated under reduced pressure. The mixture is dissolved in dichloromethane and passed through silica gel column chromatography. The resulting solution is concentrated under reduced pressure to provide intermediate 2 (15.8 g, 50.9 mmol). The yield of the intermediate 2 is 85%.

Intermediate 3

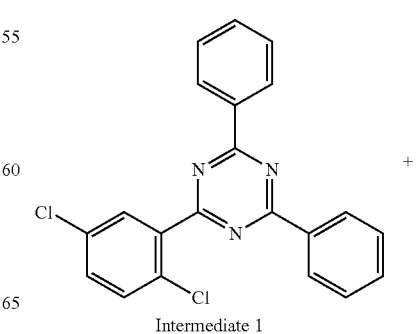

Intermediate 1

-continued

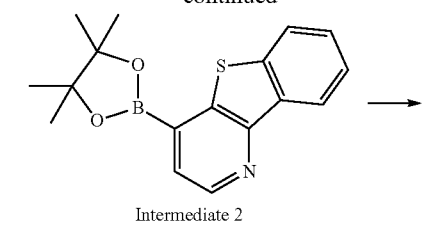

Intermediate 2

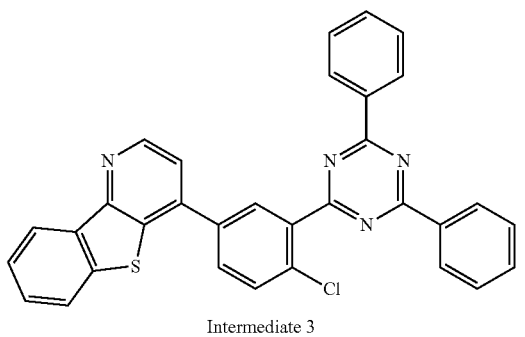

Intermediate 3

Under an argon atmosphere, to a mixture of the intermediate 1 (18.2 g, 48.0 mmol), the intermediate 2 (14.9 g, 48.0 mmol), tris(dibenzylideneacetone) dipalladium(0) (1.10 g, 2.20 mmol), X-phos (2.29 g, 4.79 mmol), and potassium acetate (13.3 g, 96.01 mmol), 1,4=dioxane (600 mL) is added, and the mixture is stirred under heating and refluxing for 8 hours. After completing the reaction, the mixture is cooled to room temperature, toluene (300 mL) and water (300 mL) are added, the phases are separated, and then organic phase is concentrated under reduced pressure. The mixture is dissolved in dichloromethane and passed through silica gel column chromatography. The resulting solution is concentrated under reduced pressure to provide intermediate 3 (11.4 g, 21.6 mmol). The yield of the intermediate 3 is 45%.

Compound (8)

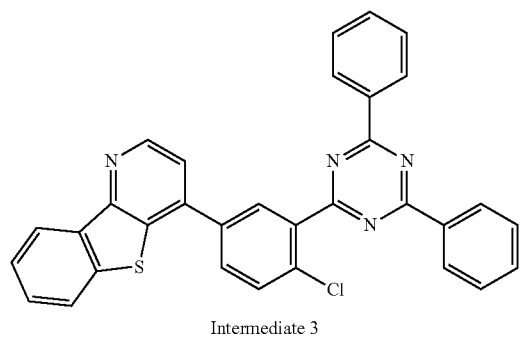

Intermediate 3

-continued

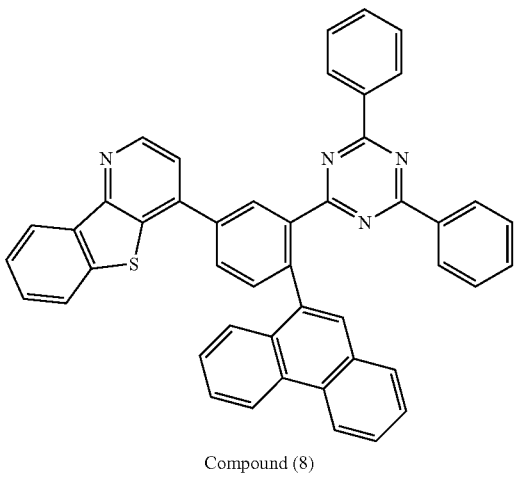

Compound (8)

Compound (8) is obtained by the same synthesis, as, in the synthesis of the compound (2) except that the intermediate 3 is used instead of 4-[3-chloro-5-(4,6-diphenyl-1,3,5-triazin-2-yl)phenyl]benzothiopheno[3,2-b]pyridine, and 9-phenahthrylborohic acid is used, instead of 9-H-carbazole. The yield is 20%. The result of mass analysis is m/e=668, and the aforementioned compound (8) (exact mass: 668.20) is identified.

Example 9: Compound (9)

Intermediate 4

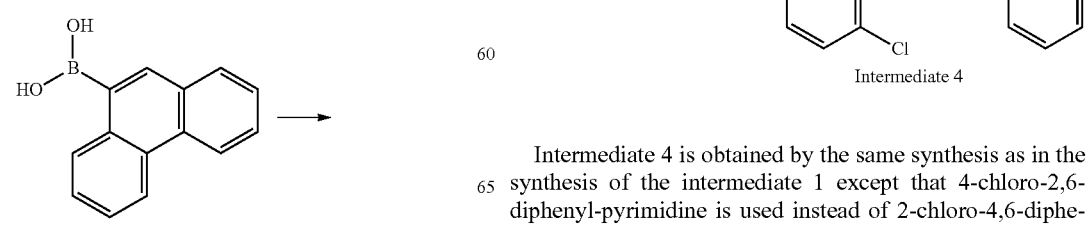

Intermediate 4

Intermediate 4 is obtained by the same synthesis as in the synthesis of the intermediate 1 except that 4-chloro-2,6-diphenyl-pyrimidine is used instead of 2-chloro-4,6-diphenyl-1,3,5-triazine. The yield is 70%.

1175

Intermediate 5

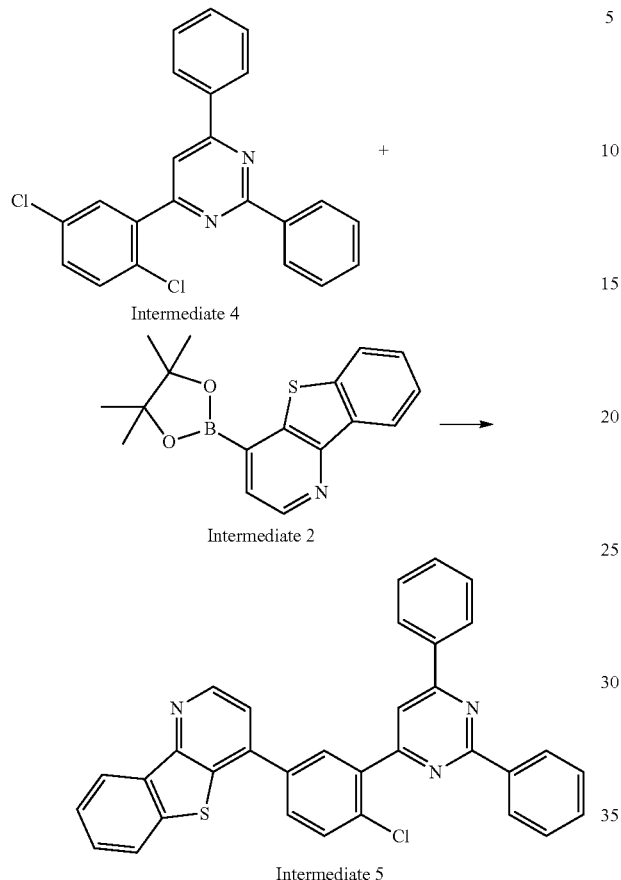

Intermediate 4

Intermediate 2

Intermediate 5

Intermediate 5 is obtained by the same synthesis as in the synthesis of the intermediate 3 except that the intermediate 4 is used instead of the intermediate 1. The yield is 45%.

Compound (9)

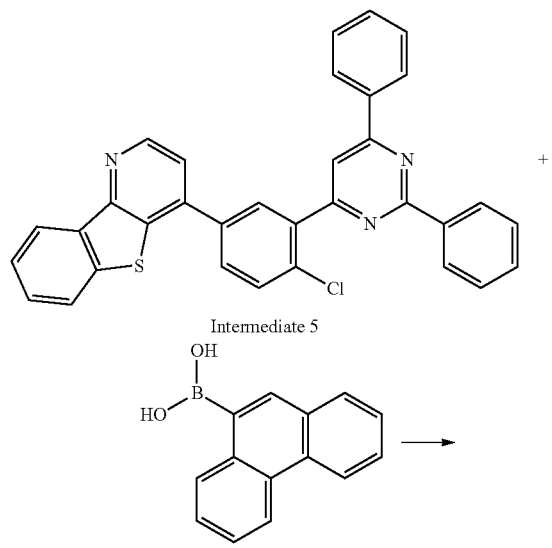

Intermediate 5

1176

-continued

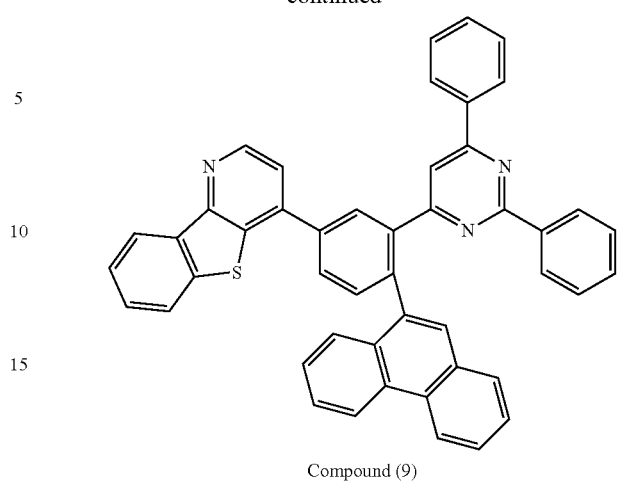

Compound (9)

Compound (9) is obtained by the same synthesis as in the synthesis of the compound (2) except that the intermediate 5 is used instead of 4-[3-chloro-5-(4,6-diphenyl-1,3,5-triazin-2-yl)phenyl]benzothiopheno[3,2-b]pyridine, and 9-phenanthrylboronic acid is used instead of 9-H-carbazole. The yield is 25%. The result of mass analysis is m/e=667, and the aforementioned compound (9) (exact mass: 667.21) is identified.

Example 10: Compound (10)

Intermediate 6

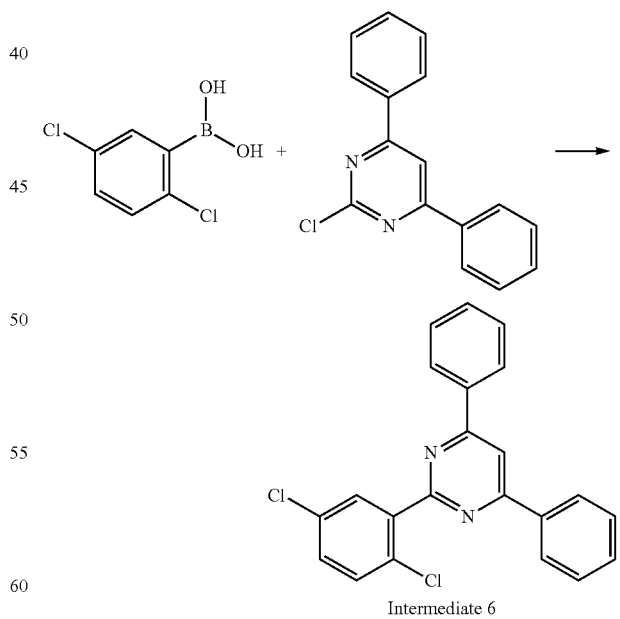

Intermediate 6

Intermediate 6 is obtained by the same synthesis as in the synthesis of the intermediate 1 except that 2-chloro-4,6-diphenyl-pyrimidine is used instead of 2-chloro-4,6-diphenyl-1,3,5-triazine. The yield is 60%.

Intermediate 7

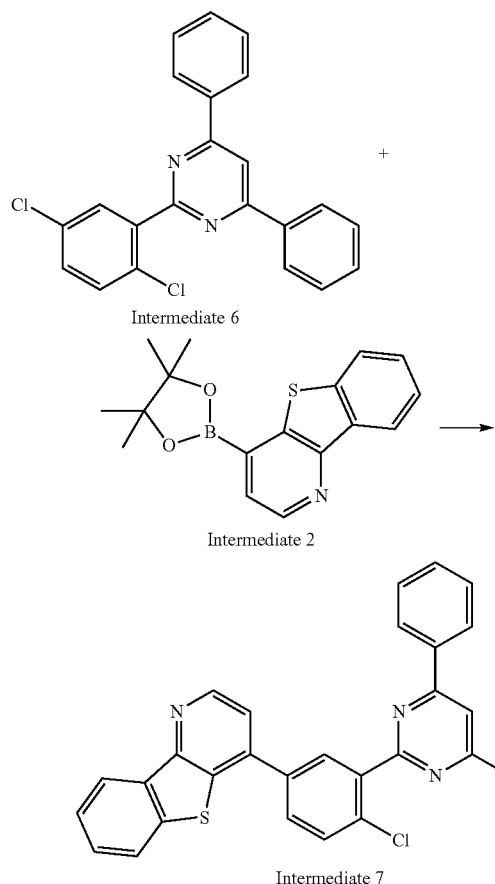

Intermediate 7 is obtained by the same synthesis as in the synthesis of the intermediate 3 except that the intermediate 6 is used instead of the intermediate 1. The yield is 40%.

Compound (10)

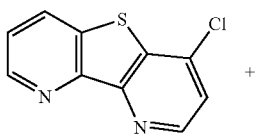

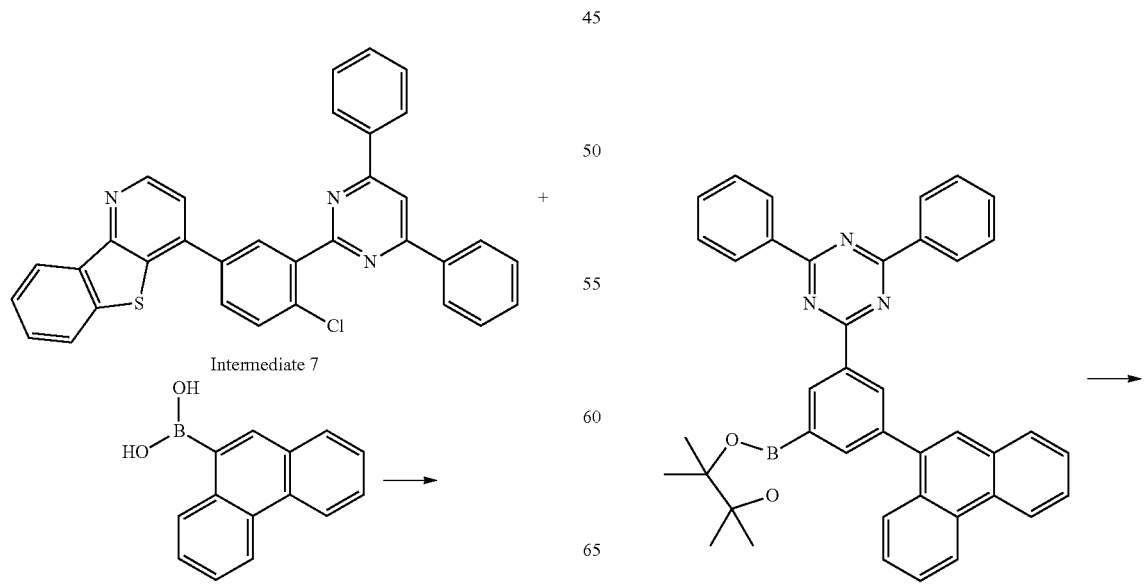

Compound (10)

Compound (10) is obtained by the same synthesis as in the synthesis of the compound (2) except that the intermediate 7 is used instead of 4-[3-chloro-5-(4,6-diphenyl-1,3,5-triazin-2-yl)phenyl]benzothiopheno[3,2-b]pyridine, and 9-phenanthrylboronic acid is used instead of 9H-carbazole. The yield is 25%. The result of mass analysis is m/e=667, and the aforementioned compound (10) (exact mass: 667.21) is identified.

Compound K:

-continued

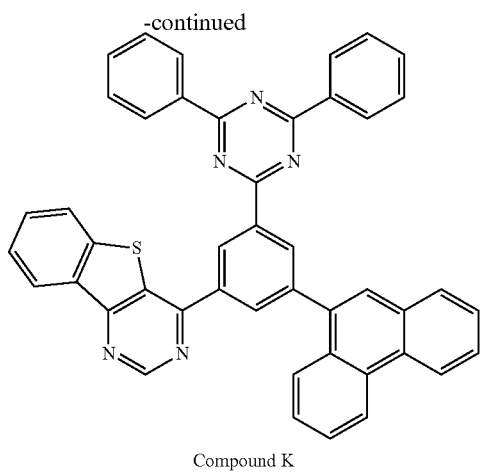

Compound K

Compound K is obtained by the same synthesis as in the synthesis of the compound (1) except that 4-iodobenzofuro[3,2-b]pyridine is used instead of 4-iodobenzothiopheno[3,2-b]pyridine. The yield is 55%. The result of mass analysis is m/e=669, and the aforementioned compound K (exact mass: 669.20) is identified.

Compound N:

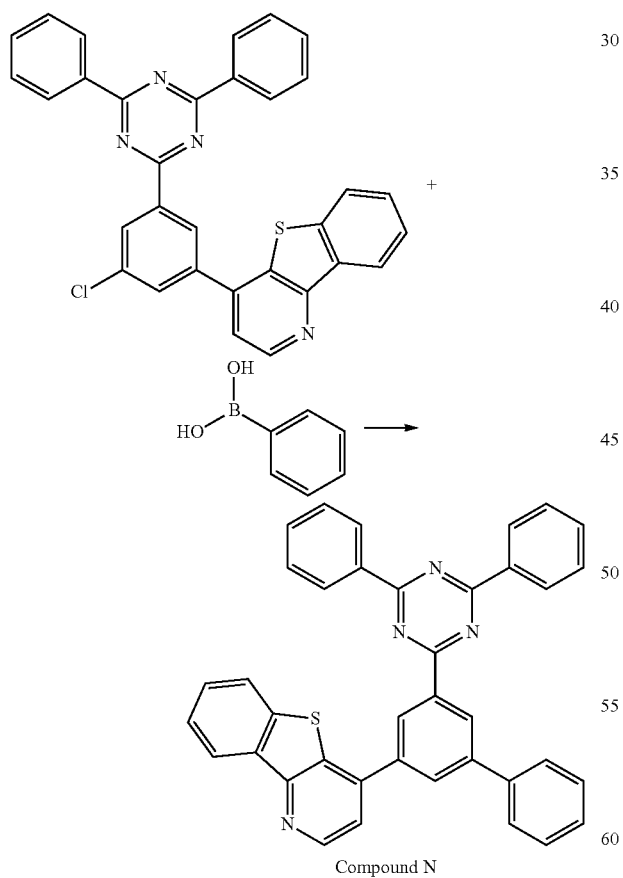

Compound N

Compound N

Compound N is obtained by the same synthesis as in the synthesis of the compound (2) except that phenylboronic acid is used instead of 9-H-carbazole. The yield is 50%. The result of mass analysis is m/e=568, and the aforementioned compound N (exact mass: 568.17) is identified.

Compound P:

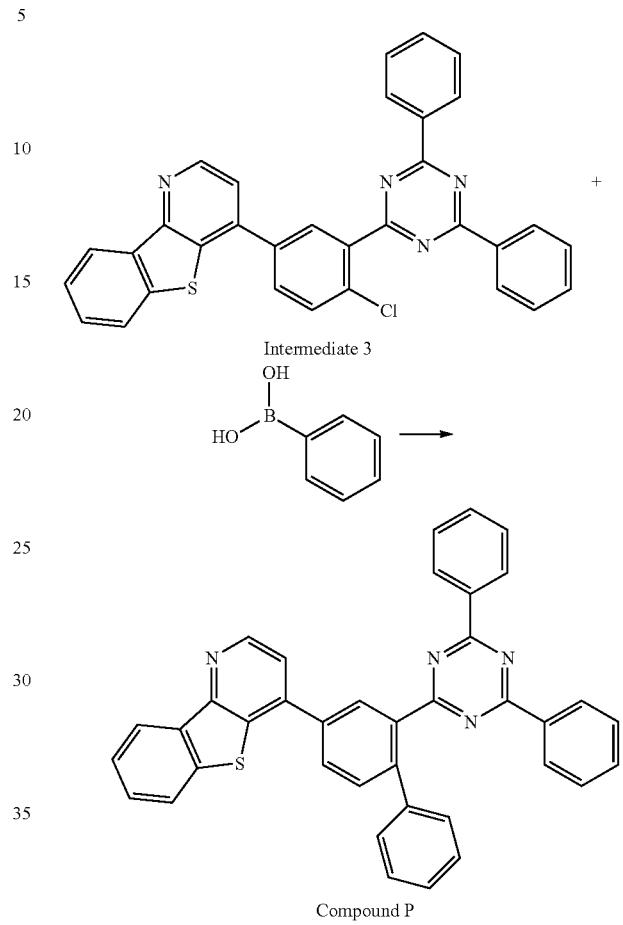

Compound P

Compound P is obtained by the same synthesis as in the synthesis of the compound (2) except that the intermediate 3 is used instead of 4-[3-chloro-5-(4,6-diphenyl-1,3,5-triazin-2-yl)phenyl]benzothiopheno[3,2-b]pyridine, and phenylboronic acid is used instead of 9-H-carbazole. The yield is 30%. The result of mass analysis is m/e=568, and the aforementioned compound P (exact mass: 568.17) is identified.

II Device Examples

Comparative Application Example C1

A glass substrate with 120 nm-thick indium-tin-oxide (ITO) transparent electrode (manufactured by Geomatec Co., Ltd.) used as an anode is first cleaned with isopropanol in an ultrasonic bath for 10 min. To eliminate any possible organic-residues, the substrate is exposed to an ultraviolet light and ozone for further 30 min. This treatment also improves the hole injection-properties of the ITO. The cleaned substrate is mounted on a substrate holder and loaded into a vacuum chamber. Thereafter, the organic materials specified below are applied by vapor deposition to the ITO substrate at a rate of approx. 0.2-1 Å/sec at about $10^{-6}$-$10^{-8}$ mbar. As a hole injection layer, 5 nm-thick of compound A is applied. Then 100 nm-thick of compound B and 5 nm-thick of compound C are applied as a first and a second hole transporting layers, respectively. Subsequently, a mixture of 3% by weight of an emitter compound D and 97% by weight of a host (compound E) are applied to form a 15 nm-thick of fluorescent-emitting layer. On the emitting layer, 5 nm-thick compound F is applied as a first electron transporting layer. Subsequently, a mixture of 50% by weight of compound G and 50% by weight of compound H are applied to form a 25 nm-thick of a second electron transporting layer. Finally, 1 nm-thick Compound H is deposited as an electron injection layer and 80 nm-thick Al is then deposited as a cathode to complete the device. The device is sealed with a glass lid and a getter in an inert nitrogen atmosphere with less than 1 ppm of water and oxygen.

Compound A

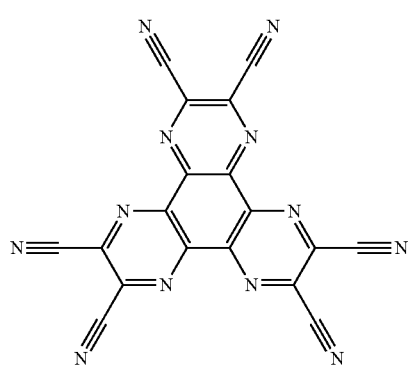

Compound B

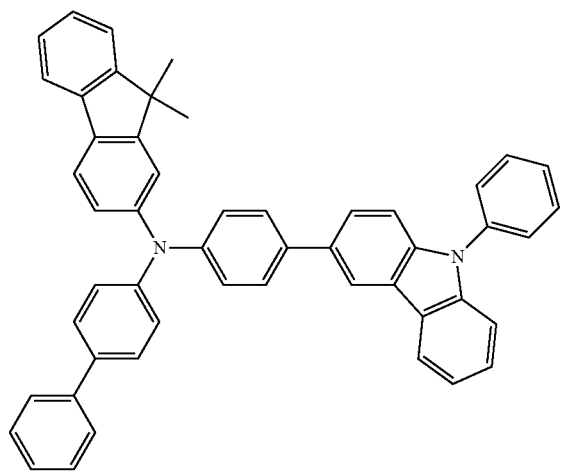

-continued

Compound C

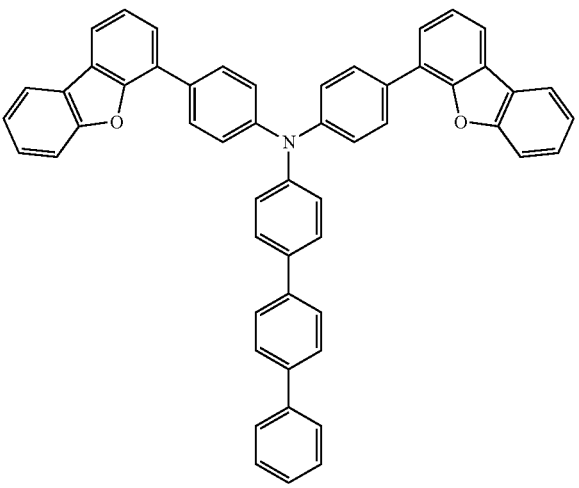

Compound D

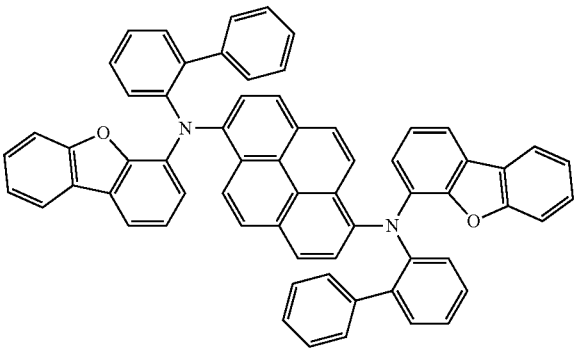

Compound E

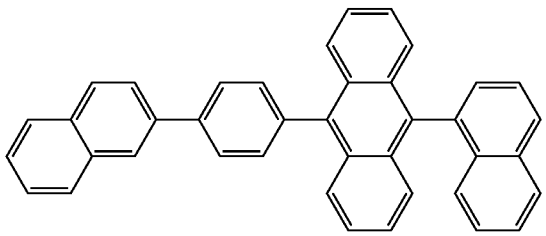

Compound F

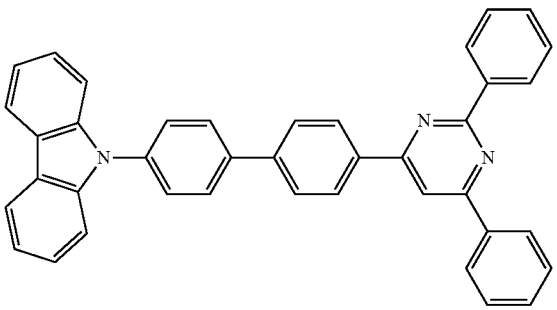

Compound G

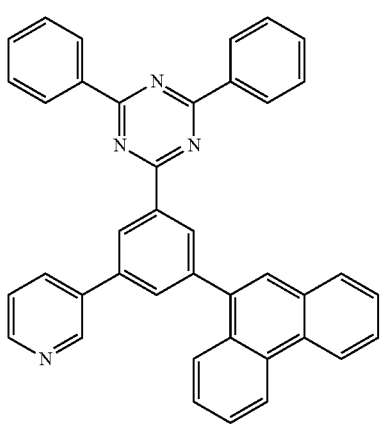

Compound H

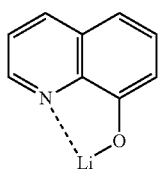

Compound I

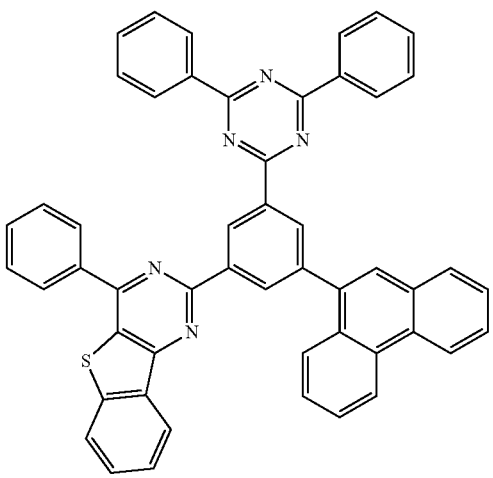

Compound J

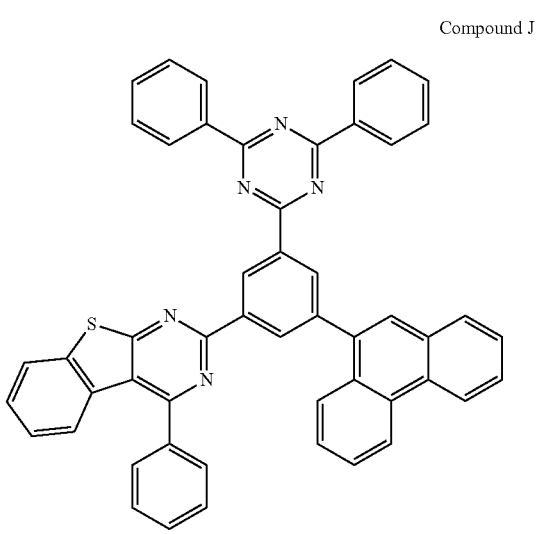

Compound K

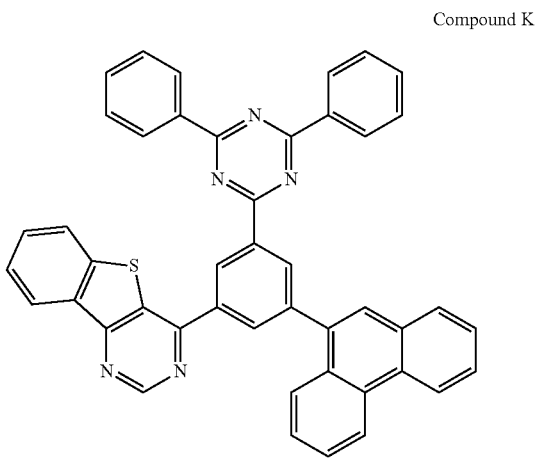

OLED Characterization

To characterize the OLED, electroluminescence spectra are recorded at various currents and voltages. In addition, the current-voltage characteristic is measured in combination with the luminance to determine luminous efficiency and external quantum efficiency (EQE). Driving Voltage U and EQE are given at a current density of 10 mA/cm², and 97% lifetime (LT97), the time spent until the initial luminance at 50 mA/cm² is reduced to 97%, is recorded.

Comparative Application Examples C2 to C7 and Inventive Application Examples 1 to 6

Comparative Application Example C1 is repeated except that the compound G is replaced by compound I (Comparative Application Example C2), compound J (Comparative Application Example C3), compound K (Comparative Application Example C4), compound L (Comparative Application Example C5), compound M (Comparative Application Example C6), compound N (Comparative Application Example C7), compound (1) according to preparation example 1 (Inventive Application Example 1), compound (3) according to preparation example 3 (Inventive Application Example 2), compound (4) according to preparation example 4 (Inventive Application Example 3), compound (5) according to preparation example 5 (Inventive Application Example 4), compound (6) according to preparation example 6 (Inventive Application Example 5) and compound (7) according to preparation example 7 (Inventive Application Example 6), respectively. The device results are shown in Table 1.

Compound L
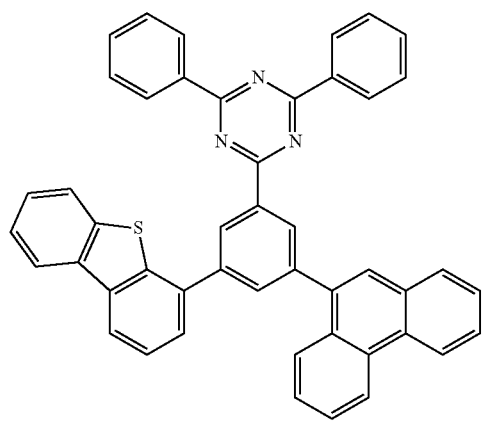
Compound (1)
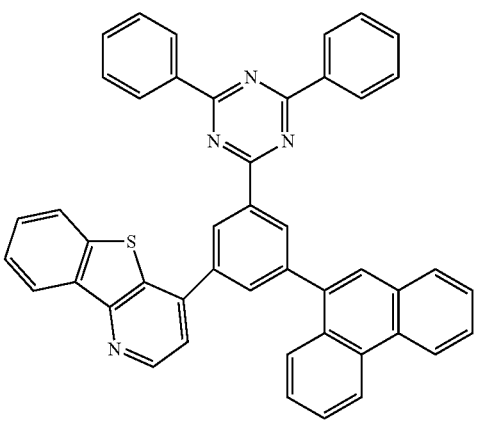
Compound M
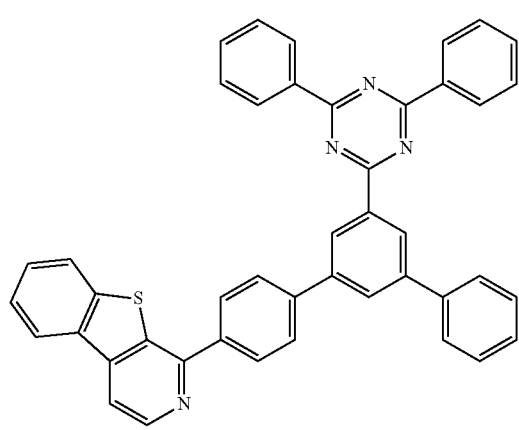
Compound (3)
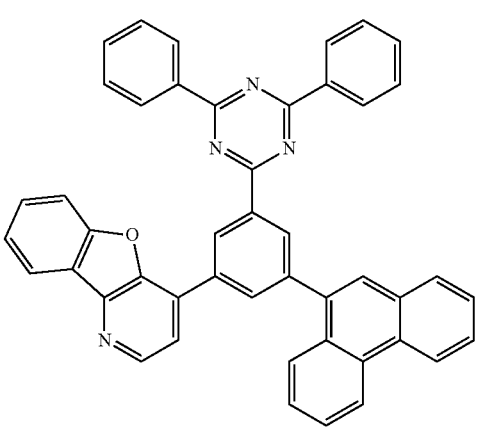
Compound N
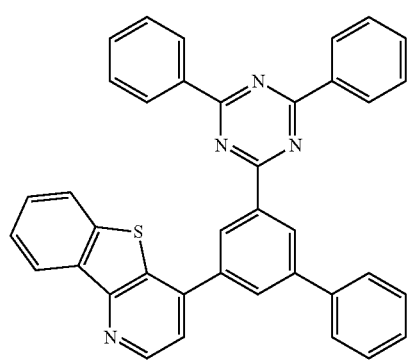
Compound (4)
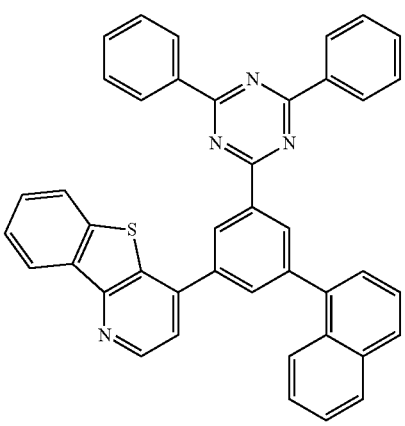

-continued

Compound (5)

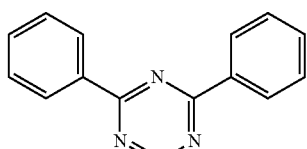

Compound (6)

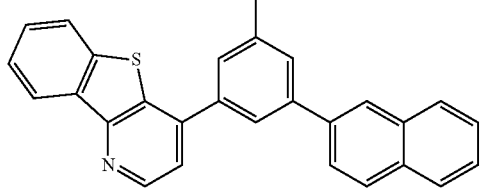

Compound (7)

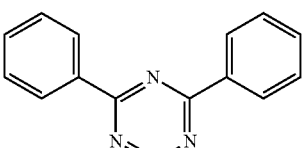

TABLE 1

| Appl. Ex. | Second Electron Transporting Layer | EQE [%] | LT97 [hrs] |
|---|---|---|---|
| Comp. Appl. Ex. C1 | Compound G | 9.6 | 85 |
| Comp. Appl. Ex. C2 | Compound I | 8.8 | 90 |
| Comp. Appl. Ex. C3 | Compound J | 8.0 | 95 |
| Comp. Appl. Ex. C4 | Compound K | 8.0 | 100 |
| Comp. Appl.-Ex. C5 | Compound L | 8.9 | 45 |
| Comp. Appl. Ex. C6 | Compound M | 8.9 | 50 |
| Comp. Appl. Ex. C7 | Compound N | 9.3 | 95 |
| Appl. Ex. 1 | Compound (1) | 10.0 | 160 |
| Appl. Ex. 2 | Compound (3) | 10.0 | 155 |
| Appl. Ex. 3 | Compound (4) | 9.8 | 145 |
| Appl. Ex. 4 | Compound (5) | 9.8 | 140 |

TABLE 1-continued

| Appl. Ex. | Second Electron Transporting Layer | EQE [%] | LT97 [hrs] |
|---|---|---|---|
| Appl. Ex. 5 | Compound (6) | 9.8 | 130 |
| Appl. Ex. 6 | Compound (7) | 9.9 | 110 |

The results shown in Table 1 demonstrate that the EQE is enhanced and the lifetime is-prolonged by the inventive compounds (1) and (3) to (7). In particular, the inventive compounds (1=) and (3) to (6), which are represented by the formula (Iaa), prolong the lifetime largely.

Comparative Application Example C8

Comparative Application Example C1 is repeated except that the compound G is replaced by compound O and the compound F is replaced by compound P.

Compound O

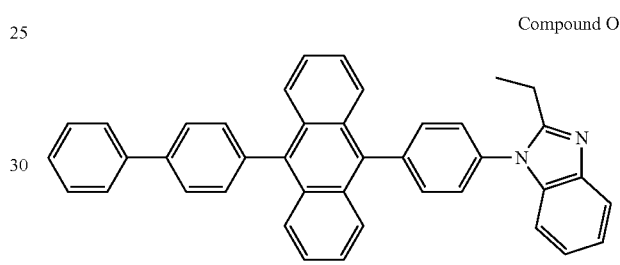

Compound P

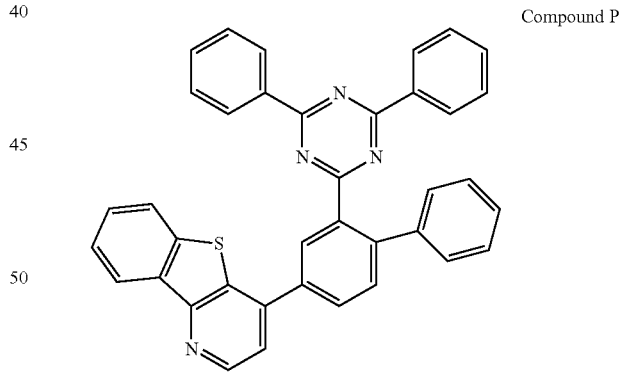

Inventive Application Examples 7 to 9

Comparative Application Example C8 is repeated except that the compound P is replaced by compound (8) according to preparation example 8 (Inventive Application Example 7), compound (9) according to preparation example 9 (Inventive Application Example 8) and compound (10) according to preparation example 10 (Inventive Application Example 9), respectively. The device results are shown in Table 2.

Compound (8)

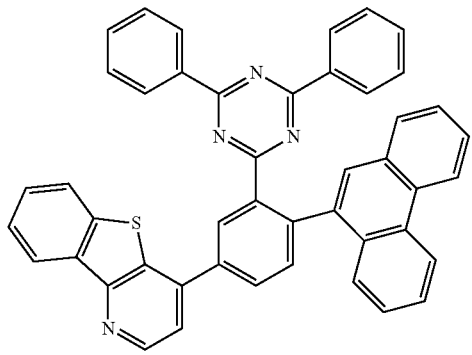

Compound (9)

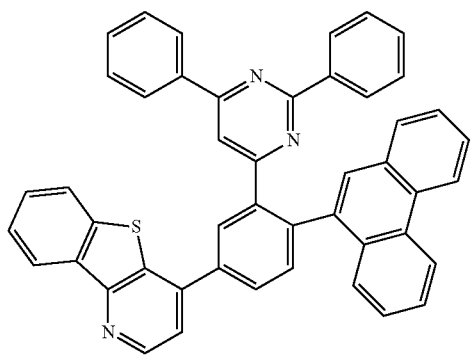

Compound (10)

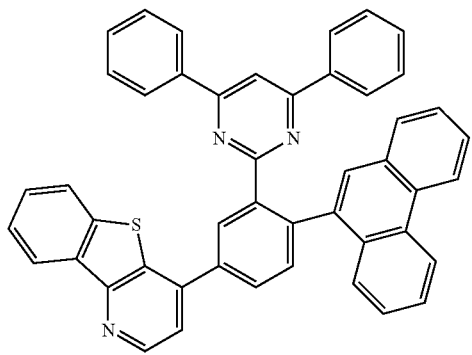

TABLE 2

| Appl. Ex. | First Electron Transporting Layer | U [V] | EQE [%] |
| --- | --- | --- | --- |
| Comp. Appl. Ex. C8 | Compound P | 4.5 | 7.9 |
| Appl. Ex. 7 | Compound (8) | 3.9 | 9.3 |
| Appl. Ex. 8 | Compound (9) | 3.8 | 9.6 |
| Appl. Ex. 9 | Compound (10) | 3.9 | 9.3 |

The results shown in Table 2 demonstrate that the driving voltage is lowered and the EQE is enhanced by the inventive compounds (8) to (10).

The invention claimed is:
1. A compound of formula (Ia):

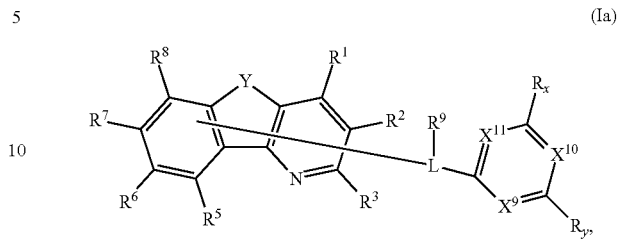

(Ia)

wherein
Y is S or O;
wherein one of $R^1$, $R^2$, $R^3$, $R^5$, $R^6$, $R^7$ and $R^8$ is

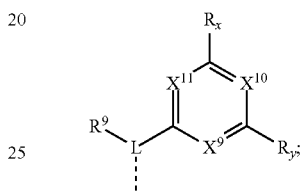

and the other of the remaining groups $R^1$, $R^2$, $R^3$, $R^5$, $R^6$, $R^7$ and $R^8$ are independently of each other H, CN, $NR^{65}R^{66}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group, which can optionally be substituted by G;
adjacent groups $R^1$ and $R^2$, $R^2$ and $R^3$, $R^5$ and $R^6$, $R^6$ and $R^7$, and $R^7$ and $R^8$ do not together form a ring
L is a trivalent $C_6$-$C_{24}$ arylene group or a trivalent $C_2$-$C_{24}$ heteroarylene group;
$R^9$ is a fused $C_{10}$-$C_{24}$ aryl group or a fused $C_{12}$-$C_{24}$ heteroaryl group;
$X^9$, $X^{10}$ and $X^{11}$ are each independently N or $CR^{10}$, whereby at least two of $X^9$, $X^{10}$ and $X^{11}$ are N;
$R^{10}$ is H, $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G;
D is —CO—, —COO—, —S—, —SO—, —SO$_2$—, —O—, —$CR^{63}$=$CR^{64}$—, —$NR^{65}$—, —$POR^{72}$—, or —C≡C—;
E is —$OR^{69}$, —$SR^{69}$, —$NR^{65}R^{66}$, —$COR^{68}$, —$COOR^{67}$, —$CONR^{65}R^{66}$ or —CN,
G is E, or a $C_1$-$C_{24}$alkyl group, an unsubstituted $C_6$-$C_{24}$aryl group, a $C_6$-$C_{24}$aryl group, which is substituted by F, $C_1$-$C_{24}$alkyl, or $C_1$-$C_{24}$alkyl which is interrupted by O, an unsubstituted $C_2$-$C_{30}$heteroaryl group, or a $C_2$-$C_{30}$heteroaryl group, which is substituted by F, $C_1$-$C_{24}$alkyl, or $C_1$-$C_{24}$alkyl which is interrupted by O;

$R^{63}$ and $R^{64}$ are independently of each other unsubstituted $C_6$-$C_{18}$aryl; $C_6$-$C_{18}$aryl which is substituted by $C_1$-$C_{18}$alkyl or $C_1$-$C_{18}$alkoxy; $C_1$-$C_{18}$alkyl; or $C_1$-$C_{18}$alkyl which is interrupted by —O—;

$R^{65}$ and $R^{66}$ form together with the carbon atoms to which they are bonded a 5- or 6-membered ring, which can optionally be part of an anellated ring system, wherein the ring and/or anellated ring system can optionally be substituted by G;

$R^{67}$ is an unsubstituted $C_6$-$C_{18}$aryl group; a $C_6$-$C_{18}$aryl group, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{68}$ is H; an unsubstituted $C_6$-$C_{18}$aryl group; a $C_6$-$C_{18}$aryl group, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{69}$ is an unsubstituted $C_6$-$C_{18}$aryl; a $C_6$-$C_{18}$aryl, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{71}$ is a $C_1$-$C_{18}$alkyl group, a $C_6$-$C_{18}$aryl group, or a $C_6$-$C_{18}$aryl group, which is substituted by $C_1$-$C_{18}$alkyl; and $R^{72}$ is a $C_1$-$C_{18}$alkyl group, an unsubstituted $C_6$-$C_{18}$aryl group, or a $C_6$-$C_{18}$aryl group, which is substituted by $C_1$-$C_{18}$aryl;

$R^{73}$ and $R^{74}$ form together with the carbon atoms to which they are bonded a 5- or 6-membered ring, which can optionally be part of an anellated ring system, wherein the ring and/or anellated ring system can optionally be substituted by G;

$R_x$ and $R_y$ are independently of each other $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{12}$aryl group, which can optionally be substituted by G, or a $C_2$-$C_{30}$heteroaryl group which can optionally be substituted by G;

wherein the dotted line is a bonding site.

2. A compound according to claim 1, wherein the compound of formula (Ia) has the formula (Iaa):

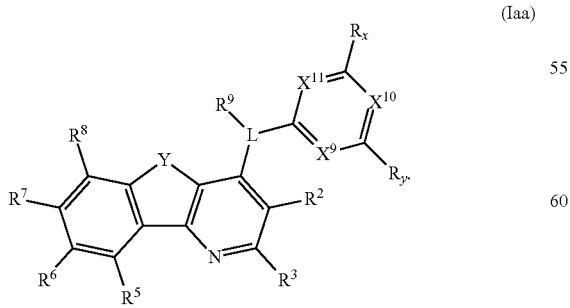

(Iaa)

3. A compound according to claim 1, wherein $R^9$ is selected from the group consisting of naphthyl, phenanthryl, anthryl, benzophenanthryl, benzanthryl, naphthacenyl, triphenylenyl, benzochrysenyl, fluorenyl, benzofluorenyl, dibenzofluorenyl, indenofluorenyl, benzindenofluorenyl, fluoranthenyl, benzofluoranthenyl, benzotriphenylenyl, benzoquinolynyl, benzoisoquinolinyl, benzoquinazolinyl, benzoquinoxalinyl, naphthoquinolinyl, naphthoisoquinolinyl, naphthoquinazolinyl, naphthoquinoxalinyl, phenanthrolinyl, benzofuroquinolinyl, benzothienoquinolinyl, carbazolyl, benzocarbazolyl, dibenzocarbazolyl, indenocarbazolyl, benzofurocarbazolyl, benzothiocarbazolyl, indrocarbazolyl, benzimidazo[1,2-a]benzimadozolyl, dibenzofuranyl, dibenzothiophenyl, benzonaphthofuranyl, benzonaphthothiophenyl, benzophenanthrofuranyl, benzophenanthrothiophenyl, wherein the groups mentioned above can optionally be substituted by G.

4. A compound according to claim 1, wherein $R^9$ is selected from the group consisting of

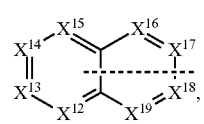

(1)

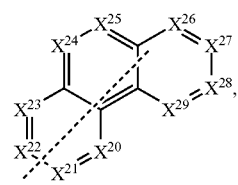

(2)

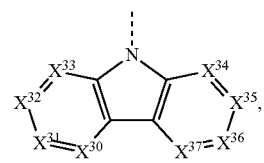

(3)

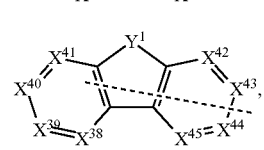

(4)

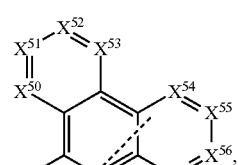

(5a)

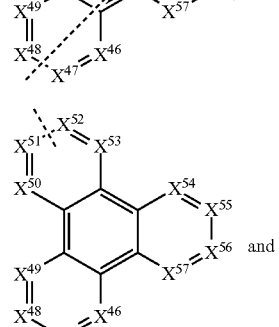

(5b) and

-continued

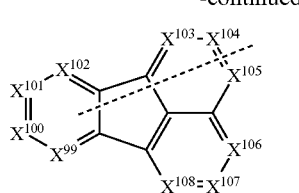
(9)

wherein
Y¹ in formula (4) is NR⁵⁸, S, O or CR⁵⁹R⁶⁰;
X¹² to X⁵⁷ are CR¹² to CR⁵⁷ or N and X⁹⁹ to X¹⁰⁸ are CR⁹⁹ to CR¹⁰⁸ or N,
wherein X¹² to X¹⁹ in formula (1) are not N,
0, 1 or 2 of X²⁰ to X²⁹ in formula (2) are N,
X³⁰ to X³⁷ in formula (3) are not N,
0, 1 or 2 of X³⁸ to X⁴⁵ in formula (4) are N, provided that formula (4) is not a fused less than C12 heteroaryl group;
0, 1 or 2 of X⁴⁶ to X⁵⁷ in formula (5a) are N,
0, 1 or 2 of X⁴⁶ to X⁵⁷ in formula (5b) are N, and
0, 1 or 2 of X⁹⁹ to X¹⁰⁸ in formula (9) are N;
whereby in formulae (1), (2), (3), (4), (5), (5b) and (9) two N atoms are not directly adjacent to each other;
R¹², R¹³, R¹⁴, R¹⁵, R¹⁶, R¹⁷, R¹⁸, R¹⁹, R²⁰, R²¹, R²², R²³, R²⁴, R²⁵, R²⁶, R²⁷, R²⁸, R²⁹, R³⁰, R³¹, R³², R³³, R³⁴, R³⁵, R³⁶, R³⁷, R³⁸, R³⁹, R⁴⁰, R⁴¹, R⁴², R⁴³, R⁴⁴, R⁴⁵, R⁴⁶, R⁴⁷, and R⁴⁸ and R⁹⁹, R¹⁰⁰, R¹⁰¹, R¹⁰², R¹⁰³, R¹⁰⁴, R¹⁰⁵, R¹⁰⁶, R¹⁰⁷ and R¹⁰⁸ are independently of each other H, NR⁷³R⁷⁴, a C₂-C₂₅alkyl group, which can optionally be substituted by E, and or interrupted by D, a C₂-C₂₅alkenyl group, which can optionally be substituted by E, and or interrupted by D, a C₂-C₂₅alkynyl group, which can optionally be substituted by E, and or interrupted by D, —OR⁶⁹, —SR⁶⁹, —COR⁶⁸, —COOR⁶⁷, a C₃C₁₈cycloalkyl group, which can optionally be substituted by G; a C₆-C₂₄aryl group, which can optionally be substituted by G, or a C₂-C₃₀heteroaryl group which can optionally be substituted by G; or two adjacent groups of the groups R¹², R¹³, R¹⁴, R¹⁵, R¹⁶, R¹⁷, R¹⁸, R¹⁹, R²⁰, R²¹, R²², R²³, R²⁴, R²⁵, R²⁶, R²⁷, R²⁸, R²⁹, R³⁰, R³¹, R³², R³³, R³⁴, R³⁵, R³⁶, R³⁷, R³⁸, R³⁹, R⁴⁰, R⁴¹, R⁴², R⁴³, R⁴⁴, R⁴⁵, R⁴⁶ and R⁴⁷ and R⁹⁹, R¹⁰⁰, R¹⁰¹, R¹⁰², R¹⁰³, R¹⁰⁴, R¹⁰⁵, R¹⁰⁶, R¹⁰⁷ and R¹⁰⁸ can optionally from together a ring, which can optionally be substituted by G;
R⁵⁸ is a C₁-C₂₅alkyl group, which can optionally be substituted by E, and or interrupted by D, a C₂-C₂₅alkenyl group, which can optionally be substituted by E, and or interrupted by D, a C₂-C₂₅alkynyl group, which can optionally be substituted by E, and or interrupted by D, a C₃C₁₈cycloalkyl group, which can optionally be substituted by G; a C₆-C₂₄aryl group, which can optionally be substituted by G, or a C₂-C₃₀heteroaryl group which can optionally be substituted by G;
R⁵⁹ and R⁶⁰ are independently of each other H; an unsubstituted C₆-C₁₈aryl group; a C₆-C₁₈alkenyl group, which is substituted by C₁-C₁₈alkyl or C₁-C₁₈alkoxy; a C₁-C₁₈alkyl group; or a C₁-C₁₈alkyl group, which is interrupted by —O—;
R⁶⁷ is an unsubstituted C₆-C₁₈aryl group; a C₆-C₁₈aryl group, which is substituted by C₁-C₁₈alkyl, or C₁-C₁₈alkoxy; a C₁-C₁₈alkyl group; or a C₁-C₁₈alkyl group, which is interrupted by —O—;

R⁶⁸ is H; an unsubstituted C₆-C₁₈aryl group; a C₆-C₁₈aryl group, which is substituted by C₁-C₁₈alkyl or C₁-C₁₈alkoxy; a C₁-C₁₈alkyl group; or a C₁-C₁₈alkyl group, which is interrupted by —O—;
R⁶⁹ is an unsubstituted C₆-C₁₈aryl; a C₆-C₁₈aryl, which is substituted by C₁-C₁₈alkyl or C₁-C₁₈alkoxy; a C₁-C₁₈alkyl group; or a C₁-C₁₈alkyl group, which is interrupted by —O—;
R⁷¹ is a C₁-C₁₈alkyl group, a C₆-C₁₈aryl group, or a C₆-C₁₈aryl group, which is substituted by C₁-C₁₈alkyl; and
R⁷² is a C₁-C₁₈alkyl group, an unsubstituted C₆-C₁₈aryl group, or a C₆-C₁₈alkyl group, which is substituted by C₁-C₁₈alkyl;
R⁷³ and R⁷⁴ form together with the carbon atoms to which they are bonded a 5- or 6-membered ring, which can optionally be part of an anellated ring system, wherein the ring and/or annelated ring system can optionally be substituted by G;
wherein the dotted lines are bonding sites.

5. A compound according to claim 4, wherein R⁹ is selected from the group consisting of

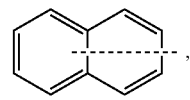
(1′)

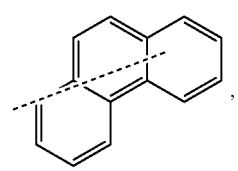
(2′)

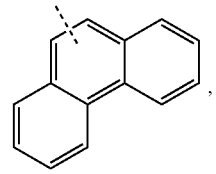
(2″)

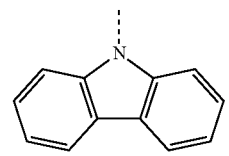
(3′)

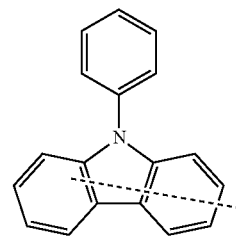
(4′)

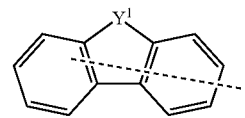
(4″)

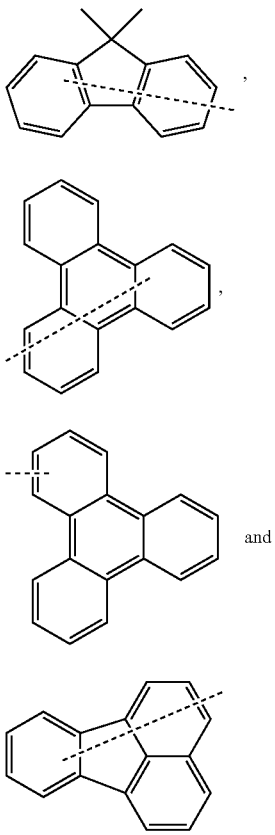

wherein $Y^1$ is O or S and the dotted lines are bonding sites.

6. The compound according to claim 1, wherein L is selected from the group consisting of

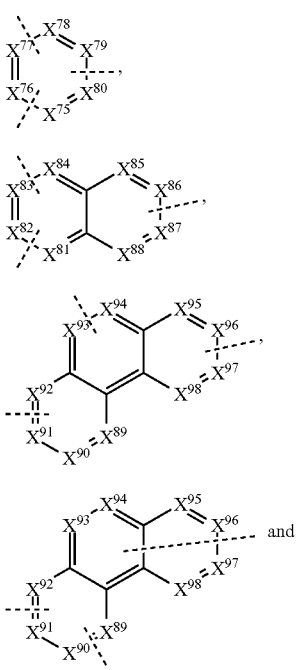

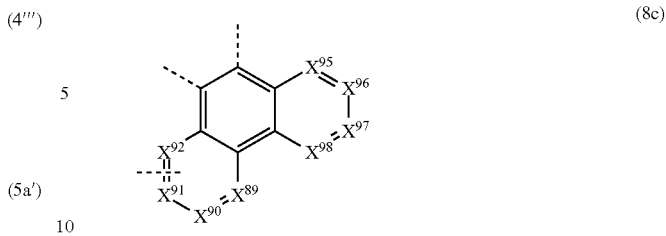

wherein $X^{75}$ to $X^{98}$ are $CR^{75}$ to $CR^{98}$ or N, wherein 0, 1, 2 or 3 of $X^{75}$ to $X^{80}$ in formula (6) are N, 0, 1 or 2, of $X^{81}$ to $X^{88}$ in formula (7) are N, 0, 1 or 2, of $X^{89}$ to $X^{98}$ in formula (8a) are N, 0, 1 or 2, of $X^{89}$ to $X^{98}$ in formula (8b) are N, 0, 1 or 2, of $X^{89}$ to $X^{98}$ in formula (8c) are N;

whereby in formulae (6), (7), (8a), (8b) and (8c) two N atoms are not directly adjacent to each other;

$R^{75}$, $R^{76}$, $R^{77}$, $R^{78}$, $R^{79}$, $R^{80}$, $R^{81}$, $R^{82}$, $R^{83}$, $R^{84}$, $R^{85}$, $R^{86}$, $R^{87}$, $R^{88}$, $R^{89}$, $R^{90}$, $R^{91}$, $R^{92}$, $R^{93}$, $R^{94}$, $R^{95}$, $R^{96}$, $R^{97}$ and $R^{98}$ are independently of each other H, $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G; or two adjacent groups of the groups $R^{75}$, $R^{76}$, $R^{77}$, $R^{78}$, $R^{79}$, $R^{80}$, $R^{81}$, $R^{82}$, $R^{83}$, $R^{84}$, $R^{85}$, $R^{86}$, $R^{87}$, $R^{88}$, $R^{89}$, $R^{90}$, $R^{91}$, $R^{92}$, $R^{93}$, $R^{94}$, $R^{95}$, $R^{96}$, $R^{97}$, and $R^{98}$ can optionally from together a ring, which can optionally be substituted by G;

$R^{67}$ is an unsubstituted $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—;

$R^{68}$ is H; an unsubstituted $C_6$-$C_{18}$aryl group; a $C_6$-$C_{18}$aryl group, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{69}$ is an unsubstituted $C_6$-$C_{18}$aryl; a $C_6$-$C_{18}$aryl, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{71}$ is a $C_1$-$C_{18}$alkyl group, a $C_6$-$C_{18}$aryl group, or a $C_6$-$C_{18}$aryl group, which is substituted by $C_1$-$C_{18}$alkyl; and $R^{72}$ is a $C_1$-$C_{18}$alkyl group, an unsubstituted $C_6$-$C_{18}$aryl group, or a $C_6$-$C_{18}$aryl group, which is substituted by $C_1$-$C_{18}$alkyl;

$R^{73}$ and $R^{74}$ form together with the carbon atoms to which they are bonded a 5- or 6-membered ring, which can optionally be part of an anellated ring system, wherein the ring and/or annelated ring system can optionally be substituted by G;

wherein the dotted lines are bonding sites.

7. The compound according to claim 6, wherein L is selected from the group consisting of

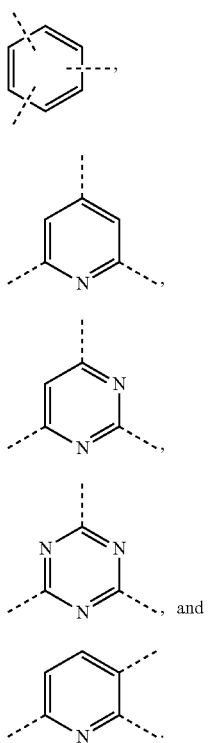

8. The compound according to claim 7, wherein L is selected from the group consisting of

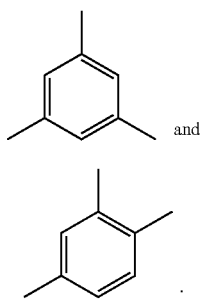

9. The compound according to claim 1, wherein Y is S.

10. An organic electronic device, comprising a compound according to claim 1.

11. The electronic device according to claim 10, which is an organic electroluminescent device.

12. The organic electroluminescent device according to claim 11, comprising an anode, a cathode, and an emitting layer between the anode and the cathode.

13. The organic electroluminescent device according to claim 12, further comprising an electron transport layer between the emitting layer and the cathode, wherein the electron transport layer comprises the compound.

14. The organic electroluminescent device according to claim 13, wherein the electron transport layer further comprises a reducing dopant.

15. The organic electroluminescent device according to claim 14, wherein the reducing dopant is at least one selected from the group consisting of an alkali metal, an alkaline earth metal, a rare earth metal, an alkali metal oxide, an alkali metal halide, an alkaline earth metal oxide, an alkaline earth metal halide, a rare earth metal oxide, a rare earth metal halide, an organic complex having an alkali metal, an organic complex having an alkaline earth metal, and an organic complex having a rare earth metal.

16. The organic electroluminescent device according to claim 12, wherein the emitting layer comprises a fluorescent dopant.

17. The organic electroluminescent device according to claim 12, wherein the emitting layer comprises the compound.

18. An apparatus selected from the group consisting of stationary visual display units; mobile visual display units; illumination units; keyboards; items of clothing; furniture; wallpaper, comprising the organic electronic device according to claim 1.

19. A hole transport layer, an electron/exciton blocking layer, an emitting layer, an electron transport layer, a hole/exciton blocking layer, an electron injection layer or a hole injection layer comprising a compound according to claim 1.

20. An electron transport layer, a hole/exciton blocking layer or an electron injection layer, comprising a compound according to claim 1.

21. A device, comprising the compound of claim 1, said device being selected from the group consisting of organic electroluminescent devices, electrophotographic photoreceptors, photoelectric converters, organic solar cells, switching elements, organic light emitting field effect transistors, and image sensors or dye lasers.

22. A process for the preparation of the compound of claim 1,
the process comprising
coupling a compound of formula (I'):

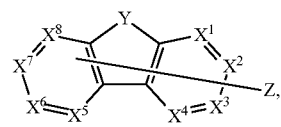

with a compound of formula:

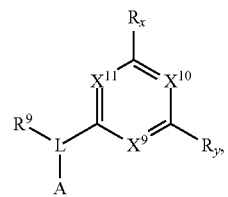

in the presence of a catalyst and in the presence of a base, wherein
Z is Hal or —B(OR")$_2$ wherein R" is H or a C$_1$-C$_3$ alkyl group or a phenyl group, provided that two R" may be same or different, and the two R"s may form a ring together with the two oxygen atoms and the boron atom;
wherein A is —B(OR")$_2$ wherein R' is H or a C$_1$-C$_3$ alkyl group or a phenyl group, provided that two R" may be same or different, and the two R"s may form a ring together with the two oxygen atoms and the boron atom, or Hal;

Hal is halogen,
Y is S or O;
$X^1$ is $CR^1$;
$X^2$ is $CR^2$;
$X^3$ is $CR^3$;
$X^4$ is $CR^4$;
$X^5$ is $CR^5$;
$X^6$ is $CR^6$;
$X^7$ is $CR^7$;
$X^8$ is $CR^8$;
wherein $R^1$, $R^2$, $R^3$, $R^5$, $R^6$, $R^7$ or $R^8$ is Z;
the other of $R^1$, $R^2$, $R^3$, $R^4$, $R^5$, $R^6$, $R^7$ and $R^8$ which are not Z are independently of each other H, CN, $NR^{65}R^{66}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group, which can optionally be substituted by G;
or adjacent groups $R^1$ and $R^2$, $R^5$ and $R^6$, $R^6$ and $R^7$, and/or $R^7$ and $R^8$ can optionally from together a ring, which can optionally be substituted by G;
L is a trivalent $C_6$-$C_{24}$ arylene group or a trivalent $C_2$-$C_{24}$ heteroarylene group;
$R^9$ is a fused $C_{10}$-$C_{24}$ aryl group or a fused $C_{12}$-$C_{24}$ heteroaryl group;
$X^9$, $X^{10}$ and $X^{11}$ are each independently N or $CR^{10}$, whereby at least two of $X^9$, $X^{10}$ and $X^{11}$ are N
$R^{10}$ is H, $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G;
D is —CO—, —COO—, —S—, —SO—, —$SO_2$—, —O—, —$CR^{63}$=$CR^{64}$—, —$NR^{65}$—, —$POR^{72}$—, or —C≡C—;
E is —$OR^{69}$, —$SR^{69}$, —$NR^{65}R^{66}$, —$COR^{68}$, —$COOR^{67}$, —$CONR^{65}R^{66}$ or —CN, G is E, or a $C_1$-$C_{24}$alkyl group, an unsubstituted $C_6$-$C_{24}$aryl group, a $C_6$-$C_{24}$aryl group, which is substituted by F, $C_1$-$C_{24}$alkyl, or $C_1$-$C_{24}$alkyl which is interrupted by O, an unsubstituted $C_2$-$C_{30}$heteroaryl group, or a $C_2$-$C_{30}$heteroaryl group, which is substituted by F, $C_1$-$C_{24}$alkyl, or $C_1$-$C_{24}$alkyl which is interrupted by O;
$R^{63}$ and $R^{64}$ are independently of each other unsubstituted $C_6$-$C_{18}$aryl; $C_6$-$C_{18}$aryl which is substituted by $C_1$-$C_{18}$alkyl or $C_1$-$C_{18}$alkoxy; $C_1$-$C_{18}$alkyl; or $C_1$-$C_{18}$alkyl which is interrupted by —O—;
$R^{65}$ and $R^{66}$ form together with the carbon atoms to which they are bonded a 5- or 6-membered ring, which can optionally be part of an anellated ring system, wherein the ring and/or annelated ring system can optionally be substituted by G;
$R^{67}$ is an unsubstituted $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—;
$R^{68}$ is H; an unsubstituted $C_6$-$C_{18}$aryl group; a $C_6$-$C_{18}$aryl group, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;
$R^{69}$ is an unsubstituted $C_6$-$C_{18}$aryl; a $C_6$-$C_{18}$aryl, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;
$R^{71}$ is a $C_1$-$C_{18}$alkyl group, a $C_6$-$C_{18}$aryl group, or a $C_6$-$C_{18}$aryl group, which is substituted by $C_1$-$C_{18}$alkyl; and
$R^{72}$ is a $C_1$-$C_{18}$alkyl group, an unsubstituted $C_6$-$C_{18}$aryl group, or a $C_6$-$C_{18}$aryl group, which is substituted by $C_1$-$C_{18}$alkyl;
$R^{73}$ and $R^{74}$ form together with the carbon atoms to which they are bonded a 5- or 6-membered ring, which can optionally be part of an anellated ring system, wherein the ring and/or annelated ring system can optionally be substituted by G;
$R_x$ and $R_y$ are independently of each other $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{12}$aryl group, which can optionally be substituted by G, or a $C_2$-$C_{30}$heteroaryl group which can optionally be substituted by G.

23. A compound of formula (Iaa):

(Iaa)

wherein
Y is S or O;
$R^2$, $R^3$, $R^5$, $R^6$, $R^7$ and $R^8$ are independently of each other H, CN, $NR^{65}R^{66}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group, which can optionally be substituted by G;
adjacent groups $R^5$ and $R^6$, $R^6$ and $R^7$, and/or $R^7$ and $R^8$ can optionally from together a ring, which can optionally be substituted by G;
L is a trivalent $C_6$-$C_{24}$ arylene group or a trivalent $C_2$-$C_{24}$ heteroarylene group;
$R^9$ is a fused $C_{10}$-$C_{24}$ aryl group or a fused $C_{12}$-$C_{24}$ heteroaryl group;

$X^9$, $X^{10}$ and $X^{11}$ are each independently N or $CR^{10}$, whereby at least two of $X^9$, $X^{10}$ and $X^{11}$ are N;

$R^{10}$ is H, $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G;

D is —CO—, —COO—, —S—, —SO—, —$SO_2$—, —O—, —$CR^{63}$=$CR^{64}$—, —$NR^{65}$—, —$POR^{72}$—, or —C≡C—;

E is —$OR^{69}$, —$SR^{69}$, —$NR^{65}R^{66}$, —$COR^{68}$, —$COOR^{67}$, —$CONR^{65}R^{66}$ or —CN,

G is E, or a $C_1$-$C_{24}$alkyl group, an unsubstituted $C_6$-$C_{24}$aryl group, a $C_6$-$C_{24}$aryl group, which is substituted by F, $C_1$-$C_{24}$alkyl, or $C_1$-$C_{24}$alkyl which is interrupted by O, an unsubstituted $C_2$-$C_{30}$heteroaryl group, or a $C_2$-$C_{30}$heteroaryl group, which is substituted by F, $C_1$-$C_{24}$alkyl, or $C_1$-$C_{24}$alkyl which is interrupted by O;

$R^{63}$ and $R^{64}$ are independently of each other unsubstituted $C_6$-$C_{18}$aryl; $C_6$-$C_{18}$aryl which is substituted by $C_1$-$C_{18}$alkyl or $C_1$-$C_{18}$alkoxy; $C_1$-$C_{18}$alkyl; or $C_1$-$C_{18}$alkyl which is interrupted by —O—;

$R^{65}$ and $R^{66}$ form together with the carbon atoms to which they are bonded a 5- or 6-membered ring, which can optionally be part of an anellated ring system, wherein the ring and/or anellated ring system can optionally be substituted by G;

$R^{67}$ is an unsubstituted $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by by —O—;

$R^{68}$ is H; an unsubstituted $C_6$-$C_{18}$aryl group; a $C_6$-$C_{18}$aryl group, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{69}$ is an unsubstituted $C_6$-$C_{18}$aryl; a $C_6$-$C_{18}$aryl, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{71}$ is a $C_1$-$C_{18}$alkyl group, a $C_6$-$C_{18}$aryl group, or a $C_6$-$C_{18}$aryl group, which is substituted by $C_1$-$C_{18}$alkyl; and $R^{72}$ is a $C_1$-$C_{18}$alkyl group, an unsubstituted $C_6$-$C_{18}$aryl group, or a $C_6$-$C_{18}$aryl group, which is substituted by $C_1$-$C_{18}$alkyl;

$R^{73}$ and $R^{74}$ form together with the carbon atoms to which they are bonded a 5- or 6-membered ring, which can optionally be part of an anellated ring system, wherein the ring and/or anellated ring system can optionally be substituted by G;

$R_x$ and $R_y$ are independently of each other $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{12}$aryl group, which can optionally be substituted by G, or a $C_2$-$C_{30}$heteroaryl group which can optionally be substituted by G;

wherein the dotted line is a bonding site.

24. The compound according to claim 23, wherein L is selected from the group consisting of

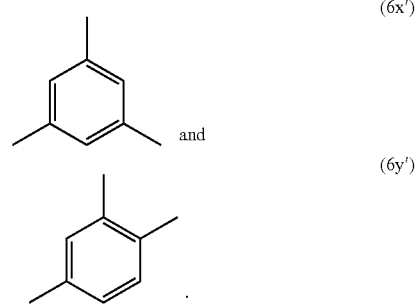

(6x')

and (6y')

25. A compound of formula (Ia):

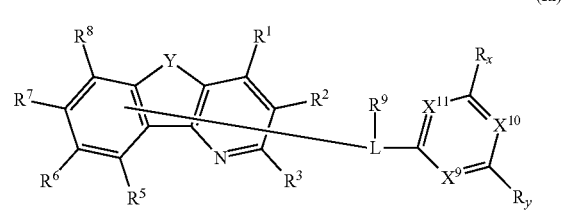

(Ia)

wherein
Y is S or O;
one of $R^1$, $R^2$, $R^3$, $R^5$, $R^6$, $R^7$ and $R^8$ is

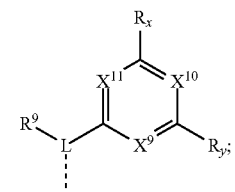

and the other of the remaining groups $R^1$, $R^2$, $R^3$, $R^5$, $R^6$, $R^7$ and $R^8$ are independently of each other H, CN, $NR^{65}R^{66}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group, which can optionally be substituted by G;

adjacent groups $R^1$ and $R^2$, $R^2$ and $R^3$, $R^5$ and $R^6$, $R^6$ and $R^7$, and $R^7$ and $R^8$ do not from together a ring;

L is a trivalent $C_6$-$C_{24}$ arylene group or a trivalent $C_2$-$C_{24}$ heteroarylene group;

$R^9$ is selected from the group consisting of naphthyl, phenanthryl, anthryl, benzophenanthryl, benzanthryl, naphthacenyl, triphenylenyl, benzochrysenyl, fluorenyl, benzofluorenyl, dibenzofluorenyl, indenofluorenyl, benzindenofluorenyl, fluoranthenyl, benzofluoranthenyl, benzotriphenylenyl, quinolyl, isoquinolyl, quinazolinyl, quinoxalinyl, benzoquinolynyl, benzoisoquinolinyl, benzoquinazolinyl, benzoquinoxalinyl, naphthoquinolinyl, naphthoisoquinolinyl, naphthoquinazolinyl, naphthoquinoxalinyl, phenanthrolinyl, benzofuroquinolinyl, benzothienoquinolinyl, carbazolyl, benzocarbazolyl, dibenzocarbazolyl, indenocarbazolyl, benzofurocarbazolyl, benzothiocarbazolyl, indrocarbazolyl, benzimidazo[1,2-a]benzimadozolyl, dibenzofuranyl, dibenzothiophenyl, benzonaphthofuranyl, benzonaphthothiophenyl, benzophenanthrofuranyl, and benzophenanthrothiophenyl, wherein the groups mentioned above can optionally be substituted by G;

$X^9$, $X^{10}$ and $X^{11}$ are each independently N or $CR^{10}$, whereby at least two of $X^9$, $X^{10}$ and $X^{11}$ are N;

$R^{10}$ is H, $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{24}$aryl group, which can optionally be substituted by G, or a $C_2$-$C_{30}$heteroaryl group which can optionally be substituted by G;

D is —CO—, —COO—, —S—, —SO—, —$SO_2$—, —O—, —$CR^{63}$=$CR^{64}$—, —$NR^{65}$—, —$POR^{72}$—, or —C≡C—;

E is —$OR^{69}$, —$SR^{69}$, —$NR^{65}R^{66}$, —$COR^{68}$, —$COOR^{67}$, —$CONR^{65}R^{66}$ or —CN,

G is E, or a $C_1$-$C_{24}$alkyl group, an unsubstituted $C_6$-$C_{24}$aryl group, a $C_6$-$C_{24}$aryl group, which is substituted by F, $C_1$-$C_{24}$alkyl, or $C_1$-$C_{24}$alkyl which is interrupted by O, an unsubstituted $C_2$-$C_{30}$heteroaryl group, or a $C_2$-$C_{30}$heteroaryl group, which is substituted by F, $C_1$-$C_{24}$alkyl, or $C_1$-$C_{24}$alkyl which is interrupted by O;

$R^{63}$ and $R^{64}$ are independently of each other unsubstituted $C_6$-$C_{18}$aryl; $C_6$-$C_{18}$aryl which is substituted by $C_1$-$C_{18}$alkyl or $C_1$-$C_{18}$alkoxy; $C_1$-$C_{18}$alkyl; or $C_1$-$C_{18}$alkyl which is interrupted by —O—;

$R^{65}$ and $R^{66}$ form together with the carbon atoms to which they are bonded a 5- or 6-membered ring, which can optionally be part of an anellated ring system, wherein the ring and/or anellated ring system can optionally be substituted by G;

$R^{67}$ is an unsubstituted $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—;

$R^{68}$ is H; an unsubstituted $C_6$-$C_{18}$aryl group; a $C_6$-$C_{18}$aryl group, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{69}$ is an unsubstituted $C_6$-$C_{18}$aryl; a $C_6$-$C_{18}$aryl, which is substituted by $C_1$-$C_{18}$alkyl or $C_1$-$C_{18}$alkoxy; a $C_1$-$C_{18}$alkyl group; or a $C_1$-$C_{18}$alkyl group, which is interrupted by —O—;

$R^{71}$ is a $C_1$-$C_{18}$alkyl group, a $C_6$-$C_{18}$aryl group, or a $C_6$-$C_{18}$aryl group, which is substituted by $C_1$-$C_{18}$alkyl; and $R^{72}$ is a $C_1$-$C_{18}$alkyl group, an unsubstituted $C_6$-$C_{18}$aryl group, or a $C_6$-$C_{18}$aryl group, which is substituted by $C_1$-$C_{18}$aryl;

$R^{73}$ and $R^{74}$ form together with the carbon atoms to which they are bonded a 5- or 6-membered ring, which can optionally be part of an anellated ring system, wherein the ring and/or anellated ring system can optionally be substituted by G;

$R_x$ and $R_y$ are independently of each other $NR^{73}R^{74}$, a $C_1$-$C_{25}$alkyl group, which can optionally be substituted by E, and or interrupted by D, a $C_2$-$C_{25}$alkenyl group, which can optionally be substituted by E, and or interrupted by D, a $C_2$-$C_{25}$alkynyl group, which can optionally be substituted by E, and or interrupted by D, —$OR^{69}$, —$SR^{69}$, —$COR^{68}$, —$COOR^{67}$, a $C_3C_{18}$cycloalkyl group, which can optionally be substituted by G; a $C_6$-$C_{12}$aryl group, which can optionally be substituted by G, or a $C_2$-$C_{30}$heteroaryl group which can optionally be substituted by G;

wherein the dotted line is a bonding site.

\* \* \* \* \*